US012059425B2

(12) United States Patent
Wu et al.

(10) Patent No.: US 12,059,425 B2
(45) Date of Patent: Aug. 13, 2024

(54) HETEROCYCLIC COMPOUNDS AND USES THEREOF

(71) Applicant: Kumquat Biosciences Inc., San Diego, CA (US)

(72) Inventors: Baogen Wu, San Diego, CA (US); Liansheng Li, San Diego, CA (US); Pingda Ren, San Diego, CA (US); Yi Liu, San Diego, CA (US); Siling Zhao, San Diego, CA (US); Xiaoming Li, San Diego, CA (US); Zhiyong Chen, San Diego, CA (US); Zhimin Zhu, San Diego, CA (US)

(73) Assignee: Kumquat Biosciences Inc., San Diego, CA (US)

( * ) Notice: Subject to any disclaimer, the term of this patent is extended or adjusted under 35 U.S.C. 154(b) by 1 day.

(21) Appl. No.: 18/439,666

(22) Filed: Feb. 12, 2024

(65) Prior Publication Data

US 2024/0226113 A1    Jul. 11, 2024

Related U.S. Application Data

(63) Continuation of application No. PCT/US2023/071743, filed on Aug. 4, 2023.

(60) Provisional application No. 63/395,649, filed on Aug. 5, 2022.

(51) Int. Cl.
*A61K 31/553* (2006.01)
*A61K 31/519* (2006.01)
*A61P 35/00* (2006.01)
*C07D 519/00* (2006.01)

(52) U.S. Cl.
CPC .......... *A61K 31/553* (2013.01); *A61K 31/519* (2013.01); *A61P 35/00* (2018.01); *C07D 519/00* (2013.01)

(58) Field of Classification Search
CPC ..... A61K 31/553; A61K 31/519; A61P 35/00; C07D 519/00
See application file for complete search history.

(56) References Cited

U.S. PATENT DOCUMENTS

| | | | |
|---|---|---|---|
| 2017/0247376 A1 | 8/2017 | Li et al. | |
| 2020/0331911 A1 | 10/2020 | Marx et al. | |
| 2022/0181118 A1 | 6/2022 | Galstyan et al. | |

FOREIGN PATENT DOCUMENTS

| | | |
|---|---|---|
| CN | 112300195 A | 2/2021 |
| CN | 112390818 A | 2/2021 |
| CN | 112552294 A | 3/2021 |
| CN | 113980032 A | 1/2022 |
| CN | 115197245 A | 10/2022 |
| CN | 116332948 A | 6/2023 |
| CN | 117486901 A | 2/2024 |
| CN | 117624190 A | 3/2024 |
| CN | 117683051 A | 3/2024 |
| WO | WO-2013155223 A1 | 10/2013 |
| WO | WO-2014143659 A1 | 9/2014 |
| WO | WO-2015054572 A1 | 4/2015 |
| WO | WO-2016044772 A1 | 3/2016 |
| WO | WO-2016119707 A1 | 8/2016 |
| WO | WO-2016164675 A1 | 10/2016 |
| WO | WO-2017058805 A1 | 4/2017 |
| WO | WO-2017172979 A1 | 10/2017 |
| WO | WO-2018206539 A1 | 11/2018 |
| WO | WO-2018217651 A1 | 11/2018 |
| WO | WO-2018218071 A1 | 11/2018 |
| WO | WO-2019099524 A1 | 5/2019 |
| WO | WO-2019110751 A1 | 6/2019 |
| WO | WO-2019215203 A1 | 11/2019 |
| WO | WO-2020035424 A1 | 2/2020 |
| WO | WO-2020035425 A1 | 2/2020 |
| WO | WO-2020081282 A1 | 4/2020 |
| WO | WO-2020097537 A2 | 5/2020 |
| WO | WO-2020113071 A1 | 6/2020 |
| WO | WO-2020146613 A1 | 7/2020 |
| WO | WO-2020177629 A1 | 9/2020 |
| WO | WO-2020221239 A1 | 11/2020 |
| WO | WO-2020239123 A1 | 12/2020 |
| WO | WO-2021000885 A1 | 1/2021 |
| WO | WO-2021018239 A1 | 2/2021 |
| WO | WO-2021041671 A1 | 3/2021 |
| WO | WO-2021108683 A1 | 6/2021 |
| WO | WO-2021118877 A1 | 6/2021 |
| WO | WO-2021219072 A1 | 11/2021 |
| WO | WO-2022015375 A1 | 1/2022 |
| WO | WO-2022042630 A1 | 3/2022 |
| WO | WO-2022068921 A1 | 4/2022 |
| WO | WO-2022076917 A1 | 4/2022 |
| WO | WO-2022105855 A1 | 5/2022 |
| WO | WO-2022132200 A1 | 6/2022 |

(Continued)

OTHER PUBLICATIONS

Aaltonen, N. et al., "Piperazine and Piperidine Triazole Ureas as Ultrapotent and Highly Selective Inhibitors of Monoacylglycerol Lipase", Chem Biol, 2013, vol. 20, pp. 379-390.

(Continued)

*Primary Examiner* — John M Mauro

(74) *Attorney, Agent, or Firm* — Wilson Sonsini Goodrich & Rosati

(57) ABSTRACT

The present disclosure provides compounds and pharmaceutically acceptable salts thereof, and methods of using the same. The compounds and methods have a range of utilities as therapeutics, diagnostics, and research tools. In particular, the subject compositions and methods are useful for reducing signaling output of certain oncogenic proteins.

20 Claims, 1 Drawing Sheet

Specification includes a Sequence Listing.

(56) References Cited

FOREIGN PATENT DOCUMENTS

| | | |
|---|---|---|
| WO | WO-2022133038 A1 | 6/2022 |
| WO | WO-2022173678 A1 | 8/2022 |
| WO | WO-2022173870 A1 | 8/2022 |
| WO | WO-2022177917 A2 | 8/2022 |
| WO | WO-2022188729 A1 | 9/2022 |
| WO | WO-2022194245 A1 | 9/2022 |
| WO | WO-2022199587 A1 | 9/2022 |
| WO | WO-2022206723 A1 | 10/2022 |
| WO | WO-2022216762 A1 | 10/2022 |
| WO | WO-2022223750 A1 | 10/2022 |
| WO | WO-2022235866 A1 | 11/2022 |
| WO | WO-2022247760 A1 | 12/2022 |
| WO | WO-2022266015 A1 | 12/2022 |
| WO | WO-2022268051 A1 | 12/2022 |
| WO | WO-2023001123 A1 | 1/2023 |
| WO | WO-2023001141 A1 | 1/2023 |
| WO | WO-2023004102 A2 | 1/2023 |
| WO | WO-2023274383 A1 | 1/2023 |
| WO | WO-2023018810 A1 | 2/2023 |
| WO | WO-2023030385 A1 | 3/2023 |
| WO | WO-2023046135 A1 | 3/2023 |
| WO | WO-2023103906 A1 | 6/2023 |
| WO | WO-2023114733 A1 | 6/2023 |
| WO | WO-2023122662 A1 | 6/2023 |
| WO | WO-2023141300 A1 | 7/2023 |
| WO | WO-2023143623 A1 | 8/2023 |
| WO | WO-2023205719 A1 | 10/2023 |
| WO | WO-2023215801 A1 | 11/2023 |
| WO | WO-2023215802 A1 | 11/2023 |
| WO | WO-2023225302 A1 | 11/2023 |
| WO | WO-2023244615 A1 | 12/2023 |
| WO | WO-2024009191 A1 | 1/2024 |
| WO | WO-2024015262 A1 | 1/2024 |
| WO | WO-2024017392 A1 | 1/2024 |
| WO | WO-2024022444 A1 | 2/2024 |
| WO | WO-2024022507 A1 | 2/2024 |
| WO | WO-2024031088 A1 | 2/2024 |
| WO | WO-2024032702 A1 | 2/2024 |
| WO | WO-2024032703 A1 | 2/2024 |
| WO | WO-2024032704 A1 | 2/2024 |
| WO | WO-2024032747 A1 | 2/2024 |
| WO | WO-2024041621 A1 | 2/2024 |
| WO | WO-2024050742 A1 | 3/2024 |
| WO | WO-2024051721 A1 | 3/2024 |
| WO | WO-2024054625 A2 | 3/2024 |

OTHER PUBLICATIONS

Bertrand, T. et al., "Structural Basis for Human Monoglyceride", J. Mol. Biol., 2010, vol. 396, pp. 663-674.

Cisar et al. Identification of ABX-1431, a Selective Inhibitor of Monoacylglycerol Lipase 1 and Clinical Candidate for Treatment of Neurological Disorders. J Med Chem 61:9062-9084 (2018).

Co-pending U.S. Appl. No. 18/506,478, inventors Li; Xiaoming et al., filed Nov. 10, 2023, Filing Receipt.

Deng, H. et al., "Monoacylglycerol lipase inhibitors: Modulators for lipid metabolism in cancer malignancy, neurological and metabolic disorders", Acta Pharm Sin B., 2020, vol. 10, No. 4, pp. 582-602.

Hyun, S. et al., "Small-Molecule Inhibitors and Degraders Targeting KRAS-Driven Cancers", Int. J. Mol. Sciences, 2021, vol. 22: 12142, pp. 1-16.

International Search Report and Written Opinion dated Nov. 24, 2023 for International Application No. PCT/US2023/071743.

McGregor, L.M., et al., "Expanding the Scope of Electrophiles Capable of Targeting K-Ras Oncogenes", Biochemistry, 2017, vol. 56, pp. 3178-3183., Supporting Information pp. S1-S24.

Morera, L. et al., "Development and Characterization of Endocannabinoid Hydrolases FAAH and MAGL Inhibitors Bearing a Benzotriazol-1-yl Carboxamide Scaffold", Bioorg Med Chem, 2012, vol. 20, pp. 6260-6275.

Patel, J.Z., et al., "Loratadine Analogues as MAGL Inhibitors", Bioorg Med Chem Lett, 2015, vol. 25, pp. 1436-1442.

Pubchem, Substance Record for SID 308914829, Jan. 30, 20, 2016.

Pubchem, Substance Record for SID 366994743 May 25, 2018.

Remsberg, J.R., et al., "ABHD17 regulation of plasma membrane palmitoylation and N-Ras-dependent cancer growth", Nat Chem Biol. Aug. 2021, vol. 17, No. 8, pp. 856-864.

Zhang, Z. et al., "Chemoselective Covalent Modification of K-Ras (G12R) with a Small Molecule Electrophile", JACS, Sep. 7, 2022, vol. 144, No. 35, pp. 15916-15921.

```
K-Ras
(SEQ ID No. 9)   mte-------yklvvv gaggvgksal tiqliqnhfv deydptieds yrkqvvidge  49

H-Ras
(SEQ ID No. 10)  mte-------yklvvv gaggvgksal tiqliqnhfv deydptieds yrkqvvidge  49

N-Ras
(SEQ ID No. 11)  mte-------yklvvv gaggvgksal tiqliqnhfv deydptieds yrkqvvidge  49

RalA
(SEQ ID No. 12)  maankpkggn slalhkvimv gsggvgksal tlqfmydefv edyeptkads yrkkvvldge  60

RalB
(SEQ ID No. 13)  maankskggs slalhkvimv gsggvgksal tlqfmydefv edyeptkads yrkkvvldge  60

K-Ras   tclldildta gqeeysamrd qymrtgegfl cvfainntks fedihhyreq ikrvkdsed-  108

H-Ras   tclldildta gqeeysamrd qymrtgegfl cvfainntks fedihqyreq ikrvkdsdd-  108

N-Ras   tclldildta gqeeysamrd qymrtgegfl cvfainnsks fadinlyreq ikrvkdsdd-  108

RalA    evqidildta gqedyaairo nyfrsgegfl cvfsitemes faatadfreq ilrvk-eden  119

RalB    evqidildta gqedyaairo nyfrsgegfl lvfsitehes ftataefreq ilrvkaeedk  120
```

HETEROCYCLIC COMPOUNDS AND USES THEREOF

CROSS-REFERENCE

This application is a continuation of International Application No. PCT/US2023/071743, filed Aug. 4, 2023, which claims the benefit of U.S. Provisional Application No. 63/395,649, filed Aug. 5, 2022, each incorporated herein by reference in its entirety.

SEQUENCE LISTING

The instant application contains a Sequence Listing which has been submitted electronically in XML format and is hereby incorporated by reference in its entirety. Said XML copy, created on Feb. 12, 2024, is named 56690_756_301_.xml and is 13,993 bytes in size.

BACKGROUND

Cancer (e.g., tumor, neoplasm, metastases) is the second leading cause of death worldwide estimated to be responsible for about 10 million deaths each year. Many types of cancers are marked with mutations in one or more proteins involved in various signaling pathways leading to unregulated growth of cancerous cells. In some cases, about 25 to 30 percent (%) of tumors are known to harbor Rat sarcoma (Ras) mutations. In particular, mutations in the Kirsten Ras oncogene (K-Ras) are one of the most frequent Ras mutations detected in human cancers, including lung adenocarcinomas (LUADs) and pancreatic ductal adenocarcinoma (PDAC).

Ras proteins have long been considered "undruggable," due to, in part, high affinity to their substrate guanosine-5'-triphosphate (GTP) and/or their smooth surfaces without any obvious targeting region. The specific G12C Ras gene mutation has been identified as a druggable target to which a number of G12C specific inhibitors have been developed. However, such therapeutics are still of limited application, as the G12C mutation in Ras exhibits a much lower prevalence rate as compared to other known Ras mutations, such as G12D and G12V. Drug resistance and lack of durability impose further limitations to such therapeutics.

SUMMARY

In view of the foregoing, there remains a considerable need for a new design of therapeutics and diagnostics that can specifically target Ras, including wildtype Ras, mutants and/or associated proteins of Ras to reduce Ras signaling output. Of particular interest are Ras inhibitors, including pan Ras inhibitors capable of inhibiting two or more Ras mutants and/or wildtype Ras, as well as mutant-selective inhibitors targeting mutant Ras proteins such as Ras G12D, G12C, G12S, G13D, and/or G12V, for the treatment of Ras-associated diseases (e.g., cancer). Such compositions and methods can be particularly useful for treating a variety of diseases including, but not limited to, cancers and neoplasia conditions. The present disclosure addresses these needs, and provides additional advantages applicable for diagnosis, prognosis, and/or treatment for a wide diversity of diseases.

In an aspect is provided a compound of Formula (A), or a pharmaceutically acceptable salt or solvate thereof:

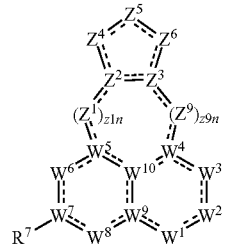

(A)

wherein:

$W^1$ is $N(R^1)$ or N;

$R^1$ is selected from hydrogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$C(O)OR^{12}$, —$OC(O)N(R^{12})(R^{13})$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20a}$;

$W^2$ is $C(R^2)$, $N(R^2)$, $C(R^2)_2$, C(O), S(O), $S(O)_2$, or N;

each $R^2$ is independently selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12a}$, —$SR^{12a}$, —$N(R^{12a})(R^{13})$, —$N=(R^{15})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20b}$;

$W^3$ is $C(R^3)$, $N(R^3)$, $C(R^3)_2$, C(O), S(O), $S(O)_2$, or N;

each $R^3$ is independently selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20c}$;

$W^4$ is $C(R^4)$, C, or N;

$R^4$ is selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —N(R$^{14}$)C(O)R$^{15}$, —S(O)$_2$R$^{15}$, —S(O)$_2$N(R$^{12}$)(R$^{13}$), —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl are optionally substituted with one, two, or three R$^{20d}$;

W$^5$ is C(R$^5$), C, or N;

R$^5$ is selected from hydrogen, halogen, —CN, C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, C$_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$), —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl are optionally substituted with one, two, or three R$^{20e}$;

W$^6$ is C(R$^6$), N(R$^6$), C(R$^6$)$_2$, C(O), S(O), S(O)$_2$, or N;

each R$^6$ is independently selected from hydrogen, halogen, —CN, C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, C$_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$), —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl are optionally substituted with one, two, or three R$^{20f}$;

W$^7$ is C(R$^{7a}$), C, or N;

R$^{7a}$ is selected from hydrogen, halogen, —CN, C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, C$_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$), —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl are optionally substituted with one, two, or three R$^{20g}$;

R$^7$ is -L$^7$—R$^{17}$;

L$^7$ is a bond, C$_1$-C$_4$alkyl, C$_2$-C$_4$alkenyl, C$_2$-C$_4$alkynyl, 2-4 membered heteroalkylene linker, —O—, —N(R$^{7d}$)—, —C(O)—, —S—, —S(O)$_2$—, —S(O)—, —P(O)R$^{7d}$—, CR$^{7c}$R$^{7c}$, —OCR$^{7c}$R$^{7c}$—, —N(R$^{7d}$) CR$^{7c}$R$^{7c}$—, —C(O)CR$^{7c}$R$^{7c}$—, —SCR$^{7c}$R$^{7c}$—, —S(O)$_2$CR$^{7c}$R$^{7c}$—, —S(O)CR$^{7c}$R$^{7c}$—, —P(O)R$^{7d}$CR$^{7c}$R$^{7c}$—, —CR$^{7c}$R$^{7c}$CR$^{7c}$R$^{7c}$—, —CR$^{7c}$R$^{7c}$O—, —CR$^{7c}$R$^{7c}$N(R$^{7d}$)—, —CR$^{7c}$R$^{7c}$C(O)O—, —CR$^{7c}$R$^{7c}$S—, —CR$^{7c}$R$^{7c}$S(O)$_2$—, —CR$^{7c}$R$^{7c}$S(O)—, —CR$^{7c}$R$^{7c}$P(O)R$^{7d}$—, —N(R$^{7d}$)C(O)—, —N(R$^{7d}$)S(O)$_2$—, —N(R$^{7d}$)S(O)—, —N(R$^{7d}$)P(O)R$^{7d}$—, —C(O)N(R$^{7d}$)—, —S(O)$_2$N(R$^{7d}$)—, —S(O)N(R$^{7d}$)—, —P(O)R$^{7d}$N(R$^{7d}$)—, —OC(O)—, —OS(O)$_2$—, —OS(O)—, —OP(O)R$^{7d}$—, —C(O)O—, —S(O)$_2$O—, —S(O)O—, or —P(O)R$^{7d}$O—; wherein the C$_1$-C$_4$alkyl, C$_2$-C$_4$alkenyl, C$_2$-C$_4$alkynyl, 2-4 membered heteroalkylene linker are optionally substituted with one, two, or three R$^{20g}$;

each R$^{7c}$ is independently selected from hydrogen, halogen, —CN, C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, C$_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$), S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl are optionally substituted with one, two, or three R$^{20g}$;

each R$^{7d}$ is independently selected from hydrogen, —CN, C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, C$_{1-9}$heteroaryl, —OR$^{12}$, —SR$^{12}$, —C(O)OR$^{12}$, —OC(O)N(R$^{12}$)(R$^{13}$), —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —S(O)$_2$R$^{15}$, —S(O)$_2$N(R$^{12}$)(R$^{13}$), —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl are optionally substituted with one, two, or three R$^{20g}$;

R$^{17}$ is selected from C$_{3-10}$cycloalkyl, 3-10 membered heterocycloalkyl, C$_{6-10}$aryl, and 5-10 membered heteroaryl, wherein C$_{3-10}$cycloalkyl, 3-10 membered heterocycloalkyl, C$_{6-10}$aryl, and 5-10 membered heteroaryl are optionally substituted with one or more R$^{20q}$; or L$^7$ is a bond and R$^{7a}$ and R$^{17}$, together with the carbon to which they are attached, form C$_{3-10}$cycloalkyl or 3-10 membered heterocycloalkyl, wherein the C$_{3-10}$cycloalkyl and 3-10 membered heterocycloalkyl are optionally substituted with one or more R$^{20q}$;

W$^8$ is C(R$^8$), N(R$^8$), C(R$^8$)$_2$, C(O), S(O), S(O)$_2$, or N;

each R$^8$ is independently selected from hydrogen, halogen, —CN, C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, C$_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$), —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl are optionally substituted with one, two, or three R$^{20h}$;

W$^9$ is C(R$^9$), C, or N;

R$^9$ is selected from hydrogen, halogen, —CN, C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, C$_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$), —S(=O)(=NH)N($R^{12}$)($R^{13}$), —CH$_2$C(O)N($R^{12}$)($R^{13}$), —CH$_2$N($R^{14}$)C(O)$R^{15}$, —CH$_2$S(O)$_2$$R^{15}$, and —CH$_2$S(O)$_2$N($R^{12}$)($R^{13}$), wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl are optionally substituted with one, two, or three $R^{20i}$;

$W^{10}$ C($R^{10}$), C, or N;

$R^{10}$ is selected from hydrogen, halogen, —CN, C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, C$_{1-9}$heteroaryl, —O$R^{12}$, —S$R^{12}$, —N($R^{12}$)($R^{13}$), —C(O)O$R^{12}$, —OC(O)N($R^{12}$)($R^{13}$), —N($R^{14}$)C(O)N($R^{12}$)($R^{13}$), —N($R^{14}$)C(O)O$R^{15}$, —N($R^{14}$)S(O)$_2$$R^{15}$, —C(O)$R^{15}$, —S(O)$R^{15}$, —OC(O)$R^{15}$, —C(O)N($R^{12}$)($R^{13}$), —C(O)C(O)N($R^{12}$)($R^{13}$), —N($R^{14}$)C(O)$R^{15}$, —S(O)$_2$$R^{15}$, —S(O)$_2$N($R^{12}$)($R^{13}$), —S(=O)(=NH)N($R^{12}$)($R^{13}$), —CH$_2$C(O)N($R^{12}$)($R^{13}$), —CH$_2$N($R^{14}$)C(O)$R^{15}$, —CH$_2$S(O)$_2$$R^{15}$, and —CH$_2$S(O)$_2$N($R^{12}$)($R^{13}$), wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl are optionally substituted with one, two, or three $R^{20j}$;

each $Z^1$ is independently C($R^{z1}$), N($R^{z1}$), C($R^{z1}$)$_2$, C(O), S(O), S(O)$_2$, O, S, or N;

z1n is 0, 1, 2, or 3; wherein if z1n is 0 then $Z^2$ is directly bonded to $W^5$;

each $R^{z1}$ is independently selected from hydrogen, halogen, —CN, C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, C$_{1-9}$heteroaryl, —O$R^{12}$, —S$R^{12}$, —N($R^{12}$)($R^{13}$), —C(O)O$R^{12}$, —OC(O)N($R^{12}$)($R^{13}$), —N($R^{14}$)C(O)N($R^{12}$)($R^{13}$), —N($R^{14}$)C(O)O$R^{15}$, —N($R^{14}$)S(O)$_2$$R^{15}$, —C(O)$R^{15}$, —S(O)$R^{15}$, —OC(O)$R^{15}$, —C(O)N($R^{12}$)($R^{13}$), —C(O)C(O)N($R^{12}$)($R^{13}$), —N($R^{14}$)C(O)$R^{15}$, —S(O)$_2$$R^{15}$, —S(O)$_2$N($R^{12}$)($R^{13}$), —S(=O)(=NH)N($R^{12}$)($R^{13}$), —CH$_2$C(O)N($R^{12}$)($R^{13}$), —CH$_2$N($R^{14}$)C(O)$R^{15}$, —CH$_2$S(O)$_2$$R^{15}$, and —CH$_2$S(O)$_2$N($R^{12}$)($R^{13}$), wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl are optionally substituted with one, two, or three $R^{20z1}$;

each $Z^9$ is independently C($R^{z9}$), N($R^{z9}$), C($R^{z9}$)$_2$, C(O), S(O), S(O)$_2$, O, S, or N;

z9n is 0, 1, 2, or 3; wherein if z9n is 0 then $Z^3$ is directly bonded to $W^4$;

each $R^{z9}$ is independently selected from hydrogen, halogen, —CN, C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, C$_{1-9}$heteroaryl, —O$R^{12}$, —S$R^{12}$, —N($R^{12}$)($R^{13}$), —C(O)O$R^{12}$, —OC(O)N($R^{12}$)($R^{13}$), —N($R^{14}$)C(O)N($R^{12}$)($R^{13}$), —N($R^{14}$)C(O)O$R^{15}$, —N($R^{14}$)S(O)$_2$$R^{15}$, —C(O)$R^{15}$, —S(O)$R^{15}$, —OC(O)$R^{15}$, —C(O)N($R^{12}$)($R^{13}$), —C(O)C(O)N($R^{12}$)($R^{13}$), —N($R^{14}$)C(O)$R^{15}$, —S(O)$_2$$R^{15}$, —S(O)$_2$N($R^{12}$)($R^{13}$), —S(=O)(=NH)N($R^{12}$)($R^{13}$), —CH$_2$C(O)N($R^{12}$)($R^{13}$), —CH$_2$N($R^{14}$)C(O)$R^{15}$, —CH$_2$S(O)$_2$$R^{15}$, and —CH$_2$S(O)$_2$N($R^{12}$)($R^{13}$), wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl are optionally substituted with one, two, or three $R^{20z9}$;

wherein the sum of z1n and z9n is 2 or 3;

$Z^2$ is C($R^{z2}$), C, or N;

$R^{z2}$ is selected from hydrogen, halogen, —CN, C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, C$_{1-9}$heteroaryl, —O$R^{12}$, —S$R^{12}$, —N($R^{12}$)($R^{13}$), —C(O)O$R^{12}$, —OC(O)N($R^{12}$)($R^{13}$), —N($R^{14}$)C(O)N($R^{12}$)($R^{13}$), —N($R^{14}$)C(O)O$R^{15}$, —N($R^{14}$)S(O)$_2$$R^{15}$, —C(O)$R^{15}$, —S(O)$R^{15}$, —OC(O)$R^{15}$, —C(O)N($R^{12}$)($R^{13}$), —C(O)C(O)N($R^{12}$)($R^{13}$), —N($R^{14}$)C(O)$R^{15}$, —S(O)$_2$$R^{15}$, —S(O)$_2$N($R^{12}$)($R^{13}$), —S(=O)(=NH)N($R^{12}$)($R^{13}$), —CH$_2$C(O)N($R^{12}$)($R^{13}$), —CH$_2$N($R^{14}$)C(O)$R^{15}$, —CH$_2$S(O)$_2$$R^{15}$, and —CH$_2$S(O)$_2$N($R^{12}$)($R^{13}$), wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl are optionally substituted with one, two, or three $R^{20z2}$;

$Z^3$ is C($R^{z3}$), C, or N;

$R^{z3}$ is selected from hydrogen, halogen, —CN, C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, C$_{1-9}$heteroaryl, —O$R^{12}$, —S$R^{12}$, —N($R^{12}$)($R^{13}$), —C(O)O$R^{12}$, —OC(O)N($R^{12}$)($R^{13}$), —N($R^{14}$)C(O)N($R^{12}$)($R^{13}$), —N($R^{14}$)C(O)O$R^{15}$, —N($R^{14}$)S(O)$_2$$R^{15}$, —C(O)$R^{15}$, —S(O)$R^{15}$, —OC(O)$R^{15}$, —C(O)N($R^{12}$)($R^{13}$), —C(O)C(O)N($R^{12}$)($R^{13}$), —N($R^{14}$)C(O)$R^{15}$, —S(O)$_2$$R^{15}$, —S(O)$_2$N($R^{12}$)($R^{13}$), —S(=O)(=NH)N($R^{12}$)($R^{13}$), —CH$_2$C(O)N($R^{12}$)($R^{13}$), —CH$_2$N($R^{14}$)C(O)$R^{15}$, —CH$_2$S(O)$_2$$R^{15}$, and —CH$_2$S(O)$_2$N($R^{12}$)($R^{13}$), wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl are optionally substituted with one, two, or three $R^{20z3}$;

$Z^4$ is a bond, $Z^{4a}$, $Z^{4a}Z^{4b}$, $Z^{4a}Z^{4b}Z^{4c}$, or $Z^{4a}Z^{4b}Z^{4c}Z^{4d}$; wherein $Z^{4a}$ is directly bonded to $Z^2$; and wherein if $Z^4$ is a bond then $Z^2$ is directly bonded to $Z^5$;

$Z^{4a}$, $Z^{4b}$, $Z^{4c}$, and $Z^{4d}$ are independently C($R^{z4}$), N($R^{z4}$), C($R^{z4}$)$_2$, C(O), S(O), S(O)$_2$, S(O)(N$R^{z4}$), O, S, or N; provided that:

i) if z9n is 0 and $Z^4$ is $Z^{4a}Z^{4b}$; then (1) $Z^{4b}$ is C($R^{z4}$), C($R^{z4}$)$_2$, C(O), S(O), S(O)$_2$, S(O)(N$R^{z4}$), O, S, or N, (2) $Z^{4b}$ is N($R^{z4}$) and $Z^{4a}$ is C(O), S(O), or S(O)$_2$; (3) $Z^{4b}$ is N($R^{z4}$) and $Z^5$ is C(O), S(O), or S(O)$_2$; or (4) $Z^{4b}$ is N($R^{z4}$) and $Z^3$ is C($R^{z3}$) or C; and ii) one $R^{z4}$, $R^{z5}$, $R^{z6}$, $R^{20z4}$, $R^{20z5}$, $R^{20z6}$, or $R^{20z}$ is independently selected from —C(O)$R^{12}$ and —N(H)C(O)$R^{12}$; wherein the one $R^{12}$ is selected from C$_{3-10}$cycloalkyl, C$_{2-9}$heterocycloalkyl, C$_{6-10}$aryl, and C$_{1-9}$heteroaryl, wherein C$_{3-10}$cycloalkyl, C$_{2-9}$heterocycloalkyl, C$_{6-10}$aryl, and C$_{1-9}$heteroaryl are optionally substituted with one, two, or three $R^{20l}$;

each $R^{z4}$ is independently selected from hydrogen, halogen, —CN, C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, C$_{1-9}$heteroaryl, —O$R^{12}$, —S$R^{12}$, —N($R^{12}$)($R^{13}$), —C(O)O$R^{12}$, —OC(O)N($R^{12}$)($R^{13}$), —N($R^{14}$)C(O)N($R^{12}$)($R^{13}$), —N($R^{14}$)C(O)O$R^{15}$, —N($R^{14}$)S(O)$_2$$R^{15}$, —C(O)$R^{12}$, —S(O)$R^{15}$, —OC(O)$R^{15}$, —C(O)N($R^{12}$)($R^{13}$), —C(O)C(O)N($R^{12}$)($R^{13}$), —N($R^{14}$)C(O)$R^{12}$, —S(O)$_2$$R^{15}$, —S(O)$_2$N($R^{12}$)($R^{13}$), —S(=O)(=NH)N($R^{12}$)($R^{13}$), —CH$_2$C(O)N($R^{12}$)($R^{13}$), —CH$_2$N($R^{14}$)C(O)$R^{15}$, —CH$_2$S(O)$_2$$R^{15}$, and —CH$_2$S(O)$_2$N($R^{12}$)($R^{13}$), wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl are optionally substituted with one, two, or three $R^{20z4}$; or two $R^{z4}$ bonded to the same carbon are joined to form C$_{2-6}$alkenyl optionally substituted with one, two, or three $R^{20z4}$;

$Z^5$ is C($R^{z5}$), N($R^{z5}$), C($R^{z5}$)$_2$, C(O), S(O), S(O)$_2$, S(O)(N$R^{z5}$), O, S, or N;

each $R^{z5}$ is independently selected from hydrogen, halogen, —CN, C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, C$_{1-9}$heteroaryl, —O$R^{12}$, —S$R^{12}$, —N($R^{12}$)($R^{13}$), —C(O)O$R^{12}$, —OC(O)N($R^{12}$)($R^{13}$), —N($R^{14}$)C(O)N $(R^{12})(R^{13})$, $-N(R^{14})C(O)OR^{15}$, $-N(R^{14})S(O)_2R^{15}$, $-C(O)R^{12}$, $-S(O)R^{15}$, $-OC(O)R^{15}$, $-C(O)N(R^{12})(R^{13})$, $-C(O)C(O)N(R^{12})(R^{13})$, $-N(R^{14})C(O)R^{12}$, $-S(O)_2R^{15}$, $-S(O)_2N(R^{12})(R^{13})$, $-S(=O)(=NH)N(R^{12})(R^{13})$, $-CH_2C(O)N(R^{12})(R^{13})$, $-CH_2N(R^{14})C(O)R^{15}$, $-CH_2S(O)_2R^{15}$, and $-CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20z5}$; or two $R^{z5}$ bonded to the same carbon are joined to form $C_{2-6}$alkenyl optionally substituted with one, two, or three $R^{20z5}$;

$Z^6$ is $C(R^{z6})$, $N(R^{z6})$, $C(R^{z6})_2$, $C(O)$, $S(O)$, $S(O)_2$, $S(O)(NR^{z6})$, O, S, or N;

each $R^{z6}$ is independently selected from hydrogen, halogen, $-CN$, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, $-OR^{12}$, $-SR^{12}$, $-N(R^{12})(R^{13})$, $-C(O)OR^{12}$, $-OC(O)N(R^{12})(R^{13})$, $-N(R^{14})C(O)N(R^{12})(R^{13})$, $-N(R^{14})C(O)OR^{15}$, $-N(R^{14})S(O)_2R^{15}$, $-C(O)R^{12}$, $-S(O)R^{15}$, $-OC(O)R^{15}$, $-C(O)N(R^{12})(R^{13})$, $-C(O)C(O)N(R^{12})(R^{13})$, $-N(R^{14})C(O)R^{12}$, $-S(O)_2R^{15}$, $-S(O)_2N(R^{12})(R^{13})$, $-S(=O)(=NH)N(R^{12})(R^{13})$, $-CH_2C(O)N(R^{12})(R^{13})$, $-CH_2N(R^{14})C(O)R^{15}$, $-CH_2S(O)_2R^{15}$, and $-CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20z6}$; or two $R^{z6}$ bonded to the same carbon are joined to form $C_{2-6}$alkenyl optionally substituted with one, two, or three $R^{20z6}$;

and further wherein the compound optionally includes one of the following:

(1) two $R^{z4}$ bonded to the same carbon atom are joined to form monocyclic $C_{3-7}$cycloalkyl or monocyclic 3-7 membered heterocycloalkyl, wherein the monocyclic $C_{3-7}$cycloalkyl and monocyclic 3-7 membered heterocycloalkyl are optionally substituted with one, two, or three $R^{20z}$;

(2) two or more $R^{z4}$ bonded to adjacent atoms are joined to form monocyclic $C_{3-7}$cycloalkyl, monocyclic 3-7 membered heterocycloalkyl, phenyl, or monocyclic 5-6 membered heteroaryl, wherein the monocyclic $C_{3-7}$cycloalkyl, monocyclic 3-7 membered heterocycloalkyl, phenyl, and monocyclic 5-6 membered heteroaryl are optionally substituted with one, two, or three $R^{20z}$;

(3) two $R^{z5}$ bonded to the same carbon atom are joined to form monocyclic $C_{3-7}$cycloalkyl or monocyclic 3-7 membered heterocycloalkyl, wherein the monocyclic $C_{3-7}$cycloalkyl and monocyclic 3-7 membered heterocycloalkyl are optionally substituted with one, two, or three $R^{20z}$;

(4) one or two $R^{z4}$ bonded to one atom and one or two $R^{z5}$ bonded to an adjacent atom are joined to form monocyclic $C_{3-7}$cycloalkyl, monocyclic 3-7 membered heterocycloalkyl, phenyl, or monocyclic 5-6 membered heteroaryl, wherein the monocyclic $C_{3-7}$cycloalkyl, monocyclic 3-7 membered heterocycloalkyl, phenyl, and monocyclic 5-6 membered heteroaryl are optionally substituted with one, two, or three $R^{20z}$;

(5) one or two $R^{z4}$ bonded to one atom and one or two $R^{z5}$ bonded to a second atom are joined to form monocyclic $C_{3-7}$cycloalkyl or monocyclic 3-7 membered heterocycloalkyl, wherein the monocyclic $C_{3-7}$cycloalkyl and monocyclic 3-7 membered heterocycloalkyl are optionally substituted with one, two, or three $R^{20z}$;

(6) two $R^{z6}$ bonded to the same carbon atom are joined to form monocyclic $C_{3-7}$cycloalkyl or monocyclic 3-7 membered heterocycloalkyl, wherein the monocyclic $C_{3-7}$cycloalkyl and monocyclic 3-7 membered heterocycloalkyl are optionally substituted with one, two, or three $R^{20z}$;

(7) one or two $R^{z5}$ bonded to one atom and one or two $R^{z6}$ bonded to an adjacent atom are joined to form monocyclic $C_{3-7}$cycloalkyl, monocyclic 3-7 membered heterocycloalkyl, phenyl, or monocyclic 5-6 membered heteroaryl, wherein the monocyclic $C_{3-7}$cycloalkyl, monocyclic 3-7 membered heterocycloalkyl, phenyl, and monocyclic 5-6 membered heteroaryl are optionally substituted with one, two, or three $R^{20z}$; or (8) one or two $R^{z4}$ bonded to one atom and one or two $R^{z6}$ bonded to a second atom are joined to form monocyclic $C_{3-7}$cycloalkyl or monocyclic 3-7 membered heterocycloalkyl, wherein the monocyclic $C_{3-7}$cycloalkyl and monocyclic 3-7 membered heterocycloalkyl are optionally substituted with one, two, or three $R^{20z}$;

each $R^{12}$ is independently selected from hydrogen, $C_{1-6}$alkyl, $C_{2-6}$alkenyl, $C_{2-6}$alkynyl, $C_{3-10}$cycloalkyl, $-CH_2-C_{3-10}$cycloalkyl, $C_{2-9}$heterocycloalkyl, $-CH_2-C_{2-9}$heterocycloalkyl, $C_{6-10}$aryl, $-CH_2-C_{6-10}$aryl, $-CH_2-C_{1-9}$heteroaryl, and $C_{1-9}$heteroaryl, wherein $C_{1-6}$alkyl, $C_{2-6}$alkenyl, $C_{2-6}$alkynyl, $C_{3-10}$cycloalkyl, $-CH_2-C_{3-10}$cycloalkyl, $C_{2-9}$heterocycloalkyl, $-CH_2-C_{2-9}$heterocycloalkyl, $C_{6-10}$aryl, $-CH_2-C_{6-10}$aryl, $-CH_2-C_{1-9}$heteroaryl, and $C_{1-9}$heteroaryl are optionally substituted with one, two, or three $R^{20l}$;

$R^{12a}$ is independently selected from hydrogen, $C_{1-6}$alkyl, $C_{2-6}$alkenyl, $C_{2-6}$alkynyl, $C_{3-10}$cycloalkyl, $-C(R^{12c})_2-C_{3-10}$cycloalkyl, $C_{2-9}$heterocycloalkyl, $-C(R^{12c})_2-C_{2-9}$heterocycloalkyl, $C_{6-10}$aryl, $-C(R^{12c})_2-C_{6-10}$aryl, $-C(R^{12c})_2-C_{1-9}$heteroaryl, and $C_{1-9}$heteroaryl, wherein $C_{1-6}$alkyl, $C_{2-6}$alkenyl, $C_{2-6}$alkynyl, $C_{3-10}$cycloalkyl, $-C(R^{12c})_2-C_{3-10}$cycloalkyl, $C_{2-9}$heterocycloalkyl, $-C(R^{12c})_2-C_{2-9}$heterocycloalkyl, $C_{6-10}$aryl, $-C(R^{12c})_2-C_{6-10}$aryl, $-C(R^{12c})_2-C_{1-9}$heteroaryl, and $C_{1-9}$heteroaryl are optionally substituted with one, two, or three $R^{20l}$;

each $R^{12c}$ is independently selected from hydrogen and $R^{20lc}$;

each $R^{13}$ is independently selected from hydrogen, $C_{1-6}$alkyl, and $C_{1-6}$haloalkyl; or $R^{12}$ and $R^{13}$, together with the nitrogen to which they are attached, form a $C_{2-9}$heterocycloalkyl ring optionally substituted with one, two, or three $R^{20m}$;

each $R^{14}$ is independently selected from hydrogen, $C_{1-6}$alkyl, and $C_{1-6}$haloalkyl;

each $R^{15}$ is independently selected from $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20o}$;

each $R^{20z1}$, $R^{20z2}$, $R^{20z3}$, $R^{20z4}$, $R^{20z5}$, $R^{20z6}$, and $R^{20z9}$ is independently selected from halogen, oxo, $-CN$, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, $-OR^{12}$, $-SR^{12}$, $-N(R^{12})(R^{13})$, $-C(O)OR^{12}$, $-OC(O)N(R^{12})(R^{13})$, $-N(R^{14})C(O)N(R^{12})(R^{13})$, $-N(R^{14})$ C(O)OR$^{15}$, —N(R$^{14}$)S(O)$_2$R$^{15}$, —C(O)R$^{12}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{12}$, —S(O)$_2$R$^{15}$, —S(O)$_2$N(R$^{12}$)(R$^{13}$), —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl are optionally substituted with one, two, or three R$^{20z}$;

each R$^{20z}$ is independently selected from halogen, oxo, —CN, C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, C$_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{12}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{12}$, —S(O)$_2$R$^{15}$, —S(O)$_2$N(R$^{12}$)(R$^{13}$), —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl are optionally substituted with one, two, or three R$^{20zz}$;

two R$^{20z}$ bonded to the same carbon atom are optionally joined to form monocyclic C$_{3-7}$cycloalkyl or monocyclic 3-7 membered heterocycloalkyl, wherein the monocyclic C$_{3-7}$cycloalkyl and monocyclic 3-7 membered heterocycloalkyl are optionally substituted with one, two, or three R$^{20zz}$; or two or more R$^{20z}$ bonded to two adjacent atoms are optionally joined to form monocyclic C$_{3-7}$cycloalkyl, monocyclic 3-7 membered heterocycloalkyl, phenyl, or monocyclic 5-6 membered heteroaryl, wherein the C$_{3-7}$cycloalkyl, monocyclic 3-7 membered heterocycloalkyl, phenyl, and monocyclic 5-6 membered heteroaryl are optionally substituted with one, two, or three R$^{20zz}$;

each R$^{20a}$, R$^{20b}$, R$^{20c}$, R$^{20d}$, R$^{20e}$, R$^{20f}$, R$^{20g}$, R$^{20h}$, R$^{20i}$, R$^{20j}$, R$^{20lc}$, R$^{20l}$, R$^{20m}$, R$^{20o}$, R$^{20q}$, and R$^{20zz}$ is independently selected from halogen, oxo, —CN, C$_{1-6}$alkyl, C$_{2-6}$alkenyl, C$_{2-6}$alkynyl, C$_{3-10}$cycloalkyl, —CH$_2$-C$_{3-10}$cycloalkyl, C$_{2-9}$heterocycloalkyl, —CH$_2$-C$_{2-9}$heterocycloalkyl, C$_{6-10}$aryl, —CH$_2$-C$_{6-10}$aryl, —CH$_2$-C$_{1-9}$heteroaryl, C$_{1-9}$heteroaryl, —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, —N(R$^{24}$)C(O)R$^{21}$, —N(R$^{24}$)S(O)$_2$R$^{25}$, —C(O)R$^{21}$, —S(O)$_2$R$^{25}$, —S(O)$_2$N(R$^{22}$)(R$^{23}$), —OCH$_2$C(O)OR$^{22}$, =NR$^{21}$, and —OC(O)R$^{25}$; two R$^{20q}$ bonded to adjacent atoms are optionally joined to form a C$_{3-10}$cycloalkyl, C$_{2-9}$heterocycloalkyl, C$_{6-10}$aryl, or C$_{1-9}$heteroaryl; wherein C$_{1-6}$alkyl, C$_{2-6}$alkenyl, C$_{2-6}$alkynyl, C$_{3-10}$cycloalkyl, —CH$_2$-C$_{3-10}$cycloalkyl, C$_{2-9}$heterocycloalkyl, —CH$_2$-C$_{2-9}$heterocycloalkyl, C$_{6-10}$aryl, —CH$_2$-C$_{6-10}$aryl, —CH$_2$-C$_{1-9}$heteroaryl, and C$_{1-9}$heteroaryl are optionally substituted with one, two, or three groups independently selected from halogen, oxo, —CN, C$_{1-6}$alkyl, C$_{1-6}$haloalkyl, C$_{1-6}$alkoxy, C$_{1-6}$haloalkoxy, —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, —N(R$^{24}$)C(O)R$^{25}$, —N(R$^{24}$)S(O)$_2$R$^{25}$, —C(O)R$^{25}$, —S(O)$_2$R$^{25}$, —S(O)$_2$N(R$^{22}$)(R$^{23}$), and —OC(O)R$^{25}$;

each R$^{21}$ is independently selected from hydrogen, C$_{1-6}$alkyl, C$_{1-6}$haloalkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl;

each R$^{22}$ is independently selected from hydrogen, C$_{1-6}$alkyl, C$_{1-6}$haloalkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl;

each R$^{23}$ is independently selected from hydrogen and C$_{1-6}$alkyl;

each R$^{24}$ is independently selected from hydrogen and C$_{1-6}$alkyl;

each R$^{25}$ is independently selected from C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl; and ===== indicates a single or double bond such that all valences are satisfied.

In an aspect is provided a compound of Formula (A), or a pharmaceutically acceptable salt or solvate thereof:

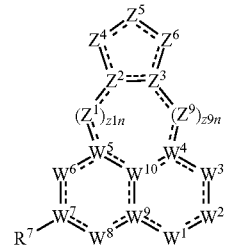

(A)

wherein:

W$^1$ is N(R$^1$) or N;

R$^1$ is selected from hydrogen, —CN, C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, C$_{1-9}$heteroaryl, —OR$^{12}$, —SR$^{12}$, —C(O)OR$^{12}$, —OC(O)N(R$^{12}$)(R$^{13}$), —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —S(O)$_2$R$^{15}$, —S(O)$_2$N(R$^{12}$)(R$^{13}$), —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl are optionally substituted with one, two, or three R$^{20a}$;

W$^2$ is C(R$^2$), N(R$^2$), C(R$^2$)$_2$, C(O), S(O), S(O)$_2$, or N;

each R$^2$ is independently selected from hydrogen, halogen, —CN, C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, C$_{1-9}$heteroaryl, —OR$^{12a}$, —SR$^{12a}$, —N(R$^{12a}$)(R$^{13}$), —N=(R$^{15}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$)—, —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl are optionally substituted with one, two, or three R$^{20b}$;

W$^3$ is C(R$^3$), N(R$^3$), C(R$^3$)$_2$, C(O), S(O), S(O)$_2$, or N;

each R$^3$ is independently selected from hydrogen, halogen, —CN, C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, $C_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$), —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three R$^{20c}$;

W$^4$ is C(R$^4$), C, or N;

R$^4$ is selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$), —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three R$^{20d}$;

W$^5$ is C(R$^5$), C, or N;

R$^5$ is selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$), —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three R$^{20e}$;

W$^6$ is C(R$^6$), N(R$^6$), C(R$^6$)$_2$, C(O), S(O), S(O)$_2$, or N;

each R$^6$ is independently selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$), —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three R$^{20f}$;

W$^7$ is C(R$^{7a}$), C, or N;

R$^{7a}$ is selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$), —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three R$^{20g}$;

R$^7$ is -L$^7$—R$^{17}$;

L$^7$ is a bond, $C_1$-$C_4$alkyl, $C_2$-$C_4$alkenyl, $C_2$-$C_4$alkynyl, 2-4 membered heteroalkylene linker, —O—, —N(R$^{7d}$)—, —C(O)—, —S—, —S(O)$_2$—, —S(O)—, —P(O)R$^{7d}$—, CR$^{7c}$R$^{7c}$—, —OCR$^{7c}$R$^{7c}$—, —N(R$^{7d}$)CR$^{7c}$R$^{7c}$—, —C(O)CR$^{7c}$R$^{7c}$—, —SCR$^{7c}$R$^{7c}$—, —S(O)$_2$CR$^{7c}$R$^{7c}$—, —S(O)CR$^{7c}$R$^{7c}$—, —P(O)R$^{7d}$CR$^{7c}$R$^{7c}$—, —CR$^{7c}$R$^{7c}$CR$^{7c}$R$^{7c}$—, —CR$^{7c}$R$^{7c}$O—, —CR$^{7c}$R$^{7c}$N(R$^{7d}$)—, —CR$^{7c}$R$^{7c}$C(O)—, —CR$^{7c}$R$^{7c}$S—, —CR$^{7c}$R$^{7c}$S(O)$_2$—, —CR$^{7c}$R$^{7c}$S(O)—, —CR$^{7c}$R$^{7c}$P(O)R$^{7d}$—, —N(R$^{7d}$)C(O)—, —N(R$^{7d}$)S(O)$_2$—, —N(R$^{7d}$)S(O)—, —N(R$^{7d}$)P(O)R$^{7d}$—, —C(O)N(R$^{7d}$)—, —S(O)$_2$N(R$^{7d}$)—, —S(O)N(R$^{7d}$)—, —P(O)R$^{7d}$N(R$^{7d}$)—, —OC(O)—, —OS(O)$_2$—, —OS(O)—, —OP(O)R$^{7d}$—, —C(O)O—, —S(O)$_2$O—, —S(O)O—, or —P(O)R$^{7d}$O—; wherein the $C_1$-$C_4$alkyl, $C_2$-$C_4$alkenyl, $C_2$-$C_4$alkynyl, 2-4 membered heteroalkylene linker are optionally substituted with one, two, or three R$^{20g}$;

each R$^{7c}$ is independently selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$), S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three R$^{20g}$;

each R$^{7d}$ is independently selected from hydrogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —OR$^{12}$, —SR$^{12}$, —C(O)OR$^{12}$, —OC(O)N(R$^{12}$)(R$^{13}$), —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —S(O)$_2$R$^{15}$, —S(O)$_2$N(R$^{12}$)(R$^{13}$), —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three R$^{20g}$;

R$^{17}$ is selected from $C_{3-10}$cycloalkyl, 3-10 membered heterocycloalkyl, $C_{6-10}$aryl, and 5-10 membered heteroaryl, wherein $C_{3-10}$cycloalkyl, 3-10 membered heterocycloalkyl, $C_{6-10}$aryl, and 5-10 membered heteroaryl are optionally substituted with one or more R$^{20q}$; or L$^7$ is a bond and R$^{7a}$ and R$^{17}$, together with the carbon to which they are attached, form $C_{3-10}$cycloalkyl or 3-10 membered heterocycloalkyl, wherein the $C_{3-10}$cycloalkyl and 3-10 membered heterocycloalkyl are optionally substituted with one or more R$^{20q}$;

W$^8$ is C(R$^8$), N(R$^8$), C(R$^8$)$_2$, C(O), S(O), S(O)$_2$, or N;

each R$^8$ is independently selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$), —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl are optionally substituted with one, two, or three R$^{20h}$;

W$^9$ is C(R$^9$), C, or N;

R$^9$ is selected from hydrogen, halogen, —CN, C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, C$_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$), —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl are optionally substituted with one, two, or three R$^{20i}$;

W$^{10}$ C(R$^{10}$), C, or N;

R$^{10}$ is selected from hydrogen, halogen, —CN, C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, C$_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$), —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl are optionally substituted with one, two, or three R$^{20j}$;

each Z$^1$ is independently C(R$^{z1}$), N(R$^{z1}$), C(R$^{z1}$)$_2$, C(O), S(O), S(O)$_2$, O, S, or N;

z1n is 0, 1, 2, or 3; wherein if z1n is 0 then Z$^2$ is directly bonded to W$^5$;

each R$^{z1}$ is independently selected from hydrogen, halogen, —CN, C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, C$_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$), —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl are optionally substituted with one, two, or three R$^{20z1}$;

each Z$^9$ is independently C(R$^{z9}$), N(R$^{z9}$), C(R$^{z9}$)$_2$, C(O), S(O), S(O)$_2$, O, S, or N;

z9n is 0, 1, 2, or 3; wherein if z9n is 0 then Z$^3$ is directly bonded to W$^4$;

each R$^{z9}$ is independently selected from hydrogen, halogen, —CN, C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, C$_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$), —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl are optionally substituted with one, two, or three R$^{20z9}$;

wherein the sum of z1n and z9n is 2 or 3;

Z$^2$ is C(R$^{z2}$), C, or N;

R$^{z2}$ is selected from hydrogen, halogen, —CN, C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, C$_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$), —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl are optionally substituted with one, two, or three R$^{20z2}$;

Z$^3$ is C(R$^{z3}$), C, or N;

R$^{z3}$ is selected from hydrogen, halogen, —CN, C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, C$_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$), —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl are optionally substituted with one, two, or three R$^{20z3}$;

Z$^4$ is a bond, Z$^{4a}$, Z$^{4a}$Z$^{4b}$, Z$^{4a}$Z$^{4b}$Z$^{4c}$, or Z$^{4a}$Z$^{4b}$Z$^{4c}$Z$^{4d}$; wherein Z$^{4a}$ is directly bonded to Z$^2$; and wherein if Z$^4$ is a bond then Z$^2$ is directly bonded to Z$^5$;

Z$^{4a}$, Z$^{4b}$, Z$^{4c}$, and Z$^{4d}$ are independently C(R$^{z4}$), N(R$^{z4}$), C(R$^{z4}$)$_2$, C(O), S(O), S(O)$_2$, S(O)(NR$^{z4}$), O, S, or N;

provided that:
   i) if z9n is 0 and Z$^4$ is Z$^{4a}$Z$^{4b}$; then (1) Z$^{4b}$ is C(R$^{z4}$), C(R$^{z4}$)$_2$, C(O), S(O), S(O)$_2$, S(O)(NR$^{z4}$), O, S, or N, (2) Z$^{4b}$ is N(R$^{z4}$) and Z$^{4a}$ is C(O), S(O), or S(O)$_2$; (3) Z$^{4b}$ is N(R$^{z4}$) and Z$^5$ is C(O), S(O), or S(O)$_2$; or (4) Z$^{4b}$ is N(R$^{z4}$) and Z$^3$ is C(R$^{z3}$) or C; and
   ii) one of R$^{z4}$, R$^{z5}$, R$^{z6}$, R$^{20z4}$, R$^{20z5}$, R$^{20z6}$, R$^{20z}$, R$^{20zz}$, or one of the joining of two substituents selected from R$^{z4}$, R$^{z5}$, R$^{z6}$, R$^{20z}$, and R$^{20zz}$ is E, wherein E is a moiety capable of covalently binding to a Ras mutant protein at an amino acid corresponding to G12D or G12S of human K-Ras mutant G12D or G12S protein, respectively:

each R$^{z4}$ is independently selected from hydrogen, halogen, —CN, C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, C$_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N $(R^{12})(R^{13})$, $-N(R^{14})C(O)OR^{15}$, $-N(R^{14})S(O)_2R^{15}$, $-C(O)R^{12}$, $-S(O)R^{15}$, $-OC(O)R^{15}$, $-C(O)N(R^{12})(R^{13})$, $-C(O)C(O)N(R^{12})(R^{13})$, $-N(R^{14})C(O)R^{12}$, $-S(O)_2R^{15}$, $-S(O)_2N(R^{12})(R^{13})$, $-S(=O)(=NH)N(R^{12})(R^{13})$, $-CH_2C(O)N(R^{12})(R^{13})$, $-CH_2N(R^{14})C(O)R^{15}$, $-CH_2S(O)_2R^{15}$, and $-CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20z4}$; or two $R^{z4}$ bonded to the same carbon are joined to form $C_{2-6}$alkenyl optionally substituted with one, two, or three $R^{20z4}$;

$Z^5$ is $C(R^{z5})$, $N(R^{z5})$, $C(R^{z5})_2$, $C(O)$, $S(O)$, $S(O)_2$, $S(O)(NR^{z5})$, O, S, or N;

each $R^{z5}$ is independently selected from hydrogen, halogen, $-CN$, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, $-OR^{12}$, $-SR^{12}$, $-N(R^{12})(R^{13})$, $-C(O)OR^{12}$, $-OC(O)N(R^{12})(R^{13})$, $-N(R^{14})C(O)N(R^{12})(R^{13})$, $-N(R^{14})C(O)OR^{15}$, $-N(R^{14})S(O)_2R^{15}$, $-C(O)R^{12}$, $-S(O)R^{15}$, $-OC(O)R^{15}$, $-C(O)N(R^{12})(R^{13})$, $-C(O)C(O)N(R^{12})(R^{13})$, $-N(R^{14})C(O)R^{12}$, $-S(O)_2R^{15}$, $-S(O)_2N(R^{12})(R^{13})$, $-S(=O)(=NH)N(R^{12})(R^{13})$, $-CH_2C(O)N(R^{12})(R^{13})$, $-CH_2N(R^{14})C(O)R^{15}$, $-CH_2S(O)_2R^{15}$, and $-CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20z5}$; or two $R^{z5}$ bonded to the same carbon are joined to form $C_{2-6}$alkenyl optionally substituted with one, two, or three $R^{20z5}$;

$Z^6$ is $C(R^{z6})$, $N(R^{z6})$, $C(R^{z6})_2$, $C(O)$, $S(O)$, $S(O)_2$, $S(O)(NR^{z6})$, O, S, or N;

each $R^{z6}$ is independently selected from hydrogen, halogen, $-CN$, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, $-OR^{12}$, $-SR^{12}$, $-N(R^{12})(R^{13})$, $-C(O)OR^{12}$, $-OC(O)N(R^{12})(R^{13})$, $-N(R^{14})C(O)N(R^{12})(R^{13})$, $-N(R^{14})C(O)OR^{15}$, $-N(R^{14})S(O)_2R^{15}$, $-C(O)R^{12}$, $-S(O)R^{15}$, $-OC(O)R^{15}$, $-C(O)N(R^{12})(R^{13})$, $-C(O)C(O)N(R^{12})(R^{13})$, $-N(R^{14})C(O)R^{12}$, $-S(O)_2R^{15}$, $-S(O)_2N(R^{12})(R^{13})$, $-S(=O)(=NH)N(R^{12})(R^{13})$, $-CH_2C(O)N(R^{12})(R^{13})$, $-CH_2N(R^{14})C(O)R^{15}$, and $-CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20z6}$; or two $R^{z6}$ bonded to the same carbon are joined to form $C_{2-6}$alkenyl optionally substituted with one, two, or three $R^{20z6}$;

and further wherein the compound optionally includes one of the following:

(1) two $R^{z4}$ bonded to the same carbon atom are joined to form monocyclic $C_{3-7}$cycloalkyl or monocyclic 3-7 membered heterocycloalkyl, wherein the monocyclic $C_{3-7}$cycloalkyl and monocyclic 3-7 membered heterocycloalkyl are optionally substituted with one, two, or three $R^{20z}$;

(2) two or more $R^{z4}$ bonded to adjacent atoms are joined to form monocyclic $C_{3-7}$cycloalkyl, monocyclic 3-7 membered heterocycloalkyl, phenyl, or monocyclic 5-6 membered heteroaryl, wherein the monocyclic $C_{3-7}$cycloalkyl, monocyclic 3-7 membered heterocycloalkyl, phenyl, and monocyclic 5-6 membered heteroaryl are optionally substituted with one, two, or three $R^{20z}$;

(3) two $R^{z5}$ bonded to the same carbon atom are joined to form monocyclic $C_{3-7}$cycloalkyl or monocyclic 3-7 membered heterocycloalkyl, wherein the monocyclic $C_{3-7}$cycloalkyl and monocyclic 3-7 membered heterocycloalkyl are optionally substituted with one, two, or three $R^{20z}$;

(4) one or two $R^{z4}$ bonded to one atom and one or two $R^{z5}$ bonded to an adjacent atom are joined to form monocyclic $C_{3-7}$cycloalkyl, monocyclic 3-7 membered heterocycloalkyl, phenyl, or monocyclic 5-6 membered heteroaryl, wherein the monocyclic $C_{3-7}$cycloalkyl, monocyclic 3-7 membered heterocycloalkyl, phenyl, and monocyclic 5-6 membered heteroaryl are optionally substituted with one, two, or three $R^{20z}$;

(5) one or two $R^{z4}$ bonded to one atom and one or two $R^{z5}$ bonded to a second atom are joined to form monocyclic $C_{3-7}$cycloalkyl or monocyclic 3-7 membered heterocycloalkyl, wherein the monocyclic $C_{3-7}$cycloalkyl and monocyclic 3-7 membered heterocycloalkyl are optionally substituted with one, two, or three $R^{20z}$;

(6) two $R^{z6}$ bonded to the same carbon atom are joined to form monocyclic $C_{3-7}$cycloalkyl or monocyclic 3-7 membered heterocycloalkyl, wherein the monocyclic $C_{3-7}$cycloalkyl and monocyclic 3-7 membered heterocycloalkyl are optionally substituted with one, two, or three $R^{20z}$;

(7) one or two $R^{z5}$ bonded to one atom and one or two $R^{z6}$ bonded to an adjacent atom are joined to form monocyclic $C_{3-7}$cycloalkyl, monocyclic 3-7 membered heterocycloalkyl, phenyl, or monocyclic 5-6 membered heteroaryl, wherein the monocyclic $C_{3-7}$cycloalkyl, monocyclic 3-7 membered heterocycloalkyl, phenyl, and monocyclic 5-6 membered heteroaryl are optionally substituted with one, two, or three $R^{20z}$; or (8) one or two $R^{z4}$ bonded to one atom and one or two $R^{z6}$ bonded to a second atom are joined to form monocyclic $C_{3-7}$cycloalkyl or monocyclic 3-7 membered heterocycloalkyl, wherein the monocyclic $C_{3-7}$cycloalkyl and monocyclic 3-7 membered heterocycloalkyl are optionally substituted with one, two, or three $R^{20z}$;

each $R^{12}$ is independently selected from hydrogen, $C_{1-6}$alkyl, $C_{2-6}$alkenyl, $C_{2-6}$alkynyl, $C_{3-10}$cycloalkyl, $-CH_2$-$C_{3-10}$cycloalkyl, $C_{2-9}$heterocycloalkyl, $-CH_2$-$C_{2-9}$heterocycloalkyl, $C_{6-10}$aryl, $-CH_2$-$C_{6-10}$aryl, $-CH_2$-$C_{1-9}$heteroaryl, and $C_{1-9}$heteroaryl, wherein $C_{1-6}$alkyl, $C_{2-6}$alkenyl, $C_{2-6}$alkynyl, $C_{3-10}$cycloalkyl, $-CH_2$-$C_{3-10}$cycloalkyl, $C_{2-9}$heterocycloalkyl, $-CH_2$-$C_{2-9}$heterocycloalkyl, $C_{6-10}$aryl, $-CH_2$-$C_{6-10}$aryl, $-CH_2$-$C_{1-9}$heteroaryl, and $C_{1-9}$heteroaryl are optionally substituted with one, two, or three $R^{20l}$;

$R^{12a}$ is independently selected from hydrogen, $C_{1-6}$alkyl, $C_{2-6}$alkenyl, $C_{2-6}$alkynyl, $C_{3-10}$cycloalkyl, $-C(R^{12c})_2$-$C_{3-10}$cycloalkyl, $C_{2-9}$heterocycloalkyl, $-C(R^{12c})_2$-$C_{2-9}$heterocycloalkyl, $C_{6-10}$aryl, $-C(R^{12c})_2$-$C_{6-10}$aryl, $-C(R^{12c})_2$-$C_{1-9}$heteroaryl, and $C_{1-9}$heteroaryl, wherein $C_{1-6}$alkyl, $C_{2-6}$alkenyl, $C_{2-6}$alkynyl, $C_{3-10}$cycloalkyl, $-C(R^{12c})_2$-$C_{3-10}$cycloalkyl, $C_{2-9}$heterocycloalkyl, $-C(R^{12c})_2$-$C_{2-9}$heterocycloalkyl, $C_{6-10}$aryl, $-C(R^{12c})_2$-$C_{6-10}$aryl, $-C(R^{12c})_2$-$C_{1-9}$heteroaryl, and $C_{1-9}$heteroaryl are optionally substituted with one, two, or three $R^{20l}$;

each $R^{12c}$ is independently selected from hydrogen and $R^{20lc}$;

each $R^{13}$ is independently selected from hydrogen, $C_{1-6}$alkyl, and $C_{1-6}$haloalkyl; or $R^{12}$ and $R^{13}$, together with the nitrogen to which they are attached, form a $C_{2-9}$heterocycloalkyl ring optionally substituted with one, two, or three $R^{20m}$;

each $R^{14}$ is independently selected from hydrogen, $C_{1-6}$alkyl, and $C_{1-6}$haloalkyl;

each $R^{15}$ is independently selected from $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20o}$;

each $R^{20z1}$, $R^{20z2}$, $R^{20z3}$, and $R^{20z9}$ is independently selected from halogen, oxo, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{12}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{12}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20z}$;

each $R^{20z4}$, $R^{20z5}$, and $R^{20z6}$ is independently selected from E, halogen, oxo, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{12}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{12}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20z}$;

each $R^{20z}$ is independently selected from halogen, oxo, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{12}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{12}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20zz}$;

two $R^{20z}$ bonded to the same carbon atom are optionally joined to form monocyclic $C_{3-7}$cycloalkyl or monocyclic 3-7 membered heterocycloalkyl, wherein the monocyclic $C_{3-7}$cycloalkyl and monocyclic 3-7 membered heterocycloalkyl are optionally substituted with one, two, or three $R^{20zz}$; or two or more $R^{20z}$ bonded to two adjacent atoms are optionally joined to form monocyclic $C_{3-7}$cycloalkyl, monocyclic 3-7 membered heterocycloalkyl, phenyl, or monocyclic 5-6 membered heteroaryl, wherein the $C_{3-7}$cycloalkyl, monocyclic 3-7 membered heterocycloalkyl, phenyl, and monocyclic 5-6 membered heteroaryl are optionally substituted with one, two, or three $R^{20zz}$;

each $R^{20a}$, $R^{20b}$, $R^{20c}$, $R^{20d}$, $R^{20e}$, $R^{20f}$, $R^{20g}$, $R^{20h}$, $R^{20i}$, $R^{20j}$, $R^{20l}$, $R^{20lz}$, $R^{20m}$, $R^{20o}$, and $R^{20q}$ is independently selected from halogen, oxo, —CN, $C_{1-6}$alkyl, $C_{2-6}$alkenyl, $C_{2-6}$alkynyl, $C_{3-10}$cycloalkyl, —$CH_2$-$C_{3-10}$cycloalkyl, $C_{2-9}$heterocycloalkyl, —$CH_2$-$C_{2-9}$heterocycloalkyl, $C_{6-10}$aryl, —$CH_2$-$C_{6-10}$aryl, —$CH_2$-$C_{1-9}$heteroaryl, $C_{1-9}$heteroaryl, —$OR^{21}$, —$SR^{21}$, —$N(R^{22})(R^{23})$, —$C(O)OR^{22}$, —$C(O)N(R^{22})(R^{23})$, —$C(O)C(O)N(R^{22})(R^{23})$, —$OC(O)N(R^{22})(R^{23})$, —$N(R^{24})C(O)N(R^{22})(R^{23})$, —$N(R^{24})C(O)OR^{25}$, —$N(R^{24})C(O)R^{21}$, —$N(R^{24})S(O)_2R^{25}$, —$C(O)R^{21}$, —$S(O)_2R^{25}$, —$S(O)_2N(R^{22})(R^{23})$, —$OCH_2C(O)OR^{22}$, =$NR^{21}$, and —$OC(O)R^{25}$; two $R^{20q}$ bonded to adjacent atoms are optionally joined to form a $C_{3-10}$cycloalkyl, $C_{2-9}$heterocycloalkyl, $C_{6-10}$aryl, or $C_{1-9}$heteroaryl; wherein $C_{1-6}$alkyl, $C_{2-6}$alkenyl, $C_{2-6}$alkynyl, $C_{3-10}$cycloalkyl, —$CH_2$-$C_{3-10}$cycloalkyl, $C_{2-9}$heterocycloalkyl, —$CH_2$-$C_{2-9}$heterocycloalkyl, $C_{6-10}$aryl, —$CH_2$-$C_{6-10}$aryl, —$CH_2$-$C_{1-9}$heteroaryl, and $C_{1-9}$heteroaryl are optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —$OR^{21}$, —$SR^{21}$, —$N(R^{22})(R^{23})$, —$C(O)OR^{22}$, —$C(O)N(R^{22})(R^{23})$, —$C(O)C(O)N(R^{22})(R^{23})$, —$OC(O)N(R^{22})(R^{23})$, —$N(R^{24})C(O)N(R^{22})(R^{23})$, —$N(R^{24})C(O)OR^{25}$, —$N(R^{24})C(O)R^{25}$, —$N(R^{24})S(O)_2R^{25}$, —$C(O)R^{25}$, —$S(O)_2R^{25}$, —$S(O)_2N(R^{22})(R^{23})$, and —$OC(O)R^{25}$;

each $R^{20zz}$ is independently selected from E, halogen, oxo, —CN, $C_{1-6}$alkyl, $C_{2-6}$alkenyl, $C_{2-6}$alkynyl, $C_{3-10}$cycloalkyl, —$CH_2$-$C_{3-10}$cycloalkyl, $C_{2-9}$heterocycloalkyl, —$CH_2$-$C_{2-9}$heterocycloalkyl, $C_{6-10}$aryl, —$CH_2$-$C_{6-10}$aryl, —$CH_2$-$C_{1-9}$heteroaryl, $C_{1-9}$heteroaryl, —$OR^{21}$, —$SR^{21}$, —$N(R^{22})(R^{23})$, —$C(O)OR^{22}$, —$C(O)N(R^{22})(R^{23})$, —$C(O)C(O)N(R^{22})(R^{23})$, —$OC(O)N(R^{22})(R^{23})$, —$N(R^{24})C(O)N(R^{22})(R^{23})$, —$N(R^{24})C(O)OR^{25}$, —$N(R^{24})C(O)R^{21}$, —$N(R^{24})S(O)_2R^{25}$, —$C(O)R^{21}$, —$S(O)_2R^{25}$, —$S(O)_2N(R^{22})(R^{23})$, —$OCH_2C(O)OR^{22}$, =$NR^{21}$, and —$OC(O)R^{25}$; two $R^{20q}$ bonded to adjacent atoms are optionally joined to form a $C_{3-10}$cycloalkyl, $C_{2-9}$heterocycloalkyl, $C_{6-10}$aryl, or $C_{1-9}$heteroaryl; wherein $C_{1-6}$alkyl, $C_{2-6}$alkenyl, $C_{2-6}$alkynyl, $C_{3-10}$cycloalkyl, —$CH_2$-$C_{3-10}$cycloalkyl, $C_{2-9}$heterocycloalkyl, —$CH_2$-$C_{2-9}$heterocycloalkyl, $C_{6-10}$aryl, —$CH_2$-$C_{6-10}$aryl, —$CH_2$-$C_{1-9}$heteroaryl, and $C_{1-9}$heteroaryl are optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —$OR^{21}$, —$SR^{21}$, —$N(R^{22})(R^{23})$, —$C(O)OR^{22}$, —$C(O)N R^{22})(R^{23})$, —$C(O)C(O)N(R^{22})(R^{23})$, —$OC(O)N(R^{22})(R^{23})$, —$N(R^{24})C(O)N(R^{22})(R^{23})$, —$N(R^{24})C(O)OR^{25}$, —$N(R^{24})C(O)R^{25}$, —$N(R^{24})S(O)_2R^{25}$, —$C(O)R^{25}$, —$S(O)_2R^{25}$, —$S(O)_2N(R^{22})(R^{23})$, and —$OC(O)R^{25}$;

each $R^{21}$ is independently selected from hydrogen, $C_{1-6}$alkyl, $C_{1-6}$haloalkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl;

each $R^{22}$ is independently selected from hydrogen, $C_{1-6}$alkyl, $C_{1-6}$haloalkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl;

each $R^{23}$ is independently selected from hydrogen and $C_{1-6}$alkyl;

each $R^{24}$ is independently selected from hydrogen and $C_{1-6}$alkyl;

each $R^{25}$ is independently selected from $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; and ----- indicates a single or double bond such that all valences are satisfied.

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, one $R^{z4}$, $R^{z5}$, $R^{z6}$, $R^{20z4}$, $R^{20z5}$, $R^{20z6}$, or $R^{20z}$ is independently —C(O)$R^{12}$ or —N(H)C(O)$R^{12}$; wherein the one $R^{12}$ is $C_{1-9}$heteroaryl, wherein $C_{1-9}$heteroaryl is optionally substituted with one, two, or three $R^{20l}$.

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, one $R^{z4}$, $R^{z5}$, $R^{z6}$, $R^{20z4}$, $R^{20z5}$, $R^{20z6}$, or $R^{20z}$ is independently —C(O)$R^{12}$ or —N(H)C(O)$R^{12}$; wherein the one $R^{12}$ is selected from $C_{2-9}$heterocycloalkyl; wherein $C_{2-9}$heterocycloalkyl is optionally substituted with one, two, or three $R^{20l}$.

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, one $R^{z4}$ is independently selected from $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl; wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are substituted with one, two, or three $R^{20z}$, and one $R^{20z4}$ is selected from —C(O)$R^{12}$ and —N(H)C(O)$R^{12}$; wherein the one $R^{12}$ is selected from $C_{3-10}$cycloalkyl, $C_{2-9}$heterocycloalkyl, $C_{6-10}$aryl, and $C_{1-9}$heteroaryl, wherein $C_{3-10}$cycloalkyl, $C_{2-9}$heterocycloalkyl, $C_{6-10}$aryl, and $C_{1-9}$heteroaryl are optionally substituted with one, two, or three $R^{20l}$.

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, one $R^{z5}$ is independently selected from $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are substituted with one, two, or three $R^{20z5}$; and one $R^{20z5}$ is selected from —C(O)$R^{12}$ and —N(H)C(O)$R^{12}$; wherein the one $R^{12}$ is selected from $C_{3-10}$cycloalkyl, $C_{2-9}$heterocycloalkyl, $C_{6-10}$aryl, and $C_{1-9}$heteroaryl, wherein $C_{3-10}$cycloalkyl, $C_{2-9}$heterocycloalkyl, $C_{6-10}$aryl, and $C_{1-9}$heteroaryl are optionally substituted with one, two, or three $R^{20l}$.

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, one $R^{z6}$ is independently selected from $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are substituted with one, two, or three $R^{20z6}$; and one $R^{20z6}$ is selected from —C(O)$R^{12}$ and —N(H)C(O)$R^{12}$; wherein the one $R^{12}$ is selected from $C_{3-10}$cycloalkyl, $C_{2-9}$heterocycloalkyl, $C_{6-10}$aryl, and $C_{1-9}$heteroaryl, wherein $C_{3-10}$cycloalkyl, $C_{2-9}$heterocycloalkyl, $C_{6-10}$aryl, and $C_{1-9}$heteroaryl are optionally substituted with one, two, or three $R^{20l}$.

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, one $R^{z4}$ is independently selected from $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl; wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are substituted with one, two, or three $R^{20z4}$; wherein one $R^{20z4}$ is selected from $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl; wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are substituted with one, two, or three $R^{20z}$; and one $R^{20z}$ is selected from —C(O)$R^{12}$ and —N(H)C(O)$R^{12}$; wherein the one $R^{12}$ is selected from $C_{3-10}$cycloalkyl, $C_{2-9}$heterocycloalkyl, $C_{6-10}$aryl, and $C_{1-9}$heteroaryl, wherein $C_{3-10}$cycloalkyl, $C_{2-9}$heterocycloalkyl, $C_{6-10}$aryl, and $C_{1-9}$heteroaryl are optionally substituted with one, two, or three $R^{20l}$.

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, one $R^{z5}$ is independently selected from $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl; wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are substituted with one, two, or three $R^{20z5}$; wherein one $R^{20z5}$ is selected from $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl; wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are substituted with one, two, or three $R^{20z}$; and one $R^{20z}$ is selected from —C(O)$R^{12}$ and —N(H)C(O)$R^{12}$; wherein the one $R^{12}$ is selected from $C_{3-10}$cycloalkyl, $C_{2-9}$heterocycloalkyl, $C_{6-10}$aryl, and $C_{1-9}$heteroaryl, wherein $C_{3-10}$cycloalkyl, $C_{2-9}$heterocycloalkyl, $C_{6-10}$aryl, and $C_{1-9}$heteroaryl are optionally substituted with one, two, or three $R^{20l}$.

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, one $R^{z6}$ is independently selected from $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl; wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are substituted with one, two, or three $R^{20z6}$; wherein one $R^{20z6}$ is selected from $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl; wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are substituted with one, two, or three $R^{20z}$; and one $R^{20z}$ is selected from —C(O)$R^{12}$ and —N(H)C(O)$R^{12}$; wherein the one $R^{12}$ is selected from $C_{3-10}$cycloalkyl, $C_{2-9}$heterocycloalkyl, $C_{6-10}$aryl, and $C_{1-9}$heteroaryl; wherein $C_{3-10}$cycloalkyl, $C_{2-9}$heterocycloalkyl, $C_{6-10}$aryl, and $C_{1-9}$heteroaryl are optionally substituted with one, two, or three $R^{20l}$.

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, two or more $R^{z4}$, $R^{z5}$, or $R^{z6}$ are joined to form a cycle substituted with one, two, or three $R^{20z}$; and one $R^{20z}$ is selected from —C(O)$R^{12}$ and —N(H)C(O)$R^{12}$; wherein the one $R^{12}$ is selected from $C_{3-10}$cycloalkyl, $C_{2-9}$heterocycloalkyl, $C_{6-10}$aryl, and $C_{1-9}$heteroaryl; wherein $C_{3-10}$cycloalkyl, $C_{2-9}$heterocycloalkyl, $C_{6-10}$aryl, and $C_{1-9}$heteroaryl are optionally substituted with one, two, or three $R^{20l}$.

In an aspect is provided a compound of Formula (A), or a pharmaceutically acceptable salt or solvate thereof:

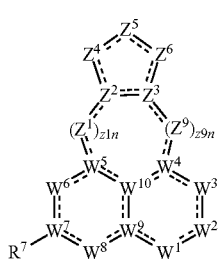

(A)

wherein:
$W^1$ is N($R^1$) or N;
$R^1$ is selected from hydrogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —O$R^{12}$, —S$R^{12}$, —C(O)O$R^{12}$, —OC(O)N($R^{12}$)($R^{13}$), —C(O)$R^{15}$, —S(O)$R^{15}$, —OC(O)$R^{15}$, —C(O)N($R^{12}$)($R^{13}$), —C(O)C(O)N($R^{12}$)($R^{13}$), —S(O)$_2$$R^{15}$, —S(O)$_2$N($R^{12}$)($R^{13}$), —S(=O)(=NH)N($R^{12}$)($R^{13}$), —CH$_2$C(O)N($R^{12}$)($R^{13}$), —CH$_2$N($R^{14}$)C(O)$R^{15}$, —CH$_2$S(O)$_2$$R^{15}$, and —CH$_2$S(O)$_2$N($R^{12}$)($R^{13}$), wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20a}$;
$W^2$ is C($R^2$), N($R^2$), C($R^2$)$_2$, C(O), S(O), S(O)$_2$, or N;
each $R^2$ is independently selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —O$R^{12a}$, —S$R^{12a}$, —N($R^{12a}$)($R^{13}$), —N=($R^{15}$), —C(O)O$R^{12}$, —OC(O)N($R^{12}$)($R^{13}$), —N($R^{14}$)C(O)N($R^{12}$)($R^{13}$), —N($R^{14}$)C(O)O$R^{15}$, —N($R^{14}$)S(O)$_2$$R^{15}$, —C(O)$R^{15}$, —S(O)$R^{15}$, —OC(O)$R^{15}$, —C(O)N($R^{12}$)($R^{13}$), —C(O)C(O)N($R^{12}$)($R^{13}$), —N($R^{14}$)C(O)$R^{15}$, —S(O)$_2$$R^{15}$, —S(O)$_2$N($R^{12}$)($R^{13}$)—, —S(=O)(=NH)N($R^{12}$)($R^{13}$), —CH$_2$C(O)N($R^{12}$)($R^{13}$), —CH$_2$N($R^{14}$)C(O)$R^{15}$, —CH$_2$S(O)$_2$$R^{15}$, and —CH$_2$S(O)$_2$N($R^{12}$)($R^{13}$), wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20b}$;
$W^3$ is C($R^3$), N($R^3$), C($R^3$)$_2$, C(O), S(O), S(O)$_2$, or N;
each $R^3$ is independently selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —O$R^{12}$, —S$R^{12}$, —N($R^{12}$)($R^{13}$), —C(O)O$R^{12}$, —OC(O)N($R^{12}$)($R^{13}$), —N($R^{14}$)C(O)N($R^{12}$)($R^{13}$), —N($R^{14}$)C(O)O$R^{15}$, —N($R^{14}$)S(O)$_2$$R^{15}$, —C(O)$R^{15}$, —S(O)$R^{15}$, —OC(O)$R^{15}$, —C(O)N($R^{12}$)($R^{13}$), —C(O)C(O)N($R^{12}$)($R^{13}$), —N($R^{14}$)C(O)$R^{15}$, —S(O)$_2$$R^{15}$, —S(O)$_2$N($R^{12}$)($R^{13}$), —S(=O)(=NH)N($R^{12}$)($R^{13}$), —CH$_2$C(O)N($R^{12}$)($R^{13}$), —CH$_2$N($R^{14}$)C(O)$R^{15}$, —CH$_2$S(O)$_2$$R^{15}$, and —CH$_2$S(O)$_2$N($R^{12}$)($R^{13}$), wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20c}$;
$W^4$ is C($R^4$), C, or N;
$R^4$ is selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —O$R^{12}$, —S$R^{12}$, —N($R^{12}$)($R^{13}$), —C(O)O$R^{12}$, —OC(O)N($R^{12}$)($R^{13}$), —N($R^{14}$)C(O)N($R^{12}$)($R^{13}$), —N($R^{14}$)C(O)O$R^{15}$, —N($R^{14}$)S(O)$_2$$R^{15}$, —C(O)$R^{15}$, —S(O)$R^{15}$, —OC(O)$R^{15}$, —C(O)N($R^{12}$)($R^{13}$), —C(O)C(O)N($R^{12}$)($R^{13}$), —N($R^{14}$)C(O)$R^{15}$, —S(O)$_2$$R^{15}$, —S(O)$_2$N($R^{12}$)($R^{13}$), —S(=O)(=NH)N($R^{12}$)($R^{13}$), —CH$_2$C(O)N($R^{12}$)($R^{13}$), —CH$_2$N($R^{14}$)C(O)$R^{15}$, —CH$_2$S(O)$_2$$R^{15}$, and —CH$_2$S(O)$_2$N($R^{12}$)($R^{13}$), wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20d}$;
$W^5$ is C($R^5$), C, or N;
$R^5$ is selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —O$R^{12}$, —S$R^{12}$, —N($R^{12}$)($R^{13}$), —C(O)O$R^{12}$, —OC(O)N($R^{12}$)($R^{13}$), —N($R^{14}$)C(O)N($R^{12}$)($R^{13}$), —N($R^{14}$)C(O)O$R^{15}$, —N($R^{14}$)S(O)$_2$$R^{15}$, —C(O)$R^{15}$, —S(O)$R^{15}$, —OC(O)$R^{15}$, —C(O)N($R^{12}$)($R^{13}$), —C(O)C(O)N($R^{12}$)($R^{13}$), —N($R^{14}$)C(O)$R^{15}$, —S(O)$_2$$R^{15}$, —S(O)$_2$N($R^{12}$)($R^{13}$), —S(=O)(=NH)N($R^{12}$)($R^{13}$), —CH$_2$C(O)N($R^{12}$)($R^{13}$), —CH$_2$N($R^{14}$)C(O)$R^{15}$, —CH$_2$S(O)$_2$$R^{15}$, and —CH$_2$S(O)$_2$N($R^{12}$)($R^{13}$), wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20e}$;
$W^6$ is C($R^6$), N($R^6$), C($R^6$)$_2$, C(O), S(O), S(O)$_2$, or N;
each $R^6$ is independently selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —O$R^{12}$, —S$R^{12}$, —N($R^{12}$)($R^{13}$), —C(O)O$R^{12}$, —OC(O)N($R^{12}$)($R^{13}$), —N($R^{14}$)C(O)N($R^{12}$)($R^{13}$), —N($R^{14}$)C(O)O$R^{15}$, —N($R^{14}$)S(O)$_2$$R^{15}$, —C(O)$R^{15}$, —S(O)$R^{15}$, —OC(O)$R^{15}$, —C(O)N($R^{12}$)($R^{13}$), —C(O)C(O)N($R^{12}$)($R^{13}$), —N($R^{14}$)C(O)$R^{15}$, —S(O)$_2$$R^{15}$, —S(O)$_2$N($R^{12}$)($R^{13}$), —S(=O)(=NH)N($R^{12}$)($R^{13}$), —CH$_2$C(O)N($R^{12}$)($R^{13}$), —CH$_2$N($R^{14}$)C(O)$R^{15}$, —CH$_2$S(O)$_2$$R^{15}$, and —CH$_2$S(O)$_2$N($R^{12}$)($R^{13}$), wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20f}$;
$W^7$ is C($R^{7a}$), C, or N;
$R^{7a}$ is selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —O$R^{12}$, —S$R^{12}$, —N($R^{12}$)($R^{13}$), —C(O)O$R^{12}$, —OC(O)N($R^{12}$)($R^{13}$), —N($R^{14}$)C(O)N($R^{12}$)($R^{13}$), —N($R^{14}$)C(O)O$R^{15}$, —N($R^{14}$)S(O)$_2$$R^{15}$, —C(O)$R^{15}$, —S(O)$R^{15}$, —OC(O)$R^{15}$, —C(O)N($R^{12}$)($R^{13}$), —C(O)C(O)N($R^{12}$)($R^{13}$), —N($R^{14}$)C(O)$R^{15}$, —S(O)$_2$$R^{15}$, —S(O)$_2$N($R^{12}$)($R^{13}$), —S(=O)(=NH)N($R^{12}$)($R^{13}$), —CH$_2$C(O)N($R^{12}$)($R^{13}$), —CH$_2$N($R^{14}$)C(O)$R^{15}$, —CH$_2$S(O)$_2$$R^{15}$, and —CH$_2$S(O)$_2$N($R^{12}$)($R^{13}$), wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20g}$;
$R^7$ is -$L^7$—$R^{17}$;
$L^7$ is a bond, $C_1$-$C_4$alkyl, $C_2$-$C_4$alkenyl, $C_2$-$C_4$alkynyl, 2-4 membered heteroalkylene linker, —O—, —N(R$^{7d}$)—, —C(O)—, —S—, —S(O)$_2$—, —S(O)—, —P(O)R$^{7d}$—, CR$^{7c}$R$^{7c}$—, —OCR$^{7c}$R$^{7c}$—, —N(R$^{7d}$) CR$^{7c}$R$^{7c}$—, —C(O)CR$^{7c}$R$^{7c}$—, —SCR$^{7c}$R$^{7c}$—, —S(O)$_2$CR$^{7c}$R$^{7c}$—, —S(O)CR$^{7c}$R$^{7c}$—, —P(O) R$^{7d}$CR$^{7c}$R$^{7c}$—, —CR$^{7c}$R$^{7c}$CR$^{7c}$R$^{7c}$, —CR$^{7c}$R$^{7c}$O—, —CR$^{7c}$R$^{7c}$N(R$^{7d}$)—, —CR$^{7c}$R$^{7c}$C(O)—, —CR$^{7c}$R$^{7c}$S—, —CR$^{7c}$R$^{7c}$S(O)$_2$—, —CR$^{7c}$R$^{7c}$S (O)—, —CR$^{7c}$R$^{7c}$P(O)R$^{7d}$—, —N(R$^{7d}$)C(O)—, —N(R$^{7d}$)S(O)$_2$—, —N(R$^{7d}$)S(O)—, —N(R$^{7d}$)P(O) R$^{7d}$—, —C(O)N(R$^{7d}$)—, —S(O)$_2$N(R$^{7d}$)—, —S(O)N (R$^{7d}$)—, —P(O)R$^{7d}$N(R$^{7d}$)—, —OC(O)—, —OS(O)$_2$—, —OS(O)—, —OP(O)R$^{7d}$—, —C(O) O—, —S(O)$_2$O—, —S(O)O—, or —P(O)R$^{7d}$O—; wherein the C$_1$-C$_4$alkyl, C$_2$-C$_4$alkenyl, C$_2$-C$_4$alkynyl, 2-4 membered heteroalkylene linker are optionally substituted with one, two, or three R$^{20g}$;

each R$^{7c}$ is independently selected from hydrogen, halogen, —CN, C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, C$_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N (R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$) (R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$), S(=O)(=NH)N (R$^{12}$)(R$^{13}$), —CH$_2$C(O)N(R$^{12}$)(R$^{13}$), —CH$_2$N(R$^{14}$)C (O)R$^{15}$, —CH$_2$S(O)$_2$R$^{15}$, and —CH$_2$S(O)$_2$N(R$^{12}$) (R$^{13}$), wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl are optionally substituted with one, two, or three R$^{20g}$;

each R$^{7d}$ is independently selected from hydrogen, —CN, C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, C$_{1-9}$heteroaryl, —OR$^{12}$, —SR$^{12}$, —C(O)OR$^{12}$, —OC(O)N(R$^{12}$)(R$^{13}$), —C(O)R$^{15}$, —S(O)R$^{15}$, —OC(O)R$^{15}$, —C(O)N(R$^{12}$) (R$^{13}$), —C(O)C(O)N(R$^{12}$)(R$^{13}$), —S(O)$_2$R$^{15}$, —S(O)$_2$N(R$^{12}$)(R$^{13}$), —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl are optionally substituted with one, two, or three R$^{20g}$;

R$^{17}$ is selected from C$_{3-10}$cycloalkyl, 3-10 membered heterocycloalkyl, C$_{6-10}$aryl, and 5-10 membered heteroaryl, wherein C$_{3-10}$cycloalkyl, 3-10 membered heterocycloalkyl, C$_{6-10}$aryl, and 5-10 membered heteroaryl are optionally substituted with one or more R$^{20q}$; or L$^7$ is a bond and R$^{7a}$ and R$^{17}$, together with the carbon to which they are attached, form C$_{3-10}$cycloalkyl or 3-10 membered heterocycloalkyl, wherein the C$_{3-10}$cycloalkyl and 3-10 membered heterocycloalkyl are optionally substituted with one or more R$^{20q}$;

W$^8$ is C(R$^8$), N(R$^8$), C(R$^8$)$_2$, C(O), S(O), S(O)$_2$, or N;

each R$^8$ is independently selected from hydrogen, halogen, —CN, C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, C$_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N (R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$) (R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$), —S(=O)(=NH)N (R$^{12}$)(R$^{13}$), —CH$_2$C(O)N(R$^{12}$)(R$^{13}$), —CH$_2$N(R$^{14}$)C (O)R$^{15}$, —CH$_2$S(O)$_2$R$^{15}$, and —CH$_2$S(O)$_2$N(R$^{12}$) (R$^{13}$), wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl are optionally substituted with one, two, or three R$^{20h}$;

W$^9$ is C(R$^9$), C, or N;

R$^9$ is selected from hydrogen, halogen, —CN, C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, C$_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O) R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$), —S(=O)(=NH)N(R$^{12}$)(R$^{13}$), —CH$_2$C(O)N(R$^{12}$) (R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl are optionally substituted with one, two, or three R$^{20i}$;

W$^{10}$ C(R$^{10}$), C, or N;

R$^{10}$ is selected from hydrogen, halogen, —CN, C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, C$_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O) R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$), —S(=O)(=NH)N(R$^{12}$)(R$^{13}$), —CH$_2$C(O)N(R$^{12}$) (R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl are optionally substituted with one, two, or three R$^{20j}$;

each Z$^1$ is independently C(R$^{z1}$), N(R$^{z1}$), C(R$^{z1}$)$_2$, C(O), S(O), S(O)$_2$, O, S, or N;

z1n is 0, 1, 2, or 3; wherein if z1n is 0 then Z$^2$ is directly bonded to W$^5$;

each R$^{z1}$ is independently selected from hydrogen, halogen, —CN, C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, C$_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N (R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$) (R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$), —S(=O)(=NH)N (R$^{12}$)(R$^{13}$), —CH$_2$C(O)N(R$^{12}$)(R$^{13}$), —CH$_2$N(R$^{14}$)C (O)R$^{15}$, —CH$_2$S(O)$_2$R$^{15}$, and —CH$_2$S(O)$_2$N(R$^{12}$) (R$^{13}$), wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl are optionally substituted with one, two, or three R$^{20z1}$;

each Z$^9$ is independently C(R$^{z9}$), N(R$^{z9}$), C(R$^{z9}$)$_2$, C(O), S(O), S(O)$_2$, O, S, or N;

z9n is 0, 1, 2, or 3; wherein if z9n is 0 then Z$^3$ is directly bonded to W$^4$;

each R$^{z9}$ is independently selected from hydrogen, halogen, —CN, C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, C$_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N (R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$) (R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$), —S(=O)(=NH)N (R$^{12}$)(R$^{13}$), —CH$_2$C(O)N(R$^{12}$)(R$^{13}$), —CH$_2$N(R$^{14}$)C (O)R$^{15}$, —CH$_2$S(O)$_2$R$^{15}$, and —CH$_2$S(O)$_2$N(R$^{12}$)

($R^{13}$), wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20z9}$;

wherein the sum of z1n and z9n is 2 or 3;

$Z^2$ is $C(R^{z2})$, C, or N;

$R^{z2}$ is selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20z2}$;

$Z^3$ is $C(R^{z3})$, C, or N;

$R^{z3}$ is selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20z3}$;

$Z^4$ is a bond, $Z^{4a}$, $Z^{4a}Z^{4b}$, $Z^{4a}Z^{4b}Z^{4c}$, or $Z^{4a}Z^{4b}Z^{4c}Z^{4d}$; wherein $Z^{4a}$ is directly bonded to $Z^2$; and wherein if $Z^4$ is a bond then $Z^2$ is directly bonded to $Z^5$;

$Z^{4a}$, $Z^{4b}$, $Z^{4c}$, and $Z^{4d}$ are independently $C(R^{z4})$, $N(R^{z4})$, $C(R^{z4})_2$, C(O), S(O), $S(O)_2$, $S(O)(NR^{z4})$, O, S, or N; provided that if z9n is 0 and $Z^4$ is $Z^{4a}Z^{4b}$; then (1) $Z^{4b}$ is $C(R^{z4})$, $C(R^{z4})_2$, C(O), S(O), $S(O)_2$, $S(O)(NR^{z4})$, O, S, or N, (2) $Z^{4b}$ is $N(R^{z4})$ and $Z^{4a}$ is C(O), S(O), or $S(O)_2$; (3) $Z^{4b}$ is $N(R^{z4})$ and $Z^5$ is C(O), S(O), or $S(O)_2$; or (4) $Z^{4b}$ is $N(R^{z4})$ and $Z^3$ is $C(R^{z3})$ or C; and each $R^{z4}$ is independently selected from -$L^{z1}$-$L^{z2}$-$L^{z3}$—$R^{12}$, hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{12}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{12}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20z4}$; or two $R^{z4}$ bonded to the same carbon are joined to form $C_{2-6}$alkenyl optionally substituted with one, two, or three $R^{20z4}$;

$Z^5$ is $C(R^{z5})$, $N(R^{z5})$, $C(R^{z5})_2$, C(O), S(O), $S(O)_2$, $S(O)(NR^{z5})$, O, S, or N;

each $R^{z5}$ is independently selected from -$L^{z1}$-$L^{z2}$-$L^{z3}$—$R^{12}$, hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{12}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{12}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20z5}$; or two $R^{z5}$ bonded to the same carbon are joined to form $C_{2-6}$alkenyl optionally substituted with one, two, or three $R^{20z5}$;

$Z^6$ is $C(R^{z6})$, $N(R^{z6})$, $C(R^{z6})_2$, C(O), S(O), $S(O)_2$, $S(O)(NR^{z6})$, O, S, or N;

each $R^{z6}$ is independently selected from -$L^{z1}$-$L^{z2}$-$L^{z3}$—$R^{12}$, hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{12}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{12}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20z6}$; or two $R^{z6}$ bonded to the same carbon are joined to form $C_{2-6}$alkenyl optionally substituted with one, two, or three $R^{20z6}$;

and further wherein the compound optionally includes one of the following:

(1) two $R^{z4}$ bonded to the same carbon atom are joined to form monocyclic $C_{3-7}$cycloalkyl or monocyclic 3-7 membered heterocycloalkyl, wherein the monocyclic $C_{3-7}$cycloalkyl and monocyclic 3-7 membered heterocycloalkyl are optionally substituted with one, two, or three $R^{20z}$;

(2) two or more $R^{z4}$ bonded to adjacent atoms are joined to form monocyclic $C_{3-7}$cycloalkyl, monocyclic 3-7 membered heterocycloalkyl, phenyl, or monocyclic 5-6 membered heteroaryl, wherein the monocyclic $C_{3-7}$cycloalkyl, monocyclic 3-7 membered heterocycloalkyl, phenyl, and monocyclic 5-6 membered heteroaryl are optionally substituted with one, two, or three $R^{20z}$;

(3) two $R^{z5}$ bonded to the same carbon atom are joined to form monocyclic $C_{3-7}$cycloalkyl or monocyclic 3-7 membered heterocycloalkyl, wherein the monocyclic $C_{3-7}$cycloalkyl and monocyclic 3-7 membered heterocycloalkyl are optionally substituted with one, two, or three $R^{20z}$;

(4) one or two $R^{z4}$ bonded to one atom and one or two $R^{z5}$ bonded to an adjacent atom are joined to form monocyclic $C_{3-7}$cycloalkyl, monocyclic 3-7 membered heterocycloalkyl, phenyl, or monocyclic 5-6 membered heteroaryl, wherein the monocyclic $C_{3-7}$cycloalkyl, monocyclic 3-7 membered heterocycloalkyl, phenyl, and monocyclic 5-6 membered heteroaryl are optionally substituted with one, two, or three $R^{20z}$;

(5) one or two $R^{z4}$ bonded to one atom and one or two $R^{z5}$ bonded to a second atom are joined to form monocyclic $C_{3-7}$cycloalkyl or monocyclic 3-7 membered heterocycloalkyl, wherein the monocyclic $C_{3-7}$cycloalkyl and monocyclic 3-7 membered heterocycloalkyl are optionally substituted with one, two, or three $R^{20z}$;

(6) two $R^{z6}$ bonded to the same carbon atom are joined to form monocyclic $C_{3-7}$cycloalkyl or monocyclic 3-7 membered heterocycloalkyl, wherein the monocyclic $C_{3-7}$cycloalkyl and monocyclic 3-7 membered heterocycloalkyl are optionally substituted with one, two, or three $R^{20z}$;

(7) one or two $R^{z5}$ bonded to one atom and one or two $R^{z6}$ bonded to an adjacent atom are joined to form monocyclic $C_{3-7}$cycloalkyl, monocyclic 3-7 membered heterocycloalkyl, phenyl, or monocyclic 5-6 membered heteroaryl, wherein the monocyclic $C_{3-7}$cycloalkyl, monocyclic 3-7 membered heterocycloalkyl, phenyl, and monocyclic 5-6 membered heteroaryl are optionally substituted with one, two, or three $R^{20z}$; or (8) one or two $R^{z4}$ bonded to one atom and one or two $R^{z6}$ bonded to a second atom are joined to form monocyclic $C_{3-7}$cycloalkyl or monocyclic 3-7 membered heterocycloalkyl, wherein the monocyclic $C_{3-7}$cycloalkyl and monocyclic 3-7 membered heterocycloalkyl are optionally substituted with one, two, or three $R^{20z}$;

each $R^{12}$ is independently selected from hydrogen, $C_{1-6}$alkyl, $C_{2-6}$alkenyl, $C_{2-6}$alkynyl, $C_{3-10}$cycloalkyl, —$CH_2$-$C_{3-10}$cycloalkyl, $C_{2-9}$heterocycloalkyl, —$CH_2$-$C_{2-9}$heterocycloalkyl, $C_{6-10}$aryl, —$CH_2$-$C_{6-10}$aryl, —$CH_2$-$C_{1-9}$heteroaryl, and $C_{1-9}$heteroaryl, wherein $C_{1-6}$alkyl, $C_{2-6}$alkenyl, $C_{2-6}$alkynyl, $C_{3-10}$cycloalkyl, —$CH_2$-$C_{3-10}$cycloalkyl, $C_{2-9}$heterocycloalkyl, —$CH_2$-$C_{2-9}$heterocycloalkyl, $C_{6-10}$aryl, —$CH_2$-$C_{6-10}$aryl, —$CH_2$-$C_{1-9}$heteroaryl, and $C_{1-9}$heteroaryl are optionally substituted with one, two, or three $R^{20l}$;

$R^{12a}$ is independently selected from hydrogen, $C_{1-6}$alkyl, $C_{2-6}$alkenyl, $C_{2-6}$alkynyl, $C_{3-10}$cycloalkyl, —$C(R^{12c})_2$-$C_{3-10}$cycloalkyl, $C_{2-9}$heterocycloalkyl, —$C(R^{12c})_2$-$C_{2-9}$heterocycloalkyl, $C_{6-10}$aryl, —$C(R^{12c})_2$-$C_{6-10}$aryl, —$C(R^{12c})_2$-$C_{1-9}$heteroaryl, and $C_{1-9}$heteroaryl, wherein $C_{1-6}$alkyl, $C_{2-6}$alkenyl, $C_{2-6}$alkynyl, $C_{3-10}$cycloalkyl, —$C(R^{12c})_2$-$C_{3-10}$cycloalkyl, $C_{2-9}$heterocycloalkyl, —$C(R^{12c})_2$-$C_{2-9}$heterocycloalkyl, $C_{6-10}$aryl, —$C(R^{12c})_2$-$C_{6-10}$aryl, —$C(R^{12c})_2$-$C_{1-9}$heteroaryl, and $C_{1-9}$heteroaryl are optionally substituted with one, two, or three $R^{20l}$;

each $R^{12c}$ is independently selected from hydrogen and $R^{20lc}$;

each $R^{13}$ is independently selected from hydrogen, $C_{1-6}$alkyl, and $C_{1-6}$haloalkyl; or $R^{12}$ and $R^{13}$, together with the nitrogen to which they are attached, form a $C_{2-9}$heterocycloalkyl ring optionally substituted with one, two, or three $R^{20m}$;

each $R^{14}$ is independently selected from hydrogen, $C_{1-6}$alkyl, and $C_{1-6}$haloalkyl;

each $R^{15}$ is independently selected from $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20o}$;

each $R^{20z1}$, $R^{20z2}$, $R^{20z3}$, $R^{20z4}$, $R^{20z5}$, $R^{20z6}$, and $R^{20z9}$ is independently selected from halogen, oxo, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{12}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{12}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20z}$;

each $R^{20z}$ is independently selected from -$L^{z3}$—$R^{12}$, halogen, oxo, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{12}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{12}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20zz}$;

two $R^{20z}$ bonded to the same carbon atom are optionally joined to form monocyclic $C_{3-7}$cycloalkyl or monocyclic 3-7 membered heterocycloalkyl, wherein the monocyclic $C_{3-7}$cycloalkyl and monocyclic 3-7 membered heterocycloalkyl are optionally substituted with one, two, or three $R^{20zz}$; or two or more $R^{20z}$ bonded to two adjacent atoms are optionally joined to form monocyclic $C_{3-7}$cycloalkyl, monocyclic 3-7 membered heterocycloalkyl, phenyl, or monocyclic 5-6 membered heteroaryl, wherein the $C_{3-7}$cycloalkyl, monocyclic 3-7 membered heterocycloalkyl, phenyl, and monocyclic 5-6 membered heteroaryl are optionally substituted with one, two, or three $R^{20zz}$;

$L^{z1}$ is selected from a bond, $C_{1-6}$alkylene, $C_{2-6}$alkenylene, $C_{2-6}$alkynylene, $C_{3-10}$cycloalkylene, $C_{1-9}$heterocycloalkylene, $C_{6-10}$arylene, and $C_{1-9}$heteroarylene; wherein $C_{1-6}$alkyl, $C_{2-6}$alkenylene, $C_{2-6}$alkynylene, $C_{3-10}$cycloalkylene, $C_{1-9}$heterocycloalkylene, $C_{6-10}$arylene, and $C_{1-9}$heteroarylene are optionally substituted with one or two $R^{30z}$;

$R^{30z}$ is independently selected from halogen, oxo, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{12}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{12}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20z}$;

$L^{z2}$ is selected from a bond, $C_{1-6}$alkylene, $C_{2-6}$alkenylene, $C_{2-6}$alkynylene, $C_{3-10}$cycloalkylene, $C_{1-9}$heterocycloalkylene, $C_{6-10}$arylene, and $C_{1-9}$heteroarylene; wherein $C_{1-6}$alkyl, $C_{2-6}$alkenylene, $C_{2-6}$alkynylene, $C_{3-10}$cycloalkylene, $C_{1-9}$heterocycloalkylene, $C_{6-10}$arylene, and $C_{1-9}$heteroarylene are optionally substituted with one or two $R^{31z}$;

$R^{31z}$ is independently selected from halogen, oxo, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{12}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{12}$, —S(O)$_2$R$^{15}$, —S(O)$_2$N(R$^{12}$)(R$^{13}$), —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three R$^{20zz}$;

L$^{z3}$—R$^{12}$ is selected from:
  i. —C(O)R$^{12}$ or —N(H)C(O)R$^{12}$; wherein the R$^{12}$ of L$^{z3}$—R$^{12}$ is a 5-membered heteroaryl including two or more ring nitrogen atoms, wherein the 5-membered heteroaryl is directly bonded to the C(O) through an R$^{12}$ ring nitrogen atom and wherein R$^{12}$ is optionally substituted with one or more R$^{20l}$; and
  ii. —C(O)R$^{12}$ or —N(H)C(O)R$^{12}$; wherein the R$^{12}$ of L$^{z3}$—R$^{12}$ is a 3-membered heterocycloalkyl including one or more ring nitrogen atoms, wherein R$^{12}$ is optionally substituted with one or more R$^{20l}$;

R$^{20l}$ is independently selected from halogen, oxo, —CN, $C_{1-6}$alkyl, $C_{2-6}$alkenyl, $C_{2-6}$alkynyl, $C_{3-10}$cycloalkyl, —CH$_2$-$C_{3-10}$cycloalkyl, $C_{2-9}$heterocycloalkyl, —CH$_2$-$C_{2-9}$heterocycloalkyl, $C_{6-10}$aryl, —CH$_2$-$C_{6-10}$aryl, —CH$_2$-$C_{1-9}$heteroaryl, $C_{1-9}$heteroaryl, —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, —N(R$^{24}$)C(O)R$^{21}$, —N(R$^{24}$)S(O)$_2$R$^{25}$, —C(O)R$^{21}$, —S(O)$_2$R$^{25}$, —S(O)$_2$N(R$^{22}$)(R$^{23}$), —OCH$_2$C(O)OR$^{22}$, =NR$^{21}$, and —OC(O)R$^{25}$; two R$^{20q}$ bonded to adjacent atoms are optionally joined to form a $C_{3-10}$cycloalkyl, $C_{2-9}$heterocycloalkyl, $C_{6-10}$aryl, or $C_{1-9}$heteroaryl; wherein $C_{1-6}$alkyl, $C_{2-6}$alkenyl, $C_{2-6}$alkynyl, $C_{3-10}$cycloalkyl, —CH$_2$-$C_{3-10}$cycloalkyl, $C_{2-9}$heterocycloalkyl, —CH$_2$-$C_{2-9}$heterocycloalkyl, $C_{6-10}$aryl, —CH$_2$-$C_{6-10}$aryl, —CH$_2$-$C_{1-9}$heteroaryl, and $C_{1-9}$heteroaryl are optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, —N(R$^{24}$)C(O)R$^{25}$, —N(R$^{24}$)S(O)$_2$R$^{25}$, —C(O)R$^{25}$, —S(O)$_2$R$^{25}$, —S(O)$_2$N(R$^{22}$)(R$^{23}$), and —OC(O)R$^{25}$;

each R$^{21}$ is independently selected from hydrogen, $C_{1-6}$alkyl, $C_{1-6}$haloalkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl;

each R$^{22}$ is independently selected from hydrogen, $C_{1-6}$alkyl, $C_{1-6}$haloalkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl;

each R$^{23}$ is independently selected from hydrogen and $C_{1-6}$alkyl;

each R$^{24}$ is independently selected from hydrogen and $C_{1-6}$alkyl;

each R$^{25}$ is independently selected from $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; and ===== indicates a single or double bond such that all valences are satisfied.

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, wherein:

L$^{z1}$ is selected from a bond, $C_{1-6}$alkylene, $C_{3-10}$cycloalkylene, and $C_{1-9}$heterocycloalkylene; wherein $C_{1-6}$alkylene, $C_{3-10}$cycloalkylene, and $C_{2-9}$heterocycloalkylene are optionally substituted with one or two R$^{30z}$;

R$^{30z}$ is independently selected from halogen, oxo, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{12}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{12}$, —S(O)$_2$R$^{15}$, —S(O)$_2$N(R$^{12}$)(R$^{13}$), —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three R$^{20z}$;

L$^{z2}$ is selected from a bond, $C_{1-6}$alkylene, $C_{3-10}$cycloalkylene, and $C_{2-9}$heterocycloalkylene; wherein $C_{1-6}$alkylene, $C_{3-10}$cycloalkylene, and $C_{2-9}$heterocycloalkylene are optionally substituted with one or two R$^{31z}$;

R$^{31z}$ is independently selected from halogen, oxo, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{12}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{12}$, —S(O)$_2$R$^{15}$, —S(O)$_2$N(R$^{12}$)(R$^{13}$), —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20zz}$;

$L^{z3}$—$R^{12}$ is selected from:
  i. —C(O)$R^{12}$ or —N(H)C(O)$R^{12}$; wherein the $R^{12}$ of $L_{z3}$—$R^{12}$ is a 5-membered heteroaryl including two or more ring nitrogen atoms, wherein the 5-membered heteroaryl is directly bonded to the C(O) through an $R^{12}$ ring nitrogen atom and wherein $R^{12}$ is optionally substituted with one or more $R^{20l}$; and
  ii. —C(O)$R^{12}$ or —N(H)C(O)$R^{12}$; wherein the $R^{12}$ of $L_{z3}$—$R^{12}$ is a 3-membered heterocycloalkyl including one or more ring nitrogen atoms, wherein $R^{12}$ is optionally substituted with one or more $R^{20l}$;

$R^{20l}$ is independently selected from halogen, oxo, —CN, $C_{1-6}$alkyl, $C_{2-6}$alkenyl, $C_{2-6}$alkynyl, $C_{3-10}$cycloalkyl, —$CH_2$-$C_{3-10}$cycloalkyl, $C_{2-9}$heterocycloalkyl, —$CH_2$-$C_{2-9}$heterocycloalkyl, $C_{6-10}$aryl, —$CH_2$-$C_{6-10}$aryl, —$CH_2$-$C_{1-9}$heteroaryl, $C_{1-9}$heteroaryl, —$OR^{21}$, —$SR^{21}$, —$N(R^{22})(R^{23})$, —C(O)$OR^{22}$, —C(O)$N(R^{22})(R^{23})$, —C(O)C(O)$N(R^{22})(R^{23})$, —OC(O)$N(R^{22})(R^{23})$, —$N(R^{24})C(O)N(R^{22})(R^{23})$, —$N(R^{24})C(O)OR^{25}$, —$N(R^{24})C(O)R^{21}$, —$N(R^{24})S(O)_2R^{25}$, —C(O)$R^{21}$, —$S(O)_2R^{25}$, —$S(O)_2N(R^{22})(R^{23})$, —$OCH_2C(O)OR^{22}$, =$NR^{21}$, and —OC(O)$R^{25}$; two $R^{20q}$ bonded to adjacent atoms are optionally joined to form a $C_{3-10}$cycloalkyl, $C_{2-9}$heterocycloalkyl, $C_{6-10}$aryl, or $C_{1-9}$heteroaryl; wherein $C_{1-6}$alkyl, $C_{2-6}$alkenyl, $C_{2-6}$alkynyl, $C_{3-10}$cycloalkyl, —$CH_2$-$C_{3-10}$cycloalkyl, $C_{2-9}$heterocycloalkyl, —$CH_2$-$C_{2-9}$heterocycloalkyl, $C_{6-10}$aryl, —$CH_2$-$C_{6-10}$aryl, —$CH_2$-$C_{1-9}$heteroaryl, and $C_{1-9}$heteroaryl are optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —$OR^{21}$, —$SR^{21}$, —$N(R^{22})(R^{23})$, —C(O)$OR^{22}$, —C(O)$N(R^{22})(R^{23})$, —C(O)C(O)$N(R^{22})(R^{23})$, —OC(O)$N(R^{22})(R^{23})$, —$N(R^{24})C(O)N(R^{22})(R^{23})$, —$N(R^{24})C(O)OR^{25}$, —$N(R^{24})C(O)R^{25}$, —$N(R^{24})S(O)_2R^{25}$, —C(O)$R^{25}$, —$S(O)_2R^{25}$, —$S(O)_2N(R^{22})(R^{23})$, and —OC(O)$R^{25}$.

In embodiments of a compound of Formula (A), or a pharmaceutically acceptable salt or solvate thereof, having the formula:

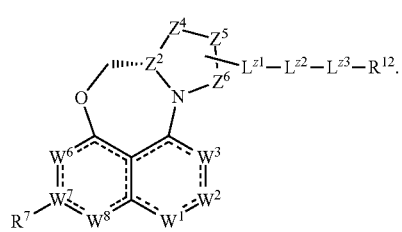

(Aa-2b)

In embodiments of a compound of Formula (A), or a pharmaceutically acceptable salt or solvate thereof, having the formula:

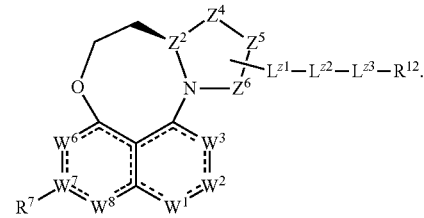

(Aa-3a)

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, wherein

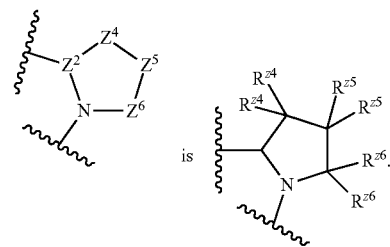

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, wherein

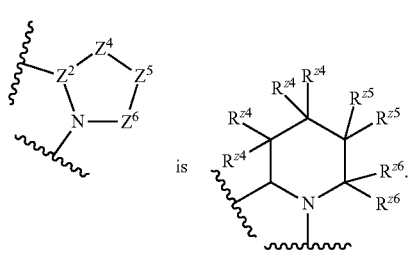

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, two $R^{z5}$ bonded to the same carbon atom are joined to form monocyclic 4-membered heterocycloalkyl, wherein the 4 membered heterocycloalkyl is substituted with one, two, or three $R^{20z}$.

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof,

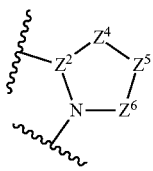

is selected from

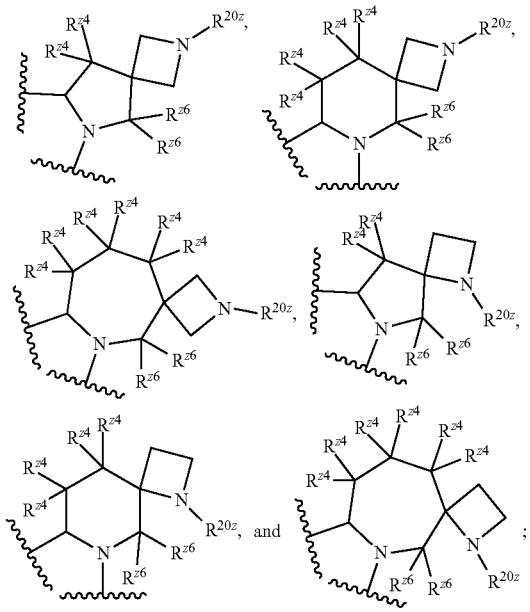

wherein the one $R^{20z}$ shown in each formula above is —C(O)R$^{12}$ or —N(H)C(O)R$^{12}$.

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, one or two $R^{z4}$ bonded to one atom and one or two $R^{z5}$ bonded to an adjacent atom are joined to form monocyclic 5-6 membered heteroaryl, wherein the monocyclic 5-6 membered heteroaryl is optionally substituted with one, two, or three $R^{20z}$.

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof,

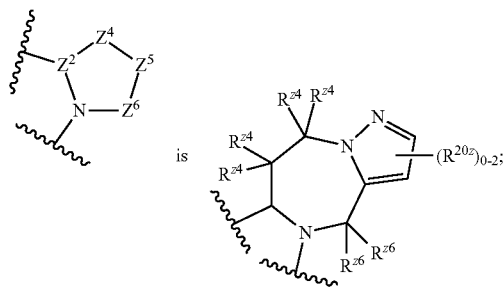

wherein one $R^{20z}$ shown in the formula above is —C(O)R$^{12}$ or —N(H)C(O)R$^{12}$.

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, z1n is 1, 2 or 3, and z9n is 1, 2, or 3. In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, $W^1$ is N. In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, $W^2$ is C(R$^2$). In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, $W^3$ is N. In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, $W^4$ is C. In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, $W^5$ is C. In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, $W^5$ is C(R$^5$). In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, $W^6$ is C(R$^6$). In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, $R^6$ is selected from hydrogen, halogen, -CN, $C_{1-6}$alkyl, and —OR$^{12}$, wherein $C_{1-6}$alkyl is optionally substituted with one, two, or three $R^{20f}$. In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, $R^6$ is halogen. In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, $W^7$ is C. In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, $W^8$ is C(R$^8$). In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, $R^8$ is selected from hydrogen, halogen, —CN, $C_{1-6}$alkyl, and —OR$^{12}$, wherein $C_{1-6}$alkyl is optionally substituted with one, two, or three $R^{20h}$. In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, $R^8$ is halogen. In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, $W^9$ is C. In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, $W^1$ is C. In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof,

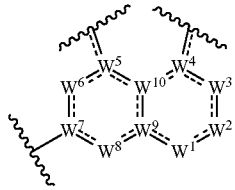

is selected from

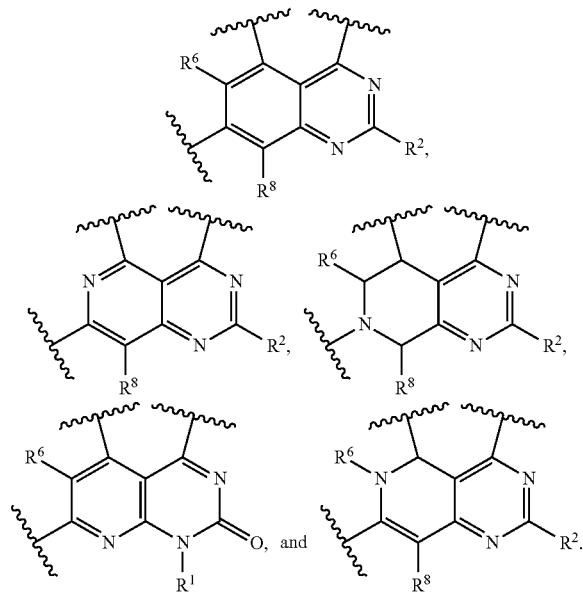

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, $L^7$ is a bond. In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, $R^{17}$ is selected from naphthalenyl and benzothiophenyl, each of which is optionally substituted with one, two, or three $R^{20q}$. In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, $R^{17}$ is substituted with one, two, or three substituents independently selected from halogen, —CN, —CH₃, —C≡CH, —OH, and —NH₂.

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, $R^{17}$ is selected from

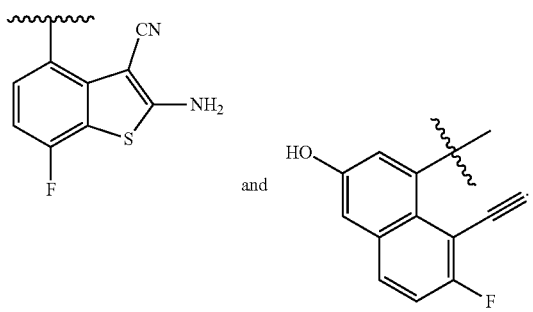

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, $R^{17}$ is selected from:

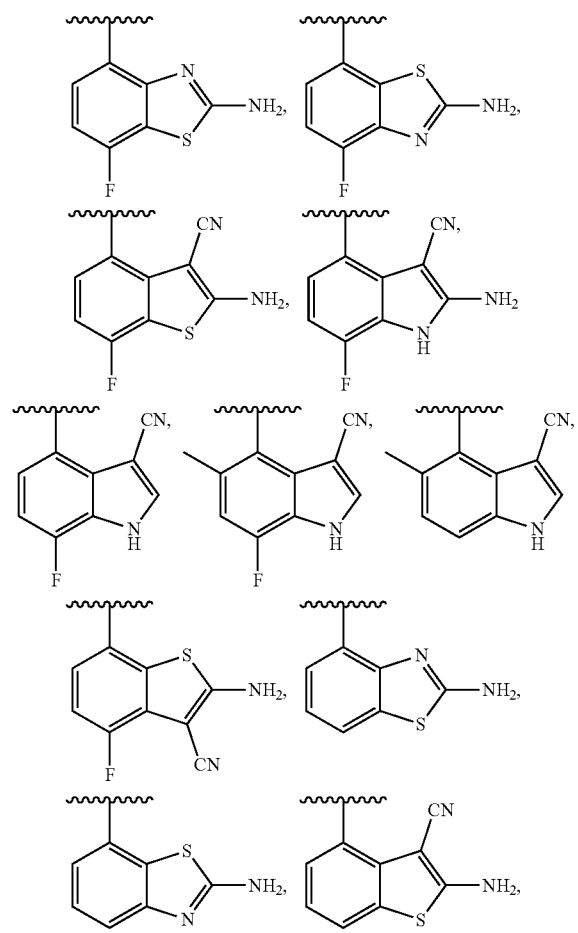

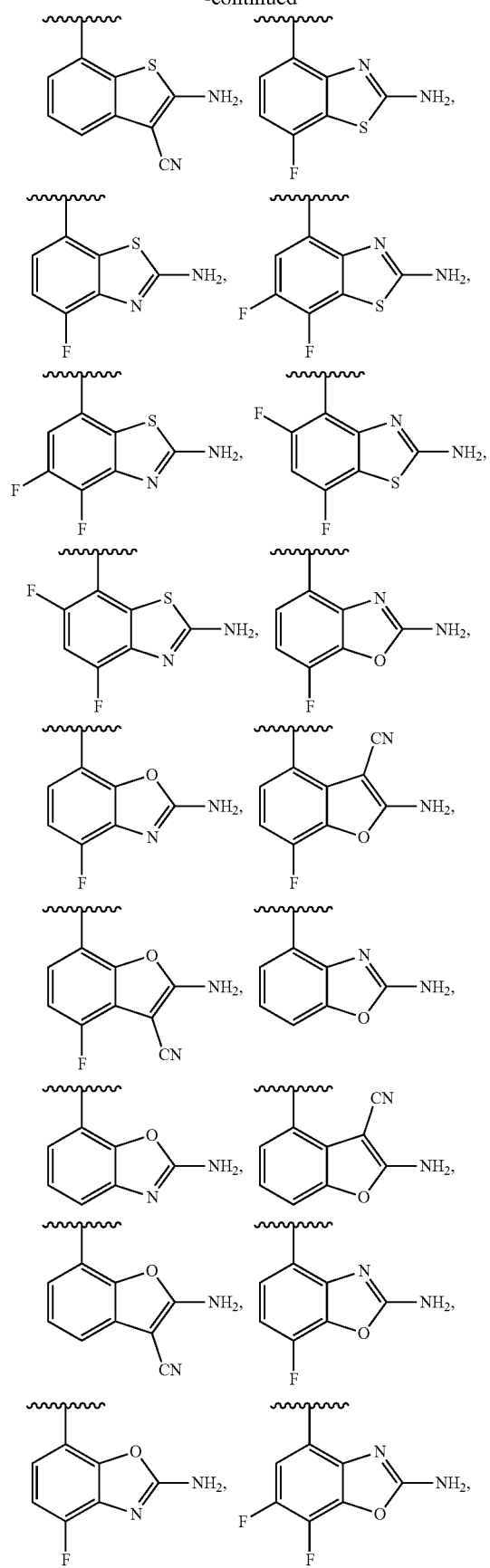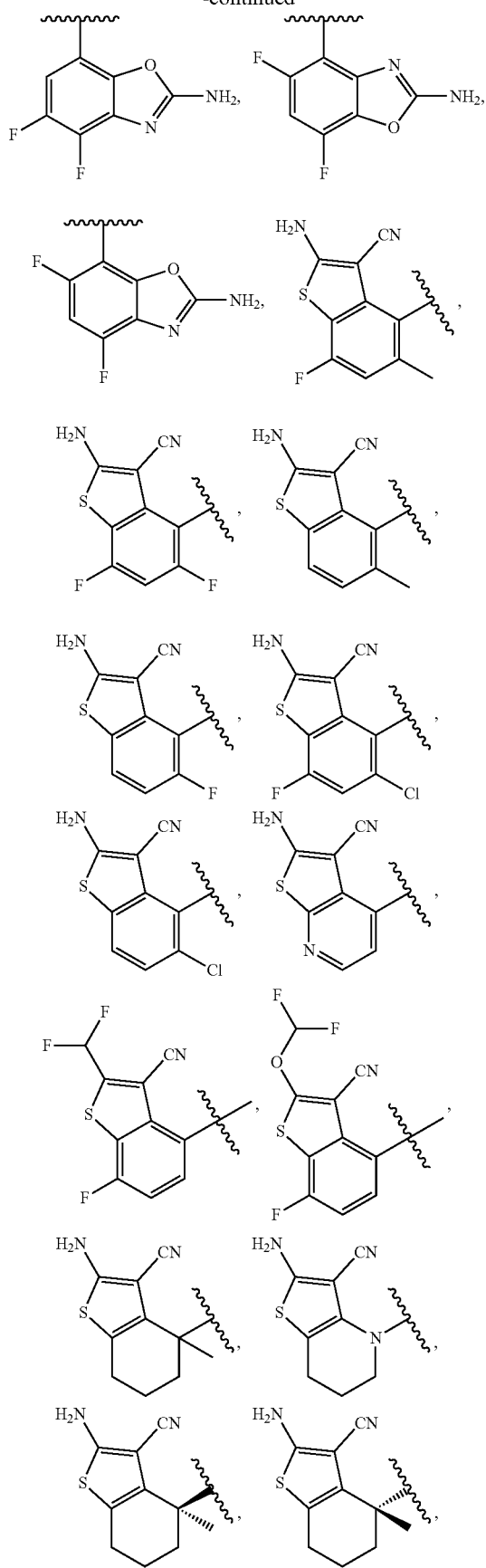

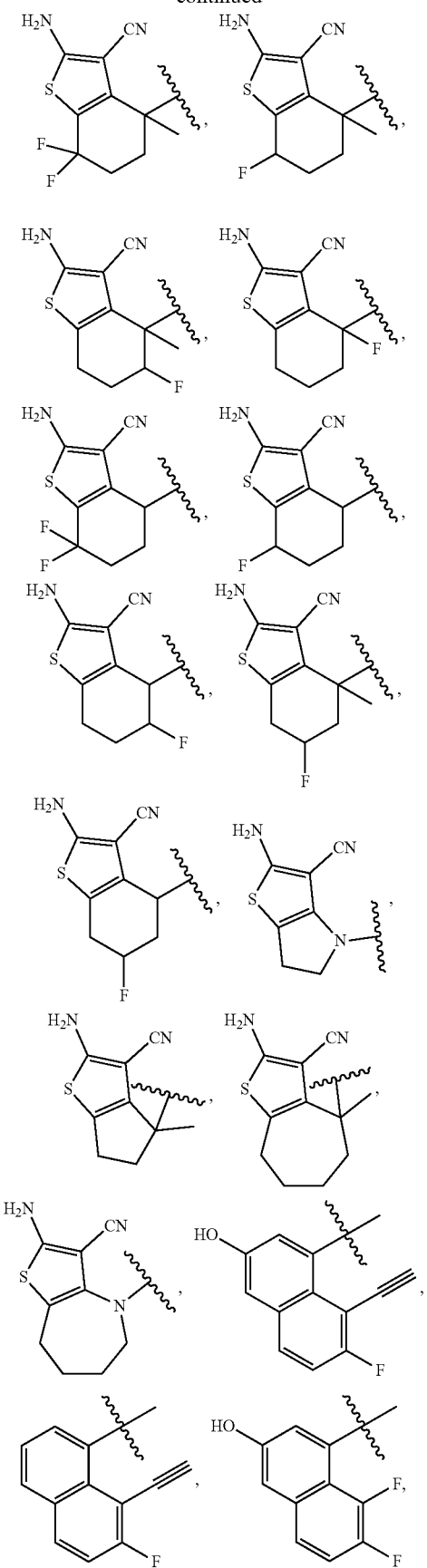
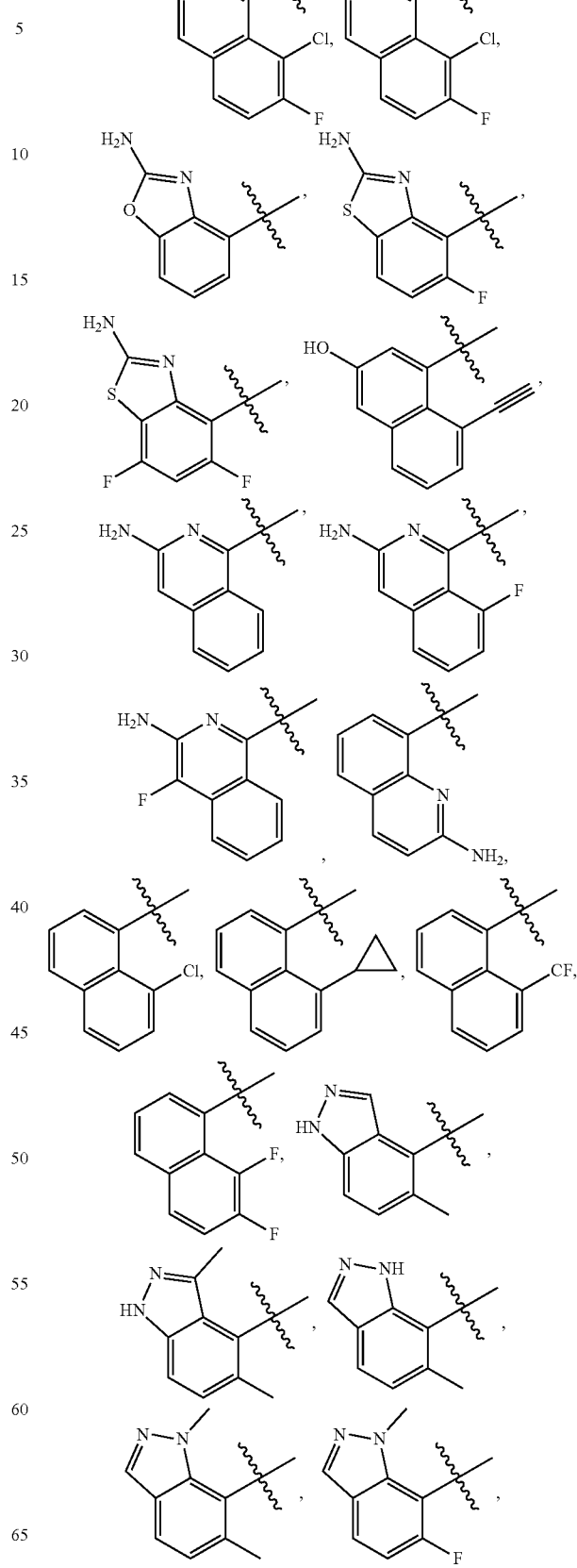

-continued
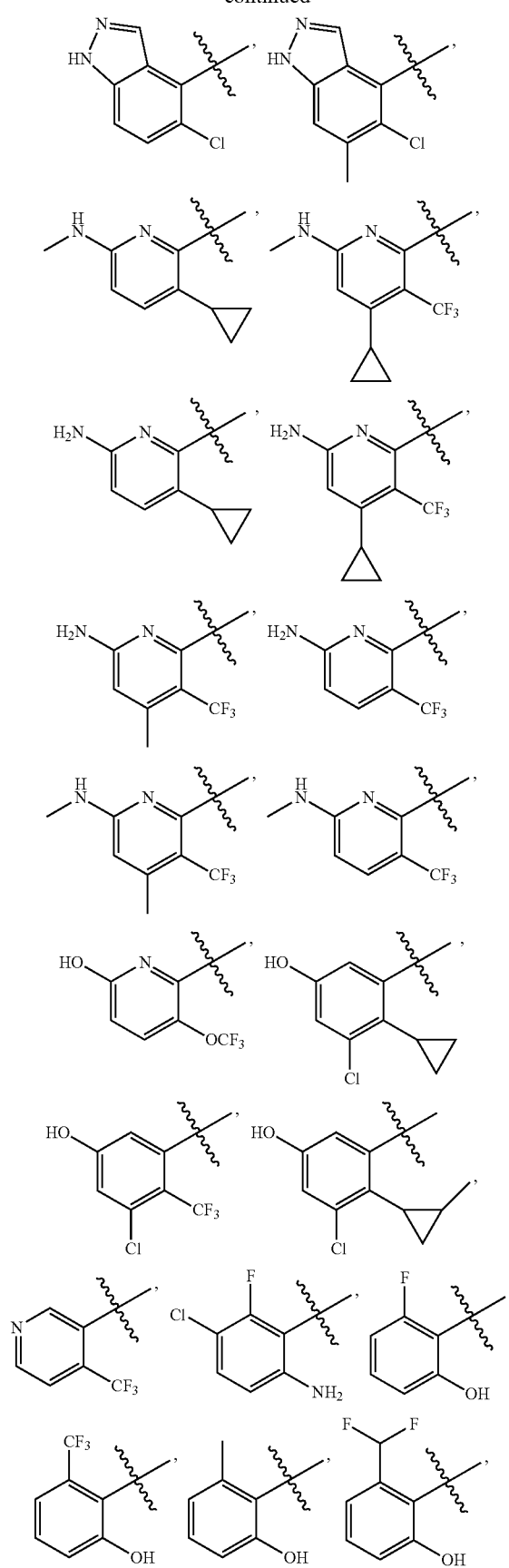
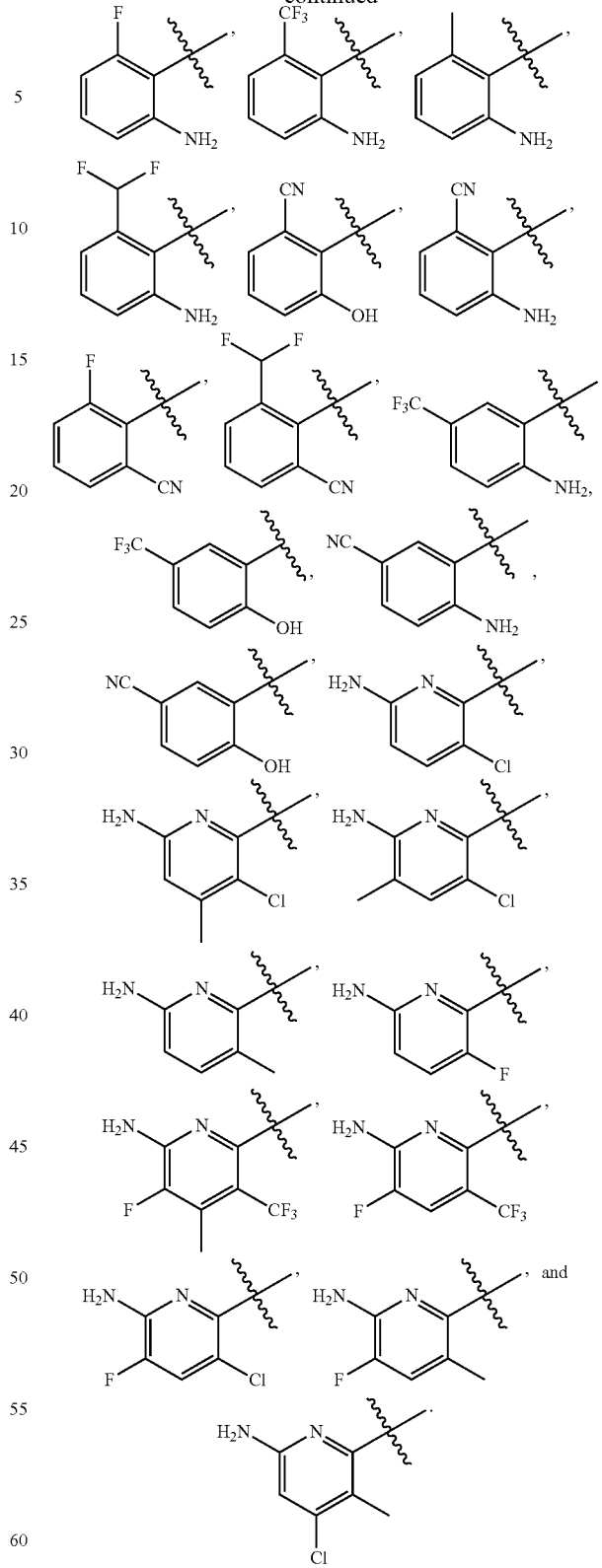
In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, $R^2$ is independently —$OR^{12a}$.

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, R² is independently selected from
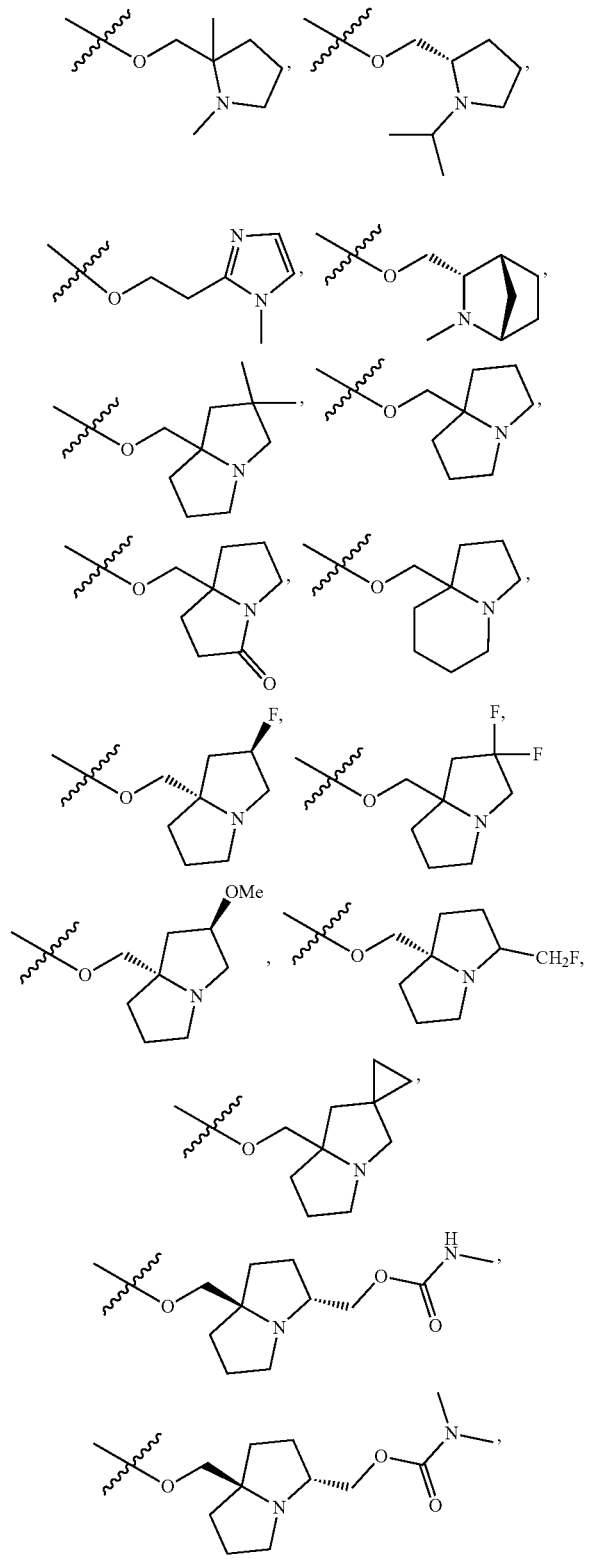
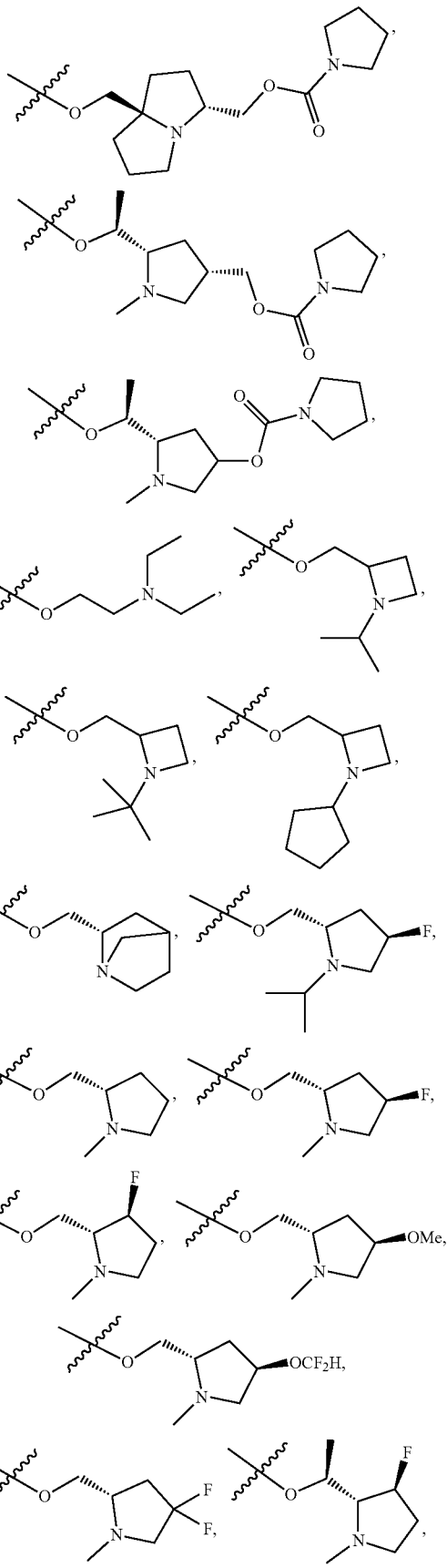

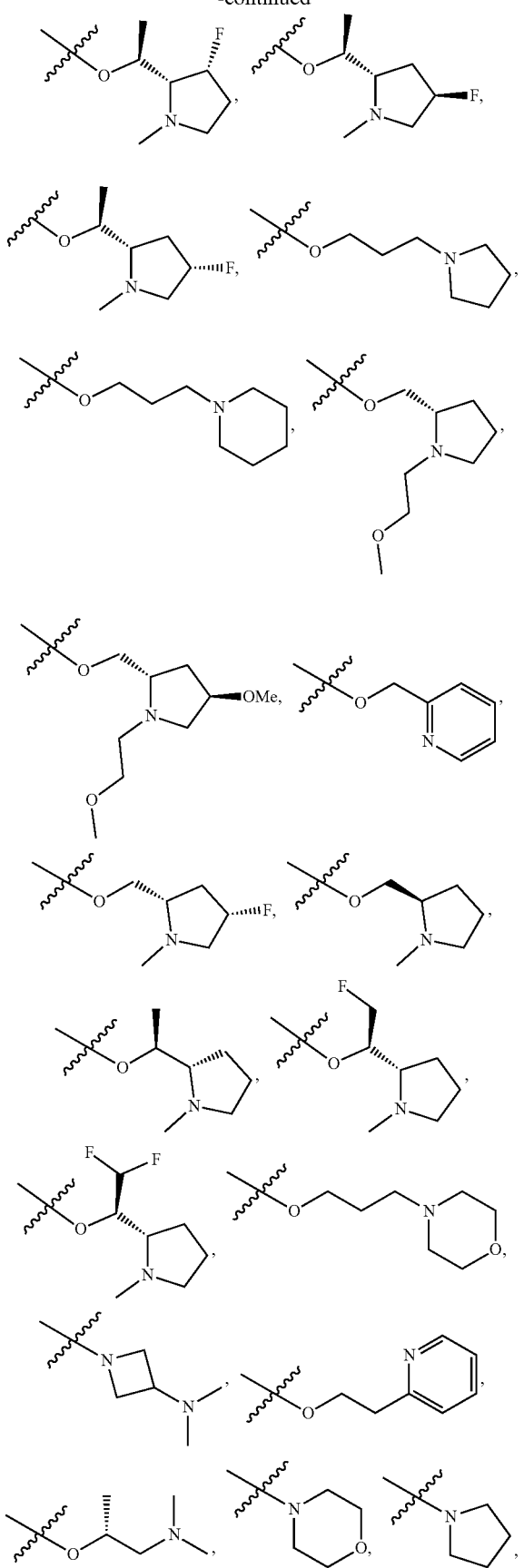
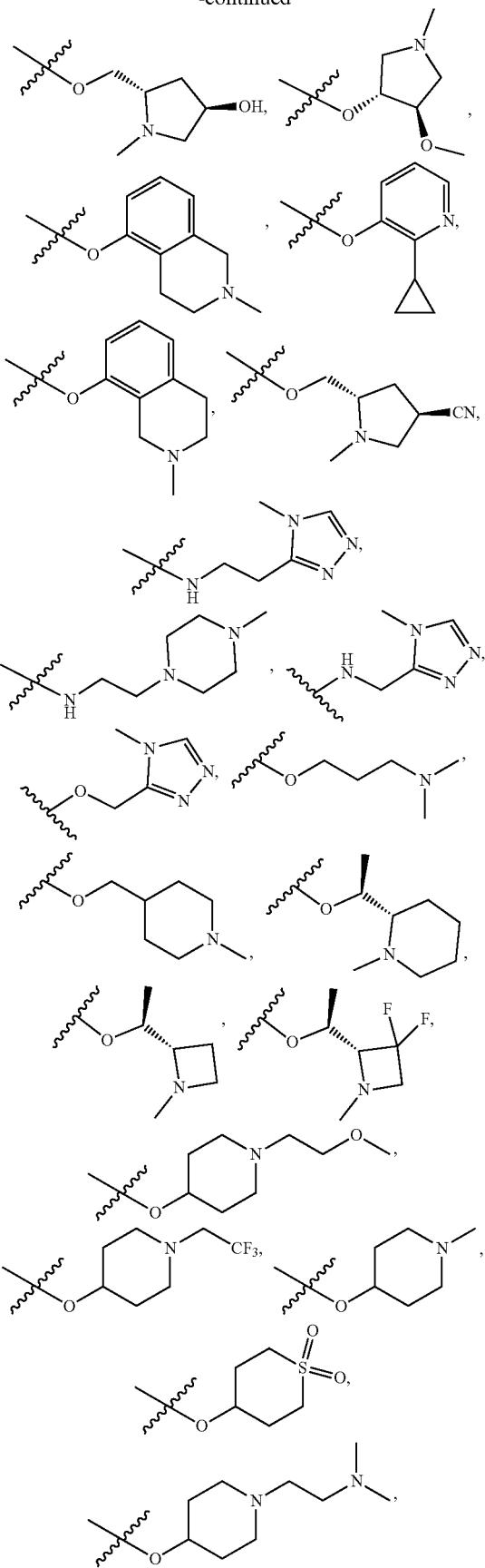

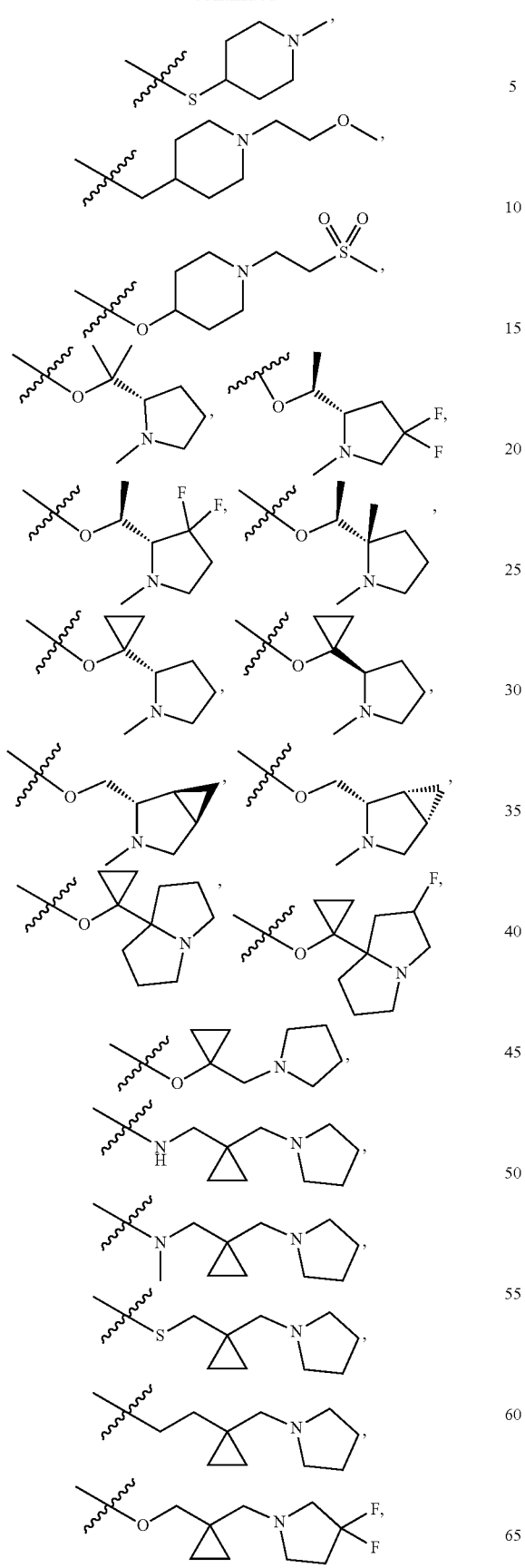
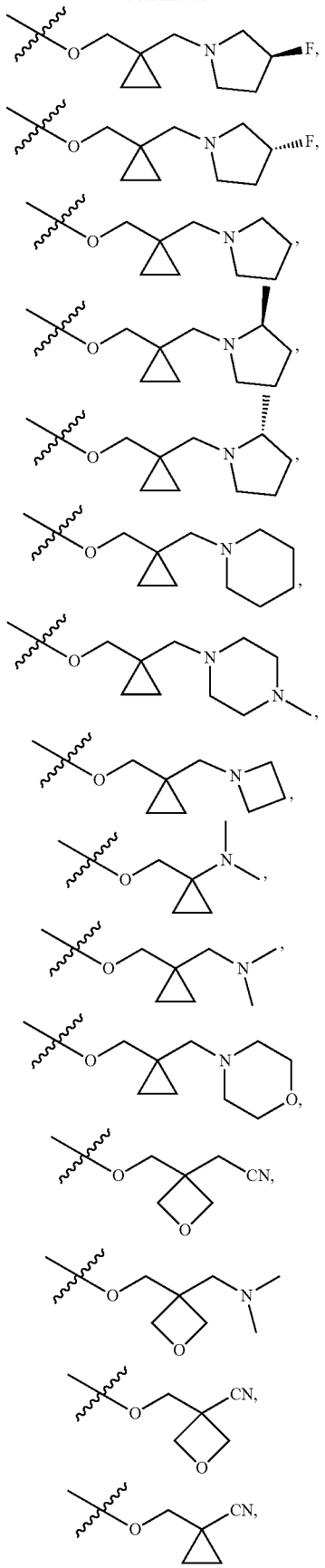

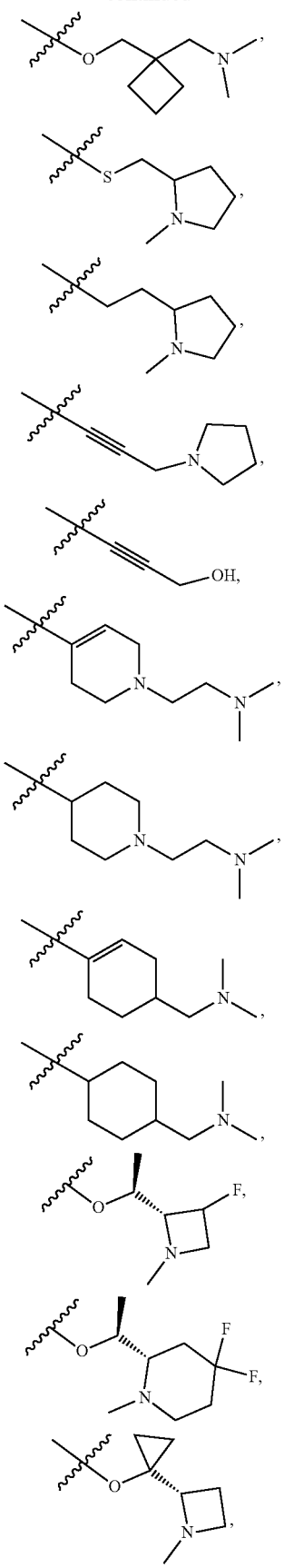
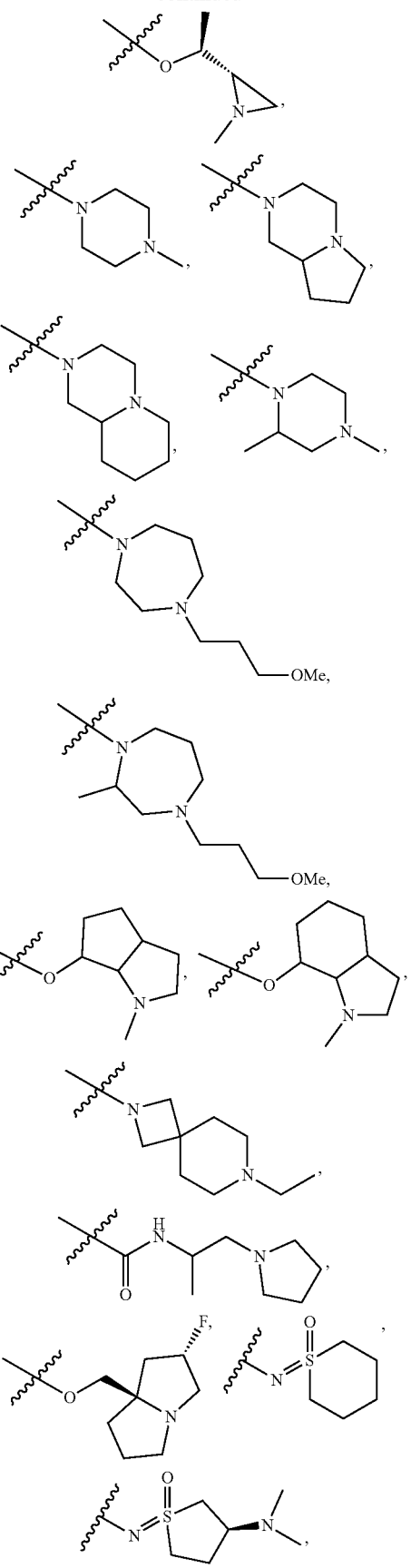

-continued

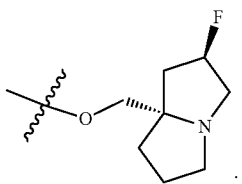 [SMILES: *OC[C@@]12CCCN1C[C@H](F)C2]

and

[structure: piperidine with O linker and N-S(O)₂-methyl sulfonamide]

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, $R^2$ is independently

[structure: fluorinated pyrrolizidine with OCH₂ linker]

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, $Z^4$ is $Z^{4a}$. In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, $Z^4$ is $Z^{4a}Z^{4b}$.

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, each $R^{z4}$ is independently selected from hydrogen, halogen, —CN, $C_{1-6}$alkyl, $C_{2-6}$alkenyl, $C_{3-10}$ cycloalkyl, $C_{2-9}$heterocycloalkyl, $C_{1-9}$heteroaryl, —$OR^{12}$, —$N(R^{12})(R^{13})$, —$N(R^{14})S(O)_2R^{15}$, —$C(O)R^{12}$, —$S(O)R^{15}$, —$OC(O)R^{15}$, —$C(O)N(R^{12})(R^{13})$, —$N(H)C(O)R^{12}$, —$S(O)_2R^{15}$, and —$S(O)_2N(R^{12})(R^{13})$—, wherein $C_{1-6}$alkyl, $C_{2-6}$alkenyl, $C_{3-10}$ cycloalkyl, $C_{2-9}$heterocycloalkyl, and $C_{1-9}$heteroaryl are optionally substituted with one, two, or three $R^{20z4}$; or two $R^{z4}$ bonded to the same carbon are joined to form a $C_{2-6}$alkenyl that is optionally substituted with one, two, or three $R^{20z4}$. In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, each $R^{z4}$ is independently selected from hydrogen, halogen, —CN, $C_{1-6}$alkyl, $C_{3-10}$ cycloalkyl, $C_{2-9}$heterocycloalkyl, $C_{1-9}$heteroaryl, —$OR^{12}$, —$N(R^{12})(R^{13})$, —$N(R^{14})S(O)_2R^{15}$, and —$S(O)_2R^{15}$, wherein $C_{1-6}$alkyl, $C_{3-10}$ cycloalkyl, $C_{2-9}$heterocycloalkyl, and $C_{1-9}$heteroaryl are optionally substituted with one, two, or three $R^{20z4}$; or two $R^{z4}$ bonded to the same carbon are joined to form a $C_{2-6}$alkenyl that is optionally substituted with one, two, or three $R^{20z4}$. In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, each $R^{z5}$ is independently selected from hydrogen, halogen, —CN, $C_{1-6}$alkyl, $C_{2-6}$alkenyl, $C_{3-10}$ cycloalkyl, $C_{2-9}$heterocycloalkyl, $C_{1-9}$heteroaryl, —$OR^{12}$, —$N(R^{12})(R^{13})$, —$N(R^{14})S(O)_2R^{15}$, —$C(O)R^{12}$, —$S(O)R^{15}$, —$OC(O)R^{15}$, —$C(O)N(R^{12})(R^{13})$, —$N(H)C(O)R^{12}$, —$S(O)_2R^{15}$, and —$S(O)_2N(R^{12})(R^{13})$—, wherein $C_{1-6}$alkyl, $C_{2-6}$alkenyl, $C_{3-10}$ cycloalkyl, $C_{2-9}$heterocycloalkyl, and $C_{1-9}$heteroaryl are optionally substituted with one, two, or three $R^{20z5}$; or two $R^{z5}$ bonded to the same carbon are joined to form a $C_{2-6}$alkenyl that is optionally substituted with one, two, or three $R^{20z5}$. In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, each $R^{z5}$ is independently selected from hydrogen, halogen, —CN, $C_{1-6}$alkyl, $C_{3-10}$ cycloalkyl, $C_{2-9}$heterocycloalkyl, $C_{1-9}$heteroaryl, —$OR^{12}$, —$N(R^{12})(R^{13})$, —$N(R^{14})S(O)_2R^{15}$, and —$S(O)_2R^{15}$, wherein $C_{1-6}$alkyl, $C_{3-10}$ cycloalkyl, $C_{2-9}$heterocycloalkyl, and $C_{1-9}$heteroaryl are optionally substituted with one, two, or three $R^{20z5}$; or two $R^{z5}$ bonded to the same carbon are joined to form a $C_{2-6}$alkenyl that is optionally substituted with one, two, or three $R^{20z5}$. In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, each $R^{z6}$ is independently selected from hydrogen, halogen, —CN, $C_{1-6}$alkyl, $C_{2-6}$alkenyl, $C_{3-10}$ cycloalkyl, $C_{2-9}$heterocycloalkyl, $C_{1-9}$heteroaryl, —$OR^{12}$, —$N(R^{12})(R^{13})$, —$N(R^{14})S(O)_2R^{15}$, —$C(O)R^{12}$, —$S(O)R^{15}$, —$OC(O)R^{15}$, —$C(O)N(R^{12})(R^{13})$, —$N(H)C(O)R^{12}$, —$S(O)_2R^{15}$, and —$S(O)_2N(R^{12})(R^{13})$—, wherein $C_{1-6}$alkyl, $C_{2-6}$alkenyl, $C_{3-10}$ cycloalkyl, $C_{2-9}$heterocycloalkyl, and $C_{1-9}$heteroaryl are optionally substituted with one, two, or three $R^{20z6}$; or two $R^{z6}$ bonded to the same carbon are joined to form a $C_{2-6}$alkenyl that is optionally substituted with one, two, or three $R^{20z6}$. In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, each $R^{z6}$ is independently selected from hydrogen, halogen, —CN, $C_{1-6}$alkyl, $C_{3-10}$ cycloalkyl, $C_{2-9}$heterocycloalkyl, $C_{1-9}$heteroaryl, —$OR^{12}$, —$N(R^{12})(R^{13})$, —$N(R^{14})S(O)_2R^{15}$, and —$S(O)_2R^{15}$, wherein $C_{1-6}$alkyl, $C_{3-10}$ cycloalkyl, $C_{2-9}$heterocycloalkyl, and $C_{1-9}$heteroaryl are optionally substituted with one, two, or three $R^{20z6}$; or two $R^{z6}$ bonded to the same carbon are joined to form a $C_{2-6}$alkenyl that is optionally substituted with one, two, or three $R^{20z6}$. In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, each $R^{20z}$ is independently selected from hydrogen, halogen, oxo, —CN, $C_{1-6}$alkyl, $C_{2-6}$alkenyl, $C_{3-10}$ cycloalkyl, $C_{2-9}$heterocycloalkyl, $C_{1-9}$heteroaryl, —$OR^{12}$, —$N(R^{12})(R^{13})$, —$N(R^{14})S(O)_2R^{15}$, —$C(O)R^{12}$, —$S(O)R^{15}$, —$OC(O)R^{15}$, —$C(O)N(R^{12})(R^{13})$, —$N(H)C(O)R^{12}$, —$S(O)_2R^{15}$, and —$S(O)_2N(R^{12})(R^{13})$—, wherein $C_{1-6}$alkyl, $C_{2-6}$alkenyl, $C_{3-10}$ cycloalkyl, $C_{2-9}$heterocycloalkyl, and $C_{1-9}$heteroaryl are optionally substituted with one, two, or three $R^{20zz}$; or two $R^{20z}$ bonded to the same carbon are joined to form a $C_{2-6}$alkenyl that is optionally substituted with one, two, or three $R^{20zz}$. In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, each $R^{20z}$ is independently selected from hydrogen, halogen, oxo, —CN, $C_{1-6}$alkyl, $C_{3-10}$cycloalkyl, $C_{2-9}$heterocycloalkyl, $C_{1-9}$heteroaryl, —N($R^{12}$)($R^{13}$), —N($R^{14}$)S(O)$_2$$R^{15}$, and —S(O)$_2$$R^{15}$, wherein $C_{1-6}$alkyl, $C_{3-10}$cycloalkyl, $C_{2-9}$heterocycloalkyl, and $C_{1-9}$heteroaryl are optionally substituted with one, two, or three $R^{20zz}$; or two $R^{20z}$ bonded to the same carbon are joined to form a $C_{2-6}$alkenyl that is optionally substituted with one, two, or three $R^{20zz}$.

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, one $R^{z4}$, $R^{z5}$, $R^{z6}$, $R^{20z4}$, $R^{20z5}$, $R^{20z6}$, or $R^{20z}$ is independently selected from —C(O)$R^{12}$ and —N(H)C(O)$R^{12}$; and the $R^{12}$ of the —C(O)$R^{12}$ or —N(H)C(O)$R^{12}$ is selected from

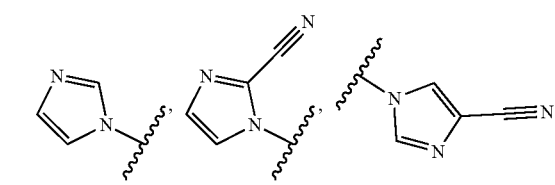

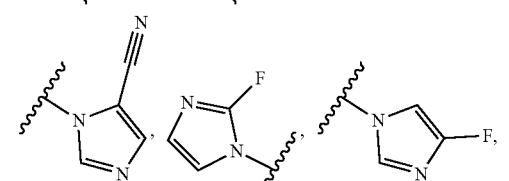

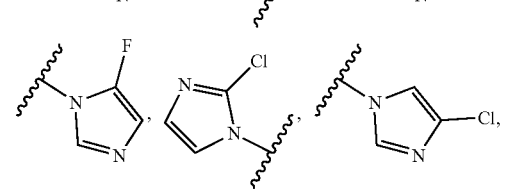

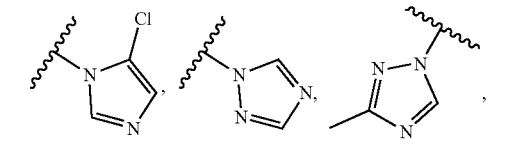

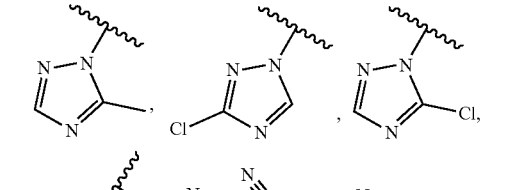

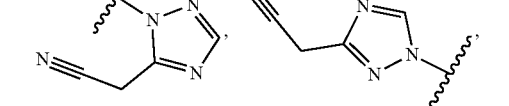

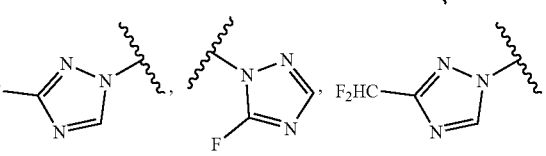

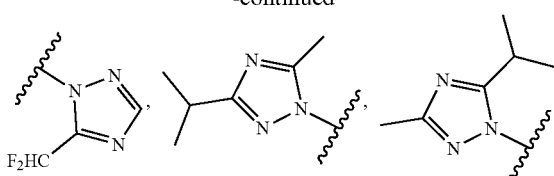

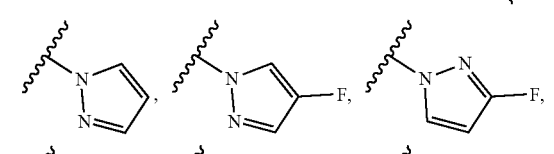

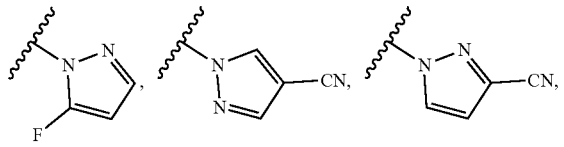

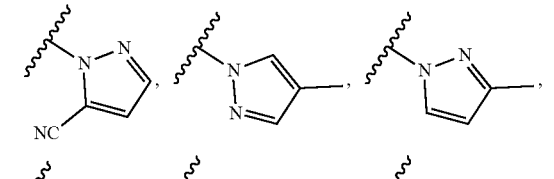

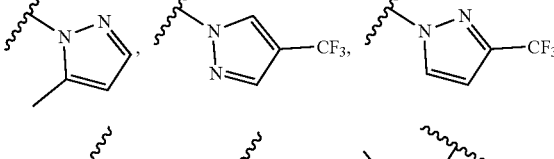

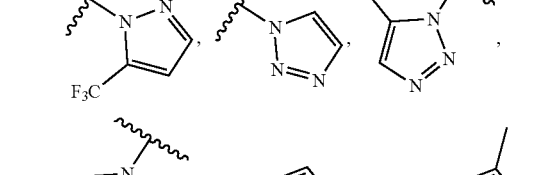

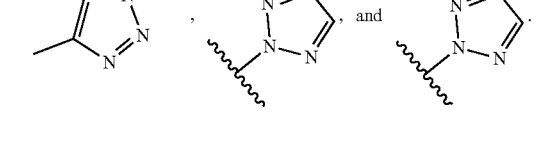

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, one $R^{z4}$, $R^{z5}$, $R^{z6}$, $R^{20z4}$, $R^{20z5}$, $R^{20z6}$, or $R^{20z}$ is independently selected from —C(O)$R^{12}$ and —N(H)C(O)$R^{12}$; and the $R^{12}$ of the —C(O)$R^{12}$ or —N(H)C(O)$R^{12}$ is selected from

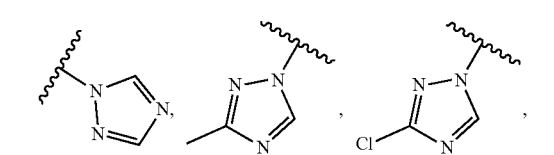

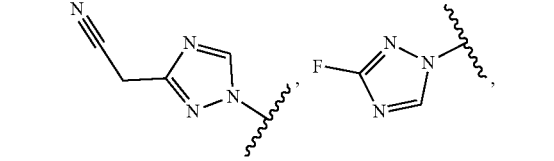

-continued

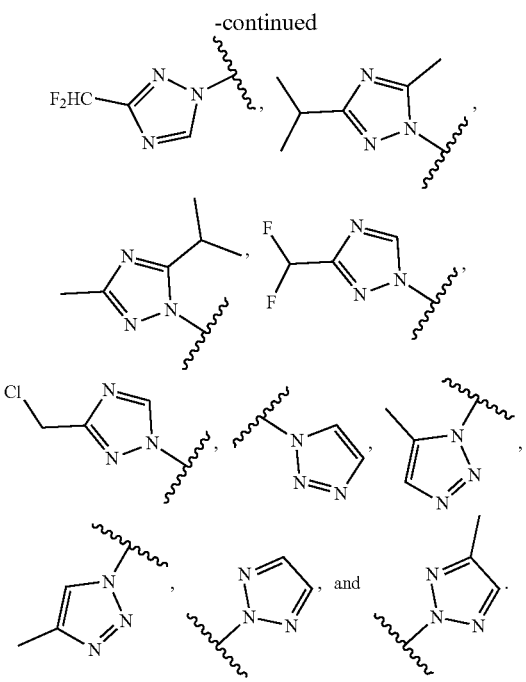

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, one $R^{z4}$, $R^{z5}$, $R^{z6}$, $R^{20z4}$, $R^{20z5}$, $R^{20z6}$, or $R^{20z}$ is independently selected from —C(O)$R^{12}$ and —N(H)C(O)$R^{12}$; and the $R^{12}$ of the —C(O)$R^{12}$ or —N(H)C(O)$R^{12}$ is selected from

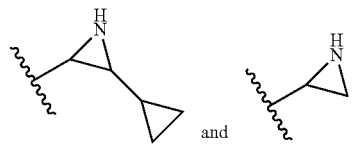

In an aspect is provided a pharmaceutical composition including a compound described herein (e.g., compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B), or a pharmaceutically acceptable salt or solvate thereof, and a pharmaceutically acceptable excipient.

In an aspect is provided a method of treating cancer in a subject in need thereof, including administering to the subject a therapeutically effective amount of a compound described herein (e.g., compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B), or a pharmaceutically acceptable salt or solvate thereof.

In an aspect is provided a method of treating cancer in a subject including a Ras mutant protein, the method including: modifying the Ras mutant protein of the subject by administering to the subject a compound, wherein the compound is characterized in that upon contacting the Ras mutant protein, the Ras mutant protein is modified covalently at a residue corresponding to residue 12 of SEQ ID No: 1, the that the modified Ras mutant protein exhibits reduced Ras signaling output.

In embodiments, the cancer is a solid tumor. In embodiments, the cancer is a hematological cancer.

In an aspect is provided a method of modulating signaling output of a Ras protein, including contacting a Ras protein with an effective amount of a compound described herein (e.g., compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B), or a pharmaceutically acceptable salt or solvate thereof, thereby modulating the signaling output of the Ras protein.

In embodiments, the method includes administering an additional agent.

In an aspect is provided a compound of Formula (A), or a pharmaceutically acceptable salt or solvate thereof:

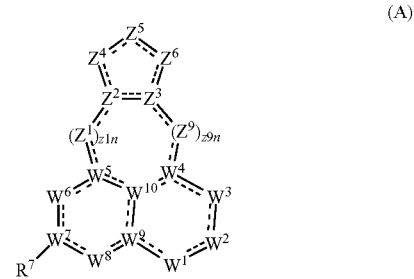

(A)

wherein:
$W^1$ is N($R^1$) or N;
$R^1$ is selected from hydrogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —O$R^{12}$, —S$R^{12}$, —C(O)O$R^{12}$, —OC(O)N($R^{12}$)($R^{13}$), —C(O)$R^{15}$, —S(O)$R^{15}$, —OC(O)$R^{15}$, —C(O)N($R^{12}$)($R^{13}$), —C(O)C(O)N($R^{12}$)($R^{13}$), —S(O)$_2$$R^{15}$, —S(O)$_2$N($R^{12}$)($R^{13}$), —S(=O)(=NH)N($R^{12}$)($R^{13}$), —CH$_2$C(O)N($R^{12}$)($R^{13}$), —CH$_2$N($R^{14}$)C(O)$R^{15}$, —CH$_2$S(O)$_2$$R^{15}$, and —CH$_2$S(O)$_2$N($R^{12}$)($R^{13}$), wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20a}$;
$W^2$ is C($R^2$), N($R^2$), C($R^2$)$_2$, C(O), S(O), S(O)$_2$, or N;
each $R^2$ is independently selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —O$R^{12a}$, —S$R^{12a}$, —N($R^{12a}$)($R^{13}$), —N=($R^{15}$), —C(O)O$R^{12}$, —OC(O)N($R^{12}$)($R^{13}$), —N($R^{14}$)C(O)N($R^{12}$)($R^{13}$), —N($R^{14}$)C(O)O$R^{15}$, —N($R^{14}$)S(O)$_2$$R^{15}$, —C(O)$R^{15}$, —S(O)$R^{15}$, —OC(O)$R^{15}$, —C(O)N($R^{12}$)($R^{13}$), —C(O)C(O)N($R^{12}$)($R^{13}$), —N($R^{14}$)C(O)$R^{15}$, —S(O)$_2$$R^{15}$, —S(O)$_2$N($R^{12}$)($R^{13}$)—, —S(=O)(=NH)N($R^{12}$)($R^{13}$), —CH$_2$C(O)N($R^{12}$)($R^{13}$), —CH$_2$N($R^{14}$)C(O)$R^{15}$, —CH$_2$S(O)$_2$$R^{15}$, and —CH$_2$S(O)$_2$N($R^{12}$)($R^{13}$), wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20b}$;
$W^3$ is C($R^3$), N($R^3$), C($R^3$)$_2$, C(O), S(O), S(O)$_2$, or N;
each $R^3$ is independently selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —O$R^{12}$, —S$R^{12}$, —N($R^{12}$)($R^{13}$), —C(O)O$R^{12}$, —OC(O)N($R^{12}$)($R^{13}$), —N($R^{14}$)C(O)N $(R^{12})(R^{13})$, $-N(R^{14})C(O)OR^{15}$, $-N(R^{14})S(O)_2R^{15}$, $-C(O)R^{15}$, $-S(O)R^{15}$, $-OC(O)R^{15}$, $-C(O)N(R^{12})(R^{13})$, $-C(O)C(O)N(R^{12})(R^{13})$, $-N(R^{14})C(O)R^{15}$, $-S(O)_2R^{15}$, $-S(O)_2N(R^{12})(R^{13})$, $-S(=O)(=NH)N(R^{12})(R^{13})$, $-CH_2C(O)N(R^{12})(R^{13})$, $-CH_2N(R^{14})C(O)R^{15}$, $-CH_2S(O)_2R^{15}$, and $-CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20c}$;

$W^4$ is $C(R^4)$, C, or N;

$R^4$ is selected from hydrogen, halogen, $-CN$, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, $-OR^{12}$, $-SR^{12}$, $-N(R^{12})(R^{13})$, $-C(O)OR^{12}$, $-OC(O)N(R^{12})(R^{13})$, $-N(R^{14})C(O)N(R^{12})(R^{13})$, $-N(R^{14})C(O)OR^{15}$, $-N(R^{14})S(O)_2R^{15}$, $-C(O)R^{15}$, $-S(O)R^{15}$, $-OC(O)R^{15}$, $-C(O)N(R^{12})(R^{13})$, $-C(O)C(O)N(R^{12})(R^{13})$, $-N(R^{14})C(O)R^{15}$, $-S(O)_2R^{15}$, $-S(O)_2N(R^{12})(R^{13})$, $-S(=O)(=NH)N(R^{12})(R^{13})$, $-CH_2C(O)N(R^{12})(R^{13})$, $-CH_2N(R^{14})C(O)R^{15}$, $-CH_2S(O)_2R^{15}$, and $-CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20d}$;

$W^5$ is $C(R^5)$, C, or N;

$R^5$ is selected from hydrogen, halogen, $-CN$, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, $-OR^{12}$, $-SR^{12}$, $-N(R^{12})(R^{13})$, $-C(O)OR^{12}$, $-OC(O)N(R^{12})(R^{13})$, $-N(R^{14})C(O)N(R^{12})(R^{13})$, $-N(R^{14})C(O)OR^{15}$, $-N(R^{14})S(O)_2R^{15}$, $-C(O)R^{15}$, $-S(O)R^{15}$, $-OC(O)R^{15}$, $-C(O)N(R^{12})(R^{13})$, $-C(O)C(O)N(R^{12})(R^{13})$, $-N(R^{14})C(O)R^{15}$, $-S(O)_2R^{15}$, $-S(O)_2N(R^{12})(R^{13})$, $-S(=O)(=NH)N(R^{12})(R^{13})$, $-CH_2C(O)N(R^{12})(R^{13})$, $-CH_2N(R^{14})C(O)R^{15}$, $-CH_2S(O)_2R^{15}$, and $-CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20e}$;

$W^6$ is $C(R^6)$, $N(R^6)$, $C(R^6)_2$, $C(O)$, $S(O)$, $S(O)_2$, or N;

each $R^6$ is independently selected from hydrogen, halogen, $-CN$, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, $-OR^{12}$, $-SR^{12}$, $-N(R^{12})(R^{13})$, $-C(O)OR^{12}$, $-OC(O)N(R^{12})(R^{13})$, $-N(R^{14})C(O)N(R^{12})(R^{13})$, $-N(R^{14})C(O)OR^{15}$, $-N(R^{14})S(O)_2R^{15}$, $-C(O)R^{15}$, $-S(O)R^{15}$, $-OC(O)R^{15}$, $-C(O)N(R^{12})(R^{13})$, $-C(O)C(O)N(R^{12})(R^{13})$, $-N(R^{14})C(O)R^{15}$, $-S(O)_2R^{15}$, $-S(O)_2N(R^{12})(R^{13})$, $-S(=O)(=NH)N(R^{12})(R^{13})$, $-CH_2C(O)N(R^{12})(R^{13})$, $-CH_2N(R^{14})C(O)R^{15}$, $-CH_2S(O)_2R^{15}$, and $-CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20f}$;

$W^7$ is $C(R^{7a})$, C, or N;

$R^{7a}$ is selected from hydrogen, halogen, $-CN$, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, $-OR^{12}$, $-SR^{12}$, $-N(R^{12})(R^{13})$, $-C(O)OR^{12}$, $-OC(O)N(R^{12})(R^{13})$, $-N(R^{14})C(O)N(R^{12})(R^{13})$, $-N(R^{14})C(O)OR^{15}$, $-N(R^{14})S(O)_2R^{15}$, $-C(O)R^{15}$, $-S(O)R^{15}$, $-OC(O)R^{15}$, $-C(O)N(R^{12})(R^{13})$, $-C(O)C(O)N(R^{12})(R^{13})$, $-N(R^{14})C(O)R^{15}$, $-S(O)_2R^{15}$, $-S(O)_2N(R^{12})(R^{13})$, $-S(=O)(=NH)N(R^{12})(R^{13})$, $-CH_2C(O)N(R^{12})(R^{13})$, $-CH_2N(R^{14})C(O)R^{15}$, $-CH_2S(O)_2R^{15}$, and $-CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20g}$;

$R^7$ is $-L^7-R^{17}$;

$L^7$ is a bond, $C_1$-$C_4$alkyl, $C_2$-$C_4$alkenyl, $C_2$-$C_4$alkynyl, 2-4 membered heteroalkylene linker, $-O-$, $-N(R^{7d})-$, $-C(O)-$, $-S-$, $-S(O)_2-$, $-S(O)-$, $-P(O)R^{7d}-$, $CR^{7c}R^{7c}$, $-OCR^{7c}R^{7c}-$, $-N(R^{7d})CR^{7c}R^{7c}-$, $-C(O)CR^{7c}R^{7c}-$, $-SCR^{7c}R^{7c}-$, $-S(O)_2CR^{7c}R^{7c}-$, $-S(O)CR^{7c}R^{7c}-$, $-P(O)R^{7d}CR^{7c}R^{7c}-$, $-CR^{7c}R^{7c}CR^{7c}R^{7c}-$, $-CR^{7c}R^{7c}O-$, $-CR^{7c}R^{7c}N(R^{7d})-$, $-CR^{7c}R^{7c}C(O)-$, $-CR^{7c}R^{7c}S-$, $-CR^{7c}R^{7c}S(O)_2-$, $-CR^{7c}R^{7c}S(O)-$, $-CR^{7c}R^{7c}P(O)R^{7d}-$, $-N(R^{7d})C(O)-$, $-N(R^{7d})S(O)_2-$, $-N(R^{7d})S(O)-$, $-N(R^{7d})P(O)R^{7d}-$, $-C(O)N(R^{7d})-$, $-S(O)_2N(R^{7d})-$, $-S(O)N(R^{7d})-$, $-P(O)R^{7d}N(R^{7d})-$, $-OC(O)-$, $-OS(O)_2-$, $-OS(O)-$, $-OP(O)R^{7d}-$, $-C(O)O-$, $-S(O)_2O-$, $-S(O)O-$, or $-P(O)R^{7d}O-$; wherein the $C_1$-$C_4$alkyl, $C_2$-$C_4$alkenyl, $C_2$-$C_4$alkynyl, 2-4 membered heteroalkylene linker are optionally substituted with one, two, or three $R^{20g}$;

each $R^{7c}$ is independently selected from hydrogen, halogen, $-CN$, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, $-OR^{12}$, $-SR^{12}$, $-N(R^{12})(R^{13})$, $-C(O)OR^{12}$, $-OC(O)N(R^{12})(R^{13})$, $-N(R^{14})C(O)N(R^{12})(R^{13})$, $-N(R^{14})C(O)OR^{15}$, $-N(R^{14})S(O)_2R^{15}$, $-C(O)R^{15}$, $-S(O)R^{15}$, $-OC(O)R^{15}$, $-C(O)N(R^{12})(R^{13})$, $-C(O)C(O)N(R^{12})(R^{13})$, $-N(R^{14})C(O)R^{15}$, $-S(O)_2R^{15}$, $-S(O)_2N(R^{12})(R^{13})$, $S(=O)(=NH)N(R^{12})(R^{13})$, $-CH_2C(O)N(R^{12})(R^{13})$, $-CH_2N(R^{14})C(O)R^{15}$, $-CH_2S(O)_2R^{15}$, and $-CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20g}$;

each $R^{7d}$ is independently selected from hydrogen, $-CN$, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, $-OR^{12}$, $-SR^{12}$, $-C(O)OR^{12}$, $-OC(O)N(R^{12})(R^{13})$, $-C(O)R^{15}$, $-S(O)R^{15}$, $-OC(O)R^{15}$, $-C(O)N(R^{12})(R^{13})$, $-C(O)C(O)N(R^{12})(R^{13})$, $-S(O)_2R^{15}$, $-S(O)_2N(R^{12})(R^{13})$, $-S(=O)(=NH)N(R^{12})(R^{13})$, $-CH_2C(O)N(R^{12})(R^{13})$, $-CH_2N(R^{14})C(O)R^{15}$, $-CH_2S(O)_2R^{15}$, and $-CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20g}$;

$R^{17}$ is selected from $C_{3-10}$cycloalkyl, 3-10 membered heterocycloalkyl, $C_{6-10}$aryl, and 5-10 membered heteroaryl, wherein $C_{3-10}$cycloalkyl, 3-10 membered heterocycloalkyl, $C_{6-10}$aryl, and 5-10 membered heteroaryl are optionally substituted with one or more $R^{20q}$;

$W^8$ is $C(R^8)$, $N(R^8)$, $C(R^8)_2$, $C(O)$, $S(O)$, $S(O)_2$, or N;

each $R^8$ is independently selected from hydrogen, halogen, $-CN$, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, $-OR^{12}$, $-SR^{12}$, $-N(R^{12})(R^{13})$, $-C(O)OR^{12}$, $-OC(O)N(R^{12})(R^{13})$, $-N(R^{14})C(O)N(R^{12})(R^{13})$, $-N(R^{14})C(O)OR^{15}$, $-N(R^{14})S(O)_2R^{15}$, $-C(O)R^{15}$, $-S(O)R^{15}$, $-OC(O)R^{15}$, $-C(O)N(R^{12})(R^{13})$, $-C(O)C(O)N(R^{12})(R^{13})$, $-N(R^{14})C(O)R^{15}$, $-S(O)_2R^{15}$, $-S(O)_2N(R^{12})(R^{13})$, $-S(=O)(=NH)N(R^{12})(R^{13})$, $-CH_2C(O)N(R^{12})(R^{13})$, $-CH_2N(R^{14})C$ (O)R$^{15}$, —CH$_2$S(O)$_2$R$^{15}$, and —CH$_2$S(O)$_2$N(R$^{12}$)(R$^{13}$), wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl are optionally substituted with one, two, or three R$^{20h}$;

W$^9$ is C(R$^9$), C, or N;

R$^9$ is selected from hydrogen, halogen, —CN, C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, C$_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$), —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl are optionally substituted with one, two, or three R$^{20i}$;

W$^{10}$ C(R$^{10}$), C, or N;

R$^{10}$ is selected from hydrogen, halogen, —CN, C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, C$_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$), —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl are optionally substituted with one, two, or three R$^{20j}$;

each Z$^1$ is independently C(R$^{z1}$), N(R$^{z1}$), C(R$^{z1}$)$_2$, C(O), S(O), S(O)$_2$, O, S, or N;

z1n is 0, 1, 2, 3, or 4; wherein if z1n is 0 then Z$^2$ is directly bonded to W$^5$;

each R$^{z1}$ is independently selected from hydrogen, halogen, —CN, C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, C$_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$), —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl are optionally substituted with one, two, or three R$^{20z1}$;

each Z$^9$ is independently C(R$^{z9}$), N(R$^{z9}$), C(R$^{z9}$)$_2$, C(O), S(O), S(O)$_2$, O, S, or N;

Z$^2$ is C(R$^{z2}$), C, or N;

R$^{z2}$ is selected from hydrogen, halogen, —CN, C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, C$_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$), —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein C$_{1-6}$alkyl, C$_{2-6}$alkynyl, C$_{3-10}$cycloalkyl, C$_{2-9}$heterocycloalkyl, C$_{6-10}$aryl, and C$_{1-9}$heteroaryl are optionally substituted with one, two, or three R$^{20z2}$;

Z$^3$ is C(R$^{z3}$), C, or N;

R$^{z3}$ is selected from hydrogen, halogen, —CN, C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, C$_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$), —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl are optionally substituted with one, two, or three R$^{20z3}$;

Z$^4$ is a bond, Z$^{4a}$, Z$^{4a}$Z$^{4b}$, Z$^{4a}$Z$^{4b}$Z$^{4c}$, Z$^{4a}$Z$^{4b}$Z$^{4c}$Z$^{4d}$, or Z$^{4a}$Z$^{4b}$Z$^{4c}$Z$^{4d}$Z$^{4e}$; wherein Z$^{4a}$ is directly bonded to Z$^2$; and wherein if Z$^4$ is a bond then Z$^2$ is directly bonded to Z$^5$;

Z$^{4a}$, Z$^{4b}$, Z$^{4c}$, Z$^{4d}$, and Z$^{4e}$ are independently C(R$^{z4}$), N(R$^{z4}$), C(R$^{z4}$)$_2$, C(O), S(O), S(O)$_2$, S(O)(NR$^{z4}$), O, S, or N;

provided that if z9n is 0 and Z$^4$ is Z$^{4a}$Z$^{4b}$; then (1) Z$^{4b}$ is C(R$^{z4}$), C(R$^{z4}$)$_2$, C(O), S(O), S(O)$_2$, S(O)(NR$^{z4}$), O, S, or N, (2) Z$^{4b}$ is N(R$^{z4}$) and Z$^{4a}$ is C(O), S(O), or S(O)$_2$; (3) Z$^{4b}$ is N(R$^{z4}$) and Z$^5$ is C(O), S(O), or S(O)$_2$; or (4) Z$^{4b}$ is N(R$^{z4}$) and Z$^3$ is C(R$^{z3}$) or C;

each R$^{z4}$ is independently selected from hydrogen, halogen, —CN, C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, C$_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{12}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{12}$, —S(O)$_2$R$^{15}$, —S(O)$_2$N(R$^{12}$)(R$^{13}$), —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl are optionally substituted with one, two, or three R$^{20z4}$; or two R$^{z4}$ bonded to the same carbon are joined to form C$_{2-6}$alkenyl optionally substituted with one, two, or three R$^{20z4}$;

Z$^5$ is C(R$^{z5}$), N(R$^{z5}$), C(R$^{z5}$)$_2$, C(O), S(O), S(O)$_2$, S(O)(NR$^{z5}$), O, S, or N;

each R$^{z5}$ is independently selected from hydrogen, halogen, —CN, C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, C$_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{12}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{12}$, —S(O)$_2$R$^{15}$, —S(O)$_2$N(R$^{12}$)(R$^{13}$), —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl are optionally substituted with one, two, or three R$^{20z5}$; or two R$^{z5}$ bonded to the same carbon are joined to form C$_{2-6}$alkenyl optionally substituted with one, two, or three R$^{20z5}$;

$Z^6$ is $C(R^{z6})$, $N(R^{z6})$, $C(R^{z6})_2$, $C(O)$, $S(O)$, $S(O)_2$, $S(O)(NR^{z6})$, O, S, or N;

each $R^{z6}$ is independently selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{12}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{12}$, —S(O)$_2$R$^{15}$, —S(O)$_2$N(R$^{12}$)(R$^{13}$), —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20z6}$; or two $R^{z6}$ bonded to the same carbon are joined to form $C_{2-6}$alkenyl optionally substituted with one, two, or three $R^{20z6}$;

and further wherein the compound optionally includes one of the following:

(1) two $R^{z4}$ bonded to the same carbon atom are joined to form monocyclic $C_{3-7}$cycloalkyl or monocyclic 3-7 membered heterocycloalkyl, wherein the monocyclic $C_{3-7}$cycloalkyl and monocyclic 3-7 membered heterocycloalkyl are optionally substituted with one, two, or three $R^{20z}$;

(2) two or more $R^{z4}$ bonded to adjacent atoms are joined to form monocyclic $C_{3-7}$cycloalkyl, monocyclic 3-7 membered heterocycloalkyl, phenyl, or monocyclic 5-6 membered heteroaryl, wherein the monocyclic $C_{3-7}$cycloalkyl, monocyclic 3-7 membered heterocycloalkyl, phenyl, and monocyclic 5-6 membered heteroaryl are optionally substituted with one, two, or three $R^{20z}$;

(3) two $R^{z5}$ bonded to the same carbon atom are joined to form monocyclic $C_{3-7}$cycloalkyl or monocyclic 3-7 membered heterocycloalkyl, wherein the monocyclic $C_{3-7}$cycloalkyl and monocyclic 3-7 membered heterocycloalkyl are optionally substituted with one, two, or three $R^{20z}$;

(4) one or two $R^{z4}$ bonded to one atom and one or two $R^{z5}$ bonded to an adjacent atom are joined to form monocyclic $C_{3-7}$cycloalkyl, monocyclic 3-7 membered heterocycloalkyl, phenyl, or monocyclic 5-6 membered heteroaryl, wherein the monocyclic $C_{3-7}$cycloalkyl, monocyclic 3-7 membered heterocycloalkyl, phenyl, and monocyclic 5-6 membered heteroaryl are optionally substituted with one, two, or three $R^{20z}$;

(5) one or two $R^{z4}$ bonded to one atom and one or two $R^{z5}$ bonded to a second atom are joined to form monocyclic $C_{3-7}$cycloalkyl or monocyclic 3-7 membered heterocycloalkyl, wherein the monocyclic $C_{3-7}$cycloalkyl and monocyclic 3-7 membered heterocycloalkyl are optionally substituted with one, two, or three $R^{20z}$;

(6) two $R^{z6}$ bonded to the same carbon atom are joined to form monocyclic $C_{3-7}$cycloalkyl or monocyclic 3-7 membered heterocycloalkyl, wherein the monocyclic $C_{3-7}$cycloalkyl and monocyclic 3-7 membered heterocycloalkyl are optionally substituted with one, two, or three $R^{20z}$;

(7) one or two $R^{z5}$ bonded to one atom and one or two $R^{z6}$ bonded to an adjacent atom are joined to form monocyclic $C_{3-7}$cycloalkyl, monocyclic 3-7 membered heterocycloalkyl, phenyl, or monocyclic 5-6 membered heteroaryl, wherein the monocyclic $C_{3-7}$cycloalkyl, monocyclic 3-7 membered heterocycloalkyl, phenyl, and monocyclic 5-6 membered heteroaryl are optionally substituted with one, two, or three $R^{20z}$; or (8) one or two $R^{z4}$ bonded to one atom and one or two $R^{z6}$ bonded to a second atom are joined to form monocyclic $C_{3-7}$cycloalkyl or monocyclic 3-7 membered heterocycloalkyl, wherein the monocyclic $C_{3-7}$cycloalkyl and monocyclic 3-7 membered heterocycloalkyl are optionally substituted with one, two, or three $R^{20z}$;

two $R^{20z}$ bonded to the same carbon atom are optionally joined to form monocyclic $C_{3-7}$cycloalkyl or monocyclic 3-7 membered heterocycloalkyl, wherein the monocyclic $C_{3-7}$cycloalkyl and monocyclic 3-7 membered heterocycloalkyl are optionally substituted with one, two, or three $R^{20zz}$; or two or more $R^{20z}$ bonded to two adjacent atoms are optionally joined to form monocyclic $C_{3-7}$cycloalkyl, monocyclic 3-7 membered heterocycloalkyl, phenyl, or monocyclic 5-6 membered heteroaryl, wherein the $C_{3-7}$cycloalkyl, monocyclic 3-7 membered heterocycloalkyl, phenyl, and monocyclic 5-6 membered heteroaryl are optionally substituted with one, two, or three $R^{20zz}$;

each $Z^9$ is independently $C(R^{z9})$, $N(R^{z9})$, $C(R^{z9})_2$, $C(O)$, $S(O)$, $S(O)_2$, O, S, or N;

z9n is 0, 1, 2, 3, or 4; wherein if z9n is 0 then $Z^3$ is directly bonded to $W^4$;

each $R^{z9}$ is independently selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$), —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20z9}$;

wherein the sum of z1n and z9n is 2, 3, or 4;

each $R^{12}$ is independently selected from hydrogen, $C_{1-6}$alkyl, $C_{2-6}$alkenyl, $C_{2-6}$alkynyl, $C_{3-10}$cycloalkyl, —CH$_2$-$C_{3-10}$cycloalkyl, $C_{2-9}$heterocycloalkyl, —CH$_2$-$C_{2-9}$heterocycloalkyl, $C_{6-10}$aryl, —CH$_2$-$C_{6-10}$aryl, —CH$_2$-$C_{1-9}$heteroaryl, and $C_{1-9}$heteroaryl, wherein $C_{1-6}$alkyl, $C_{2-6}$alkenyl, $C_{2-6}$alkynyl, $C_{3-10}$cycloalkyl, —CH$_2$-$C_{3-10}$cycloalkyl, $C_{2-9}$heterocycloalkyl, —CH$_2$-$C_{2-9}$heterocycloalkyl, $C_{6-10}$aryl, —CH$_2$-$C_{6-10}$aryl, —CH$_2$-$C_{1-9}$heteroaryl, and $C_{1-9}$heteroaryl are optionally substituted with one, two, or three $R^{20l}$;

$R^{12a}$ is independently selected from hydrogen, $C_{1-6}$alkyl, $C_{2-6}$alkenyl, $C_{2-6}$alkynyl, $C_{3-10}$cycloalkyl, —C(R$^{12c}$)$_2$-$C_{3-10}$cycloalkyl, $C_{2-9}$heterocycloalkyl, —C(R$^{12c}$)$_2$-$C_{2-9}$heterocycloalkyl, $C_{6-10}$aryl, —C(R$^{12c}$)$_2$-$C_{6-10}$aryl, —C(R$^{12c}$)$_2$-$C_{1-9}$heteroaryl, and $C_{1-9}$heteroaryl, wherein $C_{1-6}$alkyl, $C_{2-6}$alkenyl, $C_{2-6}$alkynyl, $C_{3-10}$cycloalkyl, —C(R$^{12c}$)$_2$-$C_{3-10}$cycloalkyl, $C_{2-9}$heterocycloalkyl, —C(R$^{12c}$)$_2$-$C_{2-9}$heterocycloalkyl, $C_{6-10}$aryl, —C(R$^{12c}$)$_2$-$C_{6-10}$aryl, —C(R$^{12c}$)$_2$-$C_{1-9}$heteroaryl, and $C_{1-9}$heteroaryl are optionally substituted with one, two, or three $R^{20l}$;

each $R^{12c}$ is independently selected from hydrogen and $R^{20lc}$;

each $R^{13}$ is independently selected from hydrogen, $C_{1-6}$alkyl, and $C_{1-6}$haloalkyl; or $R^{12}$ and $R^{13}$, together with the nitrogen to which they are attached, form a $C_{2-9}$heterocycloalkyl ring optionally substituted with one, two, or three $R^{20m}$;

each $R^{14}$ is independently selected from hydrogen, $C_{1-6}$alkyl, and $C_{1-6}$haloalkyl;

each $R^{15}$ is independently selected from $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20o}$;

each $R^{20z1}$, $R^{20z2}$, $R^{20z3}$, $R^{20z4}$, $R^{20z5}$, $R^{20z6}$, and $R^{20z9}$ is independently selected from halogen, oxo, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{12}$, —$S(O)R^{15}$, —$C(O)N(R^{12})(R^{13})$, —$C(O)C(O)N(R^{12})(R^{13})$, —$N(R^{14})C(O)R^{12}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20z}$;

each $R^{20z}$ is independently selected from halogen, oxo, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{12}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{12}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20zz}$;

each $R^{20a}$, $R^{20b}$, $R^{20c}$, $R^{20d}$, $R^{20e}$, $R^{20f}$, $R^{20g}$, $R^{20h}$, $R^{20i}$, $R^{20j}$, $R^{20l}$, $R^{20lc}$, $R^{20m}$, $R^{20o}$, $R^{20q}$, and $R^{20zz}$ is independently selected from halogen, oxo, —CN, $C_{1-6}$alkyl, $C_{2-6}$alkenyl, $C_{2-6}$alkynyl, $C_{3-10}$cycloalkyl, —$CH_2$-$C_{3-10}$cycloalkyl, $C_{2-9}$heterocycloalkyl, —$CH_2$-$C_{2-9}$heterocycloalkyl, $C_{6-10}$aryl, —$CH_2$-$C_{6-10}$aryl, —$CH_2$-$C_{1-9}$heteroaryl, $C_{1-9}$heteroaryl, —$OR^{21}$, —$SR^{21}$, —$N(R^{22})(R^{23})$, —$C(O)OR^{22}$, —$C(O)N(R^{22})(R^{23})$, —$C(O)C(O)N(R^{22})(R^{23})$, —$OC(O)N(R^{22})(R^{23})$, —$N(R^{24})C(O)N(R^{22})(R^{23})$, —$N(R^{24})C(O)OR^{25}$, —$N(R^{24})C(O)R^{21}$, —$N(R^{24})S(O)_2R^{25}$, —$C(O)R^{21}$, —$S(O)_2R^{25}$, —$S(O)_2N(R^{22})(R^{23})$, —$OCH_2C(O)OR^{22}$, =$NR^{21}$, and —$OC(O)R^{25}$; two $R^{20q}$ bonded to adjacent atoms are optionally joined to form a $C_{3-10}$cycloalkyl, $C_{2-9}$heterocycloalkyl, $C_{6-10}$aryl, or $C_{1-9}$heteroaryl; wherein $C_{1-6}$alkyl, $C_{2-6}$alkenyl, $C_{2-6}$alkynyl, $C_{3-10}$cycloalkyl, —$CH_2$-$C_{3-10}$cycloalkyl, $C_{2-9}$heterocycloalkyl, —$CH_2$-$C_{2-9}$heterocycloalkyl, $C_{6-10}$aryl, —$CH_2$-$C_{6-10}$aryl, —$CH_2$-$C_{1-9}$heteroaryl, and $C_{1-9}$heteroaryl are optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —$OR^{21}$, —$SR^{21}$, —$N(R^{22})(R^{23})$, —$C(O)OR^{22}$, —$C(O)N(R^{22})(R^{23})$, —$C(O)C(O)N(R^{22})(R^{23})$, —$OC(O)N(R^{22})(R^{23})$, —$N(R^{24})C(O)N(R^{22})(R^{23})$, —$N(R^{24})C(O)OR^{25}$, —$N(R^{24})C(O)R^{25}$, —$N(R^{24})S(O)_2R^{25}$, —$C(O)R^{25}$, —$S(O)_2R^{25}$, —$S(O)_2N(R^{22})(R^{23})$, and —$OC(O)R^{25}$;

each $R^{21}$ is independently selected from hydrogen, $C_{1-6}$alkyl, $C_{1-6}$haloalkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl;

each $R^{22}$ is independently selected from hydrogen, $C_{1-6}$alkyl, $C_{1-6}$haloalkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl;

each $R^{23}$ is independently selected from hydrogen and $C_{1-6}$alkyl;

each $R^{24}$ is independently selected from hydrogen and $C_{1-6}$alkyl;

each $R^{25}$ is independently selected from $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; and ===== indicates a single or double bond such that all valences are satisfied.

In embodiments, the compound has the formula:

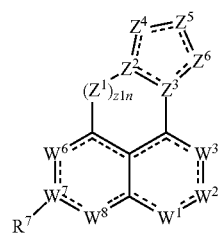

(A-1)

In embodiments, the compound has the formula:

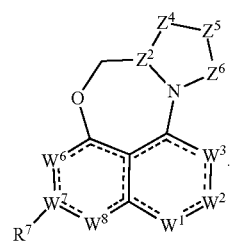

(A-2)

In embodiments, the compound has the formula:

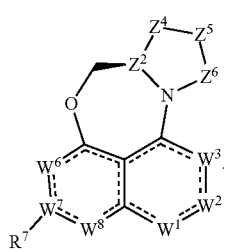

(A-2a)

In embodiments, the compound has the formula:
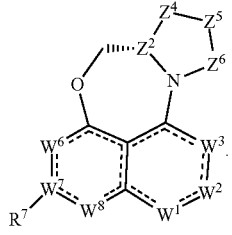
(A-2b)
In embodiments, the compound has the formula:
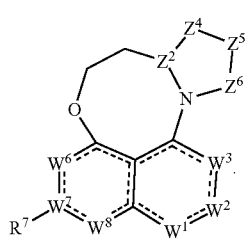
(A-3)
In embodiments, the compound has the formula:
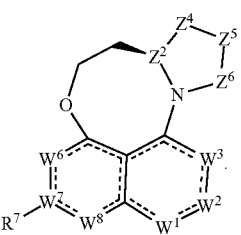
(A-3a)
In embodiments, the compound has the formula:
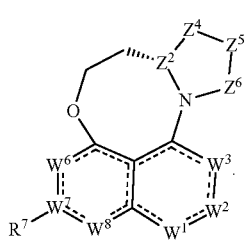
(A-3b)
In embodiments, the compound has the formula:
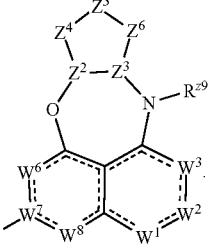
(A-6f)
In embodiments,
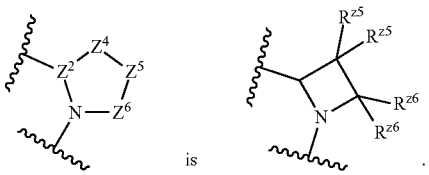
is
In embodiments,
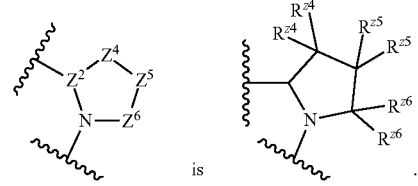
is
In embodiments,
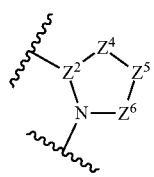
is selected from
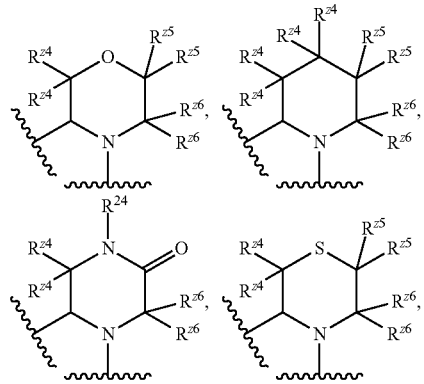

-continued
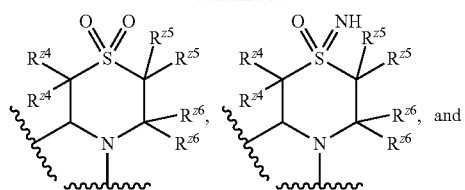
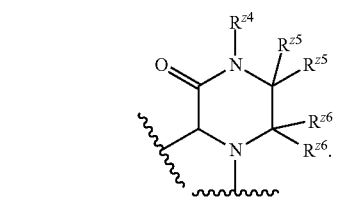
In embodiments,
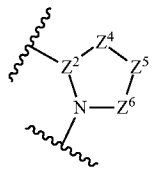
is selected from
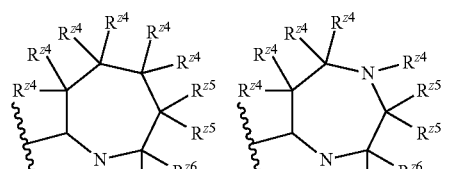
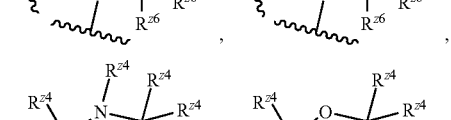
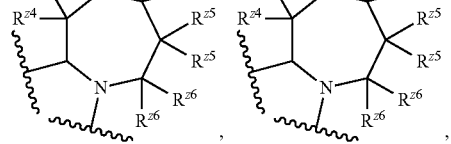
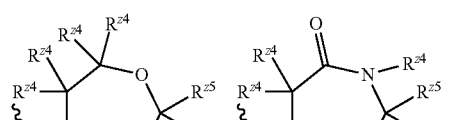
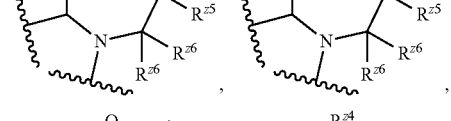
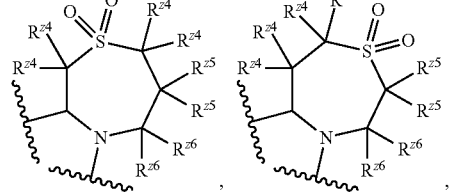
-continued
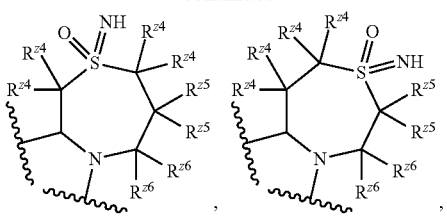
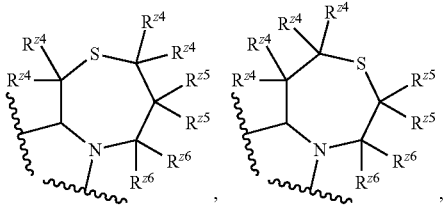
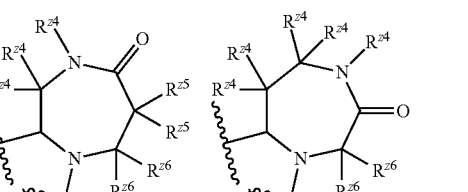
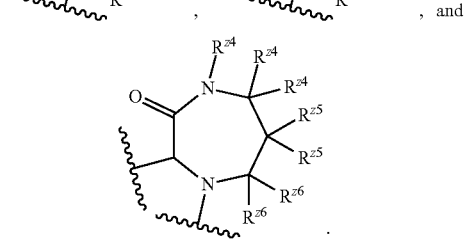
In embodiments,
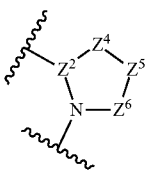
is selected from
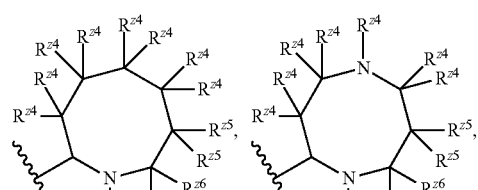
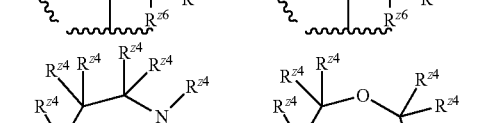
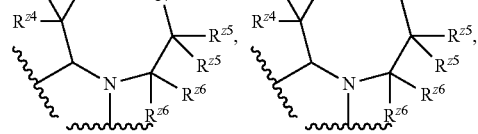

-continued

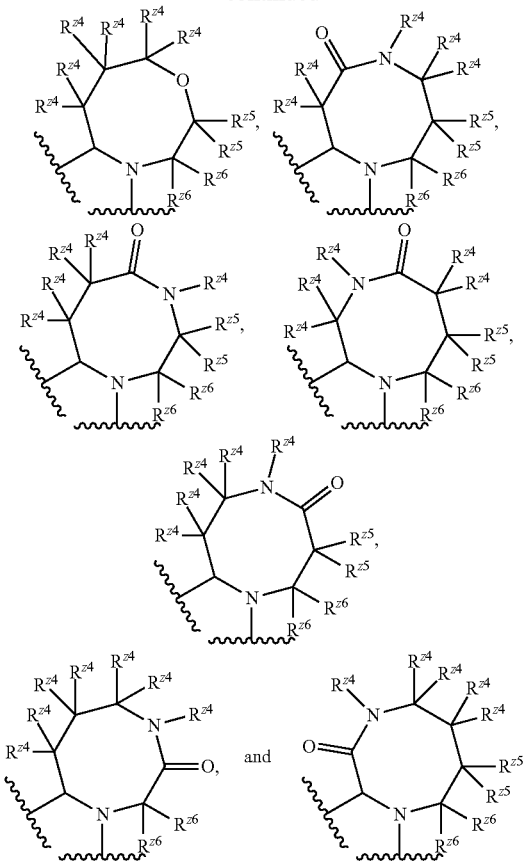

In embodiments, two $R^{z5}$ bonded to the same carbon atom are joined to form monocyclic $C_{3-7}$cycloalkyl or monocyclic 3-7 membered heterocycloalkyl, wherein the monocyclic $C_{3-7}$cycloalkyl and monocyclic 3-7 membered heterocycloalkyl are optionally substituted with one, two, or three $R^{20z}$. In embodiments, two $R^{z5}$ bonded to the same carbon atom are joined to form monocyclic 4-membered heterocycloalkyl, wherein the 4 membered heterocycloalkyl is substituted with one, two, or three $R^{20z}$.

In embodiments,

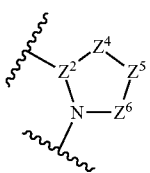

is selected from

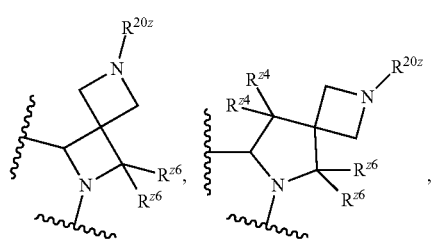

-continued

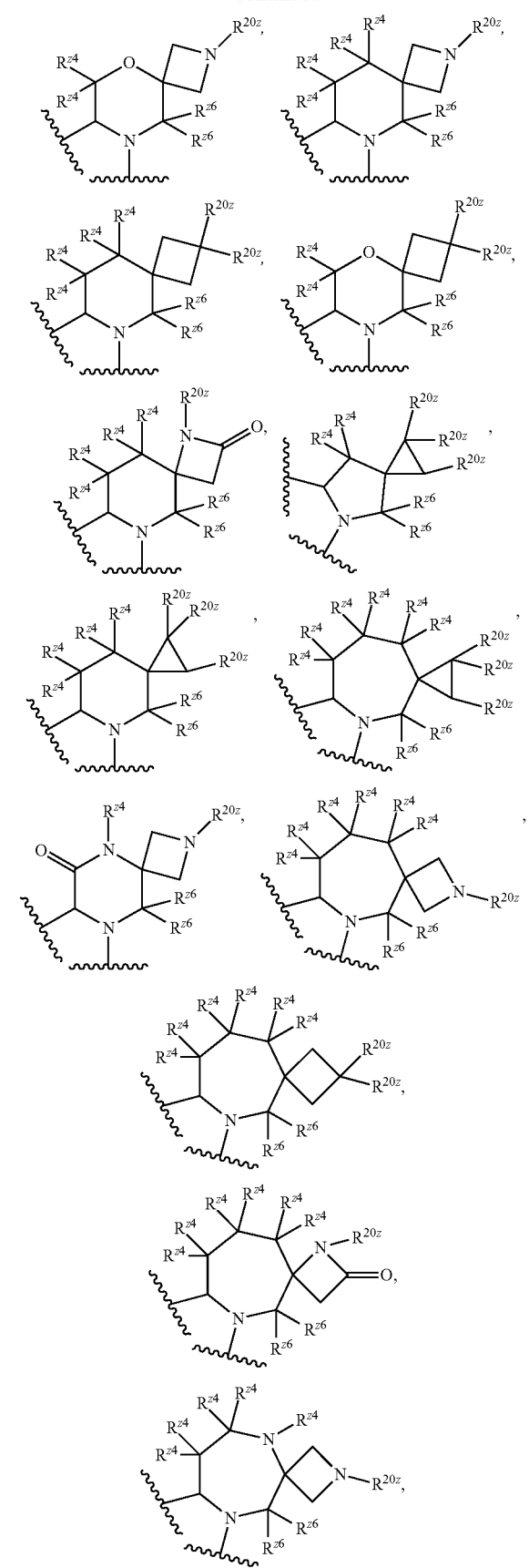

-continued
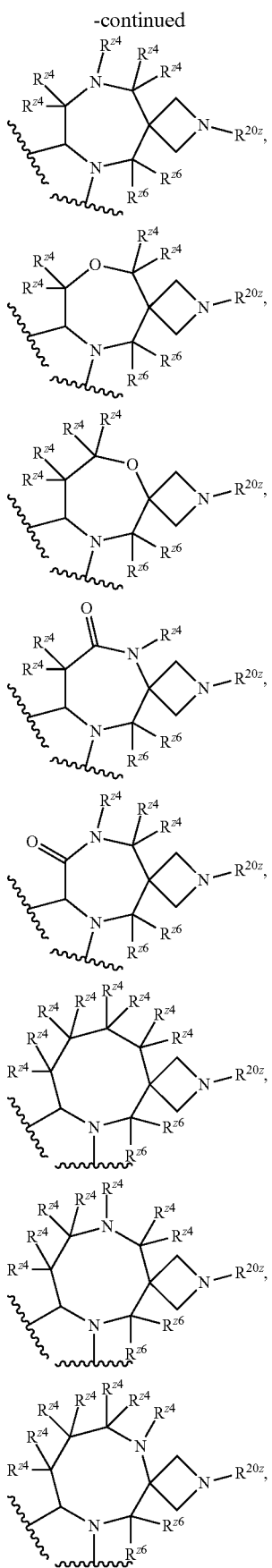
-continued
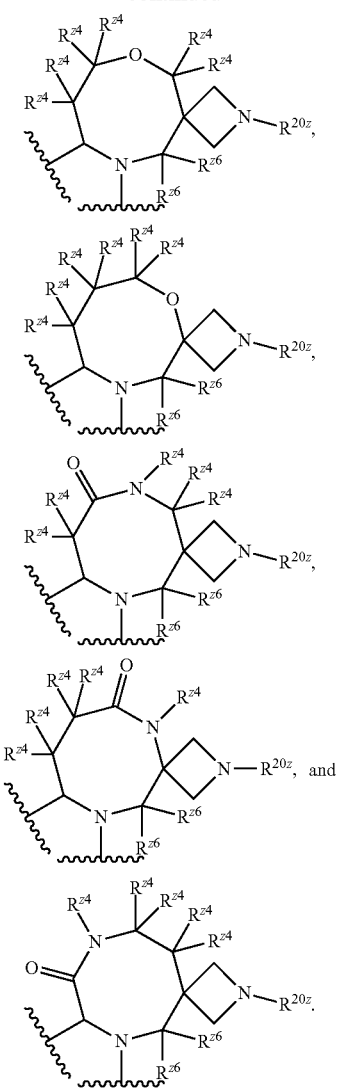
In embodiments,
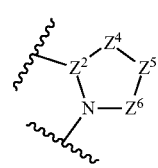
is selected from
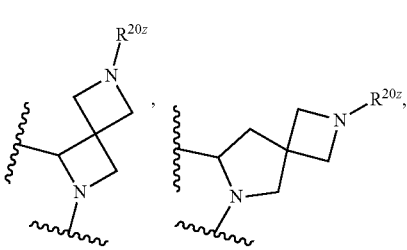

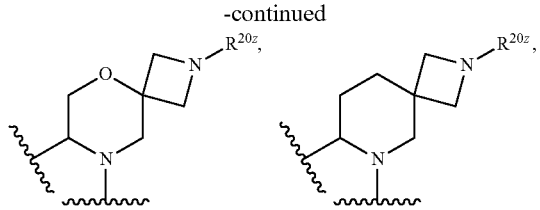
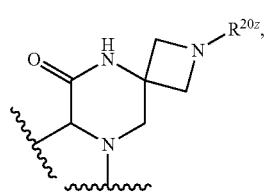
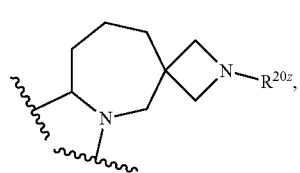
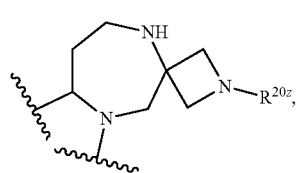
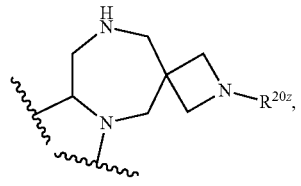
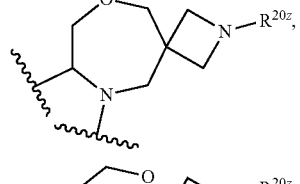
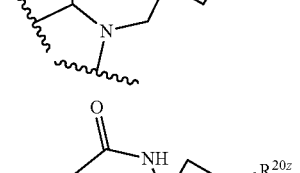
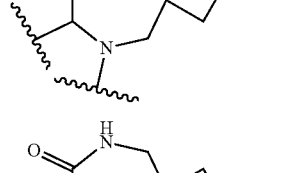
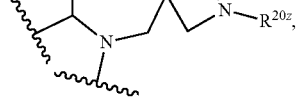
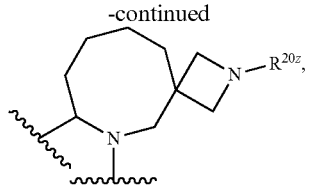
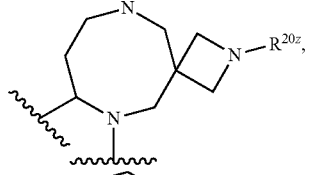
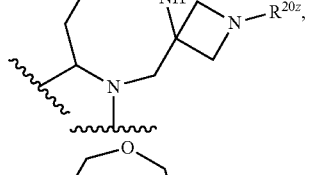
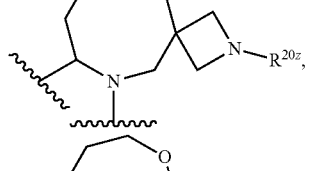
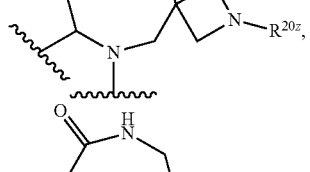
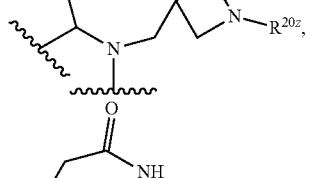
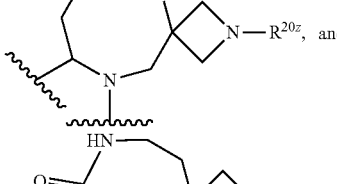

In embodiments, one or two $R^{z4}$ bonded to one atom and one or two $R^{z5}$ bonded to an adjacent atom are joined to form monocyclic $C_{3-7}$cycloalkyl, monocyclic 3-7 membered heterocycloalkyl, phenyl, or monocyclic 5-6 membered heteroaryl, wherein the monocyclic $C_{3-7}$cycloalkyl, monocyclic 3-7 membered heterocycloalkyl, phenyl, and monocyclic 5-6 membered heteroaryl are optionally substituted with one, two, or three $R^{20z}$. In embodiments, one or two $R^{z4}$ bonded to one atom and one or two $R^{z5}$ bonded to an adjacent atom are joined to form monocyclic 5-6 membered heteroaryl, wherein the monocyclic 5-6 membered heteroaryl is optionally substituted with one, two, or three $R^{20z}$. In embodiments, the monocyclic 5-6 membered heteroaryl formed by the joining of one or two $R^{z4}$ bonded to one atom and one or two $R^{z5}$ bonded to an adjacent atom, is a triazolyl, pyrazolyl, imidazolyl, pyrrolyl, furanyl, thienyl, oxazolyl, isooxazolyl, pyridyl, pyridazinyl, pyrimidinyl, or pyrazinyl; each optionally substituted with one, two, or three $R^{20z}$. In embodiments, the monocyclic 5-6 membered heteroaryl formed by the joining of one or two $R^{z4}$ bonded to one atom and one or two $R^{z5}$ bonded to an adjacent atom, is a pyrazolyl optionally substituted with one, two, or three $R^{20z}$.

In embodiments,

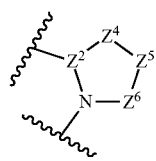

is selected from

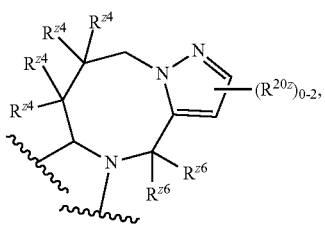

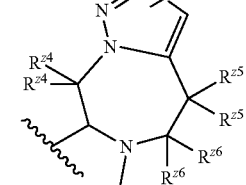

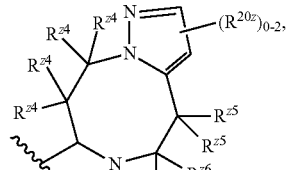

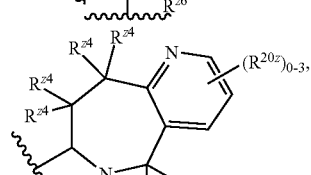

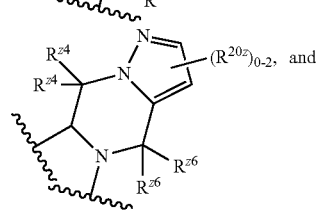

-continued

In embodiments,

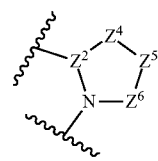

is selected from

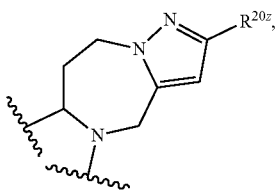

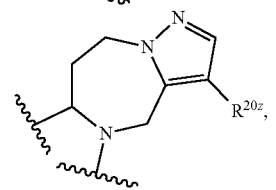

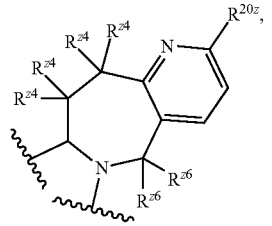

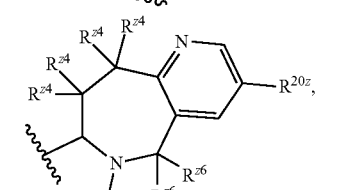

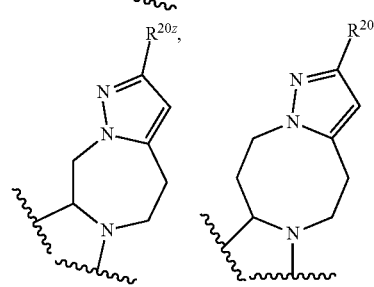

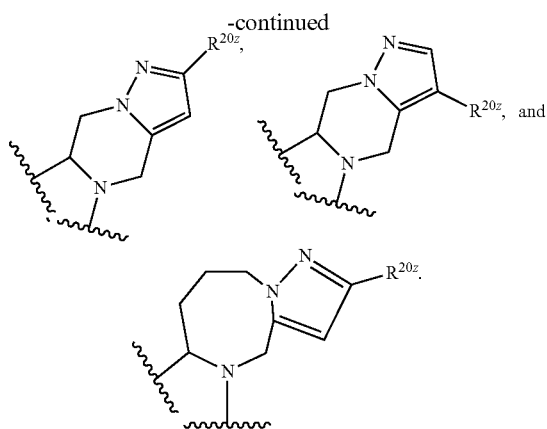

In embodiments, z1n is 1, 2 or 3, and z9n is 1, 2, or 3. In embodiments, z1n is 0. In embodiments, z9n is 0.

In embodiments, $W^1$ is N. In embodiments, $W^1$ is $N(R^1)$.

In embodiments, $W^2$ is $C(R^2)$. In embodiments, $W^2$ is $N(R^2)$. In embodiments, $W^2$ is $C(O)$.

In embodiments, $W^3$ is N. In embodiments, $W^3$ is $C(R^3)$.

In embodiments, $W^4$ is C.

In embodiments, $W^5$ is C. In embodiments, $W^5$ is $C(R^5)$.

In embodiments, $W^6$ is $C(R^6)$. In embodiments, $W^6$ is $N(R^6)$. In embodiments, $R^6$ is selected from hydrogen, halogen, —CN, $C_{1-6}$alkyl, $C_{3-6}$cycloalkyl, —$OR^{12}$, —$SR^{12}$, —$N(R^{12})(R^{13})$, —$C(O)OR^{12}$, —$C(O)R^{15}$, —$C(O)N(R^{12})(R^{13})$, —$S(O)_2R^{15}$, and —$S(O)_2N(R^{12})(R^{13})$, wherein $C_{1-6}$alkyl and $C_{3-6}$cycloalkyl are optionally substituted with one, two, or three $R^{20f}$. In embodiments, $R^6$ is selected from hydrogen, halogen, —CN, $C_{1-6}$alkyl, and —$OR^{12}$, wherein $C_{1-6}$alkyl is optionally substituted with one, two, or three $R^{20f}$. In embodiments, $R^6$ is halogen. In embodiments, $W^6$ is N.

In embodiments, $W^7$ is C. In embodiments, $W^7$ is $C(R^{7a})$. In embodiments, $W^7$ is N.

In embodiments, $W^8$ is $C(R^8)$. In embodiments, $R^8$ is selected from hydrogen, halogen, —CN, $C_{1-6}$alkyl, —$OR^{12}$, —$SR^{12}$, —$N(R^{12})(R^{13})$, —$C(O)OR^{12}$, —$C(O)R^{15}$, —$C(O)N(R^{12})(R^{13})$, —$S(O)_2R^{15}$, and —$S(O)_2N(R^{12})(R^{13})$, wherein $C_{1-6}$alkyl is optionally substituted with one, two, or three $R^{20h}$. In embodiments, $R^8$ is selected from hydrogen, halogen, —CN, $C_{1-6}$alkyl, and —$OR^{12}$, wherein $C_{1-6}$alkyl is optionally substituted with one, two, or three $R^{20h}$. In embodiments, $R^8$ is halogen. In embodiments, $W^8$ is N.

In embodiments, $W^9$ is C.

In embodiments, $W^{10}$ is C.

In embodiments,

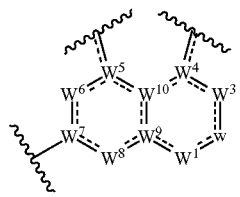

is selected from

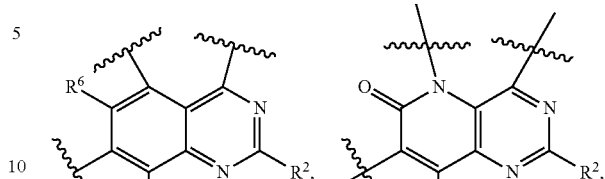

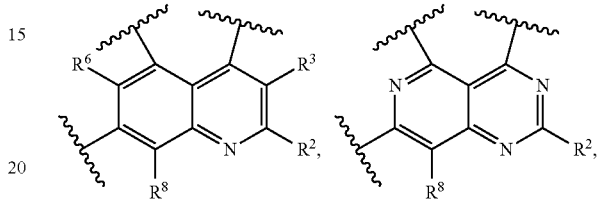

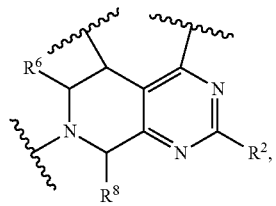

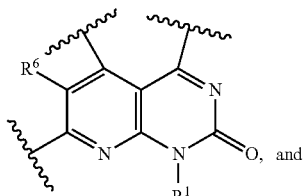

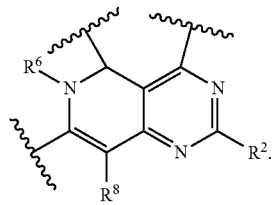

In embodiments, $L^7$ is a bond.

In embodiments, $R^{17}$ is selected from $C_{6-10}$aryl and 5-10 membered heteroaryl, each of which is optionally substituted with one, two, or three $R^{20q}$. In embodiments, $R^{17}$ is selected from $C_{10}$ aryl and 9-membered heteroaryl, each of which is optionally substituted with one, two, or three $R^{20q}$. In embodiments, $R^{17}$ is selected from naphthalenyl and benzothiophenyl, each of which is optionally substituted with one, two, or three $R^{20q}$. In embodiments, $R^{17}$ is substituted with one, two, or three substituents independently selected from halogen, —CN, $C_{1-3}$alkyl, $C_{2-3}$alkenyl, $C_{2-3}$alkynyl, —$OR^{21}$, and —$N(R^{22})(R^{23})$. In embodiments, $R^{17}$ is substituted with one, two, or three substituents independently selected from halogen, —CN, —$CH_3$, —C≡CH, —OH, and —$NH_2$. In embodiments, $R^{17}$ is substituted with —F, —CN, and —$NH_2$. In embodiments, $R^{17}$ is selected from

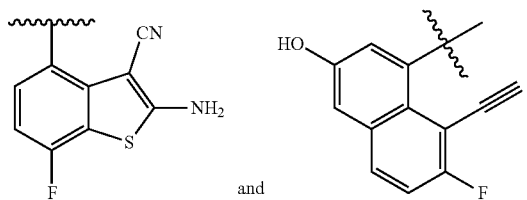

and

In embodiments, $R^{17}$ is selected from

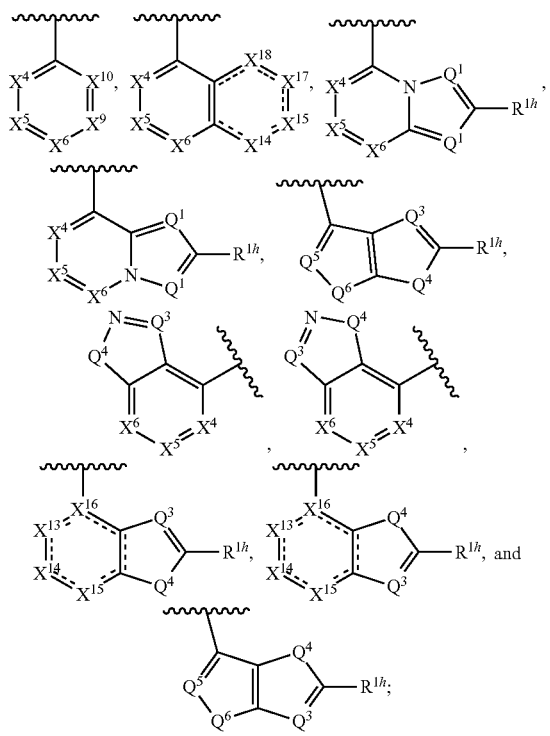

$Q^1$, $Q^3$, and $Q^5$ are independently selected from N and $C(R^{1d})$;

$Q^4$ and $Q^6$ are independently selected from O, S, $C(R^{1a})(R^{1b})$, and $N(R^{1c})$;

$X^4$, $X^5$, $X^6$, $X^9$, $X^{10}$ are independently selected from $C(R^{1a})$ and N;

$X^{13}$ is selected from a bond, $C(R^{1a})(R^{1b})$, $C(O)C(R^{1a})(R^{1b})$, $C(R^{1a})(R^{1b})C(R^{1a})(R^{1b})$, $C(R^{1a})(R^{1b})N(R^{1c})$, and $N(R^{1c})$;

$X^{14}$, $X^{15}$, $X^{17}$, $X^{18}$ are independently selected from C(O), $C(R^{1a})$, N, $C(R^{1a})(R^{1b})$, and $N(R^{1c})$;

$X^{16}$ are independently selected from C, N, and $C(R^{1a})$;

each $R^{1a}$, $R^{1b}$, $R^{1d}$, and $R^{1h}$ is independently selected from hydrogen, halogen, —CN, $C_{1-6}$alkyl, $C_{1-6}$haloalkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$hetero- cycloalkyl, $C_{6-10}$aryl, and $C_{1-9}$heteroaryl are optionally substituted with one, two, or three $R^{20q}$; or $R^{1a}$ and $R^{1b}$ bonded to the same carbon are joined to form a 3-10 membered heterocycloalkyl ring or a $C_{3-10}$cycloalkyl ring, wherein the 3-10 membered heterocycloalkyl ring or $C_{3-10}$cycloalkyl ring are optionally substituted with one, two, or three $R^{20q}$; or two $R^{1a}$ bonded to adjacent atoms are joined to form a 3-10 membered heterocycloalkyl ring, a $C_{6-10}$aryl ring, a 5-12 membered heteroaryl ring, or a $C_{3-10}$cycloalkyl ring, wherein the 3-10 membered heterocycloalkyl ring, $C_{6-10}$aryl ring, 5-12 membered heteroaryl ring, or $C_{3-10}$cycloalkyl ring are optionally substituted with one, two, or three $R^{20q}$; or $R^{1h}$ and one of $R^{1a}$, $R^{1b}$, $R^{1c}$, and $R^{1d}$ bonded to adjacent atoms are joined to form a 3-10 membered heterocycloalkyl ring, a $C_{6-10}$aryl ring, a 5-12 membered heteroaryl ring, or a $C_{3-10}$cycloalkyl ring, wherein the 3-10 membered heterocycloalkyl ring, a $C_{6-10}$aryl ring, a 5-12 membered heteroaryl ring, and $C_{3-10}$cycloalkyl ring are optionally substituted with one, two, or three $R^{20q}$; and each $R^{1c}$ is independently selected from hydrogen, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20q}$;

In embodiments, $R^{17}$ is selected from:

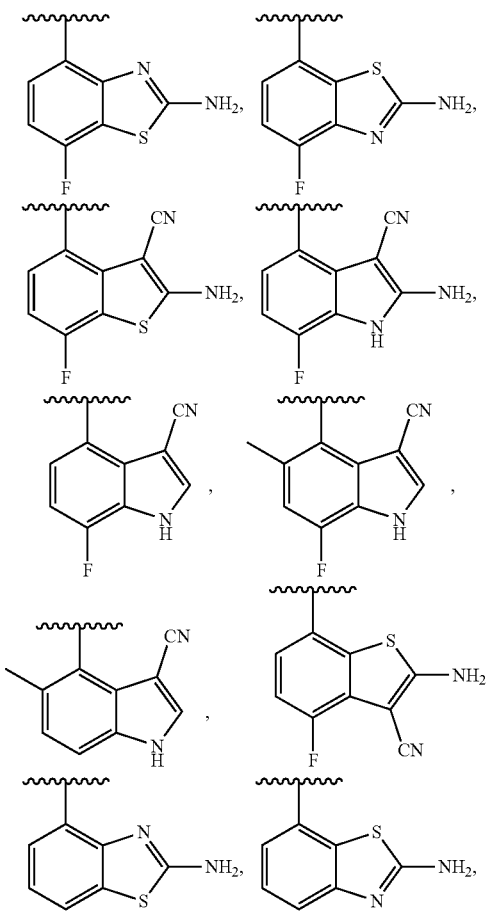

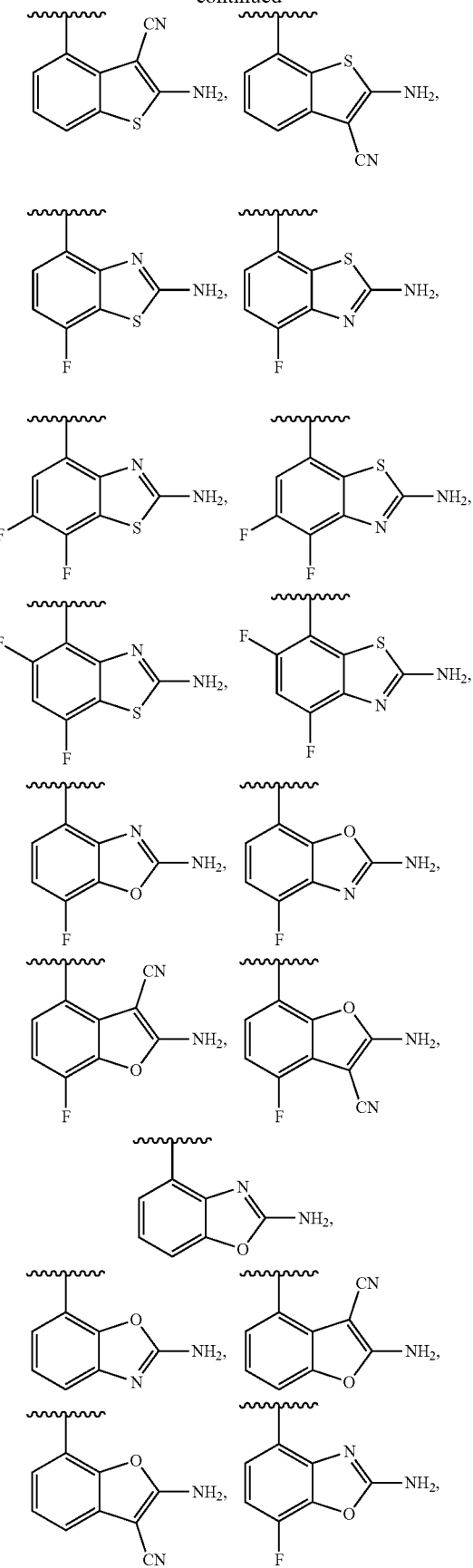
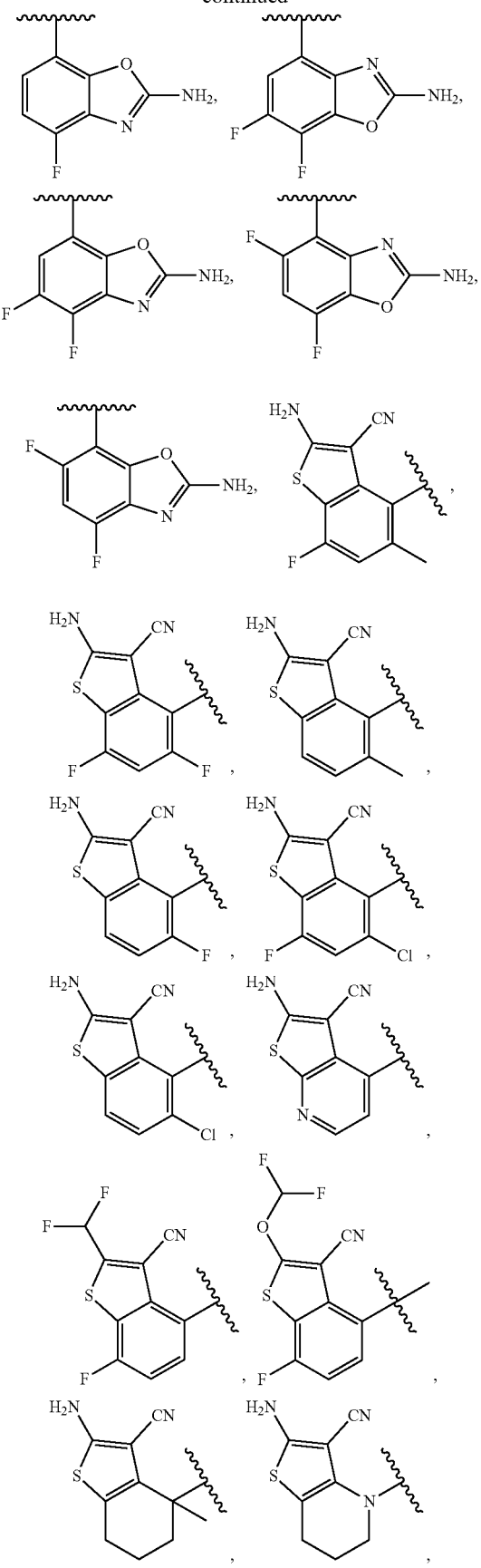

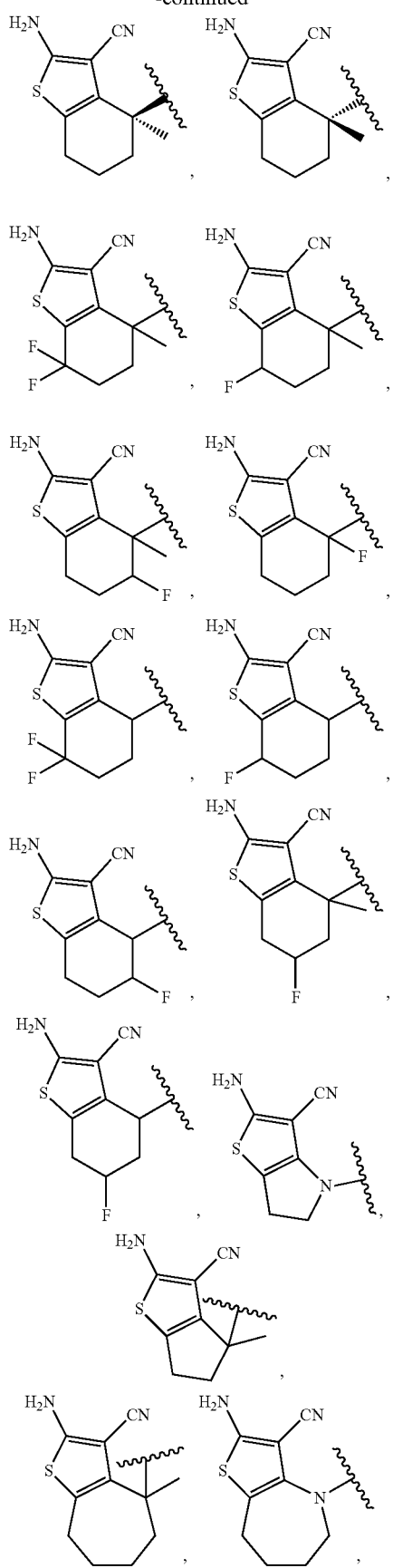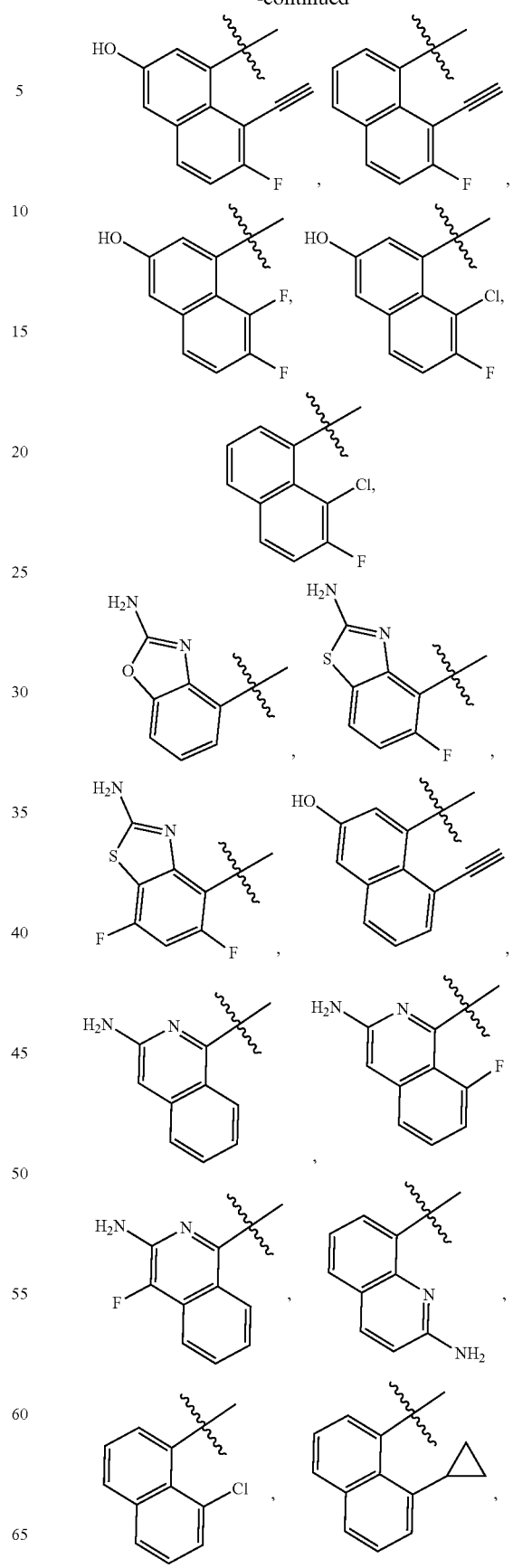

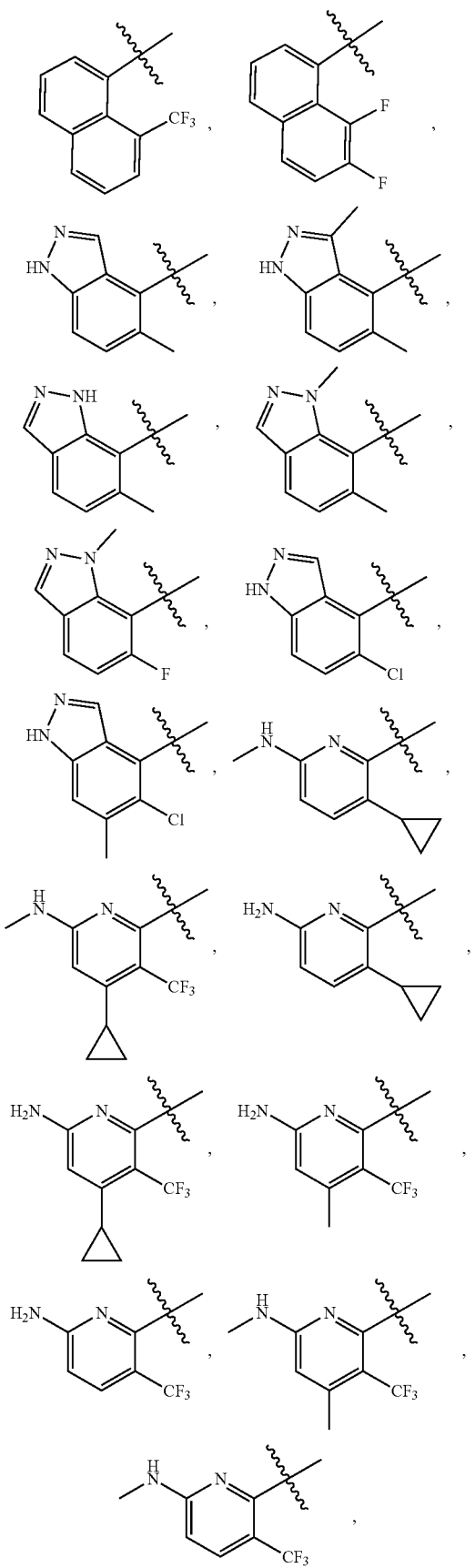
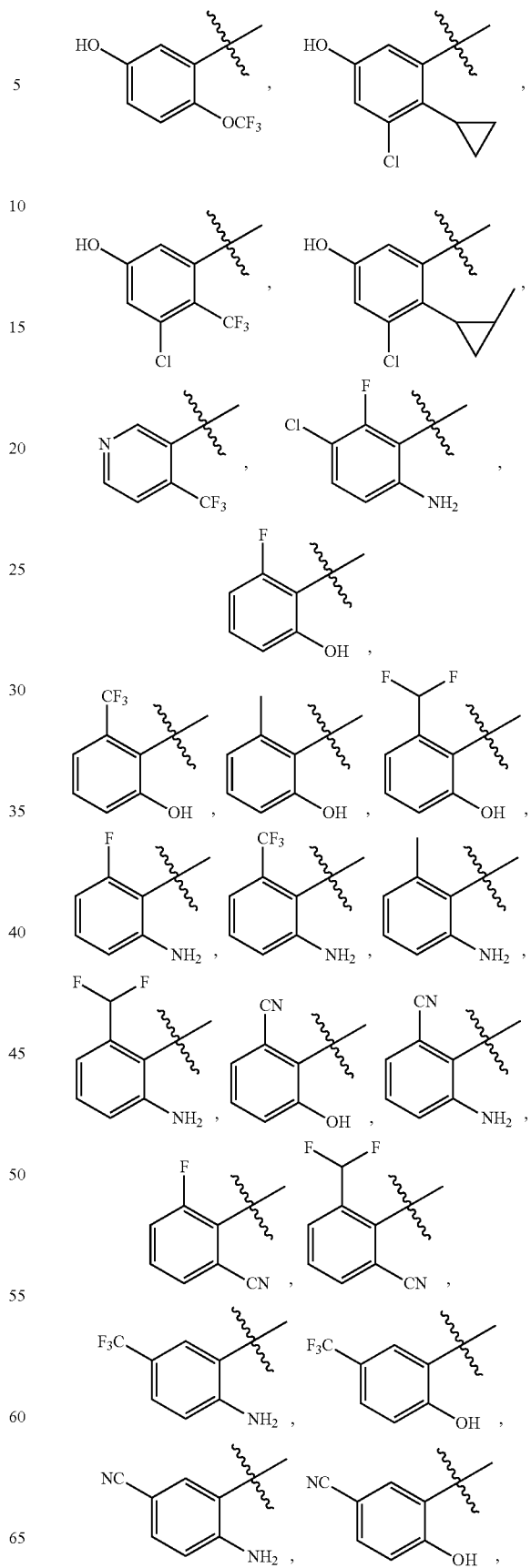

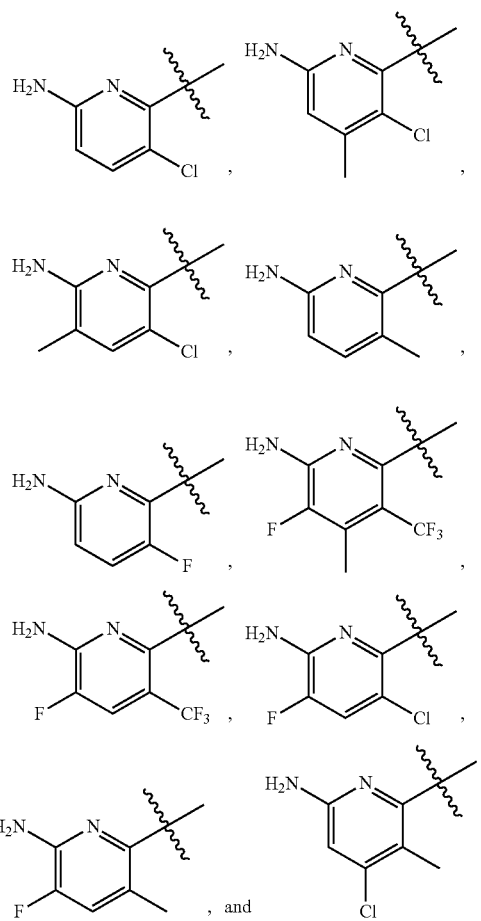
In embodiments, $R^2$ is independently —$OR^{12a}$.
In embodiments, $R^2$ is independently selected from
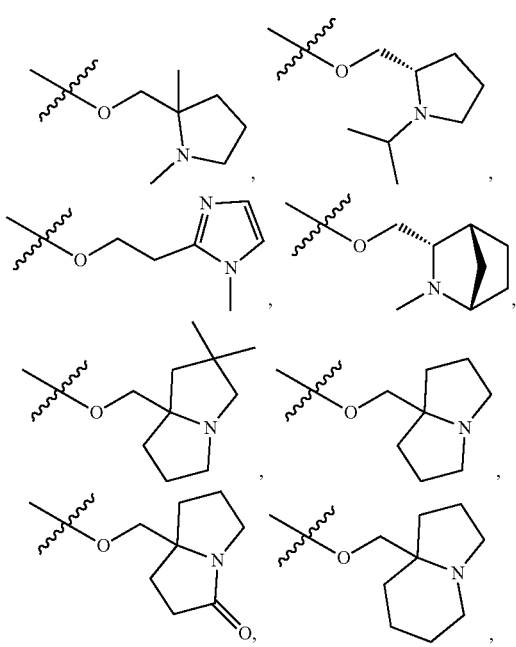
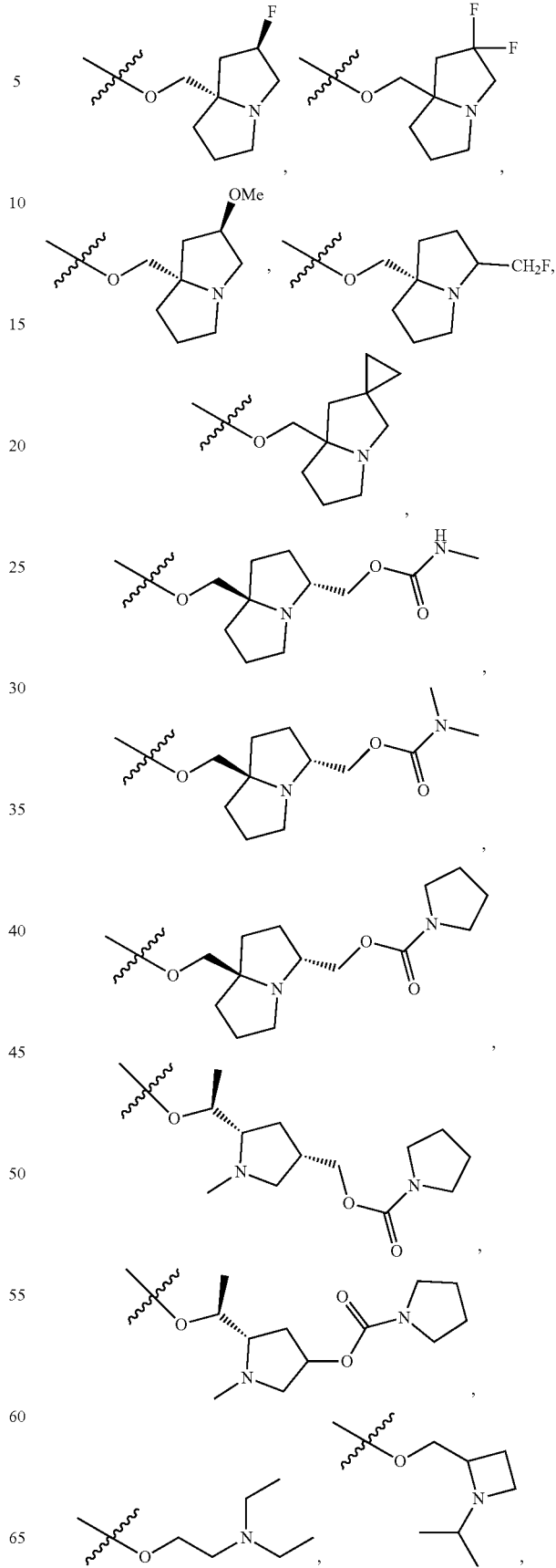

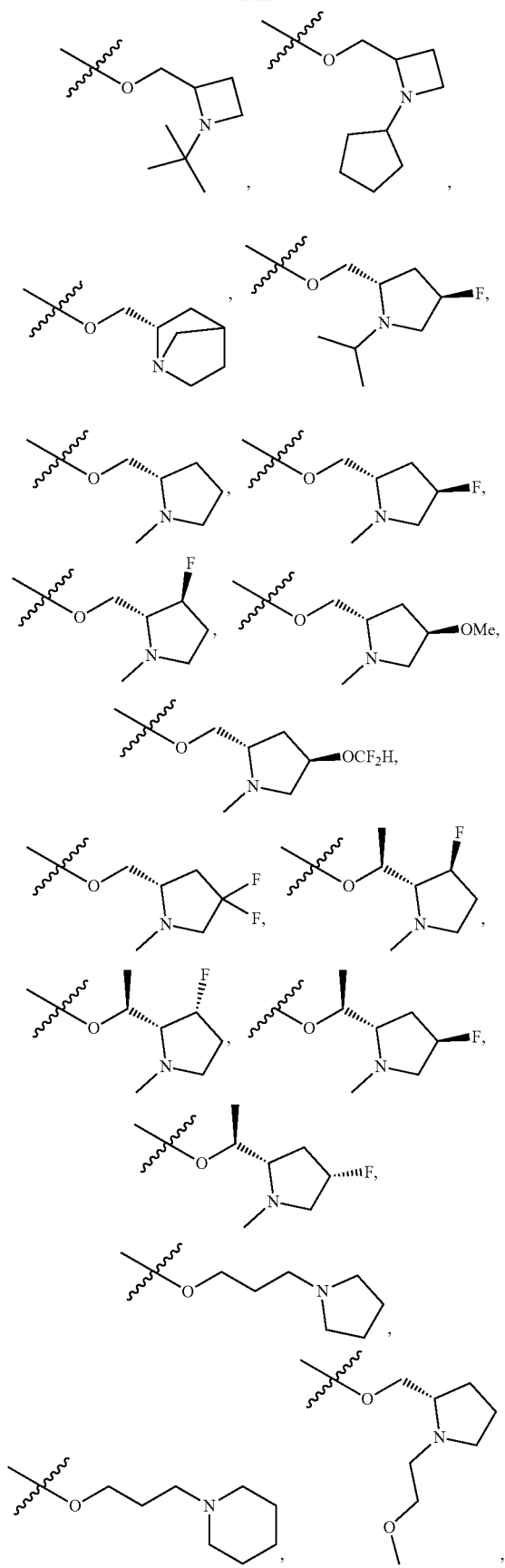
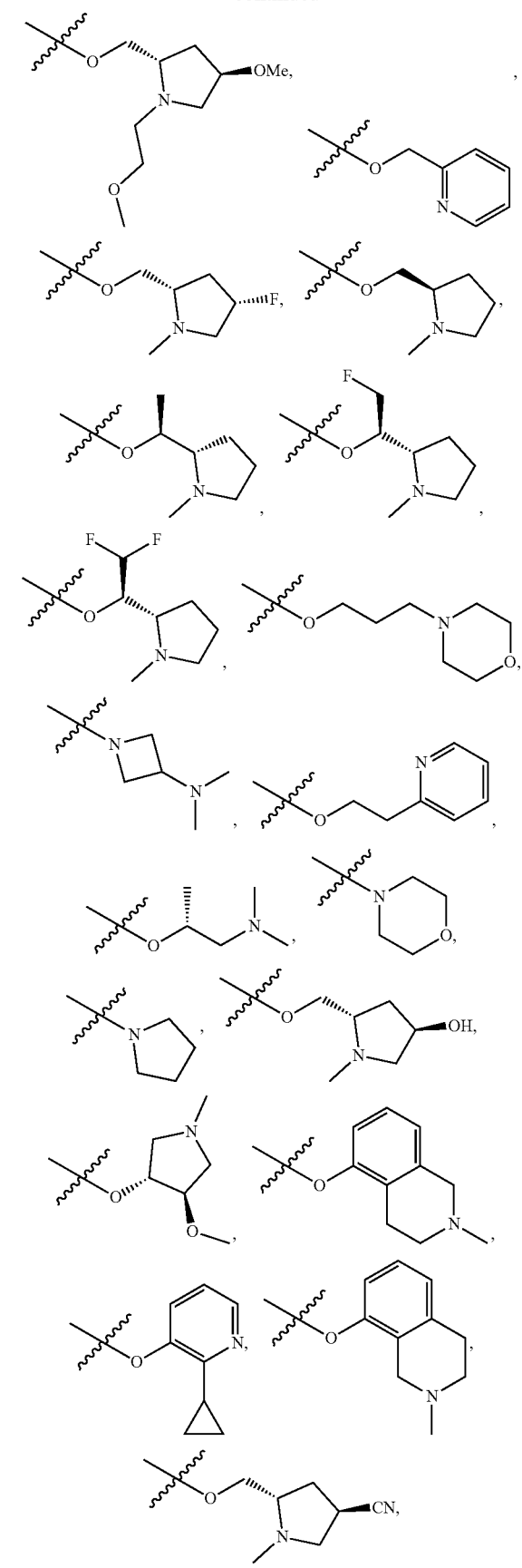

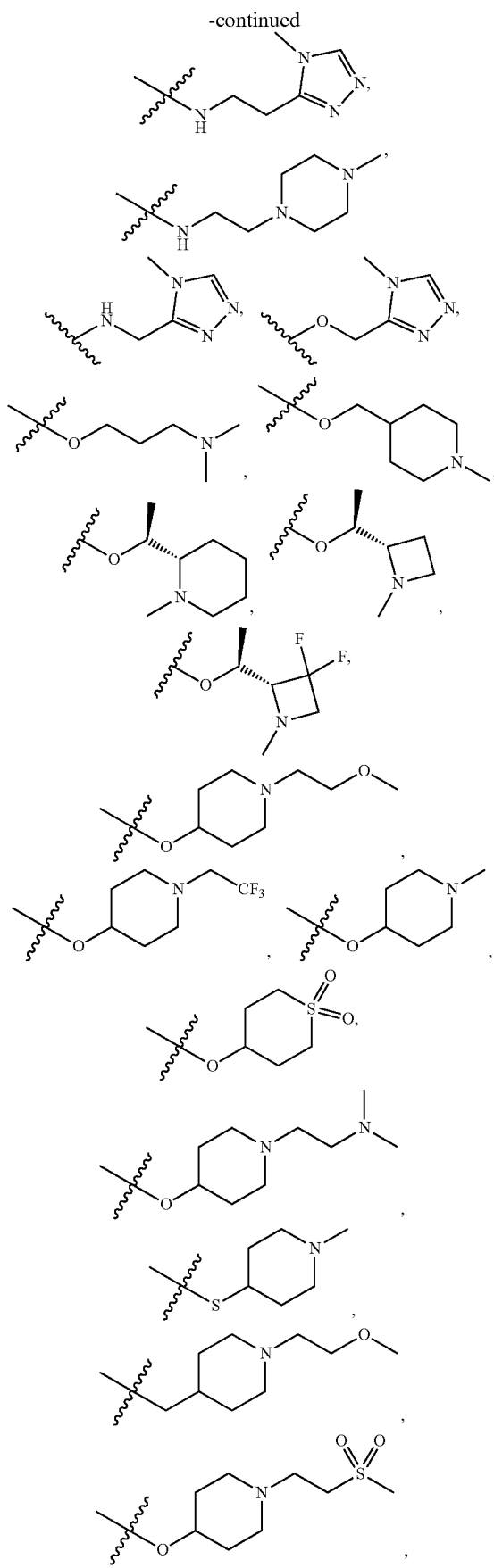
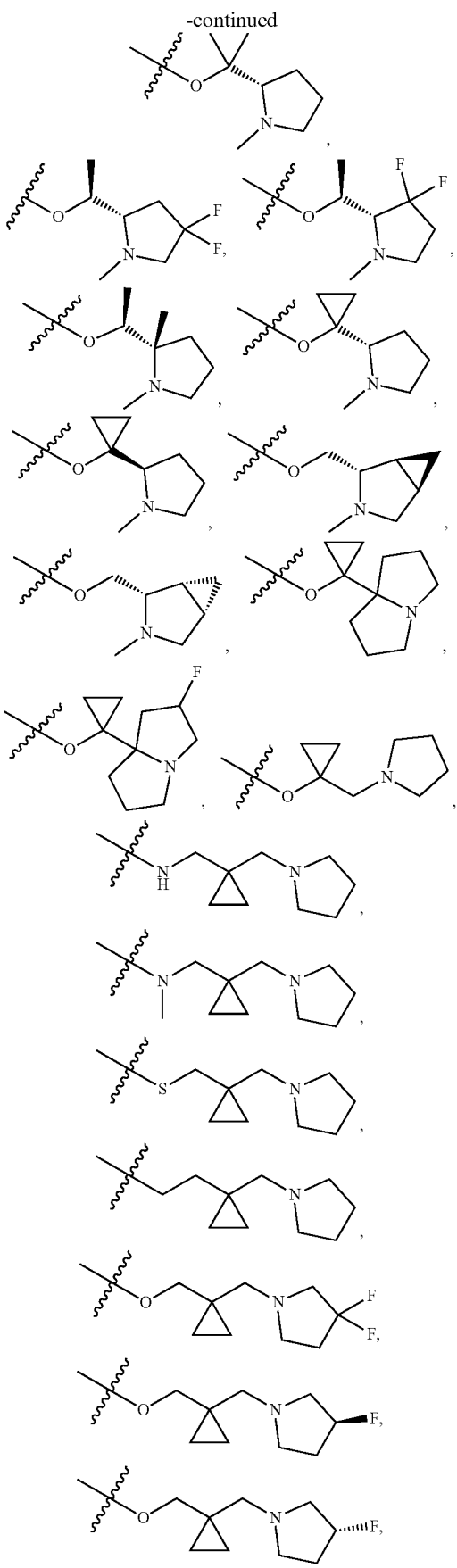

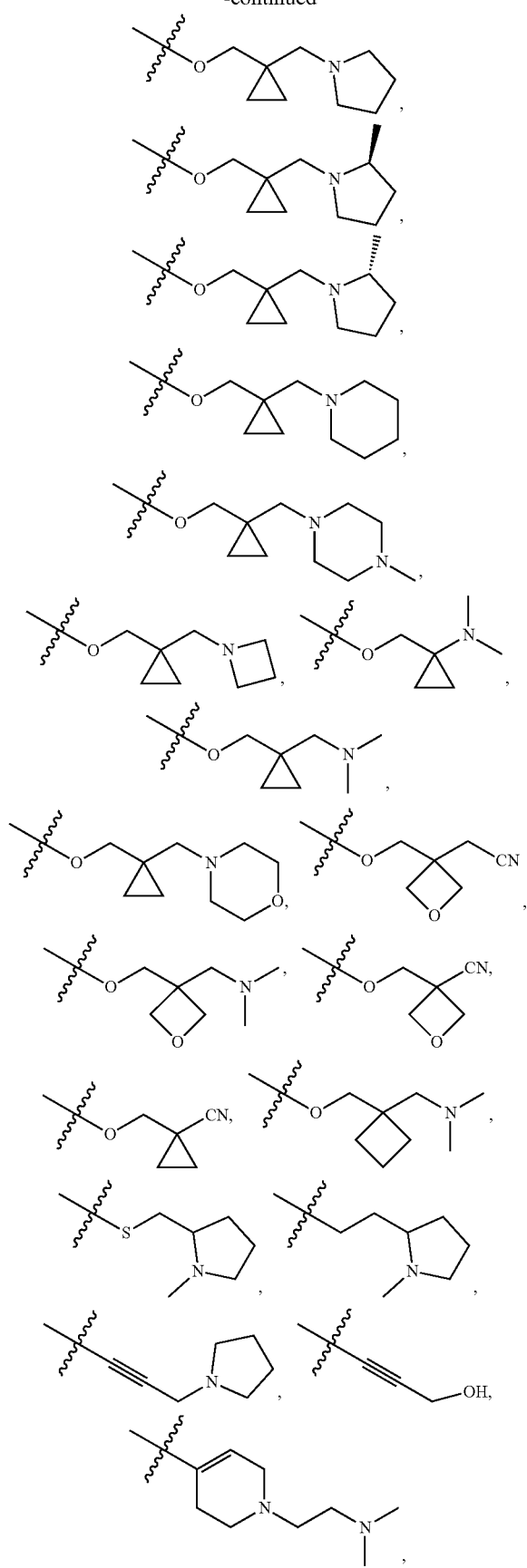
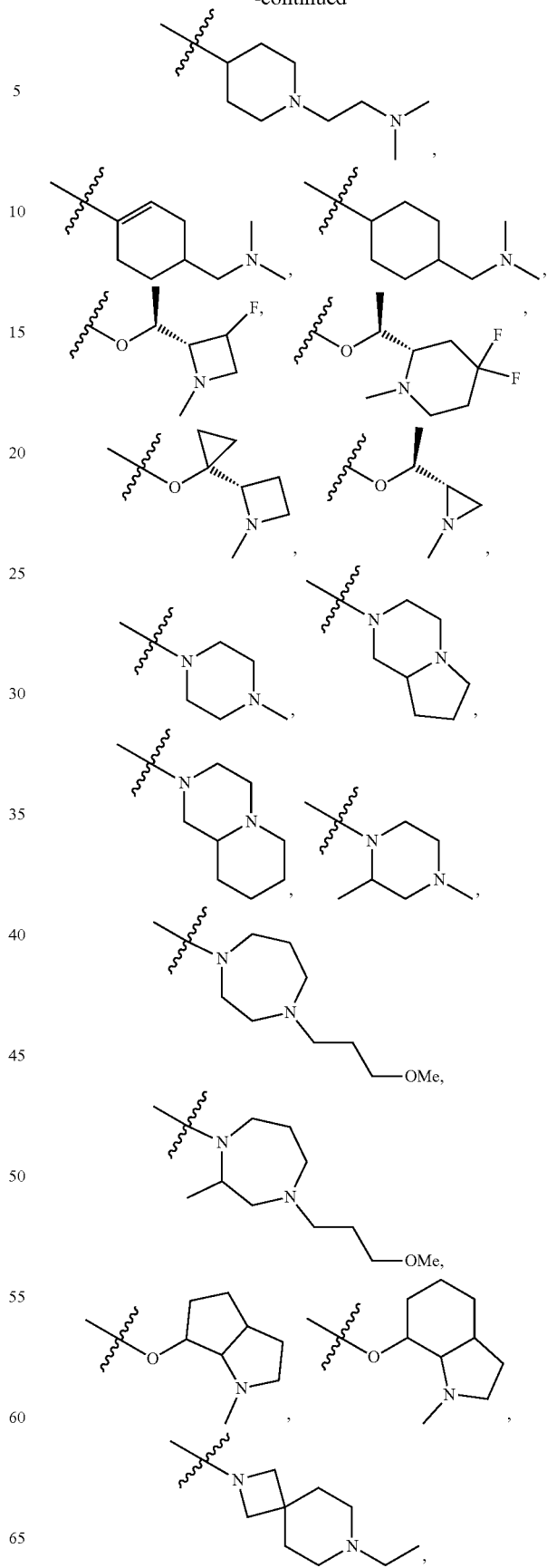

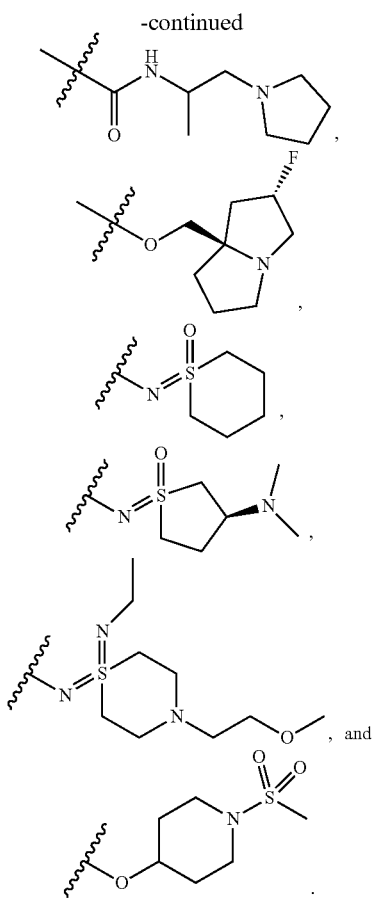

In embodiments, $R^2$ is independently

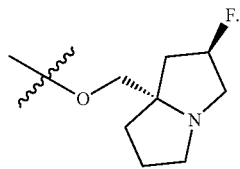 [SMILES: *OC[C@@]12CCCN1C[C@H](F)C2]

In embodiments, $Z^4$ is a bond, $Z^{4a}$, $Z^{4a}Z^{4b}$, $Z^{4a}Z^{4b}Z^{4c}$, $Z^{4a}Z^{4b}Z^{4c}Z^{4d}$, or $Z^{4a}Z^{4b}Z^{4c}Z^{4d}Z^{4e}$;. In embodiments, $Z^4$ is $Z^{4a}$. In embodiments, $Z^4$ is $Z^{4a}Z^{4b}$. In embodiments, $Z^4$ is $Z^{4a}Z^{4b}Z^{4c}$. In embodiments, $Z^4$ is $Z^{4a}Z^{4b}Z^{4c}Z^{4d}$. In embodiments, $Z^4$ is $Z^{4a}Z^{4b}Z^{4c}Z^{4d}Z^{4e}$.

In embodiments, each $R^{z4}$ is independently selected from hydrogen, halogen, —CN, $C_{1-6}$alkyl, $C_{2-6}$alkenyl, $C_{3-10}$cycloalkyl, $C_{2-9}$heterocycloalkyl, $C_{1-9}$heteroaryl, —$OR^{12}$, —$N(R^{12})(R^{13})$, —$N(R^{14})S(O)_2R^{15}$, —$C(O)R^{12}$, —$S(O)R^{15}$, —$OC(O)R^{15}$, —$C(O)N(R^{12})(R^{13})$, —$N(R^{14})C(O)R^{12}$, —$S(O)_2R^{15}$, and —$S(O)_2N(R^{12})(R^{13})$—, wherein $C_{1-6}$alkyl, $C_{2-6}$alkenyl, $C_{3-10}$cycloalkyl, $C_{2-9}$heterocycloalkyl, and $C_{1-9}$heteroaryl are optionally substituted with one, two, or three $R^{20z4}$; or two $R^{z4}$ bonded to the same carbon are joined to form a $C_{2-6}$alkenyl that is optionally substituted with one, two, or three $R^{20z4}$. In embodiments, each $R^{z4}$ is independently selected from hydrogen, halogen, —CN, $C_{1-6}$alkyl, $C_{3-10}$cycloalkyl, $C_{2-9}$heterocycloalkyl, $C_{1-9}$heteroaryl, —$OR^{12}$, —$N(R^{12})(R^{13})$, —$N(R^{14})S(O)_2R^{15}$, and —$S(O)_2R^{15}$, wherein $C_{1-6}$alkyl, $C_{3-10}$cycloalkyl, $C_{2-9}$heterocycloalkyl, and $C_{1-9}$heteroaryl are optionally substituted with one, two, or three $R^{20z4}$; or two $R^{z4}$ bonded to the same carbon are joined to form a $C_{2-6}$alkenyl that is optionally substituted with one, two, or three $R^{20z4}$.

In embodiments, each $R^{z5}$ is independently selected from hydrogen, halogen, —CN, $C_{1-6}$alkyl, $C_{2-6}$alkenyl, $C_{3-10}$cycloalkyl, $C_{2-9}$heterocycloalkyl, $C_{1-9}$heteroaryl, —$OR^{12}$, —$N(R^{12})(R^{13})$, —$N(R^{14})S(O)_2R^{15}$, —$C(O)R^{12}$, —$S(O)R^{15}$, —$OC(O)R^{15}$, —$C(O)N(R^{12})(R^{13})$, —$N(R^{14})C(O)R^{12}$, —$S(O)_2R^{15}$, and —$S(O)_2N(R^{12})(R^{13})$—, wherein $C_{1-6}$alkyl, $C_{2-6}$alkenyl, $C_{3-10}$cycloalkyl, $C_{2-9}$heterocycloalkyl, and $C_{1-9}$heteroaryl are optionally substituted with one, two, or three $R^{20z5}$; or two $R^{z5}$ bonded to the same carbon are joined to form a $C_{2-6}$alkenyl that is optionally substituted with one, two, or three $R^{20z5}$. In embodiments, each $R^{z5}$ is independently selected from hydrogen, halogen, —CN, $C_{1-6}$alkyl, $C_{3-10}$cycloalkyl, $C_{2-9}$heterocycloalkyl, $C_{1-9}$heteroaryl, —$OR^{12}$, —$N(R^{12})(R^{13})$, —$N(R^{14})S(O)_2R^{15}$, and —$S(O)_2R^{15}$, wherein $C_{1-6}$alkyl, $C_{3-10}$cycloalkyl, $C_{2-9}$heterocycloalkyl, and $C_{1-9}$heteroaryl are optionally substituted with one, two, or three $R^{20z5}$; or two $R^{z5}$ bonded to the same carbon are joined to form a $C_{2-6}$alkenyl that is optionally substituted with one, two, or three $R^{20z5}$.

In embodiments, each $R^{z6}$ is independently selected from hydrogen, halogen, —CN, $C_{1-6}$alkyl, $C_{2-6}$alkenyl, $C_{3-10}$cycloalkyl, $C_{2-9}$heterocycloalkyl, $C_{1-9}$heteroaryl, —$OR^{12}$, —$N(R^{12})(R^{13})$, —$N(R^{14})S(O)_2R^{15}$, —$C(O)R^{12}$, —$S(O)R^{15}$, —$OC(O)R^{15}$, —$C(O)N(R^{12})(R^{13})$, —$N(R^{14})C(O)R^{12}$, —$S(O)_2R^{15}$, and —$S(O)_2N(R^{12})(R^{13})$—, wherein $C_{1-6}$alkyl, $C_{2-6}$alkenyl, $C_{3-10}$cycloalkyl, $C_{2-9}$heterocycloalkyl, and $C_{1-9}$heteroaryl are optionally substituted with one, two, or three $R^{20z6}$; or two $R^{z6}$ bonded to the same carbon are joined to form a $C_{2-6}$alkenyl that is optionally substituted with one, two, or three $R^{20z6}$.

In embodiments, each $R^{z6}$ is independently selected from hydrogen, halogen, —CN, $C_{1-6}$alkyl, $C_{3-10}$cycloalkyl, $C_{2-9}$heterocycloalkyl, $C_{1-9}$heteroaryl, —$OR^{12}$, —$N(R^{12})(R^{13})$, —$N(R^{14})S(O)_2R^{15}$, and —$S(O)_2R^{15}$, wherein $C_{1-6}$alkyl, $C_{3-10}$cycloalkyl, $C_{2-9}$heterocycloalkyl, and $C_{1-9}$heteroaryl are optionally substituted with one, two, or three $R^{20z6}$; or two $R^{z6}$ bonded to the same carbon are joined to form a $C_{1-6}$alkenyl that is optionally substituted with one, two, or three $R^{20z6}$.

In embodiments, each $R^{20z}$ is independently selected from hydrogen, halogen, oxo, —CN, $C_{1-6}$alkyl, $C_{2-6}$alkenyl, $C_{3-10}$cycloalkyl, $C_{2-9}$heterocycloalkyl, $C_{1-9}$heteroaryl, —$OR^{12}$, —$N(R^{12})(R^{13})$, —$N(R^{14})S(O)_2R^{15}$, —$C(O)R^{12}$, —$S(O)R^{15}$, —$OC(O)R^{15}$, —$C(O)N(R^{12})(R^{13})$, —$N(R^{14})C(O)R^{12}$, —$S(O)_2R^{15}$, and —$S(O)_2N(R^{12})(R^{13})$—, wherein $C_{1-6}$alkyl, $C_{2-6}$alkenyl, $C_{3-10}$cycloalkyl, $C_{2-9}$heterocycloalkyl, and $C_{1-9}$heteroaryl are optionally substituted with one, two, or three $R^{20zz}$; or two $R^{20z}$ bonded to the same carbon are joined to form a $C_{2-6}$alkenyl that is optionally substituted with one, two, or three $R^{20zz}$. In embodiments, each $R^{20z}$ is independently selected from hydrogen, halogen, —CN, $C_{1-6}$alkyl, $C_{3-10}$cycloalkyl, $C_{2-9}$heterocycloalkyl, $C_{1-9}$heteroaryl, —$OR^{12}$, —$N(R^{12})(R^{13})$, —$N(R^{14})S(O)_2R^{15}$, and —$S(O)_2R^{15}$, wherein $C_{1-6}$alkyl, $C_{3-10}$cycloalkyl, $C_{2-9}$heterocycloalkyl, and $C_{1-9}$heteroaryl are optionally substituted with one, two, or three $R^{20zz}$; or two $R^{20z}$ bonded to the same carbon are joined to form a $C_{2-6}$alkenyl that is optionally substituted with one, two, or three $R^{20zz}$. In embodiments, each $R^{20z}$ is independently oxo.

In an aspect is provided a compound having the formula A-$L^{AB}$-B wherein

A is a monovalent form of a compound described herein;

$L^{AB}$ is a covalent linker bonded to A and B; and

B is a monovalent form of a degradation enhancer.

In embodiments, the degradation enhancer is capable of binding a protein selected from E3A, mdm2, APC, EDD1, SOCS/BC-box/eloBC/CUL5/RING, LNXp80, CBX4, CBLL1, HACE1, HECTD1, HECTD2, HECTD3, HECTD4, HECW1, HECW2, HERC1, HERC2, HERC3, HERC4, HER5, HERC6, HUWE1, ITCH, NEDD4, NEDD4L, PPIL2, PRPF19, PIAS1, PIAS2, PIAS3, PIAS4, RANBP2, RNF4, RBX1, SMURF1, SMURF2, STUB1, TOPORS, TRIP12, UBE3A, UBE3B, UBE3C, UBE3D, UBE4A, UBE4B, UBOX5, UBR5, VHL (von-Hippel-Lindau ubiquitin ligase), WWP1, WWP2, Parkin, MKRN1, CMA (chaperon-mediated autophage), SCFb-TRCP (Skip-Cullin-F box (Beta-TRCP) ubiquitin complex), b-TRCP (b-transducing repeat-containing protein), cIAP1 (cellular inhibitor of apoptosis protein 1), APC/C (anaphase-promoting complex/cyclosome), CRBN (cereblon), CUL4-RBX1-DDB1-CRBN (CRL4$^{CRBN}$) ubiquitin ligase, XIAP, IAP, KEAP1, DCAF15, RNF114, DCAF16, AhR, SOCS2, KLHL12, UBR2, SPOP, KLHL3, KLHL20, KLHDC2, SPSB1, SPSB2, SPSB4, SOCS6, FBXO4, FBXO31, BTRC, FBW7, CDC20, PML, TRIM21, TRIM24, TRIM33, GID4, avadomide, iberdomide, and CC-885. In embodiments, the degradation enhancer is capable of binding a protein selected from UBE2A, UBE2B, UBE2C, UBE2D1, UBE2D2, UBE2D3, UBE2DR, UBE2E1, UBE2E2, UBE2E3, UBE2F, UBE2G1, UBE2G2, UBE2H, UBE2I, UBE2J1, UBE2J2, UBE2K, UBE2L3, UBE2L6, UBE2L1, UBE2L2, UBE2L4, UBE2M, UBE2N, UBE2O, UBE2Q1, UBE2Q2, UBE2R1, UBE2R2, UBE2S, UBE2T, UBE2U, UBE2V1, UBE2V2, UBE2W, UBE2Z, ATG3, BIRC6, and UFC1. In embodiments, $L^{AB}$ is -$L^{AB1}$-$L^{AB2}$-$L^{AB3}$-$L^{AB4}$-$L^{AB5}$-;

$L^{AB1}$, $L^{AB2}$, $L^{AB3}$, $L^{AB4}$, and $L^{AB5}$ are independently a bond, —O—, —N($R^{14}$)—, —C(O)—, —N($R^{14}$)C(O)—, —C(O)N($R^{14}$)—, —S—, —S(O)$_2$—, —S(O)—, —S(O)$_2$N($R^{14}$)—, —S(O)N($R^{14}$)—, —N($R^{14}$)S(O)—, —N($R^{14}$)S(O)$_2$—, $C_{1-6}$alkylene, (—O-$C_{1-6}$alkyl)$_z$-, (-$C_{1-6}$alkyl-O)$_z$-, $C_{2-6}$alkenylene, $C_{2-6}$alkynylene, $C_{1-6}$haloalkylene, $C_{3-12}$cycloalkylene, $C_{1-11}$heterocycloalkylene, $C_{6-12}$arylene, or $C_{1-11}$heteroarylene, wherein $C_{1-6}$alkylene, $C_{2-6}$alkenylene, $C_{2-6}$alkynylene, $C_{1-6}$haloalkylene, $C_{3-12}$cycloalkylene, $C_{1-11}$heterocycloalkylene, $C_{6-12}$arylene, or $C_{1-11}$heteroarylene, are optionally substituted with one, two, or three $R^{20n}$; wherein each $C_{1-6}$alkyl of (—O-$C_{1-6}$alkyl)$_z$- and (-$C_{1-6}$alkyl-O)z- is optionally substituted with one, two, or three $R^{20n}$;

z is independently an integer from 0 to 10;

each $R^{12}$ is independently selected from hydrogen, $C_{1-6}$alkyl, $C_{2-6}$alkenyl, $C_{2-6}$alkynyl, $C_{3-10}$cycloalkyl, —CH$_2$-$C_{3-10}$cycloalkyl, $C_{2-9}$heterocycloalkyl, —CH$_2$-$C_{2-9}$heterocycloalkyl, $C_{6-10}$aryl, —CH$_2$-$C_{6-10}$aryl, —CH$_2$-$C_{1-9}$heteroaryl, and $C_{1-9}$heteroaryl, wherein $C_{1-6}$alkyl, $C_{2-6}$alkenyl, $C_{2-6}$alkynyl, $C_{3-10}$cycloalkyl, —CH$_2$-$C_{3-10}$cycloalkyl, $C_{2-9}$heterocycloalkyl, —CH$_2$-$C_{2-9}$heterocycloalkyl, $C_{6-10}$aryl, —CH$_2$-$C_{6-10}$aryl, —CH$_2$-$C_{1-9}$heteroaryl, and $C_{1-9}$heteroaryl are optionally substituted with one, two, or three $R^{20l}$;

each $R^{13}$ is independently selected from hydrogen, $C_{1-6}$alkyl, and $C_{1-6}$haloalkyl; or $R^{12}$ and $R^{13}$, together with the nitrogen to which they are attached, form a $C_{2-9}$heterocycloalkyl ring optionally substituted with one, two, or three $R^{20m}$;

each $R^{14}$ is independently selected from hydrogen, $C_{1-6}$alkyl, and $C_{1-6}$haloalkyl;

each $R^{15}$ is independently selected from $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20o}$;

each $R^{20l}$, $R^{20m}$, $R^{20n}$, and $R^{20o}$ are each independently selected from halogen, —CN, $C_{1-6}$alkyl, $C_{2-6}$alkenyl, $C_{2-6}$alkynyl, $C_{3-10}$cycloalkyl, —CH$_2$-$C_{3-10}$cycloalkyl, $C_{2-9}$heterocycloalkyl, —CH$_2$-$C_{2-9}$heterocycloalkyl, $C_{6-10}$aryl, —CH$_2$-$C_{6-10}$aryl, —CH$_2$-$C_{1-9}$heteroaryl, $C_{1-9}$heteroaryl, —OR$^{21}$, —SR$^{21}$, —N($R^{22}$)($R^{23}$), —C(O)OR$^{22}$, —C(O)N($R^{22}$)($R^{23}$), —C(O)C(O)N($R^{22}$)($R^{23}$), —OC(O)N($R^{22}$)($R^{23}$), —N($R^{24}$)C(O)N($R^{22}$)($R^{23}$), —N($R^{24}$)C(O)OR$^{25}$, —N($R^{24}$)C(O)R$^{25}$, —N($R^{24}$)S(O)$_2$R$^{25}$, —C(O)R$^{25}$, —S(O)$_2$R$^{25}$, —S(O)$_2$N($R^{22}$)($R^{23}$), —OCH$_2$C(O)OR$^{22}$, and —OC(O)R$^{25}$, wherein $C_{1-6}$alkyl, $C_{2-6}$alkenyl, $C_{2-6}$alkynyl, $C_{3-10}$cycloalkyl, —CH$_2$-$C_{3-10}$cycloalkyl, $C_{2-9}$heterocycloalkyl, —CH$_2$-$C_{2-9}$heterocycloalkyl, $C_{6-10}$aryl, —CH$_2$-$C_{6-10}$aryl, —CH$_2$-$C_{1-9}$heteroaryl, and $C_{1-9}$heteroaryl are optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —OR$^{21}$, —SR$^{21}$, —N($R^{22}$)($R^{23}$), —C(O)OR$^{22}$, —C(O)N($R^{22}$)($R^{23}$), —C(O)C(O)N($R^{22}$)($R^{23}$), —OC(O)N($R^{22}$)($R^{23}$), —N($R^{24}$)C(O)N($R^{22}$)($R^{23}$), —N($R^{24}$)C(O)OR$^{25}$, —N($R^{24}$)C(O)R$^{25}$, —N($R^{24}$)S(O)$_2$R$^{25}$, —C(O)R$^{25}$, —S(O)$_2$R$^{25}$, —S(O)$_2$N($R^{22}$)($R^{23}$), and —OC(O)R$^{25}$;

each $R^{21}$ is independently selected from H, $C_{1-6}$alkyl, $C_{1-6}$haloalkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl;

each $R^{22}$ is independently selected from H, $C_{1-6}$alkyl, $C_{1-6}$haloalkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl;

each $R^{23}$ is independently selected from H and $C_{1-6}$alkyl;

each $R^{24}$ is independently selected from H and $C_{1-6}$alkyl; and each $R^{25}$ is independently selected from $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl.

In embodiments, $L^{AB}$ is —(O-$C_2$alkyl)$_z$- and z is an integer from 1 to 10. In embodiments, $L^{AB}$ is -(C$_2$alkyl-O—)$_z$- and z is an integer from 1 to 10. In embodiments, $L^{AB}$ is —(CH$_2$)$_{zz1}$L$^{AB2}$(CH$_2$O)$_{zz2}$-, wherein $L^{AB2}$ is a bond, a 5 or 6 membered heterocycloalkylene or heteroarylene, phenylene, -(C$_2$-C$_4$)alkynylene, —SO$_2$— or —NH—; and zz1 and zz2 are independently an integer from 0 to 10.

In embodiments, $L^{AB}$ is —(CH$_2$)$_{zz1}$(CH$_2$O)$_{zz2}$-, wherein zz1 and zz2 are each independently an integer from 0 to 10. In embodiments, $L^{AB}$ is a PEG linker. In embodiments, B is a monovalent form of a compound selected from

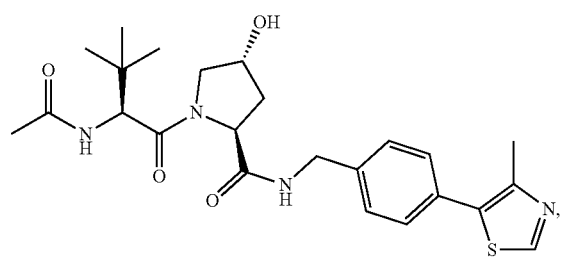

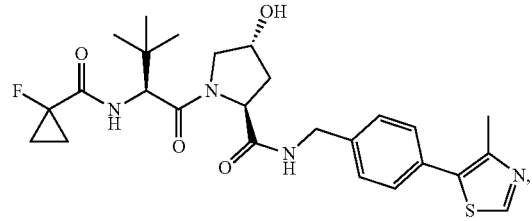
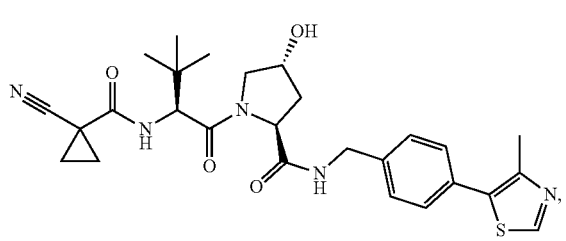
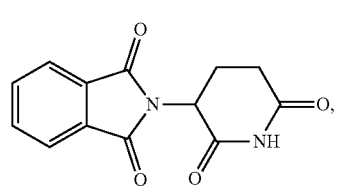
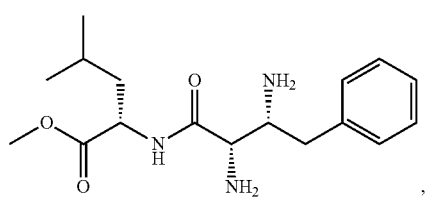
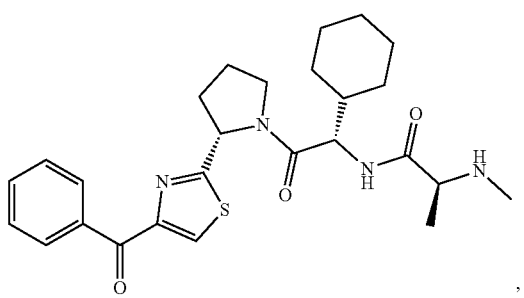
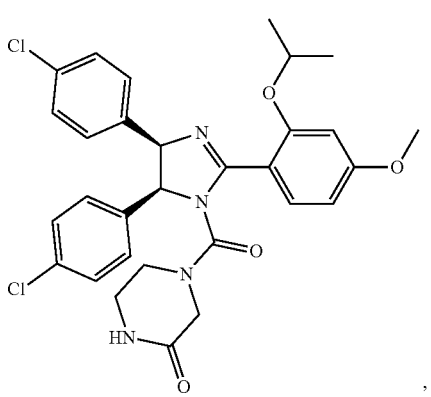

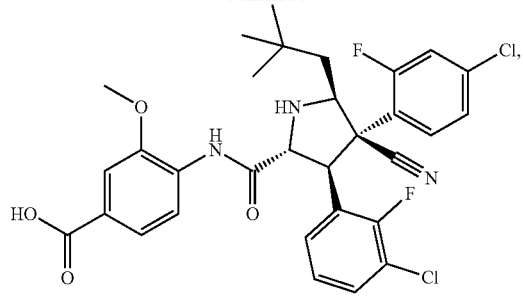
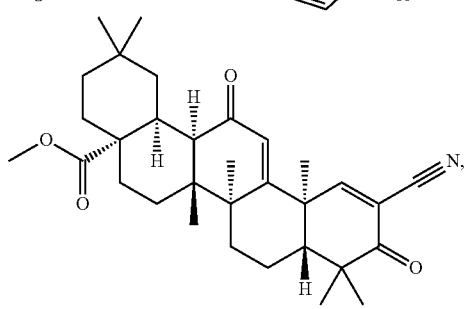
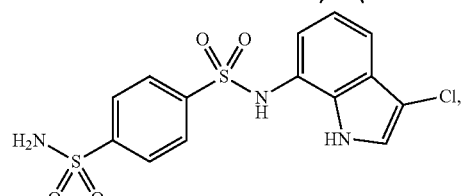
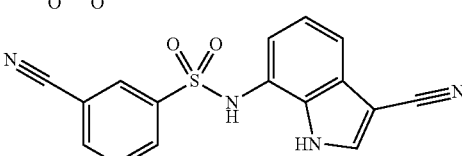
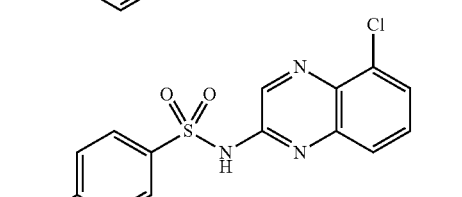
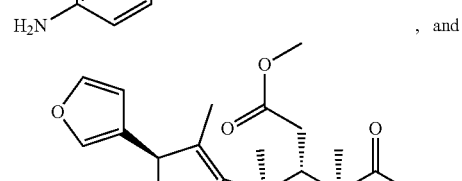
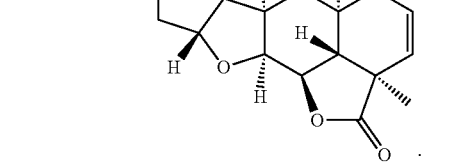

In an aspect is provided a pharmaceutical composition comprising a compound described herein, or a pharmaceutically acceptable salt or solvate thereof, and a pharmaceutically acceptable excipient.

In an aspect is provided a method of treating cancer in a subject in need thereof, comprising administering to the subject a therapeutically effective amount of a compound described herein, or a pharmaceutically acceptable salt or solvate thereof.

In an aspect is provided a method of treating cancer in a subject comprising a Ras mutant protein, the method comprising: modifying the Ras mutant protein of said subject by administering to said subject a compound, wherein the compound is characterized in that upon contacting the Ras mutant protein, said Ras mutant protein is modified covalently at a residue corresponding to residue 12 of SEQ ID No: 1, such that said modified Ras mutant protein exhibits reduced Ras signaling output.

In embodiments, the cancer is a solid tumor or a hematological cancer.

In an aspect is provided a method of modulating signaling output of a Ras protein, comprising contacting a Ras protein with an effective amount of a compound described herein, or a pharmaceutically acceptable salt or solvate thereof, thereby modulating the signaling output of the Ras protein.

In an aspect is provided a method of inhibiting cell growth, comprising administering an effective amount of a compound described herein, or a pharmaceutically acceptable salt or solvate thereof, to a cell expressing a Ras protein, thereby inhibiting growth of said cells.

In embodiments, the method includes administering an additional agent. In embodiments, the additional agent comprises (1) an inhibitor of MEK; (2) an inhibitor of epidermal growth factor receptor (EGFR) and/or of mutants thereof; (3) an immunotherapeutic agent; (4) a taxane; (5) an antimetabolite; (6) an inhibitor of FGFR1 and/or FGFR2 and/or FGFR3 and/or of mutants thereof; (7) a mitotic kinase inhibitor; (8) an anti-angiogenic drug; (9) a topoisomerase inhibitor; (10) a platinum-containing compound; (12) an inhibitor of c-MET and/or of mutants thereof; (13) an inhibitor of BCR-ABL and/or of mutants thereof; (14) an inhibitor of ErbB2 (Her2) and/or of mutants thereof; (15) an inhibitor of AXL and/or of mutants thereof; (16) an inhibitor of NTRK1 and/or of mutants thereof; (17) an inhibitor of RET and/or of mutants thereof; (18) an inhibitor of A-Raf and/or B-Raf and/or C-Raf and/or of mutants thereof; (19) an inhibitor of ERK and/or of mutants thereof; (20) an MDM2 inhibitor; (21) an inhibitor of mTOR; (23) an inhibitor of IGF1/2 and/or of IGF1-R; (24) an inhibitor of CDK9; (25) an inhibitor of farnesyl transferase; (26) an inhibitor of SHIP pathway; (27) an inhibitor of SRC; (28) an inhibitor of JAK; (29) a PARP inhibitor, (31) a ROS1 inhibitor; (32) an inhibitor of SHP pathway, or (33) an inhibitor of Src, FLT3, HDAC, VEGFR, PDGFR, LCK, Bcr-Abl or AKT; (34) an inhibitor of KrasG12C mutant; (35) a SHC inhibitor (e.g., PP2, AID371185); (36) a GAB inhibitor; (38) a PI-3 kinase inhibitor; (39) a MARPK inhibitor; (40) CDK4/6 inhibitor; (41) MAPK inhibitor; (42) SHP2 inhibitor; (43) checkpoint immune blockade agents; (44) SOS1 inhibitor; or (45) a SOS 2 inhibitor. In embodiments, the additional agent comprises an inhibitor of SHP2 selected from RMC-4630, ERAS-601,

TNO155

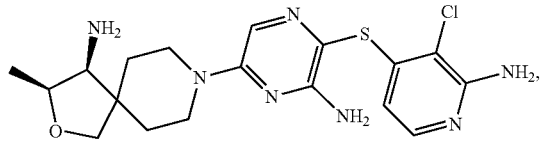

-continued

JAB-3068

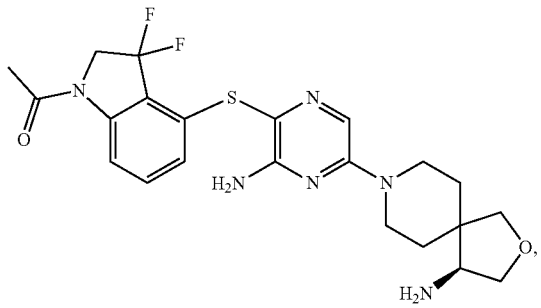

IACS-13909/BBP-398

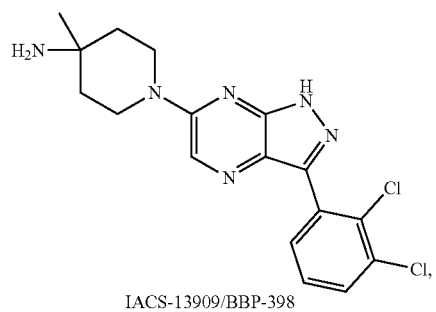

SHP099

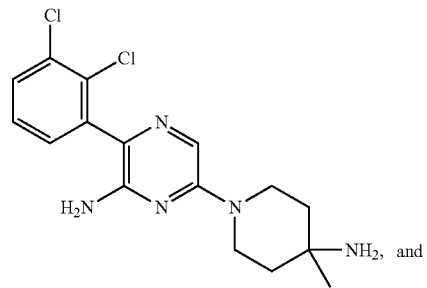
and

RMC-4550

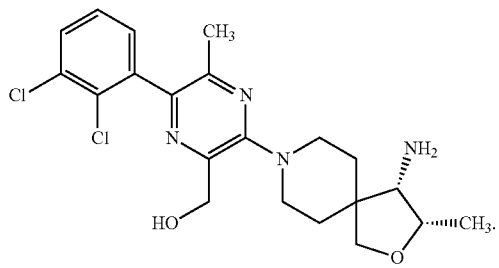

In embodiments, the additional agent comprises an inhibitor of SOS selected from RMC-5845, BI-1701963,

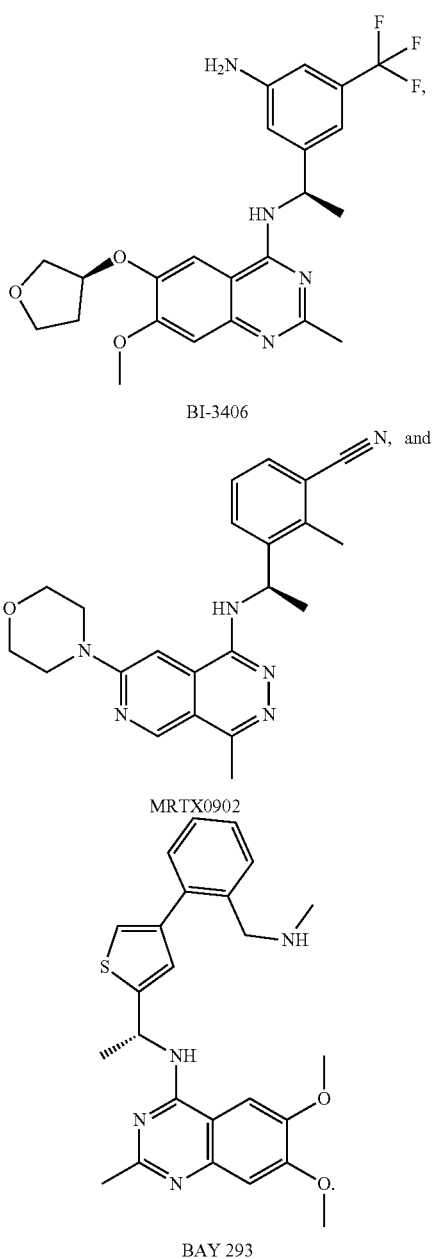

BI-3406

MRTX0902

BAY 293

In embodiments, the additional agent comprises an inhibitor of EGFR selected from afatinib, erlotinib, gefitinib, lapatinib, cetuximab panitumumab, osimertinib, olmutinib, and EGF-816. In embodiments, the additional agent comprises an inhibitor of MEK selected from trametinib, cobimetinib, binimetinib, selumetinib, refametinib, and AZD6244. In embodiments, the additional agent comprises an inhibitor of ERK selected from ulixertinib, MK-8353, LTT462, AZD0364, SCH772984, BIX02189, LY3214996, and ravoxertinib. In embodiments, the additional agent comprises an inhibitor of CDK4/6 selected from palbociclib, ribociclib, and abemaciclib. In embodiments, the additional agent comprises an inhibitor of BRAF selected from sorafenib, vemurafenib, dabrafenib, encorafenib, regorafenib, and GDC-879.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 1 depicts a sequence alignment of various wild type Ras proteins including K-Ras, H-Ras, N-Ras, RalA, RalB, from top to bottom.

DETAILED DESCRIPTION

The practice of some embodiments disclosed herein employ, unless otherwise indicated, conventional techniques of immunology, biochemistry, chemistry, molecular biology, microbiology, cell biology, genomics and recombinant DNA, which are within the skill of the art. See for example Sambrook and Green, Molecular Cloning: A Laboratory Manual, $4^{th}$ Edition (2012); the series Current Protocols in Molecular Biology (F. M. Ausubel, et al. eds.); the series Methods In Enzymology (Academic Press, Inc.), PCR 2: A Practical Approach (M. J. MacPherson, B. D. Hames and G. R. Taylor eds. (1995)), Harlow and Lane, eds. (1988) Antibodies, A Laboratory Manual, and Culture of Animal Cells: A Manual of Basic Technique and Specialized Applications, $6^{th}$ Edition (R. I. Freshney, ed. (2010)).

Unless defined otherwise, all technical and scientific terms used herein have the same meaning as is commonly understood to which the claimed subject matter belongs. In the event that there are a plurality of definitions for terms herein, those in this section prevail. All patents, patent applications, publications and published nucleotide and amino acid sequences (e.g., sequences available in GenBank or other databases) referred to herein are incorporated by reference. Where reference is made to a URL or other such identifier or address, it is understood that such identifiers can change and particular information on the internet can come and go, but equivalent information can be found by searching the internet. Reference thereto evidences the availability and public dissemination of such information.

It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

The section headings used herein are for organizational purposes only and are not to be construed as limiting the subject matter described.

Definition of standard chemistry terms may be found in reference works, including but not limited to, Carey and Sundberg "Advanced Organic Chemistry 4$^{th}$ Ed." Vols. A (2000) and B (2001), Plenum Press, New York. Unless otherwise indicated, conventional methods of mass spectroscopy, NMR, HPLC, protein chemistry, biochemistry, recombinant DNA techniques and pharmacology.

Unless specific definitions are provided, the nomenclature employed in connection with, and the laboratory procedures and techniques of, analytical chemistry, synthetic organic chemistry, and medicinal and pharmaceutical chemistry described herein are those recognized in the field. Standard techniques can be used for chemical syntheses, chemical analyses, pharmaceutical preparation, formulation, and delivery, and treatment of patients. Standard techniques can be used for recombinant DNA, oligonucleotide synthesis, and tissue culture and transformation (e.g., electroporation, lipofection). Reactions and purification techniques can be performed e.g., using kits of manufacturer's specifications or as commonly accomplished in the art or as described herein. The foregoing techniques and procedures can be generally performed of conventional methods and as described in various general and more specific references that are cited and discussed throughout the present specification.

It is to be understood that the methods and compositions described herein are not limited to the particular methodology, protocols, cell lines, constructs, and reagents described herein and as such may vary. It is also to be understood that the terminology used herein is for the purpose of describing particular embodiments only, and is not intended to limit the scope of the methods, compounds, compositions described herein.

As used herein, $C_1$-$C_x$ includes $C_1$-$C_2$, $C_1$-$C_3$ . . . $C_1$-$C_x$. $C_1$-$C_x$ refers to the number of carbon atoms that make up the moiety to which it designates (excluding optional substituents).

An "alkyl" group refers to a straight or branched hydrocarbon chain radical consisting solely of carbon and hydrogen atoms, containing no unsaturation. In some embodiments, the "alkyl" group may have 1 to 18, 1 to 12, 1 to 10, 1 to 8, or 1 to 6 carbon atoms (whenever it appears herein, a numerical range such as "1 to 6" refers to each integer in the given range; e.g., "1 to 6 carbon atoms" means that the alkyl group may consist of 1 carbon atom, 2 carbon atoms, 3 carbon atoms, etc., up to and including 6 carbon atoms, although the present definition also covers the occurrence of the term "alkyl" where no numerical range is designated). The alkyl group of the compounds described herein may be designated as "$C_1$-$C_6$alkyl" or similar designations. By way of example only, "$C_1$-$C_6$alkyl" indicates that there are one to six carbon atoms in the alkyl chain, i.e., the alkyl chain is selected from the group consisting of methyl, ethyl, n-propyl, iso-propyl, n-butyl, iso-butyl, sec-butyl, t-butyl, n-pentyl, iso-pentyl, neo-pentyl, and hexyl. Alkyl groups can be substituted or unsubstituted. Depending on the structure, an alkyl group can be a monoradical or a diradical (i.e., an alkylene group).

An "alkoxy" refers to a "—O-alkyl" group, where alkyl is as defined herein.

The term "alkenyl" refers to a straight or branched hydrocarbon chain radical group consisting solely of carbon and hydrogen atoms, containing at least one carbon-carbon double bond. Non-limiting examples of an alkenyl group include —CH=$CH_2$, —C($CH_3$)=$CH_2$, —CH=CH$CH_3$, —CH=C($CH_3$)$_2$ and —C($CH_3$)=CH$CH_3$. In some embodiments, an alkenyl group may have 2 to 6 carbons.

Alkenyl groups can be substituted or unsubstituted. Depending on the structure, an alkenyl group can be a monoradical or a diradical (i.e., an alkenylene group).

The term "alkynyl" refers to a straight or branched hydrocarbon chain radical group consisting solely of carbon and hydrogen atoms, containing at least one carbon-carbon triple bond. Non-limiting examples of an alkynyl group include —C≡CH, C≡C$CH_3$, —C≡C$CH_2$$CH_3$ and —C≡C$CH_2$$CH_2$$CH_3$. In some embodiments, an alkynyl group can have 2 to 6 carbons. Alkynyl groups can be substituted or unsubstituted. Depending on the structure, an alkynyl group can be a monoradical or a diradical (i.e., an alkynylene group).

"Amino" refers to a —$NH_2$ group.

The term "alkylamine" or "alkylamino" refers to the —N(alkyl)$_x$H$_y$ group, where alkyl is as defined herein and x and y are selected from the group x=1, y=1 and x=2, y=0. When x=2, the alkyl groups, taken together with the nitrogen to which they are attached, can optionally form a cyclic ring system. "Dialkylamino" refers to a —N(alkyl)$_2$ group, where alkyl is as defined herein.

The term "aromatic" refers to a planar ring having a delocalized n-electron system containing 4n+2 π electrons, where n is an integer. Aromatic rings can be formed from five, six, seven, eight, nine, or more than nine atoms. Aromatics can be optionally substituted. The term "aromatic" includes both aryl groups (e.g., phenyl, naphthalenyl) and heteroaryl groups (e.g., pyridinyl, quinolinyl).

As used herein, the term "aryl" refers to a monocyclic aromatic ring wherein each of the atoms forming the ring is a carbon atom (e.g., phenyl) or a polycyclic ring system (e.g., bicyclic or tricyclic) wherein 1) at least one ring is carbocyclic and aromatic, 2) a bond to the remainder of the compound is directly bonded to a carbocyclic aromatic ring of the aryl ring system, and 3) the carbocyclic aromatic ring of the aryl ring system of 2) is not directly bonded (e.g., fused) to a heteroaryl ring in the polycyclic ring system. Aryl rings can be formed by five, six, seven, eight, nine, or more than nine carbon atoms. Aryl groups can be optionally substituted. Examples of aryl groups include, but are not limited to phenyl, and naphthalenyl. Depending on the structure, an aryl group can be a monoradical or a diradical (i.e., an arylene group). As used herein, the aryl radical is a monocyclic, bicyclic, or tricyclic ring system. In embodiments, an aryl is a monocyclic ring. In embodiments, an aryl is a fused ring polycyclic system. In embodiments, an aryl is a bridged ring polycyclic system. In some embodiments the aryl is a "fused ring aryl" wherein the aryl ring is fused with a cycloalkyl or a heterocycloalkyl ring. In embodiments, an aryl is a "fused bicyclic" aryl wherein the two rings of the aryl group share one bond.

"Carboxy" refers to —$CO_2$H. In some embodiments, carboxy moieties may be replaced with a "carboxylic acid bioisostere", which refers to a functional group or moiety that exhibits similar physical and/or chemical properties as a carboxylic acid moiety. A carboxylic acid bioisostere has similar biological properties to that of a carboxylic acid group. A compound with a carboxylic acid moiety can have the carboxylic acid moiety exchanged with a carboxylic acid bioisostere and have similar physical and/or biological properties when compared to the carboxylic acid-containing compound. For example, in one embodiment, a carboxylic acid bioisostere would ionize at physiological pH to roughly the same extent as a carboxylic acid group. Examples of bioisosteres of a carboxylic acid include, but are not limited to,

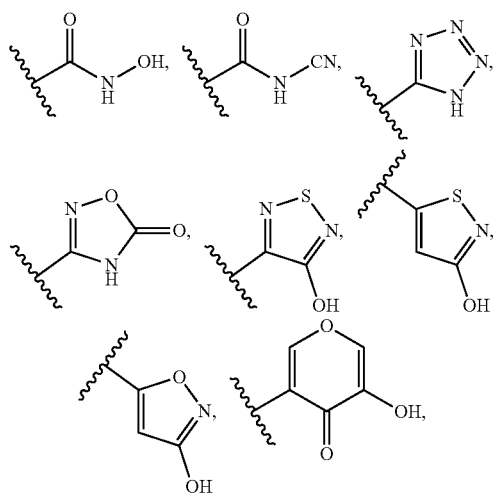

and the like.

The term "cycloalkyl" refers to a monocyclic carbocyclic saturated or partially unsaturated non-aromatic ring or a polycyclic carbocyclic (i.e., does not include heteroatom(s)) ring system (e.g., bicyclic or tricyclic) wherein 1) at least one ring is carbocyclic saturated or partially unsaturated and non-aromatic, 2) a bond to the remainder of the compound is directly bonded to a carbocyclic saturated or partially unsaturated non-aromatic ring of the ring system, and 3) the carbocyclic saturated or partially unsaturated non-aromatic ring of the ring system of 2) is not directly bonded (e.g., fused or spirocyclic) to a heterocycloalkyl ring in the polycyclic ring system. Cycloalkyls may be saturated or partially unsaturated. In some embodiments, a cycloalkyl ring is a spirocyclic cycloalkyl ring. In embodiments, a cycloalkyl is a monocyclic ring. In embodiments, a cycloalkyl is a fused ring polycyclic system. In embodiments, a cycloalkyl is a bridged ring polycyclic system. In embodiments, a cycloalkyl is a spirocyclic polycyclic ring system. In some embodiments, cycloalkyl groups include groups having from 3 to 10 ring atoms. Depending on the structure, a cycloalkyl group can be a monoradical or a diradical (i.e., a cycloalkylene group). In embodiments, a cycloalkyl is a "fused bicyclic" cycloalkyl wherein the two rings of the cycloalkyl group share one bond.

The terms "heteroaryl" or, alternatively, "heteroaromatic" refers to an monocyclic aryl group that includes one or more ring heteroatoms selected from nitrogen, oxygen and sulfur; or a polycyclic ring system (e.g., bicyclic or tricyclic) wherein 1) at least one ring is aromatic and includes one or more heteroatoms selected from nitrogen, oxygen and sulfur and 2) a bond to the remainder of the compound is directly bonded to an aromatic ring including one or more heteroatoms selected from nitrogen, oxygen and sulfur or an aromatic ring directly bonded (e.g., fused) to an aromatic ring including one or more heteroatoms selected from nitrogen, oxygen and sulfur, of the aryl ring system. As used herein, the heteroaryl radical may be a monocyclic, bicyclic, or tricyclic ring system, wherein at least one of the rings in the ring system is fully unsaturated (i.e., aromatic) and includes a heteroatom. In embodiments, a heteroaryl is a monocyclic ring. In embodiments, a heteroaryl is a fused ring polycyclic system. In embodiments, a heteroaryl is a bridged ring polycyclic system. In some embodiments is a "fused ring heteroaryl" wherein the heteroaryl ring is fused with a cycloalkyl, aryl, or heterocycloalkyl ring. An N-containing "heteroaromatic" or "heteroaryl" moiety refers to an aromatic group in which at least one of the skeletal atoms of the ring is a nitrogen atom. Depending on the structure, a heteroaryl group can be a monoradical or a diradical (i.e., a heteroarylene group). In embodiments, a heteroaryl is a "fused bicyclic" heteroaryl wherein the two rings of the heteroaryl group share one bond.

A "heterocycloalkyl" group or "heteroalicyclic" group refers to a cycloalkyl group, wherein at least one skeletal ring atom of a saturated or partially unsaturated non-aromatic ring is a heteroatom selected from nitrogen, oxygen, phosphorus, and sulfur. A heterocycloalkyl refers to a monocyclic saturated or partially unsaturated non-aromatic ring including one or more heteroatoms or a polycyclic ring system (e.g., bicyclic or tricyclic) wherein 1) at least one ring is saturated or partially unsaturated, non-aromatic, and includes one or more heteroatoms and 2) a bond to the remainder of the compound is directly bonded to a ring of the ring system that is a saturated or partially unsaturated and non-aromatic ring that includes one or more heteroatoms or a non-aromatic ring directly bonded (e.g., fused, spiro) to a saturated or partially unsaturated and non-aromatic ring that includes one or more heteroatoms of the ring system. Heterocycloalkyls may be saturated or partially unsaturated. The term heterocycloalkyl also includes all ring forms of the carbohydrates, including but not limited to the monosaccharides, the disaccharides and the oligosaccharides. In some embodiments, a heterocycloalkyl ring is a spirocyclic heterocycloalkyl ring. In embodiments, a heterocycloalkyl is a monocyclic ring. In embodiments, a heterocycloalkyl is a fused ring polycyclic system. In embodiments, a heterocycloalkyl is a bridged ring polycyclic system. In embodiments, a heterocycloalkyl is a spirocyclic polycyclic ring system. Unless otherwise noted, heterocycloalkyls have from 2 to 13 carbons in the ring or ring system. It is understood that when referring to the number of carbon atoms in a heterocycloalkyl, the number of carbon atoms in the heterocycloalkyl is not the same as the total number of atoms (including the heteroatoms) that make up the heterocycloalkyl (i.e. skeletal atoms of the heterocycloalkyl ring). Depending on the structure, a heterocycloalkyl group can be a monoradical or a diradical (i.e., a heterocycloalkylene group). In embodiments, a heterocycloalkyl is a "fused bicyclic" heterocycloalkyl wherein the two rings of the heterocycloalkyl group share one bond.

The term "halo" or, alternatively, "halogen" means fluoro, chloro, bromo and iodo.

The abbreviations "Fmoc", "Ac", "Bn", "PMB", "Tr", "Ts", "Boc", and "Cbz" are used in accordance with their well understood common meanings in Chemistry and mean the monovalent chemical substituents fluorenylmethyloxycarbonyl, acetyl, benzyl, p-methoxybenzyl, trityl or triphenylmethyl, tosyl, tert-butyloxycarbonyl, and carbobenzyloxy, respectively. The term "monovalent" is used herein in accordance with its well understood meaning in Chemistry and refers to the ability of a substituent to form one covalent bond with another substituent or compound capable of forming a covalent bond. In a related manner, the term "divalent" refers to a substituent or compound capable of forming two covalent bonds, for example a linker capable of covalently connecting two monovalent substituents or compounds.

The term "haloalkyl" refers to an alkyl group that is substituted with one or more halogens. The halogens may be the same or they may be different. Non-limiting examples of haloalkyls include —$CH_2Cl$, —$CF_3$, —$CHF_2$, —$CH_2CF_3$, —$CF_2CF_3$, and the like.

The terms "fluoroalkyl" and "fluoroalkoxy" include alkyl and alkoxy groups, respectively, that are substituted with one or more fluorine atoms. Non-limiting examples of fluoroalkyls include —$CF_3$, —$CHF_2$, —$CH_2F$, —$CH_2CF_3$, —$CF_2CF_3$, —$CF_2CF_2CF_3$, —$CF(CH_3)_3$, and the like. Non-limiting examples of fluoroalkoxy groups, include —$OCF_3$, —$OCHF_2$, —$OCH_2F$, —$OCH_2CF_3$, —$OCF_2CF_3$, —$OCF_2CF_2CF_3$, —$OCF(CH_3)_2$, and the like.

The term "heteroalkyl" refers to an alkyl radical where one or more skeletal chain atoms is selected from an atom other than carbon, e.g., oxygen, nitrogen, sulfur, phosphorus, silicon, or combinations thereof. The heteroatom(s) may be placed at any interior position of the heteroalkyl group. Examples include, but are not limited to, —$CH_2$—O—$CH_3$, —$CH_2$—$CH_2$—O—$CH_3$, —$CH_2$—NH—$CH_3$, —$CH_2$—$CH_2$—NH—$CH_3$, —$CH_2$—N($CH_3$)—$CH_3$, —$CH_2$—$CH_2$—NH—$CH_3$, —$CH_2$—$CH_2$—N($CH_3$)—$CH_3$, —$CH_2S$—$CH_2$—$CH_3$, —$CH_2$—$CH_2$—S(O)—$CH_3$, —$CH_2$—$CH_2$—S(O)$_2$—$CH_3$, —$CH_2$—NH—$OCH_3$, —$CH_2$—O—Si($CH_3$)$_3$, —$CH_2$—CH═N—$OCH_3$, and —CH═CH—N($CH_3$)—$CH_3$. In addition, up to two heteroatoms may be consecutive, such as, by way of example, —$CH_2$—NH—$OCH_3$ and —$CH_2$—O—Si($CH_3$)$_3$. Excluding the number of heteroatoms, a "heteroalkyl" may have from 1 to 6 carbon atoms.

The term "heteroalkylene linker" refers to a divalent alkyl radical where one or more skeletal chain atoms is selected from an atom other than carbon, e.g., oxygen, nitrogen, sulfur, phosphorus, silicon, or combinations thereof. In some embodiments, the heteroatom(s) may be placed at any interior position of the heteroalkyl group. In some embodiments, the heteroatom(s) may be placed at one or both terminal positions of the heteroalkylene linker (i e , position(s) directly bonded to portion(s) of the molecule other than the heteroalkylene linker) Examples include, but are not limited to, —$CH_2$—O—$CH_2$—, —$CH_2$—$CH_2$—O—$CH_2$—, —$CH_2$—NH—$CH_2$—, —$CH_2$—$CH_2$—NH—$CH_2$—, —$CH_2$—N($CH_3$)—$CH_2$—, —$CH_2$—$CH_2$—N($CH_3$)—$CH_2$—, —$CH_2$—S—$CH_2$—$CH_2$—, —$CH_2$—$CH_2$—S(O)—$CH_2$—, —$CH_2$—$CH_2$—S(O)$_2$—$CH_2$—, —$CH_2$—NH—O—$CH_2$—, —$CH_2$—O—Si($CH_3$)$_2$—, —$CH_2$—CH═N—O—$CH_2$—, and —CH═CH—N($CH_3$)—$CH_2$—. Examples include, but are not limited to, —$CH_2$—O—, —$CH_2$—$CH_2$—O—, —$CH_2$—NH—, —$CH_2$—$CH_2$—NH—, —$CH_2$—N($CH_3$)—, —$CH_2$—$CH_2$—N($CH_3$)—, —$CH_2$—S—, —$CH_2$—$CH_2$—S—, —$CH_2$—$CH_2$—S(O)—, —$CH_2$—$CH_2$—S(O)$_2$—, —$CH_2$—S(O)—, —$CH_2$—S(O)$_2$—, —$CH_2$—$CH_2$—S(O)—, —$CH_2$—$CH_2$—$CH_2$—S(O)$_2$—, —$CH_2$—$CH_2$—$CH_2$—O—, —$CH_2$—$CH_2$—$CH_2$—O—, —$CH_2$—$CH_2$—$CH_2$—S—, —$CH_2$—$CH_2$—$CH_2$—S—, —$CH_2$—$CH_2$—NH—, —$CH_2$—$CH_2$—$CH_2$—NH—, —$CH_2$—$CH_2$—$CH_2$—N($CH_3$)—, —$CH_2$—$CH_2$—$CH_2$—N($CH_3$)—, —$CH_2$—NH—O—, —O—Si($CH_3$)$_2$—, —$CH_2$—CH═N—O—, and —CH═CH—N($CH_3$)—. Examples include, but are not limited to, —O—$CH_2$—, —O—$CH_2$—$CH_2$—, —NH—$CH_2$—, —NH—$CH_2$—$CH_2$—, —N($CH_3$)—$CH_2$—, —N($CH_3$)—$CH_2$—$CH_2$—, —S—$CH_2$—, —S—$CH_2$—$CH_2$—, —S(O)—$CH_2$—, —S(O)$_2$—$CH_2$—$CH_2$—, —S(O)—$CH_2$—, —S(O)$_2$—$CH_2$—, —S(O)—$CH_2$—$CH_2$—, —S(O)$_2$—$CH_2$—$CH_2$—$CH_2$—, —O—$CH_2$—$CH_2$—$CH_2$—, —O—$CH_2$—$CH_2$—$CH_2$—, —S—$CH_2$—$CH_2$—$CH_2$—, —S—$CH_2$—$CH_2$—$CH_2$—, —NH—$CH_2$—$CH_2$—, —NH—$CH_2$—$CH_2$—$CH_2$—, —N($CH_3$)—$CH_2$—$CH_2$—, —N($CH_3$)—$CH_2$—$CH_2$—$CH_2$—, —N($CH_3$)—$CH_2$—$CH_2$—$CH_2$—, —O—NH—$CH_2$—, —Si($CH_3$)$_2$—O—, —O—N═CH—$CH_2$—, and —N($CH_3$)'CH═CH—. In addition, up to two heteroatoms may be consecutive, such as, by way of example, —$CH_2$—NH—O— and —O—Si($CH_3$)$_2$—. Examples include, but are not limited to, —P(O)($CH_3$)—$CH_2$—, —P(O)($CH_3$)—$CH_2$—$CH_2$—, —P(O)($CH_3$)—$CH_2$—$CH_2$—$CH_2$—, —$CH_2$—P(O)($CH_3$)—, —$CH_2$—$CH_2$—P(O)($CH_3$)—, and —$CH_2$—$CH_2$—$CH_2$—P(O)($CH_3$)—. In addition, up to two heteroatoms may be consecutive, such as, by way of example, —$CH_2$—NH—O— and —O—Si($CH_3$)$_2$—. A "heteroalkylene linker" may have from 2 to 4 main chain atoms unless specified otherwise.

The term "oxo" refers to the ═O radical.

The term "bond" or "single bond" refers to a chemical bond between two atoms, or two moieties when the atoms joined by the bond are considered to be part of larger substructure.

The term "moiety" refers to a specific segment or functional group of a molecule. Chemical moieties are often recognized chemical entities embedded in or appended to a molecule.

The suffix "-di-yl" will be understood to mean the substituent or linker is a divalent substituent or linker.

As used herein, the substituent "R" appearing by itself and without a number designation refers to a substituent selected from among from alkyl, haloalkyl, heteroalkyl, alkenyl, cycloalkyl, aryl, heteroaryl (bonded through a ring carbon), and heterocycloalkyl.

"Optional" or "optionally" means that a subsequently described event or circumstance may or may not occur and that the description includes instances when the event or circumstance occurs and instances in which it does not.

The term "optionally substituted" or "substituted" means, unless otherwise specified, that the referenced group may be substituted with one or more additional group(s) individually and independently selected from alkyl, cycloalkyl, aryl, heteroaryl, heterocycloalkyl, —OH, alkoxy, aryloxy, alkylthio, arylthio, alkylsulfoxide, arylsulfoxide, alkylsulfone, arylsulfone, —CN, alkyne, $C_1$-$C_6$alkylalkyne, halo, acyl, acyloxy, —$CO_2$H, —$CO_2$-alkyl, nitro, haloalkyl, fluoroalkyl, and amino, including mono- and di-substituted amino groups (e.g. —$NH_2$, —NHR, —$NR_2$), and the protected derivatives thereof. By way of example, an optional substituents may be $L^sR^s$, wherein each $L^s$ is independently selected from a bond, —O—, —C(═O)—, —S—, —S(═O)—, —S(═O)$_2$—, —NH—, —NHC(O)—, —C(O)NH—, S(═O)$_2$NH—, —NHS(═O)$_2$, —OC(O)NH—, —NHC(O)O—, -($C_1$-$C_6$alkyl)-, or -($C_2$-$C_6$alkenyl)-; and each $R^s$ is independently selected from among H, ($C_1$-$C_6$alkyl), ($C_3$-$C_8$cycloalkyl), aryl, heteroaryl, heterocycloalkyl, and $C_1$-$C_6$heteroalkyl. The protecting groups that may form the protective derivatives of the above substituents are found in sources such as Greene and Wuts, above.

"Pharmaceutically acceptable salt" includes both acid and base addition salts. A pharmaceutically acceptable salt of any one of the compounds described herein is intended to encompass any and all pharmaceutically suitable salt forms. Preferred pharmaceutically acceptable salts of the compounds described herein are pharmaceutically acceptable acid addition salts and pharmaceutically acceptable base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid, hydroiodic acid, hydrofluoric acid, phosphorous acid, and the like. Also included are salts that are formed with organic acids such as aliphatic mono- and dicarboxylic acids, phenyl-substituted alkanoic acids, hydroxy alkanoic acids, alkanedioic acids, aromatic acids, aliphatic and. aromatic sulfonic acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Exemplary salts thus include sulfates, pyrosulfates, bisulfates, sulfites, bisulfites, nitrates, phosphates, monohydrogenphosphates, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, fumarates, maleates, mandelates, benzoates, chlorobenzoates, methylbenzoates, dinitrobenzoates, phthalates, benzenesulfonates, toluenesulfonates, phenylacetates, citrates, lactates, malates, tartrates, methanesulfonates, and the like. Also contemplated are salts of amino acids, such as arginates, gluconates, and galacturonates (see, for example, Berge S. M. et al., "Pharmaceutical Salts," *Journal of Pharmaceutical Science,* 66:1-19 (1997)). Acid addition salts of basic compounds are, in some embodiments, prepared by contacting the free base forms with a sufficient amount of the desired acid to produce the salt according to methods and techniques with which a skilled artisan is familiar.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. Pharmaceutically acceptable base addition salts are, in some embodiments, formed with metals or amines, such as alkali and alkaline earth metals or organic amines Salts derived from inorganic bases include, but are not limited to, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N,N-dibenzylethylenediamine, chloroprocaine, hydrabamine, choline, betaine, ethylenediamine, ethylenedianiline, N-methylglucamine, glucosamine, methylglucamine, theobromine, purines, piperazine, piperidine, N-ethylpiperidine, polyamine resins and the like. See Berge et al., supra.

The terms "polypeptide", "peptide" and "protein" are used interchangeably herein to refer to polymers of amino acids of any length. The polymer may be linear or branched, it may comprise modified amino acids, and it may be interrupted by non-amino acids. The terms also encompass an amino acid polymer that has been modified; for example, disulfide bond formation, glycosylation, lipidation, acetylation, phosphorylation, or any other manipulation, such as conjugation with a labeling component. As used herein the term "amino acid" refers to either natural and/or unnatural or synthetic amino acids, including glycine and both the D or L optical isomers, and amino acid analogs and peptidomimetics.

The terms "polynucleotide", "nucleotide", "nucleotide sequence", "nucleic acid" and "oligonucleotide" are used interchangeably. They refer to a polymeric form of nucleotides of any length, either deoxyribonucleotides or ribonucleotides, or analogs thereof. Polynucleotides may have any three dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA, ribosomal RNA, short interfering RNA (siRNA), short-hairpin RNA (shRNA), micro-RNA (miRNA), ribozymes, cDNA, recombinant polynucleotides, branched polynucleotides, plasmids, vectors, isolated DNA of any sequence, isolated RNA of any sequence, nucleic acid probes, and primers. A polynucleotide may comprise one or more modified nucleotides, such as methylated nucleotides and nucleotide analogs, such as peptide nucleic acid (PNA), Morpholino and locked nucleic acid (LNA), glycol nucleic acid (GNA), threose nucleic acid (TNA), 2'-fluoro, 2'-OMe, and phosphorothiolated DNA. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component or other conjugation target.

As used herein, "expression" refers to the process by which a polynucleotide is transcribed from a DNA template (such as into and mRNA or other RNA transcript) and/or the process by which a transcribed mRNA is subsequently translated into peptides, polypeptides, or proteins. Transcripts and encoded polypeptides may be collectively referred to as "gene product." If the polynucleotide is derived from genomic DNA, expression may include splicing of the mRNA in a eukaryotic cell.

The terms "subject," "individual," and "patient" are used interchangeably herein to refer to a vertebrate, preferably a mammal, more preferably a human. Mammals include, but are not limited to, murines, simians, humans, farm animals, sport animals, and pets. Tissues, cells, and their progeny of a biological entity obtained in vivo or cultured in vitro are also encompassed.

The terms "agent" or "therapeutic agent", "therapeutic capable agent" or "treatment agent" are used interchangeably and refer to a molecule or compound that confers some beneficial effect upon administration to a subject. The beneficial effect includes enablement of diagnostic determinations; amelioration of a disease, symptom, disorder, or pathological condition; reducing or preventing the onset of a disease, symptom, disorder or condition; and generally counteracting a disease, symptom, disorder or pathological condition.

As used herein, "treatment" or "treating," or "palliating" or "ameliorating" are used interchangeably. These terms refer to an approach for obtaining beneficial or desired results including but not limited to a therapeutic benefit and/or a prophylactic benefit. By therapeutic benefit is meant any therapeutically relevant improvement in or effect on one or more diseases, conditions, or symptoms under treatment. For prophylactic benefit, the compositions may be administered to a subject at risk of developing a particular disease, condition, or symptom, or to a subject reporting one or more of the physiological symptoms of a disease, even though the disease, condition, or symptom may not have yet been manifested. Typically, prophylactic benefit includes reducing the incidence and/or worsening of one or more diseases, conditions, or symptoms under treatment (e.g. as between treated and untreated populations, or between treated and untreated states of a subject).

The term "effective amount" or "therapeutically effective amount" refers to the amount of an agent that is sufficient to effect beneficial or desired results. The therapeutically effective amount may vary depending upon one or more of: the subject and disease condition being treated, the weight and age of the subject, the severity of the disease condition, the manner of administration and the like, which can readily be determined by one of ordinary skill in the art. An effective amount of an active agent may be administered in a single dose or in multiple doses. A component may be described herein as having at least an effective amount, or at least an amount effective, such as that associated with a particular goal or purpose, such as any described herein. The term "effective amount" also applies to a dose that will provide an image for detection by an appropriate imaging method. The specific dose may vary depending on one or more of: the particular agent chosen, the dosing regimen to be followed, whether it is administered in combination with other compounds, timing of administration, the tissue to be imaged, and the physical delivery system in which it is carried.

The term "in vivo" refers to an event that takes place in a subject's body.

The term "ex vivo" refers to an event that first takes place outside of the subject's body for a subsequent in vivo application into a subject's body. For example, an ex vivo preparation may involve preparation of cells outside of a subject's body for the purpose of introduction of the prepared cells into the same or a different subject's body.

The term "in vitro" refers to an event that takes place outside of a subject's body. For example, an in vitro assay encompasses any assay run outside of a subject's body. In vitro assays encompass cell-based assays in which cells alive or dead are employed. In vitro assays also encompass a cell-free assay in which no intact cells are employed.

The term "Ras" or "RAS" refers to a protein in the Rat sarcoma (Ras) superfamily of small GTPases, such as in the Ras subfamily. The Ras superfamily includes, but is not limited to, the Ras subfamily, Rho subfamily, Rab subfamily, Rap subfamily, Arf subfamily, Ran subfamily, Rheb subfamily, RGK subfamily, Rit subfamily, Miro subfamily, and Unclassified subfamily. In some embodiments, a Ras protein is selected from the group consisting of KRAS (also used interchangeably herein as K-Ras, K-ras, Kras), HRAS (or H-Ras), NRAS (or N-Ras), MRAS (or M-Ras), ERAS (or E-Ras), RRAS2 (or R-Ras2), RALA (or RalA), RALB (or RalB), RIT1, and any combination thereof, such as from KRAS, HRAS, NRAS, RALA, RALB, and any combination thereof. The terms "mutant Ras" and "Ras mutant," as used interchangeably herein, refer to a Ras protein with one or more amino acid mutations, such as with respect to a common reference sequence such as a wild-type (WT) sequence. In some embodiments, a mutant Ras is selected from a mutant KRAS, mutant HRAS, mutant NRAS, mutant MRAS, mutant ERAS, mutant RRAS2, mutant RALA, mutant RALB, mutant RIT1, and any combination thereof, such as from a mutant KRAS, mutant HRAS, mutant NRAS, mutant RALA, mutant RALB, and any combination thereof. In some embodiments, a mutation can be an introduced mutation, a naturally occurring mutation, or a non-naturally occurring mutation. In some embodiments, a mutation can be a substitution (e.g., a substituted amino acid), insertion (e.g., addition of one or more amino acids), or deletion (e.g., removal of one or more amino acids). In some embodiments, two or more mutations can be consecutive, non-consecutive, or a combination thereof. In some embodiments, a mutation can be present at any position of Ras. In some embodiments, a mutation can be present at position 12, 13, 62, 92, 95, or any combination thereof of Ras of SEQ ID No. 2 when optimally aligned. In some embodiments, a mutant Ras may comprise about or at least about 1, 2, 3, 4, 5, 6, 7, 8, 9, 10, 11, 12, 13, 14, 15, 16, 17, 18, 19, 20, 25, 30, 35, 40, 45, 50, or more than 50 mutations. In some embodiments, a mutant Ras may comprise up to about 1, 2, 3, 4, 5, 6, 7, 8, 9, 10, 11, 12, 13, 14, 15, 16, 17, 18, 19, 20, 25, 30, 35, 40, 45, or 50 mutations. In some embodiments, the mutant Ras is about or up to about 500, 400, 300, 250, 240, 233, 230, 220, 219, 210, 208, 206, 204, 200, 195, 190, 189, 188, 187, 186, 185, 180, 175, 174, 173, 172, 171, 170, 169, 168, 167, 166, 165, 160, 155, 150, 125, 100, 90, 80, 70, 60, 50, or fewer than 50 amino acids in length. In some embodiments, an amino acid of a mutation is a proteinogenic, natural, standard, non-standard, non-canonical, essential, non-essential, or non-natural amino acid. In some embodiments, an amino acid of a mutation has a positively charged side chain, a negatively charged side chain, a polar uncharged side chain, a non-polar side chain, a hydrophobic side chain, a hydrophilic side chain, an aliphatic side chain, an aromatic side chain, a cyclic side chain, an acyclic side chain, a basic side chain, or an acidic side chain. In some embodiments, a mutation comprises a reactive moiety. In some embodiments, a substituted amino acid comprises a reactive moiety. In some embodiments, a mutant Ras can be further modified, such as by conjugation with a detectable label. In some embodiments, a mutant Ras is a full-length or truncated polypeptide. For example, a mutant Ras can be a truncated polypeptide comprising residues 1-169 or residues 11-183 (e.g., residues 11-183 of a mutant RALA or mutant RALB).

As used herein, the term "corresponding to" or "corresponds to" as applied to an amino acid residue in a polypeptide sequence refers to the correspondence of such amino acid relative to a reference sequence when optimally aligned (e.g., taking into consideration of gaps, insertions and mismatches; wherein alignment may be primary sequence alignment or three dimensional structural alignment of the folded proteins). For instance, the serine residue in a Ras G12S mutant refers to the serine corresponding to residue 12 of SEQ ID No. 4, which can serve as a reference sequence.). For instance, the aspartate residue in a Ras G12D mutant refers to the aspartate corresponding to residue 12 of SEQ ID No. 2, which can serve as a reference sequence. When an amino acid of a mutant Ras protein corresponds to an amino acid position in the WT Ras protein, it will be understood that although the mutant Ras protein amino acid may be a different amino acid (e.g., G12D wherein the wildtype G at position 12 is replaced by an aspartate at position 12 of SEQ ID. No. 1), the mutant amino acid is at the position corresponding to the wildtype amino acid (e.g., of SEQ ID No. 1). In embodiments, a modified Ras mutant protein disclosed herein may comprise truncations at C-terminus, or truncations at the N-terminal end preceding the serine residue. The serine residue in such N-terminal truncated modified mutant is still considered corresponding to position 12 of SEQ ID No. 1. In addition, serine residue at position 12 of SEQ ID No. 4 finds a corresponding residue in SEQ ID Nos. 6 and 8. "Prodrug" as used herein is meant to indicate a compound that may be converted under physiological conditions or by solvolysis to a biologically active compound described herein. The term "prodrug" refers to a precursor of a biologically active compound that is pharmaceutically acceptable. A prodrug may be inactive when administered to a subject, but is converted in vivo to an active compound, for example, by hydrolysis. The prodrug compound may offer advantages of solubility, tissue compatibility and/or delayed release in a mammalian organism (see, e.g., Bundgard, H., Design of Prodrugs (1985), pp. 7-9, 21-24 (Elsevier, Amsterdam). A discussion of prodrugs is provided in Higuchi, T., et al., "Pro-drugs as Novel Delivery Systems," A.C.S. Symposium Series, Vol. 14, and in Bioreversible Carriers in Drug Design, ed. Edward B. Roche, American Pharmaceutical Association and Pergamon Press, 1987, both of which are incorporated in full by reference herein. A "prodrug" can be any covalently bonded carriers, that release the active compound in vivo when such prodrug is administered to a mammalian subject. Prodrugs of an active compound, as described herein, may be prepared by modifying functional groups present in the active compound in such a way that the modifications are cleaved, either in routine manipulation or in vivo, to the parent active compound.

The term "leaving group" is used herein in accordance with their well understood meanings in Chemistry and refers to an atom or group of atoms which breaks away from the rest of the molecule, taking with it the electron pair which used to be the bond between the leaving group and the rest of the molecule.

A "degradation enhancer" is a compound capable of binding a ubiquitin ligase protein (e.g., E3 ubiquitin ligase protein) or a compound capable of binding a protein that is capable of binding to a ubiquitin ligase protein to form a protein complex capable of conjugating a ubiquitin protein to a target protein. In embodiments, the degradation enhancer is capable of binding to an E3 ubiquitin ligase protein or a protein complex comprising an E3 ubiquitin ligase protein. In embodiments, the degradation enhancer is capable of binding to an E2 ubiquitin-conjugating enzyme. In embodiments, the degradation enhancer is capable of binding to a protein complex comprising an E2 ubiquitin-conjugating enzyme and an E3 ubiquitin ligase protein.

⁓⁓⁓⁓ drawn across a bond or at the end of a bond or a dashed bond " - - - " indicates the location of a bond disconnection or attachment (e.g., location of a bond to another atom) of the depicted chemical formula or atom to a substituent, a further component of a molecule, or an atom. For example,

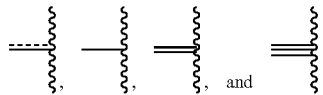

indicate a single or double bond, single bond, double bond, and triple bond, respectively, wherein the ⌇ is as defined immediately above.

Compounds

In an aspect is provided a compound of Formula (A), or a pharmaceutically acceptable salt or solvate thereof:

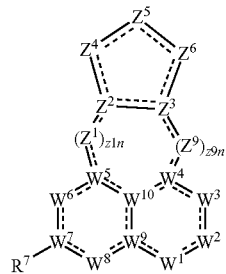

(A)

wherein:

$W^1$ is $N(R^1)$ or N;

$R^1$ is selected from hydrogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$C(O)OR^{12}$, —$OC(O)N(R^{12})(R^{13})$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$S(O)_2R^{15}$, —$S(O)_2N(R^{12})(R^{13})$, $S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20a}$;

$W^2$ is $C(R^2)$, $N(R^2)$, $C(R^2)_2$, $C(O)$, $S(O)$, $S(O)_2$, or N;

each $R^2$ is independently selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12a}$, —$SR^{12a}$, —$N(R^{12a})(R^{13})$, —$N=(R^{15})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20b}$;

$W^3$ is $C(R^3)$, $N(R^3)$, $C(R^3)_2$, $C(O)$, $S(O)$, $S(O)_2$, or N;

each $R^3$ is independently selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$, $S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20c}$;

$W^4$ is $C(R^4)$, C, or N;

$R^4$ is selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)

$R^{15}$, —C(O)N($R^{12}$)($R^{13}$), —C(O)C(O)N($R^{12}$)($R^{13}$), —N($R^{14}$)C(O)$R^{15}$, —S(O)$_2R^{15}$, —S(O)$_2$N($R^{12}$)($R^{13}$), S(=O)(=NH)N($R^{12}$)($R^{13}$), —CH$_2$C(O)N($R^{12}$)($R^{13}$), —CH$_2$N($R^{14}$)C(O)$R^{15}$, —CH$_2$S(O)$_2R^{15}$, and —CH$_2$S(O)$_2$N($R^{12}$)($R^{13}$), wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20d}$;

$W^5$ is C($R^5$), C, or N;

$R^5$ is selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —O$R^{12}$, —S$R^{12}$, —N($R^{12}$)($R^{13}$), —C(O)O$R^{12}$, —OC(O)N($R^{12}$)($R^{13}$), —N($R^{14}$)C(O)N($R^{12}$)($R^{13}$), —N($R^{14}$)C(O)O$R^{15}$, —N($R^{14}$)S(O)$_2R^{15}$, —C(O)$R^{15}$, —S(O)$R^{15}$, —OC(O)$R^{15}$, —C(O)N($R^{12}$)($R^{13}$), —C(O)C(O)N($R^{12}$)($R^{13}$), —N($R^{14}$)C(O)$R^{15}$, —S(O)$_2R^{15}$, —S(O)$_2$N($R^{12}$)($R^{13}$), —S(=O)(=NH)N($R^{12}$)($R^{13}$), —CH$_2$C(O)N($R^{12}$)($R^{13}$), —CH$_2$N($R^{14}$)C(O)$R^{15}$, —CH$_2$S(O)$_2R^{15}$, and —CH$_2$S(O)$_2$N($R^{12}$)($R^{13}$), wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20e}$;

$W^6$ is C($R^6$), N($R^6$), C($R^6$)$_2$, C(O), S(O), S(O)$_2$, or N;

each $R^6$ is independently selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —O$R^{12}$, —S$R^{12}$, —N($R^{12}$)($R^{13}$), —C(O)O$R^{12}$, —OC(O)N($R^{12}$)($R^{13}$), —N($R^{14}$)C(O)N($R^{12}$)($R^{13}$), —N($R^{14}$)C(O)O$R^{15}$, —N($R^{14}$)S(O)$_2R^{15}$, —C(O)$R^{15}$, —S(O)$R^{15}$, —OC(O)$R^{15}$, —C(O)N($R^{12}$)($R^{13}$), —C(O)C(O)N($R^{12}$)($R^{13}$), —N($R^{14}$)C(O)$R^{15}$, —S(O)$_2R^{15}$, —S(O)$_2$N($R^{12}$)($R^{13}$), —S(=O)(=NH)N($R^{12}$)($R^{13}$), —CH$_2$C(O)N($R^{12}$)($R^{13}$), —CH$_2$N($R^{14}$)C(O)$R^{15}$, —CH$_2$S(O)$_2R^{15}$, and —CH$_2$S(O)$_2$N($R^{12}$)($R^{13}$), wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20f}$;

$W^7$ is C($R^{7a}$), C, or N;

$R^{7a}$ is selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —O$R^{12}$, —S$R^{12}$, —N($R^{12}$)($R^{13}$), —C(O)O$R^{12}$, —OC(O)N($R^{12}$)($R^{13}$), —N($R^{14}$)C(O)N($R^{12}$)($R^{13}$), —N($R^{14}$)C(O)O$R^{15}$, —N($R^{14}$)S(O)$_2R^{15}$, —C(O)$R^{15}$, —S(O)$R^{15}$, —OC(O)$R^{15}$, —C(O)N($R^{12}$)($R^{13}$), —C(O)C(O)N($R^{12}$)($R^{13}$), —N($R^{14}$)C(O)$R^{15}$, —S(O)$_2R^{15}$, —S(O)$_2$N($R^{12}$)($R^{13}$), —S(=O)(=NH)N($R^{12}$)($R^{13}$), —CH$_2$C(O)N($R^{12}$)($R^{13}$), —CH$_2$N($R^{14}$)C(O)$R^{15}$, —CH$_2$S(O)$_2R^{15}$, and —CH$_2$S(O)$_2$N($R^{12}$)($R^{13}$), wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20g}$;

$R^7$ is -$L^7$—$R^{17}$;

$L^7$ is a bond, $C_1$-$C_4$alkyl, $C_2$-$C_4$alkenyl, $C_2$-$C_4$alkynyl, 2-4 membered heteroalkylene linker, —O—, —N($R^{7d}$)—, —C(O)—, —S—, —S(O)$_2$—, —S(O)—, —P(O)$R^{7d}$—, C$R^{7c}R^{7c}$, —OC$R^{7c}R^{7c}$—, —N($R^{7d}$)C$R^{7c}R^{7c}$—, —C(O)C$R^{7c}R^{7c}$—, —SC$R^{7c}R^{7c}$—, —S(O)$_2$C$R^{7c}R^{7c}$—, —S(O)C$R^{7c}R^{7c}$—, —P(O)$R^{7d}$C$R^{7c}R^{7c}$—, —C$R^{7c}R^{7c}$C$R^{7c}R^{7c}$—, —C$R^{7c}R^{7c}$O—, —C$R^{7c}R^{7c}$N($R^{7d}$)—, —C$R^{7c}R^{7c}$C(O)—, —C$R^{7c}R^{7c}$S—, —C$R^{7c}R^{7c}$S(O)$_2$—, —C$R^{7c}R^{7c}$S(O)—, —C$R^{7c}R^{7c}$P(O)$R^{7d}$—, —N($R^{7d}$)C(O)—, —N($R^{7d}$)S(O)$_2$—, —N($R^{7d}$)S(O)—, —N($R^{7d}$)P(O)$R^{7d}$—, —C(O)N($R^{7d}$)—, —S(O)$_2$N($R^{7d}$)—, —S(O)N($R^{7d}$)—, —P(O)$R^{7d}$N($R^{7d}$)—, —OC(O)—, —OS(O)$_2$—, —OS(O)—, —OP(O)$R^{7d}$—, —C(O)O—, —S(O)$_2$O—, —S(O)O—, or —P(O)$R^{7d}$O—;

wherein the $C_1$-$C_4$alkyl, $C_2$-$C_4$alkenyl, $C_2$-$C_4$alkynyl, 2-4 membered heteroalkylene linker are optionally substituted with one, two, or three $R^{20g}$;

each $R^{7c}$ is independently selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —O$R^{12}$, —S$R^{12}$, —N($R^{12}$)($R^{13}$), —C(O)O$R^{12}$, —OC(O)N($R^{12}$)($R^{13}$), —N($R^{14}$)C(O)N($R^{12}$)($R^{13}$), —N($R^{14}$)C(O)O$R^{15}$, —N($R^{14}$)S(O)$_2R^{15}$, —C(O)$R^{15}$, —S(O)$R^{15}$, —OC(O)$R^{15}$, —C(O)N($R^{12}$)($R^{13}$), —C(O)C(O)N($R^{12}$)($R^{13}$), —N($R^{14}$)C(O)$R^{15}$, —S(O)$_2R^{15}$, —S(O)$_2$N($R^{12}$)($R^{13}$), S(=O)(=NH)N($R^{12}$)($R^{13}$), —CH$_2$C(O)N($R^{12}$)($R^{13}$), —CH$_2$N($R^{14}$)C(O)$R^{15}$, —CH$_2$S(O)$_2R^{15}$, and —CH$_2$S(O)$_2$N($R^{12}$)($R^{13}$), wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20g}$;

each $R^{7d}$ is independently selected from hydrogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —O$R^{12}$, —S$R^{12}$, —C(O)O$R^{12}$, —OC(O)N($R^{12}$)($R^{13}$), —C(O)$R^{15}$, —S(O)$R^{15}$, —OC(O)$R^{15}$, —C(O)N($R^{12}$)($R^{13}$), —C(O)C(O)N($R^{12}$)($R^{13}$), —S(O)$_2R^{15}$, —S(O)$_2$N($R^{12}$)($R^{13}$), —S(=O)(=NH)N($R^{12}$)($R^{13}$), —CH$_2$C(O)N($R^{12}$)($R^{13}$), —CH$_2$N($R^{14}$)C(O)$R^{15}$, —CH$_2$S(O)$_2R^{15}$, and —CH$_2$S(O)$_2$N($R^{12}$)($R^{13}$), wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20g}$;

$R^{17}$ is selected from $C_{3-10}$cycloalkyl, 3-10 membered heterocycloalkyl, $C_{6-10}$aryl, and 5-10 membered heteroaryl, wherein $C_{3-10}$cycloalkyl, 3-10 membered heterocycloalkyl, $C_{6-10}$aryl, and 5-10 membered heteroaryl are optionally substituted with one or more $R^{20q}$;

$W^8$ is C($R^8$), N($R^8$), C($R^8$)$_2$, C(O), S(O), S(O)$_2$, or N;

each $R^8$ is independently selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —O$R^{12}$, —S$R^{12}$, —N($R^{12}$)($R^{13}$), —C(O)O$R^{12}$, —OC(O)N($R^{12}$)($R^{13}$), —N($R^{14}$)C(O)N($R^{12}$)($R^{13}$), —N($R^{14}$)C(O)O$R^{15}$, —N($R^{14}$)S(O)$_2R^{15}$, —C(O)$R^{15}$, —S(O)$R^{15}$, —OC(O)$R^{15}$, —C(O)N($R^{12}$)($R^{13}$), —C(O)C(O)N($R^{12}$)($R^{13}$), —N($R^{14}$)C(O)$R^{15}$, —S(O)$_2R^{15}$, —S(O)$_2$N($R^{12}$)($R^{13}$), —S(=O)(=NH)N($R^{12}$)($R^{13}$), —CH$_2$C(O)N($R^{12}$)($R^{13}$), —CH$_2$N($R^{14}$)C(O)$R^{15}$, —CH$_2$S(O)$_2R^{15}$, and —CH$_2$S(O)$_2$N($R^{12}$)($R^{13}$), wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20h}$;

$W^9$ is C($R^9$), C, or N;

$R^9$ is selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —O$R^{12}$, —S$R^{12}$, —N($R^{12}$)($R^{13}$), —C(O)O$R^{12}$, —OC(O)N($R^{12}$)($R^{13}$), —N($R^{14}$)C(O)N($R^{12}$)($R^{13}$), —N($R^{14}$)C(O)O$R^{15}$, —N($R^{14}$)S(O)$_2R^{15}$, —C(O)$R^{15}$, —S(O)$R^{15}$, —OC(O)$R^{15}$, —C(O)N($R^{12}$)($R^{13}$), —C(O)C(O)N($R^{12}$)($R^{13}$), —N($R^{14}$)C(O)$R^{15}$, —S(O)$_2R^{15}$, —S(O)$_2$N($R^{12}$)($R^{13}$), —S(=O)(=NH)N($R^{12}$)($R^{13}$), —CH$_2$C(O)N($R^{12}$)($R^{13}$), —CH$_2$N($R^{14}$)C(O)$R^{15}$, —CH$_2$S(O)$_2R^{15}$, and —CH$_2$S(O)$_2$N($R^{12}$)($R^{13}$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20i}$;

$W^{10}$ $C(R^{10})$, C, or N;

$R^{10}$ is selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20j}$;

each $Z^1$ is independently $C(R^{z1})$, $N(R^{z1})$, $C(R^{z1})_2$, $C(O)$, $S(O)$, $S(O)_2$, O, S, or N;

z1n is 0, 1, 2, 3, or 4; wherein if z1n is 0 then $Z^2$ is directly bonded to $W^5$;

each $R^{z1}$ is independently selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20z1}$;

$Z^2$ is $C(R^{z2})$, C, or N;

$R^{z2}$ is selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20z2}$;

$Z^3$ is $C(R^{z3})$, C, or N;

$R^{z3}$ is selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20z3}$;

$Z^4$ is a bond, $Z^{4a}$, $Z^{4a}Z^{4b}$, $Z^{4a}Z^{4b}Z^{4c}$, $Z^{4a}Z^{4b}Z^{4c}Z^{4d}$, or $Z^{4a}Z^{4b}Z^{4c}Z^{4d}Z^{4e}$; wherein $Z^{4a}$ is directly bonded to $Z^2$; and wherein if $Z^4$ is a bond then $Z^2$ is directly bonded to $Z^5$;

$Z^{4a}$, $Z^{4b}$, $Z^{4c}$, $Z^{4d}$, and $Z^{4e}$ are independently $C(R^{z4})$, $N(R^{z4})$, $C(R^{z4})_2$, $C(O)$, $S(O)$, $S(O)_2$, $S(O)(NR^{z4})$, O, S, or N;

$Z^{4a}$, $Z^{4b}$, $Z^{4c}$, $Z^{4d}$, and $Z^{4e}$ are independently $C(R^{z4})$, $N(R^{z4})$, $C(R^{z4})_2$, $C(O)$, $S(O)$, $S(O)_2$, $S(O)(NR^{z4})$, O, S, or N;

provided that if z9n is 0 and $Z^4$ is $Z^{4a}Z^{4b}$; then (1) $Z^{4b}$ is $C(R^{z4})$, $C(R^{z4})_2$, $C(O)$, $S(O)$, $S(O)_2$, $S(O)(NR^{z4})$, O, S, or N, (2) $Z^{4b}$ is $N(R^{z4})$ and $Z^{4a}$ is $C(O)$, $S(O)$, or $S(O)_2$; (3) $Z^{4b}$ is $N(R^{z4})$ and $Z^5$ is $C(O)$, $S(O)$, or $S(O)_2$; or (4) $Z^{4b}$ is $N(R^{z4})$ and $Z^3$ is $C(R^{z3})$ or C;

each $R^{z4}$ is independently selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{12}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{12}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20z4}$; or two $R^{z4}$ bonded to the same carbon are joined to form $C_{2-6}$alkenyl optionally substituted with one, two, or three $R^{20z4}$;

$Z^5$ is $C(R^{z5})$, $N(R^{z5})$, $C(R^{z5})_2$, $C(O)$, $S(O)$, $S(O)_2$, $S(O)(NR^{z5})$, O, S, or N;

each $R^{z5}$ is independently selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{12}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{12}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20z5}$; or two $R^{z5}$ bonded to the same carbon are joined to form $C_{2-6}$alkenyl optionally substituted with one, two, or three $R^{20z5}$;

$Z^6$ is $C(R^{z6})$, $N(R^{z6})$, $C(R^{z6})_2$, $C(O)$, $S(O)$, $S(O)_2$, $S(O)(NR^{z6})$, O, S, or N;

each $R^{z6}$ is independently selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{12}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{12}$, —$S(O)_2R^{15}$, —$S(O)_2N(R^{12})(R^{13})$, —$S(=O)(=NH)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20z6}$; or two $R^{z6}$ bonded to the same carbon are joined to form $C_{2-6}$alkenyl optionally substituted with one, two, or three $R^{20z6}$;

and further wherein the compound optionally includes one of the following:

(1) two $R^{z4}$ bonded to the same carbon atom are joined to form monocyclic $C_{3-7}$cycloalkyl or monocyclic 3-7 membered heterocycloalkyl, wherein the monocyclic $C_{3-7}$cycloalkyl and monocyclic 3-7 membered heterocycloalkyl are optionally substituted with one, two, or three $R^{20z}$;

(2) two or more $R^{z4}$ bonded to adjacent atoms are joined to form monocyclic $C_{3-7}$cycloalkyl, monocyclic 3-7 membered heterocycloalkyl, phenyl, or monocyclic 5-6 membered heteroaryl, wherein the monocyclic $C_{3-7}$cycloalkyl, monocyclic 3-7 membered heterocycloalkyl, phenyl, and monocyclic 5-6 membered heteroaryl are optionally substituted with one, two, or three $R^{20z}$;

(3) two $R^{z5}$ bonded to the same carbon atom are joined to form monocyclic $C_{3-7}$cycloalkyl or monocyclic 3-7 membered heterocycloalkyl, wherein the monocyclic $C_{3-7}$cycloalkyl and monocyclic 3-7 membered heterocycloalkyl are optionally substituted with one, two, or three $R^{20z}$;

(4) one or two $R^{z4}$ bonded to one atom and one or two $R^{z5}$ bonded to an adjacent atom are joined to form monocyclic $C_{3-7}$cycloalkyl, monocyclic 3-7 membered heterocycloalkyl, phenyl, or monocyclic 5-6 membered heteroaryl, wherein the monocyclic $C_{3-7}$cycloalkyl, monocyclic 3-7 membered heterocycloalkyl, phenyl, and monocyclic 5-6 membered heteroaryl are optionally substituted with one, two, or three $R^{20z}$;

(5) one or two $R^{z4}$ bonded to one atom and one or two $R^{z5}$ bonded to a second atom are joined to form monocyclic $C_{3-7}$cycloalkyl or monocyclic 3-7 membered heterocycloalkyl, wherein the monocyclic $C_{3-7}$cycloalkyl and monocyclic 3-7 membered heterocycloalkyl are optionally substituted with one, two, or three $R^{20z}$;

(6) two $R^{z6}$ bonded to the same carbon atom are joined to form monocyclic $C_{3-7}$cycloalkyl or monocyclic 3-7 membered heterocycloalkyl, wherein the monocyclic $C_{3-7}$cycloalkyl and monocyclic 3-7 membered heterocycloalkyl are optionally substituted with one, two, or three $R^{20z}$;

(7) one or two $R^{z5}$ bonded to one atom and one or two $R^{z6}$ bonded to an adjacent atom are joined to form monocyclic $C_{3-7}$cycloalkyl, monocyclic 3-7 membered heterocycloalkyl, phenyl, or monocyclic 5-6 membered heteroaryl, wherein the monocyclic $C_{3-7}$cycloalkyl, monocyclic 3-7 membered heterocycloalkyl, phenyl, and monocyclic 5-6 membered heteroaryl are optionally substituted with one, two, or three $R^{20z}$; or (8) one or two $R^{z4}$ bonded to one atom and one or two $R^{z6}$ bonded to a second atom are joined to form monocyclic $C_{3-7}$cycloalkyl or monocyclic 3-7 membered heterocycloalkyl, wherein the monocyclic $C_{3-7}$cycloalkyl and monocyclic 3-7 membered heterocycloalkyl are optionally substituted with one, two, or three $R^{20z}$;

two $R^{20z}$ bonded to the same carbon atom are optionally joined to form monocyclic $C_{3-7}$cycloalkyl or monocyclic 3-7 membered heterocycloalkyl, wherein the monocyclic $C_{3-7}$cycloalkyl and monocyclic 3-7 membered heterocycloalkyl are optionally substituted with one, two, or three $R^{20zz}$; or two or more $R^{20z}$ bonded to two adjacent atoms are optionally joined to form monocyclic $C_{3-7}$cycloalkyl, monocyclic 3-7 membered heterocycloalkyl, phenyl, or monocyclic 5-6 membered heteroaryl, wherein the $C_{3-7}$cycloalkyl, monocyclic 3-7 membered heterocycloalkyl, phenyl, and monocyclic 5-6 membered heteroaryl are optionally substituted with one, two, or three $R^{20zz}$;

each $Z^9$ is independently $C(R^{z9})$, $N(R^{z9})$, $C(R^{z9})_2$, $C(O)$, $S(O)$, $S(O)_2$, O, S, or N;

z9n is 0, 1, 2, 3, or 4; wherein if z9n is 0 then $Z^3$ is directly bonded to $W^4$;

each $R^{z9}$ is independently selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20z9}$;

wherein the sum of z1n and z9n is 2, 3, or 4;

each $R^{12}$ is independently selected from hydrogen, $C_{1-6}$alkyl, $C_{2-6}$alkenyl, $C_{2-6}$alkynyl, $C_{3-10}$cycloalkyl, —$CH_2$-$C_{3-10}$cycloalkyl, $C_{2-9}$heterocycloalkyl, —$CH_2$-$C_{2-9}$heterocycloalkyl, $C_{6-10}$aryl, —$CH_2$-$C_{6-10}$aryl, —$CH_2$-$C_{1-9}$heteroaryl, and $C_{1-9}$heteroaryl, wherein $C_{1-6}$alkyl, $C_{2-6}$alkenyl, $C_{2-6}$alkynyl, $C_{3-10}$cycloalkyl, —$CH_2$-$C_{3-10}$cycloalkyl, $C_{2-9}$heterocycloalkyl, —$CH_2$-$C_{2-9}$heterocycloalkyl, $C_{6-10}$aryl, —$CH_2$-$C_{6-10}$aryl, —$CH_2$-$C_{1-9}$heteroaryl, and $C_{1-9}$heteroaryl are optionally substituted with one, two, or three $R^{20l}$;

$R^{12a}$ is independently selected from hydrogen, $C_{1-6}$alkyl, $C_{2-6}$alkenyl, $C_{2-6}$alkynyl, $C_{3-10}$cycloalkyl, —$C(R^{12c})_2$-$C_{3-10}$cycloalkyl, $C_{2-9}$heterocycloalkyl, —$C(R^{12c})_2$-$C_{2-9}$heterocycloalkyl, $C_{6-10}$aryl, —$C(R^{12c})_2$-$C_{6-10}$aryl, —$C(R^{12c})_2$-$C_{1-9}$heteroaryl, and $C_{1-9}$heteroaryl, wherein $C_{1-6}$alkyl, $C_{2-6}$alkenyl, $C_{2-6}$alkynyl, $C_{3-10}$cycloalkyl, —$C(R^{12c})_2$-$C_{3-10}$cycloalkyl, $C_{2-9}$heterocycloalkyl, —$C(R^{12c})_2$-$C_{2-9}$heterocycloalkyl, $C_{6-10}$aryl, —$C(R^{12c})_2$-$C_{6-10}$aryl, —$C(R^{12c})_2$-$C_{1-9}$heteroaryl, and $C_{1-9}$heteroaryl are optionally substituted with one, two, or three $R^{20l}$;

each $R^{12c}$ is independently selected from hydrogen and $R^{20lc}$;

each $R^{13}$ is independently selected from hydrogen, $C_{1-6}$alkyl, and $C_{1-6}$haloalkyl; or $R^{12}$ and $R^{13}$, together with the nitrogen to which they are attached, form a $C_{2-9}$heterocycloalkyl ring optionally substituted with one, two, or three $R^{20m}$;

each $R^{14}$ is independently selected from hydrogen, $C_{1-6}$alkyl, and $C_{1-6}$haloalkyl;

each $R^{15}$ is independently selected from $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20o}$;

each $R^{20z1}$, $R^{20z2}$, $R^{20z3}$, $R^{20z4}$, $R^{20z5}$, $R^{20z6}$, and $R^{20z9}$ is independently selected from halogen, oxo, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{12}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{12}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20z}$;

each $R^{20z}$ is independently selected from halogen, oxo, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{12}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{12}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20zz}$;

each $R^{20a}$, $R^{20b}$, $R^{20c}$, $R^{20d}$, $R^{20e}$, $R^{20f}$, $R^{20g}$, $R^{20h}$, $R^{20i}$, $R^{20j}$, $R^{20l}$, $R^{20lc}$, $R^{20m}$, $R^{20o}$, $R^{20q}$, and $R^{20zz}$ is independently selected from halogen, oxo, —CN, $C_{1-6}$alkyl, $C_{2-6}$alkenyl, $C_{2-6}$alkynyl, $C_{3-10}$cycloalkyl, —$CH_2$-$C_{3-10}$cycloalkyl, $C_{2-9}$heterocycloalkyl, —$CH_2$-$C_{2-9}$heterocycloalkyl, $C_{6-10}$aryl, —$CH_2$-$C_{6-10}$aryl, —$CH_2$-$C_{1-9}$heteroaryl, $C_{1-9}$heteroaryl, —$OR^{21}$, —$SR^{21}$, —$N(R^{22})(R^{23})$, —$C(O)OR^{22}$, —$C(O)N(R^{22})(R^{23})$, —$C(O)C(O)N(R^{22})(R^{23})$, —$OC(O)N(R^{22})(R^{23})$, —$N(R^{24})C(O)N(R^{22})(R^{23})$, —$N(R^{24})C(O)OR^{25}$, —$N(R^{24})C(O)R^{21}$, —$N(R^{24})S(O)_2R^{25}$, —$C(O)R^{21}$, —$S(O)_2R^{25}$, —$S(O)_2N(R^{22})(R^{23})$, —$OCH_2C(O)OR^{22}$, =$NR^{21}$, and —$OC(O)R^{25}$; two $R^{20q}$ bonded to adjacent atoms are optionally joined to form a $C_{3-10}$cycloalkyl, $C_{2-9}$heterocycloalkyl, $C_{6-10}$aryl, or $C_{1-9}$heteroaryl; wherein $C_{1-6}$alkyl, $C_{2-6}$alkenyl, $C_{2-6}$alkynyl, $C_{3-10}$cycloalkyl, —$CH_2$-$C_{3-10}$cycloalkyl, $C_{2-9}$heterocycloalkyl, —$CH_2$-$C_{2-9}$heterocycloalkyl, $C_{6-10}$aryl, —$CH_2$-$C_{6-10}$aryl, —$CH_2$-$C_{1-9}$heteroaryl, and $C_{1-9}$heteroaryl are optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —$OR^{21}$, —$SR^{21}$, —$N(R^{22})(R^{23})$, —$C(O)OR^{22}$, —$C(O)N(R^{22})(R^{23})$, —$C(O)C(O)N(R^{22})(R^{23})$, —$OC(O)N(R^{22})(R^{23})$, —$N(R^{24})C(O)N(R^{22})(R^{23})$, —$N(R^{24})C(O)OR^{25}$, —$N(R^{24})C(O)R^{25}$, —$N(R^{24})S(O)_2R^{25}$, —$C(O)R^{25}$, —$S(O)_2R^{25}$, —$S(O)_2N(R^{22})(R^{23})$, and —$OC(O)R^{25}$;

each $R^{21}$ is independently selected from hydrogen, $C_{1-6}$alkyl, $C_{1-6}$haloalkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl;

each $R^{22}$ is independently selected from hydrogen, $C_{1-6}$alkyl, $C_{1-6}$haloalkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl;

each $R^{23}$ is independently selected from hydrogen and $C_{1-6}$alkyl;

each $R^{24}$ is independently selected from hydrogen and $C_{1-6}$alkyl;

each $R^{25}$ is independently selected from $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; and ═══ indicates a single or double bond such that all valences are satisfied.

In embodiments, the compound has the formula:

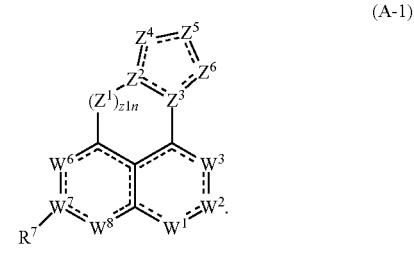

(A-1)

In embodiments, the compound has the formula:

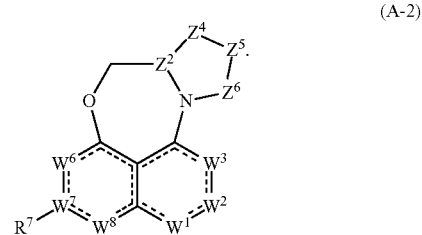

(A-2)

In embodiments, the compound has the formula:

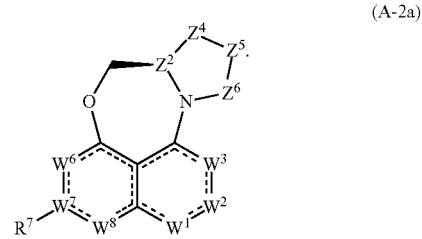

(A-2a)

In embodiments, the compound has the formula:

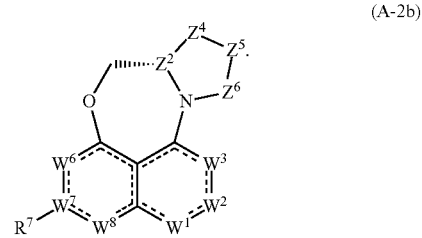

(A-2b)

In embodiments, the compound has the formula:

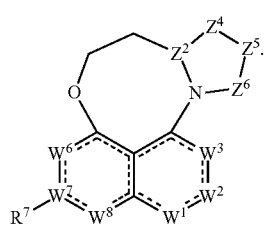
(A-3)

In embodiments, the compound has the formula:

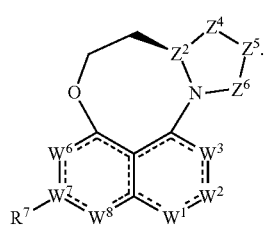
(A-3a)

In embodiments, the compound has the formula:

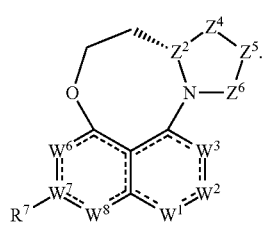
(A-3b)

In embodiments, the compound has the formula:

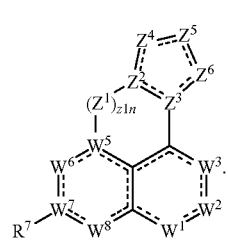
formula (A-4)

In embodiments, the compound has the formula:

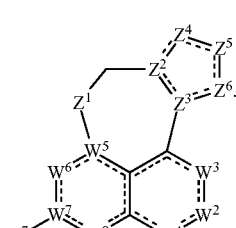
formula (A-4a)

In embodiments, the compound has the formula:

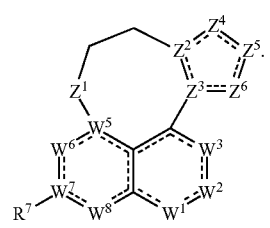
formula (A-4b)

In embodiments, the compound has the formula:

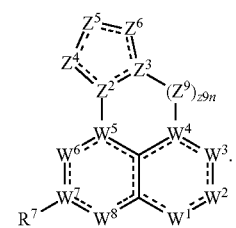
formula (A-5)

In embodiments, the compound has the formula:

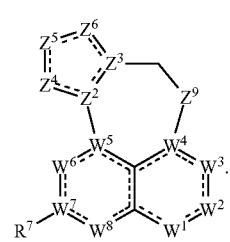
formula (A-5a)

In embodiments, the compound has the formula:

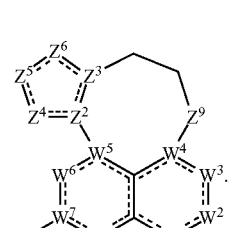
formula (A-5b)

In embodiments, the compound has the formula:

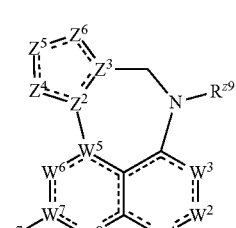
formula (A-5c)

In embodiments, the compound has the formula:

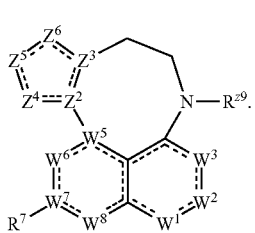

formula (A-5d)

In embodiments, the compound has the formula:

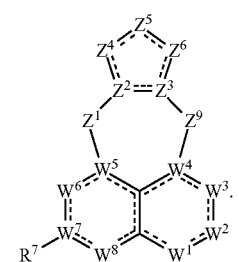

formula (A-6)

In embodiments, the compound has the formula:

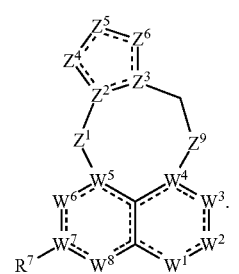

formula (A-6a)

In embodiments, the compound has the formula:

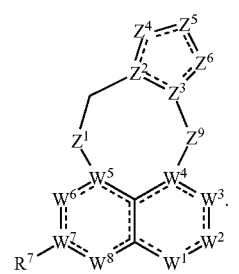

formula (A-6b)

In embodiments, the compound has the formula:

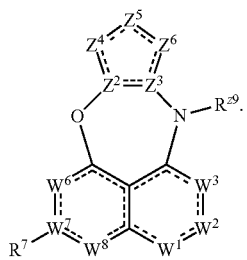

formula (A-6c)

In embodiments, the compound has the formula:

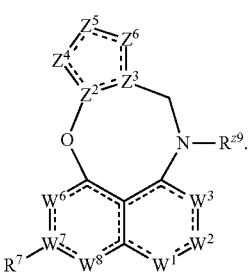

formula (A-6d)

In embodiments, the compound has the formula:

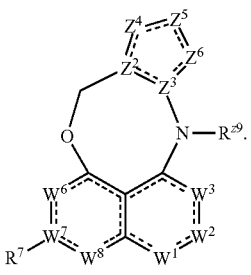

formula (A-6e)

In embodiments, the compound has the formula:

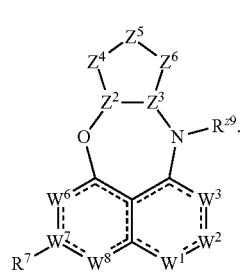

formula (A-6f)

In embodiments,
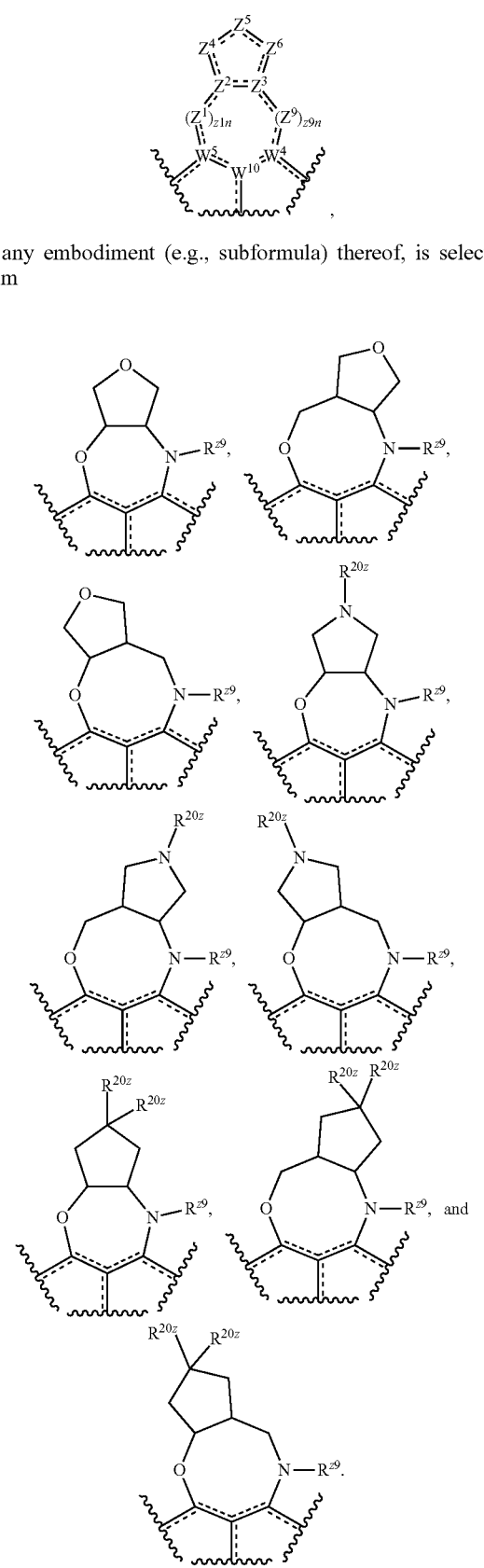
or any embodiment (e.g., subformula) thereof, is selected from
In embodiments,
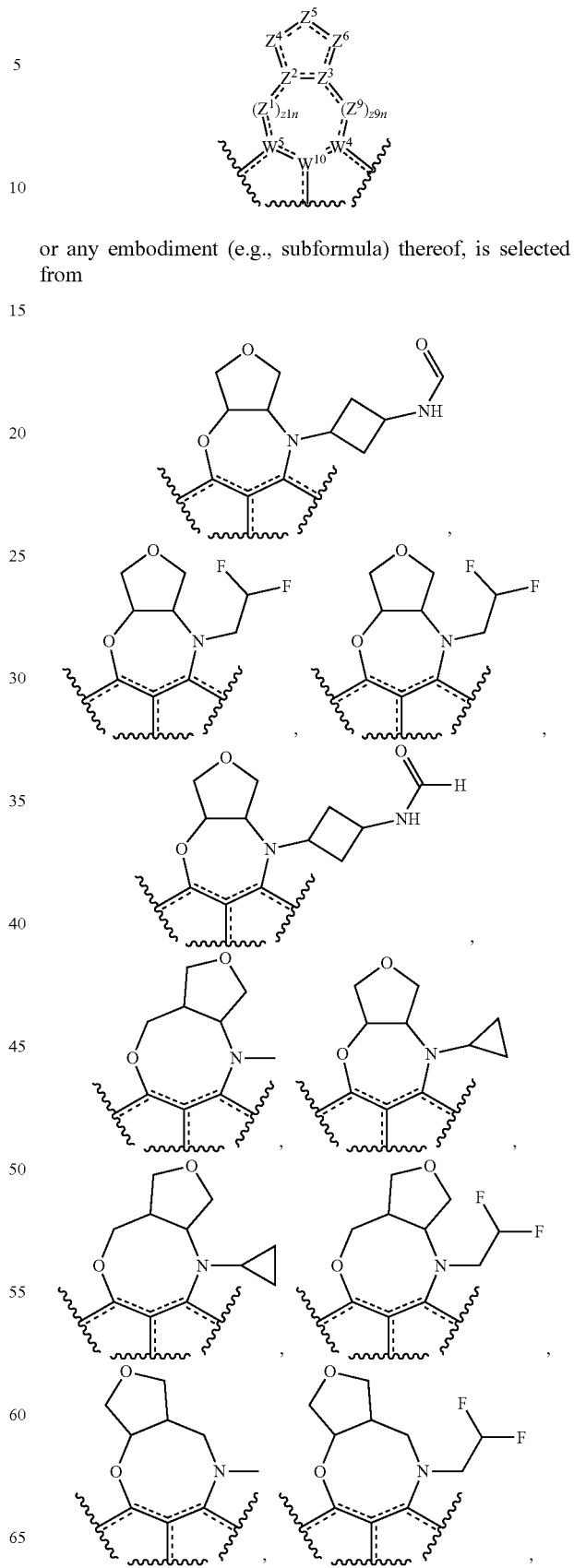
or any embodiment (e.g., subformula) thereof, is selected from -continued

[chemical structures]

, and

-continued

[chemical structure]

.

In embodiments,

[chemical structures] is .

In embodiments,

[chemical structures] is .

In embodiments,

[chemical structure]

is selected from

[chemical structures]

,

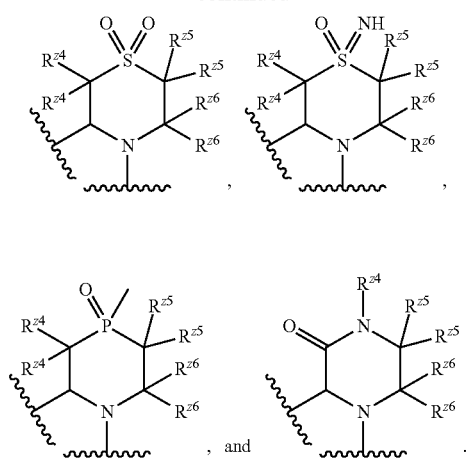
In embodiments,
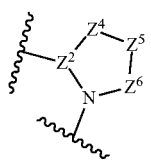
is selected from
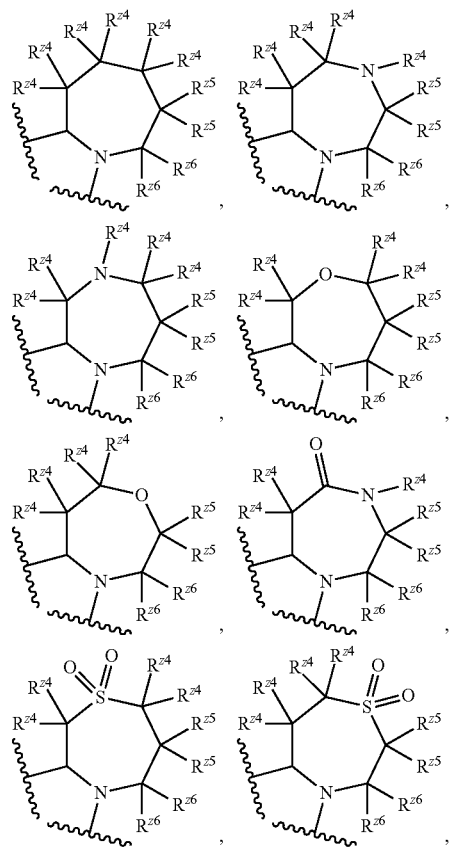
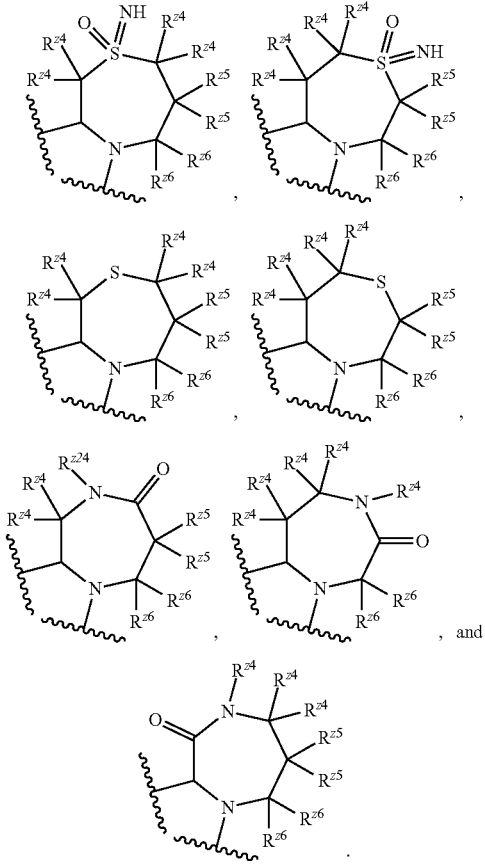
In embodiments,
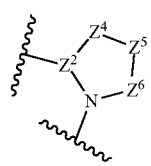
is selected from
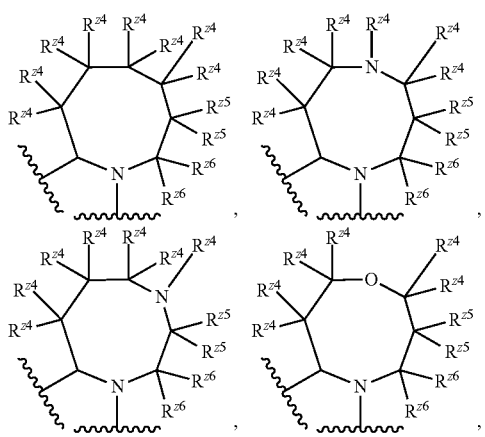

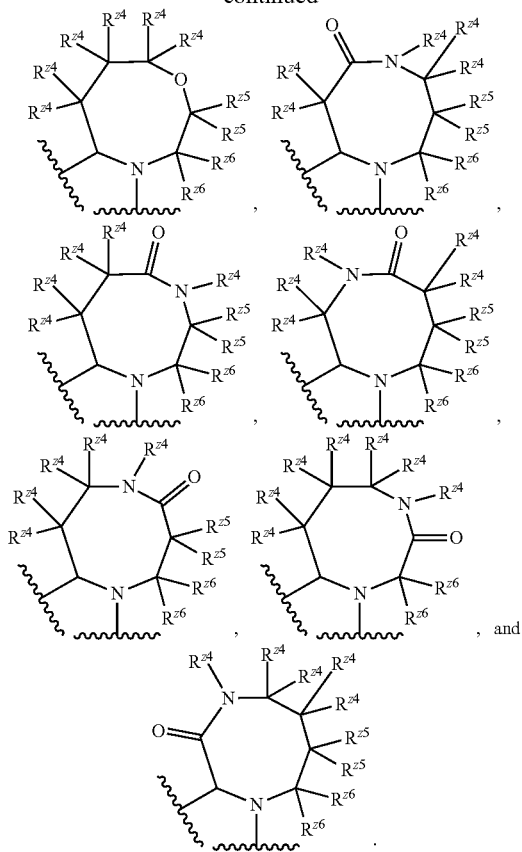

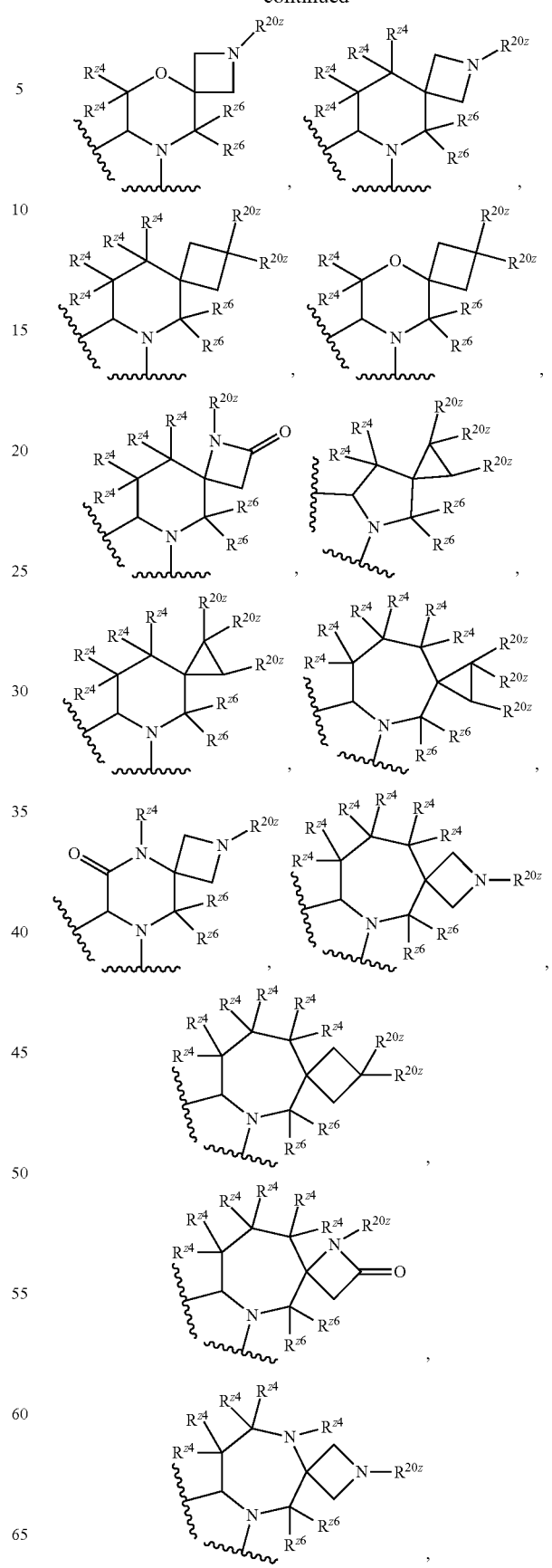

In embodiments, two $R^{z5}$ bonded to the same carbon atom are joined to form monocyclic $C_{3-7}$cycloalkyl or monocyclic 3-7 membered heterocycloalkyl, wherein the monocyclic $C_{3-7}$cycloalkyl and monocyclic 3-7 membered heterocycloalkyl are optionally substituted with one, two, or three $R^{20z}$. In embodiments, two $R^{z5}$ bonded to the same carbon atom are joined to form monocyclic 4-membered heterocycloalkyl, wherein the 4 membered heterocycloalkyl is substituted with one, two, or three $R^{20z}$.

In embodiments,

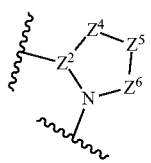

is selected from

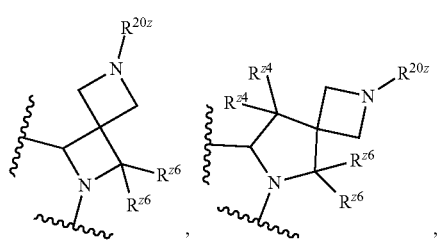

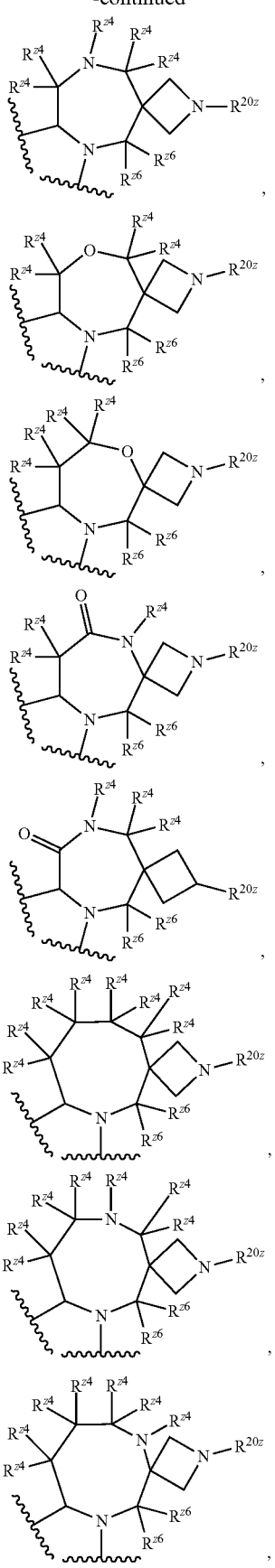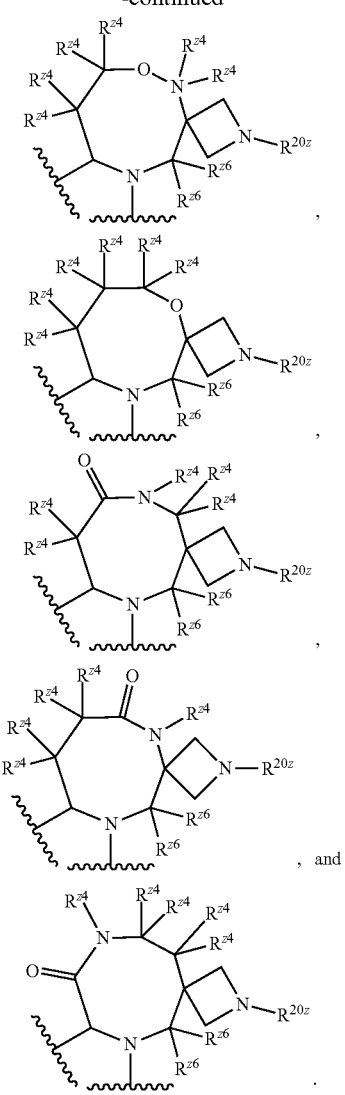
In embodiments,
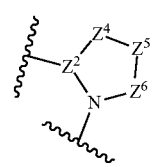
is selected from
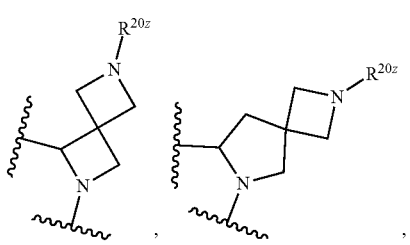

-continued

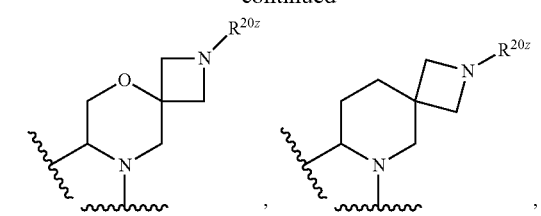

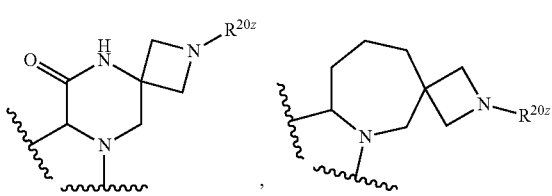

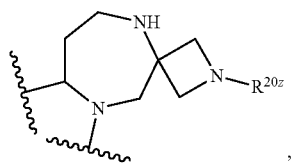

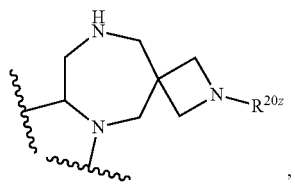

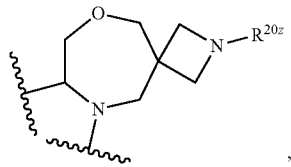

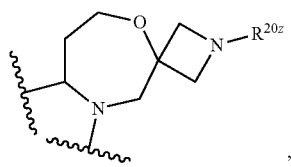

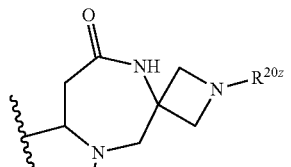

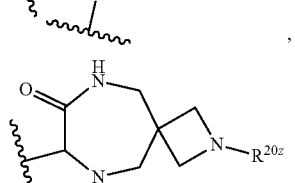

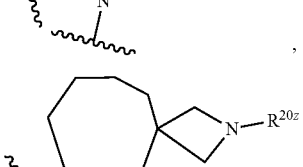

-continued

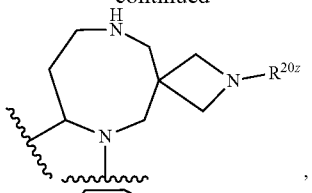

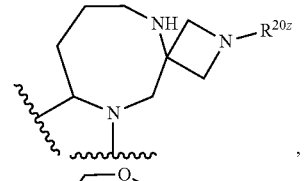

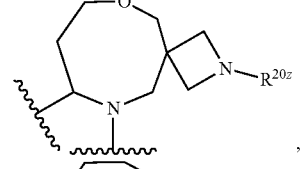

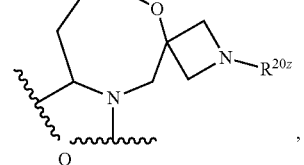

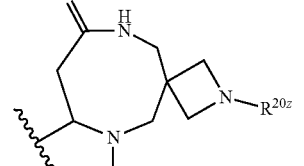

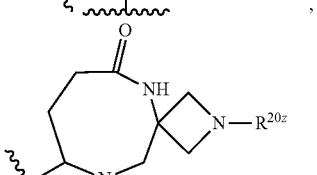

, and

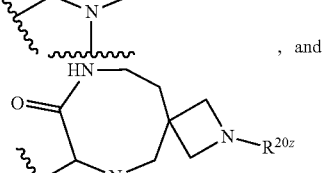

In embodiments, one or two $R^{z4}$ bonded to one atom and one or two $R^{z5}$ bonded to an adjacent atom are joined to form monocyclic $C_{3-7}$cycloalkyl, monocyclic 3-7 membered heterocycloalkyl, phenyl, or monocyclic 5-6 membered heteroaryl, wherein the monocyclic $C_{3-7}$cycloalkyl, monocyclic 3-7 membered heterocycloalkyl, phenyl, and monocyclic 5-6 membered heteroaryl are optionally substituted with one, two, or three $R^{20z}$. In embodiments, one or two $R^{z4}$ bonded to one atom and one or two $R^{z5}$ bonded to an adjacent atom are joined to form monocyclic 5-6 membered heteroaryl, wherein the monocyclic 5-6 membered heteroaryl is optionally substituted with one, two, or three $R^{20z}$. In embodiments, the monocyclic 5-6 membered heteroaryl formed by the joining of one or two $R^{z4}$ bonded to one atom and one or two $R^{z5}$ bonded to an adjacent atom, is a triazolyl, pyrazolyl, imidazolyl, pyrrolyl, furanyl, thienyl, oxazolyl, isooxazolyl, pyridyl, pyridazinyl, pyrimidinyl, or pyrazinyl;

each optionally substituted with one, two, or three $R^{20z}$. In embodiments, the monocyclic 5-6 membered heteroaryl formed by the joining of one or two $R^{z4}$ bonded to one atom and one or two $R^{z5}$ bonded to an adjacent atom, is a pyrazolyl optionally substituted with one, two, or three $R^{20z}$.

In embodiments,

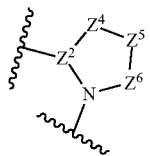

is selected from

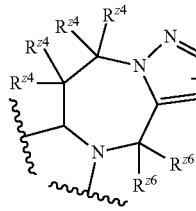 , 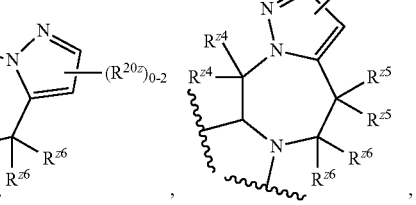 ,

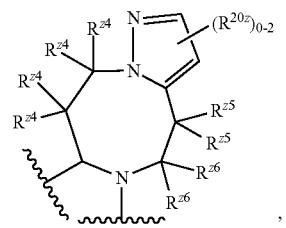 ,

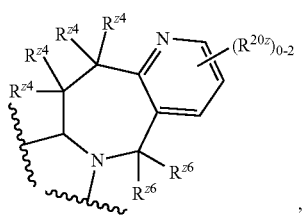 ,

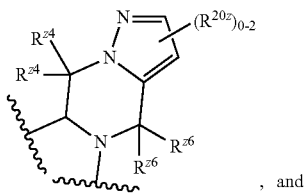 , and

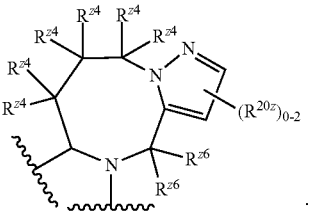 .

In embodiments,

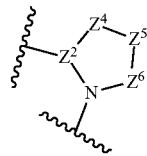

is selected from

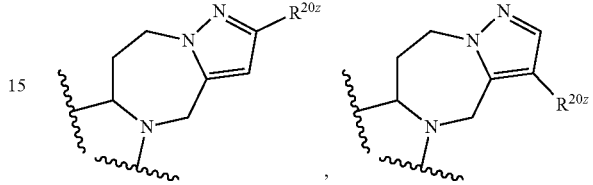 ,

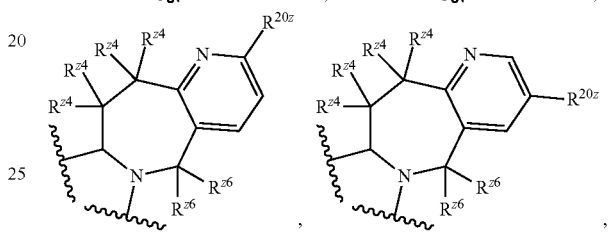 ,

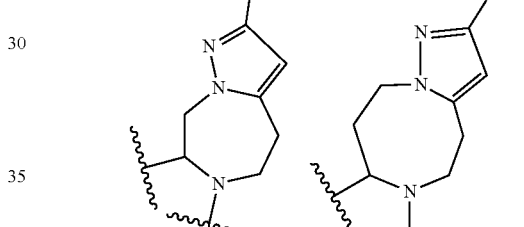 ,

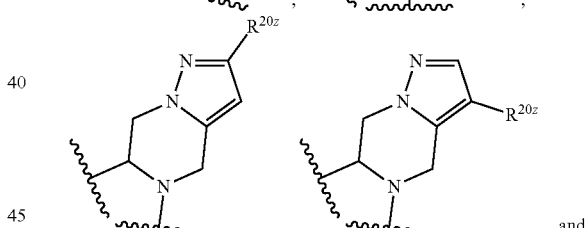 , and

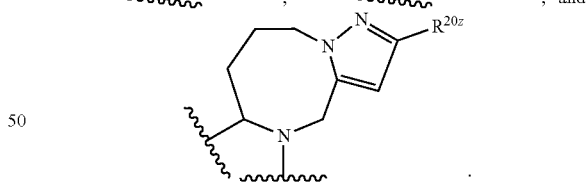

In embodiments, z1n is 1, 2 or 3, and z9n is 1, 2, or 3. In embodiments, z1n is 0. In embodiments, z9n is 0.

In embodiments, $W^1$ is N. In embodiments, $W^1$ is $N(R^1)$.
In embodiments, $W^2$ is $C(R^2)$. In embodiments, $W^2$ is $N(R^2)$. In embodiments, $W^2$ is C(O).
In embodiments, $W^3$ is N. In embodiments, $W^3$ is $C(R^3)$. In embodiments, $W^3$ is N. In embodiments, $W^3$ is O. In embodiments, $W^3$ is S. In embodiments, $W^3$ is C(O). In embodiments, $W^3$ is S(O). In embodiments, $W^3$ is $S(O)_2$. In embodiments, $W^3$ is $C(R^3)$. In embodiments, $W^3$ is $C(R^3)$ $(R^{3a})$. In embodiments, $R^3$ is independently selected from hydrogen, halogen, —CN, $C_{1-6}$alkyl, —$OR^{12}$, —$SR^{12}$, —$N(R^{12})(R^{13})$, —$C(O)OR^{12}$, —$C(O)R^{15}$, —$C(O)N(R^{12})$ ($R^{13}$), —S(O)$_2$R$^{15}$, and —S(O)$_2$N(R$^{12}$)(R$^{13}$)—, wherein C$_{1-6}$alkyl is optionally substituted with one, two, or three R$^{20c}$. In embodiments, R$^3$ is independently selected from hydrogen, halogen, —CN, C$_{1-6}$alkyl, and —OR$^{12}$, wherein C$_{1-6}$alkyl is optionally substituted with one, two, or three R$^{20c}$. In embodiments, R$^3$ is hydrogen.

In embodiments, R$^3$ is independently hydrogen. In embodiments, R$^3$ is independently halogen. In embodiments, R$^3$ is independently —CN. In embodiments, R$^3$ is independently —OR$^{12}$. In embodiments, R$^3$ is independently —SR$^{12}$. In embodiments, R$^3$ is independently —N(R$^{12}$)(R$^{13}$). In embodiments, R$^3$ is independently —C(O)OR$^{12}$. In embodiments, R$^3$ is independently —OC(O)N(R$^{12}$)(R$^{13}$). In embodiments, R$^3$ is independently —N(R$^{14}$)C(O)N(R$^{12}$)(R$^{13}$). In embodiments, R$^3$ is independently —N(R$^{14}$)C(O)OR$^{15}$. In embodiments, R$^3$ is independently —N(R$^{14}$)S(O)$_2$R$^{15}$. In embodiments, R$^3$ is independently —C(O)R$^{15}$. In embodiments, R$^3$ is independently —S(O)R$^{15}$. In embodiments, R$^3$ is independently —OC(O)R$^{15}$. In embodiments, R$^3$ is independently —C(O)N(R$^{12}$)(R$^{13}$). In embodiments, R$^3$ is independently —C(O)C(O)N(R$^{12}$)(R$^{13}$). In embodiments, R$^3$ is independently —N(R$^{14}$)C(O)R$^{15}$. In embodiments, R$^3$ is independently —S(O)$_2$R$^{15}$. In embodiments, R$^3$ is independently —S(O)$_2$N(R$^{12}$)(R$^{13}$)—. In embodiments, R$^3$ is independently —S(=O)(=NH)N(R$^{12}$)(R$^{13}$). In embodiments, R$^3$ is independently —CH$_2$C(O)N(R$^{12}$)(R$^{13}$). In embodiments, R$^3$ is independently —CH$_2$N(R$^{14}$)C(O)R$^{15}$. In embodiments, R$^3$ is independently —CH$_2$S(O)$_2$R$^{15}$. In embodiments, R$^3$ is independently —CH$_2$S(O)$_2$N(R$^{12}$)(R$^{13}$).

In embodiments of the compound, R$^3$ is independently methyl optionally substituted with one or two R$^{20c}$. In further embodiments of the compound, R$^3$ is independently methyl. In some embodiments of the compound, R$^3$ is independently ethyl optionally substituted with one, two, or three R$^{20c}$. In embodiments of the compound, R$^3$ is independently ethyl. In some embodiments of the compound, R$^3$ is independently propyl optionally substituted with one, two, or three R$^{20c}$. In embodiments of the compound, R$^3$ is independently propyl.

In embodiments, R$^3$ is independently —CN. In embodiments, R$^3$ is independently C$_{1-6}$alkyl optionally substituted with one, two, or three R$^{20b}$. In embodiments, R$^3$ is independently C$_{2-6}$alkenyl optionally substituted with one, two, or three R$^{20b}$. In embodiments, R$^3$ is independently C$_{2-6}$alkynyl optionally substituted with one, two, or three R$^{20a}$. In embodiments, R$^3$ is independently C$_{3-10}$cycloalkyl optionally substituted with one, two, or three R$^{20b}$. In embodiments, R$^3$ is independently C$_{2-9}$heterocycloalkyl optionally substituted with one, two, or three R$^{20b}$. In embodiments, R$^3$ is independently C$_{6-10}$aryl optionally substituted with one, two, or three R$^{20b}$. In embodiments, R$^3$ is independently C$_{1-9}$heteroaryl optionally substituted with one, two, or three R$^{20b}$. In embodiments, R$^3$ is independently —OR$^{12}$. In embodiments, R$^3$ is independently —C(O)OR$^{12}$. In embodiments, R$^3$ is independently —OC(O)N(R$^{12}$)(R$^{13}$). In embodiments, R$^3$ is independently —C(O)R$^{15}$. In embodiments, R$^3$ is independently halogen. In embodiments, R$^3$ is independently —N(R$^{12}$)(R$^{13}$). In embodiments, R$^3$ is independently —NH$_2$.

In embodiments, W$^4$ is C.

In embodiments, W$^5$ is C. In embodiments, W$^5$ is C(R$^5$).

In embodiments, W$^6$ is C(R$^6$). In embodiments, W$^6$ is N(R$^6$). In embodiments, R$^6$ is independently selected from hydrogen, halogen, —CN, C$_{1-6}$alkyl, C$_{3-6}$cycloalkyl, —OR$^{12}$, —SR$^{12}$, —N(R$^{12}$)(R$^{13}$), —C(O)OR$^{12}$, —C(O)R$^{15}$, —C(O)N(R$^{12}$)(R$^{13}$), —S(O)$_2$R$^{15}$, and —S(O)$_2$N(R$^{12}$)(R$^{13}$), wherein C$_{1-6}$alkyl and C$_{3-6}$cycloalkyl are optionally substituted with one, two, or three R$^{20f}$. In embodiments, R$^6$ independently is selected from hydrogen, halogen, —CN, C$_{1-6}$alkyl, and —OR$^{12}$, wherein C$_{1-6}$alkyl is optionally substituted with one, two, or three R$^{20f}$. In embodiments, R$^6$ is halogen. In embodiments, W$^6$ is N.

In embodiments, R$^6$ is independently hydrogen. In embodiments, R$^6$ is independently halogen. In embodiments, R$^6$ is independently —CN. In embodiments, R$^6$ is independently —OR$^{12}$. In embodiments, R$^6$ is independently —SR$^{12}$. In embodiments, R$^6$ is independently —N(R$^{12}$)(R$^{13}$). In embodiments, R$^6$ is independently —C(O)R$^{12}$. In embodiments, R$^6$ is independently —OC(O)N(R$^{12}$)(R$^{13}$). In embodiments, R$^6$ is independently —N(R$^{14}$)C(O)N(R$^{12}$)(R$^{13}$). In embodiments, R$^6$ is independently —N(R$^{14}$)C(O)OR$^{15}$. In embodiments, R$^6$ is independently —N(R$^{14}$)S(O)$_2$R$^{15}$. In embodiments, R$^6$ is independently —C(O)R$^{15}$. In embodiments, R$^6$ is independently —S(O)R$^{15}$. In embodiments, R$^6$ is independently —OC(O)R$^{15}$. In embodiments, R$^6$ is independently —C(O)N(R$^{12}$)(R$^{13}$). In embodiments, R$^6$ is independently —C(O)C(O)N(R$^{12}$)(R$^{13}$). In embodiments, R$^6$ is independently —N(R$^{14}$)C(O)R$^{15}$. In embodiments, R$^6$ is independently —S(O)$_2$R$^{15}$. In embodiments, R$^6$ is independently —S(O)$_2$N(R$^{12}$)(R$^{13}$)—. In embodiments, R$^6$ is independently —S(=O)(=NH)N(R$^{12}$)(R$^{13}$). In embodiments, R$^6$ is independently —CH$_2$C(O)N(R$^{12}$)(R$^{13}$). In embodiments, R$^6$ is independently —CH$_2$N(R$^{14}$)C(O)R$^{15}$. In embodiments, R$^6$ is independently —CH$_2$S(O)$_2$R$^{15}$. In embodiments, R$^6$ is independently —CH$_2$S(O)$_2$N(R$^{12}$)(R$^{13}$).

In select embodiments of the compound, R$^6$ is independently C$_{1-6}$alkyl optionally substituted with one, two, or three R$^{20f}$. In some embodiments, R$^6$ is independently C$_{2-6}$alkenyl optionally substituted with one, two, or three R$^{20f}$. In some embodiments, R$^6$ is independently C$_{2-6}$alkynyl optionally substituted with one, two, or three R$^{20f}$. In some embodiments, R$^6$ is independently C$_{3-10}$cycloalkyl optionally substituted with one, two, or three R$^{20f}$. In some embodiments, R$^6$ is independently C$_{2-9}$heterocycloalkyl optionally substituted with one, two, or three R$^{20f}$. In some embodiments, R$^6$ is independently C$_{6-10}$aryl optionally substituted with one, two, or three R$^{20f}$.

In some embodiments, R$^6$ is independently C$_{1-9}$heteroaryl optionally substituted with one, two, or three R$^{20f}$.

In additional embodiments, R$^6$ is independently hydrogen.

In embodiments of the compound, R$^6$ is independently methyl optionally substituted with one or two R$^{20f}$. In further embodiments of the compound, R$^6$ is independently methyl. In some embodiments of the compound, R$^6$ is independently ethyl optionally substituted with one, two, or three R$^{20f}$. In embodiments of the compound, R$^6$ is independently ethyl. In some embodiments of the compound, R$^6$ is independently propyl optionally substituted with one, two, or three R$^{20f}$. In embodiments of the compound, R$^6$ is independently propyl.

In embodiments, W$^7$ is C. In embodiments, W$^7$ is C(R$^{7a}$). In embodiments, W$^7$ is N.

In embodiments, R$^{7a}$ is hydrogen. In embodiments, R$^{7a}$ is halogen. In embodiments, R$^{7a}$ is —CN. In embodiments, R$^{7a}$ is —OR$^{12}$. In embodiments, R$^{7a}$ is —SR$^{12}$. In embodiments, R$^{7a}$ is —N(R$^{12}$)(R$^{13}$). In embodiments, R$^{7a}$ is —C(O)R$^{12}$. In embodiments, R$^{7a}$ is —OC(O)N(R$^{12}$)(R$^{13}$). In embodiments, R$^{7a}$ is —N(R$^{14}$)C(O)N(R$^{12}$)(R$^{13}$). In embodiments, R$^{7a}$ is —N(R$^{14}$)C(O)OR$^{15}$. In embodiments, R$^{7a}$ is —N(R$^{14}$)S(O)$_2$R$^{15}$. In embodiments, R$^{7a}$ is —C(O)R$^{15}$. In embodiments, R$^{7a}$ is —S(O)R$^{15}$. In embodiments, R$^{7a}$ is —OC(O)R$^{15}$. In embodiments, R$^{7a}$ is —C(O)N(R$^{12}$)

($R^{13}$). In embodiments, $R^{7a}$ is —C(O)C(O)N($R^{12}$)($R^{13}$). In embodiments, $R^{7a}$ is —N($R^{14}$)C(O)$R^{15}$. In embodiments, $R^{7a}$ is —S(O)$_2$$R^{15}$. In embodiments, $R^{7a}$ is —S(O)$_2$N($R^{12}$)($R^{13}$)—. In embodiments, $R^{7a}$ is —S(=O)(=NH)N($R^{12}$)($R^{13}$). In embodiments, $R^{7a}$ is —CH$_2$C(O)N($R^{12}$)($R^{13}$). In embodiments, $R^{7a}$ is —CH$_2$N($R^{14}$)C(O)$R^{15}$. In embodiments, $R^{7a}$ is —CH$_2$S(O)$_2$$R^{15}$. In embodiments, $R^{7a}$ is —CH$_2$S(O)$_2$N($R^{12}$)($R^{13}$).

In select embodiments of the compound, $R^{7a}$ is independently $C_{1-6}$alkyl optionally substituted with one, two, or three $R^{20g}$. In some embodiments, $R^{7a}$ is independently $C_{2-6}$alkenyl optionally substituted with one, two, or three $R^{20g}$. In some embodiments, $R^{7a}$ is independently $C_{2-6}$alkynyl optionally substituted with one, two, or three $R^{20g}$. In some embodiments, $R^{7a}$ is independently $C_{3-10}$cycloalkyl optionally substituted with one, two, or three $R^{20g}$. In some embodiments, $R^{7a}$ is independently $C_{2-9}$heterocycloalkyl optionally substituted with one, two, or three $R^{20g}$. In some embodiments, $R^{7a}$ is independently $C_{6-10}$aryl optionally substituted with one, two, or three $R^{20g}$. In some embodiments, $R^{7a}$ is independently $C_{1-9}$heteroaryl optionally substituted with one, two, or three $R^{20g}$. In additional embodiments, $R^{7a}$ is independently hydrogen.

In embodiments of the compound, $R^{7a}$ is independently methyl optionally substituted with one or two $R^{20g}$. In further embodiments of the compound, $R^{7a}$ is independently methyl. In some embodiments of the compound, $R^{7a}$ is independently ethyl optionally substituted with one, two, or three $R^{20g}$. In embodiments of the compound, $R^{7a}$ is independently ethyl. In some embodiments of the compound, $R^{7a}$ is independently propyl optionally substituted with one, two, or three $R^{20g}$. In embodiments of the compound, $R^{7a}$ is independently propyl.

In embodiments, $W^8$ is independently C($R^8$). In embodiments, $R^8$ is independently selected from hydrogen, halogen, —CN, $C_{1-6}$alkyl, —O$R^{12}$, —S$R^{12}$, —N($R^{12}$)($R^{13}$), —C(O)O$R^{12}$, —C(O)$R^{15}$, —C(O)N($R^{12}$)($R^{13}$), —S(O)$_2$$R^{15}$, and —S(O)$_2$N($R^{12}$)($R^{13}$), wherein $C_{1-6}$alkyl is optionally substituted with one, two, or three $R^{20h}$. In embodiments, $R^8$ is independently selected from hydrogen, halogen, —CN, $C_{1-6}$alkyl, and —O$R^{12}$, wherein $C_{1-6}$alkyl is optionally substituted with one, two, or three $R^{20h}$. In embodiments, $R^8$ is independently halogen. In embodiments, $W^8$ is independently N.

In embodiments, $R^8$ is independently selected from hydrogen, halogen, —CN, $C_{1-6}$alkyl, —O$R^{12}$, —S$R^{12}$, —N($R^{12}$)($R^{13}$), —C(O)O$R^{12}$, —C(O)$R^{15}$, —C(O)N($R^{12}$)($R^{13}$), —S(O)$_2$$R^{15}$, and —S(O)$_2$N($R^{12}$)($R^{13}$)—, wherein $C_{1-6}$alkyl is optionally substituted with one, two, or three $R^{20h}$. In embodiments, $R^8$ is independently selected from hydrogen, halogen, —CN, $C_{1-6}$alkyl, and —O$R^{12}$, wherein $C_{1-6}$alkyl is optionally substituted with one, two, or three $R^{20h}$. In embodiments, $R^{8a}$ is independently selected from hydrogen, halogen, —CN, $C_{1-6}$alkyl, —O$R^{12}$, —S$R^{12}$, —N($R^{12}$)($R^{13}$), —C(O)O$R^{12}$, —C(O)$R^{15}$, —C(O)N($R^{12}$)($R^{13}$), —S(O)$_2$$R^{15}$, and —S(O)$_2$N($R^{12}$)($R^{13}$)—, wherein $C_{1-6}$alkyl is optionally substituted with one, two, or three $R^{20h}$. In embodiments, $R^{8a}$ is independently selected from hydrogen, halogen, —CN, $C_{1-6}$alkyl, and —O$R^{12}$, wherein $C_{1-6}$alkyl is optionally substituted with one, two, or three $R^{20h}$. In embodiments, $W^8$ is independently N($R^{8b}$). In embodiments, $R^8$b is independently hydrogen.

In embodiments, $R^8$ is independently hydrogen. In embodiments, $R^8$ is independently halogen. In embodiments, $R^8$ is independently —CN. In embodiments, $R^8$ is independently $C_{1-6}$alkyl. In embodiments, $R^8$ is independently $C_{2-6}$alkenyl. In embodiments, $R^8$ is independently $C_{2-6}$alkynyl. In embodiments, $R^8$ is independently $C_{3-10}$cycloalkyl. In embodiments, $R^8$ is independently $C_{2-9}$heterocycloalkyl. In embodiments, $R^8$ is independently $C_{6-10}$aryl. In embodiments, $R^8$ is independently $C_{1-9}$heteroaryl.

In embodiments, $R^8$ is independently $C_{1-6}$alkyl optionally substituted with one, two, or three $R^{20h}$. In embodiments, $R^8$ is independently $C_{2-6}$alkenyl optionally substituted with one, two, or three $R^{20h}$. In embodiments, $R^8$ is independently $C_{2-6}$alkynyl optionally substituted with one, two, or three $R^{20h}$. In embodiments, $R^8$ is independently $C_{3-10}$cycloalkyl optionally substituted with one, two, or three $R^{20h}$. In embodiments, $R^8$ is independently $C_{2-9}$heterocycloalkyl optionally substituted with one, two, or three $R^{20h}$. In embodiments, $R^8$ is independently $C_{6-10}$aryl optionally substituted with one, two, or three $R^{20h}$. In embodiments, $R^8$ is independently $C_{1-9}$heteroaryl optionally substituted with one, two, or three $R^{20h}$.

In embodiments, $R^8$ is independently —O$R^{12}$. In embodiments, $R^8$ is independently —S$R^{12}$. In embodiments, $R^8$ is independently —N($R^{12}$)($R^{13}$). In embodiments, $R^8$ is independently —C(O)$R^{12}$. In embodiments, $R^8$ is independently —OC(O)N($R^{12}$)($R^{13}$). In embodiments, $R^8$ is independently —N($R^{14}$)C(O)N($R^{12}$)($R^{13}$). In embodiments, $R^8$ is independently —N($R^{14}$)C(O)O$R^{15}$. In embodiments, $R^8$ is independently —N($R^{14}$)S(O)$_2$$R^{15}$. In embodiments, $R^8$ is independently —C(O)$R^{15}$. In embodiments, $R^8$ is independently —S(O)$R^{15}$. In embodiments, $R^8$ is independently —OC(O)$R^{15}$. In embodiments, $R^8$ is independently —C(O)N($R^{12}$)($R^{13}$). In embodiments, $R^8$ is independently —C(O)C(O)N($R^{12}$)($R^{13}$). In embodiments, $R^8$ is independently —N($R^{14}$)C(O)$R^{15}$. In embodiments, $R^8$ is independently —S(O)$_2$$R^{15}$. In embodiments, $R^8$ is independently —S(O)$_2$N($R^{12}$)($R^{13}$). In embodiments, $R^8$ is independently S(=O)(=NH)N($R^{12}$)($R^{13}$). In embodiments, $R^8$ is independently —CH$_2$C(O)N($R^{12}$)($R^{13}$). In embodiments, $R^8$ is independently —CH$_2$N($R^{14}$)C(O)$R^{15}$. In embodiments, $R^8$ is independently —CH$_2$S(O)$_2$$R^{15}$. In embodiments, $R^8$ is independently —CH$_2$S(O)$_2$N($R^{12}$)($R^{13}$).

In embodiments, $W^9$ is C. In embodiments, $W^{10}$ is C.

In embodiments,

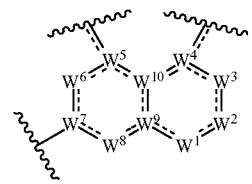

is selected from

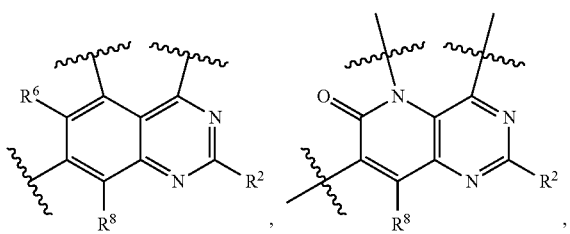

-continued
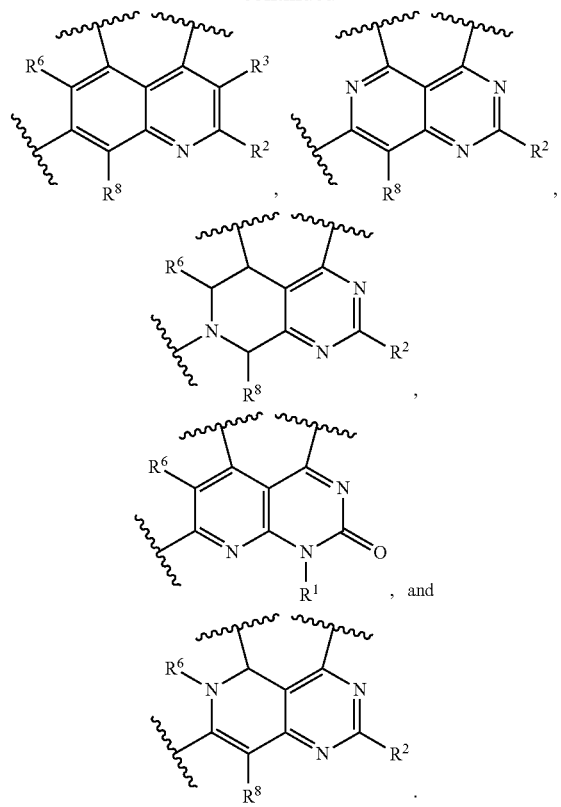
, and
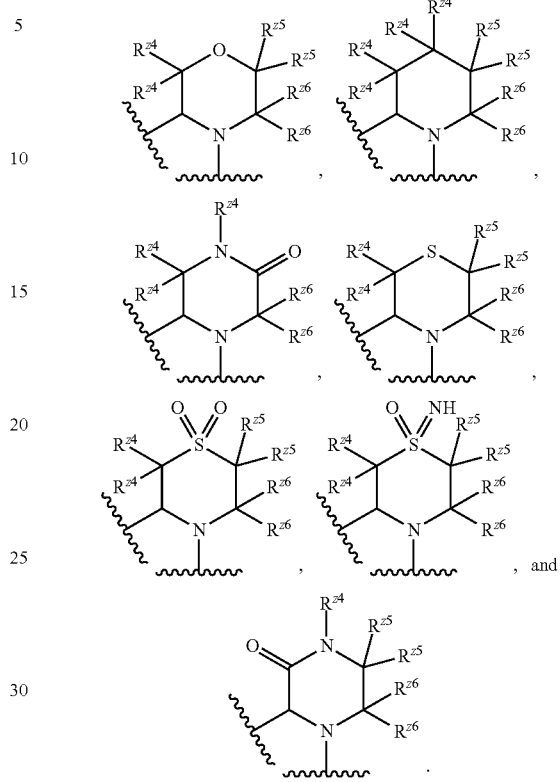
, and
In embodiments,
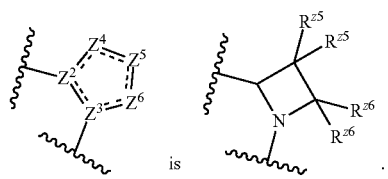
is
In embodiments,
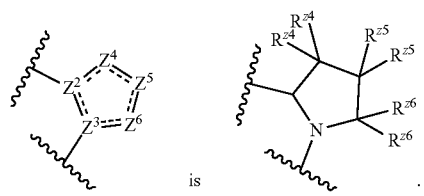
is
In embodiments,
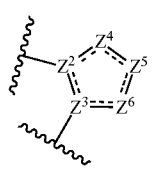
is selected from
In embodiments,
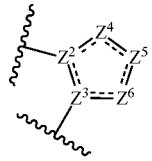
is selected from
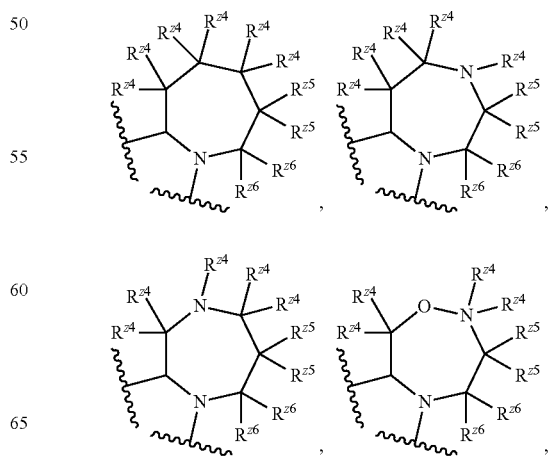
, -continued
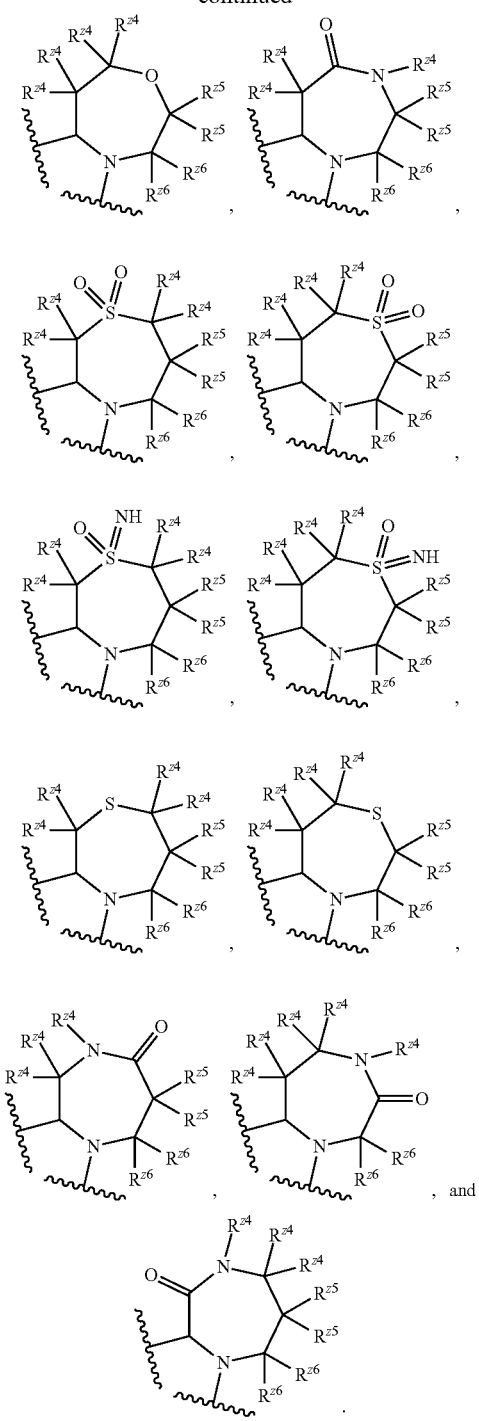
In embodiments,
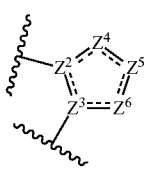
is selected from
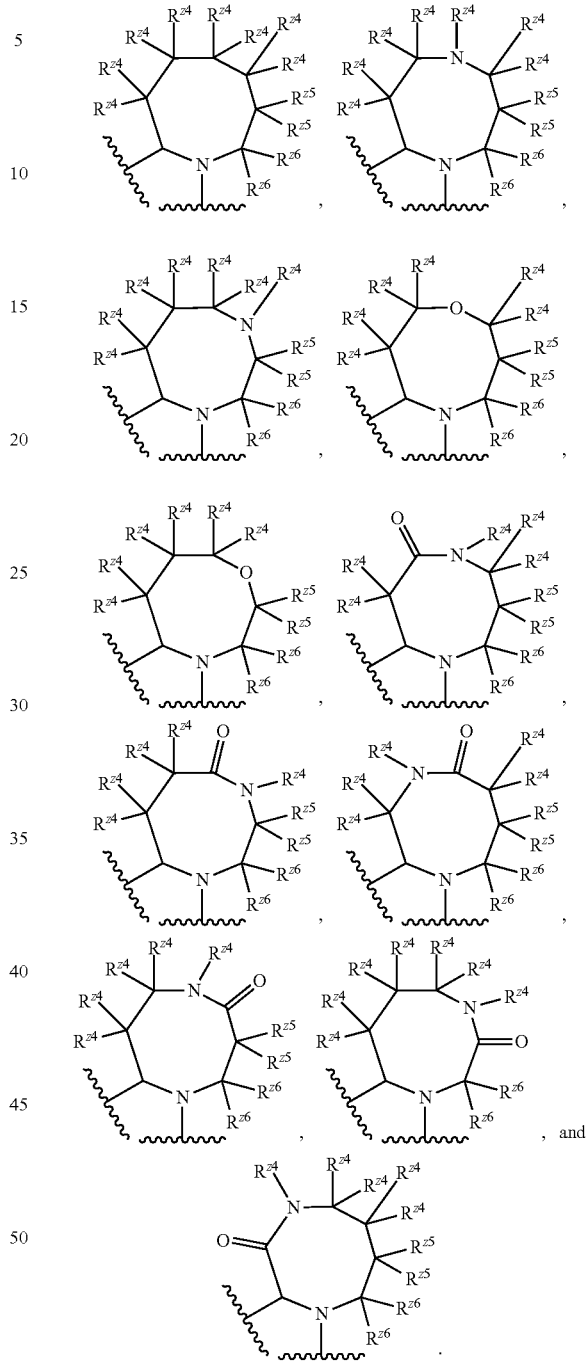
In embodiments,
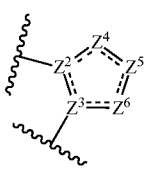

is selected from
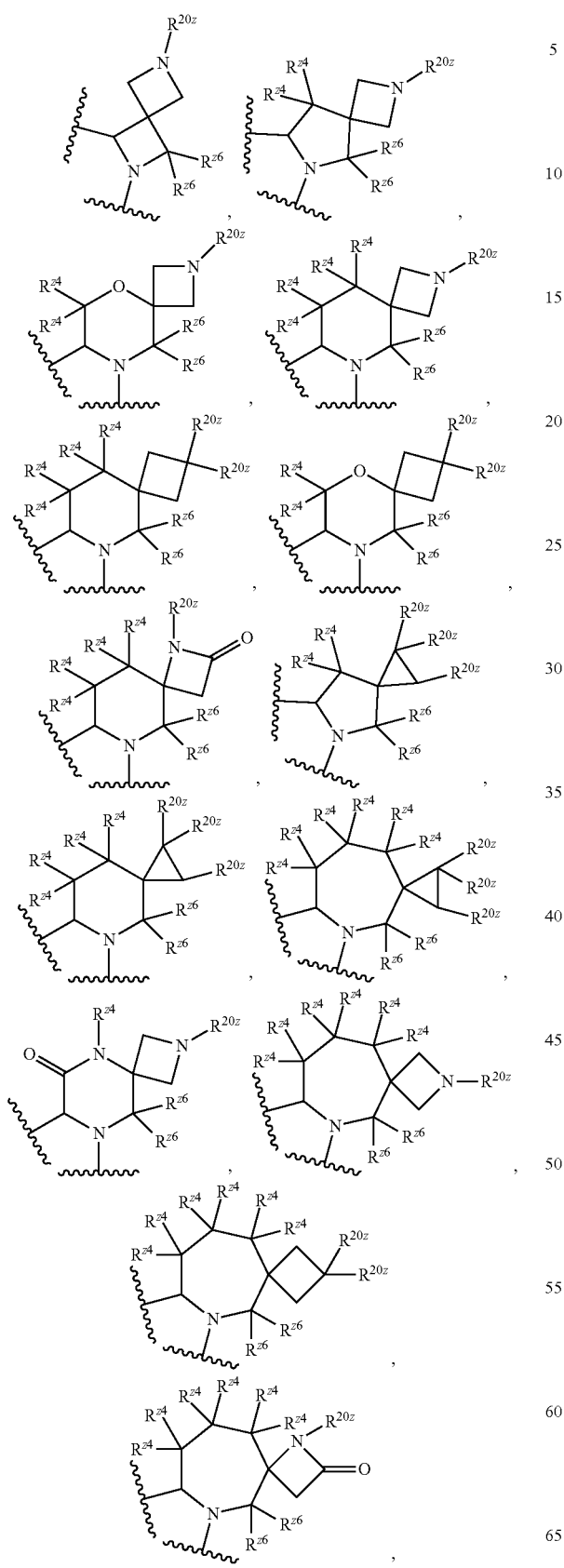
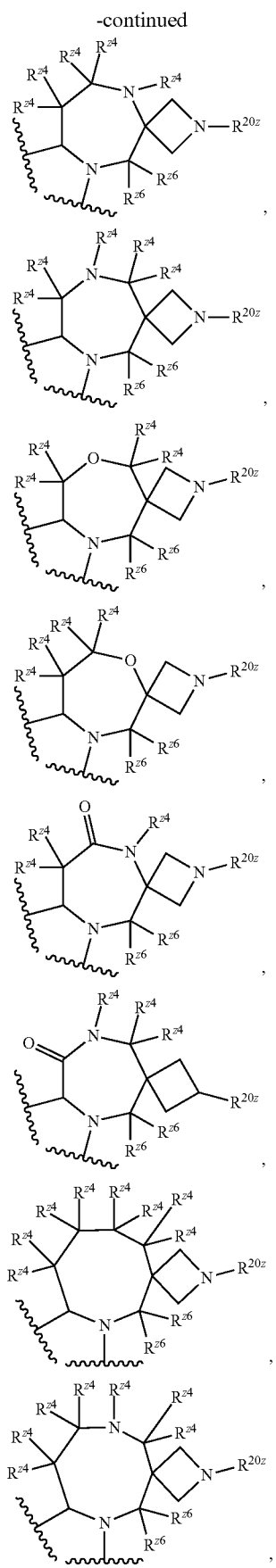

-continued
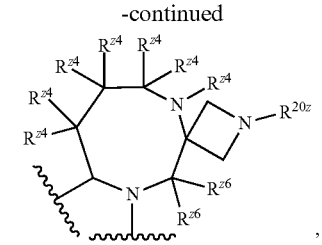,
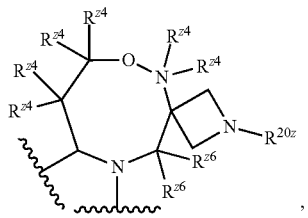,
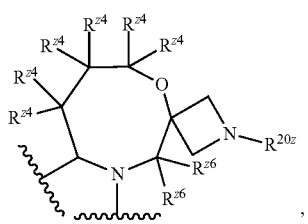,
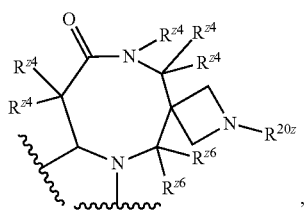,
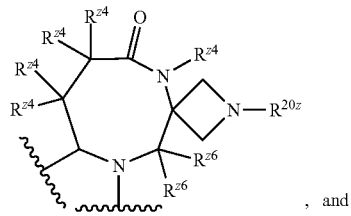, and
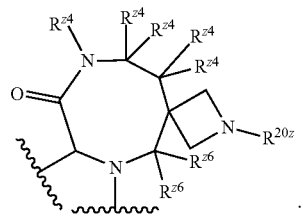.
In embodiments,
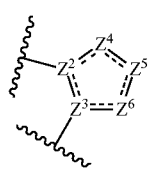 is selected from
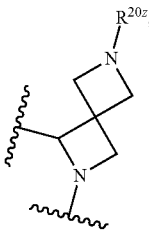 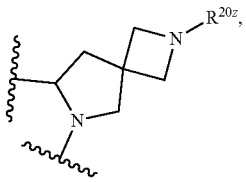,
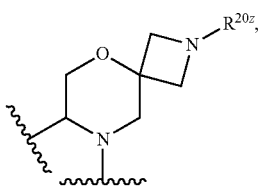 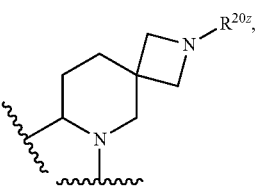,
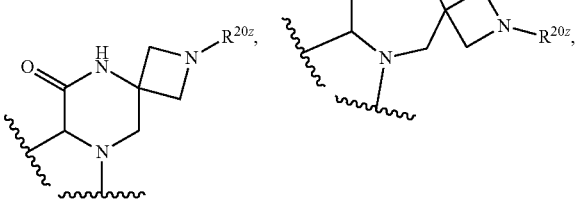,
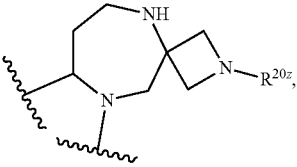,
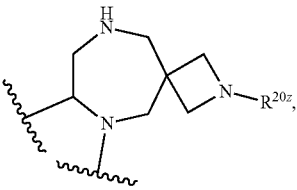,
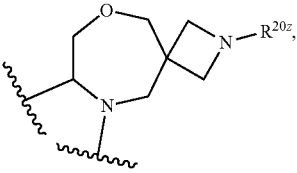,
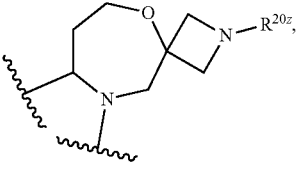,
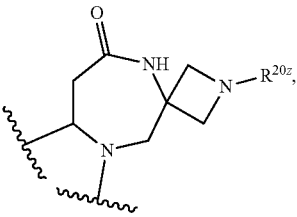, -continued
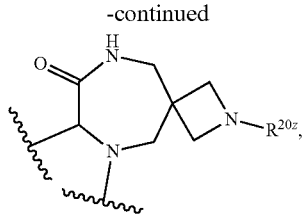
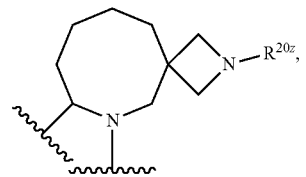
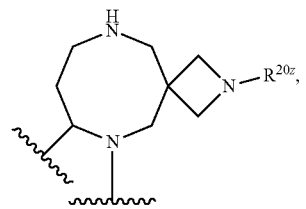
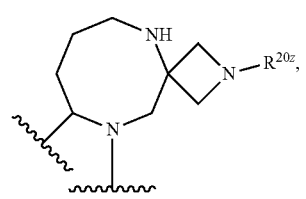

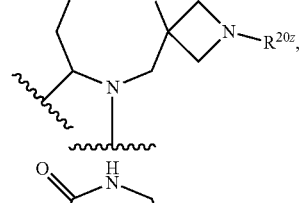
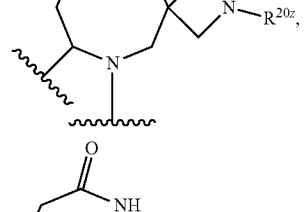
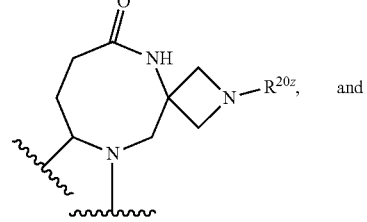 and
-continued
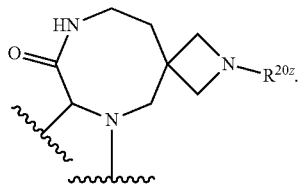
In embodiments,
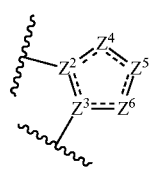
is selected from
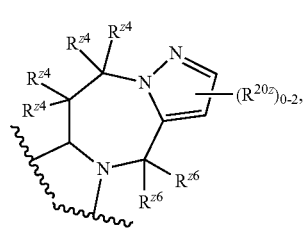
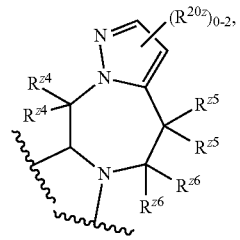
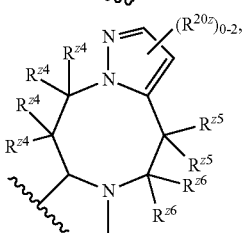
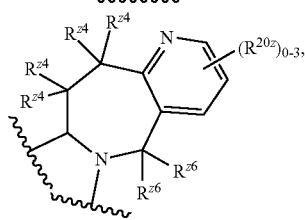
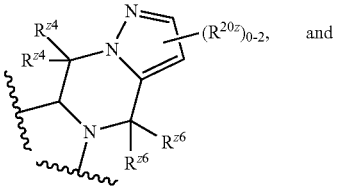 and -continued
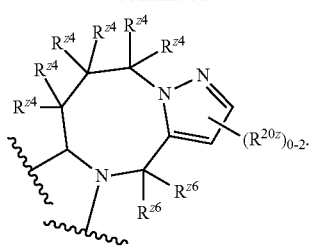
In embodiments,
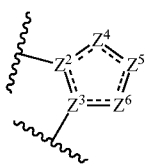
is selected from
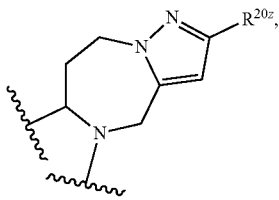
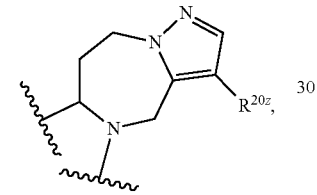
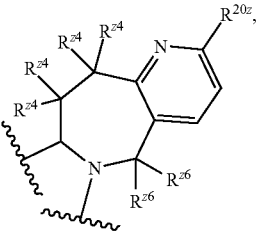
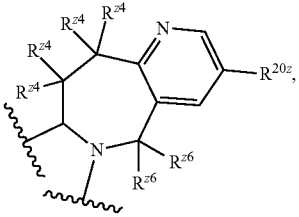
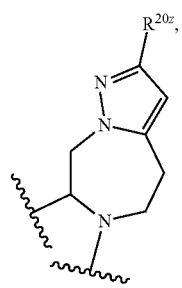
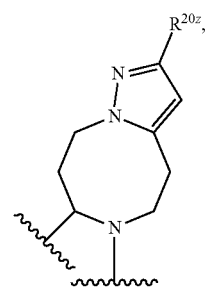
-continued
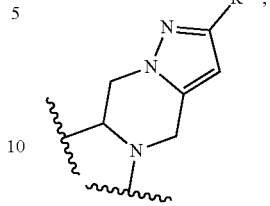
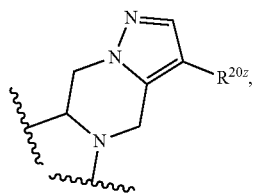
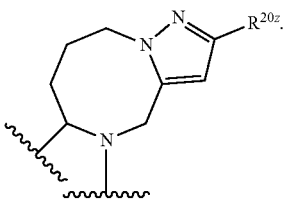
In embodiments,
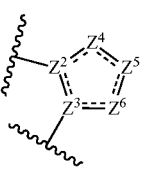
is
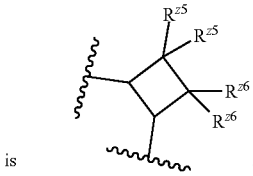
In embodiments,
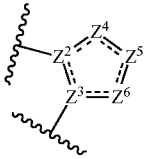
is
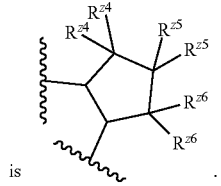
In embodiments,
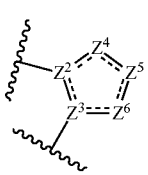
is selected from
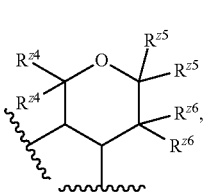
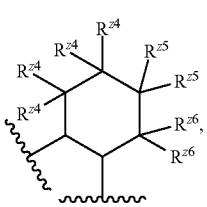

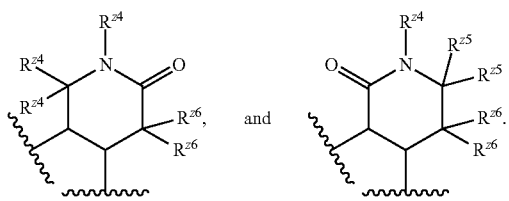
and
In embodiments,
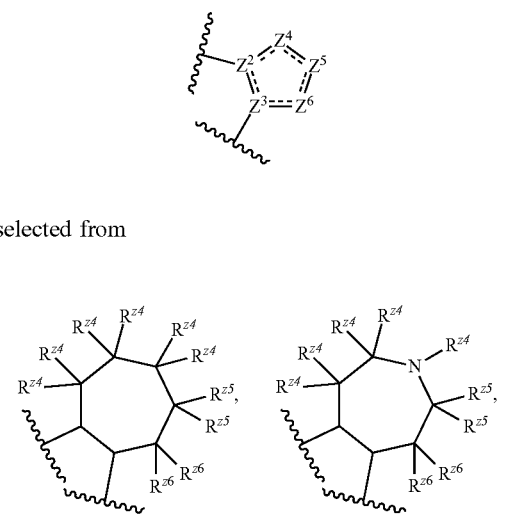
is selected from
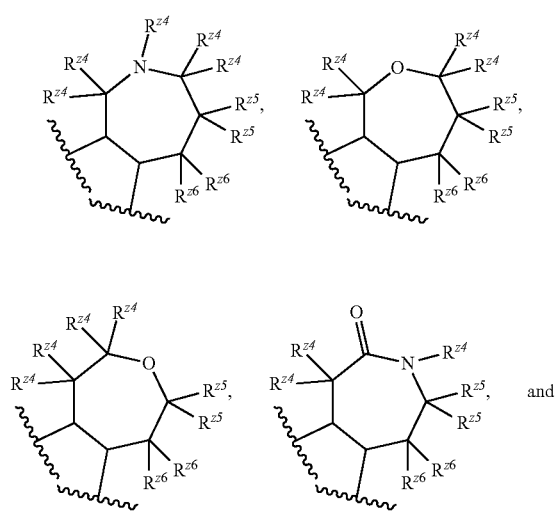
and
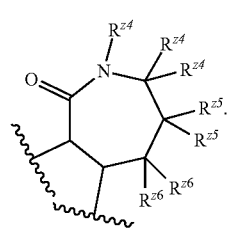
In embodiments,
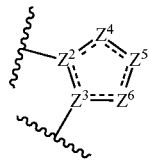
is selected from
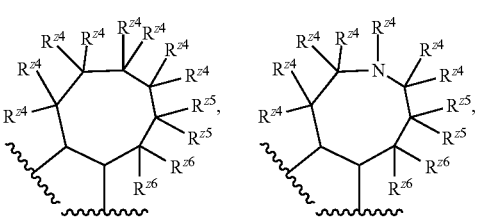
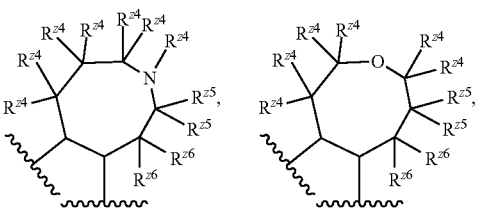
and
In embodiments,
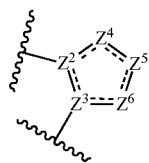

is selected from
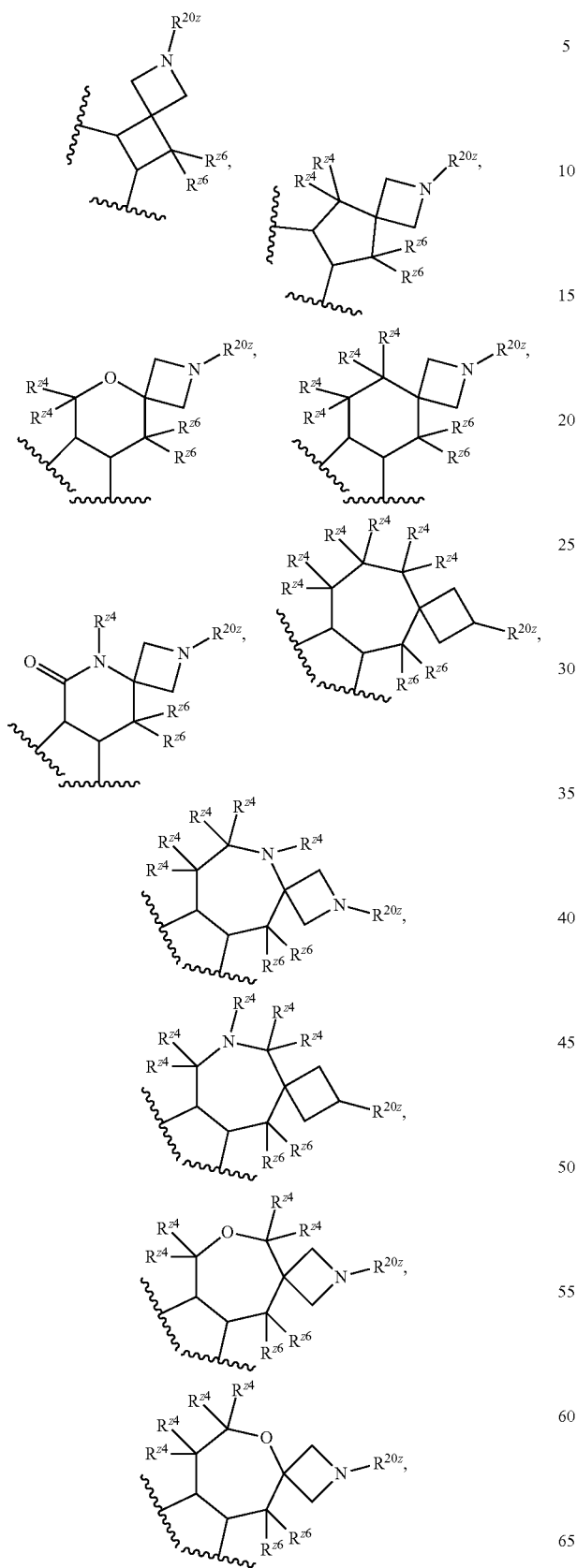
-continued
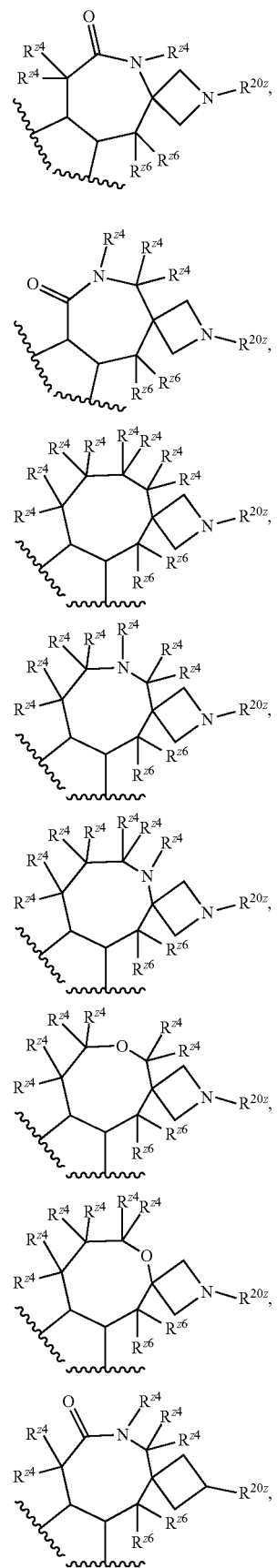

-continued
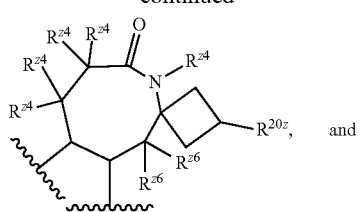
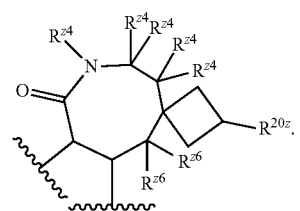
In embodiments,
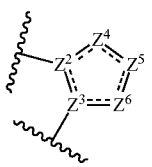
is selected from
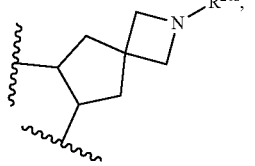
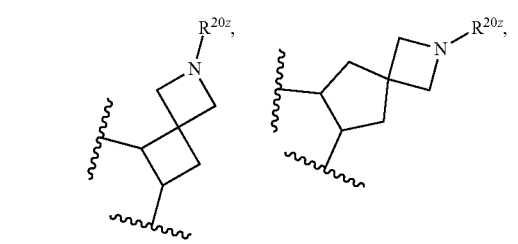
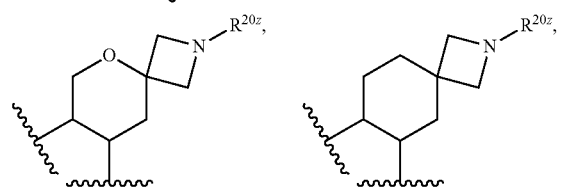
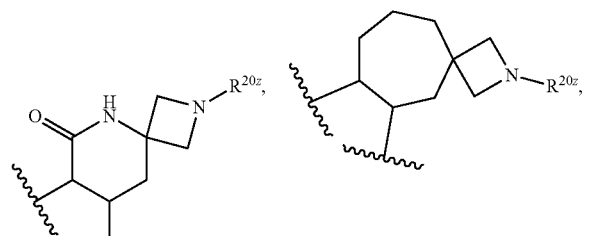
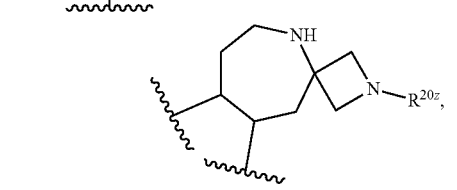
-continued
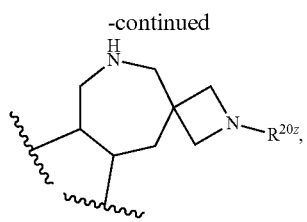
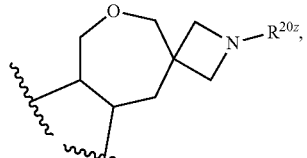
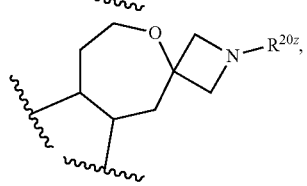
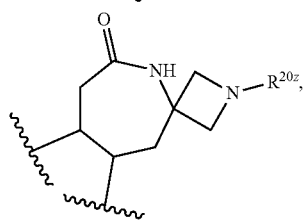
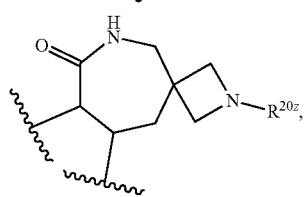
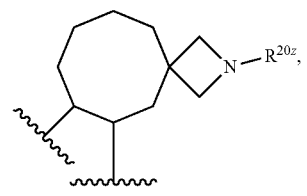
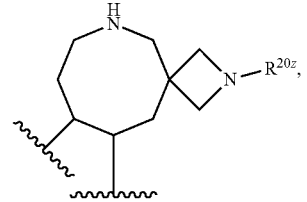
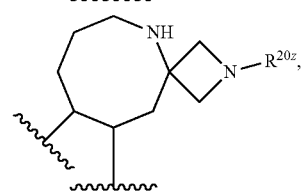
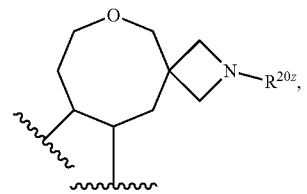

-continued
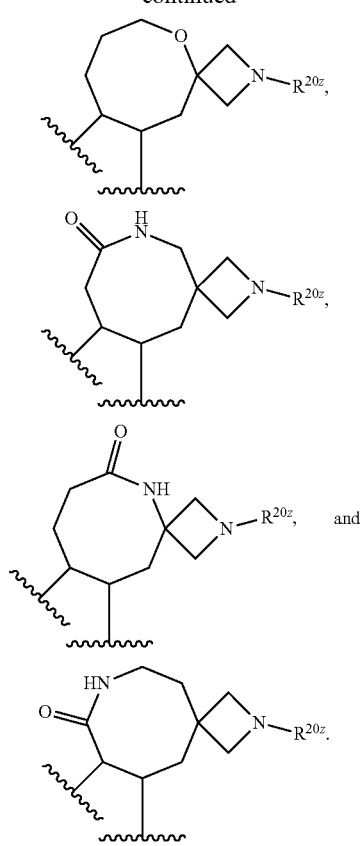
In embodiments,
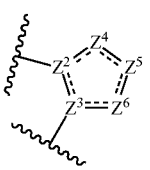
is selected from
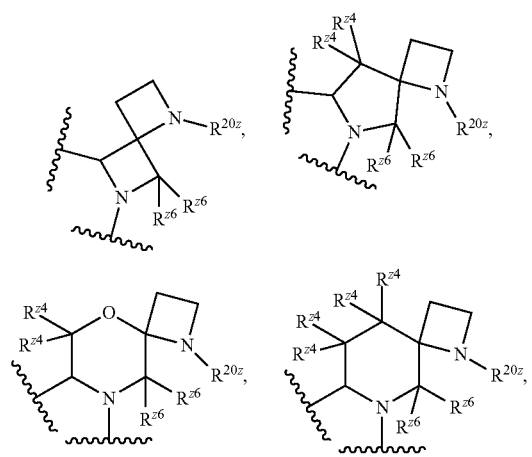
-continued
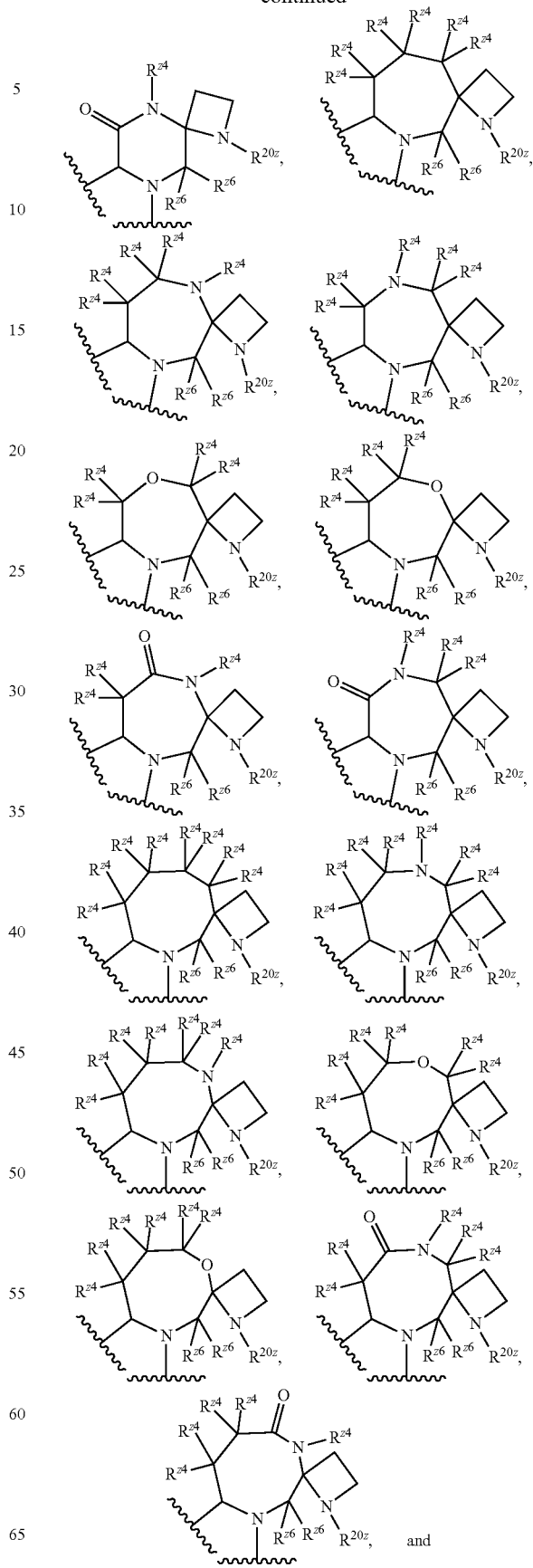
and -continued
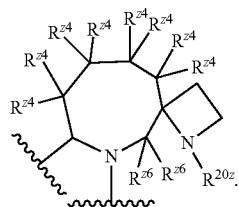
In embodiments,
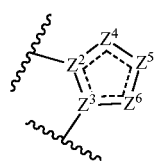
is selected from
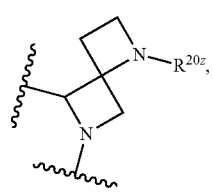 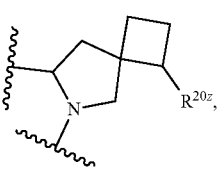
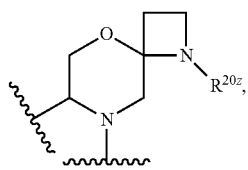 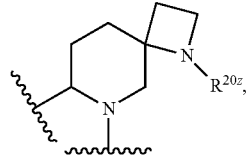
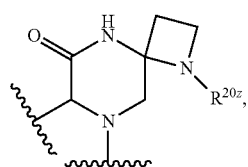 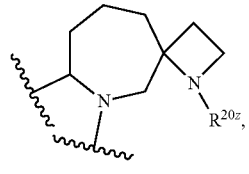
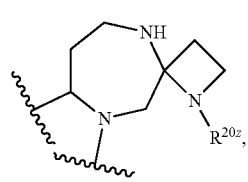 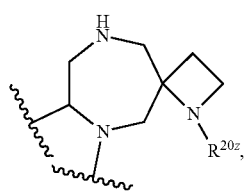
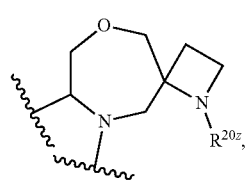 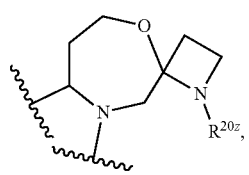
-continued
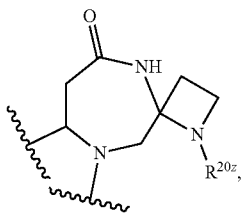 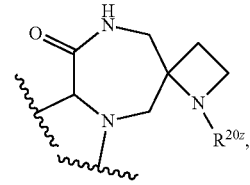
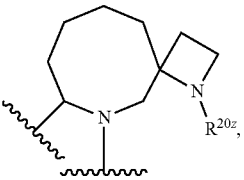 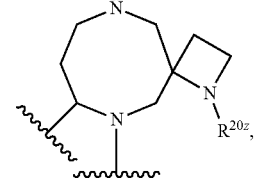
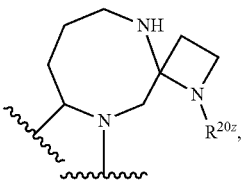 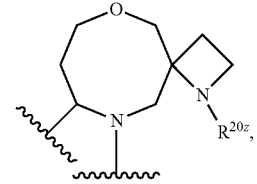
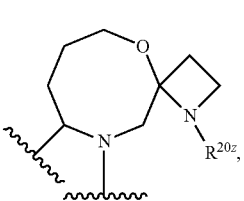 and 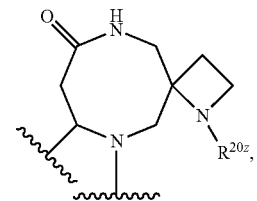.
In embodiments,
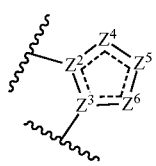
is selected from
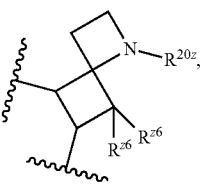 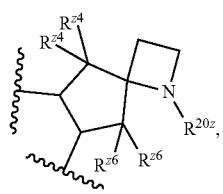

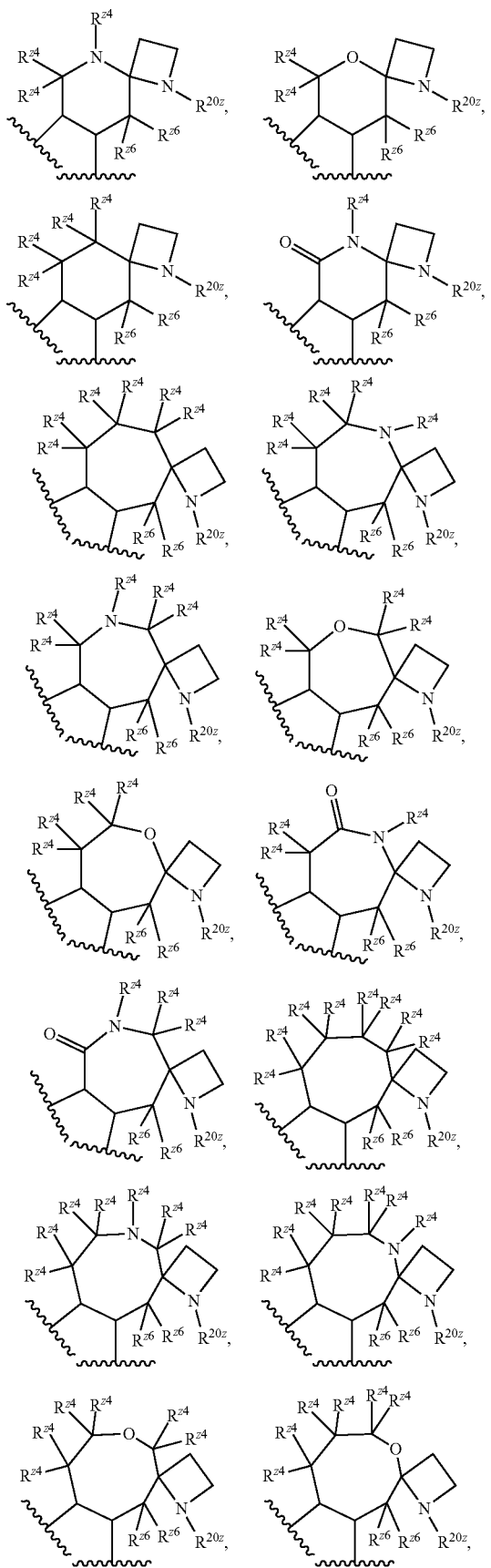
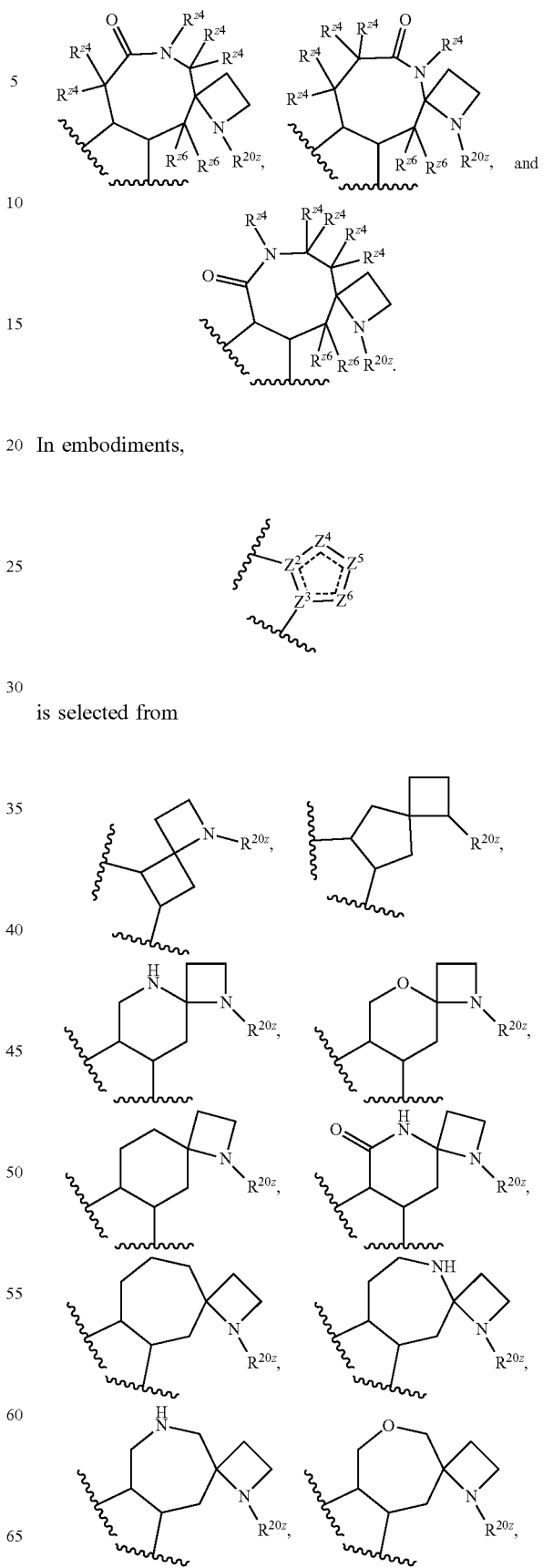
In embodiments,
is selected from

-continued
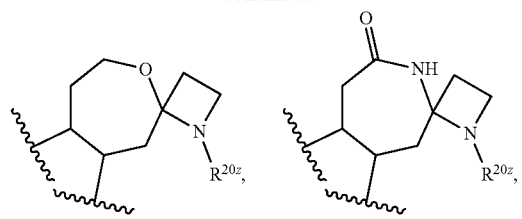
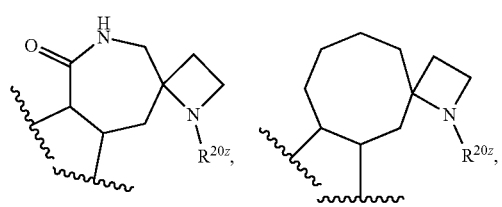
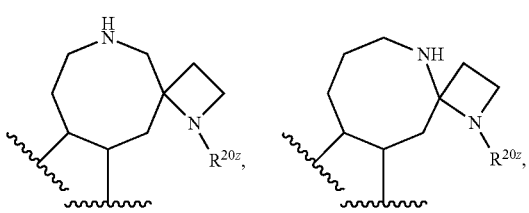
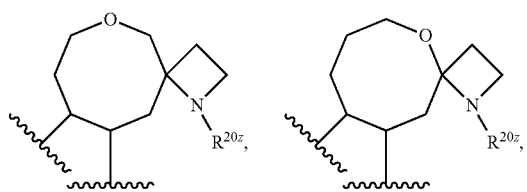
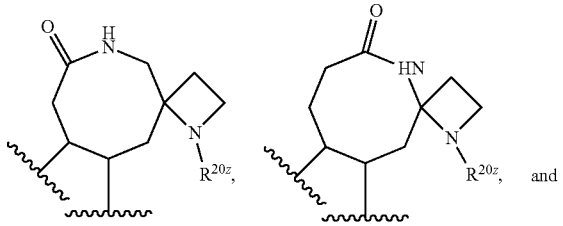
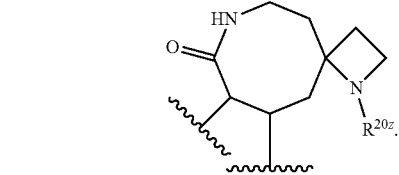
In embodiments,
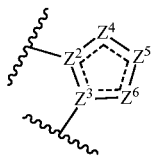
is selected from
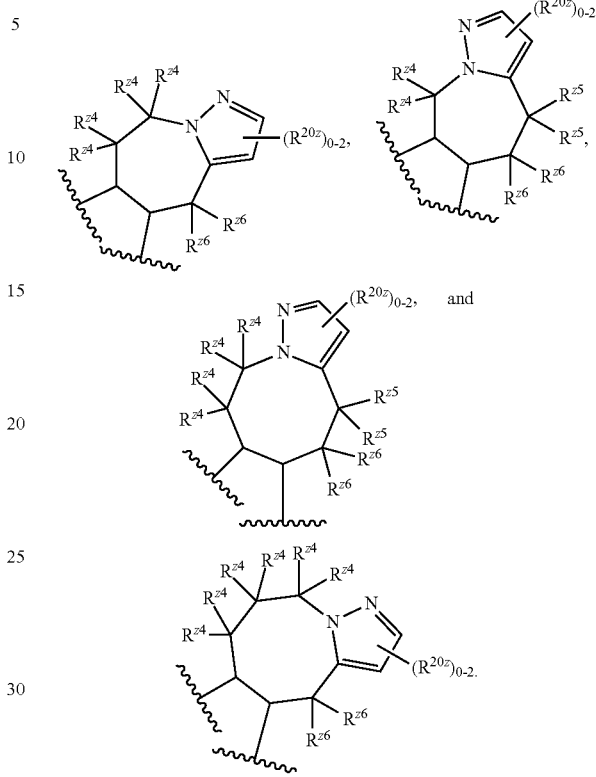
In embodiments,
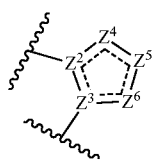
is selected from
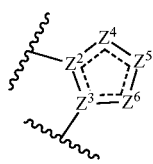
In embodiments,
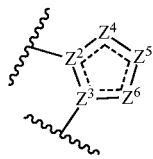

is selected from
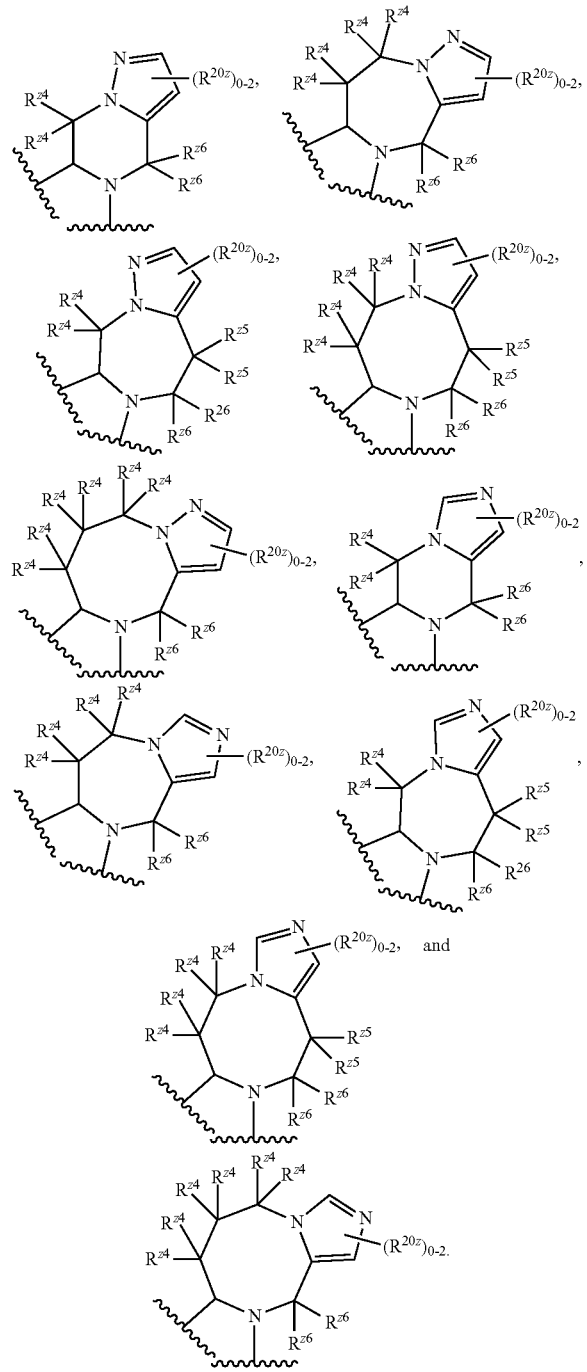
In embodiments,
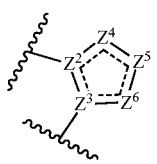
is selected from
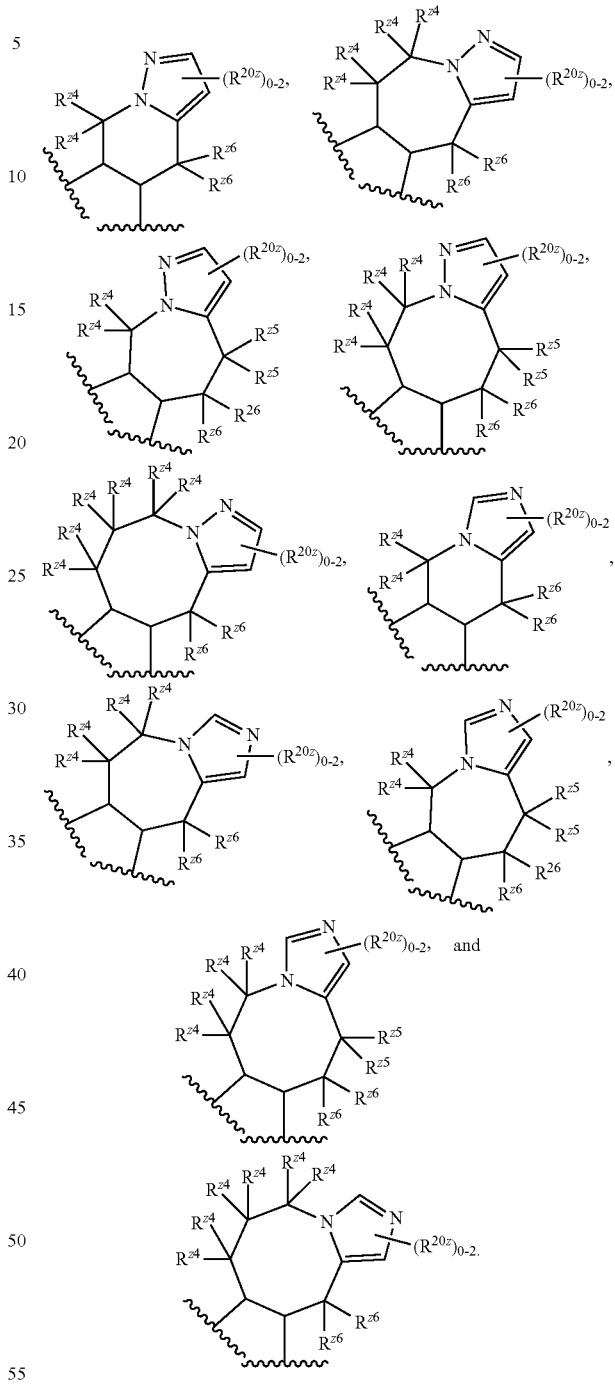
In embodiments,
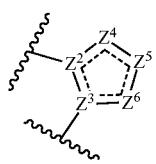

is selected from
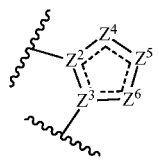
In embodiments,
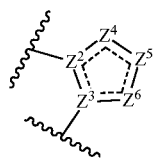
is selected from
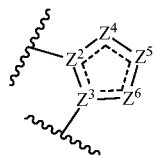
In embodiments,
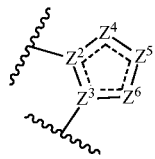
is selected from
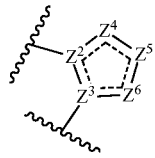
In embodiments,
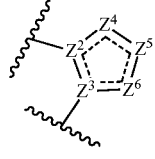
is selected from
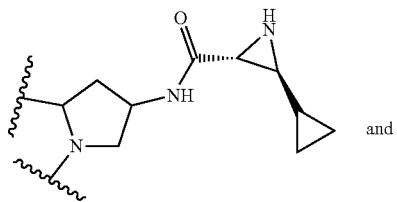
and
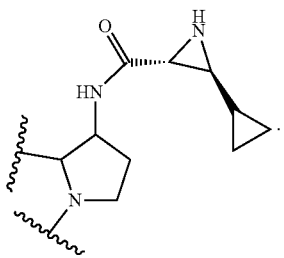
In embodiments,
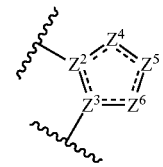
is selected from
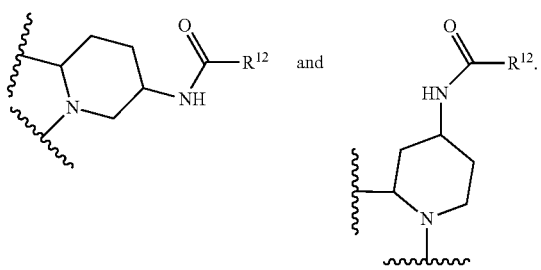
In embodiments,
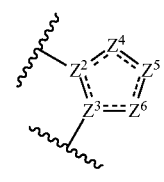

is selected from
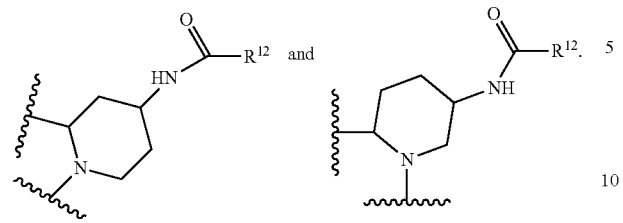
In embodiments,
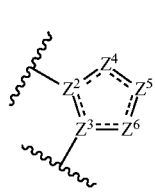
is selected from
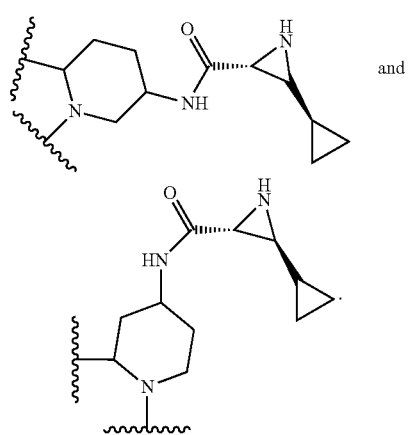
In embodiments,
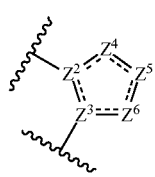
is selected from
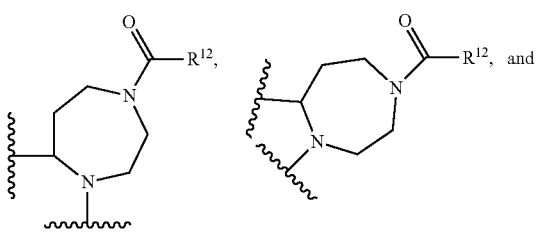
-continued
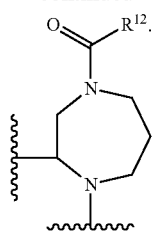
In embodiments,
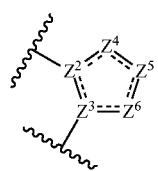
is selected from
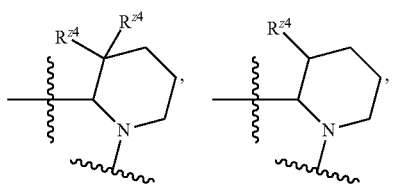
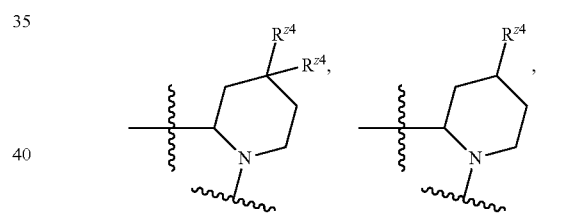
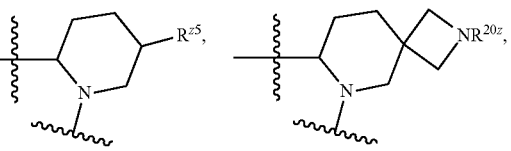
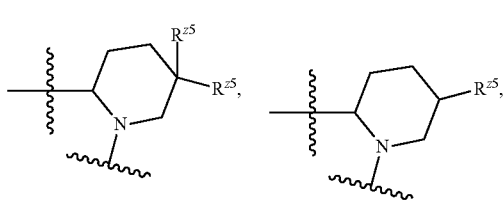
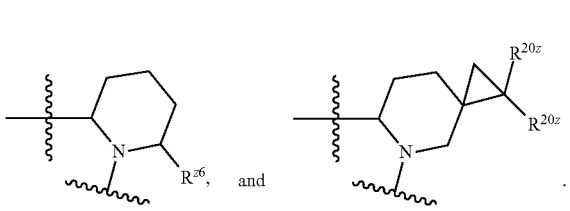

In embodiments, 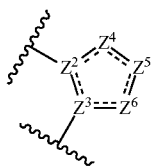
is selected from
is selected from
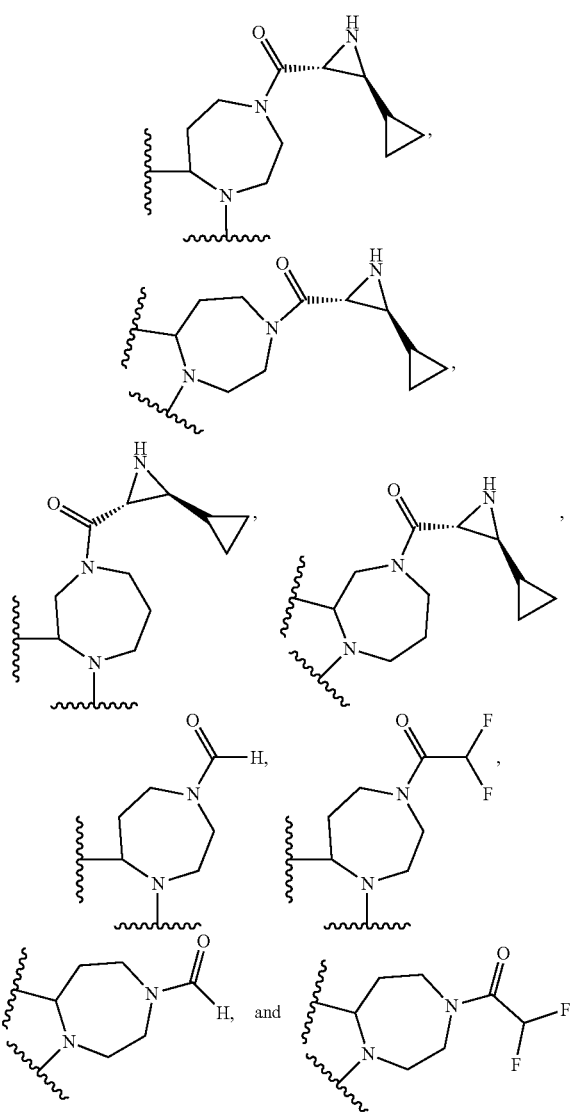
In embodiments, 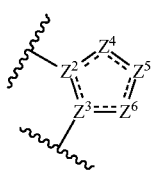
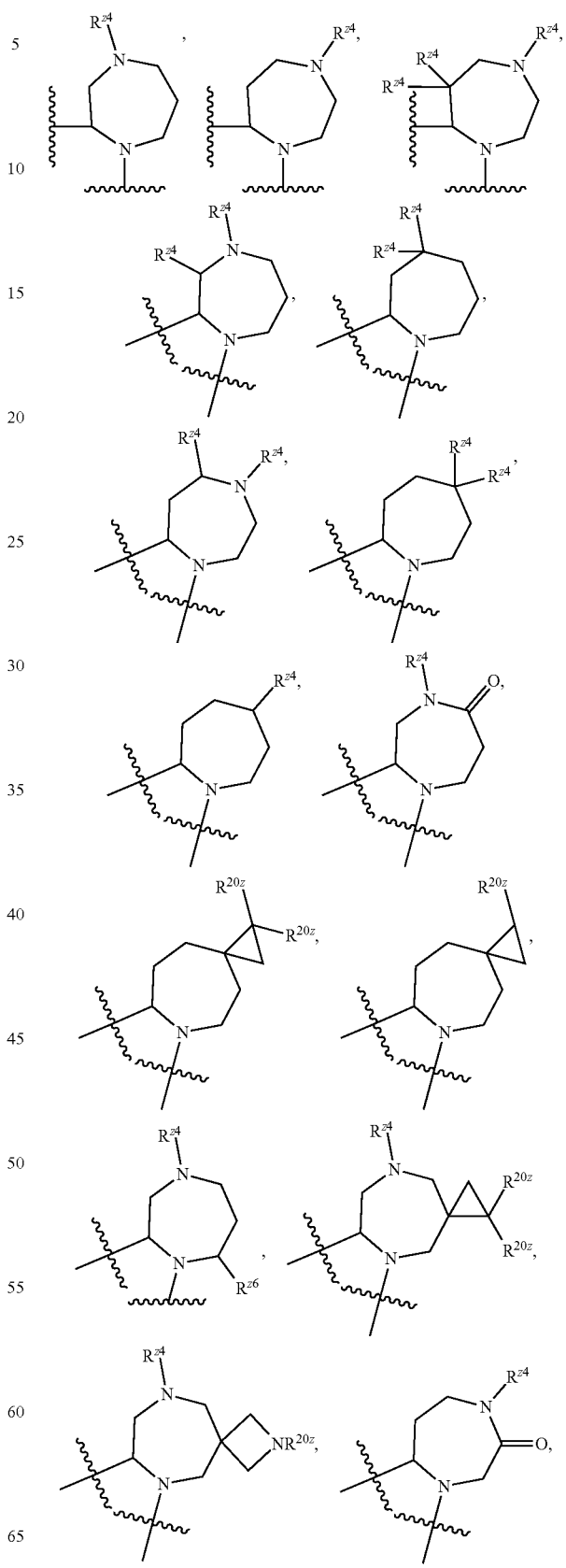

-continued
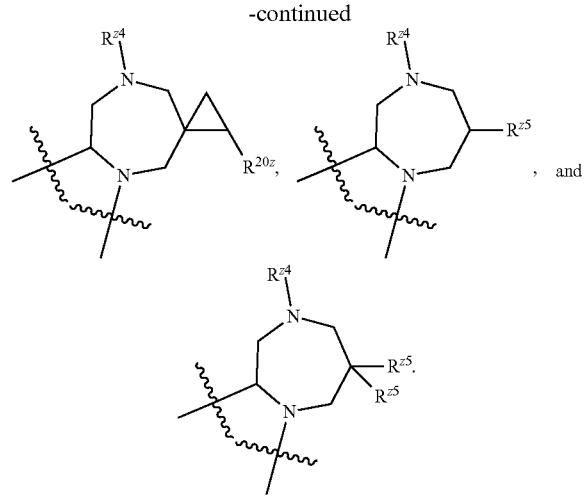
In embodiments,
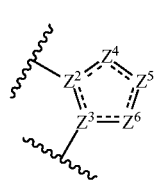
is selected from
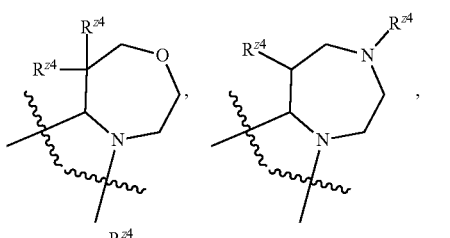
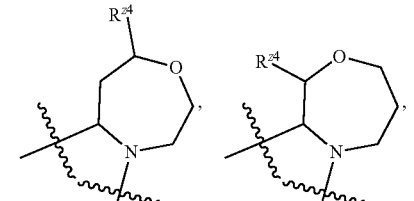
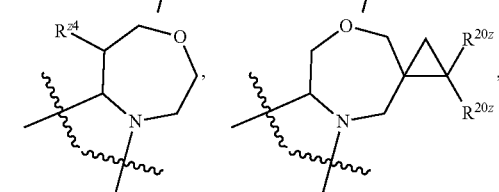
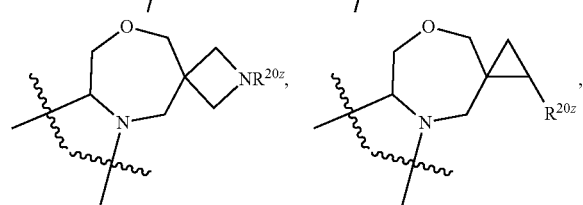
-continued
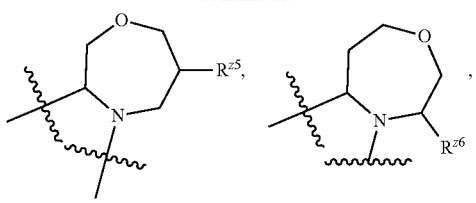
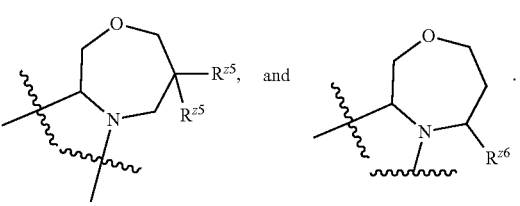
In embodiments,
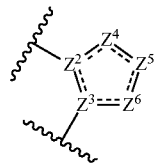
is selected from
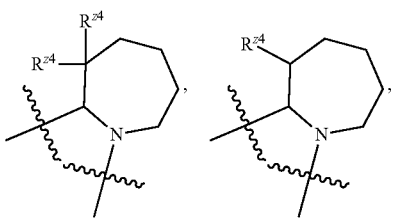
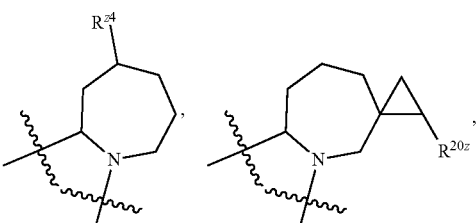
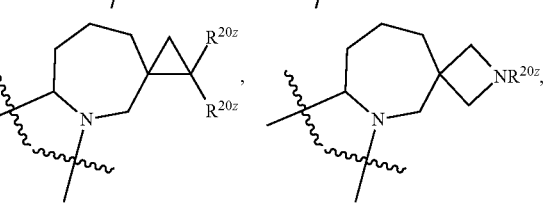

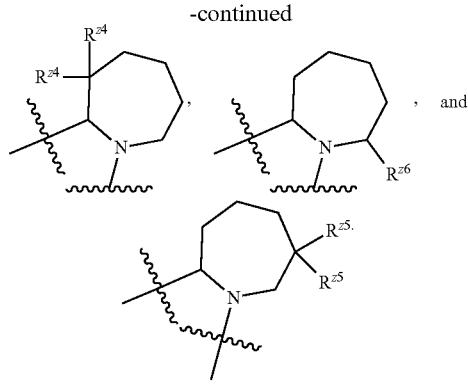
In embodiments,
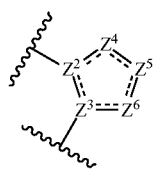
is selected from
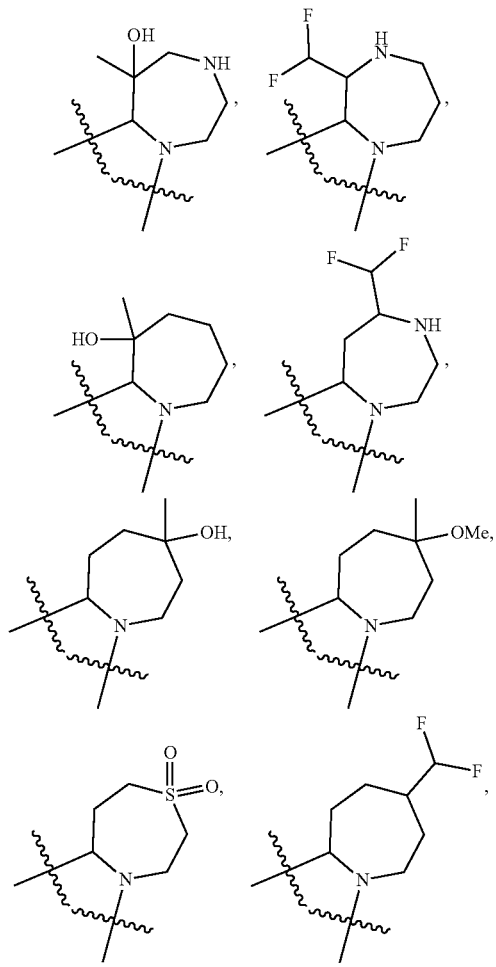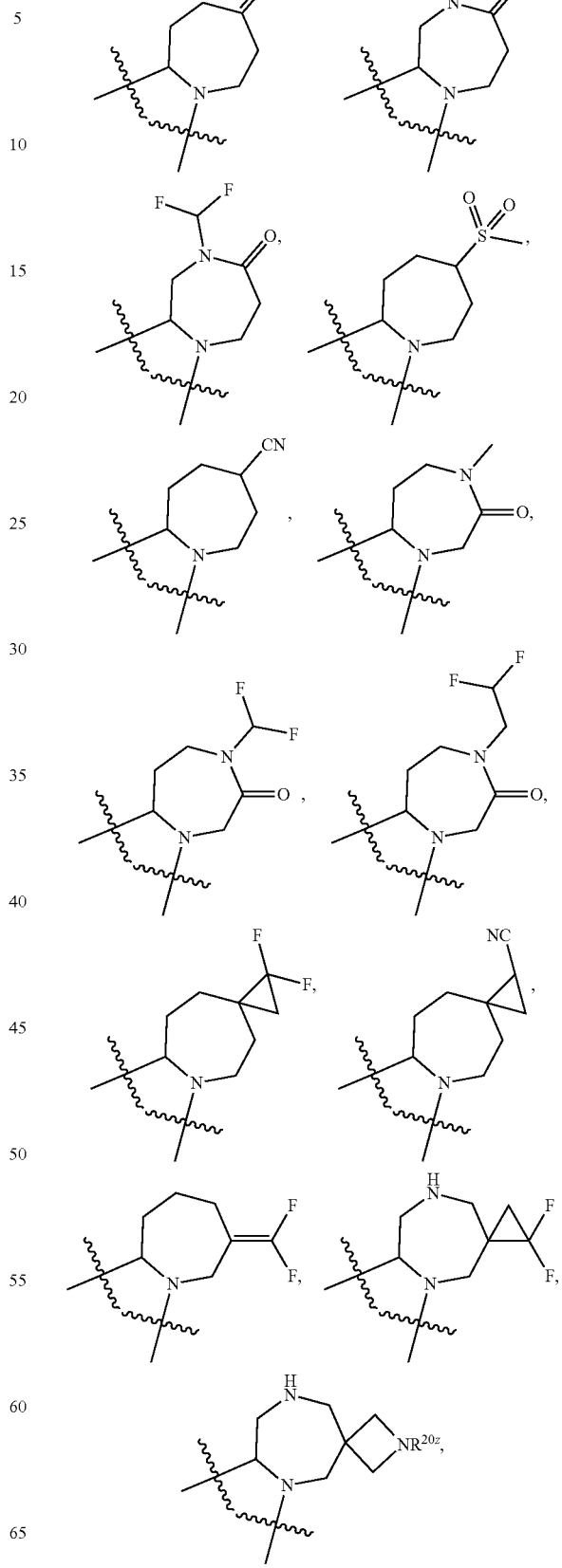

-continued
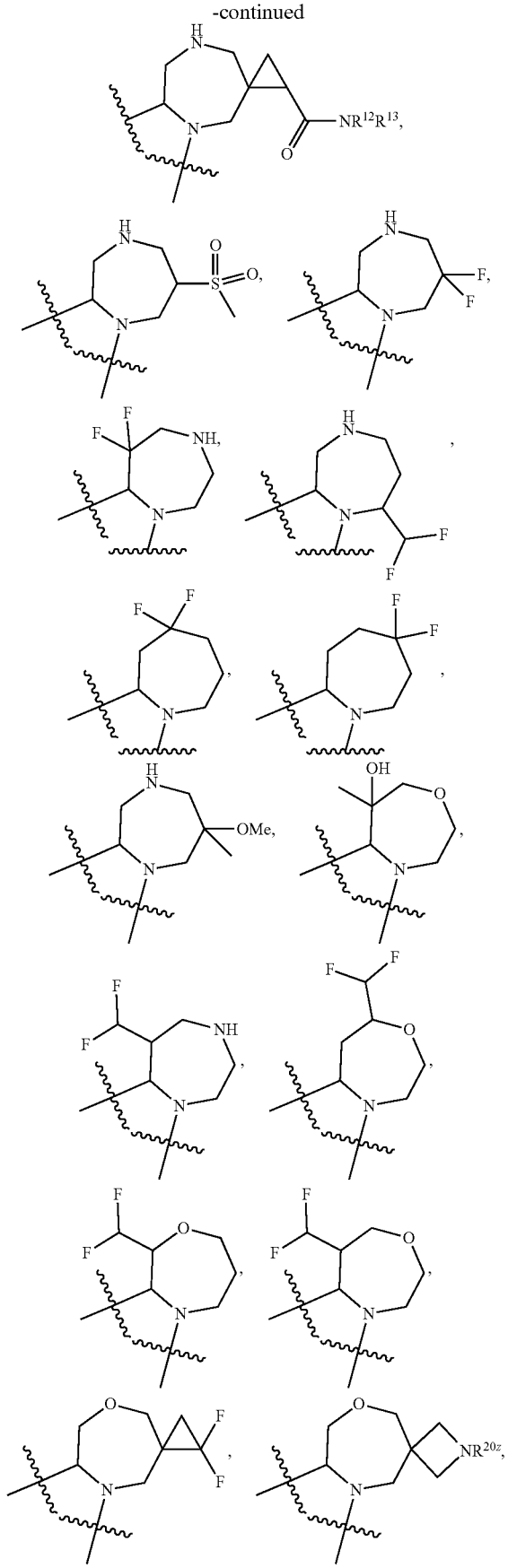
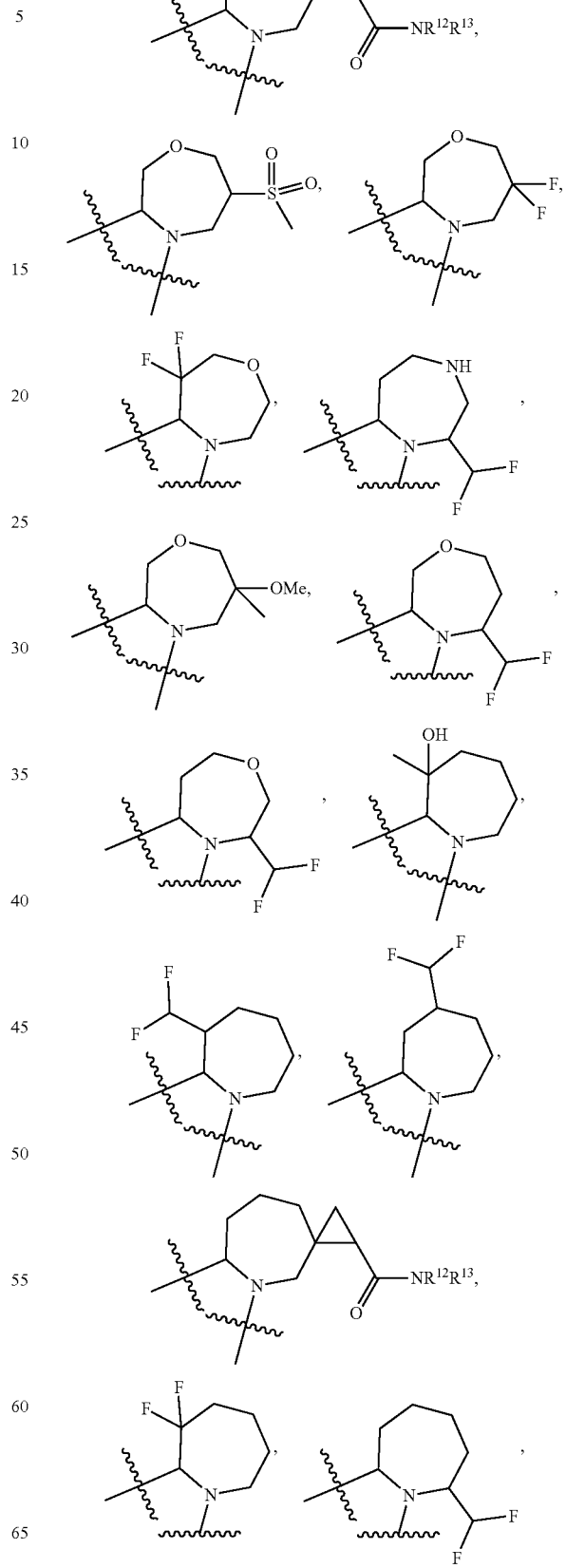

-continued
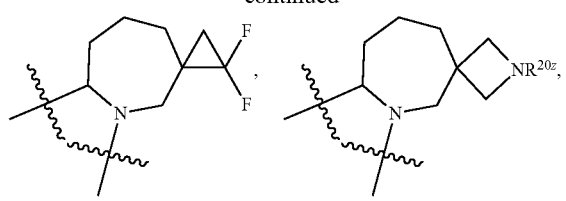
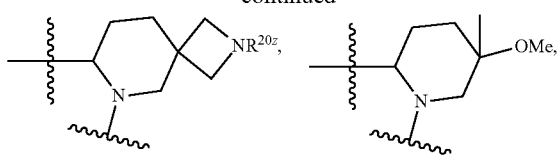
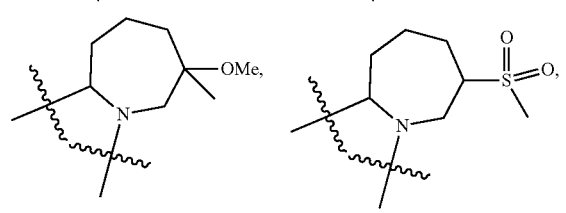
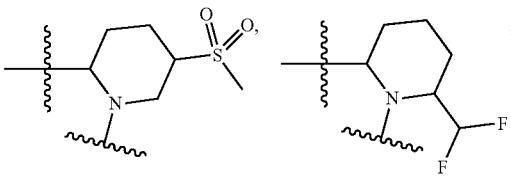
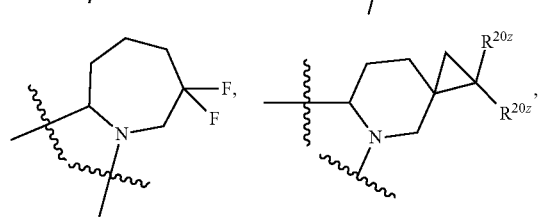
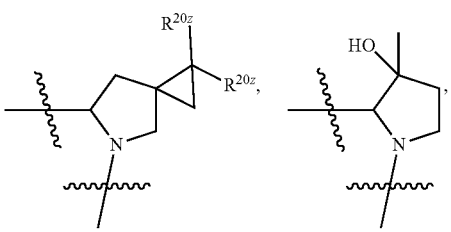
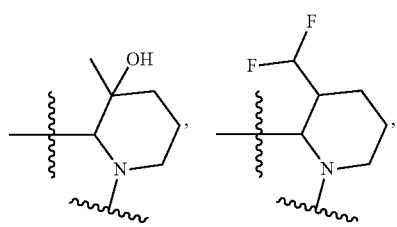
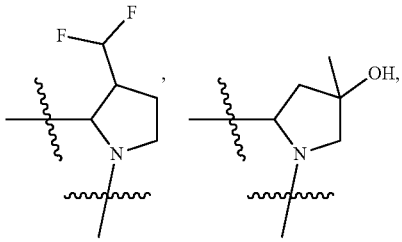
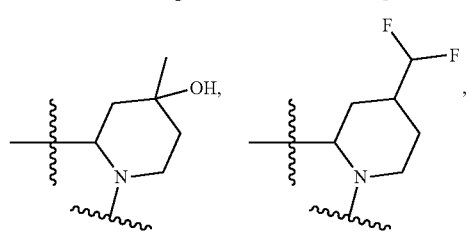
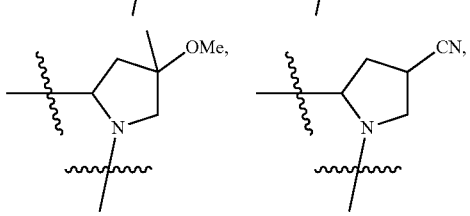
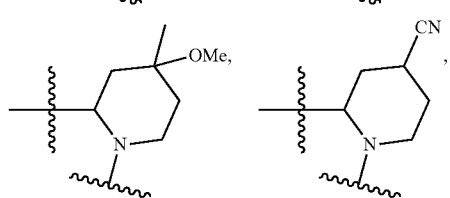
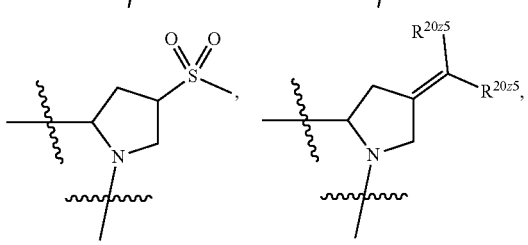
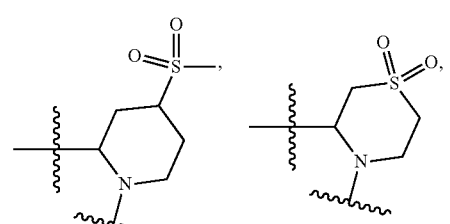
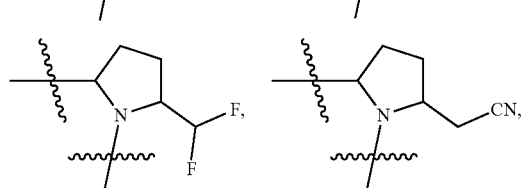
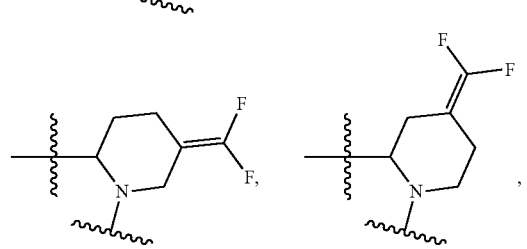
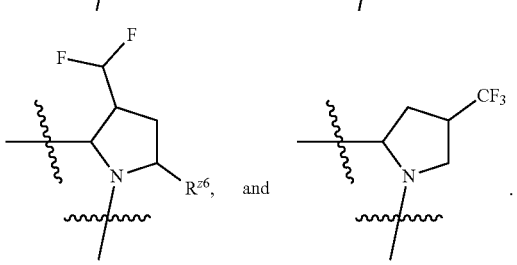

In embodiments,
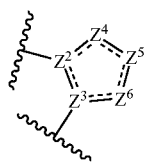
is selected from
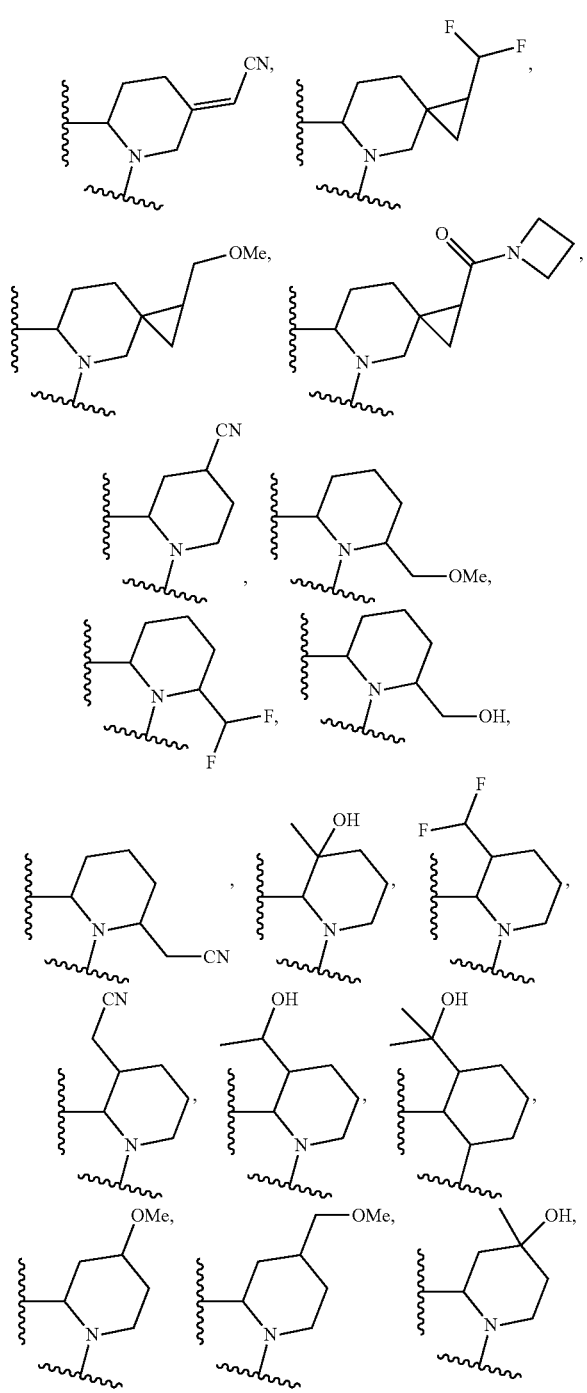
-continued
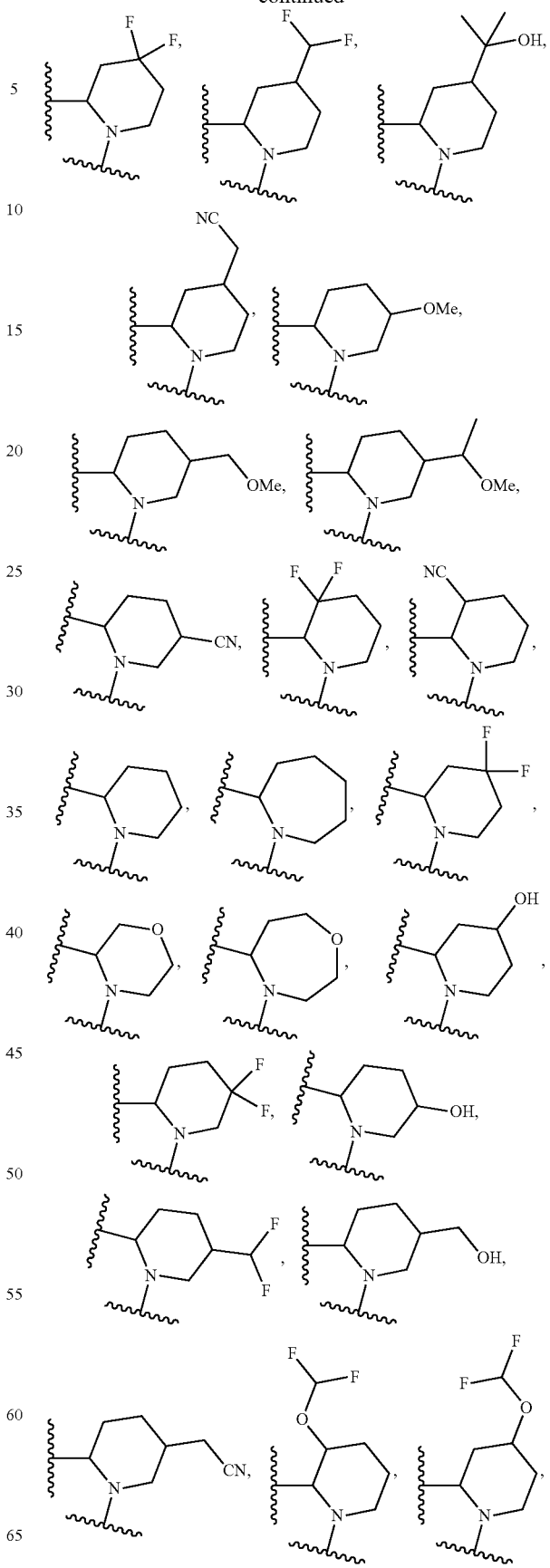

-continued
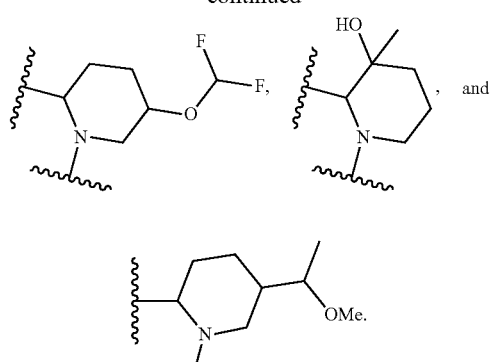
In embodiments,
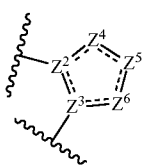
is selected from
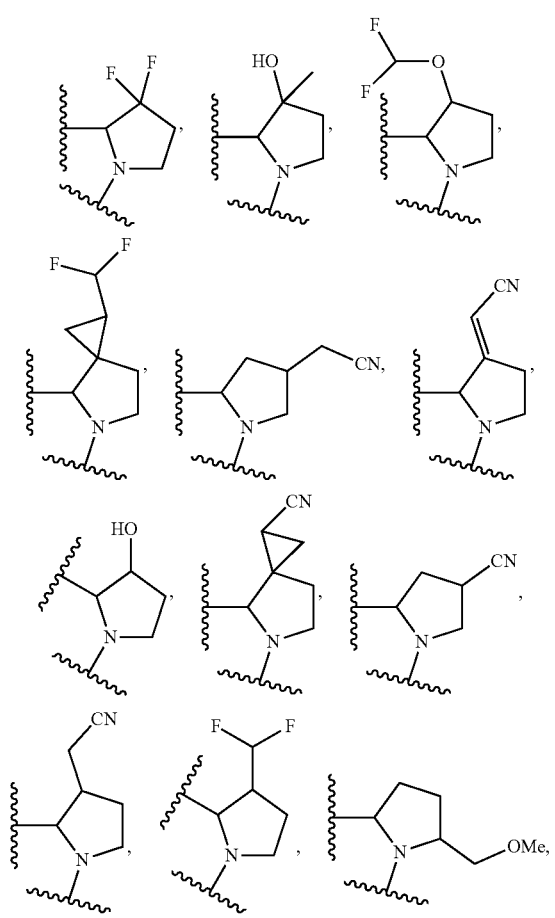
-continued
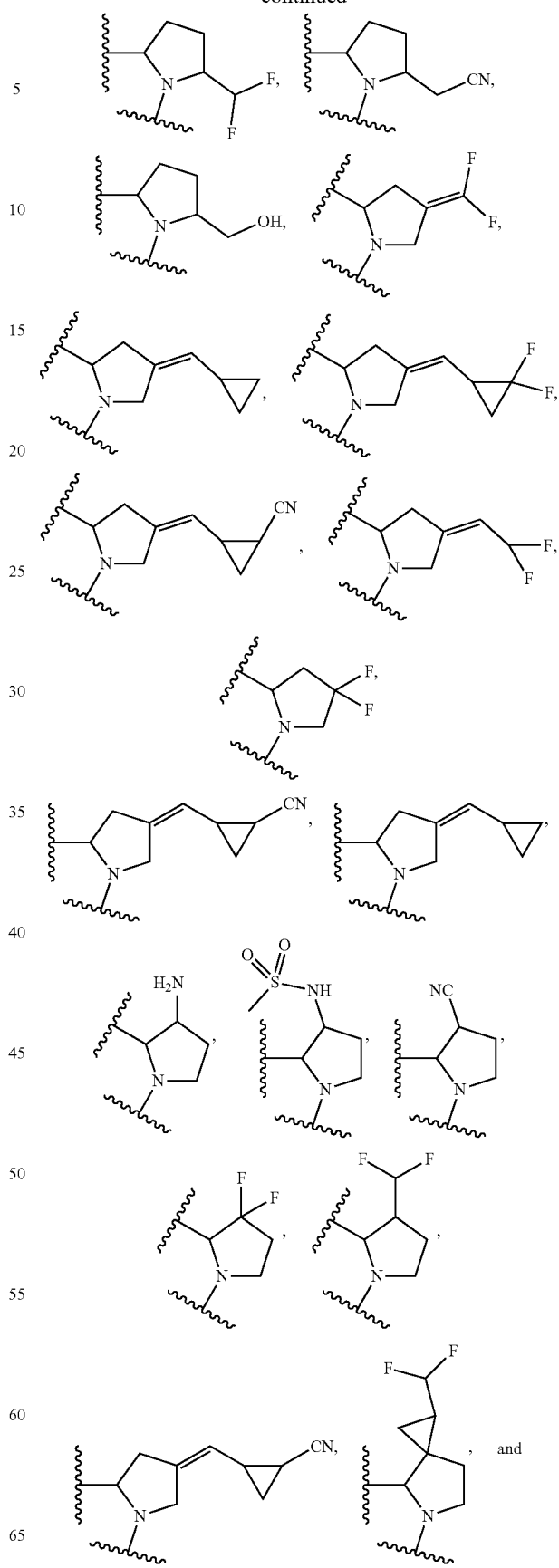

In embodiments,
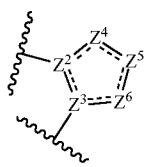
is selected from

-continued
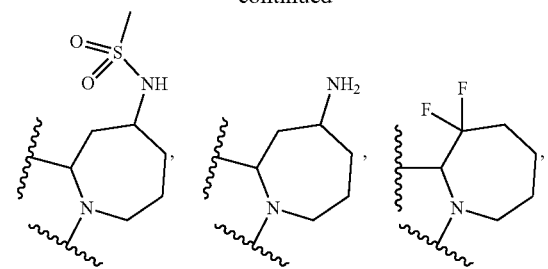
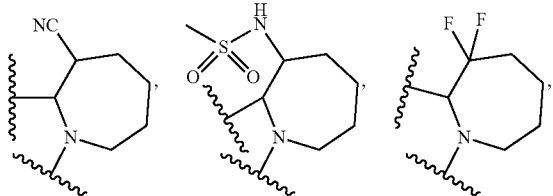
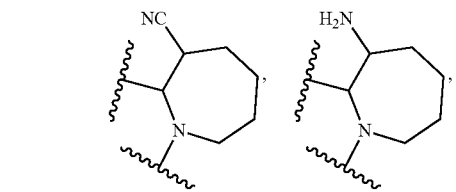
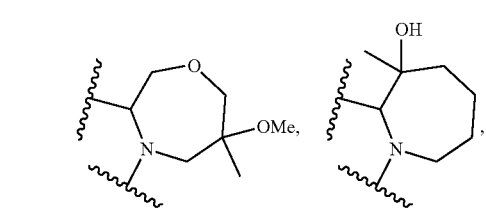
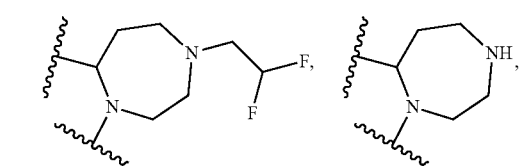
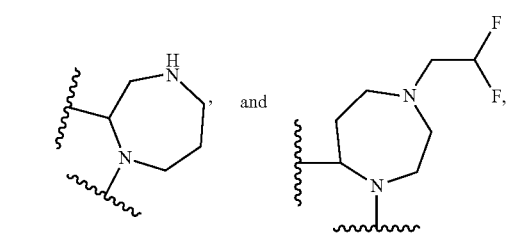
is selected from
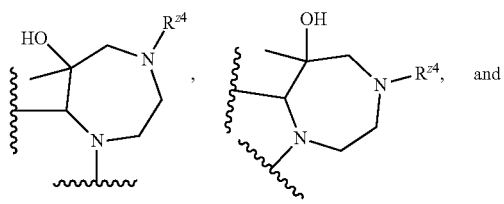
In embodiments,
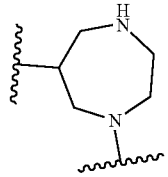
is selected from
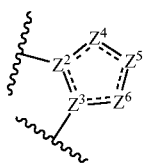
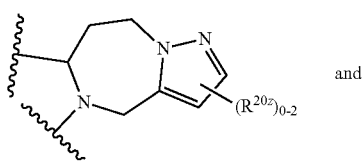
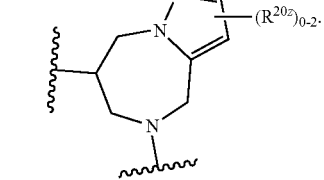
In embodiments,
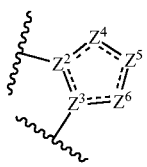
is selected from
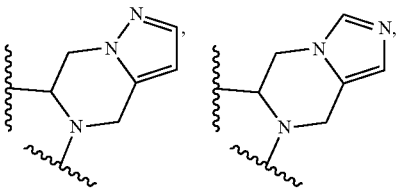

-continued
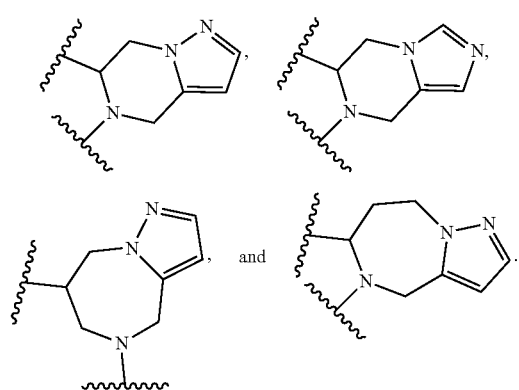
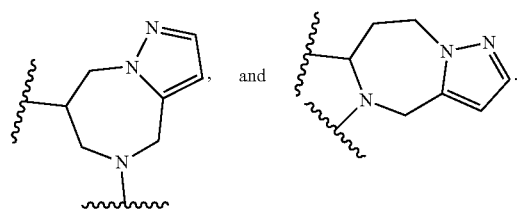
In embodiments,
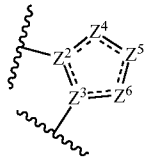
is selected from
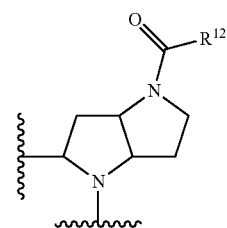   and   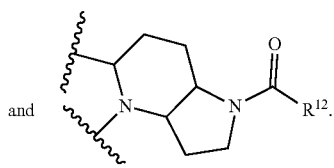
In embodiments,
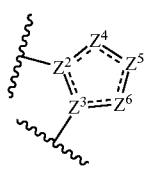
is selected from
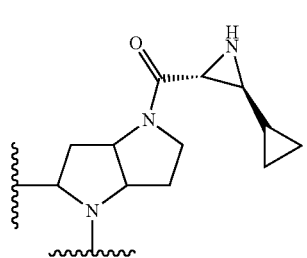   and
-continued
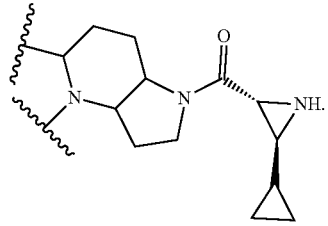
In embodiments,
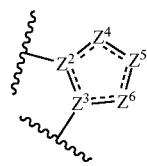
is selected from
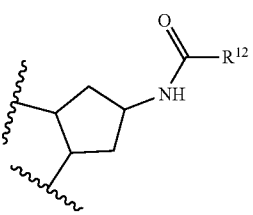   and   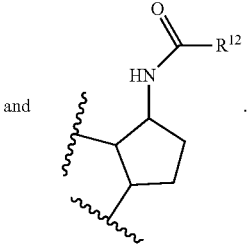
In embodiments,
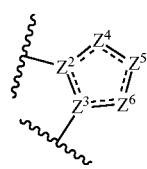
is selected from
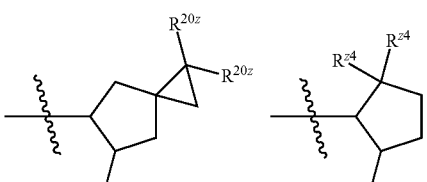
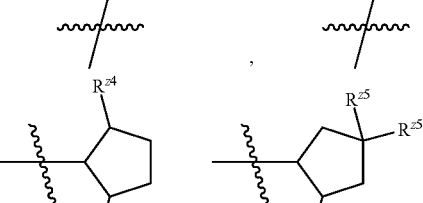
, and 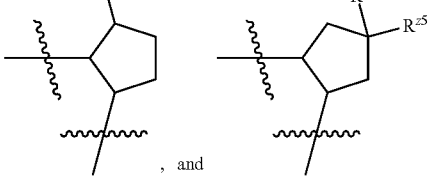

In embodiments,
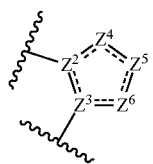
is selected from
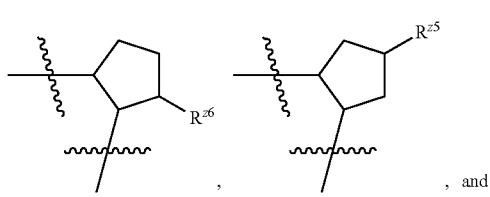
In embodiments,
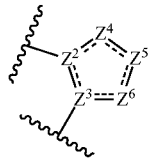
is selected from
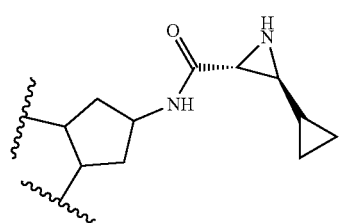
and
In embodiments,
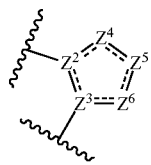
is selected from
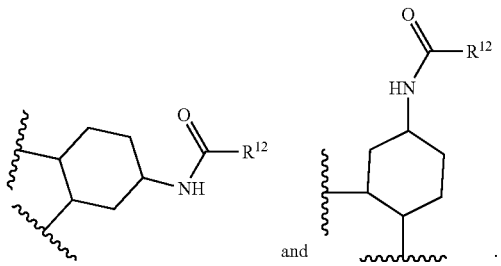
and
In embodiments,
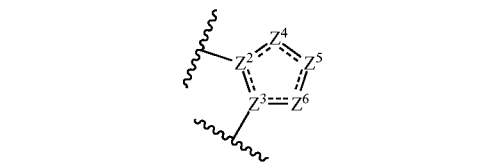
is selected from
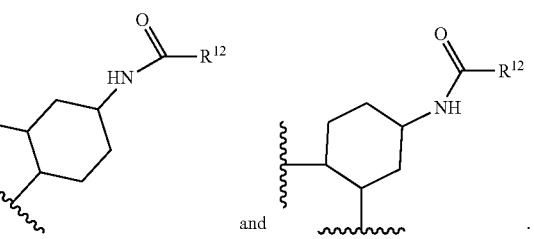
and
In embodiments,
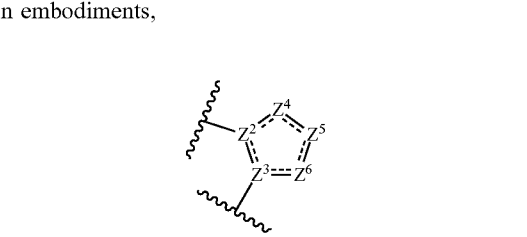
is selected from
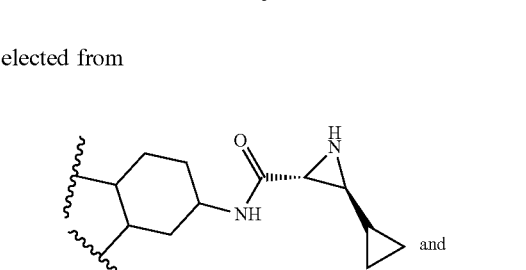
and -continued
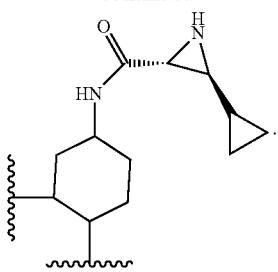
In embodiments,
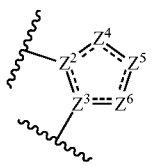
is selected from
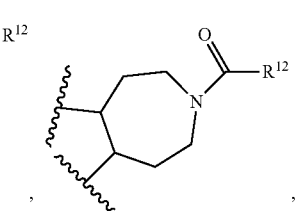, and
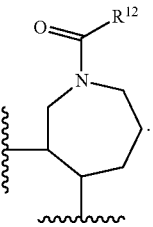
In embodiments,
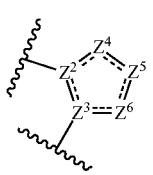
is selected from
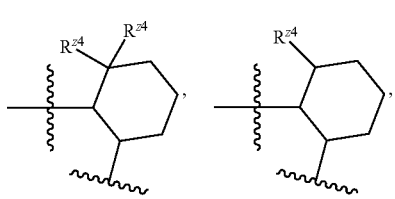
-continued
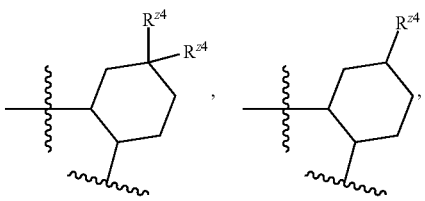

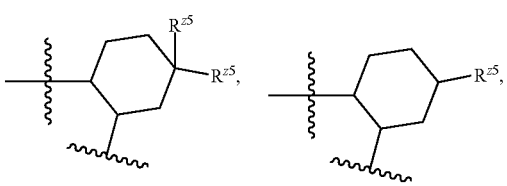
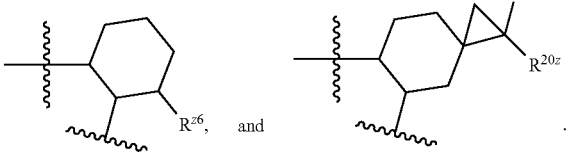 and
In embodiments,
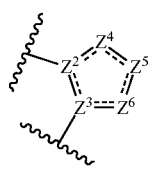
is selected from
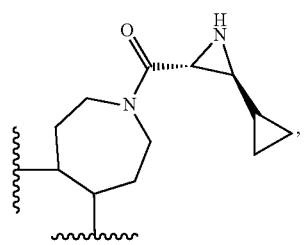
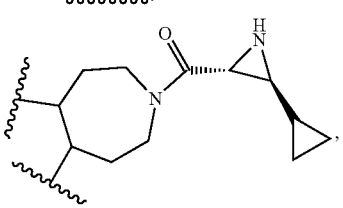

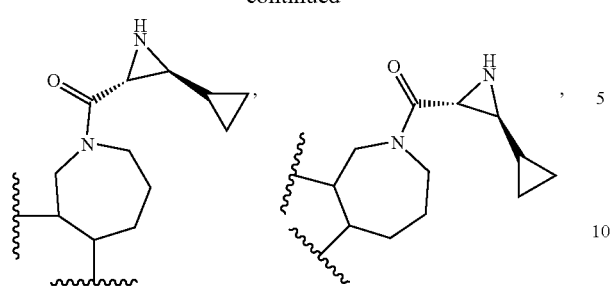
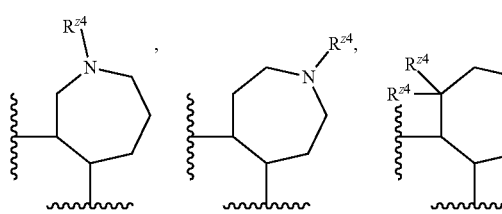
In embodiments,
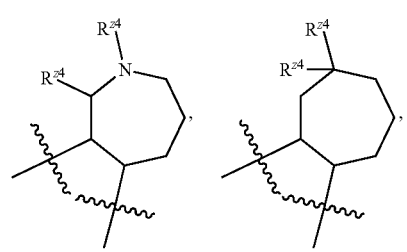
is selected from
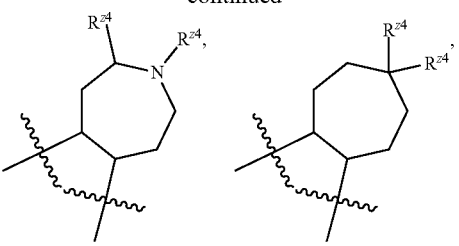
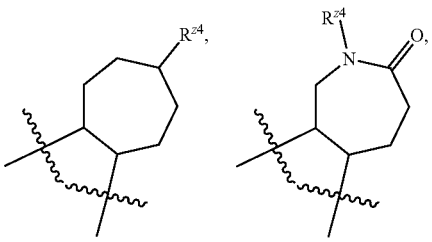
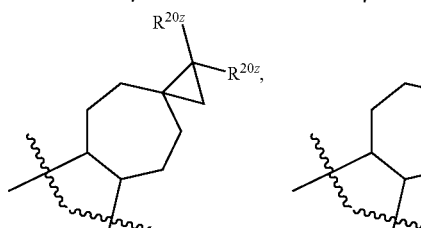
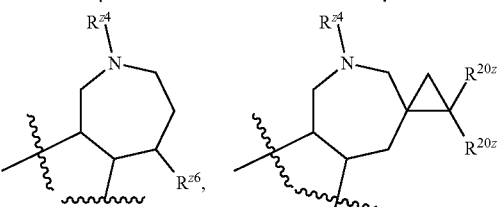
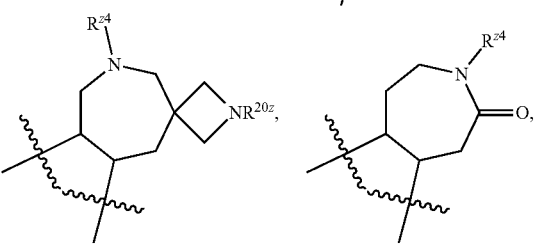
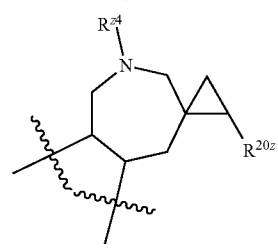
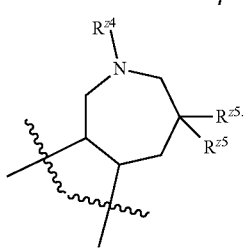

In embodiments,
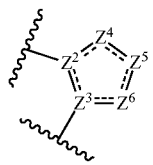
is selected from
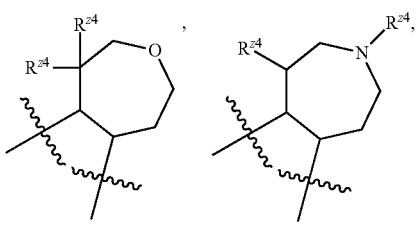
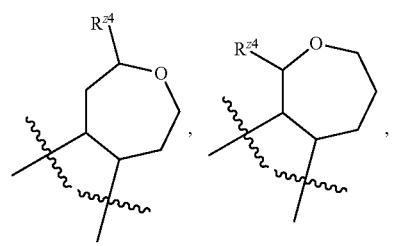
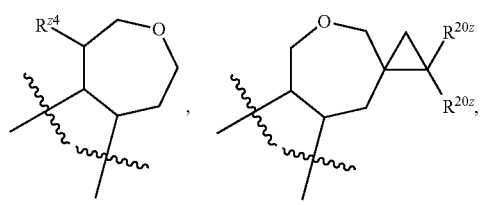
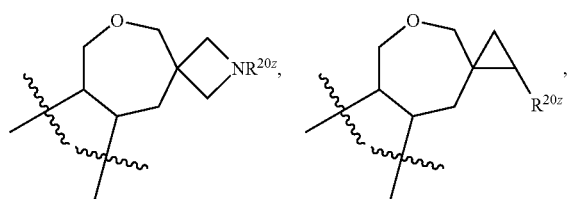
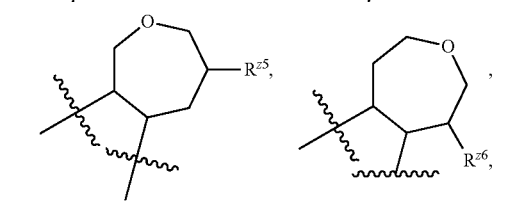
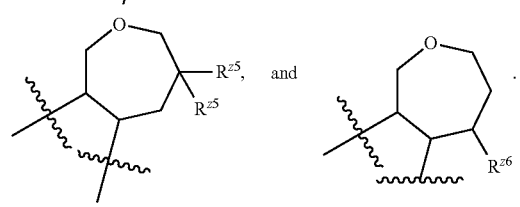
In embodiments,
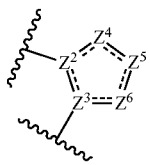
is selected from
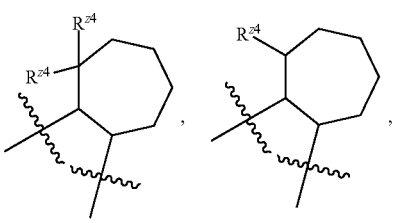
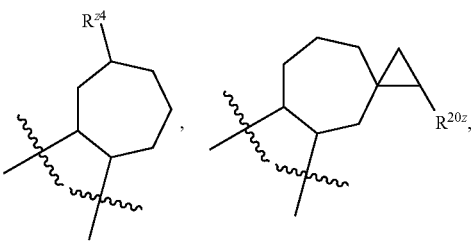
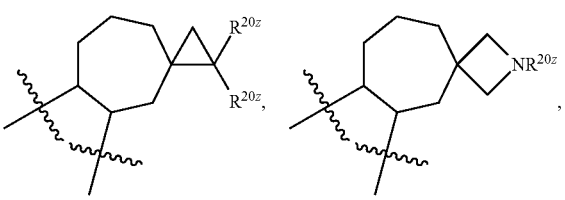
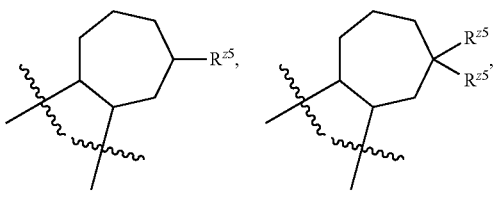
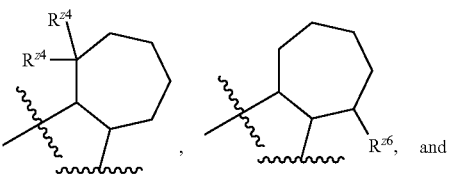
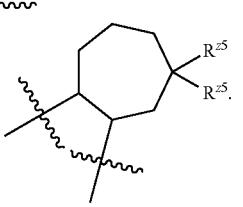

In embodiments,
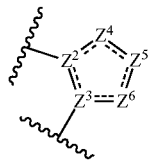
is selected from
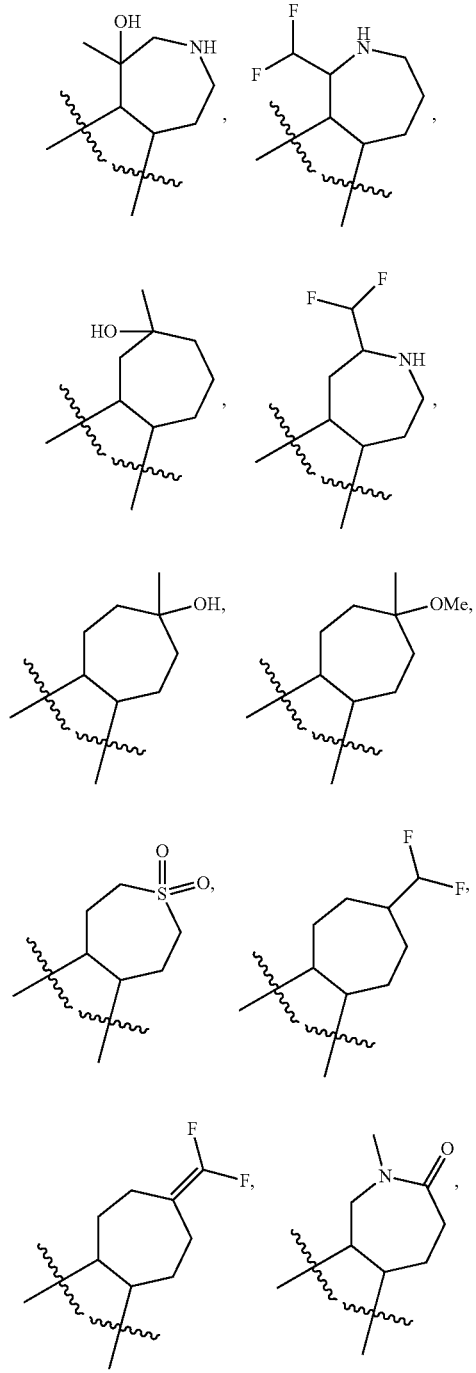
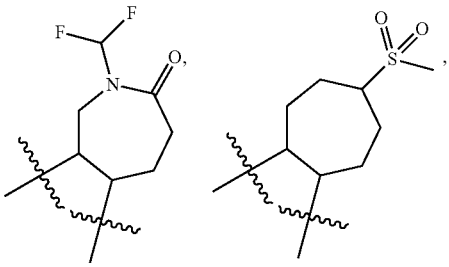
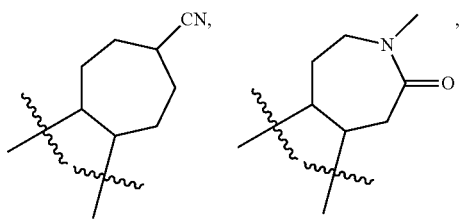
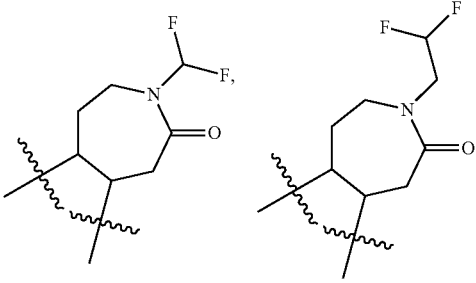
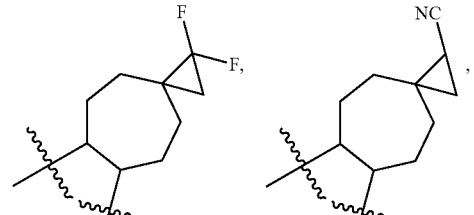
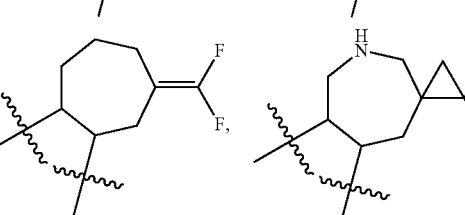
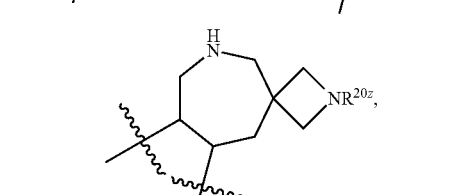
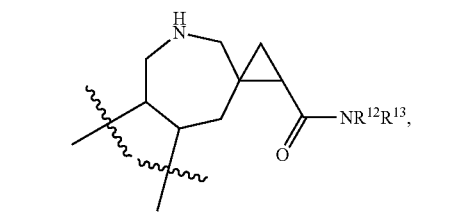

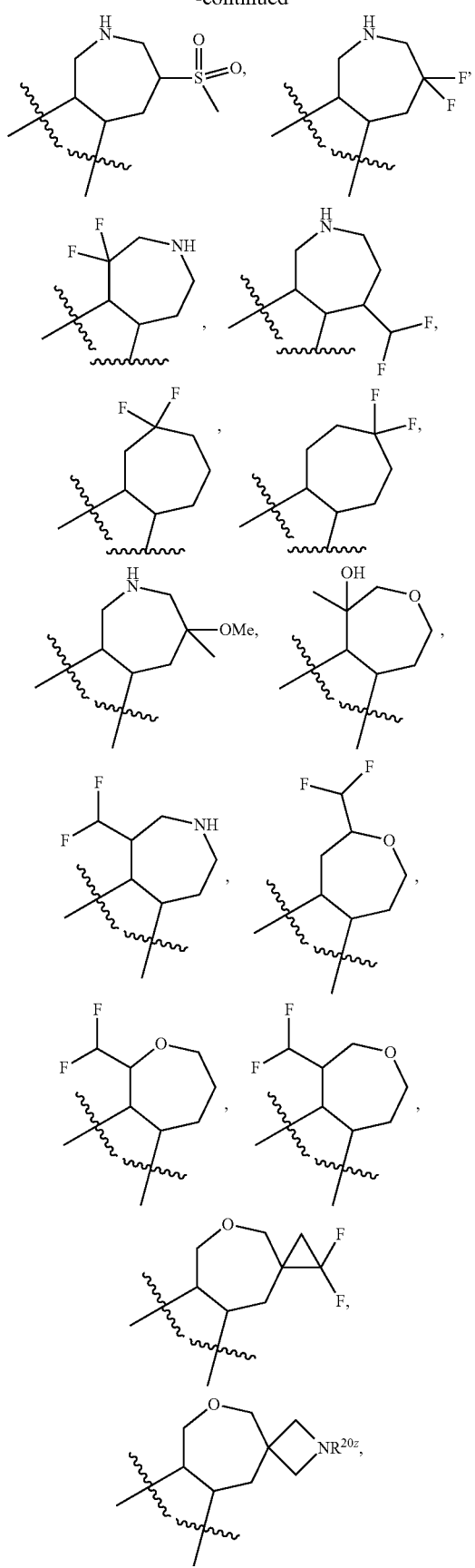
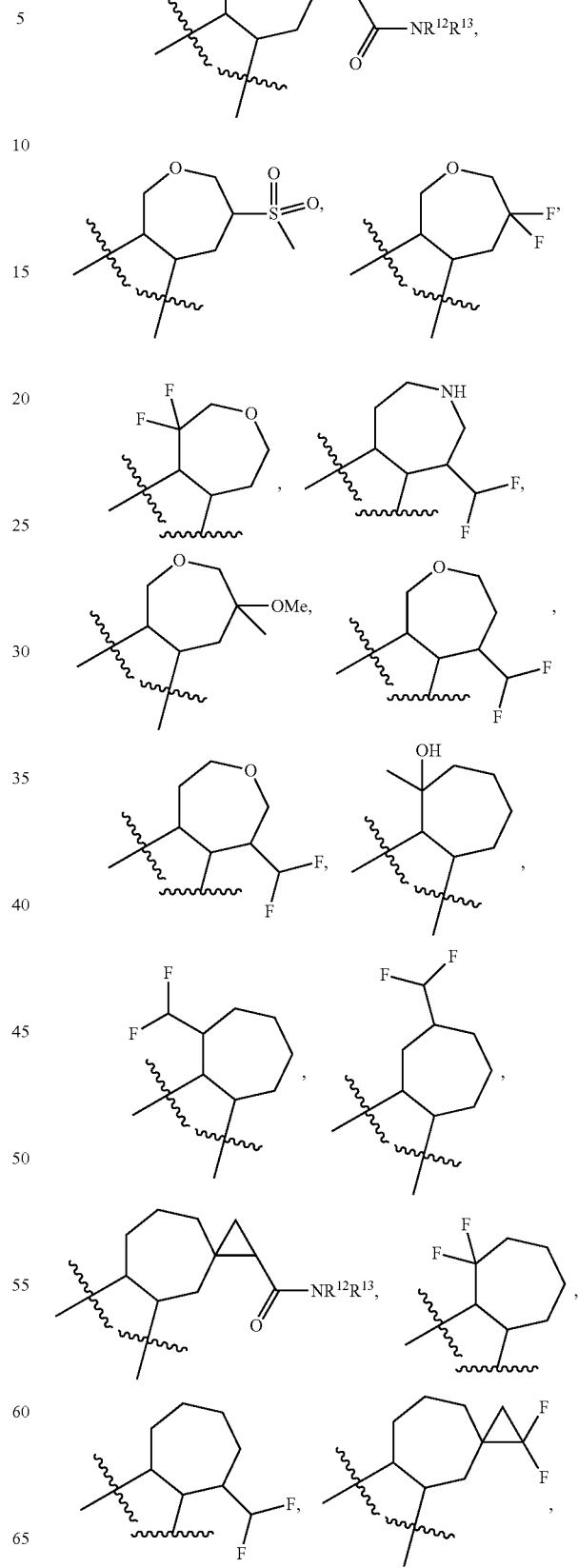

211
-continued
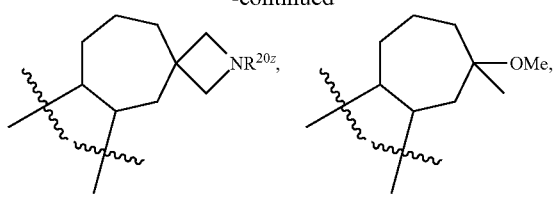
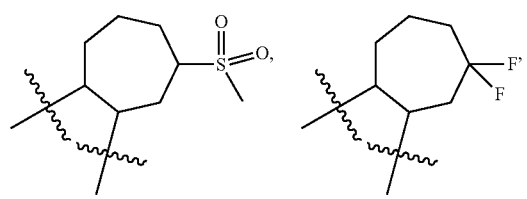
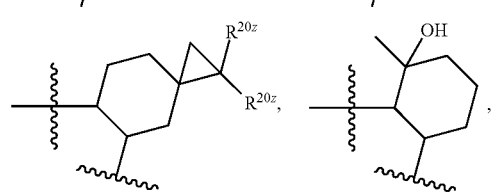
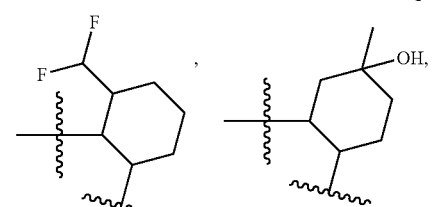
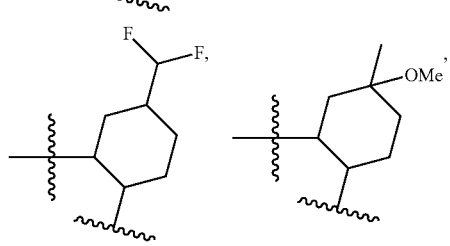
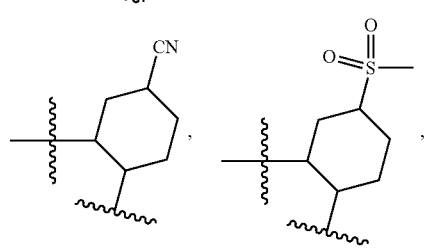
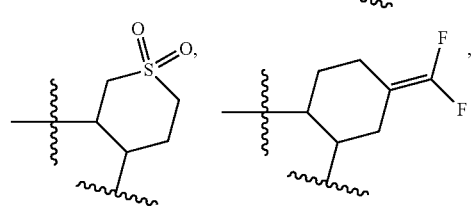
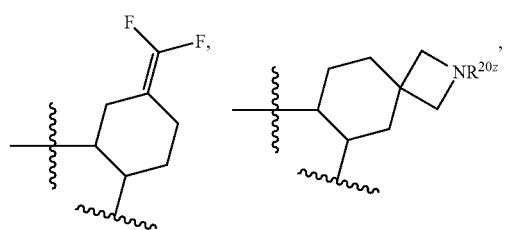
212
-continued
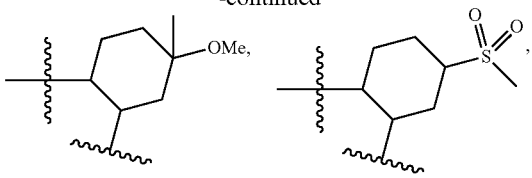
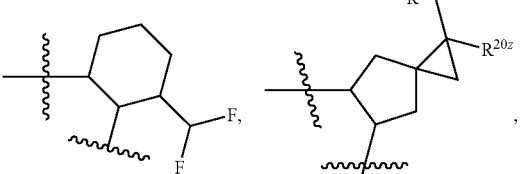
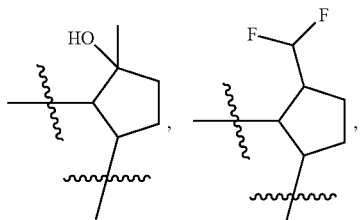
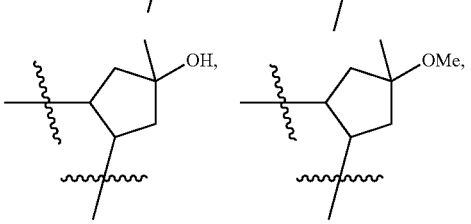
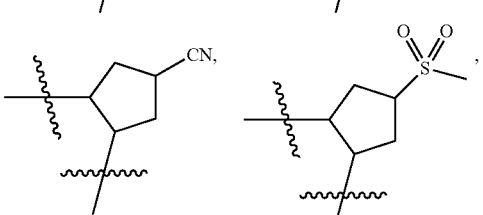
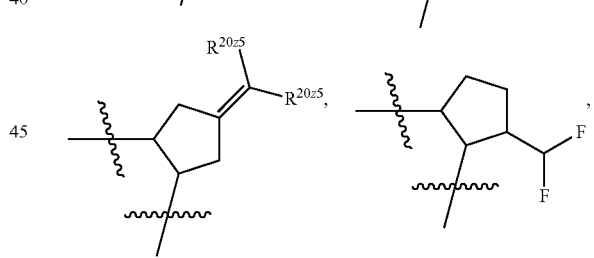
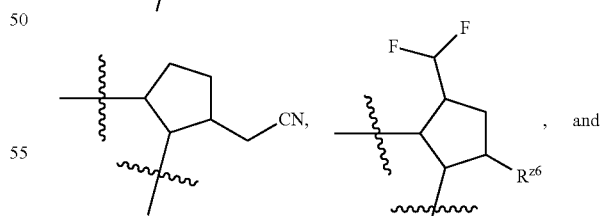
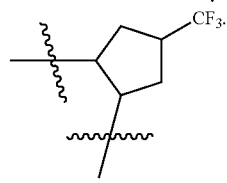

In embodiments,
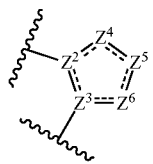
is selected from
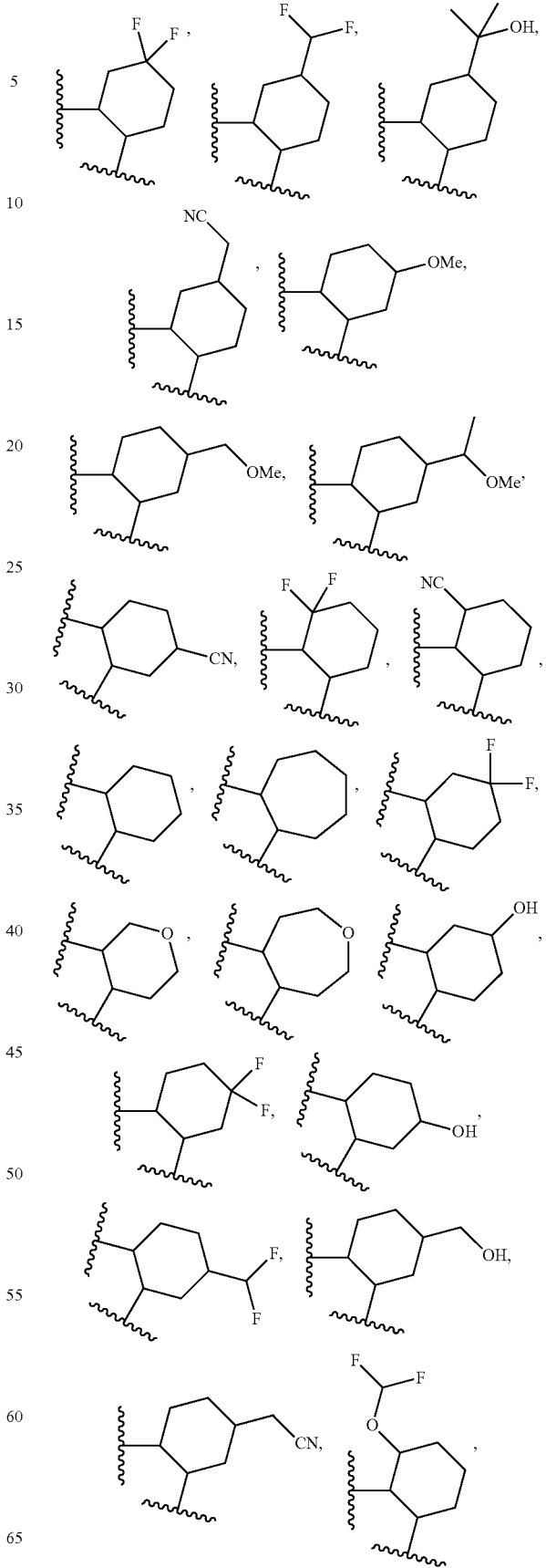

-continued
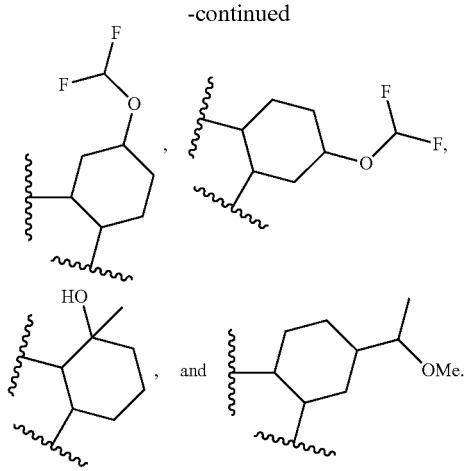
In embodiments,
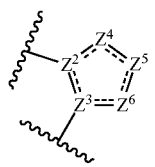
is selected from
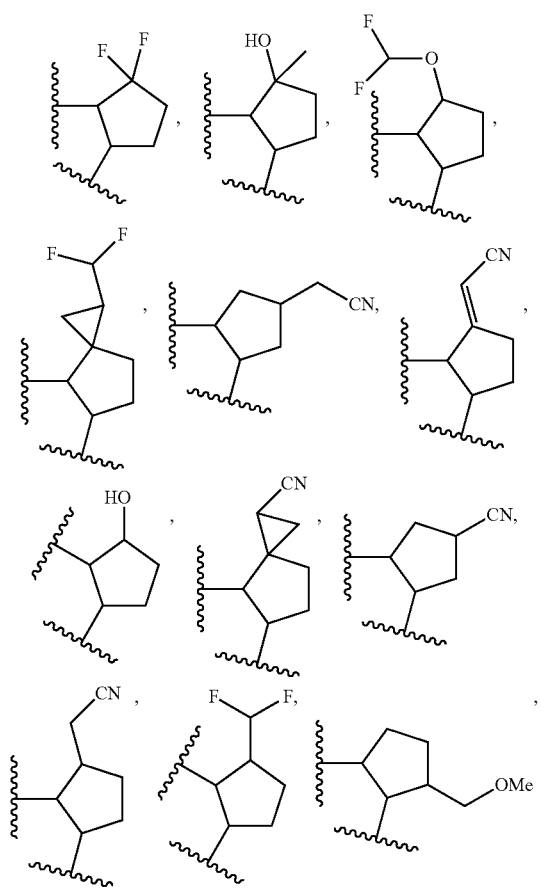
-continued
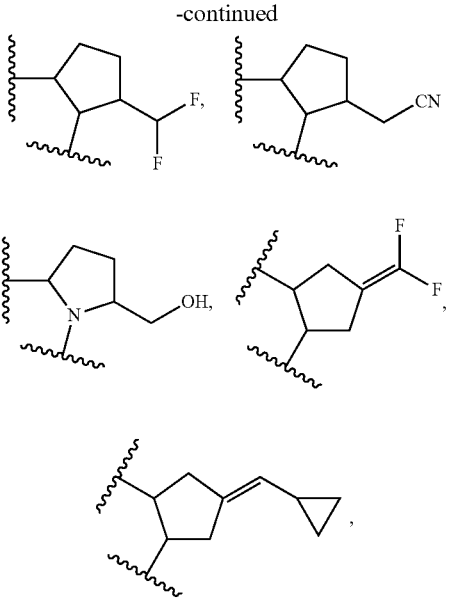
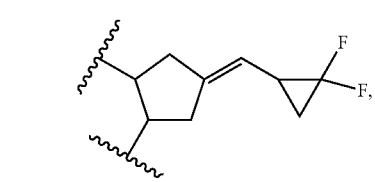
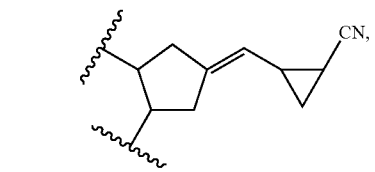
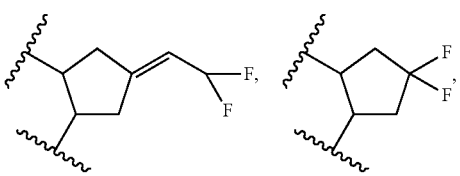
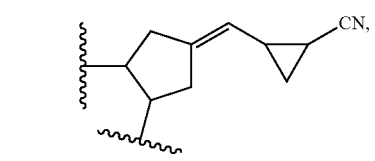
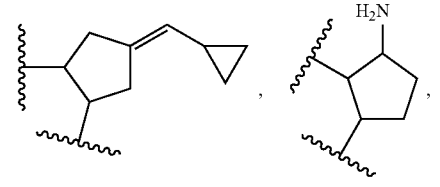
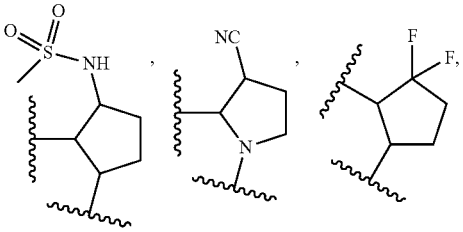

217
-continued
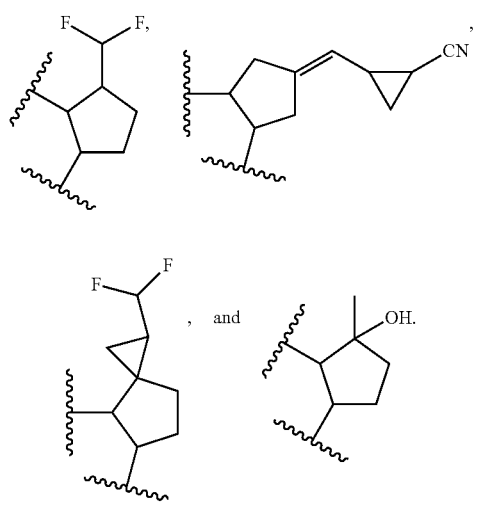
In embodiments,
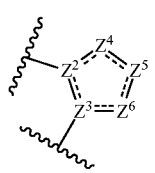
is selected from
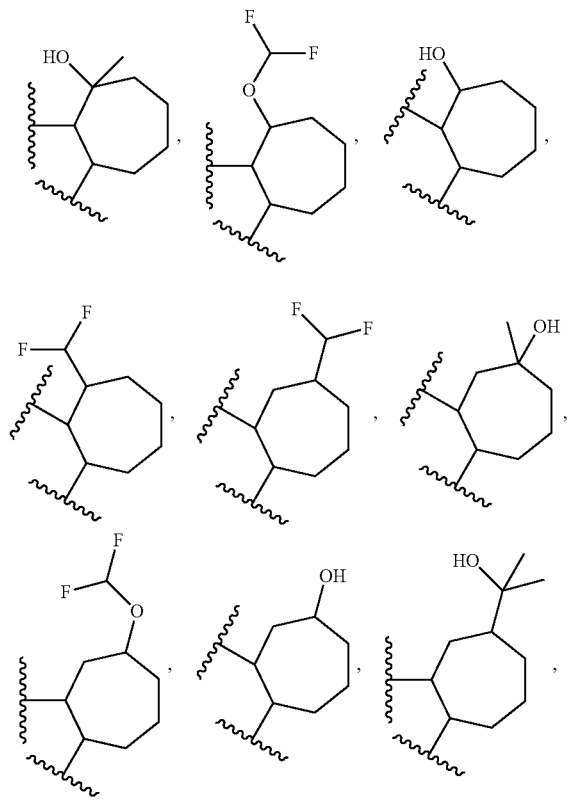
218
-continued
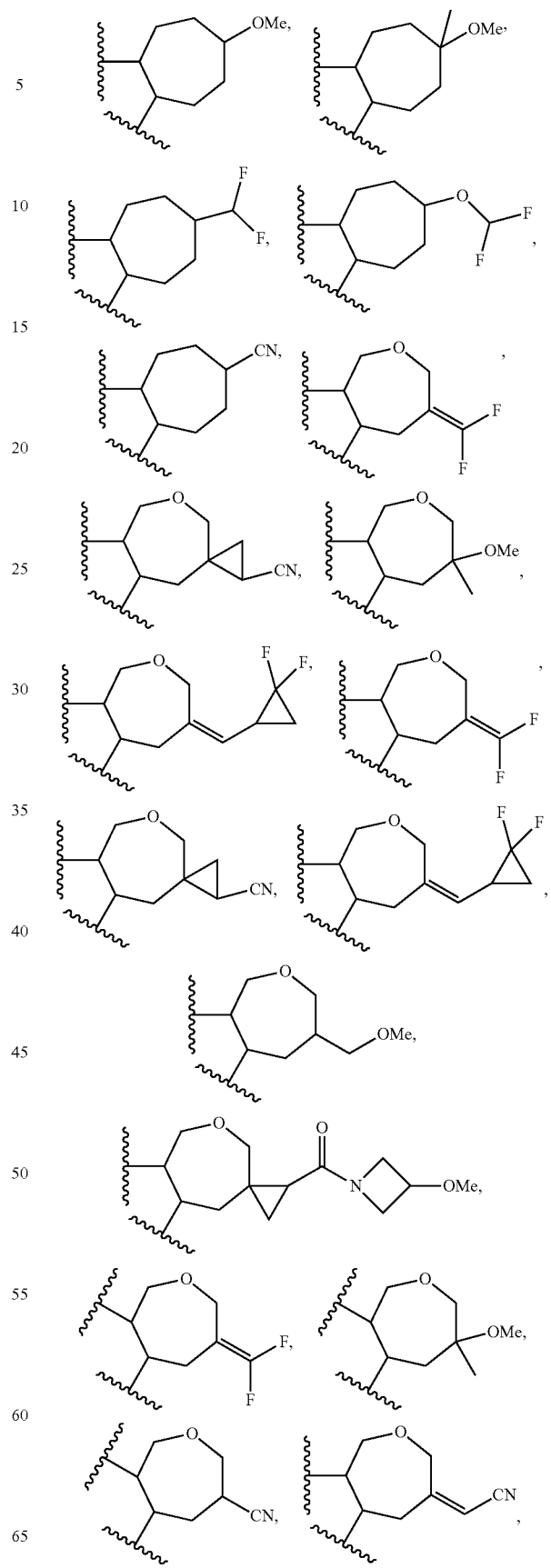

-continued
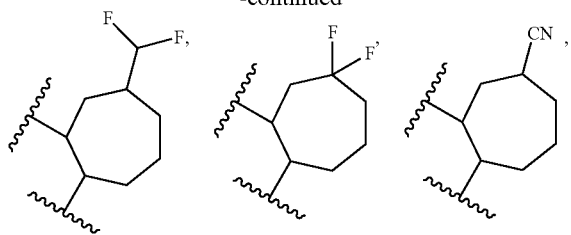
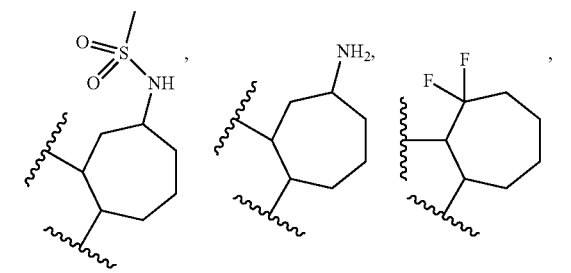
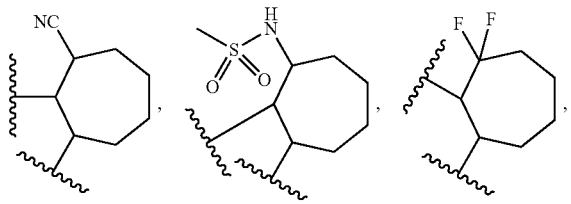
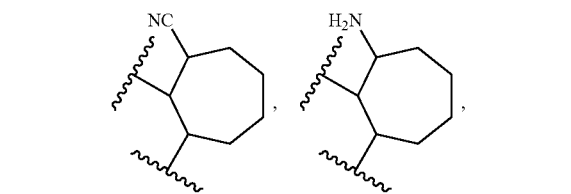
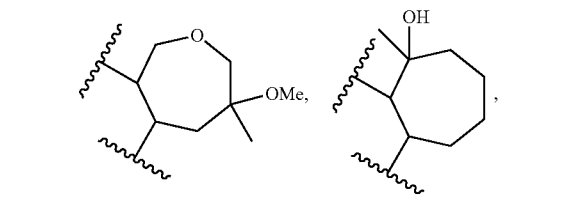
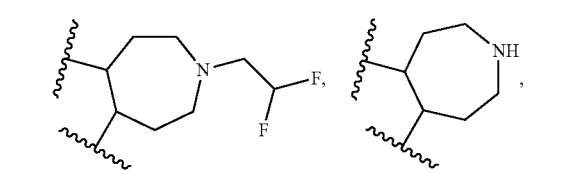
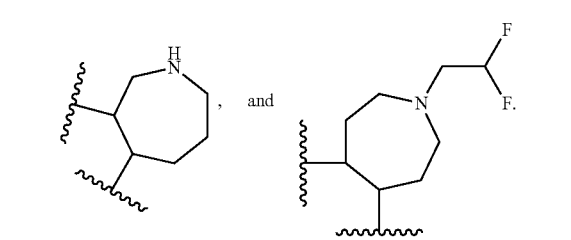
In embodiments,
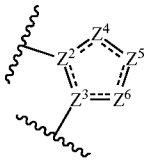
is selected from
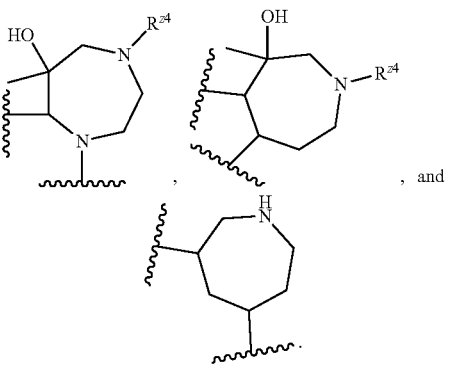
In embodiments,
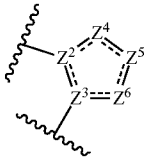
is selected from
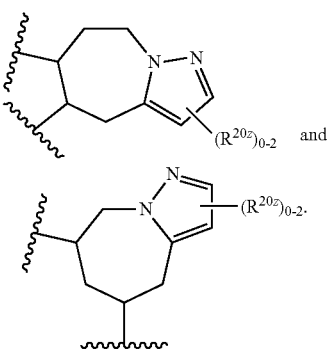
In embodiments,
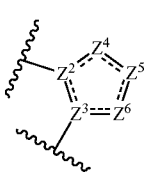

is selected from
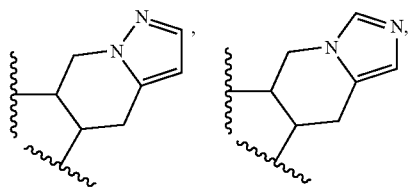
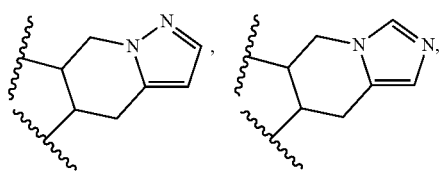
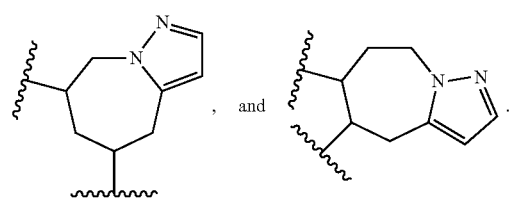
In embodiments,
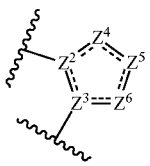
is selected from
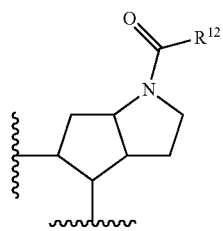
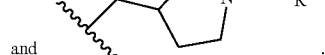
In embodiments,
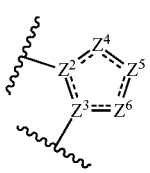
is selected from
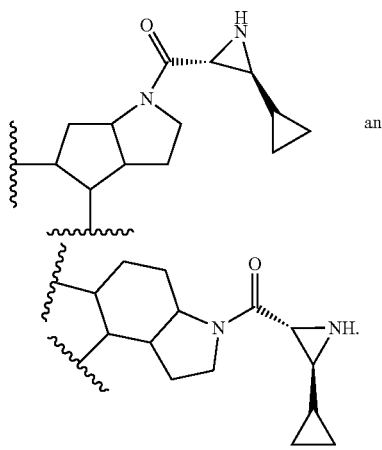
and
In embodiments,
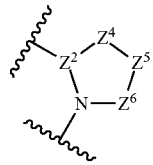
is selected from
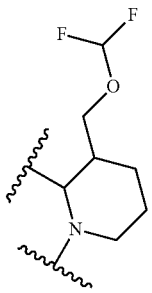
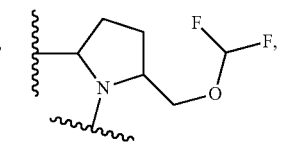
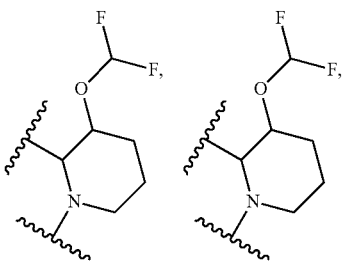

223
-continued
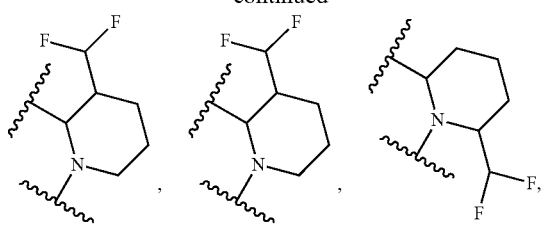
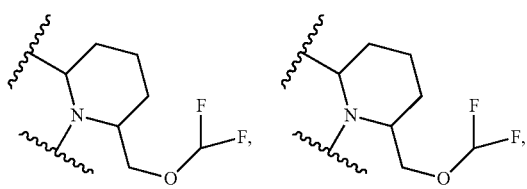
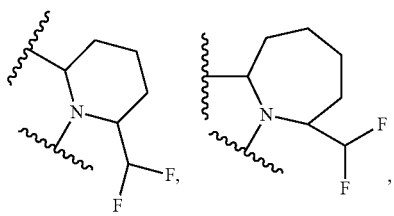
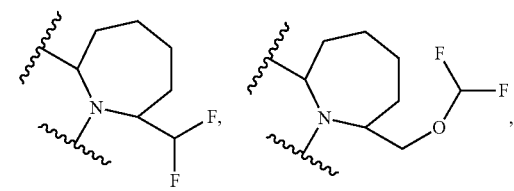
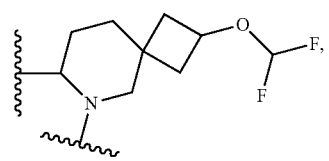
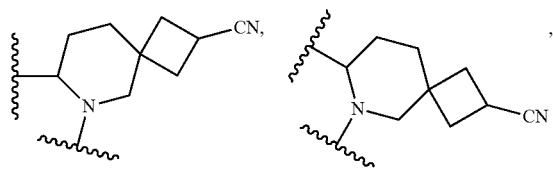
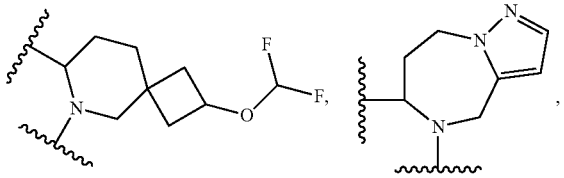
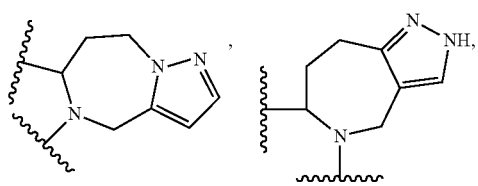
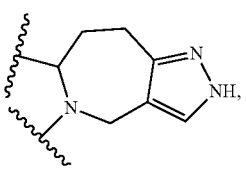
224
-continued
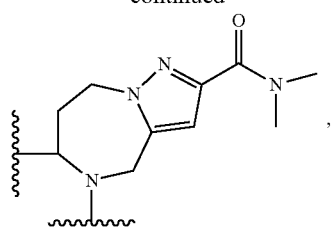
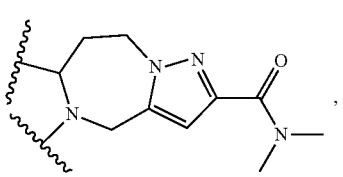
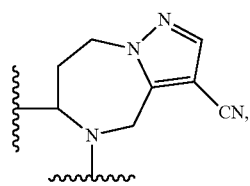
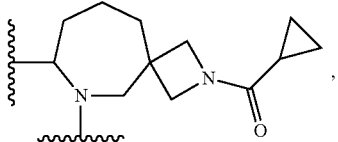
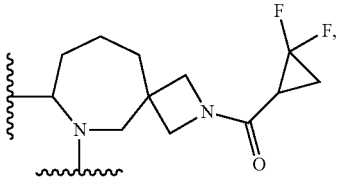
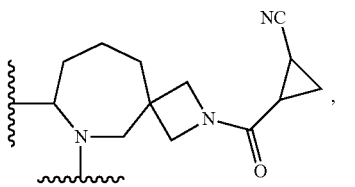
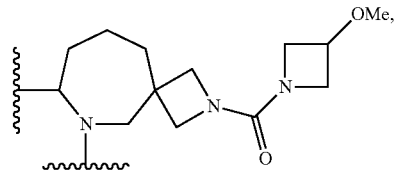
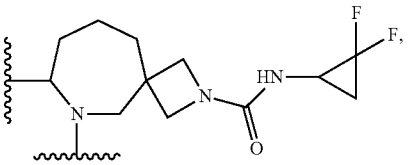
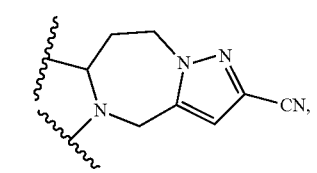

-continued
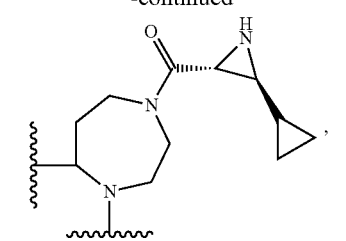
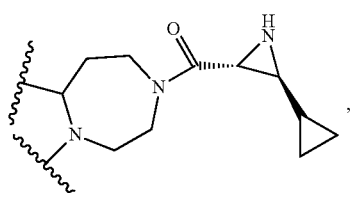
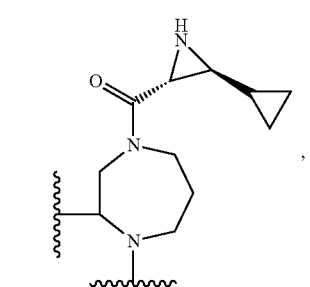
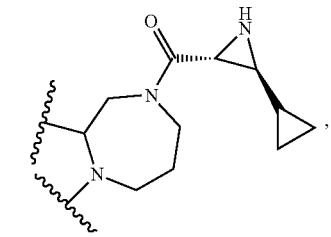
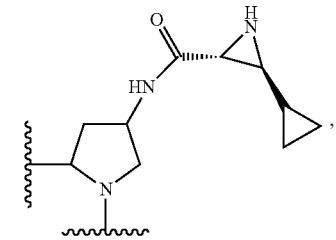
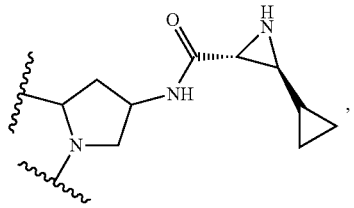
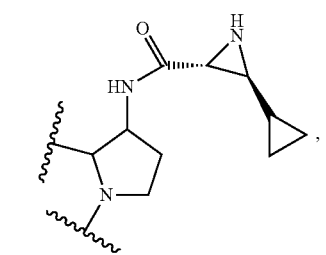
-continued
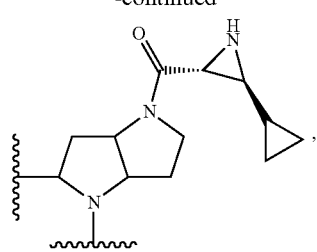
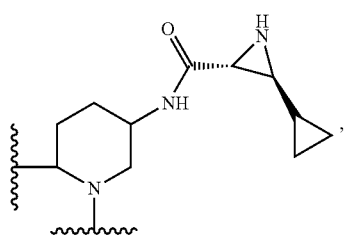
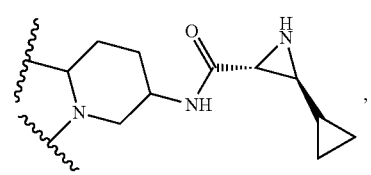
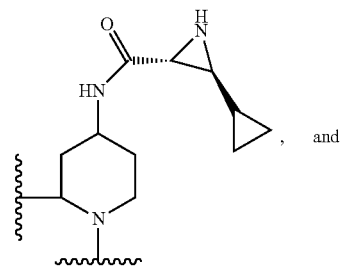
, and
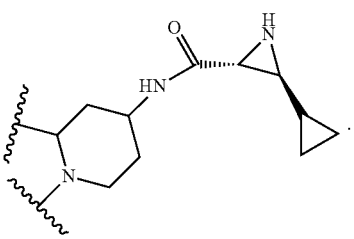
.
In embodiments,
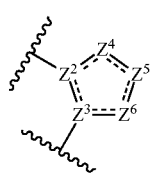

is selected from
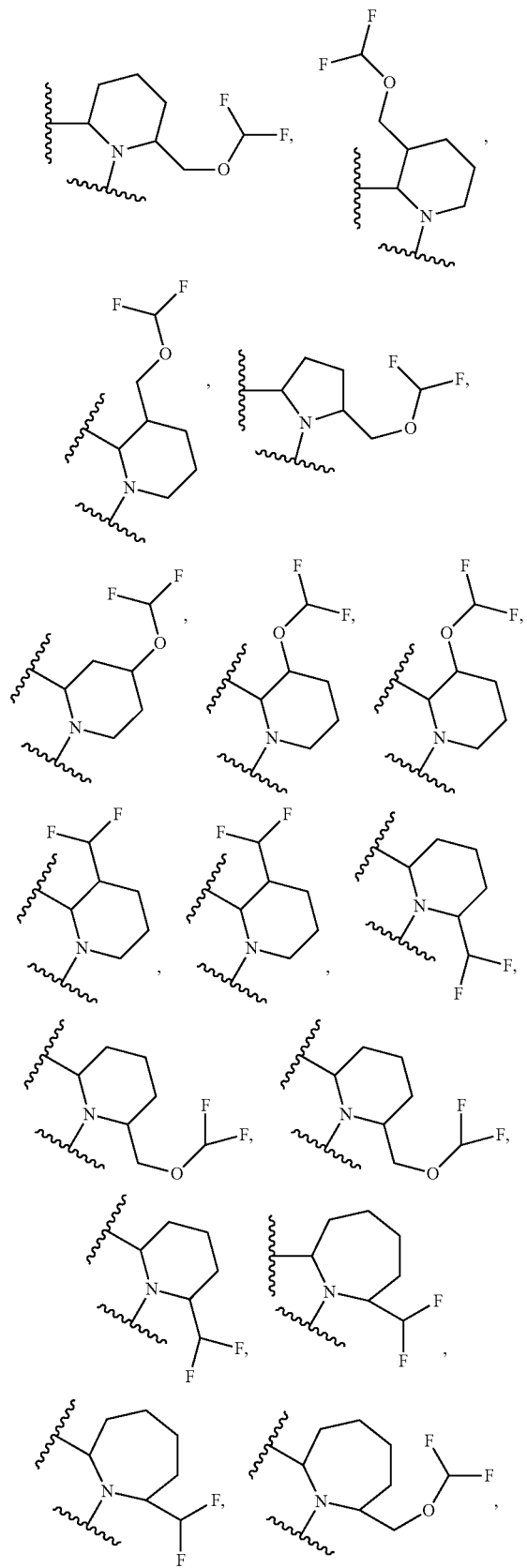
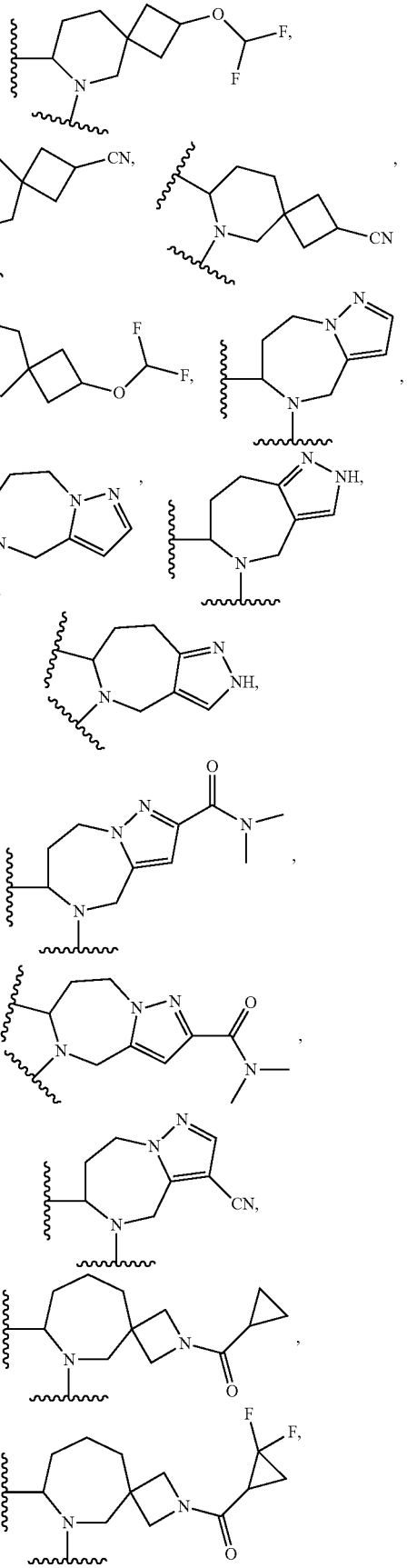

229
-continued
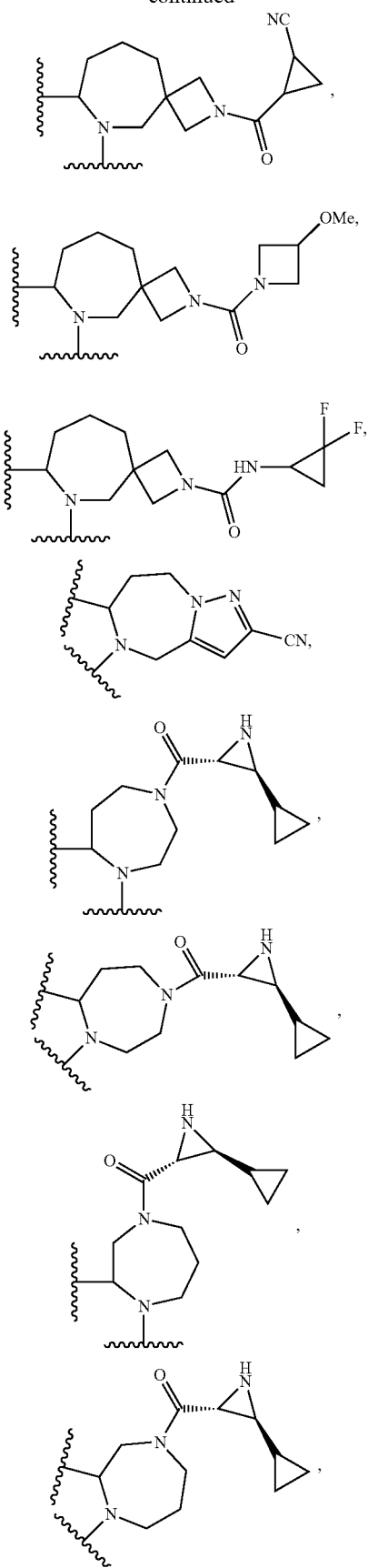
230
-continued
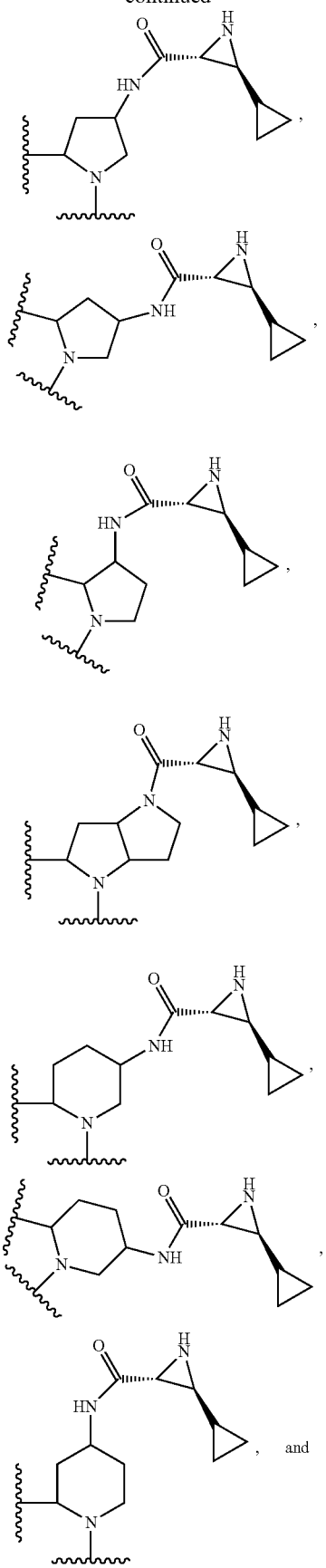

231

-continued

[Chemical structure showing a piperidine ring with an amide linkage to a cyclopropyl-substituted aziridine]

In embodiments, two $R^{z4}$ of $Z^{4a}$ are joined to form a monocyclic 3-7 membered heterocycloalkyl optionally substituted with one, two, or three $R^{20z}$. In embodiments, two $R^{z4}$ of $Z^{4a}$ are joined to form a monocyclic 3 membered heterocycloalkyl optionally substituted with one, two, or three $R^{20z}$. In embodiments, two $R^{z4}$ of $Z^{4a}$ are joined to form a monocyclic 4 membered heterocycloalkyl optionally substituted with one, two, or three $R^{20z}$. In embodiments, two $R^{z4}$ of $Z^{4a}$ are joined to form a monocyclic 5 membered heterocycloalkyl optionally substituted with one, two, or three $R^{20z}$. In embodiments, two $R^4$ of $Z^4$ a are joined to form a monocyclic 6 membered heterocycloalkyl optionally substituted with one, two, or three $R^{20z}$. In embodiments, two $R^{z4}$ of $Z^{4a}$ are joined to form a monocyclic 7 membered heterocycloalkyl optionally substituted with one, two, or three $R^{20z}$. In embodiments, two $R^{4a}$ of $Z^{4a}$ are joined to form an azetidine optionally substituted with one, two, or three $R^{20z}$ (e.g., $R^{20z}$ substitution on ring N). In embodiments, two $R^{z4}$ of $Z^{4a}$ are joined to form a pyrrolidine optionally substituted with one, two, or three $R^{20z}$ (e.g., $R^{20z}$ substitution on ring N). In embodiments, two $R^{z4}$ of $Z^{4a}$ are joined to form a piperidine optionally substituted with one, two, or three $R^{20z}$ (e.g., $R^{20z}$ substitution on ring N). In embodiments, two $R^{z4}$ of $Z^{4a}$ are joined to form a monocyclic $C_{3-7}$cycloalkyl optionally substituted with one, two, or three $R^{20z}$. In embodiments, two $R^{z4}$ of $Z^{4a}$ are joined to form a monocyclic $C_3$cycloalkyl optionally substituted with one, two, or three $R^{20z}$. In embodiments, two $R^{z4}$ of $Z^{4a}$ are joined to form a monocyclic $C_4$cycloalkyl optionally substituted with one, two, or three $R^{20z}$. In embodiments, two $R^{z4}$ of $Z^{4a}$ are joined to form a monocyclic $C_5$cycloalkyl optionally substituted with one, two, or three $R^{20z}$. In embodiments, two $R^{z4}$ of $Z^{4a}$ are joined to form a monocyclic $C_6$cycloalkyl optionally substituted with one, two, or three $R^{20z}$. In embodiments, two $R^{z4}$ of $Z^{4a}$ are joined to form a monocyclic $C_7$cycloalkyl optionally substituted with one, two, or three $R^{20z}$.

In embodiments, two $R^{z4}$ of $Z^{4b}$ are joined to form a monocyclic 3-7 membered heterocycloalkyl optionally substituted with one, two, or three $R^{20z}$. In embodiments, two $R^{z4}$ of $Z^{4b}$ are joined to form a monocyclic 3 membered heterocycloalkyl optionally substituted with one, two, or three $R^{20z}$. In embodiments, two $R^{z4}$ of $Z^{4b}$ are joined to form a monocyclic 4 membered heterocycloalkyl optionally substituted with one, two, or three $R^{20z}$. In embodiments, two $R^{z4}$ of $Z^{4b}$ are joined to form a monocyclic 5 membered heterocycloalkyl optionally substituted with one, two, or three $R^{20z}$. In embodiments, two $R^{z4}$ of $Z^{4b}$ are joined to form a monocyclic 6 membered heterocycloalkyl optionally substituted with one, two, or three $R^{20z}$. In embodiments, two $R^{z4}$ of $Z^{4b}$ are joined to form a monocyclic 7 membered heterocycloalkyl optionally substituted with one, two, or three $R^{20z}$. In embodiments, two $R^{z4}$ of $Z^{4b}$ are joined to form an azetidine optionally substituted with one, two, or three $R^{20z}$ (e.g., $R^{20z}$ substitution on ring N). In embodiments, two $R^{z4}$ of $Z^{4b}$ are joined to form a pyrrolidine optionally substituted with one, two, or three $R^{20z}$ (e.g., $R^{20z}$ substitution on ring N). In embodiments, two $R^{z4}$ of $Z^{4b}$ are joined to form a piperidine optionally substituted with one, two, or three $R^{20z}$ (e.g., $R^{20z}$ substitution on ring N). In embodiments, two $R^{z4}$ of $Z^{4b}$ are joined to form a monocyclic $C_{3-7}$cycloalkyl optionally substituted with one, two, or three $R^{20z}$. In embodiments, two $R^{z4}$ of $Z^{4b}$ are joined to form a monocyclic $C_3$cycloalkyl optionally substituted with one, two, or three $R^{20z}$. In embodiments, two $R^{z4}$ of $Z^{4b}$ are joined to form a monocyclic $C_4$cycloalkyl optionally substituted with one, two, or three $R^{20z}$. In embodiments, two $R^{z4}$ of $Z^{4b}$ are joined to form a monocyclic $C_5$cycloalkyl optionally substituted with one, two, or three $R^{20z}$. In embodiments, two $R^{z4}$ of $Z^{4b}$ are joined to form a monocyclic $C_6$cycloalkyl optionally substituted with one, two, or three $R^{20z}$. In embodiments, two $R^{z4}$ of $Z^{4b}$ are joined to form a monocyclic $C_7$cycloalkyl optionally substituted with one, two, or three $R^{20z}$.

In embodiments, two $R^{z4}$ of $Z^{4c}$ are joined to form a monocyclic 3-7 membered heterocycloalkyl optionally substituted with one, two, or three $R^{20z}$. In embodiments, two $R^{z4}$ of $Z^{4c}$ are joined to form a monocyclic 3 membered heterocycloalkyl optionally substituted with one, two, or three $R^{20z}$. In embodiments, two $R^{z4}$ of $Z^{4c}$ are joined to form a monocyclic 4 membered heterocycloalkyl optionally substituted with one, two, or three $R^{20z}$. In embodiments, two $R^{z4}$ of $Z^{4c}$ are joined to form a monocyclic 5 membered heterocycloalkyl optionally substituted with one, two, or three $R^{20z}$. In embodiments, two $R^{z4}$ of $Z^{4c}$ are joined to form a monocyclic 6 membered heterocycloalkyl optionally substituted with one, two, or three $R^{20z}$. In embodiments, two $R^{z4}$ of $Z^{4c}$ are joined to form a monocyclic 7 membered heterocycloalkyl optionally substituted with one, two, or three $R^{20z}$. In embodiments, two $R^{z4}$ of $Z^{4c}$ are joined to form an azetidine optionally substituted with one, two, or three $R^{20z}$ (e.g., $R^{20z}$ substitution on ring N). In embodiments, two $R^{z4}$ of $Z^{4c}$ are joined to form a pyrrolidine optionally substituted with one, two, or three $R^{20z}$ (e.g., $R^{20z}$ substitution on ring N). In embodiments, two $R^{z4}$ of $Z^{4c}$ are joined to form a piperidine optionally substituted with one, two, or three $R^{20z}$ (e.g., $R^{20z}$ substitution on ring N). In embodiments, two $R^{z4}$ of $Z^{4c}$ are joined to form a monocyclic $C_{3-7}$cycloalkyl optionally substituted with one, two, or three $R^{20z}$. In embodiments, two $R^{z4}$ of $Z^{4c}$ are joined to form a monocyclic $C_3$cycloalkyl optionally substituted with one, two, or three $R^{20z}$. In embodiments, two $R^{z4}$ of $Z^{4c}$ are joined to form a monocyclic $C_4$cycloalkyl optionally substituted with one, two, or three $R^{20z}$. In embodiments, two $R^{z4}$ of $Z^{4c}$ are joined to form a monocyclic $C_5$cycloalkyl optionally substituted with one, two, or three $R^{20z}$. In embodiments, two $R^{z4}$ of $Z^{4c}$ are joined to form a monocyclic $C_6$cycloalkyl optionally substituted with one, two, or three $R^{20z}$. In embodiments, two $R^{z4}$ of $Z^{4c}$ are joined to form a monocyclic $C_7$cycloalkyl optionally substituted with one, two, or three $R^{20z}$.

In embodiments, two $R^{z4}$ of $Z^{4d}$ are joined to form a monocyclic 3-7 membered heterocycloalkyl optionally substituted with one, two, or three $R^{20z}$. In embodiments, two $R^{z4}$ of $Z^{4d}$ are joined to form a monocyclic 3 membered heterocycloalkyl optionally substituted with one, two, or three $R^{20z}$. In embodiments, two $R^{z4}$ of $Z^{4d}$ are joined to form a monocyclic 4 membered heterocycloalkyl optionally substituted with one, two, or three $R^{20z}$. In embodiments, two $R^{z4}$ of $Z^{4d}$ are joined to form a monocyclic 5 membered heterocycloalkyl optionally substituted with one, two, or three $R^{20z}$. In embodiments, two $R^{z4}$ of $Z^{4d}$ are joined to form a monocyclic 6 membered heterocycloalkyl optionally substituted with one, two, or three $R^{20z}$. In embodiments, two $R^{z4}$ of $Z^{4d}$ are joined to form a monocyclic 7 membered heterocycloalkyl optionally substituted with one, two, or three $R^{20z}$. In embodiments, two $R^{z4}$ of $Z^{4d}$ are joined to form an azetidine optionally substituted with one, two, or three $R^{20z}$ (e.g., $R^{20z}$ substitution on ring N). In embodiments, two $R^{z4}$ of $Z^{4d}$ are joined to form a pyrrolidine optionally substituted with one, two, or three $R^{20z}$ (e.g., $R^{20z}$ substitution on ring N). In embodiments, two $R^{z4}$ of $Z^{4d}$ are joined to form a piperidine optionally substituted with one, two, or three $R^{20z}$ (e.g., $R^{20z}$ substitution on ring N). In embodiments, two $R^{z4}$ of $Z^{4d}$ are joined to form a monocyclic $C_{3-7}$cycloalkyl optionally substituted with one, two, or three $R^{20z}$. In embodiments, two $R^{z4}$ of $Z^{4d}$ are joined to form a monocyclic $C_3$cycloalkyl optionally substituted with one, two, or three $R^{20z}$. In embodiments, two $R^{z4}$ of $Z^{4d}$ are joined to form a monocyclic $C_4$cycloalkyl optionally substituted with one, two, or three $R^{20z}$. In embodiments, two $R^{z4}$ of $Z^{4d}$ are joined to form a monocyclic $C_5$cycloalkyl optionally substituted with one, two, or three $R^{20z}$. In embodiments, two $R^{z4}$ of $Z^{4d}$ are joined to form a monocyclic $C_6$cycloalkyl optionally substituted with one, two, or three $R^{20z}$. In embodiments, two $R^{z4}$ of $Z^{4d}$ are joined to form a monocyclic $C_7$cycloalkyl optionally substituted with one, two, or three $R^{20z}$.

In embodiments, two $R^{z4}$ of $Z^{4e}$ are joined to form a monocyclic 3-7 membered heterocycloalkyl optionally substituted with one, two, or three $R^{20z}$. In embodiments, two $R^{z4}$ of $Z^{4e}$ are joined to form a monocyclic 3 membered heterocycloalkyl optionally substituted with one, two, or three $R^{20z}$. In embodiments, two $R^{z4}$ of $Z^{4e}$ are joined to form a monocyclic 4 membered heterocycloalkyl optionally substituted with one, two, or three $R^{20z}$. In embodiments, two $R^{z4}$ of $Z^{4e}$ are joined to form a monocyclic 5 membered heterocycloalkyl optionally substituted with one, two, or three $R^{20z}$. In embodiments, two $R^{z4}$ of $Z^{4e}$ are joined to form a monocyclic 6 membered heterocycloalkyl optionally substituted with one, two, or three $R^{20z}$. In embodiments, two $R^{z4}$ of $Z^{4e}$ are joined to form a monocyclic 7 membered heterocycloalkyl optionally substituted with one, two, or three $R^{20z}$. In embodiments, two $R^{z4}$ of $Z^{4e}$ are joined to form an azetidine optionally substituted with one, two, or three $R^{20z}$ (e.g., $R^{20z}$ substitution on ring N). In embodiments, two $R^{z4}$ of $Z^{4e}$ are joined to form a pyrrolidine optionally substituted with one, two, or three $R^{20z}$ (e.g., $R^{20z}$ substitution on ring N). In embodiments, two $R^{z4}$ of $Z^{4e}$ are joined to form a piperidine optionally substituted with one, two, or three $R^{20z}$ (e.g., $R^{20z}$ substitution on ring N). In embodiments, two $R^{z4}$ of $Z^{4e}$ are joined to form a monocyclic $C_{3-7}$cycloalkyl optionally substituted with one, two, or three $R^{20z}$. In embodiments, two $R^{z4}$ of $Z^{4e}$ are joined to form a monocyclic $C_3$cycloalkyl optionally substituted with one, two, or three $R^{20z}$. In embodiments, two $R^{z4}$ of $Z^{4e}$ are joined to form a monocyclic $C_4$cycloalkyl optionally substituted with one, two, or three $R^{20z}$. In embodiments, two $R^{z4}$ of $Z^{4e}$ are joined to form a monocyclic $C_5$cycloalkyl optionally substituted with one, two, or three $R^{20z}$. In embodiments, two $R^{z4}$ of $Z^{4e}$ are joined to form a monocyclic $C_6$cycloalkyl optionally substituted with one, two, or three $R^{20z}$. In embodiments, two $R^{z4}$ of $Z^{4e}$ are joined to form a monocyclic $C_7$cycloalkyl optionally substituted with one, two, or three $R^{20z}$.

In embodiments, two $R^{z5}$ of $Z^5$ are joined to form a monocyclic 3-7 membered heterocycloalkyl optionally substituted with one, two, or three $R^{20z}$. In embodiments, two $R^{z5}$ of $Z^5$ are joined to form a monocyclic 3 membered heterocycloalkyl optionally substituted with one, two, or three $R^{20z}$. In embodiments, two $R^{z5}$ of $Z^5$ are joined to form a monocyclic 4 membered heterocycloalkyl optionally substituted with one, two, or three $R^{20z}$. In embodiments, two $R^{z5}$ of $Z^5$ are joined to form a monocyclic 5 membered heterocycloalkyl optionally substituted with one, two, or three $R^{20z}$. In embodiments, two $R^{z5}$ of $Z^5$ are joined to form a monocyclic 6 membered heterocycloalkyl optionally substituted with one, two, or three $R^{20z}$. In embodiments, two $R^{z5}$ of $Z^5$ are joined to form a monocyclic 7 membered heterocycloalkyl optionally substituted with one, two, or three $R^{20z}$. In embodiments, two $R^{z5}$ of $Z^5$ are joined to form an azetidine optionally substituted with one, two, or three $R^{20z}$ (e.g., $R^{20z}$ substitution on ring N). In embodiments, two $R^{z5}$ of $Z^5$ are joined to form a pyrrolidine optionally substituted with one, two, or three $R^{20z}$ (e.g., $R^{20z}$ substitution on ring N). In embodiments, two $R^{z5}$ of $Z^5$ are joined to form a piperidine optionally substituted with one, two, or three $R^{20z}$ (e.g., $R^{20z}$ substitution on ring N). In embodiments, two $R^{z5}$ of $Z^5$ are joined to form a monocyclic $C_{3-7}$cycloalkyl optionally substituted with one, two, or three R20z. In embodiments, two $R^{z5}$ of $Z^5$ are joined to form a monocyclic $C_3$cycloalkyl optionally substituted with one, two, or three $R^{20z}$. In embodiments, two $R^{z5}$ of $Z^5$ are joined to form a monocyclic $C_4$cycloalkyl optionally substituted with one, two, or three $R^{20z}$. In embodiments, two $R^{z5}$ of $Z^5$ are joined to form a monocyclic $C_5$cycloalkyl optionally substituted with one, two, or three $R^{20z}$. In embodiments, two $R^{z5}$ of $Z^5$ are joined to form a monocyclic $C_6$cycloalkyl optionally substituted with one, two, or three $R^{20z}$. In embodiments, two $R^{z5}$ of $Z^5$ are joined to form a monocyclic $C_7$cycloalkyl optionally substituted with one, two, or three $R^{20z}$.

In embodiments, two $R^{z6}$ of $Z^6$ are joined to form a monocyclic 3-7 membered heterocycloalkyl optionally substituted with one, two, or three $R^{20z}$. In embodiments, two $R^{z6}$ of $Z^6$ are joined to form a monocyclic 3 membered heterocycloalkyl optionally substituted with one, two, or three $R^{20z}$. In embodiments, two $R^{z6}$ of $Z^6$ are joined to form a monocyclic 4 membered heterocycloalkyl optionally substituted with one, two, or three $R^{20z}$. In embodiments, two $R^{z6}$ of $Z^6$ are joined to form a monocyclic 5 membered heterocycloalkyl optionally substituted with one, two, or three $R^{20z}$. In embodiments, two $R^{z6}$ of $Z^6$ are joined to form a monocyclic 6 membered heterocycloalkyl optionally substituted with one, two, or three $R^{20z}$. In embodiments, two $R^{z6}$ of $Z^6$ are joined to form a monocyclic 7 membered heterocycloalkyl optionally substituted with one, two, or three $R^{20z}$. In embodiments, two $R^{z6}$ of $Z^6$ are joined to form an azetidine optionally substituted with one, two, or three $R^{20z}$ (e.g., $R^{20z}$ substitution on ring N). In embodiments, two $R^{z6}$ of $Z^6$ are joined to form a pyrrolidine optionally substituted with one, two, or three $R^{20z}$ (e.g., $R^{20z}$ substitution on ring N). In embodiments, two $R^{z6}$ of $Z^6$ are joined to form a piperidine optionally substituted with one, two, or three $R^{20z}$ (e.g., $R^{20z}$ substitution on ring N). In embodiments, two $R^{z6}$ of $Z^6$ are joined to form a monocyclic $C_{3-7}$cycloalkyl optionally substituted with one, two, or three $R^{20z}$. In embodiments, two $R^{z6}$ of $Z^6$ are joined to form a monocyclic $C_3$cycloalkyl optionally substituted with one, two, or three $R^{20z}$. In embodiments, two $R^{z6}$ of $Z^6$ are joined to form a monocyclic $C_4$cycloalkyl optionally substituted with one, two, or three $R^{20z}$. In embodiments, two $R^{z6}$ of $Z^6$ are joined to form a monocyclic $C_5$cycloalkyl optionally substituted with one, two, or three $R^{20z}$. In embodiments, two $R^{z6}$ of $Z^6$ are joined to form a monocyclic $C_6$cycloalkyl optionally substituted with one, two, or three $R^{20z}$. In embodiments, two $R^{z6}$ of $Z^6$ are joined to form a monocyclic $C_7$cycloalkyl optionally substituted with one, two, or three $R^{20z}$.

In embodiments, one or two $R^{z4}$ of $Z^{4a}$ and one or two $R^{z4}$ of $Z^{4b}$ are joined to form a monocyclic $C_{3-7}$cycloalkyl, monocyclic 3-7 membered heterocycloalkyl, phenyl, or monocyclic 5-6 membered heteroaryl, wherein the monocyclic $C_{3-7}$cycloalkyl, monocyclic 3-7 membered heterocycloalkyl, phenyl, and monocyclic 5-6 membered heteroaryl are optionally substituted with one, two, or three $R^{20z}$.

In embodiments, one or two $R^{z4}$ of $Z^{4a}$ and one or two $R^{z4}$ of $Z^{4b}$ are joined to form a monocyclic $C_{3-7}$cycloalkyl optionally substituted with one, two, or three $R^{20z}$. In embodiments, one or two $R^{z4}$ of $Z^{4a}$ and one or two $R^{z4}$ of $Z^{4b}$ are joined to form a monocyclic 3-7 membered heterocycloalkyl optionally substituted with one, two, or three $R^{20z}$. In embodiments, one or two $R^{z4}$ of $Z^{4a}$ and one or two $R^{z4}$ of $Z^{4b}$ are joined to form a pyrrolidine optionally substituted with one, two, or three $R^{20z}$ (e.g., $R^{20z}$ substitution on ring N). In embodiments, one or two $R^{z4}$ of $Z^{4a}$ and one or two $R^{z4}$ of $Z^{4b}$ are joined to form a phenyl optionally substituted with one, two, or three $R^{20z}$. In embodiments, one or two $R^{z4}$ of $Z^{4a}$ and one or two $R^{z4}$ of $Z^{4b}$ are joined to form a monocyclic 5-6 membered heteroaryl optionally substituted with one, two, or three $R^{20z}$. In embodiments, one or two $R^{z4}$ of $Z^{4a}$ and one or two $R^{z4}$ of $Z^{4b}$ are joined to form a monocyclic 5 membered heteroaryl optionally substituted with one, two, or three $R^{20z}$. In embodiments, one or two $R^{z4}$ of $Z^{4a}$ and one or two $R^{z4}$ of $Z^{4b}$ are joined to form a monocyclic 6 membered heteroaryl optionally substituted with one, two, or three $R^{20z}$. In embodiments, one or two $R^{z4}$ of $Z^{4a}$ and one or two $R^{z4}$ of $Z^{4b}$ are joined to form a pyrazole optionally substituted with one, two, or three $R^{20z}$. In embodiments, one or two $R^{z4}$ of $Z^{4a}$ and one or two $R^{z4}$ of $Z^{4b}$ are joined to form a triazole optionally substituted with one, two, or three $R^{20z}$. In embodiments, one or two $R^{z4}$ of $Z^{4a}$ and one or two $R^{z4}$ of $Z^{4b}$ are joined to form a imidazole optionally substituted with one, two, or three $R^{20z}$. In embodiments, one or two $R^{z4}$ of $Z^4$a and one or two $R^{z4}$ of $Z^{4b}$ are joined to form a pyrrole optionally substituted with one, two, or three $R^{20z}$. In embodiments, one or two $R^{z4}$ of $Z^4$a and one or two $R^{z4}$ of $Z^{4b}$ are joined to form a pyrimidine optionally substituted with one, two, or three $R^{20z}$.

In embodiments, one or two $R^{z4}$ of $Z^{4b}$ and one or two $R^{z4}$ of $Z^{4c}$ are joined to form a monocyclic $C_{3-7}$cycloalkyl optionally substituted with one, two, or three $R^{20z}$. In embodiments, one or two $R^{z4}$ of $Z^{4b}$ and one or two $R^{z4}$ of $Z^{4c}$ are joined to form a monocyclic 3-7 membered heterocycloalkyl optionally substituted with one, two, or three $R^{20z}$. In embodiments, one or two $R^{z4}$ of $Z^{4b}$ of $Z^{4c}$ and one or two $R^{z4}$ of $Z^{4c}$ are joined to form a pyrrolidine optionally substituted with one, two, or three $R^{20z}$ (e.g., $R^{20z}$ on ring N). In embodiments, one or two $R^{z4}$ of $Z^{4b}$ and one or two $R^{z4}$ of $Z^{4c}$ are joined to form a phenyl optionally substituted with one, two, or three $R^{20z}$. In embodiments, one or two $R^{z4}$ of $Z^{4b}$ and one or two $R^{z4}$ of $Z^{4c}$ are joined to form a monocyclic 5-6 membered heteroaryl optionally substituted with one, two, or three $R^{20z}$. In embodiments, one or two $R^{z4}$ of $Z^{4b}$ and one or two $R^{z4}$ of $Z^{4c}$ are joined to form a monocyclic 5 membered heteroaryl optionally substituted with one, two, or three $R^{20z}$. In embodiments, one or two $R^{z4}$ of $Z^{4b}$ and one or two $R^{z4}$ of $Z^{4c}$ are joined to form a monocyclic 6 membered heteroaryl optionally substituted with one, two, or three $R^{20z}$. In embodiments, one or two $R^{z4}$ of $Z^{4b}$ and one or two $R^{z4}$ of $Z^{4c}$ are joined to form a pyrazole optionally substituted with one, two, or three $R^{20z}$. In embodiments, one or two $R^{z4}$ of $Z^{4b}$ and one or two $R^{z4}$ of $Z^{4c}$ are joined to form a triazole optionally substituted with one, two, or three $R^{20z}$. In embodiments, one or two $R^{z4}$ of $Z^{4b}$ and one or two $R^{z4}$ of $Z^{4c}$ are joined to form a imidazole optionally substituted with one, two, or three $R^{20z}$. In embodiments, one or two $R^{z4}$ of $Z^{4b}$ and one or two $R^{z4}$ of $Z^{4c}$ are joined to form a pyrrole optionally substituted with one, two, or three $R^{20z}$. In embodiments, one or two $R^{z4}$ of $Z^{4b}$ and one or two $R^{z4}$ of $Z^{4c}$ are joined to form a pyrimidine optionally substituted with one, two, or three $R^{20z}$.

In embodiments, one or two $R^{z4}$ of $Z^{4c}$ and one or two $R^{z4}$ of $Z^{4d}$ are joined to form a monocyclic $C_{3-7}$cycloalkyl optionally substituted with one, two, or three $R^{20z}$. In embodiments, one or two $R^{z4}$ of $Z^{4c}$ and one or two $R^{z4}$ of $Z^{4d}$ are joined to form a monocyclic 3-7 membered heterocycloalkyl optionally substituted with one, two, or three $R^{20z}$. In embodiments, one or two $R^{z4}$ of $Z^{4c}$ and one or two $R^{z4}$ of $Z^{4d}$ are joined to form a pyrrolidine optionally substituted with one, two, or three $R^{20z}$ (e.g., $R^{20z}$ substitution on ring N). In embodiments, one or two $R^{z4}$ of $Z^{4c}$ and one or two $R^{z4}$ of $Z^{4d}$ are joined to form a phenyl optionally substituted with one, two, or three $R^{20z}$. In embodiments, one or two $R^{z4}$ of $Z^{4c}$ and one or two $R^{z4}$ of $Z^{4d}$ are joined to form a monocyclic 5-6 membered heteroaryl optionally substituted with one, two, or three $R^{20z}$. In embodiments, one or two $R^{z4}$ of $Z^{4c}$ and one or two $R^{z4}$ of $Z^{4d}$ are joined to form a monocyclic 5 membered heteroaryl optionally substituted with one, two, or three $R^{20z}$. In embodiments, one or two $R^{z4}$ are and one or two $R^{z4}$ of $Z^{4d}$ are joined to form a monocyclic 6 membered heteroaryl optionally substituted with one, two, or three $R^{20z}$. In embodiments, one or two $R^{z4}$ of $Z^{4c}$ and one or two $R^{z4}$ of $Z^{4d}$ are joined to form a pyrazole optionally substituted with one, two, or three $R^{20z}$. In embodiments, one or two $R^{z4}$ of $Z^{4c}$ and one or two $R^{z4}$ of $Z^{4d}$ are joined to form a triazole optionally substituted with one, two, or three $R^{20z}$. In embodiments, one or two $R^{z4}$ of $Z^{4c}$ and one or two $R^{z4}$ of $Z^{4d}$ are joined to form a imidazole optionally substituted with one, two, or three $R^{20z}$. In embodiments, one or two $R^{z4}$ of $Z^{4c}$ and one or two $R^{z4}$ of $Z^{4d}$ are joined to form a pyrrole optionally substituted with one, two, or three $R^{20z}$. In embodiments, one or two $R^{z4}$ of $Z^{4c}$ and one or two $R^{z4}$ of $Z^{4d}$ are joined to form a pyrimidine optionally substituted with one, two, or three $R^{20z}$.

In embodiments, one or two $R^{z4}$ of $Z^{4d}$ and one or two $R^{z4}$ of $Z^{4e}$ are joined to form a monocyclic $C_{3-7}$cycloalkyl optionally substituted with one, two, or three $R^{20z}$. In embodiments, one or two $R^{z4}$ of $Z^{4d}$ and one or two $R^{z4}$ of $Z^{4e}$ are joined to form a monocyclic 3-7 membered heterocycloalkyl optionally substituted with one, two, or three $R^{20z}$. In embodiments, one or two $R^{z4}$ of $Z^{4d}$ and one or two $R^{z4}$ of $Z^{4e}$ are joined to form a pyrrolidine optionally substituted with one, two, or three $R^{20z}$ (e.g., $R^{20z}$ substitution on ring N). In embodiments, one or two $R^{z4}$ of $Z^{4d}$ and one or two $R^{z4}$ of $Z^{4e}$ are joined to form a phenyl optionally substituted with one, two, or three $R^{20z}$. In embodiments, one or two $R^{z4}$ of $Z^{4d}$ and one or two $R^{z4}$ of $Z^{4e}$ are joined to form a monocyclic 5-6 membered heteroaryl optionally substituted with one, two, or three $R^{20z}$. In embodiments, one or two $R^{z4}$ of $Z^{4d}$ and one or two $R^{z4}$ of $Z^{4e}$ are joined to form a monocyclic 5 membered heteroaryl optionally substituted with one, two, or three $R^{20z}$. In embodiments, one or two $R^{z4}$ of $Z^{4d}$ and one or two $R^{z4}$ of $Z^{4e}$ are joined to form a monocyclic 6 membered heteroaryl optionally substituted with one, two, or three $R^{20z}$. In embodiments, one or two $R^{z4}$ of $Z^{4d}$ and one or two $R^{z4}$ of $Z^{4e}$ are joined to form a pyrazole optionally substituted with one, two, or three $R^{20z}$. In embodiments, one or two $R^{z4}$ of $Z^{4d}$ and one or two $R^{z4}$ of $Z^{4e}$ are joined to form a triazole optionally substituted with one, two, or three $R^{20z}$. In embodiments, one or two $R^{z4}$ of $Z^{4d}$ and one or two $R^{z4}$ of $Z^{4e}$ are joined to form a imidazole optionally substituted with one, two, or three $R^{20z}$. In embodiments, one or two $R^{z4}$ of $Z^{4d}$ and one or two $R^{z4}$ of $Z^{4e}$ are joined to form a pyrrole optionally substituted with one, two, or three $R^{20z}$. In embodiments, one or two $R^{z4}$ of $Z^{4d}$ and one or two $R^{z4}$ of $Z^{4e}$ are joined to form a pyrimidine optionally substituted with one, two, or three $R^{20z}$.

In embodiments, one or two $R^{z4}$ of $Z^{4e}$ and one or two $R^{z5}$ of $Z^5$ are joined to form a monocyclic $C_{3-7}$cycloalkyl optionally substituted with one, two, or three $R^{20z}$. In embodiments, one or two $R^{z4}$ of $Z^{4e}$ and one or two $R^{z5}$ of $Z^5$ are joined to form a monocyclic 3-7 membered heterocycloalkyl optionally substituted with one, two, or three $R^{20z}$. In embodiments, one or two $R^{z4}$ of $Z^{4e}$ and one or two $R^{z5}$ of $Z^5$ are joined to form a pyrrolidine optionally substituted with one, two, or three $R^{20z}$ (e.g., $R^{20z}$ substitution on ring N). In embodiments, one or two $R^{z4}$ of $Z^{4e}$ and one or two $R^{z5}$ of $Z^5$ are joined to form a phenyl optionally substituted with one, two, or three $R^{20z}$. In embodiments, one or two $R^{z4}$ of $Z^{4e}$ and one or two $R^{z5}$ of $Z^5$ are joined to form a monocyclic 5-6 membered heteroaryl optionally substituted with one, two, or three $R^{20z}$. In embodiments, one or two $R^{z4}$ of $Z^{4e}$ and one or two $R^{z5}$ of $Z^5$ are joined to form a monocyclic 5 membered heteroaryl optionally substituted with one, two, or three $R^{20z}$. In embodiments, one or two $R^{z4}$ of $Z^{4e}$ and one or two $R^{z5}$ of $Z^5$ are joined to form a monocyclic 6 membered heteroaryl optionally substituted with one, two, or three $R^{20z}$. In embodiments, one or two $R^{z4}$ of $Z^{4e}$ and one or two $R^{z5}$ of $Z^5$ are joined to form a pyrazole optionally substituted with one, two, or three $R^{20z}$. In embodiments, one or two $R^{z4}$ of $Z^{4e}$ and one or two $R^{z5}$ of $Z^5$ are joined to form a triazole optionally substituted with one, two, or three $R^{20z}$. In embodiments, one or two $R^{z4}$ of $Z^{4e}$ and one or two $R^{z5}$ of $Z^5$ are joined to form a imidazole optionally substituted with one, two, or three $R^{20z}$. In embodiments, one or two $R^{z4}$ of $Z^{4e}$ and one or two $R^{z5}$ of $Z^5$ are joined to form a pyrrole optionally substituted with one, two, or three $R^{20z}$. In embodiments, one or two $R^{z4}$ of $Z^{4e}$ and one or two $R^{z5}$ of $Z^5$ are joined to form a pyrimidine optionally substituted with one, two, or three $R^{20z}$.

In embodiments, one or two $R^{z5}$ of $Z^5$ and one or two $R^{z6}$ of $Z^6$ are joined to form a monocyclic $C_{3-7}$cycloalkyl optionally substituted with one, two, or three $R^{20z}$. In embodiments, one or two $R^{z5}$ of $Z^5$ and one or two $R^{z6}$ of $Z^6$ are joined to form a monocyclic 3-7 membered heterocycloalkyl optionally substituted with one, two, or three $R^{20z}$. In embodiments, one or two $R^{z5}$ of $Z^5$ and one or two $R^{z6}$ of $Z^6$ are joined to form a pyrrolidine optionally substituted with one, two, or three $R^{20z}$ (e.g., $R^{20z}$ on ring N). In embodiments, one or two $R^{z5}$ of $Z^5$ and one or two $R^{z6}$ of $Z^6$ are joined to form a phenyl optionally substituted with one, two, or three $R^{20z}$. In embodiments, one or two $R^{z5}$ of $Z^5$ and one or two $R^{z6}$ of $Z^6$ are joined to form a monocyclic 5-6 membered heteroaryl optionally substituted with one, two, or three $R^{20z}$. In embodiments, one or two $R^{z5}$ of $Z^5$ and one or two $R^{z6}$ of $Z^6$ are joined to form a monocyclic 5 membered heteroaryl optionally substituted with one, two, or three $R^{20z}$. In embodiments, one or two $R^{z5}$ of $Z^5$ and one or two $R^{z6}$ of $Z^6$ are joined to form a monocyclic 6 membered heteroaryl optionally substituted with one, two, or three $R^{20z}$. In embodiments, one or two $R^{z5}$ of $Z^5$ and one or two $R^{z6}$ of $Z^6$ are joined to form a pyrazole optionally substituted with one, two, or three $R^{20z}$. In embodiments, one or two $R^{z5}$ of $Z^5$ and one or two $R^{z6}$ of $Z^6$ are joined to form a triazole optionally substituted with one, two, or three $R^{20z}$. In embodiments, one or two $R^{z5}$ of $Z^5$ and one or two $R^{z6}$ of $Z^6$ are joined to form a imidazole optionally substituted with one, two, or three $R^{20z}$. In embodiments, one or two $R^{z5}$ of $Z^5$ and one or two $R^{z6}$ of $Z^6$ are joined to form a pyrrole optionally substituted with one, two, or three $R^{20z}$. In embodiments, one or two $R^{z5}$ of $Z^5$ and one or two $R^{z6}$ of $Z^6$ are joined to form a pyrimidine optionally substituted with one, two, or three $R^{20z}$.

In embodiments, two $R^{z4}$ bonded to the same carbon atom are joined to form monocyclic $C_{3-7}$cycloalkyl or monocyclic 3-7 membered heterocycloalkyl, wherein the monocyclic $C_{3-7}$cycloalkyl and monocyclic 3-7 membered heterocycloalkyl are optionally substituted with one, two, or three $R^{20z}$. In embodiments, two $R^{z4}$ bonded to the same carbon atom are joined to form monocyclic $C_{3-7}$cycloalkyl optionally substituted with one, two, or three $R^{20z}$. In embodiments, two $R^{z4}$ bonded to the same carbon atom are joined to form monocyclic 3-7 membered heterocycloalkyl optionally substituted with one, two, or three $R^{20z}$.

In embodiments, two or more $R^{z4}$ bonded to adjacent atoms are joined to form monocyclic $C_{3-7}$cycloalkyl, monocyclic 3-7 membered heterocycloalkyl, phenyl, or monocyclic 5-6 membered heteroaryl, wherein the monocyclic $C_{3-7}$cycloalkyl, monocyclic 3-7 membered heterocycloalkyl, phenyl, and monocyclic 5-6 membered heteroaryl are optionally substituted with one, two, or three $R^{20z}$. In embodiments, two or more $R^{z4}$ bonded to adjacent atoms are joined to form monocyclic $C_{3-7}$cycloalkyl optionally substituted with one, two, or three $R^{20z}$. In embodiments, two or more $R^{z4}$ bonded to adjacent atoms are joined to form monocyclic 3-7 membered heterocycloalkyl optionally substituted with one, two, or three $R^{20z}$. In embodiments, two or more $R^{z4}$ bonded to adjacent atoms are joined to form phenyl optionally substituted with one, two, or three $R^{20z}$. In embodiments, two or more $R^{z4}$ bonded to adjacent atoms are joined to form monocyclic 5-6 membered heteroaryl optionally substituted with one, two, or three $R^{20z}$.

In embodiments, two $R^{z5}$ bonded to the same carbon atom are joined to form monocyclic $C_{3-7}$cycloalkyl or monocyclic 3-7 membered heterocycloalkyl, wherein the monocyclic $C_{3-7}$cycloalkyl and monocyclic 3-7 membered heterocycloalkyl are optionally substituted with one, two, or three $R^{20z}$. In embodiments, two $R^{z5}$ bonded to the same carbon atom are joined to form monocyclic $C_{3-7}$cycloalkyl optionally substituted with one, two, or three $R^{20z}$. In embodiments, two $R^{z5}$ bonded to the same carbon atom are joined to form monocyclic 3-7 membered heterocycloalkyl optionally substituted with one, two, or three $R^{20z}$.

In embodiments, one or two $R^{z4}$ bonded to the atom and one or two $R^{z5}$ bonded to an adjacent atom are joined to form monocyclic $C_{3-7}$cycloalkyl, monocyclic 3-7 membered heterocycloalkyl, phenyl, or monocyclic 5-6 membered heteroaryl, wherein the monocyclic $C_{3-7}$cycloalkyl, monocyclic 3-7 membered heterocycloalkyl, phenyl, and monocyclic 5-6 membered heteroaryl are optionally substituted with one, two, or three $R^{20z}$. In embodiments, one or two $R^{z4}$ bonded to the atom and one or two $R^{z5}$ bonded to an adjacent atom are joined to form monocyclic $C_{3-7}$cycloalkyl optionally substituted with one, two, or three $R^{20z}$. In embodiments, one or two $R^{z4}$ bonded to the atom and one or two $R^{z5}$ bonded to an adjacent atom are joined to form monocyclic 3-7 membered heterocycloalkyl optionally substituted with one, two, or three $R^{20z}$. In embodiments one or two $R^{z4}$ bonded to the atom and one or two $R^{z5}$ bonded to an adjacent atom are joined to form phenyl optionally substituted with one, two, or three $R^{20z}$. In embodiments, one or two $R^{z4}$ bonded to the atom and one or two $R^{z5}$ bonded to an adjacent atom are joined to form monocyclic 5-6 membered heteroaryl optionally substituted with one, two, or three $R^{20z}$.

In embodiments, one or two $R^{z4}$ bonded to one atom and one or two $R^{z5}$ bonded to a second atom are joined to form monocyclic $C_{3-7}$cycloalkyl or monocyclic 3-7 membered heterocycloalkyl, wherein the monocyclic $C_{3-7}$cycloalkyl and monocyclic 3-7 membered heterocycloalkyl are optionally substituted with one, two, or three $R^{20z}$;

In embodiments, two $R^6$ bonded to the same carbon atom are joined to form monocyclic $C_{3-7}$cycloalkyl or monocyclic 3-7 membered heterocycloalkyl, wherein the monocyclic $C_{3-7}$cycloalkyl and monocyclic 3-7 membered heterocycloalkyl are optionally substituted with one, two, or three $R^{20z}$. In embodiments, one or two $R^{z4}$ bonded to one atom and one or two $R^{z5}$ bonded to a second atom are joined to form monocyclic $C_{3-7}$cycloalkyl optionally substituted with one, two, or three $R^{20z}$. In embodiments, one or two $R^{z4}$ bonded to one atom and one or two $R^{z5}$ bonded to a second atom are joined to form monocyclic 3-7 membered heterocycloalkyl optionally substituted with one, two, or three $R^{20z}$. In embodiments, one or two $R^{z4}$ bonded to one atom and one or two $R^{z5}$ bonded to a second atom are joined to form phenyl optionally substituted with one, two, or three $R^{20z}$. In embodiments, one or two $R^{z4}$ bonded to one atom and one or two $R^{z5}$ bonded to a second atom are joined to form monocyclic 5-6 membered heteroaryl optionally substituted with one, two, or three $R^{20z}$.

In embodiments, one or two $R^{z5}$ bonded to the atom and one or two $R^{z6}$ bonded to an adjacent atom are joined to form monocyclic $C_{3-7}$cycloalkyl, monocyclic 3-7 membered heterocycloalkyl, phenyl, or monocyclic 5-6 membered heteroaryl, wherein the monocyclic $C_{3-7}$cycloalkyl, monocyclic 3-7 membered heterocycloalkyl, phenyl, and monocyclic 5-6 membered heteroaryl are optionally substituted with one, two, or three $R^{20z}$. In embodiments, one or two $R^{z5}$ bonded to the atom and one or two $R^{z6}$ bonded to an adjacent atom are joined to form monocyclic $C_{3-7}$cycloalkyl optionally substituted with one, two, or three $R^{20z}$. In embodiments, one or two $R^{z5}$ bonded to the atom and one or two $R^{z6}$ bonded to an adjacent atom are joined to form monocyclic 3-7 membered heterocycloalkyl optionally substituted with one, two, or three $R^{20z}$. In embodiments, one or two $R^{z5}$ bonded to the atom and one or two $R^{z6}$ bonded to an adjacent atom are joined to form phenyl optionally substituted with one, two, or three $R^{20z}$. In embodiments, one or two $R^{z5}$ bonded to the atom and one or two $R^{z6}$ bonded to an adjacent atom are joined to form monocyclic 5-6 membered heteroaryl optionally substituted with one, two, or three $R^{20z}$.

In embodiments, one or two $R^{z4}$ bonded to one atom and one or two $R^{z6}$ bonded to a second atom are joined to form monocyclic $C_{4-7}$cycloalkyl or monocyclic 4-7 membered heterocycloalkyl, wherein the monocyclic $C_{4-7}$cycloalkyl and monocyclic 4-7 membered heterocycloalkyl are optionally substituted with one, two, or three $R^{20z}$. In embodiments, one or two $R^{z4}$ bonded to one atom and one or two $R^{z6}$ bonded to a second atom are joined to form monocyclic $C_{4-7}$cycloalkyl optionally substituted with one, two, or three $R^{20z}$. In embodiments, one or two $R^{z4}$ bonded to one atom and one or two $R^{z6}$ bonded to a second atom are joined to form monocyclic 4-7 membered heterocycloalkyl optionally substituted with one, two, or three $R^{20z}$. In embodiments one or two $R^{z4}$ bonded to one atom and one or two $R^{z6}$ bonded to a second atom are joined to form phenyl optionally substituted with one, two, or three $R^{20z}$. In embodiments, one or two $R^{z4}$ bonded to one atom and one or two $R^{z6}$ bonded to a second atom are joined to form monocyclic 5-6 membered heteroaryl optionally substituted with one, two, or three $R^{20z}$.

In embodiments, two $R^{20z}$ bonded to the same carbon atom are optionally joined to form monocyclic $C_{3-7}$cycloalkyl or monocyclic 3-7 membered heterocycloalkyl, wherein the monocyclic $C_{3-7}$cycloalkyl and monocyclic 3-7 membered heterocycloalkyl are optionally substituted with one, two, or three $R^{20z}$. In embodiments, two $R^{20z}$ bonded to the same carbon atom are optionally joined to form monocyclic $C_{3-7}$cycloalkyl optionally substituted with one, two, or three $R^{20z}$. In embodiments, two $R^{20z}$ bonded to the same carbon atom are optionally joined to form monocyclic 3-7 membered heterocycloalkyl optionally substituted with one, two, or three $R^{20z}$.

In embodiments, two or more $R^{20z}$ bonded to two adjacent atoms are optionally joined to form monocyclic $C_{3-7}$cycloalkyl, monocyclic 3-7 membered heterocycloalkyl, phenyl, or monocyclic 5-6 membered heteroaryl, wherein the $C_{3-7}$cycloalkyl, monocyclic 3-7 membered heterocycloalkyl, phenyl, and monocyclic 5-6 membered heteroaryl are optionally substituted with one, two, or three $R^{20z}$. In embodiments, two or more $R^{20z}$ bonded to two adjacent atoms are optionally joined to form monocyclic $C_{3-7}$cycloalkyl optionally substituted with one, two, or three $R^{20z}$. In embodiments, two or more $R^{20z}$ bonded to two adjacent atoms are optionally joined to form monocyclic 3-7 membered heterocycloalkyl optionally substituted with one, two, or three $R^{20z}$. In embodiments, two or more $R^{20z}$ bonded to two adjacent atoms are optionally joined to form phenyl optionally substituted with one, two, or three $R^{20z}$. In embodiments, two or more $R^{20z}$ bonded to two adjacent atoms are optionally joined to form monocyclic 5-6 membered heteroaryl optionally substituted with one, two, or three $R^{20z}$.

In embodiments, each $Z^1$ is independently $C(R^{z1})$, $N(R^{z1})$, $C(R^{z1})_2$, $C(O)$, $S(O)$, $S(O)_2$, O, S, or N. In embodiments, each $Z^1$ is independently $C(R^{z1})$. In embodiments, each $Z^1$ is independently $N(R^{z1})$. In embodiments, each $Z^1$ is independently $C(R^{z1})_2$. In embodiments, each $Z^1$ is independently $C(O)$. In embodiments, each $Z^1$ is independently $S(O)$. In embodiments, each $Z^1$ is independently $S(O)_2$. In embodiments, each $Z^1$ is independently O. In embodiments, each $Z^1$ is independently S. In embodiments, each $Z^1$ is independently N.

In embodiments, z1n is 0. In embodiments, z1n is 1. In embodiments, z1n is 2. In embodiments, z1n is 3. In embodiments, z1n is 4.

In embodiments, $Z^2$ is $C(R^{z2})$. In embodiments, $Z^2$ is C. In embodiments, $Z^2$ is N.

In embodiments, $Z^3$ is $C(R^{z3})$. In embodiments, $Z^3$ is C. In embodiments, $Z^3$ is N.

In embodiments, $Z^4$ is a bond. In embodiments, $Z^4$ is $Z^{4a}$. In embodiments, $Z^4$ is $Z^{4a}Z^{4b}$. In embodiments, $Z^4$ is $Z^{4a}Z^{4b}Z^{4c}$. In embodiments, $Z^4$ is $Z^4$ is $Z^{4a}Z^{4b}Z^{4c}Z^{4d}$. In embodiments, $Z^4$ is $Z^4$ is $Z^{4a}Z^{4b}Z^{4c}Z^{4d}Z^{4e}$. $Z^{4a}$ is directly bonded to $Z^2$.

In embodiments, $Z^{4a}$ is $C(R^{z4})$. In embodiments, $Z^{4a}$ is $N(R^{z4})$. In embodiments, $Z^{4a}$ is $C(R^{z4})_2$. In embodiments, $Z^{4a}$ is $C(O)$. In embodiments, $Z^{4a}$ is $S(O)$. In embodiments, $Z^{4a}$ is $S(O)_2$. In embodiments, $Z^{4a}$ is O. In embodiments, $Z^{4a}$ is S. In embodiments, $Z^{4a}$ is N. In embodiments, $Z^{4a}$ is $S(O)(NR^{z4})$.

In embodiments, $Z^{4b}$ b is $C(R^{z4})$. In embodiments, $Z^{4b}$ is $N(R^{z4})$. In embodiments, $Z^{4b}$ is $C(R^{z4})_2$. In embodiments, $Z^{4b}$ is $C(O)$. In embodiments, $Z^4$ b is $S(O)$. In embodiments, $Z^4$ b is $S(O)_2$. In embodiments, $Z^4$ b is O. In embodiments, $Z^4$ b is S. In embodiments, $Z^{4b}$ b is N. In embodiments, $Z^{4b}$ is $S(O)(NR^{z4})$.

In embodiments, $Z^{4c}$ is $C(R^{z4})$. In embodiments, $Z^{4c}$ is $N(R^{z4})$. In embodiments, $Z^{4c}$ is $C(R^{z4})_2$. In embodiments, $Z^{4c}$ is $C(O)$. In embodiments, $Z^{4c}$ is $S(O)$. In embodiments, $Z^{4c}$ is $S(O)_2$. In embodiments, $Z^{4c}$ is O. In embodiments, $Z^{4c}$ is S. In embodiments, $Z^{4c}$ is N. In embodiments, $Z^{4c}$ is $S(O)(NR^{z4})$.

In embodiments, $Z^{4d}$ is $C(R^{z4})$. In embodiments, $Z^{4d}$ is $N(R^{z4})$. In embodiments, $Z^{4d}$ is $C(R^{z4})_2$. In embodiments, $Z^{4d}$ is $C(O)$. In embodiments, $Z^{4d}$ is $S(O)$. In embodiments, $Z^{4d}$ is $S(O)_2$. In embodiments, $Z^{4d}$ is O. In embodiments, $Z^{4d}$ is S. In embodiments, $Z^{4d}$ is N. In embodiments, $Z^{4d}$ is $S(O)(NR^{z4})$.

In embodiments, $Z^{4e}$ is $C(R^{z4})$. In embodiments, $Z^{4e}$ is $N(R^{z4})$. In embodiments, $Z^{4e}$ is $C(R^{z4})_2$. In embodiments, $Z^{4e}$ is $C(O)$. In embodiments, $Z^{4e}$ is $S(O)$. In embodiments, $Z^{4e}$ is $S(O)_2$. In embodiments, $Z^{4e}$ is O. In embodiments, $Z^{4e}$ is S. In embodiments, $Z^{4e}$ is N. In embodiments, $Z^{4e}$ is $S(O)(NR^{z4})$.

In embodiments, if z9n is 0 and $Z^4$ is $Z^{4a}Z^{4b}$ then $Z^{4b}$ is $C(R^{z4})$, $C(R^{z4})_2$, $C(O)$, $S(O)$, $S(O)_2$, O, S, or N. In embodiments, if z9n is 0 and $Z^4$ is $Z^{4a}Z^{4b}$ then $Z^{4b}$ is $N(R^{z4})$ and $Z^{4a}$ is $C(O)$. In embodiments, if z9n is 0 and $Z^4$ is $Z^{4a}Z^{4b}$ then $Z^{4b}$ is $N(R^{z4})$ and $Z^5$ is $C(O)$. In embodiments, if z9n is 0 and $Z^4$ is $Z^{4a}Z^{4b}$ then $Z^{4b}$ is $N(R^{z4})$ and $Z^3$ is $C(R^{z3})$ or C. In embodiments, if z9n is 0 and $Z^4$ is $Z^{4a}Z^{4b}$ then $Z^{4b}$ is $C(R^{z4})$. In embodiments, if z9n is 0 and $Z^4$ is $Z^{4a}Z^{4b}$ then $Z^{4b}$ is $C(R^{z4})_2$. In embodiments, if z9n is 0 and $Z^4$ is $Z^{4a}Z^{4b}$ then $Z^{4b}$ is $C(O)$. In embodiments, if z9n is 0 and $Z^4$ is $Z^{4a}Z^{4b}$ then $Z^{4b}$ is $S(O)$. In embodiments, if z9n is 0 and $Z^4$ is $Z^{4a}Z^{4b}$ then $Z^{4b}$ is $S(O)_2$. In embodiments, if z9n is 0 and $Z^4$ is $Z^{4a}Z^{4b}$ then $Z^{4b}$ is O. In embodiments, if z9n is 0 and $Z^4$ is $Z^{4a}Z^{4b}$ then $Z^{4b}$ is S. In embodiments, if z9n is 0 and $Z^4$ is $Z^{4a}Z^{4b}$ then $Z^{4b}$ is N. In embodiments, if z9n is 0 and $Z^4$ is $Z^{4a}Z^{4b}$ then $Z^{4b}$ is $C(R^{z4})$, $C(R^{z4})_2$, $C(O)$, $S(O)$, $S(O)_2$, $S(O)(NR^{z4})$, O, S, or N. In embodiments, if z9n is 0 and $Z^4$ is $Z^{4a}Z^{4b}$; then $Z^{4b}$ is $N(R^{z4})$ and $Z^{4a}$ is $C(O)$, $S(O)$, or $S(O)_2$. In embodiments, if z9n is 0 and $Z^4$ is $Z^{4a}Z^{4b}$; then $Z^{4b}$ is $N(R^{z4})$ and $Z^5$ is $C(O)$, $S(O)$, or $S(O)_2$. In embodiments, if z9n is 0 and $Z^4$ is $Z^{4a}Z^{4b}$; then $Z^{4b}$ is $N(R^{z4})$ and $Z^3$ is $C(R^{z3})$ or C.

In embodiments, $Z^5$ is $C(R^{z5})$. In embodiments, $Z^5$ is $N(R^{z5})$. In embodiments, $Z^5$ is $C(R^{z5})_2$. In embodiments, $Z^5$ is $C(O)$. In embodiments, $Z^5$ is $S(O)$. In embodiments, $Z^5$ is $S(O)_2$. In embodiments, $Z^5$ is O. In embodiments, $Z^5$ is S. In embodiments, $Z^5$ is N. In embodiments, $Z^5$ is $S(O)(NR^5)$.

In embodiments, $Z^6$ is $C(R^{z6})$. In embodiments, $Z^6$ is $N(R^{z6})$. In embodiments, $Z^6$ is $C(R^{z6})_2$. In embodiments, $Z^6$ is $C(O)$. In embodiments, $Z^6$ is $S(O)$. In embodiments, $Z^6$ is $S(O)_2$. In embodiments, $Z^6$ is O. In embodiments, $Z^6$ is S. In embodiments, $Z^6$ is N. In embodiments, $Z^6$ is $S(O)(NR^6)$.

In embodiments, each $Z^9$ is independently $C(R^{z9})$. In embodiments, each $Z^9$ is independently $N(R^{z9})$, $C(R^{z9})_2$. In embodiments, each $Z^9$ is independently $C(O)$. In embodiments, each $Z^9$ is independently $S(O)$. In embodiments, each $Z^9$ is independently $S(O)_2$. In embodiments, each $Z^9$ is independently O. In embodiments, each $Z^9$ is independently S. In embodiments, each $Z^9$ is independently N.

In embodiments, z9n is 0. In embodiments, z9n is 1. In embodiments, z9n is 2. In embodiments, z9n is 3. In embodiments, z9n is 4.

In embodiments, the sum of z1n and z9n is 2. In embodiments, the sum of z1n and z9n is 3. In embodiments, the sum of z1n and z9n is 4.

In embodiments, $R^{z1}$ is independently hydrogen. In embodiments, $R^{z1}$ is independently halogen. In embodiments, $R^{z1}$ is independently —CN. In embodiments, $R^{z1}$ is independently —$OR^{12}$. In embodiments, $R^{z1}$ is independently —$SR^{12}$. In embodiments, $R^{z1}$ is independently —$N(R^{12})(R^{13})$. In embodiments, $R^{z1}$ is independently —$C(O)R^{12}$. In embodiments, $R^{z1}$ is independently —$OC(O)N(R^{12})(R^{13})$. In embodiments, $R^{z1}$ is independently —$N(R^{14})C(O)N(R^{12})(R^{13})$. In embodiments, $R^{z1}$ is independently —$N(R^{14})C(O)OR^{15}$. In embodiments, $R^{z1}$ is independently —$N(R^{14})S(O)_2R^{15}$. In embodiments, $R^{z1}$ is independently —$C(O)R^{12}$. In embodiments, $R^{z1}$ is independently —$S(O)R^{15}$. In embodiments, $R^{z1}$ is independently —$OC(O)R^{15}$. In embodiments, $R^{z1}$ is independently —$C(O)N(R^{12})(R^{13})$. In embodiments, $R^{z1}$ is independently —$C(O)C(O)N(R^{12})(R^{13})$. In embodiments, $R^{z1}$ is independently —$N(R^{14})C(O)R^{12}$. In embodiments, $R^{z1}$ is independently —$S(O)_2R^{15}$. In embodiments, $R^{z1}$ is independently —$S(O)_2N(R^{12})(R^{13})$—. In embodiments, $R^{z1}$ is independently —$S(=O)(=NH)N(R^{12})(R^{13})$. In embodiments, $R^{z1}$ is independently —$CH_2C(O)N(R^{12})(R^{13})$. In embodiments, $R^{z1}$ is independently —$CH_2N(R^{14})C(O)R^{15}$. In embodiments, $R^{z1}$ is independently —$CH_2S(O)_2R^{15}$. In embodiments, $R^{z1}$ is independently —$CH_2S(O)_2N(R^{12})(R^{13})$.

In select embodiments of the compound, $R^{z1}$ is independently $C_{1-6}$alkyl optionally substituted with one, two, or three $R^{20z1}$. In some embodiments, $R^{z1}$ is independently $C_{2-6}$alkenyl optionally substituted with one, two, or three $R^{20z1}$. In some embodiments, $R^{z1}$ is independently $C_{2-6}$alkynyl optionally substituted with one, two, or three $R^{20z1}$. In some embodiments, $R^{z1}$ is independently $C_{3-10}$cycloalkyl optionally substituted with one, two, or three $R^{20z1}$. In some embodiments, $R^{z1}$ is independently $C_{1-9}$heterocycloalkyl optionally substituted with one, two, or three $R^{20z1}$. In some embodiments, $R^{z1}$ is independently $C_{6-10}$aryl optionally substituted with one, two, or three $R^{20z1}$. In some embodiments, $R^{z1}$ is independently $C_{1-9}$heteroaryl optionally substituted with one, two, or three $R^{20z1}$. In embodiments of the compound, $R^{z1}$ is independently methyl optionally substituted with one or two $R^{20z1}$. In further embodiments of the compound, $R^{z1}$ is independently methyl. In some embodiments of the compound, $R^{z1}$ is independently ethyl optionally substituted with one, two, or three $R^{20z1}$. In embodiments of the compound, $R^{z1}$ is independently ethyl. In some embodiments of the compound, $R^{z1}$ is independently propyl optionally substituted with one, two, or three $R^{20z1}$. In embodiments of the compound, $R^{z1}$ is independently propyl. In embodiments, two $R^{z1}$ bonded to the same carbon are joined to form $C_{2-6}$alkenyl optionally substituted with one, two, or three $R^{20z1}$.

In embodiments, $R^{z2}$ is independently hydrogen. In embodiments, $R^{z2}$ is independently halogen. In embodiments, $R^{z2}$ is independently —CN. In embodiments, $R^{z2}$ is independently —$OR^{12}$. In embodiments, $R^{z2}$ is independently —$SR^{12}$. In embodiments, $R^{z2}$ is independently —$N(R^{12})(R^{13})$. In embodiments, $R^{z2}$ is independently —$C(O)R^{12}$. In embodiments, $R^{z2}$ is independently —$OC(O)N(R^{12})(R^{13})$. In embodiments, $R^{z2}$ is independently —$N(R^{14})C(O)N(R^{12})(R^{13})$. In embodiments, $R^{z2}$ is independently —$N(R^{14})C(O)OR^{15}$. In embodiments, $R^{z2}$ is independently —$N(R^{14})S(O)_2R^{15}$. In embodiments, $R^{z2}$ is independently —$C(O)R^{12}$. In embodiments, $R^{z2}$ is independently —$S(O)R^{15}$. In embodiments, $R^{z2}$ is independently —$OC(O)R^{15}$. In embodiments, $R^{z2}$ is independently —$C(O)N(R^{12})(R^{13})$. In embodiments, $R^{z2}$ is independently —$C(O)C(O)N(R^{12})(R^{13})$. In embodiments, $R^{z2}$ is independently —$N(R^{14})C(O)R^{12}$. In embodiments, $R^{z2}$ is independently —S(O)$_2$R$^{15}$. In embodiments, R$^{z2}$ is independently —S(O)$_2$N(R$^{12}$)(R$^{13}$)—. In embodiments, R$^{z2}$ is independently —S(=O)(=NH)N(R$^{12}$)(R$^{13}$). In embodiments, R$^{z2}$ is independently —CH$_2$C(O)N(R$^{12}$)(R$^{13}$). In embodiments, R$^{z2}$ is independently —CH$_2$N(R$^{14}$)C(O)R$^{15}$. In embodiments, R$^{z2}$ is independently —CH$_2$S(O)$_2$R$^{15}$. In embodiments, R$^{z2}$ is independently —CH$_2$S(O)$_2$N(R$^{12}$)(R$^{13}$).

In select embodiments of the compound, R$^{z2}$ is independently C$_{1-6}$alkyl optionally substituted with one, two, or three R$^{20z2}$. In some embodiments, R$^{z2}$ is independently C$_{2-6}$alkenyl optionally substituted with one, two, or three R$^{20z2}$. In some embodiments, R$^{z2}$ is independently C$_{2-6}$alkynyl optionally substituted with one, two, or three R$^{20z2}$. In some embodiments, R$^{z2}$ is independently C$_{3-10}$cycloalkyl optionally substituted with one, two, or three R$^{20z2}$. In some embodiments, R$^{z2}$ is independently C$_{1-9}$heterocycloalkyl optionally substituted with one, two, or three R$^{20z2}$. In some embodiments, R$^{z2}$ is independently C$_{6-10}$aryl optionally substituted with one, two, or three R$^{20z2}$. In some embodiments, R$^{z2}$ is independently C$_{1-9}$heteroaryl optionally substituted with one, two, or three R$^{20z2}$. In embodiments of the compound, R$^{z2}$ is independently methyl optionally substituted with one or two R$^{20z2}$. In further embodiments of the compound, R$^{z2}$ is independently methyl. In some embodiments of the compound, R$^{z2}$ is independently ethyl optionally substituted with one, two, or three R$^{20z2}$. In embodiments of the compound, R$^{z2}$ is independently ethyl. In some embodiments of the compound, R$^{z2}$ is independently propyl optionally substituted with one, two, or three R$^{20z2}$. In embodiments of the compound, R$^{z2}$ is independently propyl. In embodiments, two R$^{z2}$ bonded to the same carbon are joined to form C$_{2-6}$alkenyl optionally substituted with one, two, or three R$^{20z2}$.

In embodiments, R$^{z3}$ is independently hydrogen. In embodiments, R$^{z3}$ is independently halogen. In embodiments, R$^{z3}$ is independently —CN. In embodiments, R$^{z3}$ is independently —OR$^{12}$. In embodiments, R$^{z3}$ is independently —SR$^{12}$. In embodiments, R$^{z3}$ is independently —N(R$^{12}$)(R$^{13}$). In embodiments, R$^{z3}$ is independently —C(O)R$^{12}$. In embodiments, R$^{z3}$ is independently —OC(O)N(R$^{12}$)(R$^{13}$). In embodiments, R$^{z3}$ is independently —N(R$^{14}$)C(O)N(R$^{12}$)(R$^{13}$). In embodiments, R$^{z3}$ is independently —N(R$^{14}$)C(O)OR$^{15}$. In embodiments, R$^{z3}$ is independently —N(R$^{14}$)S(O)$_2$R$^{15}$. In embodiments, R$^{z3}$ is independently —C(O)R$^{12}$. In embodiments, R$^{z3}$ is independently —S(O)R$^{15}$. In embodiments, R$^{z3}$ is independently —OC(O)R$^{15}$. In embodiments, R$^{z3}$ is independently —C(O)N(R$^{12}$)(R$^{13}$). In embodiments, R$^{z3}$ is independently —C(O)C(O)N(R$^{12}$)(R$^{13}$). In embodiments, R$^{z3}$ is independently —N(R$^{14}$)C(O)R$^{12}$. In embodiments, R$^{z3}$ is independently —S(O)$_2$R$^{15}$. In embodiments, R$^{z3}$ is independently —S(O)$_2$N(R$^{12}$)(R$^{13}$)—. In embodiments, R$^{z3}$ is independently —S(=O)(=NH)N(R$^{12}$)(R$^{13}$). In embodiments, R$^{z3}$ is independently —CH$_2$C(O)N(R$^{12}$)(R$^{13}$). In embodiments, R$^{z3}$ is independently —CH$_2$N(R$^{14}$)C(O)R$^{15}$. In embodiments, R$^{z3}$ is independently —CH$_2$S(O)$_2$R$^{15}$. In embodiments, R$^{z3}$ is independently —CH$_2$S(O)$_2$N(R$^{12}$)(R$^{13}$).

In select embodiments of the compound, R$^{z3}$ is independently C$_{1-6}$alkyl optionally substituted with one, two, or three R$^{20z3}$. In some embodiments, R$^{z3}$ is independently C$_{2-6}$alkenyl optionally substituted with one, two, or three R$^{20z3}$. In some embodiments, R$^{z3}$ is independently C$_{2-6}$alkynyl optionally substituted with one, two, or three R$^{20z3}$. In some embodiments, R$^{z3}$ is independently C$_{3-10}$cycloalkyl optionally substituted with one, two, or three R$^{20z3}$. In some embodiments, R$^{z3}$ is independently C$_{1-9}$heterocycloalkyl optionally substituted with one, two, or three R$^{20z3}$. In some embodiments, R$^{z3}$ is independently C$_{6-10}$aryl optionally substituted with one, two, or three R$^{20z3}$. In some embodiments, R$^{z3}$ is independently C$_{1-9}$heteroaryl optionally substituted with one, two, or three R$^{20z3}$. In embodiments of the compound, R$^{z3}$ is independently methyl optionally substituted with one or two R$^{20z3}$. In further embodiments of the compound, R$^{z3}$ is independently methyl. In some embodiments of the compound, R$^{z3}$ is independently ethyl optionally substituted with one, two, or three R$^{20z3}$. In embodiments of the compound, R$^{z3}$ is independently ethyl. In some embodiments of the compound, R$^{z3}$ is independently propyl optionally substituted with one, two, or three R$^{20z3}$. In embodiments of the compound, R$^{z3}$ is independently propyl. In embodiments, two R$^{z3}$ bonded to the same carbon are joined to form C$_{2-6}$alkenyl optionally substituted with one, two, or three R$^{20z3}$.

In embodiments, R$^{z4}$ is independently hydrogen. In embodiments, R$^{z4}$ is independently halogen. In embodiments, R$^{z4}$ is independently —CN. In embodiments, R$^{z4}$ is independently —OR$^{12}$. In embodiments, R$^{z4}$ is independently —SR$^{12}$. In embodiments, R$^{z4}$ is independently —N(R$^{12}$)(R$^{13}$). In embodiments, R$^{z4}$ is independently —C(O)R$^{12}$. In embodiments, R$^{z4}$ is independently —OC(O)N(R$^{12}$)(R$^{13}$). In embodiments, R$^{z4}$ is independently —N(R$^{14}$)C(O)N(R$^{12}$)(R$^{13}$). In embodiments, R$^{z4}$ is independently —N(R$^{14}$)C(O)OR$^{15}$. In embodiments, R$^{z4}$ is independently —N(R$^{14}$)S(O)$_2$R$^{15}$. In embodiments, R$^{z4}$ is independently —C(O)R$^{12}$. In embodiments, R$^{z4}$ is independently —S(O)R$^{15}$. In embodiments, R$^{z4}$ is independently —OC(O)R$^{15}$. In embodiments, R$^{z4}$ is independently —C(O)N(R$^{12}$)(R$^{13}$). In embodiments, R$^{z4}$ is independently —C(O)C(O)N(R$^{12}$)(R$^{13}$). In embodiments, R$^{z4}$ is independently —N(R$^{14}$)C(O)R$^{12}$. In embodiments, R$^{z4}$ is independently —S(O)$_2$R$^{15}$. In embodiments, R$^{z4}$ is independently —S(O)$_2$N(R$^{12}$)(R$^{13}$)—. In embodiments, R$^{z4}$ is independently —S(=O)(=NH)N(R$^{12}$)(R$^{13}$). In embodiments, R$^{z4}$ is independently —CH$_2$C(O)N(R$^{12}$)(R$^{13}$). In embodiments, R$^{z4}$ is independently —CH$_2$N(R$^{14}$)C(O)R$^{15}$. In embodiments, R$^{z4}$ is independently —CH$_2$S(O)$_2$R$^{15}$. In embodiments, R$^{z4}$ is independently —CH$_2$S(O)$_2$N(R$^{12}$)(R$^{13}$).

In select embodiments of the compound, R$^{z4}$ is independently C$_{1-6}$alkyl optionally substituted with one, two, or three R$^{20z4}$. In some embodiments, R$^{z4}$ is independently C$_{2-6}$alkenyl optionally substituted with one, two, or three R$^{20z4}$. In some embodiments, R$^{z4}$ is independently C$_{2-6}$alkynyl optionally substituted with one, two, or three R$^{20z4}$. In some embodiments, R$^{z4}$ is independently C$_{3-10}$cycloalkyl optionally substituted with one, two, or three R$^{20z4}$. In some embodiments, R$^{z4}$ is independently C$_{1-9}$heterocycloalkyl optionally substituted with one, two, or three R$^{20z4}$. In some embodiments, R$^{z4}$ is independently C$_{6-10}$aryl optionally substituted with one, two, or three R$^{20z4}$. In some embodiments, R$^{z4}$ is independently C$_{1-9}$heteroaryl optionally substituted with one, two, or three R$^{20z4}$. In embodiments of the compound, R$^{z4}$ is independently methyl optionally substituted with one or two R$^{20z4}$. In further embodiments of the compound, R$^{z4}$ is independently methyl. In some embodiments of the compound, R$^{z4}$ is independently ethyl optionally substituted with one, two, or three R$^{20z4}$. In embodiments of the compound, R$^{z4}$ is independently ethyl. In some embodiments of the compound, R$^{z4}$ is independently propyl optionally substituted with one, two, or three R$^{20z4}$. In embodiments of the compound, R$^{z4}$ is independently propyl. In embodiments, two R$^{z4}$ bonded to the same carbon are joined to form C$_{2-6}$alkenyl optionally substituted with one, two, or three R$^{20z4}$.

In embodiments, $R^{z5}$ is independently hydrogen. In embodiments, $R^{z5}$ is independently halogen. In embodiments, $R^{z5}$ is independently —CN. In embodiments, $R^{z5}$ is independently —$OR^{12}$. In embodiments, $R^{z5}$ is independently —$SR^{12}$. In embodiments, $R^{z5}$ is independently —$N(R^{12})(R^{13})$. In embodiments, $R^{z5}$ is independently —$C(O)R^{12}$. In embodiments, $R^{z5}$ is independently —$OC(O)N(R^{12})(R^{13})$. In embodiments, $R^{z5}$ is independently —$N(R^{14})C(O)N(R^{12})(R^{13})$. In embodiments, $R^{z5}$ is independently —$N(R^{14})C(O)R^{15}$. In embodiments, $R^{z5}$ is independently —$N(R^{14})S(O)_2R^{15}$. In embodiments, $R^{z5}$ is independently —$C(O)R^{12}$. In embodiments, $R^{z5}$ is independently —$S(O)R^{15}$. In embodiments, $R^{z5}$ is independently —$OC(O)R^{15}$. In embodiments, $R^{z5}$ is independently —$C(O)N(R^{12})(R^{13})$. In embodiments, $R^{z5}$ is independently —$C(O)C(O)N(R^{12})(R^{13})$. In embodiments, $R^{z5}$ is independently —$N(R^{14})C(O)R^{12}$. In embodiments, $R^{z5}$ is independently —$S(O)_2R^{15}$. In embodiments, $R^{z5}$ is independently —$S(O)_2N(R^{12})(R^{13})$—. In embodiments, $R^{z5}$ is independently —$S(=O)(=NH)N(R^{12})(R^{13})$. In embodiments, $R^{z5}$ is independently —$CH_2C(O)N(R^{12})(R^{13})$. In embodiments, $R^{z5}$ is independently —$CH_2N(R^{14})C(O)R^{15}$. In embodiments, $R^{z5}$ is independently —$CH_2S(O)_2R^{15}$. In embodiments, $R^{z5}$ is independently —$CH_2S(O)_2N(R^{12})(R^{13})$.

In select embodiments of the compound, $R^{z5}$ is independently $C_{1-6}$alkyl optionally substituted with one, two, or three $R^{20z5}$. In some embodiments, $R^{z5}$ is independently $C_{2-6}$alkenyl optionally substituted with one, two, or three $R^{20z5}$. In some embodiments, $R^{z5}$ is independently $C_{2-6}$alkynyl optionally substituted with one, two, or three $R^{20z5}$. In some embodiments, $R^{z5}$ is independently $C_{3-10}$cycloalkyl optionally substituted with one, two, or three $R^{20z5}$. In some embodiments, $R^{z5}$ is independently $C_{1-9}$heterocycloalkyl optionally substituted with one, two, or three $R^{20z5}$. In some embodiments, $R^{z5}$ is independently $C_{6-10}$aryl optionally substituted with one, two, or three $R^{20z5}$. In some embodiments, $R^{z5}$ is independently $C_{1-9}$heteroaryl optionally substituted with one, two, or three $R^{20z5}$. In embodiments of the compound, $R^{z5}$ is independently methyl optionally substituted with one or two $R^{20z5}$. In further embodiments of the compound, $R^{z5}$ is independently methyl. In some embodiments of the compound, $R^{z5}$ is independently ethyl optionally substituted with one, two, or three $R^{20z5}$. In embodiments of the compound, $R^{z5}$ is independently ethyl. In some embodiments of the compound, $R^{z5}$ is independently propyl optionally substituted with one, two, or three $R^{20z5}$. In embodiments of the compound, $R^{z5}$ is independently propyl. In embodiments, two $R^{z5}$ bonded to the same carbon are joined to form $C_{2-6}$alkenyl optionally substituted with one, two, or three $R^{20z5}$.

In embodiments, $R^{z6}$ is independently hydrogen. In embodiments, $R^{z6}$ is independently halogen. In embodiments, $R^{z6}$ is independently —CN. In embodiments, $R^{z6}$ is independently —$OR^{12}$. In embodiments, $R^{z6}$ is independently —$SR^{12}$. In embodiments, $R^{z6}$ is independently —$N(R^{12})(R^{13})$. In embodiments, $R^{z6}$ is independently —$C(O)R^{12}$. In embodiments, $R^{z6}$ is independently —$OC(O)N(R^{12})(R^{13})$. In embodiments, $R^{z6}$ is independently —$N(R^{14})C(O)N(R^{12})(R^{13})$. In embodiments, $R^{z6}$ is independently —$N(R^{14})C(O)R^{15}$. In embodiments, $R^{z6}$ is independently —$N(R^{14})S(O)_2R^{15}$. In embodiments, $R^{z6}$ is independently —$C(O)R^{12}$. In embodiments, $R^{z6}$ is independently —$S(O)R^{15}$. In embodiments, $R^{z6}$ is independently —$OC(O)R^{15}$. In embodiments, $R^{z6}$ is independently —$C(O)N(R^{12})(R^{13})$. In embodiments, $R^{z6}$ is independently —$C(O)C(O)N(R^{12})(R^{13})$. In embodiments, $R^{z6}$ is independently —$N(R^{14})C(O)R^{12}$. In embodiments, $R^{z6}$ is independently —$S(O)_2R^{15}$. In embodiments, $R^{z6}$ is independently —$S(O)_2N(R^{12})(R^{13})$—. In embodiments, $R^{z6}$ is independently —$S(=O)(=NH)N(R^{12})(R^{13})$. In embodiments, $R^{z6}$ is independently —$CH_2C(O)N(R^{12})(R^{13})$. In embodiments, $R^{z6}$ is independently —$CH_2N(R^{14})C(O)R^{15}$. In embodiments, $R^{z6}$ is independently —$CH_2S(O)_2R^{15}$. In embodiments, $R^{z6}$ is independently —$CH_2S(O)_2N(R^{12})(R^{13})$.

In select embodiments of the compound, $R^{z6}$ is independently $C_{1-6}$alkyl optionally substituted with one, two, or three $R^{20z6}$. In some embodiments, $R^{z6}$ is independently $C_{2-6}$alkenyl optionally substituted with one, two, or three $R^{20z6}$. In some embodiments, $R^{z6}$ is independently $C_{2-6}$alkynyl optionally substituted with one, two, or three $R^{20z6}$. In some embodiments, $R^{z6}$ is independently $C_{3-10}$cycloalkyl optionally substituted with one, two, or three $R^{20z6}$. In some embodiments, $R^{z6}$ is independently $C_{1-9}$heterocycloalkyl optionally substituted with one, two, or three $R^{20z6}$. In some embodiments, $R^{z6}$ is independently $C_{6-10}$aryl optionally substituted with one, two, or three $R^{20z6}$. In some embodiments, $R^{z6}$ is independently $C_{1-9}$heteroaryl optionally substituted with one, two, or three $R^{20z6}$. In embodiments of the compound, $R^{z6}$ is independently methyl optionally substituted with one or two $R^{20z6}$. In further embodiments of the compound, $R^{z6}$ is independently methyl. In some embodiments of the compound, $R^{z6}$ is independently ethyl optionally substituted with one, two, or three $R^{20z6}$. In embodiments of the compound, $R^{z6}$ is independently ethyl. In some embodiments of the compound, $R^{z6}$ is independently propyl optionally substituted with one, two, or three $R^{20z6}$. In embodiments of the compound, $R^{z6}$ is independently propyl. In embodiments, two $R^{z6}$ bonded to the same carbon are joined to form $C_{2-6}$alkenyl optionally substituted with one, two, or three $R^{20z6}$. In embodiments, one of $R^{z4}$, $R^{z5}$, $R^{z6}$, $R^{20z}$, and $R^{20zz}$ is (1) optionally bonded to a nitrogen atom; and (2) selected from the group consisting of

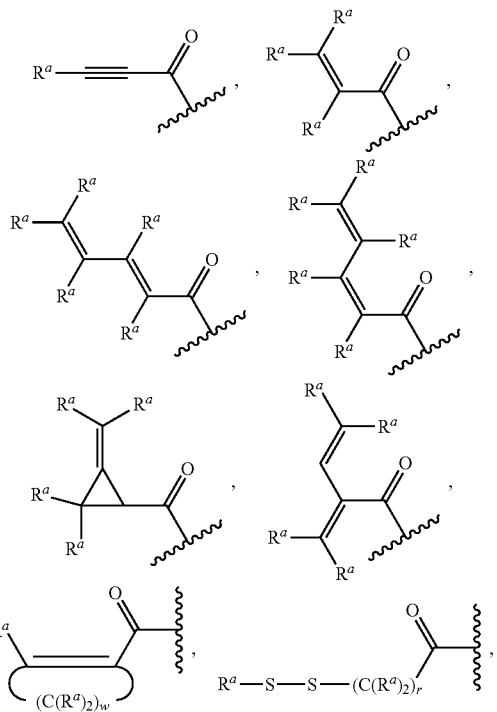

-continued

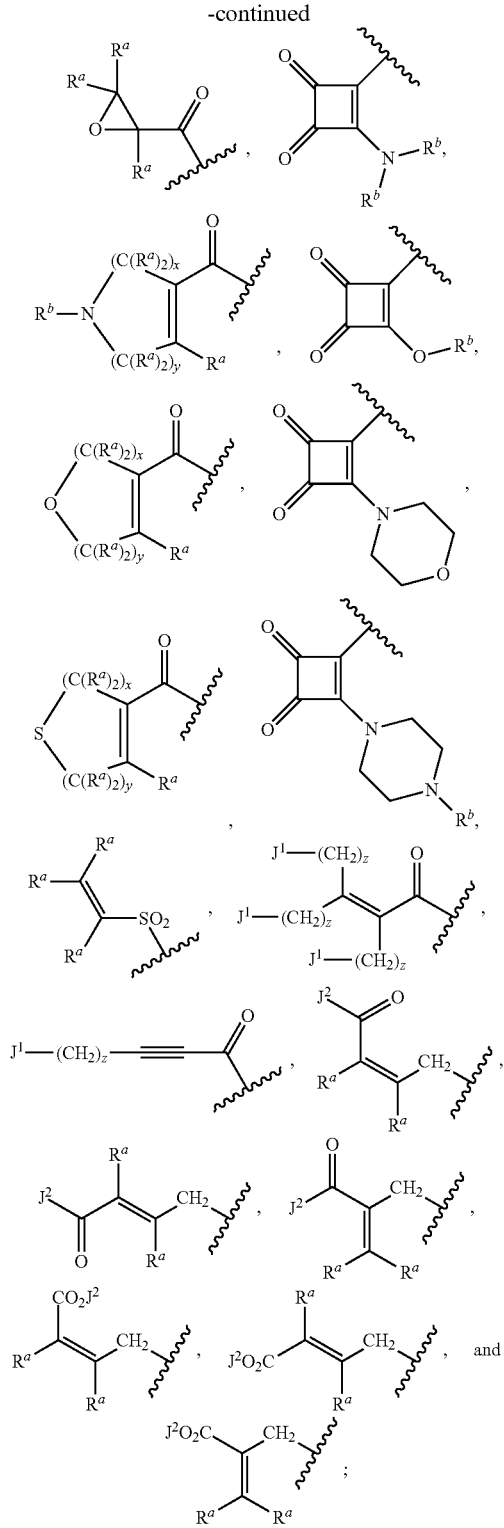

where each $R^a$ is independently hydrogen, $C_{1-6}$alkyl, carboxy, $C_{1-6}$carboalkoxy, phenyl, $C_{2-7}$carboalkyl, $R^c$—(C$(R^b)_2)_z$—, $R^c$—(C$(R^b)_2)_w$-M-(C$(R^b)_2)_r$-, $(R^d)(R^e)$CH-M-(C$(R^b)_2)_r$-, or Het-$J^3$-(C$(R^b)_2)_r$-; each $R^b$ is independently hydrogen, $C_{1-6}$alkyl, $C_{2-6}$alkenyl, $C_{2-6}$alkynyl, $C_{3-6}$cycloalkyl, $C_{2-7}$carboalkyl, $C_{2-7}$carboxyalkyl, phenyl, or phenyl optionally substituted with one or more halogen, $C_{1-6}$alkoxy, trifluoromethyl, amino, $C_{1-3}$alkylamino, $C_{2-6}$dialkylamino, nitro, azido, halomethyl, $C_{2-7}$alkoxymethyl, $C_{2-7}$alkanoyloxymethyl, $C_{1-6}$alkylthio, hydroxy, carboxyl, $C_{2-7}$carboalkoxy, phenoxy, phenyl, thiophenoxy, benzoyl, benzyl, phenylamino, benzylamino, $C_{1-6}$alkanoylamino, or $C_{1-6}$alkyl; each $R^c$ is independently —$NR^bR^b$ or —$OR^b$; $R^d$ and $R^e$ are each, independently, —(C$(R^b)_2)_r$—$NR^bR^b$, or —(C$(R^b)_2)_r$—$OR^b$; each $J^1$ is independently hydrogen, chlorine, fluorine, or bromine; $J^2$ is $C_{1-6}$alkyl or hydrogen; each M is independently —$N(R^b)$—, —O—, —N[(C$(R^b)_2)_w$—$NR^bR^b$]—, or —N[(C$(R^b)_2)_w$—$OR^b$]—; each $J^3$ is independently —$N(R^b)$—, —O—, or a bond; each Het is independently a heterocycle, optionally mono- or di-substituted on carbon or nitrogen with $R^b$ and optionally mono-substituted on carbon with —$CH_2OR^b$; wherein the heterocycle is selected from the group consisting of morpholine, thiomorpholine, thiomorpholine S-oxide, thiomorpholine S,S-dioxide, piperidine, pyrrolidine, aziridine, imidazole, 1,2,3-triazole, 1,2,4-triazole, tetrazole, piperazine, tetrahydrofuran, and tetrahydropyran; each r is independently 1-4; each w is independently 2-4; x is 0-1; y is 0-4, and each z is independently 1-6; wherein the sum of x+y is 2-4.

In embodiments, one of $R^{z4}$, $R^{z5}$, $R^{z6}$, $R^{20z}$, and $R^{20zz}$ is (1) optionally bonded to a nitrogen atom; and (2) selected from the group consisting of

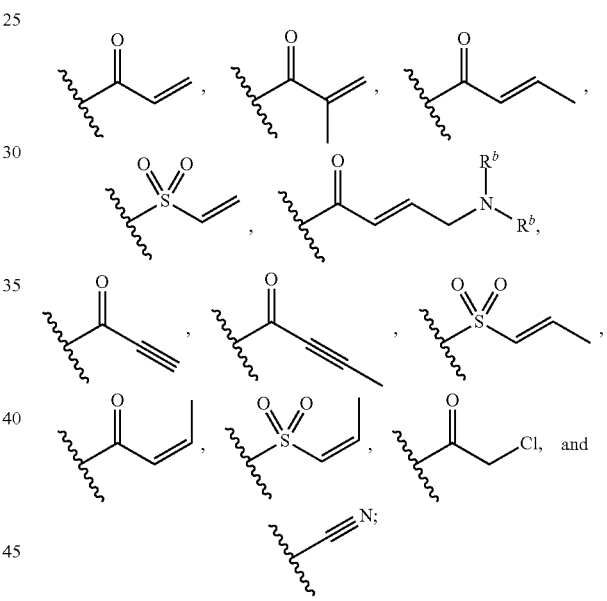

where each $R^b$ is independently selected from the group consisting of hydrogen, hydroxyl, $C_1$-$C_6$ alkoxy, and $C_1$-$C_6$ alkyl, or two $R^b$ optionally join to form heterocycle having 3-12 ring atoms or $C_3$-$C_6$ cycloalkyl.

In embodiments, one of $R^{z4}$, $R^{z5}$, $R^{z6}$, $R^{20z}$, and $R^{20zz}$ is (1) optionally bonded to a nitrogen atom; and (2) selected from the group consisting of

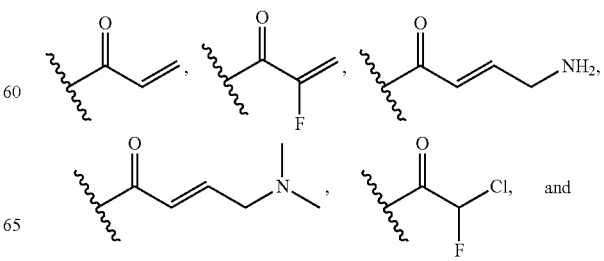

-continued

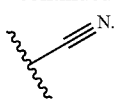

In embodiments, one of $R^{z4}$, $R^{z5}$, $R^{z6}$, $R^{20z}$, and $R^{20zz}$ is (1) optionally bonded to a nitrogen atom; and (2) selected from

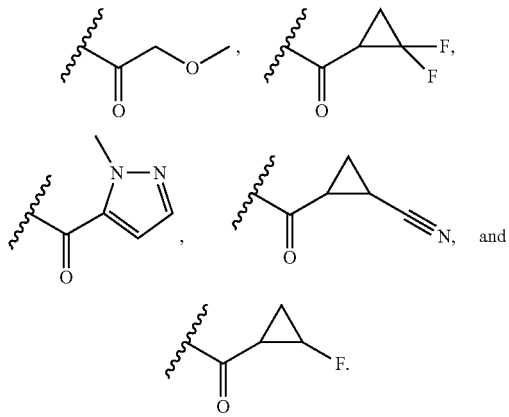

In embodiments, one of $R^{z4}$, $R^{z5}$, $R^{z6}$, $R^{20z}$, and $R^{20zz}$ is (1) optionally bonded to a nitrogen atom; and (2) selected from

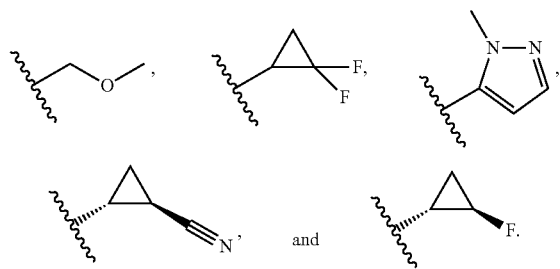

In embodiments, one of $R^{z4}$, $R^{z5}$, $R^{z6}$, $R^{20z}$, and $R^{20zz}$ is (1) optionally bonded to a nitrogen atom; and (2) selected from

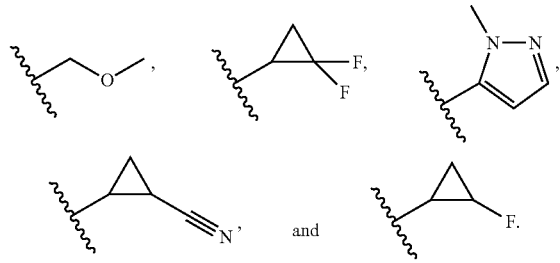

In embodiments, one of $R^{z4}$, $R^{z5}$, $R^{z6}$, $R^{20z}$, and $R^{20zz}$ is (1) optionally bonded to a nitrogen atom; and (2) selected from

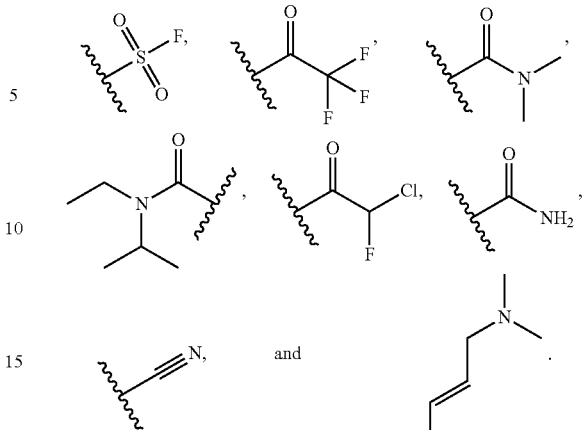

In embodiments, one of $R^{z4}$, $R^{z5}$, $R^{z6}$, $R^{20z}$, and $R^{20zz}$ is (1) optionally bonded to a nitrogen atom; and (2) selected from

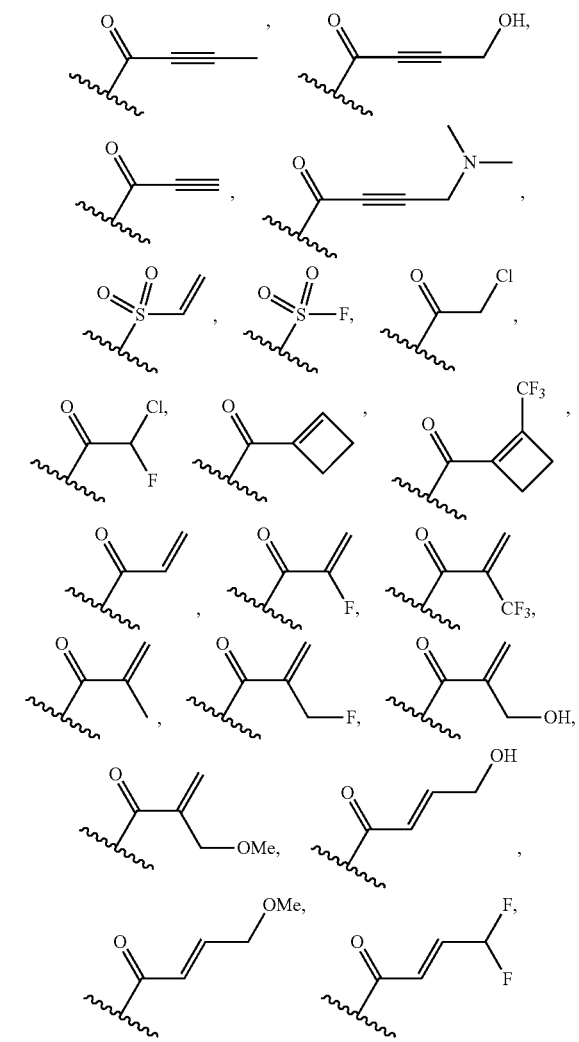

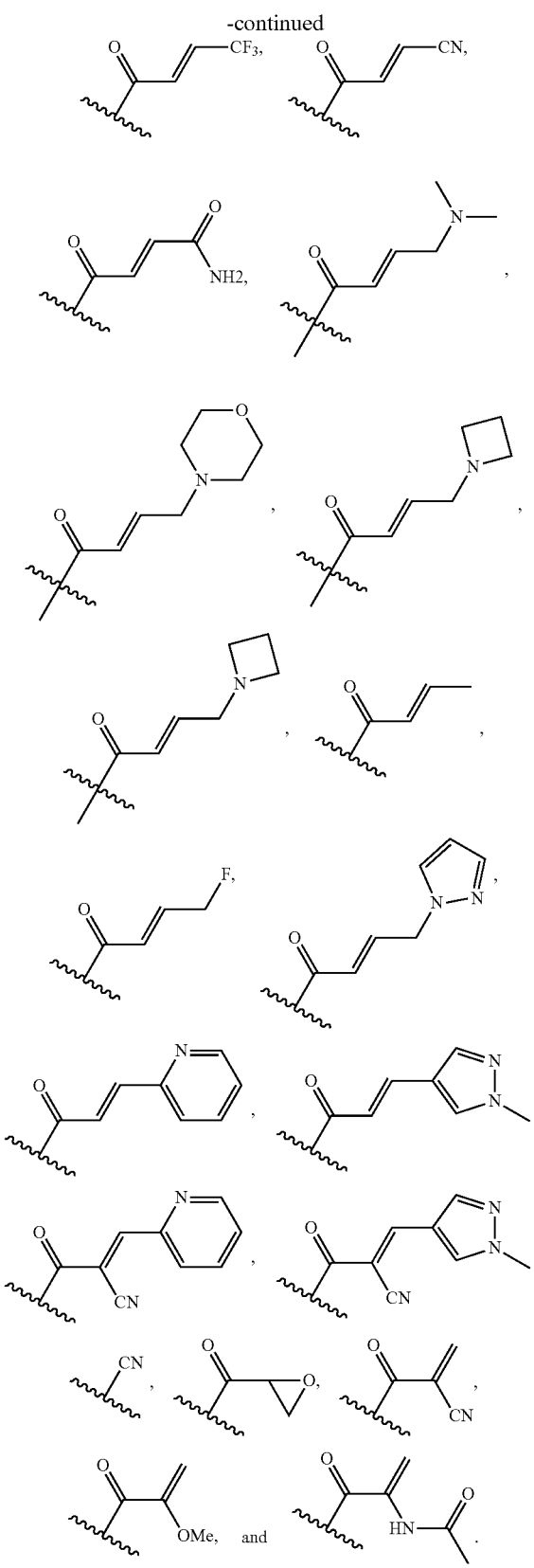
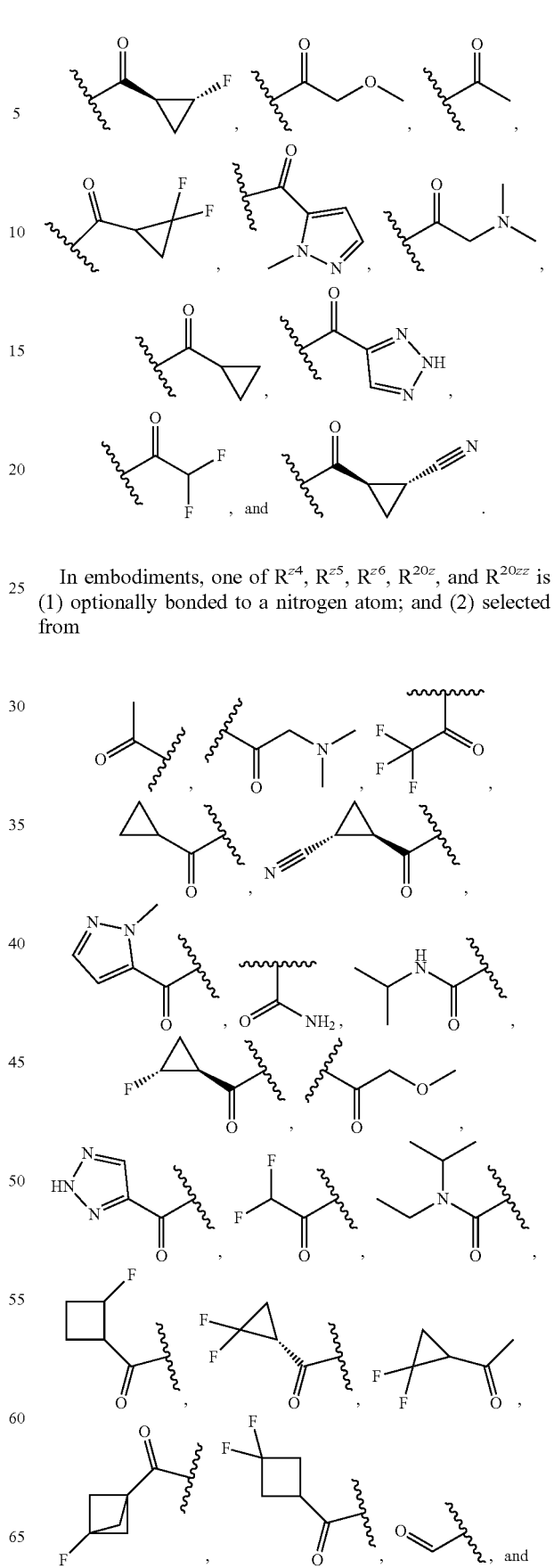
In embodiments, one of $R^{z4}$, $R^{z5}$, $R^{z6}$, $R^{20z}$, and $R^{20zz}$ is (1) optionally bonded to a nitrogen atom; and (2) selected from
In embodiments, one of $R^{z4}$, $R^{z5}$, $R^{z6}$, $R^{20z}$, and $R^{20zz}$ is (1) optionally bonded to a nitrogen atom; and (2) selected from

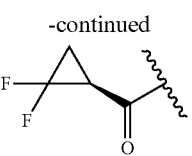
In embodiments, one of $R^{z4}$, $R^{z5}$, $R^{z6}$, $R^{20z}$, and $R^{20zz}$ is selected from
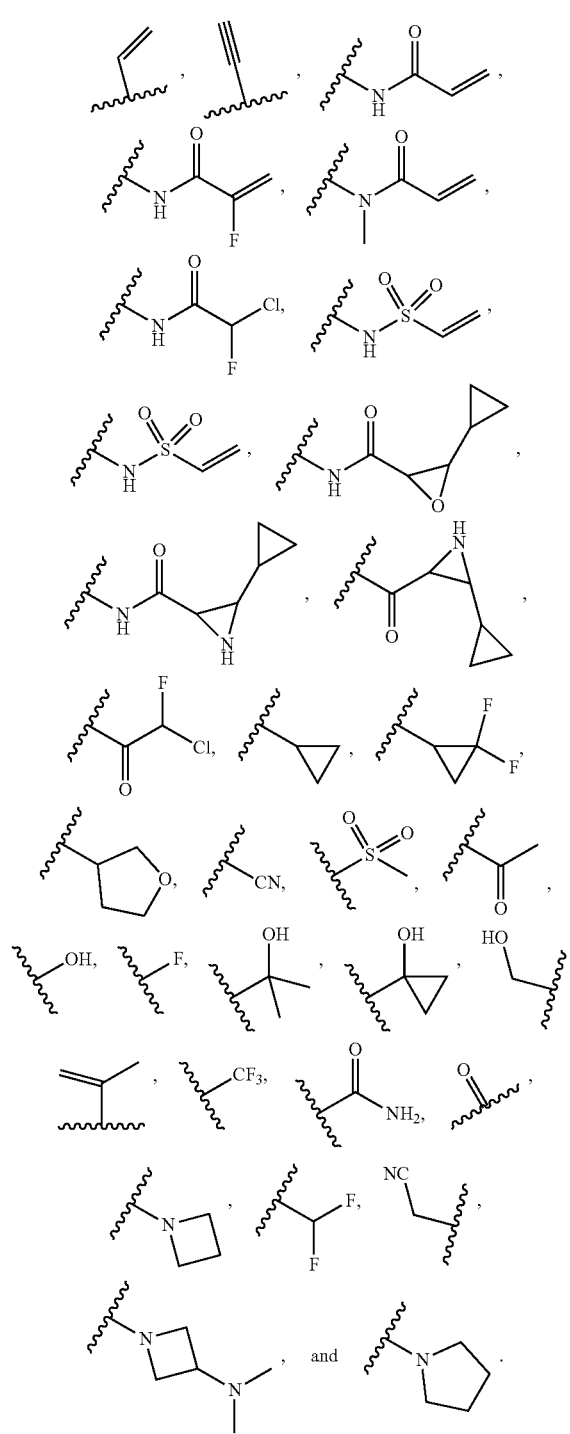
In embodiments, one of $R^{z4}$, $R^{z5}$, $R^{z6}$, $R^{20z}$, and $R^{20zz}$ is (1) optionally bonded to a nitrogen atom; and (2) selected from
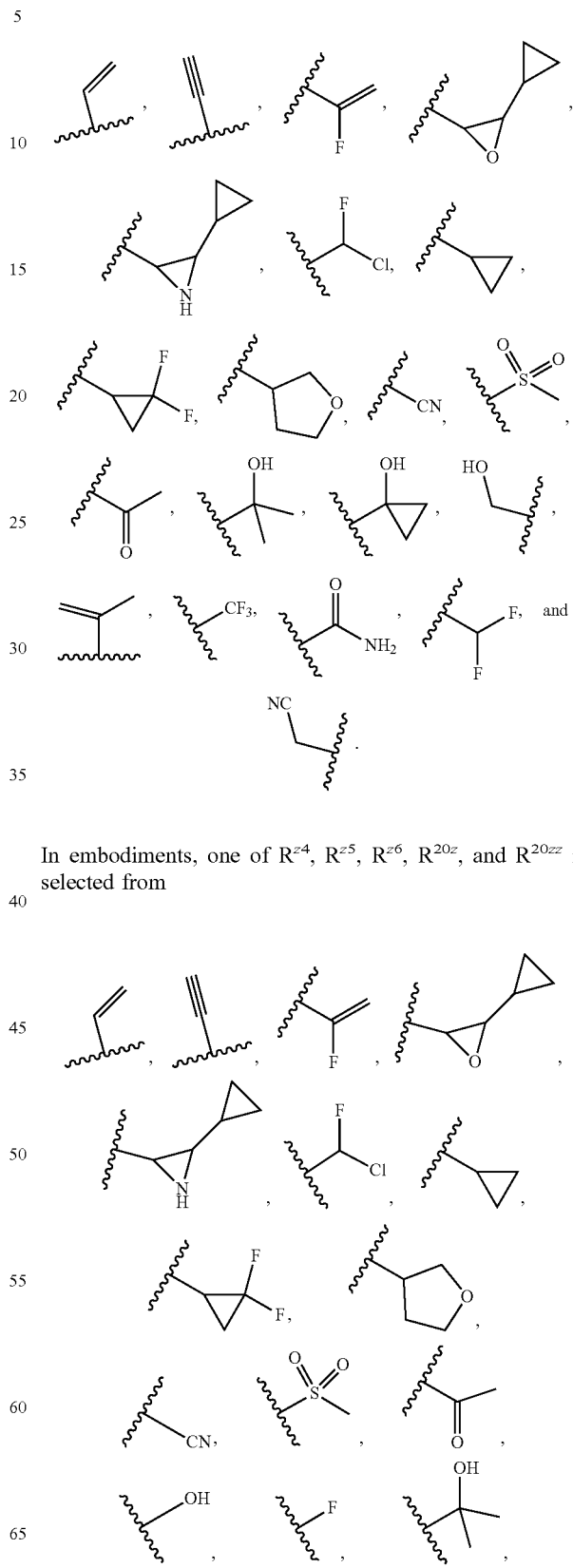
In embodiments, one of $R^{z4}$, $R^{z5}$, $R^{z6}$, $R^{20z}$, and $R^{20zz}$ is selected from -continued

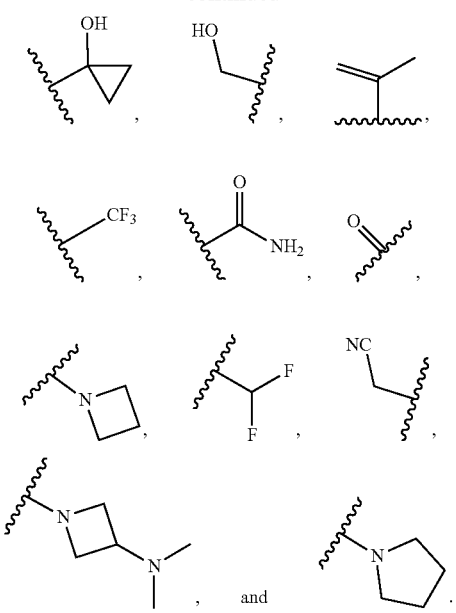

In embodiments, one of $R^{z4}$, $R^{z5}$, $R^{z6}$, $R^{20z}$, and $R^{20zz}$ is

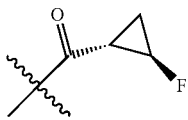

and is optionally bonded to a nitrogen atom.

In embodiments, one of $R^{z4}$, $R^{z5}$, $R^{z6}$, $R^{20z}$, and $R^{20zz}$ is (1) optionally bonded to a nitrogen atom; and (2) selected from:

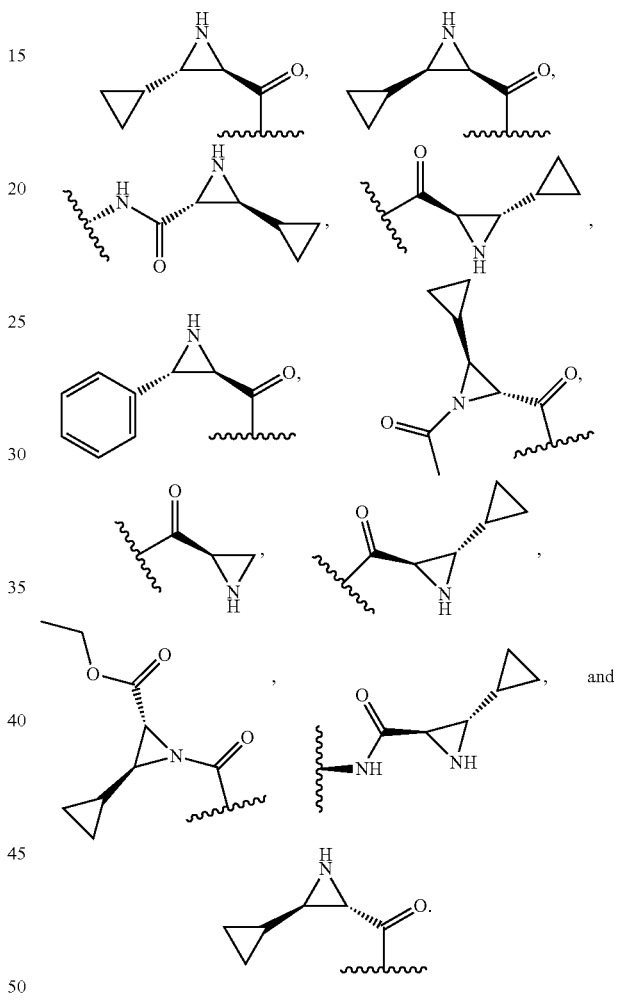

In embodiments, one of $R^{z4}$, $R^{z5}$, $R^{z6}$, $R^{20z}$, and $R^{20zz}$ is

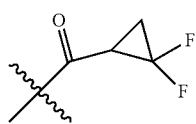 [SMILES: *C(=O)C1CC1(F)F]

and is optionally bonded to a nitrogen atom. In embodiments, one of $R^{z4}$, $R^{z5}$, $R^{z6}$, $R^{20z}$, and $R^{20zz}$ is

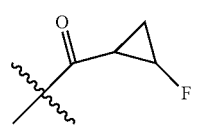 [SMILES: *C(=O)C1CC1F]

and is optionally bonded to a nitrogen atom. In embodiments, one of $R^{z4}$, $R^{z5}$, $R^{z6}$, $R^{20z}$, and $R^{20zz}$ is

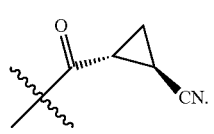 [SMILES: *C(=O)[C@@H]1C[C@H]1C#N]

and is optionally bonded to a nitrogen atom. In embodiments, one of $R^{z4}$, $R^{z5}$, $R^{z6}$, $R^{20z}$, and $R^{20zz}$ is

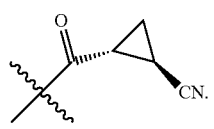 [SMILES: *C(=O)[C@@H]1C[C@H]1C#N]

In embodiments, one of $R^{z4}$, $R^{z5}$, $R^{z6}$, $R^{20z}$, and $R^{20zz}$ is selected from:

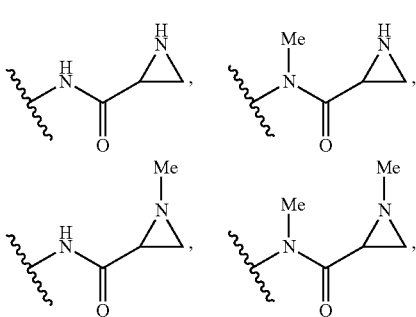

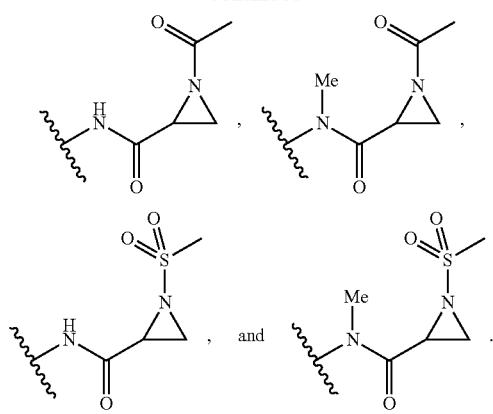
In embodiments, one of $R^{z4}$, $R^{z5}$, $R^{z6}$, $R^{20z}$, and $R^{20zz}$ is selected from:
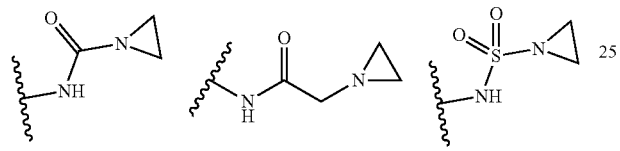
In embodiments, one of $R^{z4}$, $R^{z5}$, $R^{z6}$, $R^{20z}$, and $R^{20zz}$ is (1) optionally bonded to a nitrogen atom; and (2) selected from:
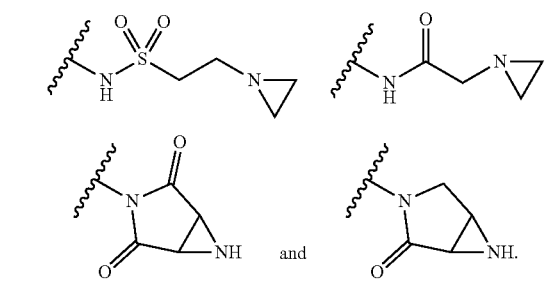
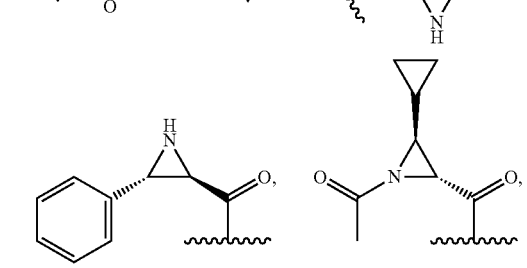
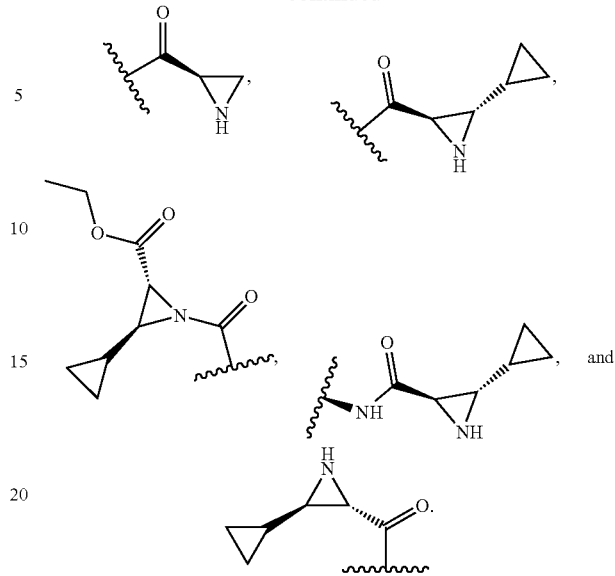
In embodiments, one of $R^{z4}$, $R^{z5}$, $R^{z6}$, $R^{20z}$, and $R^{20zz}$ is selected from:
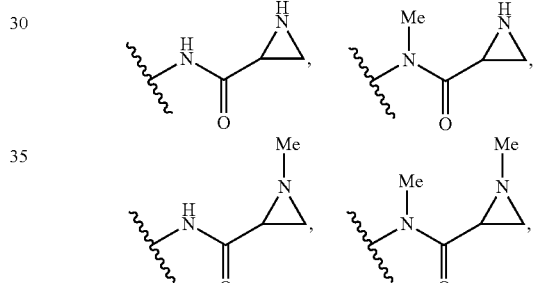
In embodiments, one of $R^{z4}$, $R^{z5}$, $R^{z6}$, $R^{20z}$, and $R^{20zz}$ is selected from:
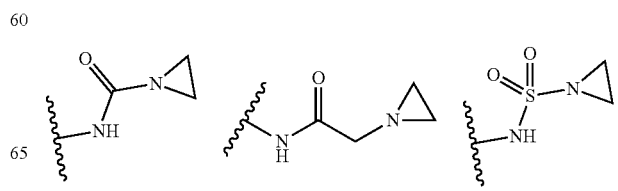

-continued
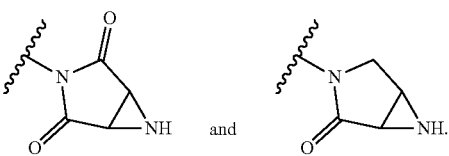
In embodiments, one of $R^{z4}$, $R^{z5}$, $R^{z6}$, $R^{20z}$, and $R^{20zz}$ is (1) optionally bonded to a nitrogen atom; and (2) selected from:
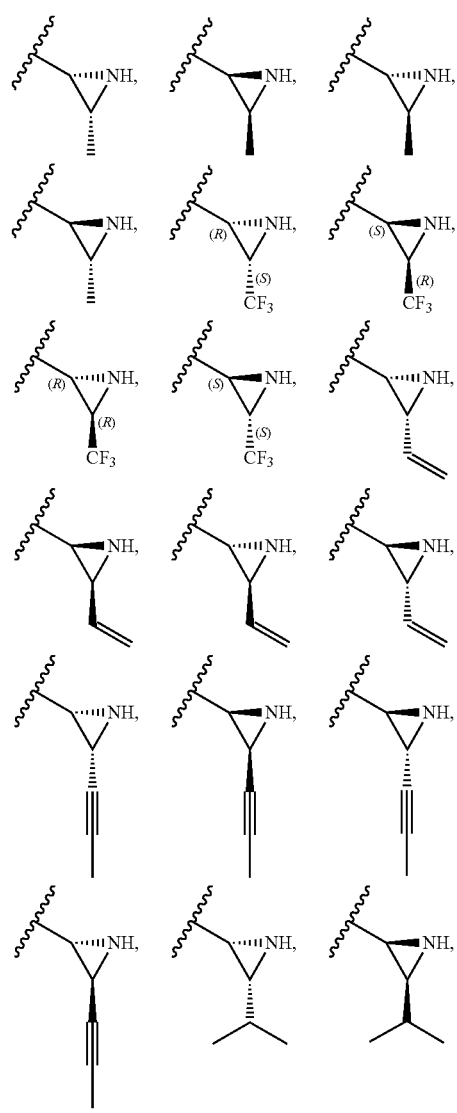
-continued
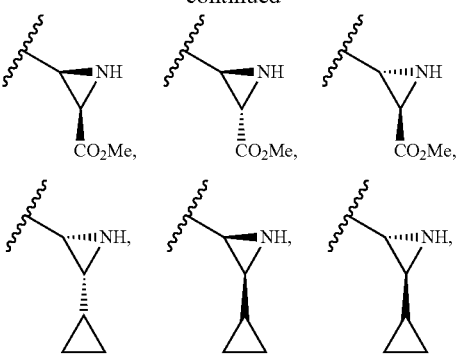
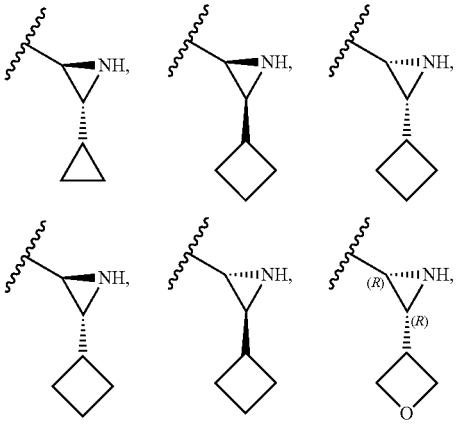
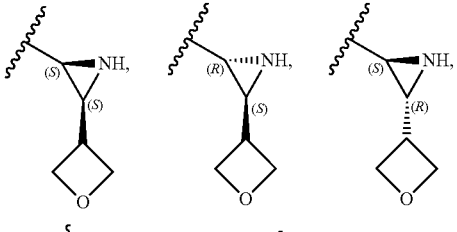
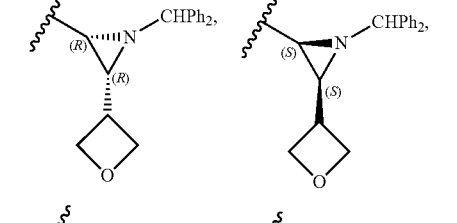
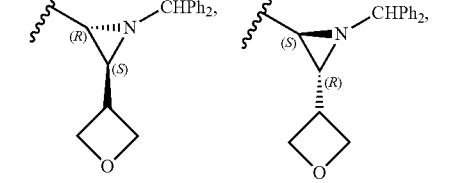
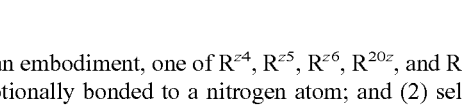
In an embodiment, one of $R^{z4}$, $R^{z5}$, $R^{z6}$, $R^{20z}$, and $R^{20zz}$ is (1) optionally bonded to a nitrogen atom; and (2) selected
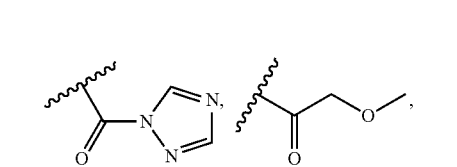

261
-continued

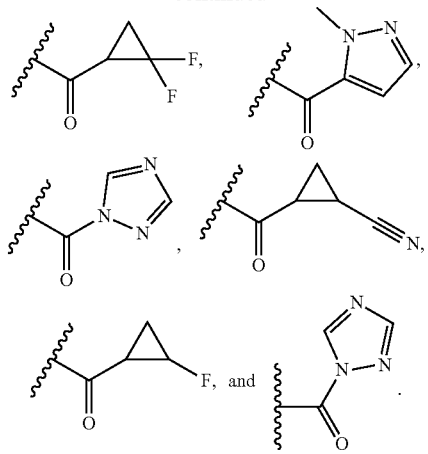

In an embodiment, one of $R^{z4}$, $R^{z5}$, $R^{z6}$, $R^{20z}$, and $R^{20zz}$ is (1) optionally bonded to a nitrogen atom; and (2) selected

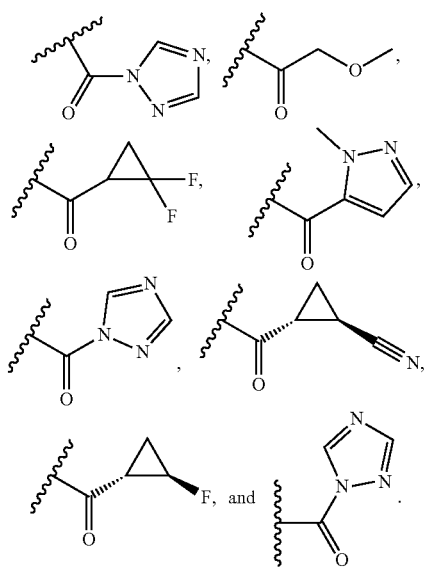

In an embodiment, one of $R^{z4}$, $R^{z5}$, $R^{z6}$, $R^{20z}$, and $R^{20zz}$ is (1) optionally bonded to a nitrogen atom; and (2) selected

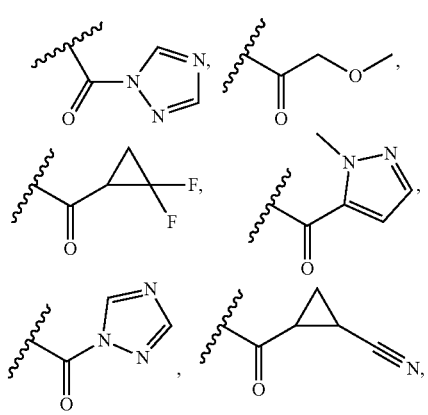

262
-continued

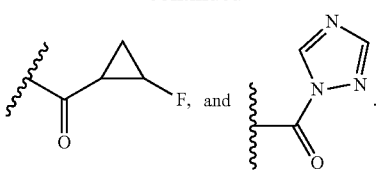

In an embodiment, one of $R^{z4}$, $R^{z5}$, $R^{z6}$, $R^{20z}$, and $R^{20zz}$ is (1) optionally bonded to a nitrogen atom; and (2) selected from

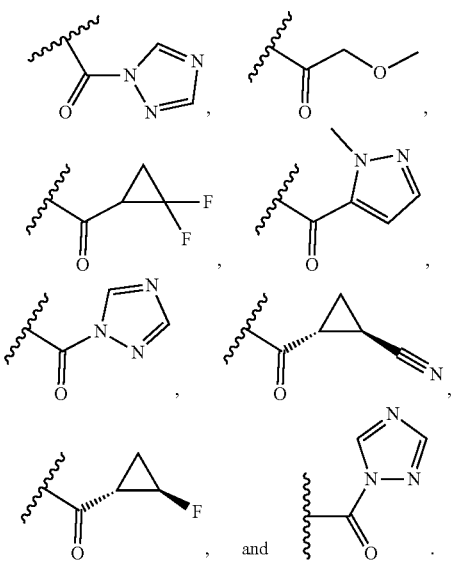

In embodiments, one of $R^{z4}$, $R^{z5}$, $R^{z6}$, $R^{20z}$, and $R^{20zz}$ is (1) optionally bonded to a nitrogen atom; and (2) selected from

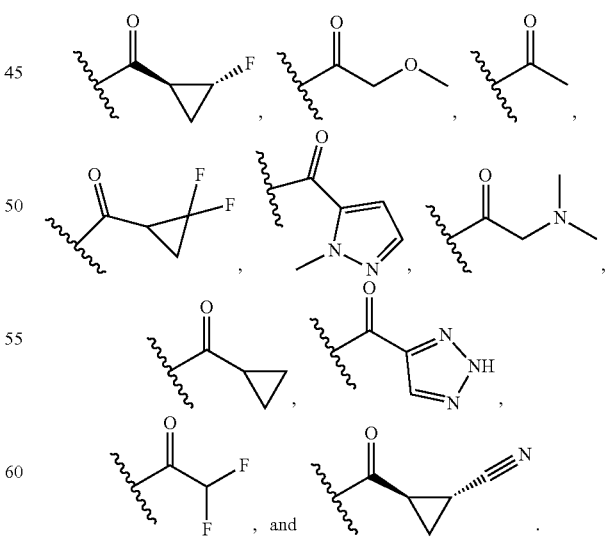

In embodiments, one of $R^{z4}$, $R^{z5}$, $R^{z6}$, $R^{20z}$, and $R^{20zz}$ is (1) optionally bonded to a nitrogen atom; and (2) selected from

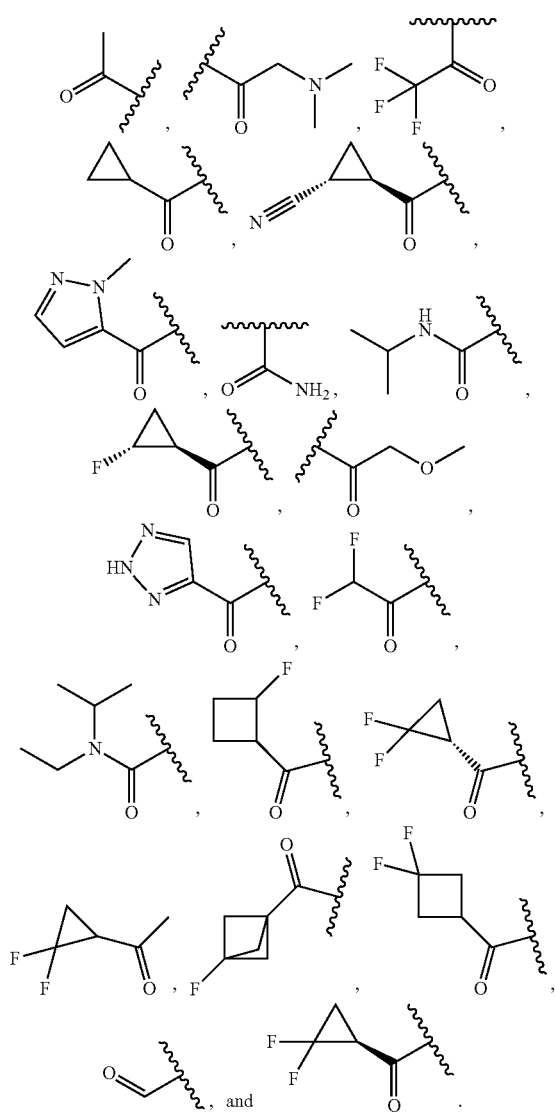
In some embodiments, one of $R^{z4}$, $R^{z5}$, $R^{z6}$, $R^{20z}$, and $R^{20zz}$ is selected from
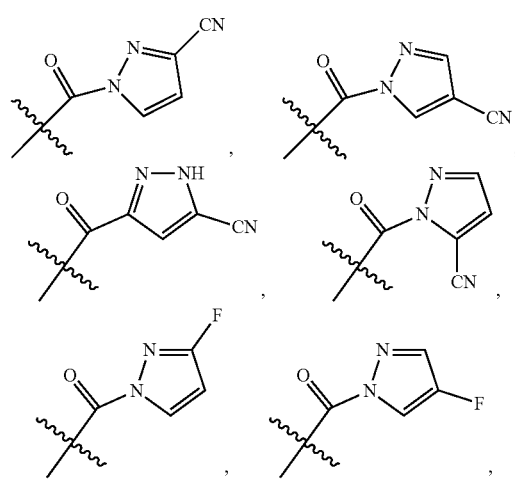
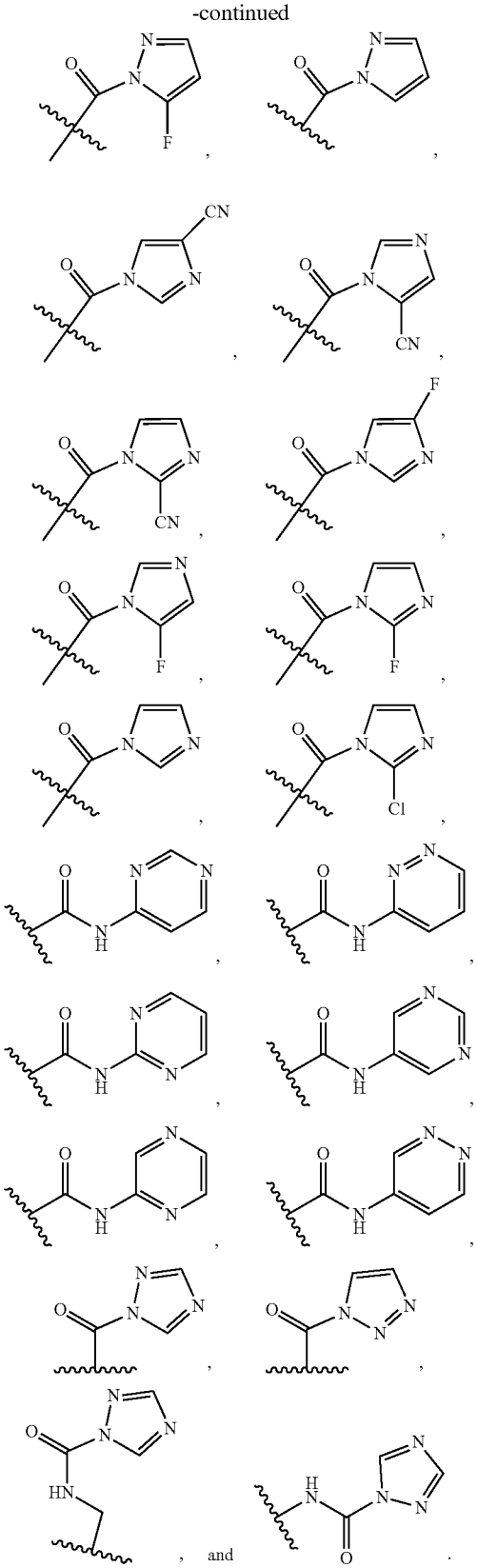
In some embodiments, one of $R^{z4}$, $R^{z5}$, $R^{z6}$, $R^{20z}$, and $R^{20zz}$ is (1) optionally bonded to a nitrogen atom; and (2) selected from

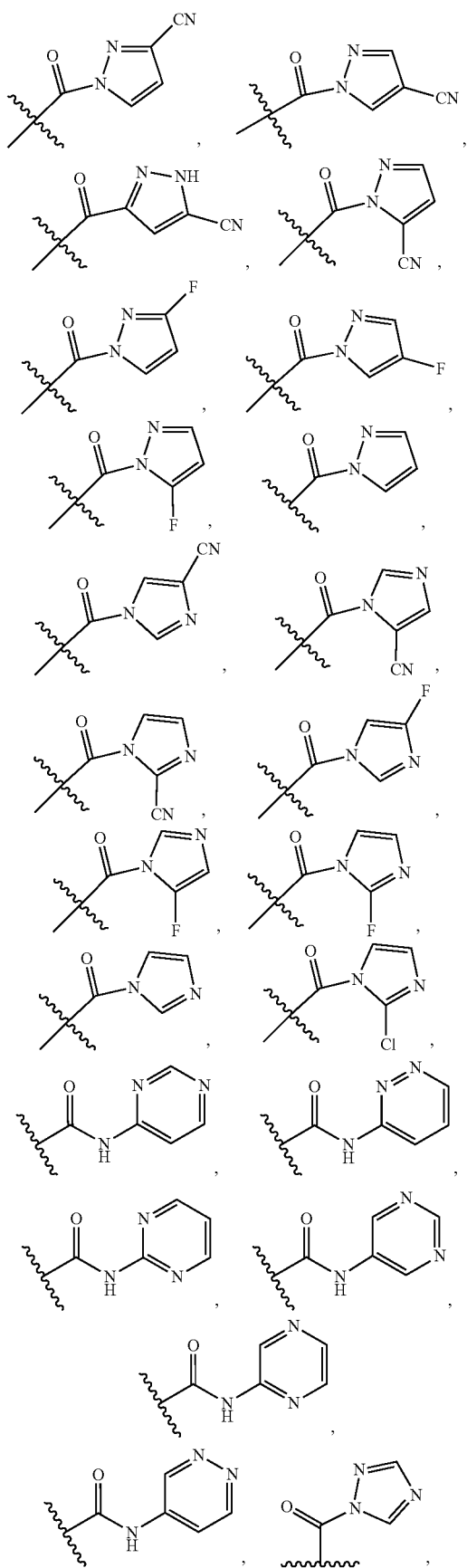
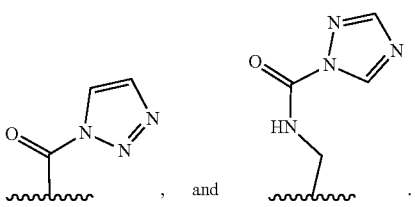
In some embodiments, one of $R^{z4}$, $R^{z5}$, $R^{z6}$, $R^{20z}$, and $R^{20zz}$ is (1) optionally bonded to a nitrogen atom; and (2) selected from
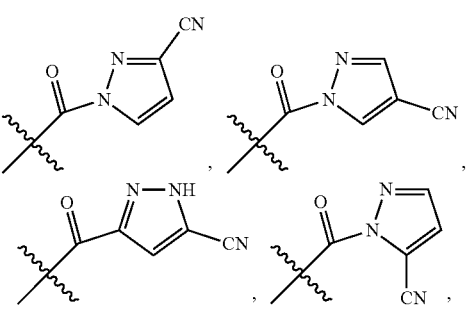
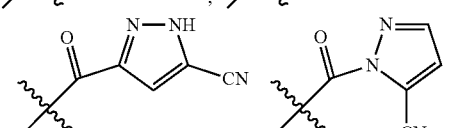
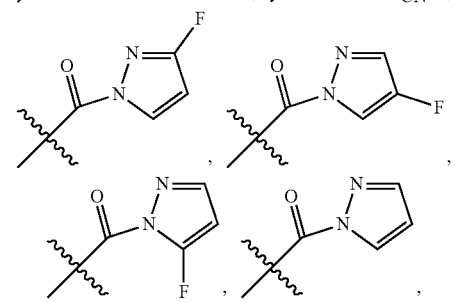
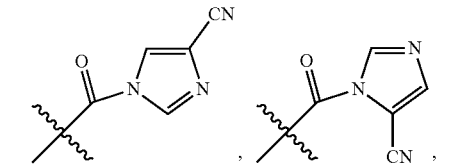
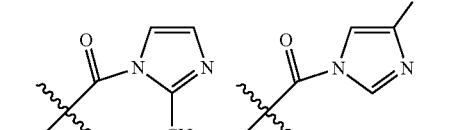
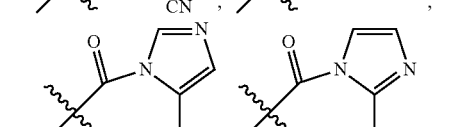
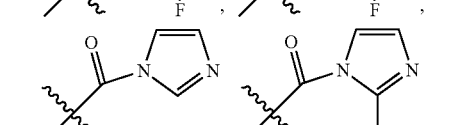
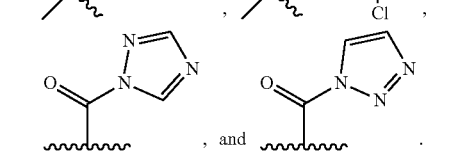

In some embodiments, one of $R^{z4}$, $R^{z5}$, $R^{z6}$, $R^{20z}$, and $R^{20zz}$ is (1) optionally bonded to a nitrogen atom; and (2) selected from
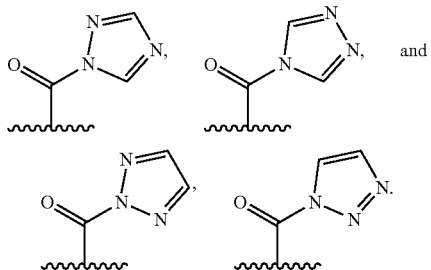
and
In embodiments, $R^{12}$ is independently selected from:
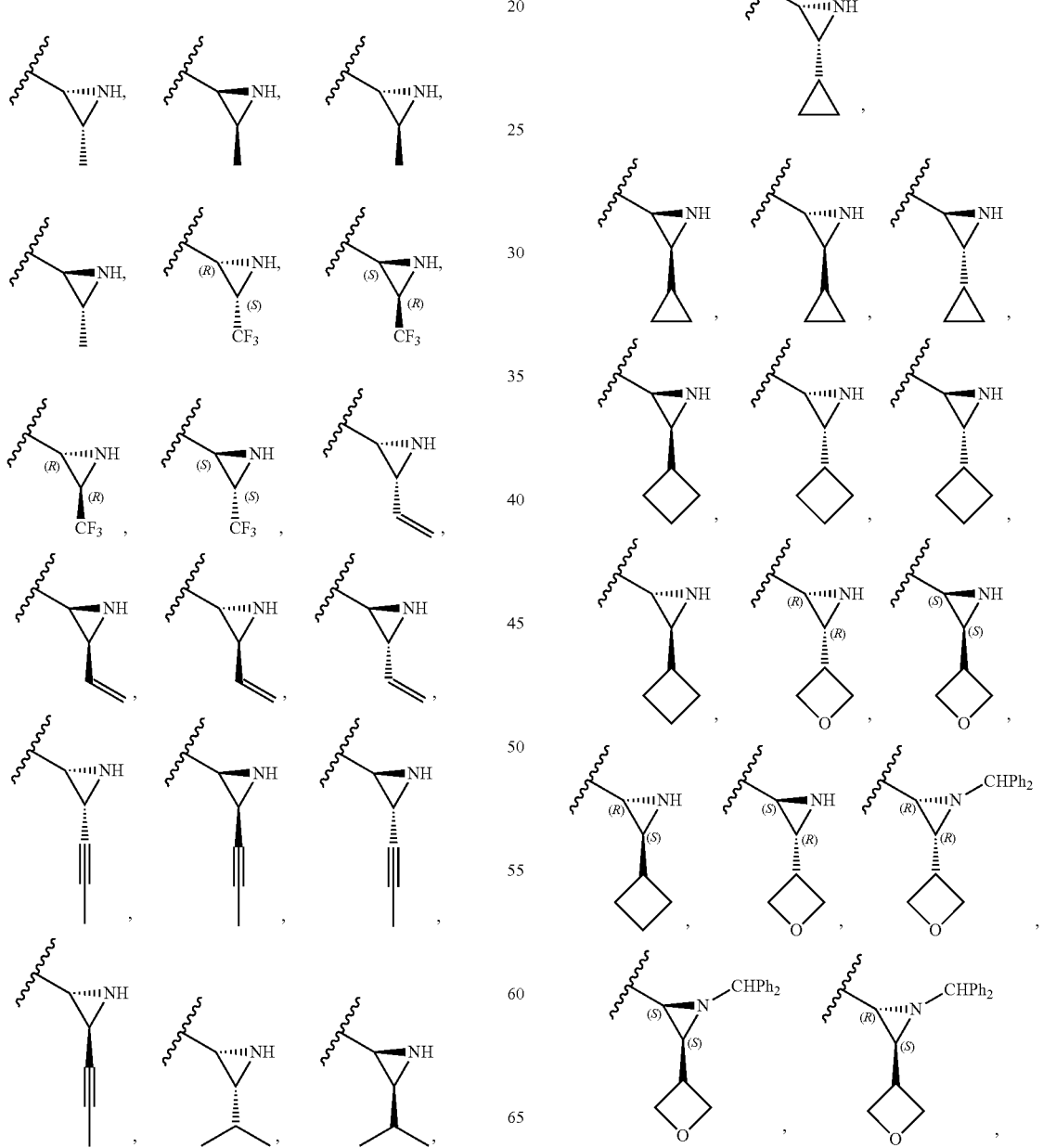
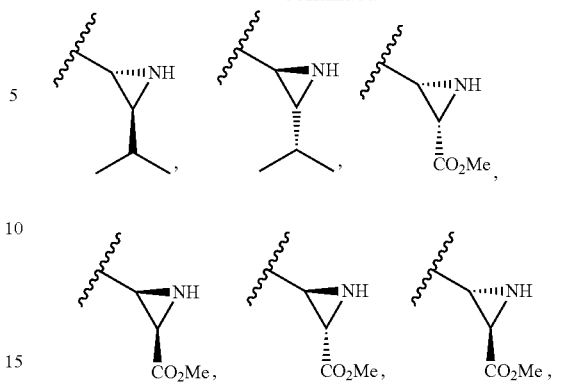

-continued
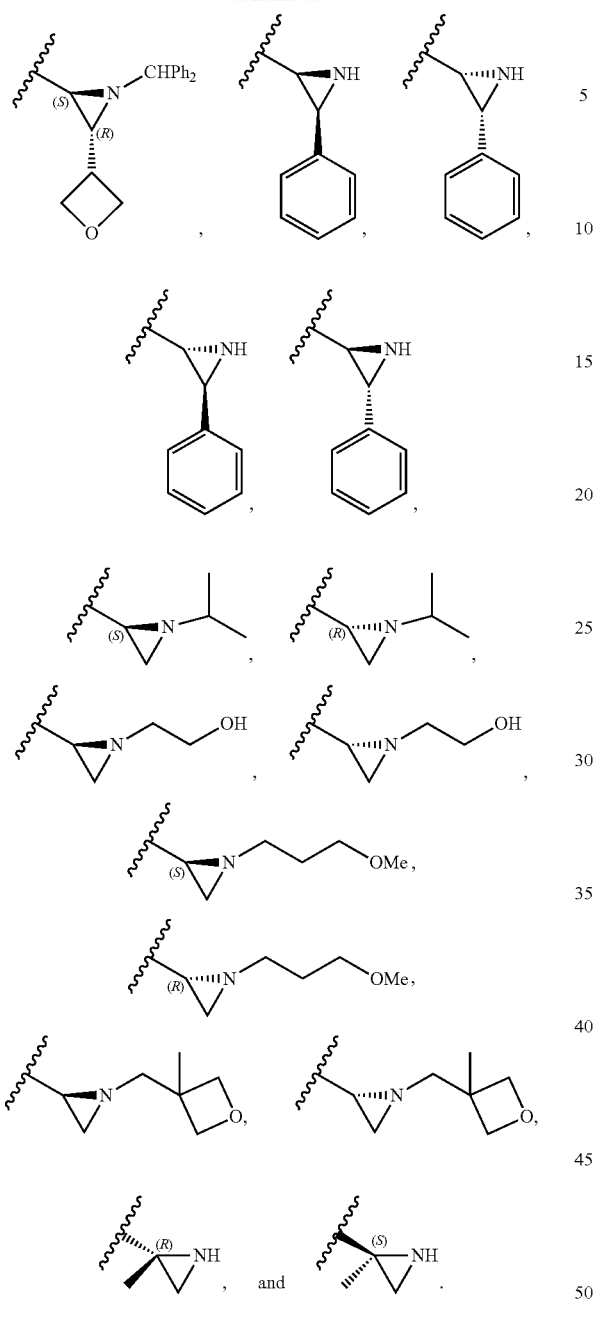
In embodiments, R[15] is independently selected from:
-continued
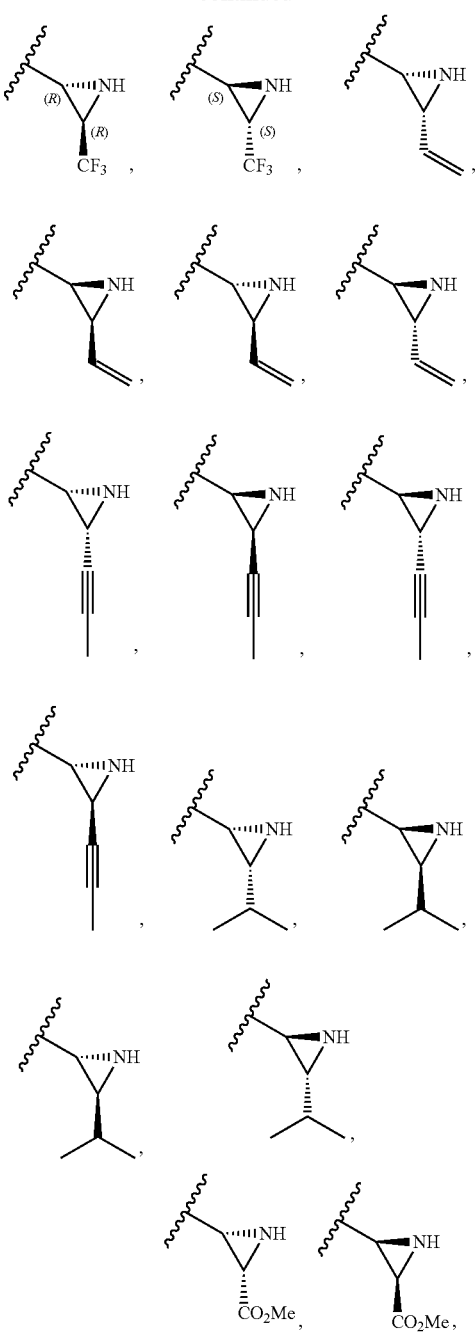

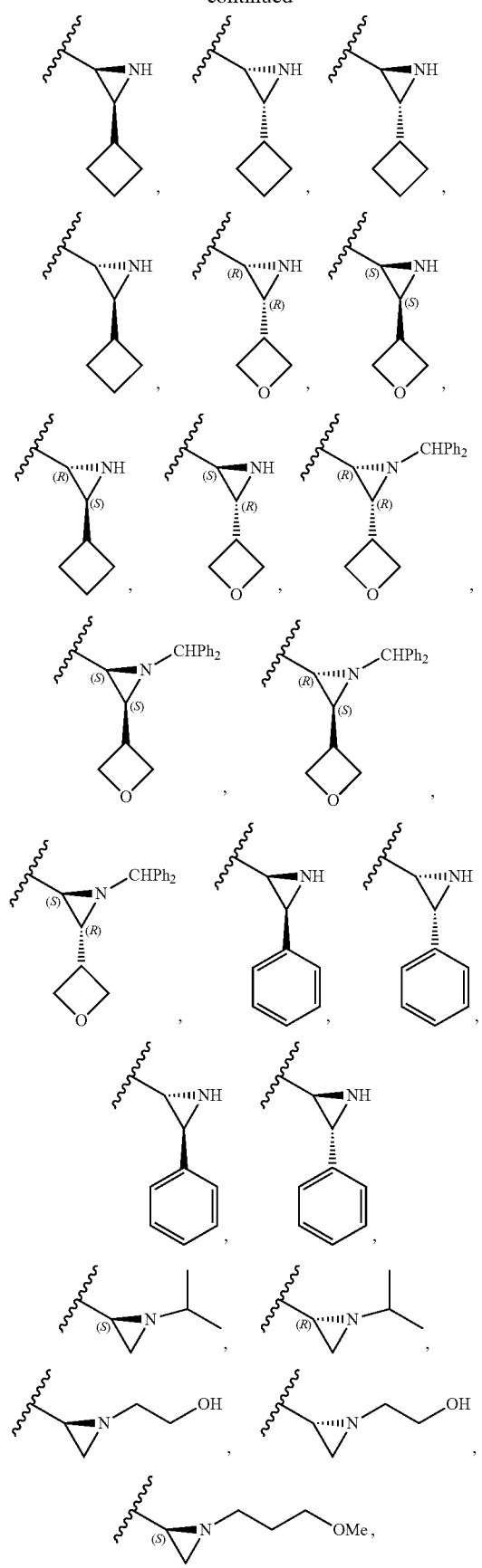
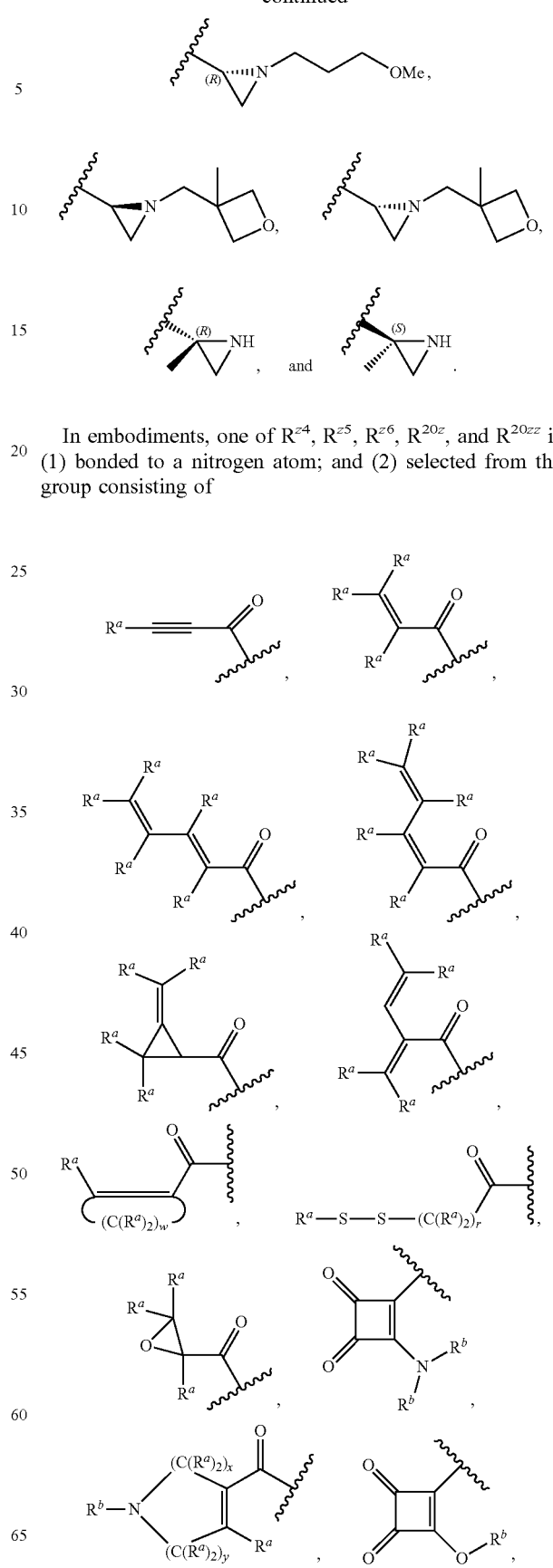
In embodiments, one of $R^{z4}$, $R^{z5}$, $R^{z6}$, $R^{20z}$, and $R^{20zz}$ is (1) bonded to a nitrogen atom; and (2) selected from the group consisting of -continued

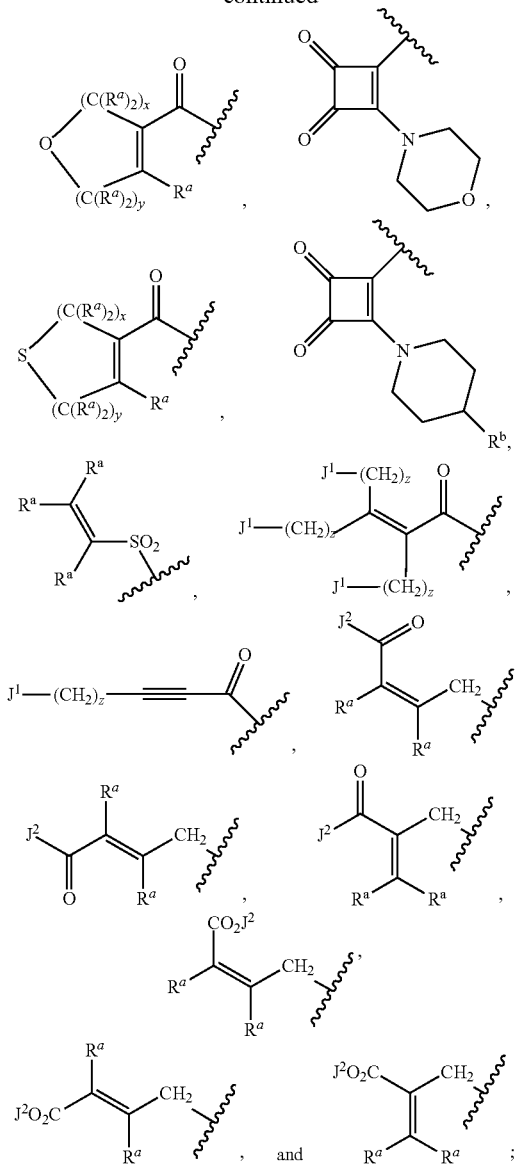

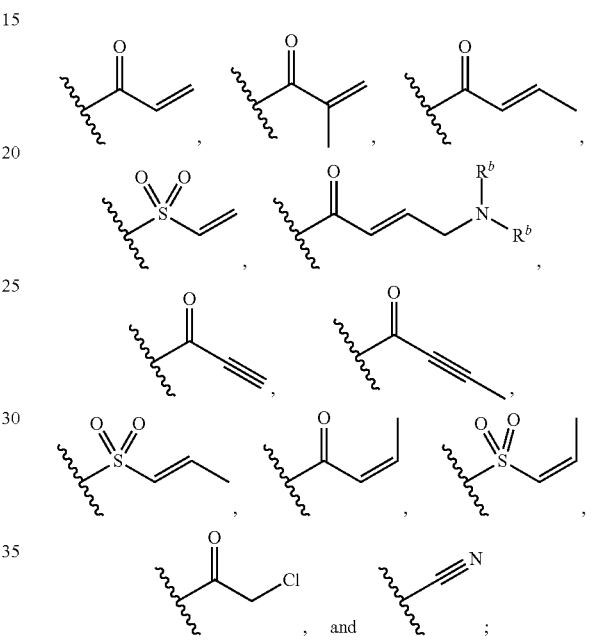

where each $R^a$ is independently hydrogen, $C_{1-6}$alkyl, carboxy, $C_{1-6}$carboalkoxy, phenyl, $C_{2-7}$carboalkyl, $R^c$—$C(R^b)_2)_z$-, $R^c$—$(C(R^b)_2)_w$-M-$(C(R^b)_2)_r$-, $(R^d)(R^e)$CH-M-$(C(R^b)_2)_r$-, or Het-J$^3$-$(C(R^b)_2)_r$-; each $R^b$ is independently hydrogen, $C_{1-6}$alkyl, $C_{2-6}$alkenyl, $C_{2-6}$alkynyl, $C_{3-6}$cycloalkyl, $C_{2-7}$carboalkyl, $C_{2-7}$carboxyalkyl, phenyl, or phenyl optionally substituted with one or more halogen, $C_{1-6}$alkoxy, trifluoromethyl, amino, $C_{1-3}$alkylamino, $C_{2-6}$dialkylamino, nitro, azido, halomethyl, $C_{2-7}$alkoxymethyl, $C_{2-7}$alkanoyloxymethyl, $C_{1-6}$alkylthio, hydroxy, carboxyl, $C_{2-7}$carboalkoxy, phenoxy, phenyl, thiophenoxy, benzoyl, benzyl, phenylamino, benzylamino, $C_{1-6}$alkanoylamino, or $C_{1-6}$alkyl; each $R^c$ is independently —$NR^bR^b$ or —$OR^b$; $R^d$ and $R^e$ are each, independently, —$(C(R^b)_2)_r$—$NR^bR^b$, or —$(C(R^b)_2)_r$—$OR^b$; each $J^1$ is independently hydrogen, chlorine, fluorine, or bromine; $J^2$ is $C_{1-6}$alkyl or hydrogen; each M is independently —$N(R^b)$—, —O—, —$N[(C(R^b)_2)_w$—$NR^bR^b]$—, or —$N[(C(R^b)_2)_w$—$OR^b]$—; each $J^3$ is independently —$N(R^b)$—, —O—, or a bond; each Het is independently a heterocycle, optionally mono- or di-substituted on carbon or nitrogen with $R^b$ and optionally mono-substituted on carbon with —$CH_2OR^b$; wherein the heterocycle is selected from the group consisting of morpholine, thiomorpholine, thiomorpholine S-oxide, thiomorpholine S,S-dioxide, piperidine, pyrrolidine, aziridine, imidazole, 1,2,3-triazole, 1,2,4-triazole, tetrazole, piperazine, tetrahydrofuran, and tetrahydropyran; each r is independently 1-4; each w is independently 2-4; x is 0-1; y is 0-4, and each z is independently 1-6; wherein the sum of x+y is 2-4.

In embodiments, one of $R^{z4}$, $R^{z5}$, $R^{z6}$, $R^{20z}$, and $R^{20zz}$ is (1) bonded to a nitrogen atom; and (2) selected from the group consisting of

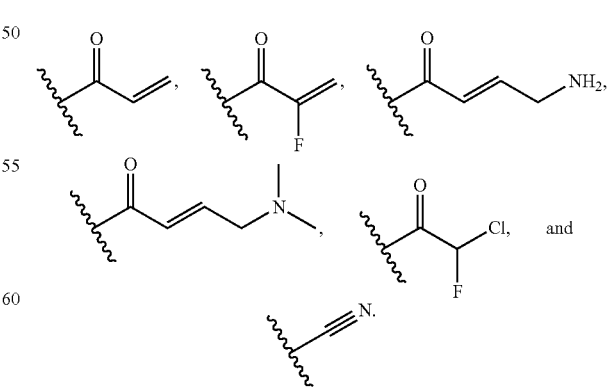

where each $R^b$ is independently selected from the group consisting of hydrogen, hydroxyl, $C_1$-$C_6$ alkoxy, and $C_1$-$C_6$ alkyl, or two $R^b$ optionally join to form heterocycle having 3-12 ring atoms or $C_3$-$C_6$ cycloalkyl.

In embodiments, one of $R^{z4}$, $R^{z5}$, $R^{z6}$, $R^{20z}$, and $R^{20zz}$ is (1) bonded to a nitrogen atom; and (2) selected from the group consisting of In embodiments, one of $R^{z4}$, $R^{z5}$, $R^{z6}$, $R^{20z}$, and $R^{20zz}$ is (1) bonded to a nitrogen atom; and (2) selected from

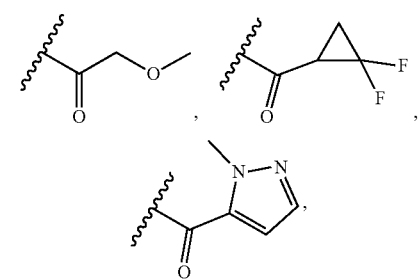
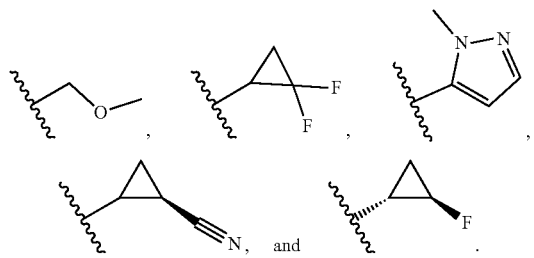
In embodiments, one of $R^{z4}$, $R^{z5}$, $R^{z6}$, $R^{20z}$, and $R^{20zz}$ is (1) bonded to a nitrogen atom; and (2) selected from
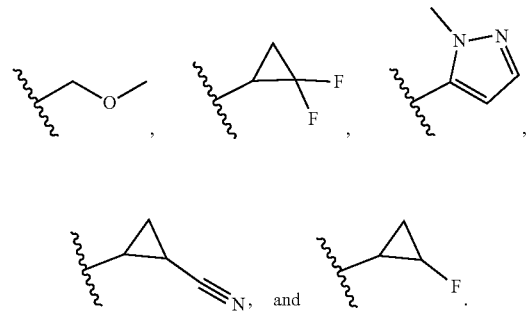
In embodiments, one of $R^{z4}$, $R^{z5}$, $R^{z6}$, $R^{20z}$, and $R^{20zz}$ is (1) bonded to a nitrogen atom; and (2) selected from
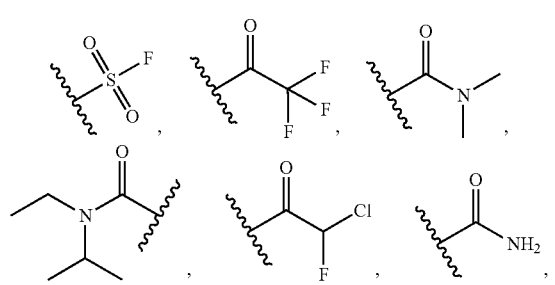
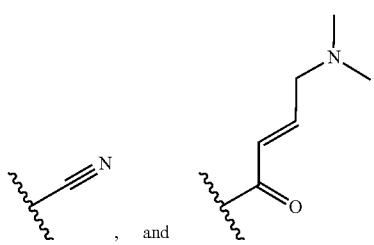
In embodiments, one of $R^{z4}$, $R^{z5}$, $R^{z6}$, $R^{20z}$, and $R^{20zz}$ is (1) bonded to a nitrogen atom; and (2) selected from

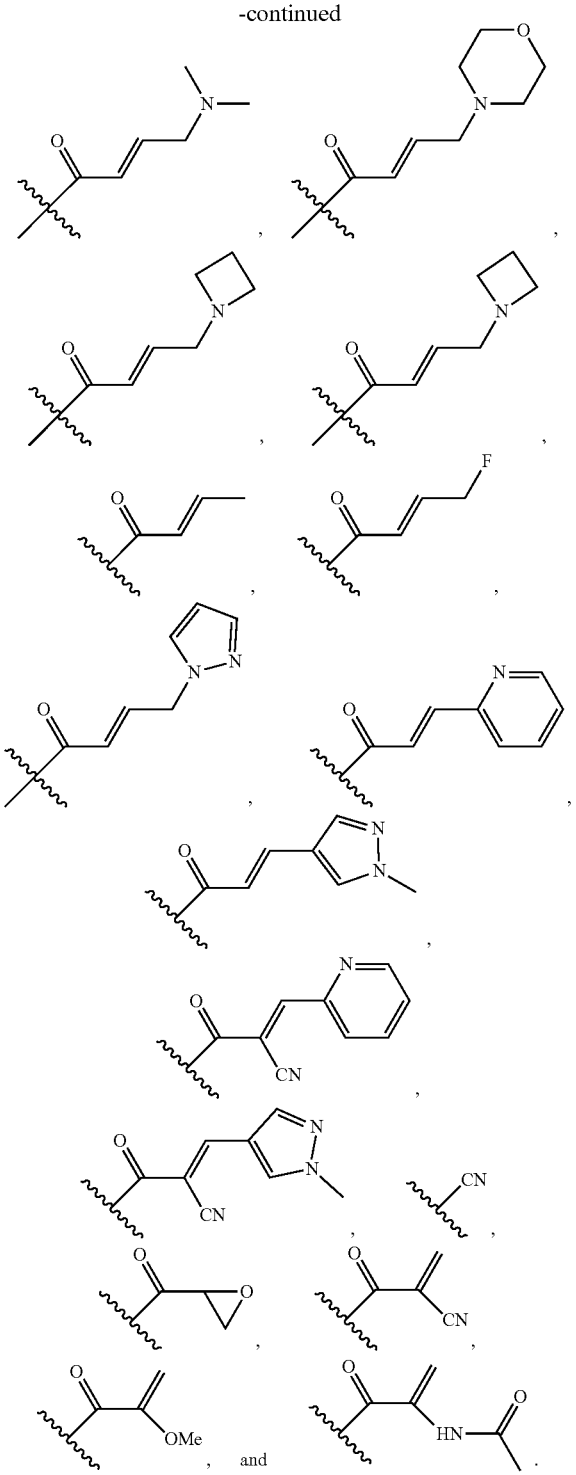
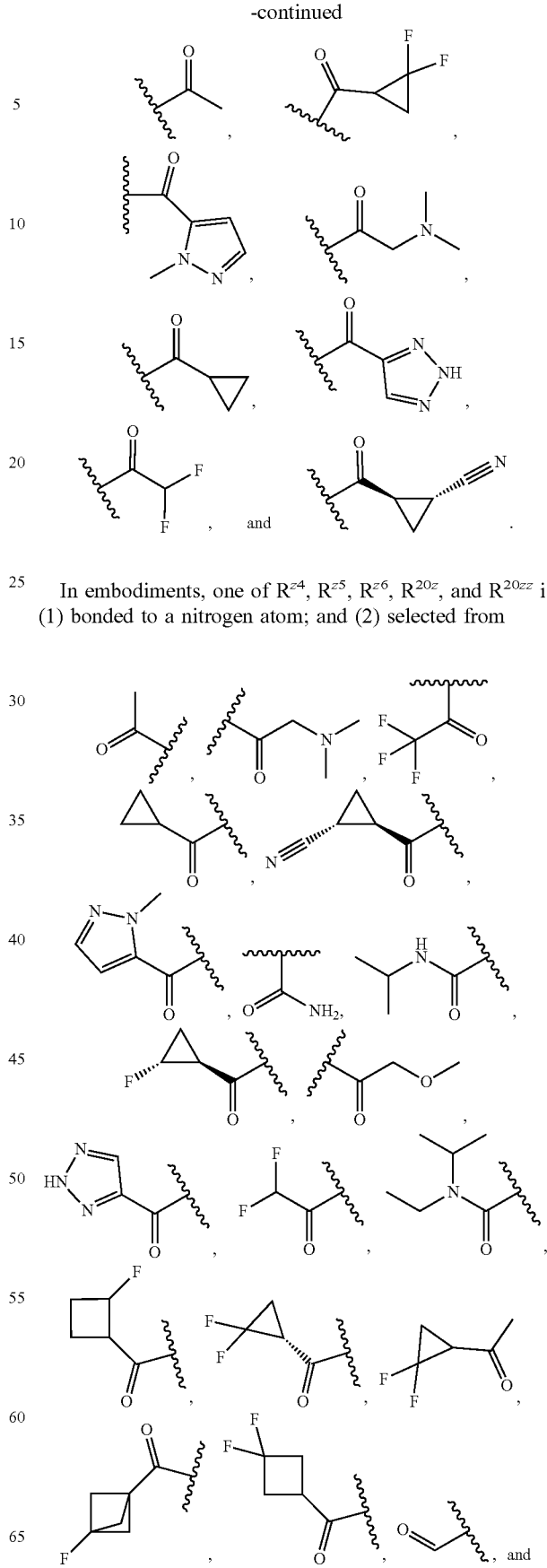
In embodiments, one of $R^{z4}$, $R^{z5}$, $R^{z6}$, $R^{20z}$, and $R^{20zz}$ is (1) bonded to a nitrogen atom; and (2) selected from
In embodiments, one of $R^{z4}$, $R^{z5}$, $R^{z6}$, $R^{20z}$, and $R^{20zz}$ is (1) bonded to a nitrogen atom; and (2) selected from

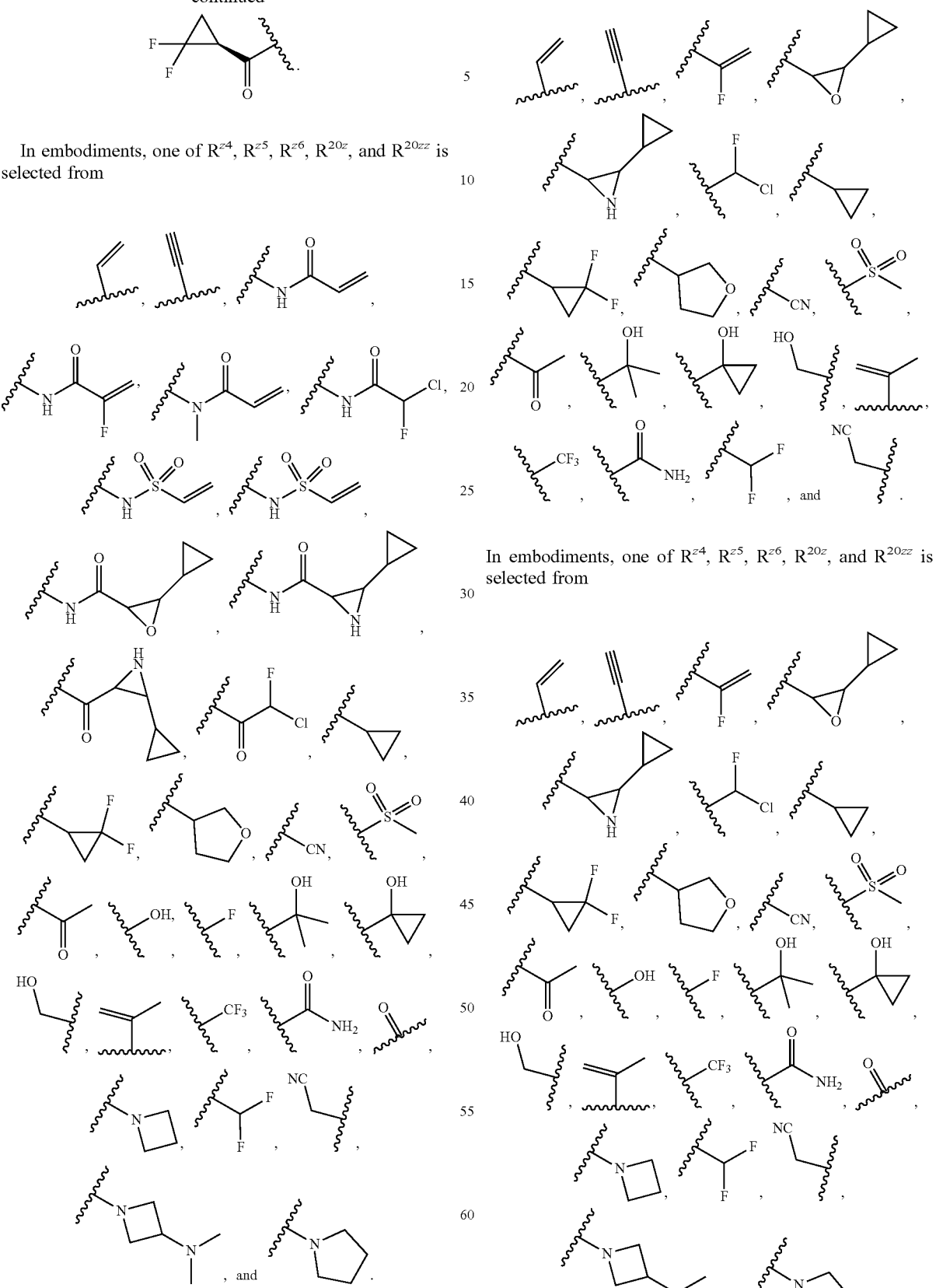
In embodiments, one of $R^{z4}$, $R^{z5}$, $R^{z6}$, $R^{20z}$, and $R^{20zz}$ is selected from
In embodiments, one of $R^{z4}$, $R^{z5}$, $R^{z6}$, $R^{20z}$, and $R^{20zz}$ is selected from
In embodiments, one of $R^{z4}$, $R^{z5}$, $R^{z6}$, $R^{20z}$, and $R^{20zz}$ is (1) bonded to a nitrogen atom; and (2) selected from In embodiments, one of $R^{z4}$, $R^{z5}$, $R^{z6}$, $R^{20z}$, and $R^{20zz}$ is

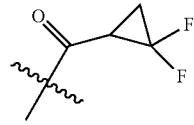

and is bonded to a nitrogen atom. In embodiments, one of $R^{z4}$, $R^{z5}$, $R^{z6}$, $R^{20z}$, and $R^{20zz}$ is

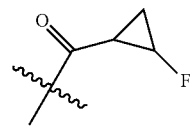 [SMILES: *C(=O)C1CC1F]

and is bonded to a nitrogen atom. In embodiments, one of $R^{z4}$, $R^{z5}$, $R^{z6}$, $R^{20z}$, and $R^{20zz}$ is

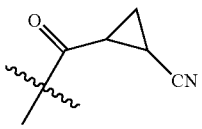 [SMILES: *C(=O)C1CC1C#N]

and is bonded to a nitrogen atom. In embodiments, one of $R^{z4}$, $R^{z5}$, $R^{z6}$, $R^{20z}$, and $R^{20zz}$ is

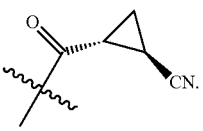 [SMILES: *C(=O)[C@@H]1C[C@H]1C#N]

In embodiments, one of $R^{z4}$, $R^{z5}$, $R^{z6}$, $R^{20z}$, and $R^{20zz}$ is

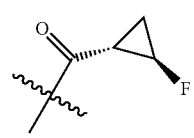 [SMILES: *C(=O)[C@@H]1C[C@H]1F]

and is bonded to a nitrogen atom.

In embodiments, one of $R^{z4}$, $R^{z5}$, $R^{z6}$, $R^{20z}$, and $R^{20zz}$ is (1) bonded to a nitrogen atom; and (2) selected from:

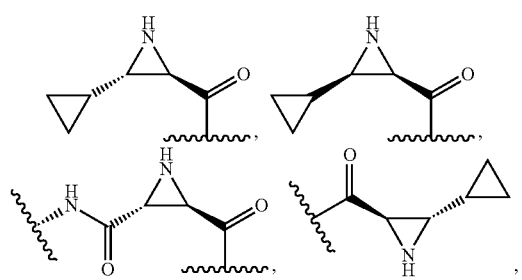

-continued

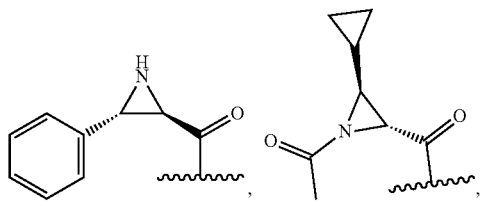

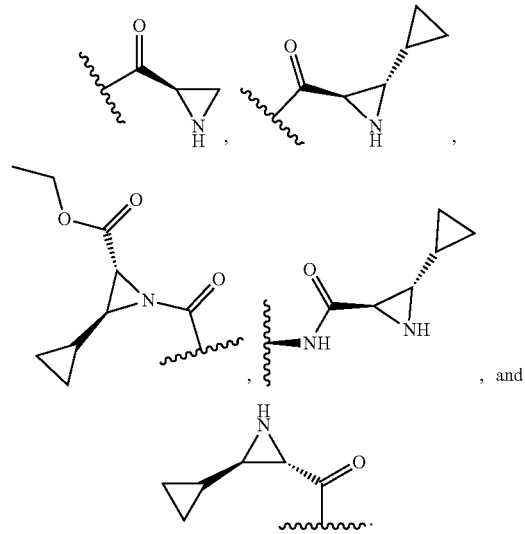

In embodiments, one of $R^{z4}$, $R^{z5}$, $R^{z6}$, $R^{20z}$, and $R^{20zz}$ is selected from:

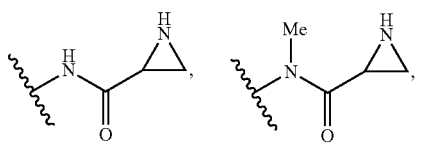

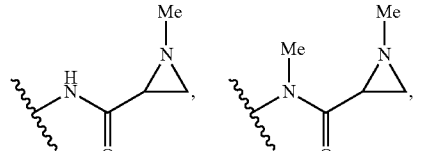

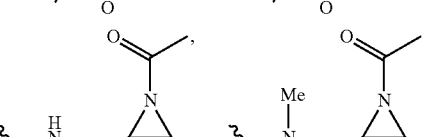

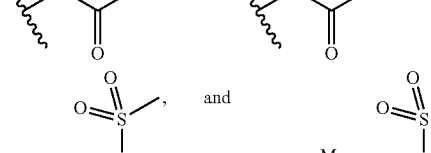

In embodiments, one of $R^{z4}$, $R^{z5}$, $R^{z6}$, $R^{20z}$, and $R^{20zz}$ is selected from:

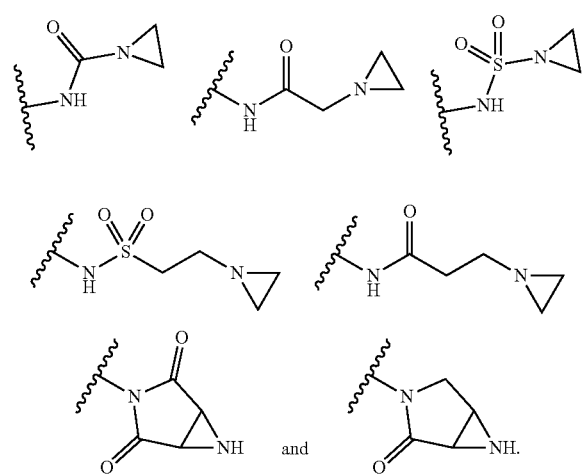
In embodiments, one of $R^{z4}$, $R^{z5}$, $R^{z6}$, $R^{20z}$, and $R^{20zz}$ is (1) bonded to a nitrogen atom; and (2) selected from:
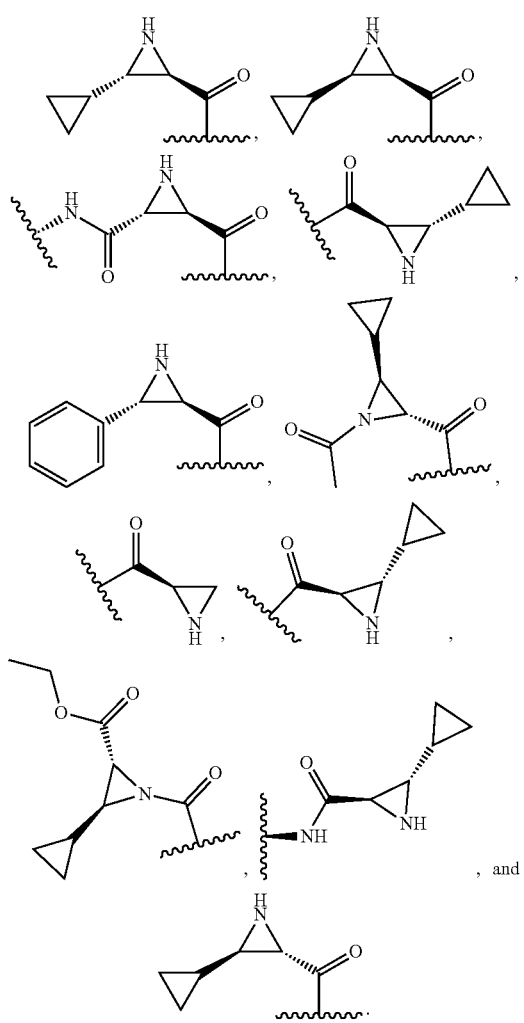
In embodiments, one of $R^{z4}$, $R^{z5}$, $R^{z6}$, $R^{20z}$, and $R^{20zz}$ is selected from:
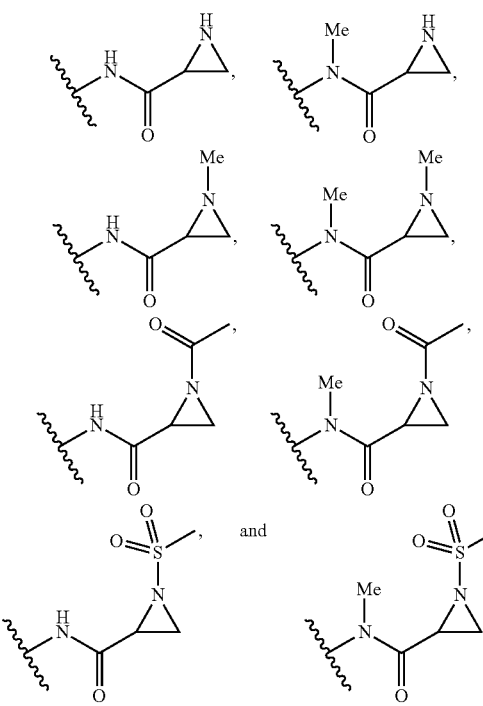
In embodiments, one of $R^{z4}$, $R^{z5}$, $R^{z6}$, $R^{20z}$, and $R^{20zz}$ is (1) bonded to a nitrogen atom; and (2) selected from:
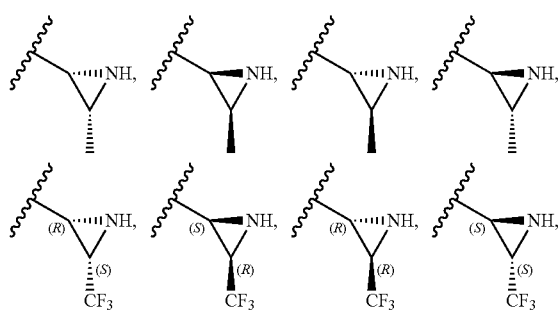

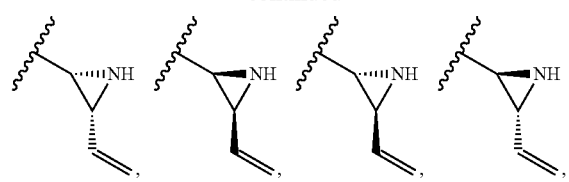
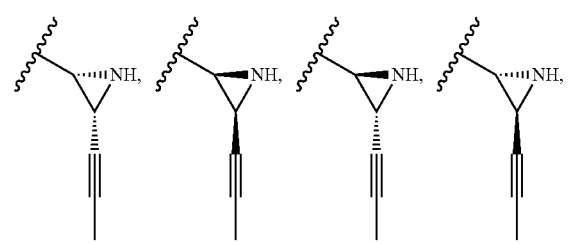
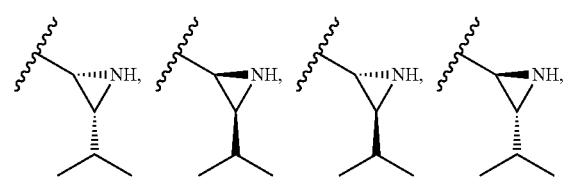
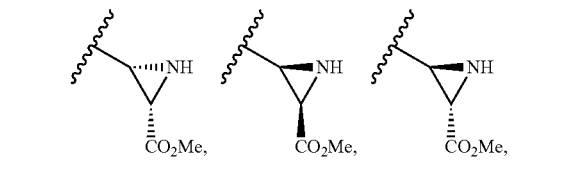
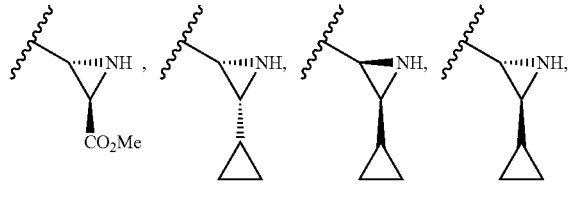
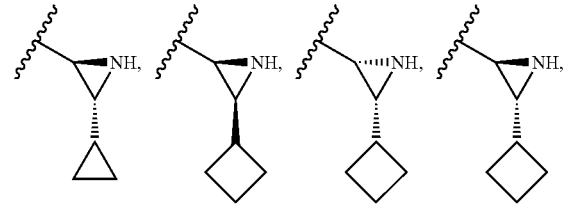
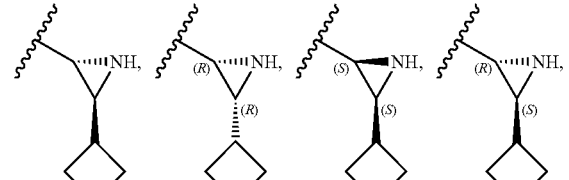
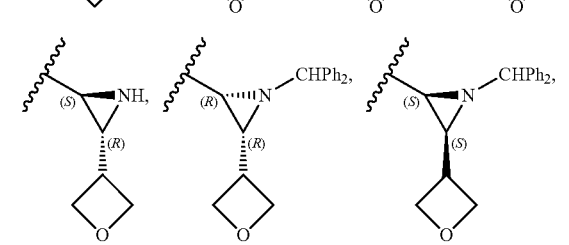
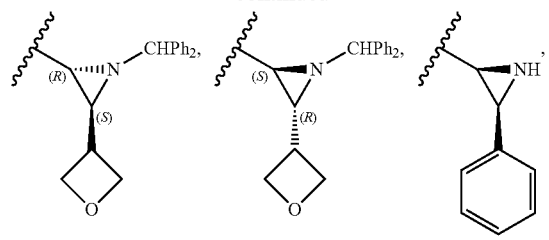
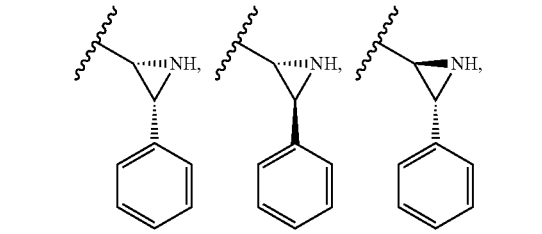
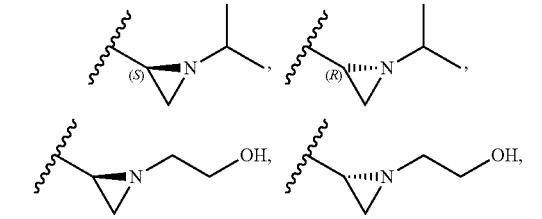
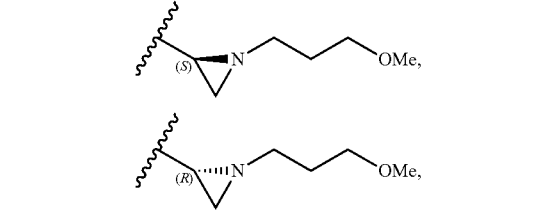
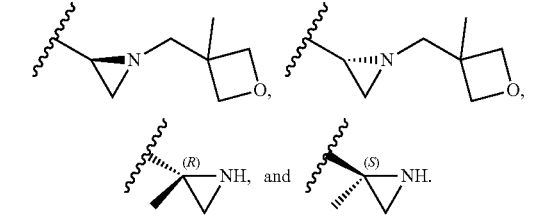
In an embodiment, one of $R^{z4}$, $R^{z5}$, $R^{z6}$, $R^{20z}$, and $R^{20zz}$ is (1) bonded to a nitrogen atom; and (2) selected from
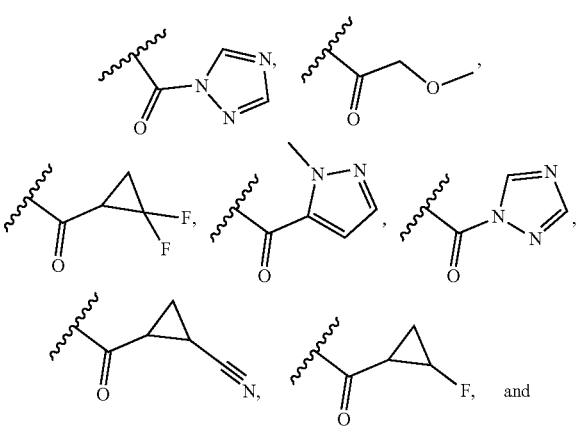

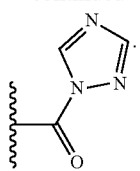

In an embodiment, one of $R^{z4}$, $R^{z5}$, $R^{z6}$, $R^{20z}$, and $R^{20zz}$ is (1) bonded to a nitrogen atom; and (2) selected from

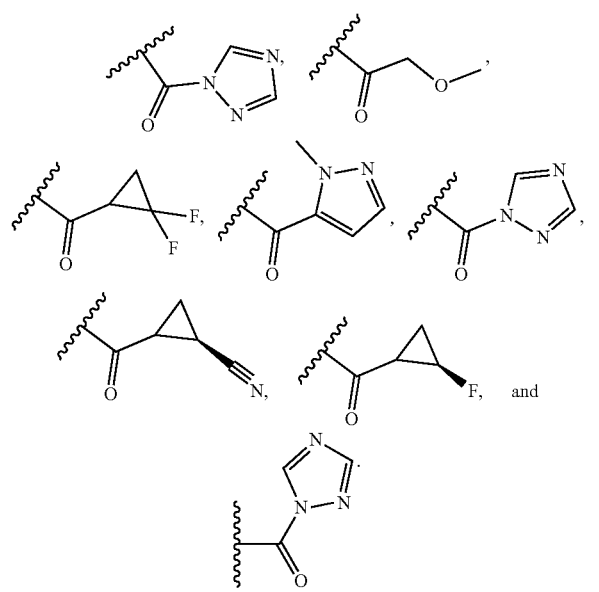

In an embodiment, one of $R^{z4}$, $R^{z5}$, $R^{z6}$, $R^{20z}$, and $R^{20zz}$ is (1) bonded to a nitrogen atom; and (2) selected from

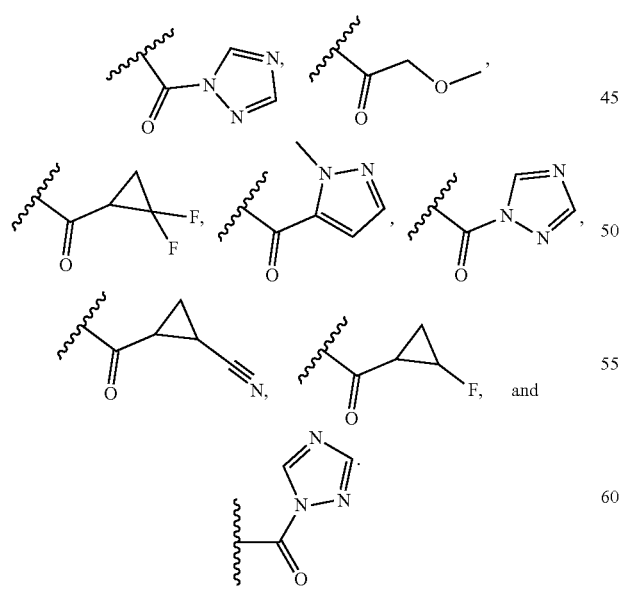

In an embodiment, one of $R^{z4}$, $R^{z5}$, $R^{z6}$, $R^{20z}$, and $R^{20zz}$ is (1) bonded to a nitrogen atom; and (2) selected from

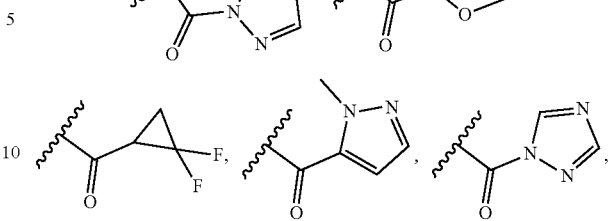

In embodiments, one of $R^{z4}$, $R^{z5}$, $R^{z6}$, $R^{20z}$, and $R^{20zz}$ is (1) bonded to a nitrogen atom; and (2) selected from

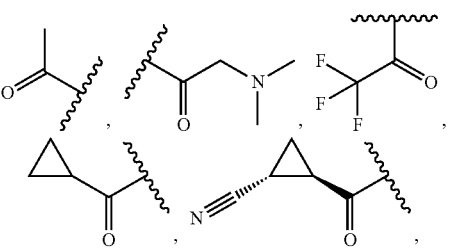

In embodiments, one of $R^{z4}$, $R^{z5}$, $R^{z6}$, $R^{20z}$, and $R^{20zz}$ is (1) bonded to a nitrogen atom; and (2) selected from -continued
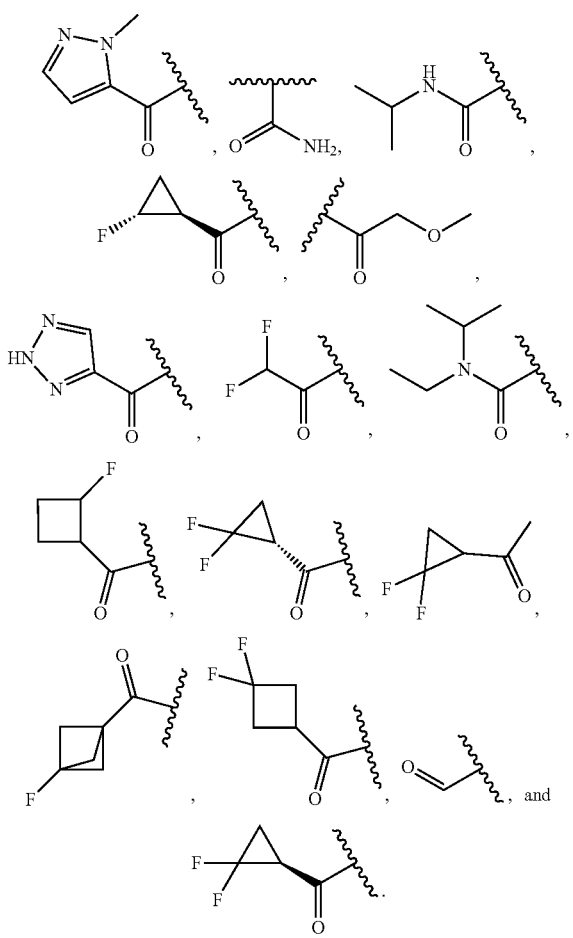
In some embodiments, one of $R^{z4}$, $R^{z5}$, $R^{z6}$, $R^{20z}$, and $R^{20zz}$ is selected from
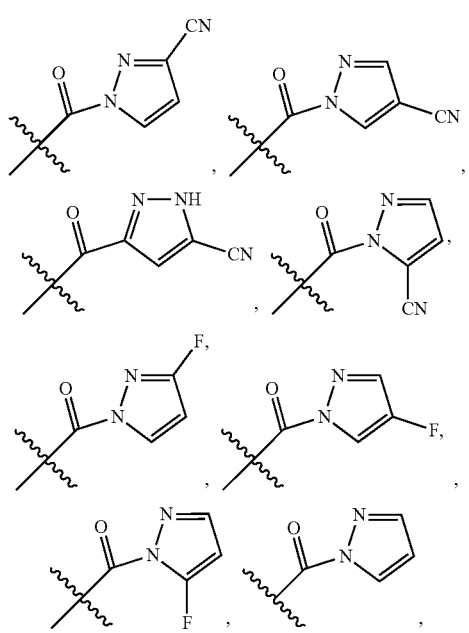
-continued
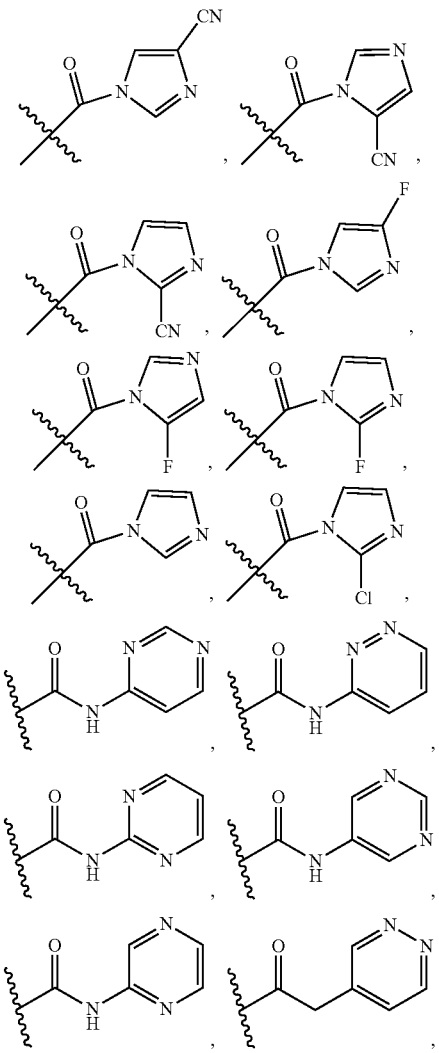
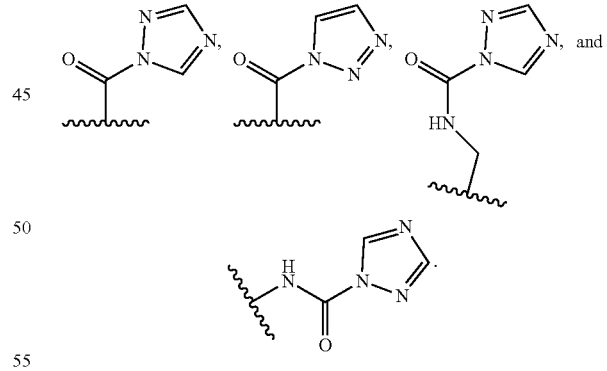
In some embodiments, one of $R^{z4}$, $R^{z5}$, $R^{z6}$, $R^{20z}$, and $R^{20zz}$ is (1) bonded to a nitrogen atom; and (2) selected from
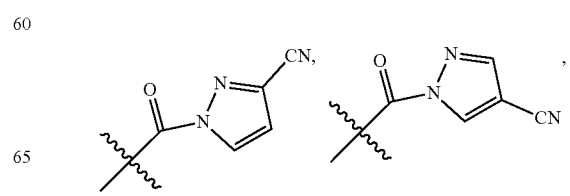

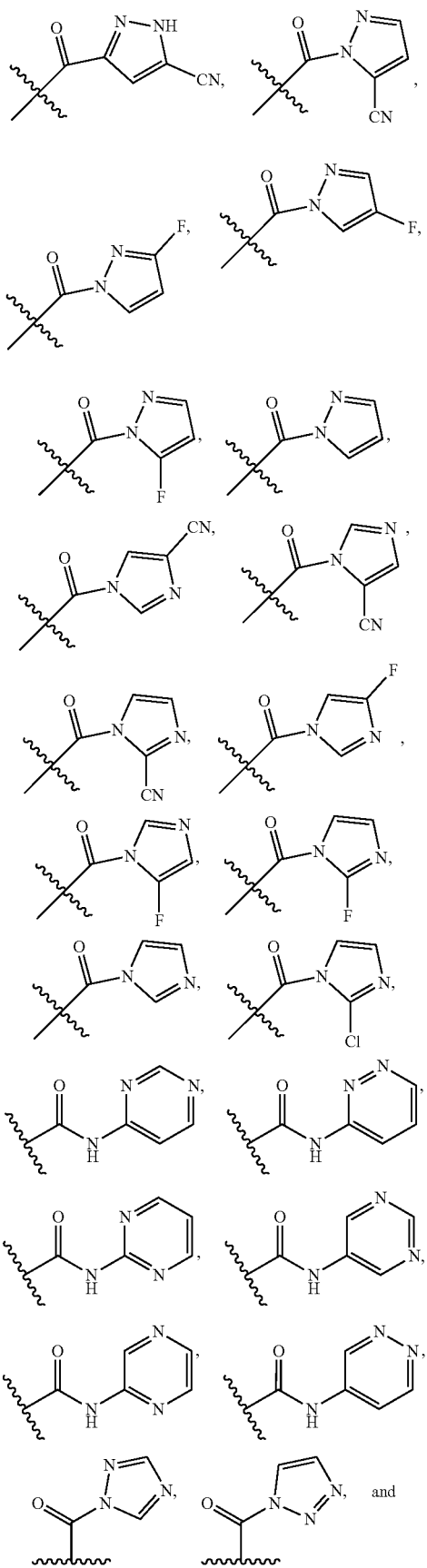
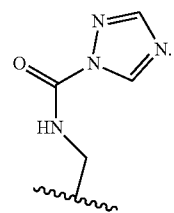
In some embodiments, one of $R^{z4}$, $R^{z5}$, $R^{z6}$, $R^{20z}$, and $R^{20zz}$ is (1) bonded to a nitrogen atom; and (2) selected from
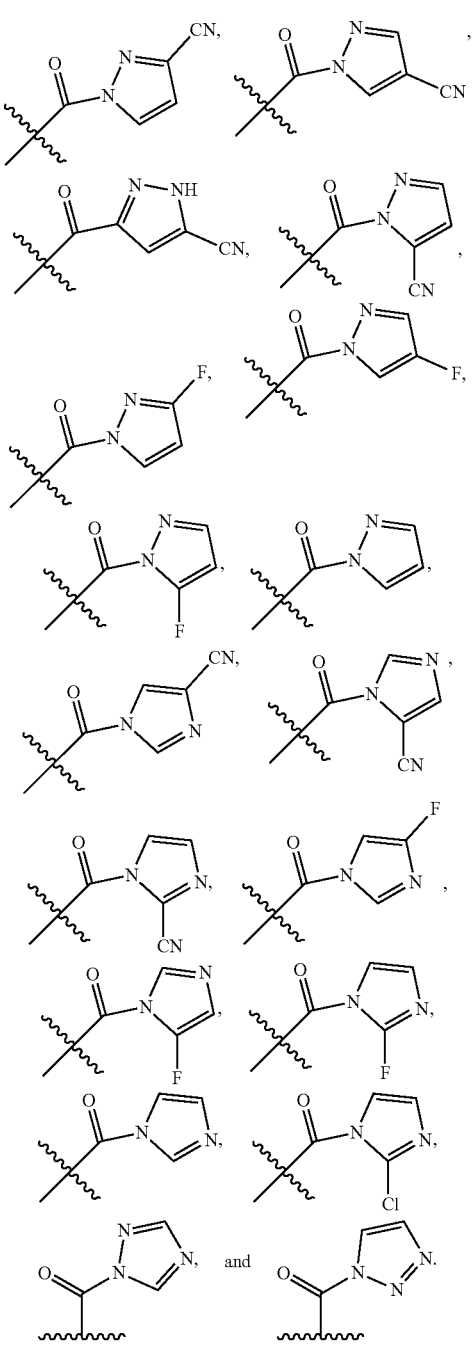

In some embodiments, one of $R^{z4}$, $R^{z5}$, $R^{z6}$, $R^{20z}$, and $R^{20zz}$ is (1) bonded to a nitrogen atom; and (2) selected from

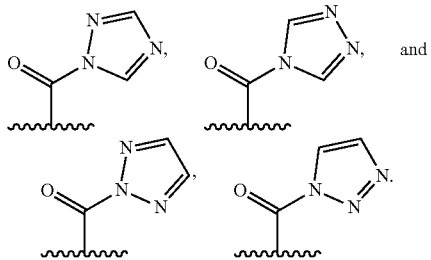

and

In embodiments, $R^{z9}$ is independently hydrogen. In embodiments, $R^{z9}$ is independently halogen. In embodiments, $R^{z9}$ is independently —CN. In embodiments, $R^{z9}$ is independently —OR$^{12}$. In embodiments, $R^{z9}$ is independently —SR$^{12}$. In embodiments, $R^{z9}$ is independently —N(R$^{12}$)(R$^{13}$). In embodiments, $R^{z9}$ is independently —C(O)R$^{12}$. In embodiments, $R^{z9}$ is independently —OC(O)N(R$^{12}$)(R$^{13}$). In embodiments, $R^{z9}$ is independently —N(R$^{14}$)C(O)N(R$^{12}$)(R$^{13}$). In embodiments, $R^{z9}$ is independently —N(R$^{14}$)C(O)R$^{15}$. In embodiments, $R^{z9}$ is independently —N(R$^{14}$)S(O)$_2$R$^{15}$. In embodiments, $R^{z9}$ is independently —C(O)R$^{12}$. In embodiments, $R^{z9}$ is independently —S(O)R$^{15}$. In embodiments, $R^{z9}$ is independently —OC(O)R$^{15}$. In embodiments, $R^{z9}$ is independently —C(O)N(R$^{12}$)(R$^{13}$). In embodiments, $R^{z9}$ is independently —C(O)C(O)N(R$^{12}$)(R$^{13}$). In embodiments, $R^{z9}$ is independently —N(R$^{14}$)C(O)R$^{12}$. In embodiments, $R^{z9}$ is independently —S(O)$_2$R$^{15}$. In embodiments, $R^{z9}$ is independently —S(O)$_2$N(R$^{12}$)(R$^{13}$)—. In embodiments, $R^{z9}$ is independently —S(=O)(=NH)N(R$^{12}$)(R$^{13}$). In embodiments, $R^{z9}$ is independently —CH$_2$C(O)N(R$^{12}$)(R$^{13}$). In embodiments, $R^{z9}$ is independently —CH$_2$N(R$^{14}$)C(O)R$^{15}$. In embodiments, $R^{z9}$ is independently —CH$_2$S(O)$_2$R$^{15}$. In embodiments, $R^{z9}$ is independently —CH$_2$S(O)$_2$N(R$^{12}$)(R$^{13}$).

In select embodiments of the compound, $R^{z9}$ is independently $C_{1-6}$alkyl optionally substituted with one, two, or three $R^{20z9}$. In some embodiments, $R^{z9}$ is independently $C_{2-6}$alkenyl optionally substituted with one, two, or three $R^{20z9}$. In some embodiments, $R^{z9}$ is independently $C_{2-6}$alkynyl optionally substituted with one, two, or three $R^{20z9}$. In some embodiments, $R^{z9}$ is independently $C_{3-10}$cycloalkyl optionally substituted with one, two, or three $R^{20z9}$. In some embodiments, $R^{z9}$ is independently $C_{2-9}$heterocycloalkyl optionally substituted with one, two, or three $R^{20z9}$. In some embodiments, $R^{z9}$ is independently $C_{6-10}$aryl optionally substituted with one, two, or three $R^{20z9}$. In some embodiments, $R^{z9}$ is independently $C_{1-9}$heteroaryl optionally substituted with one, two, or three $R^{20z9}$. In embodiments of the compound, $R^{z9}$ is independently methyl optionally substituted with one or two $R^{20z9}$. In further embodiments of the compound, $R^{z9}$ is independently methyl. In some embodiments of the compound, $R^{z9}$ is independently ethyl optionally substituted with one, two, or three $R^{20z9}$. In embodiments of the compound, $R^{z9}$ is independently ethyl. In some embodiments of the compound, $R^{z9}$ is independently propyl optionally substituted with one, two, or three $R^{20z9}$. In embodiments of the compound, $R^{z9}$ is independently propyl. In embodiments, two $R^{z9}$ bonded to the same carbon are joined to form $C_{2-6}$alkenyl optionally substituted with one, two, or three $R^{20z9}$;

In embodiments, $R^{20z1}$ is independently halogen. In embodiments, $R^{20z1}$ is independently —CN. In embodiments, $R^{20z1}$ is independently —OR$^{12}$. In embodiments, $R^{20z1}$ is independently —SR$^{12}$. In embodiments, $R^{20z1}$ is independently —N(R$^{12}$)(R$^{13}$). In embodiments, $R^{20z1}$ is independently —C(O)R$^{12}$. In embodiments, $R^{20z1}$ is independently —OC(O)N(R$^{12}$)(R$^{13}$). In embodiments, $R^{20z1}$ is independently —N(R$^{14}$)C(O)N(R$^{12}$)(R$^{13}$). In embodiments, $R^{20z1}$ is independently —N(R$^{14}$)C(O)R$^{15}$. In embodiments, $R^{20z1}$ is independently —N(R$^{14}$)S(O)$_2$R$^{15}$. In embodiments, $R^{20z1}$ is independently —C(O)R$^{12}$. In embodiments, $R^{20z1}$ is independently —S(O)R$^{15}$. In embodiments, $R^{20z1}$ is independently —OC(O)R$^{15}$. In embodiments, $R^{20z1}$ is independently —C(O)N(R$^{12}$)(R$^{13}$). In embodiments, $R^{20z1}$ is independently —C(O)C(O)N(R$^{12}$)(R$^{13}$). In embodiments, $R^{20z1}$ is independently —N(R$^{14}$)C(O)R$^{12}$. In embodiments, $R^{20z1}$ is independently —S(O)$_2$R$^{15}$. In embodiments, $R^{20z1}$ is independently —S(O)$_2$N(R$^{12}$)(R$^{13}$)—. In embodiments, $R^{20z1}$ is independently —S(=O)(=NH)N(R$^{12}$)(R$^{13}$). In embodiments, $R^{20z1}$ is independently —CH$_2$C(O)N(R$^{12}$)(R$^{13}$). In embodiments, $R^{20z1}$ is independently —CH$_2$N(R$^{14}$)C(O)R$^{15}$. In embodiments, $R^{20z1}$ is independently —CH$_2$S(O)$_2$R$^{15}$. In embodiments, $R^{20z1}$ is independently —CH$_2$S(O)$_2$N(R$^{12}$)(R$^{13}$). In embodiments, $R^{20z1}$ is independently —OH. In embodiments, $R^{20z1}$ is independently —SH. In embodiments, $R^{20z1}$ is independently —NH$_2$. In embodiments, $R^{20z1}$ is independently —C(O)H. In embodiments, $R^{20z1}$ is independently —C(O)CH$_3$.

In select embodiments of the compound, $R^{20z1}$ is independently $C_{1-6}$alkyl optionally substituted with one, two, or three $R^{20z}$. In some embodiments, $R^{20z1}$ is independently $C_{2-6}$alkenyl optionally substituted with one, two, or three $R^{20z}$. In some embodiments, R 20 z 1 is independently $C_{2-6}$alkynyl optionally substituted with one, two, or three $R^{20z}$. In some embodiments, $R^{20z1}$ is independently $C_{3-10}$cycloalkyl optionally substituted with one, two, or three $R^{20z}$. In some embodiments, $R^{20z1}$ is independently $C_{2-9}$heterocycloalkyl optionally substituted with one, two, or three $R^{20z}$. In some embodiments, $R^{20z1}$ is independently $C_{6-10}$aryl optionally substituted with one, two, or three $R^{20z}$. In some embodiments, $R^{20z1}$ is independently $C_{1-9}$heteroaryl optionally substituted with one, two, or three $R^{20z}$. In embodiments of the compound, $R^{20z1}$ is independently methyl optionally substituted with one or two $R^{20z}$. In further embodiments of the compound, $R^{20z1}$ is independently methyl. In some embodiments of the compound, $R^{20z1}$ is independently ethyl optionally substituted with one, two, or three $R^{20z}$. In embodiments of the compound, $R^{20z1}$ is independently ethyl. In some embodiments of the compound, $R^{20z1}$ is independently propyl optionally substituted with one, two, or three $R^{20z}$. In embodiments of the compound, $R^{20z1}$ is independently propyl.

In embodiments, $R^{20z2}$ is independently halogen. In embodiments, $R^{20z2}$ is independently —CN. In embodiments, $R^{20z2}$ is independently —OR$^{12}$. In embodiments, $R^{20z2}$ is independently —SR$^{12}$. In embodiments, $R^{20z2}$ is independently —N(R$^{12}$)(R$^{13}$). In embodiments, $R^{20z2}$ is independently —C(O)R$^{12}$. In embodiments, $R^{20z2}$ is independently —OC(O)N(R$^{12}$)(R$^{13}$). In embodiments, $R^{20z2}$ is independently —N(R$^{14}$)C(O)N(R$^{12}$)(R$^{13}$). In embodiments, $R^{20z2}$ is independently —N(R$^{14}$)C(O)OR$^{15}$. In embodiments, $R^{20z2}$ is independently —N(R$^{14}$)S(O)$_2$R$^{15}$. In embodiments, $R^{20z2}$ is independently —C(O)R$^{12}$. In embodiments, $R^{20z2}$ is independently —S(O)R$^{15}$. In embodiments, $R^{20z2}$ is independently —OC(O)R$^{15}$. In embodiments, $R^{20z2}$ is independently —C(O)N(R$^{12}$)(R$^{13}$). In embodiments, $R^{20z2}$ is independently —C(O)C(O)N(R$^{12}$)

($R^{13}$). In embodiments, $R^{20z2}$ is independently —N($R^{14}$)C(O)$R^{12}$. In embodiments, $R^{20z2}$ is independently —S(O)$_2$$R^{15}$. In embodiments, $R^{20z2}$ is independently —S(O)$_2$N($R^{12}$)($R^{13}$)—. In embodiments, $R^{20z2}$ is independently —S(=O)(=NH)N($R^{12}$)($R^{13}$). In embodiments, $R^{20z2}$ is independently —CH$_2$C(O)N($R^{12}$)($R^{13}$). In embodiments, $R^{20z2}$ is independently —CH$_2$N($R^{14}$)C(O)$R^{15}$. In embodiments, $R^{20z2}$ is independently —CH$_2$S(O)$_2$$R^{15}$. In embodiments, $R^{20z2}$ is independently —CH$_2$S(O)$_2$N($R^{12}$)($R^{13}$). In embodiments, $R^{20z2}$ is independently —OH. In embodiments, $R^{20z2}$ is independently —SH. In embodiments, $R^{20z2}$ is independently —NH$_2$. In embodiments, $R^{20z2}$ is independently —C(O)H. In embodiments, $R^{20z2}$ is independently —C(O)CH$_3$.

In select embodiments of the compound, $R^{20z2}$ is independently $C_{1-6}$alkyl optionally substituted with one, two, or three $R^{20z}$. In some embodiments, $R^{20z2}$ is independently $C_{2-6}$alkenyl optionally substituted with one, two, or three $R^{20z}$. In some embodiments, $R^{20z2}$ is independently $C_{2-6}$alkynyl optionally substituted with one, two, or three $R^{20z}$. In some embodiments, $R^{20z2}$ is independently $C_{3-10}$cycloalkyl optionally substituted with one, two, or three $R^{20z}$. In some embodiments, $R^{20z2}$ is independently $C_{1-9}$heterocycloalkyl optionally substituted with one, two, or three $R^{20z}$. In some embodiments, $R^{20z2}$ is independently $C_{6-10}$aryl optionally substituted with one, two, or three $R^{20z}$. In some embodiments, $R^{20z2}$ is independently $C_{1-9}$heteroaryl optionally substituted with one, two, or three $R^{20z}$. In embodiments of the compound, $R^{20z2}$ is independently methyl optionally substituted with one or two $R^{20z}$. In further embodiments of the compound, $R^{20z2}$ is independently methyl. In some embodiments of the compound, $R^{20z2}$ is independently ethyl optionally substituted with one, two, or three $R^{20z}$. In embodiments of the compound, $R^{20z2}$ is independently ethyl. In some embodiments of the compound, $R^{20z2}$ is independently propyl optionally substituted with one, two, or three $R^{20z}$. In embodiments of the compound, $R^{20z2}$ is independently propyl.

In embodiments, $R^{20z3}$ is independently halogen. In embodiments, $R^{20z3}$ is independently —CN. In embodiments, $R^{20z3}$ is independently —OR$^{12}$. In embodiments, $R^{20z3}$ is independently —SR$^{12}$. In embodiments, $R^{20z3}$ is independently —N($R^{12}$)($R^{13}$). In embodiments, $R^{20z3}$ is independently —C(O)$R^{12}$. In embodiments, $R^{20z3}$ is independently —OC(O)N($R^{12}$)($R^{13}$). In embodiments, $R^{20z3}$ is independently —N($R^{14}$)C(O)N($R^{12}$)($R^{13}$). In embodiments, $R^{20z3}$ is independently —N($R^{14}$)C(O)OR$^{15}$. In embodiments, $R^{20z3}$ is independently —N($R^{14}$)S(O)$_2$$R^{15}$. In embodiments, $R^{20z3}$ is independently —C(O)$R^{12}$. In embodiments, $R^{20z3}$ is independently —S(O)$R^{15}$. In embodiments, $R^{20z3}$ is independently —OC(O)$R^{15}$. In embodiments, $R^{20z3}$ is independently —C(O)N($R^{12}$)($R^{13}$). In embodiments, $R^{20z3}$ is independently —C(O)C(O)N($R^{12}$)($R^{13}$). In embodiments, $R^{20z3}$ is independently —N($R^{14}$)C(O)$R^{12}$. In embodiments, $R^{20z3}$ is independently —S(O)$_2$$R^{15}$. In embodiments, $R^{20z3}$ is independently —S(O)$_2$N($R^{12}$)($R^{13}$)—. In embodiments, $R^{20z3}$ is independently —S(=O)(=NH)N($R^{12}$)($R^{13}$). In embodiments, $R^{20z3}$ is independently —CH$_2$C(O)N($R^{12}$)($R^{13}$). In embodiments, $R^{20z3}$ is independently —CH$_2$N($R^{14}$)C(O)$R^{15}$. In embodiments, $R^{20z3}$ is independently —CH$_2$S(O)$_2$$R^{15}$. In embodiments, $R^{20z3}$ is independently —CH$_2$S(O)$_2$N($R^{12}$)($R^{13}$). In embodiments, $R^{20z3}$ is independently —OH. In embodiments, $R^{20z3}$ is independently —SH. In embodiments, $R^{20z3}$ is independently —NH$_2$. In embodiments, $R^{20z3}$ is independently —C(O)H. In embodiments, $R^{20z3}$ is independently —C(O)CH$_3$.

In select embodiments of the compound, $R^{20z3}$ is independently $C_{1-6}$alkyl optionally substituted with one, two, or three $R^{20z}$. In some embodiments, $R^{20z3}$ is independently $C_{2-6}$alkenyl optionally substituted with one, two, or three $R^{20z}$. In some embodiments, $R^{20z3}$ is independently $C_{2-6}$alkynyl optionally substituted with one, two, or three $R^{20z}$. In some embodiments, $R^{20z3}$ is independently $C_{3-10}$cycloalkyl optionally substituted with one, two, or three $R^{20z}$. In some embodiments, $R^{20z3}$ is independently $C_{1-9}$heterocycloalkyl optionally substituted with one, two, or three $R^{20z}$. In some embodiments, $R^{20z3}$ is independently $C_{6-10}$aryl optionally substituted with one, two, or three $R^{20z}$. In some embodiments, $R^{20z3}$ is independently $C_{1-9}$heteroaryl optionally substituted with one, two, or three $R^{20z}$. In embodiments of the compound, $R^{20z3}$ is independently methyl optionally substituted with one or two $R^{20z}$. In further embodiments of the compound, $R^{20z3}$ is independently methyl. In some embodiments of the compound, $R^{20z3}$ is independently ethyl optionally substituted with one, two, or three $R^{20z}$. In embodiments of the compound, $R^{20z3}$ is independently ethyl. In some embodiments of the compound, $R^{20z3}$ is independently propyl optionally substituted with one, two, or three $R^{20z}$. In embodiments of the compound, $R^{20z3}$ is independently propyl.

In embodiments, $R^{20z4}$ is independently halogen. In embodiments, $R^{20z4}$ is independently —CN. In embodiments, $R^{20z4}$ is independently —OR$^{12}$. In embodiments, $R^{20z4}$ is independently —SR$^{12}$. In embodiments, $R^{20z4}$ is independently —N($R^{12}$)($R^{13}$). In embodiments, $R^{20z4}$ is independently —C(O)$R^{12}$. In embodiments, $R^{20z4}$ is independently —OC(O)N($R^{12}$)($R^{13}$). In embodiments, $R^{20z4}$ is independently —N($R^{14}$)C(O)N($R^{12}$)($R^{13}$). In embodiments, $R^{20z4}$ is independently —N($R^{14}$)C(O)OR$^{15}$. In embodiments, $R^{20z4}$ is independently —N($R^{14}$)S(O)$_2$$R^{15}$. In embodiments, $R^{20z4}$ is independently —C(O)$R^{12}$. In embodiments, $R^{20z4}$ is independently —S(O)$R^{15}$. In embodiments, $R^{20z4}$ is independently —OC(O)$R^{15}$. In embodiments, $R^{20z4}$ is independently —C(O)N($R^{12}$)($R^{13}$). In embodiments, $R^{20z4}$ is independently —C(O)C(O)N($R^{12}$)($R^{13}$). In embodiments, $R^{20z4}$ is independently —N($R^{14}$)C(O)$R^{12}$. In embodiments, $R^{20z4}$ is independently —S(O)$_2$$R^{15}$. In embodiments, $R^{20z4}$ is independently —S(O)$_2$N($R^{12}$)($R^{13}$)—. In embodiments, $R^{20z4}$ is independently —S(=O)(=NH)N($R^{12}$)($R^{13}$). In embodiments, $R^{20z4}$ is independently —CH$_2$C(O)N($R^{12}$)($R^{13}$). In embodiments, $R^{20z4}$ is independently —CH$_2$N($R^{14}$)C(O)$R^{15}$. In embodiments, $R^{20z4}$ is independently —CH$_2$S(O)$_2$$R^{15}$. In embodiments, $R^{20z4}$ is independently —CH$_2$S(O)$_2$N($R^{12}$)($R^{13}$). In embodiments, $R^{20z4}$ is independently —OH. In embodiments, $R^{20z4}$ is independently —SH. In embodiments, $R^{20z4}$ is independently —NH$_2$. In embodiments, $R^{20z4}$ is independently —C(O)H. In embodiments, $R^{20z4}$ is independently —C(O)CH$_3$.

In select embodiments of the compound, $R^{20z4}$ is independently $C_{1-6}$alkyl optionally substituted with one, two, or three $R^{20z}$. In some embodiments, $R^{20z4}$ is independently $C_{2-6}$alkenyl optionally substituted with one, two, or three $R^{20z}$. In some embodiments, $R^{20z4}$ is independently $C_{2-6}$alkynyl optionally substituted with one, two, or three $R^{20z}$. In some embodiments, $R^{20z4}$ is independently $C_{3-10}$cycloalkyl optionally substituted with one, two, or three $R^{20z}$. In some embodiments, $R^{20z4}$ is independently $C_{1-9}$heterocycloalkyl optionally substituted with one, two, or three $R^{20z}$. In some embodiments, $R^{20z4}$ is independently $C_{6-10}$aryl optionally substituted with one, two, or three $R^{20z}$. In some embodiments, $R^{20z4}$ is independently $C_{1-9}$heteroaryl optionally substituted with one, two, or three $R^{20z}$. In embodiments of the compound, $R^{20z4}$ is independently methyl optionally substituted with one or two $R^{20z}$. In further embodiments of the compound, $R^{20z4}$ is independently methyl. In some embodiments of the compound, $R^{20z4}$ is independently ethyl optionally substituted with one, two, or three $R^{20z}$. In embodiments of the compound, $R^{20z4}$ is independently ethyl. In some embodiments of the compound, $R^{20z4}$ is independently propyl optionally substituted with one, two, or three $R^{20z}$. In embodiments of the compound, $R^{20z4}$ is independently propyl.

In embodiments, $R^{20z5}$ is independently halogen. In embodiments, $R^{20z5}$ is independently —CN. In embodiments, $R^{20z5}$ is independently —$OR^{12}$. In embodiments, $R^{20z5}$ is independently —$SR^{12}$. In embodiments, $R^{20z5}$ is independently —$N(R^{12})(R^{13})$. In embodiments, $R^{20z5}$ is independently —$C(O)R^{12}$. In embodiments, $R^{20z5}$ is independently —$OC(O)N(R^{12})(R^{13})$. In embodiments, $R^{20z5}$ is independently —$N(R^{14})C(O)N(R^{12})(R^{13})$. In embodiments, $R^{20z5}$ is independently —$N(R^{14})C(O)OR^{15}$. In embodiments, $R^{20z5}$ is independently —$N(R^{14})S(O)_2R^{15}$. In embodiments, $R^{20z5}$ is independently —$C(O)R^{12}$. In embodiments, $R^{20z5}$ is independently —$S(O)R^{15}$. In embodiments, $R^{20z5}$ is independently —$OC(O)R^{15}$. In embodiments, $R^{20z5}$ is independently —$C(O)N(R^{12})(R^{13})$. In embodiments, $R^{20z5}$ is independently —$C(O)C(O)N(R^{12})(R^{13})$. In embodiments, $R^{20z5}$ is independently —$N(R^{14})C(O)R^{12}$. In embodiments, $R^{20z5}$ is independently —$S(O)_2R^{15}$. In embodiments, $R^{20z5}$ is independently —$S(O)_2N(R^{12})(R^{13})$—. In embodiments, $R^{20z5}$ is independently —$S(=O)(=NH)N(R^{12})(R^{13})$. In embodiments, $R^{20z5}$ is independently —$CH_2C(O)N(R^{12})(R^{13})$. In embodiments, $R^{20z5}$ is independently —$CH_2N(R^{14})C(O)R^{15}$. In embodiments, $R^{20z5}$ is independently —$CH_2S(O)_2R^{15}$. In embodiments, $R^{20z5}$ is independently —$CH_2S(O)_2N(R^{12})(R^{13})$. In embodiments, $R^{20z5}$ is independently —OH. In embodiments, $R^{20z5}$ is independently —SH. In embodiments, $R^{20z5}$ is independently —$NH_2$. In embodiments, $R^{20z5}$ is independently —C(O)H. In embodiments, $R^{20z5}$ is independently —$C(O)CH_3$.

In select embodiments of the compound, $R^{20z5}$ is independently $C_{1-6}$alkyl optionally substituted with one, two, or three $R^{20z}$. In some embodiments, $R^{20z5}$ is independently $C_{2-6}$alkenyl optionally substituted with one, two, or three $R^{20z}$. In some embodiments, $R^{20z5}$ is independently $C_{2-6}$alkynyl optionally substituted with one, two, or three $R^{20z}$. In some embodiments, $R^{20z5}$ is independently $C_{3-10}$cycloalkyl optionally substituted with one, two, or three $R^{20z}$. In some embodiments, $R^{20z5}$ is independently $C_{1-9}$heterocycloalkyl optionally substituted with one, two, or three $R^{20z}$. In some embodiments, $R^{20z5}$ is independently $C_{6-10}$aryl optionally substituted with one, two, or three $R^{20z}$. In some embodiments, $R^{20z5}$ is independently $C_{1-9}$heteroaryl optionally substituted with one, two, or three $R^{20z}$. In embodiments of the compound, $R^{20z5}$ is independently methyl optionally substituted with one or two $R^{20z}$. In further embodiments of the compound, $R^{20z5}$ is independently methyl. In some embodiments of the compound, $R^{20z5}$ is independently ethyl optionally substituted with one, two, or three $R^{20z}$. In embodiments of the compound, $R^{20z5}$ is independently ethyl. In some embodiments of the compound, $R^{20z5}$ is independently propyl optionally substituted with one, two, or three $R^{20z}$. In embodiments of the compound, $R^{20z5}$ is independently propyl.

In embodiments, $R^{20z6}$ is independently halogen. In embodiments, $R^{20z6}$ is independently —CN. In embodiments, $R^{20z6}$ is independently —$OR^{12}$. In embodiments, $R^{20z6}$ is independently —$SR^{12}$. In embodiments, $R^{20z6}$ is independently —$N(R^{12})(R^{13})$. In embodiments, $R^{20z6}$ is independently —$C(O)R^{12}$. In embodiments, $R^{20z6}$ is independently —$OC(O)N(R^{12})(R^{13})$. In embodiments, $R^{20z6}$ is independently —$N(R^{14})C(O)N(R^{12})(R^{13})$. In embodiments, $R^{20z6}$ is independently —$N(R^{14})C(O)R^{15}$. In embodiments, $R^{20z6}$ is independently —$N(R^{14})S(O)_2R^{15}$. In embodiments, $R^{20z6}$ is independently —$C(O)R^{12}$. In embodiments, $R^{20z6}$ is independently —$S(O)R^{15}$. In embodiments, $R^{20z6}$ is independently —$OC(O)R^{15}$. In embodiments, $R^{20z6}$ is independently —$C(O)N(R^{12})(R^{13})$. In embodiments, $R^{20z6}$ is independently —$C(O)C(O)N(R^{12})(R^{13})$. In embodiments, $R^{20z6}$ is independently —$N(R^{14})C(O)R^{12}$. In embodiments, $R^{20z6}$ is independently —$S(O)_2R^{15}$. In embodiments, $R^{20z6}$ is independently —$S(O)_2N(R^{12})(R^{13})$—. In embodiments, $R^{20z6}$ is independently —$S(=O)(=NH)N(R^{12})(R^{13})$. In embodiments, $R^{20z6}$ is independently —$CH_2C(O)N(R^{12})(R^{13})$. In embodiments, $R^{20z6}$ is independently —$CH_2N(R^{14})C(O)R^{15}$. In embodiments, $R^{20z6}$ is independently —$CH_2S(O)_2R^{15}$. In embodiments, $R^{20z6}$ is independently —$CH_2S(O)_2N(R^{12})(R^{13})$. In embodiments, $R^{20z6}$ is independently —OH. In embodiments, $R^{20z6}$ is independently —SH. In embodiments, $R^{20z6}$ is independently —$NH_2$. In embodiments, $R^{20z6}$ is independently —C(O)H. In embodiments, $R^{20z6}$ is independently —$C(O)CH_3$.

In select embodiments of the compound, $R^{20z6}$ is independently $C_{1-6}$alkyl optionally substituted with one, two, or three $R^{20z}$. In some embodiments, $R^{20z6}$ is independently $C_{2-6}$alkenyl optionally substituted with one, two, or three $R^{20z}$. In some embodiments, $R^{20z6}$ is independently $C_{2-6}$alkynyl optionally substituted with one, two, or three $R^{20z}$. In some embodiments, $R^{20z6}$ is independently $C_{3-10}$cycloalkyl optionally substituted with one, two, or three $R^{20z}$. In some embodiments, $R^{20z6}$ is independently $C_{1-9}$heterocycloalkyl optionally substituted with one, two, or three $R^{20z}$. In some embodiments, $R^{20z6}$ is independently $C_{6-10}$aryl optionally substituted with one, two, or three $R^{20z}$. In some embodiments, $R^{20z6}$ is independently $C_{1-9}$heteroaryl optionally substituted with one, two, or three $R^{20z}$. In embodiments of the compound, $R^{20z6}$ is independently methyl optionally substituted with one or two $R^{20z}$. In further embodiments of the compound, $R^{20z6}$ is independently methyl. In some embodiments of the compound, $R^{20z6}$ is independently ethyl optionally substituted with one, two, or three $R^{20z}$. In embodiments of the compound, $R^{20z6}$ is independently ethyl. In some embodiments of the compound, $R^{20z6}$ is independently propyl optionally substituted with one, two, or three $R^{20z}$. In embodiments of the compound, $R^{20z6}$ is independently propyl.

In embodiments, $R^{20z9}$ is independently halogen. In embodiments, $R^{20z9}$ is independently —CN. In embodiments, $R^{20z9}$ is independently —$OR^{12}$. In embodiments, $R^{20z9}$ is independently —$SR^{12}$. In embodiments, $R^{20z9}$ is independently —$N(R^{12})(R^{13})$. In embodiments, $R^{20z9}$ is independently —$C(O)R^{12}$. In embodiments, $R^{20z9}$ is independently —$OC(O)N(R^{12})(R^{13})$. In embodiments, $R^{20z9}$ is independently —$N(R^{14})C(O)N(R^{12})(R^{13})$. In embodiments, $R^{20z9}$ is independently —$N(R^{14})C(O)OR^{15}$. In embodiments, $R^{20z9}$ is independently —$N(R^{14})S(O)_2R^{15}$. In embodiments, $R^{20z9}$ is independently —$C(O)R^{12}$. In embodiments, $R^{20z9}$ is independently —$S(O)R^{15}$. In embodiments, $R^{20z9}$ is independently —$OC(O)R^{15}$. In embodiments, $R^{20z9}$ is independently —$C(O)N(R^{12})(R^{13})$. In embodiments, $R^{20z9}$ is independently —$C(O)C(O)N(R^{12})(R^{13})$. In embodiments, $R^{20z9}$ is independently —$N(R^{14})C(O)R^{12}$. In embodiments, $R^{20z9}$ is independently —$S(O)_2R^{15}$. In embodiments, $R^{20z9}$ is independently —$S(O)_2N(R^{12})(R^{13})$—. In embodiments, $R^{20z9}$ is independently —$S(=O)(=NH)N(R^{12})(R^{13})$. In embodiments, $R^{20z9}$ is independently —CH$_2$C(O)N(R$^{12}$)(R$^{13}$). In embodiments, R$^{20z9}$ is independently —CH$_2$N(R$^{14}$)C(O)R$^{15}$. In embodiments, R$^{20z9}$ is independently —CH$_2$S(O)$_2$R$^{15}$. In embodiments, R$^{20z9}$ is independently —CH$_2$S(O)$_2$N(R$^{12}$)(R$^{13}$). In embodiments, R$^{20z9}$ is independently —OH. In embodiments, R$^{20z9}$ is independently —SH. In embodiments, R$^{20z9}$ is independently —NH$_2$. In embodiments, R$^{20z9}$ is independently —C(O)H. In embodiments, R$^{20z9}$ is independently —C(O)CH$_3$.

In select embodiments of the compound, R$^{20z9}$ is independently C$_{1-6}$alkyl optionally substituted with one, two, or three R$^{20z}$. In some embodiments, R$^{20z9}$ is independently C$_{2-6}$alkenyl optionally substituted with one, two, or three R$^{20z}$. In some embodiments, R$^{20z9}$ is independently C$_{2-6}$alkynyl optionally substituted with one, two, or three R$^{20z}$. In some embodiments, R$^{20z9}$ is independently C$_{3-10}$cycloalkyl optionally substituted with one, two, or three R$^{20z}$. In some embodiments, R$^{20z9}$ is independently C$_{1-9}$heterocycloalkyl optionally substituted with one, two, or three R$^{20z}$. In some embodiments, R$^{20z9}$ is independently C$_{6-10}$aryl optionally substituted with one, two, or three R$^{20z}$. In some embodiments, R$^{20z9}$ is independently C$_{1-9}$heteroaryl optionally substituted with one, two, or three R$^{20z}$. In embodiments of the compound, R$^{20z9}$ is independently methyl optionally substituted with one or two R$^{20z}$. In further embodiments of the compound, R$^{20z9}$ is independently methyl. In some embodiments of the compound, R$^{20z9}$ is independently ethyl optionally substituted with one, two, or three R$^{20z}$. In embodiments of the compound, R$^{20z9}$ is independently ethyl. In some embodiments of the compound, R$^{20z9}$ is independently propyl optionally substituted with one, two, or three R$^{20z}$. In embodiments of the compound, R$^{20z9}$ is independently propyl.

In embodiments, R$^{20z}$ is independently halogen. In embodiments, R$^{20z}$ is independently oxo. In embodiments, R$^{20z}$ is independently —CN. In embodiments, R$^{20z}$ is independently —OR$^{12}$. In embodiments, R$^{20z}$ is independently —SR$^{12}$. In embodiments, R$^{20z}$ is independently —N(R$^{12}$)(R$^{13}$). In embodiments, R$^{20z}$ is independently —C(O)R$^{12}$. In embodiments, R$^{20z}$ is independently —OC(O)N(R$^{12}$)(R$^{13}$). In embodiments, R$^{20z}$ is independently —N(R$^{14}$)C(O)N(R$^{12}$)(R$^{13}$). In embodiments, R$^{20z}$ is independently —N(R$^{14}$)C(O)R$^{15}$. In embodiments, R$^{20z}$ is independently —N(R$^{14}$)S(O)$_2$R$^{15}$. In embodiments, R$^{20z}$ is independently —C(O)R$^{12}$. In embodiments, R$^{20z}$ is independently —S(O)R$^{15}$. In embodiments, R$^{20z}$ is independently —OC(O)R$^{15}$. In embodiments, R$^{20z}$ is independently —C(O)N(R$^{12}$)(R$^{13}$). In embodiments, R$^{20z}$ is independently —C(O)C(O)N(R$^{12}$)(R$^{13}$). In embodiments, R$^{20z}$ is independently —N(R$^{14}$)C(O)R$^{12}$. In embodiments, R$^{20z}$ is independently —S(O)$_2$R$^{15}$. In embodiments, R$^{20z}$ is independently —S(O)$_2$N(R$^{12}$)(R$^{13}$)—. In embodiments, R$^{20z}$ is independently —S(=O)(=NH)N(R$^{12}$)(R$^{13}$). In embodiments, R$^{20z}$ is independently —CH$_2$C(O)N(R$^{12}$)(R$^{13}$). In embodiments, R$^{20z}$ is independently —CH$_2$N(R$^{14}$)C(O)R$^{15}$. In embodiments, R$^{20z}$ is independently —CH$_2$S(O)$_2$R$^{15}$. In embodiments, R$^{20z}$ is independently —CH$_2$S(O)$_2$N(R$^{12}$)(R$^{13}$). In embodiments, R$^{20z}$ is independently —OH. In embodiments, R$^{20z}$ is independently —SH. In embodiments, R$^{20z}$ is independently —NH$_2$. In embodiments, R$^{20z}$ is independently —C(O)H. In embodiments, R$^{20z}$ is independently —C(O)CH$_3$.

In select embodiments of the compound, R$^{20z}$ is independently C$_{1-6}$alkyl optionally substituted with one, two, or three R$^{20zz}$. In some embodiments, R$^{20z}$ is independently C$_{2-6}$alkenyl optionally substituted with one, two, or three R$^{20zz}$. In some embodiments, R$^{20z}$ is independently C$_{2-6}$alkynyl optionally substituted with one, two, or three R$^{20zz}$. In some embodiments, R$^{20z}$ is independently C$_{3-10}$cycloalkyl optionally substituted with one, two, or three R$^{20zz}$. In some embodiments, R$^{20z}$ is independently C$_{2-9}$heterocycloalkyl optionally substituted with one, two, or three R$^{20zz}$. In some embodiments, R$^{20z}$ is independently C$_{6-10}$aryl optionally substituted with one, two, or three R$^{20zz}$. In some embodiments, R$^{20z}$ is independently C$_{1-9}$heteroaryl optionally substituted with one, two, or three R$^{20zz}$. In embodiments of the compound, R$^{20z}$ is independently methyl optionally substituted with one or two R$^{20zz}$. In further embodiments of the compound, R$^{20z}$ is independently methyl. In some embodiments of the compound, R$^{20z}$ is independently ethyl optionally substituted with one, two, or three R$^{20zz}$. In embodiments of the compound, R$^{20z}$ is independently ethyl. In some embodiments of the compound, R$^{20z}$ is independently propyl optionally substituted with one, two, or three R$^{20zz}$. In embodiments of the compound, R$^{20z}$ is independently propyl.

In embodiments, two R$^{20z}$ bonded to the same carbon atom are independently joined to form monocyclic C$_{3-7}$cycloalkyl optionally substituted with one, two, or three R$^{20zz}$. In embodiments, two R$^{20z}$ bonded to the same carbon atom are independently joined to form monocyclic C$_{3-7}$cycloalkyl. In embodiments, two R$^{20z}$ bonded to the same carbon atom are independently joined to form monocyclic C$_3$cycloalkyl optionally substituted with one, two, or three R$^{20zz}$. In embodiments, two R$^{20z}$ bonded to the same carbon atom are independently joined to form monocyclic C$_3$cycloalkyl. In embodiments, two R$^{20z}$ bonded to the same carbon atom are independently joined to form monocyclic C$_4$cycloalkyl optionally substituted with one, two, or three R$^{20zz}$. In embodiments, two R$^{20z}$ bonded to the same carbon atom are independently joined to form monocyclic C$_4$cycloalkyl. In embodiments, two R$^{20z}$ bonded to the same carbon atom are independently joined to form monocyclic C$_5$cycloalkyl optionally substituted with one, two, or three R$^{20zz}$. In embodiments, two R$^{20z}$ bonded to the same carbon atom are independently joined to form monocyclic C$_5$cycloalkyl. In embodiments, two R$^{20z}$ bonded to the same carbon atom are independently joined to form monocyclic C$_6$cycloalkyl optionally substituted with one, two, or three R$^{20zz}$. In embodiments, two R$^{20z}$ bonded to the same carbon atom are independently joined to form monocyclic C$_6$cycloalkyl. In embodiments, two R$^{20z}$ bonded to the same carbon atom are independently joined to form monocyclic C$_7$cycloalkyl optionally substituted with one, two, or three R$^{20zz}$. In embodiments, two R$^{20z}$ bonded to the same carbon atom are independently joined to form monocyclic C$_7$cycloalkyl.

In embodiments, two R$^{20z}$ bonded to the same carbon atom are independently joined to form monocyclic 3-7 membered heterocycloalkyl optionally substituted with one, two, or three R$^{20zz}$. In embodiments, two R$^{20z}$ bonded to the same carbon atom are independently joined to form monocyclic 3-7 membered heterocycloalkyl. In embodiments, two R$^{20z}$ bonded to the same carbon atom are independently joined to form monocyclic 3 membered heterocycloalkyl optionally substituted with one, two, or three R$^{20zz}$. In embodiments, two R$^{20z}$ bonded to the same carbon atom are independently joined to form monocyclic 3 membered heterocycloalkyl. In embodiments, two R$^{20z}$ bonded to the same carbon atom are independently joined to form monocyclic 4 membered heterocycloalkyl optionally substituted with one, two, or three R$^{20zz}$. In embodiments, two R$^{20z}$ bonded to the same carbon atom are independently joined to form monocyclic 4 membered heterocycloalkyl. In embodiments, two R$^{20z}$ bonded to the same carbon atom are independently joined to form monocyclic 5 membered heterocycloalkyl optionally substituted with one, two, or three $R^{20zz}$. In embodiments, two $R^{20z}$ bonded to the same carbon atom are independently joined to form monocyclic 5 membered heterocycloalkyl. In embodiments, two $R^{20z}$ bonded to the same carbon atom are independently joined to form monocyclic 6 membered heterocycloalkyl optionally substituted with one, two, or three $R^{20zz}$. In embodiments, two $R^{20z}$ bonded to the same carbon atom are independently joined to form monocyclic 6 membered heterocycloalkyl. In embodiments, two $R^{20z}$ bonded to the same carbon atom are independently joined to form monocyclic 7 membered heterocycloalkyl optionally substituted with one, two, or three $R^{20zz}$. In embodiments, two $R^{20z}$ bonded to the same carbon atom are independently joined to form monocyclic 7 membered heterocycloalkyl.

In embodiments, two or more $R^{20z}$ bonded to two adjacent atoms are independently joined to form monocyclic $C_{3-7}$cycloalkyl optionally substituted with one, two, or three $R^{20zz}$. In embodiments, two or more $R^{20z}$ bonded to two adjacent atoms are independently joined to form monocyclic $C_{3-7}$cycloalkyl. In embodiments, two or more $R^{20z}$ bonded to two adjacent atoms are independently joined to form monocyclic $C_3$cycloalkyl optionally substituted with one, two, or three $R^{20zz}$. In embodiments, two or more $R^{20z}$ bonded to two adjacent atoms are independently joined to form monocyclic $C_3$cycloalkyl. In embodiments, two or more $R^{20z}$ bonded to two adjacent atoms are independently joined to form monocyclic $C_4$cycloalkyl optionally substituted with one, two, or three $R^{20zz}$. In embodiments, two or more $R^{20z}$ bonded to two adjacent atoms are independently joined to form monocyclic $C_4$cycloalkyl. In embodiments, two or more $R^{20z}$ bonded to two adjacent atoms are independently joined to form monocyclic $C_5$cycloalkyl optionally substituted with one, two, or three $R^{20zz}$. In embodiments, two or more $R^{20z}$ bonded to two adjacent atoms are independently joined to form monocyclic $C_5$cycloalkyl. In embodiments, two or more $R^{20z}$ bonded to two adjacent atoms are independently joined to form monocyclic $C_6$cycloalkyl optionally substituted with one, two, or three $R^{20zz}$. In embodiments, two or more $R^{20z}$ bonded to two adjacent atoms are independently joined to form monocyclic $C_6$cycloalkyl. In embodiments, two or more $R^{20z}$ bonded to two adjacent atoms are independently joined to form monocyclic $C_7$cycloalkyl optionally substituted with one, two, or three $R^{20zz}$. In embodiments, two or more $R^{20z}$ bonded to two adjacent atoms are independently joined to form monocyclic $C_7$cycloalkyl. In embodiments, two or more $R^{20z}$ bonded to two adjacent atoms are independently joined to form monocyclic 3-7 membered heterocycloalkyl optionally substituted with one, two, or three $R^{20zz}$. In embodiments, two or more $R^{20z}$ bonded to two adjacent atoms are independently joined to form monocyclic 3-7 membered heterocycloalkyl. In embodiments, two or more $R^{20z}$ bonded to two adjacent atoms are independently joined to form monocyclic 3 membered heterocycloalkyl optionally substituted with one, two, or three $R^{20zz}$. In embodiments, two or more $R^{20z}$ bonded to two adjacent atoms are independently joined to form monocyclic 3 membered heterocycloalkyl. In embodiments, two or more $R^{20z}$ bonded to two adjacent atoms are independently joined to form monocyclic 4 membered heterocycloalkyl optionally substituted with one, two, or three $R^{20zz}$. In embodiments, two or more $R^{20z}$ bonded to two adjacent atoms are independently joined to form monocyclic 4 membered heterocycloalkyl. In embodiments, two or more $R^{20z}$ bonded to two adjacent atoms are independently joined to form monocyclic 5 membered heterocycloalkyl optionally substituted with one, two, or three $R^{20zz}$. In embodiments, two or more $R^{20z}$ bonded to two adjacent atoms are independently joined to form monocyclic 5 membered heterocycloalkyl. In embodiments, two or more $R^{20z}$ bonded to two adjacent atoms are independently joined to form monocyclic 6 membered heterocycloalkyl optionally substituted with one, two, or three $R^{20zz}$. In embodiments, two or more $R^{20z}$ bonded to two adjacent atoms are independently joined to form monocyclic 6 membered heterocycloalkyl. In embodiments, two or more $R^{20z}$ bonded to two adjacent atoms are independently joined to form monocyclic 7 membered heterocycloalkyl optionally substituted with one, two, or three $R^{20zz}$. In embodiments, two or more $R^{20z}$ bonded to two adjacent atoms are independently joined to form monocyclic 7 membered heterocycloalkyl. In embodiments, two or more $R^{20z}$ bonded to two adjacent atoms are independently joined to form phenyl optionally substituted with one, two, or three $R^{20zz}$. In embodiments, two or more $R^{20z}$ bonded to two adjacent atoms are independently joined to form phenyl. In embodiments, two or more $R^{20z}$ bonded to two adjacent atoms are independently joined to form monocyclic 5-6 membered heteroaryl optionally substituted with one, two, or three $R^{20zz}$. In embodiments, two or more $R^{20z}$ bonded to two adjacent atoms are independently joined to form monocyclic 5-6 membered heteroaryl. In embodiments, two or more $R^{20z}$ bonded to two adjacent atoms are independently joined to form monocyclic 5 membered heteroaryl optionally substituted with one, two, or three $R^{20zz}$. In embodiments, two or more $R^{20z}$ bonded to two adjacent atoms are independently joined to form monocyclic 5 membered heteroaryl. In embodiments, two or more $R^{20z}$ bonded to two adjacent atoms are independently joined to form monocyclic 6 membered heteroaryl optionally substituted with one, two, or three $R^{20zz}$. In embodiments, two or more $R^{20z}$ bonded to two adjacent atoms are independently joined to form monocyclic 6 membered heteroaryl.

In embodiments, $L^7$ is a bond.

In embodiments, $L^7$ is a bond. In embodiments, $L^7$ is —O—. In embodiments, $L^7$ is —N($R^{7d}$)—. In embodiments, $L^7$ is —C(O)—. In embodiments, $L^7$ is —S—. In embodiments, $L^7$ is —S(O)$_2$—. In embodiments, $L^7$ is —S(O)—. In embodiments, $L^7$ is —NH—. In embodiments, $L^7$ is CH$_2$. In embodiments, $L^7$ is —OCH$_2$—. In embodiments, $L^7$ is —N(H)CH$_2$—. In embodiments, $L^7$ is —C(O)CH$_2$—. In embodiments, $L^7$ is —SCH$_2$—. In embodiments, $L^7$ is —S(O)$_2$CH$_2$—. In embodiments, $L^7$ is —S(O)CH$_2$—. In embodiments, $L^7$ is —P(O)(CH$_3$)CH$_2$—. In embodiments, $L^7$ is —CH$_2$CH$_2$—. In embodiments, $L^7$ is —CH$_2$O—. In embodiments, $L^7$ is —CH$_2$N(H)—. In embodiments, $L^7$ is —CH$_2$C(O)—. In embodiments, $L^7$ is —CH$_2$S—. In embodiments, $L^7$ is —CH$_2$S(O)$_2$—. In embodiments, $L^7$ is —CH$_2$S(O)—. In embodiments, $L^7$ is —CH$_2$P(O)CH$_3$—. In embodiments, $L^7$ is —N(H)C(O)—. In embodiments, $L^7$ is —N(H)P(O)CH$_3$—. In embodiments, $L^7$ is —C(O)N(H)—. In embodiments, $L^7$ is —CH$_2$CH$_2$CH$_2$—. In embodiments, $L^7$ is —OCH$_2$CH$_2$—. In embodiments, $L^7$ is —N(H)CH$_2$CH$_2$—. In embodiments, $L^7$ is —C(O)CH$_2$CH$_2$—. In embodiments, $L^7$ is —SCH$_2$CH$_2$—. In embodiments, $L^7$ is —S(O)$_2$CH$_2$CH$_2$—. In embodiments, $L^7$ is —S(O)CH$_2$CH$_2$—. In embodiments, $L^7$ is —P(O)(CH$_3$)CH$_2$CH$_2$—. In embodiments, $L^7$ is —CH$_2$CH$_2$O—. In embodiments, $L^7$ is —CH$_2$CH$_2$N(H)—. In embodiments, $L^7$ is —CH$_2$CH$_2$C(O)—. In embodiments, $L^7$ is —CH$_2$CH$_2$S—. In embodiments, $L^7$ is —CH$_2$CH$_2$S(O)$_2$—. In embodiments, $L^7$ is —CH$_2$CH$_2$S(O)—. In embodiments, $L^7$ is —CH$_2$CH$_2$P(O)(CH$_3$)—. In embodiments, $L^7$ is —CH$_2$CH$_2$CH$_2$CH$_2$—. In embodiments, $L^7$ is $C_{1-4}$alkylene optionally substituted with one, two or three $R^{20g}$. In embodiments, $L^7$ is $C_1$alkylene optionally substituted with one, two or three $R^{20g}$. In embodiments, $L^7$ is $C_2$alkylene optionally substituted with one, two or three $R^{20g}$g. In embodiments, $L^7$ is $C_3$alkylene optionally substituted with one, two or three $R^{20g}$. In embodiments, $L^7$ is $C_4$alkylene optionally substituted with one, two or three $R^{20g}$. In embodiments, $L^7$ is 2-4 membered heteroalkylene linker optionally substituted with one, two or three $R^{20g}$. In embodiments, $L^7$ is 2 membered heteroalkylene linker optionally substituted with one, two or three $R^{20g}$. In embodiments, $L^7$ is 3 membered heteroalkylene linker optionally substituted with one, two or three $R^{20g}$. In embodiments, $L^7$ is 4 membered heteroalkylene linker optionally substituted with one, two or three $R^{20g}$.

In select embodiments of the compound, $R^{7c}$ is independently $C_{1-6}$alkyl optionally substituted with one, two, or three $R^{20g}$. In some embodiments, $R^{7c}$ is independently $C_{2-6}$alkenyl optionally substituted with one, two, or three $R^{20g}$. In some embodiments, $R^{7c}$ is independently $C_{2-6}$alkynyl optionally substituted with one, two, or three $R^{20g}$. In some embodiments, $R^{7c}$ is independently $C_{3-10}$cycloalkyl optionally substituted with one, two, or three $R^{20g}$. In some embodiments, $R^{7c}$ is independently $C_{1-9}$heterocycloalkyl optionally substituted with one, two, or three $R^{20g}$. In some embodiments, $R^{7c}$ is independently $C_{6-10}$aryl optionally substituted with one, two, or three $R^{20g}$. In some embodiments, $R^{7c}$ is independently $C_{1-9}$heteroaryl optionally substituted with one, two, or three $R^{20g}$. In additional embodiments, $R^{7c}$ is independently hydrogen.

In select embodiments of the compound, $R^{7d}$ is independently $C_{1-6}$alkyl optionally substituted with one, two, or three $R^{20g}$. In some embodiments, $R^{7d}$ is independently $C_{2-6}$alkenyl optionally substituted with one, two, or three $R^{20g}$. In some embodiments, $R^{7d}$ is independently $C_{2-6}$alkynyl optionally substituted with one, two, or three $R^{20g}$. In some embodiments, R 7d is independently $C_{3-10}$cycloalkyl optionally substituted with one, two, or three $R^{20g}$. In some embodiments, $R^{7d}$ is independently $C_{2-9}$heterocycloalkyl optionally substituted with one, two, or three $R^{20g}$. In some embodiments, $R^{7d}$ is independently $C_{6-10}$aryl optionally substituted with one, two, or three $R^{20g}$. In some embodiments, $R^{7d}$ is independently $C_{1-9}$heteroaryl optionally substituted with one, two, or three $R^{20g}$. In additional embodiments, $R^{7d}$ is independently hydrogen.

In some embodiments, $R^7$ is $R^{17}$.

In some embodiments, $R^{17}$ is selected from a $C_{3-10}$cycloalkyl, 3-10 membered heterocycloalkyl, $C_{6-10}$aryl, and 5-10 membered heteroaryl, wherein the $C_{3-10}$cycloalkyl, 3-10 membered heterocycloalkyl, $C_{6-10}$aryl, and 5-10 membered heteroaryl are optionally substituted with one, two, three, four, five, six, or seven $R^{20q}$.

In some embodiments, $L^7$ is a bond and $R^{7a}$ and $R^{17}$, together with the carbon to which they are attached, form $C_{3-10}$cycloalkyl or 3-10 membered heterocycloalkyl, wherein the $C_{3-10}$cycloalkyl and 3-10 membered heterocycloalkyl are optionally substituted with one or more $R^{20q}$.

In some embodiments, $R^{17}$ is selected from a bicyclic $C_{4-10}$cycloalkyl, bicyclic 4-10 membered heterocycloalkyl, bicyclic $C_{7-10}$aryl, and bicyclic 6-10 membered heteroaryl, wherein the bicyclic $C_{4-10}$cycloalkyl, bicyclic 4-10 membered heterocycloalkyl, bicyclic $C_{7-10}$aryl, and bicyclic 6-10 membered heteroaryl are optionally substituted with one, two, three, four, five, six, or seven $R^{20q}$.

In some embodiments, $R^{17}$ is selected from a bridged bicyclic $C_{4-10}$cycloalkyl, bridged bicyclic 4-10 membered heterocycloalkyl, bridged bicyclic $C_{7-10}$aryl, and bridged bicyclic 6-10 membered heteroaryl, wherein the bridged bicyclic $C_{4-10}$cycloalkyl, bridged bicyclic 4-10 membered heterocycloalkyl, bridged bicyclic $C_{7-10}$aryl, and bridged bicyclic 6-10 membered heteroaryl are optionally substituted with one, two, three, four, five, six, or seven $R^{20q}$.

In some embodiments, $R^{17}$ is selected from a fused bicyclic $C_{4-10}$cycloalkyl, fused bicyclic 4-10 membered heterocycloalkyl, fused bicyclic $C_{7-10}$aryl, and fused bicyclic 6-10 membered heteroaryl, wherein the fused bicyclic $C_{4-10}$cycloalkyl, fused bicyclic 4-10 membered heterocycloalkyl, fused bicyclic $C_{7-10}$aryl, and fused bicyclic 6-10 membered heteroaryl are optionally substituted with one, two, three, four, five, six, or seven $R^{20q}$.

In select embodiments, $R^{17}$ is a $C_{3-10}$cycloalkyl optionally substituted with one, two, three, four, five, six, or seven $R^{20q}$. In additional embodiments, $R^{17}$ is a 3-10 membered heterocycloalkyl optionally substituted with one, two, three, four, five, six, or seven $R^{20q}$. In further embodiments, $R^{17}$ is a $C_{6-10}$aryl optionally substituted with one, two, three, four, five, six, or seven $R^{20q}$. In some embodiments, $R^{17}$ is a 5 to 10 membered heteroaryl optionally substituted with one, two, three, four, five, six, or seven $R^{20q}$. In embodiments, $R^{17}$ is a $C_{3-10}$cycloalkyl. In select embodiments, $R^{17}$ is a 3-10 membered heterocycloalkyl. In additional embodiments, $R^{17}$ is a $C_{6-10}$aryl. In some embodiments, $R^{17}$ is a 5 to 10 membered heteroaryl. In some embodiments, $R^{17}$ is a monocyclic $C_{3-9}$cycloalkyl optionally substituted with one, two, three, four, five, six, or seven $R^{20q}$. In embodiments, $R^{17}$ is a monocyclic 3-9 membered heterocycloalkyl optionally substituted with one, two, three, four, five, six, or seven $R^{20q}$. In additional embodiments, $R^{17}$ is a monocyclic phenyl optionally substituted with one, two, three, four, or five $R^{20q}$. In further embodiments, $R^{17}$ is a monocyclic 5 to 6 membered heteroaryl optionally substituted with one, two, three, four, or five $R^{20q}$. In some embodiments, $R^{17}$ is a spirocyclic $C_{5-10}$cycloalkyl optionally substituted with one, two, three, four, five, six, or seven $R^{20q}$. In embodiments, $R^{17}$ is a spirocyclic 5-10 membered heterocycloalkyl optionally substituted with one, two, three, four, five, six, or seven $R^{20q}$. In additional embodiments, $R^{17}$ is a fused $C_{4-10}$cycloalkyl optionally substituted with one, two, three, four, five, six, or seven $R^{20q}$. In further embodiments, $R^{17}$ is a fused 4-10 membered heterocycloalkyl optionally substituted with one, two, three, four, five, six, or seven $R^{20q}$. In further embodiments, $R^{17}$ is a fused $C_{7-10}$aryl, optionally substituted with one, two, three, four, five, six, or seven $R^{20q}$. In some embodiments, $R^{17}$ is a fused 6 to 10 membered heteroaryl optionally substituted with one, two, three, four, five, six, or seven $R^{20q}$.

In embodiments, $R^{17}$ is selected from $C_{6-10}$aryl and 5-10 membered heteroaryl, each of which is optionally substituted with one, two, or three $R^{20q}$. In embodiments, $R^{17}$ is selected from $C_{10}$ aryl and 9-membered heteroaryl, each of which is optionally substituted with one, two, or three $R^{20q}$. In embodiments, $R^{17}$ is selected from naphthalenyl and benzothiophenyl, each of which is optionally substituted with one, two, or three $R^{20q}$. In embodiments, $R^{17}$ is substituted with one, two, or three substituents independently selected from halogen, —CN, $C_{1-3}$alkyl, $C_{2-3}$alkenyl, $C_{2-3}$alkynyl, —$OR^{21}$, and —$N(R^{22})(R^{23})$. In embodiments, $R^{17}$ is substituted with one, two, or three substituents independently selected from halogen, —CN, —$CH_3$, —C≡CH, —OH, and —$NH_2$. In embodiments, $R^{17}$ is substituted with —F, —CN, and —$NH_2$. In embodiments, $R^{17}$ is selected from

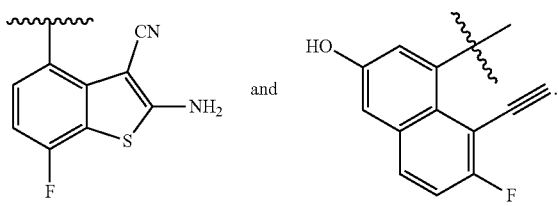 [SMILES: *c1ccc(F)c2sc(N)c(C#N)c12 ; *c1cc(O)cc2ccc(F)c(C#C)c12]

and

In embodiments, $R^{17}$ is selected from

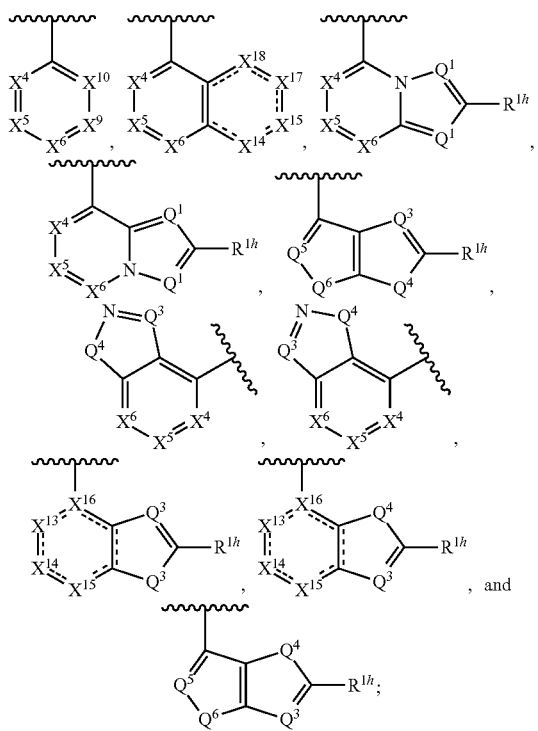

$Q^1$, $Q^3$, and $Q^5$ are independently selected from N and $C(R^{1d})$;

$Q^4$ and $Q^6$ are independently selected from O, S, $C(R^{1a})(R^{1b})$, and $N(R^{1c})$;

$X^4$, $X^5$, $X^6$, $X^9$, $X^{10}$ are independently selected from $C(R^{1a})$ and N;

$X^{13}$ is selected from a bond, $C(R^{1a})$, N, C(O), $C(R^{1a})(R^{1b})$, $C(O)C(R^{1a})(R^{1b})$, $C(R^{1a})(R^{1b})C(R^{1a})(R^{1b})$, $C(R^{1a})(R^{1b})N(R^{1c})$, and $N(R^{1c})$;

$X^{14}$, $X^{15}$, $X^{17}$, $X^{18}$ are independently selected from C(O), $C(R^{1a})$, N, $C(R^{1a})(R^{1b})$, and $N(R^{1c})$;

$X^{16}$ are independently selected from C, N, and $C(R^{1a})$;

each $R^{1b}$, $R^{1b}$, $R^{1d}$, and $R^{1h}$ is independently selected from hydrogen, halogen, —CN, $C_{1-6}$alkyl, $C_{1-6}$haloalkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20q}$; or $R^{1a}$ and $R^{1b}$ bonded to the same carbon are joined to form a 3-10 membered heterocycloalkyl ring or a $C_{3-10}$cycloalkyl ring, wherein the 3-10 membered heterocycloalkyl ring or $C_{3-10}$cycloalkyl ring are optionally substituted with one, two, or three $R^{20q}$; or two $R^{1a}$ bonded to adjacent atoms are joined to form a 3-10 membered heterocycloalkyl ring, a $C_{6-10}$aryl ring, a 5-12 membered heteroaryl ring, or a $C_{3-10}$cycloalkyl ring, wherein the 3-10 membered heterocycloalkyl ring, $C_{6-10}$aryl ring, 5-12 membered heteroaryl ring, or $C_{3-10}$cycloalkyl ring are optionally substituted with one, two, or three $R^{20q}$; or $R^{1h}$ and one of $R^{1a}$, $R^{1b}$, $R^{1c}$, and $R^{1d}$ bonded to adjacent atoms are joined to form a 3-10 membered heterocycloalkyl ring, a $C_{6-10}$aryl ring, a 5-12 membered heteroaryl ring, or a $C_{3-10}$cycloalkyl ring, wherein the 3-10 membered heterocycloalkyl ring, a $C_{6-10}$aryl ring, a 5-12 membered heteroaryl ring, and $C_{3-10}$cycloalkyl ring are optionally substituted with one, two, or three $R^{20q}$; and each $R^{1c}$ is independently selected from hydrogen, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20q}$.

In embodiments, $Q^1$ is N. In embodiments, $Q^1$ is $C(R^{1d})$. In embodiments, $Q^3$ is N. In embodiments, $Q^3$ is $C(R^{1d})$. In embodiments, $Q^5$ is N. In embodiments, $Q^5$ is $C(R^{1d})$.

In embodiments, $Q^4$ is O. In embodiments, $Q^4$ is S. In embodiments, $Q^4$ is $C(R^{1a})(R^{1b})$. In embodiments, $Q^4$ is $N(R^{1a})$. In embodiments, $Q^6$ is O. In embodiments, $Q^6$ is S. In embodiments, $Q^6$ is $C(R^{1a})(R^{1b})$. In embodiments, $Q^6$ is $N(R^{1a})$.

In embodiments, $X^4$ is $C(R^{1a})$. In embodiments, $X^4$ is N. In embodiments, $X^5$ is $C(R^{1a})$. In embodiments, $X^5$ is N. In embodiments, $X^6$ is $C(R^{1a})$. In embodiments, $X^6$ is N. In embodiments, $X^9$ is $C(R^{1a})$. In embodiments, $X^9$ is N. In embodiments, $X^{10}$ is $C(R^{1a})$. In embodiments, $X^{10}$ is N.

In embodiments, $X^{13}$ is a bond. In embodiments, $X^{13}$ is $C(R^{1a})$. In embodiments, $X^{13}$ is N. In embodiments, $X^{13}$ is C(O). In embodiments, $X^{13}$ is $C(R^{1a})(R^{1b})$. In embodiments, $X^{13}$ is $C(O)C(R^{1a})(R^{1b})$. In embodiments, $X^{13}$ is $C(R^{1a})(R^{1b})C(R^{1a})(R^{1b})$. In embodiments, $X^{13}$ is $C(R^{1a})(R^{1b})N(R^{1c})$. In embodiments, $X^{13}$ is $N(R^{1a})$.

In embodiments, $X^{14}$ is $C(R^{1a})$. In embodiments, $X^{14}$ is N. In embodiments, $X^{14}$ is C(O). In embodiments, $X^{14}$ is $C(R^{1a})(R^{1b})$. In embodiments, $X^{14}$ is $N(R^{1a})$. In embodiments, $X^{15}$ is $C(R^{1a})$. In embodiments, $X^{15}$ is N. In embodiments, $X^{15}$ is C(O). In embodiments, $X^{15}$ is $C(R^{1a})(R^{1b})$. In embodiments, $X^{15}$ is $N(R^{1a})$. In embodiments, $X^{17}$ is $C(R^{1a})$. In embodiments, $X^{17}$ is N. In embodiments, $X^{17}$ is C(O). In embodiments, $X^{17}$ is $C(R^{1a})(R^{1b})$. In embodiments, $X^{17}$ is $N(R^{1a})$. In embodiments, $X^{18}$ is $C(R^{1a})$. In embodiments, $X^{18}$ is N. In embodiments, $X^{18}$ is C(O). In embodiments, $X^{18}$ is $C(R^{1a})(R^{1b})$. In embodiments, $X^{18}$ is $N(R^{1a})$.

In embodiments, $X^{16}$ is C. In embodiments, $X^{16}$ is N. In embodiments, $X^{16}$ is $C(R^{1a})$.

In some embodiments, each $R^{1a}$ is independently hydrogen. In some embodiments, each $R^{1a}$ is independently halogen. In some embodiments, each $R^{1a}$ is independently oxo. In some embodiments, each $R^{1a}$ is independently —CN. In some embodiments, each $R^{1a}$ is independently $C_{1-6}$alkyl. In some embodiments, each $R^{1a}$ is independently $C_{2-6}$alkenyl. In some embodiments, each $R^{1a}$ is independently $C_{2-6}$alkynyl. In some embodiments, each $R^{1a}$ is independently $C_{3-10}$cycloalkyl. In some embodiments, each $R^{1a}$ is independently $C_{1-9}$heterocycloalkyl. In some embodiments, each $R^{1a}$ is independently $C_{6-10}$aryl. In some embodiments, each $R^{1a}$ is independently $C_{1-9}$heteroaryl. In some embodiments, each $R^{1a}$ is independently —$OR^{12}$. In some embodiments, each $R^{1a}$ is independently —$SR^{12}$. In some embodiments, each $R^{1a}$ is independently —$N(R^{12})(R^{13})$. In some embodiments, each $R^{1a}$ is independently —$C(O)R^{12}$. In some embodiments, each $R^{1a}$ is independently —$OC(O)N(R^{12})(R^{13})$. In some embodiments, each $R^{1a}$ is independently —$N(R^{14})C(O)N(R^{12})(R^{13})$. In some embodiments, each $R^{1a}$ is independently —$N(R^{14})C(O)R^{15}$. In some embodiments, each $R^{1a}$ is independently —$N(R^{14})S(O)_2R^{15}$. In some embodiments, each $R^{1a}$ is independently —$C(O)R^{15}$. In some embodiments, each $R^{1a}$ is independently —$S(O)R^{15}$. In some embodiments, each $R^{1a}$ is independently —$OC(O)R^{15}$. In some embodiments, each $R^{1a}$ is independently —$C(O)N(R^{12})(R^{13})$. In some embodiments, each $R^{1a}$ is independently —$C(O)C(O)N(R^{12})(R^{13})$. In some embodiments, each $R^{1a}$ is independently —$N(R^{14})C(O)R^{15}$. In some embodiments, each $R^{1a}$ is independently —$C(O)C(O)N(R^{12})(R^{13})$. In some embodiments, each $R^{1a}$ is independently —$S(O)_2R^{15}$. In some embodiments, each $R^{1a}$ is independently —$S(O)_2N(R^{12})(R^{13})$. In some embodiments, each $R^{1a}$ is independently —$S(=O)(=NH)N(R^{12})(R^{13})$. In some embodiments, each $R^{1a}$ is independently —$CH_2C(O)N(R^{12})(R^{13})$. In some embodiments, each $R^{1a}$ is independently —$CH_2N(R^{14})C(O)R^{15}$. In some embodiments, each $R^{1a}$ is independently —$CH_2S(O)_2R^{15}$. In some embodiments, each $R^{1a}$ is independently —$CH_2S(O)_2N(R^{12})(R^{13})$. In some embodiments, each $R^{1a}$ is independently $C_{1-6}$alkyl substituted with one, two, or three $R^{20q}$. In some embodiments, each $R^{1a}$ is independently $C_{2-6}$alkenyl substituted with one, two, or three $R^{20q}$. In some embodiments, each $R^{1a}$ is independently $C_{2-6}$alkynyl substituted with one, two, or three $R^{20q}$. In some embodiments, each $R^{1a}$ is independently $C_{3-10}$cycloalkyl substituted with one, two, or three $R^{20q}$. In some embodiments, each $R^{1a}$ is independently $C_{1-9}$heterocycloalkyl substituted with one, two, or three $R^{20q}$. In some embodiments, each $R^{1a}$ is independently $C_{6-10}$aryl substituted with one, two, or three $R^{20q}$. In some embodiments, each $R^{1a}$ is independently $C_{1-9}$heteroaryl substituted with one, two, or three $R^{20q}$. In embodiments, $R^{1a}$ is independently halogen. In embodiments, $R^{1a}$ is independently F. In embodiments, $R^{1a}$ is independently Cl. In embodiments, $R^{1a}$ is independently Br. In embodiments, $R^{1a}$ is independently I. In embodiments, $R^{1a}$ is independently $R^{1a}$ is independently oxo. In embodiments, $R^{1a}$ is independently —CN. In embodiments, $R^{1a}$ is independently $C_{1-6}$alkyl. In embodiments, $R^{1a}$ is independently methyl. In embodiments, $R^{1a}$ is independently ethyl. In embodiments, $R^{1a}$ is independently isopropyl. In embodiments, $R^{1a}$ is independently $C_{2-6}$alkenyl. In embodiments, $R^{1a}$ is independently $C_{2-6}$alkynyl. In embodiments, $R^{1a}$ is independently $C_{1-6}$haloalkyl. In embodiments, $R^{1a}$ is independently —$CF_3$. In embodiments, $R^{1a}$ is independently $C_{3-12}$cycloalkyl. In embodiments, $R^{1a}$ is independently $C_{2-11}$heterocycloalkyl. In embodiments, $R^{1a}$ is independently $C_{6-12}$aryl. In embodiments, $R^{1a}$ is independently $C_{1-11}$heteroaryl. In embodiments, $R^{1a}$ is independently —OH. In embodiments, $R^{1a}$ is independently —$OCH_3$. In embodiments, $R^{1a}$ is independently —SH. In embodiments, $R^{1a}$ is independently —$SCH_3$. In embodiments, $R^{1a}$ is independently —$N(CH_3)_2$. In embodiments, $R^{1a}$ is independently —$N(H)_2$. In embodiments, $R^{1a}$ is independently —$C(O)OH$. In embodiments, $R^{1a}$ is independently —$C(O)OCH_3$. In embodiments, $R^{1a}$ is independently —$OC(O)N(H)_2$. In embodiments, $R^{1a}$ is independently —$OC(O)N(CH_3)_2$. In embodiments, $R^{1a}$ is independently —$N(H)C(O)N(CH_3)_2$. In embodiments, $R^{1a}$ is independently —$N(H)C(O)N(H)_2$. In embodiments, $R^{1a}$ is independently —$N(H)C(O)OH$. In embodiments, $R^{1a}$ is independently —$N(H)C(O)OCH_3$. In embodiments, $R^{1a}$ is independently —$N(H)S(O)_2CH_3$. In embodiments, $R^{1a}$ is independently —$C(O)CH_3$. In embodiments, $R^{1a}$ is independently —$C(O)H$. In embodiments, $R^{1a}$ is independently —$S(O)CH_3$. In embodiments, $R^{1a}$ is independently —$OC(O)CH_3$. In embodiments, $R^{1a}$ is independently —$OC(O)H$. In embodiments, $R^{1a}$ is independently —$C(O)N(CH_3)_2$. In embodiments, $R^{1a}$ is independently —$C(O)C(O)N(CH_3)_2$. In embodiments, $R^{1a}$ is independently —$N(H)C(O)H$. In embodiments, $R^{1a}$ is independently —$N(H)C(O)CH_3$. In embodiments, $R^{1a}$ is independently —$S(O)_2CH_3$. In embodiments, $R^{1a}$ is independently —$S(O)_2N(H)_2$. In embodiments, $R^{1a}$ is independently —$S(O)_2N(CH_3)_2$. In embodiments, $R^{1a}$ is independently $S(=O)(=NH)N(H)_2$. In embodiments, $R^{1a}$ is independently $S(=O)(=NH)N(CH_3)_2$. In embodiments, $R^{1a}$ is independently —$CH_2C(O)N(H)_2$. In embodiments, $R^{1a}$ is independently —$CH_2C(O)N(CH_3)_2$. In embodiments, $R^{1a}$ is independently —$CH_2N(H)C(O)H$. In embodiments, $R^{1a}$ is independently —$CH_2N(H)C(O)CH_3$. In embodiments, $R^{1a}$ is independently —$CH_2S(O)_2H$. In embodiments, $R^{1a}$ is independently —$CH_2S(O)_2CH_3$. In embodiments, $R^{1a}$ is independently and —$CH_2S(O)_2N(CH_3)_2$. In embodiments, $R^{1a}$ is independently and —$CH_2S(O)_2N(H)_2$.

In some embodiments, each $R^{1b}$ is independently hydrogen. In some embodiments, each $R^{1b}$ is independently halogen. In some embodiments, each $R^{1b}$ is independently oxo. In some embodiments, each $R^{1b}$ is independently —CN. In some embodiments, each $R^{1b}$ is independently $C_{1-6}$alkyl. In some embodiments, each $R^{1b}$ is independently $C_{2-6}$alkenyl. In some embodiments, each $R^{1b}$ is independently $C_{2-6}$alkynyl. In some embodiments, each $R^{1b}$ is independently $C_{3-10}$cycloalkyl. In some embodiments, each $R^{1b}$ is independently $C_{2-9}$heterocycloalkyl. In some embodiments, each $R^{1b}$ is independently $C_{6-10}$aryl. In some embodiments, each $R^{1b}$ is independently $C_{1-9}$heteroaryl. In some embodiments, each $R^{1b}$ is independently —$OR^{12}$. In some embodiments, each $R^{1b}$ is independently —$SR^{12}$. In some embodiments, each $R^{1b}$ is independently —$N(R^{12})(R^{13})$. In some embodiments, each $R^{1b}$ is independently —$C(O)R^{12}$. In some embodiments, each $R^{1b}$ is independently —$OC(O)N(R^{12})(R^{13})$. In some embodiments, each $R^{1b}$ is independently —$N(R^{14})C(O)N(R^{12})(R^{13})$. In some embodiments, each $R^{1b}$ is independently —$N(R^{14})C(O)OR^{15}$. In some embodiments, each $R^{1b}$ is independently —$N(R^{14})S(O)_2R^{15}$. In some embodiments, each $R^{1b}$ is independently —$C(O)R^{15}$. In some embodiments, each $R^{1b}$ is independently —$S(O)R^{15}$. In some embodiments, each $R^{1b}$ is independently —$OC(O)R^{15}$. In some embodiments, each $R^{1b}$ is independently —$C(O)N(R^{12})(R^{13})$. In some embodiments, each $R^{1b}$ is independently —$C(O)C(O)N(R^{12})(R^{13})$. In some embodiments, each $R^{1b}$ is independently —$N(R^{14})C(O)R^{15}$. In some embodiments, each $R^{1b}$ is independently —$C(O)C(O)N(R^{12})(R^{13})$. In some embodiments, each $R^{1b}$ is independently —$S(O)_2R^{15}$. In some embodiments, each $R^{1b}$ is independently —$S(O)_2N(R^{12})(R^{13})$. In some embodiments, each $R^{1b}$ is independently —$S(=O)(=NH)N(R^{12})(R^{13})$. In some embodiments, each $R^{1b}$ is independently —$CH_2C(O)N(R^{12})(R^{13})$. In some embodiments, each $R^{1b}$ is independently —$CH_2N(R^{14})C(O)R^{15}$. In some embodiments, each $R^{1b}$ is independently —$CH_2S(O)_2R^{15}$. In some embodiments, each $R^{1b}$ is independently —$CH_2S(O)_2N(R^{12})(R^{13})$. In some embodiments, each $R^{1b}$ is independently $C_{1-6}$alkyl substituted with one, two, or three $R^{20q}$. In some embodiments, each $R^{1b}$ is independently $C_{2-6}$alkenyl substituted with one, two, or three $R^{20q}$. In some embodiments, each $R^{1b}$ is independently $C_{2-6}$alkynyl substituted with one, two, or three $R^{20q}$. In some embodiments, each $R^{1b}$ is independently $C_{3-10}$cycloalkyl substituted with one, two, or three $R^{20q}$. In some embodiments, each $R^{1b}$ is independently $C_{2-9}$heterocycloalkyl substituted with one, two, or three $R^{20q}$. In some embodiments, each $R^{1b}$ is independently $C_{6-10}$aryl substituted with one, two, or three $R^{20q}$. In some embodiments, each $R^{1b}$ is independently $C_{1-9}$heteroaryl substituted with one, two, or three $R^{20q}$. In embodiments, $R^{1b}$ is independently halogen. In embodiments, $R^{1b}$ is independently F. In embodiments, $R^{1b}$ is independently Cl. In embodiments, $R^{1b}$ is independently Br. In embodiments, $R^{1b}$ is independently I. In embodiments, $R^{1b}$ is independently $R^{1b}$ is independently oxo. In embodiments, $R^{1b}$ is independently —CN. In embodiments, $R^{1b}$ is independently $C_{1-6}$alkyl. In embodiments, $R^{1b}$ is independently methyl. In embodiments, $R^{1b}$ is independently ethyl. In embodiments, $R^{1b}$ is independently isopropyl. In embodiments, $R^{1b}$ is independently $C_{2-6}$alkenyl. In embodiments, $R^{1b}$ is independently $C_{2-6}$alkynyl. In embodiments, $R^{1b}$ is independently $C_{1-6}$haloalkyl. In embodiments, $R^{1b}$ is independently —$CF_3$. In embodiments, $R^{1b}$ is independently $C_{3-12}$cycloalkyl. In embodiments, $R^{1b}$ is independently $C_{2-11}$heterocycloalkyl. In embodiments, $R^{1b}$ is independently $C_{6-12}$aryl. In embodiments, $R^{1b}$ is independently $C_{1-11}$heteroaryl. In embodiments, $R^{1b}$ is independently —OH. In embodiments, $R^{1b}$ is independently —$OCH_3$. In embodiments, $R^{1b}$ is independently —SH. In embodiments, $R^{1b}$ is independently —$SCH_3$. In embodiments, $R^{1b}$ is independently —$N(CH_3)_2$. In embodiments, $R^{1b}$ is independently —$N(H)_2$. In embodiments, $R^{1b}$ is independently —C(O)OH. In embodiments, $R^{1b}$ is independently —$C(O)OCH_3$. In embodiments, $R^{1b}$ is independently —$OC(O)N(H)_2$. In embodiments, $R^{1b}$ is independently —$OC(O)N(CH_3)_2$. In embodiments, $R^{1b}$ is independently —$N(H)C(O)N(CH_3)_2$. In embodiments, $R^{1b}$ is independently —$N(H)C(O)N(H)_2$. In embodiments, $R^{1b}$ is independently —N(H)C(O)OH. In embodiments, $R^{1b}$ is independently —$N(H)C(O)OCH_3$. In embodiments, $R^{1b}$ is independently —$N(H)S(O)_2CH_3$. In embodiments, $R^{1b}$ is independently —$C(O)CH_3$. In embodiments, $R^{1b}$ is independently —C(O)H. In embodiments, $R^{1b}$ is independently —$S(O)CH_3$. In embodiments, $R^{1b}$ is independently —$OC(O)CH_3$. In embodiments, $R^{1b}$ is independently —OC(O)H. In embodiments, $R^{1b}$ is independently —$C(O)N(CH_3)_2$. In embodiments, $R^{1b}$ is independently —$C(O)C(O)N(CH_3)_2$. In embodiments, $R^{1b}$ is independently —N(H)C(O)H. In embodiments, $R^{1b}$ is independently -$N(H)C(O)CH_3$. In embodiments, $R^{1b}$ is independently —$S(O)_2CH_3$. In embodiments, $R^{1b}$ is independently —$S(O)_2N(H)_2$. In embodiments, $R^{1b}$ is independently —$S(O)_2N(CH_3)_2$. In embodiments, $R^{1b}$ is independently $S(=O)(=NH)N(H)_2$. In embodiments, $R^{1b}$ is independently $S(=O)(=NH)N(CH_3)_2$. In embodiments, $R^{1b}$ is independently —$CH_2C(O)N(H)_2$. In embodiments, $R^{1b}$ is independently —$CH_2C(O)N(CH_3)_2$. In embodiments, $R^{1b}$ is independently —$CH_2N(H)C(O)H$. In embodiments, $R^{1b}$ is independently —$CH_2N(H)C(O)CH_3$. In embodiments, $R^{1b}$ is independently —$CH_2S(O)_2H$. In embodiments, $R^{1b}$ is independently —$CH_2S(O)_2CH_3$. In embodiments, $R^{1b}$ is independently and —$CH_2S(O)_2N(CH_3)_2$. In embodiments, $R^{1b}$ is independently and —$CH_2S(O)_2N(H)_2$.

In some embodiments, each $R^{1d}$ is independently hydrogen. In some embodiments, each $R^{1d}$ is independently halogen. In some embodiments, each $R^{1d}$ is independently oxo. In some embodiments, each $R^{1d}$ is independently —CN. In some embodiments, each $R^{1d}$ is independently $C_{1-6}$alkyl. In some embodiments, each $R^{1d}$ is independently $C_{2-6}$alkenyl. In some embodiments, each $R^{1d}$ is independently $C_{2-6}$alkynyl. In some embodiments, each $R^{1d}$ is independently $C_{3-10}$cycloalkyl. In some embodiments, each $R^{1d}$ is independently $C_{1-9}$heterocycloalkyl. In some embodiments, each $R^{1d}$ is independently $C_{6-10}$aryl. In some embodiments, each $R^{1d}$ is independently $C_{1-9}$heteroaryl. In some embodiments, each $R^{1d}$ is independently —$OR^{12}$. In some embodiments, each $R^{1d}$ is independently —$SR^{12}$. In some embodiments, each $R^{1d}$ is independently —$N(R^{12})(R^{13})$. In some embodiments, each $R^{1d}$ is independently —$C(O)R^{12}$. In some embodiments, each $R^{1d}$ is independently —$OC(O)N(R^{12})(R^{13})$. In some embodiments, each $R^{1d}$ is independently —$N(R^{14})C(O)N(R^{12})(R^{13})$. In some embodiments, each $R^{1d}$ is independently —$N(R^{14})C(O)R^{15}$. In some embodiments, each $R^{1d}$ is independently —$N(R^{14})S(O)_2R^{15}$. In some embodiments, each $R^{1d}$ is independently —$C(O)R^{15}$. In some embodiments, each $R^{1d}$ is independently —$S(O)R^{15}$. In some embodiments, each $R^{1d}$ is independently —$OC(O)R^{15}$. In some embodiments, each $R^{1d}$ is independently —$C(O)N(R^{12})(R^{13})$. In some embodiments, each $R^{1d}$ is independently —$C(O)C(O)N(R^{12})(R^{13})$. In some embodiments, each $R^{1d}$ is independently —$N(R^{14})C(O)R^{15}$. In some embodiments, each $R^{1d}$ is independently —$C(O)C(O)N(R^{12})(R^{13})$. In some embodiments, each $R^{1d}$ is independently —$S(O)_2R^{15}$. In some embodiments, each $R^{1d}$ is independently —$S(O)_2N(R^{12})(R^{13})$. In some embodiments, each $R^{1d}$ is independently —$S(=O)(=NH)N(R^{12})(R^{13})$. In some embodiments, each $R^{1d}$ is independently —$CH_2C(O)N(R^{12})(R^{13})$. In some embodiments, each $R^{1d}$ is independently —$CH_2N(R^{14})C(O)R^{15}$. In some embodiments, each $R^{1d}$ is independently —$CH_2S(O)_2R^{15}$. In some embodiments, each $R^{1d}$ is independently —$CH_2S(O)_2N(R^{12})(R^{13})$. In some embodiments, each $R^{1d}$ is independently $C_{1-6}$alkyl substituted with one, two, or three $R^{20q}$. In some embodiments, each $R^{1d}$ is independently $C_{2-6}$alkenyl substituted with one, two, or three $R^{20q}$. In some embodiments, each $R^{1d}$ is independently $C_{2-6}$alkynyl substituted with one, two, or three $R^{20q}$. In some embodiments, each $R^{1d}$ is independently $C_{3-10}$cycloalkyl substituted with one, two, or three $R^{20q}$. In some embodiments, each $R^{1d}$ is independently $C_{1-9}$heterocycloalkyl substituted with one, two, or three $R^{20q}$. In some embodiments, each $R^{1d}$ is independently $C_{6-10}$aryl substituted with one, two, or three $R^{20q}$. In some embodiments, each $R^{1d}$ is independently $C_{1-9}$heteroaryl substituted with one, two, or three $R^{20q}$. In embodiments, $R^{1d}$ is independently halogen. In embodiments, $R^{1d}$ is independently F. In embodiments, $R^{1d}$ is independently Cl. In embodiments, $R^{1d}$ is independently Br. In embodiments, $R^{1d}$ is independently I. In embodiments, $R^{1d}$ is independently $R^{1d}$ is independently oxo. In embodiments, $R^{1d}$ is independently —CN. In embodiments, $R^{1d}$ is independently $C_{1-6}$alkyl. In embodiments, $R^{1d}$ is independently methyl. In embodiments, $R^{1d}$ is independently ethyl. In embodiments, $R^{1d}$ is independently isopropyl. In embodiments, $R^{1d}$ is independently $C_{2-6}$alkenyl. In embodiments, $R^{1d}$ is independently $C_{2-6}$alkynyl. In embodiments, $R^{1d}$ is independently $C_{1-6}$haloalkyl. In embodiments, $R^{1d}$ is independently —$CF_3$. In embodiments, $R^{1d}$ is independently $C_{3-12}$cycloalkyl. In embodiments, $R^{1d}$ is independently $C_{2-11}$heterocycloalkyl. In embodiments, $R^{1d}$ is independently $C_{6-12}$aryl. In embodiments, $R^{1d}$ is independently $C_{1-11}$heteroaryl. In embodiments, $R^{1d}$ is independently —OH. In embodiments, $R^{1d}$ is independently —$OCH_3$. In embodiments, $R^{1d}$ is independently —SH. In embodiments, $R^{1d}$ is independently —$SCH_3$. In embodiments, $R^{1d}$ is independently —N(CH$_3$)$_2$. In embodiments, $R^{1d}$ is independently —N(H)$_2$. In embodiments, $R^{1d}$ is independently —C(O)OH. In embodiments, $R^{1d}$ is independently —C(O)OCH$_3$. In embodiments, $R^{1d}$ is independently —OC(O)N(H)$_2$. In embodiments, $R^{1d}$ is independently —OC(O)N(CH$_3$)$_2$. In embodiments, $R^{1d}$ is independently —N(H)C(O)N(CH$_3$)$_2$. In embodiments, $R^{1d}$ is independently —N(H)C(O)N(H)$_2$. In embodiments, $R^{1d}$ is independently —N(H)C(O)OH. In embodiments, $R^{1d}$ is independently —N(H)C(O)OCH$_3$. In embodiments, $R^{1d}$ is independently —N(H)S(O)$_2$CH$_3$. In embodiments, $R^{1d}$ is independently —C(O)CH$_3$. In embodiments, $R^{1d}$ is independently —C(O)H. In embodiments, $R^{1d}$ is independently —S(O)CH$_3$. In embodiments, $R^{1d}$ is independently —OC(O)CH$_3$. In embodiments, $R^{1d}$ is independently —OC(O)H. In embodiments, $R^{1d}$ is independently —C(O)N(CH$_3$)$_2$. In embodiments, $R^{1d}$ is independently —C(O)C(O)N(CH$_3$)$_2$. In embodiments, $R^{1d}$ is independently —N(H)C(O)H. In embodiments, $R^{1d}$ is independently —N(H)C(O)CH$_3$. In embodiments, $R^{1d}$ is independently —S(O)$_2$CH$_3$. In embodiments, $R^{1d}$ is independently —S(O)$_2$N(H)$_2$. In embodiments, $R^{1d}$ is independently —S(O)$_2$N(CH$_3$)$_2$. In embodiments, $R^{1d}$ is independently S(=O)(=NH)N(H)$_2$. In embodiments, $R^{1d}$ is independently S(=O)(=NH)N(CH$_3$)$_2$. In embodiments, $R^{1d}$ is independently —CH$_2$C(O)N(H)$_2$. In embodiments, $R^{1d}$ is independently —CH$_2$C(O)N(CH$_3$)$_2$. In embodiments, $R^{1d}$ is independently —CH$_2$N(H)C(O)H. In embodiments, $R^{1d}$ is independently —CH$_2$N(H)C(O)CH$_3$. In embodiments, $R^{1d}$ is independently —CH$_2$S(O)$_2$H. In embodiments, $R^{1d}$ is independently —CH$_2$S(O)$_2$CH$_3$. In embodiments, $R^{1d}$ is independently and —CH$_2$S(O)$_2$N(CH$_3$)$_2$. In embodiments, $R^{1d}$ is independently and —CH$_2$S(O)$_2$N(H)$_2$.

In some embodiments, each $R^{1h}$ is independently hydrogen. In some embodiments, each $R^{1h}$ is independently halogen. In some embodiments, each $R^{1h}$ is independently oxo. In some embodiments, each $R^{1h}$ is independently —CN. In some embodiments, each $R^{1h}$ is independently $C_{1-6}$alkyl. In some embodiments, each $R^{1h}$ is independently $C_{2-6}$alkenyl. In some embodiments, each $R^{1h}$ is independently $C_{2-6}$alkynyl. In some embodiments, each $R^{1h}$ is independently $C_{3-10}$cycloalkyl. In some embodiments, each $R^{1h}$ is independently $C_{2-9}$heterocycloalkyl. In some embodiments, each $R^{1h}$ is independently $C_{6-10}$aryl. In some embodiments, each $R^{1h}$ is independently $C_{1-9}$heteroaryl. In some embodiments, each $R^{1h}$ is independently —OR$^{12}$. In some embodiments, each $R^{1h}$ is independently —SR$^{12}$. In some embodiments, each $R^{1h}$ is independently —N(R$^{12}$)(R$^{13}$). In some embodiments, each $R^{1h}$ is independently —C(O)R$^{12}$. In some embodiments, each $R^{1h}$ is independently —OC(O)N(R$^{12}$)(R$^{13}$). In some embodiments, each $R^{1h}$ is independently —N(R$^{14}$)C(O)N(R$^{12}$)(R$^{13}$). In some embodiments, each $R^{1h}$ is independently —N(R$^{14}$)C(O)R$^{15}$. In some embodiments, each $R^{1h}$ is independently —N(R$^{14}$)S(O)$_2$R$^{15}$. In some embodiments, each $R^{1h}$ is independently —C(O)R$^{15}$. In some embodiments, each $R^{1h}$ is independently —S(O)R$^{15}$. In some embodiments, each $R^{1h}$ is independently —OC(O)R$^{15}$. In some embodiments, each $R^{1h}$ is independently —C(O)N(R$^{12}$)(R$^{13}$). In some embodiments, each $R^{1h}$ is independently —C(O)C(O)N(R$^{12}$)(R$^{13}$). In some embodiments, each $R^{1h}$ is independently —N(R$^{14}$)C(O)R$^{15}$. In some embodiments, each $R^{1h}$ is independently —C(O)C(O)N(R$^{12}$)(R$^{13}$). In some embodiments, each $R^{1h}$ is independently —S(O)$_2$R$^{15}$. In some embodiments, each $R^{1h}$ is independently —S(O)$_2$N(R$^{12}$)(R$^{13}$). In some embodiments, each $R^{1h}$ is independently —S(=O)(=NH)N(R$^{12}$)(R$^{13}$). In some embodiments, each $R^{1h}$ is independently —CH$_2$C(O)N(R$^{12}$)(R$^{13}$). In some embodiments, each $R^{1h}$ is independently —CH$_2$N(R$^{14}$)C(O)R$^{15}$. In some embodiments, each $R^{1h}$ is independently —CH$_2$S(O)$_2$R$^{15}$. In some embodiments, each $R^{1h}$ is independently —CH$_2$S(O)$_2$N(R$^{12}$)(R$^{13}$). In some embodiments, each $R^{1h}$ is independently $C_{1-6}$alkyl substituted with one, two, or three $R^{20q}$. In some embodiments, each $R^{1h}$ is independently $C_{2-6}$alkenyl substituted with one, two, or three $R^{20q}$. In some embodiments, each $R^{1h}$ is independently $C_{2-6}$alkynyl substituted with one, two, or three $R^{20q}$. In some embodiments, each $R^{1h}$ is independently $C_{3-10}$cycloalkyl substituted with one, two, or three $R^{20q}$. In some embodiments, each $R^{1h}$ is independently $C_{1-9}$heterocycloalkyl substituted with one, two, or three $R^{20q}$. In some embodiments, each $R^{1h}$ is independently $C_{6-10}$aryl substituted with one, two, or three $R^{20q}$. In some embodiments, each $R^{1h}$ is independently $C_{1-9}$heteroaryl substituted with one, two, or three $R^{20q}$. In embodiments, $R^{1h}$ is independently halogen. In embodiments, $R^{1h}$ is independently F. In embodiments, $R^{1h}$ is independently Cl. In embodiments, $R^{1h}$ is independently Br. In embodiments, $R^{1h}$ is independently I. In embodiments, $R^{1h}$ is independently $R^{1h}$ is independently oxo. In embodiments, $R^{1h}$ is independently —CN. In embodiments, $R^{1h}$ is independently $C_{1-6}$alkyl. In embodiments, $R^{1h}$ is independently methyl. In embodiments, $R^{1h}$ is independently ethyl. In embodiments, $R^{1h}$ is independently isopropyl. In embodiments, $R^{1h}$ is independently $C_{2-6}$alkenyl. In embodiments, $R^{1h}$ is independently $C_{2-6}$alkynyl. In embodiments, $R^{1h}$ is independently $C_{1-6}$haloalkyl. In embodiments, $R^{1h}$ is independently —CF$_3$. In embodiments, $R^{1h}$ is independently $C_{3-12}$cycloalkyl. In embodiments, $R^{1h}$ is independently $C_{2-11}$heterocycloalkyl. In embodiments, $R^{1h}$ is independently $C_{6-12}$aryl. In embodiments, $R^{1h}$ is independently $C_{1-11}$heteroaryl. In embodiments, $R^{1h}$ is independently —OH. In embodiments, $R^{1h}$ is independently —OCH$_3$. In embodiments, $R^{1h}$ is independently —SH. In embodiments, $R^{1h}$ is independently —SCH$_3$. In embodiments, $R^{1h}$ is independently —N(CH$_3$)$_2$. In embodiments, $R^{1h}$ is independently —N(H)$_2$. In embodiments, $R^{1h}$ is independently —C(O)OH. In embodiments, $R^{1h}$ is independently —C(O)OCH$_3$. In embodiments, $R^{1h}$ is independently —OC(O)N(H)$_2$. In embodiments, $R^{1h}$ is independently —OC(O)N(CH$_3$)$_2$. In embodiments, $R^{1h}$ is independently —N(H)C(O)N(CH$_3$)$_2$. In embodiments, $R^{1h}$ is independently —N(H)C(O)N(H)$_2$. In embodiments, $R^{1h}$ is independently —N(H)C(O)OH. In embodiments, $R^{1h}$ is independently —N(H)C(O)OCH$_3$. In embodiments, $R^{1h}$ is independently —N(H)S(O)$_2$CH$_3$. In embodiments, $R^{1h}$ is independently —C(O)CH$_3$. In embodiments, $R^{1h}$ is independently —C(O)H. In embodiments, $R^{1h}$ is independently —S(O)CH$_3$. In embodiments, $R^{1h}$ is independently —OC(O)CH$_3$. In embodiments, $R^{1h}$ is independently —OC(O)H. In embodiments, $R^{1h}$ is independently —C(O)N(CH$_3$)$_2$. In embodiments, $R^{1h}$ is independently —C(O)C(O)N(CH$_3$)$_2$. In embodiments, $R^{1h}$ is independently —N(H)C(O)H. In embodiments, $R^{1h}$ is independently —N(H)C(O)CH$_3$. In embodiments, $R^{1h}$ is independently —S(O)$_2$CH$_3$. In embodiments, $R^{1h}$ is independently —S(O)$_2$N(H)$_2$. In embodiments, $R^{1h}$ is independently —S(O)$_2$N(CH$_3$)$_2$. In embodiments, $R^{1h}$ is independently S(=O)(=NH)N(H)$_2$. In embodiments, $R^{1h}$ is independently S(=O)(=NH)N(CH$_3$)$_2$. In embodiments, $R^{1h}$ is independently —CH$_2$C(O)N(H)$_2$. In embodiments, $R^{1h}$ is independently —CH$_2$C(O)N(CH$_3$)$_2$. In embodiments, $R^{1h}$ is independently —CH$_2$N(H)C(O)H. In embodiments, $R^{1h}$ is independently —CH$_2$N(H)C(O)CH$_3$. In embodiments, $R^{1h}$ is independently —CH$_2$S(O)$_2$H. In embodiments, $R^{1h}$ is independently —CH$_2$S(O)$_2$CH$_3$. In embodiments, $R^{1h}$ is independently and —CH$_2$S(O)$_2$N(CH$_3$)$_2$. In embodiments, R$^{1h}$ is independently and —CH$_2$S(O)$_2$N(H)$_2$.

In some embodiments, each R$^{1c}$ is independently hydrogen. In some embodiments, each R$^{1c}$ is independently C$_{1-6}$alkyl. In some embodiments, each R$^{1c}$ is independently C$_{2-6}$alkenyl. In some embodiments, each R$^{1c}$ is independently C$_{2-6}$alkynyl. In some embodiments, each R$^{1c}$ is independently C$_{3-10}$cycloalkyl. In some embodiments, each R$^{1c}$ is independently C$_{1-9}$heterocycloalkyl. In some embodiments, each R$^{1c}$ is independently C$_{6-10}$aryl. In some embodiments, each R$^{1c}$ is independently C$_{1-9}$heteroaryl. In some embodiments, each R$^{1c}$ is independently C$_{1-6}$alkyl substituted with one, two, or three R$^{20q}$. In some embodiments, each R$^{1c}$ is independently C$_{2-6}$alkenyl substituted with one, two, or three R$^{20q}$. In some embodiments, each R$^{1c}$ is independently C$_{2-6}$alkynyl substituted with one, two, or three R$^{20q}$. In some embodiments, each R$^{1c}$ is independently C$_{3-10}$cycloalkyl substituted with one, two, or three R$^{20q}$. In some embodiments, each R$^{1c}$ is independently C$_{2-9}$heterocycloalkyl substituted with one, two, or three R$^{20q}$. In some embodiments, each R$^{1c}$ is independently C$_{6-10}$aryl substituted with one, two, or three R$^{20q}$. In some embodiments, each R$^{1c}$ is independently C$_{1-9}$heteroaryl substituted with one, two, or three R$^{20q}$. In embodiments, R$^{1c}$ is independently C$_{1-6}$alkyl. In embodiments, R$^{1c}$ is independently methyl. In embodiments, R$^{1c}$ is independently ethyl. In embodiments, R$^{1c}$ is independently isopropyl. In embodiments, R$^{1c}$ is independently C$_{2-6}$alkenyl. In embodiments, R$^{1c}$ is independently C$_{2-6}$alkynyl. In embodiments, R$^{1c}$ is independently C$_{1-6}$haloalkyl. In embodiments, R$^{1c}$ is independently —CF$_3$. In embodiments, R$^{1c}$ is independently C$_{3-12}$cycloalkyl. In embodiments, R$^{1c}$ is independently C$_{2-11}$heterocycloalkyl. In embodiments, R$^{1c}$ is independently C$_{6-12}$aryl. In embodiments, R$^{1c}$ is independently C$_{1-11}$heteroaryl.

In embodiments, R$^{1a}$ and R$^{1b}$ bonded to the same carbon are joined to form a 4-7 membered heterocycloalkyl ring or a C$_{4-7}$cycloalkyl ring, wherein the 4-7 membered heterocycloalkyl ring or C$_{4-7}$cycloalkyl ring are optionally substituted with one, two, or three R$^{20q}$. In embodiments, two R$^{1a}$ bonded to adjacent atoms are joined to form a 4-7 membered heterocycloalkyl ring, a phenyl ring, a 5-6 membered heteroaryl ring, or a C$_{4-7}$cycloalkyl ring, wherein the 4-7 membered heterocycloalkyl ring, phenyl ring, 5-6 membered heteroaryl ring, or C$_{4-7}$cycloalkyl ring are optionally substituted with one, two, or three R$^{20q}$. In embodiments, R$^{1h}$ and one of R$^{1a}$, R$^{1b}$, R$^{1c}$, and R$^{1d}$ bonded to adjacent atoms are joined to form a 4-7 membered heterocycloalkyl ring, a phenyl ring, a 5-6 membered heteroaryl ring, or a C$_{4-7}$cycloalkyl ring, wherein the 4-7 membered heterocycloalkyl ring, phenyl ring, 5-6 membered heteroaryl ring, or C$_{4-7}$cycloalkyl ring are optionally substituted with one, two, or three R$^{20q}$.

In embodiments, R$^{17}$ is selected from:

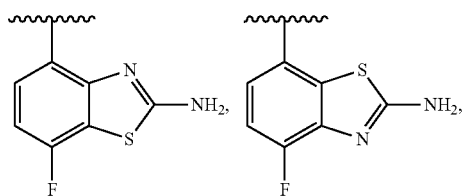

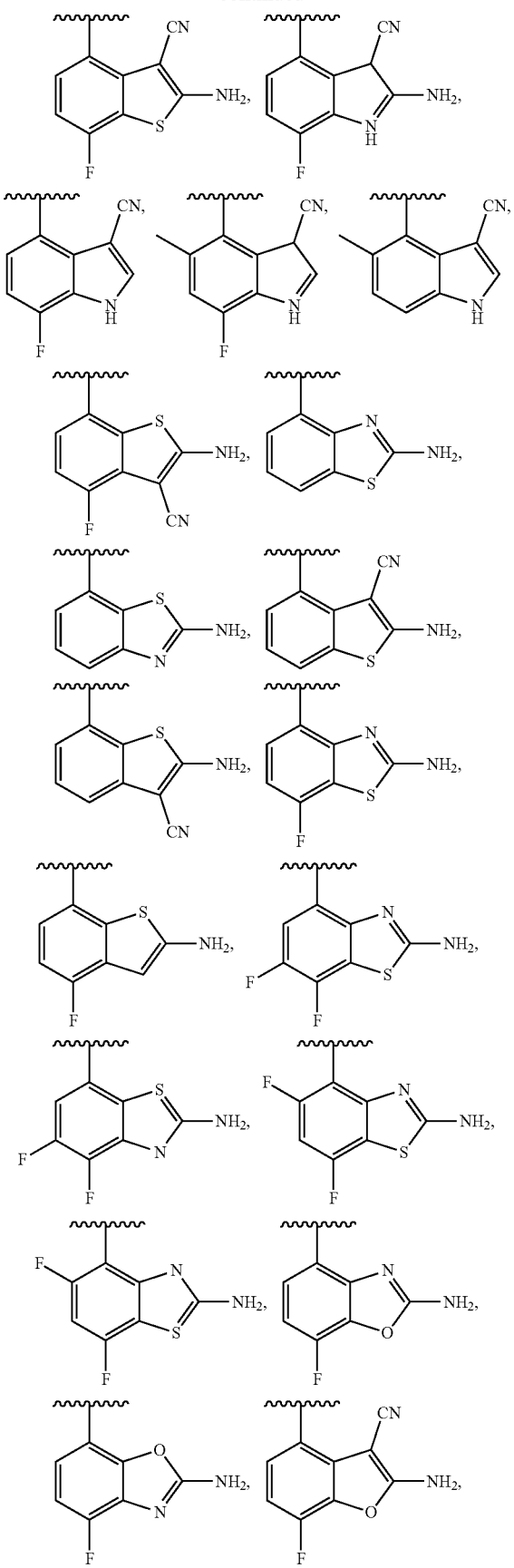

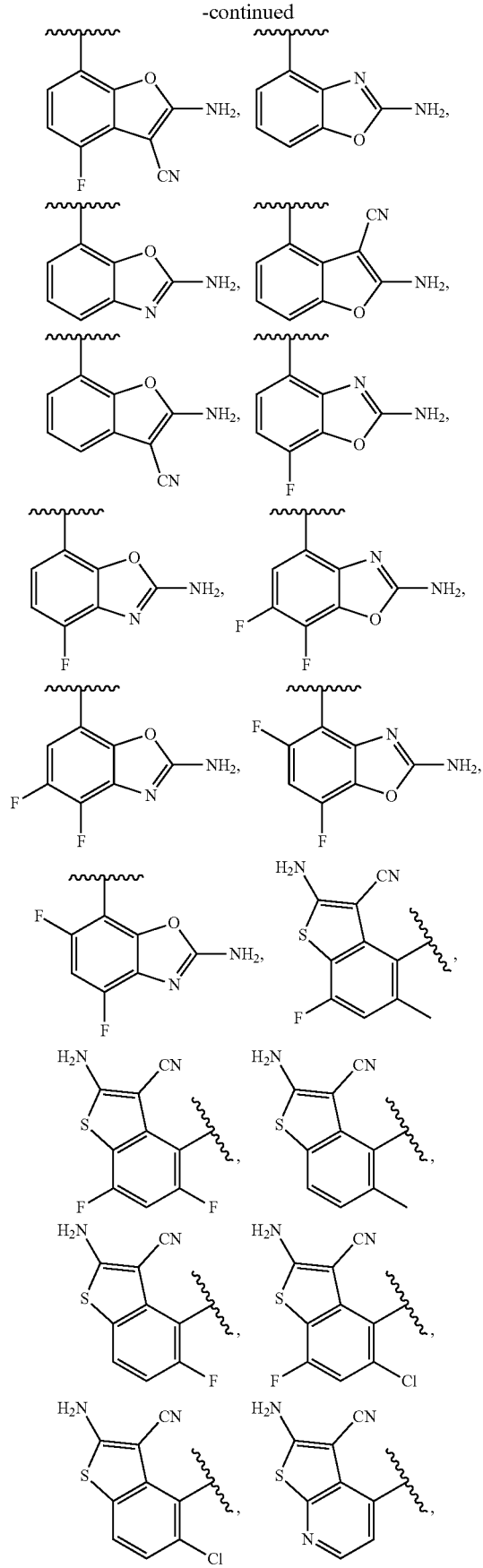
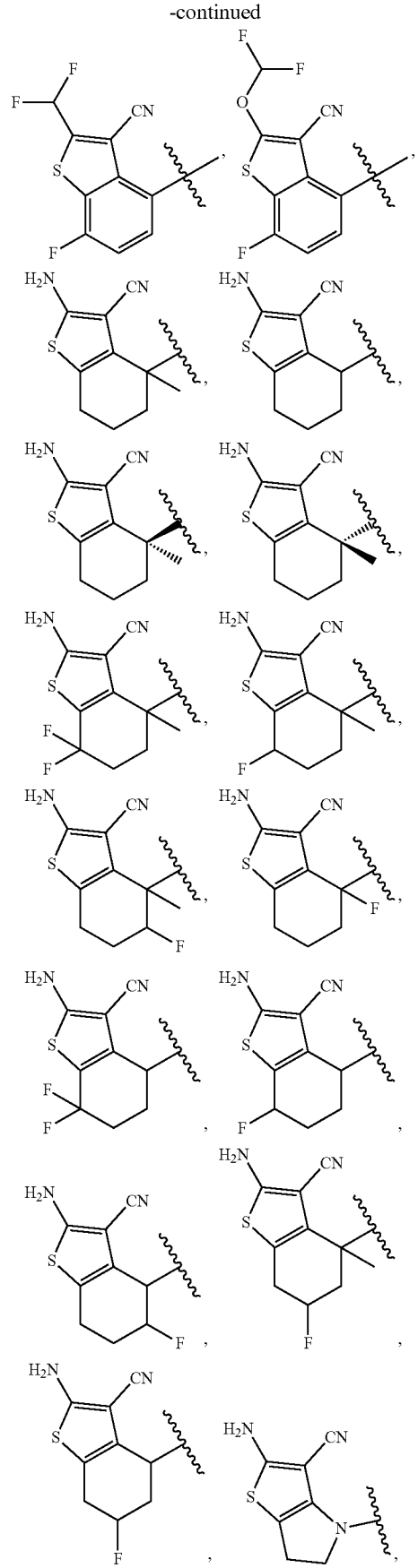

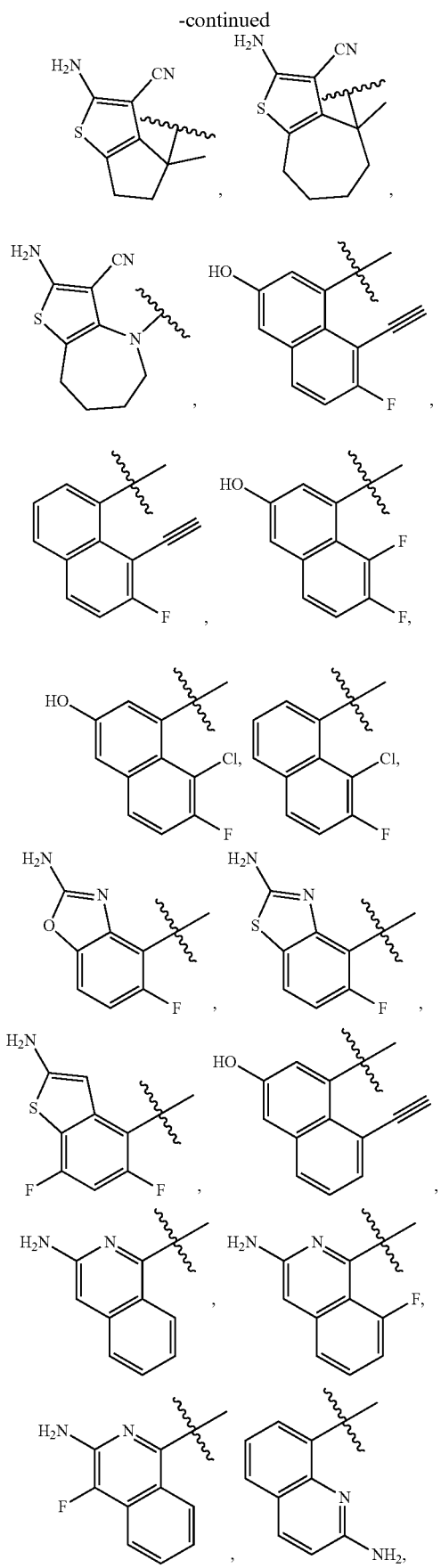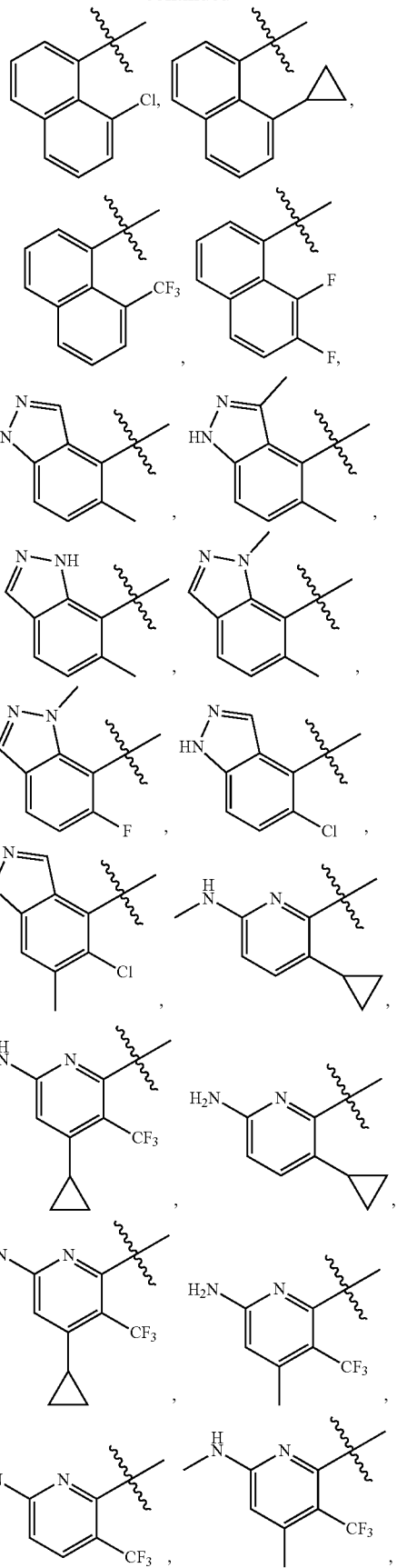

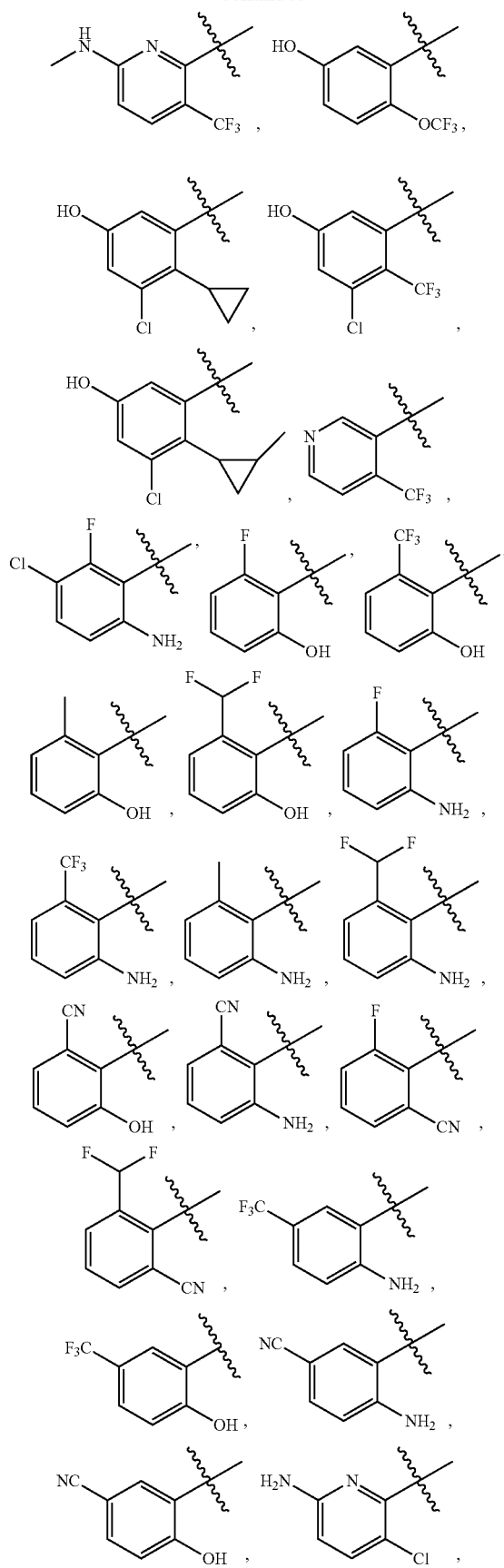
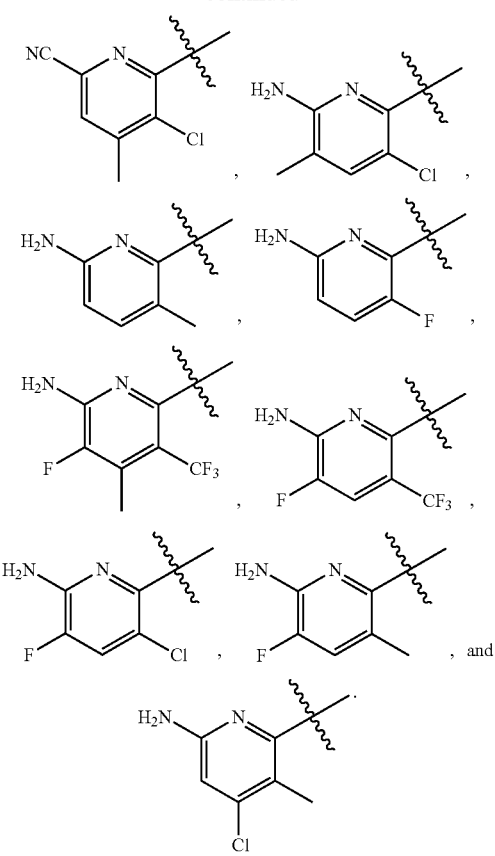
In embodiments, $L^7$ is a bond and $R^{7a}$ and $R^{17}$, together with the carbon to which they are attached, form $C_{3-10}$cycloalkyl or 3-10 membered heterocycloalkyl, wherein the $C_{3-10}$cycloalkyl and 3-10 membered heterocycloalkyl are optionally substituted with one or more $R^{20q}$. In embodiments,
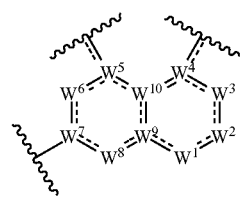
is selected from
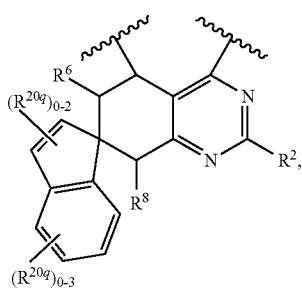

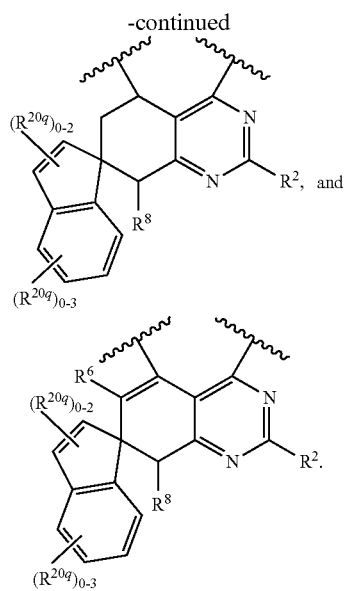

In embodiments, $R^2$ is independently hydrogen. In embodiments, $R^2$ is independently halogen. In embodiments, $R^2$ is independently —CN. In embodiments, $R^2$ is independently —$OR^{12aa}$. In embodiments, $R^2$ is independently —$SR^{12a}$. In embodiments, $R^2$ is independently —$N(R^{12a})(R^{13})$. In embodiments, $R^2$ is independently —$C(O)R^{12}$. In embodiments, $R^2$ is independently —$OC(O)N(R^{12})(R^{13})$. In embodiments, $R^2$ is independently —$N(R^{14})C(O)N(R^{12})(R^{13})$. In embodiments, $R^2$ is independently —$N(R^{14})C(O)OR^{15}$. In embodiments, $R^2$ is independently —$N(R^{14})S(O)_2R^{15}$. In embodiments, $R^2$ is independently —$C(O)R^{15}$. In embodiments, $R^2$ is independently —$S(O)R^{15}$. In embodiments, $R^2$ is independently —$OC(O)R^{15}$. In embodiments, $R^2$ is independently —$C(O)N(R^{12})(R^{13})$. In embodiments, $R^2$ is independently —$C(O)C(O)N(R^{12})(R^{13})$. In embodiments, $R^2$ is independently —$N(R^{14})C(O)R^{15}$. In embodiments, $R^2$ is independently —$S(O)_2R^{15}$. In embodiments, $R^2$ is independently —$S(O)_2N(R^{12})(R^{13})$—. In embodiments, $R^2$ is independently —$S(=O)(=NH)N(R^{12})(R^{13})$. In embodiments, $R^2$ is independently —$CH_2C(O)N(R^{12})(R^{13})$. In embodiments, $R^2$ is independently —$CH_2N(R^{14})C(O)R^{15}$. In embodiments, $R^2$ is independently —$CH_2S(O)_2R^{15}$. In embodiments, $R^2$ is independently —$CH_2S(O)_2N(R^{12})(R^{13})$.

In embodiments, $R^2$ is independently —$R^{12a}$. In embodiments, $R^2$ is independently —$SR^{12a}$. In embodiments, $R^2$ is independently —$N(R^{12a})(R^{13})$.

In select embodiments of the compound, $R^2$ is independently $C_{1-6}$alkyl optionally substituted with one, two, or three $R^{20b}$. In some embodiments, $R^2$ is independently $C_{2-6}$alkenyl optionally substituted with one, two, or three $R^{20b}$. In some embodiments, $R^2$ is independently $C_{2-6}$alkynyl optionally substituted with one, two, or three $R^{20b}$. In some embodiments, $R^2$ is independently $C_{3-10}$cycloalkyl optionally substituted with one, two, or three $R^{20b}$. In some embodiments, $R^2$ is independently $C_{1-9}$heterocycloalkyl optionally substituted with one, two, or three $R^{20b}$. In some embodiments, $R^2$ is independently $C_{6-10}$aryl optionally substituted with one, two, or three $R^{20b}$. In some embodiments, $R^2$ is independently $C_{1-9}$heteroaryl optionally substituted with one, two, or three $R^{20b}$. In additional embodiments, $R^2$ is independently hydrogen.

In some embodiments, $R^2$ is independently $C_{1-9}$heterocycloalkyl optionally substituted with one, two, or three $R^{20b}$. In some embodiments, $R^2$ is independently (monocyclic $C_{2-8}$heterocycloalkyl) optionally substituted with one, two, or three $R^{20b}$. In some embodiments, $R^2$ is independently (monocyclic $C_{3-5}$heterocycloalkyl) optionally substituted with one, two, or three $R^{20b}$. In some embodiments, $R^2$ is independently (spirocyclic $C_{1-9}$heterocycloalkyl) optionally substituted with one, two, or three $R^{20b}$. In some embodiments, $R^2$ is independently (spirocyclic $C_{3-9}$heterocycloalkyl) optionally substituted with one, two, or three $R^{20b}$. In some embodiments, $R^2$ is independently (fused $C_{1-9}$heterocycloalkyl) optionally substituted with one, two, or three $R^{20b}$. In some embodiments, $R^2$ is independently (spirocyclic $C_{6-8}$heterocycloalkyl) optionally substituted with one, two, or three $R^{20b}$.

In embodiments of the compound, $R^2$ is independently methyl optionally substituted with one or two $R^{20b}$. In further embodiments of the compound, $R^2$ is independently methyl. In some embodiments of the compound, $R^2$ is independently ethyl optionally substituted with one, two, or three $R^{20b}$. In embodiments of the compound, $R^2$ is independently ethyl. In some embodiments of the compound, $R^2$ is independently propyl optionally substituted with one, two, or three $R^{20b}$. In embodiments of the compound, $R^2$ is independently propyl.

In embodiments, $R^2$ is independently

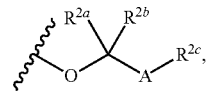

wherein: $R^{2a}$ and $R^{2b}$ are independently selected from hydrogen, halogen, and $C_{1-3}$alkyl; A is selected from a bond, $C(CH_3)_2$, $C_{3-10}$cycloalkyl, and $C_{2-9}$heterocycloalkyl, wherein $C_{3-10}$cycloalkyl and $C_{2-9}$heterocycloalkyl are optionally substituted with one, two, or three substituents selected from halogen, $C_{1-3}$alkyl, $C_{1-3}$haloalkyl, —OH, and $C_{1-3}$alkyl-OH; and $R^{2c}$ is independently selected from hydrogen, halogen, $C_{1-6}$alkyl, $C_{2-6}$alkenyl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$, and —$S(=O)(=NH)N(R^{12})(R^{13})$, wherein $C_{1-6}$alkyl and $C_{2-6}$alkenyl are optionally substituted with one, two, or three substituents selected from halogen, $C_{3-10}$cycloalkyl, $C_{2-9}$heterocycloalkyl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$, and —$S(=O)(=NH)N(R^{12})(R^{13})$. In some embodiments, $R^{2a}$ and $R^{2b}$ are each hydrogen; A is selected from a bond, $C(CH_3)_2$, $C_{3-6}$cycloalkyl, and $C_{2-9}$heterocycloalkyl, wherein $C_{3-6}$cycloalkyl and $C_{2-9}$heterocycloalkyl are optionally substituted with one, two, or three substituents selected from halogen, $C_{1-3}$alkyl, —OH, and $C_{1-3}$alkyl-OH; and $R^{2c}$ is independently selected from hydrogen, halogen, and $C_{1-6}$alkyl, wherein $C_{1-6}$alkyl is optionally substituted with halogen, —$OR^{12}$, —$N(R^{12})(R^{13})$, —$OC(O)N(R^{12})(R^{13})$, —$N(R^{14})C(O)N(R^{12})(R^{13})$, —$C(O)N(R^{12})(R^{13})$, —$S(O)_2N(R^{12})(R^{13})$, or —$S(=O)(=NH)N(R^{12})(R^{13})$.

In embodiments, $R^2$ is independently

[structure: wavy-O-CH(CH3)-pyrrolidine with N-methyl]

In embodiments, $R^2$ is independently

[structure: wavy-O-CH2-pyrrolizidine with F substituent]

In embodiments, $R^2$ is independently —$OR^{12a}$.

In some embodiments, $R^{12a}$ is independently hydrogen. In some embodiments, $R^{12a}$ is independently $C_{1-6}$alkyl. In some embodiments, $R^{12a}$ is independently $C_{2-6}$alkenyl. In some embodiments, $R^{12a}$ is independently $C_{2-6}$alkynyl. In some embodiments, $R^{12a}$ is independently $C_{3-10}$cycloalkyl. In some embodiments, $R^{12a}$ is independently —$C(R^{12c})_2$-$C_{3-10}$cycloalkyl. In some embodiments, $R^{12a}$ is independently $C_{1-9}$heterocycloalkyl. In some embodiments, $R^{12a}$ is independently —$C(R^{12c})_2$-$C_{1-9}$heterocycloalkyl. In some embodiments, $R^{12a}$ is independently $C_{6-10}$aryl. In some embodiments, $R^{12a}$ is independently —$C(R^{12c})_2$-$C_{6-10}$aryl. In some embodiments, $R^{12a}$ is independently —$C(R^{12c})_2$-$C_{1-9}$heteroaryl. In some embodiments, $R^{12a}$ is independently $C_{1-9}$heteroaryl.

In some embodiments, $R^{12a}$ is independently $C_{1-6}$alkyl optionally substituted with one, two, or three $R^{20l}$. In some embodiments, $R^{12a}$ is independently $C_{2-6}$alkenyl optionally substituted with one, two, or three $R^{20l}$. In some embodiments, $R^{12a}$ is independently $C_{2-6}$alkynyl optionally substituted with one, two, or three $R^{20l}$. In some embodiments, $R^{12a}$ is independently $C_{3-10}$cycloalkyl optionally substituted with one, two, or three $R^{20l}$. In some embodiments, $R^{12a}$ is independently —$C(R^{12c})_2$-$C_{3-10}$cycloalkyl optionally substituted with one, two, or three $R^{20l}$. In some embodiments, $R^{12a}$ is independently $C_{1-9}$heterocycloalkyl optionally substituted with one, two, or three $R^{20l}$. In some embodiments, $R^{12a}$ is independently —$C(R^{12c})_2$-$C_{1-9}$heterocycloalkyl optionally substituted with one, two, or three $R^{20l}$. In some embodiments, $R^{12a}$ is independently $C_{6-10}$aryl optionally substituted with one, two, or three $R^{20l}$. In some embodiments, $R^{12a}$ is independently —$C(R^{12c})_2$-$C_{6-10}$aryl optionally substituted with one, two, or three $R^{20l}$. In some embodiments, $R^{12a}$ is independently —$C(R^{12c})_2$-$C_{1-9}$heteroaryl optionally substituted with one, two, or three $R^{20l}$. In some embodiments, $R^{12a}$ is independently $C_{1-9}$heteroaryl optionally substituted with one, two, or three $R^{20l}$.

In some embodiments, $R^2$ is independently In some embodiments, $R^{12a}$ is independently $C_{3-10}$cycloalkyl optionally substituted with one, two, or three $R^{20l}$. In some embodiments, $R^{12a}$ is independently —$CH_2$-$C_{3-10}$cycloalkyl optionally substituted with one, two, or three $R^{20l}$. In some embodiments, $R^{12a}$ is independently $C_{2-9}$heterocycloalkyl optionally substituted with one, two, or three $R^{20l}$. In some embodiments, $R^{12a}$ is independently —$CH_2$-$C_{1-9}$heterocycloalkyl optionally substituted with one, two, or three $R^{20l}$. In some embodiments, $R^{12a}$ is independently $C_{6-10}$aryl optionally substituted with one, two, or three $R^{20l}$. In some embodiments, $R^{12a}$ is independently —$CH_2$-$C_{6-10}$aryl optionally substituted with one, two, or three $R^{20l}$. In some embodiments, $R^{12a}$ is independently —$CH_2$-$C_{1-9}$heteroaryl optionally substituted with one, two, or three $R^{20l}$. In some embodiments, $R^{12a}$ is independently $C_{1-9}$heteroaryl optionally substituted with one, two, or three $R^{20l}$. In additional embodiments, $R^{12a}$ is independently hydrogen.

In some embodiments, $R^{12a}$ is independently $C_{2-9}$heterocycloalkyl optionally substituted with one, two, or three $R^{20l}$. In some embodiments, $R^{12a}$ is independently (monocyclic $C_{2-8}$heterocycloalkyl) optionally substituted with one, two, or three $R^{20l}$. In some embodiments, $R^{12a}$ is independently (monocyclic $C_{3-5}$heterocycloalkyl) optionally substituted with one, two, or three $R^{20l}$. In some embodiments, $R^{12a}$ is independently (spirocyclic $C_{2-11}$heterocycloalkyl) optionally substituted with one, two, or three $R^{20l}$. In some embodiments, $R^{12a}$ is independently (spirocyclic $C_{3-11}$heterocycloalkyl) optionally substituted with one, two, or three $R^{20l}$. In some embodiments, $R^{12a}$ is independently (fused $C_{2-11}$heterocycloalkyl) optionally substituted with one, two, or three $R^{20l}$. In some embodiments, $R^{12a}$ is independently (spirocyclic $C_{6-8}$heterocycloalkyl) optionally substituted with one, two, or three $R^{20l}$.

In some embodiments, $R^{12a}$ is independently —$CH_2$-$C_{1-9}$heterocycloalkyl optionally substituted with one, two, or three $R^{20l}$. In some embodiments, $R^{12a}$ is independently —$CH_2$-(monocyclic $C_{2-8}$heterocycloalkyl) optionally substituted with one, two, or three $R^{20l}$. In some embodiments, $R^{12a}$ is independently —$CH_2$-(monocyclic $C_{3-5}$heterocycloalkyl) optionally substituted with one, two, or three $R^{20l}$. In some embodiments, $R^{12a}$ is independently —$CH_2$-(spirocyclic $C_{2-11}$heterocycloalkyl) optionally substituted with one, two, or three $R^{20l}$. In some embodiments, $R^{12a}$ is independently —$CH_2$-(spirocyclic $C_{3-11}$heterocycloalkyl) optionally substituted with one, two, or three $R^{20l}$. In some embodiments, $R^{12a}$ is independently —$CH_2$-(fused $C_{2-11}$heterocycloalkyl) optionally substituted with one, two, or three $R^{20l}$. In some embodiments, $R^{12a}$ is independently —$CH_2$-(spirocyclic $C_{6-8}$heterocycloalkyl) optionally substituted with one, two, or three $R^{20l}$.

In some embodiments, $R^{12a}$ is independently $C_{3-10}$cycloalkyl. In some embodiments, $R^{12a}$ is independently -$C_{1-6}$alkyl-$C_{3-10}$cycloalkyl. In some embodiments, $R^{12a}$ is independently -$C_{2-6}$alkenyl-$C_{3-10}$cycloalkyl. In some embodiments, $R^{12a}$ is independently -$C_{2-6}$alkynyl-$C_{3-10}$cycloalkyl. In some embodiments, $R^{12a}$ is independently —$C(R^{12c})_2$-$C_{3-10}$cycloalkyl. In some embodiments, $R^{12a}$ is independently $C_{2-9}$heterocycloalkyl. In some embodiments, $R^{12a}$ is independently -$C_{1-6}$alkyl-$C_{1-9}$heterocycloalkyl. In some embodiments, $R^{12a}$ is independently -$C_{2-6}$alkenyl-$C_{1-9}$heterocycloalkyl. In some embodiments, $R^{12a}$ is independently -$C_{2-6}$alkynyl-$C_{2-9}$heterocycloalkyl. In some embodiments, $R^{12a}$ is independently —$C(R^{12c})_2$-$C_{1-9}$heterocycloalkyl. In some embodiments, $R^{12a}$ is independently —$C(R^{12c})_2$-$C_{6-10}$aryl. In some embodiments, $R^{12a}$ is independently -$C_{1-6}$alkyl-$C_{6-10}$aryl. In some embodiments, $R^{12a}$ is independently -$C_{2-6}$alkenyl-$C_{6-10}$aryl. In some embodiments, $R^{12a}$ is independently -$C_{2-6}$alkynyl-$C_{6-10}$aryl. In some embodiments, $R^{12a}$ is independently and $C_{6-10}$aryl. In some embodiments, $R^{12a}$ is independently —$C(R^{12c})_2$-$C_{1-9}$heteroaryl. In some embodiments, $R^{12a}$ is independently -$C_{1-6}$alkyl-$C_{1-9}$heteroaryl. In some embodiments, $R^{12a}$ is independently -$C_{2-6}$alkenyl-$C_{1-9}$heteroaryl. In some embodiments, $R^{12a}$ is independently -$C_{2-6}$alkynyl-$C_{1-9}$heteroaryl. In some embodiments, $R^{12a}$ is independently $C_{1-9}$heteroaryl. In some embodiments, $R^{12a}$ is independently $C_{3-10}$cycloalkyl optionally substituted with one, two, or three $R^{20l}$. In some embodiments, $R^{12a}$ is independently -$C_{1-6}$alkyl-$C_{3-10}$cycloalkyl optionally substituted with one, two, or three $R^{20l}$. In some embodiments, $R^{12a}$ is independently -$C_{2-6}$alkenyl-$C_{3-10}$cycloalkyl optionally substituted with one, two, or three $R^{20l}$. In some embodiments, $R^{12a}$ is independently -$C_{2-6}$alkynyl-$C_{3-10}$cycloalkyl optionally substituted with one, two, or three $R^{20l}$. In some embodiments, $R^{12a}$ is independently —C($R^{12c}$)$_2$-$C_{3-10}$cycloalkyl optionally substituted with one, two, or three $R^{20l}$. In some embodiments, $R^{12a}$ is independently $C_{1-9}$heterocycloalkyl optionally substituted with one, two, or three $R^{20l}$. In some embodiments, $R^{12a}$ is independently -$C_{1-6}$alkyl-$C_{1-9}$heterocycloalkyl optionally substituted with one, two, or three $R^{20l}$. In some embodiments, $R^{12a}$ is independently -$C_{2-6}$alkenyl-$C_{2-9}$heterocycloalkyl optionally substituted with one, two, or three $R^{20l}$. In some embodiments, $R^{12a}$ is independently -$C_{2-6}$alkynyl-$C_{2-9}$heterocycloalkyl optionally substituted with one, two, or three $R^{20l}$. In some embodiments, $R^{12a}$ is independently —C($R^{12c}$)$_2$-$C_{2-9}$heterocycloalkyl optionally substituted with one, two, or three $R^{20l}$. In some embodiments, $R^{12a}$ is independently —C($R^{12c}$)$_2$-$C_{6-10}$aryl optionally substituted with one, two, or three $R^{20l}$. In some embodiments, $R^{12a}$ is independently -$C_{1-6}$alkyl-$C_{6-10}$aryl optionally substituted with one, two, or three $R^{20l}$. In some embodiments, $R^{12a}$ is independently -$C_{2-6}$alkenyl-$C_{6-10}$aryl optionally substituted with one, two, or three $R^{20l}$. In some embodiments, $R^{12a}$ is independently -$C_{2-6}$alkynyl-$C_{6-10}$aryl optionally substituted with one, two, or three $R^{20l}$. In some embodiments, $R^{12a}$ is independently and $C_{6-10}$aryl optionally substituted with one, two, or three $R^{20l}$. In some embodiments, $R^{12a}$ is independently —C($R^{12c}$)$_2$-$C_{1-9}$heteroaryl optionally substituted with one, two, or three $R^{20l}$. In some embodiments, $R^{12a}$ is independently -$C_{1-6}$alkyl-$C_{1-9}$heteroaryl optionally substituted with one, two, or three $R^{20l}$. In some embodiments, $R^{12a}$ is independently -$C_{2-6}$alkenyl-$C_{1-9}$heteroaryl optionally substituted with one, two, or three $R^{20l}$. In some embodiments, $R^{12a}$ is independently -$C_{2-6}$alkynyl-$C_{1-9}$heteroaryl optionally substituted with one, two, or three $R^{20l}$. In some embodiments, $R^{12a}$ is independently $C_{1-9}$heteroaryl optionally substituted with one, two, or three $R^{20l}$.

In embodiments, $R^2$ is independently selected from

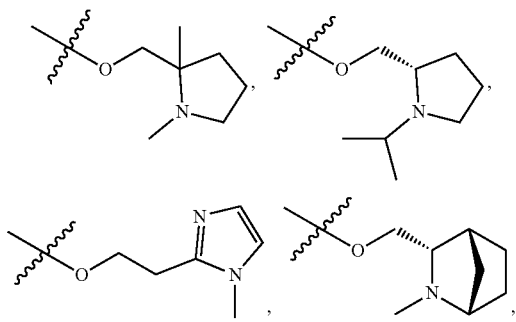

-continued

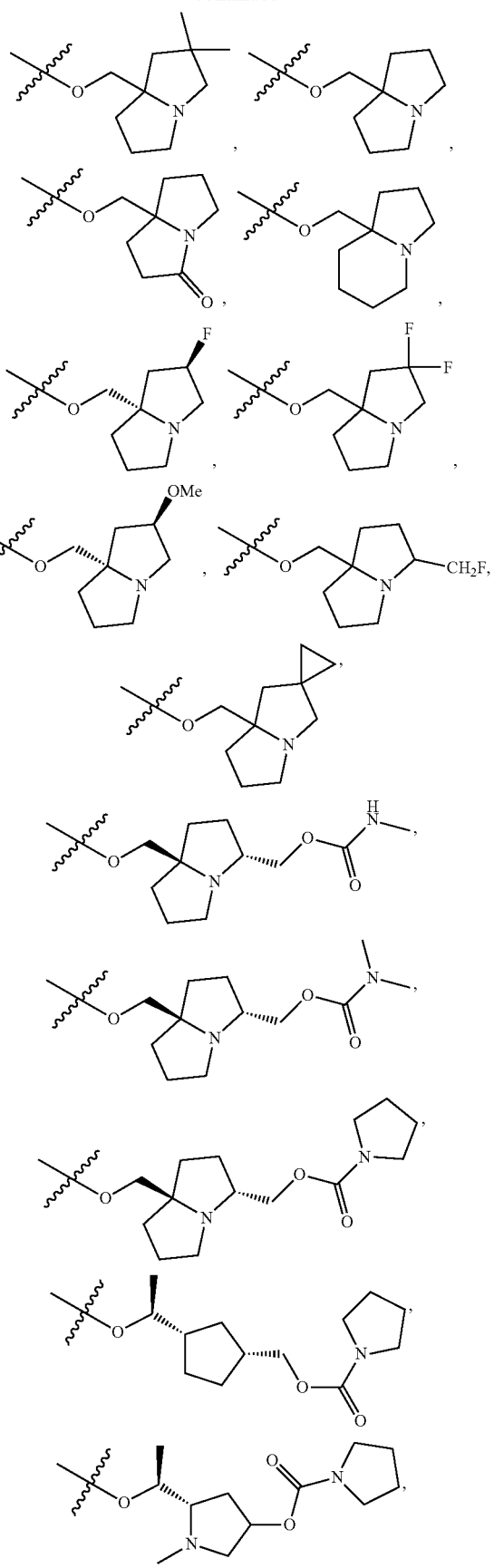

-continued
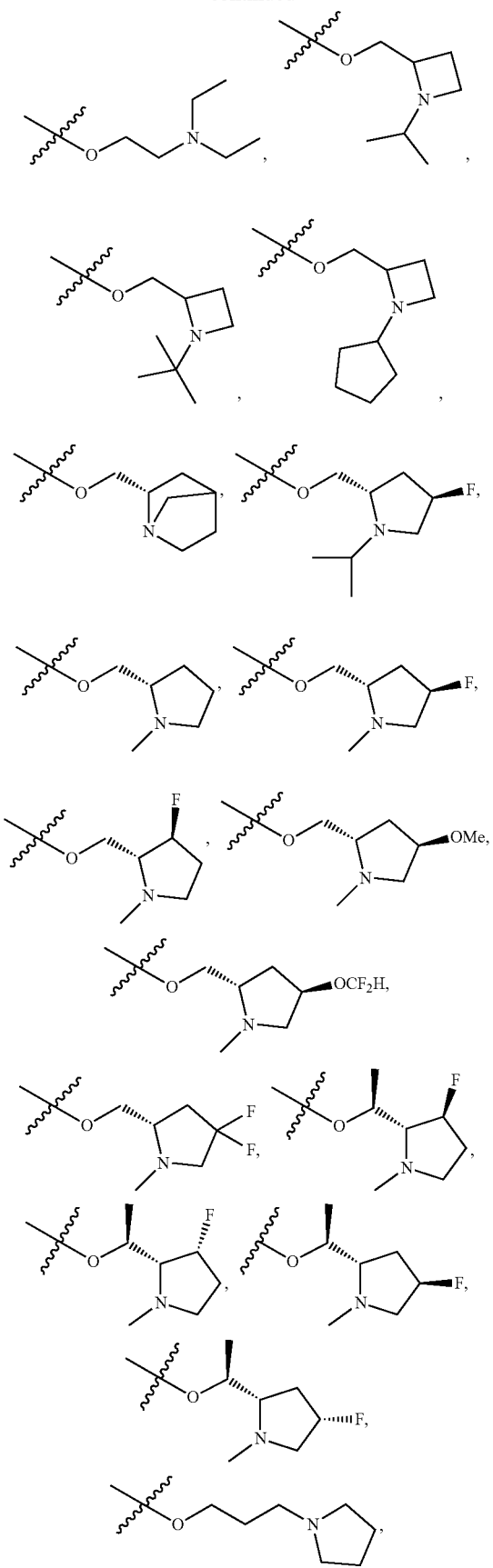
-continued
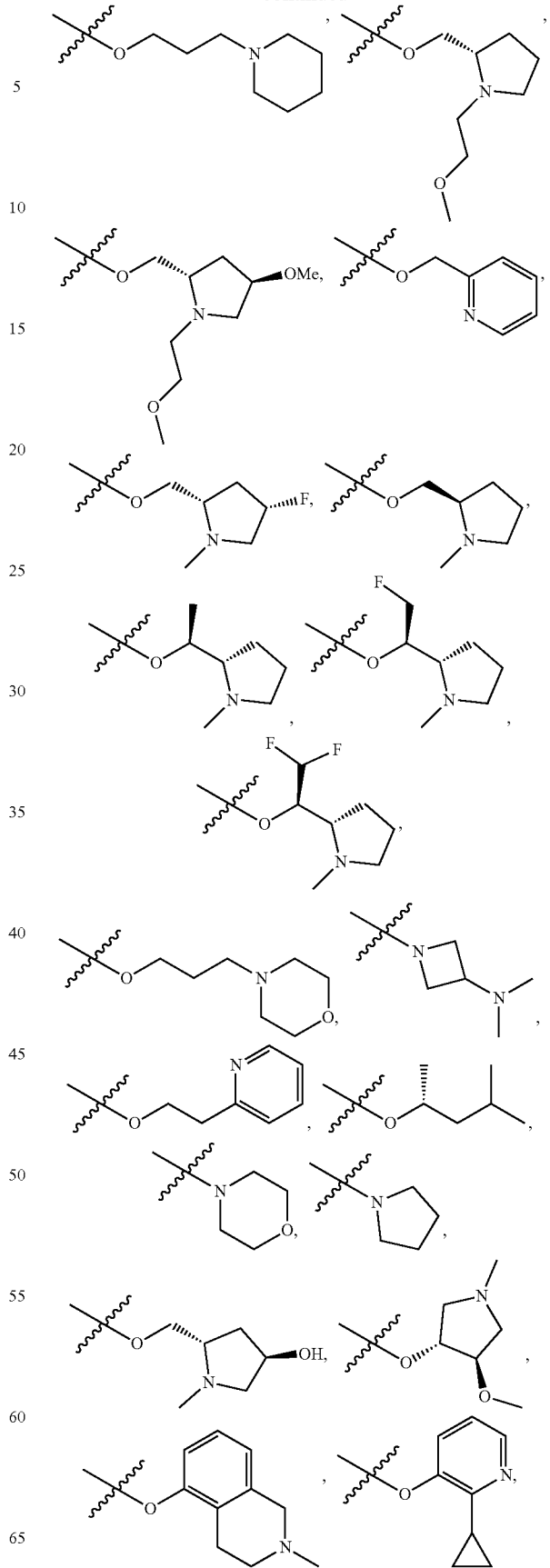

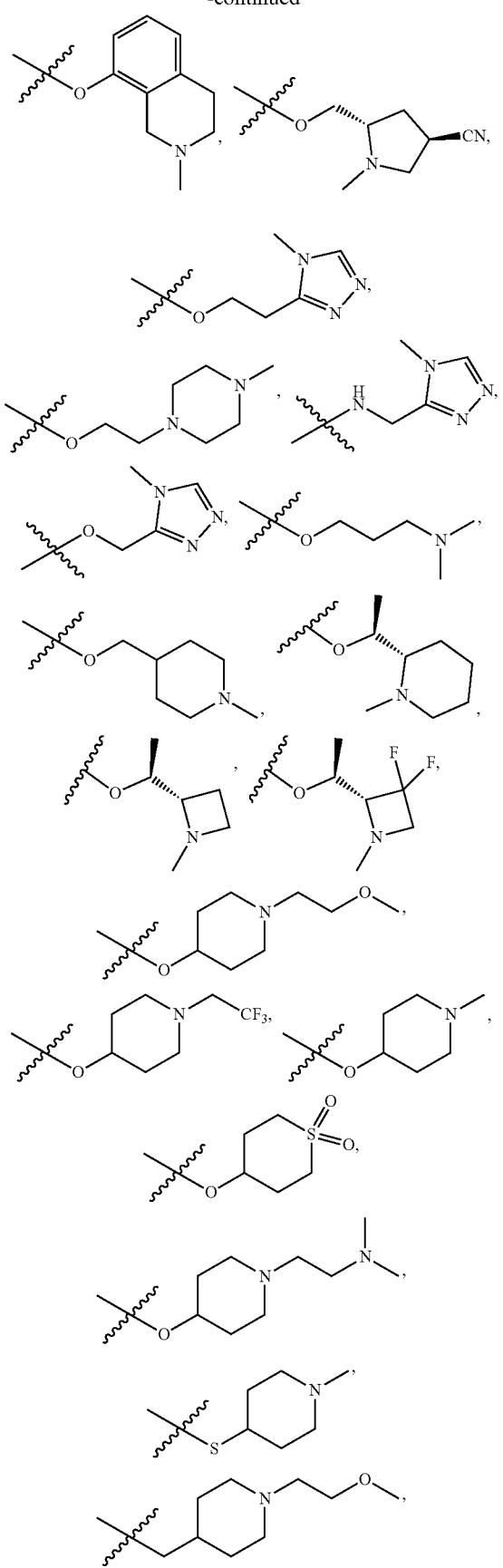
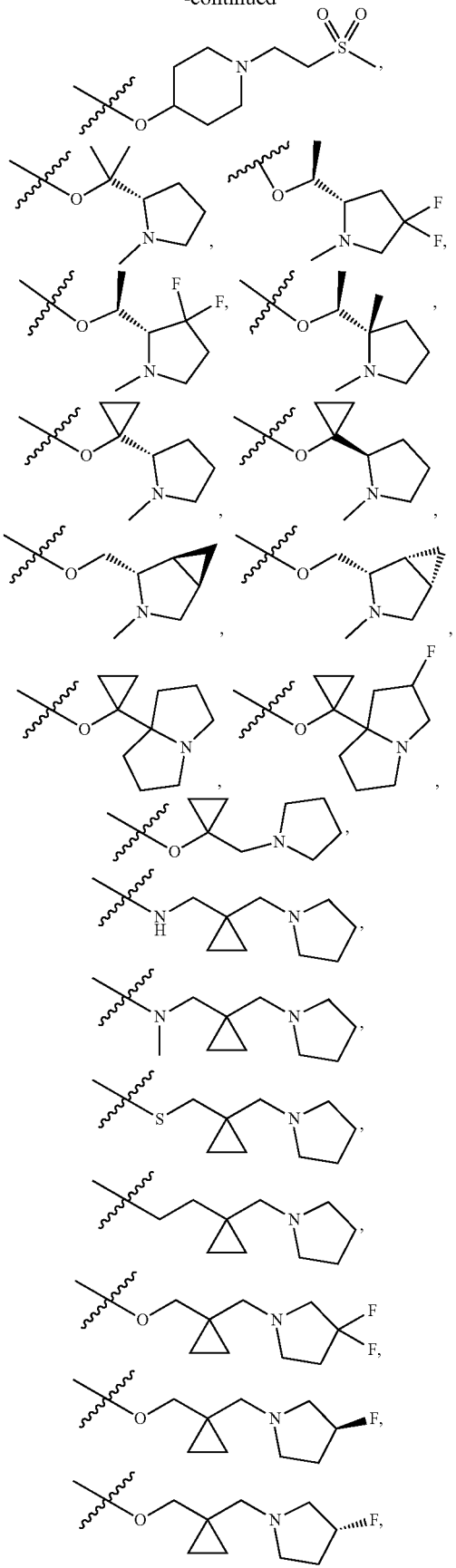

331
-continued
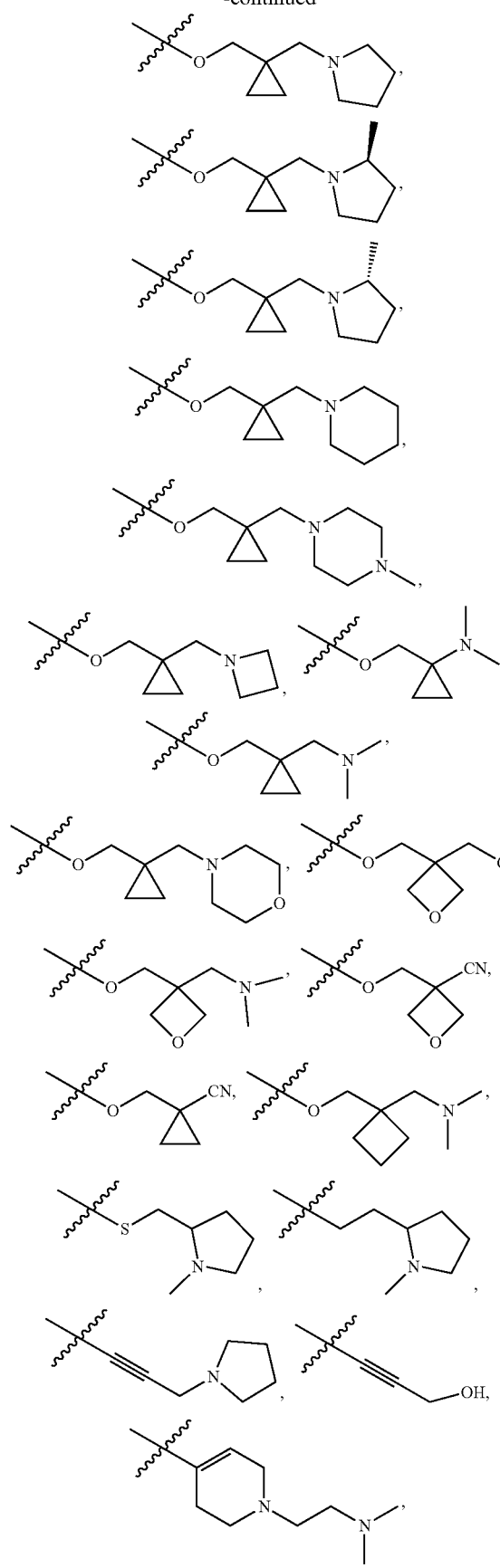
332
-continued
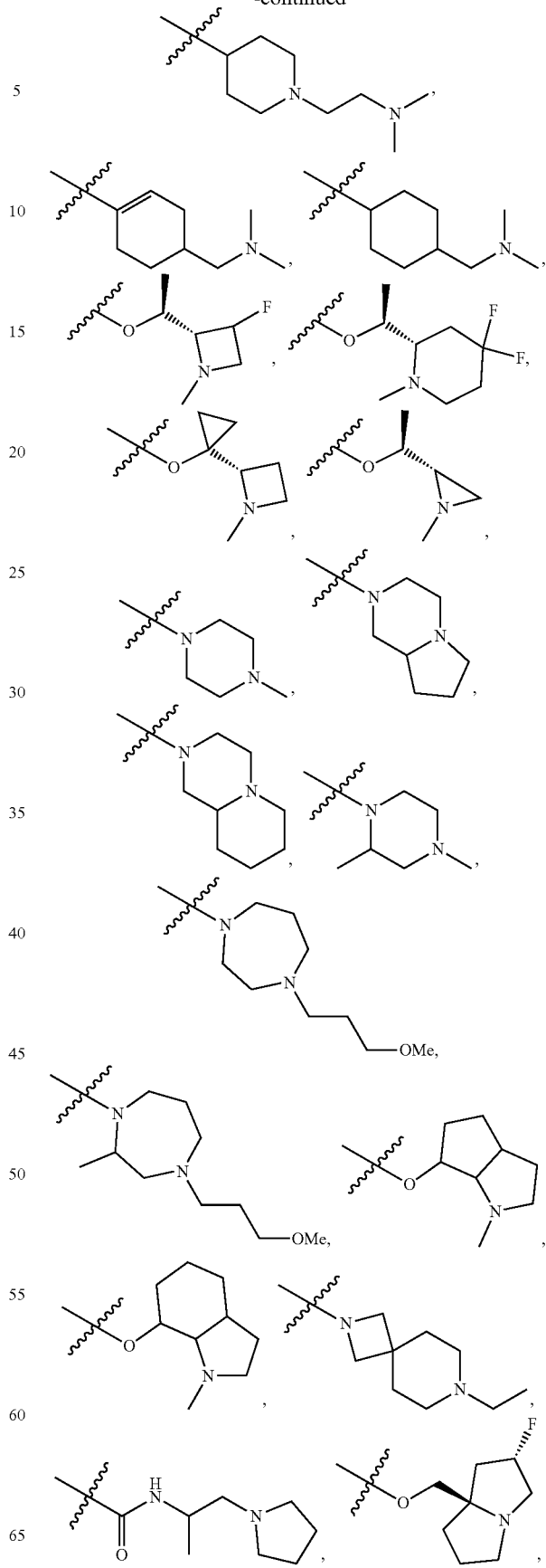

In embodiments, $Z^4$ is a bond, $Z^{4a}$, $Z^{4a}Z^{4b}$, $Z^{4a}Z^{4b}Z^{4c}$, $Z^{4a}Z^{4b}Z^{4c}Z^{4d}$, or $Z^{4a}Z^{4b}Z^{4c}Z^{4d}Z^{4e}$. In embodiments, $Z^4$ is $Z^{4a}$. In embodiments, $Z^4$ is $Z^{4a}Z^{4b}$. In embodiments, $Z^4$ is $Z^{4a}Z^{4b}Z^{4c}$. In embodiments, $Z^4$ is $Z^{4a}Z^{4b}Z^{4c}Z^{4d}$. In embodiments, $Z^4$ is $Z^{4a}Z^{4b}Z^{4c}Z^{4d}Z^{4e}$.

In embodiments, each $R^{z4}$ is independently selected from hydrogen, halogen, —CN, $C_{1-6}$alkyl, $C_{2-6}$alkenyl, $C_{3-10}$cycloalkyl, $C_{2-9}$heterocycloalkyl, $C_{1-9}$heteroaryl, —OR$^{12}$, —N(R$^{12}$)(R$^{13}$), —N(R$^{14}$)S(O)$_2$R$^{15}$, —C(O)R$^{12}$, —S(O)R$^{15}$, —OC(O)R$^{15}$, —C(O)N(R$^{12}$)(R$^{13}$), —N(R$^{14}$)C(O)R$^{12}$, —S(O)$_2$R$^{15}$, and —S(O)$_2$N(R$^{12}$)(R$^{13}$)—, wherein $C_{1-6}$alkyl, $C_{2-6}$alkenyl, $C_{3-10}$cycloalkyl, $C_{2-9}$heterocycloalkyl, and $C_{1-9}$heteroaryl are optionally substituted with one, two, or three $R^{20z4}$; or two $R^{z4}$ bonded to the same carbon are joined to form a $C_{2-6}$alkenyl that is optionally substituted with one, two, or three $R^{20z4}$. In embodiments, each $R^{z4}$ is independently selected from hydrogen, halogen, —CN, $C_{1-6}$alkyl, $C_{3-10}$cycloalkyl, $C_{2-9}$heterocycloalkyl, $C_{1-9}$heteroaryl, —OR$^{12}$, —N(R$^{12}$)(R$^{13}$), —N(R$^{14}$)S(O)$_2$R$^{15}$, and —S(O)$_2$R$^{15}$, wherein $C_{1-6}$alkyl, $C_{3-10}$cycloalkyl, $C_{2-9}$heterocycloalkyl, and $C_{1-9}$heteroaryl are optionally substituted with one, two, or three $R^{20z4}$; or two $R^{z4}$ bonded to the same carbon are joined to form a $C_{2-6}$alkenyl that is optionally substituted with one, two, or three $R^{20z4}$.

In embodiments, each $R^{z5}$ is independently selected from hydrogen, halogen, —CN, $C_{1-6}$alkyl, $C_{2-6}$alkenyl, $C_{3-10}$cycloalkyl, $C_{2-9}$heterocycloalkyl, $C_{1-9}$heteroaryl, —OR$^{12}$, —N(R$^{12}$)(R$^{13}$), —N(R$^{14}$)S(O)$_2$R$^{15}$, —C(O)R$^{12}$, —S(O)R$^{15}$, —OC(O)R$^{15}$, —C(O)N(R$^{12}$)(R$^{13}$), —N(R$^{14}$)C(O)R$^{12}$, —S(O)$_2$R$^{15}$, and —S(O)$_2$N(R$^{12}$)(R$^{13}$)—, wherein $C_{1-6}$alkyl, $C_{2-6}$alkenyl, $C_{3-10}$cycloalkyl, $C_{2-9}$heterocycloalkyl, and $C_{1-9}$heteroaryl are optionally substituted with one, two, or three $R^{20z5}$; or two $R^{z5}$ bonded to the same carbon are joined to form a $C_{2-6}$alkenyl that is optionally substituted with one, two, or three $R^{20z5}$. In embodiments, each $R^{z5}$ is independently selected from hydrogen, halogen, —CN, $C_{1-6}$alkyl, $C_{3-10}$cycloalkyl, $C_{2-9}$heterocycloalkyl, $C_{1-9}$heteroaryl, —OR$^{12}$, —N(R$^{12}$)(R$^{13}$), —N(R$^{14}$)S(O)$_2$R$^{15}$, and —S(O)$_2$R$^{15}$, wherein $C_{1-6}$alkyl, $C_{3-10}$cycloalkyl, $C_{2-9}$heterocycloalkyl, and $C_{1-9}$heteroaryl are optionally substituted with one, two, or three $R^{20z5}$; or two $R^{z5}$ bonded to the same carbon are joined to form a $C_{2-6}$alkenyl that is optionally substituted with one, two, or three $R^{20z5}$.

In embodiments, each $R^{z6}$ is independently selected from hydrogen, halogen, —CN, $C_{1-6}$alkyl, $C_{2-6}$alkenyl, $C_{3-10}$cycloalkyl, $C_{2-9}$heterocycloalkyl, $C_{1-9}$heteroaryl, —OR$^{12}$, —N(R$^{12}$)(R$^{13}$), —N(R$^{14}$)S(O)$_2$R$^{15}$, —C(O)R$^{12}$, —S(O)R$^{15}$, —OC(O)R$^{15}$, —C(O)N(R$^{12}$)(R$^{13}$), —N(R$^{14}$)C(O)R$^{12}$, —S(O)$_2$R$^{15}$, and —S(O)$_2$N(R$^{12}$)(R$^{13}$)—, wherein $C_{1-6}$alkyl, $C_{2-6}$alkenyl, $C_{3-10}$cycloalkyl, $C_{2-9}$heterocycloalkyl, and $C_{1-9}$heteroaryl are optionally substituted with one, two, or three $R^{20z6}$; or two $R^{z6}$ bonded to the same carbon are joined to form a $C_{2-6}$alkenyl that is optionally substituted with one, two, or three $R^{20z6}$.

In embodiments, each $R^{z6}$ is independently selected from hydrogen, halogen, —CN, $C_{1-6}$alkyl, $C_{3-10}$cycloalkyl, $C_{2-9}$heterocycloalkyl, $C_{1-9}$heteroaryl, —OR$^{12}$, —N(R$^{12}$)(R$^{13}$), —N(R$^{14}$)S(O)$_2$R$^{15}$, and —S(O)$_2$R$^{15}$, wherein $C_{1-6}$alkyl, $C_{3-10}$cycloalkyl, $C_{2-9}$heterocycloalkyl, and $C_{1-9}$heteroaryl are optionally substituted with one, two, or three $R^{20z6}$; or two $R^{z6}$ bonded to the same carbon are joined to form a $C_{2-6}$alkenyl that is optionally substituted with one, two, or three $R^{20z6}$.

In embodiments, each $R^{20z}$ is independently selected from hydrogen, halogen, oxo, —CN, $C_{1-6}$alkyl, $C_{2-6}$alkenyl, $C_{3-10}$cycloalkyl, $C_{2-9}$heterocycloalkyl, $C_{1-9}$heteroaryl, —OR$^{12}$, —N(R$^{12}$)(R$^{13}$), —N(R$^{14}$)S(O)$_2$R$^{15}$, —C(O)R$^{12}$, —S(O)R$^{15}$, —OC(O)R$^{15}$, —C(O)N(R$^{12}$)(R$^{13}$), —N(R$^{14}$)C(O)R$^{12}$, —S(O)$_2$R$^{15}$, and —S(O)$_2$N(R$^{12}$)(R$^{13}$)—, wherein $C_{1-6}$alkyl, $C_{2-6}$alkenyl, $C_{3-10}$cycloalkyl, $C_{2-9}$heterocycloalkyl, and $C_{1-9}$heteroaryl are optionally substituted with one, two, or three $R^{20zz}$; or two $R^{20z}$ bonded to the same carbon are joined to form a $C_{2-6}$alkenyl that is optionally substituted with one, two, or three $R^{20zz}$. In embodiments, each $R^{20z}$ is independently selected from hydrogen, oxo, halogen, —CN, $C_{1-6}$alkyl, $C_{3-10}$cycloalkyl, $C_{2-9}$heterocycloalkyl, $C_{1-9}$heteroaryl, —OR$^{12}$, —N(R$^{12}$)(R$^{13}$), —N(R$^{14}$)S(O)$_2$R$^{15}$, and —S(O)$_2$R$^{15}$, wherein $C_{1-6}$alkyl, $C_{3-10}$cycloalkyl, $C_{2-9}$heterocycloalkyl, and $C_{1-9}$heteroaryl are optionally substituted with one, two, or three $R^{20zz}$; or two $R^{20z}$ bonded to the same carbon are joined to form a $C_{2-6}$alkenyl that is optionally substituted with one, two, or three $R^{20zz}$.

In some embodiments, $R^{12}$ is independently hydrogen. In some embodiments, $R^{12}$ is independently $C_{1-6}$alkyl. In some embodiments, $R^{12}$ is independently $C_{2-6}$alkenyl. In some embodiments, $R^{12}$ is independently $C_{2-6}$alkynyl. In some embodiments, $R^{12}$ is independently $C_{3-10}$cycloalkyl. In some embodiments, $R^{12}$ is independently $C_{1-9}$heterocycloalkyl. In some embodiments, $R^{12}$ is independently $C_{6-10}$aryl. In some embodiments, $R^{12}$ is independently $C_{1-9}$heteroaryl.

In some embodiments, $R^{12}$ is independently $C_{1-6}$alkyl optionally substituted with one, two, or three $R^{20l}$. In some embodiments, $R^{12}$ is independently $C_{2-6}$alkenyl optionally substituted with one, two, or three $R^{20l}$. In some embodiments, $R^{12}$ is independently $C_{2-6}$alkynyl optionally substituted with one, two, or three $R^{20l}$. In some embodiments, $R^{12}$ is independently $C_{3-10}$cycloalkyl optionally substituted with one, two, or three $R^{20l}$. In some embodiments, $R^{12}$ is independently $C_{2-9}$heterocycloalkyl optionally substituted with one, two, or three $R^{20l}$. In some embodiments, $R^{12}$ is independently $C_{6-10}$aryl optionally substituted with one, two, or three $R^{20l}$. In some embodiments, $R^{12}$ is independently $C_{1-9}$heteroaryl optionally substituted with one, two, or three $R^{20l}$.

In some embodiments, $R^{12}$ is independently $C_{3-10}$cycloalkyl optionally substituted with one, two, or three $R^{20l}$. In some embodiments, $R^{12}$ is independently —CH$_2$-$C_{3-10}$cycloalkyl optionally substituted with one, two, or three $R^{20l}$. In some embodiments, $R^{12}$ is independently $C_{1-9}$heterocycloalkyl optionally substituted with one, two, or three $R^{20l}$. In some embodiments, $R^{12}$ is independently —CH$_2$-$C_{1-9}$heterocycloalkyl optionally substituted with one, two, or three $R^{20l}$. In some embodiments, $R^{12}$ is independently $C_{6-10}$aryl optionally substituted with one, two, or three $R^{20l}$.

In some embodiments, $R^{12}$ is independently —$CH_2$-$C_{6-10}$aryl optionally substituted with one, two, or three $R^{20l}$. In some embodiments, $R^{12}$ is independently —$CH_2$-$C_{1-9}$heteroaryl optionally substituted with one, two, or three $R^{20l}$. In some embodiments, $R^{12}$ is independently $C_{1-9}$heteroaryl optionally substituted with one, two, or three $R^{20l}$. In additional embodiments, $R^{12}$ is independently hydrogen.

In some embodiments, $R^{12}$ is independently $C_{1-9}$heterocycloalkyl optionally substituted with one, two, or three $R^{20l}$. In some embodiments, $R^{12}$ is independently (monocyclic $C_{2-8}$heterocycloalkyl) optionally substituted with one, two, or three $R^{20l}$. In some embodiments, $R^{12}$ is independently (monocyclic $C_{3-5}$heterocycloalkyl) optionally substituted with one, two, or three $R^{20l}$. In some embodiments, $R^{12}$ is independently (spirocyclic $C_{2-11}$heterocycloalkyl) optionally substituted with one, two, or three $R^{20l}$. In some embodiments, $R^{12}$ is independently (spirocyclic $C_{3-11}$heterocycloalkyl) optionally substituted with one, two, or three $R^{20l}$. In some embodiments, $R^{12}$ is independently (fused $C_{2-11}$heterocycloalkyl) optionally substituted with one, two, or three $R^{20l}$. In some embodiments, $R^{12}$ is independently (spirocyclic $C_{6-8}$heterocycloalkyl) optionally substituted with one, two, or three $R^{20l}$.

In some embodiments, $R^{12}$ is independently —$CH_2$-$C_{1-9}$heterocycloalkyl optionally substituted with one, two, or three $R^{20l}$. In some embodiments, $R^{12}$ is independently —$CH_2$-(monocyclic $C_{2-8}$heterocycloalkyl) optionally substituted with one, two, or three $R^{20l}$. In some embodiments, $R^{12}$ is independently —$CH_2$-(monocyclic $C_{3-5}$heterocycloalkyl) optionally substituted with one, two, or three $R^{20l}$. In some embodiments, $R^{12}$ is independently —$CH_2$-(spirocyclic $C_{2-11}$heterocycloalkyl) optionally substituted with one, two, or three $R^{20l}$. In some embodiments, $R^{12}$ is independently —$CH_2$-(spirocyclic $C_{3-11}$heterocycloalkyl) optionally substituted with one, two, or three $R^{20l}$. In some embodiments, $R^{12}$ is independently —$CH_2$-(fused $C_{2-11}$heterocycloalkyl) optionally substituted with one, two, or three $R^{20l}$. In some embodiments, $R^{12}$ is independently —$CH_2$-(spirocyclic $C_{6-8}$heterocycloalkyl) optionally substituted with one, two, or three $R^{20l}$.

In embodiments, $R^{12}$ is independently 5 membered heteroaryl optionally substituted with one, two, or three $R^{20l}$. In embodiments, $R^{12}$ is independently 6 membered heteroaryl optionally substituted with one, two, or three $R^{20l}$. In embodiments, $R^{12}$ is independently 7 membered heteroaryl optionally substituted with one, two, or three $R^{20l}$. In embodiments, $R^{12}$ is independently 8 membered heteroaryl optionally substituted with one, two, or three $R^{20l}$. In embodiments, $R^{12}$ is independently 9 membered heteroaryl optionally substituted with one, two, or three $R^{20l}$. In embodiments, $R^{12}$ is independently 10 membered heteroaryl optionally substituted with one, two, or three $R^{20l}$.

In embodiments, $R^{12}$ is independently 5 membered heteroaryl, including one or more nitrogen ring atoms, which is optionally substituted with one, two, or three $R^{20l}$. In embodiments, $R^{12}$ is independently 6 membered heteroaryl, including one or more nitrogen ring atoms, which is optionally substituted with one, two, or three $R^{20l}$. In embodiments, $R^{12}$ is independently 7 membered heteroaryl, including one or more nitrogen ring atoms, which is optionally substituted with one, two, or three $R^{20l}$. In embodiments, $R^{12}$ is independently 8 membered heteroaryl, including one or more nitrogen ring atoms, which is optionally substituted with one, two, or three $R^{20l}$. In embodiments, $R^{12}$ is independently 9 membered heteroaryl, including one or more nitrogen ring atoms, which is optionally substituted with one, two, or three $R^{20l}$. In embodiments, $R^{12}$ is independently 10 membered heteroaryl, including one or more nitrogen ring atoms, which is optionally substituted with one, two, or three $R^{20l}$.

In embodiments, $R^{12}$ is independently 3 membered heterocycloalkyl optionally substituted with one, two, or three $R^{20l}$. In embodiments, $R^{12}$ is independently 4 membered heterocycloalkyl optionally substituted with one, two, or three $R^{20l}$. In embodiments, $R^{12}$ is independently 5 membered heterocycloalkyl optionally substituted with one, two, or three $R^{20l}$. In embodiments, $R^{12}$ is independently 6 membered heterocycloalkyl optionally substituted with one, two, or three $R^{20l}$. In embodiments, $R^{12}$ is independently 7 membered heterocycloalkyl optionally substituted with one, two, or three $R^{20l}$. In embodiments, $R^{12}$ is independently 8 membered heterocycloalkyl optionally substituted with one, two, or three $R^{20l}$. In embodiments, $R^{12}$ is independently 9 membered heterocycloalkyl optionally substituted with one, two, or three $R^{20l}$. In embodiments, $R^{12}$ is independently 10 membered heterocycloalkyl optionally substituted with one, two, or three $R^{20l}$.

In embodiments, $R^{12}$ is independently 3 membered heterocycloalkyl, including one or more nitrogen ring atoms, which is optionally substituted with one, two, or three $R^{20l}$. In embodiments, $R^{12}$ is independently 4 membered heterocycloalkyl, including one or more nitrogen ring atoms, which is optionally substituted with one, two, or three $R^{20l}$. In embodiments, $R^{12}$ is independently 5 membered heterocycloalkyl, including one or more nitrogen ring atoms, which is optionally substituted with one, two, or three $R^{20l}$. In embodiments, $R^{12}$ is independently 6 membered heterocycloalkyl, including one or more nitrogen ring atoms, which is optionally substituted with one, two, or three $R^{20l}$. In embodiments, $R^{12}$ is independently 7 membered heterocycloalkyl, including one or more nitrogen ring atoms, which is optionally substituted with one, two, or three $R^{20l}$. In embodiments, $R^{12}$ is independently 8 membered heterocycloalkyl, including one or more nitrogen ring atoms, which is optionally substituted with one, two, or three $R^{20l}$. In embodiments, $R^{12}$ is independently 9 membered heterocycloalkyl, including one or more nitrogen ring atoms, which is optionally substituted with one, two, or three $R^{20l}$. In embodiments, $R^{12}$ is independently 10 membered heterocycloalkyl, including one or more nitrogen ring atoms, which is optionally substituted with one, two, or three $R^{20l}$.

In embodiments, the $R^{12}$ heteroaryl is substituted with halogen. In embodiments, the $R^{12}$ heteroaryl is substituted with oxo. In embodiments, the $R^{12}$ heteroaryl is substituted with —CN. In embodiments, the $R^{12}$ heteroaryl is substituted with $C_{1-6}$alkyl optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —$OR^{21}$, —$SR^{21}$, —$N(R^{22})(R^{23})$, —$C(O)OR^{22}$, —$C(O)N(R^{22})(R^{23})$, —$C(O)C(O)N(R^{22})(R^{23})$, —$OC(O)N(R^{22})(R^{23})$, —$N(R^{24})C(O)N(R^{22})(R^{23})$, —$N(R^{24})C(O)OR^{25}$, —$N(R^{24})C(O)R^{25}$, —$N(R^{24})S(O)_2R^{25}$, —$C(O)R^{25}$, —$S(O)_2R^{25}$, —$S(O)_2N(R^{22})(R^{23})$, and —$OC(O)R^{25}$. In embodiments, the $R^{12}$ heteroaryl is substituted with $C_{2-6}$alkenyl optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —$OR^{21}$, —$SR^{21}$, —$N(R^{22})(R^{23})$, —$C(O)OR^{22}$, —$C(O)N(R^{22})(R^{23})$, —$C(O)C(O)N(R^{22})(R^{23})$, —$OC(O)N(R^{22})(R^{23})$, —$N(R^{24})C(O)N(R^{22})(R^{23})$, —$N(R^{24})C(O)OR^{25}$, —$N(R^{24})C(O)R^{25}$, —$N(R^{24})S(O)_2R^{25}$, —$C(O)R^{25}$, —$S(O)_2R^{25}$, —$S(O)_2N(R^{22})(R^{23})$, and —$OC(O)R^{25}$. In embodiments, the $R^{12}$ heteroaryl is substituted with $C_{2-6}$alkynyl optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, N(R$^{24}$)C(O)R$^{25}$, —N(R$^{24}$)S(O)$_2$R$^{25}$, —C(O)R$^{25}$, —S(O)$_2$R$^{25}$, —S(O)$_2$N(R$^{21}$)(R$^{23}$), and —OC(O)R$^{25}$. In embodiments, the R$^{12}$ heteroaryl is substituted with $C_{3-10}$cycloalkyl optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, —N(R$^{24}$)C(O)R$^{25}$, —N(R$^{24}$)S(O)$_2$R$^{25}$, —C(O)R$^{25}$, —S(O)$_2$R$^{25}$, —S(O)$_2$N(R$^{22}$)(R$^{23}$), and —OC(O)R$^{25}$. In embodiments, the R$^{12}$ heteroaryl is substituted with —CH$_2$-$C_{3-10}$cycloalkyl optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, N(R$^{24}$)C(O)R$^{25}$, —N(R$^{24}$)S(O)$_2$R$^{25}$, —C(O)R$^{25}$, —S(O)$_2$R$^{25}$, —S(O)$_2$N(R$^{22}$)(R$^{23}$) and —OC(O)R$^{25}$. In embodiments, the R$^{12}$ heteroaryl is substituted with $C_{2-9}$heterocycloalkyl optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, —N(R$^{24}$)C(O)R$^{25}$, —N(R$^{24}$)S(O)$_2$R$^{25}$, —C(O)R$^{25}$, —S(O)$_2$R$^{25}$, —S(O)$_2$N(R$^{22}$)(R$^{23}$), and —OC(O)R$^{25}$. In embodiments, the R$^{12}$ heteroaryl is substituted with —CH$_2$-$C_{2-9}$heterocycloalkyl optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, C(O)OR$^{25}$, —N(R$^{24}$)C(O)R$^{25}$, —N(R$^{24}$)S(O)$_2$R$^{25}$, —C(O)R$^{25}$, —S(O)$_2$R$^{25}$, —S(O)$_2$N(R$^{22}$)(R$^{23}$), and —OC(O)R$^{25}$. In embodiments, the R$^{12}$ heteroaryl is substituted with $C_{6-10}$aryl optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, —N(R$^{24}$)C(O)R$^{25}$, —N(R$^{24}$)S(O)$_2$R$^{25}$, —C(O)R$^{25}$, —S(O)$_2$R$^{25}$, —S(O)$_2$N(R$^{22}$)(R$^{23}$), and —OC(O)R$^{25}$. In embodiments, the R$^{12}$ heteroaryl is substituted with —CH$_2$-$C_{6-10}$aryl optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, —N(R$^{24}$)C(O)R$^{25}$, —N(R$^{24}$)S(O)$_2$R$^{25}$, —C(O)R$^{25}$, —S(O)$_2$R$^{25}$, —S(O)$_2$N(R$^{22}$)(R$^{23}$), and —OC(O)R$^{25}$. In embodiments, the R$^{12}$ heteroaryl is substituted with —CH$_2$-$C_{1-9}$heteroaryl optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, C(O)OR$^{25}$, —N(R$^{24}$)C(O)R$^{25}$, —N(R$^{24}$)S(O)$_2$R$^{25}$, —C(O)R$^{25}$, —S(O)$_2$R$^{25}$, —S(O)$_2$N(R$^{22}$)(R$^{23}$), and —OC(O)R$^{25}$. In embodiments, the R$^{12}$ heteroaryl is substituted with $C_{1-9}$heteroaryl optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, —N(R$^{24}$)C(O)R$^{25}$, —N(R$^{24}$)S(O)$_2$R$^{25}$, —C(O)R$^{25}$, —S(O)$_2$R$^{25}$, —S(O)$_2$N(R$^{22}$)(R$^{23}$), and —OC(O)R$^{25}$. In embodiments, the R$^{12}$ heteroaryl is substituted with —OR$^{21}$. In embodiments, the R$^{12}$ heteroaryl is substituted with —SR$^{21}$. In embodiments, the R$^{12}$ heteroaryl is substituted with —N(R$^{22}$)(R$^{23}$). In embodiments, the R$^{12}$ heteroaryl is substituted with —C(O)OR$^{22}$. In embodiments, the R$^{12}$ heteroaryl is substituted with —C(O)N(R$^{22}$)(R$^{23}$). In embodiments, the R$^{12}$ heteroaryl is substituted with —C(O)C(O)N(R$^{22}$)(R$^{23}$). In embodiments, the R$^{12}$ heteroaryl is substituted with —OC(O)N(R$^{22}$)(R$^{23}$). In embodiments, the R$^{12}$ heteroaryl is substituted with —N(R$^{24}$)C(O)N(R$^{22}$)(R$^{23}$). In embodiments, the R$^{12}$ heteroaryl is substituted with —N(R$^{24}$)C(O)OR$^{25}$. In embodiments, the R$^{12}$ heteroaryl is substituted with —N(R$^{24}$)C(O)R$^{21}$. In embodiments, the R$^{12}$ heteroaryl is substituted with —N(R$^{24}$)S(O)$_2$R$^{25}$. In embodiments, the R$^{12}$ heteroaryl is substituted with —C(O)R$^{21}$. In embodiments, the R$^{12}$ heteroaryl is substituted with —S(O)$_2$R$^{25}$. In embodiments, the R$^{12}$ heteroaryl is substituted with —S(O)$_2$N(R$^{22}$)(R$^{23}$). In embodiments, the R$^{12}$ heteroaryl is substituted with —OCH$_2$C(O)OR$^{22}$. In embodiments, the R$^{12}$ heteroaryl is substituted with —OC(O)R$^{25}$. In embodiments, the R$^{12}$ heteroaryl is substituted with F. In embodiments, the R$^{12}$ heteroaryl is substituted with Cl. In embodiments, the R$^{12}$ heteroaryl is substituted with Br. In embodiments, the R$^{12}$ heteroaryl is substituted with I. In embodiments, the R$^{12}$ heteroaryl is substituted with unsubstituted methyl. In embodiments, the R$^{12}$ heteroaryl is substituted with —CFH$_2$. In embodiments, the R$^{12}$ heteroaryl is substituted with —CHF$_2$. In embodiments, the R$^{12}$ heteroaryl is substituted with —CF$_3$. In embodiments, the R$^{12}$ heteroaryl is substituted with $C_{1-6}$haloalkyl.

In some embodiments, each R$^{13}$ is independently hydrogen. In some embodiments, each R$^{13}$ is independently $C_{1-6}$alkyl. In some embodiments, each R$^{13}$ is independently $C_{1-6}$haloalkyl. In some embodiments, each R$^{12}$ and R$^{13}$, together with the nitrogen to which they are attached, form a $C_{2-9}$heterocycloalkyl ring optionally substituted with one, two, or three R$^{20m}$.

In some embodiments, each R$^{14}$ is independently hydrogen. In some embodiments, each R$^{14}$ is independently $C_{1-6}$alkyl. In some embodiments, each R$^{14}$ is independently $C_{1-6}$haloalkyl.

In some embodiments, each R$^{15}$ is independently $C_{1-6}$alkyl. In some embodiments, each R$^{15}$ is independently $C_{2-6}$alkenyl. In some embodiments, each R$^{15}$ is independently $C_{2-6}$alkynyl. In some embodiments, each R$^{15}$ is independently $C_{3-10}$cycloalkyl. In some embodiments, each R$^{15}$ is independently $C_{2-9}$heterocycloalkyl. In some embodiments, each R$^{15}$ is independently $C_{6-10}$aryl. In some embodiments, each R$^{15}$ is independently $C_{1-9}$heteroaryl.

In some embodiments, each R$^{15}$ is independently $C_{1-6}$alkyl substituted with one, two, or three R$^{20o}$. In some embodiments, each R$^{15}$ is independently $C_{2-6}$alkenyl substituted with one, two, or three R$^{20o}$. In some embodiments, each R$^{15}$ is independently $C_{2-6}$alkynyl substituted with one, two, or three R$^{20o}$. In some embodiments, each R$^{15}$ is independently $C_{3-10}$cycloalkyl substituted with one, two, or three $R^{20o}$. In some embodiments, each $R^{15}$ is independently $C_{1-9}$heterocycloalkyl substituted with one, two, or three $R^{20o}$. In some embodiments, each $R^{15}$ is independently $C_{6-10}$aryl substituted with one, two, or three $R^{20o}$. In some embodiments, each $R^{15}$ is independently $C_{1-9}$heteroaryl substituted with one, two, or three $R^{20o}$. In some embodiments, each $R^{15}$ is independently ethenyl substituted with one, two, or three $R^{20o}$. In some embodiments, each $R^{15}$ is independently propenyl substituted with one, two, or three $R^{20o}$. In some embodiments, each $R^{15}$ is independently butenyl substituted with one, two, or three $R^{20o}$. In some embodiments, each $R^{15}$ is independently ethenyl. In some embodiments, each $R^{15}$ is independently propenyl. In some embodiments, each $R^{15}$ is independently butenyl.

A compound of Formula (A), or a pharmaceutically acceptable salt or solvate thereof:

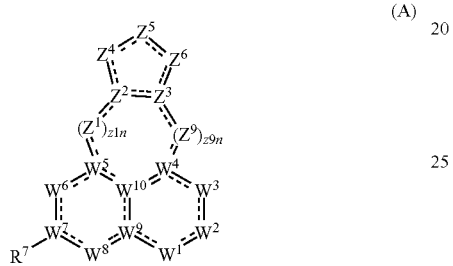

(A)

wherein:

$W^1$ is $N(R^1)$ or N;

$R^1$ is selected from hydrogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$C(O)OR^{12}$, —$OC(O)N(R^{12})(R^{13})$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20a}$;

$W^2$ is $C(R^2)$, $N(R^2)$, $C(R^2)_2$, C(O), S(O), $S(O)_2$, or N;

each $R^2$ is independently selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12a}$, —$SR^{12a}$, —$N(R^{12a})(R^{13})$, —$N=(R^{15})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$—, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20b}$;

$W^3$ is $C(R^3)$, $N(R^3)$, $C(R^3)_2$, C(O), S(O), $S(O)_2$, or N;

each $R^3$ is independently selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20c}$;

$W^4$ is $C(R^4)$, C, or N;

$R^4$ is selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20d}$;

$W^5$ is $C(R^5)$, C, or N;

$R^5$ is selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20e}$;

$W^6$ is $C(R^6)$, $N(R^6)$, $C(R^6)_2$, C(O), S(O), $S(O)_2$, or N;

each $R^6$ is independently selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20f}$;

$W^7$ is $C(R^{7a})$, C, or N;

$R^{7a}$ is selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20g}$;

$R^7$ is -$L^7$—$R^{17}$;

$L^7$ is a bond, $C_1$-$C_4$alkyl, $C_2$-$C_4$alkenyl, $C_2$-$C_4$alkynyl, 2-4 membered heteroalkylene linker, —O—, —N($R^{7d}$)—, —C(O)—, —S—, —S(O)$_2$—, —S(O)—, —P(O)$R^{7d}$—, $CR^{7c}R^{7c}$, —$OCR^{7c}R^{7c}$—, —N($R^{7d}$)$CR^{7c}R^{7c}$—, —C(O)$CR^{7c}R^{7c}$—, —$SCR^{7c}R^{7c}$—, —S(O)$_2$$CR^{7c}R^{7c}$—, —S(O)$CR^{7c}R^{7c}$—, —P(O)$R^{7d}$$CR^{7c}R^{7c}$—, —$CR^{7c}R^{7c}CR^{7c}R^{7c}$—, —$CR^{7c}R^{7c}$O—, —$CR^{7c}R^{7c}$N($R^{7d}$)—, —$CR^{7c}R^{7c}$C(O)—, —$CR^{7c}R^{7c}$S—, —$CR^{7c}R^{7c}$S(O)$_2$—, —$CR^{7c}R^{7c}$S(O)—, —$CR^{7c}R^{7c}$P(O)$R^{7d}$—, —N($R^{7d}$)C(O)—, —N($R^{7d}$)S(O)$_2$—, —N($R^{7d}$)S(O)—, —N($R^{7d}$)P(O)$R^{7d}$—, —C(O)N($R^{7d}$)—, —S(O)$_2$N($R^{7d}$)—, —S(O)N($R^{7d}$)—, —P(O)$R^{7d}$N($R^{7d}$)—, —OC(O)—, —OS(O)$_2$—, —OS(O)—, —OP(O)$R^{7d}$—, —C(O)O—, —S(O)$_2$O—, —S(O)O—, or —P(O)$R^{7d}$O—; wherein the $C_1$-$C_4$alkyl, $C_2$-$C_4$alkenyl, $C_2$-$C_4$alkynyl, 2-4 membered heteroalkylene linker are optionally substituted with one, two, or three $R^{20g}$;

each $R^{7c}$ is independently selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —N($R^{12}$)($R^{13}$), —C(O)$OR^{12}$, —OC(O)N($R^{12}$)($R^{13}$), —N($R^{14}$)C(O)N($R^{12}$)($R^{13}$), —N($R^{14}$)C(O)$OR^{15}$, —N($R^{14}$)S(O)$_2$$R^{15}$, —C(O)$R^{15}$, —S(O)$R^{15}$, —OC(O)$R^{15}$, —C(O)N($R^{12}$)($R^{13}$), —C(O)C(O)N($R^{12}$)($R^{13}$), —N($R^{14}$)C(O)$R^{15}$, —S(O)$_2$$R^{15}$, —S(O)$_2$N($R^{12}$)($R^{13}$), S(=O)(=NH)N($R^{12}$)($R^{13}$), —CH$_2$C(O)N($R^{12}$)($R^{13}$), —CH$_2$N($R^{14}$)C(O)$R^{15}$, —CH$_2$S(O)$_2$$R^{15}$, and —CH$_2$S(O)$_2$N($R^{12}$)($R^{13}$), wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20g}$;

each $R^{7d}$ is independently selected from hydrogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —C(O)$OR^{12}$, —OC(O)N($R^{12}$)($R^{13}$), —C(O)$R^{15}$, —S(O)$R^{15}$, —OC(O)$R^{15}$, —C(O)N($R^{12}$)($R^{13}$), —C(O)C(O)N($R^{12}$)($R^{13}$), —S(O)$_2$$R^{15}$, —S(O)$_2$N($R^{12}$)($R^{13}$), —S(=O)(=NH)N($R^{12}$)($R^{13}$), —CH$_2$C(O)N($R^{12}$)($R^{13}$), —CH$_2$N($R^{14}$)C(O)$R^{15}$, —CH$_2$S(O)$_2$$R^{15}$, and —CH$_2$S(O)$_2$N($R^{12}$)($R^{13}$), wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20g}$;

$R^{17}$ is selected from $C_{3-10}$cycloalkyl, 3-10 membered heterocycloalkyl, $C_{6-10}$aryl, and 5-10 membered heteroaryl, wherein $C_{3-10}$cycloalkyl, 3-10 membered heterocycloalkyl, $C_{6-10}$aryl, and 5-10 membered heteroaryl are optionally substituted with one or more $R^{20q}$; or $L^7$ is a bond and $R^{7a}$ and $R^{17}$, together with the carbon to which they are attached, form $C_{3-10}$cycloalkyl or 3-10 membered heterocycloalkyl, wherein the $C_{3-10}$cycloalkyl and 3-10 membered heterocycloalkyl are optionally substituted with one or more $R^{20q}$;

$W^8$ is $C(R^8)$, $N(R^8)$, $C(R^8)_2$, $C(O)$, $S(O)$, $S(O)_2$, or N;

each $R^8$ is independently selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —N($R^{12}$)($R^{13}$), —C(O)$OR^{12}$, —OC(O)N($R^{12}$)($R^{13}$), —N($R^{14}$)C(O)N($R^{12}$)($R^{13}$), —N($R^{14}$)C(O)$OR^{15}$, —N($R^{14}$)S(O)$_2$$R^{15}$, —C(O)$R^{15}$, —S(O)$R^{15}$, —OC(O)$R^{15}$, —C(O)N($R^{12}$)($R^{13}$), —C(O)C(O)N($R^{12}$)($R^{13}$), —N($R^{14}$)C(O)$R^{15}$, —S(O)$_2$$R^{15}$, —S(O)$_2$N($R^{12}$)($R^{13}$), —S(=O)(=NH)N($R^{12}$)($R^{13}$), —CH$_2$C(O)N($R^{12}$)($R^{13}$), —CH$_2$N($R^{14}$)C(O)$R^{15}$, —CH$_2$S(O)$_2$$R^{15}$, and —CH$_2$S(O)$_2$N($R^{12}$)($R^{13}$), wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20h}$;

$W^9$ is $C(R^9)$, C, or N;

$R^9$ is selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —N($R^{12}$)($R^{13}$), —C(O)$OR^{12}$, —OC(O)N($R^{12}$)($R^{13}$), —N($R^{14}$)C(O)N($R^{12}$)($R^{13}$), —N($R^{14}$)C(O)$OR^{15}$, —N($R^{14}$)S(O)$_2$$R^{15}$, —C(O)$R^{15}$, —S(O)$R^{15}$, —OC(O)$R^{15}$, —C(O)N($R^{12}$)($R^{13}$), —C(O)C(O)N($R^{12}$)($R^{13}$), —N($R^{14}$)C(O)$R^{15}$, —S(O)$_2$$R^{15}$, —S(O)$_2$N($R^{12}$)($R^{13}$), —S(=O)(=NH)N($R^{12}$)($R^{13}$), —CH$_2$C(O)N($R^{12}$)($R^{13}$), —CH$_2$N($R^{14}$)C(O)$R^{15}$, —CH$_2$S(O)$_2$$R^{15}$, and —CH$_2$S(O)$_2$N($R^{12}$)($R^{13}$), wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20i}$;

$W^{10}$ $C(R^{10})$, C, or N;

$R^{10}$ is selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —N($R^{12}$)($R^{13}$), —C(O)$OR^{12}$, —OC(O)N($R^{12}$)($R^{13}$), —N($R^{14}$)C(O)N($R^{12}$)($R^{13}$), —N($R^{14}$)C(O)$OR^{15}$, —N($R^{14}$)S(O)$_2$$R^{15}$, —C(O)$R^{15}$, —S(O)$R^{15}$, —OC(O)$R^{15}$, —C(O)N($R^{12}$)($R^{13}$), —C(O)C(O)N($R^{12}$)($R^{13}$), —N($R^{14}$)C(O)$R^{15}$, —S(O)$_2$$R^{15}$, —S(O)$_2$N($R^{12}$)($R^{13}$), —S(=O)(=NH)N($R^{12}$)($R^{13}$), —CH$_2$C(O)N($R^{12}$)($R^{13}$), —CH$_2$N($R^{14}$)C(O)$R^{15}$, —CH$_2$S(O)$_2$$R^{15}$, and —CH$_2$S(O)$_2$N($R^{12}$)($R^{13}$), wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20j}$;

each $Z^1$ is independently $C(R^{z1})$, $N(R^{z1})$, $C(R^{z1})_2$, $C(O)$, $S(O)$, $S(O)_2$, O, S, or N;

z1n is 0, 1, 2, 3, or 4; wherein if z1n is 0 then $Z^2$ is directly bonded to $W^5$;

each $R^{z1}$ is independently selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —N($R^{12}$)($R^{13}$), —C(O)$OR^{12}$, —OC(O)N($R^{12}$)($R^{13}$), —N($R^{14}$)C(O)N($R^{12}$)($R^{13}$), —N($R^{14}$)C(O)$OR^{15}$, —N($R^{14}$)S(O)$_2$$R^{15}$, —C(O)$R^{15}$, —S(O)$R^{15}$, —OC(O)$R^{15}$, —C(O)N($R^{12}$)($R^{13}$), —C(O)C(O)N($R^{12}$)($R^{13}$), —N($R^{14}$)C(O)$R^{15}$, —S(O)$_2$$R^{15}$, —S(O)$_2$N($R^{12}$)($R^{13}$), —S(=O)(=NH)N($R^{12}$)($R^{13}$), —CH$_2$C(O)N($R^{12}$)($R^{13}$), —CH$_2$N($R^{14}$)C(O)$R^{15}$, —CH$_2$S(O)$_2$$R^{15}$, and —CH$_2$S(O)$_2$N($R^{12}$)($R^{13}$), wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20z1}$;

$Z^2$ is $C(R^{z2})$, C, or N;

$R^{z2}$ is selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —N($R^{12}$)($R^{13}$), —C(O)$OR^{12}$, —OC(O)N($R^{12}$)($R^{13}$), —N($R^{14}$)C(O)N($R^{12}$)($R^{13}$), —N($R^{14}$)C(O)$OR^{15}$, —N($R^{14}$)S(O)$_2$$R^{15}$, —C(O)$R^{15}$, —S(O)$R^{15}$, —OC(O)$R^{15}$, —C(O)N($R^{12}$)($R^{13}$), —C(O)C(O)N($R^{12}$)($R^{13}$), —N($R^{14}$)C(O)$R^{15}$, —S(O)$_2$$R^{15}$, —S(O)$_2$N($R^{12}$)($R^{13}$), —S(=O)(=NH)N($R^{12}$)($R^{13}$), —CH$_2$C(O)N($R^{12}$)

($R^{13}$), —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20z2}$;

$Z^3$ is $C(R^{z3})$, C, or N;

$R^{z3}$ is selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20z3}$;

$Z^4$ is a bond, $Z^{4a}$, $Z^{4a}Z^{4b}$, $Z^{4a}Z^{4b}Z^{4c}$, $Z^{4a}Z^{4b}Z^{4c}Z^{4d}$, or $Z^{4a}Z^{4b}Z^{4c}Z^{4d}Z^{4e}$; wherein $Z^{4a}$ is directly bonded to $Z^2$; and wherein if $Z^4$ is a bond then $Z^2$ is directly bonded to $Z^5$;

$Z^{4a}$, $Z^{4b}$, $Z^{4c}$, $Z^{4d}$, and $Z^{4e}$ are independently $C(R^{z4})$, $N(R^{z4})$, $C(R^{z4})_2$, C(O), S(O), $S(O)_2$, $S(O)(NR^{z4})$, $P(O)(R^{z4})$, O, S, or N;

provided that if z9n is 0 and $Z^4$ is $Z^{4a}Z^{4b}$; then (1) $Z^{4b}$ is $C(R^{z4})$, $C(R^{z4})_2$, C(O), S(O), $S(O)_2$, $S(O)(NR^{z4})$, $P(O)(R^{z4})$, O, S, or N, (2) $Z^{4b}$ is $N(R^{z4})$ and $Z^{4a}$ is C(O), S(O), $S(O)_2$; $S(O)(NR^{z4})$, or $P(O)(R^{z4})$; (3) $Z^{4b}$ is $N(R^{z4})$ and $Z^5$ is C(O), S(O), $S(O)_2$, $S(O)(NR^{z4})$, or $P(O)(R^{z5})$; or (4) $Z^{4b}$ is $N(R^{z4})$ and $Z^3$ is $C(R^{z3})$ or C;

each $R^{z4}$ is independently selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{12}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{12}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20z4}$; or two $R^{z4}$ bonded to the same carbon are joined to form $C_{2-6}$alkenyl optionally substituted with one, two, or three $R^{20z4}$;

$Z^5$ is $C(R^{z5})$, $N(R^{z5})$, $C(R^{z5})_2$, C(O), S(O), $S(O)_2$, $S(O)(NR^{z5})$, O, S, or N;

each $R^{z5}$ is independently selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{12}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{12}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20z5}$; or two $R^{z5}$ bonded to the same carbon are joined to form $C_{2-6}$alkenyl optionally substituted with one, two, or three $R^{20z5}$;

$Z^6$ is $C(R^{z6})$, $N(R^{z6})$, $C(R^{z6})_2$, C(O), S(O), $S(O)_2$, $S(O)(NR^{z6})$, O, S, or N;

each $R^{z6}$ is independently selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{12}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{12}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20z6}$; or two $R^{z6}$ bonded to the same carbon are joined to form $C_{2-6}$alkenyl optionally substituted with one, two, or three $R^{20z6}$;

and further wherein the compound optionally includes one of the following:

(1) two $R^{z4}$ bonded to the same carbon atom are joined to form monocyclic $C_{3-7}$cycloalkyl or monocyclic 3-7 membered heterocycloalkyl, wherein the monocyclic $C_{3-7}$cycloalkyl and monocyclic 3-7 membered heterocycloalkyl are optionally substituted with one, two, or three $R^{20z}$;

(2) two or more $R^{z4}$ bonded to adjacent atoms are joined to form monocyclic $C_{3-7}$cycloalkyl, monocyclic 3-7 membered heterocycloalkyl, phenyl, or monocyclic 5-6 membered heteroaryl, wherein the monocyclic $C_{3-7}$cycloalkyl, monocyclic 3-7 membered heterocycloalkyl, phenyl, and monocyclic 5-6 membered heteroaryl are optionally substituted with one, two, or three $R^{20z}$;

(3) two $R^{z5}$ bonded to the same carbon atom are joined to form monocyclic $C_{3-7}$cycloalkyl or monocyclic 3-7 membered heterocycloalkyl, wherein the monocyclic $C_{3-7}$cycloalkyl and monocyclic 3-7 membered heterocycloalkyl are optionally substituted with one, two, or three $R^{20z}$;

(4) one or two $R^{z4}$ bonded to one atom and one or two $R^{z5}$ bonded to an adjacent atom are joined to form monocyclic $C_{3-7}$cycloalkyl, monocyclic 3-7 membered heterocycloalkyl, phenyl, or monocyclic 5-6 membered heteroaryl, wherein the monocyclic $C_{3-7}$cycloalkyl, monocyclic 3-7 membered heterocycloalkyl, phenyl, and monocyclic 5-6 membered heteroaryl are optionally substituted with one, two, or three $R^{20z}$;

(5) one or two $R^{z4}$ bonded to one atom and one or two $R^{z5}$ bonded to a second atom are joined to form monocyclic $C_{3-7}$cycloalkyl or monocyclic 3-7 membered heterocycloalkyl, wherein the monocyclic $C_{3-7}$cycloalkyl and monocyclic 3-7 membered heterocycloalkyl are optionally substituted with one, two, or three $R^{20z}$;

(6) two $R^{z6}$ bonded to the same carbon atom are joined to form monocyclic $C_{3-7}$cycloalkyl or monocyclic 3-7 membered heterocycloalkyl, wherein the monocyclic $C_{3-7}$cycloalkyl and monocyclic 3-7 membered heterocycloalkyl are optionally substituted with one, two, or three $R^{20z}$;

(7) one or two $R^{z5}$ bonded to one atom and one or two $R^{z6}$ bonded to an adjacent atom are joined to form monocyclic $C_{3-7}$cycloalkyl, monocyclic 3-7 membered heterocycloalkyl, phenyl, or monocyclic 5-6 membered heteroaryl, wherein the monocyclic $C_{3-7}$cycloalkyl, monocyclic 3-7 membered heterocycloalkyl, phenyl, and monocyclic 5-6 membered heteroaryl are optionally substituted with one, two, or three $R^{20z}$; or (8) one or two $R^{z4}$ bonded to one atom and one or two $R^{z6}$ bonded to a second atom are joined to form monocyclic $C_{3-7}$cycloalkyl or monocyclic 3-7 membered heterocycloalkyl, wherein the monocyclic $C_{3-7}$cycloalkyl and monocyclic 3-7 membered heterocycloalkyl are optionally substituted with one, two, or three $R^{20z}$;

two $R^{20z}$ bonded to the same carbon atom are optionally joined to form monocyclic $C_{3-7}$cycloalkyl or monocyclic 3-7 membered heterocycloalkyl, wherein the monocyclic $C_{3-7}$cycloalkyl and monocyclic 3-7 membered heterocycloalkyl are optionally substituted with one, two, or three $R^{20zz}$; or two or more $R^{20z}$ bonded to two adjacent atoms are optionally joined to form monocyclic $C_{3-7}$cycloalkyl, monocyclic 3-7 membered heterocycloalkyl, phenyl, or monocyclic 5-6 membered heteroaryl, wherein the $C_{3-7}$cycloalkyl, monocyclic 3-7 membered heterocycloalkyl, phenyl, and monocyclic 5-6 membered heteroaryl are optionally substituted with one, two, or three $R^{20zz}$;

each $Z^9$ is independently $C(R^{z9})$, $N(R^{z9})$, $C(R^{z9})_2$, $C(O)$, $S(O)$, $S(O)_2$, $O$, $S$, or $N$;

z9n is 0, 1, 2, 3, or 4; wherein if z9n is 0 then $Z^3$ is directly bonded to $W^4$;

each $R^{z9}$ is independently selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20z9}$;

wherein the sum of z1n and z9n is 2, 3, or 4;

each $R^{12}$ is independently selected from hydrogen, $C_{1-6}$alkyl, $C_{2-6}$alkenyl, $C_{2-6}$alkynyl, $C_{3-10}$cycloalkyl, —$CH_2$-$C_{3-10}$cycloalkyl, $C_{2-9}$heterocycloalkyl, —$CH_2$-$C_{2-9}$heterocycloalkyl, $C_{6-10}$aryl, —$CH_2$-$C_{6-10}$aryl, —$CH_2$-$C_{1-9}$heteroaryl, and $C_{1-9}$heteroaryl, wherein $C_{1-6}$alkyl, $C_{2-6}$alkenyl, $C_{2-6}$alkynyl, $C_{3-10}$cycloalkyl, —$CH_2$-$C_{3-10}$cycloalkyl, $C_{2-9}$heterocycloalkyl, —$CH_2$-$C_{2-9}$heterocycloalkyl, $C_{6-10}$aryl, —$CH_2$-$C_{6-10}$aryl, —$CH_2$-$C_{1-9}$heteroaryl, and $C_{1-9}$heteroaryl are optionally substituted with one, two, or three $R^{20l}$;

$R^{12a}$ is independently selected from hydrogen, $C_{1-6}$alkyl, $C_{2-6}$alkenyl, $C_{2-6}$alkynyl, $C_{3-10}$cycloalkyl, —$C(R^{12c})_2$-$C_{3-10}$cycloalkyl, $C_{2-9}$heterocycloalkyl, —$C(R^{12c})_2$-$C_{2-9}$heterocycloalkyl, $C_{6-10}$aryl, —$C(R^{12c})_2$-$C_{6-10}$aryl, —$C(R^{12c})_2$-$C_{1-9}$heteroaryl, and $C_{1-9}$heteroaryl, wherein $C_{1-6}$alkyl, $C_{2-6}$alkenyl, $C_{2-6}$alkynyl, $C_{3-10}$cycloalkyl, —$C(R^{12c})_2$-$C_{3-10}$cycloalkyl, $C_{2-9}$heterocycloalkyl, —$C(R^{12c})_2$-$C_{2-9}$heterocycloalkyl, $C_{6-10}$aryl, —$C(R^{12c})_2$-$C_{6-10}$aryl, —$C(R^{12c})_2$-$C_{1-9}$heteroaryl, and $C_{1-9}$heteroaryl are optionally substituted with one, two, or three $R^{20l}$;

each $R^{12c}$ is independently selected from hydrogen and $R^{20lc}$;

each $R^{13}$ is independently selected from hydrogen, $C_{1-6}$alkyl, and $C_{1-6}$haloalkyl; or $R^{12}$ and $R^{13}$, together with the nitrogen to which they are attached, form a $C_{2-9}$heterocycloalkyl ring optionally substituted with one, two, or three $R^{20m}$;

each $R^{14}$ is independently selected from hydrogen, $C_{1-6}$alkyl, and $C_{1-6}$haloalkyl;

each $R^{15}$ is independently selected from $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20o}$;

each $R^{20z1}$, $R^{20z2}$, $R^{20z3}$, $R^{20z4}$, $R^{20z5}$, $R^{20z6}$, and $R^{20z9}$ is independently selected from halogen, oxo, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{12}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{12}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20z}$;

each $R^{20z}$ is independently selected from halogen, oxo, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{12}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{12}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20zz}$;

each $R^{20a}$, $R^{20b}$, $R^{20c}$, $R^{20d}$, $R^{20e}$, $R^{20f}$, $R^{20g}$, $R^{20h}$, $R^{20i}$, $R^{20j}$, $R^{20l}$, $R^{20lc}$, $R^{20m}$, $R^{20o}$, $R^{20q}$, and $R^{20zz}$ is independently selected from halogen, oxo, —CN, $C_{1-6}$alkyl, $C_{2-6}$alkenyl, $C_{2-6}$alkynyl, $C_{3-10}$cycloalkyl, —$CH_2$-$C_{3-10}$cycloalkyl, $C_{2-9}$heterocycloalkyl, —$CH_2$-$C_{2-9}$heterocycloalkyl, $C_{6-10}$aryl, —$CH_2$-$C_{6-10}$aryl, —$CH_2$-$C_{1-9}$heteroaryl, $C_{1-9}$heteroaryl, —$OR^{21}$, —$SR^{21}$, —$N(R^{22})(R^{23})$, —$C(O)OR^{22}$, —$C(O)N(R^{22})(R^{23})$, —$C(O)C(O)N(R^{22})(R^{23})$, —$OC(O)N(R^{22})(R^{23})$, —$N(R^{24})C(O)N(R^{22})(R^{23})$, —$N(R^{24})C(O)OR^{25}$, —$N(R^{24})C(O)R^{21}$, —$N(R^{24})S(O)_2R^{25}$, —$C(O)R^{21}$, —$S(O)_2R^{25}$, —$S(O)_2N(R^{22})(R^{23})$, —$OCH_2C(O)OR^{22}$, =$NR^{21}$, and —$OC(O)R^{25}$; two $R^{20q}$ bonded to adjacent atoms are optionally joined to form a $C_{3-10}$cycloalkyl, $C_{2-9}$heterocycloalkyl, $C_{6-10}$aryl, or $C_{1-9}$heteroaryl; wherein $C_{1-6}$alkyl, $C_{2-6}$alkenyl, $C_{2-6}$alkynyl, $C_{3-10}$cycloalkyl, —$CH_2$-$C_{3-10}$cycloalkyl, $C_{2-9}$heterocycloalkyl, —$CH_2$-$C_{2-9}$heterocycloalkyl, $C_{6-10}$aryl, —CH$_2$-C$_{6-10}$aryl, —CH$_2$-C$_{1-9}$heteroaryl, and C$_{1-9}$heteroaryl are optionally substituted with one, two, or three groups independently selected from halogen, oxo, —CN, C$_{1-6}$alkyl, C$_{1-6}$haloalkyl, C$_{1-6}$alkoxy, C$_{1-6}$haloalkoxy, —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, —N(R$^{24}$)C(O)R$^{25}$, —N(R$^{24}$)S(O)$_2$R$^{25}$, —C(O)R$^{25}$, —S(O)$_2$R$^{25}$, —S(O)$_2$N(R$^{22}$)(R$^{23}$), and —OC(O)R$^{25}$;

each R$^{21}$ is independently selected from hydrogen, C$_{1-6}$alkyl, C$_{1-6}$haloalkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl;

each R$^{22}$ is independently selected from hydrogen, C$_{1-6}$alkyl, C$_{1-6}$haloalkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl;

each R$^{23}$ is independently selected from hydrogen and C$_{1-6}$alkyl;

each R$^{24}$ is independently selected from hydrogen and C$_{1-6}$alkyl;

each R$^{25}$ is independently selected from C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl; and ----- indicates a single or double bond such that all valences are satisfied.

In embodiments,

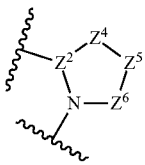

is selected from

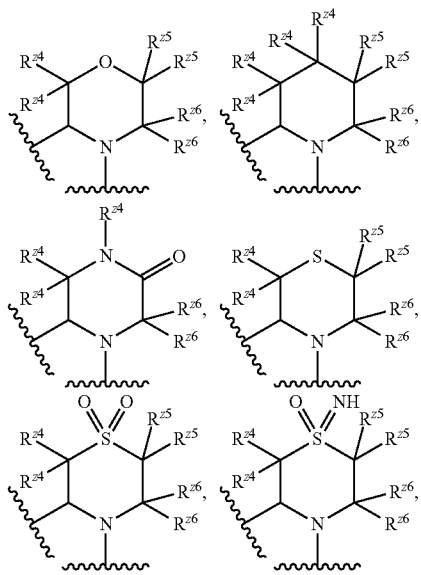

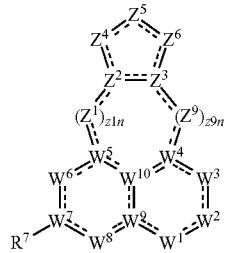

In some embodiments, the present disclosure provides a compound of Formula (A), or a pharmaceutically acceptable salt or solvate thereof:

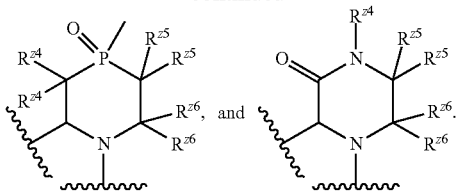

(A)

wherein:
W$^1$ is N, W$^2$ is C(R$^2$), W$^3$ is N, W$^4$ is C, W$^5$ is C, W$^6$ is C(R$^6$), W$^7$ is C, W$^8$ is C(R$^8$), W$^9$ is C, and W$^{10}$ is C;
W$^1$ is N, W$^2$ is C(R$^2$), W$^3$ is N, W$^4$ is C, W$^5$ is C, W$^6$ is N, W$^7$ is C, W$^8$ is C(R$^8$), W$^9$ is C, W$^{10}$ is C;
W$^1$ is N, W$^2$ is C(R$^2$), W$^3$ is N, W$^4$ is C, W$^5$ is C(R$^5$), W$^6$ is C(R$^6$)$_2$, W$^7$ is N, W$^8$ is C(R$^8$)$_2$, W$^9$ is C, W$^{10}$ is C; or
W$^1$ is N(R$^1$), W$^2$ is C(O), W$^3$ is N, W$^4$ is C, W$^5$ is C, W$^6$ is C(R$^6$), W$^7$ is C, W$^8$ is N, W$^9$ is C, W$^{10}$ is C;
R$^1$ is selected from C$_{6-10}$aryl and C$_{1-9}$heteroaryl, wherein C$_{6-10}$aryl and C$_{1-9}$heteroaryl are optionally substituted with one, two, or three substituents independently selected from C$_{1-6}$alkyl;
R$^2$ is selected from hydrogen, C$_{1-6}$alkyl, C$_{2-6}$alkenyl, C$_{3-10}$cycloalkyl, C$_{2-9}$heterocycloalkyl, C$_{6-10}$aryl, C$_{1-9}$heteroaryl, —OR$^{12a}$, —SR$^{12a}$, —N(R$^{12a}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$), —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein C$_{1-6}$alkyl, C$_{2-6}$alkenyl, C$_{3-10}$cycloalkyl, C$_{2-9}$heterocycloalkyl, C$_{6-10}$aryl, and C$_{1-9}$heteroaryl are optionally substituted with one, two, or three R$^{20b}$;
R$^5$ is selected from hydrogen, halogen, C$_{1-6}$alkyl, C$_{1-6}$haloalkyl, —OR$^{12}$, and —N(R$^{12}$)(R$^{13}$);
each R$^6$ is independently selected from hydrogen, halogen, C$_{1-6}$alkyl, C$_{1-6}$haloalkyl, —OR$^{12}$, and —N(R$^{12}$)(R$^{13}$);
R$^7$ is -L$^7$—R$^{17}$;
L$^7$ is a bond, C$_1$-C$_4$alkyl, C$_2$-C$_4$alkenyl, C$_2$-C$_4$alkynyl, 2-4 membered heteroalkylene linker, —O—, —N(R$^{7d}$)—, —C(O)—, —S—, —S(O)$_2$—, —S(O)—, —P(O)R$^{7d}$—, CR$^{7c}$R$^{7c}$—, —OCR$^{7c}$R$^{7c}$—, —N(R$^{7d}$)CR$^{7c}$R$^{7c}$—, —C(O)CR$^{7c}$R$^{7c}$—, —SCR$^{7c}$R$^{7c}$—, —S(O)$_2$CR$^{7c}$R$^{7c}$—, —S(O)CR$^{7c}$R$^{7c}$—, —P(O)R$^{7d}$CR$^{7c}$R$^{7c}$—, —CR$^{7c}$R$^{7c}$CR$^{7c}$R$^{7c}$—, —CR$^{7c}$R$^{7c}$O—, —CR$^{7c}$R$^{7c}$N(R$^{7d}$)—, —CR$^{7c}$R$^{7c}$C(O)—, —CR$^{7c}$R$^{7c}$S—, —CR$^{7c}$R$^{7c}$S(O)$_2$—, —CR$^{7c}$R$^{7c}$S(O)—, —CR$^{7c}$R$^{7c}$P(O)R$^{7d}$—, —N(R$^{7d}$)C(O)—, —N(R$^{7d}$)S(O)$_2$—, —N(R$^{7d}$)S(O)—, —N(R$^{7d}$)P(O)R$^{7d}$—, —C(O)N(R$^{7d}$)—, —S(O)$_2$N(R$^{7d}$)—, —S(O)N(R$^{7d}$)—, —P(O)R$^{7d}$N(R$^{7d}$)—, —OC(O)—, —OS(O)$_2$—, —OS(O)—, —OP(O)R$^{7d}$—, —C(O)O—, —S(O)$_2$O—, —S(O)O—, or —P(O)R$^{7d}$O—; wherein the C$_1$-C$_4$alkyl, C$_2$-C$_4$alkenyl, C$_2$-C$_4$alkynyl, 2-4 membered heteroalkylene linker are optionally substituted with one, two, or three R$^{20g}$;

each R$^{7c}$ is independently selected from hydrogen, halogen, —CN, C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, C$_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$), S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl are optionally substituted with one, two, or three R$^{20g}$;

each R$^{7d}$ is independently selected from hydrogen, —CN, C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, C$_{1-9}$heteroaryl, —OR$^{12}$, —SR$^{12}$, —C(O)OR$^{12}$, —OC(O)N(R$^{12}$)(R$^{13}$), —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —S(O)$_2$R$^{15}$, —S(O)$_2$N(R$^{12}$)(R$^{13}$), —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl are optionally substituted with one, two, or three R$^{20g}$;

R$^{17}$ is selected from C$_{3-10}$cycloalkyl, 3-10 membered heterocycloalkyl, C$_{6-10}$aryl, and 5-10 membered heteroaryl, wherein C$_{3-10}$cycloalkyl, 3-10 membered heterocycloalkyl, C$_{6-10}$aryl, and 5-10 membered heteroaryl are optionally substituted with one or more R$^{20q}$;

each R$^8$ is independently selected from hydrogen, halogen, C$_{1-6}$alkyl, C$_{1-6}$haloalkyl, —OR$^{12}$, and —N(R$^{12}$)(R$^{13}$);

each Z$^1$ is independently C(R$^{z1}$)$_2$ or O;

z1n is 0, 1, 2, 3; wherein if z1n is 0 then Z$^2$ is directly bonded to W$^5$;

each R$^{z1}$ is independently selected from hydrogen, halogen, C$_{1-6}$alkyl, —OR$^{12}$, —N(R$^{12}$)(R$^{13}$), —N(R$^{14}$)C(O)N(R$^{12}$)(R$^{13}$), —C(O)R$^{15}$, —S(O)R$^{15}$, —C(O)N(R$^{12}$)(R$^{13}$), —N(R$^{14}$)C(O)R$^{15}$, —S(O)$_2$R$^{15}$, and —S(O)$_2$N(R$^{12}$)(R$^{13}$), wherein C$_{1-6}$alkyl is optionally substituted with one, two, or three R$^{20z1}$;

Z$^2$ is CH or N;

Z$^3$ is CH or N;

Z$^4$ is a bond, Z$^{4a}$, Z$^{4a}$Z$^{4b}$, Z$^{4a}$Z$^{4b}$Z$^{4c}$, Z$^{4a}$Z$^{4b}$Z$^{4c}$Z$^{4d}$, or Z$^{4a}$Z$^{4b}$Z$^{4c}$Z$^{4d}$Z$^{4e}$; wherein Z$^{4a}$ is directly bonded to Z$^2$; and wherein if Z$^4$ is a bond then Z$^2$ is directly bonded to Z$^5$;

Z$^{4a}$, Z$^{4b}$, Z$^{4c}$, Z$^{4d}$, and Z$^{4e}$ are independently N(R$^{z4}$), C(R$^{z4}$)$_2$, C(O), or O;

provided that if z9n is 0 and Z$^4$ is Z$^{4a}$Z$^{4b}$; then (1) Z$^{4b}$ is C(R$^{z4}$)$_2$, C(O), or O, (2) Z$^{4b}$ is N(R$^{z4}$) and Z$^{4a}$ is C(O); or (3) Z$^{4b}$ is N(R$^{z4}$) and Z$^3$ is CH;.

each R$^{z4}$ is independently selected from hydrogen, halogen, —CN, C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, C$_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{12}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{12}$, —S(O)$_2$R$^{15}$, —S(O)$_2$N(R$^{12}$)(R$^{13}$), S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl are optionally substituted with one, two, or three R$^{20z4}$; or two R$^{z4}$ bonded to the same carbon are joined to form C$_{2-6}$alkenyl optionally substituted with one, two, or three R$^{20z4}$;

Z$^5$ is N(R$^{z5}$), C(R$^{z5}$)$_2$, or O;

each R$^{z5}$ is independently selected from hydrogen, halogen, —CN, C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, C$_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{12}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{12}$, —S(O)$_2$R$^{15}$, —S(O)$_2$N(R$^{12}$)(R$^{13}$), S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl are optionally substituted with one, two, or three R$^{20z5}$; or two R$^{z5}$ bonded to the same carbon are joined to form C$_{2-6}$alkenyl optionally substituted with one, two, or three R$^{20z5}$;

Z$^6$ is C(R$^{z6}$)$_2$;

each R$^{z6}$ is independently selected from hydrogen, halogen, —CN, C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, C$_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{12}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{12}$, —S(O)$_2$R$^{15}$, —S(O)$_2$N(R$^{12}$)(R$^{13}$), S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl are optionally substituted with one, two, or three R$^{20z6}$; or two R$^{z6}$ bonded to the same carbon are joined to form C$_{2-6}$alkenyl optionally substituted with one, two, or three R$^{20z6}$;

each Z$^9$ is independently N(R$^{z9}$), C(R$^{z9}$)$_2$, or O;

z9n is 0, 1, or 2; wherein if z9n is 0 then Z$^3$ is directly bonded to W$^4$;

each R$^{z9}$ is independently selected from hydrogen, halogen, —CN, C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, C$_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{12}$, —S(O)$_2$R$^{15}$, —S(O)$_2$N(R$^{12}$)(R$^{13}$), S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)

($R^{13}$), wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20z9}$;

wherein the sum of z1n and z9n is 2, 3, or 4;

each $R^{12}$ is independently selected from hydrogen, $C_{1-6}$alkyl, $C_{2-6}$alkenyl, $C_{2-6}$alkynyl, $C_{3-10}$cycloalkyl, —$CH_2$-$C_{3-10}$cycloalkyl, $C_{2-9}$heterocycloalkyl, —$CH_2$-$C_{2-9}$heterocycloalkyl, $C_{6-10}$aryl, —$CH_2$-$C_{6-10}$aryl, —$CH_2$-$C_{1-9}$heteroaryl, and $C_{1-9}$heteroaryl, wherein $C_{1-6}$alkyl, $C_{2-6}$alkenyl, $C_{2-6}$alkynyl, $C_{3-10}$cycloalkyl, —$CH_2$-$C_{3-10}$cycloalkyl, $C_{2-9}$heterocycloalkyl, —$CH_2$-$C_{2-9}$heterocycloalkyl, $C_{6-10}$aryl, —$CH_2$-$C_{6-10}$aryl, —$CH_2$-$C_{1-9}$heteroaryl, and $C_{1-9}$heteroaryl are optionally substituted with one, two, or three $R^{20l}$;

each $R^{12a}$ is independently selected from hydrogen, $C_{1-6}$alkyl, $C_{2-6}$alkenyl, $C_{2-6}$alkynyl, $C_{3-10}$cycloalkyl, —$C(R^{12c})_2$-$C_{3-10}$cycloalkyl, $C_{2-9}$heterocycloalkyl, —$C(R^{12c})_2$-$C_{2-9}$heterocycloalkyl, $C_{6-10}$aryl, —$C(R^{12c})_2$-$C_{6-10}$aryl, —$C(R^{12c})_2$-$C_{1-9}$heteroaryl, and $C_{1-9}$heteroaryl, wherein $C_{1-6}$alkyl, $C_{2-6}$alkenyl, $C_{2-6}$alkynyl, $C_{3-10}$cycloalkyl, —$C(R^{12c})_2$-$C_{3-10}$cycloalkyl, $C_{2-9}$heterocycloalkyl, —$C(R^{12c})_2$-$C_{2-9}$heterocycloalkyl, $C_{6-10}$aryl, —$C(R^{12c})_2$-$C_{6-10}$aryl, —$C(R^{12c})_2$-$C_{1-9}$heteroaryl, and $C_{1-9}$heteroaryl are optionally substituted with one, two, or three $R^{20l}$;

each $R^{12c}$ is independently selected from hydrogen and $R^{20lc}$;

each $R^{13}$ is independently selected from hydrogen, $C_{1-6}$alkyl, and $C_{1-6}$haloalkyl; or $R^{12}$ and $R^{13}$, together with the nitrogen to which they are attached, form a $C_{1-9}$heterocycloalkyl ring optionally substituted with one, two, or three $R^{20m}$;

each $R^{14}$ is independently selected from hydrogen, $C_{1-6}$alkyl, and $C_{1-6}$haloalkyl;

each $R^{15}$ is independently selected from $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20o}$;

each $R^{20z1}$, $R^{20z4}$, $R^{20z5}$, $R^{20z6}$, and $R^{20z9}$ is independently selected from halogen, oxo, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{12}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{12}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20z}$;

each $R^{20z}$ is independently selected from halogen, oxo, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{12}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{12}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})$ ($R^{13}$), wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20zz}$;

each $R^{20b}$, $R^{20g}$, $R^{20l}$, $R^{20lc}$, $R^{20m}$, $R^{20o}$, $R^{20q}$, and $R^{20zz}$ is independently selected from halogen, oxo, —CN, $C_{1-6}$alkyl, $C_{2-6}$alkenyl, $C_{2-6}$alkynyl, $C_{3-10}$cycloalkyl, —$CH_2$-$C_{3-10}$cycloalkyl, $C_{2-9}$heterocycloalkyl, —$CH_2$-$C_{2-9}$heterocycloalkyl, $C_{6-10}$aryl, —$CH_2$-$C_{6-10}$aryl, —$CH_2$-$C_{1-9}$heteroaryl, $C_{1-9}$heteroaryl, —$OR^{21}$, —$SR^{21}$, —$N(R^{22})(R^{23})$, —$C(O)OR^{22}$, —$C(O)N(R^{22})(R^{23})$, —$C(O)C(O)N(R^{22})(R^{23})$, —$OC(O)N(R^{22})(R^{23})$, —$N(R^{24})C(O)N(R^{22})(R^{23})$, —$N(R^{24})C(O)OR^{25}$, —$N(R^{24})C(O)R^{21}$, —$N(R^{24})S(O)_2R^{25}$, —$C(O)R^{21}$, —$S(O)_2R^{25}$, —$S(O)_2N(R^{22})(R^{23})$, —$OCH_2C(O)OR^{22}$, and —$OC(O)R^{25}$; wherein $C_{1-6}$alkyl, $C_{2-6}$alkenyl, $C_{2-6}$alkynyl, $C_{3-10}$cycloalkyl, —$CH_2$-$C_{3-10}$cycloalkyl, $C_{2-9}$heterocycloalkyl, —$CH_2$-$C_{2-9}$heterocycloalkyl, $C_{6-10}$aryl, —$CH_2$-$C_{6-10}$aryl, —$CH_2$-$C_{1-9}$heteroaryl, and $C_{1-9}$heteroaryl are optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —$OR^{21}$, —$SR^{21}$, —$N(R^{22})(R^{23})$, —$C(O)OR^{22}$, —$C(O)N(R^{22})(R^{23})$, —$C(O)C(O)N(R^{22})(R^{23})$, —$OC(O)N(R^{22})(R^{23})$, —$N(R^{24})C(O)N(R^{22})(R^{23})$, —$N(R^{24})C(O)OR^{25}$, —$N(R^{24})C(O)R^{25}$, —$N(R^{24})S(O)_2R^{25}$, —$C(O)R^{25}$, —$S(O)_2R^{25}$, —$S(O)_2N(R^{22})(R^{23})$, and —$OC(O)R^{25}$;

each $R^{21}$ is independently selected from hydrogen, $C_{1-6}$alkyl, $C_{1-6}$haloalkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl;

each $R^{22}$ is independently selected from hydrogen, $C_{1-6}$alkyl, $C_{1-6}$haloalkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl;

each $R^{23}$ is independently selected from hydrogen and $C_{1-6}$alkyl;

each $R^{24}$ is independently selected from hydrogen and $C_{1-6}$alkyl;

each $R^{25}$ is independently selected from $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; and ===== indicates a single or double bond such that all valences are satisfied.

In some embodiments, the present disclosure provides a compound of Formula (A), or a pharmaceutically acceptable salt or solvate thereof:

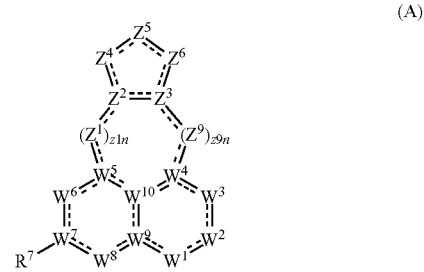

(A)

wherein:

$W^1$ is N, $W^2$ is $C(R^2)$, $W^3$ is N, $W^4$ is C, $W^5$ is C, $W^6$ is $C(R^6)$, $W^7$ is C, $W^8$ is $C(R^8)$, $W^9$ is C, and $W^{10}$ is C;

$R^2$ is selected from —$OR^{12a}$;

$R^6$ is selected from halogen;

$R^7$ is selected from 5-10 membered heteroaryl optionally substituted with one or more $R^{20q}$;

$R^8$ is selected from halogen;

each $Z^1$ is independently $C(R^{z1})_2$ or O;

z1n is 1, 2, or 3;

each $R^{z1}$ is independently selected from hydrogen, halogen, $C_{1-3}$alkyl, $C_{1-3}$haloalkyl, and —OH;

$Z^2$ is CH;

$Z^3$ is CH or N;

$Z^4$ is $Z^{4a}$, $Z^{4a}Z^{4b}$, $Z^{4a}Z^{4b}Z^{4c}$, or $Z^{4a}Z^{4b}Z^{4c}Z^{4d}$; wherein $Z^{4a}$ is directly bonded to $Z^2$;

$Z^{4a}$, $Z^{4b}$, $Z^{4c}$, and $Z^{4d}$ are independently $N(R^{z4})$, $C(R^{z4})_2$, C(O), or O;

provided that if z9n is 0 and $Z^4$ is $Z^{4a}Z^{4b}$; then (1) $Z^{4b}$ is $C(R^{z4})_2$, C(O), or O, (2) $Z^{4b}$ is $N(R^{z4})$ and $Z^{4a}$ is C(O); or (3) $Z^{4b}$ is $N(R^{z4})$ and $Z^3$ is CH;.

each $R^{z4}$ is independently selected from hydrogen, halogen, —CN, $C_{1-6}$alkyl, $C_{2-6}$alkenyl, $C_{2-6}$alkynyl, —$OR^{12}$, —$N(R^{12})(R^{13})$, —$N(R^{14})C(O)N(R^{12})(R^{13})$, —$C(O)R^{12}$, and —$C(O)N(R^{12})(R^{13})$, wherein $C_{1-6}$alkyl, $C_{2-6}$alkenyl, and $C_{2-6}$alkynyl are optionally substituted with one, two, or three $R^{20z4}$; or two $R^{z4}$ bonded to the same carbon are joined to form $C_{2-6}$alkenyl optionally substituted with one, two, or three $R^{20z4}$;

$Z^5$ is $N(R^{z5})$, $C(R^{z5})_2$, or O;

each $R^{z5}$ is independently selected from hydrogen, halogen, —CN, $C_{1-6}$alkyl, $C_{2-6}$alkenyl, $C_{2-6}$alkynyl, —$OR^{12}$, —$N(R^{12})(R^{13})$, —$N(R^{14})C(O)N(R^{12})(R^{13})$, —$C(O)R^{12}$, and —$C(O)N(R^{12})(R^{13})$, wherein $C_{1-6}$alkyl, $C_{2-6}$alkenyl, and $C_{2-6}$alkynyl are optionally substituted with one, two, or three $R^{20z5}$; or two $R^{z5}$ bonded to the same carbon are joined to form $C_{2-6}$alkenyl optionally substituted with one, two, or three $R^{20z5}$;

$Z^6$ is $C(R^{z6})_2$;

each $R^{z6}$ is independently selected from hydrogen, halogen, —CN, $C_{1-6}$alkyl, $C_{2-6}$alkenyl, $C_{2-6}$alkynyl, —$OR^{12}$, —$N(R^{12})(R^{13})$, —$N(R^{14})C(O)N(R^{12})(R^{13})$, —$C(O)R^{12}$, and —$C(O)N(R^{12})(R^{13})$, wherein $C_{1-6}$alkyl, $C_{2-6}$alkenyl, and $C_{2-6}$alkynyl are optionally substituted with one, two, or three $R^{20z6}$; or two $R^{z6}$ bonded to the same carbon are joined to form $C_{2-6}$alkenyl optionally substituted with one, two, or three $R^{20z6}$;

$Z^9$ is $N(R^{z9})$;

z9n is 0 or 1; wherein if z9n is 0 then $Z^3$ is directly bonded to $W^4$;

each $R^{z9}$ is independently selected from hydrogen, $C_{1-3}$alkyl, and $C_{1-3}$haloalkyl;

wherein the sum of z1n and z9n is 2, 3, or 4;

each $R^{12}$ is independently selected from hydrogen, $C_{1-6}$alkyl, $C_{2-6}$alkenyl, $C_{2-6}$alkynyl, $C_{3-10}$cycloalkyl, —$CH_2$-$C_{3-10}$cycloalkyl, $C_{2-9}$heterocycloalkyl, —$CH_2$-$C_{2-9}$heterocycloalkyl, $C_{6-10}$aryl, —$CH_2$-$C_{6-10}$aryl, —$CH_2$-$C_{1-9}$heteroaryl, and $C_{1-9}$heteroaryl, wherein $C_{1-6}$alkyl, $C_{2-6}$alkenyl, $C_{2-6}$alkynyl, $C_{3-10}$cycloalkyl, —$CH_2$-$C_{3-10}$cycloalkyl, $C_{2-9}$heterocycloalkyl, —$CH_2$-$C_{2-9}$heterocycloalkyl, $C_{6-10}$aryl, —$CH_2$-$C_{6-10}$aryl, —$CH_2$-$C_{1-9}$heteroaryl, and $C_{1-9}$heteroaryl are optionally substituted with one, two, or three $R^{20l}$;

each $R^{12a}$ is independently selected from hydrogen, $C_{1-6}$alkyl, $C_{2-6}$alkenyl, $C_{2-6}$alkynyl, $C_{3-10}$cycloalkyl, —$C(R^{12c})_2$-$C_{3-10}$cycloalkyl, $C_{2-9}$heterocycloalkyl, —$C(R^{12c})_2$-$C_{2-9}$heterocycloalkyl, $C_{6-10}$aryl, —$C(R^{12c})_2$-$C_{6-10}$aryl, —$C(R^{12c})_2$-$C_{1-9}$heteroaryl, and $C_{1-9}$heteroaryl, wherein $C_{1-6}$alkyl, $C_{2-6}$alkenyl, $C_{2-6}$alkynyl, $C_{3-10}$cycloalkyl, —$C(R^{12c})_2$-$C_{3-10}$cycloalkyl, $C_{2-9}$heterocycloalkyl, —$C(R^{12c})_2$-$C_{2-9}$hetero-
cycloalkyl, $C_{6-10}$aryl, —$C(R^{12c})_2$-$C_{6-10}$aryl, —$C(R^{12c})_2$-$C_{1-9}$heteroaryl, and $C_{1-9}$heteroaryl are optionally substituted with one, two, or three $R^{20l}$;

each $R^{12c}$ is independently selected from hydrogen and $R^{20lc}$;

each $R^{13}$ is independently selected from hydrogen, $C_{1-6}$alkyl, and $C_{1-6}$haloalkyl; or $R^{12}$ and $R^{13}$, together with the nitrogen to which they are attached, form a $C_{1-9}$heterocycloalkyl ring optionally substituted with one, two, or three $R^{20m}$;

each $R^{14}$ is independently selected from hydrogen, $C_{1-6}$alkyl, and $C_{1-6}$haloalkyl;

each $R^{15}$ is independently selected from $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20o}$;

each $R^{20z4}$, $R^{20z5}$, and $R^{20z6}$ is independently selected from halogen, oxo, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})S(O)N(R^{12})(R^{13})$, —$N(R^{14})C(O)OR^{15}$, —$N(R^{14})S(O)_2R^{15}$, —$C(O)R^{12}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{12}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20z}$;

each $R^{20z}$ is independently selected from halogen, oxo, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{12}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{12}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20zz}$;

each $R^{20l}$, $R^{20lc}$, $R^{20m}$, $R^{20o}$, $R^{20q}$, and $R^{20zz}$ is independently selected from halogen, oxo, —CN, $C_{1-6}$alkyl, $C_{2-6}$alkenyl, $C_{2-6}$alkynyl, $C_{3-10}$cycloalkyl, —$CH_2$-$C_{3-10}$cycloalkyl, $C_{2-9}$heterocycloalkyl, —$CH_2$-$C_{2-9}$heterocycloalkyl, $C_{6-10}$aryl, —$CH_2$-$C_{6-10}$aryl, —$CH_2$-$C_{1-9}$heteroaryl, $C_{1-9}$heteroaryl, —$OR^{21}$, —$SR^{21}$, —$N(R^{22})(R^{23})$, —$C(O)OR^{22}$, —$C(O)N(R^{22})(R^{23})$, —$C(O)C(O)N(R^{22})(R^{23})$, —$OC(O)N(R^{22})(R^{23})$, —$N(R^{24})C(O)N(R^{22})(R^{23})$, —$N(R^{24})C(O)OR^{25}$, —$N(R^{24})C(O)R^{21}$, —$N(R^{24})S(O)_2R^{25}$, —$C(O)R^{21}$, —$S(O)_2R^{25}$, —$S(O)_2N(R^{22})(R^{23})$, —$OCH_2C(O)OR^{22}$, and —$OC(O)R^{25}$; wherein $C_{1-6}$alkyl, $C_{2-6}$alkenyl, $C_{2-6}$alkynyl, $C_{3-10}$cycloalkyl, —$CH_2$-$C_{3-10}$cycloalkyl, $C_{2-9}$heterocycloalkyl, —$CH_2$-$C_{2-9}$heterocycloalkyl, $C_{6-10}$aryl, —$CH_2$-$C_{6-10}$aryl, —$CH_2$-$C_{1-9}$heteroaryl, and $C_{1-9}$heteroaryl are optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —$OR^{21}$, —$SR^{21}$, —$N(R^{22})(R^{23})$, —C(O)OR²², —C(O)N(R²²)(R²³), —C(O)C(O)N(R²²)(R²³), —OC(O)N(R²²)(R²³), —N(R²⁴)C(O)N(R²²)(R²³), —N(R²⁴)C(O)OR²⁵, —N(R²⁴)C(O)R²⁵, —N(R²⁴)S(O)₂R²⁵, —C(O)R²⁵, —S(O)₂R²⁵, —S(O)₂N(R²²)(R²³), and —OC(O)R²⁵;

each $R^{21}$ is independently selected from hydrogen, $C_{1-6}$alkyl, $C_{1-6}$haloalkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl;

each $R^{22}$ is independently selected from hydrogen, $C_{1-6}$alkyl, $C_{1-6}$haloalkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl;

each $R^{23}$ is independently selected from hydrogen and $C_{1-6}$alkyl;

each $R^{24}$ is independently selected from hydrogen and $C_{1-6}$alkyl;

each $R^{25}$ is independently selected from $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; and ----- indicates a single or double bond such that all valences are satisfied.

In some embodiments, the compound of Formula (A) is a compound of the formula

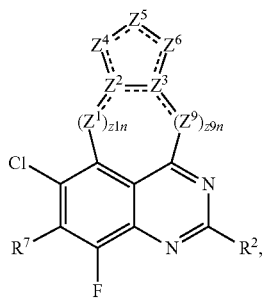

such as

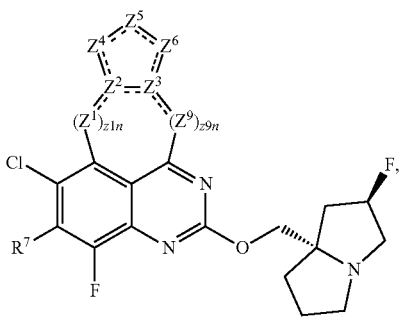

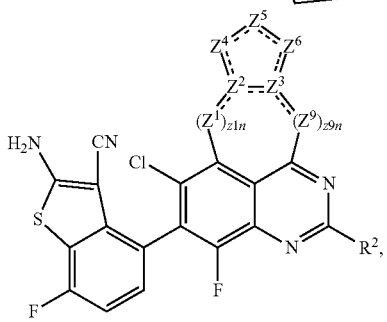

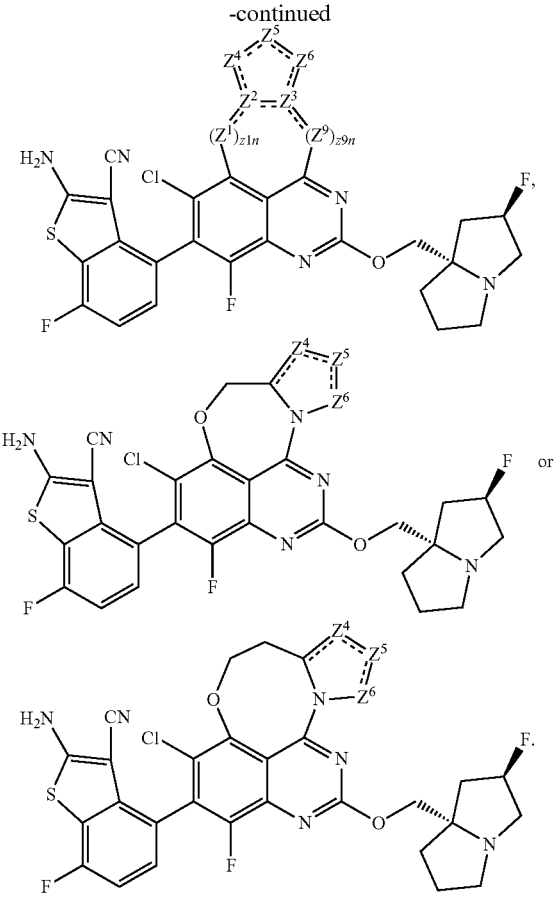

In an aspect is provided a compound of Formula (A), or a pharmaceutically acceptable salt or solvate thereof:

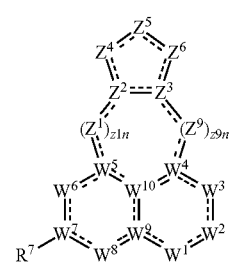

(A)

wherein:

$W^1$ is $N(R^1)$ or N;

$R^1$ is selected from hydrogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —OR¹², —SR¹², —C(O)OR¹², —OC(O)N(R¹²)(R¹³), —C(O)R¹⁵, —S(O)R¹⁵, —OC(O)R¹⁵, —C(O)N(R¹²)(R¹³), —C(O)C(O)N(R¹²)(R¹³), —S(O)₂R¹⁵, —S(O)₂N(R¹²)(R¹³), —S(=O)(=NH)N(R¹²)(R¹³), —CH₂C(O)N(R¹²)(R¹³), —CH₂N(R¹⁴)C(O)R¹⁵, —CH₂S(O)₂R¹⁵, and —CH₂S(O)₂N(R¹²)(R¹³), wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20a}$;

$W^2$ is $C(R^2)$, $N(R^2)$, $C(R^2)_2$, $C(O)$, $S(O)$, $S(O)_2$, or N;

each $R^2$ is independently selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12a}$, —$SR^{12a}$, —$N(R^{12a})(R^{13})$, —$N=(R^{15})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$—, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20b}$;

$W^3$ is $C(R^3)$, $N(R^3)$, $C(R^3)_2$, $C(O)$, $S(O)$, $S(O)_2$, or N;

each $R^3$ is independently selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20c}$;

$W^4$ is $C(R^4)$, C, or N;

$R^4$ is selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20d}$;

$W^5$ is $C(R^5)$, C, or N;

$R^5$ is selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20e}$;

$W^6$ is $C(R^6)$, $N(R^6)$, $C(R^6)_2$, $C(O)$, $S(O)$, $S(O)_2$, or N;

each $R^6$ is independently selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20f}$;

$W^7$ is $C(R^{7a})$, C, or N;

$R^{7a}$ is selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20g}$;

$R^7$ is -$L^7$—$R^{17}$;

$L^7$ is a bond, $C_1$-$C_4$alkyl, $C_2$-$C_4$alkenyl, $C_2$-$C_4$alkynyl, 2-4 membered heteroalkylene linker, —O—, —$N(R^{7d})$—, —$C(O)$—, —S—, —$S(O)_2$—, —$S(O)$—, —$P(O)R^{7d}$—, $CR^{7c}R^{7c}$—, —$OCR^{7c}R^{7c}$—, —$N(R^{7d})CR^{7c}R^{7c}$—, —$C(O)CR^{7c}R^{7c}$—, —$SCR^{7c}R^{7c}$—, —$S(O)_2CR^{7c}R^{7c}$—, —$S(O)CR^{7c}R^{7c}$—, —$P(O)R^{7d}CR^{7c}R^{7c}$—, —$CR^{7c}R^{7c}CR^{7c}R^{7c}$—, —$CR^{7c}R^{7c}O$—, —$CR^{7c}R^{7c}N(R^{7d})$—, —$CR^{7c}R^{7c}C(O)$—, —$CR^{7c}R^{7c}S$—, —$CR^{7c}R^{7c}S(O)_2$—, —$CR^{7c}R^{7c}S(O)$—, —$CR^{7c}R^{7c}P(O)R^{7d}$—, —$N(R^{7d})C(O)$—, —$N(R^{7d})S(O)_2$—, —$N(R^{7d})S(O)$—, —$N(R^{7d})P(O)R^{7d}$—, —$C(O)N(R^{7d})$—, —$S(O)_2N(R^{7d})$—, —$S(O)N(R^{7d})$—, —$P(O)R^{7d}N(R^{7d})$—, —$OC(O)$—, —$OS(O)_2$—, —$OS(O)$—, —$OP(O)R^{7d}$—, —$C(O)O$—, —$S(O)_2O$—, —$S(O)O$—, or —$P(O)R^{7d}O$—; wherein the $C_1$-$C_4$alkyl, $C_2$-$C_4$alkenyl, $C_2$-$C_4$alkynyl, 2-4 membered heteroalkylene linker are optionally substituted with one, two, or three $R^{20g}$;

each $R^{7c}$ is independently selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$, $S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20g}$;

each $R^{7d}$ is independently selected from hydrogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$C(O)OR^{12}$, —$OC(O)N(R^{12})(R^{13})$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2$ $R^{15}$, and —CH$_2$S(O)$_2$N(R$^{12}$)(R$^{13}$), wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl are optionally substituted with one, two, or three R$^{20g}$;

R$^{17}$ is selected from C$_{3-10}$cycloalkyl, 3-10 membered heterocycloalkyl, C$_{6-10}$aryl, and 5-10 membered heteroaryl, wherein C$_{3-10}$cycloalkyl, 3-10 membered heterocycloalkyl, C$_{6-10}$aryl, and 5-10 membered heteroaryl are optionally substituted with one or more R$^{20q}$; or L$^7$ is a bond and R$^{7a}$ and R$^{17}$, together with the carbon to which they are attached, form C$_{3-10}$cycloalkyl or 3-10 membered heterocycloalkyl, wherein the C$_{3-10}$cycloalkyl and 3-10 membered heterocycloalkyl are optionally substituted with one or more R$^{20q}$;

W$^8$ is C(R$^8$), N(R$^8$), C(R$^8$)$_2$, C(O), S(O), S(O)$_2$, or N;

each R$^8$ is independently selected from hydrogen, halogen, —CN, C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, C$_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$), —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl are optionally substituted with one, two, or three R$^{20h}$;

W$^9$ is C(R$^9$), C, or N;

R$^9$ is selected from hydrogen, halogen, —CN, C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, C$_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$), —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl are optionally substituted with one, two, or three R$^{20i}$;

W$^{10}$ C(R$^{10}$), C, or N;

R$^{10}$ is selected from hydrogen, halogen, —CN, C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, C$_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$), —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl are optionally substituted with one, two, or three R$^{20j}$;

each Z$^1$ is independently C(R$^{z1}$), N(R$^{z1}$), C(R$^{z1}$)$_2$, C(O), S(O), S(O)$_2$, O, S, or N;

z1n is 0, 1, 2, or 3; wherein if z1n is 0 then Z$^2$ is directly bonded to W$^5$;

each R$^{z1}$ is independently selected from hydrogen, halogen, —CN, C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, C$_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$), —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl are optionally substituted with one, two, or three R$^{20z1}$;

each Z$^9$ is independently C(R$^{z9}$), N(R$^{z9}$), C(R$^{z9}$)$_2$, C(O), S(O), S(O)$_2$, O, S, or N;

z9n is 0, 1, 2, or 3; wherein if z9n is 0 then Z$^3$ is directly bonded to W$^4$;

each R$^{z9}$ is independently selected from hydrogen, halogen, —CN, C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, C$_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$), —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl are optionally substituted with one, two, or three R$^{20z9}$;

wherein the sum of z1n and z9n is 2 or 3;

Z$^2$ is C(R$^{z2}$), C, or N;

R$^{z2}$ is selected from hydrogen, halogen, —CN, C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, C$_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$), —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl are optionally substituted with one, two, or three R$^{20z2}$;

Z$^3$ is C(R$^{z3}$), C, or N;

R$^{z3}$ is selected from hydrogen, halogen, —CN, C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, C$_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$), —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl are optionally substituted with one, two, or three R$^{20z3}$;

Z$^4$ is a bond, Z$^{4a}$, Z$^{4a}$Z$^{4b}$, Z$^{4a}$Z$^{4b}$Z$^{4c}$, or Z$^{4a}$Z$^{4b}$Z$^{4c}$Z$^{4d}$; wherein Z$^{4a}$ is directly bonded to Z$^2$; and wherein if Z$^4$ is a bond then Z$^2$ is directly bonded to Z$^5$;

Z$^{4a}$, Z$^{4b}$, Z$^{4c}$, and Z$^{4d}$ are independently C(R$^{z4}$), N(R$^{z4}$), C(R$^{z4}$)$_2$, C(O), S(O), S(O)$_2$, S(O)(NR$^{z4}$), O, S, or N;

provided that:
i) if z9n is 0 and $Z^4$ is $Z^{4a}Z^{4b}$; then (1) $Z^{4b}$ is $C(R^{z4})$, $C(R^{z4})_2$, C(O), S(O), S(O)$_2$, S(O)(NR$^{z4}$), O, S, or N, (2) $Z^{4b}$ is N(R$^{z4}$) and $Z^{4a}$ is C(O), S(O), or S(O)$_2$; (3) $Z^{4b}$ is N(R$^{z4}$) and $Z^5$ is C(O), S(O), or S(O)$_2$; or (4) $Z^{4b}$ is N(R$^{z4}$) and $Z^3$ is C(R$^{z3}$) or C; and
ii) one or more $R^{z4}$, $R^{z5}$, $R^{z6}$, $R^{20z4}$, $R^{20z5}$, $R^{20z6}$, or $R^{20z}$ is independently selected from —C(O)R$^{12}$ and —N(H)C(O)R$^{12}$; wherein the one or more $R^{12}$ are independently selected from $C_{3-10}$cycloalkyl, $C_{2-9}$heterocycloalkyl, $C_{6-10}$aryl, and $C_{1-9}$heteroaryl, wherein $C_{3-10}$cycloalkyl, $C_{2-9}$heterocycloalkyl, $C_{6-10}$aryl, and $C_{1-9}$heteroaryl are optionally substituted with one, two, or three $R^{20l}$;

each $R^{z4}$ is independently selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{12}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{12}$, —S(O)$_2$R$^{15}$, —S(O)$_2$N(R$^{12}$)(R$^{13}$), —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20z4}$; or two $R^{z4}$ bonded to the same carbon are joined to form $C_{2-6}$alkenyl optionally substituted with one, two, or three $R^{20z4}$;

$Z^5$ is C(R$^{z5}$), N(R$^{z5}$), C(R$^{z5}$)$_2$, C(O), S(O), S(O)$_2$, S(O)(NR$^{z5}$), O, S, or N;

each $R^{z5}$ is independently selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{12}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{12}$, —S(O)$_2$R$^{15}$, —S(O)$_2$N(R$^{12}$)(R$^{13}$), —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20z5}$; or two $R^{z5}$ bonded to the same carbon are joined to form $C_{2-6}$alkenyl optionally substituted with one, two, or three $R^{20z5}$;

$Z^6$ is C(R$^{z6}$), N(R$^{z6}$), C(R$^{z6}$)$_2$, C(O), S(O), S(O)$_2$, S(O)(NR$^{z6}$), O, S, or N;

each $R^{z6}$ is independently selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{12}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{12}$, —S(O)$_2$R$^{15}$, —S(O)$_2$N(R$^{12}$)(R$^{13}$), —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20z6}$; or two $R^{z6}$ bonded to the same carbon are joined to form $C_{2-6}$alkenyl optionally substituted with one, two, or three $R^{20z6}$;

and further wherein the compound optionally includes one of the following:

(1) two $R^{z4}$ bonded to the same carbon atom are joined to form monocyclic $C_{3-7}$cycloalkyl or monocyclic 3-7 membered heterocycloalkyl, wherein the monocyclic $C_{3-7}$cycloalkyl and monocyclic 3-7 membered heterocycloalkyl are optionally substituted with one, two, or three $R^{20z}$;

(2) two or more $R^{z4}$ bonded to adjacent atoms are joined to form monocyclic $C_{3-7}$cycloalkyl, monocyclic 3-7 membered heterocycloalkyl, phenyl, or monocyclic 5-6 membered heteroaryl, wherein the monocyclic $C_{3-7}$cycloalkyl, monocyclic 3-7 membered heterocycloalkyl, phenyl, and monocyclic 5-6 membered heteroaryl are optionally substituted with one, two, or three $R^{20z}$;

(3) two $R^{z5}$ bonded to the same carbon atom are joined to form monocyclic $C_{3-7}$cycloalkyl or monocyclic 3-7 membered heterocycloalkyl, wherein the monocyclic $C_{3-7}$cycloalkyl and monocyclic 3-7 membered heterocycloalkyl are optionally substituted with one, two, or three $R^{20z}$;

(4) one or two $R^{z4}$ bonded to one atom and one or two $R^{z5}$ bonded to an adjacent atom are joined to form monocyclic $C_{3-7}$cycloalkyl, monocyclic 3-7 membered heterocycloalkyl, phenyl, or monocyclic 5-6 membered heteroaryl, wherein the monocyclic $C_{3-7}$cycloalkyl, monocyclic 3-7 membered heterocycloalkyl, phenyl, and monocyclic 5-6 membered heteroaryl are optionally substituted with one, two, or three $R^{20z}$;

(5) one or two $R^{z4}$ bonded to one atom and one or two $R^{z5}$ bonded to a second atom are joined to form monocyclic $C_{3-7}$cycloalkyl or monocyclic 3-7 membered heterocycloalkyl, wherein the monocyclic $C_{3-7}$cycloalkyl and monocyclic 3-7 membered heterocycloalkyl are optionally substituted with one, two, or three $R^{20z}$;

(6) two $R^{z6}$ bonded to the same carbon atom are joined to form monocyclic $C_{3-7}$cycloalkyl or monocyclic 3-7 membered heterocycloalkyl, wherein the monocyclic $C_{3-7}$cycloalkyl and monocyclic 3-7 membered heterocycloalkyl are optionally substituted with one, two, or three $R^{20z}$;

(7) one or two $R^{z5}$ bonded to one atom and one or two $R^{z6}$ bonded to an adjacent atom are joined to form monocyclic $C_{3-7}$cycloalkyl, monocyclic 3-7 membered heterocycloalkyl, phenyl, or monocyclic 5-6 membered heteroaryl, wherein the monocyclic $C_{3-7}$cycloalkyl, monocyclic 3-7 membered heterocycloalkyl, phenyl, and monocyclic 5-6 membered heteroaryl are optionally substituted with one, two, or three $R^{20z}$; or (8) one or two $R^{z4}$ bonded to one atom and one or two $R^{z6}$ bonded to a second atom are joined to form monocyclic $C_{3-7}$cycloalkyl or monocyclic 3-7 membered heterocycloalkyl, wherein the monocyclic $C_{3-7}$cycloalkyl and monocyclic 3-7 membered heterocycloalkyl are optionally substituted with one, two, or three $R^{20z}$;

each $R^{12}$ is independently selected from hydrogen, $C_{1-6}$alkyl, $C_{2-6}$alkenyl, $C_{2-6}$alkynyl, $C_{3-10}$cycloalkyl, —CH$_2$-$C_{3-10}$cycloalkyl, $C_{2-9}$heterocycloalkyl, —CH$_2$-$C_{2-9}$heterocycloalkyl, $C_{6-10}$aryl, —CH$_2$-$C_{6-10}$aryl, —CH$_2$-

$C_{1-9}$heteroaryl, and $C_{1-9}$heteroaryl, wherein $C_{1-6}$alkyl, $C_{2-6}$alkenyl, $C_{2-6}$alkynyl, $C_{3-10}$cycloalkyl, —$CH_2$-$C_{3-10}$cycloalkyl, $C_{2-9}$heterocycloalkyl, —$CH_2$-$C_{2-9}$heterocycloalkyl, $C_{6-10}$aryl, —$CH_2$-$C_{6-10}$aryl, —$CH_2$-$C_{1-9}$heteroaryl, and $C_{1-9}$heteroaryl are optionally substituted with one, two, or three $R^{20l}$;

$R^{12a}$ is independently selected from hydrogen, $C_{1-6}$alkyl, $C_{2-6}$alkenyl, $C_{2-6}$alkynyl, $C_{3-10}$cycloalkyl, —$C(R^{12c})_2$-$C_{3-10}$cycloalkyl, $C_{2-9}$heterocycloalkyl, —$C(R^{12c})_2$-$C_{2-9}$heterocycloalkyl, $C_{6-10}$aryl, —$C(R^{12c})_2$-$C_{6-10}$aryl, —$C(R^{12c})_2$-$C_{1-9}$heteroaryl, and $C_{1-9}$heteroaryl, wherein $C_{1-6}$alkyl, $C_{2-6}$alkenyl, $C_{2-6}$alkynyl, $C_{3-10}$cycloalkyl, —$C(R^{12c})_2$-$C_{3-10}$cycloalkyl, $C_{2-9}$heterocycloalkyl, —$C(R^{12c})_2$-$C_{2-9}$heterocycloalkyl, $C_{6-10}$aryl, —$C(R^{12c})_2$-$C_{6-10}$aryl, —$C(R^{12c})_2$-$C_{1-9}$heteroaryl, and $C_{1-9}$heteroaryl are optionally substituted with one, two, or three $R^{20l}$;

each $R^{12c}$ is independently selected from hydrogen and $R^{20lc}$;

each $R^{13}$ is independently selected from hydrogen, $C_{1-6}$alkyl, and $C_{1-6}$haloalkyl; or $R^{12}$ and $R^{13}$, together with the nitrogen to which they are attached, form a $C_{2-9}$heterocycloalkyl ring optionally substituted with one, two, or three $R^{20m}$;

each $R^{14}$ is independently selected from hydrogen, $C_{1-6}$alkyl, and $C_{1-6}$haloalkyl;

each $R^{15}$ is independently selected from $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20o}$;

each $R^{20z1}$, $R^{20z2}$, $R^{20z3}$, $R^{20z4}$, $R^{20z5}$, $R^{20z6}$, and $R^{20z9}$ is independently selected from halogen, oxo, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{12}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{12}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20z}$;

each $R^{20z}$ is independently selected from halogen, oxo, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{12}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{12}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20zz}$;

two $R^{20z}$ bonded to the same carbon atom are optionally joined to form monocyclic $C_{3-7}$cycloalkyl or monocyclic 3-7 membered heterocycloalkyl, wherein the monocyclic $C_{3-7}$cycloalkyl and monocyclic 3-7 membered heterocycloalkyl are optionally substituted with one, two, or three $R^{20zz}$; or two or more $R^{20z}$ bonded to two adjacent atoms are optionally joined to form monocyclic $C_{3-7}$cycloalkyl, monocyclic 3-7 membered heterocycloalkyl, phenyl, or monocyclic 5-6 membered heteroaryl, wherein the $C_{3-7}$cycloalkyl, monocyclic 3-7 membered heterocycloalkyl, phenyl, and monocyclic 5-6 membered heteroaryl are optionally substituted with one, two, or three $R^{20zz}$;

each $R^{20a}$, $R^{20b}$, $R^{20c}$, $R^{20d}$, $R^{20e}$, $R^{20f}$, $R^{20g}$, $R^{20h}$, $R^{20i}$, $R^{20j}$, $R^{20lc}$, $R^{20l}$, $R^{20m}$, $R^{20o}$, $R^{20q}$, and $R^{20zz}$ is independently selected from halogen, oxo, —CN, $C_{1-6}$alkyl, $C_{2-6}$alkenyl, $C_{2-6}$alkynyl, $C_{3-10}$cycloalkyl, —$CH_2$-$C_{3-10}$cycloalkyl, $C_{2-9}$heterocycloalkyl, —$CH_2$-$C_{2-9}$heterocycloalkyl, $C_{6-10}$aryl, —$CH_2$-$C_{6-10}$aryl, —$CH_2$-$C_{1-9}$heteroaryl, $C_{1-9}$heteroaryl, —$OR^{21}$, —$SR^{21}$, —$N(R^{22})(R^{23})$, —$C(O)OR^{22}$, —$C(O)N(R^{22})(R^{23})$, —$C(O)C(O)N(R^{22})(R^{23})$, —$OC(O)N(R^{22})(R^{23})$, —$N(R^{24})C(O)N(R^{22})(R^{23})$, —$N(R^{24})C(O)OR^{25}$, —$N(R^{24})C(O)R^{21}$, —$N(R^{24})S(O)_2R^{25}$, —$C(O)R^{21}$, —$S(O)_2R^{25}$, —$S(O)_2N(R^{22})(R^{23})$, —$OCH_2C(O)OR^{22}$, =$NR^{21}$, and —$OC(O)R^{25}$; two $R^{20q}$ bonded to adjacent atoms are optionally joined to form a $C_{3-10}$cycloalkyl, $C_{2-9}$heterocycloalkyl, $C_{6-10}$aryl, or $C_{1-9}$heteroaryl; wherein $C_{1-6}$alkyl, $C_{2-6}$alkenyl, $C_{2-6}$alkynyl, $C_{3-10}$cycloalkyl, —$CH_2$-$C_{3-10}$cycloalkyl, $C_{2-9}$heterocycloalkyl, —$CH_2$-$C_{2-9}$heterocycloalkyl, $C_{6-10}$aryl, —$CH_2$-$C_{6-10}$aryl, —$CH_2$-$C_{1-9}$heteroaryl, and $C_{1-9}$heteroaryl are optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —$OR^{21}$, —$SR^{21}$, —$N(R^{22})(R^{23})$, —$C(O)OR^{22}$, —$C(O)N(R^{22})(R^{23})$, —$C(O)C(O)N(R^{22})(R^{23})$, —$OC(O)N(R^{22})(R^{23})$, —$N(R^{24})C(O)N(R^{22})(R^{23})$, —$N(R^{24})C(O)OR^{25}$, —$N(R^{24})C(O)R^{25}$, —$N(R^{24})S(O)_2R^{25}$, —$C(O)R^{25}$, —$S(O)_2R^{25}$, —$S(O)_2N(R^{22})(R^{23})$, and —$OC(O)R^{25}$;

each $R^{21}$ is independently selected from hydrogen, $C_{1-6}$alkyl, $C_{1-6}$haloalkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl;

each $R^{22}$ is independently selected from hydrogen, $C_{1-6}$alkyl, $C_{1-6}$haloalkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl;

each $R^{23}$ is independently selected from hydrogen and $C_{1-6}$alkyl;

each $R^{24}$ is independently selected from hydrogen and $C_{1-6}$alkyl;

each $R^{25}$ is independently selected from $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; and ===== indicates a single or double bond such that all valences are satisfied.

In an aspect is provided a compound of Formula (A), or a pharmaceutically acceptable salt or solvate thereof:

(A)

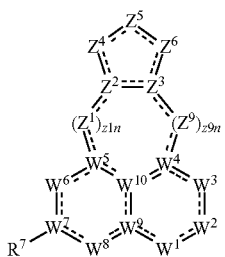

wherein:

$W^1$ is $N(R^1)$ or N;

$R^1$ is selected from hydrogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$C(O)OR^{12}$, —$OC(O)N(R^{12})(R^{13})$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20a}$;

$W^2$ is $C(R^2)$, $N(R^2)$, $C(R^2)_2$, $C(O)$, $S(O)$, $S(O)_2$, or N;

each $R^2$ is independently selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12a}$, —$SR^{12a}$, —$N(R^{12a})(R^{13})$, —$N=(R^{15})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$—, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20b}$;

$W^3$ is $C(R^3)$, $N(R^3)$, $C(R^3)_2$, $C(O)$, $S(O)$, $S(O)_2$, or N;

each $R^3$ is independently selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$CH_2S(O)_2R^{15}$, and —$CH_2S(O)_2N(R^{12})(R^{13})$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20c}$;

$W^4$ is $C(R^4)$, C, or N;

$R^4$ is selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20d}$;

$W^5$ is $C(R^5)$, C, or N;

$R^5$ is selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20e}$;

$W^6$ is $C(R^6)$, $N(R^6)$, $C(R^6)_2$, $C(O)$, $S(O)$, $S(O)_2$, or N;

each $R^6$ is independently selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20f}$;

$W^7$ is $C(R^{7a})$, C, or N;

$R^{7a}$ is selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20g}$;

$R^7$ is -$L^7$—$R^{17}$;

$L^7$ is a bond, $C_1$-$C_4$alkyl, $C_2$-$C_4$alkenyl, $C_2$-$C_4$alkynyl, 2-4 membered heteroalkylene linker, —O—, —$N(R^{7d})$—, —$C(O)$—, —S—, —$S(O)_2$—, —$S(O)$—, —$P(O)R^{7d}$—, $CR^{7c}R^{7c}$, —$OCR^{7c}R^{7c}$—, —$N(R^{7d})CR^{7c}R^{7c}$—, —$C(O)CR^{7c}R^{7c}$—, —$SCR^{7c}R^{7c}$—, —$S(O)_2CR^{7c}R^{7c}$—, —$S(O)CR^{7c}R^{7c}$—, —$P(O)R^{7d}CR^{7c}R^{7c}$—, —$CR^{7c}R^{7c}CR^{7c}R^{7c}$—, —$CR^{7c}R^{7c}O$—, —$CR^{7c}R^{7c}N(R^{7d})$—, —$CR^{7c}R^{7c}C(O)$—, —$CR^{7c}R^{7c}S$—, —$CR^{7c}R^{7c}S(O)_2$—, —$CR^{7c}R^{7c}S(O)$—, —$CR^{7c}R^{7c}P(O)R^{7d}$—, —$N(R^{7d})C(O)$—, —$N(R^{7d})S(O)_2$—, —$N(R^{7d})S(O)$—, —$N(R^{7d})P(O)R^{7d}$—, —$C(O)N(R^{7d})$—, —$S(O)_2N(R^{7d})$—, —$S(O)N(R^{7d})$—, —$P(O)R^{7d}N(R^{7d})$—, —$OC(O)$—, —OS(O)$_2$—, —OS(O)—, —OP(O)R$^{7d}$—, —C(O)O—, —S(O)$_2$O—, —S(O)O—, or —P(O)R$^{7d}$O—; wherein the C$_1$-C$_4$alkyl, C$_2$-C$_4$alkenyl, C$_2$-C$_4$alkynyl, 2-4 membered heteroalkylene linker are optionally substituted with one, two, or three R$^{20g}$;

each R$^{7c}$ is independently selected from hydrogen, halogen, —CN, C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, C$_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$), S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl are optionally substituted with one, two, or three R$^{20g}$;

each R$^{7d}$ is independently selected from hydrogen, —CN, C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, C$_{1-9}$heteroaryl, —OR$^{12}$, —SR$^{12}$, —C(O)OR$^{12}$, —OC(O)N(R$^{12}$)(R$^{13}$), —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —S(O)$_2$R$^{15}$, —S(O)$_2$N(R$^{12}$)(R$^{13}$), —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl are optionally substituted with one, two, or three R$^{20g}$;

R$^{17}$ is selected from C$_{3-10}$cycloalkyl, 3-10 membered heterocycloalkyl, C$_{6-10}$aryl, and 5-10 membered heteroaryl, wherein C$_{3-10}$cycloalkyl, 3-10 membered heterocycloalkyl, C$_{6-10}$aryl, and 5-10 membered heteroaryl are optionally substituted with one or more R$^{20q}$; or L$^7$ is a bond and R$^{7a}$ and R$^{17}$, together with the carbon to which they are attached, form C$_{3-10}$cycloalkyl or 3-10 membered heterocycloalkyl, wherein the C$_{3-10}$cycloalkyl and 3-10 membered heterocycloalkyl are optionally substituted with one or more R$^{20q}$;

W$^8$ is C(R$^8$), N(R$^8$), C(R$^8$)$_2$, C(O), S(O), S(O)$_2$, or N;

each R$^8$ is independently selected from hydrogen, halogen, —CN, C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, C$_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$), —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl are optionally substituted with one, two, or three R$^{20h}$;

W$^9$ is C(R$^9$), C, or N;

R$^9$ is selected from hydrogen, halogen, —CN, C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, C$_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$), —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl are optionally substituted with one, two, or three R$^{20i}$;

W$^{10}$ C(R$^{10}$), C, or N;

R$^{10}$ is selected from hydrogen, halogen, —CN, C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, C$_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$), —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl are optionally substituted with one, two, or three R$^{20j}$;

each Z$^1$ is independently C(R$^{z1}$), N(R$^{z1}$), C(R$^{z1}$)$_2$, C(O), S(O), S(O)$_2$, O, S, or N;

z1n is 0, 1, 2, or 3; wherein if z1n is 0 then Z$^2$ is directly bonded to W$^5$;

each R$^{z1}$ is independently selected from hydrogen, halogen, —CN, C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, C$_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$), —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl are optionally substituted with one, two, or three R$^{20z1}$;

each Z$^9$ is independently C(R$^{z9}$), N(R$^{z9}$), C(R$^{z9}$)$_2$, C(O), S(O), S(O)$_2$, O, S, or N;

z9n is 0, 1, 2, or 3; wherein if z9n is 0 then Z$^3$ is directly bonded to W$^4$;

each R$^{z9}$ is independently selected from hydrogen, halogen, —CN, C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, C$_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$), —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl are optionally substituted with one, two, or three R$^{20z9}$;

wherein the sum of z1n and z9n is 2 or 3;

Z$^2$ is C(R$^{z2}$), C, or N;

R$^{z2}$ is selected from hydrogen, halogen, —CN, C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, C$_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)

$R^{15}$, —C(O)N($R^{12}$)($R^{13}$), —C(O)C(O)N($R^{12}$)($R^{13}$), —N($R^{14}$)C(O)$R^{15}$, —S(O)$_2R^{15}$, —S(O)$_2$N($R^{12}$)($R^{13}$), —S(=O)(=NH)N($R^{12}$)($R^{13}$), —CH$_2$C(O)N($R^{12}$)($R^{13}$), —CH$_2$N($R^{14}$)C(O)$R^{15}$, —CH$_2$S(O)$_2R^{15}$, and —CH$_2$S(O)$_2$N($R^{12}$)($R^{13}$), wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20z2}$;

$Z^3$ is C($R^{z3}$), C, or N;

$R^{z3}$ is selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —O$R^{12}$, —S$R^{12}$, —N($R^{12}$)($R^{13}$), —C(O)O$R^{12}$, —OC(O)N($R^{12}$)($R^{13}$), —N($R^{14}$)C(O)N($R^{12}$)($R^{13}$), —N($R^{14}$)C(O)O$R^{15}$, —N($R^{14}$)S(O)$_2R^{15}$, —C(O)$R^{15}$, —S(O)$R^{15}$, —OC(O)$R^{15}$, —C(O)N($R^{12}$)($R^{13}$), —C(O)C(O)N($R^{12}$)($R^{13}$), —N($R^{14}$)C(O)$R^{15}$, —S(O)$_2R^{15}$, —S(O)$_2$N($R^{12}$)($R^{13}$), —S(=O)(=NH)N($R^{12}$)($R^{13}$), —CH$_2$C(O)N($R^{12}$)($R^{13}$), —CH$_2$N($R^{14}$)C(O)$R^{15}$, —CH$_2$S(O)$_2R^{15}$, and —CH$_2$S(O)$_2$N($R^{12}$)($R^{13}$), wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20z3}$;

$Z^4$ is a bond, $Z^{4a}$, $Z^{4a}Z^{4b}$, $Z^{4a}Z^{4b}Z^{4c}$, or $Z^{4a}Z^{4b}Z^{4c}Z^{4d}$; wherein $Z^{4a}$ is directly bonded to $Z^2$; and wherein if $Z^4$ is a bond then $Z^2$ is directly bonded to $Z^5$;

$Z^{4a}$, $Z^{4b}$, $Z^{4c}$, and $Z^{4d}$ are independently C($R^{z4}$), N($R^{z4}$), C($R^{z4}$)$_2$, C(O), S(O), S(O)$_2$, S(O)(N$R^{z4}$), O, S, or N; provided that:
  i) if z9n is 0 and $Z^4$ is $Z^{4a}Z^{4b}$; then (1) $Z^{4b}$ is C($R^{z4}$), C($R^{z4}$)$_2$, C(O), S(O), S(O)$_2$, S(O)(N$R^{z4}$), O, S, or N, (2) $Z^{4b}$ is N($R^{z4}$) and $Z^{4a}$ is C(O), S(O), or S(O)$_2$; (3) $Z^{4b}$ is N($R^{z4}$) and $Z^5$ is C(O), S(O), or S(O)$_2$; or (4) $Z^{4b}$ is N($R^{z4}$) and $Z^3$ is C($R^{z3}$) or C; and
  ii) one or more of $R^{z4}$, $R^{z5}$, $R^{z6}$, $R^{20z4}$, $R^{20z5}$, $R^{20z6}$, $R^{20z}$, $R^{20zz}$, or one or more of the joining of two substituents selected from $R^{z4}$, $R^{z5}$, $R^{z6}$, $R^{20z}$, and $R^{20zz}$ is E, wherein E is a moiety capable of covalently binding to a Ras mutant protein at an amino acid corresponding to G12D or G12S of human K-Ras mutant G12D or G12S protein, respectively:

each $R^{z4}$ is independently selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —O$R^{12}$, —S$R^{12}$, —N($R^{12}$)($R^{13}$), —C(O)O$R^{12}$, —OC(O)N($R^{12}$)($R^{13}$), —N($R^{14}$)C(O)N($R^{12}$)($R^{13}$), —N($R^{14}$)C(O)O$R^{15}$, —N($R^{14}$)S(O)$_2R^{15}$, —C(O)$R^{12}$, —S(O)$R^{15}$, —OC(O)$R^{15}$, —C(O)N($R^{12}$)($R^{13}$), —C(O)C(O)N($R^{12}$)($R^{13}$), —N($R^{14}$)C(O)$R^{12}$, —S(O)$_2R^{15}$, —S(O)$_2$N($R^{12}$)($R^{13}$), —S(=O)(=NH)N($R^{12}$)($R^{13}$), —CH$_2$C(O)N($R^{12}$)($R^{13}$), —CH$_2$N($R^{14}$)C(O)$R^{15}$, —CH$_2$S(O)$_2R^{15}$, and —CH$_2$S(O)$_2$N($R^{12}$)($R^{13}$), wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20z4}$; or two $R^{z4}$ bonded to the same carbon are joined to form $C_{2-6}$alkenyl optionally substituted with one, two, or three $R^{20z4}$;

$Z^5$ is C($R^{z5}$), N($R^{z5}$), C($R^{z5}$)$_2$, C(O), S(O), S(O)$_2$, S(O)(N$R^{z5}$), O, S, or N;

each $R^{z5}$ is independently selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —O$R^{12}$, —S$R^{12}$, —N($R^{12}$)($R^{13}$), —C(O)O$R^{12}$, —OC(O)N($R^{12}$)($R^{13}$), —N($R^{14}$)C(O)N($R^{12}$)($R^{13}$), —N($R^{14}$)C(O)O$R^{15}$, —N($R^{14}$)S(O)$_2R^{15}$, —C(O)$R^{12}$, —S(O)$R^{15}$, —OC(O)$R^{15}$, —C(O)N($R^{12}$)($R^{13}$), —C(O)C(O)N($R^{12}$)($R^{13}$), —N($R^{14}$)C(O)$R^{12}$, —S(O)$_2R^{15}$, —S(O)$_2$N($R^{12}$)($R^{13}$), —S(=O)(=NH)N($R^{12}$)($R^{13}$), —CH$_2$C(O)N($R^{12}$)($R^{13}$), —CH$_2$N($R^{14}$)C(O)$R^{15}$, —CH$_2$S(O)$_2R^{15}$, and —CH$_2$S(O)$_2$N($R^{12}$)($R^{13}$), wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20z5}$; or two $R^{z5}$ bonded to the same carbon are joined to form $C_{2-6}$alkenyl optionally substituted with one, two, or three $R^{20z5}$;

$Z^6$ is C($R^{z6}$), N($R^{z6}$), C($R^{z6}$)$_2$, C(O), S(O), S(O)$_2$, S(O)(N$R^{z6}$), O, S, or N;

each $R^{z6}$ is independently selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —O$R^{12}$, —S$R^{12}$, —N($R^{12}$)($R^{13}$), —C(O)O$R^{12}$, —OC(O)N($R^{12}$)($R^{13}$), —N($R^{14}$)C(O)N($R^{12}$)($R^{13}$), —N($R^{14}$)C(O)O$R^{15}$, —N($R^{14}$)S(O)$_2R^{15}$, —C(O)$R^{12}$, —S(O)$R^{15}$, —OC(O)$R^{15}$, —C(O)N($R^{12}$)($R^{13}$), —C(O)C(O)N($R^{12}$)($R^{13}$), —N($R^{14}$)C(O)$R^{12}$, —S(O)$_2R^{15}$, —S(O)$_2$N($R^{12}$)($R^{13}$), —S(=O)(=NH)N($R^{12}$)($R^{13}$), —CH$_2$C(O)N($R^{12}$)($R^{13}$), —CH$_2$N($R^{14}$)C(O)$R^{15}$, —CH$_2$S(O)$_2R^{15}$, and —CH$_2$S(O)$_2$N($R^{12}$)($R^{13}$), wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20z6}$; or two $R^{z6}$ bonded to the same carbon are joined to form $C_{2-6}$alkenyl optionally substituted with one, two, or three $R^{20z6}$;

and further wherein the compound optionally includes one of the following:

(1) two $R^{z4}$ bonded to the same carbon atom are joined to form monocyclic $C_{3-7}$cycloalkyl or monocyclic 3-7 membered heterocycloalkyl, wherein the monocyclic $C_{3-7}$cycloalkyl and monocyclic 3-7 membered heterocycloalkyl are optionally substituted with one, two, or three $R^{20z}$;

(2) two or more $R^{z4}$ bonded to adjacent atoms are joined to form monocyclic $C_{3-7}$cycloalkyl, monocyclic 3-7 membered heterocycloalkyl, phenyl, or monocyclic 5-6 membered heteroaryl, wherein the monocyclic $C_{3-7}$cycloalkyl, monocyclic 3-7 membered heterocycloalkyl, phenyl, and monocyclic 5-6 membered heteroaryl are optionally substituted with one, two, or three $R^{20z}$;

(3) two $R^{z5}$ bonded to the same carbon atom are joined to form monocyclic $C_{3-7}$cycloalkyl or monocyclic 3-7 membered heterocycloalkyl, wherein the monocyclic $C_{3-7}$cycloalkyl and monocyclic 3-7 membered heterocycloalkyl are optionally substituted with one, two, or three $R^{20z}$;

(4) one or two $R^{z4}$ bonded to one atom and one or two $R^{z5}$ bonded to an adjacent atom are joined to form monocyclic $C_{3-7}$cycloalkyl, monocyclic 3-7 membered heterocycloalkyl, phenyl, or monocyclic 5-6 membered heteroaryl, wherein the monocyclic $C_{3-7}$cycloalkyl, monocyclic 3-7 membered heterocycloalkyl, phenyl, and monocyclic 5-6 membered heteroaryl are optionally substituted with one, two, or three $R^{20z}$;

(5) one or two $R^{z4}$ bonded to one atom and one or two $R^{z5}$ bonded to a second atom are joined to form monocyclic $C_{3-7}$cycloalkyl or monocyclic 3-7 membered heterocycloalkyl, wherein the monocyclic $C_{3-7}$cycloalkyl and monocyclic 3-7 membered heterocycloalkyl are optionally substituted with one, two, or three $R^{20z}$;

(6) two $R^{z6}$ bonded to the same carbon atom are joined to form monocyclic $C_{3-7}$cycloalkyl or monocyclic 3-7 membered heterocycloalkyl, wherein the monocyclic $C_{3-7}$cycloalkyl and monocyclic 3-7 membered heterocycloalkyl are optionally substituted with one, two, or three $R^{20z}$;

(7) one or two $R^{z5}$ bonded to one atom and one or two $R^{z6}$ bonded to an adjacent atom are joined to form monocyclic $C_{3-7}$cycloalkyl, monocyclic 3-7 membered heterocycloalkyl, phenyl, or monocyclic 5-6 membered heteroaryl, wherein the monocyclic $C_{3-7}$cycloalkyl, monocyclic 3-7 membered heterocycloalkyl, phenyl, and monocyclic 5-6 membered heteroaryl are optionally substituted with one, two, or three $R^{20z}$; or (8) one or two $R^{z4}$ bonded to one atom and one or two $R^{z6}$ bonded to a second atom are joined to form monocyclic $C_{3-7}$cycloalkyl or monocyclic 3-7 membered heterocycloalkyl, wherein the monocyclic $C_{3-7}$cycloalkyl and monocyclic 3-7 membered heterocycloalkyl are optionally substituted with one, two, or three $R^{20z}$;

each $R^{12}$ is independently selected from hydrogen, $C_{1-6}$alkyl, $C_{2-6}$alkenyl, $C_{2-6}$alkynyl, $C_{3-10}$cycloalkyl, —CH$_2$-$C_{3-10}$cycloalkyl, $C_{2-9}$heterocycloalkyl, —CH$_2$-$C_{2-9}$heterocycloalkyl, $C_{6-10}$aryl, —CH$_2$-$C_{6-10}$aryl, —CH$_2$-$C_{1-9}$heteroaryl, and $C_{1-9}$heteroaryl, wherein $C_{1-6}$alkyl, $C_{2-6}$alkenyl, $C_{2-6}$alkynyl, $C_{3-10}$cycloalkyl, —CH$_2$-$C_{3-10}$cycloalkyl, $C_{2-9}$heterocycloalkyl, —CH$_2$-$C_{2-9}$heterocycloalkyl, $C_{6-10}$aryl, —CH$_2$-$C_{6-10}$aryl, —CH$_2$-$C_{1-9}$heteroaryl, and $C_{1-9}$heteroaryl are optionally substituted with one, two, or three $R^{20l}$;

$R^{12a}$ is independently selected from hydrogen, $C_{1-6}$alkyl, $C_{2-6}$alkenyl, $C_{2-6}$alkynyl, $C_{3-10}$cycloalkyl, —C($R^{12c}$)$_2$-$C_{3-10}$cycloalkyl, $C_{2-9}$heterocycloalkyl, —C($R^{12c}$)$_2$-$C_{2-9}$heterocycloalkyl, $C_{6-10}$aryl, —C($R^{12c}$)$_2$-$C_{6-10}$aryl, —C($R^{12c}$)$_2$-$C_{1-9}$heteroaryl, and $C_{1-9}$heteroaryl, wherein $C_{1-6}$alkyl, $C_{2-6}$alkenyl, $C_{2-6}$alkynyl, $C_{3-10}$cycloalkyl, —C($R^{12c}$)$_2$-$C_{3-10}$cycloalkyl, $C_{2-9}$heterocycloalkyl, —C($R^{12c}$)$_2$-$C_{2-9}$heterocycloalkyl, $C_{6-10}$aryl, —C($R^{12c}$)$_2$-$C_{6-10}$aryl, —C($R^{12c}$)$_2$-$C_{1-9}$heteroaryl, and $C_{1-9}$heteroaryl are optionally substituted with one, two, or three $R^{20l}$;

each $R^{12c}$ is independently selected from hydrogen and $R^{20lc}$;

each $R^{13}$ is independently selected from hydrogen, $C_{1-6}$alkyl, and $C_{1-6}$haloalkyl; or $R^{12}$ and $R^{13}$, together with the nitrogen to which they are attached, form a $C_{2-9}$heterocycloalkyl ring optionally substituted with one, two, or three $R^{20m}$;

each $R^{14}$ is independently selected from hydrogen, $C_{1-6}$alkyl, and $C_{1-6}$haloalkyl;

each $R^{15}$ is independently selected from $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20o}$;

each $R^{20z1}$, $R^{20z2}$, $R^{20z3}$, and $R^{20z9}$ is independently selected from halogen, oxo, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{12}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{12}$, —S(O)$_2$R$^{15}$, —S(O)$_2$N(R$^{12}$)(R$^{13}$), —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20z}$;

each $R^{20z4}$, $R^{20z5}$, and $R^{20z6}$ is independently selected from E, halogen, oxo, —CN, $C_{1-6}$alkyl, $C_{2-6}$alkenyl, $C_{2-6}$alkynyl, $C_{3-10}$ cycloalkyl, $C_{2-9}$heterocycloalkyl, $C_{6-10}$aryl, $C_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{12}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{12}$, —S(O)$_2$R$^{15}$, —S(O)$_2$N(R$^{12}$)(R$^{13}$), —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20z}$;

each $R^{20z}$ is independently selected from halogen, oxo, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{12}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{12}$, —S(O)$_2$R$^{15}$, —S(O)$_2$N(R$^{12}$)(R$^{13}$), —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20zz}$;

two $R^{20z}$ bonded to the same carbon atom are optionally joined to form monocyclic $C_{3-7}$cycloalkyl or monocyclic 3-7 membered heterocycloalkyl, wherein the monocyclic $C_{3-7}$cycloalkyl and monocyclic 3-7 membered heterocycloalkyl are optionally substituted with one, two, or three $R^{20zz}$; or two or more $R^{20z}$ bonded to two adjacent atoms are optionally joined to form monocyclic $C_{3-7}$cycloalkyl, monocyclic 3-7 membered heterocycloalkyl, phenyl, or monocyclic 5-6 membered heteroaryl, wherein the $C_{3-7}$cycloalkyl, monocyclic 3-7 membered heterocycloalkyl, phenyl, and monocyclic 5-6 membered heteroaryl are optionally substituted with one, two, or three $R^{20zz}$;

each $R^{20a}$, $R^{20b}$, $R^{20c}$, $R^{20d}$, $R^{20e}$, $R^{20f}$, $R^{20g}$, $R^{20h}$, $R^{20i}$, $R^{20j}$, $R^{20lc}$, $R^{20lz}$, $R^{20m}$, $R^{20o}$, $R^{20q}$, and $R^{20zz}$ is independently selected from halogen, oxo, —CN, $C_{1-6}$alkyl, $C_{2-6}$alkenyl, $C_{2-6}$alkynyl, $C_{3-10}$cycloalkyl, —CH$_2$-$C_{3-10}$cycloalkyl, $C_{2-9}$heterocycloalkyl, —CH$_2$-$C_{2-9}$heterocycloalkyl, $C_{6-10}$aryl, —CH$_2$-$C_{6-10}$aryl, —CH$_2$-$C_{1-9}$heteroaryl, $C_{1-9}$heteroaryl, —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, —N(R$^{24}$)C(O)R$^{21}$, —N(R$^{24}$)S(O)$_2$R$^{25}$, —C(O)R$^{21}$, —S(O)R$^{25}$, —S(O)$_2$N(R$^{22}$)(R$^{23}$), —OCH$_2$C(O)OR$^{22}$, =NR$^{21}$, and —OC(O)R$^{25}$; two $R^{20q}$ bonded to adjacent atoms are optionally joined to form a $C_{3-10}$cycloalkyl, $C_{2-9}$heterocycloalkyl, $C_{6-10}$aryl, or $C_{1-9}$heteroaryl; wherein $C_{1-6}$alkyl, $C_{2-6}$alkenyl, $C_{2-6}$alkynyl, $C_{3-10}$cycloalkyl, —$CH_2$-$C_{3-10}$cycloalkyl, $C_{2-9}$heterocycloalkyl, —$CH_2$-$C_{2-9}$heterocycloalkyl, $C_{6-10}$aryl, —$CH_2$-$C_{6-10}$aryl, —$CH_2$-$C_{1-9}$heteroaryl, and $C_{1-9}$heteroaryl are optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —$OR^{21}$, —$SR^{21}$, —$N(R^{22})(R^{23})$, —$C(O)OR^{22}$, —$C(O)N(R^{22})(R^{23})$, —$C(O)C(O)N(R^{22})(R^{23})$, —$OC(O)N(R^{22})(R^{23})$, —$N(R^{24})C(O)N(R^{22})(R^{23})$, —$N(R^{24})C(O)OR^{25}$, —$N(R^{24})C(O)R^{25}$, —$N(R^{24})S(O)_2R^{25}$, —$C(O)R^{25}$, —$S(O)_2R^{25}$, —$S(O)_2N(R^{22})(R^{23})$, and —$OC(O)R^{25}$;

each $R^{20zz}$ is independently selected from E, halogen, oxo, —CN, $C_{1-6}$alkyl, $C_{2-6}$alkenyl, $C_{2-6}$alkynyl, $C_{3-10}$cycloalkyl, —$CH_2$-$C_{3-10}$cycloalkyl, $C_{2-9}$heterocycloalkyl, —$CH_2$-$C_{2-9}$heterocycloalkyl, $C_{6-10}$aryl, —$CH_2$-$C_{6-10}$aryl, —$CH_2$-$C_{1-9}$heteroaryl, $C_{1-9}$heteroaryl, —$OR^{21}$, —$SR^{21}$, —$N(R^{22})(R^{23})$, —$C(O)OR^{22}$, —$C(O)N(R^{22})(R^{23})$, —$C(O)C(O)N(R^{22})(R^{23})$, —$OC(O)N(R^{22})(R^{23})$, —$N(R^{24})C(O)N(R^{22})(R^{23})$, —$N(R^{24})C(O)OR^{25}$, —$N(R^{24})C(O)R^{21}$, —$N(R^{24})S(O)_2R^{25}$, —$C(O)R^{21}$, —$S(O)_2R^{25}$, —$S(O)_2N(R^{22})(R^{23})$, —$OCH_2C(O)OR^{22}$, =$NR^{21}$, and —$OC(O)R^{25}$; two $R^{20q}$ bonded to adjacent atoms are optionally joined to form a $C_{3-10}$cycloalkyl, $C_{2-9}$heterocycloalkyl, $C_{6-10}$aryl, or $C_{1-9}$heteroaryl; wherein $C_{1-6}$alkyl, $C_{2-6}$alkenyl, $C_{2-6}$alkynyl, $C_{3-10}$cycloalkyl, —$CH_2$-$C_{3-10}$cycloalkyl, $C_{2-9}$heterocycloalkyl, —$CH_2$-$C_{2-9}$heterocycloalkyl, $C_{6-10}$aryl, —$CH_2$-$C_{6-10}$aryl, —$CH_2$-$C_{1-9}$heteroaryl, and $C_{1-9}$heteroaryl are optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —$OR^{21}$, —$SR^{21}$, —$N(R^{22})(R^{23})$, —$C(O)OR^{22}$, —$C(O)N(R^{22})(R^{23})$, —$C(O)C(O)N(R^{22})(R^{23})$, —$OC(O)N(R^{22})(R^{23})$, —$N(R^{24})C(O)N(R^{22})(R^{23})$, —$N(R^{24})C(O)OR^{25}$, —$N(R^{24})C(O)R^{25}$, —$N(R^{24})S(O)_2R^{25}$, —$C(O)R^{25}$, —$S(O)_2R^{25}$, —$S(O)_2N(R^{22})(R^{23})$, and —$OC(O)R^{25}$; each $R^{21}$ is independently selected from hydrogen, $C_{1-6}$alkyl, $C_{1-6}$haloalkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl;

each $R^{22}$ is independently selected from hydrogen, $C_{1-6}$alkyl, $C_{1-6}$haloalkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl;

each $R^{23}$ is independently selected from hydrogen and $C_{1-6}$alkyl;

each $R^{24}$ is independently selected from hydrogen and $C_{1-6}$alkyl;

each $R^{25}$ is independently selected from $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; and ===== indicates a single or double bond such that all valences are satisfied.

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, one or more $R^{z4}$, $R^{z5}$, $R^{z6}$, $R^{20z4}$, $R^{20z5}$, $R^{20z6}$, or $R^{20z}$ is independently —$C(O)R^{12}$ or —$N(H)C(O)R^{12}$; wherein the one or more $R^{12}$ is $C_{1-9}$heteroaryl, wherein $C_{1-9}$heteroaryl is optionally substituted with one, two, or three $R^{20l}$.

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, one or more $R^{z4}$, $R^{z5}$, $R^{z6}$, $R^{20z4}$, $R^{20z5}$, $R^{20z6}$, or $R^{20z}$ is independently —$C(O)R^{12}$ or —$N(H)C(O)R^{12}$; wherein the one or more $R^{12}$ is selected from $C_{2-9}$heterocycloalkyl; wherein $C_{2-9}$heterocycloalkyl is optionally substituted with one, two, or three $R^{20l}$.

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, one or more $R^{z4}$, $R^{z5}$, $R^{z6}$, $R^{20z4}$, $R^{20z5}$, $R^{20z6}$, or $R^{20z}$ is independently —$C(O)R^{12}$ or —$N(H)C(O)R^{12}$; wherein the one or more $R^{12}$ is 5 membered heteroaryl, wherein the 5 membered heteroaryl is optionally substituted with one, two, or three $R^{20l}$.

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, one or more $R^{z4}$, $R^{z5}$, $R^{z6}$, $R^{20z4}$, $R^{20z5}$, $R^{20z6}$, or $R^{20z}$ is independently —$C(O)R^{12}$ or —$N(H)C(O)R^{12}$; wherein the one or more $R^{12}$ is 5 membered heteroaryl including two, three, or four ring nitrogen atoms, wherein the 5 membered heteroaryl is optionally substituted with one, two, or three $R^{20l}$. In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, one or more $R^{z4}$, $R^{z5}$, $R^{z6}$, $R^{20z4}$, $R^{20z5}$, $R^{20z6}$, or $R^{20z}$ is independently —$C(O)R^{12}$ or —$N(H)C(O)R^{12}$; wherein the one or more $R^{12}$ is 5 membered heteroaryl including two, three, or four ring nitrogen atoms and the one $R^{12}$ is directly bonded to the C(O) of —$C(O)R^{12}$ or —$N(H)C(O)R^{12}$; wherein the 5 membered heteroaryl is optionally substituted with one, two, or three $R^{20l}$. In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, one or more $R^{z4}$, $R^{z5}$, $R^{z6}$, $R^{20z4}$, $R^{20z5}$, $R^{20z6}$, or $R^{20z}$ is independently —$C(O)R^{12}$ or —$N(H)C(O)R^{12}$; wherein the one or more $R^{12}$ is 5 membered heteroaryl including two, three, or four ring nitrogen atoms and the one $R^{12}$ is directly bonded to the C(O) of —$C(O)R^{12}$ or —$N(H)C(O)R^{12}$; wherein the 5 membered heteroaryl is substituted with one, two, or three $R^{20l}$; In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, one or more $R^{z4}$, $R^{z5}$, $R^{z6}$, $R^{20z4}$, $R^{20z5}$, $R^{20z6}$, or $R^{20z}$ is independently —$C(O)R^{12}$ or —$N(H)C(O)R^{12}$; wherein the one or more $R^{12}$ is 5 membered heteroaryl including two, three, or four ring nitrogen atoms and the one or more $R^{12}$ is directly bonded to the C(O) of —$C(O)R^{12}$ or —$N(H)C(O)R^{12}$; wherein the 5 membered heteroaryl is substituted with one $R^{20l}$.

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, one or more $R^{z4}$, $R^{z5}$, $R^{z6}$, $R^{20z4}$, $R^{20z5}$, $R^{20z6}$, or $R^{20z}$ is independently —$C(O)R^{12}$ or —$N(H)C(O)R^{12}$; wherein the one or more $R^{12}$ is an imidazole, wherein the imidazole is optionally substituted with one, two, or three $R^{20l}$. In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, one or more $R^{z4}$, $R^{z5}$, $R^{z6}$, $R^{20z4}$, $R^{20z5}$, $R^{20z6}$, or $R^{20z}$ is independently —C(O)$R^{12}$ or —N(H)C(O)$R^{12}$; wherein the one or more $R^{12}$ is an imidazole and the one $R^{12}$ is directly bonded to the C(O) of —C(O)$R^{12}$ or —N(H)C(O)$R^{12}$; wherein the imidazole is optionally substituted with one or two $R^{20l}$. In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, one or more $R^{z4}$, $R^{z5}$, $R^{z6}$, $R^{20z4}$, $R^{20z5}$, $R^{20z6}$, or $R^{20z}$ is independently —C(O)$R^{12}$ or —N(H)C(O)$R^{12}$; wherein the one or more $R^{12}$ is an imidazole and the one or more $R^{12}$ is directly bonded to the C(O) of —C(O)$R^{12}$ or —N(H)C(O)$R^{12}$; wherein the imidazole is substituted with one or two $R^{20l}$. In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, one or more $R^{z4}$, $R^{z5}$, $R^{z6}$, $R^{20z4}$, $R^{20z5}$, $R^{20z6}$, or $R^{20z}$ is independently —C(O)$R^{12}$ or —N(H)C(O)$R^{12}$; wherein the one or more $R^{12}$ is an imidazole and the one or more $R^{12}$ is directly bonded to the C(O) of —C(O)$R^{12}$ or —N(H)C(O)$R^{12}$; wherein the imidazole is substituted with one $R^{20l}$.

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, one or more $R^{z4}$, $R^{z5}$, $R^{z6}$, $R^{20z4}$, $R^{20z5}$, $R^{20z6}$, or $R^{20z}$ is independently —C(O)$R^{12}$ or —N(H)C(O)$R^{12}$; wherein the one or more $R^{12}$ is a triazole, wherein the triazole is optionally substituted with one, two, or three $R^{20l}$. In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, one or more $R^{z4}$, $R^{z5}$, $R^{z6}$, $R^{20z4}$, $R^{20z5}$, $R^{20z6}$, or $R^{20z}$ is independently —C(O)$R^{12}$ or —N(H)C(O)$R^{12}$; wherein the one or more $R^{12}$ is a triazole and the one or more $R^{12}$ is directly bonded to the C(O) of —C(O)$R^{12}$ or —N(H)C(O)$R^{12}$; wherein the triazole is optionally substituted with one, two, or three $R^{20l}$. In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, one or more $R^{z4}$, $R^{z5}$, $R^{z6}$, $R^{20z4}$, $R^{20z5}$, $R^{20z6}$, or $R^{20z}$ is independently —C(O)$R^{12}$ or —N(H)C(O)$R^{12}$; wherein the one or more $R^{12}$ is a triazole and the one or more $R^{12}$ is directly bonded to the C(O) of —C(O)$R^{12}$ or —N(H)C(O)$R^{12}$; wherein the triazole is substituted with one, two, or three $R^{20l}$. In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, one or more $R^{z4}$, $R^{z5}$, $R^{z6}$, $R^{20z4}$, $R^{20z5}$, $R^{20z6}$, or $R^{20z}$ is independently —C(O)$R^{12}$ or —N(H)C(O)$R^{12}$; wherein the one or more $R^{12}$ is a triazole and the one or more $R^{12}$ is directly bonded to the C(O) of —C(O)$R^{12}$ or —N(H)C(O)$R^{12}$; wherein the triazole is substituted with one $R^{20l}$.

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, one or more $R^{z4}$, $R^{z5}$, $R^{z6}$, $R^{20z4}$, $R^{20z5}$, $R^{20z6}$, or $R^{20z}$ is independently —C(O)$R^{12}$ or —N(H)C(O)$R^{12}$; wherein the one or more $R^{12}$ is 3 membered heterocycloalkyl, wherein the 3 membered heterocycloalkyl is optionally substituted with one, two, or three $R^{20k}$.

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, one or more $R^{z4}$, $R^{z5}$, $R^{z6}$, $R^{20z4}$, $R^{20z5}$, $R^{20z6}$, or $R^{20z}$ is independently —C(O)$R^{12}$ or —N(H)C(O)$R^{12}$; wherein the one or more $R^{12}$ is 3 membered heterocycloalkyl including one ring nitrogen atom, wherein the 3 membered heterocycloalkyl is optionally substituted with one, two, or three $R^{20l}$. In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, one or more $R^{z4}$, $R^{z5}$, $R^{z6}$, $R^{20z4}$, $R^{20z5}$, $R^{20z6}$, or $R^{20z}$ is independently —C(O)$R^{12}$ or —N(H)C(O)$R^{12}$; wherein the one or more $R^{12}$ is aziridine, wherein the aziridine is optionally substituted with one, two, or three $R^{20l}$. In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, one or more $R^{z4}$, $R^{z5}$, $R^{z6}$, $R^{20z4}$, $R^{20z5}$, $R^{20z6}$, or $R^{20z}$ is independently —C(O)$R^{12}$ or —N(H)C(O)$R^{12}$; wherein the one or more $R^{12}$ is aziridine, wherein the aziridine is optionally substituted with —S(O)$_2$$R^{15}$ and/or cyclopropyl. In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, one or more $R^{z4}$, $R^{z5}$, $R^{z6}$, $R^{20z4}$, $R^{20z5}$, $R^{20z6}$, or $R^{20z}$ is independently —C(O)$R^{12}$ or —N(H)C(O)$R^{12}$; wherein the one or more $R^{12}$ is aziridine, wherein the aziridine is substituted with —S(O)$_2$$R^{15}$. In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, one or more $R^{z4}$, $R^{z5}$, $R^{z6}$, $R^{20z4}$, $R^{20z5}$, $R^{20z6}$, or $R^{20z}$ is independently —C(O)$R^{12}$ or —N(H)C(O)$R^{12}$; wherein the one or more $R^{12}$ is aziridine, wherein the aziridine is substituted with cyclopropyl. In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, one or more $R^{z4}$, $R^{z5}$, $R^{z6}$, $R^{20z4}$, $R^{20z5}$, $R^{20z6}$, or $R^{20z}$ is independently —C(O)$R^{12}$ or —N(H)C(O)$R^{12}$; wherein the one or more $R^{12}$ is azirine, wherein the azirine is optionally substituted with one, two, or three $R^{20l}$. In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, one or more $R^{z4}$, $R^{z5}$, $R^{z6}$, $R^{20z4}$, $R^{20z5}$, $R^{20z6}$, or $R^{20z}$ is independently —C(O)$R^{12}$ or —N(H)C(O)$R^{12}$; wherein the one or more $R^{12}$ is azirine, wherein the aziridine is optionally substituted with —S(O)$_2$$R^{15}$ and/or cyclopropyl. In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, one or more $R^{z4}$, $R^{z5}$, $R^{z6}$, $R^{20z4}$, $R^{20z5}$, $R^{20z6}$, or $R^{20z}$ is independently —C(O)$R^{12}$ or —N(H)C(O)$R^{12}$; wherein the one or more $R^{12}$ is azirine, wherein the aziridine is substituted with —S(O)$_2R^{15}$. In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, one or more $R^{z4}$, $R^{z5}$, $R^{z6}$, $R^{20z4}$, $R^{20z5}$, $R^{20z6}$, or $R^{20z}$ is independently —C(O)$R^{12}$ or —N(H)C(O)$R^{12}$; wherein the one or more $R^{12}$ is azirine, wherein the aziridine is substituted with -cyclopropyl.

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, one $R^{z4}$ is independently selected from $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl; wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are substituted with one, two, or three $R^{20z4}$, and one $R^{20z4}$ is selected from —C(O)$R^{12}$ and —N(H)C(O)$R^{12}$; wherein the one $R^{12}$ is selected from $C_{3-10}$cycloalkyl, $C_{2-9}$heterocycloalkyl, $C_{6-10}$aryl, and $C_{1-9}$heteroaryl, wherein $C_{3-10}$cycloalkyl, $C_{2-9}$heterocycloalkyl, $C_{6-10}$aryl, and $C_{1-9}$heteroaryl are optionally substituted with one, two, or three $R^{20l}$.

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, one $R^{z5}$ is independently selected from $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are substituted with one, two, or three $R^{20z5}$; and one $R^{20z5}$ is selected from —C(O)$R^{12}$ and —N(H)C(O)$R^{12}$; wherein the one $R^{12}$ is selected from $C_{3-10}$cycloalkyl, $C_{2-9}$heterocycloalkyl, $C_{6-10}$aryl, and $C_{1-9}$heteroaryl, wherein $C_{3-10}$cycloalkyl, $C_{2-9}$heterocycloalkyl, $C_{6-10}$aryl, and $C_{1-9}$heteroaryl are optionally substituted with one, two, or three $R^{20l}$.

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, one $R^{z6}$ is independently selected from $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are substituted with one, two, or three $R^{20z6}$; and one $R^{20z6}$ is selected from —C(O)$R^{12}$ and —N(H)C(O)$R^{12}$; wherein the one $R^{12}$ is selected from $C_{3-10}$cycloalkyl, $C_{2-9}$heterocycloalkyl, $C_{6-10}$aryl, and $C_{1-9}$heteroaryl, wherein $C_{3-10}$cycloalkyl, $C_{2-9}$heterocycloalkyl, $C_{6-10}$aryl, and $C_{1-9}$heteroaryl are optionally substituted with one, two, or three $R^{20l}$.

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, one $R^{z4}$ is independently selected from $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl; wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are substituted with one, two, or three $R^{20z4}$; wherein one $R^{20z4}$ is selected from $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl; wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are substituted with one, two, or three $R^{20z}$; and one $R^{20z}$ is selected from —C(O)$R^{12}$ and —N(H)C(O)$R^{12}$; wherein the one $R^{12}$ is selected from $C_{3-10}$cycloalkyl, $C_{2-9}$heterocycloalkyl, $C_{6-10}$aryl, and $C_{1-9}$heteroaryl, wherein $C_{3-10}$cycloalkyl, $C_{2-9}$heterocycloalkyl, $C_{6-10}$aryl, and $C_{1-9}$heteroaryl are optionally substituted with one, two, or three $R^{20l}$.

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, one $R^{z5}$ is independently selected from $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl; wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are substituted with one, two, or three $R^{20z5}$; wherein one $R^{20z5}$ is selected from $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl; wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are substituted with one, two, or three $R^{20z}$; and one $R^{20z}$ is selected from —C(O)$R^{12}$ and —N(H)C(O)$R^{12}$; wherein the one $R^{12}$ is selected from $C_{3-10}$cycloalkyl, $C_{2-9}$heterocycloalkyl, $C_{6-10}$aryl, and $C_{1-9}$heteroaryl, wherein $C_{3-10}$cycloalkyl, $C_{2-9}$heterocycloalkyl, $C_{6-10}$aryl, and $C_{1-9}$heteroaryl are optionally substituted with one, two, or three $R^{20l}$.

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, one $R^{z6}$ is independently selected from $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl; wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are substituted with one, two, or three $R^{20z6}$; wherein one $R^{20z6}$ is selected from $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl; wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are substituted with one, two, or three $R^{20z}$; and one $R^{20z}$ is selected from —C(O)$R^{12}$ and —N(H)C(O)$R^{12}$; wherein the one $R^{12}$ is selected from $C_{3-10}$cycloalkyl, $C_{2-9}$heterocycloalkyl, $C_{6-10}$aryl, and $C_{1-9}$heteroaryl; wherein $C_{3-10}$cycloalkyl, $C_{2-9}$heterocycloalkyl, $C_{6-10}$aryl, and $C_{1-9}$heteroaryl are optionally substituted with one, two, or three $R^{20l}$.

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, two or more $R^{z4}$, $R^{z5}$, or $R^{z6}$ are joined to form a cycle substituted with one, two, or three $R^{20z}$; and one $R^{20z}$ is selected from —C(O)$R^{12}$ and —N(H)C(O)$R^{12}$; wherein the one $R^{12}$ is selected from $C_{3-10}$cycloalkyl, $C_{2-9}$heterocycloalkyl, $C_{6-10}$aryl, and $C_{1-9}$heteroaryl; wherein $C_{3-10}$cycloalkyl, $C_{2-9}$heterocycloalkyl, $C_{6-10}$aryl, and $C_{1-9}$heteroaryl are optionally substituted with one, two, or three $R^{20l}$.

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, one $R^{z4}$ is independently selected from $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl; wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are substituted with one, two, or three $R^{20z4}$, and one $R^{20z4}$ is selected from —C(O)R$^{12}$ and —N(H)C(O)R$^{12}$; wherein the one R$^{12}$ is $C_{1-9}$heteroaryl, wherein the $C_{1-9}$heteroaryl is optionally substituted with one, two, or three $R^{20l}$.

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, one $R^{z5}$ is independently selected from $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are substituted with one, two, or three $R^{20z5}$; and one $R^{20z5}$ is selected from —C(O)R$^{12}$ and —N(H)C(O)R$^{12}$; wherein the one R$^{12}$ is $C_{1-9}$heteroaryl, wherein $C_{1-9}$heteroaryl is optionally substituted with one, two, or three $R^{20l}$.

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, one $R^{z6}$ is independently selected from $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are substituted with one, two, or three $R^{20z6}$; and one $R^{20z6}$ is selected from —C(O)R$^{12}$ and —N(H)C(O)R$^{12}$; wherein the one R$^{12}$ is $C_{1-9}$heteroaryl, wherein $C_{1-9}$heteroaryl is optionally substituted with one, two, or three $R^{20l}$.

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, one $R^{z4}$ is independently selected from $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl; wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are substituted with one, two, or three $R^{20z4}$; wherein one $R^{20z4}$ is selected from $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl; wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are substituted with one, two, or three $R^{20z}$; and one $R^{20z}$ is selected from —C(O)R$^{12}$ and —N(H)C(O)R$^{12}$; wherein the one R$^{12}$ is $C_{1-9}$heteroaryl, wherein $C_{1-9}$heteroaryl is optionally substituted with one, two, or three $R^{20l}$.

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, one $R^{z5}$ is independently selected from $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are substituted with one, two, or three $R^{20z5}$; wherein one $R^{20z5}$ is selected from $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl; wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are substituted with one, two, or three $R^{20z}$; and one $R^{20z}$ is selected from —C(O)R$^{12}$ and —N(H)C(O)R$^{12}$; wherein the one R$^{12}$ is $C_{1-9}$heteroaryl, wherein $C_{1-9}$heteroaryl is optionally substituted with one, two, or three $R^{20l}$.

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, one $R^{z6}$ is independently selected from $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl; wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are substituted with one, two, or three $R^{20z6}$; wherein one $R^{20z6}$ is selected from $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl; wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are substituted with one, two, or three $R^{20z}$; and one $R^{20z}$ is selected from —C(O)R$^{12}$ and —N(H)C(O)R$^{12}$; wherein the one R$^{12}$ is $C_{1-9}$heteroaryl; wherein $C_{1-9}$heteroaryl is optionally substituted with one, two, or three $R^{20l}$.

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, two or more $R^{z4}$, $R^{z5}$, or $R^{z6}$ are joined to form a cycle substituted with one, two, or three $R^{20z}$; and one $R^{20z}$ is selected from —C(O)R$^{12}$ and —N(H)C(O)R$^{12}$; wherein the one R$^{12}$ is $C_{1-9}$heteroaryl; wherein $C_{1-9}$heteroaryl is optionally substituted with one, two, or three $R^{20l}$.

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, one $R^{z4}$ is independently selected from $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl; wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are substituted with one, two, or three $R^{20z4}$, and one $R^{20z4}$ is selected from —C(O)R$^{12}$ and —N(H)C(O)R$^{12}$; wherein the one R$^{12}$ is 5 membered heteroaryl including two, three, or four ring nitrogen atoms, wherein the 5 membered heteroaryl is optionally substituted with one, two, or three $R^{20l}$.

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, one $R^{z5}$ is independently selected from $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are substituted with one, two, or three $R^{20z5}$; and one $R^{20z5}$ is selected from —C(O)R$^{12}$ and —N(H)C(O)R$^{12}$; wherein the one R$^{12}$ is 5 membered heteroaryl including two, three, or four ring nitrogen atoms, wherein 5 membered heteroaryl is optionally substituted with one, two, or three $R^{20l}$.

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, one $R^{z6}$ is independently selected from $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are substituted with one, two, or three $R^{20z6}$; and one $R^{20z6}$ is selected from —C(O)R$^{12}$ and —N(H)C(O)R$^{12}$; wherein the one R$^{12}$ is 5 membered heteroaryl including two, three, or four ring nitrogen atoms, wherein 5 membered heteroaryl is optionally substituted with one, two, or three R$^{20l}$.

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, one R$^{z4}$ is independently selected from C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, C$_{1-9}$heteroaryl; wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl are substituted with one, two, or three R$^{20z4}$; wherein one R$^{20z4}$ is selected from C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, C$_{1-9}$heteroaryl; wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl are substituted with one, two, or three R$^{20z}$; and one R$^{20z}$ is selected from —C(O)R$^{12}$ and —N(H)C(O)R$^{12}$; wherein the one R$^{12}$ is 5 membered heteroaryl including two, three, or four ring nitrogen atoms, wherein 5 membered heteroaryl is optionally substituted with one, two, or three R$^{20l}$.

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, one R$^{z5}$ is independently selected from C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, C$_{1-9}$heteroaryl, wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl are substituted with one, two, or three R$^{20z5}$; wherein one R$^{20z5}$ is selected from C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, C$_{1-9}$heteroaryl; wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl are substituted with one, two, or three R$^{20z}$; and one R$^{20z}$ is selected from —C(O)R$^{12}$ and —N(H)C(O)R$^{12}$; wherein the one R$^{12}$ is 5 membered heteroaryl including two, three, or four ring nitrogen atoms, wherein 5 membered heteroaryl is optionally substituted with one, two, or three R$^{20l}$.

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, one R$^{z6}$ is independently selected from C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, C$_{1-9}$heteroaryl; wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl are substituted with one, two, or three R$^{20z6}$; wherein one R$^{20z6}$ is selected from C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, C$_{1-9}$heteroaryl; wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl are substituted with one, two, or three R$^{20z}$; and one R$^{20z}$ is selected from —C(O)R$^{12}$ and —N(H)C(O)R$^{12}$; wherein the one R$^{12}$ is 5 membered heteroaryl including two, three, or four ring nitrogen atoms; wherein 5 membered heteroaryl is optionally substituted with one, two, or three R$^{20l}$.

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, two or more R$^{z4}$, R$^{z5}$, or R$^{z6}$ are joined to form a cycle substituted with one, two, or three R$^{20z}$; and one R$^{20z}$ is selected from —C(O)R$^{12}$ and —N(H)C(O)R$^{12}$; wherein the one R$^{12}$ is 5 membered heteroaryl including two, three, or four ring nitrogen atoms; wherein 5 membered heteroaryl is optionally substituted with one, two, or three R$^{20l}$.

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, one R$^{z4}$ is independently selected from C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, C$_{1-9}$heteroaryl; wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl are substituted with one, two, or three R$^{20z4}$, and one R$^{20z4}$ is selected from —C(O)R$^{12}$ and —N(H)C(O)R$^{12}$; wherein the one R$^{12}$ is C$_{2-9}$heterocycloalkyl, wherein the C$_{2-9}$heterocycloalkyl is optionally substituted with one, two, or three R$^{20l}$.

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, one R$^{z5}$ is independently selected from C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, C$_{1-9}$heteroaryl, wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl are substituted with one, two, or three R$^{20z5}$; and one R$^{20z5}$ is selected from —C(O)R$^{12}$ and —N(H)C(O)R$^{12}$; wherein the one R$^{12}$ is C$_{2-9}$heterocycloalkyl, wherein C$_{1-9}$heterocycloalkyl is optionally substituted with one, two, or three R$^{20l}$.

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, one R$^{z6}$ is independently selected from C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, C$_{1-9}$heteroaryl, wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl are substituted with one, two, or three R$^{20z6}$; and one R$^{20z6}$ is selected from —C(O)R$^{12}$ and —N(H)C(O)R$^{12}$; wherein the one R$^{12}$ is C$_{2-9}$heterocycloalkyl, wherein C$_{1-9}$heterocycloalkyl is optionally substituted with one, two, or three R$^{20l}$.

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, one R$^{z4}$ is independently selected from C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, C$_{1-9}$heteroaryl; wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl are substituted with one, two, or three R$^{20z4}$; wherein one R$^{20z4}$ is selected from C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, C$_{1-9}$heteroaryl; wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl are substituted with one, two, or three R$^{20z}$; and one R$^{20z}$ is selected from —C(O)R$^{12}$ and —N(H)C(O)R$^{12}$; wherein the one R$^{12}$ is C$_{2-9}$heterocycloalkyl, wherein C$_{1-9}$heterocycloalkyl is optionally substituted with one, two, or three R$^{20l}$.

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, one R$^{z5}$ is independently selected from C$_{1-6}$alkyl, C$_{2-6}$alkenyl, C$_{2-6}$alkynyl, C$_{3-10}$cycloalkyl, C$_{2-9}$heterocycloalkyl, $C_{6-10}$aryl, $C_{1-9}$heteroaryl, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are substituted with one, two, or three $R^{20z5}$; wherein one $R^{20z5}$ is selected from $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl; wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are substituted with one, two, or three $R^{20z}$; and one $R^{20z}$ is selected from —C(O)$R^{12}$ and —N(H)C(O)$R^{12}$; wherein the one $R^{12}$ is $C_{2-9}$heterocycloalkyl, wherein $C_{1-9}$heterocycloalkyl is optionally substituted with one, two, or three $R^{20l}$.

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, one $R^{z6}$ is independently selected from $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl; wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are substituted with one, two, or three $R^{20z6}$; wherein one $R^{20z6}$ is selected from $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl; wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are substituted with one, two, or three $R^{20z}$; and one $R^{20z}$ is selected from —C(O)$R^{12}$ and —N(H)C(O)$R^{12}$; wherein the one $R^{12}$ is $C_{2-9}$heterocycloalkyl; wherein $C_{1-9}$heterocycloalkyl is optionally substituted with one, two, or three $R^{20l}$.

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, two or more $R^{z4}$, $R^{z5}$, or $R^{z6}$ are joined to form a cycle substituted with one, two, or three $R^{20z}$; and one $R^{20z}$ is selected from —C(O)$R^{12}$ and —N(H)C(O)$R^{12}$; wherein the one $R^{12}$ is $C_{2-9}$heterocycloalkyl; wherein $C_{2-9}$heterocycloalkyl is optionally substituted with one, two, or three $R^{20l}$.

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, one $R^{z4}$ is independently selected from $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl; wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are substituted with one, two, or three $R^{20z4}$, and one $R^{20z4}$ is selected from —C(O)$R^{12}$ and —N(H)C(O)$R^{12}$; wherein the one $R^{12}$ is 3 membered heterocycloalkyl including one ring nitrogen atom, wherein the 3 membered heterocycloalkyl is optionally substituted with one, two, or three $R^{20l}$.

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, one $R^{z5}$ is independently selected from $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are substituted with one, two, or three $R^{20z5}$; and one $R^{20z5}$ is selected from —C(O)$R^{12}$ and —N(H)C(O)$R^{12}$; wherein the one $R^{12}$ is 3 membered heterocycloalkyl including one ring nitrogen atom, wherein the 3 membered heterocycloalkyl is optionally substituted with one, two, or three $R^{20l}$.

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, one $R^{z6}$ is independently selected from $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are substituted with one, two, or three $R^{20z6}$; and one $R^{20z6}$ is selected from —C(O)$R^{12}$ and —N(H)C(O)$R^{12}$; wherein the one $R^{12}$ is 3 membered heterocycloalkyl including one ring nitrogen atom, wherein the 3 membered heterocycloalkyl is optionally substituted with one, two, or three $R^{20l}$.

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, one $R^{z4}$ is independently selected from $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl; wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are substituted with one, two, or three $R^{20z4}$; wherein one $R^{20z4}$ is selected from $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl; wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are substituted with one, two, or three $R^{20z}$; and one $R^{20z}$ is selected from —C(O)$R^{12}$ and —N(H)C(O)$R^{12}$; wherein the one $R^{12}$ is 3 membered heterocycloalkyl including one ring nitrogen atom, wherein the 3 membered heterocycloalkyl is optionally substituted with one, two, or three $R^{20l}$.

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, one $R^{z5}$ is independently selected from $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are substituted with one, two, or three $R^{20z5}$; wherein one $R^{20z5}$ is selected from $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl; wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are substituted with one, two, or three $R^{20z}$; and one $R^{20z}$ is selected from —C(O)$R^{12}$ and —N(H)C(O)$R^{12}$; wherein the one $R^{12}$ is 3 membered heterocycloalkyl including one ring nitrogen atom, wherein the 3 membered heterocycloalkyl is optionally substituted with one, two, or three $R^{20l}$.

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, one $R^{z6}$ is independently selected from $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl; wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are substituted with one, two, or three $R^{20z6}$; wherein one $R^{20z6}$ is selected from $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl; wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are substituted with one, two, or three $R^{20z}$; and one $R^{20z}$ is selected from —C(O)$R^{12}$ and —N(H)C(O)$R^{12}$; wherein the one $R^{12}$ is 3 membered heterocycloalkyl including one ring nitrogen atom, wherein the 3 membered heterocycloalkyl is optionally substituted with one, two, or three $R^{20l}$.

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, two or more $R^{z4}$, $R^{z5}$, or $R^{z6}$ are joined to form a cycle substituted with one, two, or three $R^{20z}$; and one $R^{20z}$ is selected from —C(O)$R^{12}$ and —N(H)C(O)$R^{12}$; wherein the one $R^{12}$ is $R^{12}$ is 3 membered heterocycloalkyl including one ring nitrogen atom, wherein the 3 membered heterocycloalkyl is optionally substituted with one, two, or three $R^{20l}$.

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, one $R^{z4}$ is independently selected from $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl; wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are substituted with one, two, or three $R^{20z4}$, and one $R^{20z4}$ is selected from —C(O)$R^{12}$ and —N(H)C(O)$R^{12}$; wherein the one $R^{12}$ is imidazole, wherein the imidazole is optionally substituted with one or two $R^{20l}$.

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, one $R^{z5}$ is independently selected from $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are substituted with one, two, or three $R^{20z5}$; and one $R^{20z5}$ is selected from —C(O)$R^{12}$ and —N(H)C(O)$R^{12}$; wherein the one $R^{12}$ is imidazole, wherein the imidazole is optionally substituted with one or two $R^{20l}$.

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, one $R^{z6}$ is independently selected from $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are substituted with one, two, or three $R^{20z6}$; and one $R^{20z6}$ is selected from —C(O)$R^{12}$ and —N(H)C(O)$R^{12}$; wherein the one $R^{12}$ is imidazole, wherein the imidazole is optionally substituted with one or two $R^{20l}$.

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, one $R^{z4}$ is independently selected from $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl; wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are substituted with one, two, or three $R^{20z}$; and one $R^{20z}$ is selected from —C(O)$R^{12}$ and —N(H)C(O)$R^{12}$; wherein the one $R^{12}$ is imidazole, wherein the imidazole is optionally substituted with one or two $R^{20l}$.

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, one $R^{z5}$ is independently selected from $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl; wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are substituted with one, two, or three $R^{20z}$; and one $R^{20z}$ is selected from —C(O)$R^{12}$ and —N(H)C(O)$R^{12}$; wherein the one $R^{12}$ is imidazole, wherein the imidazole is optionally substituted with one or two $R^{20l}$.

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, one $R^{z6}$ is independently selected from $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl; wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are substituted with one, two, or three $R^{20z}$; and one $R^{20z}$ is selected from —C(O)$R^{12}$ and —N(H)C(O)$R^{12}$; wherein the one $R^{12}$ is imidazole, wherein the imidazole is optionally substituted with one or two $R^{20l}$.

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, two or more $R^{z4}$, $R^{z5}$, or $R^{z6}$ are joined to form a cycle substituted with one, two, or three $R^{20z}$; and one $R^{20z}$ is selected from —C(O)$R^{12}$ and —N(H)C(O)$R^{12}$; wherein the one $R^{12}$ is imidazole, wherein the imidazole is optionally substituted with one or two $R^{20l}$.

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, one $R^{z4}$ is independently selected from $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl; wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are substituted with one, two, or three $R^{20z4}$, and one $R^{20z4}$ is selected from —C(O)$R^{12}$ and —N(H)C(O)$R^{12}$; wherein the one $R^{12}$ is triazole, wherein the triazole is optionally substituted with one or two $R^{20l}$.

In embodiments of a compound of Formula (A), A-1, A-2, A-2a, A-2b, A-3, A-3a, A-3b, A-4, A-4a, A-4b, A-5, A-5a, In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, one $R^{z5}$ is independently selected from $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are substituted with one, two, or three $R^{20z5}$; and one $R^{20z5}$ is selected from —C(O)R$^{12}$ and —N(H)C(O)R$^{12}$; wherein the one $R^{12}$ is triazole, wherein the triazole is optionally substituted with one or two $R^{20l}$.

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, one $R^{z6}$ is independently selected from $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are substituted with one, two, or three $R^{20z6}$; and one $R^{20z6}$ is selected from —C(O)R$^{12}$ and —N(H)C(O)R$^{12}$; wherein the one $R^{12}$ is triazole, wherein the triazole is optionally substituted with one or two $R^{20l}$.

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, one $R^{z4}$ is independently selected from $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl; wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are substituted with one, two, or three $R^{20z4}$; wherein one $R^{20z4}$ is selected from $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl; wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are substituted with one, two, or three $R^{20z}$; and one $R^{20z}$ is selected from —C(O)R$^{12}$ and —N(H)C(O)R$^{12}$; wherein the one $R^{12}$ is triazole, wherein the triazole is optionally substituted with one or two $R^{20l}$.

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, one $R^{z5}$ is independently selected from $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are substituted with one, two, or three $R^{20z5}$; wherein one $R^{20z5}$ is selected from $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl; wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are substituted with one, two, or three $R^{20z}$; and one $R^{20z}$ is selected from —C(O)R$^{12}$ and —N(H)C(O)R$^{12}$; wherein the one $R^{12}$ is triazole, wherein the triazole is optionally substituted with one or two $R^{20l}$.

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, one $R^{z6}$ is independently selected from $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl; wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are substituted with one, two, or three $R^{20z6}$; wherein one $R^{20z6}$ is selected from $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl; wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are substituted with one, two, or three $R^{20z}$; and one $R^{20z}$ is selected from —C(O)R$^{12}$ and —N(H)C(O)R$^{12}$; wherein the one $R^{12}$ is triazole, wherein the triazole is optionally substituted with one or two $R^{20l}$.

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, two or more $R^{z4}$, $R^{z5}$, or $R^{z6}$ are joined to form a cycle substituted with one, two, or three $R^{20z}$; and one $R^{20z}$ is selected from —C(O)R$^{12}$ and —N(H)C(O)R$^{12}$; wherein the one $R^{12}$ is triazole, wherein the triazole is optionally substituted with one or two $R^{20l}$.

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, one $R^{z4}$ is independently selected from $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl; wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are substituted with one, two, or three $R^{20z4}$, and one $R^{20z4}$ is selected from —C(O)R$^{12}$ and —N(H)C(O)R$^{12}$; wherein the one $R^{12}$ is aziridine, wherein the aziridine is optionally substituted with one or two $R^{20l}$.

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, one $R^{z5}$ is independently selected from $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are substituted with one, two, or three $R^{20z5}$; and one $R^{20z5}$ is selected from —C(O)R$^{12}$ and —N(H)C(O)R$^{12}$; wherein the one $R^{12}$ is aziridine, wherein the aziridine is optionally substituted with one or two $R^{20l}$.

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, one $R^{z6}$ is independently selected from $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are substituted with one, two, or three $R^{20z6}$; and one $R^{20z6}$ is selected from —C(O)R$^{12}$ and —N(H)C(O)R$^{12}$; wherein the one $R^{12}$ is aziridine, wherein the aziridine is optionally substituted with one or two $R^{20l}$.

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, one $R^{z4}$ is independently selected from $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl; wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are substituted with one, two, or three $R^{20z4}$; wherein one $R^{20z4}$ is selected from $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl; wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are substituted with one, two, or three $R^{20z}$; and one $R^{20z}$ is selected from —C(O)$R^{12}$ and —N(H)C(O)$R^{12}$; wherein the one $R^{12}$ is aziridine, wherein the aziridine is optionally substituted with one or two $R^{20l}$.

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, one $R^{z5}$ is independently selected from $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are substituted with one, two, or three $R^{20z5}$; wherein one $R^{20z5}$ is selected from $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl; wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are substituted with one, two, or three $R^{20z}$; and one $R^{20z}$ is selected from —C(O)$R^{12}$ and —N(H)C(O)$R^{12}$; wherein the one $R^{12}$ is aziridine, wherein the aziridine is optionally substituted with one or two $R^{20l}$.

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, one $R^{z6}$ is independently selected from $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl; wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are substituted with one, two, or three $R^{20z6}$; wherein one $R^{20z6}$ is selected from $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl; wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are substituted with one, two, or three $R^{20z}$; and one $R^{20z}$ is selected from —C(O)$R^{12}$ and —N(H)C(O)$R^{12}$; wherein the one $R^{12}$ is aziridine, wherein the aziridine is optionally substituted with one or two $R^{20l}$.

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, two or more $R^{z4}$, $R^{z5}$, or $R^{z6}$ are joined to form a cycle substituted with one, two, or three $R^{20z}$; and one $R^{20z}$ is selected from —C(O)$R^{12}$ and —N(H)C(O)$R^{12}$; wherein the one $R^{12}$ is aziridine, wherein the aziridine is optionally substituted with one or two $R^{20l}$.

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, one $R^{z4}$ is independently selected from $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl; wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are substituted with one, two, or three $R^{20z4}$, and one $R^{20z4}$ is selected from —C(O)$R^{12}$ and —N(H)C(O)$R^{12}$; wherein the one $R^{12}$ is aziridine, wherein the aziridine is substituted with one cyclopropyl.

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, one $R^{z5}$ is independently selected from $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are substituted with one, two, or three $R^{20z5}$; and one $R^{20z5}$ is selected from —C(O)$R^{12}$ and —N(H)C(O)$R^{12}$; wherein the one $R^{12}$ is aziridine, wherein the aziridine is substituted with one cyclopropyl.

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, one $R^{z6}$ is independently selected from $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are substituted with one, two, or three $R^{20z6}$; and one $R^{20z6}$ is selected from —C(O)$R^{12}$ and —N(H)C(O)$R^{12}$; wherein the one $R^{12}$ is aziridine, wherein the aziridine is substituted with one cyclopropyl. In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, one $R^{z4}$ is independently selected from $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl; wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are substituted with one, two, or three $R^{20z4}$; wherein one $R^{20z4}$ is selected from $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl; wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are substituted with one, two, or three $R^{20z}$; and one $R^{20z}$ is selected from —C(O)$R^{12}$ and —N(H)C(O)$R^{12}$; wherein the one $R^{12}$ is aziridine, wherein the aziridine is substituted with one cyclopropyl.

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, one $R^{z5}$ is independently selected from $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are substituted with one, two, or three $R^{20z5}$; wherein one $R^{20z5}$ is selected from $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl; wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are substituted with one, two, or three $R^{20z}$; and one $R^{20z}$ is selected from —C(O)$R^{12}$ and —N(H)C(O)$R^{12}$; wherein the one $R^{12}$ is aziridine, wherein the aziridine is substituted with one cyclopropyl.

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, one $R^{z6}$ is independently selected from $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl; wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are substituted with one, two, or three $R^{20z6}$; wherein one $R^{20z6}$ is selected from $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl; wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are substituted with one, two, or three $R^{20z}$; and one $R^{20z}$ is selected from —C(O)$R^{12}$ and —N(H)C(O)$R^{12}$; wherein the one $R^{12}$ is aziridine, wherein the aziridine is substituted with one cyclopropyl.

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, two or more $R^{z4}$, $R^{z5}$, or $R^{z6}$ are joined to form a cycle substituted with one, two, or three $R^{20z}$; and one $R^{20z}$ is selected from —C(O)$R^{12}$ and —N(H)C(O)$R^{12}$; wherein the one $R^{12}$ is aziridine, wherein the aziridine is substituted with one cyclopropyl.

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, one $R^{z4}$ is independently selected from $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl; wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are substituted with one, two, or three $R^{20z4}$, and one $R^{20z4}$ is selected from —C(O)$R^{12}$ and —N(H)C(O)$R^{12}$; wherein the one $R^{12}$ is aziridine, wherein the aziridine is substituted with —S(O)$_2$$R^{15}$.

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, one $R^{z5}$ is independently selected from $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are substituted with one, two, or three $R^{20z5}$; and one $R^{20z5}$ is selected from —C(O)$R^{12}$ and —N(H)C(O)$R^{12}$; wherein the one $R^{12}$ is aziridine, wherein the aziridine is substituted with —S(O)$_2$$R^{15}$.

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, one $R^{z6}$ is independently selected from $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are substituted with one, two, or three $R^{20z6}$; and one $R^{20z6}$ is selected from —C(O)$R^{12}$ and —N(H)C(O)$R^{12}$; wherein the one $R^{12}$ is aziridine, wherein the aziridine is substituted with —S(O)$_2$$R^{15}$.

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, one $R^{z4}$ is independently selected from $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl; wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are substituted with one, two, or three $R^{20z4}$; wherein one $R^{20z4}$ is selected from $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl; wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are substituted with one, two, or three $R^{20z}$; and one $R^{20z}$ is selected from —C(O)$R^{12}$ and —N(H)C(O)$R^{12}$; wherein the one $R^{12}$ is aziridine, wherein the aziridine is substituted with —S(O)$_2$$R^{15}$.

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, one $R^{z5}$ is independently selected from $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are substituted with one, two, or three $R^{20z5}$; wherein one $R^{20z5}$ is selected from $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl; wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are substituted with one, two, or three $R^{20z}$; and one $R^{20z}$ is selected from —C(O)$R^{12}$ and —N(H)C(O)$R^{12}$; wherein the one $R^{12}$ is aziridine, wherein the aziridine is substituted with —S(O)$_2$$R^{15}$.

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, one $R^{z6}$ is independently selected from $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl; wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are substituted with one, two, or three $R^{20z6}$; wherein one $R^{20z6}$ is selected from $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl; wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are substituted with one, two, or three $R^{20z}$; and one $R^{20z}$ is selected from —C(O)$R^{12}$ and —N(H)C(O)$R^{12}$; wherein the one $R^{12}$ is aziridine, wherein the aziridine is substituted with —S(O)$_2$$R^{15}$.

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, two or more $R^{z4}$, $R^{z5}$, or $R^{z6}$ are joined to form a cycle substituted with one, two, or three $R^{20z}$; and one $R^{20z}$ is selected from —C(O)$R^{12}$ and —N(H)C(O)$R^{12}$; wherein the one $R^{12}$ is aziridine, wherein the aziridine is substituted with —S(O)$_2$$R^{15}$.

In embodiments, E is $L^{z3}$—$R^{12}$ as described herein, including embodiments thereof. In embodiments, E is independently selected from —C(O)$R^{12}$ and —N(H)C(O)$R^{12}$; wherein the one $R^{12}$ is selected from $C_{3-10}$cycloalkyl, $C_{2-9}$heterocycloalkyl, $C_{6-10}$aryl, and $C_{1-9}$heteroaryl, wherein $C_{3-10}$cycloalkyl, $C_{2-9}$heterocycloalkyl, $C_{6-10}$aryl, and $C_{1-9}$heteroaryl are optionally substituted with one, two, or three $R^{20l}$. In embodiments, E is —C(O)$R^{12}$ or —N(H)C (O)R$^{12}$; wherein the R$^{12}$ is a 5-membered heteroaryl including two or more ring nitrogen atoms, wherein the 5-membered heteroaryl is directly bonded to the C(O) through an R$^{12}$ ring nitrogen atom and wherein R$^{12}$ is optionally substituted with one or more R$^{20l}$; and R$^{20l}$ is independently selected from halogen, oxo, —CN, C$_{1-6}$alkyl, C$_{2-6}$alkenyl, C$_{2-6}$alkynyl, C$_{3-10}$cycloalkyl, —CH$_2$-C$_{3-10}$cycloalkyl, C$_{2-9}$heterocycloalkyl, —CH$_2$-C$_{2-9}$heterocycloalkyl, C$_{6-10}$aryl, —CH$_2$-C$_{6-10}$aryl, —CH$_2$-C$_{1-9}$heteroaryl, C$_{1-9}$heteroaryl, —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, —N(R$^{24}$)C(O)R$^{21}$, —N(R$^{24}$)S(O)$_2$R$^{25}$, —C(O)R$^{21}$, —S(O)$_2$R$^{25}$, —S(O)$_2$N(R$^{22}$)(R$^{23}$), —OCH$_2$C(O)OR$^{22}$, =NR$^{21}$, and —OC(O)R$^{25}$; wherein C$_{1-6}$alkyl, C$_{2-6}$alkenyl, C$_{2-6}$alkynyl, C$_{3-10}$cycloalkyl, —CH$_2$-C$_{3-10}$cycloalkyl, C$_{2-9}$heterocycloalkyl, —CH$_2$-C$_{2-9}$heterocycloalkyl, C$_{6-10}$aryl, —CH$_2$-C$_{6-10}$aryl, —CH$_2$-C$_{1-9}$heteroaryl, and C$_{1-9}$heteroaryl are optionally substituted with one, two, or three groups independently selected from halogen, oxo, —CN, C$_{1-6}$alkyl, C$_{1-6}$haloalkyl, C$_{1-6}$alkoxy, C$_{1-6}$haloalkoxy, —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, —N(R$^{24}$)C(O)R$^{25}$, —N(R$^{24}$)S(O)$_2$R$^{25}$, —C(O)R$^{25}$, —S(O)$_2$R$^{25}$, —S(O)$_2$N(R$^{22}$)(R$^{23}$), and —OC(O)R$^{25}$. In embodiments, E is a 3-membered heterocycloalkyl including one or more ring nitrogen atoms, wherein the 3-membered heterocycloalkyl is optionally substituted with one or more R$^{20l}$; and R$^{20l}$ is independently selected from halogen, oxo, —CN, C$_{1-6}$alkyl, C$_{2-6}$alkenyl, C$_{2-6}$alkynyl, C$_{3-10}$cycloalkyl, —CH$_2$-C$_{3-10}$cycloalkyl, C$_{2-9}$heterocycloalkyl, —CH$_2$-C$_{2-9}$heterocycloalkyl, C$_{6-10}$aryl, —CH$_2$-C$_{6-10}$aryl, —CH$_2$-C$_{1-9}$heteroaryl, C$_{1-9}$heteroaryl, —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, —N(R$^{24}$)C(O)R$^{21}$, —N(R$^{24}$)S(O)$_2$R$^{25}$, —C(O)R$^{21}$, —S(O)$_2$R$^{25}$, —S(O)$_2$N(R$^{22}$)(R$^{23}$), —OCH$_2$C(O)OR$^{22}$, =NR$^{21}$, and —OC(O)R$^{25}$; wherein C$_{1-6}$alkyl, C$_{2-6}$alkenyl, C$_{2-6}$alkynyl, C$_{3-10}$cycloalkyl, —CH$_2$-C$_{3-10}$cycloalkyl, C$_{2-9}$heterocycloalkyl, —CH$_2$-C$_{2-9}$heterocycloalkyl, C$_{6-10}$aryl, —CH$_2$-C$_{6-10}$aryl, —CH$_2$-C$_{1-9}$heteroaryl, and C$_{1-9}$heteroaryl are optionally substituted with one, two, or three groups independently selected from halogen, oxo, —CN, C$_{1-6}$alkyl, C$_{1-6}$haloalkyl, C$_{1-6}$alkoxy, C$_{1-6}$haloalkoxy, —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, —N(R$^{24}$)C(O)R$^{25}$, —N(R$^{24}$)S(O)$_2$R$^{25}$, —C(O)R$^{25}$, —S(O)$_2$R$^{25}$, —S(O)$_2$N(R$^{22}$)(R$^{23}$), and —OC(O)R$^{25}$. In embodiments, E is —C(O)R$^{12}$ or —N(H)C(O)R$^{12}$; wherein the R$^{12}$ is a 3-membered heterocycloalkyl including one or more ring nitrogen atoms, wherein R$^{12}$ is optionally substituted with one or more R$^{20l}$; and R$^{20l}$ is independently selected from halogen, oxo, —CN, C$_{1-6}$alkyl, C$_{2-6}$alkenyl, C$_{2-6}$alkynyl, C$_{3-10}$cycloalkyl, —CH$_2$-C$_{3-10}$cycloalkyl, C$_{2-9}$heterocycloalkyl, —CH$_2$-C$_{2-9}$heterocycloalkyl, C$_{6-10}$aryl, —CH$_2$-C$_{6-10}$aryl, —CH$_2$-C$_{1-9}$heteroaryl, C$_{1-9}$heteroaryl, —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, —N(R$^{24}$)C(O)R$^{21}$, —N(R$^{24}$)S(O)$_2$R$^{25}$, —C(O)R$^{21}$, —S(O)$_2$R$^{25}$, —S(O)$_2$N(R$^{22}$)(R$^{23}$), —OCH$_2$C(O)OR$^{22}$, =NR$^{21}$, and —OC(O)R$^{25}$; wherein C$_{1-6}$alkyl, C$_{2-6}$alkenyl, C$_{2-6}$alkynyl, C$_{3-10}$cycloalkyl, —CH$_2$-C$_{3-10}$cycloalkyl, C$_{2-9}$heterocycloalkyl, —CH$_2$-C$_{2-9}$heterocycloalkyl, C$_{6-10}$aryl, —CH$_2$-C$_{6-10}$aryl, —CH$_2$-C$_{1-9}$heteroaryl, and C$_{1-9}$heteroaryl are optionally substituted with one, two, or three groups independently selected from halogen, oxo, —CN, C$_{1-6}$alkyl, C$_{1-6}$haloalkyl, C$_{1-6}$alkoxy, C$_{1-6}$haloalkoxy, —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, —N(R$^{24}$)C(O)R$^{25}$, —N(R$^{24}$)S(O)$_2$R$^{25}$, —C(O)R$^{25}$, —S(O)$_2$R$^{25}$, —S(O)$_2$N(R$^{22}$)(R$^{23}$), and —OC(O)R$^{25}$. In embodiments, E is —C(O)R$^{12}$ or —N(H)C(O)R$^{12}$; wherein the R$^{12}$ is independently selected from C$_{3-10}$cycloalkyl, C$_{2-9}$heterocycloalkyl, C$_{6-10}$aryl, and C$_{1-9}$heteroaryl, wherein C$_{3-10}$cycloalkyl, C$_{2-9}$heterocycloalkyl, C$_{6-10}$aryl, and C$_{1-9}$heteroaryl are optionally substituted with one, two, or three R$^{20l}$ (e.g., R$^{12}$ is a 5-membered heteroaryl including two or more ring nitrogen atoms, wherein the 5-membered heteroaryl is directly bonded to the C(O) through an R$^{12}$ ring nitrogen atom and wherein R$^{12}$ is optionally substituted with one or more R$^{20l}$; R$^{12}$ is a 3-membered heterocycloalkyl including one or more ring nitrogen atoms, wherein R$^{12}$ is optionally substituted with one or more R$^{20l}$). In embodiments, E is —C(O)R$^{12}$ or —N(H)C(O)R$^{12}$; wherein the R$^{12}$ is independently selected from

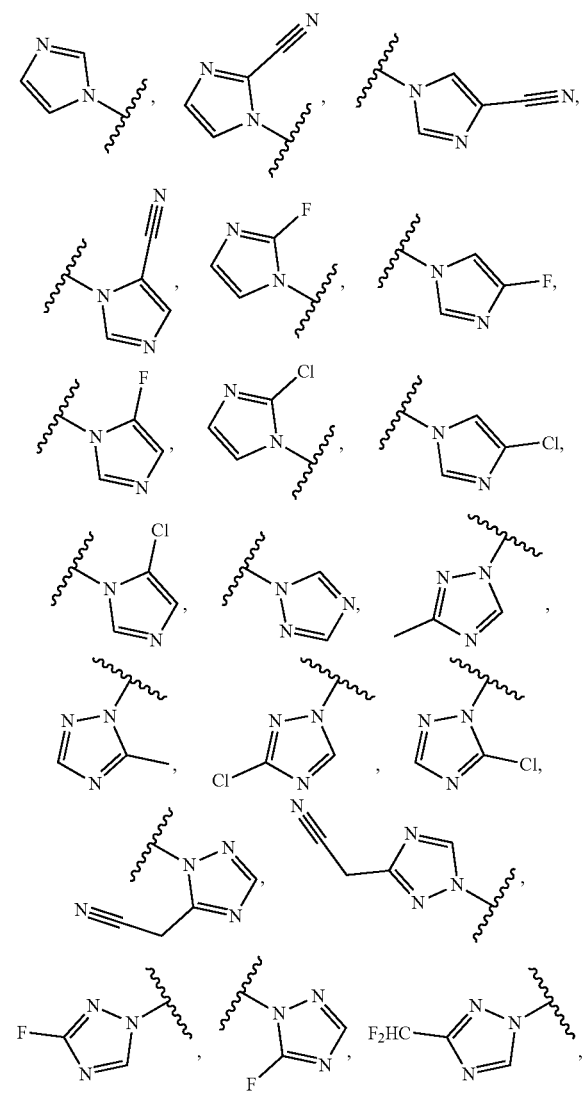

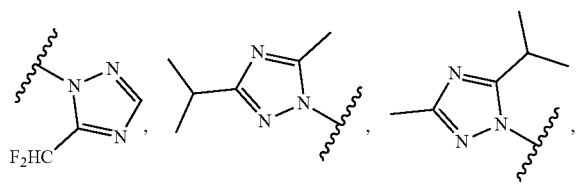
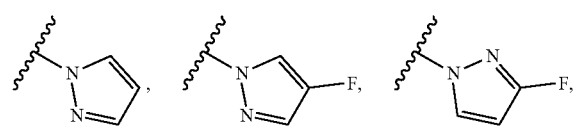
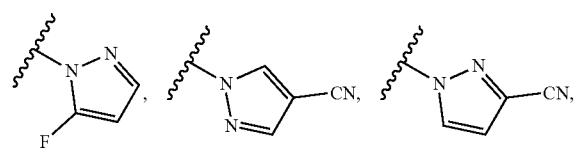
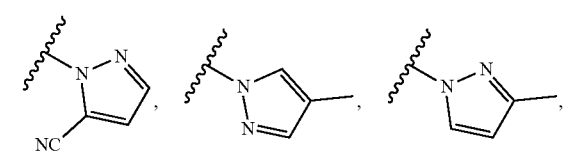
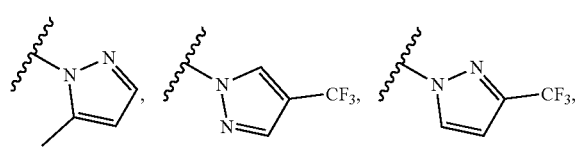
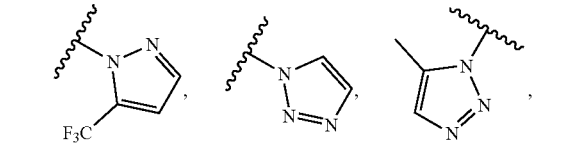
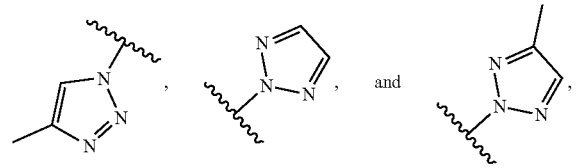

In embodiments, E is —C(O)R$^{12}$ or —N(H)C(O)R$^{12}$; wherein the R$^{12}$ is independently selected from

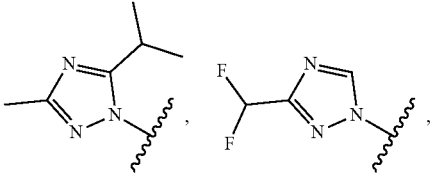
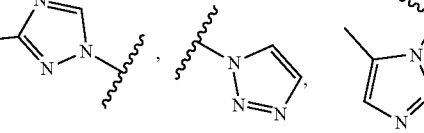
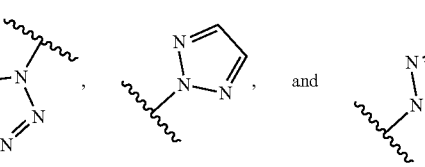

In embodiments, E is —C(O)R$^{12}$ or —N(H)C(O)R$^{12}$; wherein the R$^{12}$ is independently selected from

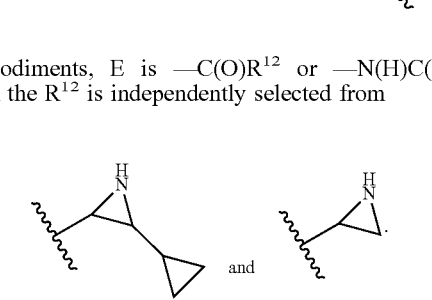

In embodiments, E is independently selected from

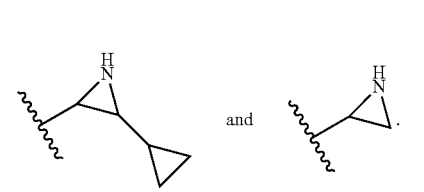

In embodiments, E is —C(O)R$^{12}$ or —N(H)C(O)R$^{12}$; wherein the R$^{12}$ is independently selected from C$_{1-9}$heteroaryl, wherein C$_{1-9}$heteroaryl is optionally substituted with one, two, or three R$^{20l}$; and R$^{20l}$ is independently selected from halogen, oxo, —CN, C$_{1-6}$alkyl, C$_{2-6}$alkenyl, C$_{2-6}$alkynyl, C$_{3-10}$cycloalkyl, —CH$_2$-C$_{3-10}$cycloalkyl, C$_{2-9}$heterocycloalkyl, —CH$_2$-C$_{2-9}$heterocycloalkyl, C$_{6-10}$aryl, —CH$_2$-C$_{6-10}$aryl, —CH$_2$-C$_{1-9}$heteroaryl, C$_{1-9}$heteroaryl, —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, —N(R$^{24}$)C(O)R$^{21}$, —N(R$^{24}$)S(O)$_2$R$^{25}$, —C(O)R$^{21}$, —S(O)$_2$R$^{25}$, —S(O)$_2$N(R$^{22}$)(R$^{23}$), —OCH$_2$C(O)OR$^{22}$, =NR$^{21}$, and —OC(O)R$^{25}$; wherein C$_{1-6}$alkyl, C$_{2-6}$alkenyl, C$_{2-6}$alkynyl, C$_{3-10}$cycloalkyl, —CH$_2$-C$_{3-10}$cycloalkyl, C$_{2-9}$heterocycloalkyl, —CH$_2$-C$_{2-9}$heterocycloalkyl, C$_{6-10}$aryl, —CH$_2$-C$_{6-10}$aryl, —CH$_2$-C$_{1-9}$heteroaryl, and C$_{1-9}$heteroaryl are optionally substituted with one, two, or three groups independently selected from halogen, oxo, —CN, C$_{1-6}$alkyl, C$_{1-6}$haloalkyl, C$_{1-6}$alkoxy, C$_{1-6}$haloalkoxy, —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, —N(R$^{24}$)C(O)R$^{25}$, —N(R$^{24}$)C(O)R$^{25}$, —N(R$^{24}$)S(O)$_2$R$^{25}$, —C(O)R$^{25}$, —S(O)$_2$R$^{25}$, —S(O)$_2$N(R$^{22}$)(R$^{23}$), and —OC(O)R$^{25}$.

In embodiments, E includes a leaving group (LG). In embodiments, the leaving group is released from the staying group by reaction with Ras protein (e.g., KRas) amino acid (e.g., corresponding to position 12 of human KRas). In embodiments, the leaving group is released from the staying group by reaction with the aspartate residue at the position corresponding to G12D of mutant human KRas G12D. In embodiments, the leaving group is released from the staying group by reaction with the serine residue at the position corresponding to G12S of mutant human Kras G12S.

As used herein, the term "leaving group" (e.g., LG) refers to an atom or group that becomes detached from an atom in the residual or main part of the substrate in a specified reaction. The residual or main part of the substrate is also referred to herein as the "staying group". Not wishing to be bound by any particular theory, the mechanism below is provided as an example to illustrate a non-limiting type of leaving group that may be found in compounds of the present disclosure. In the example below, nucleophilic attack of the parent compound by a carboxylate group of an aspartic acid residue or a hydroxyl group of a serine residue results in the cleavage of a C-LG bond, forming the depicted modified Ras protein and the leaving group (LG, shown as a portion of an E group as described herein) as two distinct molecules.

In embodiments, E is:

(i) —C(O)R$^{12}$ or —N(H)C(O)R$^{12}$; wherein the one R$^{12}$ is selected from C$_{2-9}$heterocycloalkyl and C$_{1-9}$heteroaryl, wherein C$_{2-9}$heterocycloalkyl and C$_{1-9}$heteroaryl are optionally substituted with one, two, or three R$^{20l}$; or (ii) independently selected from —NCN—R$^{4f}$;

optionally substituted with one or two R$^{4b}$;

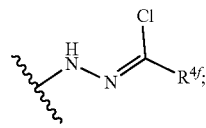

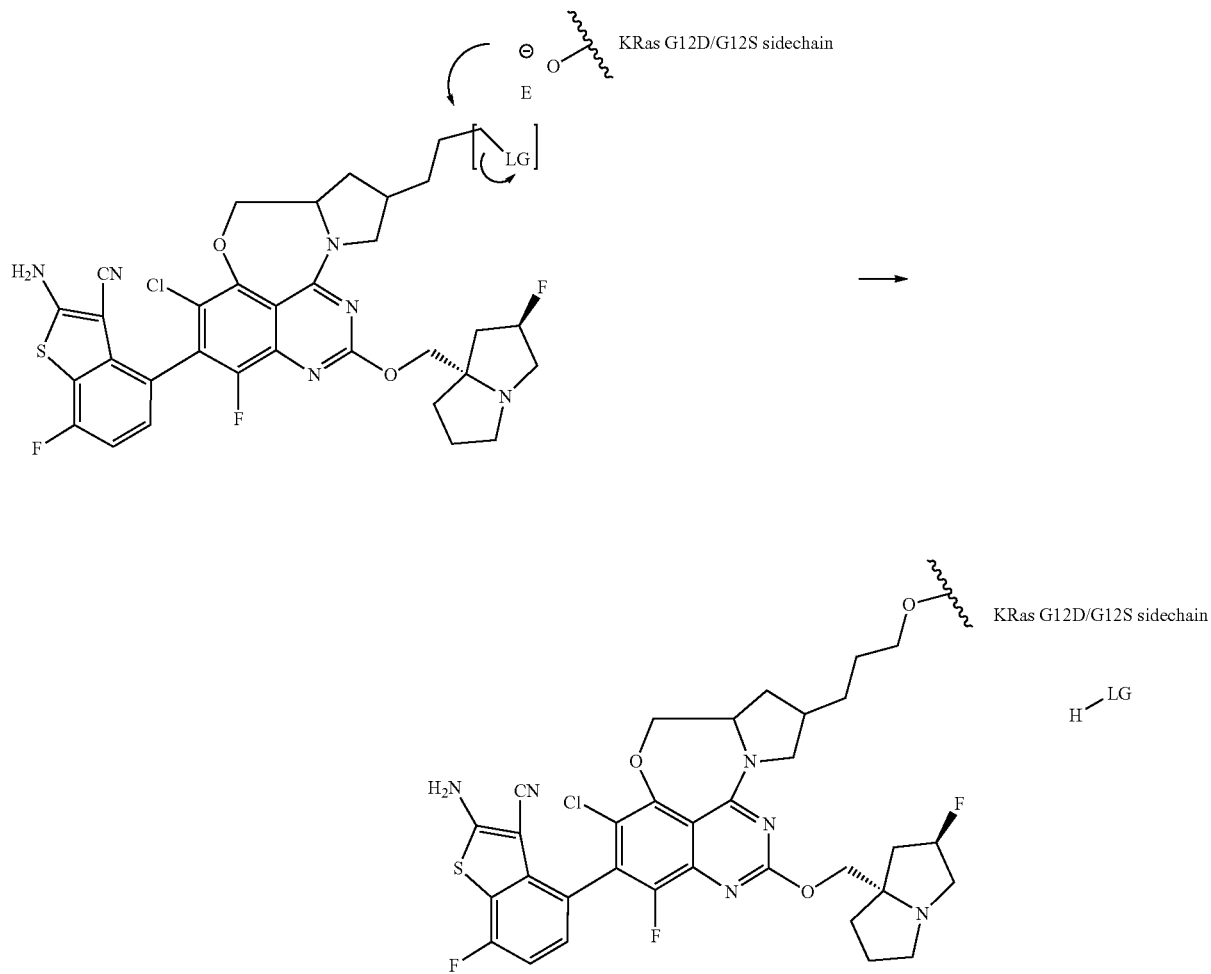

optionally substituted with one, two, three, or four R$^{4b}$;

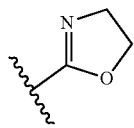

optionally substituted with one, two, three, or four R$^{4b}$;

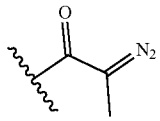

optionally substituted with one, two, or three R$^{4b}$;

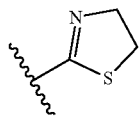 [SMILES: *C1=NCCS1]

optionally substituted with one, two, three, or four R$^{4b}$;

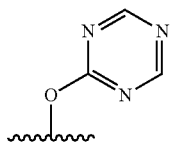 [SMILES: *Oc1ncncn1]

optionally substituted with one, two, R$^{4b}$;

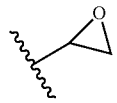

optionally substituted with one, two, or three R$^{4b}$;

optionally substituted with one, two, or three R$^{4b}$;

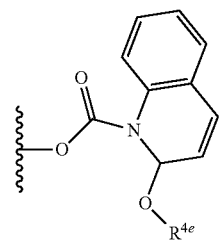

optionally substituted with one or more R$^{4b}$;

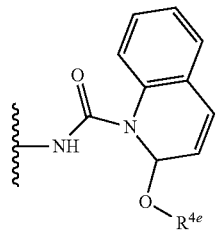

optionally substituted with one or more R$^{4b}$;

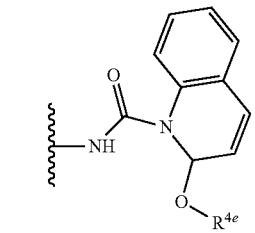

optionally substituted with one or more R$^{4b}$;

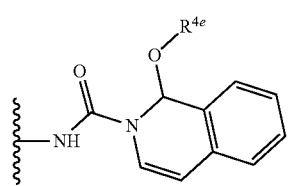

optionally substituted with one or more R$^{4b}$;

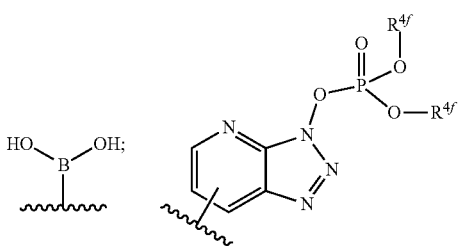

optionally substituted with one or more R$^{4b}$;

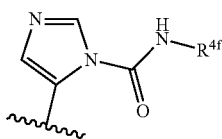

optionally substituted with one or more R$^{4b}$;

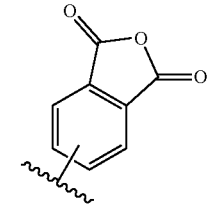

optionally substituted with one, two, or three R$^{4b}$;

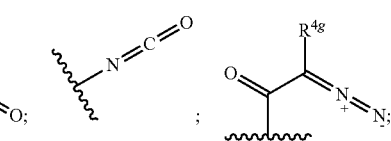

-continued

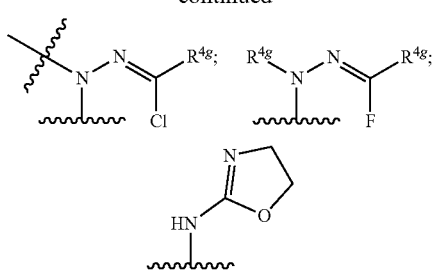

optionally substituted with one or more R<sup>4b</sup>;

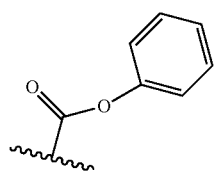 [SMILES: *C(=O)Oc1ccccc1]

optionally substituted with one or more R<sup>4b</sup>;

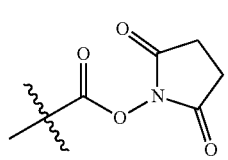 [SMILES: *C(=O)ON1C(=O)CCC1=O]

optionally substituted with one or more R<sup>4b</sup>;

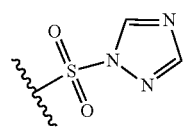 [SMILES: *S(=O)(=O)n1cncn1]

optionally substituted with one or more R<sup>4b</sup>;

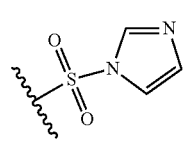 [SMILES: *S(=O)(=O)n1ccnc1]

optionally substituted with one or more R<sup>4b</sup>;

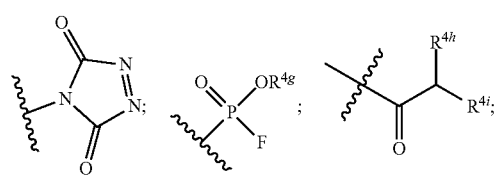

-continued

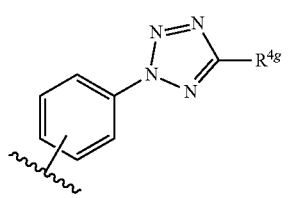

optionally substituted with one or more R<sup>4b</sup>;

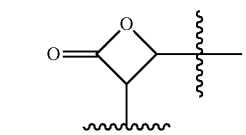 [SMILES: *C1OC(=O)C1*]

optionally substituted with one or more R<sup>4b</sup>;

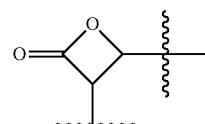

optionally substituted with one or more R<sup>4b</sup>;

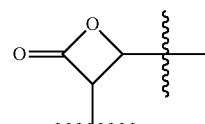

optionally substituted with one or more R<sup>4b</sup>;


optionally substituted with one or more R<sup>4b</sup>;

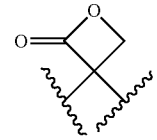 [SMILES: *C1(*)COC1=O]

optionally substituted with one or more R<sup>4b</sup>;

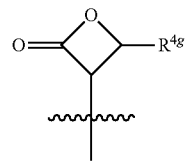

optionally substituted with one or more R<sup>4b</sup>;

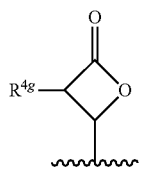

optionally substituted with one or more R<sup>4b</sup>;

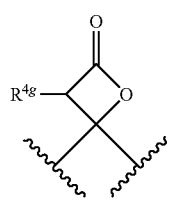

optionally substituted with one or more R<sup>4b</sup>;

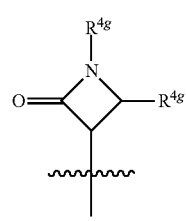

optionally substituted with one or more R<sup>4b</sup>;

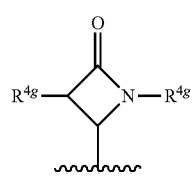

optionally substituted with one or more R<sup>4b</sup>;

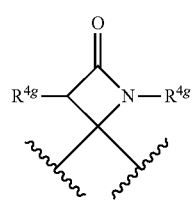

optionally substituted with one or more R<sup>4b</sup>

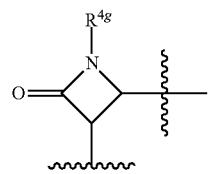

optionally substituted with one or more R<sup>4b</sup>;

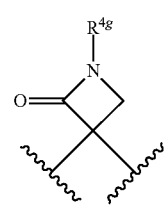

optionally substituted with one or more R<sup>4b</sup>;

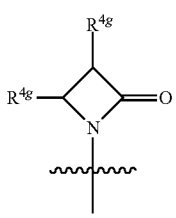

optionally substituted with one or more R<sup>4b</sup>;

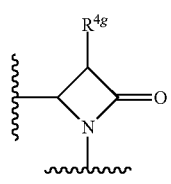

optionally substituted with one or more R<sup>4b</sup>;

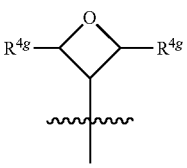

optionally substituted with one or more R<sup>4b</sup>;

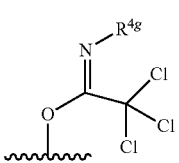

optionally substituted with one or more R⁴ᵇ;

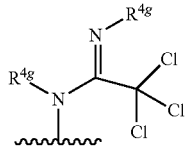

optionally substituted with one or more R⁴ᵇ;

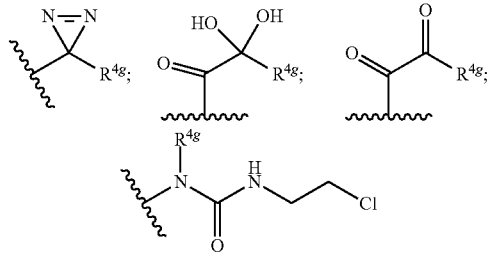

optionally substituted with one or more R⁴ᵇ;

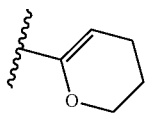 [SMILES: *C1=CCCCO1]

optionally substituted with one or more R⁴ᵇ;

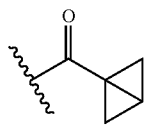 [SMILES: *C(=O)C12CC1C2]

optionally substituted with one or more R⁴ᵇ;

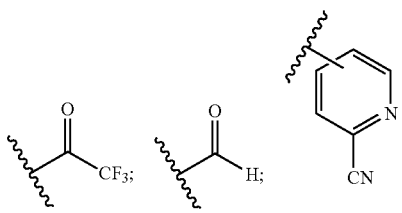

optionally substituted with one or more R⁴ᵇ; and

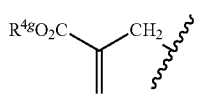

optionally substituted with one or more R⁴ᵇ;
each R⁴ᵉ is independently selected from C₁₋₆alkyl optionally substituted with one or more R²⁰ʸ;
each R⁴ᶠ is independently selected from C₁₋₆alkyl, C₂₋₆alkenyl, C₂₋₆alkynyl, C₃₋₁₀cycloalkyl, —CH₂-C₃₋₁₀cycloalkyl, C₂₋₉heterocycloalkyl, —CH₂-C₂₋₉heterocycloalkyl, C₆₋₁₀aryl, —CH₂-C₆₋₁₀aryl, —CH₂-C₁₋₉heteroaryl, C₁₋₉heteroaryl; wherein C₁₋₆alkyl, C₂₋₆alkenyl, C₂₋₆alkynyl, C₃₋₁₀cycloalkyl, —CH₂-C₃₋₁₀cycloalkyl, C₂₋₉heterocycloalkyl, —CH₂-C₂₋₉heterocycloalkyl, C₆₋₁₀aryl, —CH₂-C₆₋₁₀aryl, —CH₂-C₁₋₉heteroaryl, and C₁₋₉heteroaryl are optionally substituted with one or more R²⁰ʸ;
each R⁴ᵍ is independently selected from hydrogen and R⁴ᵇ;
each R⁴ʰ is independently selected from Cl, Br, and I;
each R⁴ⁱ is independently selected from —CN, C₁₋₆alkyl, C₂₋₆alkenyl, C₂₋₆alkynyl, C₃₋₁₂cycloalkyl, C₂₋₁₁heterocycloalkyl, C₆₋₁₂aryl, C₁₋₁₁heteroaryl, —OR¹², —SR¹², —N(R¹²)(R¹³), —C(O)OR¹², —OC(O)N(R¹²)(R¹³), —N(R¹⁴)C(O)N(R¹²)(R¹³), —N(R¹⁴)C(O)OR¹⁵, —N(R¹⁴)S(O)₂R¹⁵, —C(O)R¹², —S(O)R¹⁵, —OC(O)R¹⁵, —C(O)N(R¹²)(R¹³), —C(O)C(O)N(R¹²)(R¹³), —N(R¹⁴)C(O)R¹², —S(O)₂R¹⁵, —S(O)₂N(R¹²)(R¹³), —S(=O)(=NH)N(R¹²)(R¹³), -(C₁₋₆alkyl)—C(O)N(R¹²)(R¹³), -(C₁₋₆alkyl)—N(R¹⁴)C(O)R¹², -(C₁₋₆alkyl)—S(O)₂R¹⁵, -(C₁₋₆alkyl)—N(R¹²)(R¹³), -(C₁₋₆alkyl)—S(O)₂N(R¹²)(R¹³), and —P(=O)(R¹²)₂, wherein C₁₋₆alkyl, C₂₋₆alkenyl, C₂₋₆alkynyl, C₃₋₁₂cycloalkyl, C₂₋₁₁heterocycloalkyl, C₆₋₁₂aryl, and C₁₋₁₁heteroaryl are optionally substituted with one or more R²⁰ʸ;
each R⁴ᵇ is independently selected from halogen, oxo, —CN, C₁₋₆alkyl, C₂₋₆alkenyl, C₂₋₆alkynyl, C₃₋₁₂cycloalkyl, C₂₋₁₁heterocycloalkyl, C₆₋₁₂aryl, C₁₋₁₁heteroaryl, —N(R¹²)(R¹³), —C(O)OR¹², —OC(O)N(R¹²)(R¹³), —N(R¹⁴)C(O)N(R¹²)(R¹³), —N(R¹⁴)C(O)OR¹⁵, —N(R¹⁴)S(O)₂R¹⁵, —C(O)R¹², —S(O)R¹⁵, —OC(O)R¹⁵, —C(O)N(R¹²)(R¹³), —C(O)C(O)N(R¹²)(R¹³), —N(R¹⁴)C(O)R¹², —S(O)₂R¹⁵, —S(O)₂N(R¹²)(R¹³), —S(=O)(=NH)N(R¹²)(R¹³), -(C₁₋₆alkyl)—C(O)N(R¹²)(R¹³), -(C₁₋₆alkyl)—N(R¹⁴)C(O)R¹², -(C₁₋₆alkyl)—S(O)₂R¹⁵, -(C₁₋₆alkyl)—N(R¹²)(R¹³), -(C₁₋₆alkyl)—S(O)₂N(R¹²)(R¹³), and —P(=O)(R¹²)₂, wherein C₁₋₆alkyl, C₂₋₆alkenyl, C₂₋₆alkynyl, C₃₋₁₂cycloalkyl, C₂₋₁₁heterocycloalkyl, C₆₋₁₂aryl, and C₁₋₁₁heteroaryl are optionally substituted with one or more R²⁰ʸ;
each R²⁰ˡ, R²⁰ˡᶜ, R²⁰ᵐ, and R²⁰ᵒ is independently selected from halogen, oxo, —CN, C₁₋₆alkyl, C₂₋₆alkenyl, C₂₋₆alkynyl, C₃₋₁₀cycloalkyl, —CH₂-C₃₋₁₀cycloalkyl, C₂₋₉heterocycloalkyl, —CH₂-C₂₋₉heterocycloalkyl, C₆₋₁₀aryl, —CH₂-C₆₋₁₀aryl, —CH₂-C₁₋₉heteroaryl, C₁₋₉heteroaryl, —N(R²²)(R²³), —C(O)OR²², —C(O)N(R²²)(R²³), —C(O)C(O)N(R²²)(R²³), —OC(O)N(R²²)(R²³), —N(R²⁴)C(O)N(R²²)(R²³), —N(R²⁴)C(O)OR²⁵, —N(R²⁴)C(O)R²¹, —N(R²⁴)S(O)₂R²⁵, —C(O)R²¹, —S(O)₂R²⁵, —S(O)₂N(R²²)(R²³), —OCH₂C(O)OR²², =NR²¹, and —OC(O)R²⁵; two R²⁰ᵠ bonded to adjacent atoms are optionally joined to form a C₃₋₁₀cycloalkyl, C₂₋₉heterocycloalkyl, C₆₋₁₀aryl, or C₁₋₉heteroaryl; wherein C₁₋₆alkyl, C₂₋₆alkenyl, C₂₋₆alkynyl, C₃₋₁₀cycloalkyl, —CH₂-C₃₋₁₀cycloalkyl, C₂₋₉heterocycloalkyl, —CH₂-C₂₋₉heterocycloalkyl, C₆₋₁₀aryl, —CH₂-C₆₋₁₀aryl, —CH₂-C₁₋₉heteroaryl, and C₁₋₉heteroaryl are optionally substituted with one, two, or three groups independently selected from halogen, oxo, —CN, C₁₋₆alkyl, C₁₋₆haloalkyl, C₁₋₆alkoxy, C₁₋₆haloalkoxy, —OR²¹, —SR²¹, —N(R²²)(R²³), —C(O)OR²², —C(O)N(R²²)(R²³), —C(O)C(O)N(R²²)(R²³), —OC(O)N(R²²)(R²³), —N(R²⁴)C(O)N(R²²)(R²³), —N(R²⁴)C(O)OR²⁵, —N(R²⁴)C(O)R²⁵, —N(R²⁴)S(O)₂R²⁵, —C(O)R²⁵, —S(O)₂R²⁵, —S(O)₂N(R²²)(R²³), and —OC(O)R²⁵;

$R^{20y}$ is independently selected from halogen, oxo, —CN, $C_{1-6}$alkyl, $C_{2-6}$alkenyl, $C_{2-6}$alkynyl, $C_{3-10}$cycloalkyl, —CH$_2$-C$_{3-10}$cycloalkyl, $C_{2-9}$heterocycloalkyl, —CH$_2$-C$_{2-9}$heterocycloalkyl, $C_{6-10}$aryl, —CH$_2$-C$_{6-10}$aryl, —CH$_2$-C$_{1-9}$heteroaryl, $C_{1-9}$heteroaryl, —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, —N(R$^{24}$)C(O)R$^{21}$, —N(R$^{24}$)S(O)$_2$R$^{25}$, —C(O)R$^{21}$, —S(O)$_2$R$^{25}$, —S(O)$_2$N(R$^{22}$)(R$^{23}$), —OCH$_2$C(O)OR$^{22}$, =NR$^{21}$, and —OC(O)R$^{25}$; wherein $C_{1-6}$alkyl, $C_{2-6}$alkenyl, $C_{2-6}$alkynyl, $C_{3-10}$cycloalkyl, —CH$_2$-C$_{3-10}$cycloalkyl, $C_{2-9}$heterocycloalkyl, —CH$_2$-C$_{2-9}$heterocycloalkyl, $C_{6-10}$aryl, —CH$_2$-C$_{6-10}$aryl, —CH$_2$-C$_{1-9}$heteroaryl, and $C_{1-9}$heteroaryl are optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, —N(R$^{24}$)C(O)R$^{25}$, —N(R$^{24}$)S(O)$_2$R$^{25}$, —C(O)R$^{25}$, —S(O)$_2$R$^{25}$, —S(O)$_2$N(R$^{22}$)(R$^{23}$), and —OC(O)R$^{25}$;

each $R^{12}$ is independently selected from hydrogen, $C_{1-6}$alkyl, $C_{2-6}$alkenyl, $C_{2-6}$alkynyl, $C_{3-10}$cycloalkyl, —CH$_2$-C$_{3-10}$cycloalkyl, $C_{2-9}$heterocycloalkyl, —CH$_2$-C$_{2-9}$heterocycloalkyl, $C_{6-10}$aryl, —CH$_2$-C$_{6-10}$aryl, —CH$_2$-C$_{1-9}$heteroaryl, and $C_{1-9}$heteroaryl, wherein $C_{1-6}$alkyl, $C_{2-6}$alkenyl, $C_{2-6}$alkynyl, $C_{3-10}$cycloalkyl, —CH$_2$-C$_{3-10}$cycloalkyl, $C_{2-9}$heterocycloalkyl, —CH$_2$-C$_{2-9}$heterocycloalkyl, $C_{6-10}$aryl, —CH$_2$-C$_{6-10}$aryl, —CH$_2$-C$_{1-9}$heteroaryl, and $C_{1-9}$heteroaryl are optionally substituted with one, two, or three $R^{20l}$;

each $R^{12a}$ is independently selected from hydrogen, $C_{1-6}$alkyl, $C_{2-6}$alkenyl, $C_{2-6}$alkynyl, $C_{3-10}$cycloalkyl, —C(R$^{12c}$)$_2$-C$_{3-10}$cycloalkyl, $C_{2-9}$heterocycloalkyl, —C(R$^{12c}$)$_2$-C$_{2-9}$heterocycloalkyl, $C_{6-10}$aryl, —C(R$^{12c}$)$_2$-C$_{6-10}$aryl, —C(R$^{12c}$)$_2$-C$_{1-9}$heteroaryl, and $C_{1-9}$heteroaryl, wherein $C_{1-6}$alkyl, $C_{2-6}$alkenyl, $C_{2-6}$alkynyl, $C_{3-10}$cycloalkyl, —C(R$^{12c}$)$_2$-C$_{3-10}$cycloalkyl, $C_{2-9}$heterocycloalkyl, —C(R$^{12c}$)$_2$-C$_{2-9}$heterocycloalkyl, $C_{6-10}$aryl, —C(R$^{12c}$)$_2$-C$_{6-10}$aryl, —C(R$^{12c}$)$_2$-C$_{1-9}$heteroaryl, and $C_{1-9}$heteroaryl are optionally substituted with one, two, or three $R^{20l}$;

each $R^{12c}$ is independently selected from hydrogen and $R^{20lc}$;

each $R^{13}$ is independently selected from hydrogen, $C_{1-6}$alkyl, and $C_{1-6}$haloalkyl; or $R^{12}$ and $R^{13}$, together with the nitrogen to which they are attached, form a $C_{2-9}$heterocycloalkyl ring optionally substituted with one, two, or three $R^{20m}$;

each $R^{14}$ is independently selected from hydrogen, $C_{1-6}$alkyl, and $C_{1-6}$haloalkyl;

each $R^{15}$ is independently selected from $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20o}$;

each $R^{21}$ is independently selected from hydrogen, $C_{1-6}$alkyl, $C_{1-6}$haloalkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl;

each $R^{22}$ is independently selected from hydrogen, $C_{1-6}$alkyl, $C_{1-6}$haloalkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl;

each $R^{23}$ is independently selected from hydrogen and $C_{1-6}$alkyl;

each $R^{24}$ is independently selected from hydrogen and $C_{1-6}$alkyl; and each $R^{25}$ is independently selected from $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl.

In an aspect is provided a compound of Formula (A), or a pharmaceutically acceptable salt or solvate thereof:

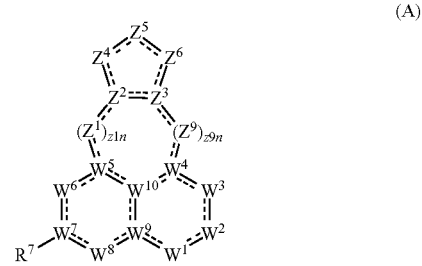

(A)

wherein:

$W^1$ is N(R$^1$) or N;

$R^1$ is selected from hydrogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —OR$^{12}$, —SR$^{12}$, —C(O)OR$^{12}$, —OC(O)N(R$^{12}$)(R$^{13}$), —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —S(O)$_2$R$^{15}$, —S(O)$_2$N(R$^{12}$)(R$^{13}$), —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20a}$;

$W^2$ is C(R$^2$), N(R$^2$), C(R$^2$)$_2$, C(O), S(O), S(O)$_2$, or N;

each $R^2$ is independently selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —OR$^{12a}$, —SR$^{12a}$, —N(R$^{12a}$)(R$^{13}$), —N=(R$^{15}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$)—, —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20b}$;

$W^3$ is C(R$^3$), N(R$^3$), C(R$^3$)$_2$, C(O), S(O), S(O)$_2$, or N;

each $R^3$ is independently selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$), —S(=O)(=NH)N ($R^{12}$)($R^{13}$), —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20c}$;

$W^4$ is $C(R^4)$, C, or N;

$R^4$ is selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20d}$;

$W^5$ is $C(R^5)$, C, or N;

$R^5$ is selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20e}$;

$W^6$ is $C(R^6)$, $N(R^6)$, $C(R^6)_2$, C(O), S(O), $S(O)_2$, or N;

each $R^6$ is independently selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20f}$;

$W^7$ is $C(R^{7a})$, C, or N;

$R^{7a}$ is selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20g}$;

$R^7$ is -$L^7$—$R^{17}$;

$L^7$ is a bond, $C_1$-$C_4$alkyl, $C_2$-$C_4$alkenyl, $C_2$-$C_4$alkynyl, 2-4 membered heteroalkylene linker, —O—, —$N(R^{7d})$—, —C(O)—, —S—, —$S(O)_2$—, —S(O)—, —$P(O)R^{7d}$—, $CR^{7c}R^{7c}$, —$OCR^{7c}R^{7c}$—, —$N(R^{7d})CR^{7c}R^{7c}$—, —$C(O)CR^{7c}R^{7c}$—, —$SCR^{7c}R^{7c}$—, —$S(O)_2CR^{7c}R^{7c}$—, —$S(O)CR^{7c}R^{7c}$—, —$P(O)R^{7d}CR^{7c}R^{7c}$—, —$CR^{7c}R^{7c}CR^{7c}R^{7c}$, —$CR^{7c}R^{7c}O$—, —$CR^{7c}R^{7c}N(R^{7d})$—, —$CR^{7c}R^{7c}C(O)$—, —$CR^{7c}R^{7c}S$—, —$CR^{7c}R^{7c}S(O)_2$—, —$CR^{7c}R^{7c}S(O)$—, —$CR^{7c}R^{7c}P(O)R^{7d}$—, —$N(R^{7d})C(O)$—, —$N(R^{7d})S(O)_2$—, —$N(R^{7d})S(O)$—, —$N(R^{7d})P(O)R^{7d}$—, —$C(O)N(R^{7d})$—, —$S(O)_2N(R^{7d})$—, —$S(O)N(R^{7d})$—, —$P(O)R^{7d}N(R^{7d})$—, —OC(O)—, —$OS(O)_2$—, —OS(O)—, —$OP(O)R^{7d}$—, —C(O)O—, —$S(O)_2O$—, —S(O)O—, or —$P(O)R^{7d}O$—; wherein the $C_1$-$C_4$alkyl, $C_2$-$C_4$alkenyl, $C_2$-$C_4$alkynyl, 2-4 membered heteroalkylene linker are optionally substituted with one, two, or three $R^{20g}$;

each $R^{7c}$ is independently selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$, $S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20g}$;

each $R^{7d}$ is independently selected from hydrogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$C(O)OR^{12}$, —$OC(O)N(R^{12})(R^{13})$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20g}$;

$R^{17}$ is selected from $C_{3-10}$cycloalkyl, 3-10 membered heterocycloalkyl, $C_{6-10}$aryl, and 5-10 membered heteroaryl, wherein $C_{3-10}$cycloalkyl, 3-10 membered heterocycloalkyl, $C_{6-10}$aryl, and 5-10 membered heteroaryl are optionally substituted with one or more $R^{20q}$; or $L^7$ is a bond and $R^{7a}$ and $R^{17}$, together with the carbon to which they are attached, form $C_{3-10}$cycloalkyl or 3-10 membered heterocycloalkyl, wherein the $C_{3-10}$cycloalkyl and 3-10 membered heterocycloalkyl are optionally substituted with one or more $R^{20q}$;

$W^8$ is $C(R^8)$, $N(R^8)$, $C(R^8)_2$, C(O), S(O), $S(O)_2$, or N;

each $R^8$ is independently selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)

(O)$R^{15}$, —$CH_2S(O)_2R^{15}$, and —$CH_2S(O)_2N(R^{12})$($R^{13}$), wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20h}$;

$W^9$ is C($R^9$), C, or N;

$R^9$ is selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —N($R^{12}$)($R^{13}$), —C(O)$OR^{12}$, —OC(O)N($R^{12}$)($R^{13}$), —N($R^{14}$)C(O)N($R^{12}$)($R^{13}$), —N($R^{14}$)C(O)$OR^{15}$, —N($R^{14}$)S(O)$_2R^{15}$, —C(O)$R^{15}$, —S(O)$R^{15}$, —OC(O)$R^{15}$, —C(O)N($R^{12}$)($R^{13}$), —C(O)C(O)N($R^{12}$)($R^{13}$), —N($R^{14}$)C(O)$R^{15}$, —S(O)$_2R^{15}$, —S(O)$_2$N($R^{12}$)($R^{13}$), —S(=O)(=NH)N($R^{12}$)($R^{13}$), —$CH_2$C(O)N($R^{12}$)($R^{13}$), —$CH_2$N($R^{14}$)C(O)$R^{15}$, —$CH_2$S(O)$_2R^{15}$, and —$CH_2$S(O)$_2$N($R^{12}$)($R^{13}$), wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20i}$;

$W^{10}$ C($R^{10}$), C, or N;

$R^{10}$ is selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —N($R^{12}$)($R^{13}$), —C(O)$OR^{12}$, —OC(O)N($R^{12}$)($R^{13}$), —N($R^{14}$)C(O)N($R^{12}$)($R^{13}$), —N($R^{14}$)C(O)$OR^{15}$, —N($R^{14}$)S(O)$_2R^{15}$, —C(O)$R^{15}$, —S(O)$R^{15}$, —OC(O)$R^{15}$, —C(O)N($R^{12}$)($R^{13}$), —C(O)C(O)N($R^{12}$)($R^{13}$), —N($R^{14}$)C(O)$R^{15}$, —S(O)$_2R^{15}$, —S(O)$_2$N($R^{12}$)($R^{13}$), —S(=O)(=NH)N($R^{12}$)($R^{13}$), —$CH_2$C(O)N($R^{12}$)($R^{13}$), —$CH_2$N($R^{14}$)C(O)$R^{15}$, —$CH_2$S(O)$_2R^{15}$, and —$CH_2$S(O)$_2$N($R^{12}$)($R^{13}$), wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20j}$;

each $Z^1$ is independently C($R^{z1}$), N($R^{z1}$), C($R^{z1}$)$_2$, C(O), S(O), S(O)$_2$, O, S, or N;

z1n is 0, 1, 2, or 3; wherein if z1n is 0 then $Z^2$ is directly bonded to $W^5$;

each $R^{z1}$ is independently selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —N($R^{12}$)($R^{13}$), —C(O)$OR^{12}$, —OC(O)N($R^{12}$)($R^{13}$), —N($R^{14}$)C(O)N($R^{12}$)($R^{13}$), —N($R^{14}$)C(O)$OR^{15}$, —N($R^{14}$)S(O)$_2R^{15}$, —C(O)$R^{15}$, —S(O)$R^{15}$, —OC(O)$R^{15}$, —C(O)N($R^{12}$)($R^{13}$), —C(O)C(O)N($R^{12}$)($R^{13}$), —N($R^{14}$)C(O)$R^{15}$, —S(O)$_2R^{15}$, —S(O)$_2$N($R^{12}$)($R^{13}$), —S(=O)(=NH)N($R^{12}$)($R^{13}$), —$CH_2$C(O)N($R^{12}$)($R^{13}$), —$CH_2$N($R^{14}$)C(O)$R^{15}$, —$CH_2$S(O)$_2R^{15}$, and —$CH_2$S(O)$_2$N($R^{12}$)($R^{13}$), wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20z1}$;

each $Z^9$ is independently C($R^{z9}$), N($R^{z9}$), C($R^{z9}$)$_2$, C(O), S(O), S(O)$_2$, O, S, or N;

z9n is 0, 1, 2, or 3; wherein if z9n is 0 then $Z^3$ is directly bonded to $W^4$;

each $R^{z9}$ is independently selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —N($R^{12}$)($R^{13}$), —C(O)$OR^{12}$, —OC(O)N($R^{12}$)($R^{13}$), —N($R^{14}$)C(O)N($R^{12}$)($R^{13}$), —N($R^{14}$)C(O)$OR^{15}$, —N($R^{14}$)S(O)$_2R^{15}$, —C(O)$R^{15}$, —S(O)$R^{15}$, —OC(O)$R^{15}$, —C(O)N($R^{12}$)($R^{13}$), —C(O)C(O)N($R^{12}$)($R^{13}$), —N($R^{14}$)C(O)$R^{15}$, —S(O)$_2R^{15}$, —S(O)$_2$N($R^{12}$)($R^{13}$), —S(=O)(=NH)N($R^{12}$)($R^{13}$), —$CH_2$C(O)N($R^{12}$)($R^{13}$), —$CH_2$N($R^{14}$)C(O)$R^{15}$, —$CH_2$S(O)$_2R^{15}$, and —$CH_2$S(O)$_2$N($R^{12}$)($R^{13}$), wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20z9}$;

wherein the sum of z1n and z9n is 2 or 3;

$Z^2$ is C($R^{z2}$), C, or N;

$R^{z2}$ is selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —N($R^{12}$)($R^{13}$), —C(O)$OR^{12}$, —OC(O)N($R^{12}$)($R^{13}$), —N($R^{14}$)C(O)N($R^{12}$)($R^{13}$), —N($R^{14}$)C(O)$OR^{15}$, —N($R^{14}$)S(O)$_2R^{15}$, —C(O)$R^{15}$, —S(O)$R^{15}$, —OC(O)$R^{15}$, —C(O)N($R^{12}$)($R^{13}$), —C(O)C(O)N($R^{12}$)($R^{13}$), —N($R^{14}$)C(O)$R^{15}$, —S(O)$_2R^{15}$, —S(O)$_2$N($R^{12}$)($R^{13}$), —S(=O)(=NH)N($R^{12}$)($R^{13}$), —$CH_2$C(O)N($R^{12}$)($R^{13}$), —$CH_2$N($R^{14}$)C(O)$R^{15}$, —$CH_2$S(O)$_2R^{15}$, and —$CH_2$S(O)$_2$N($R^{12}$)($R^{13}$), wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20z2}$;

$Z^3$ is C($R^{z3}$), C, or N;

$R^{z3}$ is selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —N($R^{12}$)($R^{13}$), —C(O)$OR^{12}$, —OC(O)N($R^{12}$)($R^{13}$), —N($R^{14}$)C(O)N($R^{12}$)($R^{13}$), —N($R^{14}$)C(O)$OR^{15}$, —N($R^{14}$)S(O)$_2R^{15}$, —C(O)$R^{15}$, —S(O)$R^{15}$, —OC(O)$R^{15}$, —C(O)N($R^{12}$)($R^{13}$), —C(O)C(O)N($R^{12}$)($R^{13}$), —N($R^{14}$)C(O)$R^{15}$, —S(O)$_2R^{15}$, —S(O)$_2$N($R^{12}$)($R^{13}$), —S(=O)(=NH)N($R^{12}$)($R^{13}$), —$CH_2$C(O)N($R^{12}$)($R^{13}$), —$CH_2$N($R^{14}$)C(O)$R^{15}$, —$CH_2$S(O)$_2R^{15}$, and —$CH_2$S(O)$_2$N($R^{12}$)($R^{13}$), wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20z3}$;

$Z^4$ is a bond, $Z^{4a}$, $Z^{4a}Z^{4b}$, $Z^{4a}Z^{4b}Z^{4c}$, or $Z^{4a}Z^{4b}Z^{4c}Z^{4d}$; wherein $Z^{4a}$ is directly bonded to $Z^2$; and wherein if $Z^4$ is a bond then $Z^2$ is directly bonded to $Z^5$;

$Z^{4a}$, $Z^{4b}$, $Z^{4c}$, and $Z^{4d}$ are independently C($R^{4a}$), N($R^{4a}$), C($R^{4a}$)$_2$, C(O), S(O), S(O)$_2$, S(O)(N$R^{4a}$), O, S, or N; provided that if z9n is 0 and $Z^4$ is $Z^{4a}Z^{4b}$; then (1) $Z^{4b}$ is C($R^{4a}$), C($R^{4a}$)$_2$, C(O), S(O), S(O)$_2$, S(O)(N$R^{4a}$), O, S, or N, (2) $Z^{4b}$ is N($R^{4a}$) and $Z^{4a}$ is C(O), S(O), or S(O)$_2$; (3) $Z^{4b}$ is N($R^{4a}$) and $Z^5$ is C(O), S(O), or S(O)$_2$; or (4) $Z^{4b}$ is N($R^{4a}$) and $Z^3$ is C($R^{z3}$) or C; and each $R^{4a}$ is independently selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —N($R^{12}$)($R^{13}$), —C(O)$OR^{12}$, —OC(O)N($R^{12}$)($R^{13}$), —N($R^{14}$)C(O)N($R^{12}$)($R^{13}$), —N($R^{14}$)C(O)$OR^{15}$, —N($R^{14}$)S(O)$_2R^{15}$, —C(O)$R^{12}$, —S(O)$R^{15}$, —OC(O)$R^{15}$, —C(O)N($R^{12}$)($R^{13}$), —C(O)C(O)N($R^{12}$)($R^{13}$), —N($R^{14}$)C(O)$R^{12}$, —S(O)$_2R^{15}$, —S(O)$_2$N($R^{12}$)($R^{13}$), —S(=O)(=NH)N($R^{12}$)($R^{13}$), —$CH_2$C(O)N($R^{12}$)($R^{13}$), —$CH_2$N($R^{14}$)C(O)$R^{15}$, —$CH_2$S(O)$_2R^{15}$, and —$CH_2$S(O)$_2$N($R^{12}$)($R^{13}$), wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20z4}$; or two $R^{4a}$ bonded to the same carbon are joined to form $C_{2-6}$alkenyl optionally substituted with one, two, or three $R^{20z4}$;

$Z^5$ is C($R^{z5}$), N($R^{z5}$), C($R^{z5}$)$_2$, C(O), S(O), S(O)$_2$, S(O)(N$R^{z5}$), O, S, or N;

each $R^{z5}$ is independently selected -$L^{z1}$-$L^{z2}$-$L^{z3}$ —$R^{12}$, from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{12}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{12}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20z5}$; or two $R^{z5}$ bonded to the same carbon are joined to form $C_{2-6}$alkenyl optionally substituted with one, two, or three $R^{20z5}$;

$Z^6$ is $C(R^{z6})$, $N(R^{z6})$, $C(R^{z6})_2$, $C(O)$, $S(O)$, $S(O)_2$, $S(O)(NR^{z6})$, O, S, or N;

each $R^{z6}$ is independently selected from -$L^{z1}$-$L^{z2}$-$L^{z3}$—$R^{12}$, hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{12}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{12}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20z6}$; or two $R^{z6}$ bonded to the same carbon are joined to form $C_{2-6}$alkenyl optionally substituted with one, two, or three $R^{20z6}$;

and further wherein the compound optionally includes one of the following:

(1) two $R^{z4}$ bonded to the same carbon atom are joined to form monocyclic $C_{3-7}$cycloalkyl or monocyclic 3-7 membered heterocycloalkyl, wherein the monocyclic $C_{3-7}$cycloalkyl and monocyclic 3-7 membered heterocycloalkyl are optionally substituted with one, two, or three $R^{20z}$;

(2) two or more $R^{z4}$ bonded to adjacent atoms are joined to form monocyclic $C_{3-7}$cycloalkyl, monocyclic 3-7 membered heterocycloalkyl, phenyl, or monocyclic 5-6 membered heteroaryl, wherein the monocyclic $C_{3-7}$cycloalkyl, monocyclic 3-7 membered heterocycloalkyl, phenyl, and monocyclic 5-6 membered heteroaryl are optionally substituted with one, two, or three $R^{20z}$;

(3) two $R^{z5}$ bonded to the same carbon atom are joined to form monocyclic $C_{3-7}$cycloalkyl or monocyclic 3-7 membered heterocycloalkyl, wherein the monocyclic $C_{3-7}$cycloalkyl and monocyclic 3-7 membered heterocycloalkyl are optionally substituted with one, two, or three $R^{20z}$;

(4) one or two $R^{z4}$ bonded to one atom and one or two $R^{z5}$ bonded to an adjacent atom are joined to form monocyclic $C_{3-7}$cycloalkyl, monocyclic 3-7 membered heterocycloalkyl, phenyl, or monocyclic 5-6 membered heteroaryl, wherein the monocyclic $C_{3-7}$cycloalkyl, monocyclic 3-7 membered heterocycloalkyl, phenyl, and monocyclic 5-6 membered heteroaryl are optionally substituted with one, two, or three $R^{20z}$;

(5) one or two $R^{z4}$ bonded to one atom and one or two $R^{z5}$ bonded to a second atom are joined to form monocyclic $C_{3-7}$cycloalkyl or monocyclic 3-7 membered heterocycloalkyl, wherein the monocyclic $C_{3-7}$cycloalkyl and monocyclic 3-7 membered heterocycloalkyl are optionally substituted with one, two, or three $R^{20z}$;

(6) two $R^{z6}$ bonded to the same carbon atom are joined to form monocyclic $C_{3-7}$cycloalkyl or monocyclic 3-7 membered heterocycloalkyl, wherein the monocyclic $C_{3-7}$cycloalkyl and monocyclic 3-7 membered heterocycloalkyl are optionally substituted with one, two, or three $R^{20z}$;

(7) one or two $R^{z5}$ bonded to one atom and one or two $R^{z6}$ bonded to an adjacent atom are joined to form monocyclic $C_{3-7}$cycloalkyl, monocyclic 3-7 membered heterocycloalkyl, phenyl, or monocyclic 5-6 membered heteroaryl, wherein the monocyclic $C_{3-7}$cycloalkyl, monocyclic 3-7 membered heterocycloalkyl, phenyl, and monocyclic 5-6 membered heteroaryl are optionally substituted with one, two, or three $R^{20z}$; or (8) one or two $R^{z4}$ bonded to one atom and one or two $R^{z6}$ bonded to a second atom are joined to form monocyclic $C_{3-7}$cycloalkyl or monocyclic 3-7 membered heterocycloalkyl, wherein the monocyclic $C_{3-7}$cycloalkyl and monocyclic 3-7 membered heterocycloalkyl are optionally substituted with one, two, or three $R^{20z}$;

each $R^{12}$ is independently selected from hydrogen, $C_{1-6}$alkyl, $C_{2-6}$alkenyl, $C_{2-6}$alkynyl, $C_{3-10}$cycloalkyl, —$CH_2$-$C_{3-10}$cycloalkyl, $C_{2-9}$heterocycloalkyl, —$CH_2$-$C_{2-9}$heterocycloalkyl, $C_{6-10}$aryl, —$CH_2$-$C_{6-10}$aryl, —$CH_2$-$C_{1-9}$heteroaryl, and $C_{1-9}$heteroaryl, wherein $C_{1-6}$alkyl, $C_{2-6}$alkenyl, $C_{2-6}$alkynyl, $C_{3-10}$cycloalkyl, —$CH_2$-$C_{3-10}$cycloalkyl, $C_{2-9}$heterocycloalkyl, —$CH_2$-$C_{2-9}$heterocycloalkyl, $C_{6-10}$aryl, —$CH_2$-$C_{6-10}$aryl, —$CH_2$-$C_{1-9}$heteroaryl, and $C_{1-9}$heteroaryl are optionally substituted with one, two, or three $R^{20l}$;

$R^{12a}$ is independently selected from hydrogen, $C_{1-6}$alkyl, $C_{2-6}$alkenyl, $C_{2-6}$alkynyl, $C_{3-10}$cycloalkyl, —$C(R^{12c})_2$-$C_{3-10}$cycloalkyl, $C_{2-9}$heterocycloalkyl, —$C(R^{12c})_2$-$C_{2-9}$heterocycloalkyl, $C_{6-10}$aryl, —$C(R^{12c})_2$-$C_{6-10}$aryl, —$C(R^{12c})_2$-$C_{1-9}$heteroaryl, and $C_{1-9}$heteroaryl, wherein $C_{1-6}$alkyl, $C_{2-6}$alkenyl, $C_{2-6}$alkynyl, $C_{3-10}$cycloalkyl, —$C(R^{12c})_2$-$C_{3-10}$cycloalkyl, $C_{2-9}$heterocycloalkyl, —$C(R^{12c})_2$-$C_{2-9}$heterocycloalkyl, $C_{6-10}$aryl, —$C(R^{12c})_2$-$C_{6-10}$aryl, —$C(R^{12c})_2$-$C_{1-9}$heteroaryl, and $C_{1-9}$heteroaryl are optionally substituted with one, two, or three $R^{20l}$;

each $R^{12c}$ is independently selected from hydrogen and $R^{20lc}$;

each $R^{13}$ is independently selected from hydrogen, $C_{1-6}$alkyl, and $C_{1-6}$haloalkyl; or $R^{12}$ and $R^{13}$, together with the nitrogen to which they are attached, form a $C_{2-9}$heterocycloalkyl ring optionally substituted with one, two, or three $R^{20m}$;

each $R^{14}$ is independently selected from hydrogen, $C_{1-6}$alkyl, and $C_{1-6}$haloalkyl;

each $R^{15}$ is independently selected from $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20o}$;

each $R^{20z1}$, $R^{20z2}$, $R^{20z3}$, $R^{20z4}$, $R^{20z5}$, $R^{20z6}$, and $R^{20z9}$ is independently selected from halogen, oxo, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{12}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{12}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20z}$;

each $R^{20z}$ is independently selected from -$L^{z3}$—$R^{12}$, halogen, oxo, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{12}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{12}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20zz}$;

two $R^{20z}$ bonded to the same carbon atom are optionally joined to form monocyclic $C_{3-7}$cycloalkyl or monocyclic 3-7 membered heterocycloalkyl, wherein the monocyclic $C_{3-7}$cycloalkyl and monocyclic 3-7 membered heterocycloalkyl are optionally substituted with one, two, or three $R^{20zz}$; or two or more $R^{20z}$ bonded to two adjacent atoms are optionally joined to form monocyclic $C_{3-7}$cycloalkyl, monocyclic 3-7 membered heterocycloalkyl, phenyl, or monocyclic 5-6 membered heteroaryl, wherein the $C_{3-7}$cycloalkyl, monocyclic 3-7 membered heterocycloalkyl, phenyl, and monocyclic 5-6 membered heteroaryl are optionally substituted with one, two, or three $R^{20zz}$;

$L^{z1}$ is selected from a bond, $C_{1-6}$alkylene, $C_{2-6}$alkenylene, $C_{2-6}$alkynylene, $C_{3-10}$cycloalkylene, $C_{1-9}$heterocycloalkylene, $C_{6-10}$arylene, and $C_{1-9}$heteroarylene; wherein $C_{1-6}$alkyl, $C_{2-6}$alkenylene, $C_{2-6}$alkynylene, $C_{3-10}$cycloalkylene, $C_{1-9}$heterocycloalkylene, $C_{6-10}$arylene, and $C_{1-9}$heteroarylene are optionally substituted with one or two $R^{30z}$;

$R^{30z}$ is independently selected from halogen, oxo, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{12}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{12}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20z}$;

$L^{z2}$ is selected from a bond, $C_{1-6}$alkylene, $C_{2-6}$alkenylene, $C_{2-6}$alkynylene, $C_{3-10}$cycloalkylene, $C_{2-9}$heterocycloalkylene, $C_{6-10}$arylene, and $C_{1-9}$heteroarylene; wherein $C_{1-6}$alkyl, $C_{2-6}$alkenylene, $C_{2-6}$alkynylene, $C_{3-10}$cycloalkylene, $C_{1-9}$heterocycloalkylene, $C_{6-10}$arylene, and $C_{1-9}$heteroarylene are optionally substituted with one or two $R^{31z}$;

$R^{31z}$ is independently selected from halogen, oxo, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{12}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{12}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20zz}$;

$L^{z3}$—$R^{12}$ is selected from:
i. —$C(O)R^{12}$ or —$N(H)C(O)R^{12}$; wherein the $R^{12}$ of $L^{z3}$—$R^{12}$ is a 5-membered heteroaryl including two or more ring nitrogen atoms, wherein the 5-membered heteroaryl is directly bonded to the C(O) through an $R^{12}$ ring nitrogen atom and wherein $R^{12}$ is optionally substituted with one or more $R^{20l}$; and
ii. —$C(O)R^{12}$ or —$N(H)C(O)R^{12}$; wherein the $R^{12}$ of $L^{z3}$—$R^{12}$ is a 3-membered heterocycloalkyl including one or more ring nitrogen atoms, wherein $R^{12}$ is optionally substituted with one or more $R^{20l}$;

$R^{20l}$ is independently selected from halogen, oxo, —CN, $C_{1-6}$alkyl, $C_{2-6}$alkenyl, $C_{2-6}$alkynyl, $C_{3-10}$cycloalkyl, —$CH_2$-$C_{3-10}$cycloalkyl, $C_{2-9}$heterocycloalkyl, —$CH_2$-$C_{2-9}$heterocycloalkyl, $C_{6-10}$aryl, —$CH_2$-$C_{6-10}$aryl, —$CH_2$-$C_{1-9}$heteroaryl, $C_{1-9}$heteroaryl, —$OR^{21}$, —$SR^{21}$, —$N(R^{22})(R^{23})$, —$C(O)OR^{22}$, —$C(O)N(R^{22})(R^{23})$, —$C(O)C(O)N(R^{22})(R^{23})$, —$OC(O)N(R^{22})(R^{23})$, —$N(R^{24})C(O)N(R^{22})(R^{23})$, —$N(R^{24})C(O)OR^{25}$, —$N(R^{24})C(O)R^{21}$, —$N(R^{24})S(O)_2R^{25}$, —$C(O)R^{21}$, —$S(O)_2R^{25}$, —$S(O)_2N(R^{22})(R^{23})$, —$OCH_2C(O)OR^{22}$, =$NR^{21}$, and —$OC(O)R^{25}$; two $R^{20q}$ bonded to adjacent atoms are optionally joined to form a $C_{3-10}$cycloalkyl, $C_{2-9}$heterocycloalkyl, $C_{6-10}$aryl, or $C_{1-9}$heteroaryl; wherein $C_{1-6}$alkyl, $C_{2-6}$alkenyl, $C_{2-6}$alkynyl, $C_{3-10}$cycloalkyl, —$CH_2$-$C_{3-10}$cycloalkyl, $C_{2-9}$heterocycloalkyl, —$CH_2$-$C_{2-9}$heterocycloalkyl, $C_{6-10}$aryl, —$CH_2$-$C_{6-10}$aryl, —$CH_2$-$C_{1-9}$heteroaryl, and $C_{1-9}$heteroaryl are optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —$OR^{12}$, —$SR^{12}$, —$N(R^{22})(R^{23})$, —$C(O)OR^{22}$, —$C(O)N(R^{22})(R^{23})$, —$C(O)C(O)N(R^{22})(R^{23})$, —$OC(O)N(R^{22})(R^{23})$, —$N(R^{24})C(O)N(R^{22})(R^{23})$, —$N(R^{24})C(O)OR^{25}$, —$N(R^{24})C(O)R^{25}$, —$N(R^{24})S(O)_2R^{25}$, —$C(O)R^{25}$, —$S(O)_2R^{25}$, —$S(O)_2N(R^{22})(R^{23})$, and —$OC(O)R^{25}$;

provided that i) one or more of $R^{z4}$, $R^{z5}$, or $R^{z6}$ is -$L^{z1}$-$L^{z2}$-$L^{z3}$—$R^{12}$; or ii) one or more of $R^{20z}$ is -$L^{z3}$—$R^{12}$;

each $R^{20a}$, $R^{20b}$, $R^{20c}$, $R^{20d}$, $R^{20e}$, $R^{20f}$, $R^{20g}$, $R^{20h}$, $R^{20i}$, $R^{20j}$, $R^{20l}$, $R^{20lc}$, $R^{20m}$, $R^{20o}$, $R^{20q}$, and $R^{20zz}$ is independently selected from halogen, oxo, —CN, $C_{1-6}$alkyl, $C_{2-6}$alkenyl, $C_{2-6}$alkynyl, $C_{3-10}$cycloalkyl, —$CH_2$-$C_{3-10}$cycloalkyl, $C_{2-9}$heterocycloalkyl, —$CH_2$-$C_{2-9}$heterocycloalkyl, $C_{6-10}$aryl, —$CH_2$-$C_{6-10}$aryl, —$CH_2$-$C_{1-9}$heteroaryl, $C_{1-9}$heteroaryl, —$OR^{21}$, —$SR^{21}$, —$N(R^{22})(R^{23})$, —$C(O)OR^{22}$, —$C(O)N(R^{22})(R^{23})$, —$C(O)C(O)N(R^{22})(R^{23})$, —$OC(O)N(R^{22})(R^{23})$, —$N(R^{24})C(O)N(R^{22})(R^{23})$, —$N(R^{24})C(O)$ OR$^{25}$, —N(R$^{24}$)C(O)R$^{21}$, —N(R$^{24}$)S(O)$_2$R$^{25}$, —C(O)R$^{21}$, —S(O)$_2$R$^{25}$, —S(O)$_2$N(R$^{22}$)(R$^{23}$), —OCH$_2$C(O)OR$^{22}$, =NR$^{21}$, and —OC(O)R$^{25}$; two R$^{20q}$ bonded to adjacent atoms are optionally joined to form a C$_{3-10}$cycloalkyl, C$_{2-9}$heterocycloalkyl, C$_{6-10}$aryl, or C$_{1-9}$heteroaryl; wherein C$_{1-6}$alkyl, C$_{2-6}$alkenyl, C$_{2-6}$alkynyl, C$_{3-10}$cycloalkyl, —CH$_2$-C$_{3-10}$cycloalkyl, C$_{2-9}$heterocycloalkyl, —CH$_2$-C$_{2-9}$heterocycloalkyl, C$_{6-10}$aryl, —CH$_2$-C$_{6-10}$aryl, —CH$_2$-C$_{1-9}$heteroaryl, and C$_{1-9}$heteroaryl are optionally substituted with one, two, or three groups independently selected from halogen, oxo, —CN, C$_{1-6}$alkyl, C$_{1-6}$haloalkyl, C$_{1-6}$alkoxy, C$_{1-6}$haloalkoxy, —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, —N(R$^{24}$)C(O)R$^{25}$, —N(R$^{24}$)S(O)$_2$R$^{25}$, —C(O)R$^{25}$, —S(O)$_2$R$^{25}$, —S(O)$_2$N(R$^{22}$)(R$^{23}$), and —OC(O)R$^{25}$;

each R$^{21}$ is independently selected from hydrogen, C$_{1-6}$alkyl, C$_{1-6}$haloalkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl;

each R$^{22}$ is independently selected from hydrogen, C$_{1-6}$alkyl, C$_{1-6}$haloalkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl;

each R$^{23}$ is independently selected from hydrogen and C$_{1-6}$alkyl;

each R$^{24}$ is independently selected from hydrogen and C$_{1-6}$alkyl;

each R$^{25}$ is independently selected from C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl; and $\overline{-----}$ indicates a single or double bond such that all valences are satisfied.

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, wherein:

L$^{z1}$ is selected from a bond, C$_{1-6}$alkylene, C$_{3-10}$cycloalkylene, and C$_{1-9}$heterocycloalkylene; wherein C$_{1-6}$alkylene, C$_{3-10}$cycloalkylene, and C$_{1-9}$heterocycloalkylene are optionally substituted with one or two R$^{30z}$;

R$^{30z}$ is independently selected from halogen, oxo, —CN, C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, C$_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{12}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{12}$, —S(O)$_2$R$^{15}$, —S(O)$_2$N(R$^{12}$)(R$^{13}$), —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl are optionally substituted with one, two, or three R$^{20z}$;

L$^{z2}$ is selected from a bond, C$_{1-6}$alkylene, C$_{3-10}$cycloalkylene, and C$_{1-9}$heterocycloalkylene; wherein C$_{1-6}$alkylene, C$_{3-10}$cycloalkylene, and C$_{1-9}$heterocycloalkylene are optionally substituted with one or two R$^{31z}$;

R$^{31z}$ is independently selected from halogen, oxo, —CN, C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, C$_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{12}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{12}$, —S(O)$_2$R$^{15}$, —S(O)$_2$N(R$^{12}$)(R$^{13}$), —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl are optionally substituted with one, two, or three R$^{20zz}$;

L$^{z3}$—R$^{12}$ is selected from:
i. —C(O)R$^{12}$ or —N(H)C(O)R$^{12}$; wherein the R$^{12}$ of L$^{z3}$—R$^{12}$ is a 5-membered heteroaryl including two or more ring nitrogen atoms, wherein the 5-membered heteroaryl is directly bonded to the C(O) through an R$^{12}$ ring nitrogen atom and wherein R$^{12}$ is optionally substituted with one or more R$^{20l}$; and
ii. —C(O)R$^{12}$ or —N(H)C(O)R$^{12}$; wherein the R$^{12}$ of L$^{3z}$—R$^{12}$ is a 3-membered heterocycloalkyl including one or more ring nitrogen atoms, wherein R$^{12}$ is optionally substituted with one or more R$^{20l}$;

R$^{20l}$ is independently selected from halogen, oxo, —CN, C$_{1-6}$alkyl, C$_{2-6}$alkenyl, C$_{2-6}$alkynyl, C$_{3-10}$cycloalkyl, —CH$_2$-C$_{3-10}$cycloalkyl, C$_{2-9}$heterocycloalkyl, —CH$_2$-C$_{2-9}$heterocycloalkyl, C$_{6-10}$aryl, —CH$_2$-C$_{6-10}$aryl, —CH$_2$-C$_{1-9}$heteroaryl, C$_{1-9}$heteroaryl, —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, —N(R$^{24}$)C(O)R$^{21}$, —N(R$^{24}$)S(O)$_2$R$^{25}$, —C(O)R$^{21}$, —S(O)$_2$R$^{25}$, —S(O)$_2$N(R$^{22}$)(R$^{23}$), —OCH$_2$C(O)OR$^{22}$, =NR$^{21}$, and —OC(O)R$^{25}$; two R$^{20q}$ bonded to adjacent atoms are optionally joined to form a C$_{3-10}$cycloalkyl, C$_{2-9}$heterocycloalkyl, C$_{6-10}$aryl, or C$_{1-9}$heteroaryl; wherein C$_{1-6}$alkyl, C$_{2-6}$alkenyl, C$_{2-6}$alkynyl, C$_{3-10}$cycloalkyl, —CH$_2$-C$_{3-10}$cycloalkyl, C$_{2-9}$heterocycloalkyl, —CH$_2$-C$_{2-9}$heterocycloalkyl, C$_{6-10}$aryl, —CH$_2$-C$_{6-10}$aryl, —CH$_2$-C$_{1-9}$heteroaryl, and C$_{1-9}$heteroaryl are optionally substituted with one, two, or three groups independently selected from halogen, oxo, —CN, C$_{1-6}$alkyl, C$_{1-6}$haloalkyl, C$_{1-6}$alkoxy, C$_{1-6}$haloalkoxy, —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, —N(R$^{24}$)C(O)R$^{25}$, —N(R$^{24}$)S(O)$_2$R$^{25}$, —C(O)R$^{25}$, —S(O)$_2$R$^{25}$, —S(O)$_2$N(R$^{22}$)(R$^{23}$), and —OC(O)R$^{25}$;

provided that i) one or more of R$^{z4}$, R$^{z5}$, or R$^{z6}$ is -L$^{z1}$-L$^{z2}$-L$^{z3}$—R$^{12}$ ; or ii) one or more of R$^{20z}$ is -L$^{z3}$—R$^{12}$.

In embodiments a compound of Formula (A) or B, or a pharmaceutically acceptable salt or solvate thereof, has the formula:

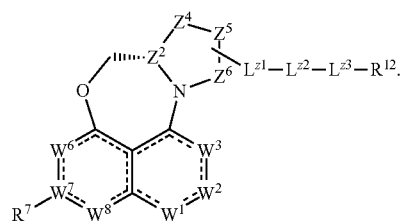

In embodiments, a compound of Formula (A) or B, or a pharmaceutically acceptable salt or solvate thereof, has the formula:

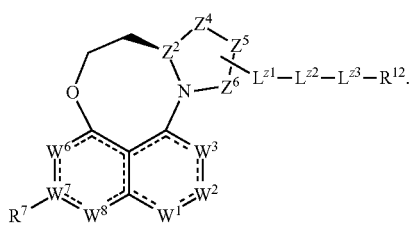

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof,

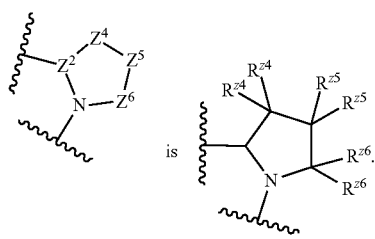

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof,

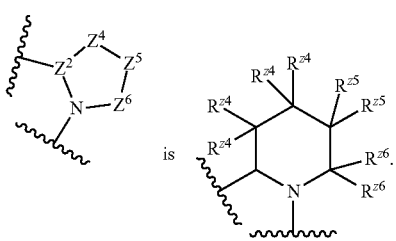

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, two $R^{z5}$ bonded to the same carbon atom are joined to form monocyclic 4-membered heterocycloalkyl, wherein the 4 membered heterocycloalkyl is substituted with one, two, or three $R^{20z}$.

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof,

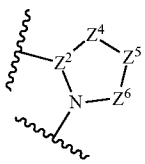 is selected from

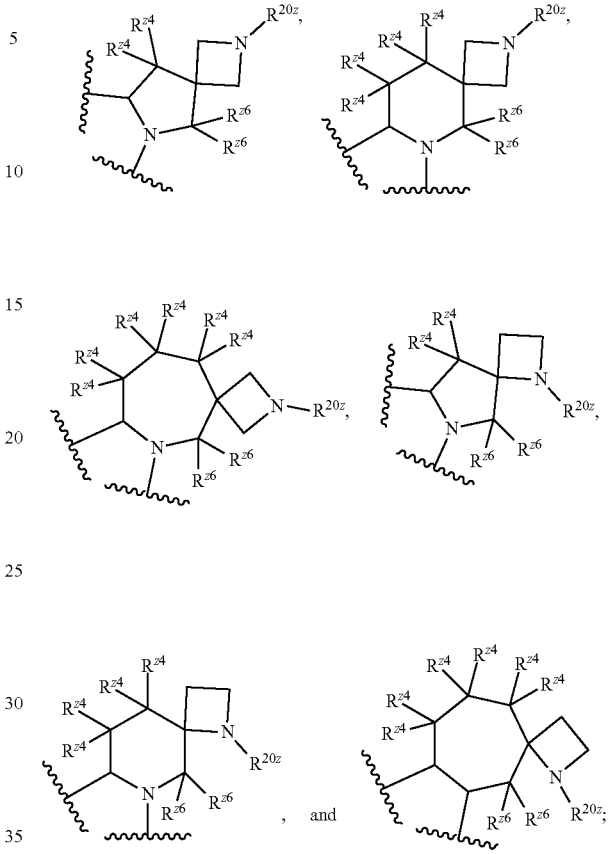

wherein the one $R^{20z}$ shown in each formula above is —C(O)$R^{12}$ or —N(H)C(O)$R^{12}$. In embodiments of the formula immediately above, $R^{12}$ is independently selected from $C_{3-10}$cycloalkyl, $C_{2-9}$heterocycloalkyl, $C_{6-10}$aryl, and $C_{1-9}$heteroaryl, wherein $C_{3-10}$cycloalkyl, $C_{2-9}$heterocycloalkyl, $C_{6-10}$aryl, and $C_{1-9}$heteroaryl are optionally substituted with one, two, or three $R^{20l}$ (e.g., $R^{12}$ is a 5-membered heteroaryl including two or more ring nitrogen atoms, wherein the 5-membered heteroaryl is directly bonded to the C(O) through an $R^{12}$ ring nitrogen atom and wherein $R^{12}$ is optionally substituted with one or more $R^{20l}$; $R^{12}$ is a 3-membered heterocycloalkyl including one or more ring nitrogen atoms, wherein $R^{12}$ is optionally substituted with one or more $R^{20l}$).

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, one or two $R^{z4}$ bonded to one atom and one or two $R^{z5}$ bonded to an adjacent atom are joined to form monocyclic 5-6 membered heteroaryl, wherein the monocyclic 5-6 membered heteroaryl is optionally substituted with one, two, or three $R^{20z}$.

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof,

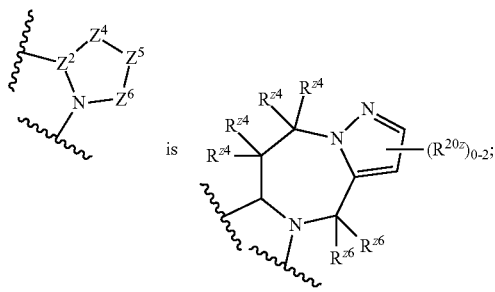 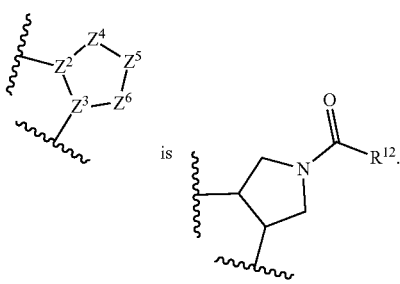

wherein one $R^{20z}$ shown in the formula above is —C(O)$R^{12}$ or —N(H)C(O)$R^{12}$. In embodiments of the formula immediately above, $R^{12}$ is independently selected from $C_{3-10}$cycloalkyl, $C_{2-9}$heterocycloalkyl, $C_{6-10}$aryl, and $C_{1-9}$heteroaryl, wherein $C_{3-10}$cycloalkyl, $C_{2-9}$heterocycloalkyl, $C_{6-10}$aryl, and $C_{1-9}$heteroaryl are optionally substituted with one, two, or three $R^{20l}$ (e.g., $R^{12}$ is a 5-membered heteroaryl including two or more ring nitrogen atoms, wherein the 5-membered heteroaryl is directly bonded to the C(O) through an $R^{12}$ ring nitrogen atom and wherein $R^{12}$ is optionally substituted with one or more $R^{20l}$; $R^{12}$ is a 3-membered heterocycloalkyl including one or more ring nitrogen atoms, wherein $R^{12}$ is optionally substituted with one or more $R^{20l}$).

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, wherein In embodiments of the formula immediately above, $R^{12}$ is independently selected from $C_{3-10}$cycloalkyl, $C_{2-9}$heterocycloalkyl, $C_{6-10}$aryl, and $C_{1-9}$heteroaryl, wherein $C_{3-10}$cycloalkyl, $C_{2-9}$heterocycloalkyl, $C_{6-10}$aryl, and $C_{1-9}$heteroaryl are optionally substituted with one, two, or three $R^{20l}$ (e.g., $R^{12}$ is a 5-membered heteroaryl including two or more ring nitrogen atoms, wherein the 5-membered heteroaryl is directly bonded to the C(O) through an $R^{12}$ ring nitrogen atom and wherein $R^{12}$ is optionally substituted with one or more $R^{20l}$; $R^{12}$ is a 3-membered heterocycloalkyl including one or more ring nitrogen atoms, wherein $R^{12}$ is optionally substituted with one or more $R^{20l}$).

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, wherein

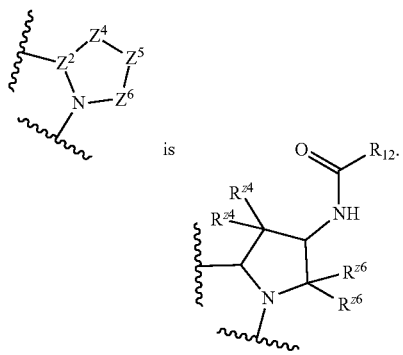 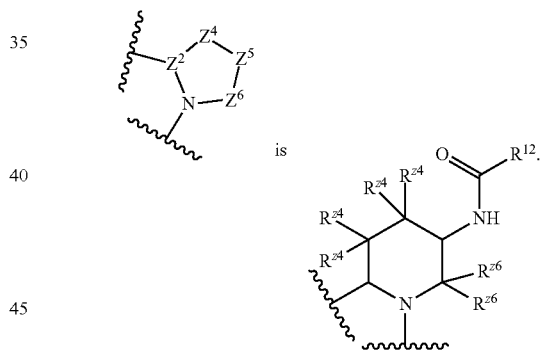

In embodiments of the formula immediately above, $R^{12}$ is independently selected from $C_{3-10}$cycloalkyl, $C_{2-9}$heterocycloalkyl, $C_{6-10}$aryl, and $C_{1-9}$heteroaryl, wherein $C_{3-10}$cycloalkyl, $C_{2-9}$heterocycloalkyl, $C_{6-10}$aryl, and $C_{1-9}$heteroaryl are optionally substituted with one, two, or three $R^{20l}$ (e.g., $R^{12}$ is a 5-membered heteroaryl including two or more ring nitrogen atoms, wherein the 5-membered heteroaryl is directly bonded to the C(O) through an $R^{12}$ ring nitrogen atom and wherein $R^{12}$ is optionally substituted with one or more $R^{20l}$; $R^{12}$ is a 3-membered heterocycloalkyl including one or more ring nitrogen atoms, wherein $R^{12}$ is optionally substituted with one or more $R^{20l}$).

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, wherein In embodiments of the formula immediately above, $R^{12}$ is independently selected from $C_{3-10}$cycloalkyl, $C_{2-9}$heterocycloalkyl, $C_{6-10}$aryl, and $C_{1-9}$heteroaryl, wherein $C_{3-10}$cycloalkyl, $C_{2-9}$heterocycloalkyl, $C_{6-10}$aryl, and $C_{1-9}$heteroaryl are optionally substituted with one, two, or three $R^{20l}$ (e.g., $R^{12}$ is a 5-membered heteroaryl including two or more ring nitrogen atoms, wherein the 5-membered heteroaryl is directly bonded to the C(O) through an $R^{12}$ ring nitrogen atom and wherein $R^{12}$ is optionally substituted with one or more $R^{20l}$; $R^{12}$ is a 3-membered heterocycloalkyl including one or more ring nitrogen atoms, wherein $R^{12}$ is optionally substituted with one or more $R^{20l}$).

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, wherein

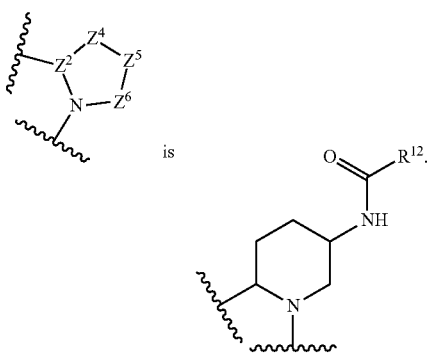

is

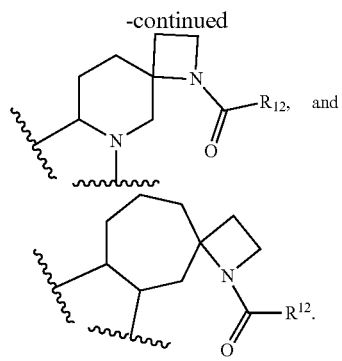

In embodiments of the formula immediately above, $R^{12}$ is independently selected from $C_{3-10}$cycloalkyl, $C_{2-9}$heterocycloalkyl, $C_{6-10}$aryl, and $C_{1-9}$heteroaryl, wherein $C_{3-10}$cycloalkyl, $C_{2-9}$heterocycloalkyl, $C_{6-10}$aryl, and $C_{1-9}$heteroaryl are optionally substituted with one, two, or three $R^{20l}$ (e.g., $R^{12}$ is a 5-membered heteroaryl including two or more ring nitrogen atoms, wherein the 5-membered heteroaryl is directly bonded to the C(O) through an $R^{12}$ ring nitrogen atom and wherein $R^{12}$ is optionally substituted with one or more $R^{20l}$; $R^{12}$ is a 3-membered heterocycloalkyl including one or more ring nitrogen atoms, wherein $R^{12}$ is optionally substituted with one or more $R^{20l}$).

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, is selected from

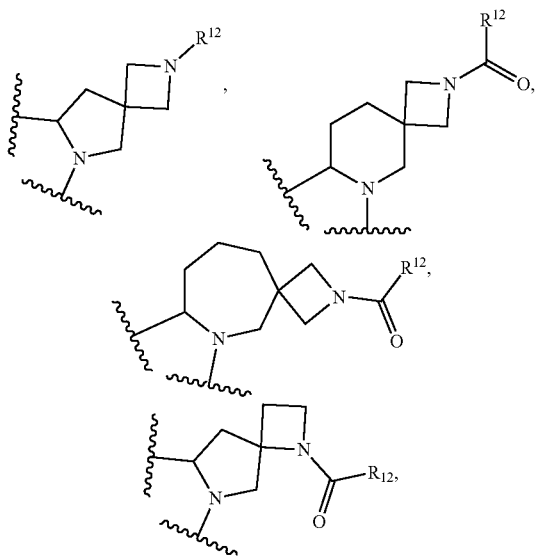

-continued

In embodiments of the formula immediately above, $R^{12}$ is independently selected from $C_{3-10}$cycloalkyl, $C_{2-9}$heterocycloalkyl, $C_{6-10}$aryl, and $C_{1-9}$heteroaryl, wherein $C_{3-10}$cycloalkyl, $C_{2-9}$heterocycloalkyl, $C_{6-10}$aryl, and $C_{1-9}$heteroaryl are optionally substituted with one, two, or three $R^{20l}$ (e.g., $R^{12}$ is a 5-membered heteroaryl including two or more ring nitrogen atoms, wherein the 5-membered heteroaryl is directly bonded to the C(O) through an $R^{12}$ ring nitrogen atom and wherein $R^{12}$ is optionally substituted with one or more $R^{20l}$; $R^{12}$ is a 3-membered heterocycloalkyl including one or more ring nitrogen atoms, wherein $R^{12}$ is optionally substituted with one or more $R^{20l}$).

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, z1n is 1, 2 or 3, and z9n is 1, 2, or 3. In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, $W^1$ is N. In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, $W^2$ is $C(R^2)$. In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, $W^3$ is N. In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, $W^4$ is C. In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, $W^5$ is C. In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, $W^5$ is $C(R^5)$. In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, $W^6$ is $C(R^6)$. In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, $R^6$ is selected from hydrogen, halogen, —CN, $C_{1-6}$alkyl, and —OR$^{12}$, wherein $C_{1-6}$alkyl is optionally substituted with one, two, or three R$^{20f}$. In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, R$^6$ is halogen. In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, W$^7$ is C. In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, W$^8$ is C(R$^8$). In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, R$^8$ is selected from hydrogen, halogen, —CN, $C_{1-6}$alkyl, and —OR$^{12}$, wherein $C_{1-6}$alkyl is optionally substituted with one, two, or three R$^{20h}$. In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, R$^8$ is halogen. In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, W$^9$ is C. In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, W$^{10}$ is C. In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof,

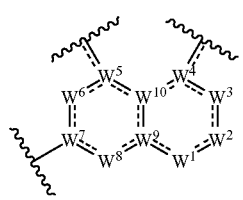

is selected from

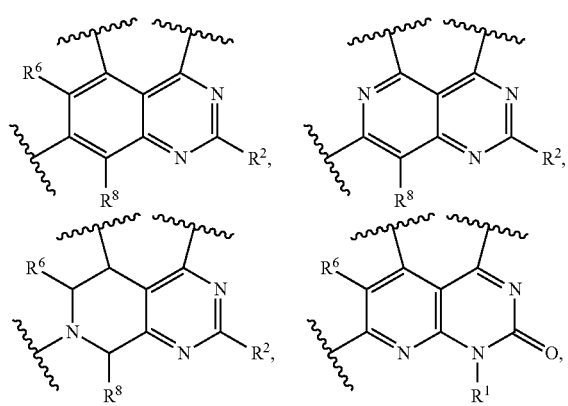

and

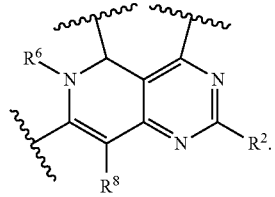

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, L$^7$ is a bond.

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, R$^{17}$ is selected from naphthalenyl and benzothiophenyl, each of which is optionally substituted with one, two, or three R$^{20q}$. In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, R$^{17}$ is substituted with one, two, or three substituents independently selected from halogen, —CN, —CH$_3$, —C≡CH, —OH, and —NH$_2$.

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, R$^{17}$ is selected from

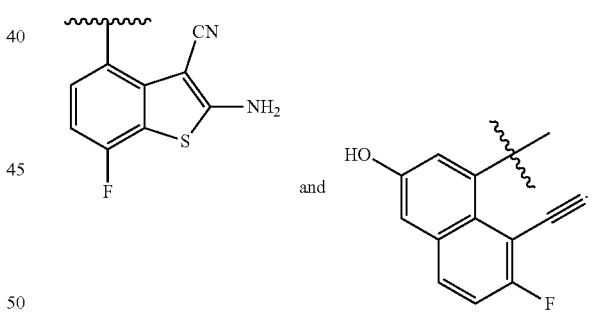

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, R$^{17}$ is selected from:

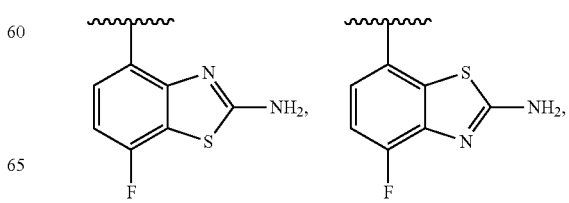

-continued
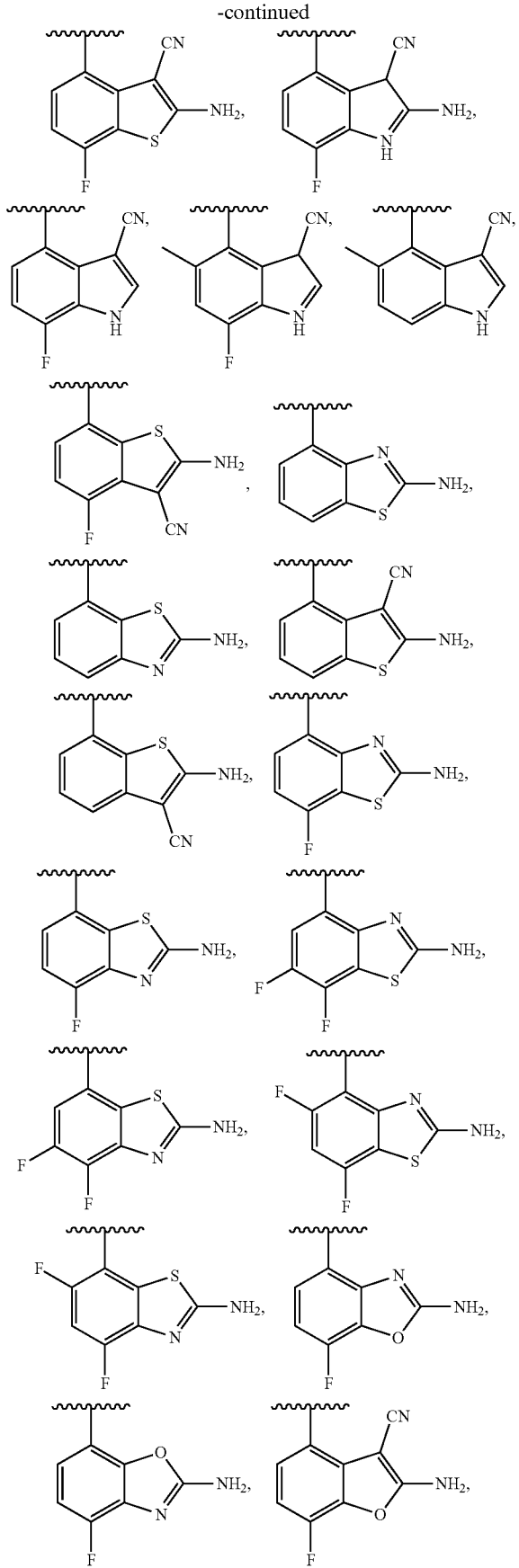
-continued
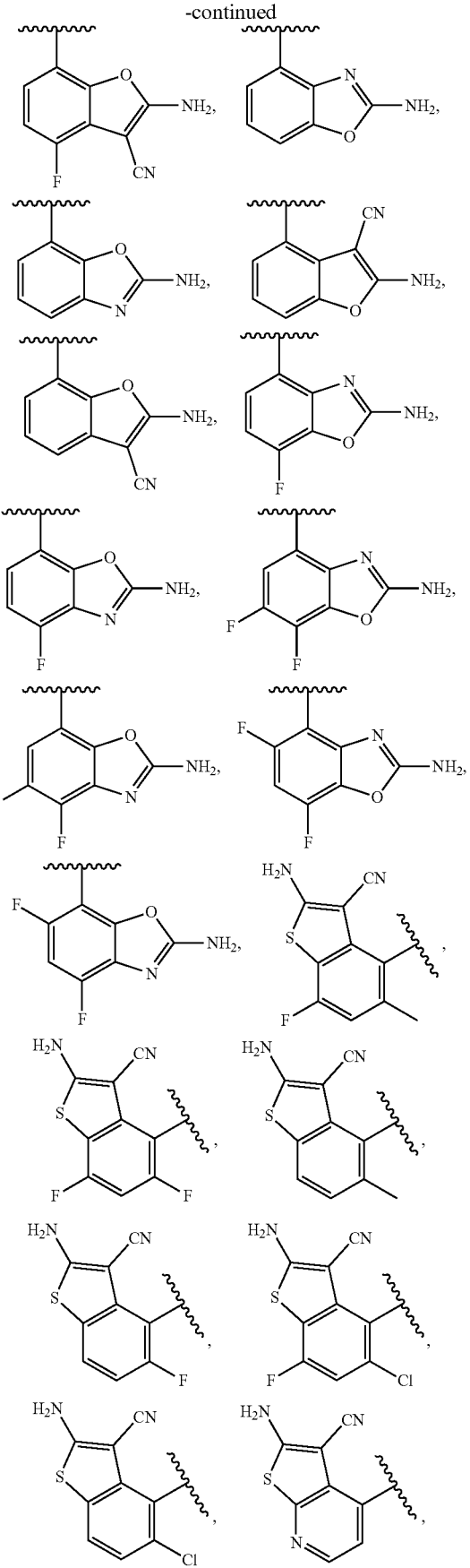

-continued
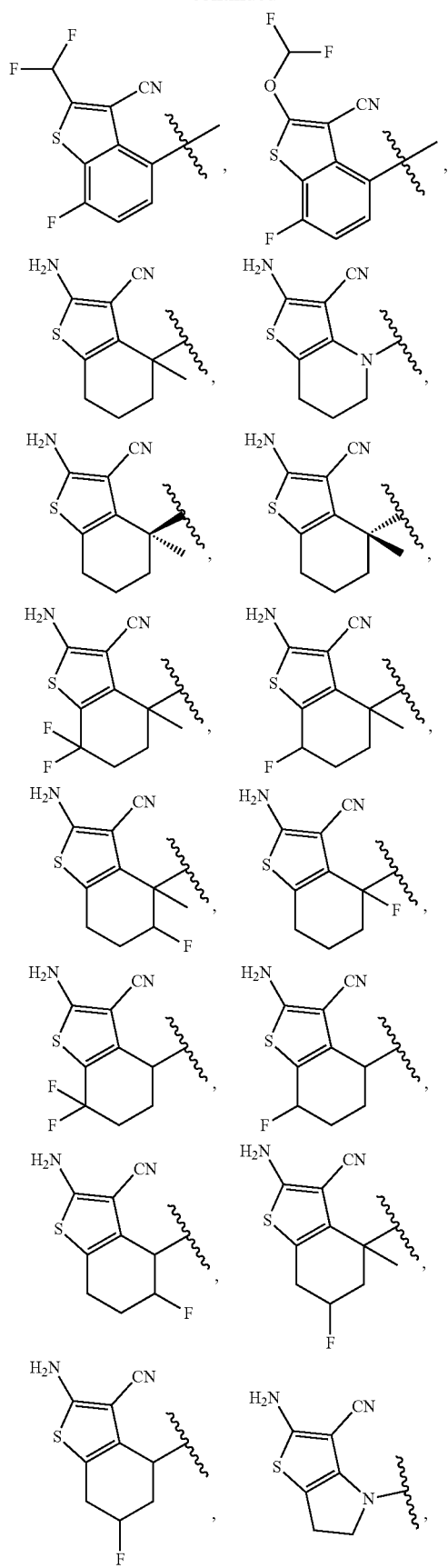
-continued
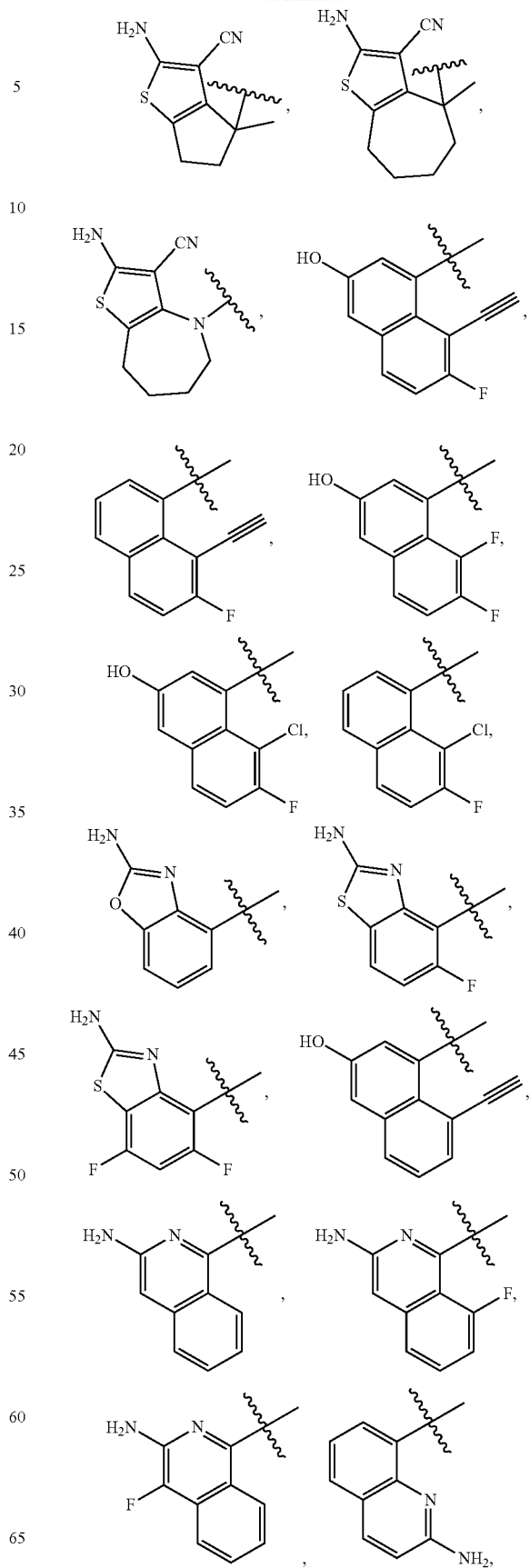

431
-continued
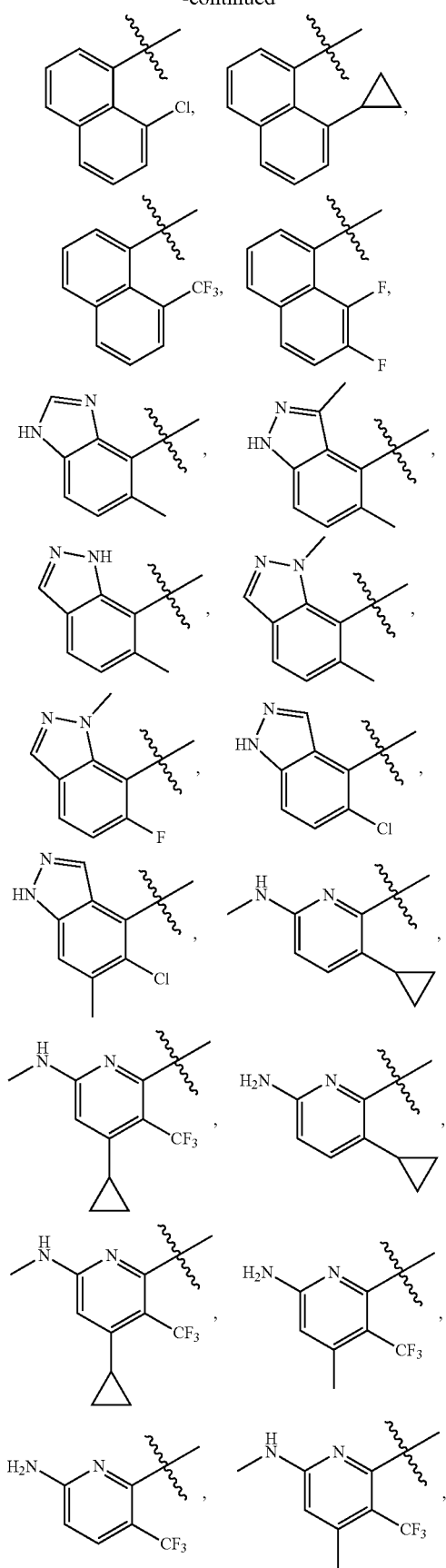
432
-continued
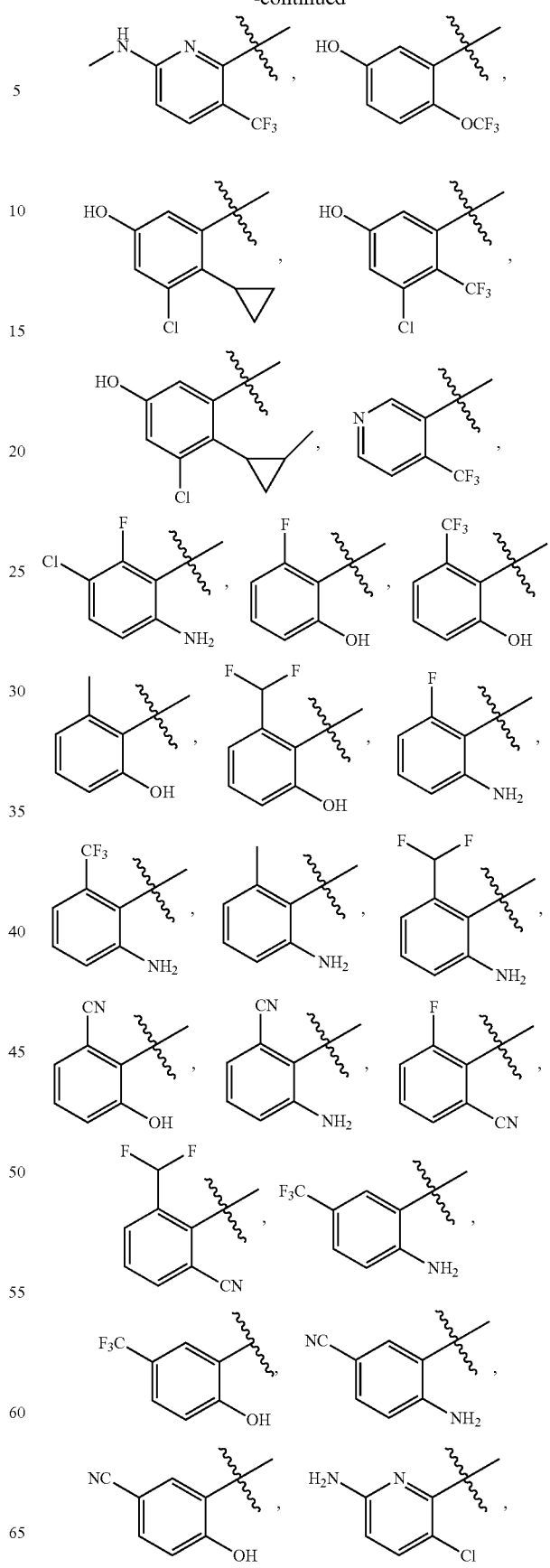

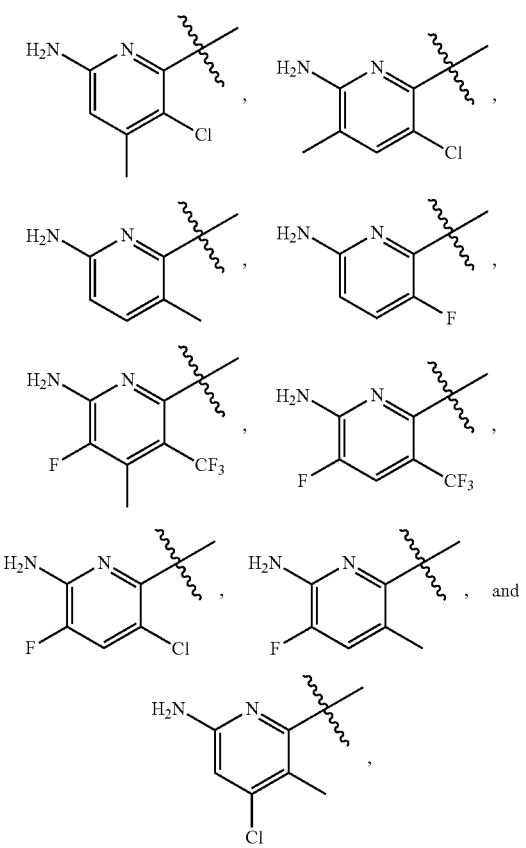

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, $R^2$ is independently —$OR^{12a}$.

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, $R^2$ is independently selected from

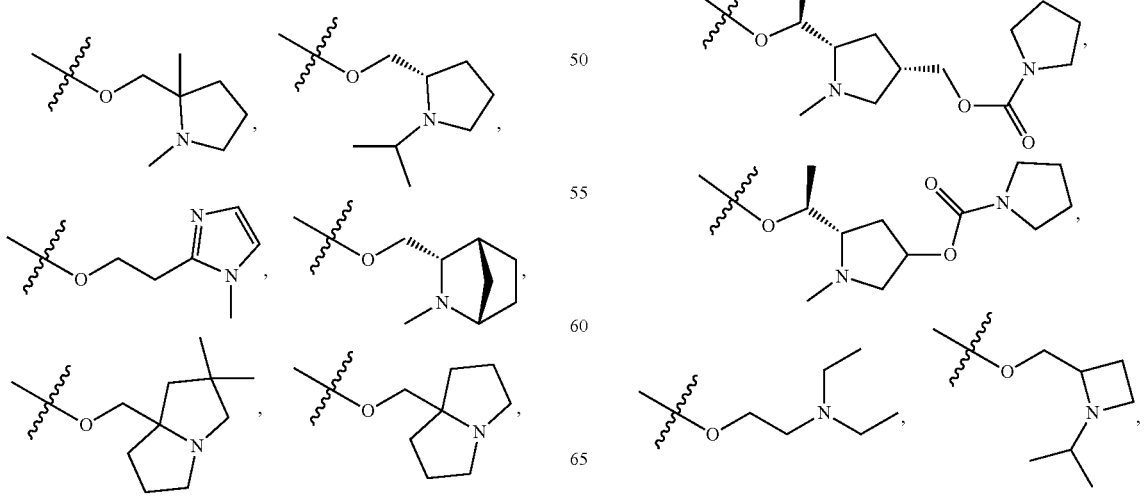

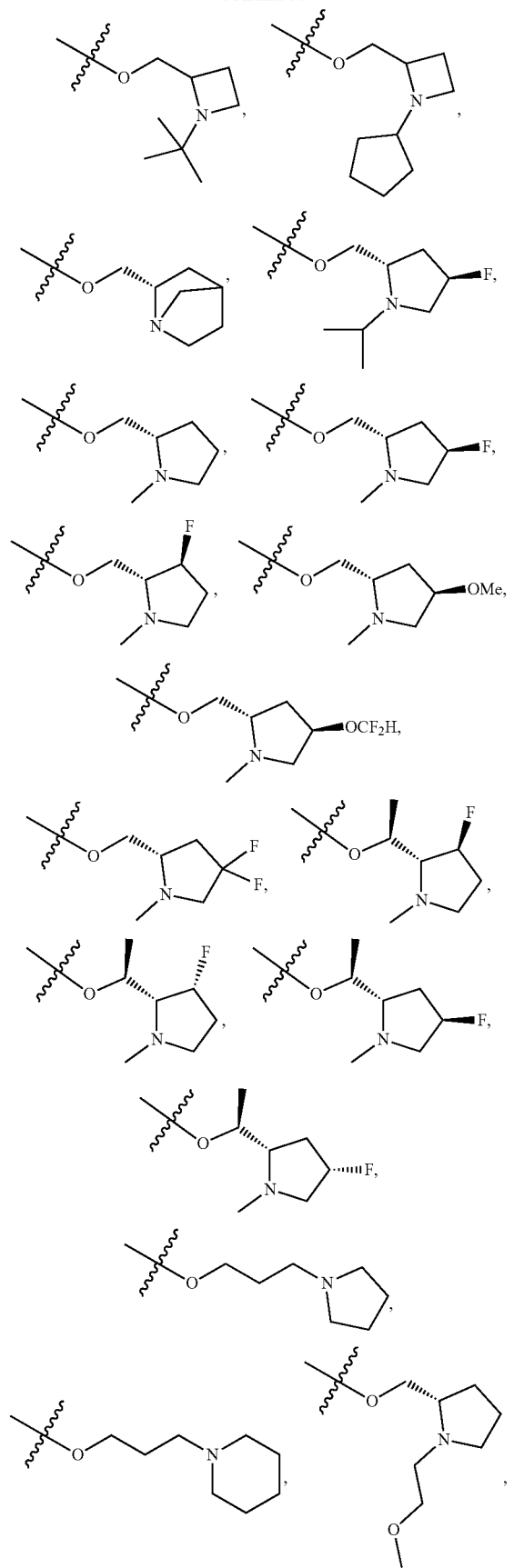
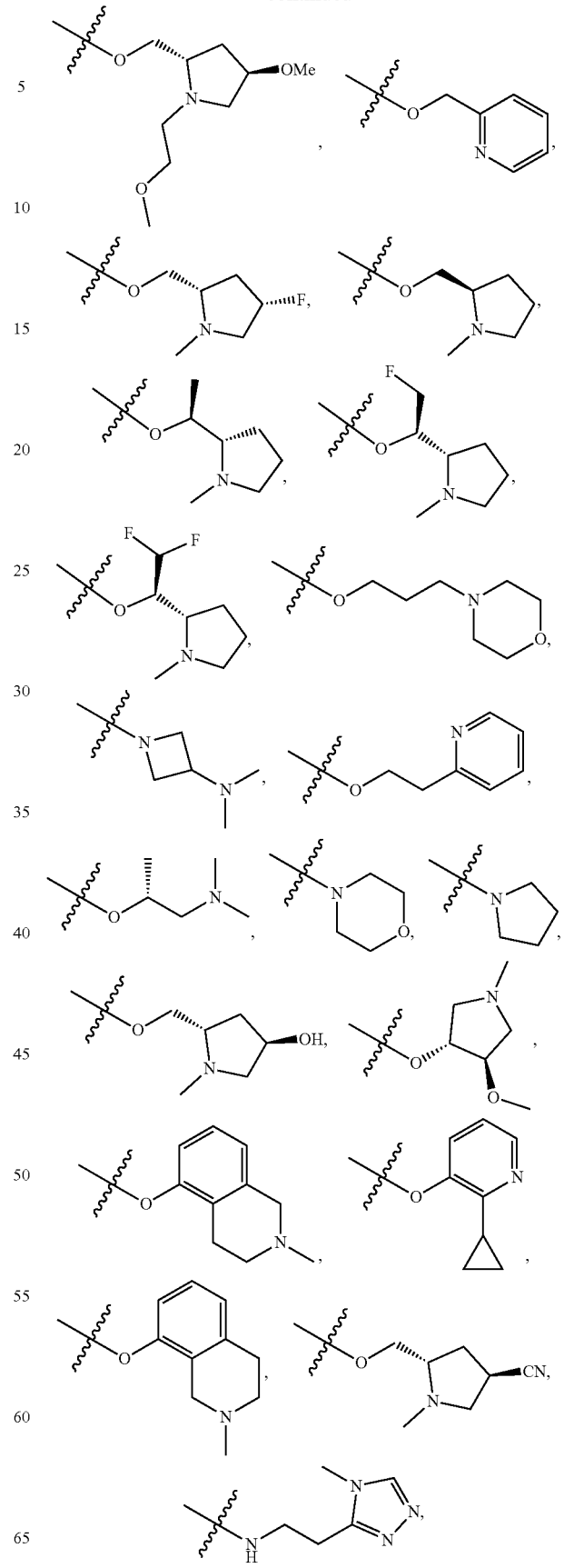

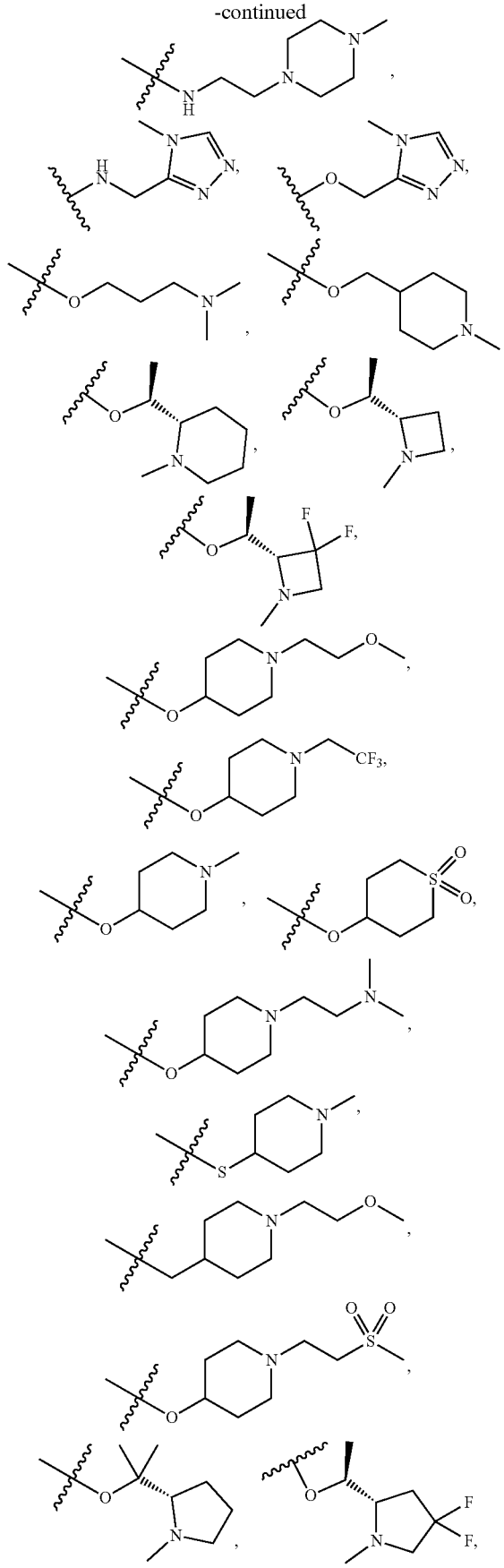
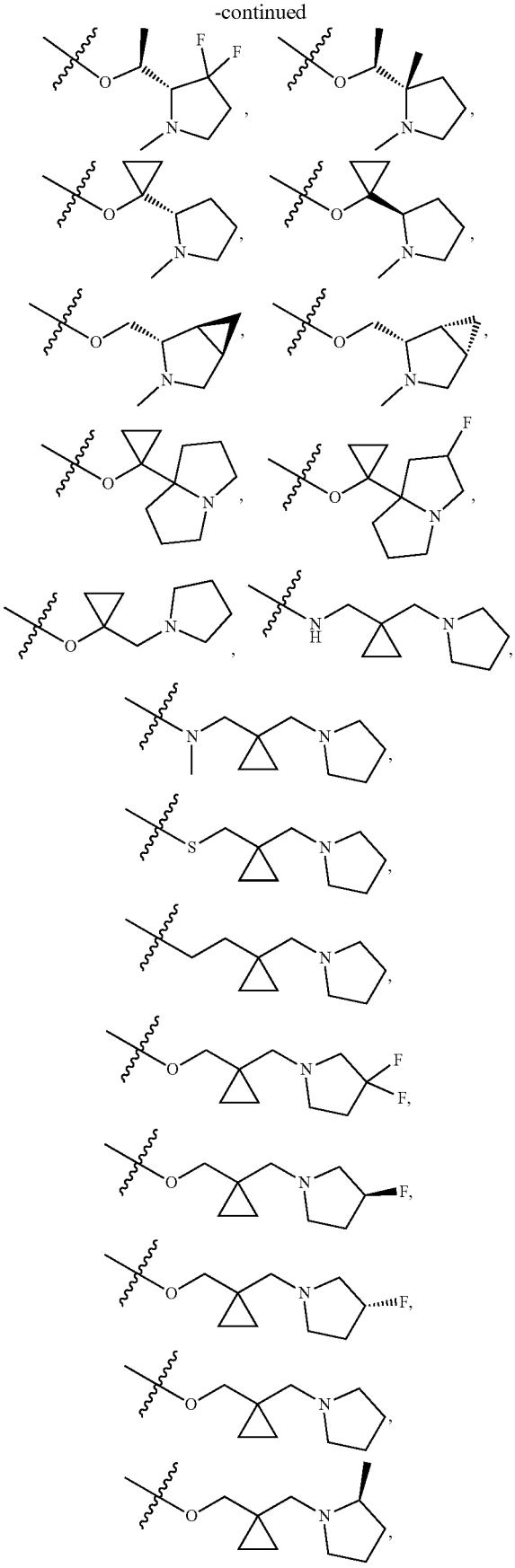

439
-continued
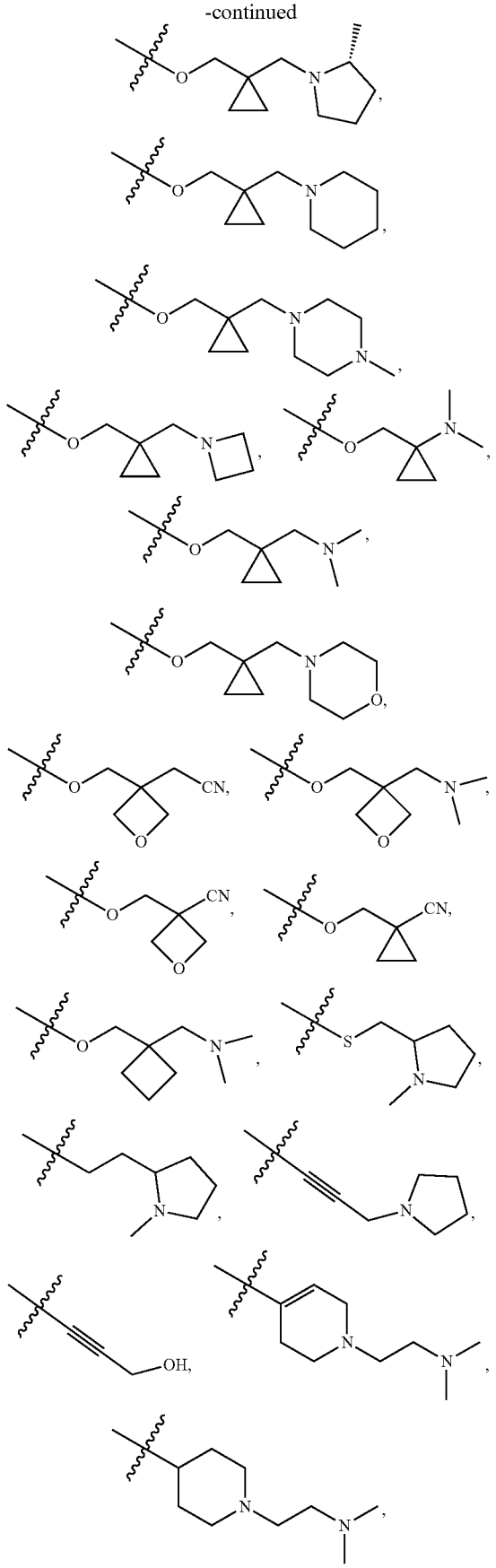
440
-continued
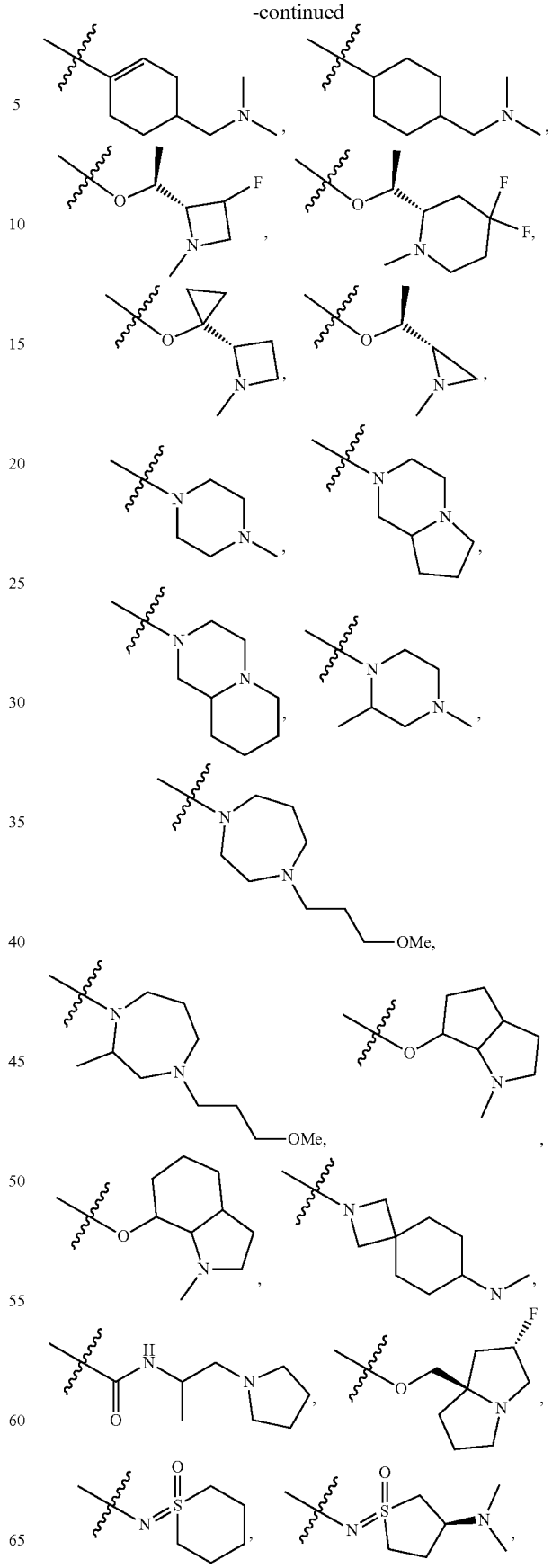

-continued

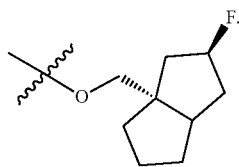 [SMILES: *OC[C@@]12CCCC1C[C@H](F)C2]
, and

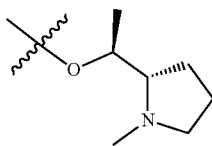
.

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, $R^2$ is independently

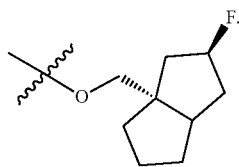 [SMILES: *OC[C@@]12CCCC1C[C@H](F)C2]

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, $R^2$ is independently

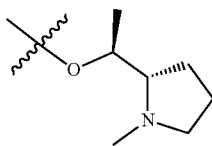

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, $Z^4$ is $Z^{4a}$. In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, $Z^4$ is $Z^{4a}Z^{4b}$. In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, each $R^{z4}$ is independently selected from hydrogen, halogen, —CN, $C_{1-6}$alkyl, $C_{2-6}$alkenyl, $C_{3-10}$cycloalkyl, $C_{2-9}$heterocycloalkyl, $C_{1-9}$heteroaryl, —$OR^{12}$, —$N(R^{12})(R^{13})$, —$N(R^{14})S(O)_2R^{15}$, —$C(O)R^{12}$, —$S(O)R^{15}$, —$OC(O)R^{15}$, —$C(O)N(R^{12})(R^{13})$, —$N(H)C(O)R^{12}$, —$S(O)_2^{15}$, and —$S(O)_2N(R^{12})(R^{13})$—, wherein $C_{1-6}$alkyl, $C_{2-6}$alkenyl, $C_{3-10}$cycloalkyl, $C_{2-9}$heterocycloalkyl, and $C_{1-9}$heteroaryl are optionally substituted with one, two, or three $R^{20z4}$; or two $R^{z4}$ bonded to the same carbon are joined to form a $C_{2-6}$alkenyl that is optionally substituted with one, two, or three $R^{20z4}$. In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, each $R^{z4}$ is independently selected from hydrogen, halogen, —CN, $C_{1-6}$alkyl, $C_{3-10}$cycloalkyl, $C_{2-9}$heterocycloalkyl, $C_{1-9}$heteroaryl, —$OR^{12}$, —$N(R^{12})(R^{13})$, —$N(R^{14})S(O)_2R^{15}$, and —$S(O)_2R^{15}$, wherein $C_{1-6}$alkyl, $C_{3-10}$cycloalkyl, $C_{2-9}$heterocycloalkyl, and $C_{1-9}$heteroaryl are optionally substituted with one, two, or three $R^{20z4}$; or two $R^{z4}$ bonded to the same carbon are joined to form a $C_{2-6}$alkenyl that is optionally substituted with one, two, or three $R^{20z4}$. In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, each $R^{z5}$ is independently selected from hydrogen, halogen, —CN, $C_{1-6}$alkyl, $C_{2-6}$alkenyl, $C_{3-10}$cycloalkyl, $C_{2-9}$heterocycloalkyl, $C_{1-9}$heteroaryl, —$OR^{12}$, —$N(R^{12})(R^{13})$, —$N(R^{14})S(O)_2R^{15}$, —$C(O)R^{12}$, —$S(O)R^{15}$, —$OC(O)R^{15}$, —$C(O)N(R^{12})(R^{13})$, —$N(H)C(O)R^{12}$, —$S(O)_2R^{15}$, and —$S(O)_2N(R^{12})(R^{13})$—, wherein $C_{1-6}$alkyl, $C_{2-6}$alkenyl, $C_{3-10}$cycloalkyl, $C_{2-9}$heterocycloalkyl, and $C_{1-9}$heteroaryl are optionally substituted with one, two, or three $R^{20z5}$; or two $R^{z5}$ bonded to the same carbon are joined to form a $C_{2-6}$alkenyl that is optionally substituted with one, two, or three $R^{20z5}$. In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, each $R^{z5}$ is independently selected from hydrogen, halogen, —CN, $C_{1-6}$alkyl, $C_{3-10}$cycloalkyl, $C_{2-9}$heterocycloalkyl, $C_{1-9}$heteroaryl, —$OR^{12}$, —$N(R^{12})(R^{13})$, —$N(R^{14})S(O)_2R^{15}$, and —$S(O)_2R^{15}$, wherein $C_{1-6}$alkyl, $C_{3-10}$cycloalkyl, $C_{2-9}$heterocycloalkyl, and $C_{1-9}$heteroaryl are optionally substituted with one, two, or three $R^{20z5}$; or two $R^{z5}$ bonded to the same carbon are joined to form a $C_{2-6}$alkenyl that is optionally substituted with one, two, or three $R^{20z5}$. In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, each $R^{z6}$ is independently selected from hydrogen, halogen, —CN, $C_{1-6}$alkyl, $C_{2-6}$alkenyl, $C_{3-10}$cycloalkyl, $C_{2-9}$heterocycloalkyl, $C_{1-9}$heteroaryl, —$OR^{12}$, —$N(R^{12})(R^{13})$, —$N(R^{14})S(O)_2R^{15}$, —$C(O)R^{12}$, —$S(O)R^{15}$, —$OC(O)R^{15}$, —$C(O)N(R^{12})(R^{13})$, —$N(H)C(O)R^{12}$, —$S(O)_2R^{15}$, and —$S(O)_2N(R^{12})(R^{13})$—, wherein $C_{1-6}$alkyl, $C_{2-6}$alkenyl, $C_{3-10}$cycloalkyl, $C_{2-9}$heterocycloalkyl, and $C_{1-9}$heteroaryl are optionally substituted with one, two, or three $R^{20z6}$; or two $R^{z6}$ bonded to the same carbon are joined to form a $C_{2-6}$alkenyl that is optionally substituted with one, two, or three $R^{20z6}$. In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, each $R^{z6}$ is independently selected from hydrogen, halogen, —CN, $C_{1-6}$alkyl, $C_{3-10}$cycloalkyl, $C_{2-9}$heterocycloalkyl, $C_{1-9}$heteroaryl, —$OR^{12}$, —$N(R^{12})(R^{13})$, —$N(R^{14})S(O)_2R^{15}$, and —$S(O)_2R^{15}$, wherein $C_{1-6}$alkyl, $C_{3-10}$cycloalkyl, $C_{2-9}$heterocycloalkyl, and $C_{1-9}$heteroaryl are optionally substituted with one, two, or three $R^{20z6}$; or two $R^{z6}$ bonded to the same carbon are joined to form a $C_{2-6}$alkenyl that is optionally substituted with one, two, or three $R^{20z6}$. In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, each $R^{20z}$ is independently selected from hydrogen, halogen, oxo, —CN, $C_{1-6}$alkyl, $C_{2-6}$alkenyl, $C_{3-10}$cycloalkyl, $C_{2-9}$heterocycloalkyl, $C_{1-9}$heteroaryl, —$OR^{12}$, —$N(R^{12})(R^{13})$, —$N(R^{14})S(O)_2R^{15}$, —$C(O)R^{12}$, —$S(O)R^{15}$, —$OC(O)R^{15}$, —$C(O)N(R^{12})(R^{13})$, —$N(H)C(O)R^{12}$, —$S(O)_2R^{15}$, and —$S(O)_2N(R^{12})(R^{13})$—, wherein $C_{1-6}$alkyl, $C_{2-6}$alkenyl, $C_{3-10}$cycloalkyl, $C_{2-9}$heterocycloalkyl, and $C_{1-9}$heteroaryl are optionally substituted with one, two, or three $R^{20zz}$; or two $R^{20z}$ bonded to the same carbon are joined to form a $C_{2-6}$alkenyl that is optionally substituted with one, two, or three $R^{20zz}$. In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, each $R^{20z}$ is independently selected from hydrogen, halogen, oxo, —CN, $C_{1-6}$alkyl, $C_{3-10}$cycloalkyl, $C_{2-9}$heterocycloalkyl, $C_{1-9}$heteroaryl, —$OR^{12}$, —$N(R^{12})(R^{13})$, —$N(R^{14})S(O)_2R^{15}$, and —$S(O)_2R^{15}$, wherein $C_{1-6}$alkyl, $C_{3-10}$cycloalkyl, $C_{2-9}$heterocycloalkyl, and $C_{1-9}$heteroaryl are optionally substituted with one, two, or three $R^{20zz}$; or two $R^{20z}$ bonded to the same carbon are joined to form a $C_{2-6}$alkenyl that is optionally substituted with one, two, or three $R^{20zz}$. In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, one or more $R^{z4}$, $R^{z5}$, $R^{z6}$, $R^{20z4}$, $R^{20z5}$, $R^{20z6}$, or $R^{20z}$ is independently selected from —$C(O)R^{12}$ and —$N(H)C(O)R^{12}$; and the $R^{12}$ of the one or more —$C(O)R^{12}$ or —$N(H)C(O)R^{12}$ is independently selected from

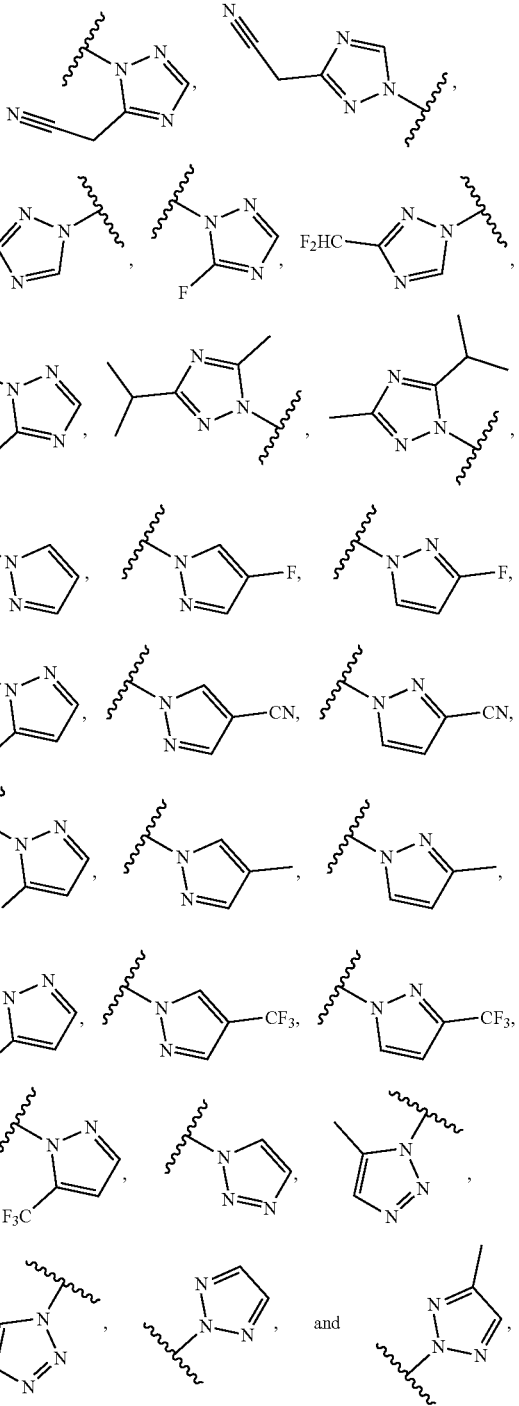

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, one or more $R^{z4}$, $R^{z5}$, $R^{z6}$, $R^{20z4}$, $R^{20z5}$, $R^{20z6}$, or $R^{20z}$ is independently selected from —$C(O)R^{12}$ and —$N(H)C(O)R^{12}$; and the $R^{12}$ of the one or more —$C(O)R^{12}$ or —$N(H)C(O)R^{12}$ is independently selected from

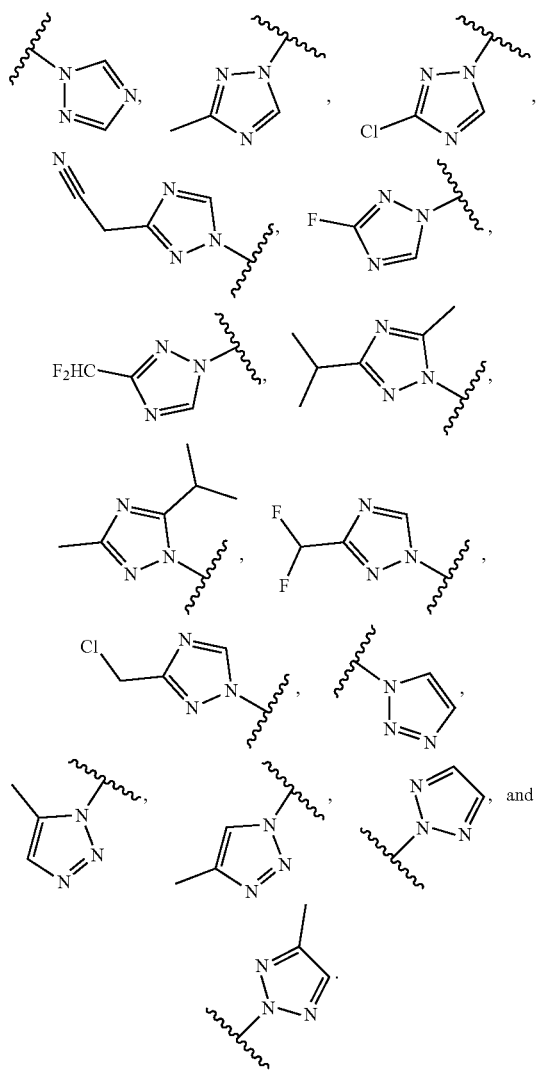

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, one or more $R^{z4}$, $R^{z5}$, $R^{z6}$, $R^{20z4}$, $R^{20z5}$, $R^{20z6}$, or $R^{20z}$ is independently selected from —C(O)R$^{12}$ and —N(H)C(O)R$^{12}$; and the R$^{12}$ of the one or more —C(O)R$^{12}$ or —N(H)C(O)R$^{12}$ is independently selected from

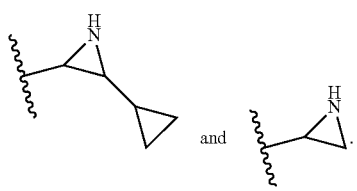

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, one or more $R^{z4}$, $R^{z5}$, $R^{z6}$, $R^{20z4}$, $R^{20z5}$, $R^{20z6}$, or $R^{20z}$ is independently selected from —C(O)R$^{12}$ and —N(H)C(O)R$^{12}$; and the R$^{12}$ of the one or more —C(O)R$^{12}$ or —N(H)C(O)R$^{12}$ is

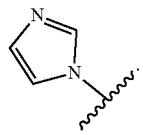

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, one or more $R^{z4}$, $R^{z5}$, $R^{z6}$, $R^{20z4}$, $R^{20z5}$, $R^{20z6}$, or $R^{20z}$ is independently selected from —C(O)R$^{12}$ and —N(H)C(O)R$^{12}$; and the R$^{12}$ of the one or more —C(O)R$^{12}$ or —N(H)C(O)R$^{12}$ is

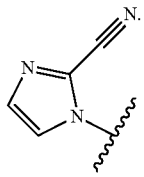 [SMILES: *n1ccnc1C#N]

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, one or more $R^{z4}$, $R^{z5}$, $R^{z6}$, $R^{20z4}$, $R^{20z5}$, $R^{20z6}$, or $R^{20z}$ is independently selected from —C(O)R$^{12}$ and —N(H)C(O)R$^{12}$; and the R$^{12}$ of the one or more —C(O)R$^{12}$ or —N(H)C(O)R$^{12}$ is

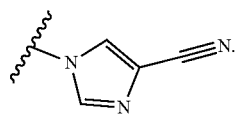 [SMILES: *n1cnc(C#N)c1]

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, one or more $R^{z4}$, $R^{z5}$, $R^{z6}$, $R^{20z4}$, $R^{20z5}$, $R^{20z6}$, or $R^{20z}$ is independently selected from —C(O)R$^{12}$ and —N(H)C(O)R$^{12}$; and the R$^{12}$ of the one or more —C(O)R$^{12}$ or —N(H)C(O)R$^{12}$ is

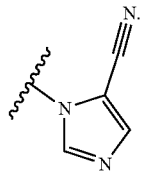

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, one or more $R^{z4}$, $R^{z5}$, $R^{z6}$, $R^{20z4}$, $R^{20z5}$, $R^{20z6}$, or $R^{20z}$ is independently selected from —C(O)$R^{12}$ and —N(H)C(O)$R^{12}$; and the $R^{12}$ of the one or more —C(O)$R^{12}$ or —N(H)C(O)$R^{12}$ is

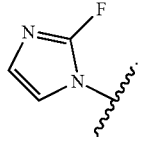

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, one or more $R^{z4}$, $R^{z5}$, $R^{z6}$, $R^{20z4}$, $R^{20z5}$, $R^{20z6}$, or $R^{20z}$ is independently selected from —C(O)$R^{12}$ and —N(H)C(O)$R^{12}$; and the $R^{12}$ of the one or more —C(O)$R^{12}$ or —N(H)C(O)$R^{12}$ is

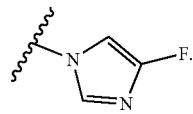 [SMILES: *n1cnc(F)c1]

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, one or more $R^{z4}$, $R^{z5}$, $R^{z6}$, $R^{20z4}$, $R^{20z5}$, $R^{20z6}$, or $R^{20z}$ is independently selected from —C(O)$R^{12}$ and —N(H)C(O)$R^{12}$; and the $R^{12}$ of the one or more —C(O)$R^{12}$ or —N(H)C(O)$R^{12}$ is

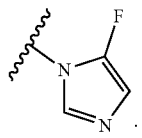 [SMILES: *n1cncc1F]

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, one or more $R^{z4}$, $R^{z5}$, $R^{z6}$, $R^{20z4}$, $R^{20z5}$, $R^{20z6}$, or $R^{20z}$ is independently selected from —C(O)$R^{12}$ and —N(H)C(O)$R^{12}$; and the $R^{12}$ of the one or more —C(O)$R^{12}$ or —N(H)C(O)$R^{12}$ is

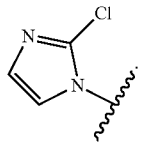

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, one or more $R^{z4}$, $R^{z5}$, $R^{z6}$, $R^{20z4}$, $R^{20z5}$, $R^{20z6}$, or $R^{20z}$ is independently selected from —C(O)$R^{12}$ and —N(H)C(O)$R^{12}$; and the $R^{12}$ of the —C(O)$R^{12}$ or —N(H)C(O)$R^{12}$ is

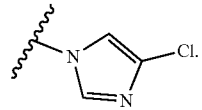 [SMILES: *n1cnc(Cl)c1]

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, one or more $R^{z4}$, $R^{z5}$, $R^{z6}$, $R^{20z4}$, $R^{20z5}$, $R^{20z6}$, or $R^{20z}$ is independently selected from —C(O)$R^{12}$ and —N(H)C(O)$R^{12}$; and the $R^{12}$ of the one or more —C(O)$R^{12}$ or —N(H)C(O)$R^{12}$ is

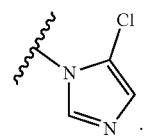 [SMILES: *n1cncc1Cl]

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, one or more $R^{z4}$, $R^{z5}$, $R^{z6}$, $R^{20z4}$, $R^{20z5}$, $R^{20z6}$, or $R^{20z}$ is independently selected from —C(O)$R^{12}$ and —N(H)C(O)$R^{12}$; and the $R^{12}$ of the one or more —C(O)$R^{12}$ or —N(H)C(O)$R^{12}$ is

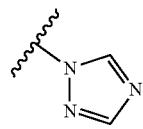

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, one or more $R^{z4}$, $R^{z5}$, $R^{z6}$, $R^{20z4}$, $R^{20z5}$, $R^{20z6}$, or $R^{20z}$ is independently selected from —C(O)$R^{12}$ and —N(H)C(O)$R^{12}$; and the $R^{12}$ of the one or more —C(O)$R^{12}$ or —N(H)C(O)$R^{12}$ is

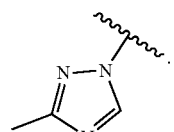

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, one or more $R^{z4}$, $R^{z5}$, $R^{z6}$, $R^{20z4}$, $R^{20z5}$, $R^{20z6}$, or $R^{20z}$ or is independently selected from —C(O)$R^{12}$ and —N(H)C(O)$R^{12}$; and the $R^{12}$ of the one or more —C(O)$R^{12}$ or —N(H)C(O)$R^{12}$ is

449

[Structure: triazole ring with N-N and N, attached via wavy bond]

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, one or more $R^{z4}$, $R^{z5}$, $R^{z6}$, $R^{20z4}$, $R^{20z5}$, $R^{20z6}$, or $R^{20z}$ is independently selected from —C(O)R$^{12}$ and —N(H)C(O)R$^{12}$; and the R$^{12}$ of the one or more —C(O)R$^{12}$ or —N(H)C(O)R$^{12}$ is

[Structure: triazole with Cl substituent]

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, one or more $R^{z4}$, $R^{z5}$, $R^{z6}$, $R^{20z4}$, $R^{20z5}$, $R^{20z6}$, or $R^{20z}$ is independently selected from —C(O)R$^{12}$ and —N(H)C(O)R$^{12}$; and the R$^{12}$ of the one or more —C(O)R$^{12}$ or —N(H)C(O)R$^{12}$ is

[Structure: triazole with Cl substituent]

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, one or more $R^{z4}$, $R^{z5}$, $R^{z6}$, $R^{20z4}$, $R^{20z5}$, $R^{20z6}$, or $R^{20z}$ is independently selected from —C(O)R$^{12}$ and —N(H)C(O)R$^{12}$; and the R$^{12}$ of the one or more —C(O)R$^{12}$ or —N(H)C(O)R$^{12}$ is

[Structure: triazole with CH2CN substituent]

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, one or more $R^{z4}$, $R^{z5}$, $R^{z6}$, $R^{20z4}$, $R^{20z5}$, $R^{20z6}$, or $R^{20z}$ is independently selected from —C(O)R$^{12}$ and —N(H)C(O)R$^{12}$; and the R$^{12}$ of the —C(O)R$^{12}$ or —N(H)C(O)R$^{12}$ is

450

[Structure: triazole with CH2CN substituent]

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, one or more $R^{z4}$, $R^{z5}$, $R^{z6}$, $R^{20z4}$, $R^{20z5}$, $R^{20z6}$, or $R^{20z}$ is independently selected from —C(O)R$^{12}$ and —N(H)C(O)R$^{12}$; and the R$^{12}$ of the one or more —C(O)R$^{12}$ or —N(H)C(O)R$^{12}$ is

[Structure: triazole with F substituent]

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, one or more $R^{z4}$, $R^{z5}$, $R^{z6}$, $R^{20z4}$, $R^{20z5}$, $R^{20z6}$, or $R^{20z}$ is independently selected from —C(O)R$^{12}$ and —N(H)C(O)R$^{12}$; and the R$^{12}$ of the —C(O)R$^{12}$ or —N(H)C(O)R$^{12}$ is

[Structure: triazole with F substituent]

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, one or more $R^{z4}$, $R^{z5}$, $R^{z6}$, $R^{20z4}$, $R^{20z5}$, $R^{20z6}$, or $R^{20z}$ is independently selected from —C(O)R$^{12}$ and —N(H)C(O)R$^{12}$; and the R$^{12}$ of the one or more —C(O)R$^{12}$ or —N(H)C(O)R$^{12}$ is

[Structure: triazole with F2HC substituent]

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, one or more $R^{z4}$, $R^{z5}$, $R^{z6}$, $R^{20z4}$, $R^{20z5}$, $R^{20z6}$, or $R^{20z}$ is independently selected from —C(O)R$^{12}$ and —N(H)C(O)R$^{12}$; and the R$^{12}$ of the one or more —C(O)R$^{12}$ or —N(H)C(O)R$^{12}$ is

451

[Structure: triazole with F₂HC substituent]

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, one or more $R^{z4}$, $R^{z5}$, $R^{z6}$, $R^{20z4}$, $R^{20z5}$, $R^{20z6}$, or $R^{20z}$ is independently selected from —C(O)R$^{12}$ and —N(H)C(O)R$^{12}$; and the R$^{12}$ of the —C(O)R$^{12}$ or —N(H)C(O)R$^{12}$ is

[Structure: triazole with isopropyl substituent]

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, one or more $R^{z4}$, $R^{z5}$, $R^{z6}$, $R^{20z4}$, $R^{20z5}$, $R^{20z6}$, or $R^{20z}$ is independently selected from —C(O)R$^{12}$ and —N(H)C(O)R$^{12}$; and the R$^{12}$ of the one or more —C(O)R$^{12}$ or —N(H)C(O)R$^{12}$ is

[Structure: triazole with isopropyl and methyl substituents]

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, one or more $R^{z4}$, $R^{z5}$, $R^{z6}$, $R^{20z4}$, $R^{20z5}$, $R^{20z6}$, or $R^{20z}$ is independently selected from —C(O)R$^{12}$ and —N(H)C(O)R$^{12}$; and the R$^{12}$ of the one or more —C(O)R$^{12}$ or —N(H)C(O)R$^{12}$ is

[Structure: pyrazole]

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, one or more $R^{z4}$, $R^{z5}$, $R^{z6}$, $R^{20z4}$, $R^{20z5}$, $R^{20z6}$, or $R^{20z}$ is independently selected from —C(O)R$^{12}$ and —N(H)C(O)R$^{12}$; and the R$^{12}$ of the one or more —C(O)R$^{12}$ or —N(H)C(O)R$^{12}$ is

452

[Structure: pyrazole with F at 4-position]

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, one or more $R^{z4}$, $R^{z5}$, $R^{z6}$, $R^{20z4}$, $R^{20z5}$, $R^{20z6}$, or $R^{20z}$ is independently selected from —C(O)R$^{12}$ and —N(H)C(O)R$^{12}$; and the R$^{12}$ of the one or more —C(O)R$^{12}$ or —N(H)C(O)R$^{12}$ is

[Structure: pyrazole with F at 3-position]

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, one or more $R^{z4}$, $R^{z5}$, $R^{z6}$, $R^{20z4}$, $R^{20z5}$, $R^{20z6}$, or $R^{20z}$ is independently selected from —C(O)R$^{12}$ and —N(H)C(O)R$^{12}$; and the R$^{12}$ of the —C(O)R$^{12}$ or —N(H)C(O)R$^{12}$ is

[Structure: pyrazole with F at 5-position]

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, one or more $R^{z4}$, $R^{z5}$, $R^{z6}$, $R^{20z4}$, $R^{20z5}$, $R^{20z6}$, or $R^{20z}$ is independently selected from —C(O)R$^{12}$ and —N(H)C(O)R$^{12}$; and the R$^{12}$ of the one or more —C(O)R$^{12}$ or —N(H)C(O)R$^{12}$ is

[Structure: pyrazole with CN substituent]

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, one or more $R^{z4}$, $R^{z5}$, $R^{z6}$, $R^{20z4}$, $R^{20z5}$, $R^{20z6}$, or $R^{20z}$ is independently selected from —C(O)R$^{12}$ and —N(H)C(O)R$^{12}$; and the R$^{12}$ of the one or more —C(O)R$^{12}$ or —N(H)C(O)R$^{12}$ is

[Structure: pyrazole linked via N, with CN substituent]

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, one or more $R^{z4}$, $R^{z5}$, $R^{z6}$, $R^{20z4}$, $R^{20z5}$, $R^{20z6}$, or $R^{20z}$ is independently selected from —C(O)$R^{12}$ and —N(H)C(O)$R^{12}$; and the $R^{12}$ of the one or more —C(O)$R^{12}$ or —N(H)C(O)$R^{12}$ is

[Structure: pyrazole with NC substituent]

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, one or more $R^{z4}$, $R^{z5}$, $R^{z6}$, $R^{20z4}$, $R^{20z5}$, $R^{20z6}$, or $R^{20z}$ is independently selected from —C(O)$R^{12}$ and —N(H)C(O)$R^{12}$; and the $R^{12}$ of the one or more —C(O)$R^{12}$ or —N(H)C(O)$R^{12}$ is

[Structure: pyrazole]

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, one or more $R^{z4}$, $R^{z5}$, $R^{z6}$, $R^{20z4}$, $R^{20z5}$, $R^{20z6}$, or $R^{20z}$ is independently selected from —C(O)$R^{12}$ and —N(H)C(O)$R^{12}$; and the $R^{12}$ of the one or more —C(O)$R^{12}$ or —N(H)C(O)$R^{12}$ is

[Structure: pyrazole with methyl substituent]

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, one or more $R^{z4}$, $R^{z5}$, $R^{z6}$, $R^{20z4}$, $R^{20z5}$, $R^{20z6}$, or $R^{20z}$ is independently selected from —C(O)$R^{12}$ and —N(H)C(O)$R^{12}$; and the $R^{12}$ of the one or more —C(O)$R^{12}$ or —N(H)C(O)$R^{12}$ is

[Structure: pyrazole with CF3 substituent]

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, one or more $R^{z4}$, $R^{z5}$, $R^{z6}$, $R^{20z4}$, $R^{20z5}$, $R^{20z6}$, or $R^{20z}$ is independently selected from —C(O)$R^{12}$ and —N(H)C(O)$R^{12}$; and the $R^{12}$ 2 of the one or more —C(O)$R^{12}$ or —N(H)C(O)$R^{12}$ is

[Structure: pyrazole with CF3 substituent]

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, one or more $R^{z4}$, $R^{z5}$, $R^{z6}$, $R^{20z4}$, $R^{20z5}$, $R^{20z6}$, or $R^{20z}$ is independently selected from —C(O)$R^{12}$ and —N(H)C(O)$R^{12}$; and the $R^{12}$ of the one or more —C(O)$R^{12}$ or —N(H)C(O)$R^{12}$ is

[Structure: pyrazole with methyl substituent]

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, one or more $R^{z4}$, $R^{z5}$, $R^{z6}$, $R^{20z4}$, $R^{20z5}$, $R^{20z6}$, or $R^{20z}$ is independently selected from —C(O)$R^{12}$ and —N(H)C(O)$R^{12}$; and the $R^{12}$ of the one or more —C(O)$R^{12}$ or —N(H)C(O)$R^{12}$ is

[Structure: pyrazole with F3C substituent]

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, one or more $R^{z4}$, $R^{z5}$, $R^{z6}$, $R^{20z4}$, $R^{20z5}$, $R^{20z6}$, or $R^{20z}$ is independently selected from —C(O)$R^{12}$ and —N(H)C(O)$R^{12}$; and the $R^{12}$ of the one or more —C(O)$R^{12}$ or —N(H)C(O)$R^{12}$ is

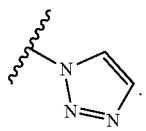

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, one or more $R^{z4}$, $R^{z5}$, $R^{z6}$, $R^{20z4}$, $R^{20z5}$, $R^{20z6}$, or $R^{20z}$ is independently selected from —C(O)$R^{12}$ and —N(H)C(O)$R^{12}$; and the $R^{12}$ of the one or more —C(O)$R^{12}$ or —N(H)C(O)$R^{12}$ is

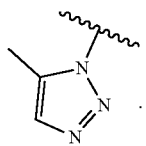

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, one or more $R^{z4}$, $R^{z5}$, $R^{z6}$, $R^{20z4}$, $R^{20z5}$, $R^{20z6}$, or $R^{20z}$ is independently selected from —C(O)$R^{12}$ and —N(H)C(O)$R^{12}$; and the $R^{12}$ of the one or more —C(O)$R^{12}$ or —N(H)C(O)$R^{12}$ is

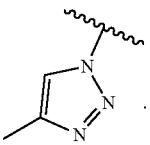 [SMILES: *n1cc(C)nn1]

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, one or more $R^{z4}$, $R^{z5}$, $R^{z6}$, $R^{20z4}$, $R^{20z5}$, $R^{20z6}$, or $R^{20z}$ is independently selected from —C(O)$R^{12}$ and —N(H)C(O)$R^{12}$; and the $R^{12}$ of the one or more —C(O)$R^{12}$ or —N(H)C(O)$R^{12}$ is

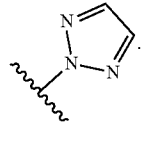 [SMILES: *n1nccn1]

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, one or more $R^{z4}$, $R^{z5}$, $R^{z6}$, $R^{20z4}$, $R^{20z5}$, $R^{20z6}$, or $R^{20z}$ is independently selected from —C(O)$R^{12}$ and —N(H)C(O)$R^{12}$; and the $R^{12}$ of the one or more —C(O)$R^{12}$ or —N(H)C(O)$R^{12}$ is

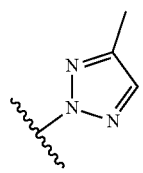

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, one or more $R^{z4}$, $R^{z5}$, $R^{z6}$, $R^{20z4}$, $R^{20z5}$, $R^{20z6}$, or $R^{20z}$ is independently selected from —C(O)$R^{12}$ and —N(H)C(O)$R^{12}$; and the $R^{12}$ of the one or more —C(O)$R^{12}$ or —N(H)C(O)$R^{12}$ is

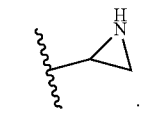 [SMILES: *C1CN1]

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, one or more $R^{z4}$, $R^{z5}$, $R^{z6}$, $R^{20z4}$, $R^{20z5}$, $R^{20z6}$, or $R^{20z}$ is independently selected from —C(O)$R^{12}$ and —N(H)C(O)$R^{12}$; and the $R^{12}$ of the one or more —C(O)$R^{12}$ or —N(H)C(O)$R^{12}$ is

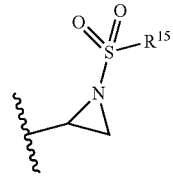

and the $R^{z5}$ of the preceding formula is methyl or ethyl.

In some embodiments, the present disclosure provides a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof:

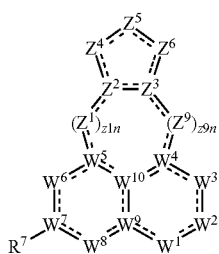
(A)

wherein:
$W^1$ is N, $W^2$ is $C(R^2)$, $W^3$ is N, $W^4$ is C, $W^5$ is C, $W^6$ is $C(R^6)$, $W^7$ is C, $W^8$ is $C(R^8)$, $W^9$ is C, and $W^{10}$ is C;
$W^1$ is N, $W^2$ is $C(R^2)$, $W^3$ is N, $W^4$ is C, $W^5$ is C, $W^6$ is N, $W^7$ is C, $W^8$ is $C(R^8)$, $W^9$ is C, $W^{10}$ is C;
$R^2$ is selected from

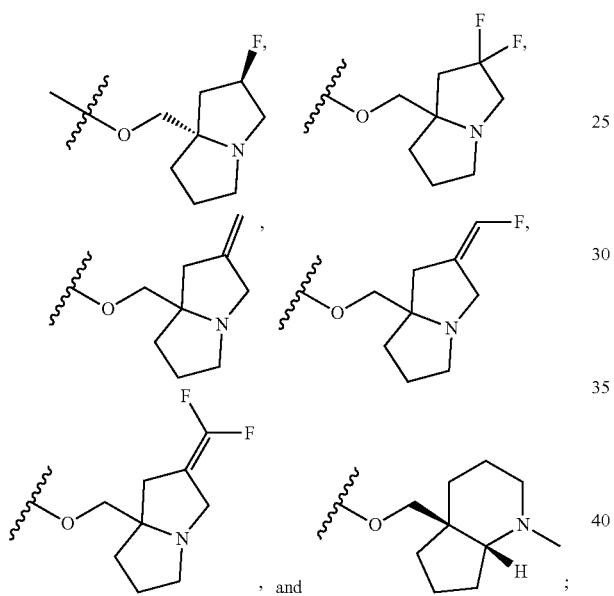

, and ;

$R^6$ is selected from hydrogen, halogen, and $C_{1-6}$haloalkyl;
$R^7$ is $-L^7-R^{17}$;
$L^7$ is a bond;
$R^{17}$ is selected from selected from

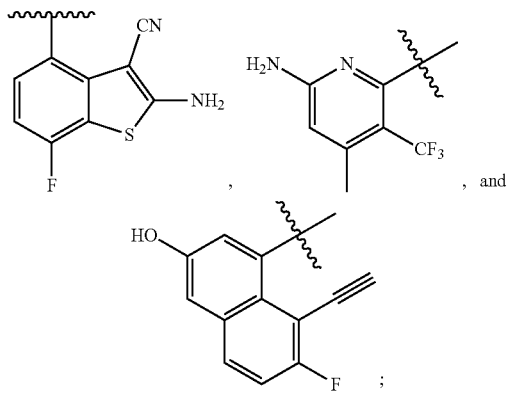

, and

;

$R^8$ is halogen;
each $Z^1$ is independently $C(R^{z1})_2$ or O;

z1n is 1, 2, or 3;
each $R^{z1}$ is independently selected from hydrogen, $C_{1-6}$alkyl, wherein $C_{1-6}$alkyl is optionally substituted with one, two, or three substituents independently selected from halogen and —OH;
$Z^2$ is CH;
$Z^3$ is CH or N;
$Z^4$ is a bond, $Z^{4a}$, $Z^{4a}Z^{4b}$, or $Z^{4a}Z^{4b}Z^{4c}$; wherein $Z^{4a}$ is directly bonded to $Z^2$; and wherein if $Z^4$ is a bond then $Z^2$ is directly bonded to $Z^5$;
$Z^{4a}$, $Z^{4b}$, and $Z^{4c}$ are independently $N(R^{z4})$ or $C(R^{z4})_2$;
provided that if z9n is 0 and $Z^4$ is $Z^{4a}Z^{4b}$; then (1) $Z^4$b is $C(R^{z4})_2$, or (2) $Z^{4b}$ is $N(R^{z4})$ and $Z^3$ is CH;.
each $R^{z4}$ is independently selected from hydrogen, halogen, —CN, $C_{1-6}$alkyl, —OH, —NH($C_{1-6}$alkyl), —C(O)H, —C(O)($C_{1-6}$alkyl), —C(O)$R^{12}$, and —N(H)C(O)$R^{12}$, wherein $C_{1-6}$alkyl, is optionally substituted with one, two, or three substituents independently selected from halogen, —OH, and —CN; wherein the $R^{12}$ is selected from

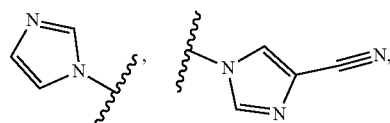

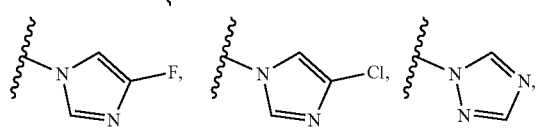

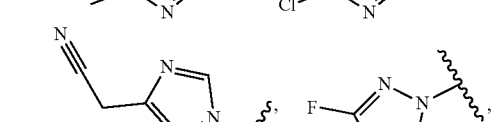

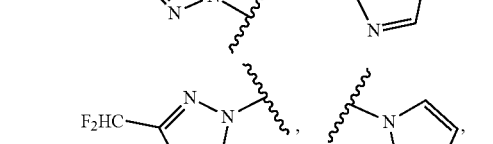

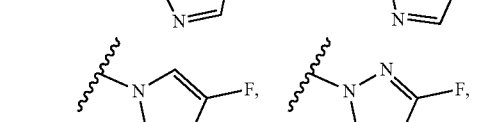

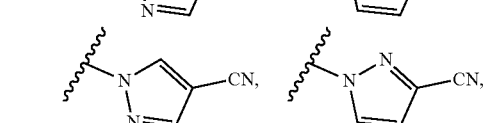

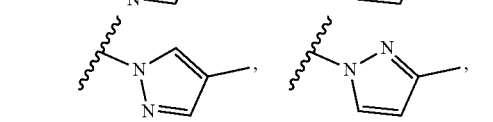

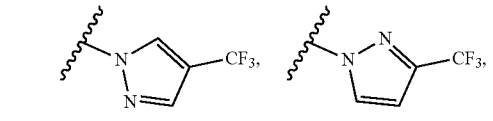

-continued

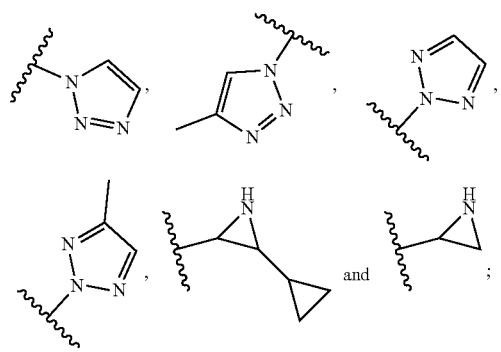

$Z^5$ is $N(R^{z5})$ or $C(R^{z5})_2$;

each $R^{z5}$ is independently selected from hydrogen, halogen, —CN, $C_{1-6}$alkyl, —OH, —O($C_{1-6}$alkyl), —NH$_2$, —NH($C_{1-6}$alkyl), —C(O)H, —C(O)($C_{1-6}$alkyl),), —C(O)R$^{12}$, and —N(H)C(O)R$^{12}$, wherein $C_{1-6}$alkyl is optionally substituted with one, two, or three substituents independently selected from halogen, —OH, —O($C_{1-6}$alkyl), —O($C_{1-6}$haloalkyl), and —CN; wherein the R$^{12}$ is selected from

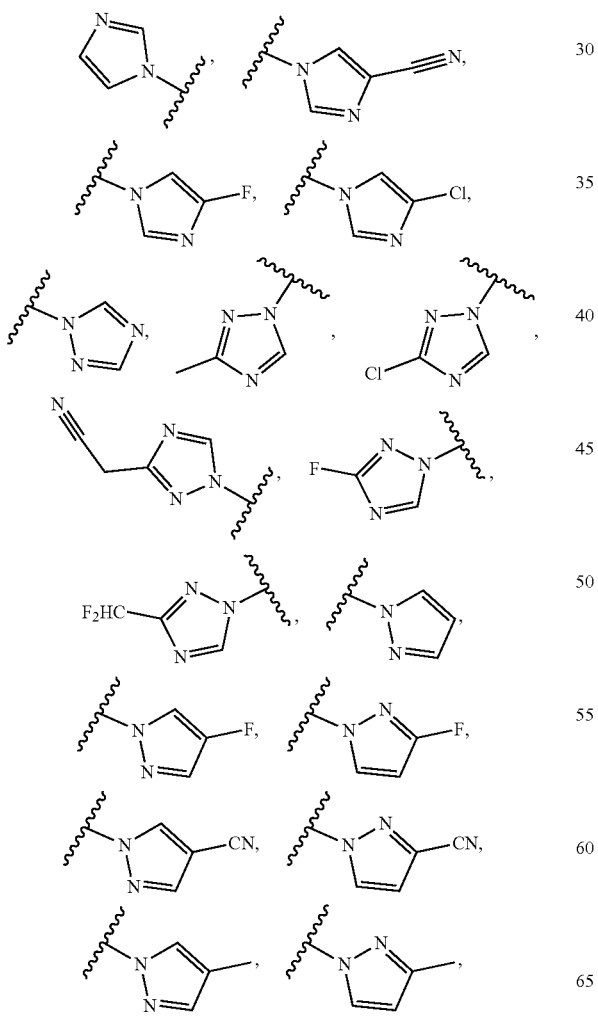

-continued

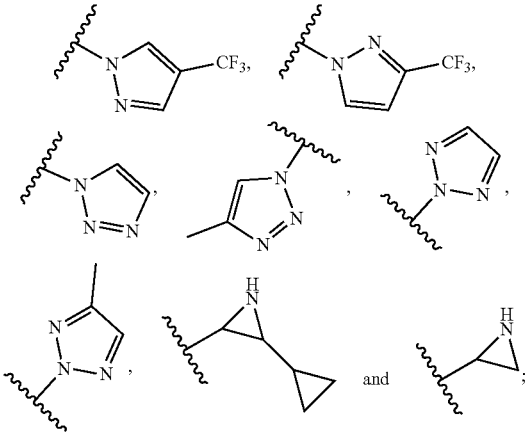

$Z^6$ is $C(R^{z6})_2$;

each $R^{z6}$ is independently selected from hydrogen, $C_{1-6}$alkyl, —C(O)R$^{12}$, and —N(H)C(O)R$^{12}$; wherein $C_{1-6}$alkyl is optionally substituted with one, two, or three substituents independently selected from halogen, —OH, —O($C_{1-6}$alkyl), and —O($C_{1-6}$haloalkyl); wherein the R$^{12}$ is selected from

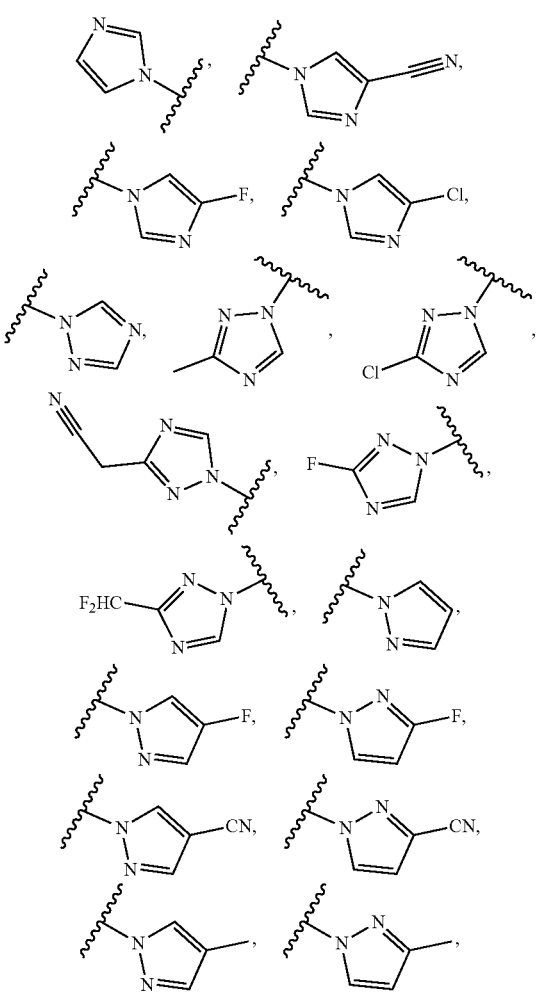

-continued

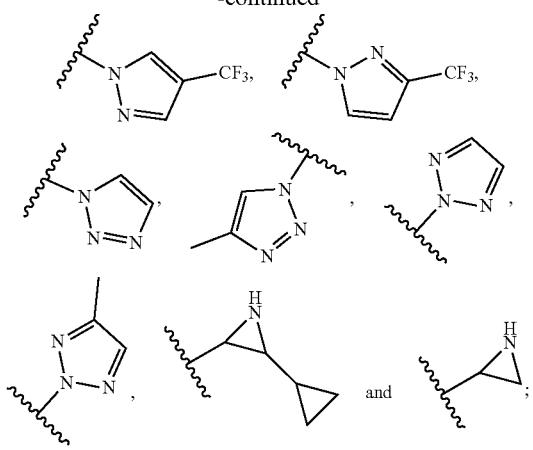

each $Z^9$ is independently $N(R^{z9})$;

z9n is 0 or 1; wherein if z9n is 0 then $Z^3$ is directly bonded to $W^4$;

each $R^{z9}$ is independently selected from hydrogen, $C_{1-6}$alkyl, and $C_{3-10}$cycloalkyl, wherein $C_{1-6}$alkyl, is optionally substituted with one, two, or three substituents independently selected from halogen, —CN, —O($C_{1-6}$alkyl), —O($C_{1-6}$haloalkyl), $C_{3-4}$cycloalkyl, 3-4 membered heterocycloalkyl, —NH($C_{1-6}$alkyl), and —N($C_{1-6}$alkyl)$_2$;

wherein the sum of z1n and z9n is 2 or 3; and one $R^{z4}$, $R^{z5}$, or $R^{z6}$, is independently selected from —C(O)R$^{12}$, and —N(H)C(O)R$^{12}$, wherein the R$^{12}$ is selected from -continued

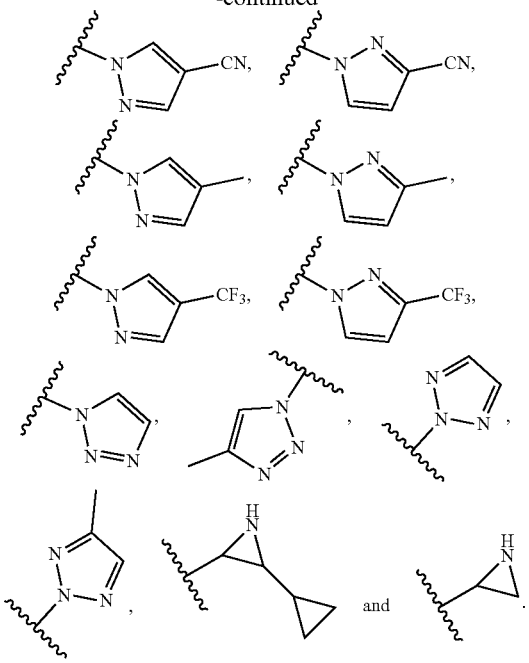

In embodiments of Formula (A) in the paragraph immediately above, $R^2$ is

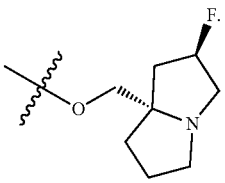 [SMILES: *OC[C@@]12CCCN1C[C@H](F)C2]

In embodiments of Formula (A) in the paragraph immediately above, $R^{17}$ is

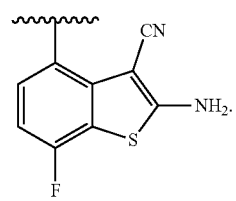 [SMILES: *c1ccc(F)c2sc(N)c(C#N)c12]

In embodiments of Formula (A) in the paragraph immediately above, $R^{17}$ is

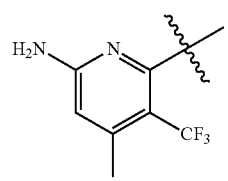

In embodiments of Formula (A) in the paragraph immediately above, $R^{17}$ is

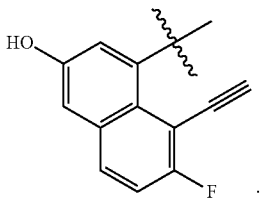 [SMILES: *c1cc(O)cc2ccc(F)c(C#C)c12]

In some embodiments, the present disclosure provides a compound of Formula (A), or a pharmaceutically acceptable salt or solvate thereof:

(A)

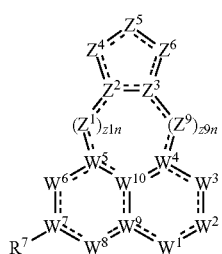

wherein:
$W^1$ is N, $W^2$ is $C(R^2)$, $W^3$ is N, $W^4$ is C, $W^5$ is C, $W^6$ is $C(R^6)$, $W^7$ is C, $W^8$ is $C(R^8)$, $W^9$ is C, and $W^{10}$ is C; $R^2$ is

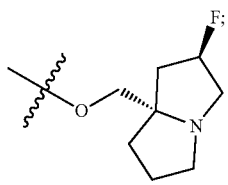 [SMILES: *OC[C@@]12CCCN1C[C@H](F)C2]

$R^6$ is selected from Cl and —$CF_3$; $R^7$ is -$L^7$—$R^{17}$; $L^7$ is a bond; $R^{17}$ is

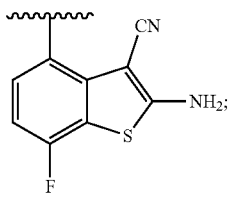 [SMILES: *c1ccc(F)c2sc(N)c(C#N)c12]

$R^8$ is F;
each $Z^1$ is independently $C(R^{z1})_2$ or O;
z1n is 1, 2, or 3;
each $R^{z1}$ is independently selected from hydrogen, $C_{1-3}$alkyl, wherein $C_{1-3}$alkyl is optionally substituted with one, two, or three substituents independently selected from halogen and —OH;
$Z^2$ is CH;
$Z^3$ is CH or N;
$Z^4$ is a bond, $Z^{4a}$, $Z^{4a}Z^{4b}$, or $Z^{4a}Z^{4b}Z^{4c}$; wherein $Z^{4a}$ is directly bonded to $Z^2$; and wherein if $Z^4$ is a bond then $Z^2$ is directly bonded to $Z^5$;
$Z^{4a}$, $Z^{4b}$, and $Z^{4c}$ are independently $N(R^{z4})$ or $C(R^{z4})_2$;

provided that if z9n is 0 and $Z^4$ is $Z^{4a}Z^{4b}$; then $Z^{4b}$ is $C(R^{z4})_2$;.

each $R^{z4}$ is independently selected from hydrogen, halogen, —CN, $C_{1-6}$alkyl, —OH, —NH($C_{1-6}$alkyl), —C(O)H, —C(O)($C_{1-6}$alkyl), —C(O)$R^{12}$, and —N(H)C(O)$R^{12}$, wherein $C_{1-6}$alkyl, is optionally substituted with one, two, or three substituents independently selected from halogen, —OH, and —CN; wherein the $R^{12}$ is selected from

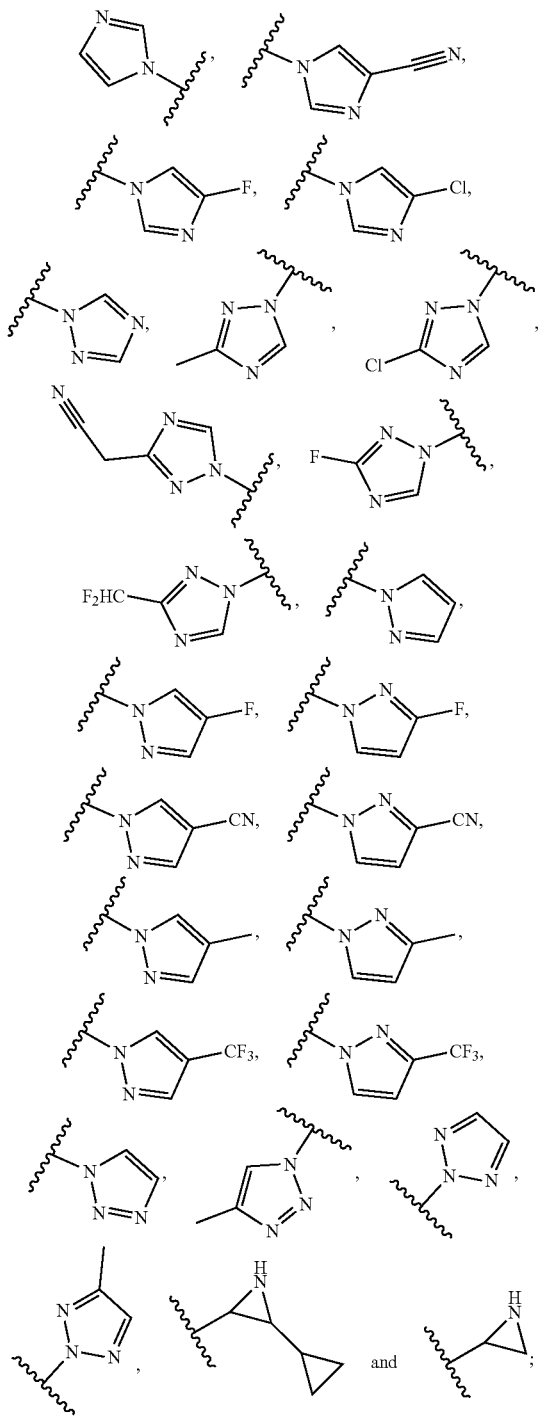

$Z^5$ is $N(R^{z5})$ or $C(R^{z5})_2$;
each $R^{z5}$ is independently selected from hydrogen, halogen, —CN, $C_{1-6}$alkyl, —OH, —O($C_{1-6}$alkyl), —$NH_2$, —NH(C$_{1-6}$alkyl), —C(O)H, —C(O)R$^{12}$, and —N(H)C(O)R$^{12}$, wherein C$_{1-6}$alkyl is optionally substituted with one, two, or three substituents independently selected from halogen, —OH, —O(C$_{1-6}$alkyl), —O(C$_{1-6}$haloalkyl), and —CN; wherein the R$^{12}$ is selected from

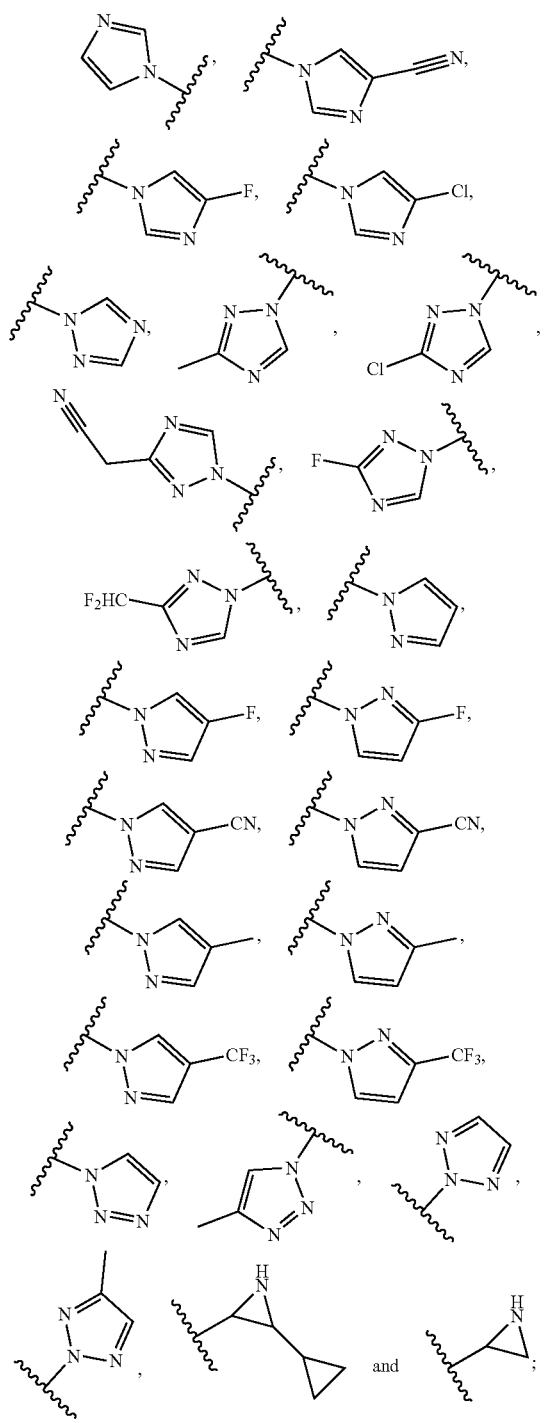

substituents independently selected from halogen, —OH, —O(C$_{1-6}$alkyl), and —O(C$_{1-3}$haloalkyl); wherein the R$^{12}$ is selected from

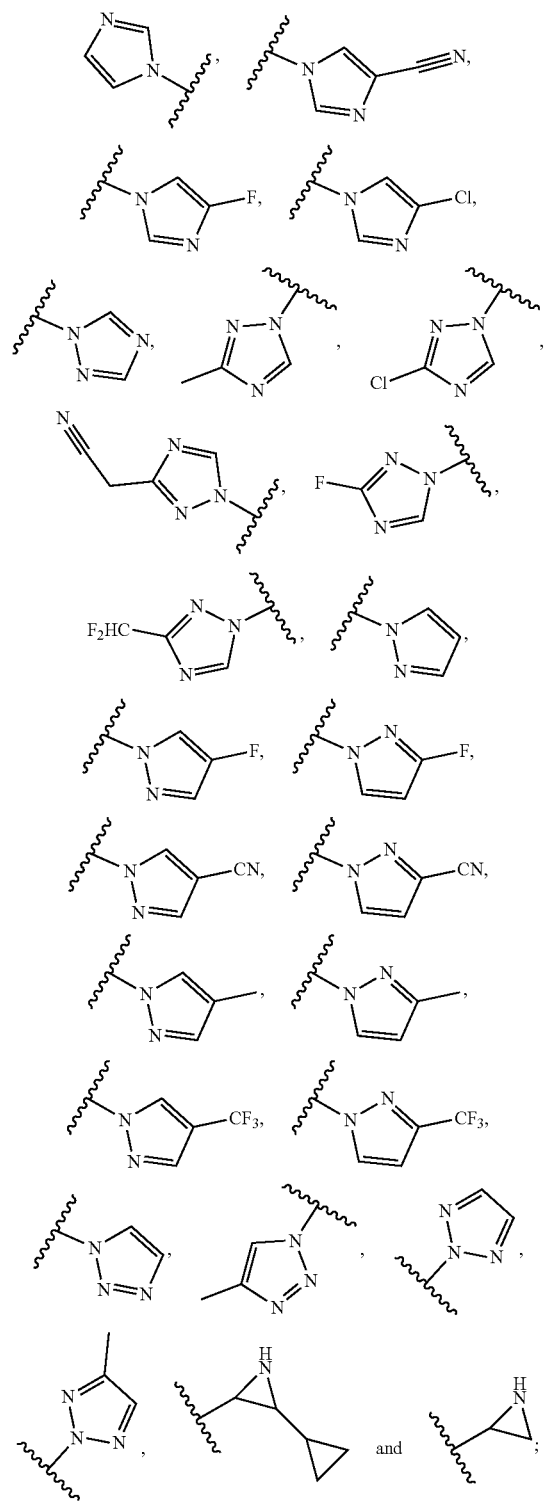

Z$^6$ is C(R$^{z6}$)$_2$;

each R$^{z6}$ is independently selected from hydrogen, C$_{1-6}$alkyl, —C(O)R$^{12}$, and —N(H)C(O)R$^{12}$; wherein C$_{1-6}$alkyl is optionally substituted with one, two, or three each Z$^9$ is independently N(R$^{z9}$);

z9n is 0 or 1; wherein if z9n is 0 then Z$^3$ is directly bonded to W$^4$;

each $R^{z9}$ is independently selected from hydrogen, $C_{1-6}$alkyl, and $C_{3-10}$cycloalkyl, wherein $C_{1-6}$alkyl, is optionally substituted with one, two, or three substituents independently selected from halogen, —CN, —O($C_{1-6}$alkyl), —O($C_{1-6}$haloalkyl), $C_{3-4}$cycloalkyl, 3-4 membered heterocycloalkyl, —NH($C_{1-6}$alkyl), and —N($C_{1-6}$alkyl)$_2$; and wherein the sum of z1n and z9n is 2 or 3; and one $R^{z4}$, $R^{z5}$, or $R^{z6}$, is independently selected from —C(O)$R^{12}$, and —N(H)C(O)$R^{12}$, wherein the $R^{12}$ is selected from

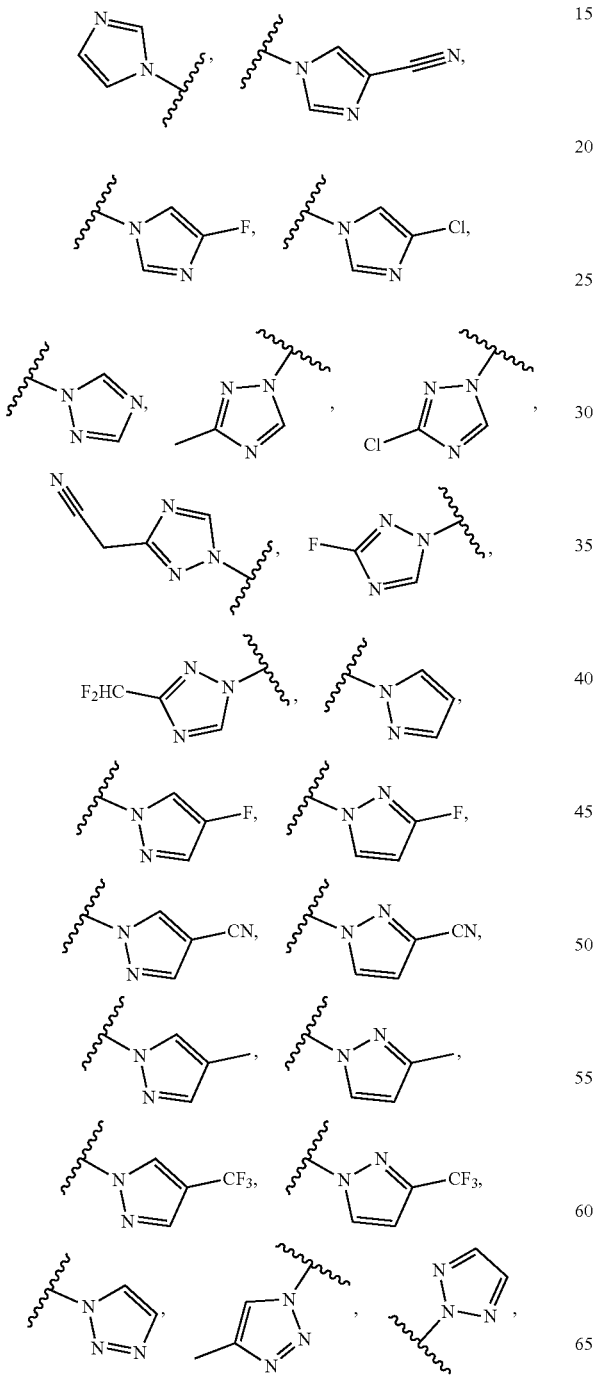

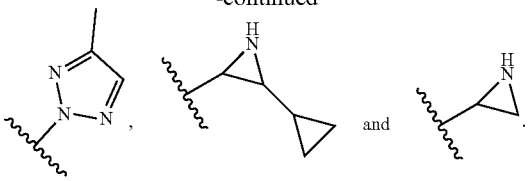

In some embodiments, the present disclosure provides a compound of Formula (A), or a pharmaceutically acceptable salt or solvate thereof:

(A)

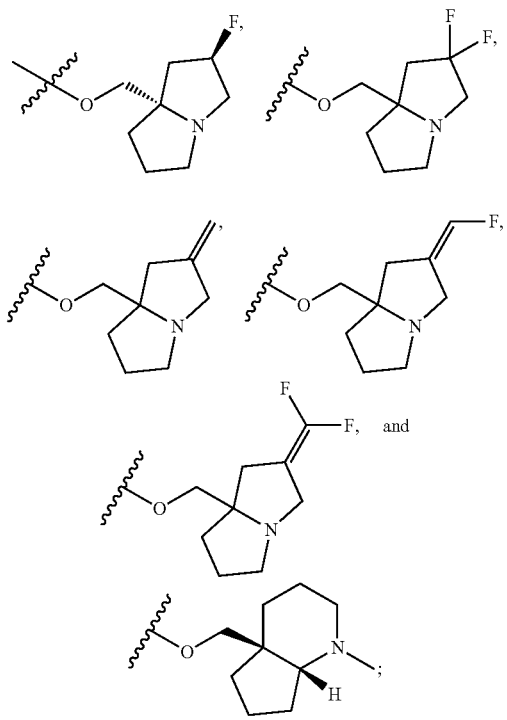

wherein:

$W^1$ is N, $W^2$ is C($R^2$), $W^3$ is N, $W^4$ is C, $W^5$ is C, $W^6$ is C($R^6$), $W^7$ is C, $W^8$ is C($R^8$), $W^9$ is C, and $R^{10}$ is C;

$W^1$ is N, $W^2$ is C($R^2$), $W^3$ is N, $W^4$ is C, $W^5$ is C, $W^6$ is N, $W^7$ is C, $W^8$ is C($R^8$), $W^9$ is C, $R^{10}$ is C;

$R^2$ is selected from $R^6$ is selected from hydrogen, halogen, and $C_{1-6}$haloalkyl;

$R^7$ is -$L^7$—$R^{17}$;

$L^7$ is a bond;

R[17] is selected from

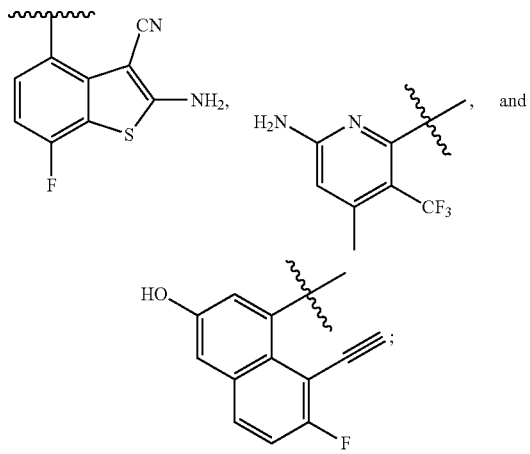

R[8] is halogen;
each Z[1] is independently C(R[z1])$_2$ or O;
z1n is 1, 2, or 3;
each R[z1] is independently selected from hydrogen, C$_{1-6}$alkyl, wherein C$_{1-6}$alkyl is optionally substituted with one, two, or three substituents independently selected from halogen and —OH;
Z[2] is CH;
Z[3] is CH or N;
Z[4] is a bond, Z[4a], Z[4a]Z[4b], or Z[4a]Z[4b]Z[4c]; wherein Z[4a] is directly bonded to Z[2]; and wherein if Z[4] is a bond then Z[2] is directly bonded to Z[5];
Z[4a], Z[4b], and Z[4c] are independently N(R[z4]) or C(R[z4])$_2$; provided that if z9n is 0 and Z[4] is Z[4a]Z[4b]; then (1) Z[4b] is C(R[z4])$_2$, or (2) Z[4b] is N(R[z4]) and Z[3] is CH;.
each R[z4] is independently selected from hydrogen, halogen, —CN, C$_{1-6}$alkyl, —OH, —NH(C$_{1-6}$alkyl), —C(O)H, and —C(O)(C$_{1-6}$alkyl), wherein C$_{1-6}$alkyl, is optionally substituted with one, two, or three substituents independently selected from halogen, —OH, and —CN;
Z[5] is C(R[z5])$_2$;
two R[z5] bonded to the same carbon atom are joined to form monocyclic C$_{3-7}$cycloalkyl or monocyclic 3-7 membered heterocycloalkyl, wherein the monocyclic C$_{3-7}$cycloalkyl and monocyclic 3-7 membered heterocycloalkyl are optionally substituted with one, two, or three R[20z];
Z[6] is C(R[z6])$_2$;
each R[z6] is independently selected from hydrogen and C$_{1-6}$alkyl; wherein C$_{1-6}$alkyl is optionally substituted with one, two, or three substituents independently selected from halogen, —OH, —O(C$_{1-6}$alkyl), and —O(C$_{1-6}$haloalkyl);
each Z[9] is independently N(R[z9]);
z9n is 0 or 1; wherein if z9n is 0 then Z[3] is directly bonded to W[4];
each R[z9] is independently selected from hydrogen, C$_{1-6}$alkyl, and C$_{3-10}$cycloalkyl, wherein C$_{1-6}$alkyl, is optionally substituted with one, two, or three substituents independently selected from halogen, —CN, —O(C$_{1-6}$alkyl), —O(C$_{1-6}$haloalkyl), C$_{3-4}$cycloalkyl, 3-4 membered heterocycloalkyl, —NH(C$_{1-6}$alkyl), and —N(C$_{1-6}$alkyl)2; and
wherein the sum of z1n and z9n is 2 or 3; and
each R[20z] is independently selected from C$_{1-6}$alkyl, —C(O)R[12], and —N(H)C(O)R[12]; wherein the R[12] is selected from

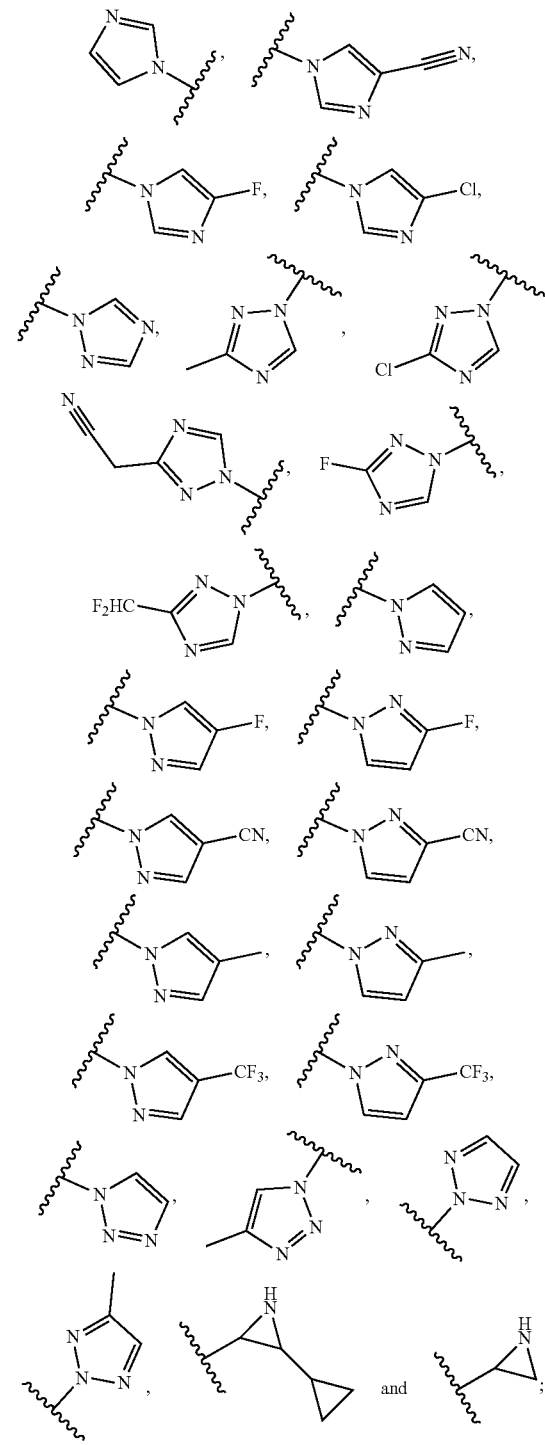

one R[20z] is selected from —C(O)R[12], and —N(H)C(O)R[12], wherein the R[12] is selected from

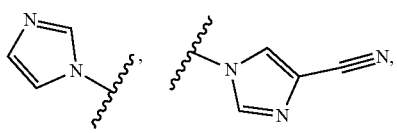

-continued

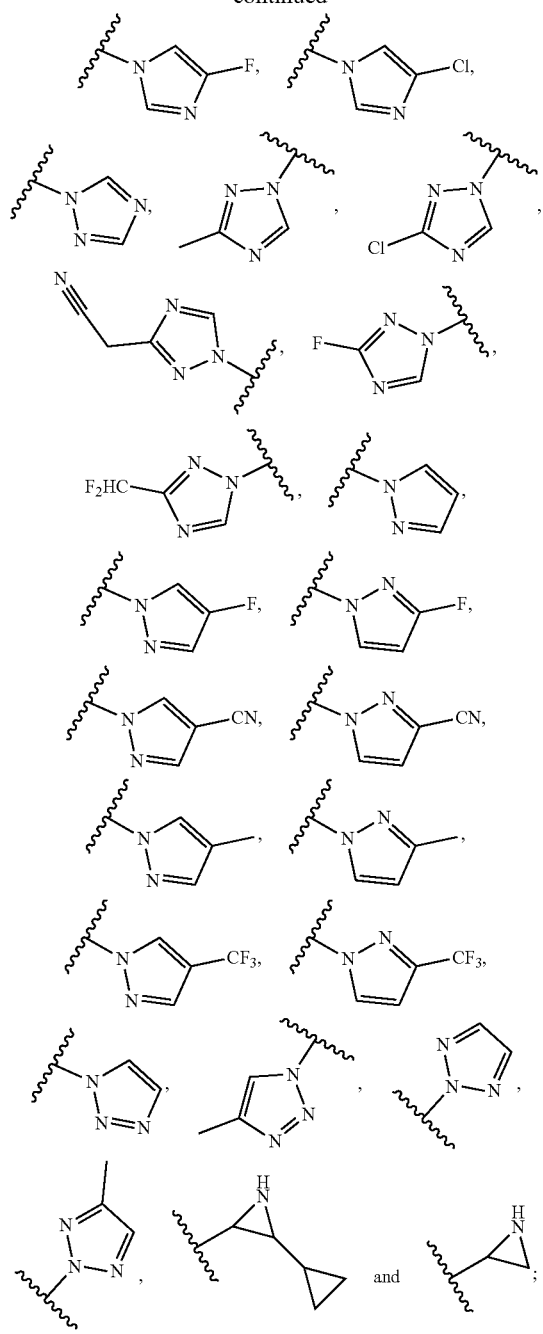

In embodiments of Formula (A) in the paragraph immediately above, R² is

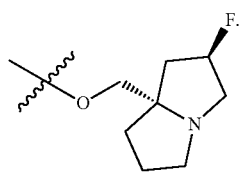 [SMILES: *OC[C@@]12CCCN1C[C@H](F)C2]

In embodiments of Formula (A) in the paragraph immediately above, R¹⁷ is

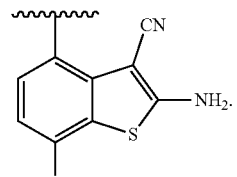

In embodiments of Formula (A) in the paragraph immediately above, R¹⁷ is

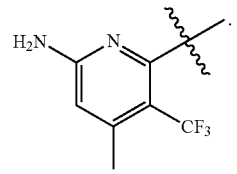 [SMILES: *c1nc(N)cc(C)c1C(F)(F)F]

In embodiments of Formula (A) in the paragraph immediately above, R¹⁷ is

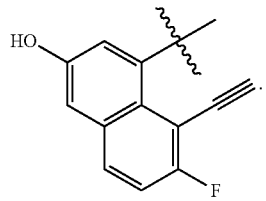 [SMILES: *c1cc(O)cc2ccc(F)c(C#C)c12]

In embodiments, the compound of Formula (A) or B has a formula selected from:

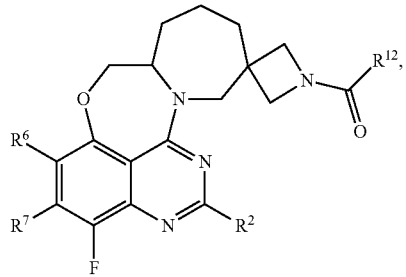

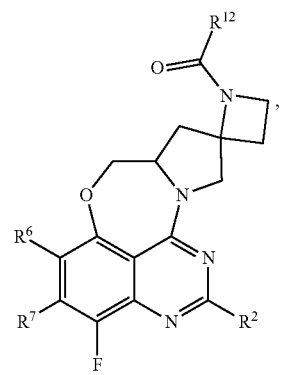

473
-continued
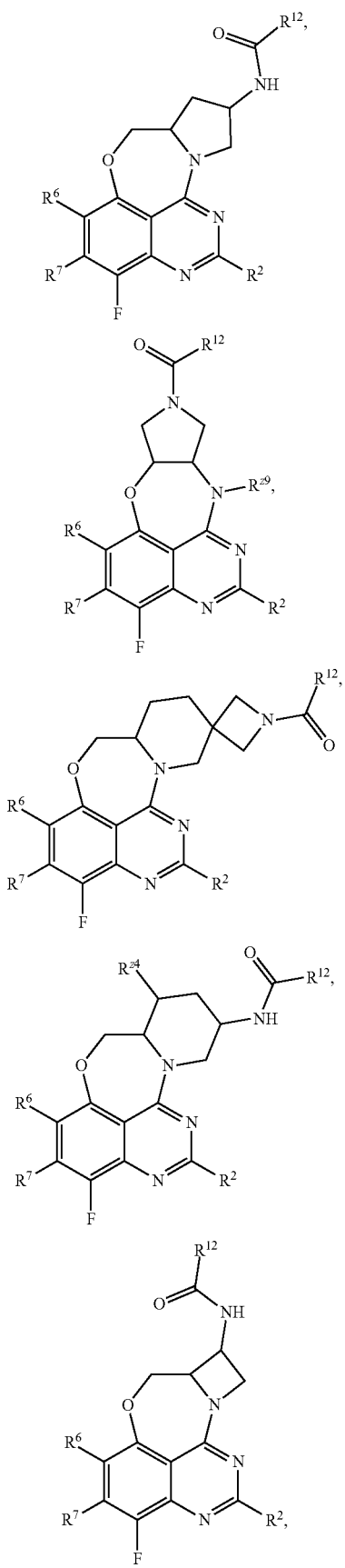
474
-continued
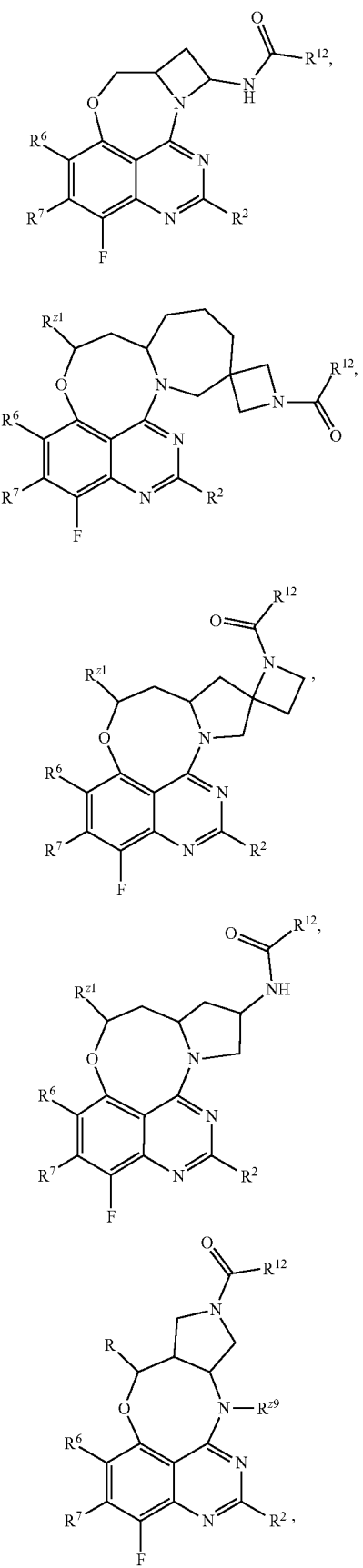

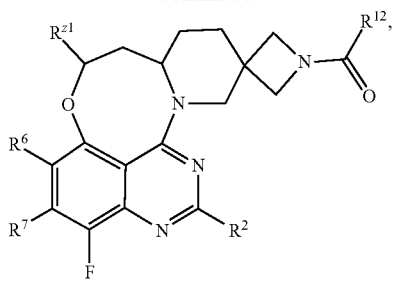
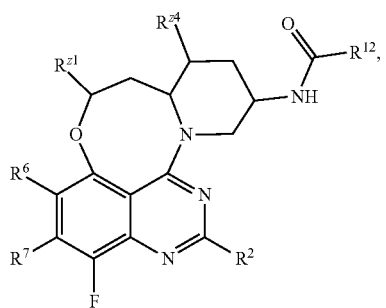
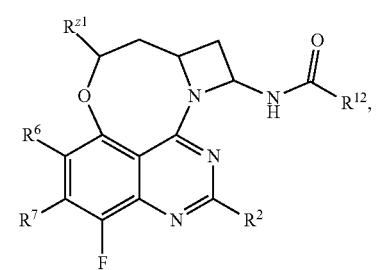
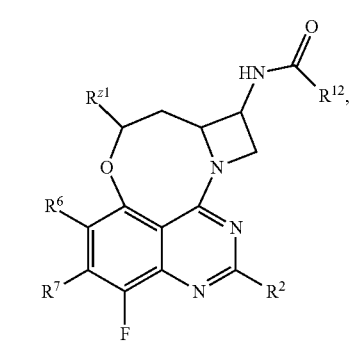
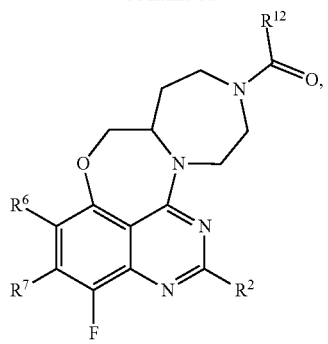
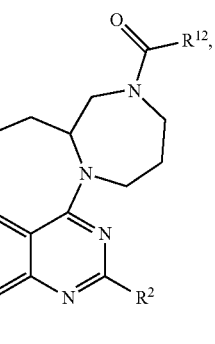
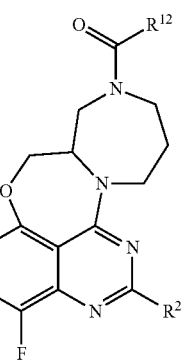
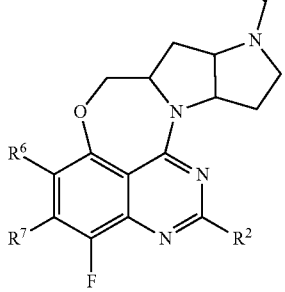
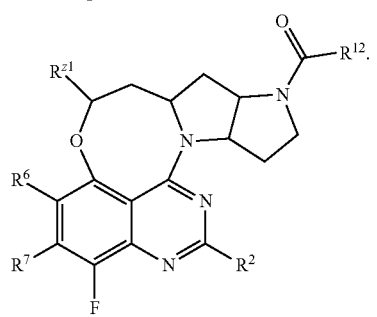

477

In embodiments of the formulae immediately above, $R^2$ is selected from

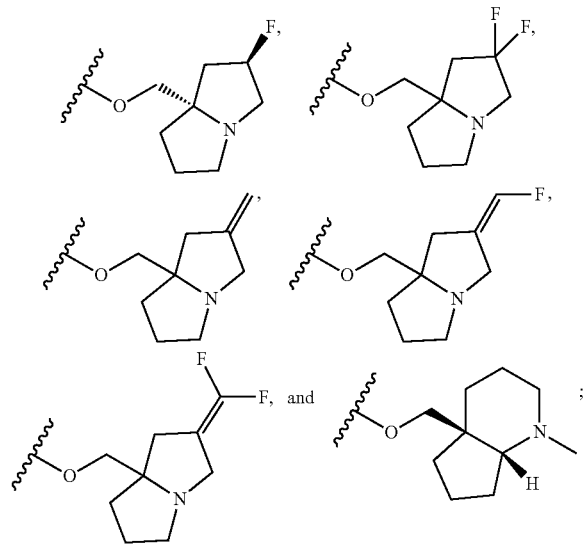

$R^6$ is selected from hydrogen, halogen, and $C_{1-6}$haloalkyl; $R^7$ is -$L^7$—$R^{17}$; $L^7$ is a bond; $R^{17\ 7}$ is selected from

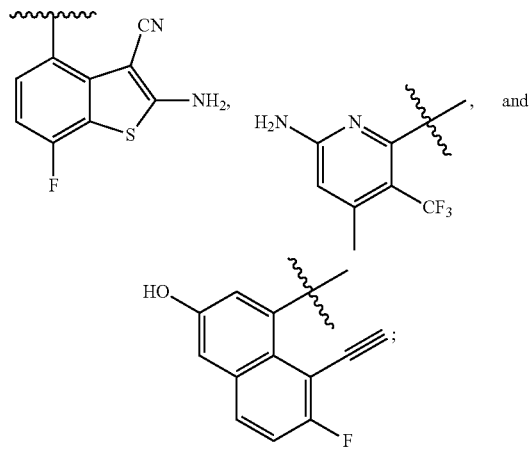

$R^{12}$ is selected from

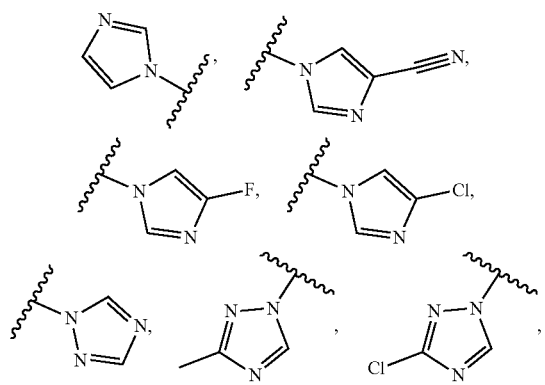

478

-continued

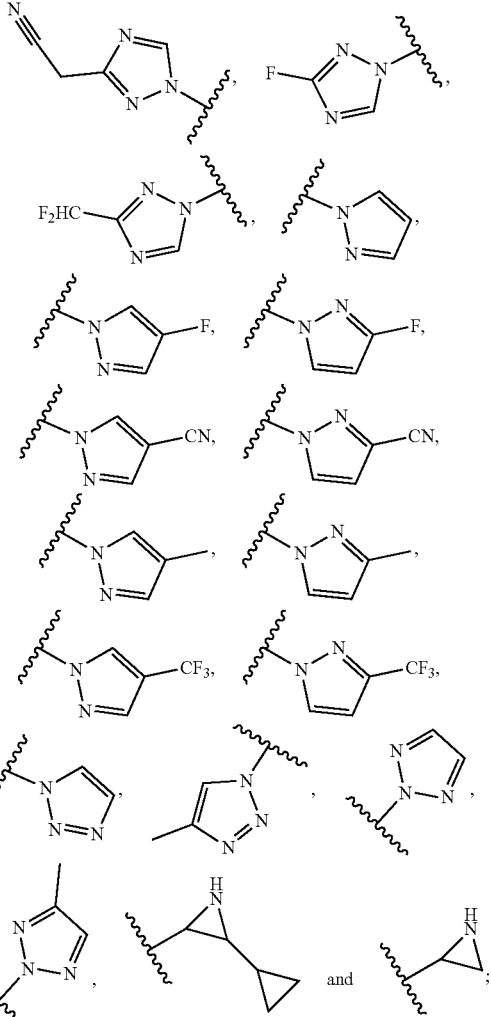

each $R^{z1}$ is independently selected from hydrogen and $C_{1-6}$alkyl, wherein $C_{1-6}$alkyl is optionally substituted with one, two, or three substituents independently selected from halogen and —OH; each $R^{z4}$ is independently selected from hydrogen, halogen, —CN, $C_{1-6}$alkyl, —OH, —NH($C_{1-6}$alkyl), —C(O)H, and —C(O)($C_{1-6}$alkyl), wherein $C_{1-6}$alkyl, is optionally substituted with one, two, or three substituents independently selected from halogen, —OH, and —CN; each $R^{z6}$ is independently selected from hydrogen and $C_{1-6}$alkyl; wherein $C_{1-6}$alkyl is optionally substituted with one, two, or three substituents independently selected from halogen, —OH, —O($C_{1-6}$alkyl), and —O($C_{1-6}$haloalkyl); and each $R^{20z}$ is independently selected from $C_{1-6}$alkyl. In embodiments of the formulae immediately above, $R^2$ is

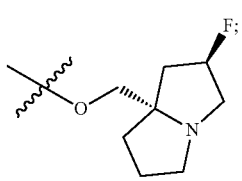

$R^6$ is selected from hydrogen, halogen, and $C_{1-6}$haloalkyl; $R^7$ is -$L^7$—$R^{17}$; $L^7$ is a bond; $R^{17}$ is

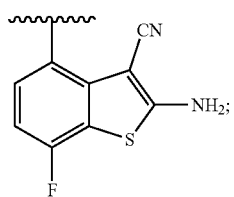 [SMILES: *c1ccc(F)c2sc(N)c(C#N)c12]

each $R^{z1}$ is independently selected from hydrogen and $C_{1-6}$alkyl, wherein $C_{1-6}$alkyl is optionally substituted with one, two, or three substituents independently selected from halogen and —OH; each $R^{z4}$ is independently selected from hydrogen, halogen, —CN, $C_{1-6}$alkyl, —OH, —NH($C_{1-6}$alkyl), —C(O)H, and —C(O)($C_{1-6}$alkyl), wherein $C_{1-6}$alkyl, is optionally substituted with one, two, or three substituents independently selected from halogen, —OH, and —CN; each $R^{z6}$ is independently selected from hydrogen and $C_{1-6}$alkyl; wherein $C_{1-6}$alkyl is optionally substituted with one, two, or three substituents independently selected from halogen, —OH, —O($C_{1-6}$alkyl), and —O($C_{1-6}$haloalkyl); and each $R^{20z}$ is independently selected from $C_{1-6}$alkyl.

In embodiments, the compound of Formula (A) or B has a formula selected from:

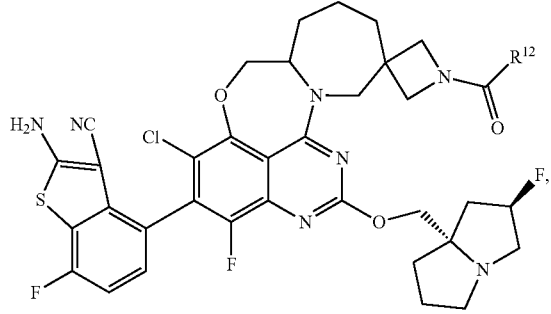

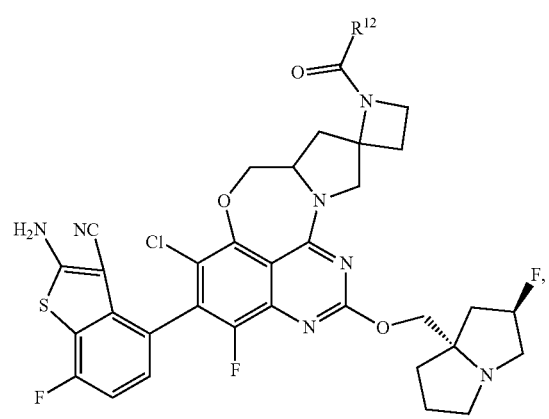

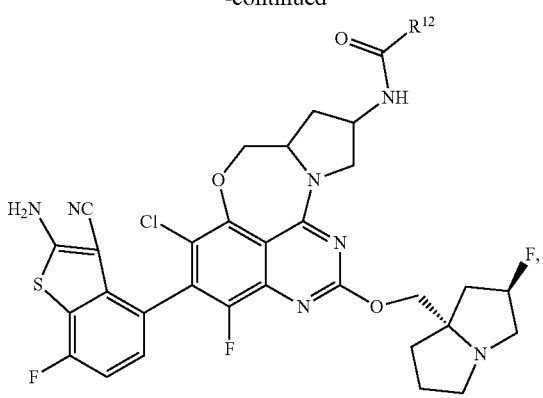

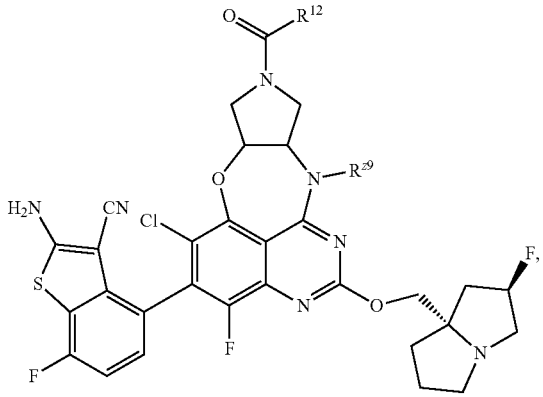

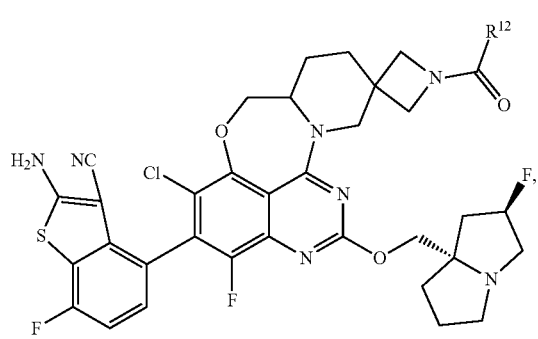

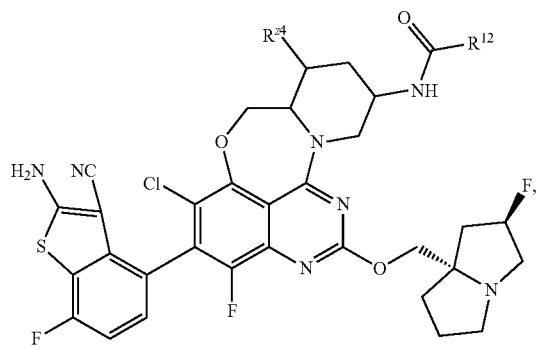

481
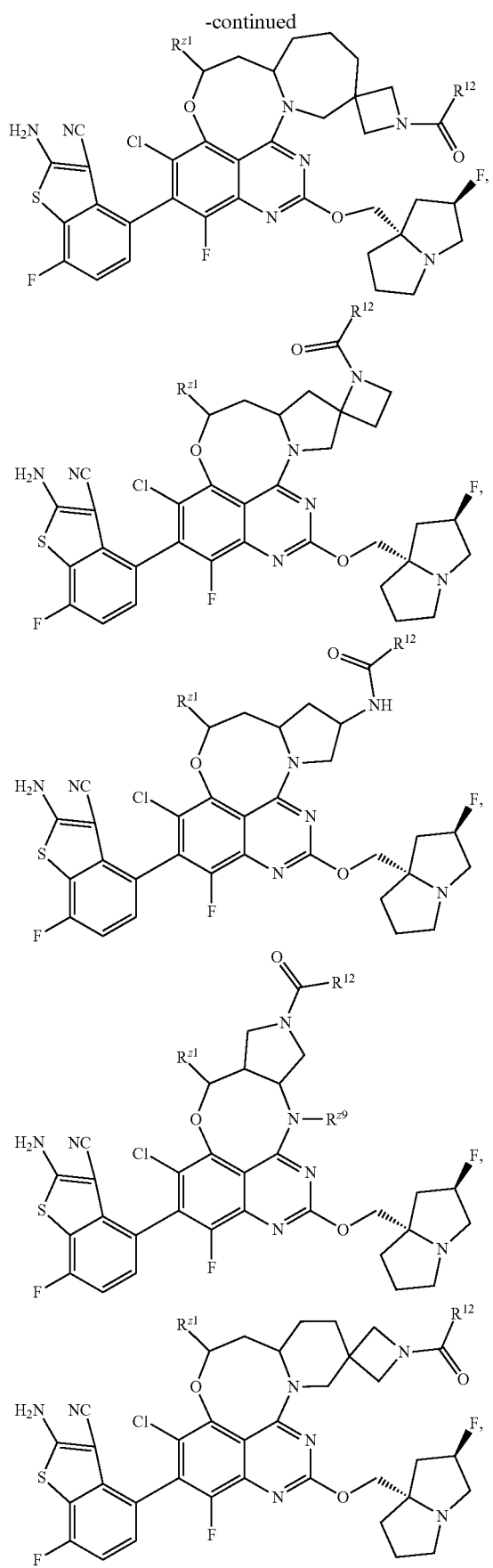
482
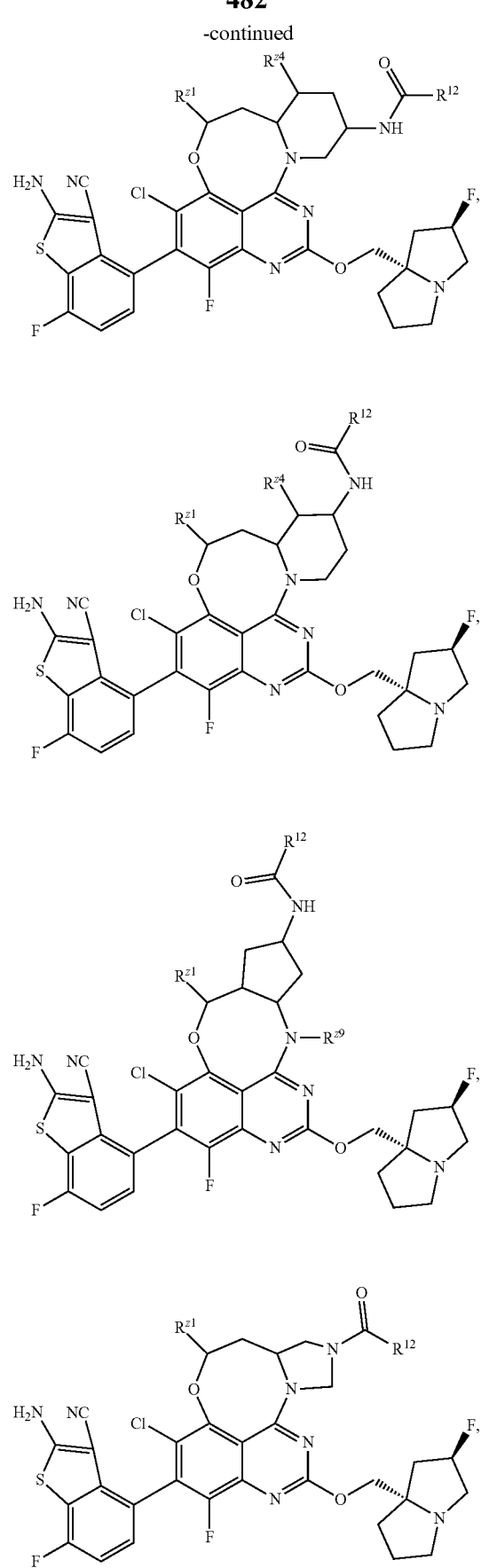

483
-continued
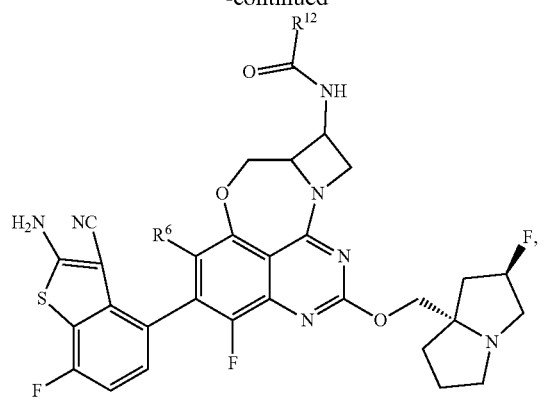
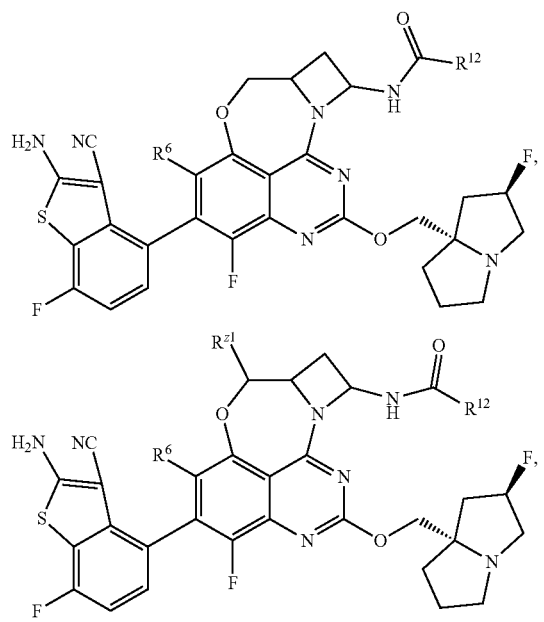
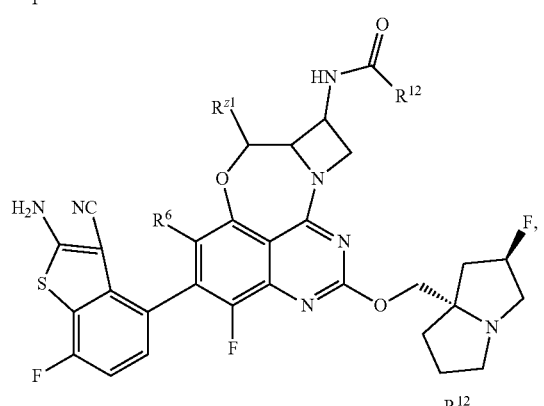
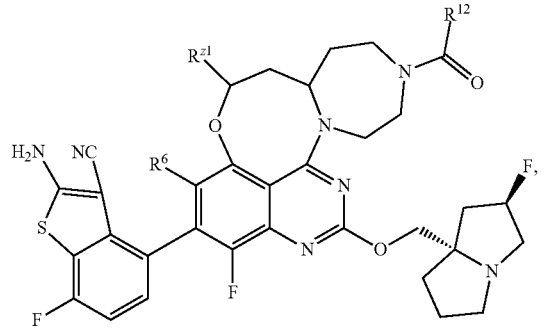
484
-continued
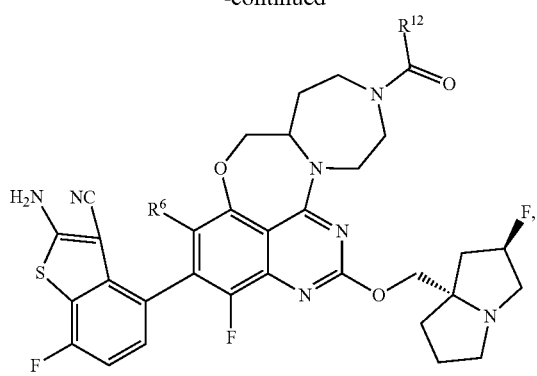
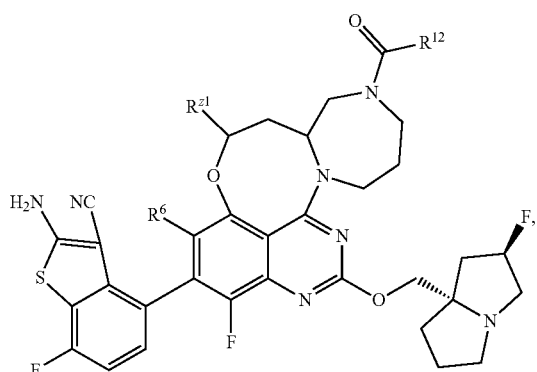
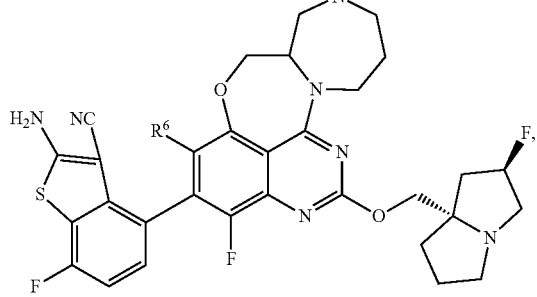
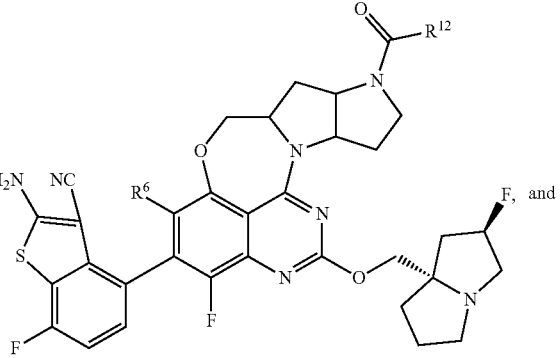
, and -continued

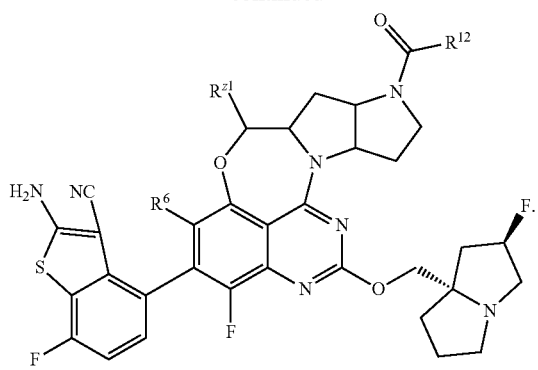

In embodiments of the formulae immediately above, $R^{12}$ is selected from

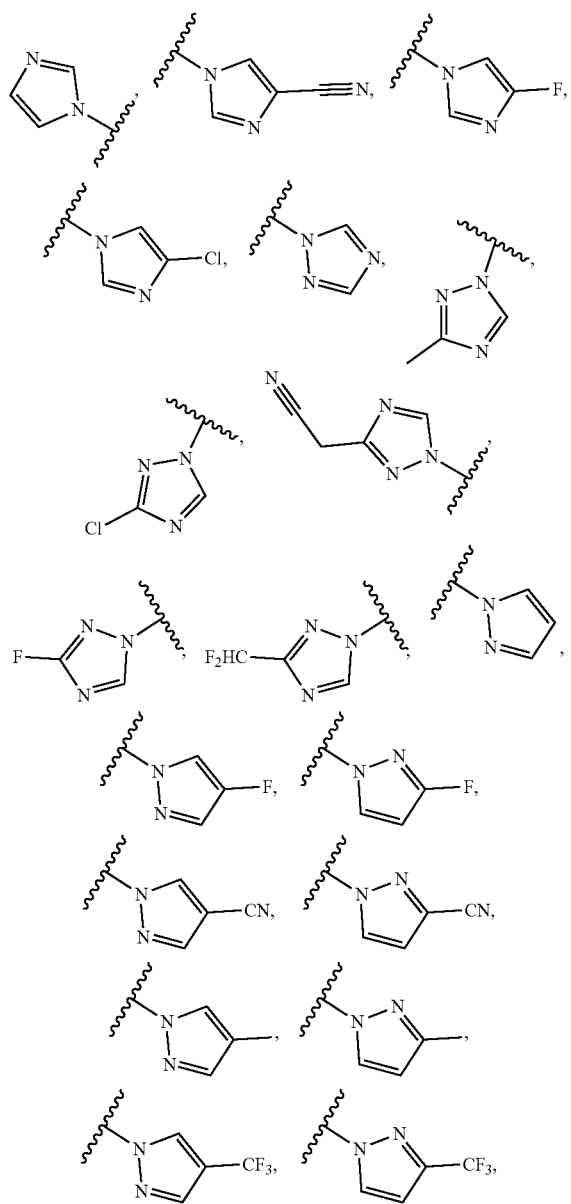

-continued

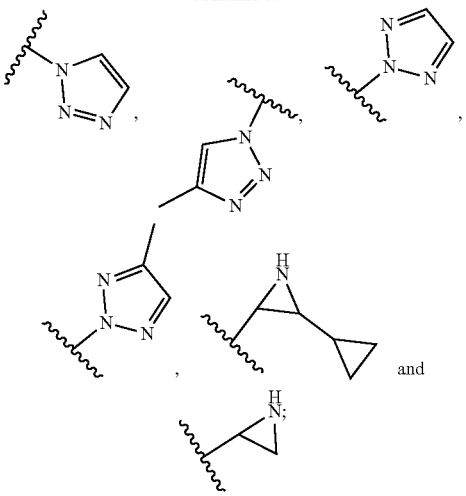

$R^6$ is selected from hydrogen, halogen, and $C_{1-2}$haloalkyl; each $R^{z1}$ is independently selected from hydrogen and $C_{1-6}$alkyl, wherein $C_{1-6}$alkyl is optionally substituted with one, two, or three substituents independently selected from halogen and —OH; each $R^{z4}$ is independently selected from hydrogen, halogen, —CN, $C_{1-6}$alkyl, —OH, —NH($C_{1-6}$alkyl), —C(O)H, and —C(O)($C_{1-6}$alkyl), wherein $C_{1-6}$alkyl, is optionally substituted with one, two, or three substituents independently selected from halogen, —OH, and —CN; each $R^{z6}$ is independently selected from hydrogen and $C_{1-6}$alkyl; wherein $C_{1-6}$alkyl is optionally substituted with one, two, or three substituents independently selected from halogen, —OH, —O($C_{1-6}$alkyl), and —O($C_{1-6}$haloalkyl); each $R^{z9}$ is independently selected from hydrogen, $C_{3-4}$cycloalkyl, and $C_{1-6}$alkyl, wherein $C_{1-6}$alkyl is optionally substituted with one, two, or three substituents independently selected from halogen, —CN, $C_{3-4}$cycloalkyl, 3-4 membered heterocycloalkyl, —NH($C_{1-6}$alkyl), —N($C_{1-6}$alkyl)$_2$, —O($C_{1-6}$alkyl), and —OH; and each $R^{20z}$ is independently selected from $C_{1-6}$alkyl. In embodiments of the formulae immediately above, $R^6$ is selected from hydrogen, halogen, and $C_1$haloalkyl; each $R^{z1}$ is independently selected from hydrogen and $C_{1-6}$alkyl, wherein $C_{1-6}$alkyl is optionally substituted with one, two, or three substituents independently selected from halogen and —OH; each $R^{z4}$ is independently selected from hydrogen, halogen, —CN, $C_{1-6}$alkyl, —OH, —NH($C_{1-6}$alkyl), —C(O)H, and —C(O)($C_{1-6}$alkyl), wherein $C_{1-6}$alkyl, is optionally substituted with one, two, or three substituents independently selected from halogen, —OH, and —CN; each $R^{z6}$ is independently selected from hydrogen and $C_{1-6}$alkyl; wherein $C_{1-6}$alkyl is optionally substituted with one, two, or three substituents independently selected from halogen, —OH, —O($C_{1-6}$alkyl), and —O($C_{1-6}$haloalkyl); each $R^{z9}$ is independently selected from hydrogen, $C_{3-4}$cycloalkyl, and $C_{1-6}$alkyl, wherein $C_{1-6}$alkyl is optionally substituted with one, two, or three substituents independently selected from halogen, —CN, $C_{3-4}$cycloalkyl, 3-4 membered heterocycloalkyl, —NH($C_{1-6}$alkyl), —N($C_{1-6}$alkyl)$_2$, —O($C_{1-6}$alkyl), and —OH; and each $R^{20z}$ is independently selected from $C_{1-6}$alkyl.

In embodiments, the compound of Formula (A) or B has a formula selected from:

487
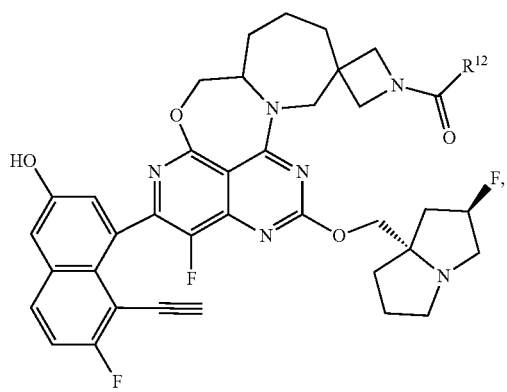
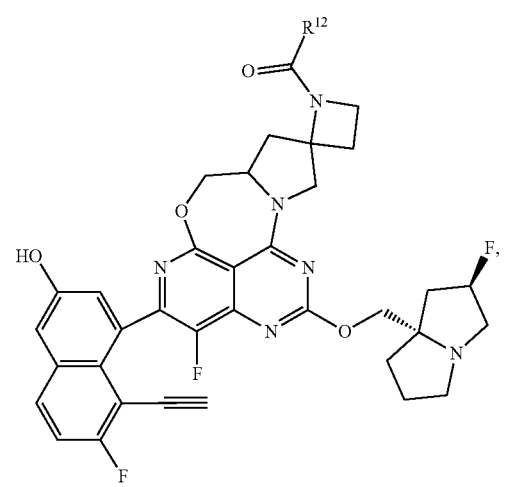
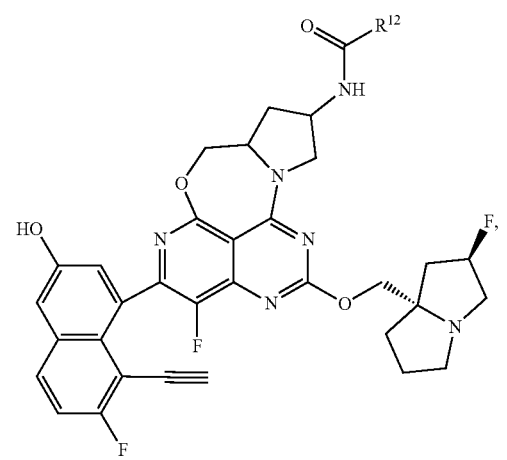
488
-continued
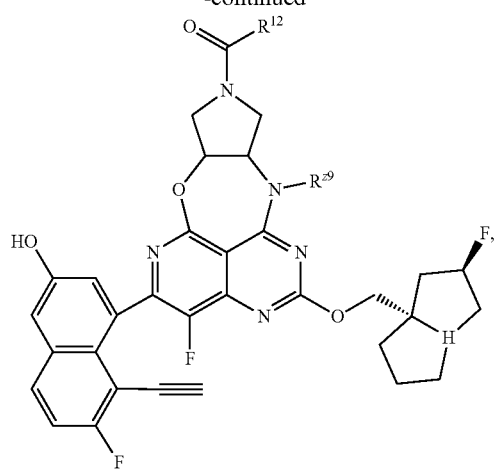
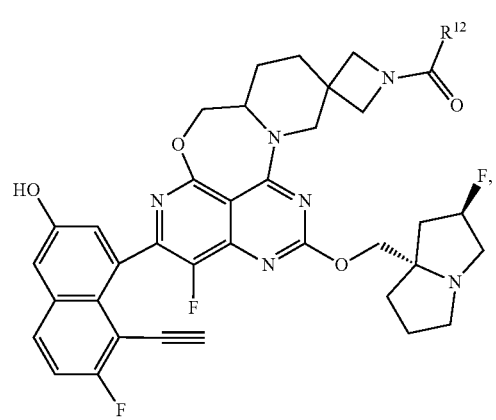
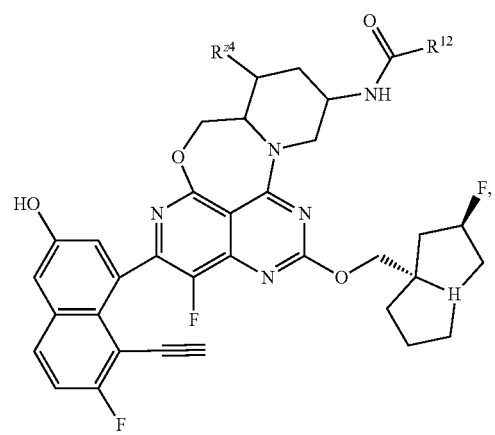
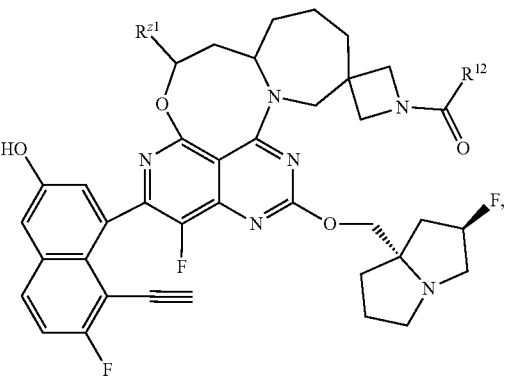

489
-continued
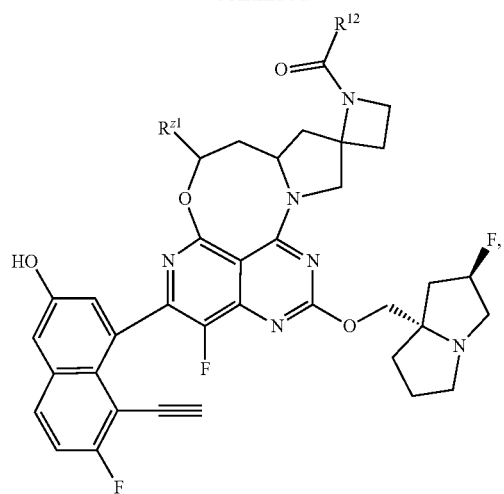
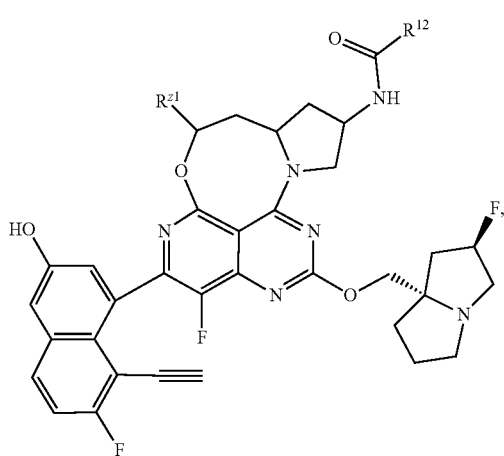
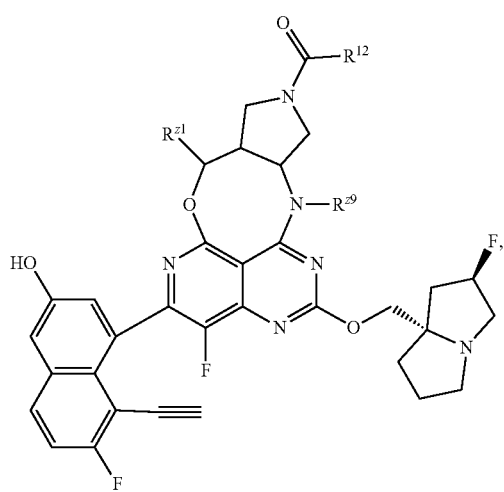
490
-continued
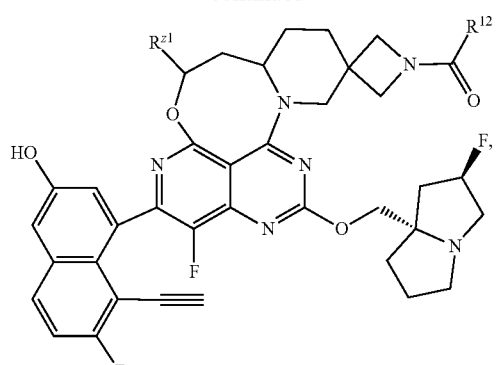
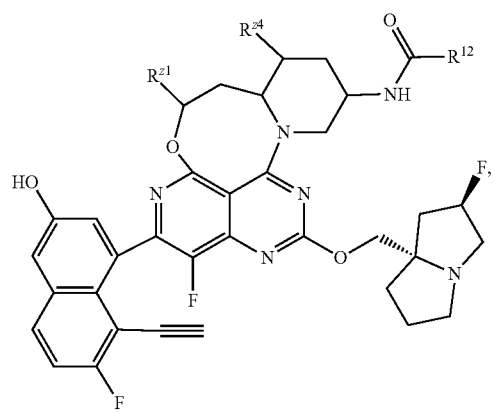
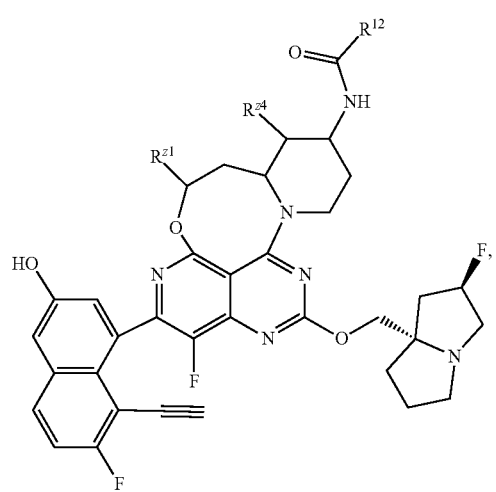

491
-continued
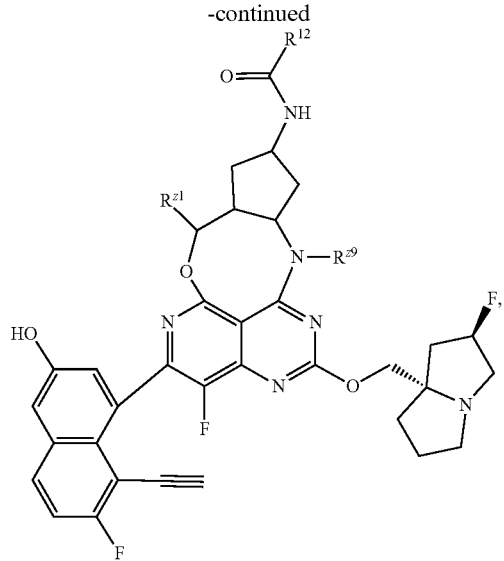
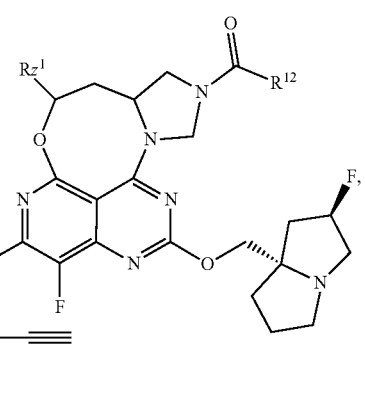
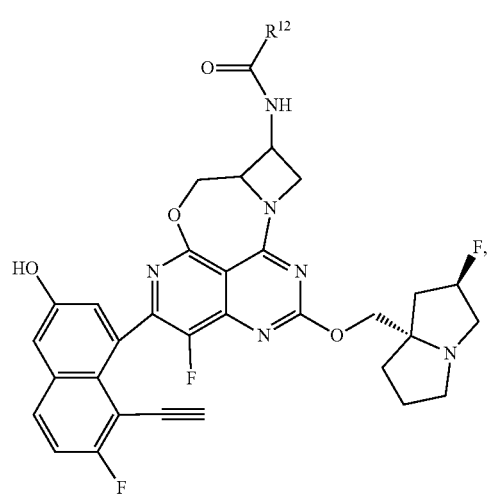
492
-continued
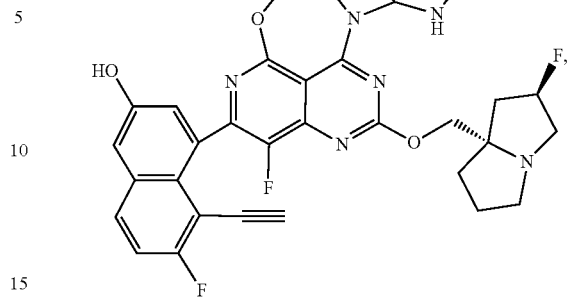
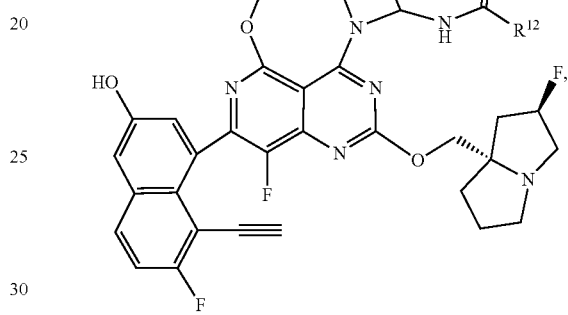
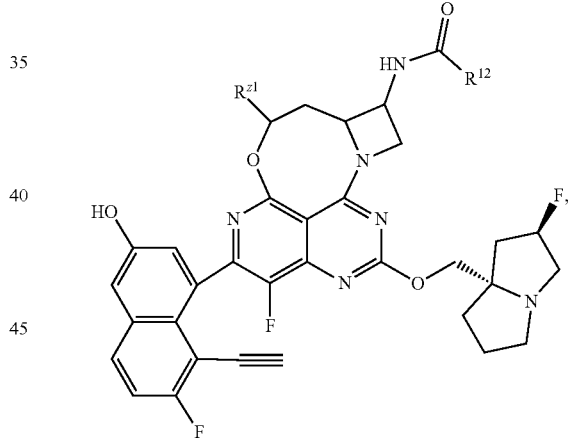
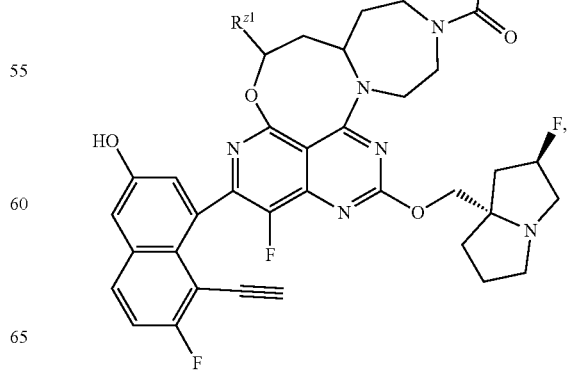

493
-continued
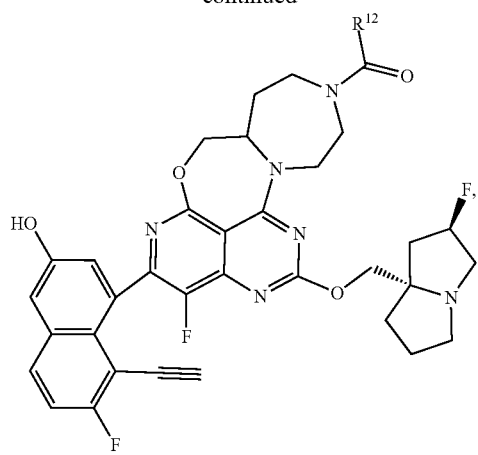
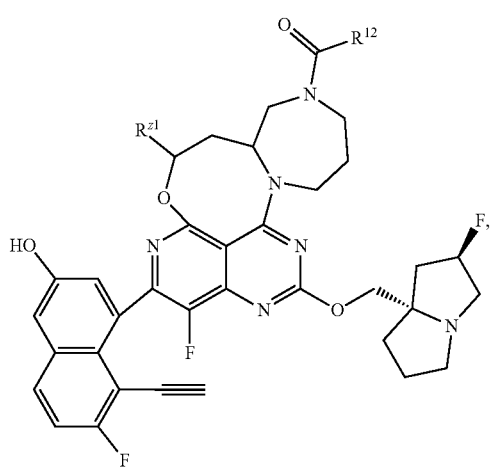
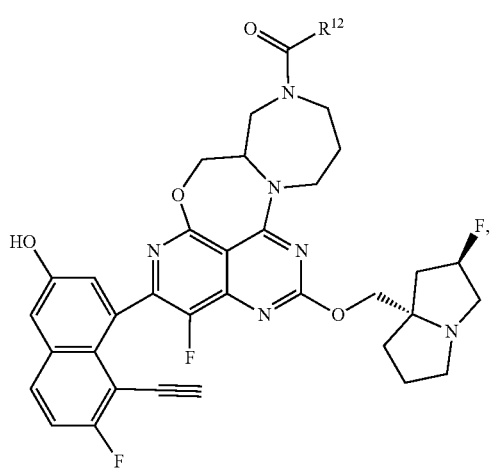
494
-continued
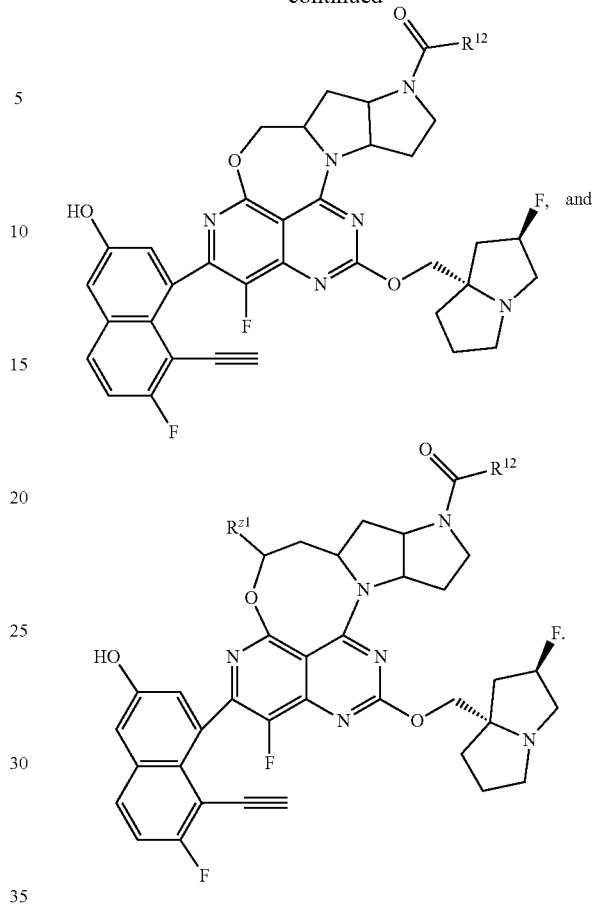
In embodiments of the formulae immediately above, $R^{12}$ is selected from
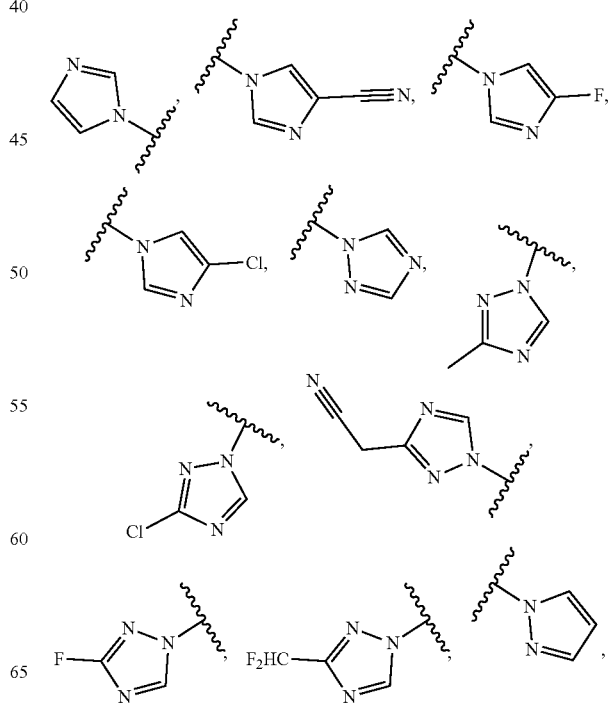

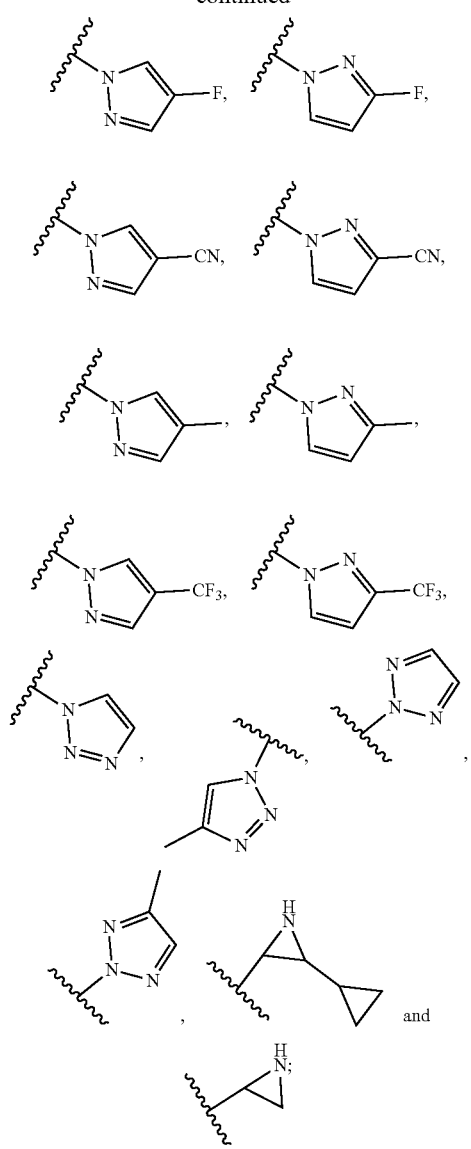

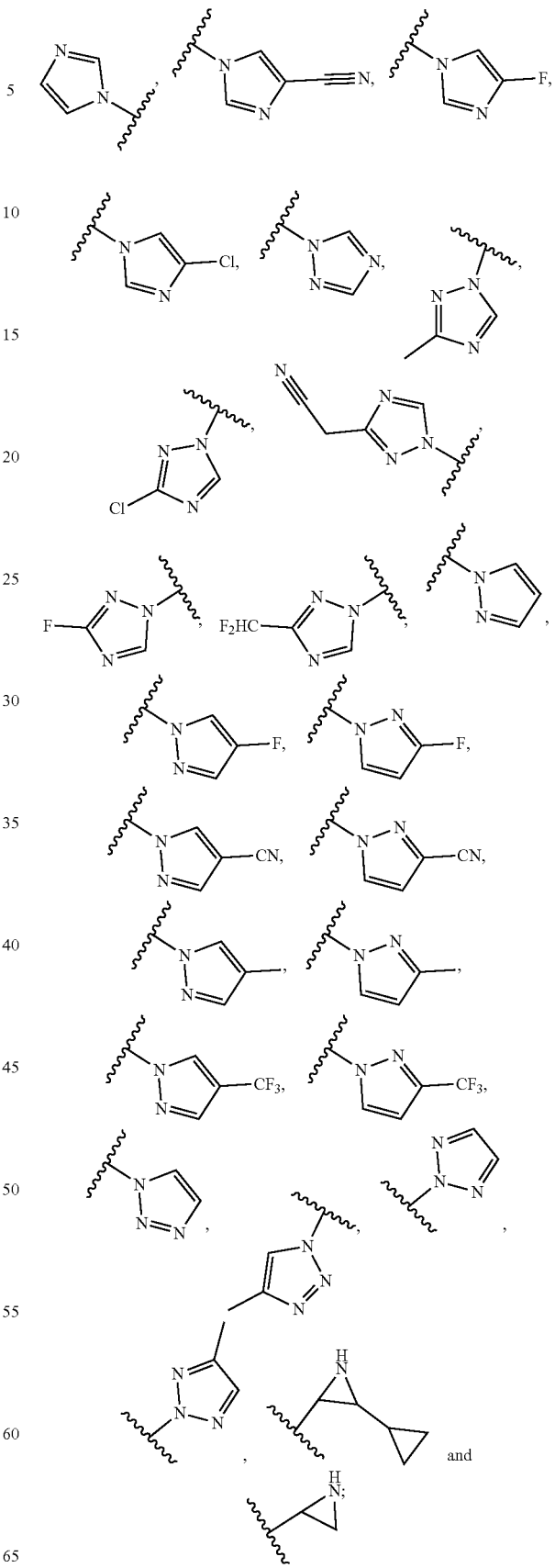

each $R^{z1}$ is independently selected from hydrogen and $C_{1-6}$alkyl, wherein $C_{1-6}$alkyl is optionally substituted with one, two, or three substituents independently selected from halogen and —OH; each $R^{z4}$ is independently selected from hydrogen, halogen, —CN, $C_{1-6}$alkyl, —OH, —NH($C_{1-6}$alkyl), —C(O)H, and —C(O)($C_{1-6}$alkyl), wherein $C_{1-6}$alkyl, is optionally substituted with one, two, or three substituents independently selected from halogen, —OH, and —CN; each $R^{z6}$ is independently selected from hydrogen and $C_{1-6}$alkyl; wherein $C_{1-6}$alkyl is optionally substituted with one, two, or three substituents independently selected from halogen, —OH, —O($C_{1-6}$alkyl), and —O($C_{1-6}$haloalkyl); each $R^{z9}$ is independently selected from hydrogen, $C_{3-4}$cycloalkyl, and $C_{1-6}$alkyl, wherein $C_{1-6}$alkyl is optionally substituted with one, two, or three substituents independently selected from halogen, —CN, $C_{3-4}$cycloalkyl, 3-4 membered heterocycloalkyl, —NH($C_{1-6}$alkyl), —N($C_{1-6}$alkyl)$_2$, —O($C_{1-6}$alkyl), and —OH; and each $R^{20z}$ is independently selected from $C_{1-6}$alkyl. In embodiments of the formulae immediately above, $R^{12}$ is selected from each $R^{z1}$ is independently selected from hydrogen and $C_{1-6}$alkyl, wherein $C_{1-6}$alkyl is optionally substituted with one, two, or three substituents independently selected from halogen and —OH; each $R^{z4}$ is independently selected from hydrogen, halogen, —CN, $C_{1-6}$alkyl, —OH, —NH($C_{1-6}$alkyl), —C(O)H, and —C(O)($C_{1-6}$alkyl), wherein $C_{1-6}$alkyl, is optionally substituted with one, two, or three substituents independently selected from halogen, —OH, and —CN; each $R^{z6}$ is independently selected from hydrogen and $C_{1-6}$alkyl; wherein $C_{1-6}$alkyl is optionally substituted with one, two, or three substituents independently selected from halogen, —OH, —O($C_{1-6}$alkyl), and —O($C_{1-6}$haloalkyl); each $R^{z9}$ is independently selected from hydrogen, $C_{3-4}$cycloalkyl, and $C_{1-6}$alkyl, wherein $C_{1-6}$alkyl is optionally substituted with one, two, or three substituents independently selected from halogen, —CN, $C_{3-4}$cycloalkyl, 3-4 membered heterocycloalkyl, —NH($C_{1-6}$alkyl), —N($C_{1-6}$alkyl)$_2$, —O($C_{1-6}$alkyl), and —OH; and each $R^{20z}$ is independently selected from $C_{1-6}$alkyl.

In embodiments, the compound of Formula (A) or B has a formula selected from:

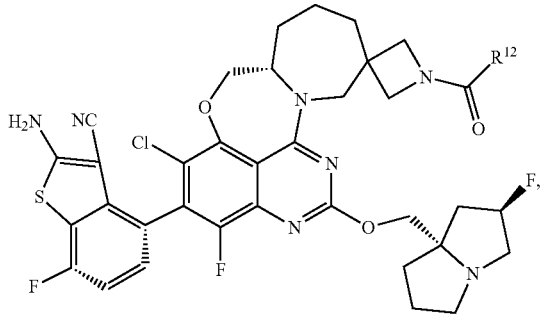

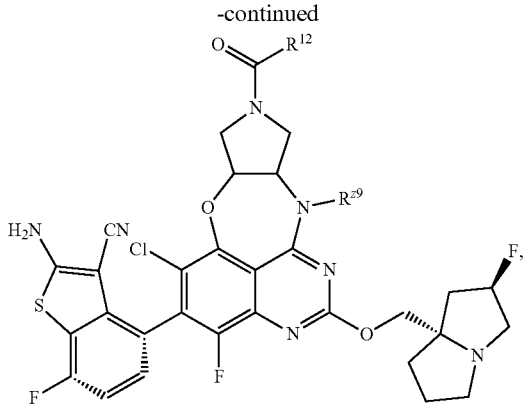

-continued

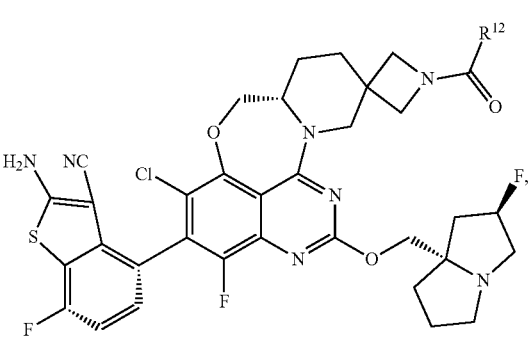

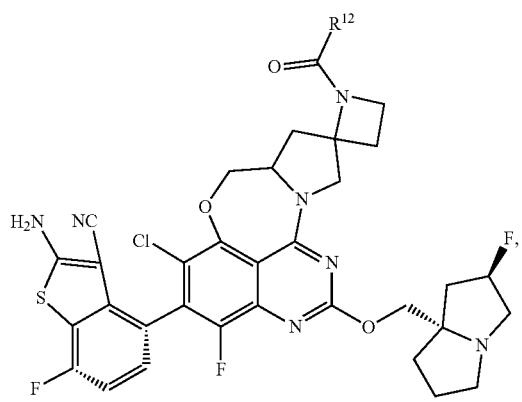

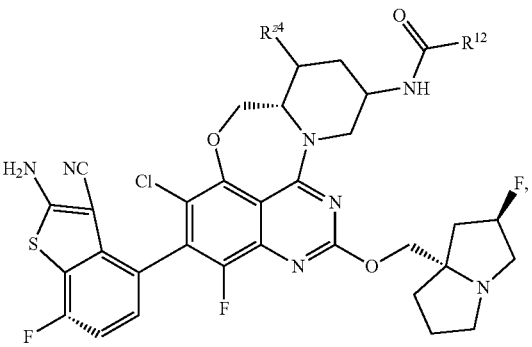

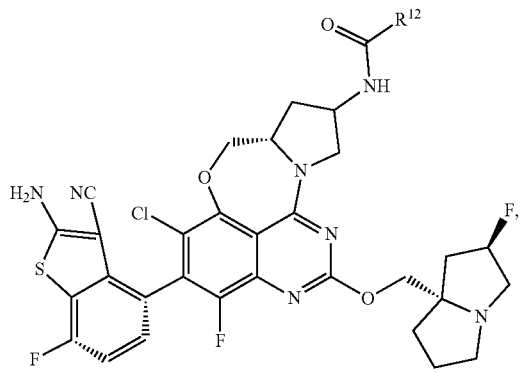

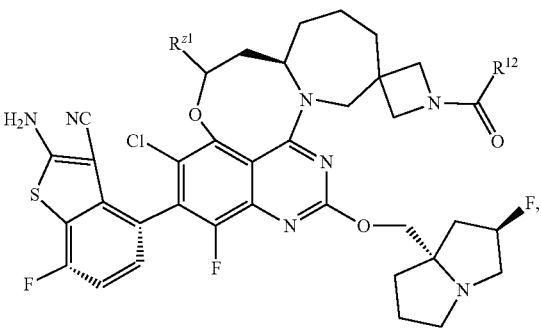

499
-continued
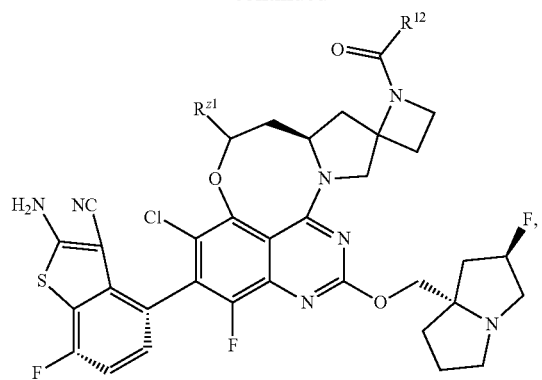
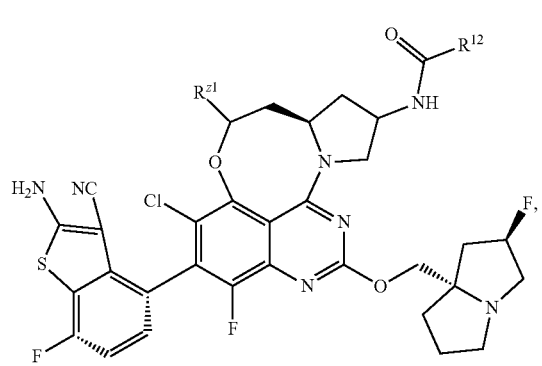
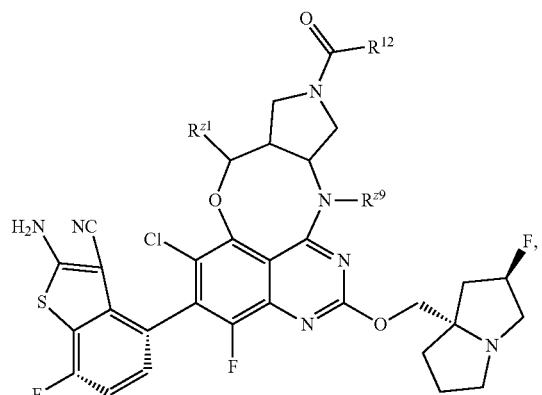
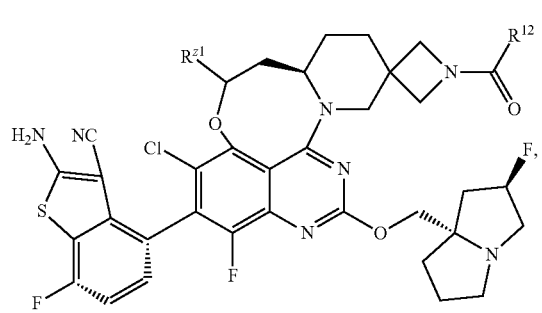
500
-continued
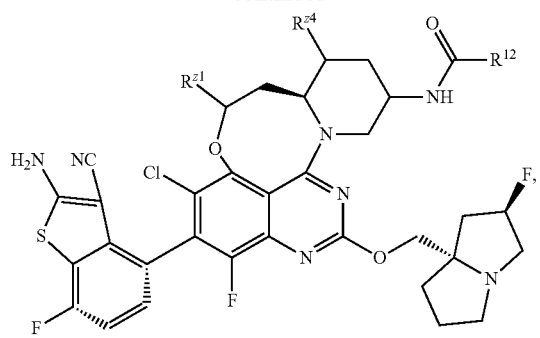
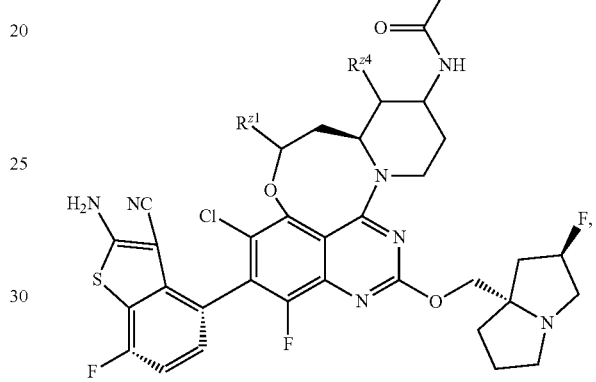
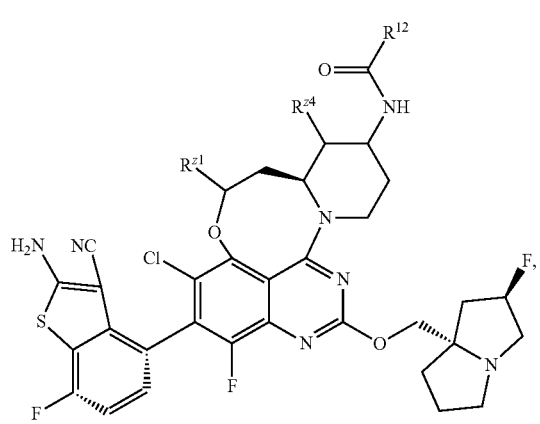
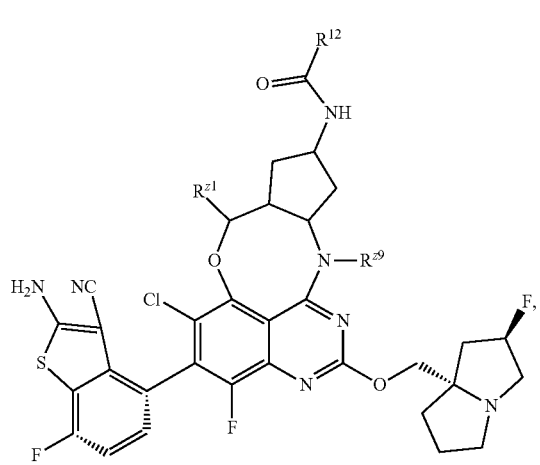
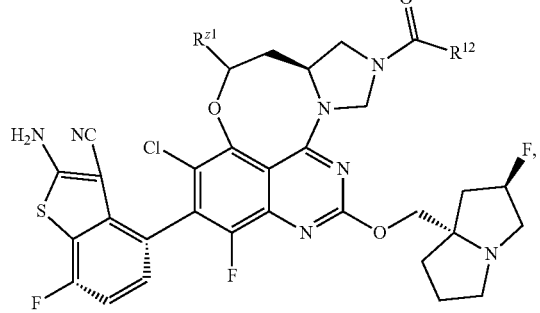

501
-continued
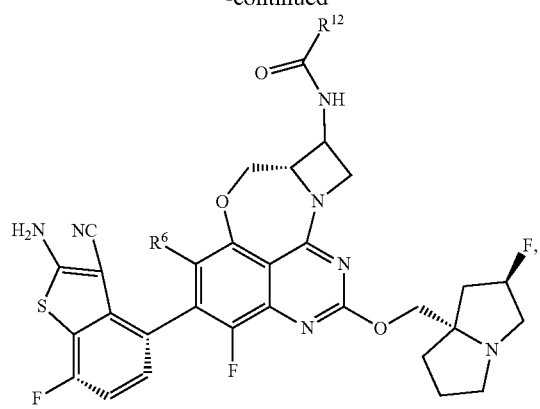
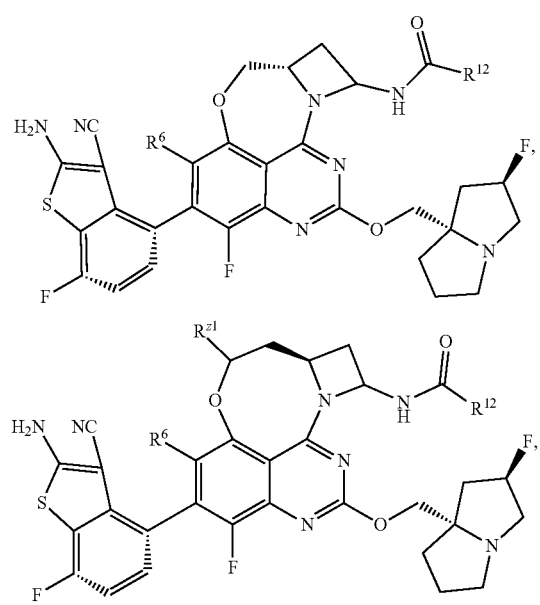
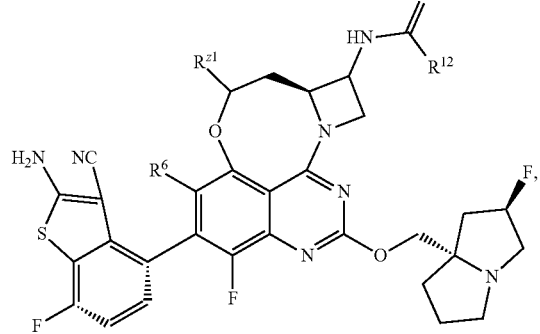
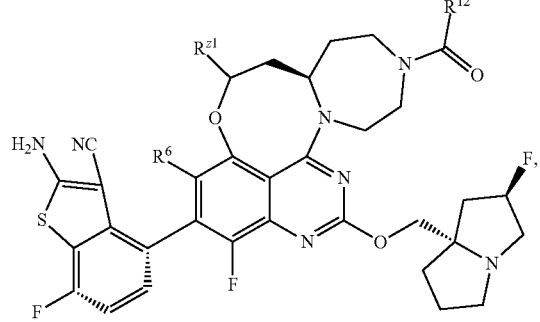
502
-continued
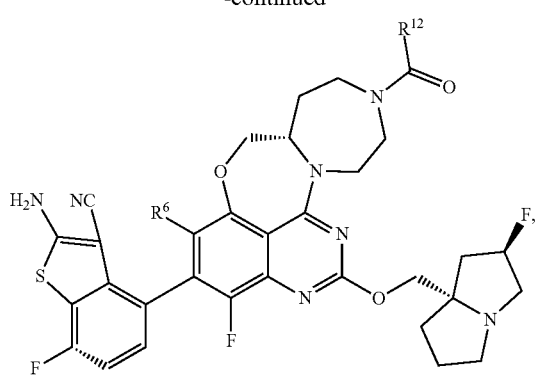
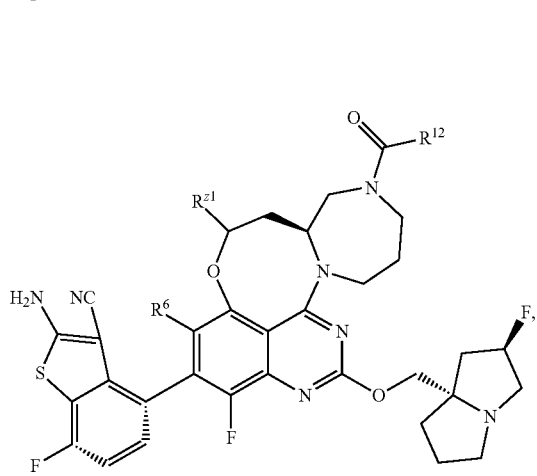

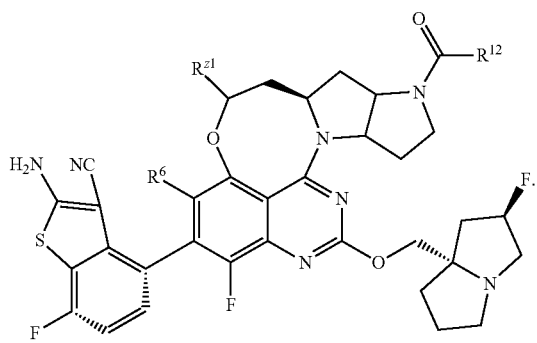

In the embodiments of the formulae immediately above, $R^{12}$ is selected from

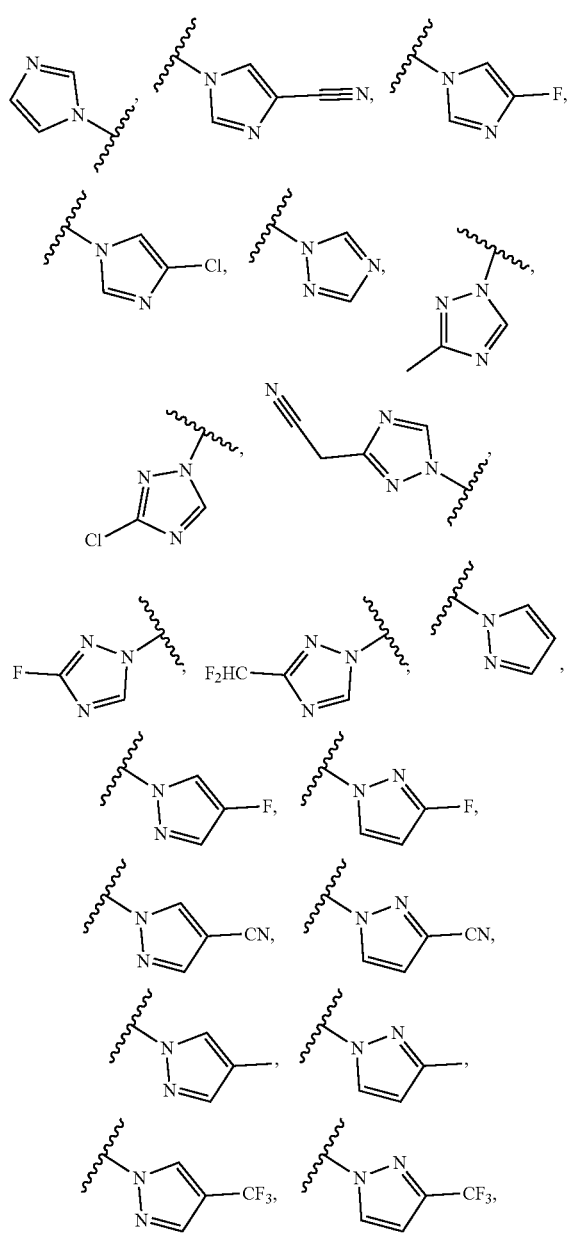

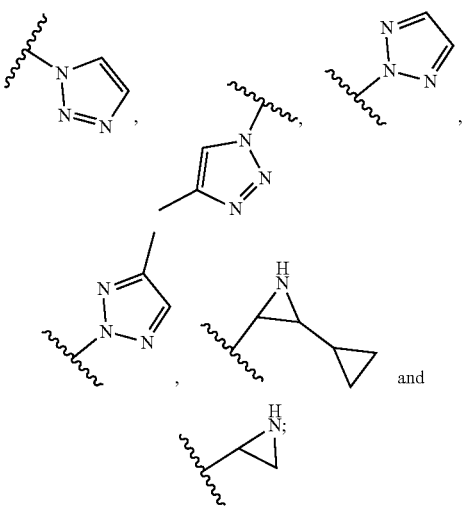

$R^6$ is selected from hydrogen, halogen, and $C_{1-2}$haloalkyl; each $R^{z1}$ is independently selected from hydrogen and $C_{1-6}$alkyl, wherein $C_{1-6}$alkyl is optionally substituted with one, two, or three substituents independently selected from halogen and —OH; each $R^{z4}$ is independently selected from hydrogen, halogen, —CN, $C_{1-6}$alkyl, —OH, —NH($C_{1-6}$alkyl), —C(O)H, and —C(O)($C_{1-6}$alkyl), wherein $C_{1-6}$alkyl, is optionally substituted with one, two, or three substituents independently selected from halogen, —OH, and —CN; each $R^{z6}$ is independently selected from hydrogen and $C_{1-6}$alkyl; wherein $C_{1-6}$alkyl is optionally substituted with one, two, or three substituents independently selected from halogen, —OH, —O($C_{1-6}$alkyl), and —O($C_{1-6}$haloalkyl); each $R^{z9}$ is independently selected from hydrogen, $C_{3-4}$cycloalkyl, and $C_{1-6}$alkyl, wherein $C_{1-6}$alkyl is optionally substituted with one, two, or three substituents independently selected from halogen, —CN, $C_{3-4}$cycloalkyl, 3-4 membered heterocycloalkyl, —NH($C_{1-6}$alkyl), —N($C_{1-6}$alkyl)$_2$, —O($C_{1-6}$alkyl), and —OH; and each $R^{20z}$ is independently selected from $C_{1-6}$alkyl. In embodiments of the formulae immediately above, $R^{12}$ is selected from -continued

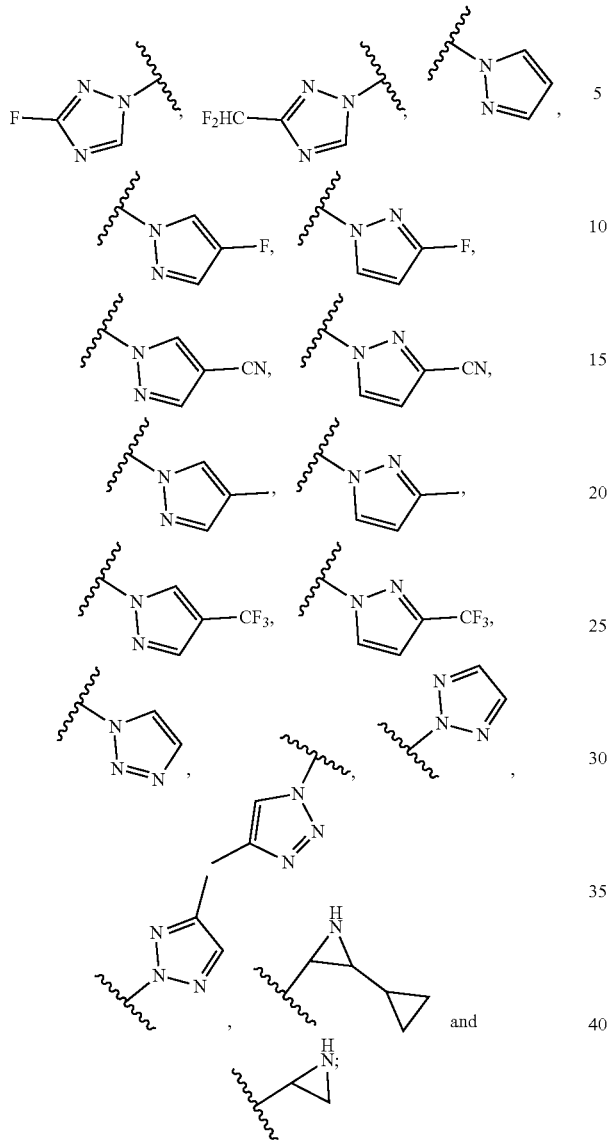

R[6] is selected from hydrogen, halogen, and C₁haloalkyl; each R[z1] is independently selected from hydrogen and $C_{1-6}$alkyl, wherein $C_{1-6}$alkyl is optionally substituted with one, two, or three substituents independently selected from halogen and —OH; each R[z4] is independently selected from hydrogen, halogen, —CN, $C_{1-6}$alkyl, —OH, —NH($C_{1-6}$alkyl), —C(O)H, and —C(O)($C_{1-6}$alkyl), wherein $C_{1-6}$alkyl, is optionally substituted with one, two, or three substituents independently selected from halogen, —OH, and —CN; each R[z6] is independently selected from hydrogen and $C_{1-6}$alkyl; wherein $C_{1-6}$alkyl is optionally substituted with one, two, or three substituents independently selected from halogen, —OH, —O($C_{1-6}$alkyl), and —O($C_{1-6}$haloalkyl); each R[z9] is independently selected from hydrogen, $C_{3-4}$cycloalkyl, and $C_{1-6}$alkyl, wherein $C_{1-6}$alkyl is optionally substituted with one, two, or three substituents independently selected from halogen, —CN, $C_{3-4}$cycloalkyl, 3-4 membered heterocycloalkyl, —NH($C_{1-6}$alkyl), —N($C_{1-6}$alkyl)₂, —O($C_{1-6}$alkyl), and —OH; and each R[20z] is independently selected from $C_{1-6}$alkyl.

In embodiments, the compound of Formula (A) or B has a formula selected from:

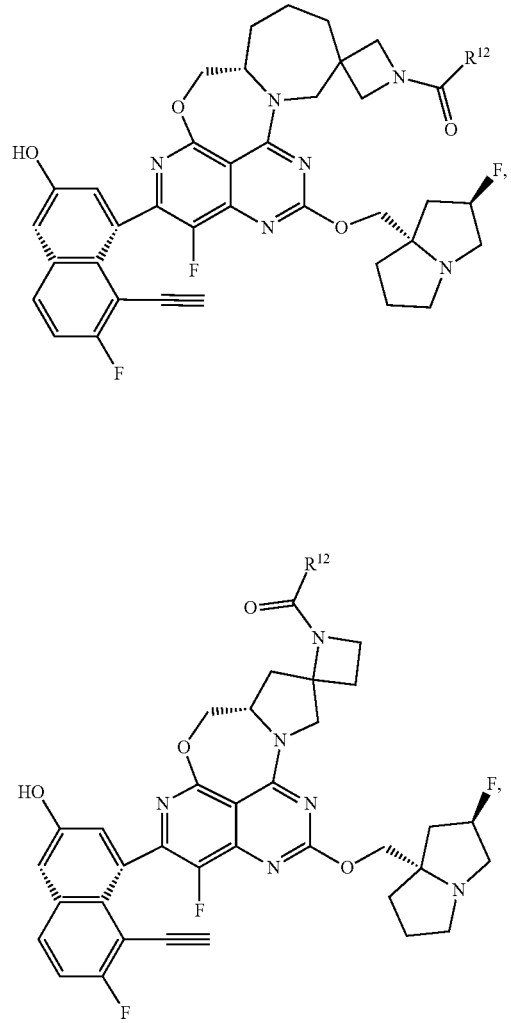

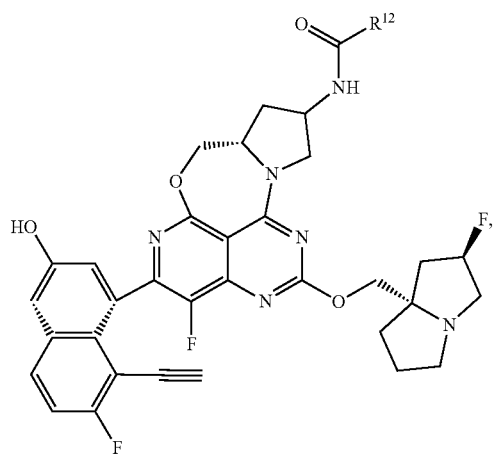

507
-continued
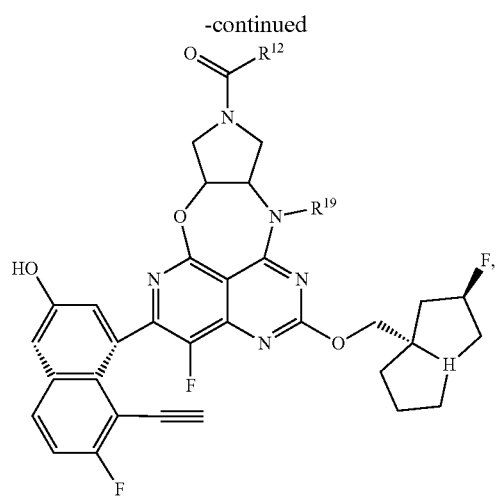
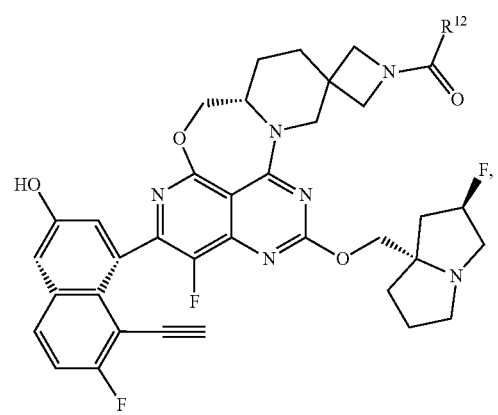
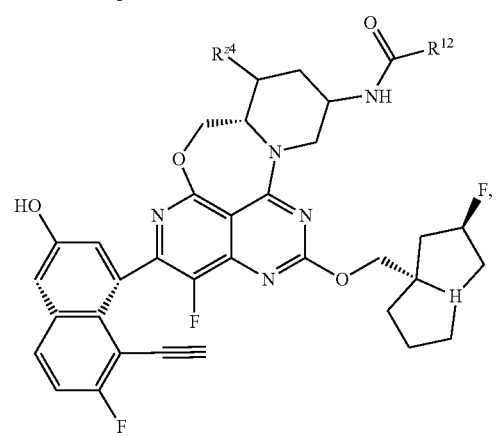
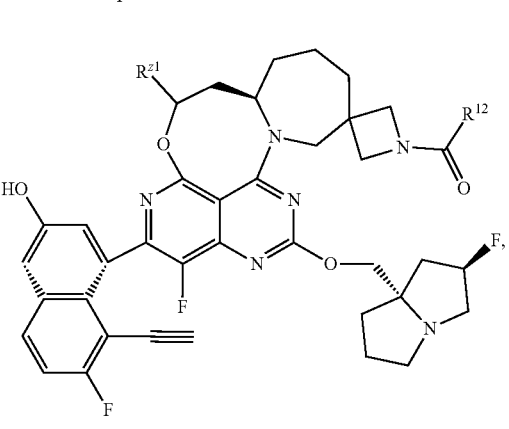
508
-continued
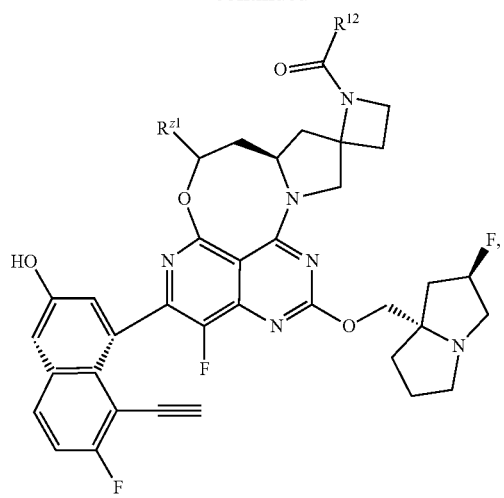
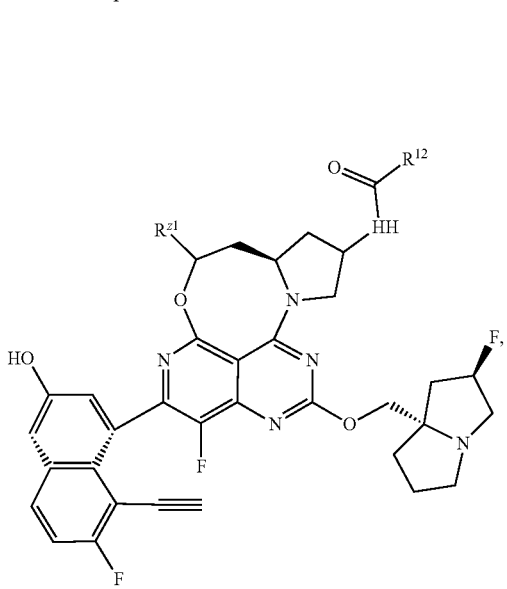
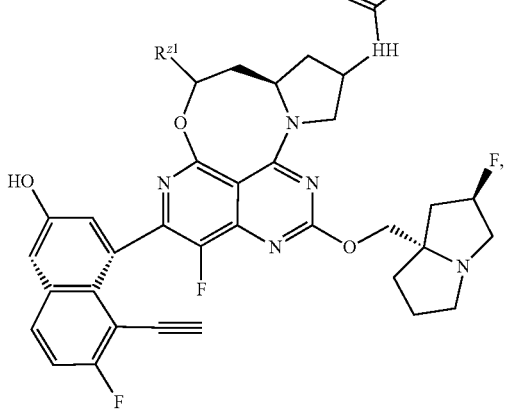
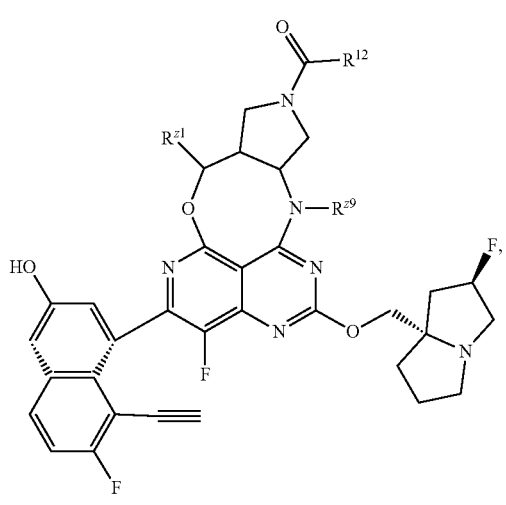
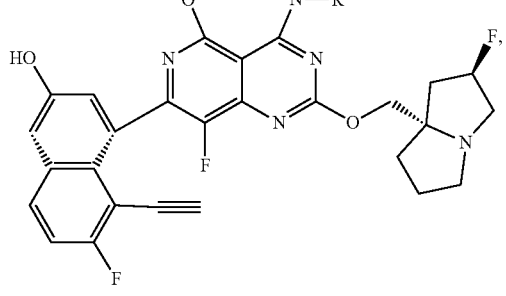

509
-continued
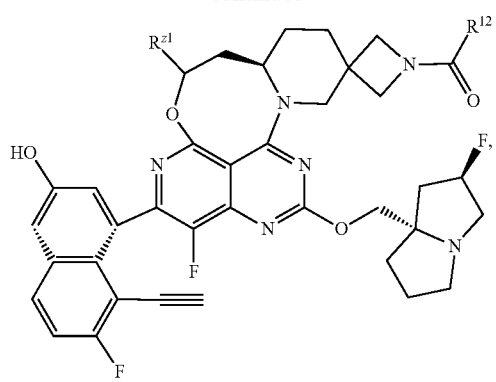
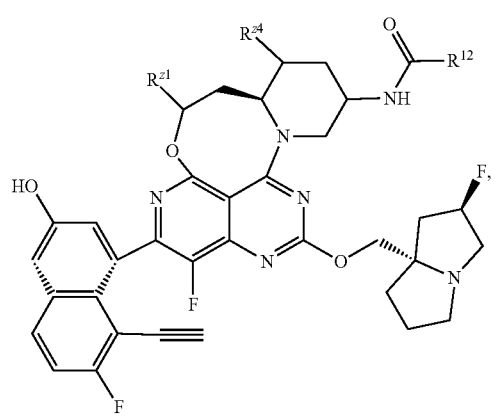
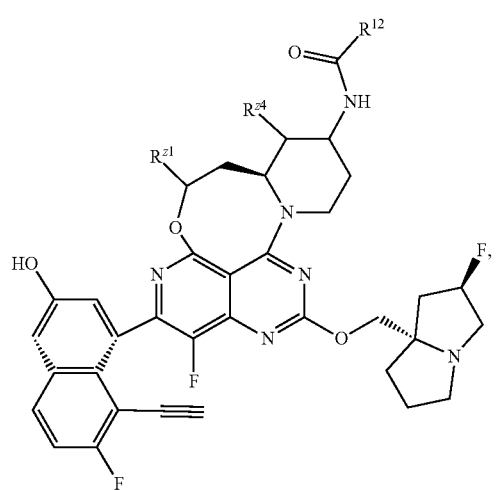
510
-continued
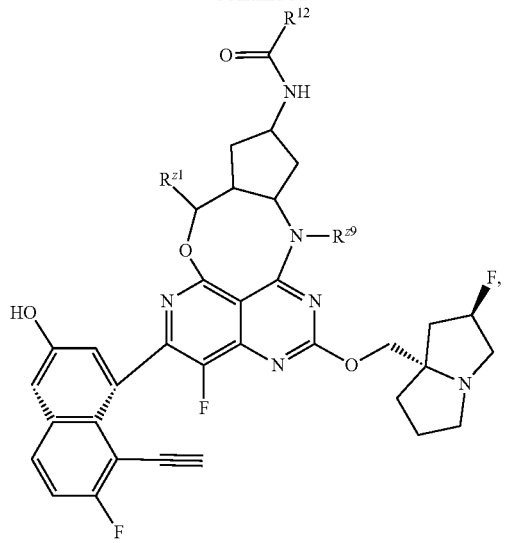
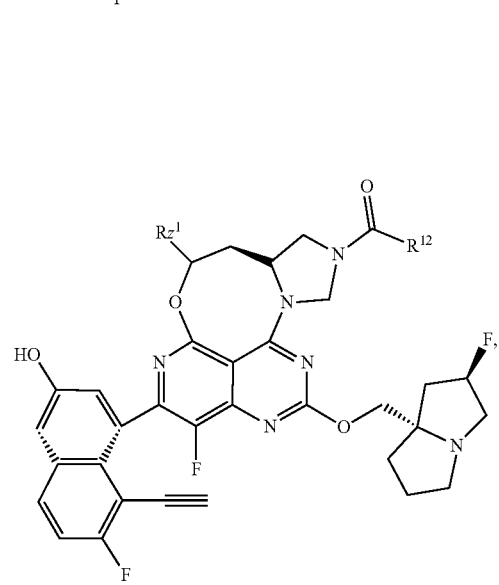
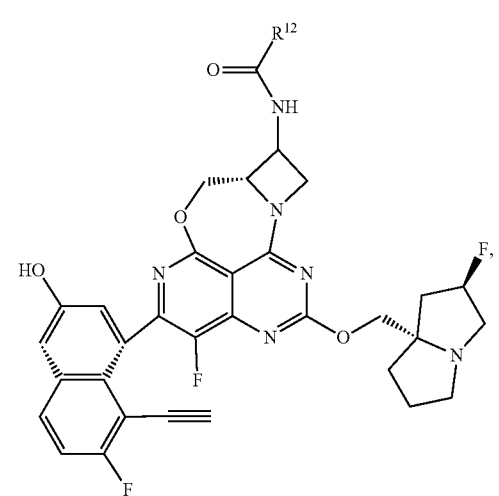

511
-continued
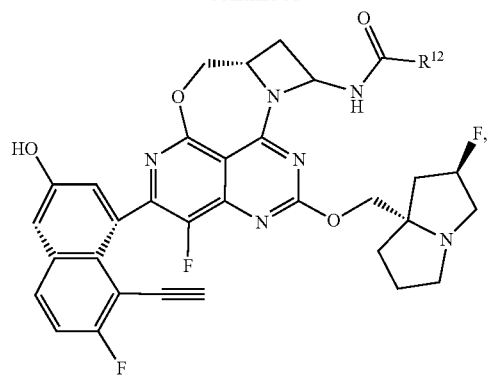
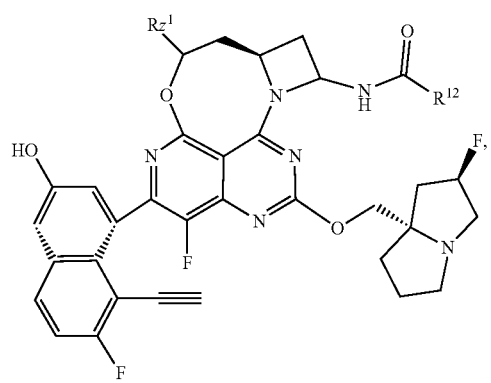
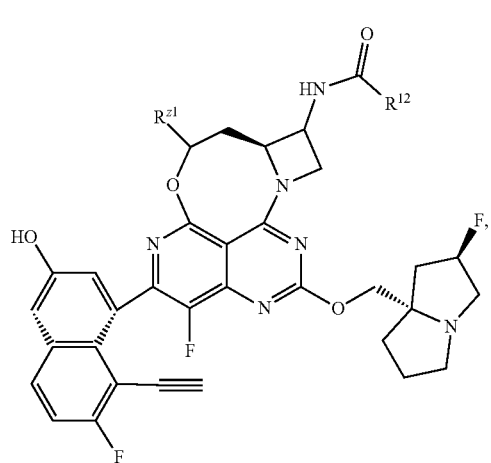
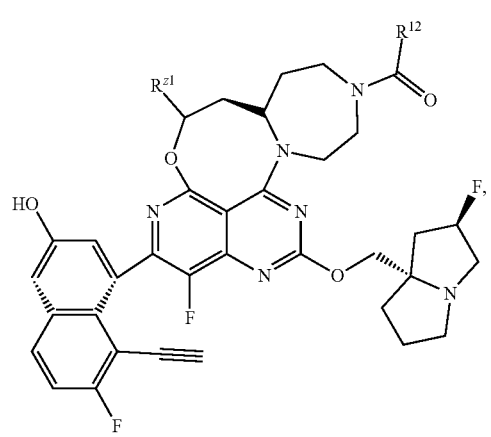
512
-continued
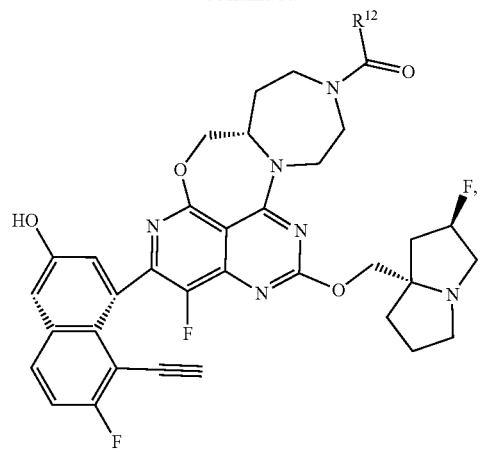
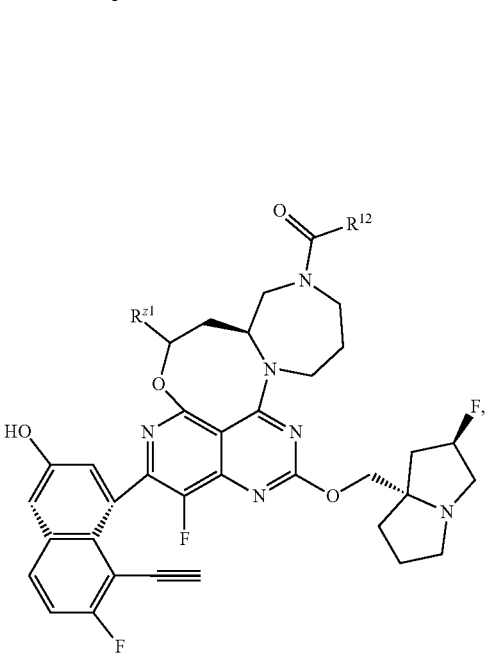
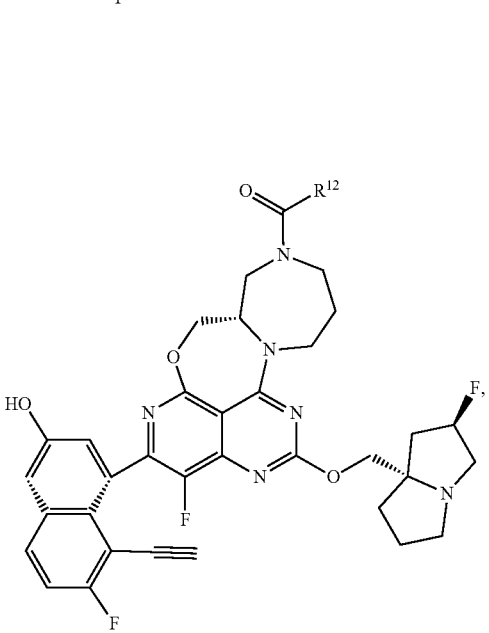

513
-continued

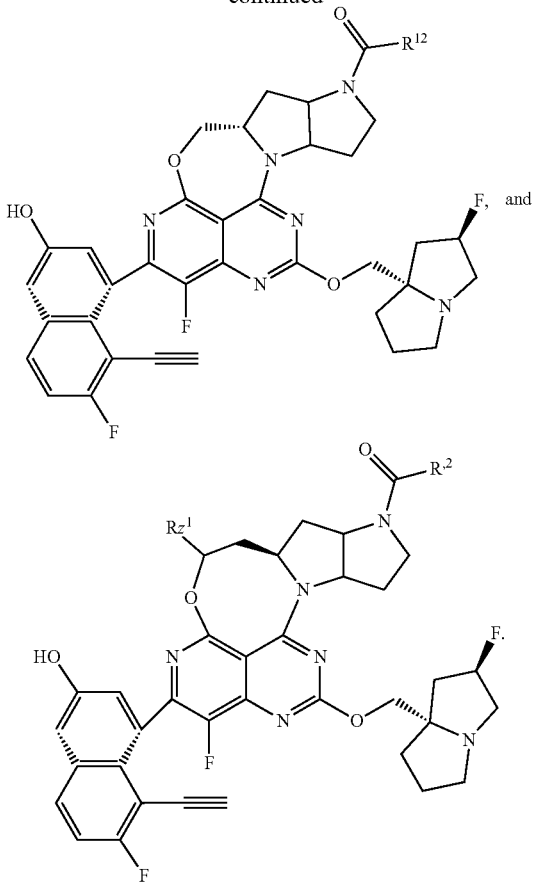

In embodiments of the formulae immediately above, $R^{12}$ is selected from

514
-continued

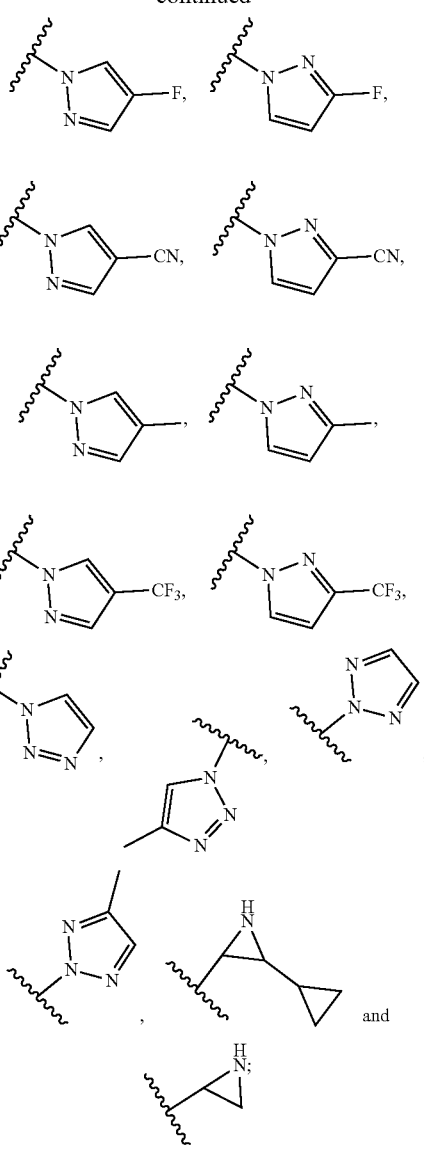

each $R^{z1}$ is independently selected from hydrogen and $C_{1-6}$alkyl, wherein $C_{1-6}$alkyl is optionally substituted with one, two, or three substituents independently selected from halogen and —OH; each $R^{z4}$ is independently selected from hydrogen, halogen, —CN, $C_{1-6}$alkyl, —OH, —NH($C_{1-6}$alkyl), —C(O)H, and —C(O)($C_{1-6}$alkyl), wherein $C_{1-6}$alkyl, is optionally substituted with one, two, or three substituents independently selected from halogen, —OH, and —CN; each $R^{z6}$ is independently selected from hydrogen and $C_{1-6}$alkyl; wherein $C_{1-6}$alkyl is optionally substituted with one, two, or three substituents independently selected from halogen, —OH, —O($C_{1-6}$alkyl), and —O($C_{1-6}$haloalkyl); each $R^{z9}$ is independently selected from hydrogen, $C_{3-4}$cycloalkyl, and $C_{1-6}$alkyl, wherein $C_{1-6}$alkyl is optionally substituted with one, two, or three substituents independently selected from halogen, —CN, $C_{3-4}$cycloalkyl, 3-4 membered heterocycloalkyl, —NH($C_{1-6}$alkyl), —N($C_{1-6}$alkyl)$_2$, —O($C_{1-6}$alkyl), and —OH; and each $R^{20z}$ is independently selected from $C_{1-6}$alkyl. In embodiments of the formulae immediately above, $R^{12}$ is selected from

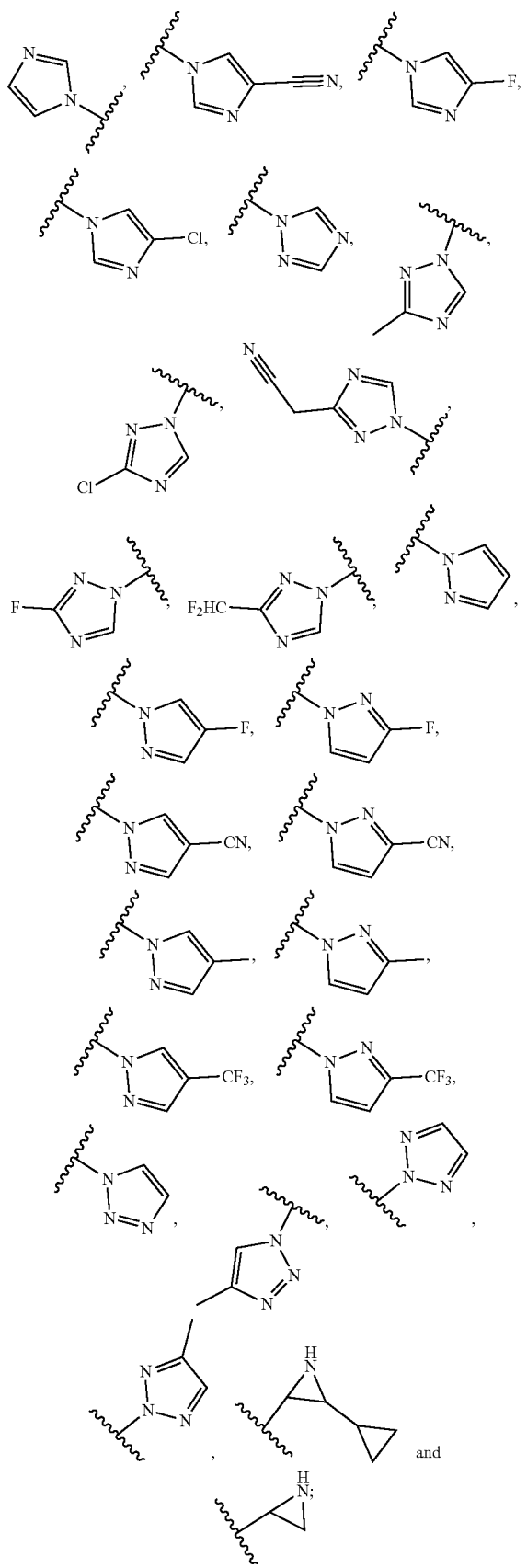

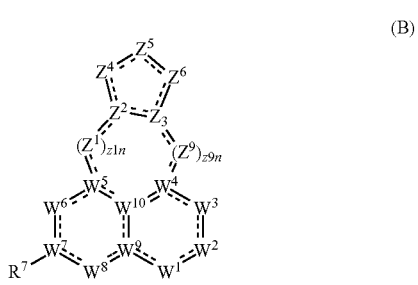

each $R^{z1}$ is independently selected from hydrogen and $C_{1-6}$alkyl, wherein $C_{1-6}$alkyl is optionally substituted with one, two, or three substituents independently selected from halogen and —OH; each $R^{z4}$ is independently selected from hydrogen, halogen, —CN, $C_{1-6}$alkyl, —OH, —NH($C_{1-6}$alkyl), —C(O)H, and —C(O)($C_{1-6}$alkyl), wherein $C_{1-6}$alkyl, is optionally substituted with one, two, or three substituents independently selected from halogen, —OH, and —CN; each $R^{z6}$ is independently selected from hydrogen and $C_{1-6}$alkyl; wherein $C_{1-6}$alkyl is optionally substituted with one, two, or three substituents independently selected from halogen, —OH, —O($C_{1-6}$alkyl), and —O($C_{1-6}$haloalkyl); each $R^{z9}$ is independently selected from hydrogen, $C_{3-4}$cycloalkyl, and $C_{1-6}$alkyl, wherein $C_{1-6}$alkyl is optionally substituted with one, two, or three substituents independently selected from halogen, —CN, $C_{3-4}$cycloalkyl, 3-4 membered heterocycloalkyl, —NH($C_{1-6}$alkyl), —N($C_{1-6}$alkyl)$_2$, —O($C_{1-6}$alkyl), and —OH; and each $R^{20z}$ is independently selected from $C_{1-6}$alkyl.

In an aspect is provided a compound of Formula (B), or a pharmaceutically acceptable salt or solvate thereof:

(B)

wherein:
$W^1$ is N($R^1$) or N;
$R^1$ is selected from hydrogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —OR$^{12}$, —SR$^{12}$, —C(O)OR$^{12}$, —OC(O)N(R$^{12}$)(R$^{13}$), —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —S(O)$_2$R$^{15}$, —S(O)$_2$N(R$^{12}$)(R$^{13}$), —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20a}$;
$W^2$ is C($R^2$), N($R^2$), C($R^2$)$_2$, C(O), S(O), S(O)$_2$, or N;
each $R^2$ is independently selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —OR$^{12a}$, —SR$^{12a}$, —N(R$^{12a}$)(R$^{13}$), —N=(R$^{15}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$)—, —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20b}$;
$W^3$ is C($R^3$), N($R^3$), C($R^3$)$_2$, C(O), S(O), S(O)$_2$, or N;

each $R^3$ is independently selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20c}$;

$W^4$ is $C(R^4)$, C, or N;

$R^4$ is selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20d}$;

$W^5$ is $C(R^5)$, C, or N;

$R^5$ is selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20e}$;

$W^6$ is $C(R^6)$, $N(R^6)$, $C(R^6)_2$, $C(O)$, $S(O)$, $S(O)_2$, or N;

each $R^6$ is independently selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20f}$;

$W^7$ is $C(R^{7a})$, C, or N;

$R^{7a}$ is selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20g}$;

$R^7$ is -$L^7$—$R^{17}$;

$L^7$ is a bond, $C_1$-$C_4$alkyl, $C_2$-$C_4$alkenyl, $C_2$-$C_4$alkynyl, 2-4 membered heteroalkylene linker, —O—, —$N(R^{7d})$—, —$C(O)$—, —S—, —$S(O)_2$—, —$S(O)$—, —$P(O)R^{7d}$—, $CR^{7c}R^{7c}$, —$OCR^{7c}R^{7c}$—, —$N(R^{7d})CR^{7c}R^{7c}$—, —$C(O)CR^{7c}R^{7c}$—, —$SCR^{7c}R^{7c}$—, —$S(O)_2CR^{7c}R^{7c}$—, —$S(O)CR^{7c}R^{7c}$—, —$P(O)R^{7d}CR^{7c}R^{7c}$—, —$CR^{7c}R^{7c}CR^{7c}R^{7c}$—, —$CR^{7c}R^{7c}O$—, —$CR^{7c}R^{7c}N(R^{7d})$—, —$CR^{7c}R^{7c}C(O)$—, —$CR^{7c}R^{7c}S$—, —$CR^{7c}R^{7c}S(O)_2$—, —$CR^{7c}R^{7c}S(O)$—, —$CR^{7c}R^{7c}P(O)R^{7d}$—, —$N(R^{7d})C(O)$—, —$N(R^{7d})S(O)_2$—, —$N(R^{7d})S(O)$—, —$N(R^{7d})P(O)R^{7d}$—, —$C(O)N(R^{7d})$—, —$S(O)_2N(R^{7d})$—, —$S(O)N(R^{7d})$—, —$P(O)R^{7d}N(R^{7d})$—, —$OC(O)$—, —$OS(O)_2$—, —$OS(O)$—, —$OP(O)R^{7d}$—, —$C(O)O$—, —$S(O)_2O$—, —$S(O)O$—, or —$P(O)R^{7d}O$—; wherein the $C_1$-$C_4$alkyl, $C_2$-$C_4$alkenyl, $C_2$-$C_4$alkynyl, 2-4 membered heteroalkylene linker are optionally substituted with one, two, or three $R^{20g}$;

each $R^{7c}$ is independently selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$, $S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20g}$;

each $R^{7d}$ is independently selected from hydrogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$C(O)OR^{12}$, —$OC(O)N(R^{12})(R^{13})$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20g}$;

$R^{17}$ is selected from $C_{3-10}$cycloalkyl, 3-10 membered heterocycloalkyl, $C_{6-10}$aryl, and 5-10 membered heteroaryl, wherein $C_{3-10}$cycloalkyl, 3-10 membered heterocycloalkyl, $C_{6-10}$aryl, and 5-10 membered heteroaryl are optionally substituted with one or more $R^{20q}$; or $L^7$ is a bond and $R^{7a}$ and $R^{17}$, together with the carbon to which they are attached, form $C_{3-10}$cycloalkyl or 3-10 membered heterocycloalkyl, wherein the $C_{3-10}$cycloalkyl and 3-10 membered heterocycloalkyl are optionally substituted with one or more $R^{20q}$;

$W^8$ is $C(R^8)$, $N(R^8)$, $C(R^8)_2$, $C(O)$, $S(O)$, $S(O)_2$, or N;

each $R^8$ is independently selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20h}$;

$W^9$ is $C(R^9)$, C, or N;

$R^9$ is selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20i}$;

$W^{10}$ $C(R^{10})$, C, or N;

$R^{10}$ is selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20j}$;

each $Z^1$ is independently $C(R^{z1})$, $N(R^{z1})$, $C(R^{z1})_2$, $C(O)$, $S(O)$, $S(O)_2$, O, S, or N;

z1n is 0, 1, 2, or 3; wherein if z1n is 0 then $Z^2$ is directly bonded to $W^5$;

each $R^{z1}$ is independently selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20z1}$;

each $Z^9$ is independently $C(R^{z9})$, $N(R^{z9})$, $C(R^{z9})_2$, $C(O)$, $S(O)$, $S(O)_2$, O, S, or N;

z9n is 0, 1, 2, or 3; wherein if z9n is 0 then $Z^3$ is directly bonded to $W^4$;

each $R^{z9}$ is independently selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20z9}$;

wherein the sum of z1n and z9n is 2 or 3;

$Z^2$ is $C(R^{z2})$, C, or N;

$R^{z2}$ is selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20z2}$;

$Z^3$ is $C(R^{z3})$, C, or N;

$R^{z3}$ is selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20z3}$;

$Z^4$ is a bond, $Z^{4a}$, $Z^{4a}Z^{4b}$, $Z^{4a}Z^{4b}Z^{4c}$, or $Z^{4a}Z^{4b}Z^{4c}Z^{4d}$; wherein $Z^{4a}$ is directly bonded to $Z^2$; and wherein if $Z^4$ is a bond then $Z^2$ is directly bonded to $Z^5$;

$Z^{4a}$, $Z^{4b}$, $Z^{4c}$, and $Z^{4d}$ are independently $C(R^{z4})$, $N(R^{z4})$, $C(R^{z4})_2$, $C(O)$, $S(O)$, $S(O)_2$, $S(O)(NR^{z4})$, O, S, or N; provided that:

i) if z9n is 0 and $Z^4$ is $Z^{4a}Z^{4b}$; then (1) $Z^{4b}$ is $C(R^{z4})$, $C(R^{z4})_2$, $C(O)$, $S(O)$, $S(O)_2$, $S(O)(NR^{z4})$, O, S, or N, (2) $Z^{4b}$ is $N(R^{z4})$ and $Z^{4a}$ is $C(O)$, $S(O)$, or $S(O)_2$; (3) $Z^{4b}$ is $N(R^{z4})$ and $Z^5$ is $C(O)$, $S(O)$, or $S(O)_2$; or (4) $Z^{4b}$ is $N(R^{z4})$ and $Z^3$ is $C(R^{z3})$ or C; and ii) one $R^{z4}$, $R^{z5}$, $R^{z6}$, $R^{20z4}$, $R^{20z5}$, $R^{20z6}$, or $R^{20z}$ is independently selected from —$C(O)R^{12}$ and —$N(H)C(O)R^{12}$; wherein the one $R^{12}$ is selected from $C_{3-10}$cycloalkyl, $C_{2-9}$heterocycloalkyl, $C_{6-10}$aryl, and $C_{1-9}$heteroaryl, wherein $C_{3-10}$cycloalkyl, $C_{2-9}$heterocycloalkyl, $C_{6-10}$aryl, and $C_{1-9}$heteroaryl are optionally substituted with one, two, or three $R^{20l}$;

each $R^{z4}$ is independently selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{12}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{12}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20z4}$; or two $R^{z4}$ bonded to the same carbon are joined to form $C_{2-6}$alkenyl optionally substituted with one, two, or three $R^{20z4}$;

$Z^5$ is $C(R^{z5})$, $N(R^{z5})$, $C(R^{z5})_2$, $C(O)$, $S(O)$, $S(O)_2$, $S(O)(NR^{z5})$, O, S, or N;

each $R^{z5}$ is independently selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{12}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{12}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20z5}$; or two $R^{z5}$ bonded to the same carbon are joined to form $C_{2-6}$alkenyl optionally substituted with one, two, or three $R^{20z5}$;

$Z^6$ is $C(R^{z6})$, $N(R^{z6})$, $C(R^{z6})_2$, $C(O)$, $S(O)$, $S(O)_2$, $S(O)(NR^{z6})$, O, S, or N;

each $R^{z6}$ is independently selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{12}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{12}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20z6}$; or two $R^{z6}$ bonded to the same carbon are joined to form $C_{2-6}$alkenyl optionally substituted with one, two, or three $R^{20z6}$;

and further wherein the compound optionally includes one of the following:

(1) two $R^{z4}$ bonded to the same carbon atom are joined to form monocyclic $C_{3-7}$cycloalkyl or monocyclic 3-7 membered heterocycloalkyl, wherein the monocyclic $C_{3-7}$cycloalkyl and monocyclic 3-7 membered heterocycloalkyl are optionally substituted with one, two, or three $R^{20z}$;

(2) two or more $R^{z4}$ bonded to adjacent atoms are joined to form monocyclic $C_{3-7}$cycloalkyl, monocyclic 3-7 membered heterocycloalkyl, phenyl, or monocyclic 5-6 membered heteroaryl, wherein the monocyclic $C_{3-7}$cycloalkyl, monocyclic 3-7 membered heterocycloalkyl, phenyl, and monocyclic 5-6 membered heteroaryl are optionally substituted with one, two, or three $R^{20z}$;

(3) two $R^{z5}$ bonded to the same carbon atom are joined to form monocyclic $C_{3-7}$cycloalkyl or monocyclic 3-7 membered heterocycloalkyl, wherein the monocyclic $C_{3-7}$cycloalkyl and monocyclic 3-7 membered heterocycloalkyl are optionally substituted with one, two, or three $R^{20z}$;

(4) one or two $R^{z4}$ bonded to one atom and one or two $R^{z5}$ bonded to an adjacent atom are joined to form monocyclic $C_{3-7}$cycloalkyl, monocyclic 3-7 membered heterocycloalkyl, phenyl, or monocyclic 5-6 membered heteroaryl, wherein the monocyclic $C_{3-7}$cycloalkyl, monocyclic 3-7 membered heterocycloalkyl, phenyl, and monocyclic 5-6 membered heteroaryl are optionally substituted with one, two, or three $R^{20z}$;

(5) one or two $R^{z4}$ bonded to one atom and one or two $R^{z5}$ bonded to a second atom are joined to form monocyclic $C_{3-7}$cycloalkyl or monocyclic 3-7 membered heterocycloalkyl, wherein the monocyclic $C_{3-7}$cycloalkyl and monocyclic 3-7 membered heterocycloalkyl are optionally substituted with one, two, or three $R^{20z}$;

(6) two $R^{z6}$ bonded to the same carbon atom are joined to form monocyclic $C_{3-7}$cycloalkyl or monocyclic 3-7 membered heterocycloalkyl, wherein the monocyclic $C_{3-7}$cycloalkyl and monocyclic 3-7 membered heterocycloalkyl are optionally substituted with one, two, or three $R^{20z}$;

(7) one or two $R^{z5}$ bonded to one atom and one or two $R^{z6}$ bonded to an adjacent atom are joined to form monocyclic $C_{3-7}$cycloalkyl, monocyclic 3-7 membered heterocycloalkyl, phenyl, or monocyclic 5-6 membered heteroaryl, wherein the monocyclic $C_{3-7}$cycloalkyl, monocyclic 3-7 membered heterocycloalkyl, phenyl, and monocyclic 5-6 membered heteroaryl are optionally substituted with one, two, or three $R^{20z}$; or (8) one or two $R^{z4}$ bonded to one atom and one or two $R^{z6}$ bonded to a second atom are joined to form monocyclic $C_{3-7}$cycloalkyl or monocyclic 3-7 membered heterocycloalkyl, wherein the monocyclic $C_{3-7}$cycloalkyl and monocyclic 3-7 membered heterocycloalkyl are optionally substituted with one, two, or three $R^{20z}$;

each $R^{12}$ is independently selected from hydrogen, $C_{1-6}$alkyl, $C_{2-6}$alkenyl, $C_{2-6}$alkynyl, $C_{3-10}$cycloalkyl, —$CH_2$-$C_{3-10}$cycloalkyl, $C_{2-9}$heterocycloalkyl, —$CH_2$-$C_{2-9}$heterocycloalkyl, $C_{6-10}$aryl, —$CH_2$-$C_{6-10}$aryl, —$CH_2$-$C_{1-9}$heteroaryl, and $C_{1-9}$heteroaryl, wherein $C_{1-6}$alkyl, $C_{2-6}$alkenyl, $C_{2-6}$alkynyl, $C_{3-10}$cycloalkyl, —$CH_2$-$C_{3-10}$cycloalkyl, $C_{2-9}$heterocycloalkyl, —$CH_2$-$C_{2-9}$heterocycloalkyl, $C_{6-10}$aryl, —$CH_2$-$C_{6-10}$aryl, —$CH_2$-$C_{1-9}$heteroaryl, and $C_{1-9}$heteroaryl are optionally substituted with one, two, or three $R^{20l}$;

$R^{12a}$ is independently selected from hydrogen, $C_{1-6}$alkyl, $C_{2-6}$alkenyl, $C_{2-6}$alkynyl, $C_{3-10}$cycloalkyl, —$C(R^{12c})_2$-$C_{3-10}$cycloalkyl, $C_{2-9}$heterocycloalkyl, —$C(R^{12c})_2$-$C_{2-9}$heterocycloalkyl, $C_{6-10}$aryl, —$C(R^{12c})_2$-$C_{6-10}$aryl, —$C(R^{12c})_2$-$C_{1-9}$heteroaryl, and $C_{1-9}$heteroaryl, wherein $C_{1-6}$alkyl, $C_{2-6}$alkenyl, $C_{2-6}$alkynyl, $C_{3-10}$cycloalkyl, $-C(R^{12c})_2-C_{3-10}$cycloalkyl, $C_{2-9}$heterocycloalkyl, $-C(R^{12c})_2-C_{2-9}$heterocycloalkyl, $C_{6-10}$aryl, $-C(R^{12c})_2-C_{6-10}$aryl, $-C(R^{12c})_2-C_{1-9}$heteroaryl, and $C_{1-9}$heteroaryl are optionally substituted with one, two, or three $R^{20l}$;

each $R^{12c}$ is independently selected from hydrogen and $R^{20lc}$;

each $R^{13}$ is independently selected from hydrogen, $C_{1-6}$alkyl, and $C_{1-6}$haloalkyl; or $R^{12}$ and $R^{13}$, together with the nitrogen to which they are attached, form a $C_{2-9}$heterocycloalkyl ring optionally substituted with one, two, or three $R^{20m}$;

each $R^{14}$ is independently selected from hydrogen, $C_{1-6}$alkyl, and $C_{1-6}$haloalkyl;

each $R^{15}$ is independently selected from $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20o}$;

each $R^{20z1}$, $R^{20z2}$, $R^{20z3}$, $R^{20z4}$, $R^{20z5}$, $R^{20z6}$, and $R^{20z9}$ is independently selected from halogen, oxo, $-CN$, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, $-OR^{12}$, $-SR^{12}$, $-N(R^{12})(R^{13})$, $-C(O)OR^{12}$, $-OC(O)N(R^{12})(R^{13})$, $-N(R^{14})C(O)N(R^{12})(R^{13})$, $-N(R^{14})C(O)OR^{15}$, $-N(R^{14})S(O)_2R^{15}$, $-C(O)R^{12}$, $-S(O)R^{15}$, $-OC(O)R^{15}$, $-C(O)N(R^{12})(R^{13})$, $-C(O)C(O)N(R^{12})(R^{13})$, $-N(R^{14})C(O)R^{12}$, $-S(O)_2R^{15}$, $-S(O)_2N(R^{12})(R^{13})$, $-S(=O)(=NH)N(R^{12})(R^{13})$, $-CH_2C(O)N(R^{12})(R^{13})$, $-CH_2N(R^{14})C(O)R^{15}$, $-CH_2S(O)_2R^{15}$, and $-CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20z}$;

each $R^{20z}$ is independently selected from halogen, oxo, $-CN$, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, $-OR^{12}$, $-SR^{12}$, $-N(R^{12})(R^{13})$, $-C(O)OR^{12}$, $-OC(O)N(R^{12})(R^{13})$, $-N(R^{14})C(O)N(R^{12})(R^{13})$, $-N(R^{14})C(O)OR^{15}$, $-N(R^{14})S(O)_2R^{15}$, $-C(O)R^{12}$, $-S(O)R^{15}$, $-OC(O)R^{15}$, $-C(O)N(R^{12})(R^{13})$, $-C(O)C(O)N(R^{12})(R^{13})$, $-N(R^{14})C(O)R^{12}$, $-S(O)_2R^{15}$, $-S(O)_2N(R^{12})(R^{13})$, $-S(=O)(=NH)N(R^{12})(R^{13})$, $-CH_2C(O)N(R^{12})(R^{13})$, $-CH_2N(R^{14})C(O)R^{15}$, $-CH_2S(O)_2R^{15}$, and $-CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20zz}$;

two $R^{20z}$ bonded to the same carbon atom are optionally joined to form monocyclic $C_{3-7}$cycloalkyl or monocyclic 3-7 membered heterocycloalkyl, wherein the monocyclic $C_{3-7}$cycloalkyl and monocyclic 3-7 membered heterocycloalkyl are optionally substituted with one, two, or three $R^{20zz}$; or two or more $R^{20z}$ bonded to two adjacent atoms are optionally joined to form monocyclic $C_{3-7}$cycloalkyl, monocyclic 3-7 membered heterocycloalkyl, phenyl, or monocyclic 5-6 membered heteroaryl, wherein the $C_{3-7}$cycloalkyl, monocyclic 3-7 membered heterocycloalkyl, phenyl, and monocyclic 5-6 membered heteroaryl are optionally substituted with one, two, or three $R^{20zz}$;

each $R^{20a}$, $R^{20b}$, $R^{20c}$, $R^{20d}$, $R^{20e}$, $R^{20f}$, $R^{20g}$, $R^{20h}$, $R^{20i}$, $R^{20j}$, $R^{20lc}$, $R^{20l}$, $R^{20m}$, $R^{20o}$, $R^{20q}$, and $R^{20zz}$ is independently selected from halogen, oxo, $-CN$, $C_{1-6}$alkyl, $C_{2-6}$alkenyl, $C_{2-6}$alkynyl, $C_{3-10}$cycloalkyl, $-CH_2-C_{3-10}$cycloalkyl, $C_{2-9}$heterocycloalkyl, $-CH_2-C_{2-9}$heterocycloalkyl, $C_{6-10}$aryl, $-CH_2-C_{6-10}$aryl, $-CH_2-C_{1-9}$heteroaryl, $C_{1-9}$heteroaryl, $-OR^{21}$, $-SR^{21}$, $-N(R^{22})(R^{23})$, $-C(O)OR^{22}$, $-C(O)N(R^{22})(R^{23})$, $-C(O)C(O)N(R^{22})(R^{23})$, $-OC(O)N(R^{22})(R^{23})$, $-N(R^{24})C(O)N(R^{22})(R^{23})$, $-N(R^{24})C(O)OR^{25}$, $-N(R^{24})C(O)R^{21}$, $-N(R^{24})S(O)_2R^{25}$, $-C(O)R^{21}$, $-S(O)_2R^{25}$, $-S(O)_2N(R^{22})(R^{23})$, $-OCH_2C(O)OR^{22}$, $=NR^{21}$, and $-OC(O)R^{25}$; two $R^{20q}$ bonded to adjacent atoms are optionally joined to form a $C_{3-10}$cycloalkyl, $C_{2-9}$heterocycloalkyl, $C_{6-10}$aryl, or $C_{1-9}$heteroaryl; wherein $C_{1-6}$alkyl, $C_{2-6}$alkenyl, $C_{2-6}$alkynyl, $C_{3-10}$cycloalkyl, $-CH_2-C_{3-10}$cycloalkyl, $C_{2-9}$heterocycloalkyl, $-CH_2-C_{2-9}$heterocycloalkyl, $C_{6-10}$aryl, $-CH_2-C_{6-10}$aryl, $-CH_2-C_{1-9}$heteroaryl, and $C_{1-9}$heteroaryl are optionally substituted with one, two, or three groups independently selected from halogen, oxo, $-CN$, $C_{1-6}$alkyl, $C_{1-6}$haloalkyl, $C_{1-6}$alkoxy, $C_{1-6}$haloalkoxy, $-OR^{21}$, $-SR^{21}$, $-N(R^{22})(R^{23})$, $-C(O)OR^{22}$, $-C(O)N(R^{22})(R^{23})$, $-C(O)C(O)N(R^{22})(R^{23})$, $-OC(O)N(R^{22})(R^{23})$, $-N(R^{24})C(O)N(R^{22})(R^{23})$, $-N(R^{24})C(O)OR^{25}$, $-N(R^{24})C(O)R^{25}$, $-N(R^{24})S(O)_2R^{25}$, $-C(O)R^{25}$, $-S(O)_2R^{25}$, $-S(O)_2N(R^{22})(R^{23})$, and $-OC(O)R^{25}$;

each $R^{21}$ is independently selected from hydrogen, $C_{1-6}$alkyl, $C_{1-6}$haloalkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl;

each $R^{21b}$ is independently selected from hydrogen, halogen, $C_{1-6}$alkyl, $C_{1-6}$haloalkyl, $C_{3-10}$cycloalkyl, and $C_{2-9}$heterocycloalkyl, or two $R^{21b}$ are taken together with the carbon atom to which they are attached to form $C_{3-10}$cycloalkyl or $C_{2-9}$heterocycloalkyl, each of which is optionally substituted with one or more substituents independently selected from halogen, $C_{1-3}$alkyl, $C_{1-3}$haloalkyl, and $-OH$;

each $R^{22}$ is independently selected from hydrogen, $C_{1-6}$alkyl, $C_{1-6}$haloalkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl;

each $R^{23}$ is independently selected from hydrogen and $C_{1-6}$alkyl;

each $R^{24}$ is independently selected from hydrogen and $C_{1-6}$alkyl;

each $R^{25}$ is independently selected from $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; and ===== indicates a single or double bond such that all valences are satisfied.

In an aspect is provided a compound of Formula (B), or a pharmaceutically acceptable salt or solvate thereof:

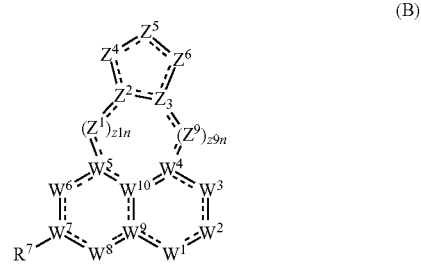

(B)

wherein:

$W^1$ is $N(R^1)$ or N;

$R^1$ is selected from hydrogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$C(O)OR^{12}$, —$OC(O)N(R^{12})(R^{13})$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20a}$;

$W^2$ is $C(R^2)$, $N(R^2)$, $C(R^2)_2$, C(O), S(O), $S(O)_2$, or N;

each $R^2$ is independently selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12a}$, —$SR^{12a}$, —$N(R^{12a})(R^{13})$, —$N=(R^{15})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$—, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20b}$;

$W^3$ is $C(R^3)$, $N(R^3)$, $C(R^3)_2$, C(O), S(O), $S(O)_2$, or N;

each $R^3$ is independently selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20c}$;

$W^4$ is $C(R^4)$, C, or N;

$R^4$ is selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20d}$;

$W^5$ is $C(R^5)$, C, or N;

$R^5$ is selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20e}$;

$W^6$ is $C(R^6)$, $N(R^6)$, $C(R^6)_2$, C(O), S(O), $S(O)_2$, or N;

each $R^6$ is independently selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20f}$;

$W^7$ is $C(R^{7a})$, C, or N;

$R^{7a}$ selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20g}$;

$R^7$ is -$L^7$—$R^{17}$;

$L^7$ is a bond, $C_1$-$C_4$alkyl, $C_2$-$C_4$alkenyl, $C_2$-$C_4$alkynyl, 2-4 membered heteroalkylene linker, —O—, —$N(R^{7d})$—, —C(O)—, —S—, —$S(O)_2$—, —S(O)—, —$P(O)R^{7d}$—, $CR^{7c}R^{7c}$—, —$OCR^{7c}$—, —$N(R^{7d})CR^{7c}R^{7c}$—, —$C(O)CR^{7c}R^{7c}$—, —$SCR^{7c}R^{7c}$—, —$S(O)_2CR^{7c}R^{7c}$—, —$S(O)CR^{7c}R^{7c}$—, —P(O)$R^{7d}CR^{7c}R^{7c}$—, —$CR^{7c}R^{7c}CR^{7c}R^{7c}$, —$CR^{7c}R^{7c}O$—, —$CR^{7c}R^{7c}N(R^{7d})$—, —$CR^{7c}R^{7c}C(O)$—, —$CR^{7c}R^{7c}S$—, —$CR^{7c}R^{7c}S(O)_2$—, —$CR^{7c}R^{7c}S(O)$—, —$CR^{7c}R^{7c}P(O)R^{7d}$—, —$N(R^{7d})C(O)$—, —$N(R^{7d})S(O)_2$—, —$N(R^{7d})S(O)$—, —$N(R^{7d})P(O)R^{7d}$—, —$C(O)N(R^{7d})$—, —$S(O)_2N(R^{7d})$—, —$S(O)N(R^{7d})$—, —$P(O)R^{7d}N(R^{7d})$—, —OC(O)—, —$OS(O)_2$—, —OS(O)—, —$OP(O)R^{7d}$—, —C(O)O—, —$S(O)_2O$—, —S(O)O—, or —$P(O)R^{7d}O$—; wherein the $C_1$-$C_4$alkyl, $C_2$-$C_4$alkenyl, $C_2$-$C_4$alkynyl, 2-4 membered heteroalkylene linker are optionally substituted with one, two, or three $R^{20g}$;

each $R^{7c}$ is independently selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —S(O)$_2$R$^{15}$, —S(O)$_2$N(R$^{12}$)(R$^{13}$), S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl are optionally substituted with one, two, or three R$^{20g}$;

each R$^{7d}$ is independently selected from hydrogen, —CN, C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, C$_{1-9}$heteroaryl, —OR$^{12}$, —SR$^{12}$, —C(O)OR$^{12}$, —OC(O)N(R$^{12}$)(R$^{13}$), —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —S(O)$_2$R$^{15}$, —S(O)$_2$N(R$^{12}$)(R$^{13}$), —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl are optionally substituted with one, two, or three R$^{20g}$;

R$^{17}$ is selected from C$_{3-10}$cycloalkyl, 3-10 membered heterocycloalkyl, C$_{6-10}$aryl, and 5-10 membered heteroaryl, wherein C$_{3-10}$cycloalkyl, 3-10 membered heterocycloalkyl, C$_{6-10}$aryl, and 5-10 membered heteroaryl are optionally substituted with one or more R$^{20q}$; or L$^7$ is a bond and R$^{7a}$ and R$^{17}$, together with the carbon to which they are attached, form C$_{3-10}$cycloalkyl or 3-10 membered heterocycloalkyl, wherein the C$_{3-10}$cycloalkyl and 3-10 membered heterocycloalkyl are optionally substituted with one or more R$^{20q}$;

W$^8$ is C(R$^8$), N(R$^8$), C(R$^8$)$_2$, C(O), S(O), S(O)$_2$, or N;

each R$^8$ is independently selected from hydrogen, halogen, —CN, C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, C$_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$), —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl are optionally substituted with one, two, or three R$^{20h}$;

W$^9$ is C(R$^9$), C, or N;

R$^9$ is selected from hydrogen, halogen, —CN, C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, C$_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$), —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl are optionally substituted with one, two, or three R$^{20i}$;

W$^{10}$ C(R$^{10}$), C, or N;

R$^{10}$ is selected from hydrogen, halogen, —CN, C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, C$_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$), —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl are optionally substituted with one, two, or three R$^{20j}$;

each Z$^1$ is independently C(R$^{z1}$), N(R$^{z1}$), C(R$^{z1}$)$_2$, C(O), S(O), S(O)$_2$, O, S, or N;

z1n is 0, 1, 2, or 3; wherein if z1n is 0 then Z$^2$ is directly bonded to W$^5$;

each R$^{z1}$ is independently selected from hydrogen, halogen, —CN, C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, C$_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$), —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl are optionally substituted with one, two, or three R$^{20z1}$;

each Z$^9$ is independently C(R$^{z9}$), N(R$^{z9}$), C(R$^{z9}$)$_2$, C(O), S(O), S(O)$_2$, O, S, or N;

z9n is 0, 1, 2, or 3; wherein if z9n is 0 then Z$^3$ is directly bonded to W$^4$;

each R$^{z9}$ is independently selected from hydrogen, halogen, —CN, C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, C$_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$), —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl are optionally substituted with one, two, or three R$^{20z9}$;

wherein the sum of z1n and z9n is 2 or 3;

Z$^2$ is C(R$^{z2}$), C, or N;

R$^{z2}$ is selected from hydrogen, halogen, —CN, C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, C$_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$), —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl are optionally substituted with one, two, or three R$^{20z2}$;

Z$^3$ is C(R$^{z3}$), C, or N;

R$^{z3}$ is selected from hydrogen, halogen, —CN, C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, C$_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$), —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl are optionally substituted with one, two, or three R$^{20z3}$;

Z$^4$ is a bond, Z$^{4a}$, Z$^{4a}$Z$^{4b}$, Z$^{4a}$Z$^{4b}$Z$^{4c}$, or Z$^{4a}$Z$^{4b}$Z$^{4c}$Z$^{4d}$; wherein Z$^{4a}$ is directly bonded to Z$^2$; and wherein if Z$^4$ is a bond then Z$^2$ is directly bonded to Z$^5$;

Z$^{4a}$, Z$^{4b}$, Z$^{4c}$, and Z$^{4d}$ are independently C(R$^{z4}$), N(R$^{z4}$), C(R$^{z4}$)$_2$, C(O), S(O), S(O)$_2$, S(O)(NR$^{z4}$), O, S, or N; provided that:

i) if z9n is 0 and Z$^4$ is Z$^{4a}$Z$^{4b}$; then (1) Z$^{4b}$ is C(R$^{z4}$), C(R$^{z4}$)$_2$, C(O), S(O), S(O)$_2$, S(O)(NR$^{z4}$), O, S, or N, (2) Z$^{4b}$ is N(R$^{z4}$) and Z$^{4a}$ is C(O), S(O), or S(O)$_2$; (3) Z$^{4b}$ is N(R$^{z4}$) and Z$^5$ is C(O), S(O), or S(O)$_2$; or (4) Z$^{4b}$ is N(R$^{z4}$) and Z$^3$ is C(R$^{z3}$) or C; and ii) one or more of R$^{z4}$, R$^{z5}$, R$^{z6}$, R$^{20z4}$, R$^{20z5}$, R$^{20z6}$, or R$^{20z}$ or one or more of the joining of two substituents selected from R$^{z4}$, R$^{z5}$, R$^{z6}$, R$^{20z}$, and R$^{20zz}$ is E, wherein E is a moiety capable of covalently binding to a Ras mutant protein at an amino acid corresponding to G12D or G12S of human K-Ras mutant G12D or G12S protein, respectively:

each R$^{z4}$ is independently selected from E, hydrogen, halogen, —CN, C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, C$_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{12}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{12}$, —S(O)$_2$R$^{15}$, —S(O)$_2$N(R$^{12}$)(R$^{13}$), —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl are optionally substituted with one, two, or three R$^{20z4}$; or two R$^{z4}$ bonded to the same carbon are joined to form C$_{2-6}$alkenyl optionally substituted with one, two, or three R$^{20z4}$;

Z$^5$ is C(R$^{z5}$), N(R$^{z5}$), C(R$^{z5}$)$_2$, C(O), S(O), S(O)$_2$, S(O)(NR$^{z5}$), O, S, or N;

each R$^{z5}$ is independently selected from E, hydrogen, halogen, —CN, C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, C$_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{12}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{12}$, —S(O)$_2$R$^{15}$, —S(O)$_2$N(R$^{12}$)(R$^{13}$), —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl are optionally substituted with one, two, or three R$^{20z5}$; or two R$^{z5}$ bonded to the same carbon are joined to form C$_{2-6}$alkenyl optionally substituted with one, two, or three R$^{20z5}$;

Z$^6$ is C(R$^{z6}$), N(R$^{z6}$), C(R$^{z6}$)$_2$, C(O), S(O), S(O)$_2$, S(O)(NR$^{z6}$), O, S, or N;

each R$^{z6}$ is independently selected from E, hydrogen, halogen, —CN, C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, C$_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{12}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{12}$, —S(O)$_2$R$^{15}$, —S(O)$_2$N(R$^{12}$)(R$^{13}$), —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl are optionally substituted with one, two, or three R$^{20z6}$; or two R$^{z6}$ bonded to the same carbon are joined to form C$_{2-6}$alkenyl optionally substituted with one, two, or three R$^{20z6}$;

and further wherein the compound optionally includes one of the following:

(1) two R$^{z4}$ bonded to the same carbon atom are joined to form monocyclic C$_{3-7}$cycloalkyl or monocyclic 3-7 membered heterocycloalkyl, wherein the monocyclic C$_{3-7}$cycloalkyl and monocyclic 3-7 membered heterocycloalkyl are optionally substituted with one, two, or three R$^{20z}$;

(2) two or more R$^{z4}$ bonded to adjacent atoms are joined to form monocyclic C$_{3-7}$cycloalkyl, monocyclic 3-7 membered heterocycloalkyl, phenyl, or monocyclic 5-6 membered heteroaryl, wherein the monocyclic C$_{3-7}$cycloalkyl, monocyclic 3-7 membered heterocycloalkyl, phenyl, and monocyclic 5-6 membered heteroaryl are optionally substituted with one, two, or three R$^{20z}$;

(3) two R$^{z5}$ bonded to the same carbon atom are joined to form monocyclic C$_{3-7}$cycloalkyl or monocyclic 3-7 membered heterocycloalkyl, wherein the monocyclic C$_{3-7}$cycloalkyl and monocyclic 3-7 membered heterocycloalkyl are optionally substituted with one, two, or three R$^{20z}$;

(4) one or two R$^{z4}$ bonded to one atom and one or two R$^{z5}$ bonded to an adjacent atom are joined to form monocyclic C$_{3-7}$cycloalkyl, monocyclic 3-7 membered heterocycloalkyl, phenyl, or monocyclic 5-6 membered heteroaryl, wherein the monocyclic C$_{3-7}$cycloalkyl, monocyclic 3-7 membered heterocycloalkyl, phenyl, and monocyclic 5-6 membered heteroaryl are optionally substituted with one, two, or three R$^{20z}$;

(5) one or two R$^{z4}$ bonded to one atom and one or two R$^{z5}$ bonded to a second atom are joined to form monocyclic C$_{3-7}$cycloalkyl or monocyclic 3-7 membered heterocycloalkyl, wherein the monocyclic C$_{3-7}$cycloalkyl and monocyclic 3-7 membered heterocycloalkyl are optionally substituted with one, two, or three R$^{20z}$;

(6) two R$^{z6}$ bonded to the same carbon atom are joined to form monocyclic C$_{3-7}$cycloalkyl or monocyclic 3-7 membered heterocycloalkyl, wherein the monocyclic C$_{3-7}$cycloalkyl and monocyclic 3-7 membered heterocycloalkyl are optionally substituted with one, two, or three R$^{20z}$;

(7) one or two R$^{z5}$ bonded to one atom and one or two R$^{z6}$ bonded to an adjacent atom are joined to form monocyclic C$_{3-7}$cycloalkyl, monocyclic 3-7 membered heterocycloalkyl, phenyl, or monocyclic 5-6 membered heteroaryl, wherein the monocyclic $C_{3-7}$cycloalkyl, monocyclic 3-7 membered heterocycloalkyl, phenyl, and monocyclic 5-6 membered heteroaryl are optionally substituted with one, two, or three $R^{20z}$; or (8) one or two $R^{z4}$ bonded to one atom and one or two $R^{z6}$ bonded to a second atom are joined to form monocyclic $C_{3-7}$cycloalkyl or monocyclic 3-7 membered heterocycloalkyl, wherein the monocyclic $C_{3-7}$cycloalkyl and monocyclic 3-7 membered heterocycloalkyl are optionally substituted with one, two, or three $R^{20z}$;

each $R^{12}$ is independently selected from hydrogen, $C_{1-6}$alkyl, $C_{2-6}$alkenyl, $C_{2-6}$alkynyl, $C_{3-10}$cycloalkyl, —$CH_2$-$C_{3-10}$cycloalkyl, $C_{2-9}$heterocycloalkyl, —$CH_2$-$C_{2-9}$heterocycloalkyl, $C_{6-10}$aryl, —$CH_2$-$C_{6-10}$aryl, —$CH_2$-$C_{1-9}$heteroaryl, and $C_{1-9}$heteroaryl, wherein $C_{1-6}$alkyl, $C_{2-6}$alkenyl, $C_{2-6}$alkynyl, $C_{3-10}$cycloalkyl, —$CH_2$-$C_{3-10}$cycloalkyl, $C_{2-9}$heterocycloalkyl, —$CH_2$-$C_{2-9}$heterocycloalkyl, $C_{6-10}$aryl, —$CH_2$-$C_{6-10}$aryl, —$CH_2$-$C_{1-9}$heteroaryl, and $C_{1-9}$heteroaryl are optionally substituted with one, two, or three $R^{20l}$;

$R^{12a}$ is independently selected from hydrogen, $C_{1-6}$alkyl, $C_{2-6}$alkenyl, $C_{2-6}$alkynyl, $C_{3-10}$cycloalkyl, —$C(R^{12c})_2$-$C_{3-10}$cycloalkyl, $C_{2-9}$heterocycloalkyl, —$C(R^{12c})_2$-$C_{2-9}$heterocycloalkyl, $C_{6-10}$aryl, —$C(R^{12c})_2$-$C_{6-10}$aryl, —$C(R^{12c})_2$-$C_{1-9}$heteroaryl, and $C_{1-9}$heteroaryl, wherein $C_{1-6}$alkyl, $C_{2-6}$alkenyl, $C_{2-6}$alkynyl, $C_{3-10}$cycloalkyl, —$C(R^{12c})_2$-$C_{3-10}$cycloalkyl, $C_{2-9}$heterocycloalkyl, —$C(R^{12c})_2$-$C_{2-9}$heterocycloalkyl, $C_{6-10}$aryl, —$C(R^{12c})_2$-$C_{6-10}$aryl, —$C(R^{12c})_2$-$C_{1-9}$heteroaryl, and $C_{1-9}$heteroaryl are optionally substituted with one, two, or three $R^{20l}$;

each $R^{12c}$ is independently selected from hydrogen and $R^{20lc}$;

each $R^{13}$ is independently selected from hydrogen, $C_{1-6}$alkyl, and $C_{1-6}$haloalkyl; or $R^{12}$ and $R^{13}$, together with the nitrogen to which they are attached, form a $C_{2-9}$heterocycloalkyl ring optionally substituted with one, two, or three $R^{20m}$;

each $R^{14}$ is independently selected from hydrogen, $C_{1-6}$alkyl, and $C_{1-6}$haloalkyl;

each $R^{15}$ is independently selected from $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20o}$;

each $R^{20z1}$, $R^{20z2}$, $R^{20z3}$, and $R^{20z9}$ is independently selected from halogen, oxo, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{12}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{12}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20z}$;

each $R^{20z4}$, $R^{20z5}$, and $R^{20z6}$ is independently selected from E, halogen, oxo, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{12}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{12}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20z}$;

each $R^{20z}$ is independently selected from E, halogen, oxo, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{12}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{12}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20zz}$;

two $R^{20z}$ bonded to the same carbon atom are optionally joined to form monocyclic $C_{3-7}$cycloalkyl or monocyclic 3-7 membered heterocycloalkyl, wherein the monocyclic $C_{3-7}$cycloalkyl and monocyclic 3-7 membered heterocycloalkyl are optionally substituted with one, two, or three $R^{20zz}$; or two or more $R^{20z}$ bonded to two adjacent atoms are optionally joined to form monocyclic $C_{3-7}$cycloalkyl, monocyclic 3-7 membered heterocycloalkyl, phenyl, or monocyclic 5-6 membered heteroaryl, wherein the $C_{3-7}$cycloalkyl, monocyclic 3-7 membered heterocycloalkyl, phenyl, and monocyclic 5-6 membered heteroaryl are optionally substituted with one, two, or three $R^{20zz}$;

each $R^{20a}$, $R^{20b}$, $R^{20c}$, $R^{20d}$, $R^{20e}$, $R^{20f}$, $R^{20g}$, $R^{20h}$, $R^{20i}$, $R^{20j}$, $R^{20lc}$, $R^{20l}$, $R^{20m}$, $R^{20o}$, and $R^{20q}$ is independently selected from halogen, oxo, —CN, $C_{1-6}$alkyl, $C_{2-6}$alkenyl, $C_{2-6}$alkynyl, $C_{3-10}$cycloalkyl, —$CH_2$-$C_{3-10}$cycloalkyl, $C_{2-9}$heterocycloalkyl, —$CH_2$-$C_{2-9}$heterocycloalkyl, $C_{6-10}$aryl, —$CH_2$-$C_{6-10}$aryl, —$CH_2$-$C_{1-9}$heteroaryl, $C_{1-9}$heteroaryl, —$OR^{21}$, —$SR^{21}$, —$N(R^{22})(R^{23})$, —$C(O)OR^{22}$, —$C(O)N(R^{22})(R^{23})$, —$C(O)C(O)N(R^{22})(R^{23})$, —$OC(O)N(R^{22})(R^{23})$, —$N(R^{24})C(O)N(R^{22})(R^{23})$, —$N(R^{24})C(O)OR^{25}$, —$N(R^{24})C(O)R^{21}$, —$N(R^{24})S(O)_2R^{25}$, —$C(O)R^{21}$, —$S(O)_2R^{25}$, —$S(O)_2N(R^{22})(R^{23})$, —$OCH_2C(O)OR^{22}$, $=NR^{21}$, and —$OC(O)R^{25}$; two $R^{20q}$ bonded to adjacent atoms are optionally joined to form a $C_{3-10}$cycloalkyl, $C_{2-9}$heterocycloalkyl, $C_{6-10}$aryl, or $C_{1-9}$heteroaryl; wherein $C_{1-6}$alkyl, $C_{2-6}$alkenyl, $C_{2-6}$alkynyl, $C_{3-10}$cycloalkyl, —$CH_2$-$C_{3-10}$cycloalkyl, $C_{2-9}$heterocycloalkyl, —$CH_2$-$C_{2-9}$heterocycloalkyl, $C_{6-10}$aryl, —$CH_2$-$C_{6-10}$aryl, —$CH_2$-$C_{1-9}$heteroaryl, and $C_{1-9}$heteroaryl are optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —$OR^{21}$, —$SR^{21}$, —$N(R^{22})(R^{23})$, —$C(O)OR^{22}$, —$C(O)N(R^{22})(R^{23})$, —$C(O)C(O)N(R^{22})(R^{23})$, —$OC(O)N(R^{22})(R^{23})$, —$N(R^{24})C(O)N(R^{22})(R^{23})$, —$N(R^{24})$ C(O)OR²⁵, —N(R²⁴)C(O)R²⁵, —N(R²⁴)S(O)₂R²⁵, —C(O)R²⁵, —S(O)₂R²⁵, —S(O)₂N(R²²)(R²³), and —OC(O)R²⁵;

each $R^{20zz}$ is independently selected from E, halogen, oxo, —CN, $C_{1-6}$alkyl, $C_{2-6}$alkenyl, $C_{2-6}$alkynyl, $C_{3-10}$cycloalkyl, —CH₂-$C_{3-10}$cycloalkyl, $C_{2-9}$heterocycloalkyl, —CH₂-$C_{2-9}$heterocycloalkyl, $C_{6-10}$aryl, —CH₂-$C_{6-10}$aryl, —CH₂-$C_{1-9}$heteroaryl, $C_{1-9}$heteroaryl, —OR²¹, —SR²¹, —N(R²²)(R²³), —C(O)OR²², —C(O)N(R²²)(R²³), —C(O)C(O)N(R²²)(R²³), —OC(O)N(R²²)(R²³), —N(R²⁴)C(O)N(R²²)(R²³), —N(R²⁴)C(O)OR²⁵, —N(R²⁴)C(O)R²¹, —N(R²⁴)S(O)₂R²⁵, —C(O)R²¹, —S(O)₂R²⁵, —S(O)₂N(R²²)(R²³), —OCH₂C(O)OR²², =NR²¹, and —OC(O)R²⁵; two $R^{20q}$ bonded to adjacent atoms are optionally joined to form a $C_{3-10}$cycloalkyl, $C_{2-9}$heterocycloalkyl, $C_{6-10}$aryl, or $C_{1-9}$heteroaryl; wherein $C_{1-6}$alkyl, $C_{2-6}$alkenyl, $C_{2-6}$alkynyl, $C_{3-10}$cycloalkyl, —CH₂-$C_{3-10}$cycloalkyl, $C_{2-9}$heterocycloalkyl, —CH₂-$C_{2-9}$heterocycloalkyl, $C_{6-10}$aryl, —CH₂-$C_{6-10}$aryl, —CH₂-$C_{1-9}$heteroaryl, and $C_{1-9}$heteroaryl are optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —OR²¹, —SR²¹, —N(R²²)(R²³), —C(O)OR²², —C(O)N(R²²)(R²³), —C(O)C(O)N(R²²)(R²³), —OC(O)N(R²²)(R²³), —N(R²⁴)C(O)N(R²²)(R²³), —N(R²⁴)C(O)OR²⁵, —N(R²⁴)C(O)R²⁵, —N(R²⁴)S(O)₂R²⁵, —C(O)R²⁵, —S(O)₂R²⁵, —S(O)₂N(R²²)(R²³), and —OC(O)R²⁵;

each $R^{21}$ is independently selected from hydrogen, $C_{1-6}$alkyl, $C_{1-6}$haloalkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl;

each $R^{21b}$ is independently selected from hydrogen, halogen, $C_{1-6}$alkyl, $C_{1-6}$haloalkyl, $C_{3-10}$cycloalkyl, and $C_{2-9}$heterocycloalkyl, or two $R^{21b}$ are taken together with the carbon atom to which they are attached to form $C_{3-10}$cycloalkyl or $C_{2-9}$heterocycloalkyl, each of which is optionally substituted with one or more substituents independently selected from halogen, $C_{1-3}$alkyl, $C_{1-3}$haloalkyl, and —OH;

each $R^{22}$ is independently selected from hydrogen, $C_{1-6}$alkyl, $C_{1-6}$haloalkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl;

each $R^{23}$ is independently selected from hydrogen and $C_{1-6}$alkyl;

each $R^{24}$ is independently selected from hydrogen and $C_{1-6}$alkyl;

each $R^{25}$ is independently selected from $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; and ----- indicates a single or double bond such that all valences are satisfied.

In an aspect is provided a compound of Formula (B), or a pharmaceutically acceptable salt or solvate thereof:

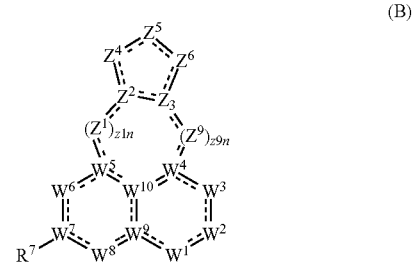

(B)

wherein:

$W^1$ is $N(R^1)$ or N;

$R^1$ is selected from hydrogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —OR¹², —SR¹², —C(O)OR¹², —OC(O)N(R¹²)(R¹³), —C(O)R¹⁵, —S(O)R¹⁵, —OC(O)R¹⁵, —C(O)N(R¹²)(R¹³), —C(O)C(O)N(R¹²)(R¹³), —S(O)₂R¹⁵, —S(O)₂N(R¹²)(R¹³), —S(=O)(=NH)N(R¹²)(R¹³), —CH₂C(O)N(R¹²)(R¹³), —CH₂N(R¹⁴)C(O)R¹⁵, —CH₂S(O)₂R¹⁵, and —CH₂S(O)₂N(R¹²)(R¹³), wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20a}$;

$W^2$ is $C(R^2)$, $N(R^2)$, $C(R^2)_2$, C(O), S(O), S(O)₂, or N;

each $R^2$ is independently selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —OR¹²ᵃ, —SR¹²ᵃ, —N(R¹²ᵃ)(R¹³), —N=(R¹⁵), —C(O)OR¹², —OC(O)N(R¹²)(R¹³), —N(R¹⁴)C(O)N(R¹²)(R¹³), —N(R¹⁴)C(O)OR¹⁵, —N(R¹⁴)S(O)₂R¹⁵, —C(O)R¹⁵, —S(O)R¹⁵, —OC(O)R¹⁵, —C(O)N(R¹²)(R¹³), —C(O)C(O)N(R¹²)(R¹³), —N(R¹⁴)C(O)R¹⁵, —S(O)₂R¹⁵, —S(O)₂N(R¹²)(R¹³)—, —S(=O)(=NH)N(R¹²)(R¹³), —CH₂C(O)N(R¹²)(R¹³), —CH₂N(R¹⁴)C(O)R¹⁵, —CH₂S(O)₂R¹⁵, and —CH₂S(O)₂N(R¹²)(R¹³), wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20b}$;

$W^3$ is $C(R^3)$, $N(R^3)$, $C(R^3)_2$, C(O), S(O), S(O)₂, or N;

each $R^3$ is independently selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —OR¹², —SR¹², —N(R¹²)(R¹³), —C(O)OR¹², —OC(O)N(R¹²)(R¹³), —N(R¹⁴)C(O)N(R¹²)(R¹³), —N(R¹⁴)C(O)OR¹⁵, —N(R¹⁴)S(O)₂R¹⁵, —C(O)R¹⁵, —S(O)R¹⁵, —OC(O)R¹⁵, —C(O)N(R¹²)(R¹³), —C(O)C(O)N(R¹²)(R¹³), —N(R¹⁴)C(O)R¹⁵, —S(O)₂R¹⁵, —S(O)₂N(R¹²)(R¹³), —S(=O)(=NH)N(R¹²)(R¹³), —CH₂C(O)N(R¹²)(R¹³), —CH₂N(R¹⁴)C(O)R¹⁵, —CH₂S(O)₂R¹⁵, and —CH₂S(O)₂N(R¹²)(R¹³), wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20c}$;

$W^4$ is $C(R^4)$, C, or N;

$R^4$ is selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —OR¹², —SR¹², —N(R¹²)(R¹³), —C(O)OR¹², —OC(O)N(R¹²)(R¹³), —N(R¹⁴)C(O)N(R¹²)(R¹³), —N(R¹⁴)C(O)OR¹⁵, —N(R¹⁴)S(O)₂R¹⁵, —C(O)R¹⁵, —S(O)R¹⁵, —OC(O)R¹⁵, —C(O)N(R¹²)(R¹³), —C(O)C(O)N(R¹²)(R¹³), —N(R$^{14}$)C(O)R$^{15}$, —S(O)$_2$R$^{15}$, —S(O)$_2$N(R$^{12}$)(R$^{13}$), —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl are optionally substituted with one, two, or three R$^{20d}$;

W$^5$ is C(R$^5$), C, or N;

R$^5$ is selected from hydrogen, halogen, —CN, C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, C$_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$), —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl are optionally substituted with one, two, or three R$^{20e}$;

W$^6$ is C(R$^6$), N(R$^6$), C(R$^6$)$_2$, C(O), S(O), S(O)$_2$, or N;

each R$^6$ is independently selected from hydrogen, halogen, —CN, C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, C$_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$), —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl are optionally substituted with one, two, or three R$^{20f}$;

W$^7$ is C(R$^{7a}$), C, or N;

R$^{7a}$ is selected from hydrogen, halogen, —CN, C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, C$_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$), —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl are optionally substituted with one, two, or three R$^{20g}$;

R$^7$ is -L$^7$—R$^{17}$;

L$^7$ is a bond, C$_1$-C$_4$alkyl, C$_2$-C$_4$alkenyl, C$_2$-C$_4$alkynyl, 2-4 membered heteroalkylene linker, —O—, —N(R$^{7d}$)—, —C(O)—, —S—, —S(O)$_2$—, —S(O)—, —P(O)R$^{7d}$—, CR$^{7c}$R$^{7c}$, —OCR$^{7c}$R$^{7c}$, —N(R$^{7d}$)CR$^{7c}$R$^{7c}$—, —C(O)CR$^{7c}$R$^{7c}$—, —SCR$^{7c}$R$^{7c}$—, —S(O)$_2$CR$^{7c}$R$^{7c}$—, —S(O)CR$^{7c}$R$^{7c}$—, —P(O)R$^{7d}$CR$^{7c}$R$^{7c}$—, —CR$^{7c}$R$^{7c}$CR$^{7c}$R$^{7c}$, —CR$^{7c}$R$^{7c}$O—, —CR$^{7c}$R$^{7c}$N(R$^{7d}$)—, —CR$^{7c}$R$^{7c}$C(O)—, —CR$^{7c}$R$^{7c}$S—, —CR$^{7c}$R$^{7c}$S(O)$_2$—, —CR$^{7c}$R$^{7c}$S(O)—, —CR$^{7c}$R$^{7c}$P(O)R$^{7d}$—, —N(R$^{7d}$)C(O)—, —N(R$^{7d}$)S(O)$_2$—, —N(R$^{7d}$)S(O)—, —N(R$^{7d}$)P(O)R$^{7d}$—, —C(O)N(R$^{7d}$)—, —S(O)$_2$N(R$^{7d}$)—, —S(O)N(R$^{7d}$)—, —P(O)R$^{7d}$N(R$^{7d}$)—, —OC(O)—, —OS(O)$_2$—, —OS(O)—, —OP(O)R$^{7d}$—, —C(O)O—, —S(O)$_2$O—, —S(O)O—, or —P(O)R$^{7d}$O—; wherein the C$_1$-C$_4$alkyl, C$_2$-C$_4$alkenyl, C$_2$-C$_4$alkynyl, 2-4 membered heteroalkylene linker are optionally substituted with one, two, or three R$^{20g}$;

each R$^{7c}$ is independently selected from hydrogen, halogen, —CN, C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, C$_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$), S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl are optionally substituted with one, two, or three R$^{20g}$;

each R$^{7d}$ is independently selected from hydrogen, —CN, C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, C$_{1-9}$heteroaryl, —OR$^{12}$, —SR$^{12}$, —C(O)OR$^{12}$, —OC(O)N(R$^{12}$)(R$^{13}$), —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —S(O)$_2$R$^{15}$, —S(O)$_2$N(R$^{12}$)(R$^{13}$), —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl are optionally substituted with one, two, or three R$^{20g}$;

R$^{17}$ is selected from C$_{3-10}$cycloalkyl, 3-10 membered heterocycloalkyl, C$_{6-10}$aryl, and 5-10 membered heteroaryl, wherein C$_{3-10}$cycloalkyl, 3-10 membered heterocycloalkyl, C$_{6-10}$aryl, and 5-10 membered heteroaryl are optionally substituted with one or more R$^{20q}$; or L$^7$ is a bond and R$^{7a}$ and R$^{17}$, together with the carbon to which they are attached, form C$_{3-10}$cycloalkyl or 3-10 membered heterocycloalkyl, wherein the C$_{3-10}$cycloalkyl and 3-10 membered heterocycloalkyl are optionally substituted with one or more R$^{20q}$;

W$^8$ is C(R$^8$), N(R$^8$), C(R$^8$)$_2$, C(O), S(O), S(O)$_2$, or N;

each R$^8$ is independently selected from hydrogen, halogen, —CN, C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, C$_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$), —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl are optionally substituted with one, two, or three R$^{20h}$;

W$^9$ is C(R$^9$), C, or N;

R$^9$ is selected from hydrogen, halogen, —CN, C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, C$_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$), —S(=O)(=NH)N($R^{12}$)($R^{13}$), —CH$_2$C(O)N($R^{12}$)($R^{13}$), —CH$_2$N($R^{14}$)C(O)$R^{15}$, —CH$_2$S(O)$_2$$R^{15}$, and —CH$_2$S(O)$_2$N($R^{12}$)($R^{13}$), wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl are optionally substituted with one, two, or three $R^{20i}$;

$W^{10}$ C($R^{10}$), C, or N;

$R^{10}$ is selected from hydrogen, halogen, —CN, C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, C$_{1-9}$heteroaryl, —O$R^{12}$, —S$R^{12}$, —N($R^{12}$)($R^{13}$), —C(O)O$R^{12}$, —OC(O)N($R^{12}$)($R^{13}$), —N($R^{14}$)C(O)N($R^{12}$)($R^{13}$), —N($R^{14}$)C(O)O$R^{15}$, —N($R^{14}$)S(O)$_2$$R^{15}$, —C(O)$R^{15}$, —S(O)$R^{15}$, —OC(O)$R^{15}$, —C(O)N($R^{12}$)($R^{13}$), —C(O)C(O)N($R^{12}$)($R^{13}$), —N($R^{14}$)C(O)$R^{15}$, —S(O)$_2$$R^{15}$, —S(O)$_2$N($R^{12}$)($R^{13}$), —S(=O)(=NH)N($R^{12}$)($R^{13}$), —CH$_2$C(O)N($R^{12}$)($R^{13}$), —CH$_2$N($R^{14}$)C(O)$R^{15}$, —CH$_2$S(O)$_2$$R^{15}$, and —CH$_2$S(O)$_2$N($R^{12}$)($R^{13}$), wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl are optionally substituted with one, two, or three $R^{20j}$;

each $Z^1$ is independently C($R^{z1}$), N($R^{z1}$), C($R^{z1}$)$_2$, C(O), S(O), S(O)$_2$, O, S, or N;

z1n is 0, 1, 2, or 3; wherein if z1n is 0 then $Z^2$ is directly bonded to $W^5$;

each $R^{z1}$ is independently selected from hydrogen, halogen, —CN, C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, C$_{1-9}$heteroaryl, —O$R^{12}$, —S$R^{12}$, —N($R^{12}$)($R^{13}$), —C(O)O$R^{12}$, —OC(O)N($R^{12}$)($R^{13}$), —N($R^{14}$)C(O)N($R^{12}$)($R^{13}$), —N($R^{14}$)C(O)O$R^{15}$, —N($R^{14}$)S(O)$_2$$R^{15}$, —C(O)$R^{15}$, —S(O)$R^{15}$, —OC(O)$R^{15}$, —C(O)N($R^{12}$)($R^{13}$), —C(O)C(O)N($R^{12}$)($R^{13}$), —N($R^{14}$)C(O)$R^{15}$, —S(O)$_2$$R^{15}$, —S(O)$_2$N($R^{12}$)($R^{13}$), —S(=O)(=NH)N($R^{12}$)($R^{13}$), —CH$_2$C(O)N($R^{12}$)($R^{13}$), —CH$_2$N($R^{14}$)C(O)$R^{15}$, —CH$_2$S(O)$_2$$R^{15}$, and —CH$_2$S(O)$_2$N($R^{12}$)($R^{13}$), wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl are optionally substituted with one, two, or three $R^{20z1}$;

each $Z^9$ is independently C($R^{z9}$), N($R^{z9}$), C($R^{z9}$)$_2$, C(O), S(O), S(O)$_2$, O, S, or N;

z9n is 0, 1, 2, or 3; wherein if z9n is 0 then $Z^3$ is directly bonded to $W^4$;

each $R^{z9}$ is independently selected from hydrogen, halogen, —CN, C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, C$_{1-9}$heteroaryl, —O$R^{12}$, —S$R^{12}$, —N($R^{12}$)($R^{13}$), —C(O)O$R^{12}$, —OC(O)N($R^{12}$)($R^{13}$), —N($R^{14}$)C(O)N($R^{12}$)($R^{13}$), —N($R^{14}$)C(O)O$R^{15}$, —N($R^{14}$)S(O)$_2$$R^{15}$, —C(O)$R^{15}$, —S(O)$R^{15}$, —OC(O)$R^{15}$, —C(O)N($R^{12}$)($R^{13}$), —C(O)C(O)N($R^{12}$)($R^{13}$), —N($R^{14}$)C(O)$R^{15}$, —S(O)$_2$$R^{15}$, —S(O)$_2$N($R^{12}$)($R^{13}$), —S(=O)(=NH)N($R^{12}$)($R^{13}$), —CH$_2$C(O)N($R^{12}$)($R^{13}$), —CH$_2$N($R^{14}$)C(O)$R^{15}$, —CH$_2$S(O)$_2$$R^{15}$, and —CH$_2$S(O)$_2$N($R^{12}$)($R^{13}$), wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl are optionally substituted with one, two, or three $R^{20z9}$;

wherein the sum of z1n and z9n is 2 or 3;

$Z^2$ is C($R^{z2}$), C, or N;

$R^{z2}$ is selected from hydrogen, halogen, —CN, C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, C$_{1-9}$heteroaryl, —O$R^{12}$, —S$R^{12}$, —N($R^{12}$)($R^{13}$), —C(O)O$R^{12}$, —OC(O)N($R^{12}$)($R^{13}$), —N($R^{14}$)C(O)N($R^{12}$)($R^{13}$), —N($R^{14}$)C(O)O$R^{15}$, —N($R^{14}$)S(O)$_2$$R^{15}$, —C(O)$R^{15}$, —S(O)$R^{15}$, —OC(O)$R^{15}$, —C(O)N($R^{12}$)($R^{13}$), —C(O)C(O)N($R^{12}$)($R^{13}$), —N($R^{14}$)C(O)$R^{15}$, —S(O)$_2$$R^{15}$, —S(O)$_2$N($R^{12}$)($R^{13}$), —S(=O)(=NH)N($R^{12}$)($R^{13}$), —CH$_2$C(O)N($R^{12}$)($R^{13}$), —CH$_2$N($R^{14}$)C(O)$R^{15}$, —CH$_2$S(O)$_2$$R^{15}$, and —CH$_2$S(O)$_2$N($R^{12}$)($R^{13}$), wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl are optionally substituted with one, two, or three $R^{20z2}$;

$Z^3$ is C($R^{z3}$), C, or N;

$R^{z3}$ is selected from hydrogen, halogen, —CN, C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, C$_{1-9}$heteroaryl, —O$R^{12}$, —S$R^{12}$, —N($R^{12}$)($R^{13}$), —C(O)O$R^{12}$, —OC(O)N($R^{12}$)($R^{13}$), —N($R^{14}$)C(O)N($R^{12}$)($R^{13}$), —N($R^{14}$)C(O)O$R^{15}$, —N($R^{14}$)S(O)$_2$$R^{15}$, —C(O)$R^{15}$, —S(O)$R^{15}$, —OC(O)$R^{15}$, —C(O)N($R^{12}$)($R^{13}$), —C(O)C(O)N($R^{12}$)($R^{13}$), —N($R^{14}$)C(O)$R^{15}$, —S(O)$_2$$R^{15}$, —S(O)$_2$N($R^{12}$)($R^{13}$), —S(=O)(=NH)N($R^{12}$)($R^{13}$), —CH$_2$C(O)N($R^{12}$)($R^{13}$), —CH$_2$N($R^{14}$)C(O)$R^{15}$, —CH$_2$S(O)$_2$$R^{15}$, and —CH$_2$S(O)$_2$N($R^{12}$)($R^{13}$), wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl are optionally substituted with one, two, or three $R^{20z3}$;

$Z^4$ is a bond, $Z^{4a}$, $Z^{4a}Z^{4b}$, $Z^{4a}Z^{4b}Z^{4c}$, or $Z^{4a}Z^{4b}Z^{4c}Z^{4d}$; wherein $Z^{4a}$ is directly bonded to $Z^2$; and wherein if $Z^4$ is a bond then $Z^2$ is directly bonded to $Z^5$;

$Z^{4a}$, $Z^{4b}$, $Z^{4c}$, and $Z^{4d}$ are independently C($R^{z4}$), N($R^{z4}$), C($R^{z4}$)$_2$, C(O), S(O), S(O)$_2$, S(O)(N$R^{z4}$), O, S, or N; provided that if z9n is 0 and $Z^4$ is $Z^{4a}Z^{4b}$; then (1) $Z^{4b}$ is C($R^{z4}$), C($R^{z4}$)$_2$, C(O), S(O), S(O)$_2$, S(O)(N$R^{z4}$), O, S, or N, (2) $Z^{4b}$ is N($R^{z4}$) and $Z^{4a}$ is C(O), S(O), or S(O)$_2$; (3) $Z^{4b}$ is N($R^{z4}$) and $Z^5$ is C(O), S(O), or S(O)$_2$; or (4) $Z^{4b}$ is N($R^{z4}$) and $Z^3$ is C($R^{z3}$) or C; and each $R^{z4}$ is independently selected from hydrogen, halogen, —CN, C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, C$_{1-9}$heteroaryl, —O$R^{12}$, —S$R^{12}$, —N($R^{12}$)($R^{13}$), —C(O)O$R^{12}$, —OC(O)N($R^{12}$)($R^{13}$), —N($R^{14}$)C(O)N($R^{12}$)($R^{13}$), —N($R^{14}$)C(O)O$R^{15}$, —N($R^{14}$)S(O)$_2$$R^{15}$, —C(O)O$R^{12}$, —S(O)$R^{15}$, —OC(O)$R^{15}$, —C(O)N($R^{12}$)($R^{13}$), —C(O)C(O)N($R^{12}$)($R^{13}$), —N($R^{14}$)C(O)$R^{12}$, —S(O)$_2$$R^{15}$, —S(O)$_2$N($R^{12}$)($R^{13}$), —S(=O)(=NH)N($R^{12}$)($R^{13}$), —CH$_2$C(O)N($R^{12}$)($R^{13}$), —CH$_2$N($R^{14}$)C(O)$R^{15}$, —CH$_2$S(O)$_2$$R^{15}$, and —CH$_2$S(O)$_2$N($R^{12}$)($R^{13}$), wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl are optionally substituted with one, two, or three $R^{20z4}$; or two $R^{z4}$ bonded to the same carbon are joined to form C$_{2-6}$alkenyl optionally substituted with one, two, or three $R^{20z4}$;

$Z^5$ is C($R^{z5}$), N($R^{z5}$), C($R^{z5}$)$_2$, C(O), S(O), S(O)$_2$, S(O)(N$R^{z5}$), O, S, or N;

each $R^{z5}$ is independently selected from -L$^{z1}$-L$^{z2}$-L$^{z3}$—$R^{12}$, hydrogen, halogen, —CN, C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, C$_{1-9}$heteroaryl, —O$R^{12}$, —S$R^{12}$, —N($R^{12}$)($R^{13}$), —C(O)O$R^{12}$, —OC(O)N($R^{12}$)($R^{13}$), —N($R^{14}$)C(O)N($R^{12}$)($R^{13}$), —N($R^{14}$)C(O)O$R^{15}$, —N($R^{14}$)S(O)$_2$$R^{15}$, —C(O)$R^{12}$, —S(O)$R^{15}$, —OC(O)$R^{15}$, —C(O)N($R^{12}$)($R^{13}$), —C(O)C(O)N($R^{12}$)($R^{13}$), —N($R^{14}$)C(O)$R^{12}$, —S(O)$_2$$R^{15}$, —S(O)$_2$N($R^{12}$)($R^{13}$), —S(=O)(=NH)N($R^{12}$)($R^{13}$), —CH$_2$C(O)N($R^{12}$)($R^{13}$), —CH$_2$N($R^{14}$)C(O)$R^{15}$, —CH$_2$S(O)$_2$$R^{15}$, and —CH$_2$S(O)$_2$N($R^{12}$)($R^{13}$), wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl are optionally substituted with one, two, or three $R^{20z5}$; or two $R^{z5}$ bonded to the same carbon are joined to form C$_{2-6}$alkenyl optionally substituted with one, two, or three R$^{20z5}$;

Z$^6$ is C(R$^{z6}$), N(R$^{z6}$), C(R$^{z6}$)$_2$, C(O), S(O), S(O)$_2$, S(O)(NR$^{z6}$), O, S, or N;

each R$^{z6}$ is independently selected from -L$^{z1}$-L$^{z2}$-L$^{z3}$—R$^{12}$, hydrogen, halogen, —CN, C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, C$_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{12}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{12}$, —S(O)$_2$R$^{15}$, —S(O)$_2$N(R$^{12}$)(R$^{13}$), —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl are optionally substituted with one, two, or three R$^{20z6}$; or two R$^{z6}$ bonded to the same carbon are joined to form C$_{2-6}$alkenyl optionally substituted with one, two, or three R$^{20z6}$;

and further wherein the compound optionally includes one of the following:

(1) two R$^{z4}$ bonded to the same carbon atom are joined to form monocyclic C$_{3-7}$cycloalkyl or monocyclic 3-7 membered heterocycloalkyl, wherein the monocyclic C$_{3-7}$cycloalkyl and monocyclic 3-7 membered heterocycloalkyl are optionally substituted with one, two, or three R$^{20z}$;

(2) two or more R$^{z4}$ bonded to adjacent atoms are joined to form monocyclic C$_{3-7}$cycloalkyl, monocyclic 3-7 membered heterocycloalkyl, phenyl, or monocyclic 5-6 membered heteroaryl, wherein the monocyclic C$_{3-7}$cycloalkyl, monocyclic 3-7 membered heterocycloalkyl, phenyl, and monocyclic 5-6 membered heteroaryl are optionally substituted with one, two, or three R$^{20z}$;

(3) two R$^{z5}$ bonded to the same carbon atom are joined to form monocyclic C$_{3-7}$cycloalkyl or monocyclic 3-7 membered heterocycloalkyl, wherein the monocyclic C$_{3-7}$cycloalkyl and monocyclic 3-7 membered heterocycloalkyl are optionally substituted with one, two, or three R$^{20z}$;

(4) one or two R$^{z4}$ bonded to one atom and one or two R$^{z5}$ bonded to an adjacent atom are joined to form monocyclic C$_{3-7}$cycloalkyl, monocyclic 3-7 membered heterocycloalkyl, phenyl, or monocyclic 5-6 membered heteroaryl, wherein the monocyclic C$_{3-7}$cycloalkyl, monocyclic 3-7 membered heterocycloalkyl, phenyl, and monocyclic 5-6 membered heteroaryl are optionally substituted with one, two, or three R$^{20z}$;

(5) one or two R$^{z4}$ bonded to one atom and one or two R$^{z5}$ bonded to a second atom are joined to form monocyclic C$_{3-7}$cycloalkyl or monocyclic 3-7 membered heterocycloalkyl, wherein the monocyclic C$_{3-7}$cycloalkyl and monocyclic 3-7 membered heterocycloalkyl are optionally substituted with one, two, or three R$^{20z}$;

(6) two R$^{z6}$ bonded to the same carbon atom are joined to form monocyclic C$_{3-7}$cycloalkyl or monocyclic 3-7 membered heterocycloalkyl, wherein the monocyclic C$_{3-7}$cycloalkyl and monocyclic 3-7 membered heterocycloalkyl are optionally substituted with one, two, or three R$^{20z}$;

(7) one or two R$^{z5}$ bonded to one atom and one or two R$^{z6}$ bonded to an adjacent atom are joined to form monocyclic C$_{3-7}$cycloalkyl, monocyclic 3-7 membered heterocycloalkyl, phenyl, or monocyclic 5-6 membered heteroaryl, wherein the monocyclic C$_{3-7}$cycloalkyl, monocyclic 3-7 membered heterocycloalkyl, phenyl, and monocyclic 5-6 membered heteroaryl are optionally substituted with one, two, or three R$^{20z}$; or (8) one or two R$^{z4}$ bonded to one atom and one or two R$^{z6}$ bonded to a second atom are joined to form monocyclic C$_{3-7}$cycloalkyl or monocyclic 3-7 membered heterocycloalkyl, wherein the monocyclic C$_{3-7}$cycloalkyl and monocyclic 3-7 membered heterocycloalkyl are optionally substituted with one, two, or three R$^{20z}$;

each R$^{12}$ is independently selected from hydrogen, C$_{1-6}$alkyl, C$_{2-6}$alkenyl, C$_{2-6}$alkynyl, C$_{3-10}$cycloalkyl, —CH$_2$-C$_{3-10}$cycloalkyl, C$_{2-9}$heterocycloalkyl, —CH$_2$-C$_{2-9}$heterocycloalkyl, C$_{6-10}$aryl, —CH$_2$-C$_{6-10}$aryl, —CH$_2$-C$_{1-9}$heteroaryl, and C$_{1-9}$heteroaryl, wherein C$_{1-6}$alkyl, C$_{2-6}$alkenyl, C$_{2-6}$alkynyl, C$_{3-10}$cycloalkyl, —CH$_2$-C$_{3-10}$cycloalkyl, C$_{2-9}$heterocycloalkyl, —CH$_2$-C$_{2-9}$heterocycloalkyl, C$_{6-10}$aryl, —CH$_2$-C$_{6-10}$aryl, —CH$_2$-C$_{1-9}$heteroaryl, and C$_{1-9}$heteroaryl are optionally substituted with one, two, or three R$^{20l}$;

R$^{12a}$ is independently selected from hydrogen, C$_{1-6}$alkyl, C$_{2-6}$alkenyl, C$_{2-6}$alkynyl, C$_{3-10}$cycloalkyl, —C(R$^{12c}$)$_2$-C$_{3-10}$cycloalkyl, C$_{2-9}$heterocycloalkyl, —C(R$^{12c}$)$_2$-C$_{2-9}$heterocycloalkyl, C$_{6-10}$aryl, —C(R$^{12c}$)$_2$-C$_{6-10}$aryl, —C(R$^{12c}$)$_2$-C$_{1-9}$heteroaryl, and C$_{1-9}$heteroaryl, wherein C$_{1-6}$alkyl, C$_{2-6}$alkenyl, C$_{2-6}$alkynyl, C$_{3-10}$cycloalkyl, —C(R$^{12c}$)$_2$-C$_{3-10}$cycloalkyl, C$_{2-9}$heterocycloalkyl, —C(R$^{12c}$)$_2$-C$_{2-9}$heterocycloalkyl, C$_{6-10}$aryl, —C(R$^{12c}$)$_2$-C$_{6-10}$aryl, —C(R$^{12c}$)$_2$-C$_{1-9}$heteroaryl, and C$_{1-9}$heteroaryl are optionally substituted with one, two, or three R$^{20l}$;

each R$^{12c}$ is independently selected from hydrogen and R$^{20lc}$;

each R$^{13}$ is independently selected from hydrogen, C$_{1-6}$alkyl, and C$_{1-6}$haloalkyl; or R$^{12}$ and R$^{13}$, together with the nitrogen to which they are attached, form a C$_{2-9}$heterocycloalkyl ring optionally substituted with one, two, or three R$^{20m}$;

each R$^{14}$ is independently selected from hydrogen, C$_{1-6}$alkyl, and C$_{1-6}$haloalkyl;

each R$^{15}$ is independently selected from C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl, wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl are optionally substituted with one, two, or three R$^{20o}$;

each R$^{20z1}$, R$^{20z2}$, R$^{20z3}$, R$^{20z4}$, R$^{20z5}$, R$^{20z6}$, and R$^{20z9}$ is independently selected from halogen, oxo, —CN, C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, C$_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{12}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{12}$, —S(O)$_2$R$^{15}$, —S(O)$_2$N(R$^{12}$)(R$^{13}$), —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl are optionally substituted with one, two, or three R$^{20z}$;

each R$^{20z}$ is independently selected from halogen, oxo, —CN, C$_{1-6}$alkyl, C$_{2-6}$alkenyl, C$_{2-6}$alkynyl, C$_{3-10}$cycloalkyl, $C_{2-9}$heterocycloalkyl, $C_{6-10}$aryl, $C_{1-9}$heteroaryl, —OR$^{12}$, —SR$^{12}$, —N(R$^{12}$)(R$^{13}$), —C(O) OR$^{12}$, —OC(O)N(R$^{12}$)(R$^{13}$), —N(R$^{14}$)C(O)N(R$^{12}$) (R$^{13}$), —N(R$^{14}$)C(O)OR$^{15}$, —N(R$^{14}$)S(O)$_2$R$^{15}$, —C(O)R$^{12}$, —S(O)R$^{15}$, —OC(O)R$^{15}$, —C(O)N(R$^{12}$) (R$^{13}$), —C(O)C(O)N(R$^{12}$)(R$^{13}$), —N(R$^{14}$)C(O)R$^{12}$, —S(O)$_2$R$^{15}$, —S(O)$_2$N(R$^{12}$)(R$^{13}$), —S(=O)(=NH)N (R$^{12}$)(R$^{13}$), —CH$_2$C(O)N(R$^{12}$)(R$^{13}$), —CH$_2$N(R$^{14}$)C (O)R$^{15}$, —CH$_2$S(O)$_2$R$^{15}$, and —CH$_2$S(O)$_2$N(R$^{12}$) (R$^{13}$), wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three R$^{20zz}$;

two R$^{20z}$ bonded to the same carbon atom are optionally joined to form monocyclic $C_{3-7}$cycloalkyl or monocyclic 3-7 membered heterocycloalkyl, wherein the monocyclic $C_{3-7}$cycloalkyl and monocyclic 3-7 membered heterocycloalkyl are optionally substituted with one, two, or three R$^{20zz}$; or two or more R$^{20z}$ bonded to two adjacent atoms are optionally joined to form monocyclic $C_{3-7}$cycloalkyl, monocyclic 3-7 membered heterocycloalkyl, phenyl, or monocyclic 5-6 membered heteroaryl, wherein the $C_{3-7}$cycloalkyl, monocyclic 3-7 membered heterocycloalkyl, phenyl, and monocyclic 5-6 membered heteroaryl are optionally substituted with one, two, or three R$^{20zz}$;

L$^{z1}$ is selected from a bond, $C_{1-6}$alkylene, $C_{2-6}$alkenylene, $C_{2-6}$alkynylene, $C_{3-10}$cycloalkylene, $C_{1-9}$heterocycloalkylene, $C_{6-10}$arylene, and $C_{1-9}$heteroarylene; wherein $C_{1-6}$alkyl, $C_{2-6}$alkenylene, $C_{2-6}$alkynylene, $C_{3-10}$cycloalkylene, $C_{1-9}$heterocycloalkylene, $C_{6-10}$arylene, and $C_{1-9}$heteroarylene are optionally substituted with one or two R$^{30z}$;

R$^{30z}$ is independently selected from halogen, oxo, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —OR$^{12}$, —SR$^{12}$, —N(R$^{12}$)(R$^{13}$), —C(O)OR$^{12}$, —OC (O)N(R$^{12}$)(R$^{13}$), —N(R$^{14}$)C(O)N(R$^{12}$)(R$^{13}$), —N(R$^{14}$) C(O)OR$^{15}$, —N(R$^{14}$)S(O)$_2$R$^{15}$, —C(O)R$^{12}$, —S(O) R$^{15}$, —OC(O)R$^{15}$, —C(O)N(R$^{12}$)(R$^{13}$), —C(O)C(O)N (R$^{12}$)(R$^{13}$), —N(R$^{14}$)C(O)R$^{12}$, —S(O)$_2$R$^{15}$, —S(O)$_2$N (R$^{12}$)(R$^{13}$), —S(=O)(=NH)N(R$^{12}$)(R$^{13}$), —CH$_2$C(O) N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three R$^{20z}$;

L$^{z2}$ is selected from a bond, $C_{1-6}$alkylene, $C_{2-6}$alkenylene, $C_{2-6}$alkynylene, $C_{3-10}$cycloalkylene, $C_{2-9}$heterocycloalkylene, $C_{6-10}$arylene, and $C_{1-9}$heteroarylene; wherein $C_{1-6}$alkyl, $C_{2-6}$alkenylene, $C_{2-6}$alkynylene, $C_{3-10}$cycloalkylene, $C_{1-9}$heterocycloalkylene, $C_{6-10}$arylene, and $C_{1-9}$heteroarylene are optionally substituted with one or two R$^{31z}$;

R$^{31z}$ is independently selected from halogen, oxo, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —OR$^{12}$, —SR$^{12}$, —N(R$^{12}$)(R$^{13}$), —C(O)OR$^{12}$, —OC (O)N(R$^{12}$)(R$^{13}$), —N(R$^{14}$)C(O)N(R$^{12}$)(R$^{13}$), —N(R$^{14}$) C(O)OR$^{15}$, —N(R$^{14}$)S(O)$_2$R$^{15}$, —C(O)R$^{12}$, —S(O) R$^{15}$, —OC(O)R$^{15}$, —C(O)N(R$^{12}$)(R$^{13}$), —C(O)C(O)N (R$^{12}$)(R$^{13}$), —N(R$^{14}$)C(O)R$^{12}$, —S(O)$_2$R$^{15}$, —S(O)$_2$N (R$^{12}$)(R$^{13}$), —S(=O)(=NH)N(R$^{12}$)(R$^{13}$), —CH$_2$C(O) N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three R$^{20zz}$;

L$^{z3}$—R$^{12}$ is selected from:
i. —C(O)R$^{12}$ or —N(H)C(O)R$^{12}$; wherein the R$^{12}$ of L$^{z3}$—R$^{12}$ is a 5-membered heteroaryl including two or more ring nitrogen atoms, wherein the 5-membered heteroaryl is directly bonded to the C(O) through an R$^{12}$ ring nitrogen atom and wherein R$^{12}$ is optionally substituted with one or more R$^{20l}$; and
ii. —C(O)R$^{12}$ or —N(H)C(O)R$^{12}$; wherein the R$^{12}$ of L$^{z3}$—R$^{12}$ is a 3-membered heterocycloalkyl including one or more ring nitrogen atoms, wherein R$^{12}$ is optionally substituted with one or more R$^{20l}$;

R$^{20l}$ is independently selected from halogen, oxo, —CN, $C_{1-6}$alkyl, $C_{2-6}$alkenyl, $C_{2-6}$alkynyl, $C_{3-10}$cycloalkyl, —CH$_2$-$C_{3-10}$cycloalkyl, $C_{2-9}$heterocycloalkyl, —CH$_2$-$C_{2-9}$heterocycloalkyl, $C_{6-10}$aryl, —CH$_2$-$C_{6-10}$aryl, —CH$_2$-$C_{1-9}$heteroaryl, $C_{1-9}$heteroaryl, —OR$^{21}$, —SR$^{21}$, —N(R$^{22}$)(R$^{23}$), —C(O)OR$^{22}$, —C(O)N(R$^{22}$) (R$^{23}$), —C(O)C(O)N(R$^{22}$)(R$^{23}$), —OC(O)N(R$^{22}$) (R$^{23}$), —N(R$^{24}$)C(O)N(R$^{22}$)(R$^{23}$), —N(R$^{24}$)C(O) OR$^{25}$, —N(R$^{24}$)C(O)R$^{21}$, —N(R$^{24}$)S(O)$_2$R$^{25}$, —C(O) R$^{21}$, —S(O)$_2$R$^{25}$, —S(O)$_2$N(R$^{22}$)(R$^{23}$), —OCH$_2$C(O) OR$^{22}$, =NR$^{21}$, and —OC(O)R$^{25}$; two R$^{20q}$ bonded to adjacent atoms are optionally joined to form a $C_{3-10}$cycloalkyl, $C_{2-9}$heterocycloalkyl, $C_{6-10}$aryl, or $C_{1-9}$heteroaryl; wherein $C_{1-6}$alkyl, $C_{2-6}$alkenyl, $C_{2-6}$alkynyl, $C_{3-10}$cycloalkyl, —CH$_2$-$C_{3-10}$cycloalkyl, $C_{2-9}$heterocycloalkyl, —CH$_2$-$C_{2-9}$heterocycloalkyl, $C_{6-10}$aryl, —CH$_2$-$C_{6-10}$aryl, —CH$_2$-$C_{1-9}$heteroaryl, and $C_{1-9}$heteroaryl are optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —OR$^{12}$, —SR$^{12}$, —N(R$^{22}$)(R$^{23}$), —C(O) OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, —N(R$^{24}$)C(O)R$^{25}$, —N(R$^{24}$)S (O)$_2$R$^{25}$, —C(O)R$^{25}$, —S(O)$_2$R$^{25}$, —S(O)$_2$N(R$^{22}$) (R$^{23}$), and —OC(O)R$^{25}$;

provided that i) one or more of R$^{z4}$, R$^{z5}$, or R$^{z6}$ is -L$^{z1}$-L$^{z2}$-L$^{z3}$—R$^{12}$; or ii) one or more of R$^{20z}$ is -L$^{z3}$—R$^{12}$;

each R$^{20a}$, R$^{20b}$, R$^{20c}$, R$^{20d}$, R$^{20e}$, R$^{20f}$, R$^{20g}$, R$^{20h}$, R$^{20i}$, R$^{20j}$, R$^{20l}$, R$^{20lc}$, R$^{20m}$, R$^{20o}$, R$^{20q}$, and R$^{20zz}$ is independently selected from halogen, oxo, —CN, $C_{1-6}$alkyl, $C_{2-6}$alkenyl, $C_{2-6}$alkynyl, $C_{3-10}$cycloalkyl, —CH$_2$-$C_{3-10}$cycloalkyl, $C_{2-9}$heterocycloalkyl, —CH$_2$-$C_{2-9}$heterocycloalkyl, $C_{6-10}$aryl, —CH$_2$-$C_{6-10}$aryl, —CH$_2$-$C_{1-9}$heteroaryl, $C_{1-9}$heteroaryl, —OR$^{21}$, —SR$^{21}$, —N(R$^{22}$)(R$^{23}$), —C(O)OR$^{22}$, —C(O)N(R$^{22}$) (R$^{23}$), —C(O)C(O)N(R$^{22}$)(R$^{23}$), —OC(O)N(R$^{22}$) (R$^{23}$), —N(R$^{24}$)C(O)N(R$^{22}$)(R$^{23}$), —N(R$^{24}$)C(O) OR$^{25}$, —N(R$^{24}$)C(O)R$^{21}$, —N(R$^{24}$)S(O)$_2$R$^{25}$, —C(O) R$^{21}$, —S(O)$_2$R$^{25}$, —S(O)$_2$N(R$^{22}$)(R$^{23}$), —OCH$_2$C(O) OR$^{22}$, =NR$^{21}$, =C(R$^{21b}$)$_2$, and —OC(O)R$^{25}$; two R$^{20q}$ bonded to adjacent atoms are optionally joined to form a $C_{3-10}$cycloalkyl, $C_{2-9}$heterocycloalkyl, $C_{6-10}$aryl, or $C_{1-9}$heteroaryl; wherein $C_{1-6}$alkyl, $C_{2-6}$alkenyl, $C_{2-6}$alkynyl, $C_{3-10}$cycloalkyl, —CH$_2$-$C_{3-10}$cycloalkyl, $C_{2-9}$heterocycloalkyl, —CH$_2$-$C_{2-9}$heterocycloalkyl, $C_{6-10}$aryl, —CH$_2$-$C_{6-10}$aryl, —CH$_2$-$C_{1-9}$heteroaryl, and $C_{1-9}$heteroaryl are optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, —N(R$^{24}$)C(O)R$^{25}$, —N(R$^{24}$)S(O)$_2$R$^{25}$, —C(O)R$^{25}$, —S(O)$_2$R$^{25}$, —S(O)$_2$N(R$^{22}$)(R$^{23}$), and —OC(O)R$^{25}$;

- each R$^{21}$ is independently selected from hydrogen, C$_{1-6}$alkyl, C$_{1-6}$haloalkyl, C$_{2-6}$alkenyl, C$_{2-6}$alkynyl, C$_{3-10}$cycloalkyl, C$_{6-10}$aryl, and C$_{1-9}$heteroaryl;
- each R$^{21b}$ is independently selected from hydrogen, halogen, C$_{1-6}$alkyl, C$_{1-6}$haloalkyl, C$_{3-10}$cycloalkyl, and C$_{2-9}$heterocycloalkyl, or two R$^{21b}$ are taken together with the carbon atom to which they are attached to form C$_{3-10}$cycloalkyl or C$_{2-9}$heterocycloalkyl, each of which is optionally substituted with one or more substituents independently selected from halogen, C$_{1-3}$alkyl, C$_{1-3}$haloalkyl, and —OH;
- each R$^{22}$ is independently selected from hydrogen, C$_{1-6}$alkyl, C$_{1-6}$haloalkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl;
- each R$^{23}$ is independently selected from hydrogen and C$_{1-6}$alkyl;
- each R$^{24}$ is independently selected from hydrogen and C$_{1-6}$alkyl;
- each R$^{25}$ is independently selected from C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl; and
- ===== indicates a single or double bond such that all valences are satisfied.

In embodiments of a compound of Formula (B), R$^2$ is selected from

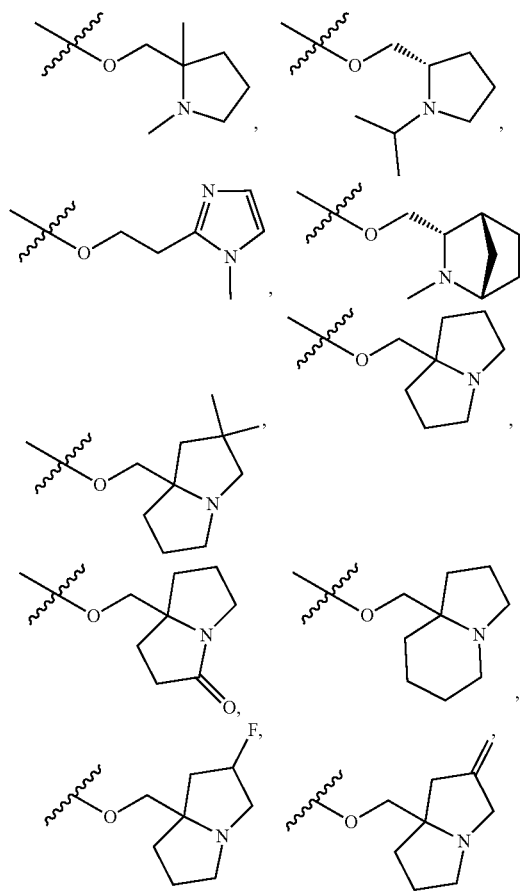

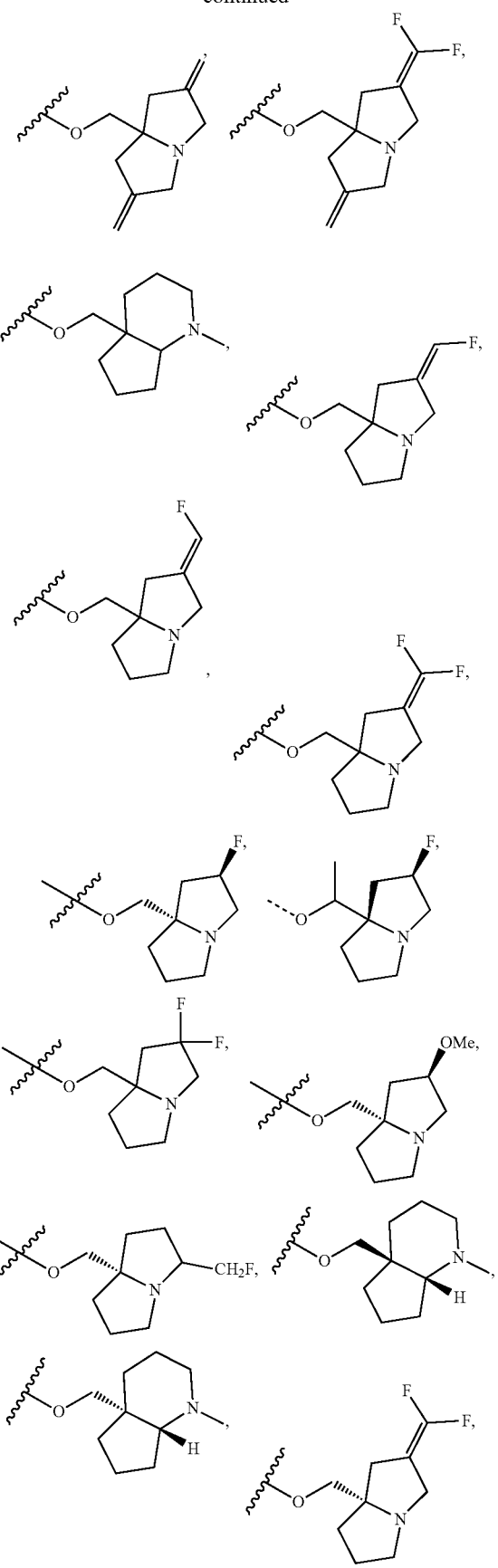

545
-continued
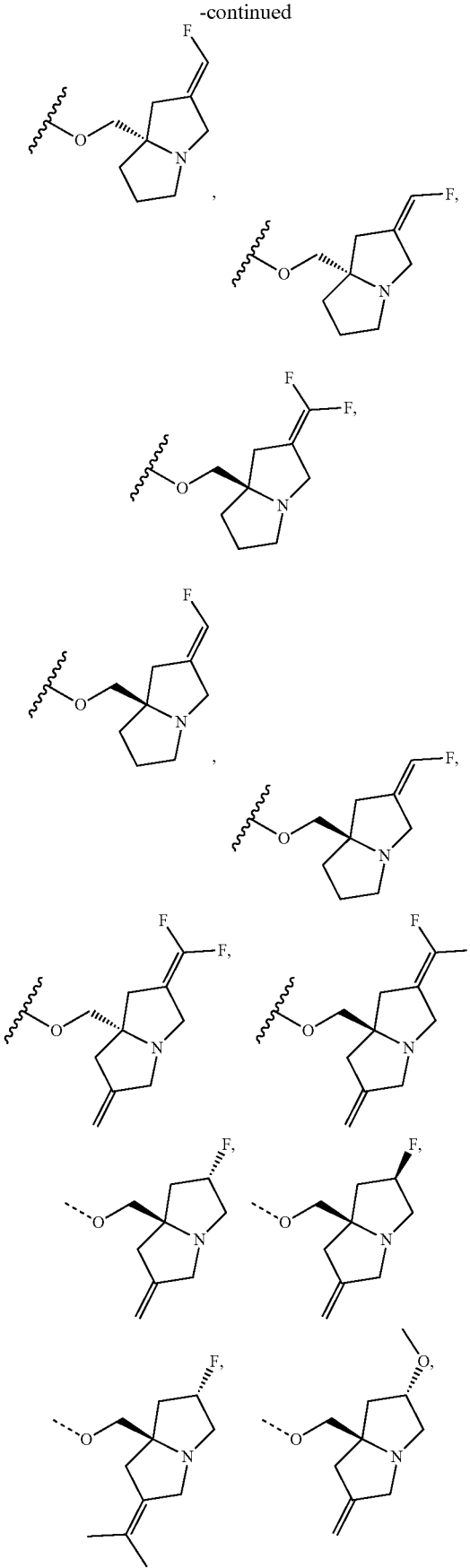
546
-continued
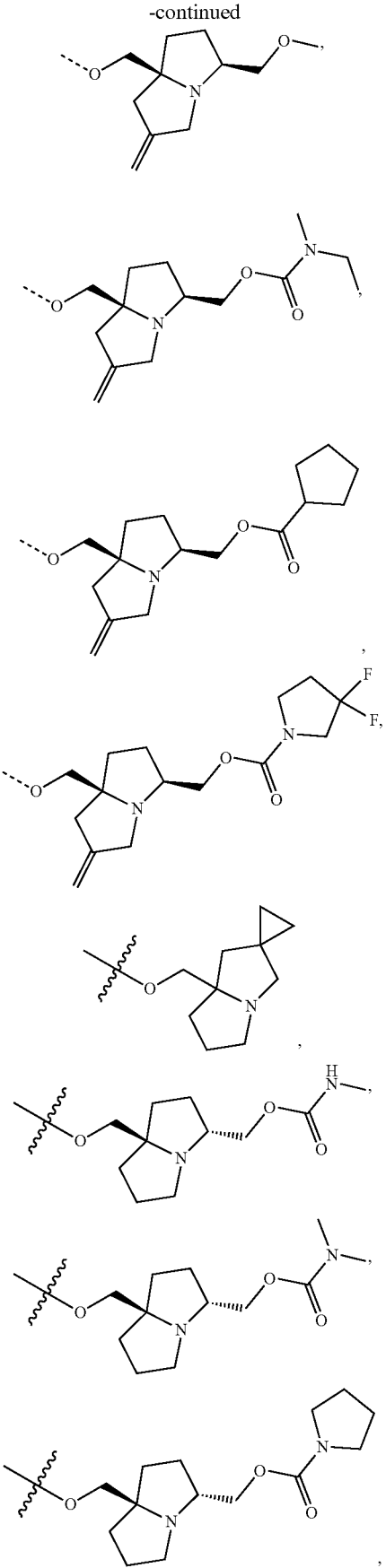

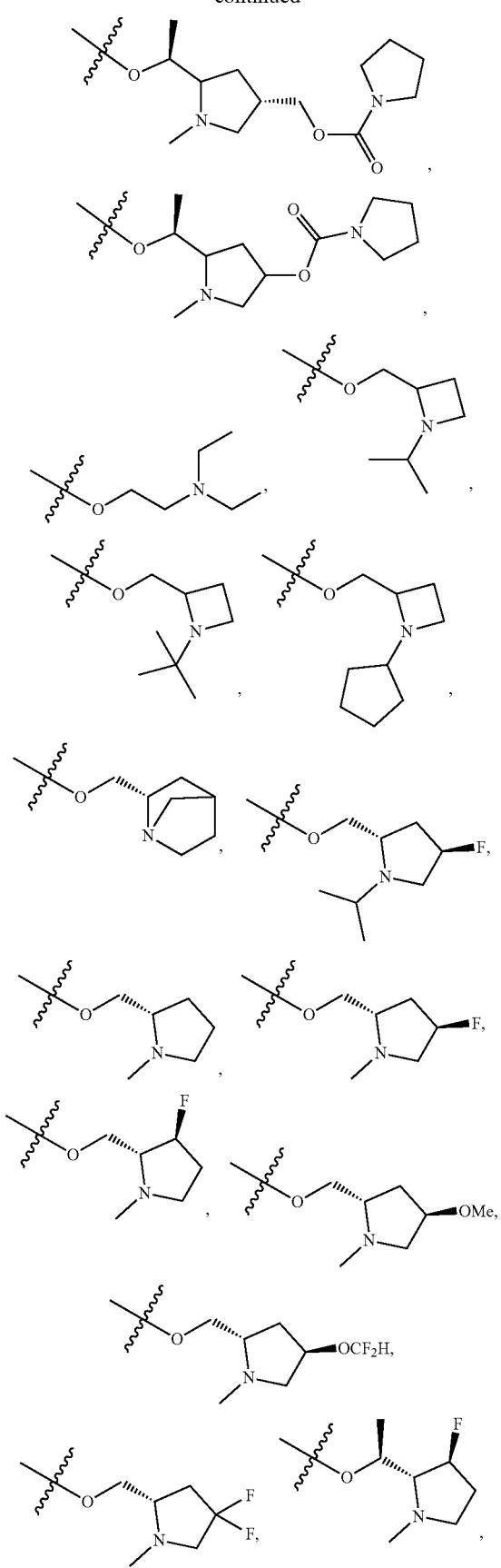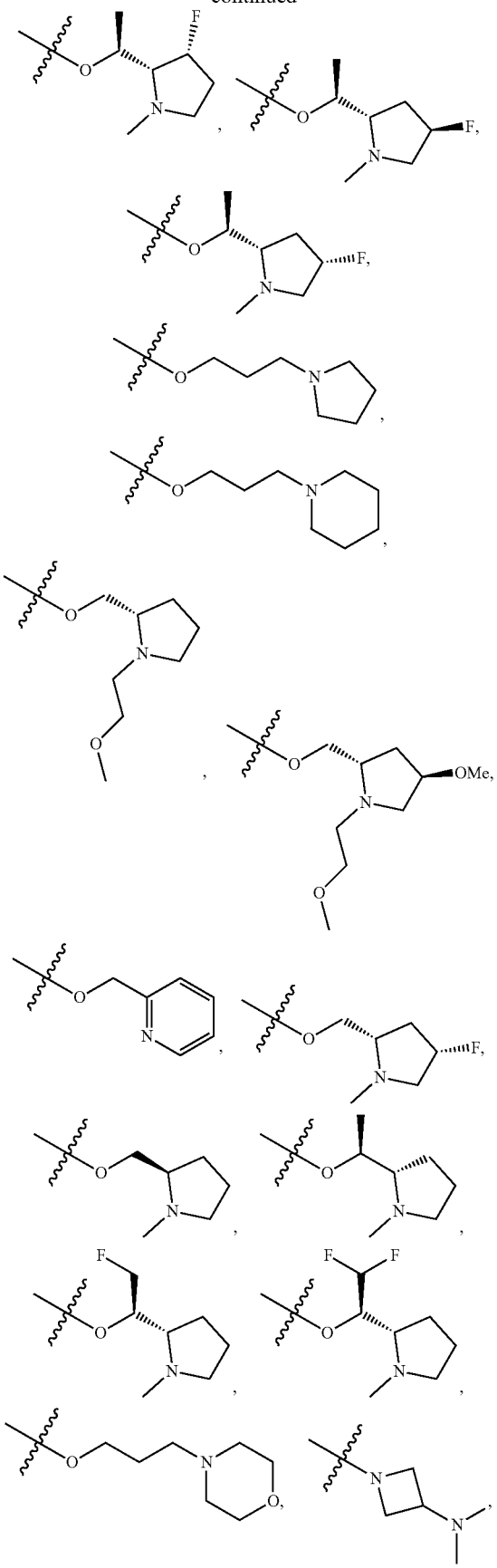

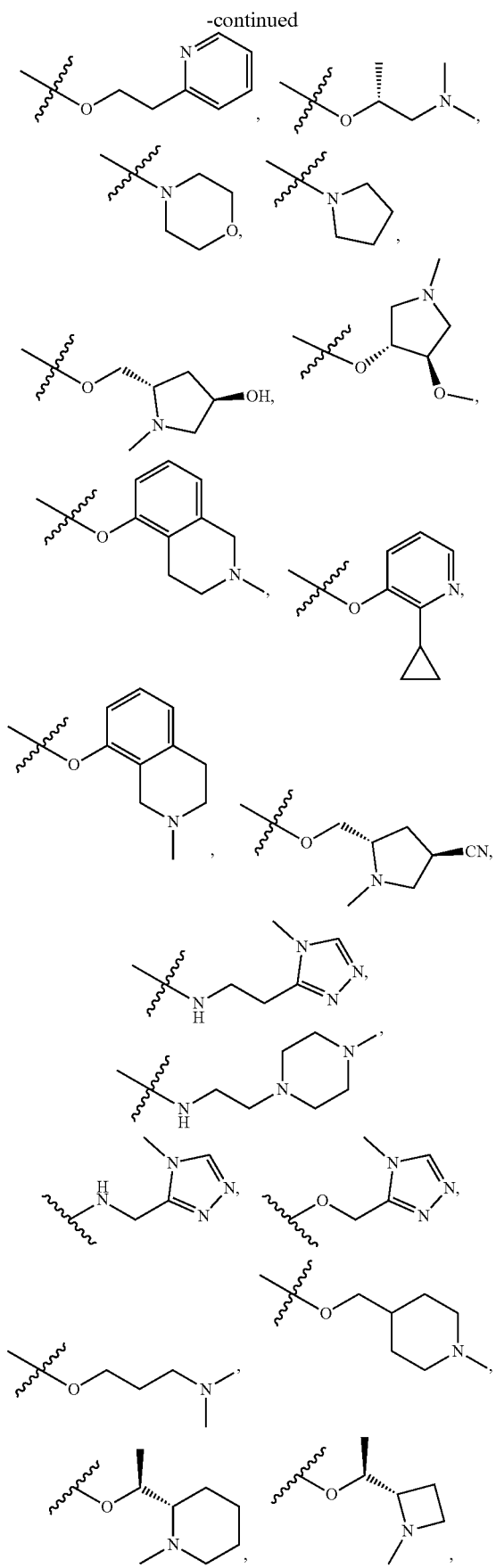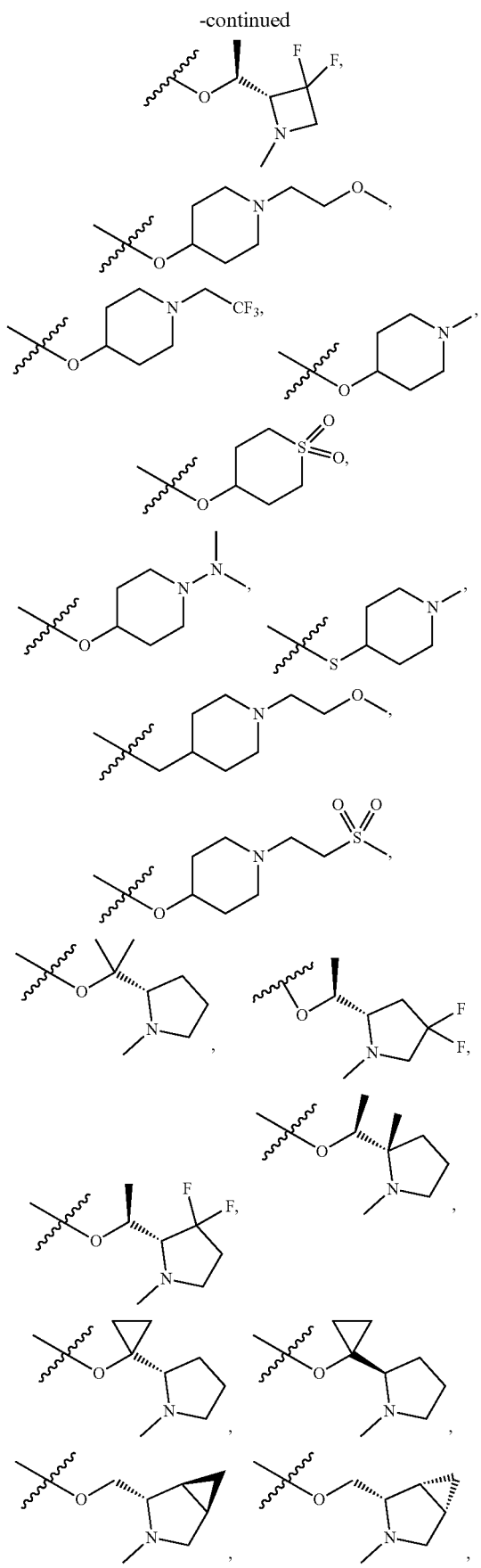

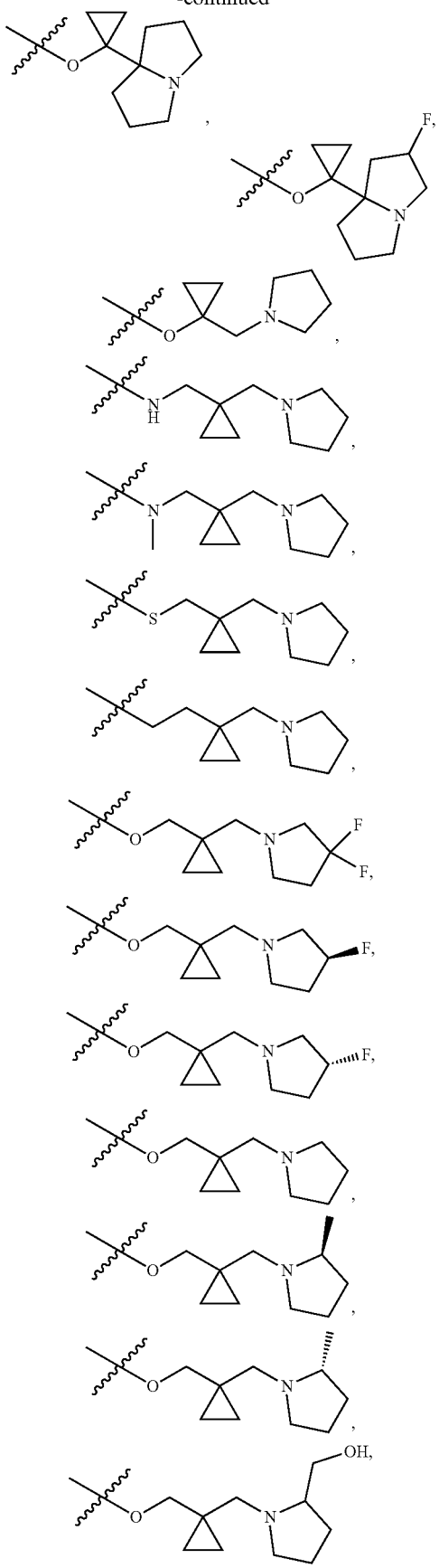
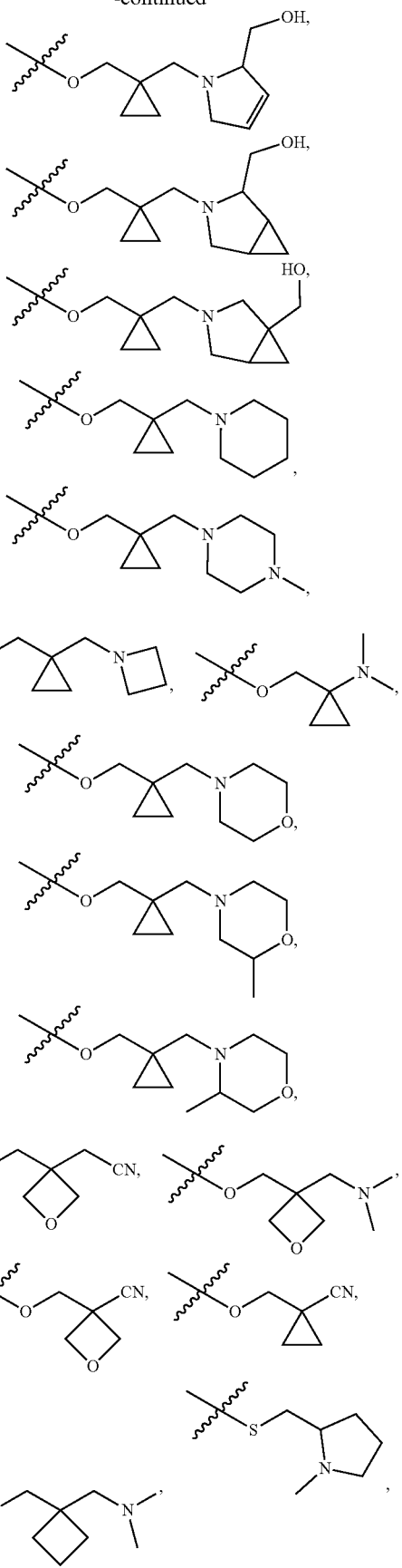

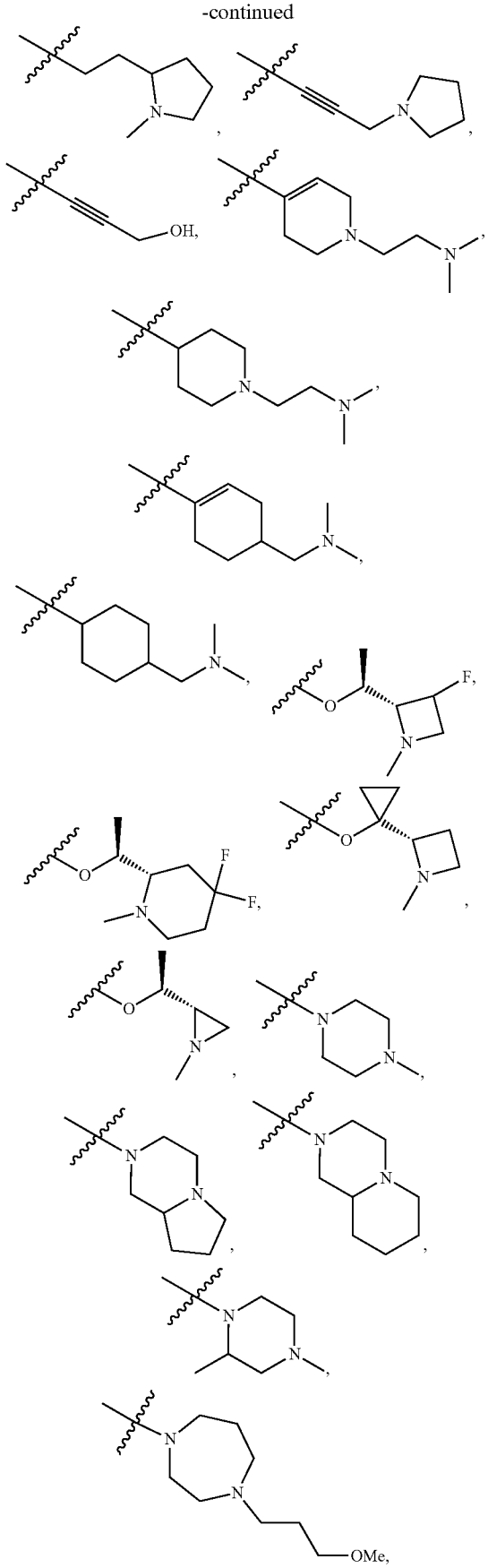
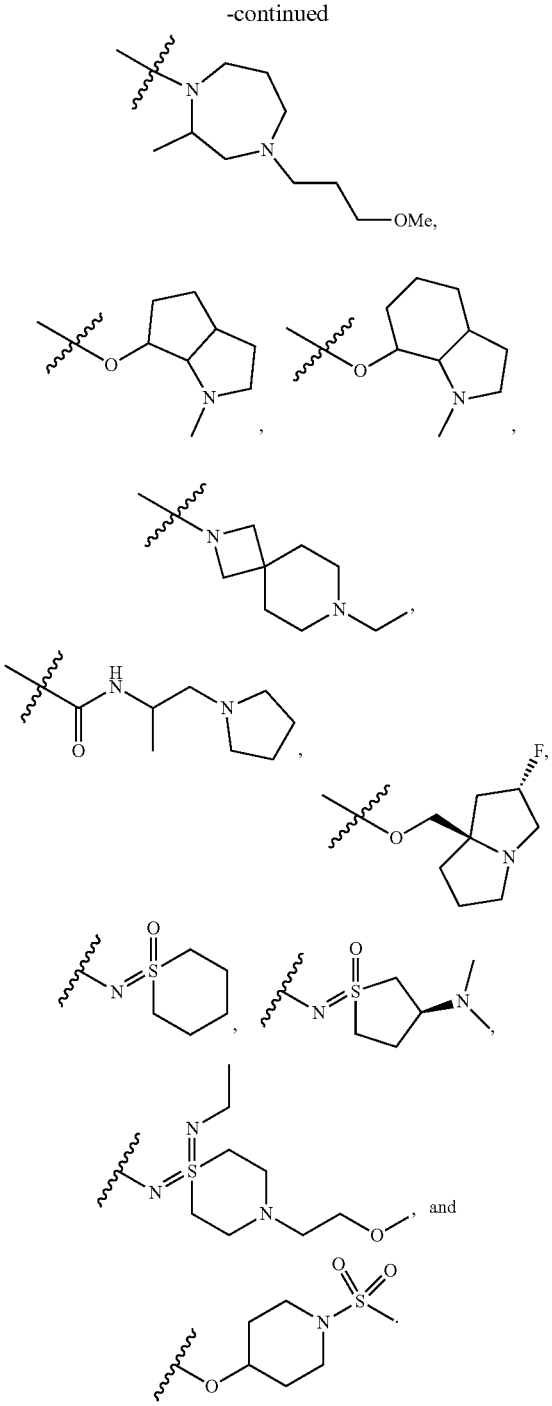
In embodiments of a compound of Formula (B), R² is selected from
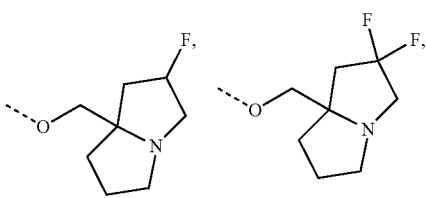

-continued

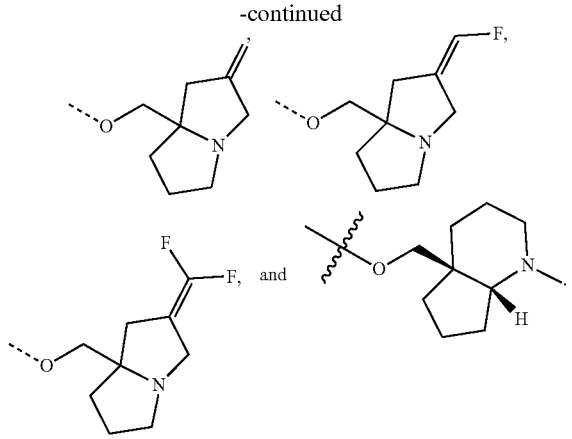

In embodiments of a compound of Formula (B), R² is selected from

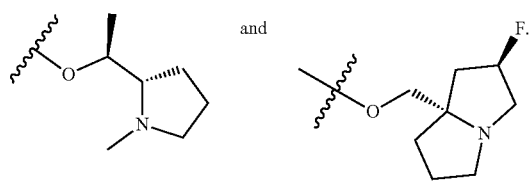

In an aspect is provided a compound of Formula (A), or a pharmaceutically acceptable salt or solvate thereof:

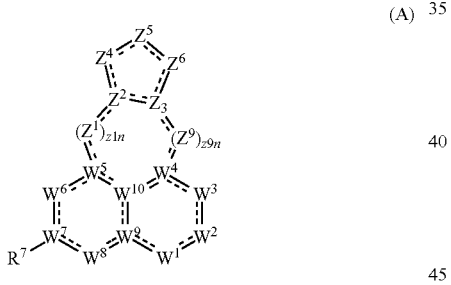

(A)

wherein:
$W^1$ is $N(R^1)$ or N;
$R^1$ is selected from hydrogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$C(O)OR^{12}$, —$OC(O)N(R^{12})(R^{13})$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20a}$;
$W^2$ is $C(R^2)$, $N(R^2)$, $C(R^2)_2$, C(O), S(O), $S(O)_2$, or N;
each $R^2$ is independently selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12a}$, —$SR^{12a}$, —$N(R^{12a})(R^{13})$, —$N=(R^{15})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20b}$;
$W^3$ is $C(R^3)$, $N(R^3)$, $C(R^3)_2$, C(O), S(O), $S(O)_2$, or N;
each $R^3$ is independently selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20c}$;
$W^4$ is $C(R^4)$, C, or N;
$R^4$ is selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20d}$;
$W^5$ is $C(R^5)$, C, or N;
$R^5$ is selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20e}$;
$W^6$ is $C(R^6)$, $N(R^6)$, $C(R^6)_2$, C(O), S(O), $S(O)_2$, or N;
each $R^6$ is independently selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})$ ($R^{13}$), wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20f}$;

$W^7$ is $C(R^{7a})$, C, or N;

$R^{7a}$ is selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20g}$;

$R^7$ is -$L^7$—$R^{17}$;

$L^7$ is a bond, $C_1$-$C_4$alkyl, $C_2$-$C_4$alkenyl, $C_2$-$C_4$alkynyl, 2-4 membered heteroalkylene linker, —O—, —$N(R^{7d})$—, —$C(O)$—, —S—, —$S(O)_2$—, —$S(O)$—, —$P(O)R^{7d}$—, $CR^{7c}R^{7c}$—, —$OCR^{7c}R^{7c}$—, —$N(R^{7d})CR^{7c}R^{7c}$—, —$C(O)CR^{7c}R^{7c}$—, —$SCR^{7c}R^{7c}$—, —$S(O)_2CR^{7c}R^{7c}$—, —$S(O)CR^{7c}R^{7c}$—, —$P(O)R^{7d}CR^{7c}R^{7c}$—, —$CR^{7c}R^{7c}CR^{7c}R^{7c}$, —$CR^{7c}R^{7c}O$—, —$CR^{7c}R^{7c}N(R^{7d})$—, —$CR^{7c}R^{7c}C(O)$—, —$CR^{7c}R^{7c}S$—, —$CR^{7c}R^{7c}S(O)_2$—, —$CR^{7c}R^{7c}S(O)$—, —$CR^{7c}R^{7c}P(O)R^{7d}$—, —$N(R^{7d})C(O)$—, —$N(R^{7d})S(O)_2$—, —$N(R^{7d})S(O)$—, —$N(R^{7d})P(O)R^{7d}$—, —$C(O)N(R^{7d})$—, —$S(O)_2N(R^{7d})$—, —$S(O)N(R^{7d})$—, —$P(O)R^{7d}N(R^{7d})$—, —$OC(O)$—, —$OS(O)_2$—, —$OS(O)$—, —$OP(O)R^{7d}$—, —$C(O)O$—, —$S(O)_2O$—, —$S(O)O$—, or —$P(O)R^{7d}O$—; wherein the $C_1$-$C_4$alkyl, $C_2$-$C_4$alkenyl, $C_2$-$C_4$alkynyl, 2-4 membered heteroalkylene linker are optionally substituted with one, two, or three $R^{20g}$;

each $R^{7c}$ is independently selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$, $S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20g}$;

each $R^{7d}$ is independently selected from hydrogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$C(O)OR^{12}$, —$OC(O)N(R^{12})(R^{13})$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20g}$;

$R^{17}$ is selected from $C_{3-10}$cycloalkyl, 3-10 membered heterocycloalkyl, $C_{6-10}$aryl, and 5-10 membered heteroaryl, wherein $C_{3-10}$cycloalkyl, 3-10 membered heterocycloalkyl, $C_{6-10}$aryl, and 5-10 membered heteroaryl are optionally substituted with one or more $R^{20q}$; or $L^7$ is a bond and $R^{7a}$ and $R^{17}$, together with the carbon to which they are attached, form $C_{3-10}$cycloalkyl or 3-10 membered heterocycloalkyl, wherein the $C_{3-10}$cycloalkyl and 3-10 membered heterocycloalkyl are optionally substituted with one or more $R^{20q}$;

$W^8$ is $C(R^8)$, $N(R^8)$, $C(R^8)_2$, C(O), S(O), $S(O)_2$, or N;

each $R^8$ is independently selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20h}$;

$W^9$ is $C(R^9)$, C, or N;

$R^9$ is selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20i}$;

$W^{10}$ $C(R^{10})$, C, or N;

$R^{10}$ is selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20j}$;

each $Z^1$ is independently $C(R^{z1})$, $N(R^{z1})$, $C(R^{z1})_2$, C(O), S(O), $S(O)_2$, O, S, or N;

z1n is 0, 1, 2, or 3; wherein if z1n is 0 then $Z^2$ is directly bonded to $W^5$;

each $R^{z1}$ is independently selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$, —$S(=O)(=NH)N $(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20z1}$;

each $Z^9$ is independently $C(R^{z9})$, $N(R^{z9})$, $C(R^{z9})_2$, $C(O)$, $S(O)$, $S(O)_2$, O, S, or N;

z9n is 0, 1, 2, or 3; wherein if z9n is 0 then $Z^3$ is directly bonded to $W^4$;

each $R^{z9}$ is independently selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20z9}$;

wherein the sum of z1n and z9n is 2 or 3;

$Z^2$ is $C(R^{z2})$, C, or N;

$R^{z2}$ is selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20z2}$;

$Z^3$ is $C(R^{z3})$, C, or N;

$R^{z3}$ is selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20z3}$;

$Z^4$ is a bond, $Z^{4a}$, $Z^{4a}Z^{4b}$, $Z^{4a}Z^{4b}Z^{4c}$, or $Z^{4a}Z^{4b}Z^{4c}Z^{4d}$; wherein $Z^{4a}$ is directly bonded to $Z^2$; and wherein if $Z^4$ is a bond then $Z^2$ is directly bonded to $Z^5$;

$Z^{4a}$, $Z^{4b}$, $Z^{4c}$, and $Z^{4d}$ are independently $C(R^{z4})$, $N(R^{z4})$, $C(R^{z4})_2$, $C(O)$, $S(O)$, $S(O)_2$, $S(O)(NR^{z4})$, O, S, or N;

provided that:
  i) if z9n is 0 and $Z^4$ is $Z^{4a}Z^{4b}$; then (1) $Z^{4b}$ is $C(R^{z4})$, $C(R^{z4})_2$, $C(O)$, $S(O)$, $S(O)_2$, $S(O)(NR^{z4})$, O, S, or N, (2) $Z^{4b}$ is $N(R^{z4})$ and $Z^{4a}$ is $C(O)$, $S(O)$, or $S(O)_2$; (3) $Z^{4b}$ is $N(R^{z4})$ and $Z^5$ is $C(O)$, $S(O)$, or $S(O)_2$; or (4) $Z^{4b}$ is $N(R^{z4})$ and $Z^3$ is $C(R^{z3})$ or C; and ii) one or more $R^{z4}$, $R^{z5}$, $R^{z6}$, $R^{20z4}$, $R^{20z5}$, $R^{20z6}$, or $R^{20z}$ or is independently selected from —$C(O)R^{12}$ and —$N(H)C(O)R^{12}$; wherein the one or more $R^{12}$ of —$C(O)R^{12}$ or —$N(H)C(O)R^{12}$, is independently selected from $C_{1-9}$heteroaryl, wherein $C_{1-9}$heteroaryl is optionally substituted with one, two, or three $R^{20l}$;

each $R^{z4}$ is independently selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{12}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{12}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20z4}$; or two $R^{z4}$ bonded to the same carbon are joined to form $C_{2-6}$alkenyl optionally substituted with one, two, or three $R^{20z4}$;

$Z^5$ is $C(R^{z5})$, $N(R^{z5})$, $C(R^{z5})_2$, $C(O)$, $S(O)$, $S(O)_2$, $S(O)(NR^{z5})$, O, S, or N;

each $R^{z5}$ is independently selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{12}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{12}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20z5}$; or two $R^{z5}$ bonded to the same carbon are joined to form $C_{2-6}$alkenyl optionally substituted with one, two, or three $R^{20z5}$;

$Z^6$ is $C(R^{z6})$, $N(R^{z6})$, $C(R^{z6})_2$, $C(O)$, $S(O)$, $S(O)_2$, $S(O)(NR^{z6})$, O, S, or N;

each $R^{z6}$ is independently selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{12}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{12}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20z6}$; or two $R^{z6}$ bonded to the same carbon are joined to form $C_{2-6}$alkenyl optionally substituted with one, two, or three $R^{20z6}$;

and further wherein the compound optionally includes one of the following:

(1) two $R^{z4}$ bonded to the same carbon atom are joined to form monocyclic $C_{3-7}$cycloalkyl or monocyclic 3-7 membered heterocycloalkyl, wherein the monocyclic $C_{3-7}$cycloalkyl and monocyclic 3-7 membered heterocycloalkyl are optionally substituted with one, two, or three $R^{20z}$;

(2) two or more $R^{z4}$ bonded to adjacent atoms are joined to form monocyclic $C_{3-7}$cycloalkyl, monocyclic 3-7 membered heterocycloalkyl, phenyl, or monocyclic 5-6 membered heteroaryl, wherein the monocyclic $C_{3-7}$cycloalkyl, monocyclic 3-7 membered heterocycloalkyl, phenyl, and monocyclic 5-6 membered heteroaryl are optionally substituted with one, two, or three $R^{20z}$;

(3) two $R^{z5}$ bonded to the same carbon atom are joined to form monocyclic $C_{3-7}$cycloalkyl or monocyclic 3-7 membered heterocycloalkyl, wherein the monocyclic $C_{3-7}$cycloalkyl and monocyclic 3-7 membered heterocycloalkyl are optionally substituted with one, two, or three $R^{20z}$;

(4) one or two $R^{z4}$ bonded to one atom and one or two $R^{z5}$ bonded to an adjacent atom are joined to form monocyclic $C_{3-7}$cycloalkyl, monocyclic 3-7 membered heterocycloalkyl, phenyl, or monocyclic 5-6 membered heteroaryl, wherein the monocyclic $C_{3-7}$cycloalkyl, monocyclic 3-7 membered heterocycloalkyl, phenyl, and monocyclic 5-6 membered heteroaryl are optionally substituted with one, two, or three $R^{20z}$;

(6) two $R^{z6}$ bonded to the same carbon atom are joined to form monocyclic $C_{3-7}$cycloalkyl or monocyclic 3-7 membered heterocycloalkyl, wherein the monocyclic $C_{3-7}$cycloalkyl and monocyclic 3-7 membered heterocycloalkyl are optionally substituted with one, two, or three $R^{20z}$;

(7) one or two $R^{z5}$ bonded to one atom and one or two $R^{z6}$ bonded to an adjacent atom are joined to form monocyclic $C_{3-7}$cycloalkyl, monocyclic 3-7 membered heterocycloalkyl, phenyl, or monocyclic 5-6 membered heteroaryl, wherein the monocyclic $C_{3-7}$cycloalkyl, monocyclic 3-7 membered heterocycloalkyl, phenyl, and monocyclic 5-6 membered heteroaryl are optionally substituted with one, two, or three $R^{20z}$; or (8) one or two $R^{z4}$ bonded to one atom and one or two $R^{z6}$ bonded to a second atom are joined to form monocyclic $C_{3-7}$cycloalkyl or monocyclic 3-7 membered heterocycloalkyl, wherein the monocyclic $C_{3-7}$cycloalkyl and monocyclic 3-7 membered heterocycloalkyl are optionally substituted with one, two, or three $R^{20z}$;

each $R^{12}$ is independently selected from hydrogen, $C_{1-6}$alkyl, $C_{2-6}$alkenyl, $C_{2-6}$alkynyl, $C_{3-10}$cycloalkyl, —$CH_2$-$C_{3-10}$cycloalkyl, $C_{2-9}$heterocycloalkyl, —$CH_2$-$C_{2-9}$heterocycloalkyl, $C_{6-10}$aryl, —$CH_2$-$C_{6-10}$aryl, —$CH_2$-$C_{1-9}$heteroaryl, and $C_{1-9}$heteroaryl, wherein $C_{1-6}$alkyl, $C_{2-6}$alkenyl, $C_{2-6}$alkynyl, $C_{3-10}$cycloalkyl, —$CH_2$-$C_{3-10}$cycloalkyl, $C_{2-9}$heterocycloalkyl, —$CH_2$-$C_{2-9}$heterocycloalkyl, $C_{6-10}$aryl, —$CH_2$-$C_{6-10}$aryl, —$CH_2$-$C_{1-9}$heteroaryl, and $C_{1-9}$heteroaryl are optionally substituted with one, two, or three $R^{20l}$;

$R^{12a}$ is independently selected from hydrogen, $C_{1-6}$alkyl, $C_{2-6}$alkenyl, $C_{2-6}$alkynyl, $C_{3-10}$cycloalkyl, —$C(R^{12c})_2$-$C_{3-10}$cycloalkyl, $C_{2-9}$heterocycloalkyl, —$C(R^{12c})_2$-$C_{2-9}$heterocycloalkyl, $C_{6-10}$aryl, —$C(R^{12c})_2$-$C_{6-10}$aryl, —$C(R^{12c})_2$-$C_{1-9}$heteroaryl, and $C_{1-9}$heteroaryl, wherein $C_{1-6}$alkyl, $C_{2-6}$alkenyl, $C_{2-6}$alkynyl, $C_{3-10}$cycloalkyl, —$C(R^{12c})_2$-$C_{3-10}$cycloalkyl, $C_{2-9}$heterocycloalkyl, —$C(R^{12c})_2$-$C_{2-9}$heterocycloalkyl, $C_{6-10}$aryl, —$C(R^{12c})_2$-$C_{6-10}$aryl, —$C(R^{12c})_2$-$C_{1-9}$heteroaryl, and $C_{1-9}$heteroaryl are optionally substituted with one, two, or three $R^{20l}$;

each $R^{12c}$ is independently selected from hydrogen and $R^{20lc}$;

each $R^{13}$ is independently selected from hydrogen, $C_{1-6}$alkyl, and $C_{1-6}$haloalkyl; or $R^{12}$ and $R^{13}$, together with the nitrogen to which they are attached, form a $C_{2-9}$heterocycloalkyl ring optionally substituted with one, two, or three $R^{20m}$;

each $R^{14}$ is independently selected from hydrogen, $C_{1-6}$alkyl, and $C_{1-6}$haloalkyl;

each $R^{15}$ is independently selected from $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20o}$;

each $R^{20z1}$, $R^{20z2}$, $R^{20z3}$, $R^{20z4}$, $R^{20z5}$, $R^{20z6}$, and $R^{20z9}$ is independently selected from halogen, oxo, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{12}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{12}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20z}$;

each $R^{20z}$ is independently selected from halogen, oxo, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{12}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{12}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20zz}$;

two $R^{20z}$ bonded to the same carbon atom are optionally joined to form monocyclic $C_{3-7}$cycloalkyl or monocyclic 3-7 membered heterocycloalkyl, wherein the monocyclic $C_{3-7}$cycloalkyl and monocyclic 3-7 membered heterocycloalkyl are optionally substituted with one, two, or three $R^{20zz}$; or two or more $R^{20z}$ bonded to two adjacent atoms are optionally joined to form monocyclic $C_{3-7}$cycloalkyl, monocyclic 3-7 membered heterocycloalkyl, phenyl, or monocyclic 5-6 membered heteroaryl, wherein the $C_{3-7}$cycloalkyl, monocyclic 3-7 membered heterocycloalkyl, phenyl, and monocyclic 5-6 membered heteroaryl are optionally substituted with one, two, or three $R^{20zz}$;

each $R^{20a}$, $R^{20b}$, $R^{20c}$, $R^{20d}$, $R^{20e}$, $R^{20f}$, $R^{20g}$, $R^{20h}$, $R^{20i}$, $R^{20j}$, $R^{20lc}$, $R^{20l}$, $R^{20m}$, $R^{20o}$, and $R^{20q}$ is independently selected from halogen, oxo, —CN, $C_{1-6}$alkyl, $C_{2-6}$alkenyl, $C_{2-6}$alkynyl, $C_{3-10}$cycloalkyl, —$CH_2$-$C_{3-10}$cycloalkyl, $C_{2-9}$heterocycloalkyl, —$CH_2$-$C_{2-9}$heterocycloalkyl, $C_{6-10}$aryl, —$CH_2$-$C_{6-10}$aryl, —$CH_2$-$C_{1-9}$heteroaryl, $C_{1-9}$heteroaryl, —$OR^{21}$, —$SR^{21}$, —$N(R^{22})(R^{23})$, —$C(O)OR^{22}$, —$C(O)N(R^{22})(R^{23})$, —$C(O)C(O)N(R^{22})(R^{23})$, —$OC(O)N(R^{22})(R^{23})$, —$N(R^{24})C(O)N(R^{22})(R^{23})$, —$N(R^{24})C(O)OR^{25}$, —$N(R^{24})C(O)R^{21}$, —$N(R^{24})S(O)_2R^{25}$, —$C(O)R^{21}$, —$S(O)_2R^{25}$, —$S(O)_2N(R^{22})(R^{23})$, —$OCH_2C(O)OR^{22}$, =$NR^{21}$, and —$OC(O)R^{25}$; two $R^{20q}$ bonded to adjacent atoms are optionally joined to form a $C_{3-10}$cycloalkyl, $C_{2-9}$heterocycloalkyl, $C_{6-10}$aryl, or $C_{1-9}$heteroaryl; wherein $C_{1-6}$alkyl, $C_{2-6}$alkenyl, $C_{2-6}$alkynyl, $C_{3-10}$cycloalkyl, —$CH_2$-$C_{3-10}$cycloalkyl, $C_{2-9}$heterocycloalkyl, —$CH_2$-$C_{2-9}$heterocycloalkyl, $C_{6-10}$aryl, —$CH_2$-$C_{6-10}$aryl, —$CH_2$-$C_{1-9}$heteroaryl, and $C_{1-9}$heteroaryl are optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —$OR^{21}$, —$SR^{21}$, —$N(R^{22})(R^{23})$, —$C(O)OR^{22}$, —$C(O)N(R^{22})(R^{23})$, —$C(O)C(O)N(R^{22})(R^{23})$, —$OC(O)N(R^{22})(R^{23})$, —$N(R^{24})C(O)N(R^{22})(R^{23})$, —$N(R^{24})C(O)OR^{25}$, —$N(R^{24})C(O)R^{25}$, —$N(R^{24})S(O)_2R^{25}$, —$C(O)R^{25}$, —$S(O)_2R^{25}$, —$S(O)_2N(R^{22})(R^{23})$, and —$OC(O)R^{25}$;

each $R^{21}$ is independently selected from hydrogen, $C_{1-6}$alkyl, $C_{1-6}$haloalkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl;

each $R^{22}$ is independently selected from hydrogen, $C_{1-6}$alkyl, $C_{1-6}$haloalkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl;

each $R^{23}$ is independently selected from hydrogen and $C_{1-6}$alkyl;

each $R^{24}$ is independently selected from hydrogen and $C_{1-6}$alkyl;

each $R^{25}$ is independently selected from $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; and ═══ indicates a single or double bond such that all valences are satisfied.

(A)

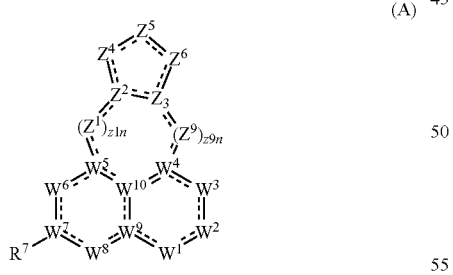

wherein:

$W^1$ is $N(R^1)$ or N;

$R^1$ is selected from hydrogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$C(O)OR^{12}$, —$OC(O)N(R^{12})(R^{13})$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20a}$;

$W^2$ is $C(R^2)$, $N(R^2)$, $C(R^2)_2$, C(O), S(O), $S(O)_2$, or N;

each $R^2$ is independently selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12a}$, —$SR^{12a}$, —$N(R^{12a})(R^{13})$, —$N$═$(R^{15})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$—, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20b}$;

$W^3$ is $C(R^3)$, $N(R^3)$, $C(R^3)_2$, C(O), S(O), $S(O)_2$, or N;

each $R^3$ is independently selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20c}$;

$W^4$ is $C(R^4)$, C, or N;

$R^4$ is selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20d}$;

$W^5$ is $C(R^5)$, C, or N;

$R^5$ is selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20e}$;

$W^6$ is $C(R^6)$, $N(R^6)$, $C(R^6)_2$, C(O), S(O), $S(O)_2$, or N;

each $R^6$ is independently selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20f}$;

$W^7$ is $C(R^{7a})$, C, or N;

$R^{7a}$ is selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20g}$;

$R^7$ is -$L^7$—$R^{17}$;

$L^7$ is a bond, $C_1$-$C_4$alkyl, $C_2$-$C_4$alkenyl, $C_2$-$C_4$alkynyl, 2-4 membered heteroalkylene linker, —O—, —$N(R^{7d})$—, —C(O)—, —S—, —$S(O)_2$—, —S(O)—, —$P(O)R^{7d}$—, —$CR^{7c}R^{7c}$—, —$OCR^{7c}R^{7c}$—, —$N(R^{7d})CR^{7c}R^{7c}$—, —$C(O)CR^{7c}R^{7c}$—, —$SCR^{7c}R^{7c}$—, —$S(O)_2CR^{7c}R^{7c}$—, —$S(O)CR^{7c}R^{7c}$—, —$P(O)R^{7d}CR^{7c}R^{7c}$—, —$CR^{7c}R^{7c}CR^{7c}R^{7c}$—, —$CR^{7c}R^{7c}O$—, —$CR^{7c}R^{7c}N(R^{7d})$—, —$CR^{7c}R^{7c}C(O)$—, —$CR^{7c}R^{7c}S$—, —$CR^{7c}R^{7c}S(O)_2$—, —$CR^{7c}R^{7c}S(O)$—, —$CR^{7c}R^{7c}P(O)R^{7d}$—, —$N(R^{7d})C(O)$—, —$N(R^{7d})S(O)_2$—, —$N(R^{7d})S(O)$—, —$N(R^{7d})P(O)R^{7d}$—, —$C(O)N(R^{7d})$—, —$S(O)_2N(R^{7d})$—, —$S(O)N(R^{7d})$—, —$P(O)R^{7d}N(R^{7d})$—, —OC(O)—, —$OS(O)_2$—, —OS(O)—, —$OP(O)R^{7d}$—, —C(O)O—, —$S(O)_2O$—, —S(O)O—, or —$P(O)R^{7d}O$—; wherein the $C_1$-$C_4$alkyl, $C_2$-$C_4$alkenyl, $C_2$-$C_4$alkynyl, 2-4 membered heteroalkylene linker are optionally substituted with one, two, or three $R^{20g}$;

each $R^{7c}$ is independently selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$, $S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20g}$;

each $R^{7d}$ is independently selected from hydrogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$C(O)OR^{12}$, —$OC(O)N(R^{12})(R^{13})$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20g}$;

$R^{17}$ is selected from $C_{3-10}$cycloalkyl, 3-10 membered heterocycloalkyl, $C_{6-10}$aryl, and 5-10 membered heteroaryl, wherein $C_{3-10}$cycloalkyl, 3-10 membered heterocycloalkyl, $C_{6-10}$aryl, and 5-10 membered heteroaryl are optionally substituted with one or more $R^{20q}$; or $L^7$ is a bond and $R^{7a}$ and $R^{17}$, together with the carbon to which they are attached, form $C_{3-10}$cycloalkyl or 3-10 membered heterocycloalkyl, wherein the $C_{3-10}$cycloalkyl and 3-10 membered heterocycloalkyl are optionally substituted with one or more $R^{20q}$;

$W^8$ is $C(R^8)$, $N(R^8)$, $C(R^8)_2$, C(O), S(O), $S(O)_2$, or N;

each $R^8$ is independently selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, and —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20h}$;

$W^9$ is $C(R^9)$, C, or N;

$R^9$ is selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20i}$;

$W^{10}$ $C(R^{10})$, C, or N;

$R^{10}$ is selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20j}$;

each $Z^1$ is independently $C(R^{z1})$, $N(R^{z1})$, $C(R^{z1})_2$, C(O), S(O), $S(O)_2$, O, S, or N;

z1n is 0, 1, 2, or 3; wherein if z1n is 0 then $Z^2$ is directly bonded to $W^5$;

each $R^{z1}$ is independently selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$), —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20z1}$;

each $Z^9$ is independently C(R$^{z9}$), N(R$^{z9}$), C(R$^{z9}$)$_2$, C(O), S(O), S(O)$_2$, O, S, or N;

z9n is 0, 1, 2, or 3; wherein if z9n is 0 then $Z^3$ is directly bonded to $W^4$;

each $R^{z9}$ is independently selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$), —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20z9}$;

wherein the sum of z1n and z9n is 2 or 3;

$Z^2$ is C(R$^{z2}$), C, or N;

$R^{z2}$ is selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$), —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20z2}$;

$Z^3$ is C(R$^{z3}$), C, or N;

$R^{z3}$ is selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$), —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20z3}$;

$Z^4$ is a bond, $Z^{4a}$, $Z^{4a}Z^{4b}$, $Z^{4a}Z^{4b}Z^{4c}$, or $Z^{4a}Z^{4b}Z^{4c}Z^{4d}$; wherein $Z^{4a}$ is directly bonded to $Z^2$; and wherein if $Z^4$ is a bond then $Z^2$ is directly bonded to $Z^5$;

$Z^{4a}$, $Z^{4b}$, $Z^{4c}$, and $Z^{4d}$ are independently C(R$^{z4}$), N(R$^{z4}$), C(R$^{z4}$)$_2$, C(O), S(O), S(O)$_2$, S(O)(NR$^{z4}$), O, S, or N; provided that:

i) if z9n is 0 and $Z^4$ is $Z^{4a}Z^{4b}$; then (1) $Z^{4b}$ is C(R$^{z4}$), C(R$^{z4}$)$_2$, C(O), S(O), S(O)$_2$, S(O)(NR$^{z4}$), O, S, or N, (2) $Z^{4b}$ is N(R$^{z4}$) and $Z^{4a}$ is C(O), S(O), or S(O)$_2$; (3) $Z^{4b}$ is N(R$^{z4}$) and $Z^5$ is C(O), S(O), or S(O)$_2$; or (4) $Z^{4b}$ is N(R$^{z4}$) and $Z^3$ is C(R$^{z3}$) or C; and ii) one or more of R$^{z4}$, R$^{z5}$, R$^{z6}$, R$^{20z4}$, R$^{20z5}$, R$^{20z6}$, or R$^{20z}$ or one or more of the joining of two substituents selected from R$^{z4}$, R$^{z5}$, R$^{z6}$, R$^{20z}$, and R$^{20zz}$ is E, wherein E is a moiety capable of covalently binding to a Ras mutant protein at an amino acid corresponding to G12D or G12S of human K-Ras mutant G12D or G12S protein, respectively:

each $R^{z4}$ is independently selected from E, hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{12}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{12}$, —S(O)$_2$R$^{15}$, —S(O)$_2$N(R$^{12}$)(R$^{13}$), —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20z4}$; or two $R^{z4}$ bonded to the same carbon are joined to form $C_{2-6}$alkenyl optionally substituted with one, two, or three $R^{20z4}$;

$Z^5$ is C(R$^{z5}$), N(R$^{z5}$), C(R$^{z5}$)$_2$, C(O), S(O), S(O)$_2$, S(O)(NR$^{z5}$), O, S, or N;

each $R^{z5}$ is independently selected from E, hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{12}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{12}$, —S(O)$_2$R$^{15}$, —S(O)$_2$N(R$^{12}$)(R$^{13}$), —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20z5}$; or two $R^{z5}$ bonded to the same carbon are joined to form $C_{2-6}$alkenyl optionally substituted with one, two, or three $R^{20z5}$;

$Z^6$ is C(R$^{z6}$), N(R$^{z6}$), C(R$^{z6}$)$_2$, C(O), S(O), S(O)$_2$, S(O)(NR$^{z6}$), O, S, or N;

each $R^{z6}$ is independently selected from E, hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{12}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{12}$, —S(O)$_2$R$^{15}$, —S(O)$_2$N(R$^{12}$)(R$^{13}$), —S(=O)(=NH)N ($R^{12}$)($R^{13}$), —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20z6}$; or two $R^{z6}$ bonded to the same carbon are joined to form $C_{2-6}$alkenyl optionally substituted with one, two, or three $R^{20z6}$;

and further wherein the compound optionally includes one of the following:

(1) two $R^{z4}$ bonded to the same carbon atom are joined to form monocyclic $C_{3-7}$cycloalkyl or monocyclic 3-7 membered heterocycloalkyl, wherein the monocyclic $C_{3-7}$cycloalkyl and monocyclic 3-7 membered heterocycloalkyl are optionally substituted with one, two, or three $R^{20z}$;

(2) two or more $R^{z4}$ bonded to adjacent atoms are joined to form monocyclic $C_{3-7}$cycloalkyl, monocyclic 3-7 membered heterocycloalkyl, phenyl, or monocyclic 5-6 membered heteroaryl, wherein the monocyclic $C_{3-7}$cycloalkyl, monocyclic 3-7 membered heterocycloalkyl, phenyl, and monocyclic 5-6 membered heteroaryl are optionally substituted with one, two, or three $R^{20z}$;

(3) two $R^{z5}$ bonded to the same carbon atom are joined to form monocyclic $C_{3-7}$cycloalkyl or monocyclic 3-7 membered heterocycloalkyl, wherein the monocyclic $C_{3-7}$cycloalkyl and monocyclic 3-7 membered heterocycloalkyl are optionally substituted with one, two, or three $R^{20z}$;

(4) one or two $R^{z4}$ bonded to one atom and one or two $R^{z5}$ bonded to an adjacent atom are joined to form monocyclic $C_{3-7}$cycloalkyl, monocyclic 3-7 membered heterocycloalkyl, phenyl, or monocyclic 5-6 membered heteroaryl, wherein the monocyclic $C_{3-7}$cycloalkyl, monocyclic 3-7 membered heterocycloalkyl, phenyl, and monocyclic 5-6 membered heteroaryl are optionally substituted with one, two, or three $R^{20z}$;

(6) two $R^{z6}$ bonded to the same carbon atom are joined to form monocyclic $C_{3-7}$cycloalkyl or monocyclic 3-7 membered heterocycloalkyl, wherein the monocyclic $C_{3-7}$cycloalkyl and monocyclic 3-7 membered heterocycloalkyl are optionally substituted with one, two, or three $R^{20z}$;

(7) one or two $R^{z5}$ bonded to one atom and one or two $R^{z6}$ bonded to an adjacent atom are joined to form monocyclic $C_{3-7}$cycloalkyl, monocyclic 3-7 membered heterocycloalkyl, phenyl, or monocyclic 5-6 membered heteroaryl, wherein the monocyclic $C_{3-7}$cycloalkyl, monocyclic 3-7 membered heterocycloalkyl, phenyl, and monocyclic 5-6 membered heteroaryl are optionally substituted with one, two, or three $R^{20z}$; or (8) one or two $R^{z4}$ bonded to one atom and one or two $R^{z6}$ bonded to a second atom are joined to form monocyclic $C_{3-7}$cycloalkyl or monocyclic 3-7 membered heterocycloalkyl, wherein the monocyclic $C_{3-7}$cycloalkyl and monocyclic 3-7 membered heterocycloalkyl are optionally substituted with one, two, or three $R^{20z}$;

each $R^{12}$ is independently selected from hydrogen, $C_{1-6}$alkyl, $C_{2-6}$alkenyl, $C_{2-6}$alkynyl, $C_{3-10}$cycloalkyl, —$CH_2$-$C_{3-10}$cycloalkyl, $C_{2-9}$heterocycloalkyl, —$CH_2$-$C_{2-9}$heterocycloalkyl, $C_{6-10}$aryl, —$CH_2$-$C_{6-10}$aryl, —$CH_2$-$C_{1-9}$heteroaryl, and $C_{1-9}$heteroaryl, wherein $C_{1-6}$alkyl, $C_{2-6}$alkenyl, $C_{2-6}$alkynyl, $C_{3-10}$cycloalkyl, —$CH_2$-$C_{3-10}$cycloalkyl, $C_{2-9}$heterocycloalkyl, —$CH_2$-$C_{2-9}$heterocycloalkyl, $C_{6-10}$aryl, —$CH_2$-$C_{6-10}$aryl, —$CH_2$-$C_{1-9}$heteroaryl, and $C_{1-9}$heteroaryl are optionally substituted with one, two, or three $R^{20l}$;

$R^{12a}$ is independently selected from hydrogen, $C_{1-6}$alkyl, $C_{2-6}$alkenyl, $C_{2-6}$alkynyl, $C_{3-10}$cycloalkyl, —$C(R^{12c})_2$-$C_{3-10}$cycloalkyl, $C_{2-9}$heterocycloalkyl, —$C(R^{12c})_2$-$C_{2-9}$heterocycloalkyl, $C_{6-10}$aryl, —$C(R^{12c})_2$-$C_{6-10}$aryl, —$C(R^{12c})_2$-$C_{1-9}$heteroaryl, and $C_{1-9}$heteroaryl, wherein $C_{1-6}$alkyl, $C_{2-6}$alkenyl, $C_{2-6}$alkynyl, $C_{3-10}$cycloalkyl, —$C(R^{12c})_2$-$C_{3-10}$cycloalkyl, $C_{2-9}$heterocycloalkyl, —$C(R^{12c})_2$-$C_{2-9}$heterocycloalkyl, $C_{6-10}$aryl, —$C(R^{12c})_2$-$C_{6-10}$aryl, —$C(R^{12c})_2$-$C_{1-9}$heteroaryl, and $C_{1-9}$heteroaryl are optionally substituted with one, two, or three $R^{20l}$;

each $R^{12c}$ is independently selected from hydrogen and $R^{20lc}$;

each $R^{13}$ is independently selected from hydrogen, $C_{1-6}$alkyl, and $C_{1-6}$haloalkyl; or $R^{12}$ and $R^{13}$, together with the nitrogen to which they are attached, form a $C_{2-9}$heterocycloalkyl ring optionally substituted with one, two, or three $R^{20m}$;

each $R^{14}$ is independently selected from hydrogen, $C_{1-6}$alkyl, and $C_{1-6}$haloalkyl;

each $R^{15}$ is independently selected from $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20o}$;

each $R^{20z1}$, $R^{20z2}$, $R^{20z3}$, and $R^{20z9}$ is independently selected from halogen, oxo, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{12}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{12}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20z}$;

each $R^{20z4}$, $R^{20z5}$, and $R^{20z6}$ is independently selected from E, halogen, oxo, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{12}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{12}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20z}$;

each $R^{20z}$ is independently selected from E, halogen, oxo, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{12}$, —$S(O)R^{15}$, —$OC(O)R^{15}$, —$C(O)N(R^{12})$ ($R^{13}$), —C(O)C(O)N($R^{12}$)($R^{13}$), —N($R^{14}$)C(O)$R^{12}$, —S(O)$_2R^{15}$, —S(O)$_2$N($R^{12}$)($R^{13}$), —S(=O)(=NH)N($R^{12}$)($R^{13}$), —CH$_2$C(O)N($R^{12}$)($R^{13}$), —CH$_2$N($R^{14}$)C(O)$R^{15}$, —CH$_2$S(O)$_2R^{15}$, and —CH$_2$S(O)$_2$N($R^{12}$)($R^{13}$), wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20zz}$;

two $R^{20z}$ bonded to the same carbon atom are optionally joined to form monocyclic $C_{3-7}$cycloalkyl or monocyclic 3-7 membered heterocycloalkyl, wherein the monocyclic $C_{3-7}$cycloalkyl and monocyclic 3-7 membered heterocycloalkyl are optionally substituted with one, two, or three $R^{20zz}$; or two or more $R^{20z}$ bonded to two adjacent atoms are optionally joined to form monocyclic $C_{3-7}$cycloalkyl, monocyclic 3-7 membered heterocycloalkyl, phenyl, or monocyclic 5-6 membered heteroaryl, wherein the $C_{3-7}$cycloalkyl, monocyclic 3-7 membered heterocycloalkyl, phenyl, and monocyclic 5-6 membered heteroaryl are optionally substituted with one, two, or three $R^{20zz}$;

each $R^{20a}$, $R^{20b}$, $R^{20c}$, $R^{20d}$, $R^{20e}$, $R^{20f}$, $R^{20g}$, $R^{20h}$, $R^{20i}$, $R^{20j}$, $R^{20l}$, $R^{20lz}$, $R^{20m}$, $R^{20o}$, and $R^{20q}$, and $R^{20zz}$ is independently selected from halogen, oxo, —CN, $C_{1-6}$alkyl, $C_{2-6}$alkenyl, $C_{2-6}$alkynyl, $C_{3-10}$cycloalkyl, —CH$_2$-$C_{3-10}$cycloalkyl, $C_{2-9}$heterocycloalkyl, —CH$_2$-$C_{2-9}$heterocycloalkyl, $C_{6-10}$aryl, —CH$_2$-$C_{6-10}$aryl, —CH$_2$-$C_{1-9}$heteroaryl, $C_{1-9}$heteroaryl, —O$R^{21}$, —S$R^{21}$, —N($R^{22}$)($R^{23}$), —C(O)O$R^{22}$, —C(O)N($R^{22}$)($R^{23}$), —C(O)C(O)N($R^{22}$)($R^{23}$), —OC(O)N($R^{22}$)($R^{23}$), —N($R^{24}$)C(O)N($R^{22}$)($R^{23}$), —N($R^{24}$)C(O)O$R^{25}$, —N($R^{24}$)C(O)$R^{21}$, —N($R^{24}$)S(O)$_2R^{25}$, —C(O)$R^{21}$, —S(O)$_2R^{25}$, —S(O)$_2$N($R^{22}$)($R^{23}$), —OCH$_2$C(O)O$R^{22}$, =N$R^{21}$, and —OC(O)$R^{25}$; two $R^{20q}$ bonded to adjacent atoms are optionally joined to form a $C_{3-10}$cycloalkyl, $C_{2-9}$heterocycloalkyl, $C_{6-10}$aryl, or $C_{1-9}$heteroaryl; wherein $C_{1-6}$alkyl, $C_{2-6}$alkenyl, $C_{2-6}$alkynyl, $C_{3-10}$cycloalkyl, —CH$_2$-$C_{3-10}$cycloalkyl, $C_{2-9}$heterocycloalkyl, —CH$_2$-$C_{2-9}$heterocycloalkyl, $C_{6-10}$aryl, —CH$_2$-$C_{6-10}$aryl, —CH$_2$-$C_{1-9}$heteroaryl, and $C_{1-9}$heteroaryl are optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —O$R^{21}$, —S$R^{21}$, —N($R^{22}$)($R^{23}$), —C(O)O$R^{22}$, —C(O)N($R^{22}$)($R^{23}$), —C(O)C(O)N($R^{22}$)($R^{23}$), —OC(O)N($R^{22}$)($R^{23}$), —N($R^{24}$)C(O)N($R^{22}$)($R^{23}$), —N($R^{24}$)C(O)O$R^{25}$, —N($R^{24}$)C(O)$R^{25}$, —N($R^{24}$)S(O)$_2R^{25}$, —C(O)$R^{25}$, —S(O)$_2R^{25}$, —S(O)$_2$N($R^{22}$)($R^{23}$), and —OC(O)$R^{25}$;

each $R^{20zz}$ is independently selected from E, halogen, oxo, —CN, $C_{1-6}$alkyl, $C_{2-6}$alkenyl, $C_{2-6}$alkynyl, $C_{3-10}$cycloalkyl, —CH$_2$-$C_{3-10}$cycloalkyl, $C_{2-9}$heterocycloalkyl, —CH$_2$-$C_{2-9}$heterocycloalkyl, $C_{6-10}$aryl, —CH$_2$-$C_{6-10}$aryl, —CH$_2$-$C_{1-9}$heteroaryl, $C_{1-9}$heteroaryl, —O$R^{21}$, —S$R^{21}$, —N($R^{22}$)($R^{23}$), —C(O)O$R^{22}$, —C(O)N($R^{22}$)($R^{23}$), —C(O)C(O)N($R^{22}$)($R^{23}$), —OC(O)N($R^{22}$)($R^{23}$), —N($R^{24}$)C(O)N($R^{22}$)($R^{23}$), —N($R^{24}$)C(O)O$R^{25}$, —N($R^{24}$)C(O)$R^{21}$, —N($R^{24}$)S(O)$_2R^{25}$, —C(O)$R^{21}$, —S(O)$_2R^{25}$, —S(O)$_2$N($R^{22}$)($R^{23}$), —OCH$_2$C(O)O$R^{22}$, =N$R^{21}$, and —OC(O)$R^{25}$; two $R^{20q}$ bonded to adjacent atoms are optionally joined to form a $C_{3-10}$cycloalkyl, $C_{2-9}$heterocycloalkyl, $C_{6-10}$aryl, or $C_{1-9}$heteroaryl; wherein $C_{1-6}$alkyl, $C_{2-6}$alkenyl, $C_{2-6}$alkynyl, $C_{3-10}$cycloalkyl, —CH$_2$-$C_{3-10}$cycloalkyl, $C_{2-9}$heterocycloalkyl, —CH$_2$-$C_{2-9}$heterocycloalkyl, $C_{6-10}$aryl, —CH$_2$-$C_{6-10}$aryl, —CH$_2$-$C_{1-9}$heteroaryl, and $C_{1-9}$heteroaryl are optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —O$R^{21}$, —S$R^{21}$, —N($R^{22}$)($R^{23}$), —C(O)O$R^{22}$, —C(O)N($R^{22}$)($R^{23}$), —C(O)C(O)N($R^{22}$)($R^{23}$), —OC(O)N($R^{22}$)($R^{23}$), —N($R^{24}$)C(O)N($R^{22}$)($R^{23}$), —N($R^{24}$)C(O)O$R^{25}$, —N($R^{24}$)C(O)$R^{25}$, —N($R^{24}$)S(O)$_2R^{25}$, —C(O)$R^{25}$, —S(O)$_2R^{25}$, —S(O)$_2$N($R^{22}$)($R^{23}$), and —OC(O)$R^{25}$;

each $R^{21}$ is independently selected from hydrogen, $C_{1-6}$alkyl, $C_{1-6}$haloalkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl;

each $R^{22}$ is independently selected from hydrogen, $C_{1-6}$alkyl, $C_{1-6}$haloalkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl;

each $R^{23}$ is independently selected from hydrogen and $C_{1-6}$alkyl;

each $R^{24}$ is independently selected from hydrogen and $C_{1-6}$alkyl;

each $R^{25}$ is independently selected from $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; and ===== indicates a single or double bond such that all valences are satisfied.

In an aspect is provided a compound of Formula (A), or a pharmaceutically acceptable salt or solvate thereof:

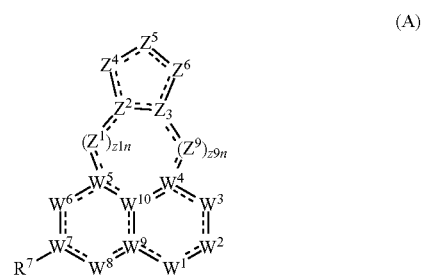

(A)

wherein:

$W^1$ is N($R^1$) or N;

$R^1$ is selected from hydrogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —O$R^{12}$, —S$R^{12}$, —C(O)O$R^{12}$, —OC(O)N($R^{12}$)($R^{13}$), —C(O)$R^{15}$, —S(O)$R^{15}$, —OC(O)$R^{15}$, —C(O)N($R^{12}$)($R^{13}$), —C(O)C(O)N($R^{12}$)($R^{13}$), —S(O)$_2R^{15}$, —S(O)$_2$N($R^{12}$)($R^{13}$), —S(=O)(=NH)N($R^{12}$)($R^{13}$), —CH$_2$C(O)N($R^{12}$)($R^{13}$), —CH$_2$N($R^{14}$)C(O)$R^{15}$, —CH$_2$S(O)$_2R^{15}$, and —CH$_2$S(O)$_2$N($R^{12}$)($R^{13}$), wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20a}$;

$W^2$ is C($R^2$), N($R^2$), C($R^2$)$_2$, C(O), S(O), S(O)$_2$, or N;

each $R^2$ is independently selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —O$R^{12a}$, —S$R^{12a}$, —N($R^{12a}$)($R^{13}$), —N=($R^{15}$), —C(O)O$R^{12}$, —OC(O)N($R^{12}$)($R^{13}$), —N($R^{14}$)C(O)N($R^{12}$)($R^{13}$), —N($R^{14}$)C(O)O$R^{15}$, —N($R^{14}$)S(O)$_2R^{15}$, —C(O)$R^{15}$, —S(O)$R^{15}$, —OC(O)$R^{15}$, —C(O)N($R^{12}$)($R^{13}$), —C(O)C(O)N($R^{12}$)($R^{13}$), —N($R^{14}$)C(O)$R^{15}$, —S(O)$_2R^{15}$, —S(O)$_2$N($R^{12}$)($R^{13}$)—, —S(=O)(=NH)N($R^{12}$)($R^{13}$), —CH$_2$C(O)N $(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20b}$;

$W^3$ is $C(R^3)$, $N(R^3)$, $C(R^3)_2$, $C(O)$, $S(O)$, $S(O)_2$, or N;

each $R^3$ is independently selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20c}$;

$W^4$ is $C(R^4)$, C, or N;

$R^4$ is selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20d}$;

$W^5$ is $C(R^5)$, C, or N;

$R^5$ is selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20e}$;

$W^6$ is $C(R^6)$, $N(R^6)$, $C(R^6)_2$, $C(O)$, $S(O)$, $S(O)_2$, or N;

each $R^6$ is independently selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20f}$;

$W^7$ is $C(R^{7a})$, C, or N;

$R^{7a}$ is selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{6-10}$aryl, and $C_{1-9}$heteroaryl are optionally substituted with one, two, or three $R^{20g}$;

$R^7$ is -$L^7$—$R^{17}$;

$L^7$ is a bond, $C_1$-$C_4$alkyl, $C_2$-$C_4$alkenyl, $C_2$-$C_4$alkynyl, 2-4 membered heteroalkylene linker, —O—, —$N(R^{7d})$—, —$C(O)$—, —S—, —$S(O)_2$—, —$S(O)$—, —$P(O)R^{7d}$—, $CR^{7c}R^{7c}$, —$OCR^{7c}R^{7c}$—, —$N(R^{7d})CR^{7c}R^{7c}$—, —$C(O)CR^{7c}R^{7c}$—, —$SCR^{7c}R^{7c}$—, —$S(O)_2CR^{7c}R^{7c}$—, —$S(O)CR^{7c}R^{7c}$—, —$P(O)R^{7d}CR^{7c}R^{7c}$—, —$CR^{7c}R^{7c}CR^{7c}R^{7c}$—, —$CR^{7c}R^{7c}O$—, —$CR^{7c}R^{7c}N(R^{7d})$—, —$CR^{7c}R^{7c}C(O)$—, —$CR^{7c}R^{7c}S$—, —$CR^{7c}R^{7c}S(O)_2$—, —$CR^{7c}R^{7c}S(O)$—, —$CR^{7c}R^{7c}P(O)R^{7d}$—, —$N(R^{7d})C(O)$—, —$N(R^{7d})S(O)_2$—, —$N(R^{7d})S(O)$—, —$N(R^{7d})P(O)R^{7d}$—, —$C(O)N(R^{7d})$—, —$S(O)_2N(R^{7d})$—, —$S(O)N(R^{7d})$—, —$P(O)R^{7d}N(R^{7d})$—, —$OC(O)$—, —$OS(O)_2$—, —$OS(O)$—, —$OP(O)R^{7d}$—, —$C(O)O$—, —$S(O)_2O$—, —$S(O)O$—, or —$P(O)R^{7d}O$—; wherein the $C_1$-$C_4$alkyl, $C_2$-$C_4$alkenyl, $C_2$-$C_4$alkynyl, 2-4 membered heteroalkylene linker are optionally substituted with one, two, or three $R^{20g}$;

each $R^{7c}$ is independently selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$, $S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20g}$;

each $R^{7d}$ is independently selected from hydrogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$C(O)OR^{12}$, —$OC(O)N(R^{12})(R^{13})$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20g}$;

$R^{17}$ is selected from $C_{3-10}$cycloalkyl, 3-10 membered heterocycloalkyl, $C_{6-10}$aryl, and 5-10 membered heteroaryl, wherein $C_{3-10}$cycloalkyl, 3-10 membered heterocycloalkyl, $C_{6-10}$aryl, and 5-10 membered heteroaryl are optionally substituted with one or more $R^{20q}$; or $L^7$ is a bond and $R^{7a}$ and $R^{17}$, together with the carbon to which they are attached, form $C_{3-10}$cycloalkyl or 3-10 membered heterocycloalkyl, wherein the $C_{3-10}$cycloalkyl and 3-10 membered heterocycloalkyl are optionally substituted with one or more $R^{20q}$;

$W^8$ is $C(R^8)$, $N(R^8)$, $C(R^8)_2$, $C(O)$, $S(O)$, $S(O)_2$, or N;

each $R^8$ is independently selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20h}$;

$W^9$ is $C(R^9)$, C, or N;

$R^9$ is selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20i}$;

$W^{10}$ $C(R^{10})$, C, or N;

$R^{10}$ is selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20j}$;

each $Z^1$ is independently $C(R^{z1})$, $N(R^{z1})$, $C(R^{z1})_2$, $C(O)$, $S(O)$, $S(O)_2$, O, S, or N;

z1n is 0, 1, 2, or 3; wherein if z1n is 0 then $Z^2$ is directly bonded to $W^5$;

each $R^{z1}$ is independently selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20z1}$;

each $Z^9$ is independently $C(R^{z9})$, $N(R^{z9})$, $C(R^{z9})_2$, $C(O)$, $S(O)$, $S(O)_2$, O, S, or N;

z9n is 0, 1, 2, or 3; wherein if z9n is 0 then $Z^3$ is directly bonded to $W^4$;

each $R^{z9}$ is independently selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20z9}$;

wherein the sum of z1n and z9n is 2 or 3;

$Z^2$ is $C(R^{z2})$, C, or N;

$R^{z2}$ is selected from halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20z2}$;

$Z^3$ is $C(R^{z3})$, C, or N;

$R^{z3}$ is selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20z3}$;

$Z^4$ is a bond, $Z^{4a}$, $Z^{4a}Z^{4b}$, $Z^{4a}Z^{4b}Z^{4c}$, or $Z^{4a}Z^{4b}Z^{4c}Z^{4d}$; wherein $Z^{4a}$ is directly bonded to $Z^2$; and wherein if $Z^4$ is a bond then $Z^2$ is directly bonded to $Z^5$;

$Z^{4a}$, $Z^{4b}$, $Z^{4c}$, and $Z^{4d}$ are independently $C(R^{z4})$, $N(R^{z4})$, $C(R^{z4})_2$, $C(O)$, $S(O)$, $S(O)_2$, $S(O)(NR^{z4})$, O, S, or N; provided that if z9n is 0 and $Z^4$ is $Z^{4a}Z^{4b}$; then (1) $Z^{4b}$ is $C(R^{z4})$, $C(R^{z4})_2$, $C(O)$, $S(O)$, $S(O)_2$, $S(O)(NR^{z4})$, O, S, or N, (2) $Z^{4b}$ is $N(R^{z4})$ and $Z^{4a}$ is $C(O)$, $S(O)$, or $S(O)_2$; (3) $Z^{4b}$ is $N(R^{z4})$ and $Z^5$ is $C(O)$, $S(O)$, or $S(O)_2$; or (4) $Z^{4b}$ is $N(R^{z4})$ and $Z^3$ is $C(R^{z3})$ or C; and each $R^{z4}$ is independently selected from -$L^{z1}$-$L^{z2}$-$L^{z3}$—$R^{12}$, hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12}$ ($R^{13}$), —C(O)O$R^{12}$, —OC(O)N($R^{12}$)($R^{13}$), —N($R^{14}$)C(O)N($R^{12}$)($R^{13}$), —N($R^{14}$)C(O)O$R^{15}$, —N($R^{14}$)S(O)$_2R^{15}$, —C(O)$R^{12}$, —S(O)$R^{15}$, —OC(O)$R^{15}$, —C(O)N($R^{12}$)($R^{13}$), —C(O)C(O)N($R^{12}$)($R^{13}$), —N($R^{14}$)C(O)$R^{12}$, —S(O)$_2R^{15}$, —S(O)$_2$N($R^{12}$)($R^{13}$), —S(=O)(=NH)N($R^{12}$)($R^{13}$), —CH$_2$C(O)N($R^{12}$)($R^{13}$), —CH$_2$N($R^{14}$)C(O)$R^{15}$, —CH$_2$S(O)$_2R^{15}$, and —CH$_2$S(O)$_2$N($R^{12}$)($R^{13}$), wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl are optionally substituted with one, two, or three $R^{20z4}$; or two $R^{z4}$ bonded to the same carbon are joined to form C$_{2-6}$alkenyl optionally substituted with one, two, or three $R^{20z4}$;

$Z^5$ is C($R^{z5}$), N($R^{z5}$), C($R^{z5}$)$_2$, C(O), S(O), S(O)$_2$, S(O)(N$R^{z5}$), O, S, or N;

each $R^{z5}$ is independently selected from -L$^{z1}$-L$^{z2}$-L$^{z3}$—$R^{12}$, hydrogen, halogen, —CN, C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, C$_{1-9}$heteroaryl, —O$R^{12}$, —S$R^{12}$, —N($R^{12}$)($R^{13}$), —C(O)O$R^{12}$, —OC(O)N($R^{12}$)($R^{13}$), —N($R^{14}$)C(O)N($R^{12}$)($R^{13}$), —N($R^{14}$)C(O)O$R^{15}$, —N($R^{14}$)S(O)$_2R^{15}$, —C(O)$R^{12}$, —S(O)$R^{15}$, —OC(O)$R^{15}$, —C(O)N($R^{12}$)($R^{13}$), —C(O)C(O)N($R^{12}$)($R^{13}$), —N($R^{14}$)C(O)$R^{12}$, —S(O)$_2R^{15}$, —S(O)$_2$N($R^{12}$)($R^{13}$), —S(=O)(=NH)N($R^{12}$)($R^{13}$), —CH$_2$C(O)N($R^{12}$)($R^{13}$), —CH$_2$N($R^{14}$)C(O)$R^{15}$, —CH$_2$S(O)$_2R^{15}$, and —CH$_2$S(O)$_2$N($R^{12}$)($R^{13}$), wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl are optionally substituted with one, two, or three $R^{20z5}$; or two $R^{z5}$ bonded to the same carbon are joined to form C$_{2-6}$alkenyl optionally substituted with one, two, or three $R^{20z5}$;

$Z^6$ is C($R^{z6}$), N($R^{z6}$), C($R^{z6}$)$_2$, C(O), S(O), S(O)$_2$, S(O)(N$R^{z6}$), O, S, or N;

each $R^{z6}$ is independently selected from -L$^{z1}$-L$^{z2}$-L$^{z3}$—$R^{12}$, hydrogen, halogen, —CN, C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, C$_{1-9}$heteroaryl, —O$R^{12}$, —S$R^{12}$, —N($R^{12}$)($R^{13}$), —C(O)O$R^{12}$, —OC(O)N($R^{12}$)($R^{13}$), —N($R^{14}$)C(O)N($R^{12}$)($R^{13}$), —N($R^{14}$)C(O)O$R^{15}$, —N($R^{14}$)S(O)$_2R^{15}$, —C(O)$R^{12}$, —S(O)$R^{15}$, —OC(O)$R^{15}$, —C(O)N($R^{12}$)($R^{13}$), —C(O)C(O)N($R^{12}$)($R^{13}$), —N($R^{14}$)C(O)$R^{12}$, —S(O)$_2R^{15}$, —S(O)$_2$N($R^{12}$)($R^{13}$), —S(=O)(=NH)N($R^{12}$)($R^{13}$), —CH$_2$C(O)N($R^{12}$)($R^{13}$), —CH$_2$N($R^{14}$)C(O)$R^{15}$, —CH$_2$S(O)$_2R^{15}$, and —CH$_2$S(O)$_2$N($R^{12}$)($R^{13}$), wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl are optionally substituted with one, two, or three $R^{20z6}$; or two $R^{z6}$ bonded to the same carbon are joined to form C$_{2-6}$alkenyl optionally substituted with one, two, or three $R^{20z6}$;

and further wherein the compound optionally includes one of the following:

(1) two $R^{z4}$ bonded to the same carbon atom are joined to form monocyclic C$_{3-7}$cycloalkyl or monocyclic 3-7 membered heterocycloalkyl, wherein the monocyclic C$_{3-7}$cycloalkyl and monocyclic 3-7 membered heterocycloalkyl are optionally substituted with one, two, or three $R^{20z}$;

(2) two or more $R^{z4}$ bonded to adjacent atoms are joined to form monocyclic C$_{3-7}$cycloalkyl, monocyclic 3-7 membered heterocycloalkyl, phenyl, or monocyclic 5-6 membered heteroaryl, wherein the monocyclic C$_{3-7}$cycloalkyl, monocyclic 3-7 membered heterocycloalkyl, phenyl, and monocyclic 5-6 membered heteroaryl are optionally substituted with one, two, or three $R^{20z}$;

(3) two $R^{z5}$ bonded to the same carbon atom are joined to form monocyclic C$_{3-7}$cycloalkyl or monocyclic 3-7 membered heterocycloalkyl, wherein the monocyclic C$_{3-7}$cycloalkyl and monocyclic 3-7 membered heterocycloalkyl are optionally substituted with one, two, or three $R^{20z}$;

(4) one or two $R^{z4}$ bonded to one atom and one or two $R^{z5}$ bonded to an adjacent atom are joined to form monocyclic C$_{3-7}$cycloalkyl, monocyclic 3-7 membered heterocycloalkyl, phenyl, or monocyclic 5-6 membered heteroaryl, wherein the monocyclic C$_{3-7}$cycloalkyl, monocyclic 3-7 membered heterocycloalkyl, phenyl, and monocyclic 5-6 membered heteroaryl are optionally substituted with one, two, or three $R^{20z}$;

(5) one or two $R^{z4}$ bonded to one atom and one or two $R^{z5}$ bonded to a second atom are joined to form monocyclic C$_{3-7}$cycloalkyl or monocyclic 3-7 membered heterocycloalkyl, wherein the monocyclic C$_{3-7}$cycloalkyl and monocyclic 3-7 membered heterocycloalkyl are optionally substituted with one, two, or three $R^{20z}$;

(6) two $R^{z6}$ bonded to the same carbon atom are joined to form monocyclic C$_{3-7}$cycloalkyl or monocyclic 3-7 membered heterocycloalkyl, wherein the monocyclic C$_{3-7}$cycloalkyl and monocyclic 3-7 membered heterocycloalkyl are optionally substituted with one, two, or three $R^{20z}$;

(7) one or two $R^{z5}$ bonded to one atom and one or two $R^{z6}$ bonded to an adjacent atom are joined to form monocyclic C$_{3-7}$cycloalkyl, monocyclic 3-7 membered heterocycloalkyl, phenyl, or monocyclic 5-6 membered heteroaryl, wherein the monocyclic C$_{3-7}$cycloalkyl, monocyclic 3-7 membered heterocycloalkyl, phenyl, and monocyclic 5-6 membered heteroaryl are optionally substituted with one, two, or three $R^{20z}$; or (8) one or two $R^{z4}$ bonded to one atom and one or two $R^{z6}$ bonded to a second atom are joined to form monocyclic C$_{3-7}$cycloalkyl or monocyclic 3-7 membered heterocycloalkyl, wherein the monocyclic C$_{3-7}$cycloalkyl and monocyclic 3-7 membered heterocycloalkyl are optionally substituted with one, two, or three $R^{20z}$;

each $R^{12}$ is independently selected from hydrogen, C$_{1-6}$alkyl, C$_{2-6}$alkenyl, C$_{2-6}$alkynyl, C$_{3-10}$cycloalkyl, —CH$_2$-C$_{3-10}$cycloalkyl, C$_{2-9}$heterocycloalkyl, —CH$_2$-C$_{2-9}$heterocycloalkyl, C$_{6-10}$aryl, —CH$_2$-C$_{6-10}$aryl, —CH$_2$-C$_{1-9}$heteroaryl, and C$_{1-9}$heteroaryl, wherein C$_{1-6}$alkyl, C$_{2-6}$alkenyl, C$_{2-6}$alkynyl, C$_{3-10}$cycloalkyl, —CH$_2$-C$_{3-10}$cycloalkyl, C$_{2-9}$heterocycloalkyl, —CH$_2$-C$_{2-9}$heterocycloalkyl, C$_{6-10}$aryl, —CH$_2$-C$_{6-10}$aryl, —CH$_2$-C$_{1-9}$heteroaryl, and C$_{1-9}$heteroaryl are optionally substituted with one, two, or three $R^{20l}$;

$R^{12a}$ is independently selected from hydrogen, C$_{1-6}$alkyl, C$_{2-6}$alkenyl, C$_{2-6}$alkynyl, C$_{3-10}$cycloalkyl, —C($R^{12c}$)$_2$-C$_{3-10}$cycloalkyl, C$_{2-9}$heterocycloalkyl, —C($R^{12c}$)$_2$-C$_{2-9}$heterocycloalkyl, C$_{6-10}$aryl, —C($R^{12c}$)$_2$-C$_{6-10}$aryl, —C($R^{12c}$)$_2$-C$_{1-9}$heteroaryl, and C$_{1-9}$heteroaryl, wherein C$_{1-6}$alkyl, C$_{2-6}$alkenyl, C$_{2-6}$alkynyl, C$_{3-10}$cycloalkyl, —C($R^{12c}$)$_2$-C$_{3-10}$cycloalkyl, C$_{2-9}$heterocycloalkyl, —C($R^{12c}$)$_2$-C$_{2-9}$heterocycloalkyl, C$_{6-10}$aryl, —C($R^{12c}$)$_2$-C$_{6-10}$aryl, —C($R^{12c}$)$_2$-C$_{1-9}$heteroaryl, and C$_{1-9}$heteroaryl are optionally substituted with one, two, or three $R^{20l}$;

each $R^{12c}$ is independently selected from hydrogen and $R^{20lc}$;

each $R^{13}$ is independently selected from hydrogen, $C_{1-6}$alkyl, and $C_{1-6}$haloalkyl; or $R^{12}$ and $R^{13}$, together with the nitrogen to which they are attached, form a $C_{2-9}$heterocycloalkyl ring optionally substituted with one, two, or three $R^{20m}$;

each $R^{14}$ is independently selected from hydrogen, $C_{1-6}$alkyl, and $C_{1-6}$haloalkyl;

each $R^{15}$ is independently selected from $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20o}$;

each $R^{20z1}$, $R^{20z2}$, $R^{20z3}$, $R^{20z4}$, $R^{20z5}$, $R^{20z6}$, and $R^{20z9}$ is independently selected from halogen, oxo, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{12}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{12}$, —S(O)$_2$R$^{15}$, —S(O)$_2$N(R$^{12}$)(R$^{13}$), —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20z}$;

each $R^{20z}$ is independently selected from -L$^{z3}$—R$^{12}$, halogen, oxo, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{12}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{12}$, —S(O)$_2$R$^{15}$, —S(O)$_2$N(R$^{12}$)(R$^{13}$), —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20zz}$;

two $R^{20z}$ bonded to the same carbon atom are optionally joined to form monocyclic $C_{3-7}$cycloalkyl or monocyclic 3-7 membered heterocycloalkyl, wherein the monocyclic $C_{3-7}$cycloalkyl and monocyclic 3-7 membered heterocycloalkyl are optionally substituted with one, two, or three $R^{20zz}$; or two or more $R^{20z}$ bonded to two adjacent atoms are optionally joined to form monocyclic $C_{3-7}$cycloalkyl, monocyclic 3-7 membered heterocycloalkyl, phenyl, or monocyclic 5-6 membered heteroaryl, wherein the $C_{3-7}$cycloalkyl, monocyclic 3-7 membered heterocycloalkyl, phenyl, and monocyclic 5-6 membered heteroaryl are optionally substituted with one, two, or three $R^{20zz}$;

$L^{z1}$ is selected from a bond, $C_{1-6}$alkylene, $C_{2-6}$alkenylene, $C_{2-6}$alkynylene, $C_{3-10}$cycloalkylene, $C_{1-9}$heterocycloalkylene, $C_{6-10}$arylene, and $C_{1-9}$heteroarylene; wherein $C_{1-6}$alkyl, $C_{2-6}$alkenylene, $C_{2-6}$alkynylene, $C_{3-10}$cycloalkylene, $C_{1-9}$heterocycloalkylene, $C_{6-10}$arylene, and $C_{1-9}$heteroarylene are optionally substituted with one or two $R^{30z}$;

$R^{30z}$ is independently selected from halogen, oxo, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{12}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{12}$, —S(O)$_2$R$^{15}$, —S(O)$_2$N(R$^{12}$)(R$^{13}$), —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20zz}$;

$L^{z2}$ is selected from a bond, $C_{1-6}$alkylene, $C_{2-6}$alkenylene, $C_{2-6}$alkynylene, $C_{3-10}$cycloalkylene, $C_{1-9}$heterocycloalkylene, $C_{6-10}$arylene, and $C_{1-9}$heteroarylene; wherein $C_{1-6}$alkyl, $C_{2-6}$alkenylene, $C_{2-6}$alkynylene, $C_{3-10}$cycloalkylene, $C_{1-9}$heterocycloalkylene, $C_{6-10}$arylene, and $C_{1-9}$heteroarylene are optionally substituted with one or two $R^{31z}$;

$R^{31z}$ is independently selected from halogen, oxo, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{12}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{12}$, —S(O)$_2$R$^{15}$, —S(O)$_2$N(R$^{12}$)(R$^{13}$), —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20zz}$;

$L^{z3}$—R$^{12}$ is selected from —C(O)R$^{12}$ or —N(H)C(O)R$^{12}$; wherein the R$^{12}$ of $L^{z3}$—R$^{12}$ is a 5-membered heteroaryl including two or more ring nitrogen atoms, wherein the 5-membered heteroaryl is directly bonded to the C(O) through an R$^{12}$ ring nitrogen atom and wherein R$^{12}$ is optionally substituted with one or more $R^{20l}$; and $R^{20l}$ is independently selected from halogen, oxo, —CN, $C_{1-6}$alkyl, $C_{2-6}$alkenyl, $C_{2-6}$alkynyl, $C_{3-10}$cycloalkyl, —CH$_2$-C$_{3-10}$cycloalkyl, $C_{2-9}$heterocycloalkyl, —CH$_2$-C$_{2-9}$heterocycloalkyl, $C_{6-10}$aryl, —CH$_2$-C$_{6-10}$aryl, —CH$_2$-C$_{1-9}$heteroaryl, $C_{1-9}$heteroaryl, —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, —N(R$^{24}$)C(O)R$^{21}$, —N(R$^{24}$)S(O)$_2$R$^{25}$, —C(O)R$^{21}$, —S(O)$_2$R$^{25}$, —S(O)$_2$N(R$^{22}$)(R$^{23}$), —OCH$_2$C(O)OR$^{22}$, =NR$^{21}$, and —OC(O)R$^{25}$; two $R^{20q}$ bonded to adjacent atoms are optionally joined to form a $C_{3-10}$cycloalkyl, $C_{2-9}$heterocycloalkyl, $C_{6-10}$aryl, or $C_{1-9}$heteroaryl; wherein $C_{1-6}$alkyl, $C_{2-6}$alkenyl, $C_{2-6}$alkynyl, $C_{3-10}$cycloalkyl, —CH$_2$-C$_{3-10}$cycloalkyl, $C_{2-9}$heterocycloalkyl, —CH$_2$-C$_{2-9}$heterocycloalkyl, $C_{6-10}$aryl, —CH$_2$-C$_{6-10}$aryl, —CH$_2$-C$_{1-9}$heteroaryl, and $C_{1-9}$heteroaryl are optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, —N(R$^{24}$)C(O)R$^{25}$, —N(R$^{24}$)S(O)$_2$R$^{25}$, —C(O)R$^{25}$, —S(O)$_2$R$^{25}$, —S(O)$_2$N(R$^{22}$)(R$^{23}$), and —OC(O)R$^{25}$;

provided that i) one or more of $R^{z4}$, $R^{z5}$, or $R^{z6}$ is -$L^1$-$L^{z2}$-$L^{z3}$—$R^{12}$; or ii) one or more of $R^{20z}$ is -$L^{z3}$—$R^{12}$;

each $R^{20a}$, $R^{20b}$, $R^{20c}$, $R^{20d}$, $R^{20e}$, $R^{20f}$, $R^{20g}$, $R^{20h}$, $R^{20i}$, $R^{20j}$, $R^{20l}$, $R^{20lc}$, $R^{20m}$, $R^{20o}$, $R^{20q}$, and $R^{20zz}$ is independently selected from halogen, oxo, —CN, $C_{1-6}$alkyl, $C_{2-6}$alkenyl, $C_{2-6}$alkynyl, $C_{3-10}$cycloalkyl, —CH$_2$-$C_{3-10}$cycloalkyl, $C_{2-9}$heterocycloalkyl, —CH$_2$-$C_{2-9}$heterocycloalkyl, $C_{6-10}$aryl, —CH$_2$-$C_{6-10}$aryl, —CH$_2$-$C_{1-9}$heteroaryl, $C_{1-9}$heteroaryl, —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, —N(R$^{24}$)C(O)R$^{21}$, —N(R$^{24}$)S(O)$_2$R$^{25}$, —C(O)R$^{21}$, —S(O)$_2$R$^{25}$, —S(O)$_2$N(R$^{22}$)(R$^{23}$), —OCH$_2$C(O)OR$^{22}$, =NR$^{21}$, and —OC(O)R$^{25}$; two R$^{20q}$ bonded to adjacent atoms are optionally joined to form a $C_{3-10}$cycloalkyl, $C_{2-9}$heterocycloalkyl, $C_{6-10}$aryl, or $C_{1-9}$heteroaryl; wherein $C_{1-6}$alkyl, $C_{2-6}$alkenyl, $C_{2-6}$alkynyl, $C_{3-10}$cycloalkyl, —CH$_2$-$C_{3-10}$cycloalkyl, $C_{2-9}$heterocycloalkyl, —CH$_2$-$C_{2-9}$heterocycloalkyl, $C_{6-10}$aryl, —CH$_2$-$C_{6-10}$aryl, —CH$_2$-$C_{1-9}$heteroaryl, and $C_{1-9}$heteroaryl are optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, —N(R$^{24}$)C(O)R$^{25}$, —N(R$^{24}$)S(O)$_2$R$^{25}$, —C(O)R$^{25}$, —S(O)$_2$R$^{25}$, —S(O)$_2$N(R$^{22}$)(R$^{23}$), and —OC(O)R$^{25}$;

each $R^{21}$ is independently selected from hydrogen, $C_{1-6}$alkyl, $C_{1-6}$haloalkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl;

each $R^{22}$ is independently selected from hydrogen, $C_{1-6}$alkyl, $C_{1-6}$haloalkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl;

each $R^{23}$ is independently selected from hydrogen and $C_{1-6}$alkyl;

each $R^{24}$ is independently selected from hydrogen and $C_{1-6}$alkyl;

each $R^{25}$ is independently selected from $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; and ═══ indicates a single or double bond such that all valences are satisfied.

In embodiments, $L^{z1}$ is a bond. In embodiments, $L^{z1}$ is $C_{1-6}$alkylene optionally substituted with one or two $R^{30z}$. In embodiments, $L^{z1}$ is $C_{2-6}$alkenylene optionally substituted with one or two $R^{30z}$. In embodiments, $L^{z1}$ is $C_{2-6}$alkynylene optionally substituted with one or two $R^{30z}$. In embodiments, $L^{z1}$ is $C_{3-10}$cycloalkylene optionally substituted with one or two $R^{30z}$. In embodiments, $L^{z1}$ is $C_{2-9}$heterocycloalkylene optionally substituted with one or two $R^{30z}$. In embodiments, $L^{z1}$ is $C_{6-10}$arylene optionally substituted with one or two $R^{30z}$. In embodiments, $L^{z1}$ is $C_{1-9}$heteroarylene optionally substituted with one or two $R^{30z}$.

In embodiments, $R^{30z}$ is halogen. In embodiments, $R^{30z}$ is oxo. In embodiments, $R^{30z}$ is —CN. In embodiments, $R^{30z}$ is $C_{1-6}$alkyl optionally substituted with one, two, or three $R^{20z}$. In embodiments, $R^{30z}$ is $C_{2-6}$alkenyl optionally substituted with one, two, or three $R^{20z}$. In embodiments, $R^{30z}$ is $C_{2-6}$alkynyl optionally substituted with one, two, or three $R^{20z}$. In embodiments, $R^{30z}$ is $C_{3-10}$cycloalkyl optionally substituted with one, two, or three $R^{20z}$. In embodiments, $R^{30z}$ is $C_{1-9}$heterocycloalkyl optionally substituted with one, two, or three $R^{20z}$. In embodiments, $R^{30z}$ is $C_{6-10}$aryl optionally substituted with one, two, or three $R^{20z}$. In embodiments, $R^{30z}$ is $C_{1-9}$heteroaryl optionally substituted with one, two, or three $R^{20z}$. In embodiments, $R^{30z}$ is —OR$^{12}$. In embodiments, $R^{30z}$ is —SR$^{12}$. In embodiments, $R^{30z}$ is —N(R$^{12}$)(R$^{13}$). In embodiments, $R^{30z}$ is —C(O)R$^{12}$. In embodiments, $R^{30z}$ is —OC(O)N(R$^{12}$)(R$^{13}$). In embodiments, $R^{30z}$ is —N(R$^{14}$)C(O)N(R$^{12}$)(R$^{13}$). In embodiments, $R^{30z}$ is —N(R$^{14}$)C(O)OR$^{15}$. In embodiments, $R^{30z}$ is —N(R$^{14}$)S(O)$_2$R$^{15}$. In embodiments, $R^{30z}$ is —C(O)R$^{12}$. In embodiments, $R^{30z}$ is —S(O)R$^{15}$. In embodiments, $R^{30z}$ is —OC(O)R$^{15}$. In embodiments, $R^{30z}$ is —C(O)N(R$^{12}$)(R$^{13}$). In embodiments, $R^{30z}$ is —C(O)C(O)N(R$^{12}$)(R$^{13}$). In embodiments, $R^{30z}$ is —N(R$^{14}$)C(O)R$^{12}$. In embodiments, $R^{30z}$ is —S(O)$_2$R$^{15}$. In embodiments, $R^{30z}$ is —S(O)$_2$N(R$^{12}$)(R$^{13}$). In embodiments, $R^{30z}$ is —S(=O)(=NH)N(R$^{12}$)(R$^{13}$). In embodiments, $R^{30z}$ is —CH$_2$C(O)N(R$^{12}$)(R$^{13}$). In embodiments, $R^{30z}$ is —CH$_2$N(R$^{14}$)C(O)R$^{15}$. In embodiments, $R^{30z}$ is —CH$_2$S(O)$_2$R$^{15}$. In embodiments, $R^{30z}$ is —CH$_2$S(O)$_2$N(R$^{12}$)(R$^{13}$). wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20z}$;

In embodiments, $L^{z2}$ is a bond. In embodiments, $L^{z2}$ is $C_{1-6}$alkylene optionally substituted with one or two $R^{31z}$. In embodiments, $L^{z2}$ is $C_{2-6}$alkenylene optionally substituted with one or two $R^{31z}$. In embodiments, $L^{z2}$ is $C_{2-6}$alkynylene optionally substituted with one or two $R^{31z}$. In embodiments, $L^{z2}$ is $C_{3-10}$cycloalkylene optionally substituted with one or two $R^{31z}$. In embodiments, $L^{z2}$ is $C_{2-9}$heterocycloalkylene optionally substituted with one or two $R^{31z}$. In embodiments, $L^{z2}$ is $C_{6-10}$arylene optionally substituted with one or two $R^{31z}$. In embodiments, $L^{z2}$ is $C_{1-9}$heteroarylene optionally substituted with one or two $R^{31z}$.

In embodiments, $R^{31z}$ is halogen. In embodiments, $R^{31z}$ is oxo. In embodiments, $R^{31z}$ is —CN. In embodiments, $R^{31z}$ is $C_{1-6}$alkyl optionally substituted with one, two, or three $R^{20zz}$. In embodiments, $R^{31z}$ is $C_{2-6}$alkenyl optionally substituted with one, two, or three $R^{20zz}$. In embodiments, $R^{31z}$ is $C_{2-6}$alkynyl optionally substituted with one, two, or three $R^{20zz}$. In embodiments, $R^{31z}$ is $C_{3-10}$cycloalkyl optionally substituted with one, two, or three $R^{20zz}$. In embodiments, $R^{31z}$ is $C_{1-9}$heterocycloalkyl optionally substituted with one, two, or three $R^{20zz}$. In embodiments, $R^{31z}$ is $C_{6-10}$aryl optionally substituted with one, two, or three $R^{20zz}$. In embodiments, $R^{31z}$ is $C_{1-9}$heteroaryl optionally substituted with one, two, or three $R^{20zz}$. In embodiments, $R^{31z}$ is —OR$^{12}$. In embodiments, $R^{31z}$ is —SR$^{12}$. In embodiments, $R^{31z}$ is —N(R$^{12}$)(R$^{13}$). In embodiments, $R^{31z}$ is —C(O)OR$^{12}$. In embodiments, $R^{31z}$ is —OC(O)N(R$^{12}$)(R$^{13}$). In embodiments, $R^{31z}$ is —N(R$^{14}$)C(O)N(R$^{12}$)(R$^{13}$). In embodiments, $R^{31z}$ is —N(R$^{14}$)C(O)OR$^{15}$. In embodiments, $R^{31z}$ is —N(R$^{14}$)S(O)$_2$R$^{15}$. In embodiments, $R^{31z}$ is —C(O)R$^{12}$. In embodiments, $R^{31z}$ is —S(O)R$^{15}$. In embodiments, $R^{31z}$ is —OC(O)R$^{15}$. In embodiments, $R^{31z}$ is —C(O)N(R$^{12}$)(R$^{13}$). In embodiments, $R^{31z}$ is —C(O)C(O)N(R$^{12}$)(R$^{13}$). In embodiments, $R^{31z}$ is —N(R$^{14}$)C(O)R$^{12}$. In embodiments, $R^{31z}$ is —S(O)$_2$R$^{15}$. In embodiments, $R^{31z}$ is —S(O)$_2$N(R$^{12}$)(R$^{13}$). In embodiments, $R^{31z}$ is —S(=O)(=NH)N(R$^{12}$)(R$^{13}$). In embodiments, $R^{31z}$ is —CH$_2$C(O)N(R$^{12}$)(R$^{13}$). In embodiments, $R^{31z}$ is —CH$_2$N(R$^{14}$)C(O)R$^{15}$. In embodiments, $R^{31z}$ is —CH$_2$S(O)$_2$R$^{15}$. In embodiments, $R^{31z}$ is —CH$_2$S(O)$_2$N(R$^{12}$)(R$^{13}$). wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20zz}$;

In embodiments, $L^{z3}$—$R^{12}$ is selected from —C(O)$R^{12}$ and —N(H)C(O)$R^{12}$; wherein the $R^{12}$ of $L^{z3}$—$R^{12}$ is a 5-membered heteroaryl including two or more ring nitrogen atoms, wherein the 5-membered heteroaryl is directly bonded to the C(O) through an $R^{12}$ ring nitrogen atom and wherein $R^{12}$ is optionally substituted with one or more $R^{20l}$.

In embodiments, $L^{z3}$—$R^{12}$ is selected from —C(O)$R^{12}$ and —N(H)C(O)$R^{12}$; wherein the $R^{12}$ of $L^{z3}$—$R^{12}$ is a 3-membered heterocycloalkyl including one or more ring nitrogen atoms, wherein $R^{12}$ is optionally substituted with one or more $R^{20l}$.

In embodiments, $R^{20l}$ is independently halogen. In embodiments, $R^{20l}$ is independently F. In embodiments, $R^{20l}$ is independently Cl. In embodiments, $R^{20l}$ is independently I. In embodiments, $R^{20l}$ is independently Br. In embodiments, $R^{20l}$ is independently unsubstituted methyl. In embodiments, $R^{20l}$ is independently unsubstituted isopropyl. In embodiments, $R^{20l}$ is independently —CHF$_2$. In embodiments, $R^{20l}$ is independently unsubstituted cyclopropyl. In embodiments, $R^{20l}$ is independently oxo. In embodiments, $R^{20l}$ is independently —CN. In embodiments, $R^{20l}$ is independently $C_{1-6}$alkyl optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —O$R^{21}$, —S$R^{21}$, —N($R^{22}$)($R^{23}$), —C(O)O$R^{22}$, —C(O)N($R^{22}$)($R^{23}$), —C(O)C(O)N($R^{22}$)($R^{23}$), —OC(O)N($R^{22}$)($R^{23}$), —N($R^{24}$)C(O)N($R^{22}$)($R^{23}$), —N($R^{24}$)C(O)N($R^{22}$)($R^{23}$), —N($R^{24}$)C(O)O$R^{25}$, —N($R^{24}$)C(O)$R^{25}$, —N($R^{24}$)S(O)$_2R^{25}$, —N($R^{24}$)S(O)$_2R^{25}$, —C(O)$R^{25}$, —S(O)$_2R^{25}$, —S(O)$_2$N($R^{22}$)($R^{23}$), and —OC(O)$R^{25}$. In embodiments, $R^{20l}$ is independently $C_{2-6}$alkenyl optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —O$R^{21}$, —S$R^{21}$, —N($R^{22}$)($R^{23}$), —C(O)O$R^{22}$, —C(O)N($R^{22}$)($R^{23}$), —C(O)C(O)N($R^{22}$)($R^{23}$), —OC(O)N($R^{22}$)($R^{23}$), —N($R^{24}$)C(O)N($R^{22}$)($R^{23}$), —N($R^{24}$)C(O)O$R^{25}$, —N($R^{24}$)C(O)$R^{25}$, —N($R^{24}$)C(O)$R^{25}$, —N($R^{24}$)S(O)$_2R^{25}$, —N($R^{24}$)S(O)$_2R^{25}$, —C(O)$R^{25}$, —S(O)$_2R^{25}$, —S(O)$_2$N($R^{22}$)($R^{23}$), and —OC(O)$R^{25}$. In embodiments, $R^{20l}$ is independently $C_{2-6}$alkynyl optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —O$R^{21}$, —S$R^{21}$, —N($R^{22}$)($R^{23}$), —C(O)O$R^{22}$, —C(O)N($R^{22}$)($R^{23}$), —C(O)C(O)N($R^{22}$)($R^{23}$), —OC(O)N($R^{22}$)($R^{23}$), —N($R^{24}$)C(O)N($R^{22}$)($R^{23}$), —N($R^{24}$)C(O)O$R^{25}$, —N($R^{24}$)C(O)$R^{25}$, —N($R^{24}$)S(O)$_2R^{25}$, —C(O)$R^{25}$, —S(O)$_2R^{25}$, —S(O)$_2$N($R^{22}$)($R^{23}$), and —OC(O)$R^{25}$. In embodiments, $R^{20l}$ is independently $C_{3-10}$cycloalkyl optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —O$R^{21}$, —S$R^{21}$, —N($R^{22}$)($R^{23}$), —C(O)O$R^{22}$, —C(O)N($R^{22}$)($R^{23}$), —C(O)C(O)N($R^{22}$)($R^{23}$), —OC(O)N($R^{22}$)($R^{23}$), —N($R^{24}$)C(O)N($R^{22}$)($R^{23}$), —N($R^{24}$)C(O)O$R^{25}$, —N($R^{24}$)C(O)$R^{25}$, —N($R^{24}$)C(O)$R^{25}$, —N($R^{24}$)S(O)$_2R^{25}$, —N($R^{24}$)S(O)$_2R^{25}$, —C(O)$R^{25}$, —S(O)$_2R^{25}$, —S(O)$_2$N($R^{22}$)($R^{23}$), and —OC(O)$R^{25}$. In embodiments, $R^{20l}$ is independently —CH$_2$-$C_{3-10}$cycloalkyl optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —O$R^{21}$, —S$R^{21}$, —N($R^{22}$)($R^{23}$), —C(O)O$R^{22}$, —C(O)N($R^{22}$)($R^{23}$), —C(O)C(O)N($R^{22}$)($R^{23}$), —OC(O)N($R^{22}$)($R^{23}$), —N($R^{24}$)C(O)N($R^{22}$)($R^{23}$), —N($R^{24}$)C(O)O$R^{25}$, —N($R^{24}$)C(O)$R^{25}$, —N($R^{24}$)S(O)$_2R^{25}$, —N($R^{24}$)S(O)$_2R^{25}$, —C(O)$R^{25}$, —S(O)$_2R^{25}$, —S(O)$_2$N($R^{22}$)($R^{23}$), and —OC(O)$R^{25}$. In embodiments, $R^{20l}$ is independently $C_{2-9}$heterocycloalkyl optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —O$R^{21}$, —S$R^{21}$, —N($R^{22}$)($R^{23}$), —C(O)O$R^{22}$, —C(O)N($R^{22}$)($R^{23}$), —C(O)C(O)N($R^{22}$)($R^{23}$), —OC(O)N($R^{22}$)($R^{23}$), —N($R^{24}$)C(O)N($R^{22}$)($R^{23}$), —N($R^{24}$)C(O)O$R^{25}$, —N($R^{24}$)C(O)$R^{25}$, —N($R^{24}$)C(O)$R^{25}$, —N($R^{24}$)S(O)$_2R^{25}$, —C(O)$R^{25}$, —S(O)$_2R^{25}$, —S(O)$_2$N($R^{22}$)($R^{23}$), and —OC(O)$R^{25}$. In embodiments, $R^{20l}$ is independently —CH$_2$-$C_{1-9}$heterocycloalkyl optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —O$R^{21}$, —S$R^{21}$, —N($R^{22}$)($R^{23}$), —N($R^{22}$)($R^{23}$), —C(O)O$R^{22}$, —C(O)N($R^{22}$)($R^{23}$), —C(O)C(O)N($R^{22}$)($R^{23}$), —OC(O)N($R^{22}$)($R^{23}$), —N($R^{24}$)C(O)N($R^{22}$)($R^{23}$), —N($R^{24}$)C(O)O$R^{25}$, —N($R^{24}$)C(O)$R^{25}$, —N($R^{24}$)C(O)$R^{25}$, —N($R^{24}$)S(O)$_2R^{25}$, —C(O)$R^{25}$, —S(O)$_2R^{25}$, —S(O)$_2$N($R^{22}$)($R^{23}$), and —OC(O)$R^{25}$. In embodiments, $R^{20l}$ is independently $C_{6-10}$aryl optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —O$R^{21}$, —S$R^{21}$, —N($R^{22}$)($R^{23}$), —C(O)O$R^{22}$, —C(O)N($R^{22}$)($R^{23}$), —C(O)C(O)N($R^{22}$)($R^{23}$), —C(O)N($R^{22}$)($R^{23}$), —N($R^{24}$)C(O)N($R^{22}$)($R^{23}$), —N($R^{24}$)C(O)O$R^{25}$, —N($R^{24}$)C(O)$R^{25}$, —N($R^{24}$)C(O)$R^{25}$, —N($R^{24}$)S(O)$_2R^{25}$, —C(O)$R^{25}$, —S(O)$_2R^{25}$, —S(O)$_2$N($R^{22}$)($R^{23}$), and —OC(O)$R^{25}$. In embodiments, $R^{20l}$ is independently —CH$_2$-$C_{6-10}$aryl optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —O$R^{21}$, —S$R^{21}$, —N($R^{22}$)($R^{23}$), —C(O)O$R^{22}$, —C(O)N($R^{22}$)($R^{23}$), —C(O)C(O)N($R^{22}$)($R^{23}$), —OC(O)N($R^{22}$)($R^{23}$), —N($R^{24}$)C(O)N($R^{22}$)($R^{23}$), —N($R^{24}$)C(O)$R^{25}$, —N($R^{24}$)C(O)O$R^{25}$, —N($R^{24}$)C(O)$R^{25}$, —N($R^{24}$)S(O)$_2R^{25}$, —N($R^{24}$)S(O)$_2R^{25}$, —C(O)$R^{25}$, —S(O)$_2R^{25}$, —S(O)$_2$N($R^{22}$)($R^{23}$), and —OC(O)$R^{25}$. In embodiments, $R^{20l}$ is independently —CH$_2$-$C_{1-9}$heteroaryl optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —O$R^{21}$, —S$R^{21}$, —N($R^{22}$)($R^{23}$), —C(O)O$R^{22}$, —C(O)N($R^{22}$)($R^{23}$), —C(O)C(O)N($R^{22}$)($R^{23}$), —OC(O)N($R^{22}$)($R^{23}$), —N($R^{24}$)C(O)N($R^{22}$)($R^{23}$), N($R^{24}$)C(O)O$R^{25}$, —N($R^{24}$)C(O)$R^{25}$, —N($R^{24}$)C(O)$R^{25}$, —N($R^{24}$)S(O)$_2R^{25}$, —C(O)$R^{25}$, —S(O)$_2R^{25}$, —S(O)$_2$N($R^{22}$)($R^{23}$), and —OC(O)$R^{25}$. In embodiments, $R^{20l}$ is independently $C_{1-9}$heteroaryl optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —O$R^{21}$, —S$R^{21}$, —N($R^{22}$)($R^{23}$), —C(O)O$R^{22}$, —C(O)N($R^{22}$)($R^{23}$), —C(O)C(O)N($R^{22}$)($R^{23}$), —OC(O)N($R^{22}$)($R^{23}$), —N($R^{24}$)C(O)N($R^{22}$)($R^{23}$), —N($R^{24}$)C(O)N($R^{22}$)($R^{23}$), —N($R^{24}$)C(O)O$R^{25}$, —N($R^{24}$)C(O)$R^{25}$, —N($R^{24}$)S(O)$_2R^{25}$, —N($R^{24}$)S(O)$_2R^{25}$, —C(O)$R^{25}$, —S(O)$_2R^{25}$, —S(O)$_2$N($R^{22}$)($R^{23}$), and —OC(O)$R^{25}$. In embodiments, $R^{20l}$ is independently —O$R^{21}$. In embodiments, $R^{20l}$ is independently —S$R^{21}$. In embodiments, $R^{20l}$ is independently —N($R^{22}$)($R^{23}$). In embodiments, $R^{20l}$ is independently —C(O)O$R^{22}$. In embodiments, $R^{20l}$ is independently —C(O)N($R^{22}$)($R^{23}$). In embodiments, $R^{20l}$ is independently —C(O)C(O)N($R^{22}$)($R^{23}$). In embodiments, $R^{20l}$ is independently —OC(O)N($R^{22}$)($R^{23}$). In embodiments, $R^{20l}$ is independently —N($R^{24}$)C(O)N($R^{22}$)($R^{23}$). In embodiments, $R^{20l}$ is independently —N($R^{24}$)C(O)O$R^{25}$. In embodiments, $R^{20l}$ is independently —N($R^{24}$)C(O)$R^{21}$. In embodiments, $R^{20l}$ is independently —N($R^{24}$)S(O)$_2R^{25}$. In embodiments, $R^{20l}$ is independently —C(O)$R^{21}$. In embodiments, $R^{20l}$ is independently —S(O)$_2R^{25}$. In embodiments, $R^{20l}$ is independently —S(O)$_2$N($R^{22}$)($R^{23}$). In embodiments, $R^{20l}$ is independently —OCH$_2$C(O)OR$^{22}$. In embodiments, $R^{20l}$ is independently =NR$^{21}$. In embodiments, $R^{20l}$ is independently —OC(O)R$^{25}$.

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof: the compound optionally includes one of the following:

(1) two $R^{z4}$ bonded to the same carbon atom are joined to form monocyclic $C_{3-7}$cycloalkyl or monocyclic 3-7 membered heterocycloalkyl, wherein the monocyclic $C_{3-7}$cycloalkyl and monocyclic 3-7 membered heterocycloalkyl are optionally substituted with one, two, or three $R^{20z}$;

(2) two or more $R^{z4}$ bonded to adjacent atoms are joined to form monocyclic $C_{3-7}$cycloalkyl, monocyclic 3-7 membered heterocycloalkyl, phenyl, or monocyclic 5-6 membered heteroaryl, wherein the monocyclic $C_{3-7}$cycloalkyl, monocyclic 3-7 membered heterocycloalkyl, phenyl, and monocyclic 5-6 membered heteroaryl are optionally substituted with one, two, or three $R^{20z}$;

(3) two $R^{z5}$ bonded to the same carbon atom are joined to form monocyclic $C_{3-7}$cycloalkyl or monocyclic 3-7 membered heterocycloalkyl, wherein the monocyclic $C_{3-7}$cycloalkyl and monocyclic 3-7 membered heterocycloalkyl are optionally substituted with one, two, or three $R^{20z}$;

(4) one or two $R^{z4}$ bonded to one atom and one or two $R^{z5}$ bonded to an adjacent atom are joined to form monocyclic $C_{3-7}$cycloalkyl, monocyclic 3-7 membered heterocycloalkyl, phenyl, or monocyclic 5-6 membered heteroaryl, wherein the monocyclic $C_{3-7}$cycloalkyl, monocyclic 3-7 membered heterocycloalkyl, phenyl, and monocyclic 5-6 membered heteroaryl are optionally substituted with one, two, or three $R^{20z}$;

(6) two $R^{z6}$ bonded to the same carbon atom are joined to form monocyclic $C_{3-7}$cycloalkyl or monocyclic 3-7 membered heterocycloalkyl, wherein the monocyclic $C_{3-7}$cycloalkyl and monocyclic 3-7 membered heterocycloalkyl are optionally substituted with one, two, or three $R^{20z}$;

(7) one or two $R^{z5}$ bonded to one atom and one or two $R^{z6}$ bonded to an adjacent atom are joined to form monocyclic $C_{3-7}$cycloalkyl, monocyclic 3-7 membered heterocycloalkyl, phenyl, or monocyclic 5-6 membered heteroaryl, wherein the monocyclic $C_{3-7}$cycloalkyl, monocyclic 3-7 membered heterocycloalkyl, phenyl, and monocyclic 5-6 membered heteroaryl are optionally substituted with one, two, or three $R^{20z}$; or (8) one or two $R^{z4}$ bonded to one atom and one or two $R^{z6}$ bonded to a second atom are joined to form monocyclic $C_{3-7}$cycloalkyl or monocyclic 3-7 membered heterocycloalkyl, wherein the monocyclic $C_{3-7}$cycloalkyl and monocyclic 3-7 membered heterocycloalkyl are optionally substituted with one, two, or three $R^{20z}$.

It will be understood that when two or more substituents are joined to form a monocyclic ring, such as when i) one or two $R^{z4}$ bonded to one atom and one or two $R^{z5}$ bonded to a second atom are joined to form monocyclic $C_{3-7}$cycloalkyl or monocyclic 3-7 membered heterocycloalkyl, wherein the monocyclic $C_{3-7}$cycloalkyl and monocyclic 3-7 membered heterocycloalkyl are optionally substituted with one, two, or three $R^{20z}$; or ii) one or two $R^{z4}$ bonded to one atom and one or two $R^{z6}$ bonded to a second atom are joined to form monocyclic $C_{3-7}$cycloalkyl or monocyclic 3-7 membered heterocycloalkyl, wherein the monocyclic $C_{3-7}$cycloalkyl and monocyclic 3-7 membered heterocycloalkyl are optionally substituted with one, two, or three $R^{20z}$; and the two atoms to which the joined substituents are bonded are themselves separated by one or more covalently bonded atoms, then the joining of substituents forms a bridged polycyclic ring system. In the above described compounds, the monocyclic ring will be understood to be any one of the new rings formed in a polycyclic bridged ring system but the joining of the two substituents will not itself add additional rings to the polycyclic ring system entirely contained in the new bridge linker between $R^{z4}$ and $R^{z5}$ or the new bridge linker between $R^{z4}$ and $R^{z6}$, and not including any atoms already included in a ring system prior to the bridge formation In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, when z9n is 0; $Z^4$ is $Z^{4a}Z^{4b}Z^{4c}$; and $Z^{4a}$, $Z^{4b}$, and $Z^{4c}$ are each independently C($R^{z4}$)$_2$; then the $R^{z4}$ of $Z^{4a}$ cannot join $R^{z5}$ to form a monocyclic 3-7 membered heterocycloalkyl, wherein the monocyclic 3-7 membered heterocycloalkyl is optionally substituted with one, two, or three $R^{20z}$.

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, $W^2$ is C($R^2$), N($R^2$), CH($R^2$), C(O), S(O), S(O)$_2$, or N; and each $R^2$ is independently selected from halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —OR$^{12a}$, —SR$^{12a}$, —N(R$^{12a}$)(R$^{13}$), —N=(R$^{15}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$)—, —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20b}$.

In embodiments of a compound of Formula (A), A-1, A-2, A-2a, A-2b, A-3, A-3a, A-3b, A-4, A-4a, A-4b, A-5, A-5a, A-5b, A-5c, A-5d, A-6, A-6a, A-6b, A-6c, A-6d, A-6e, A-6f, and/or B, or a pharmaceutically acceptable salt or solvate thereof, $Z^4$ is a bond, $Z^{4a}$, or $Z^{4a}Z^{4b}Z^{4c}$.

Any and all embodiments of a compound of Formula (A) recited herein may also be combined with an aspect reciting a compound of Formula (B) to provide an embodiment of a compound of Formula (B) with the recited limitation or scope of the embodiment of a compound of Formula (A).

Also provided is a compound selected from:

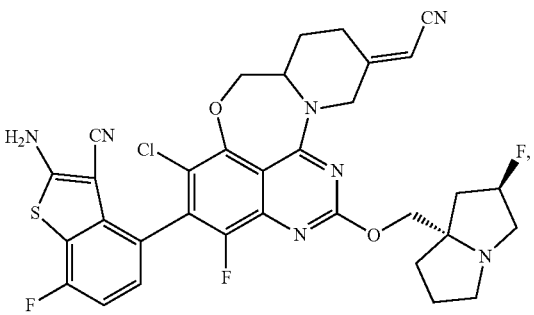

587
-continued
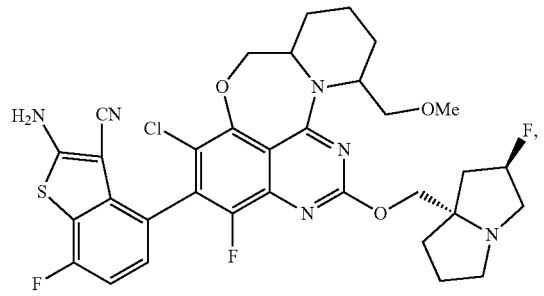
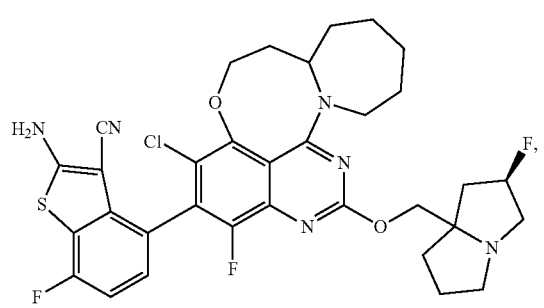
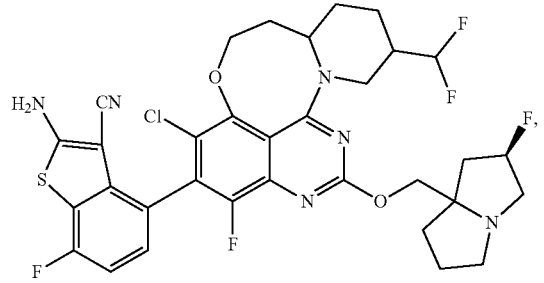
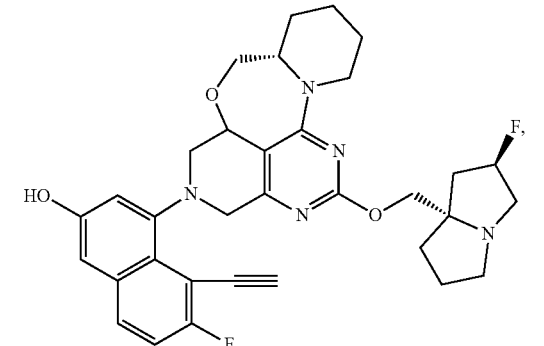
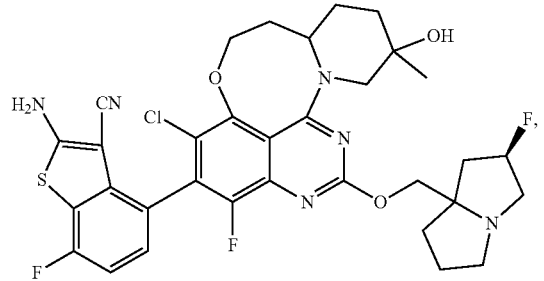
588
-continued
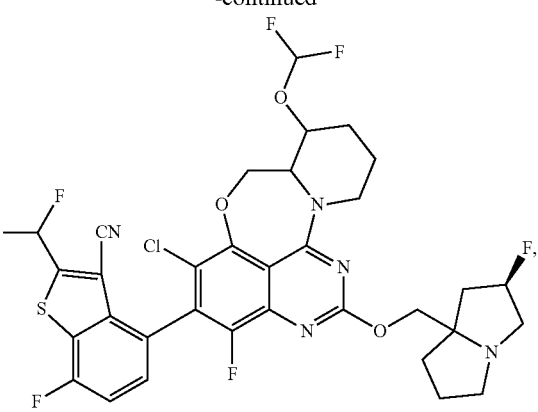
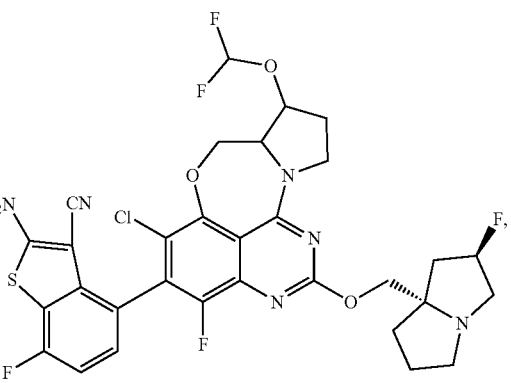
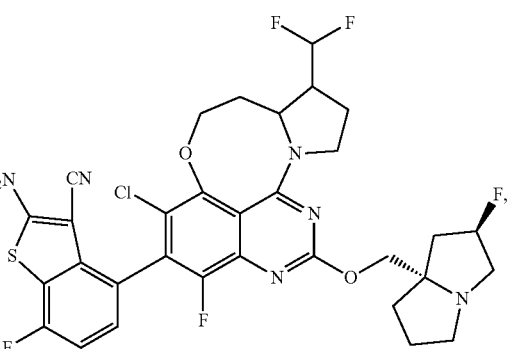
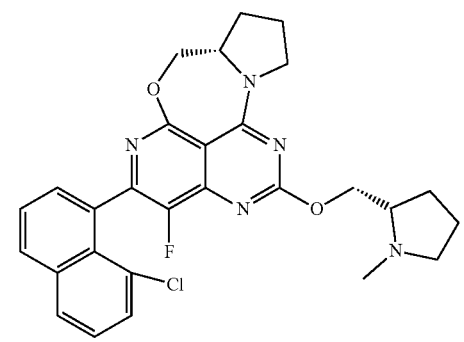

589
-continued
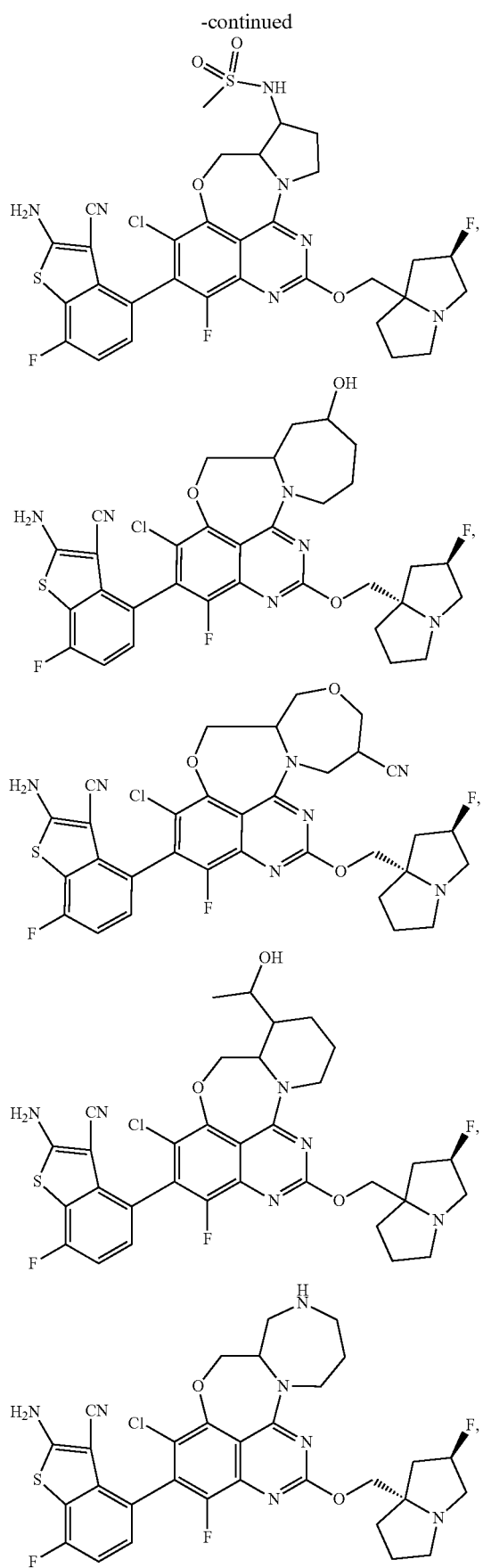
590
-continued
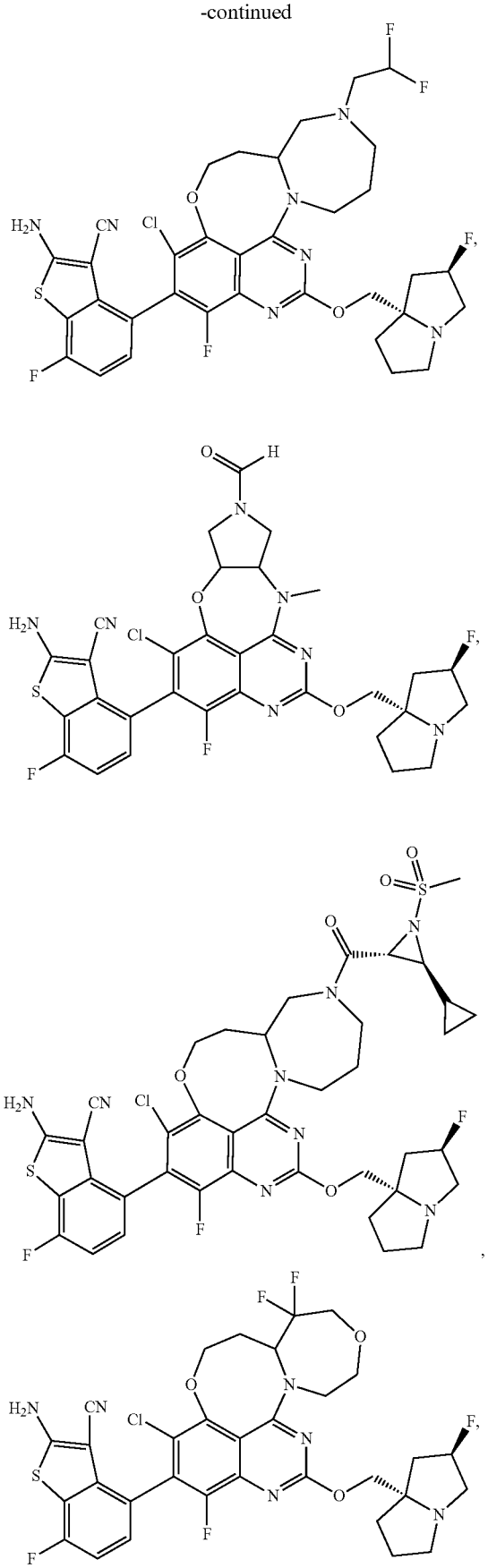

591
-continued
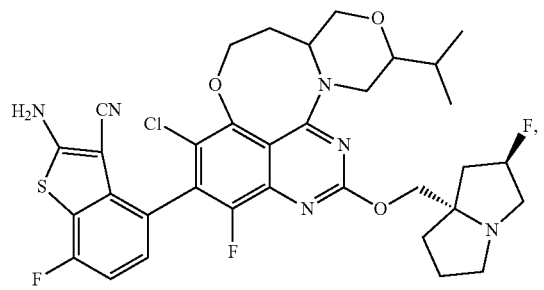
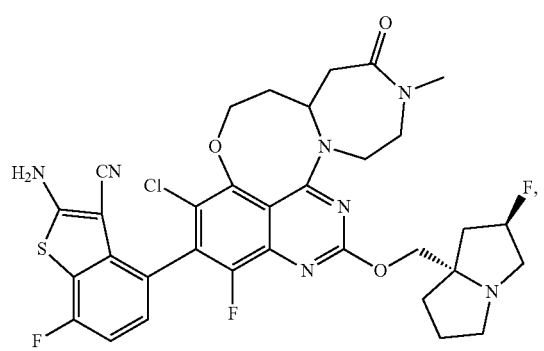
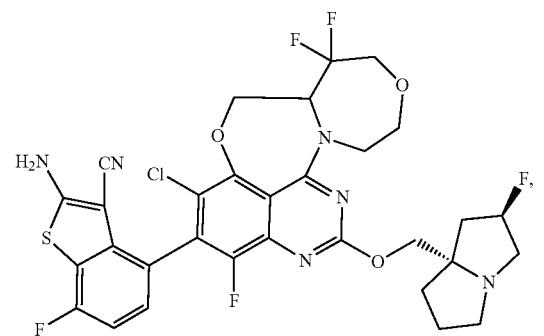
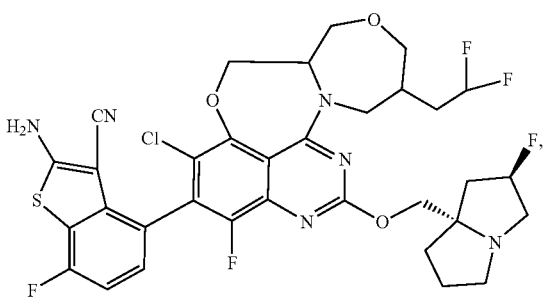
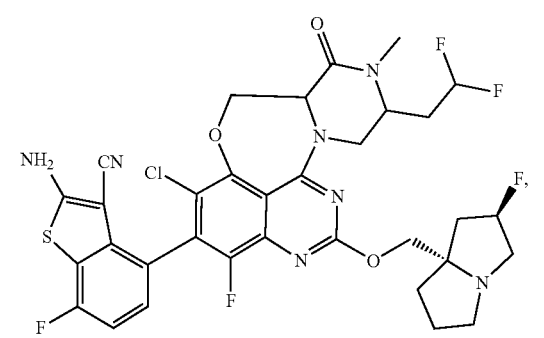
592
-continued
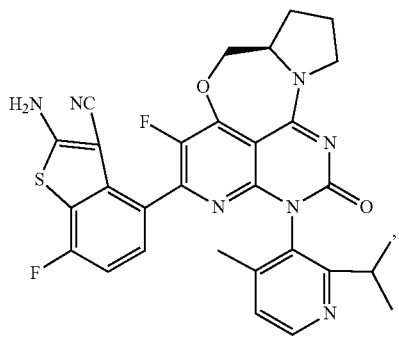
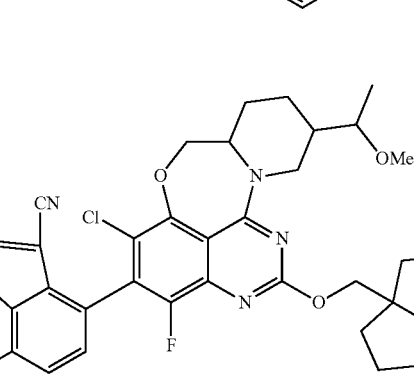
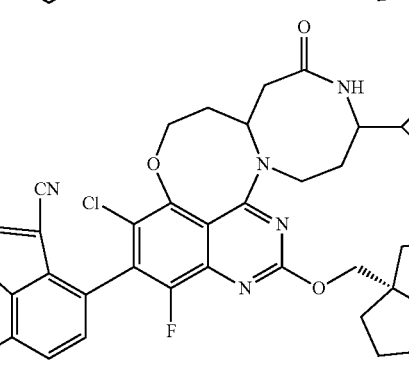
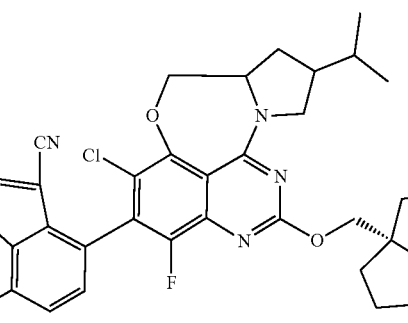
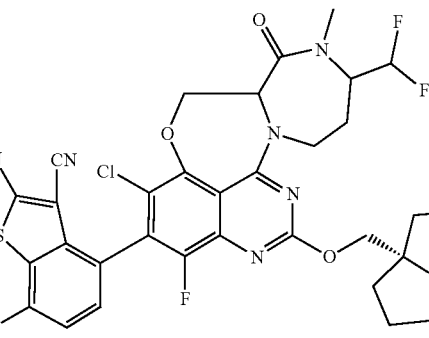

593
-continued
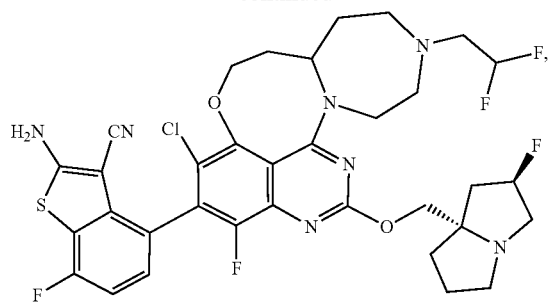
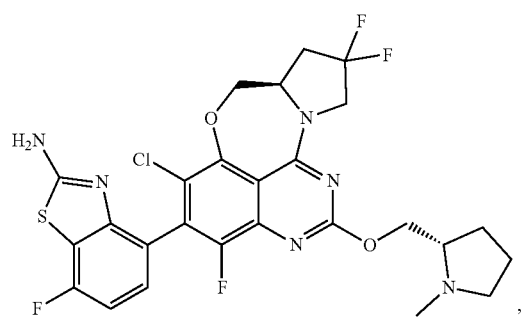
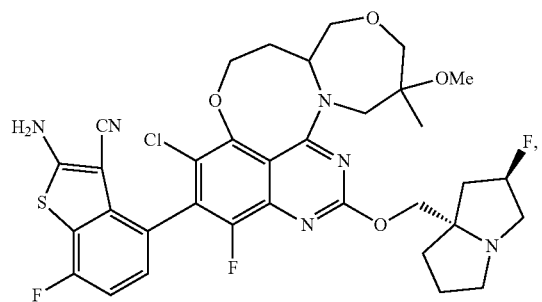
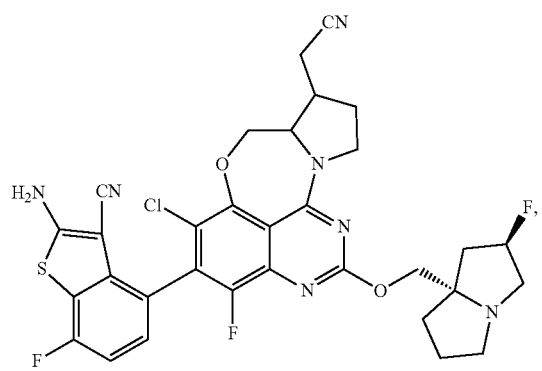
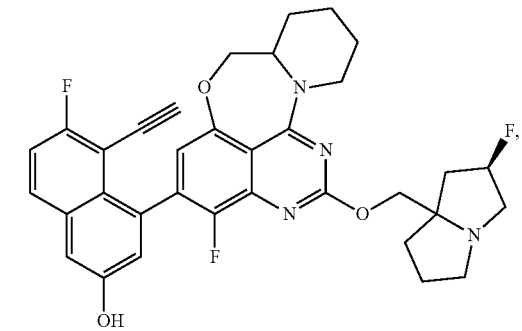
594
-continued
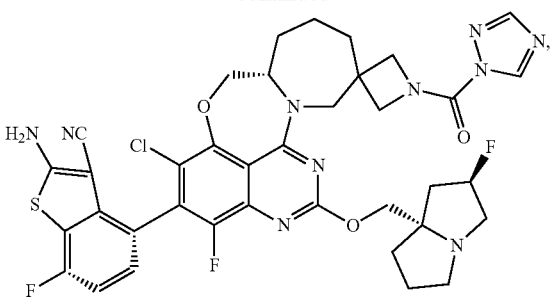
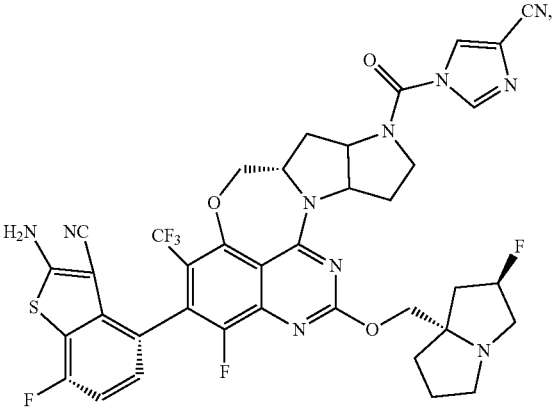
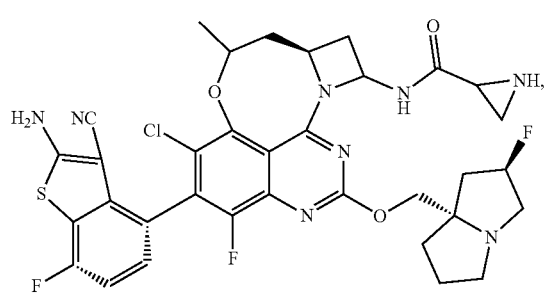
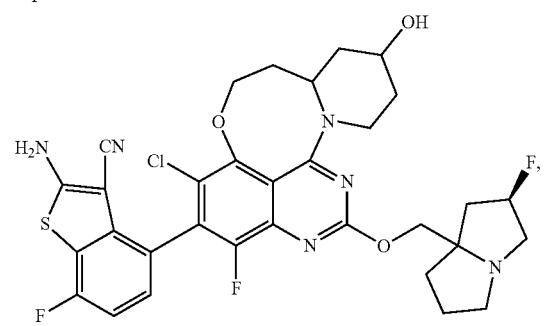
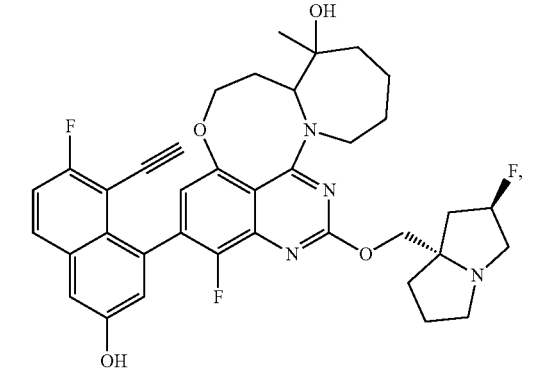

595
-continued
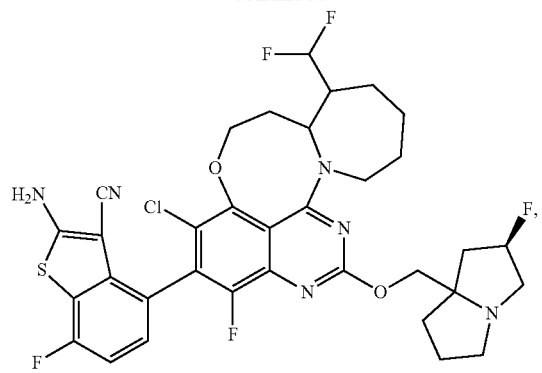
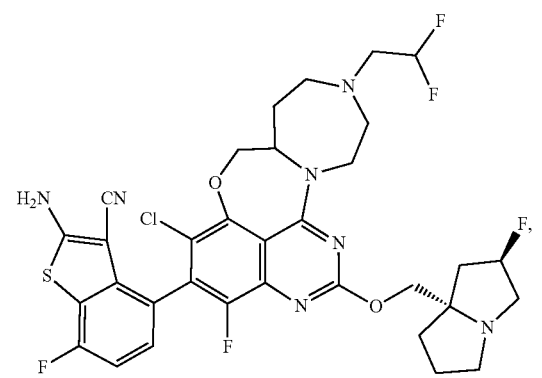
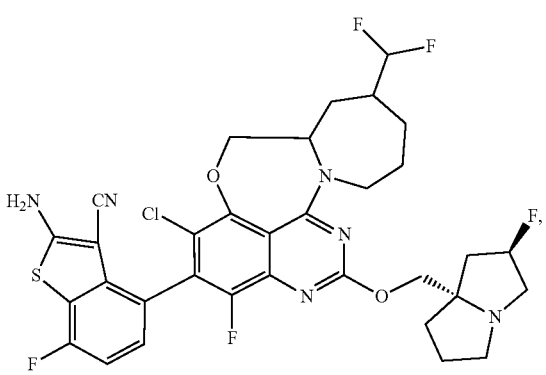
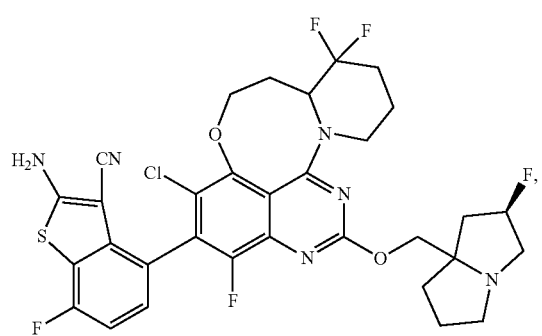
596
-continued
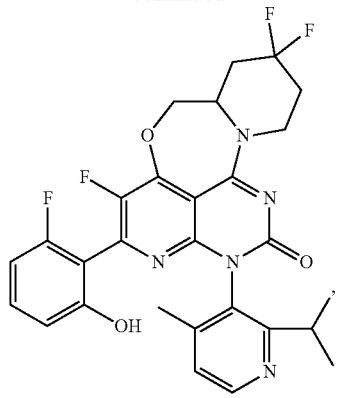
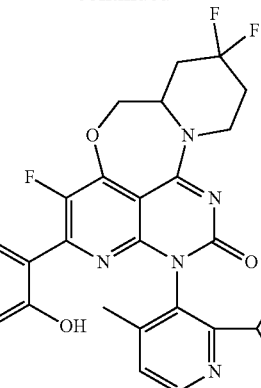
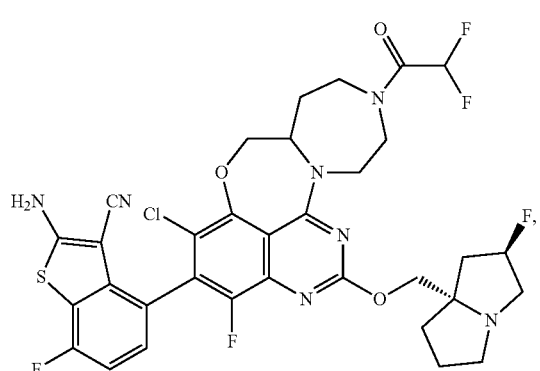
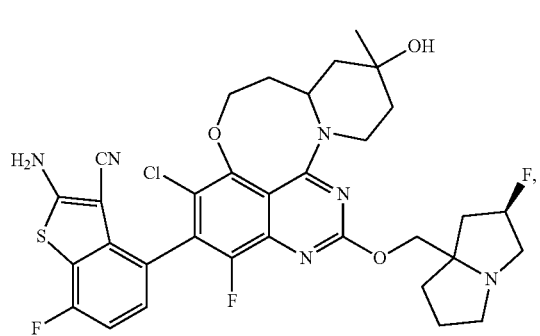

597
-continued
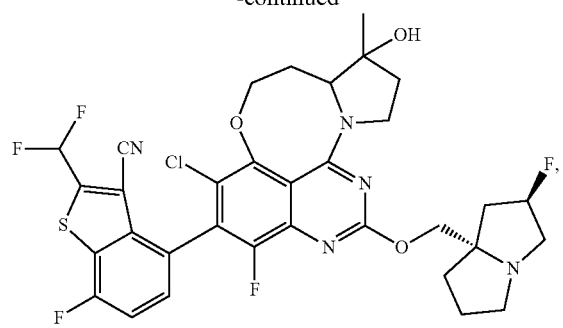
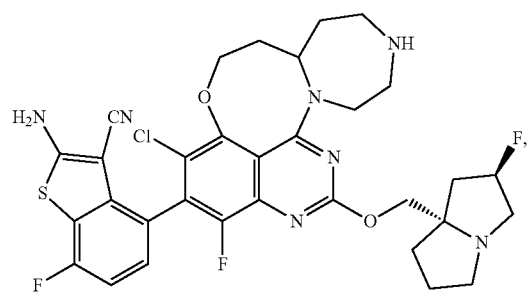
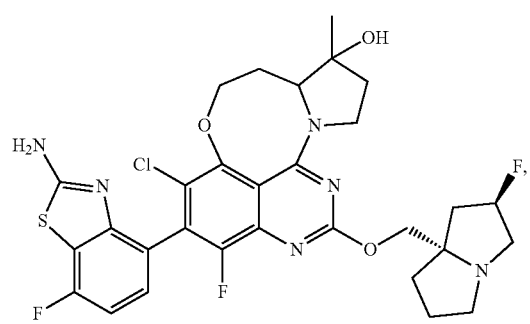
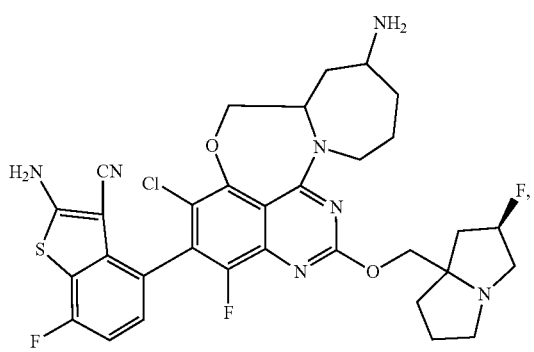
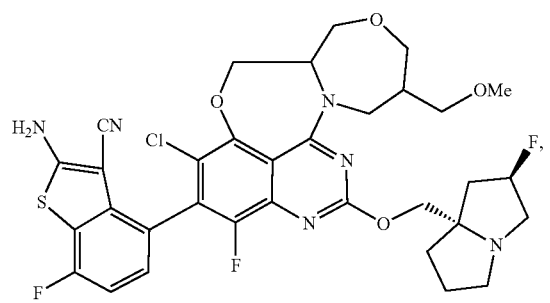
598
-continued
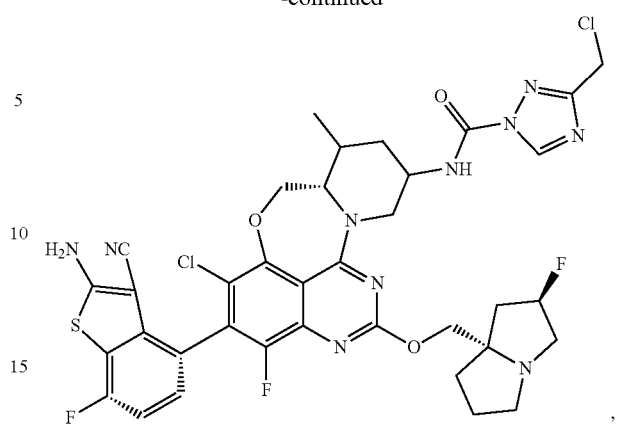
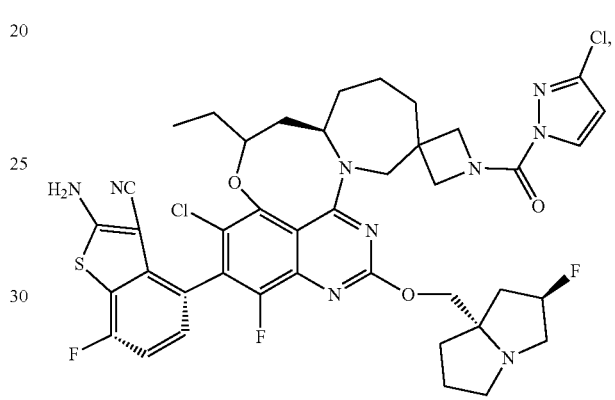
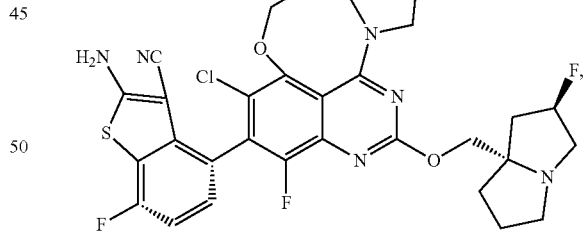
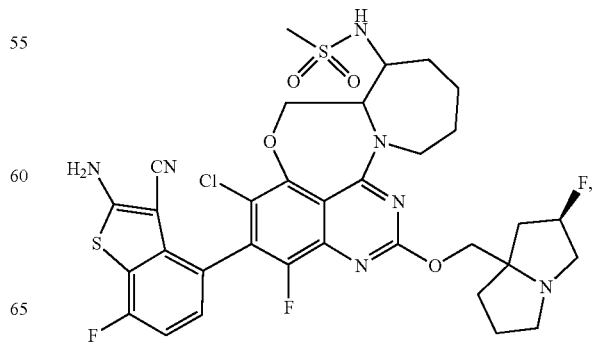

599
-continued
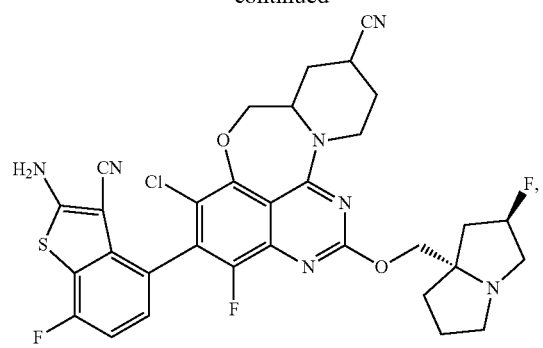
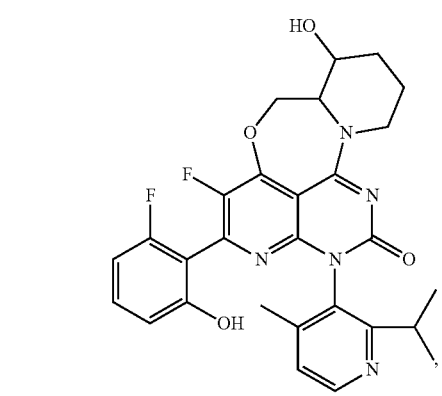
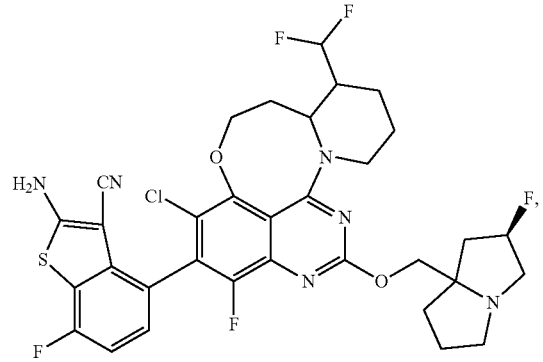
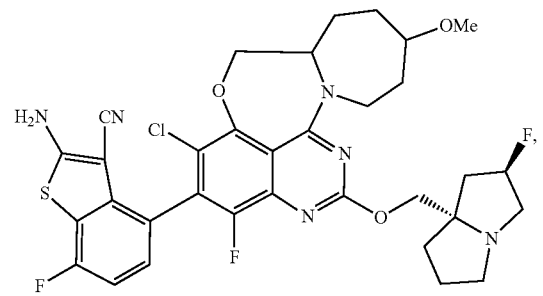
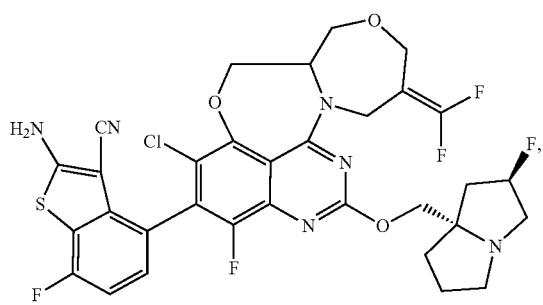
600
-continued
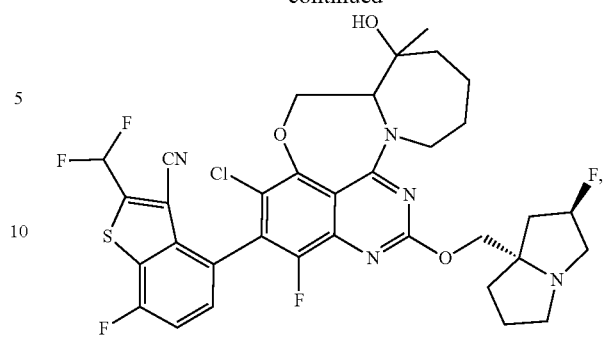
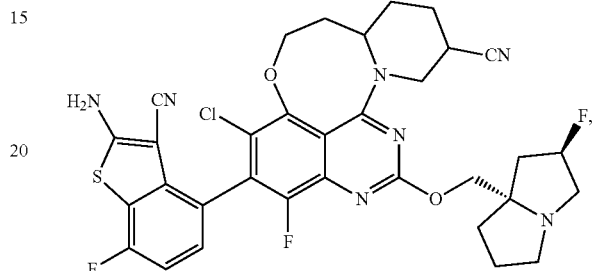
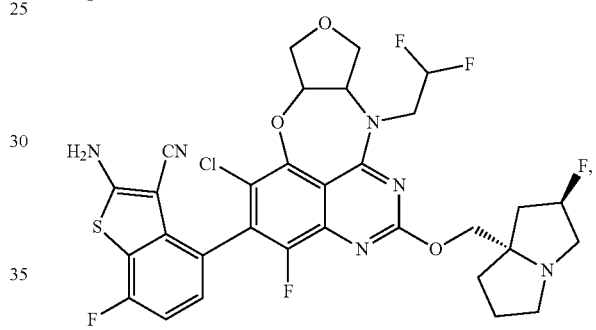
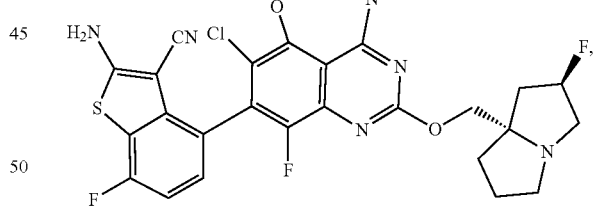
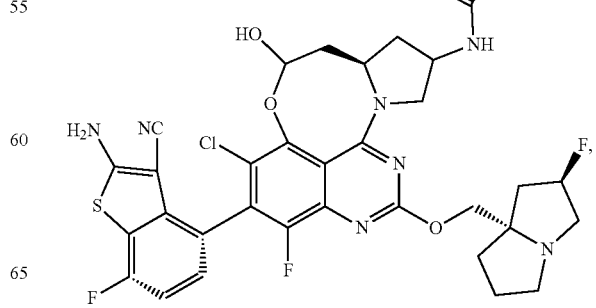

601
-continued
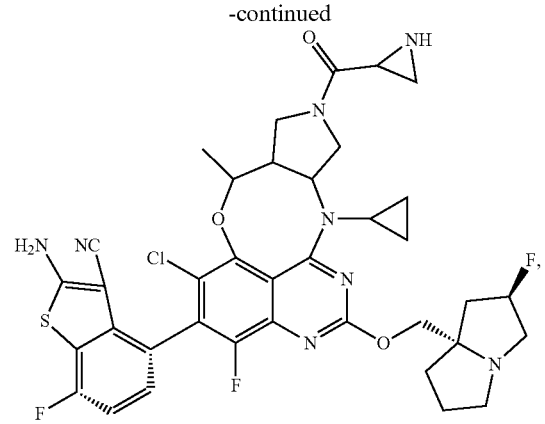
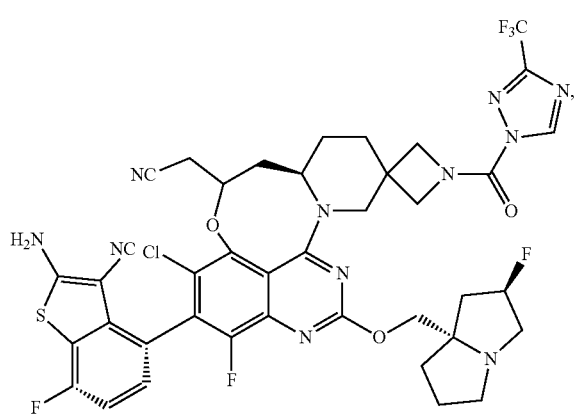
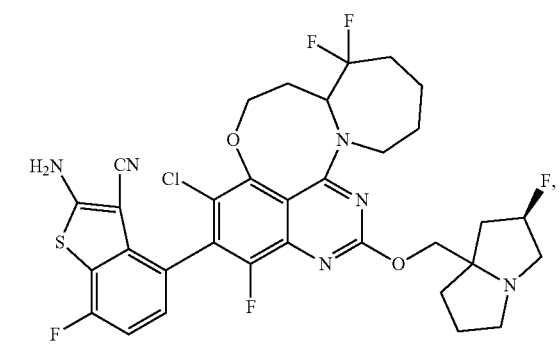
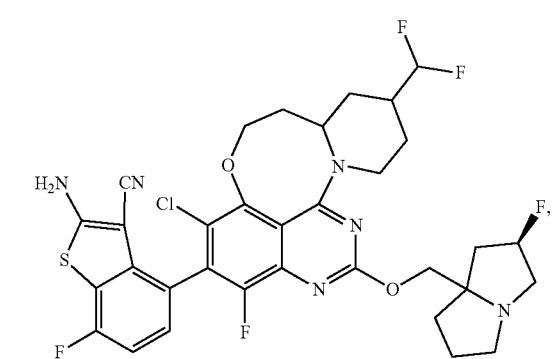
602
-continued
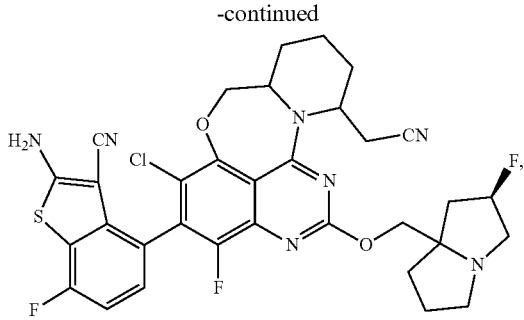
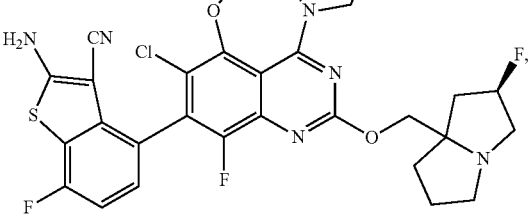
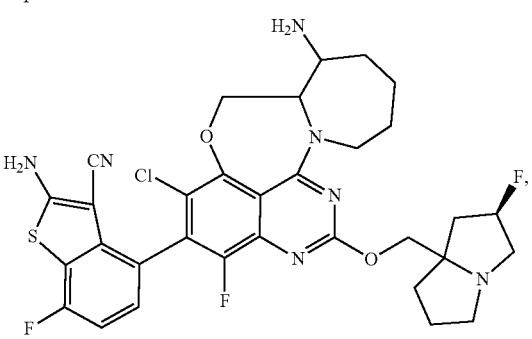
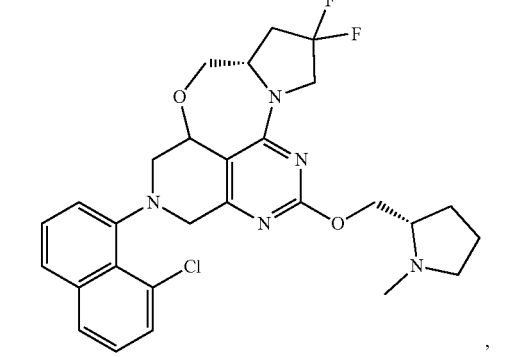
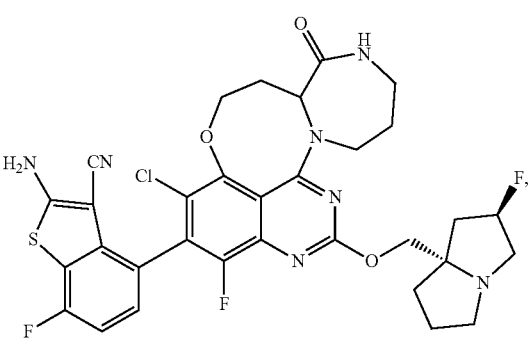

603
-continued
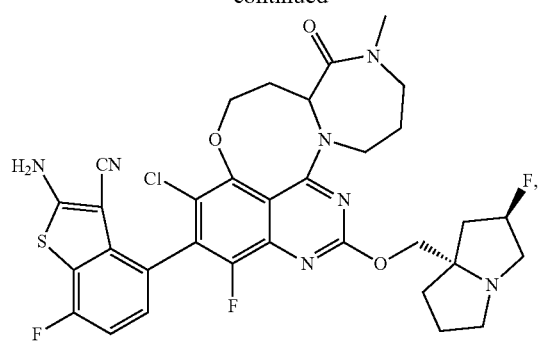
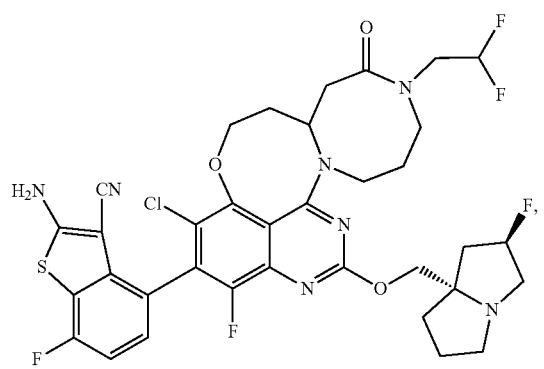
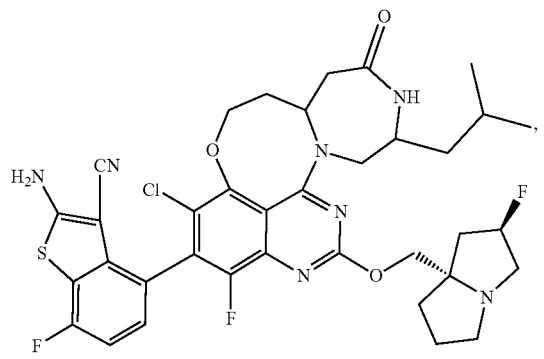
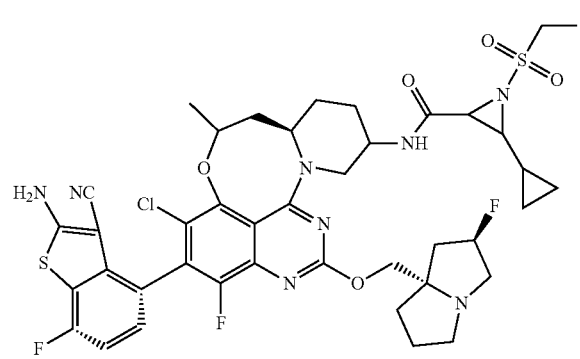
604
-continued
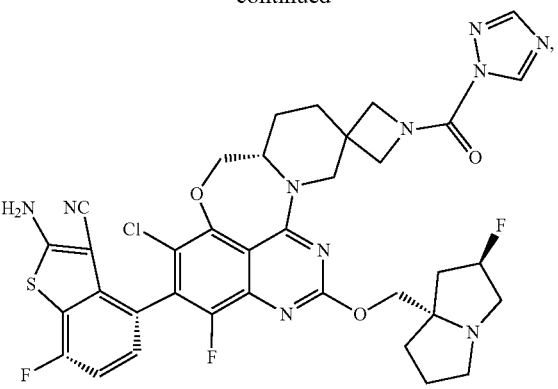
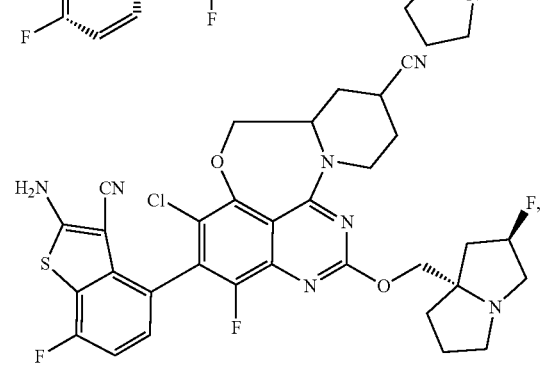
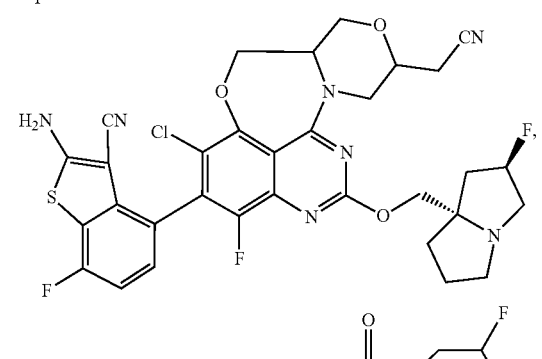
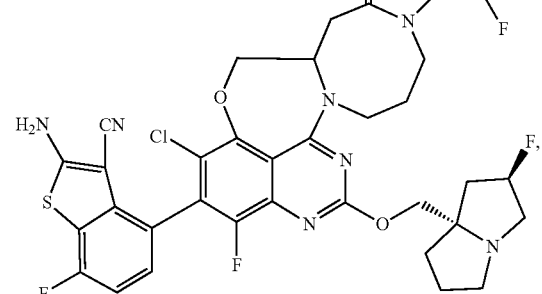
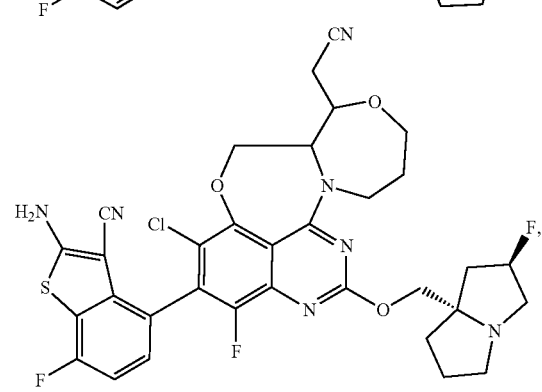

605
-continued
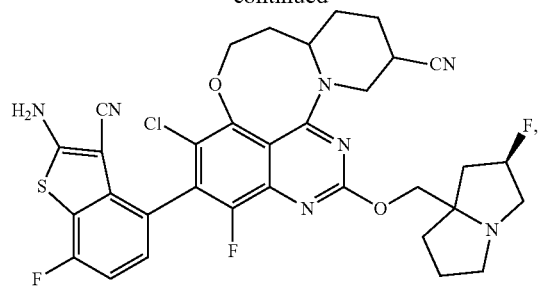
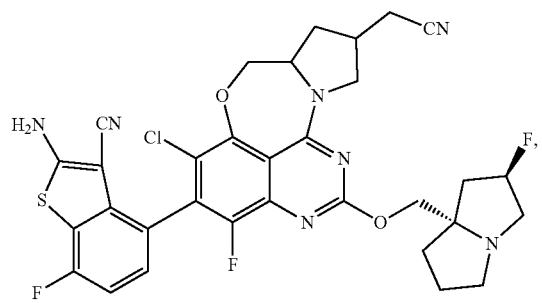
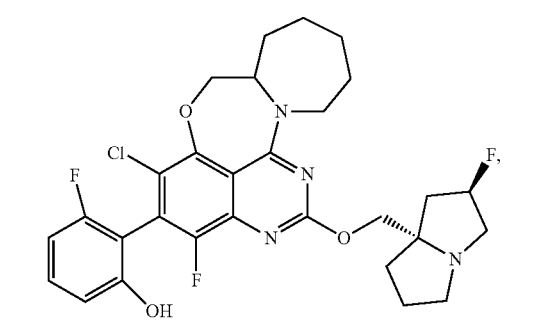
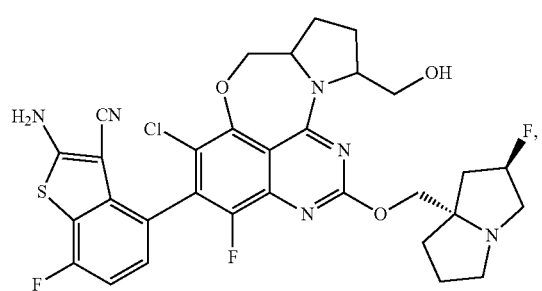
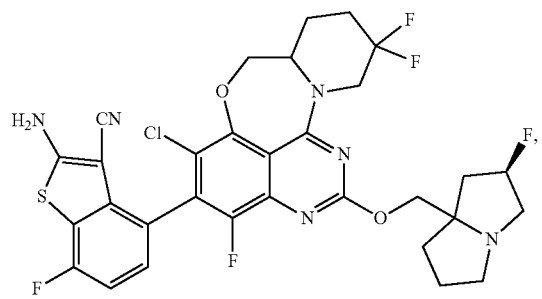
606
-continued
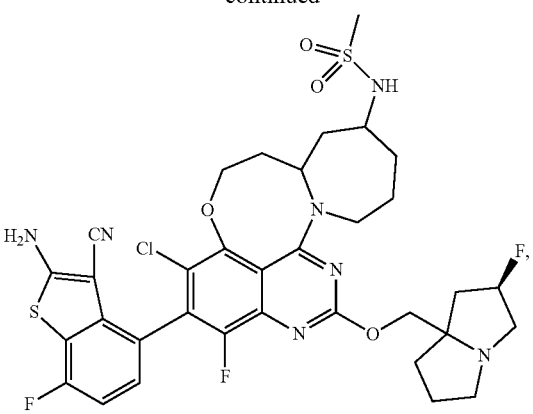
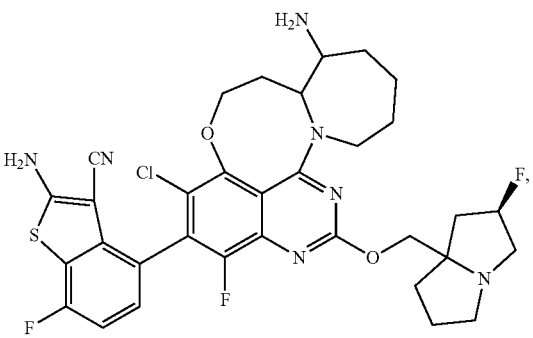
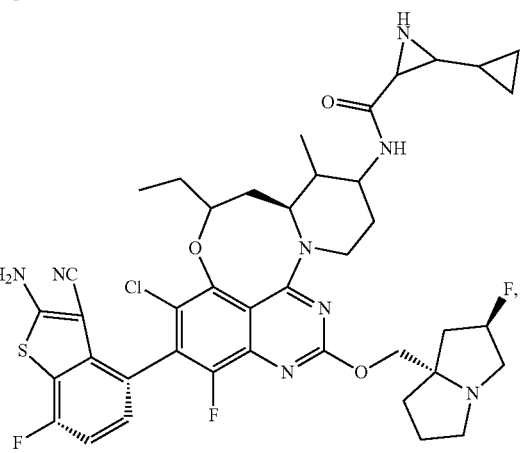
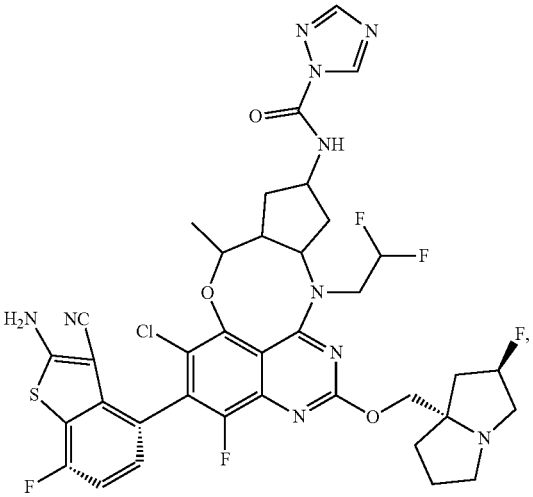

607
-continued
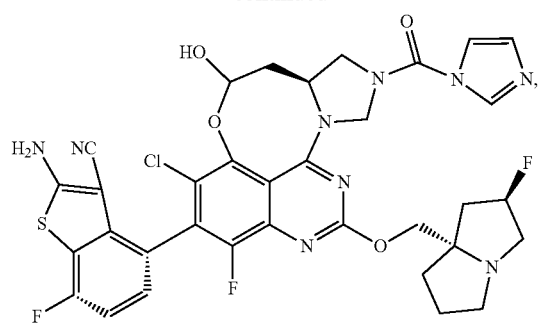
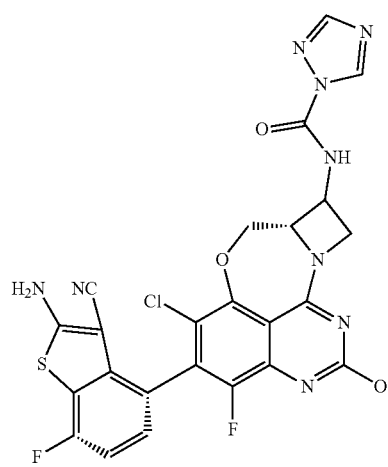
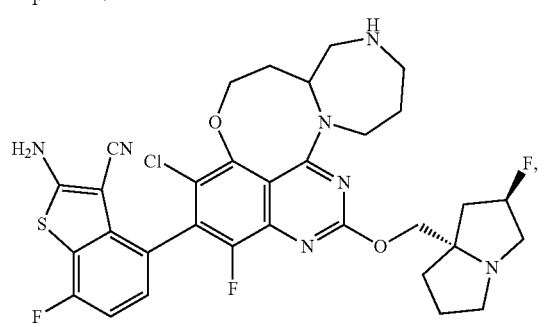
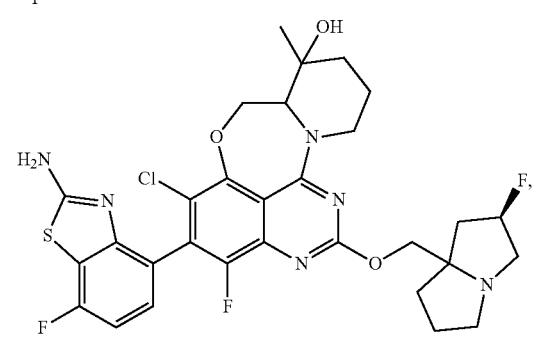
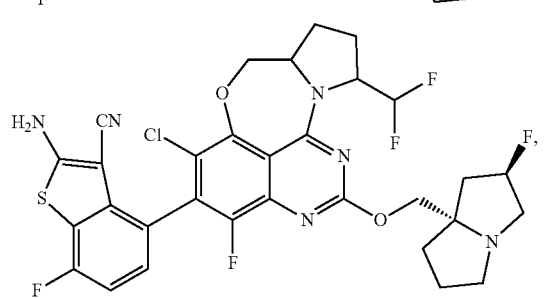
608
-continued
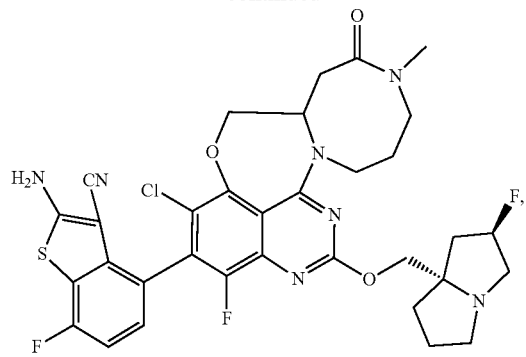
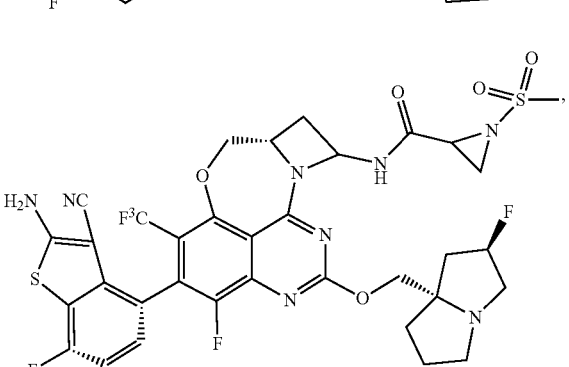
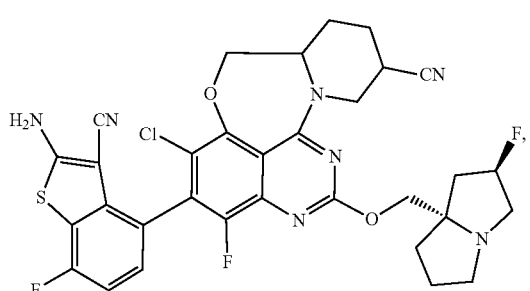
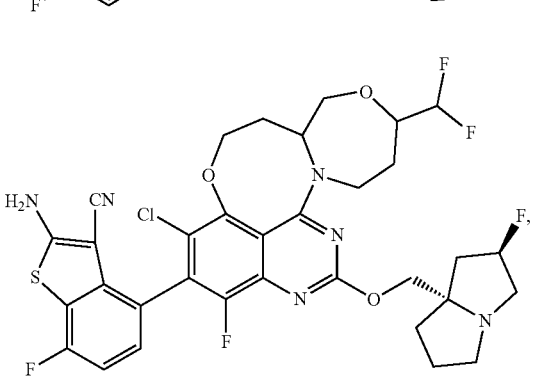
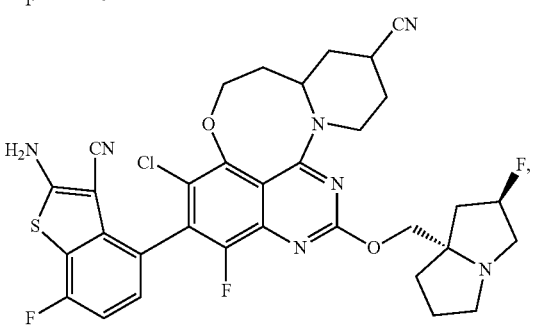

609
-continued
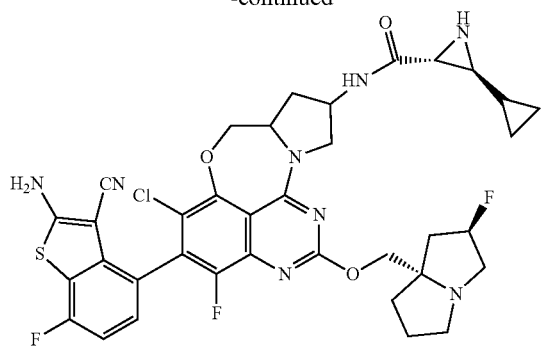
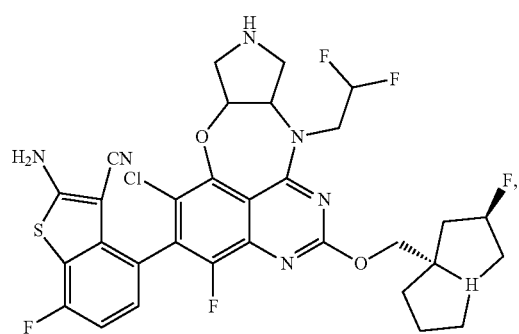
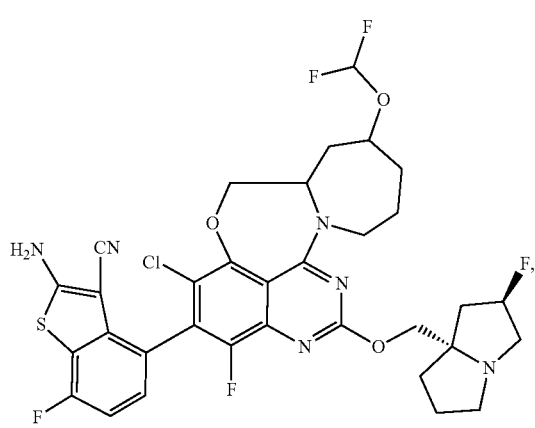
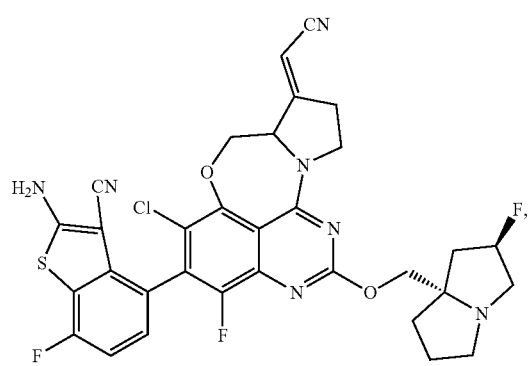
610
-continued
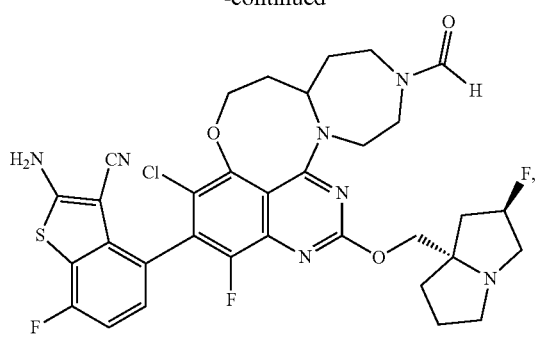
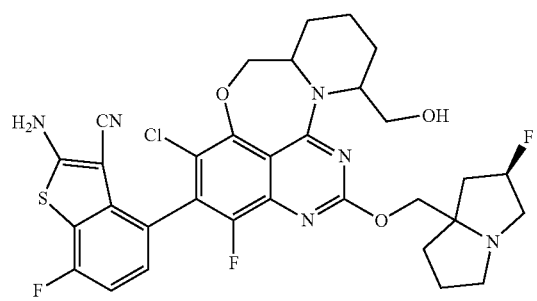
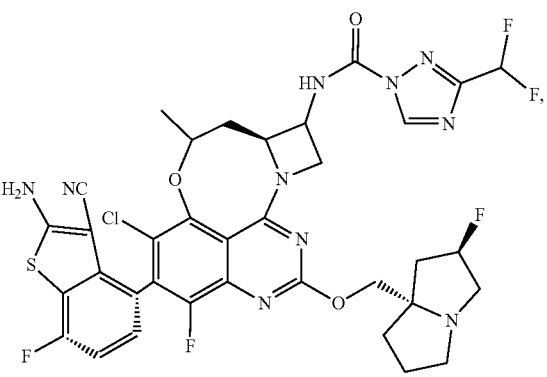
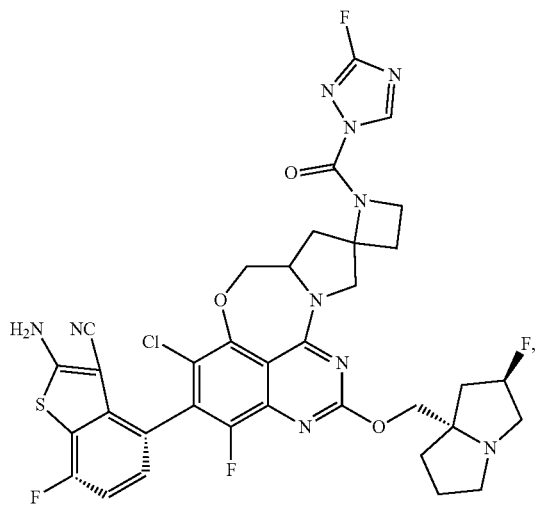

611
-continued
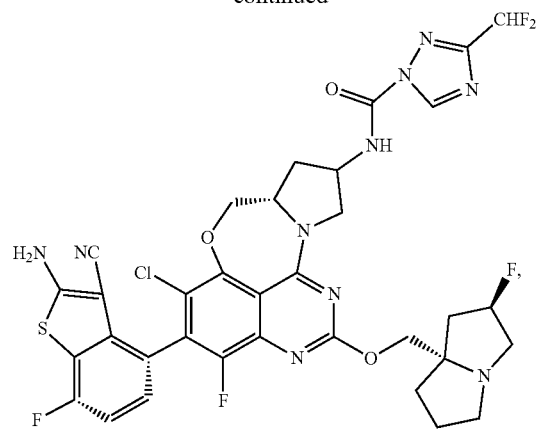
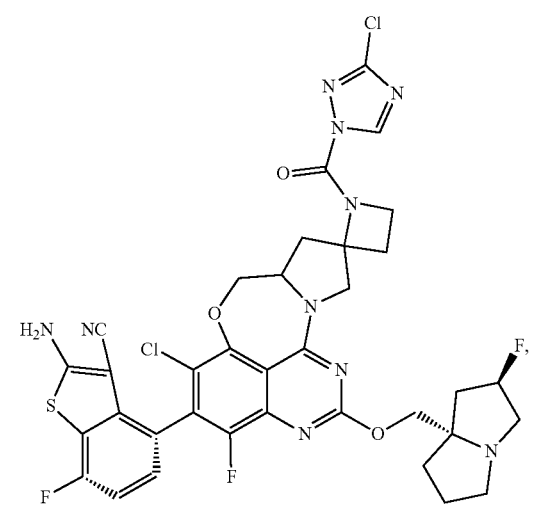
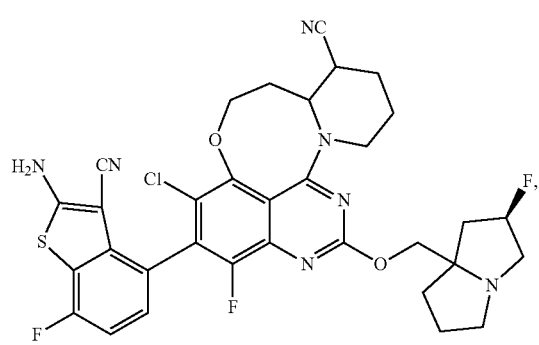
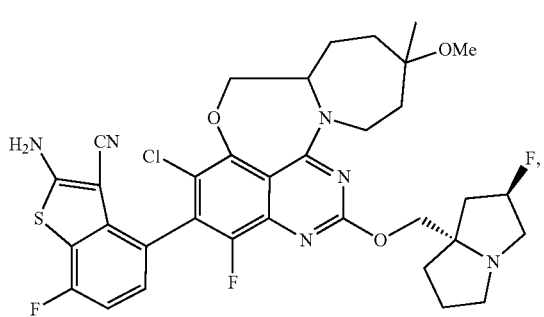
612
-continued
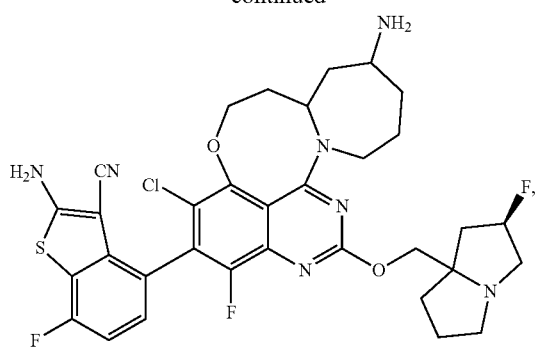
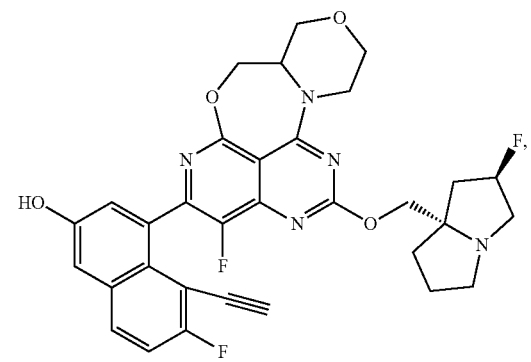
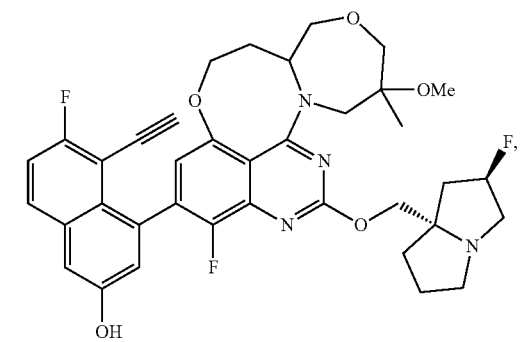
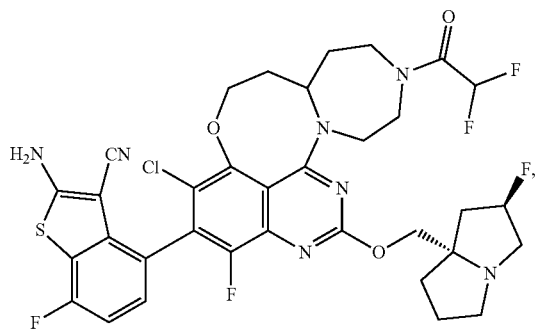
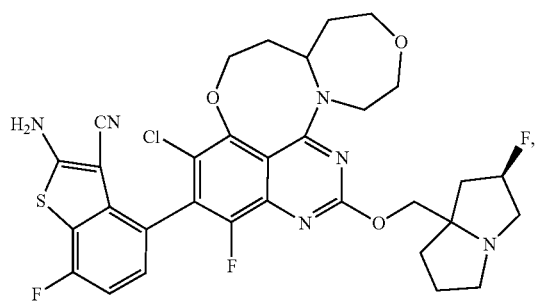

613
-continued
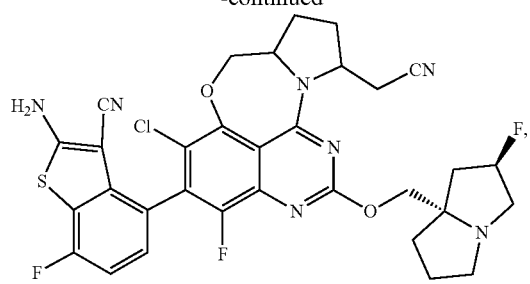
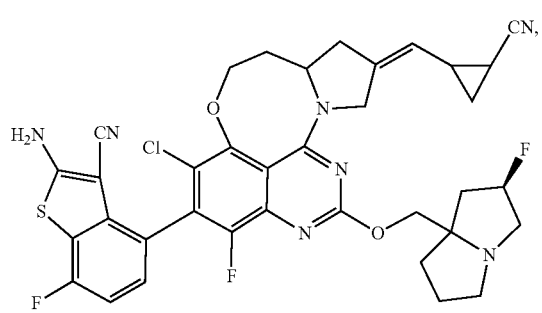
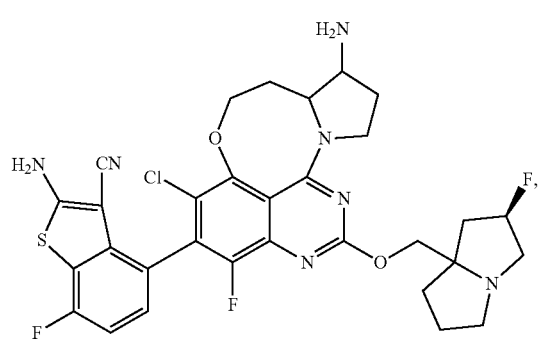
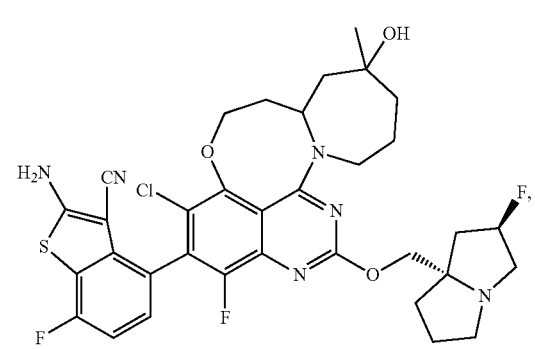
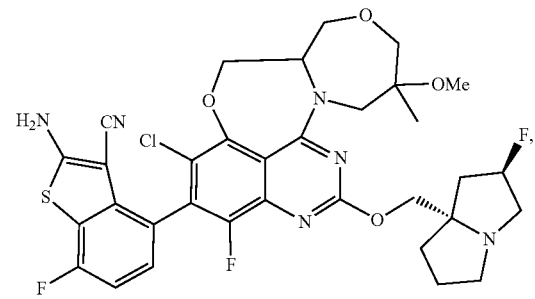
614
-continued
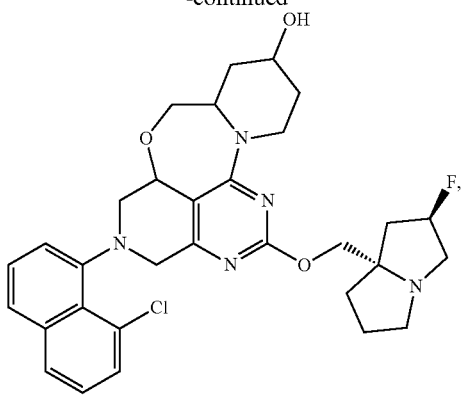
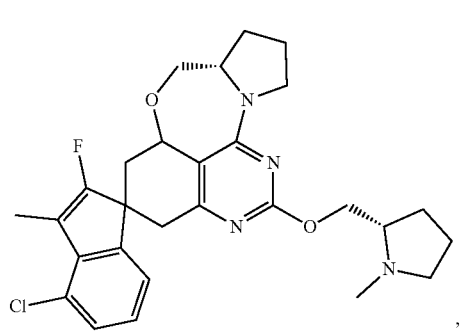
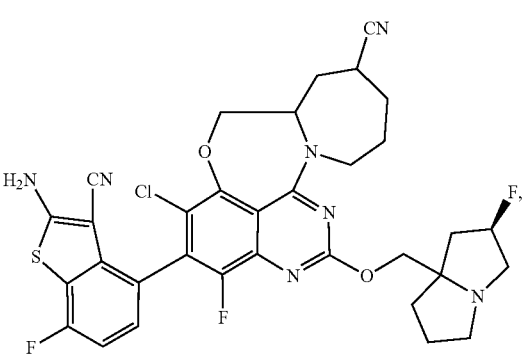
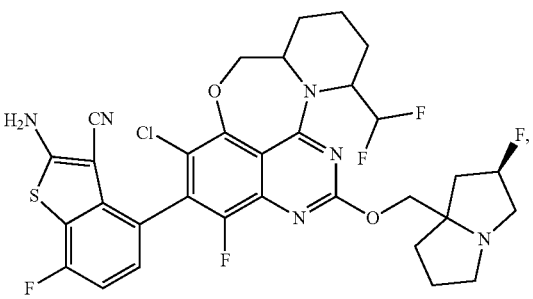

615
-continued
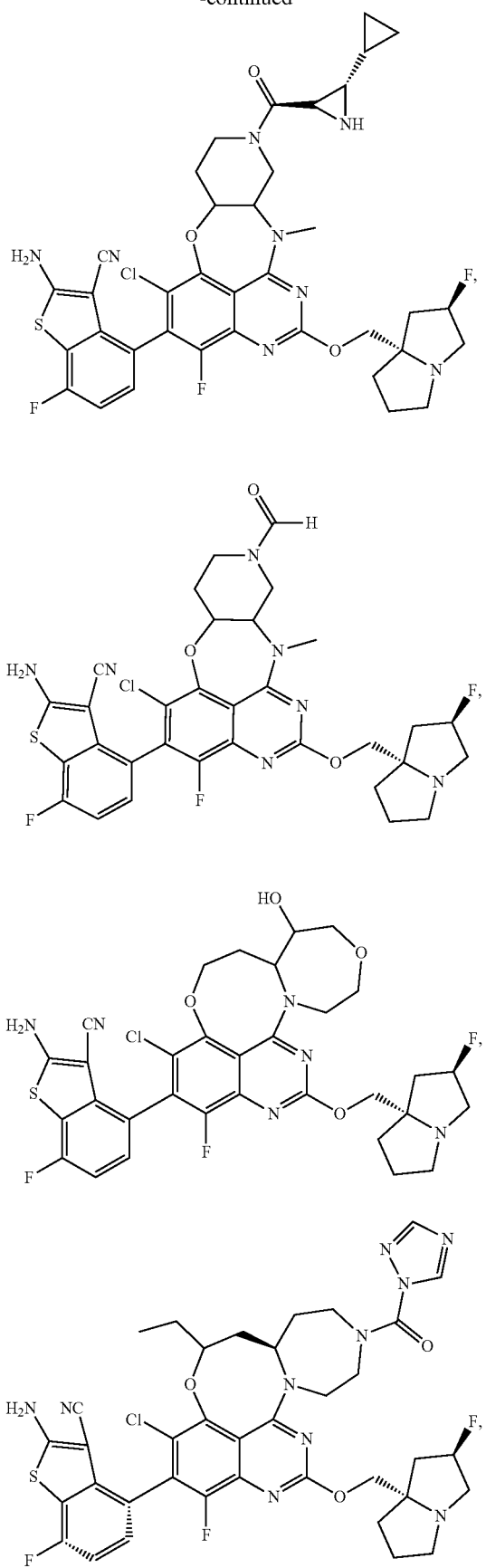
616
-continued
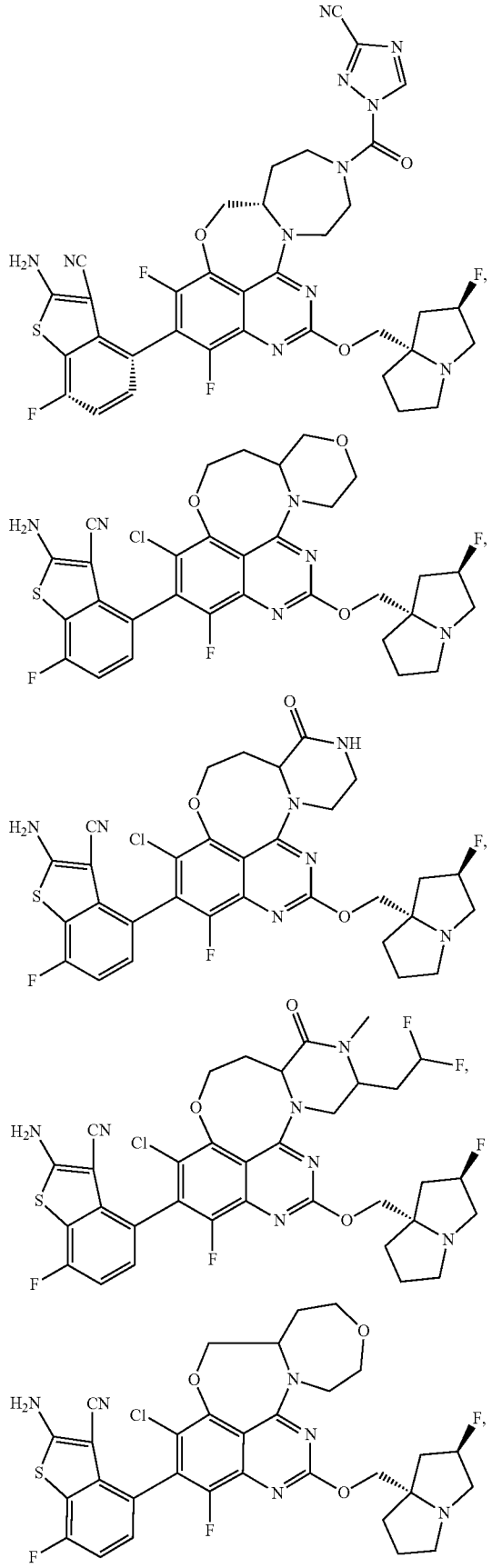

617
-continued
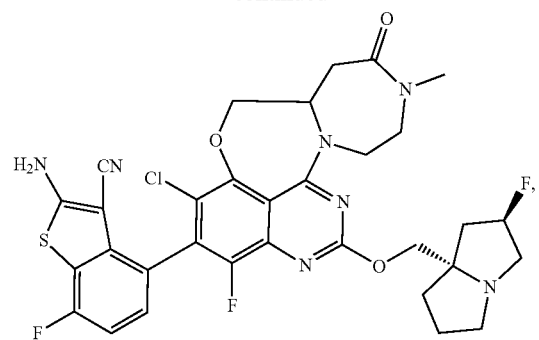
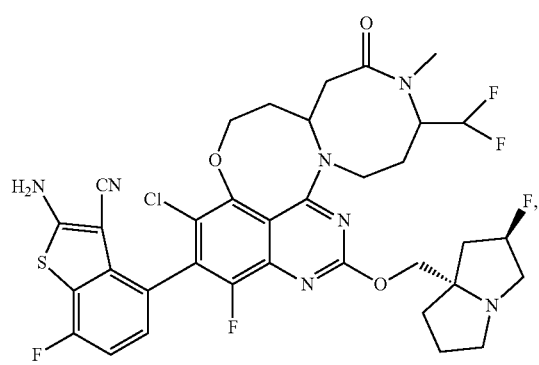
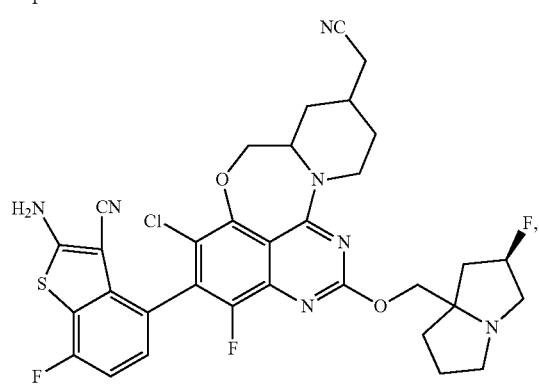
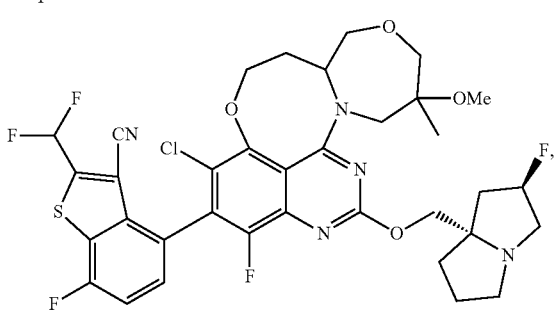
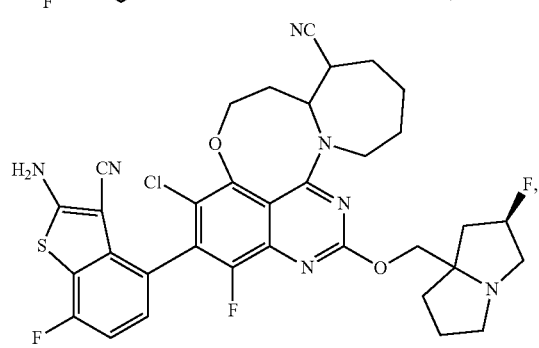
618
-continued
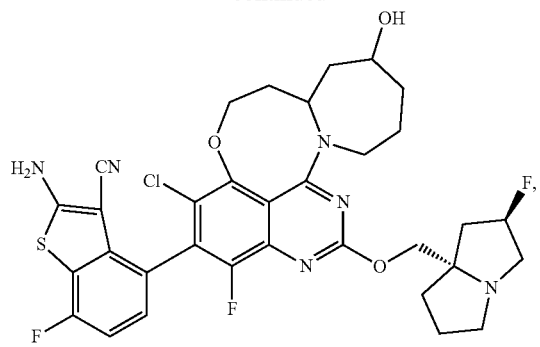
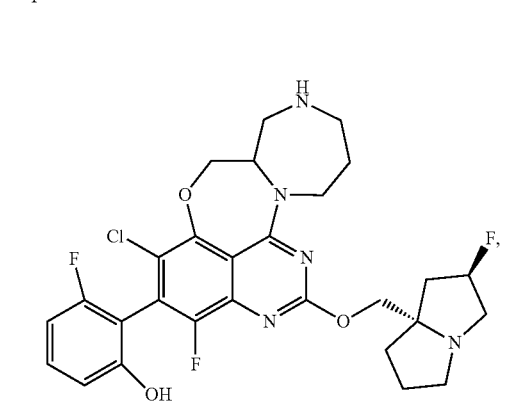
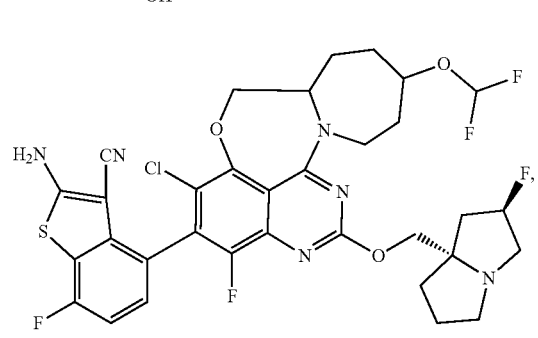
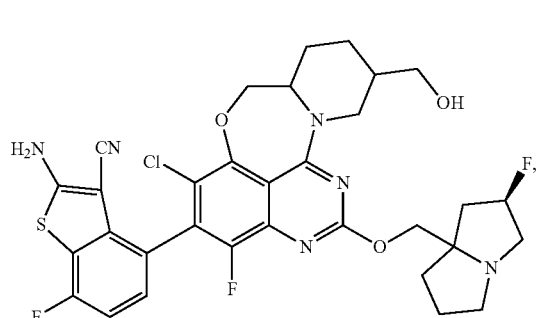
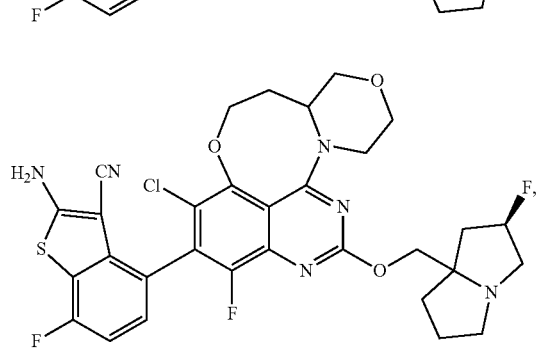

619
-continued
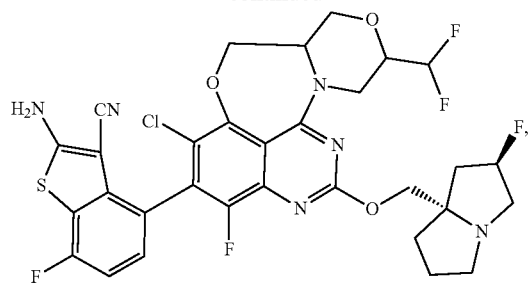
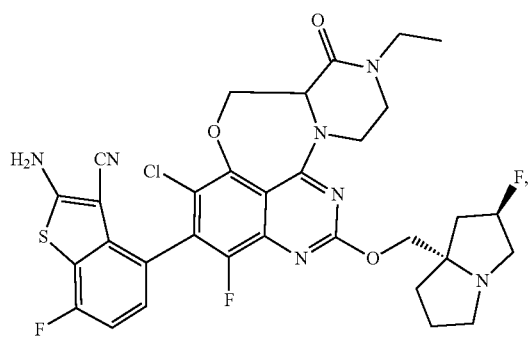
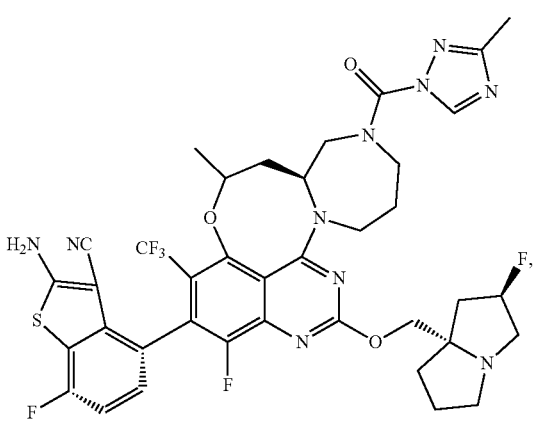
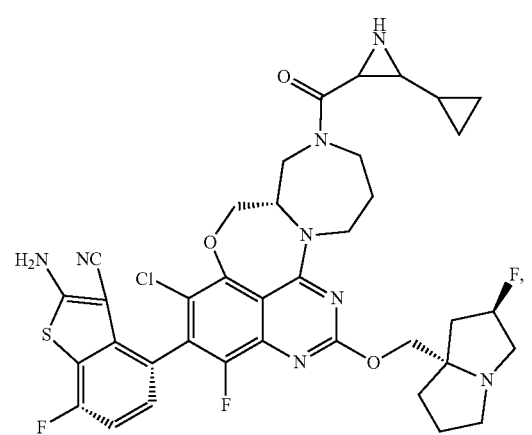
620
-continued
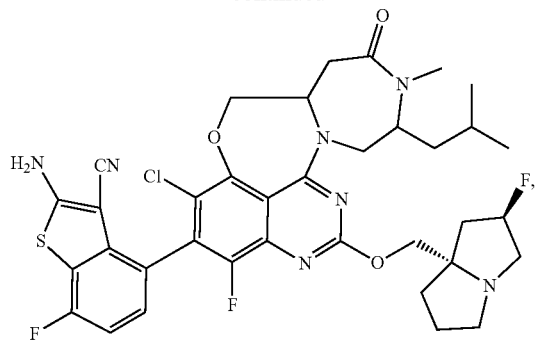
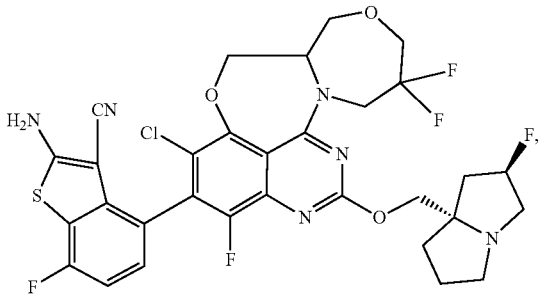
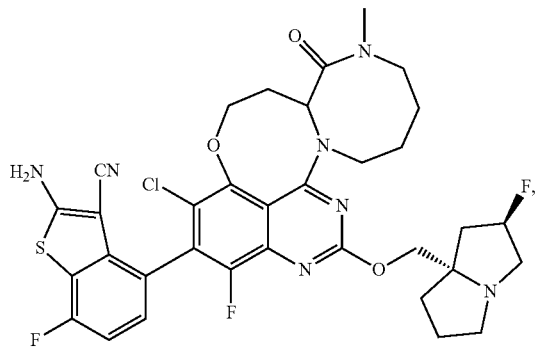
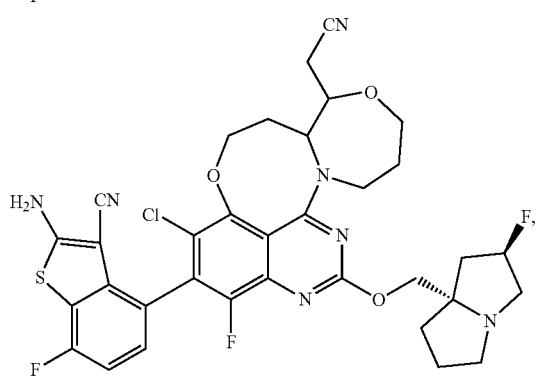
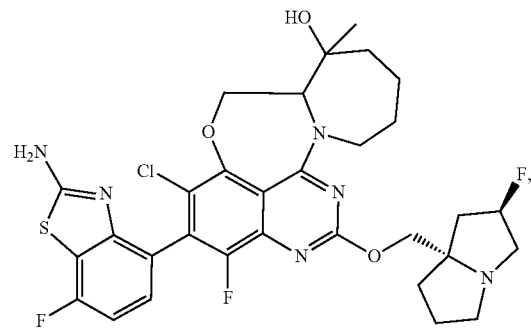

621
-continued
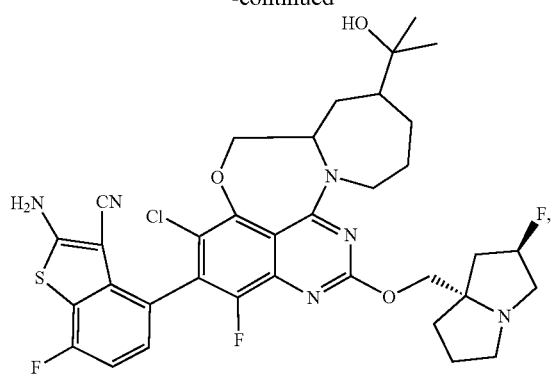
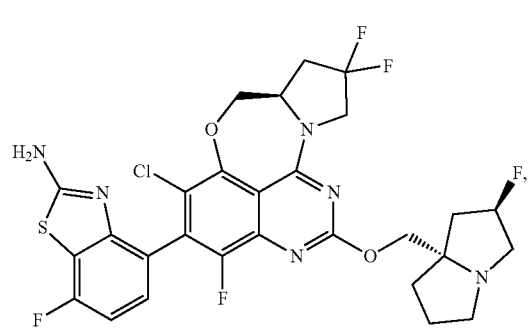
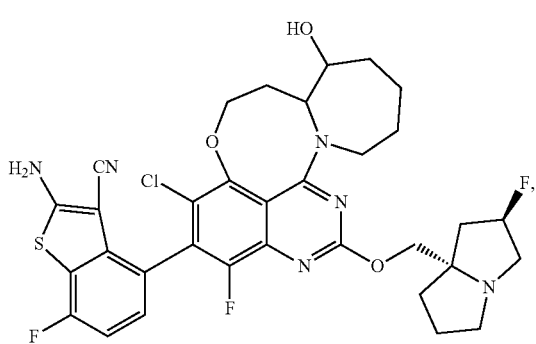
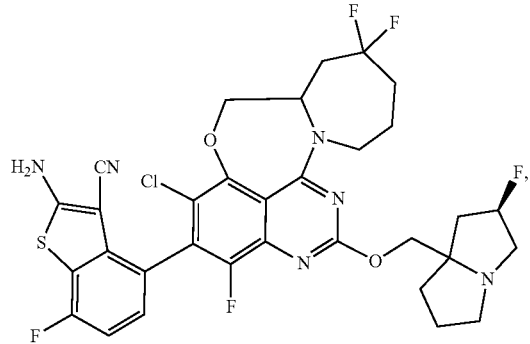
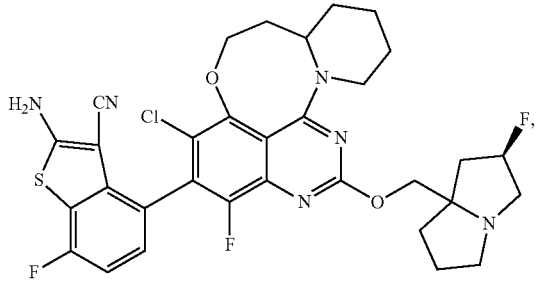
622
-continued
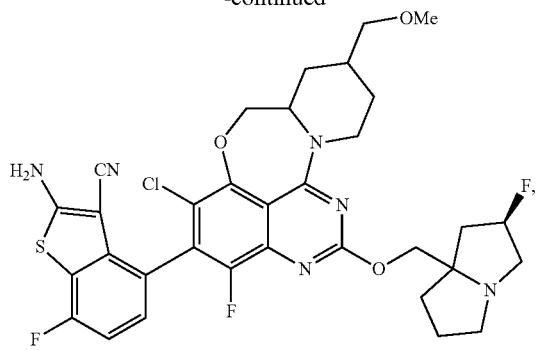
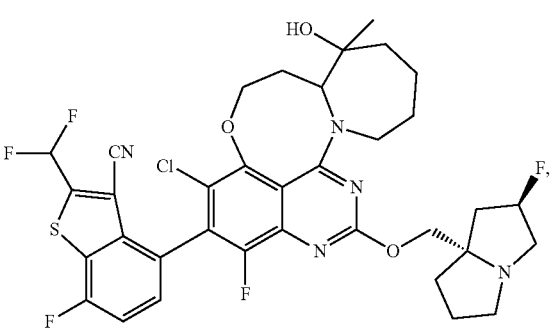
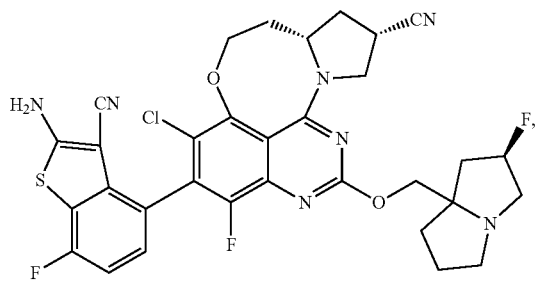 [SMILES: N#Cc1c(N)sc2c(F)ccc(-c3c(Cl)c4c5c(nc(OCC67CCCN6C[C@H](F)C7)nc5c3F)N3C[C@@H](C#N)C[C@H]3CCO4)c12]
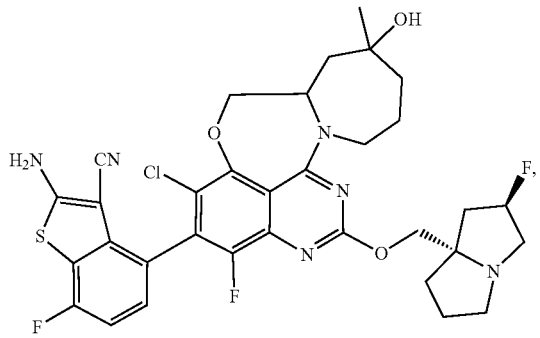
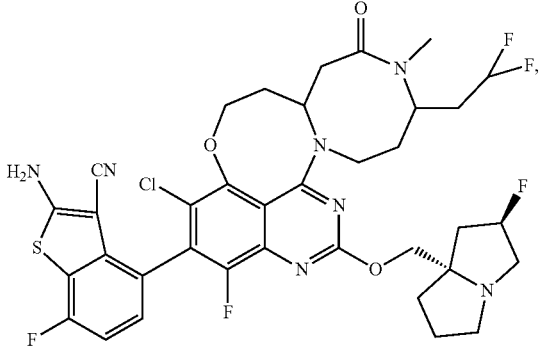

623
-continued
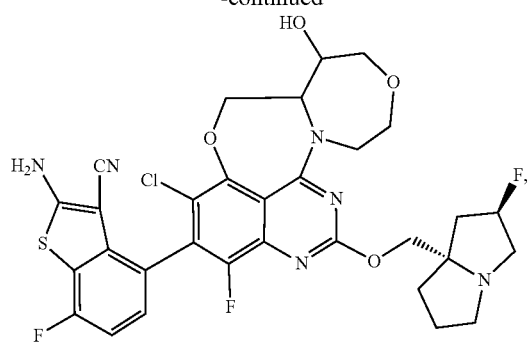
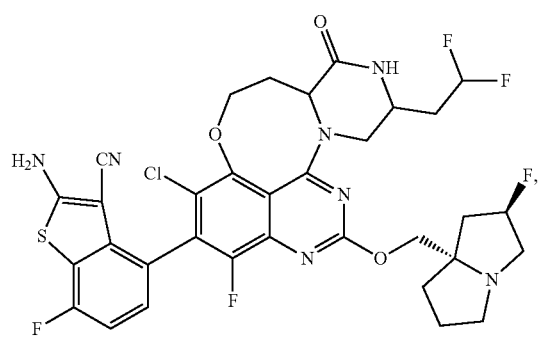
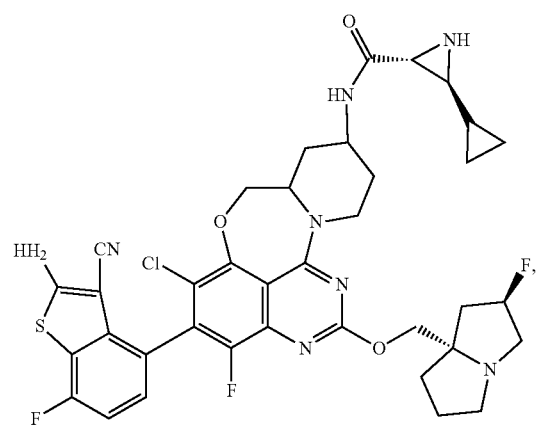
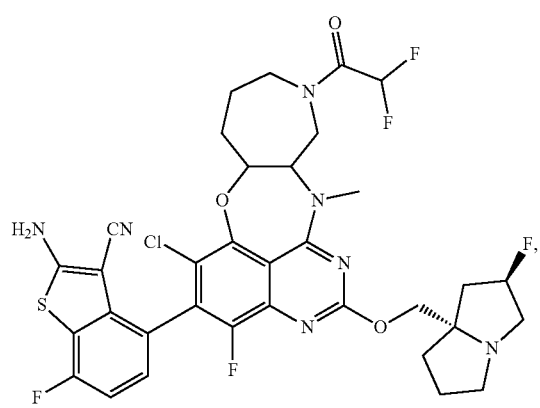
624
-continued
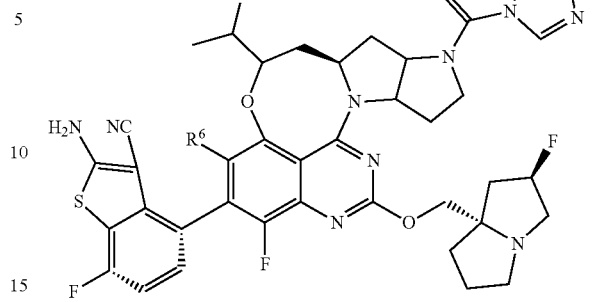
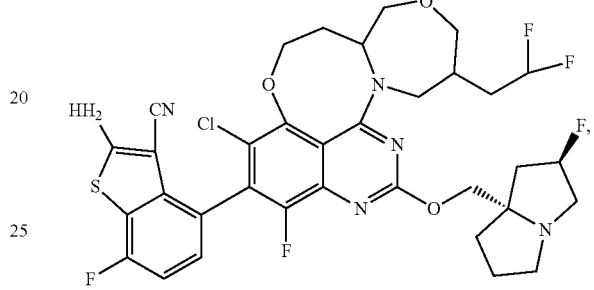
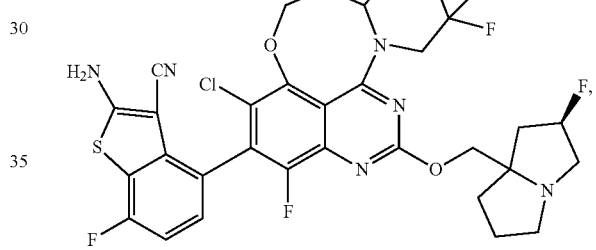
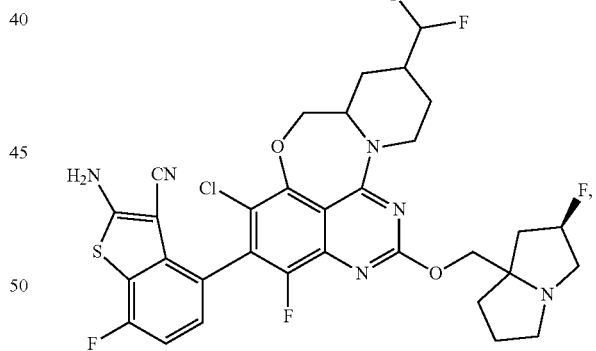
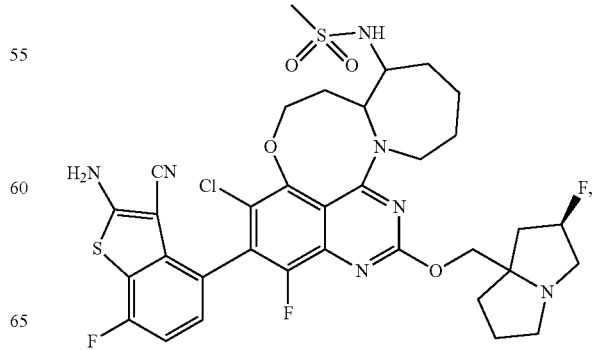

625
-continued
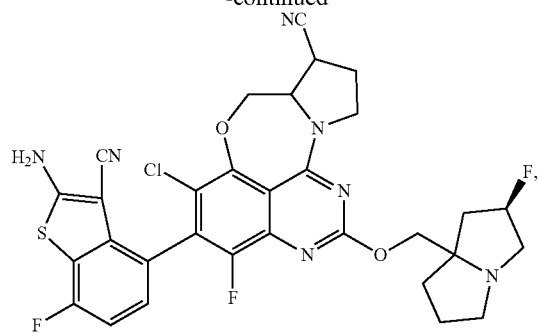
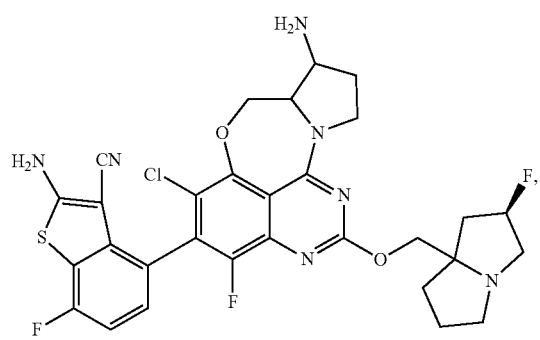
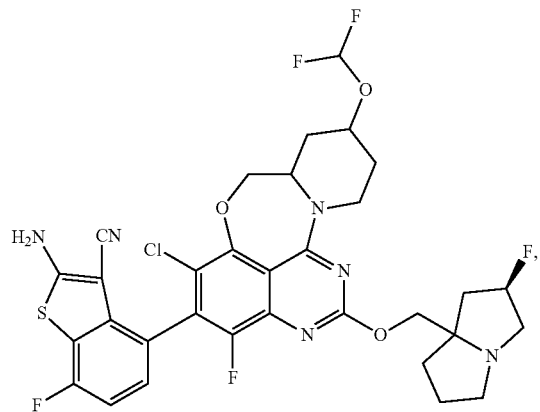
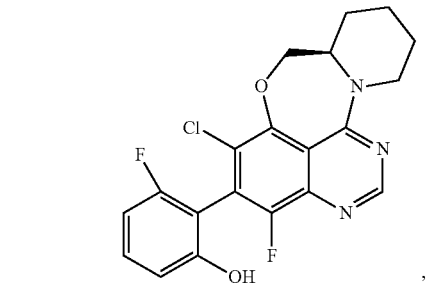
,
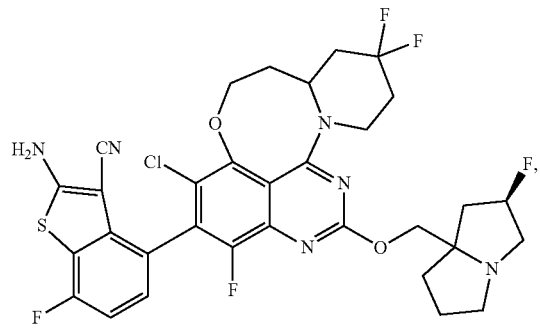
626
-continued
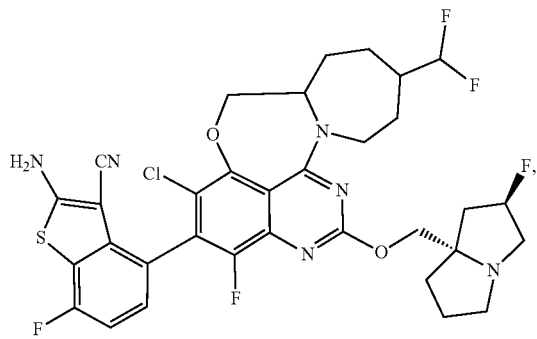
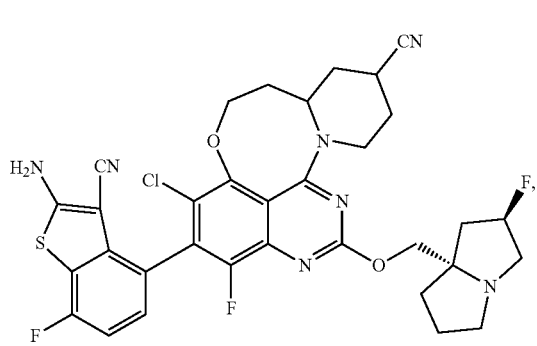
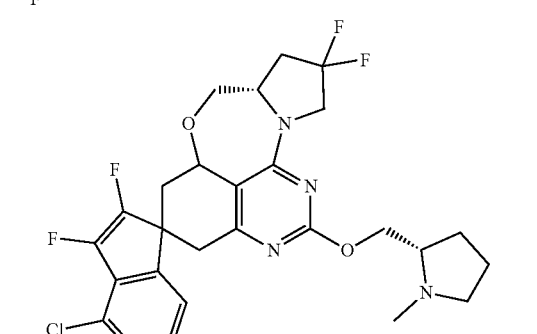
,
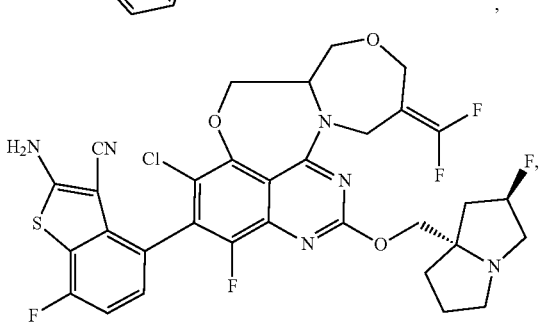
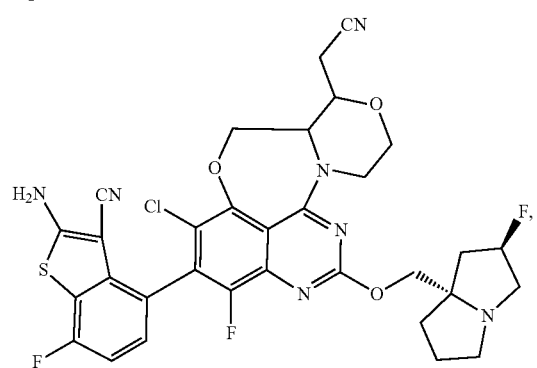

627
-continued
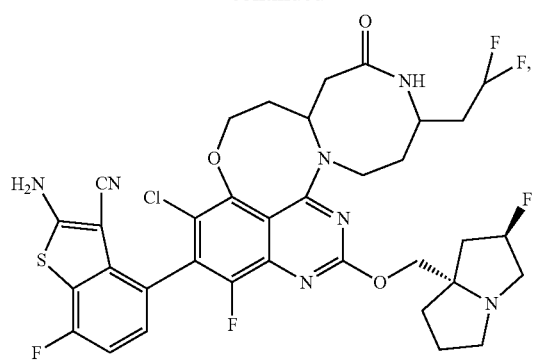
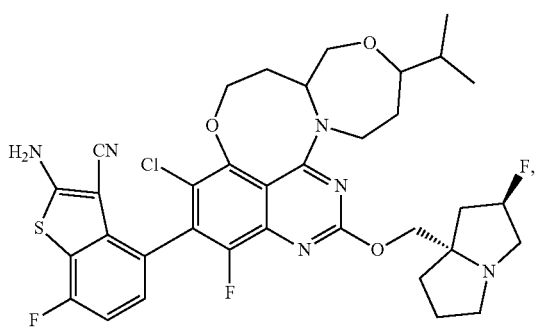
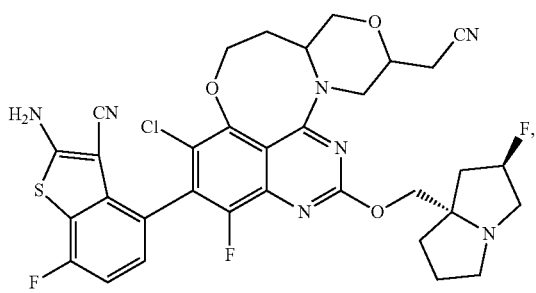
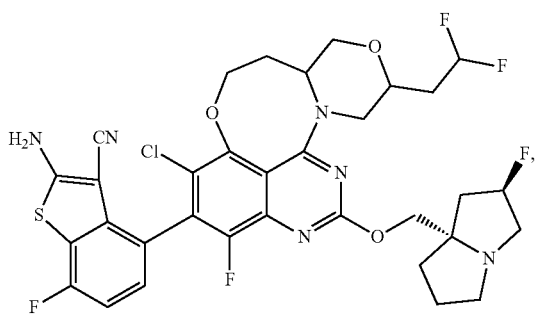
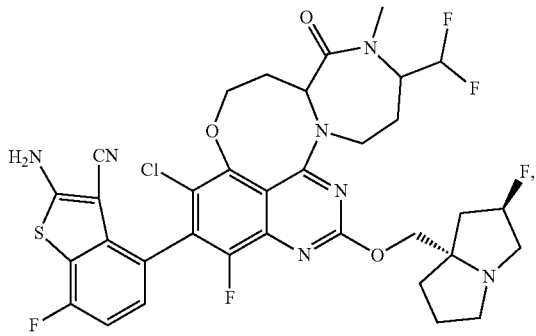
628
-continued
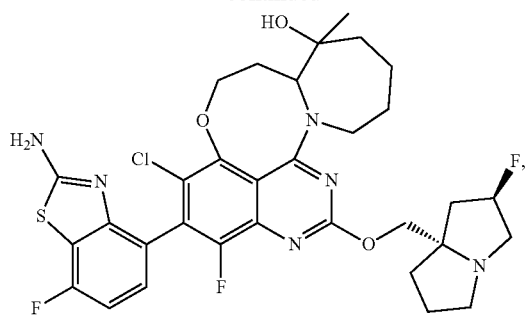
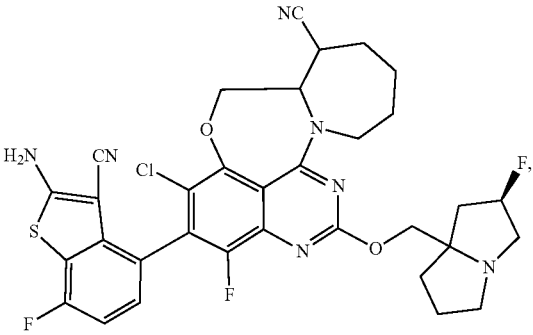
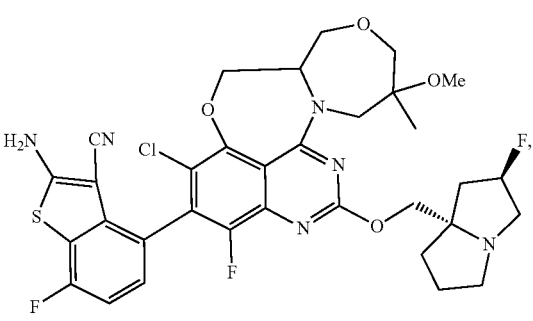
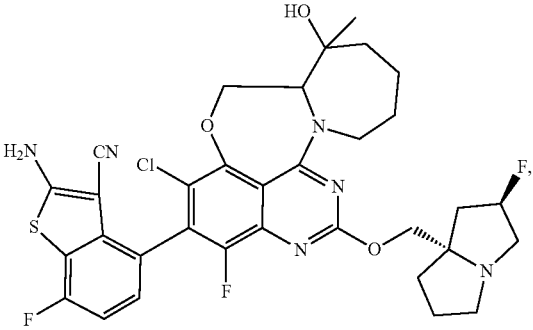
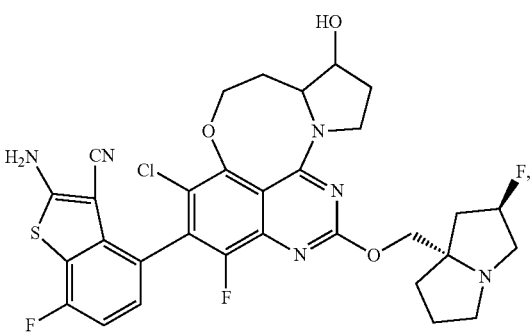

629
-continued
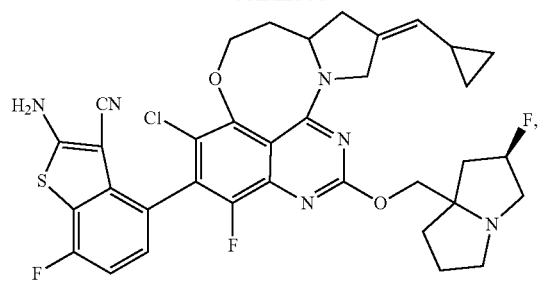
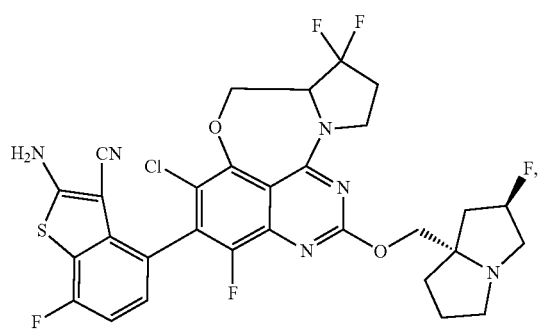
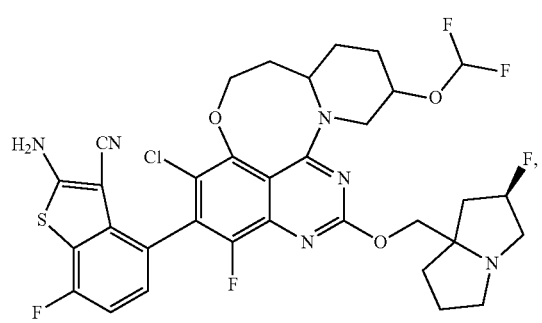
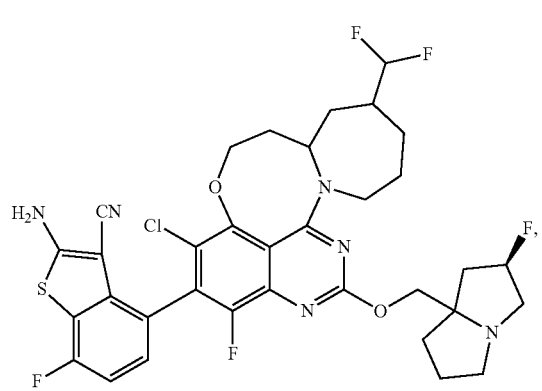
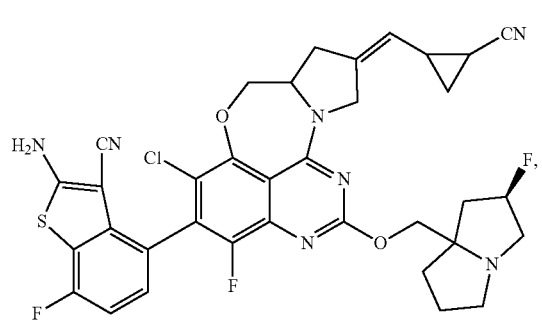
630
-continued
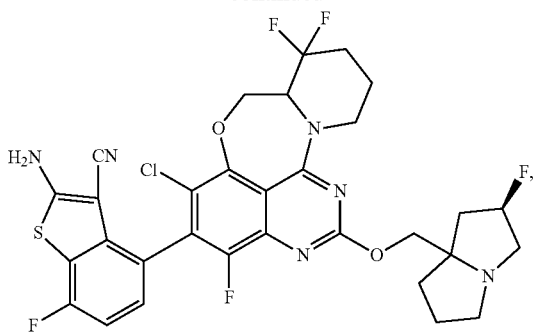
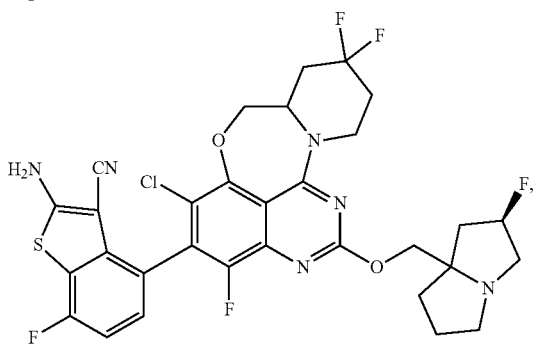
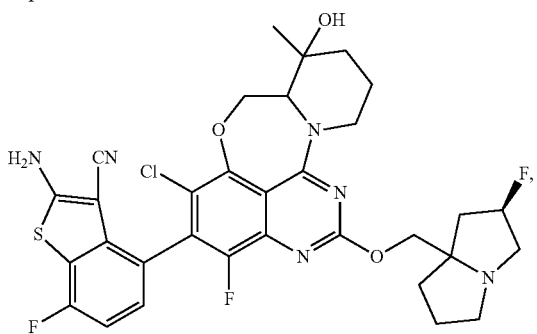
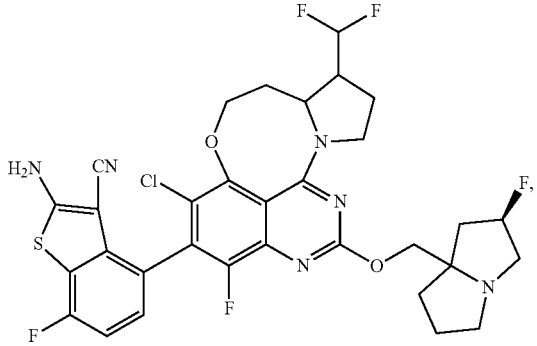
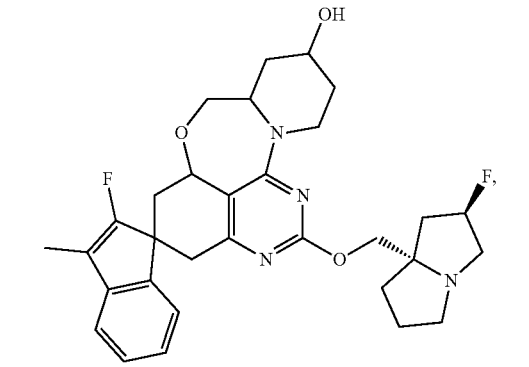

631
-continued
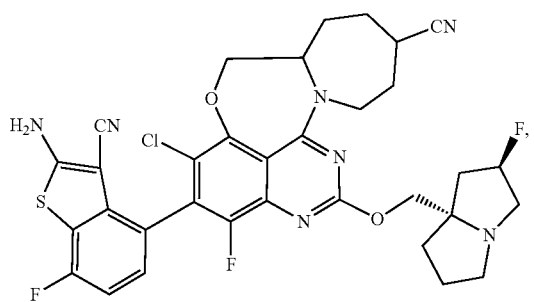
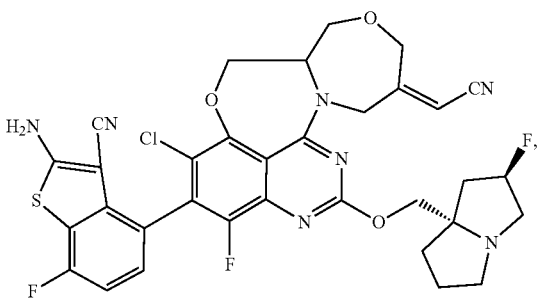
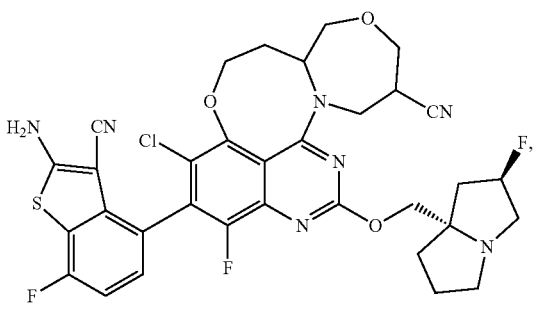
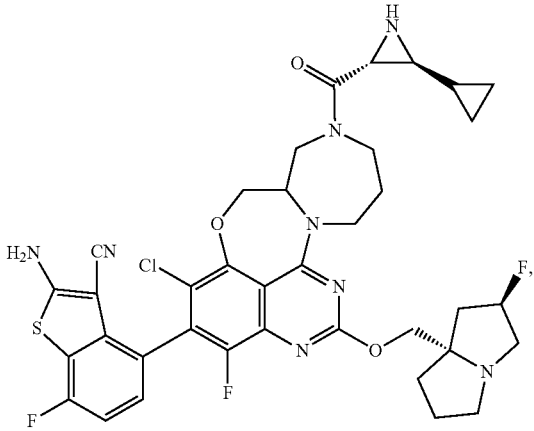
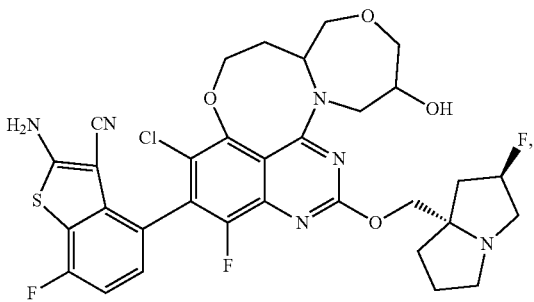
632
-continued
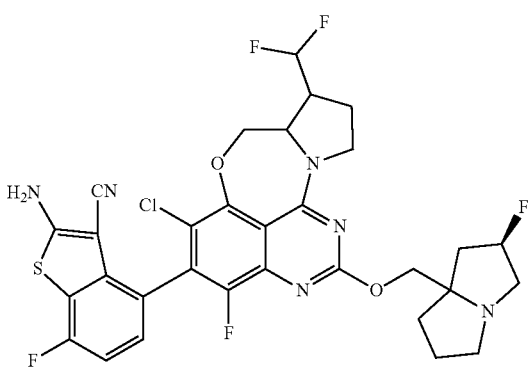
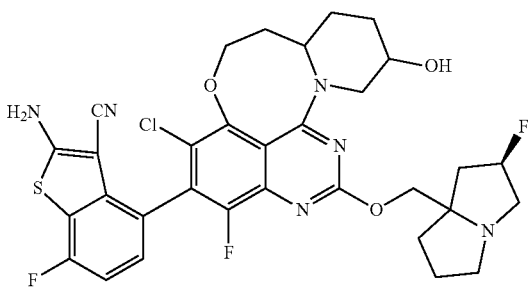
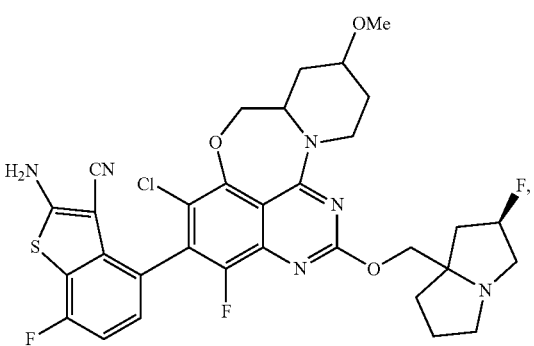
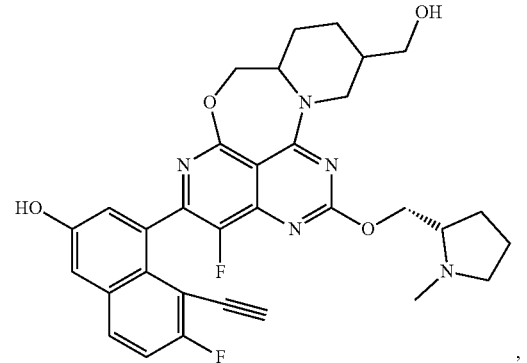
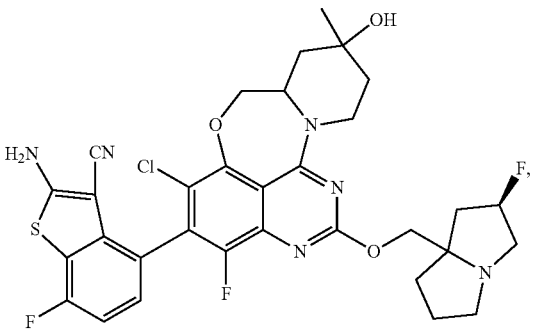

633
-continued
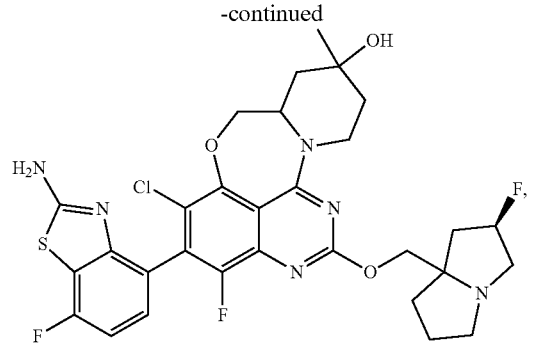
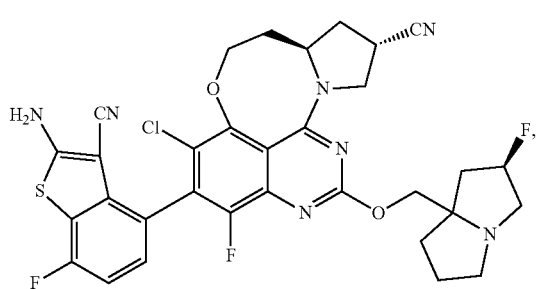
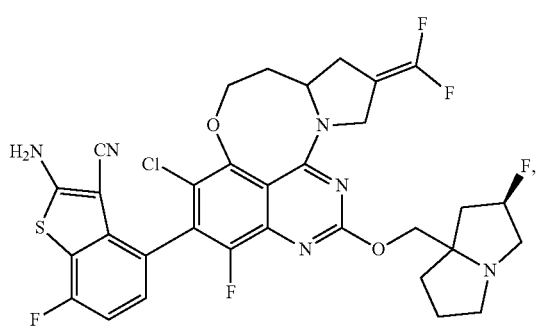
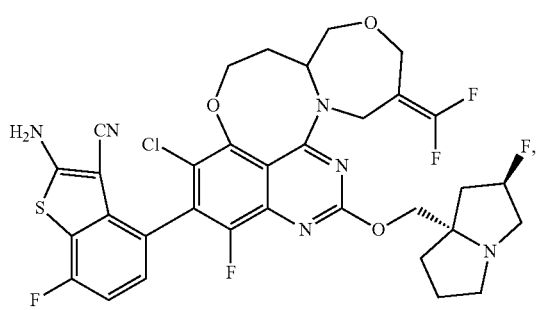
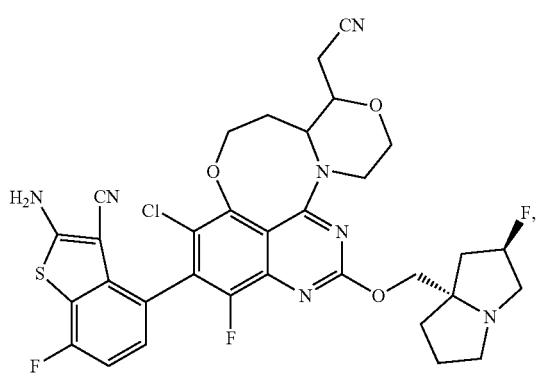
634
-continued
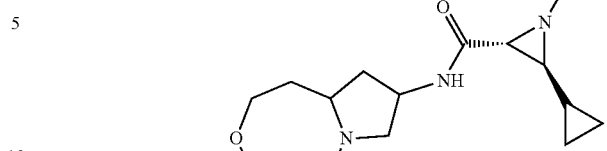
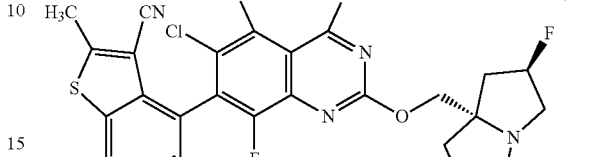
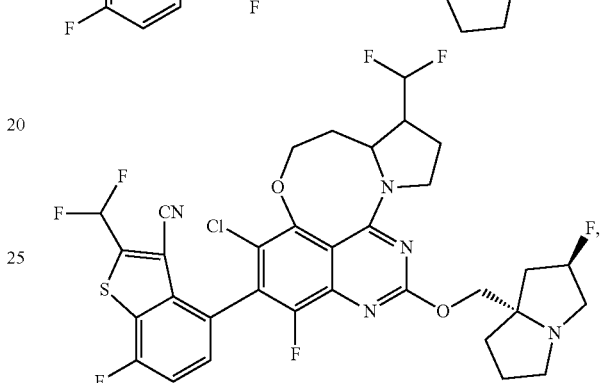
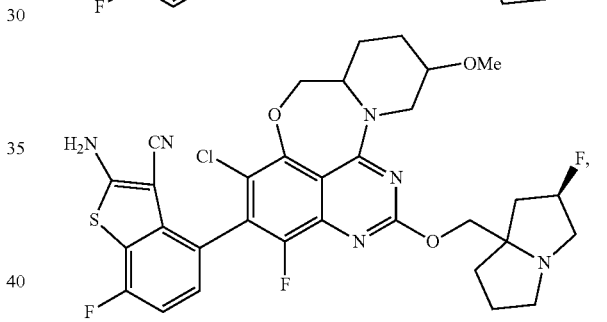
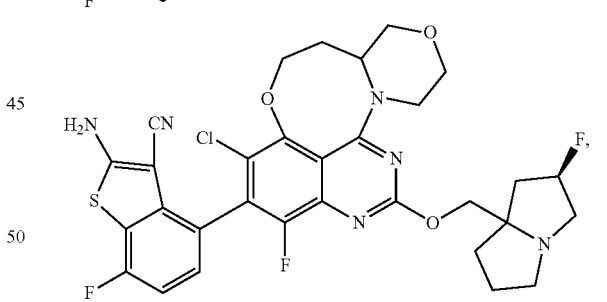
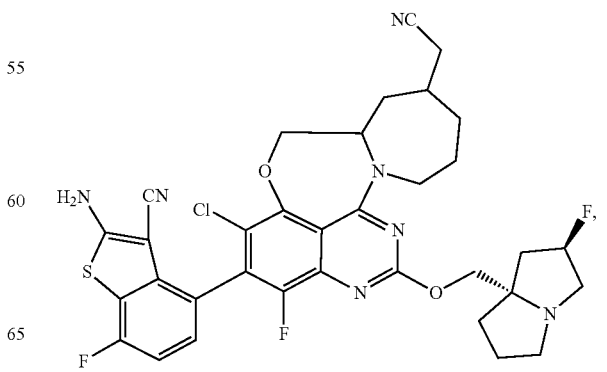

635
-continued
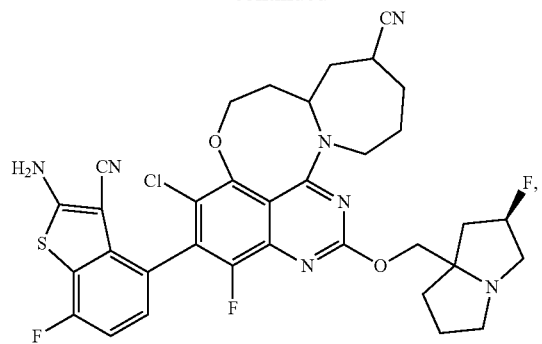
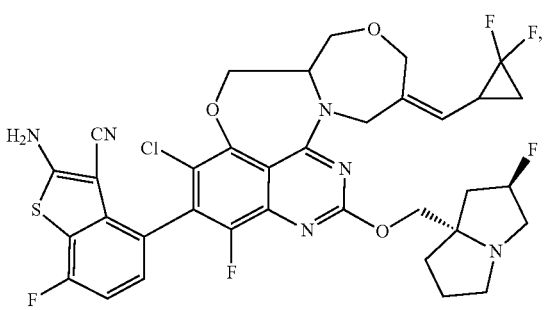
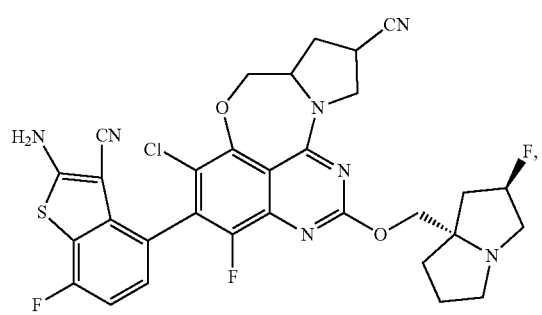
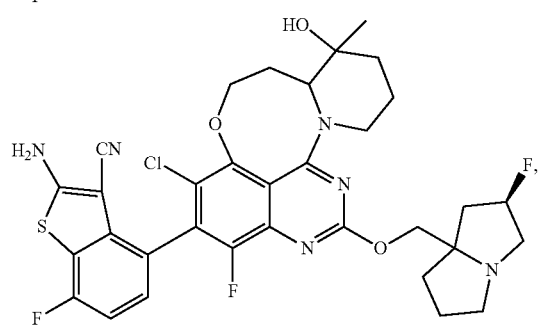
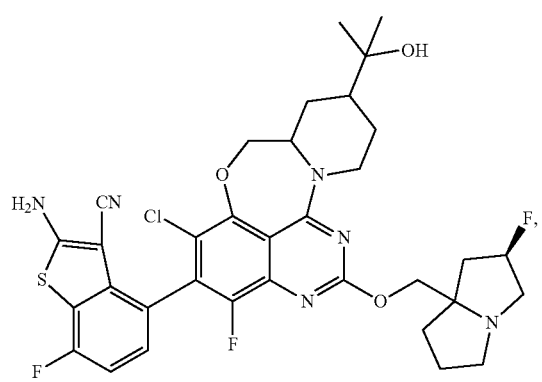
636
-continued
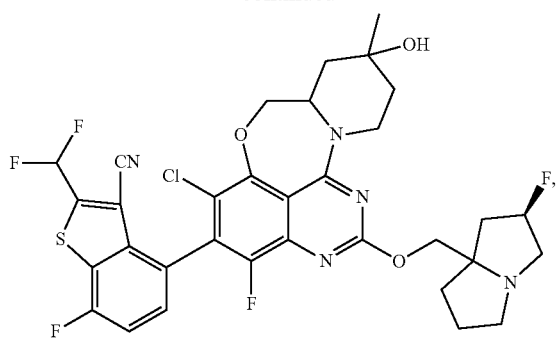
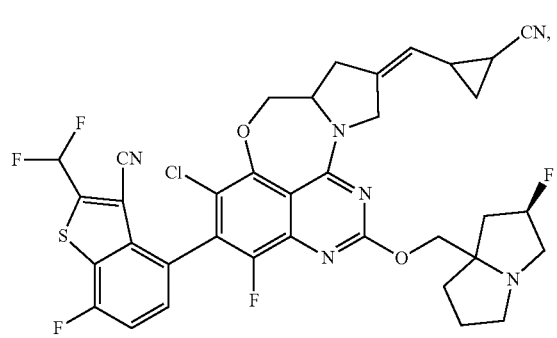
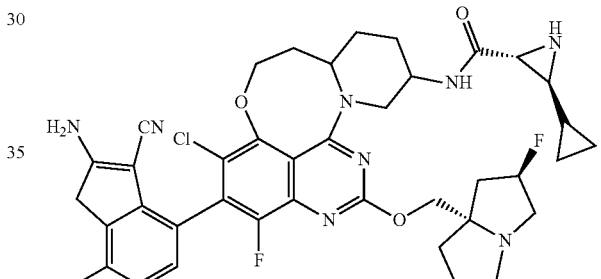
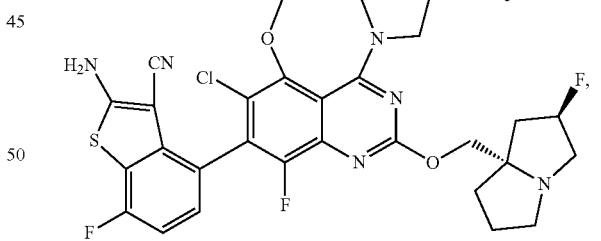
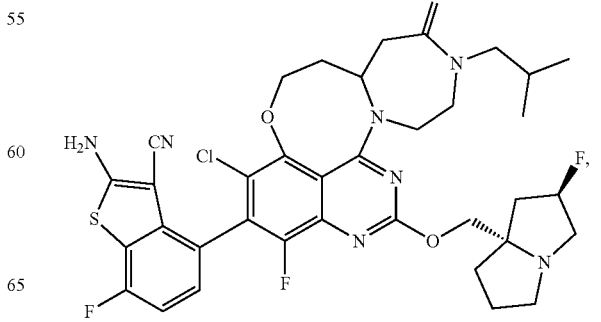

637
-continued
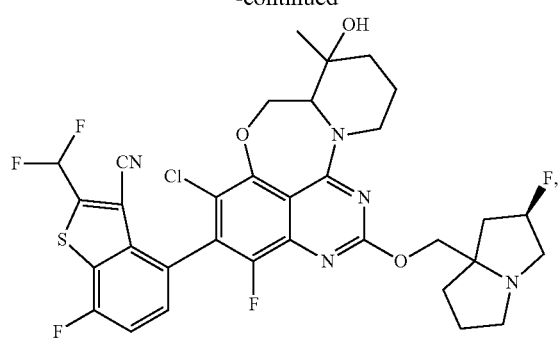
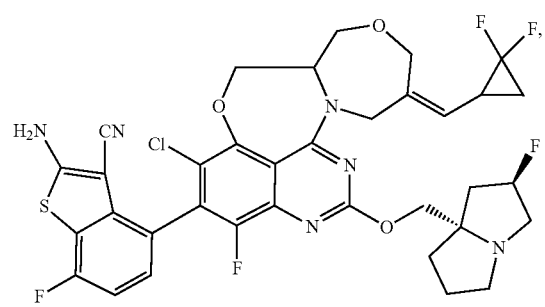
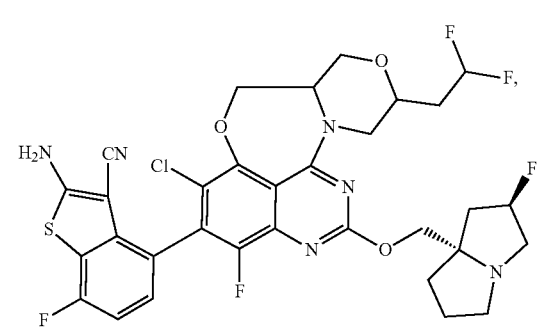
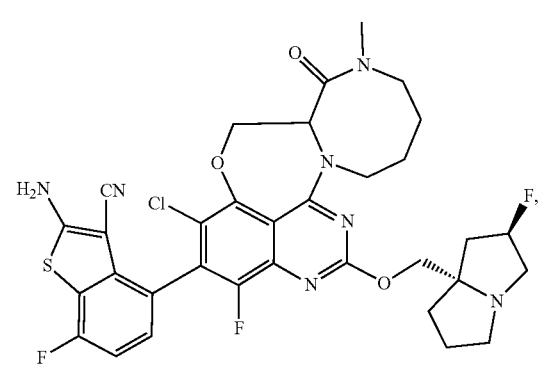
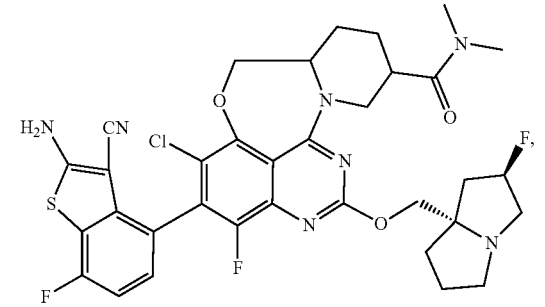
638
-continued
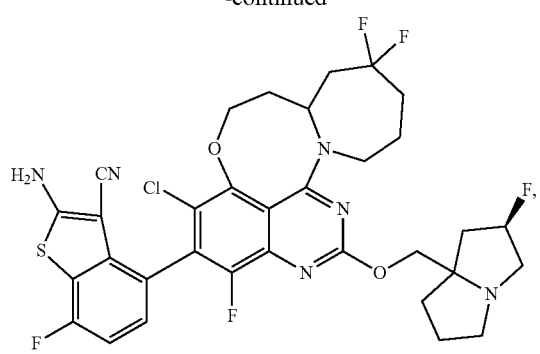
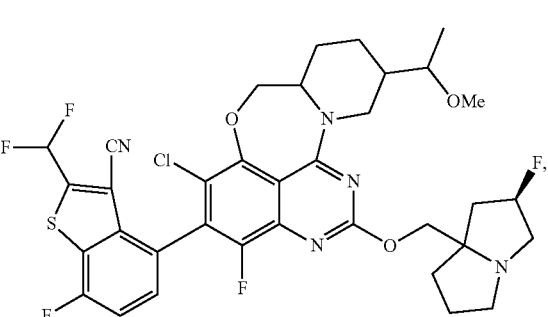
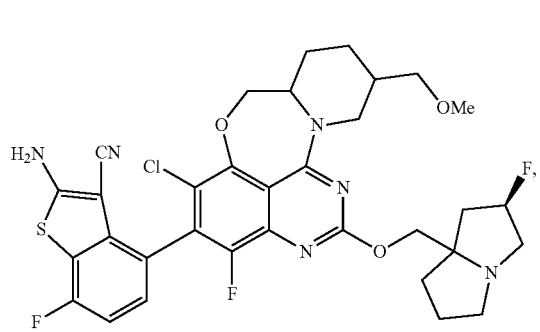
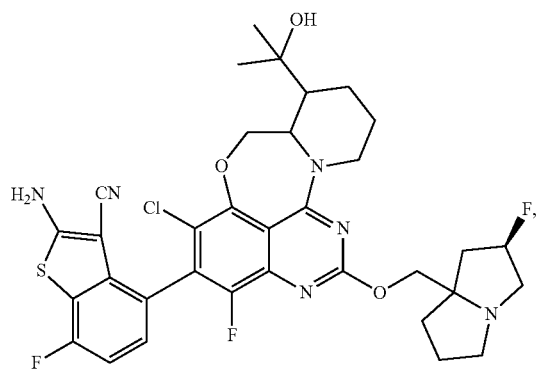
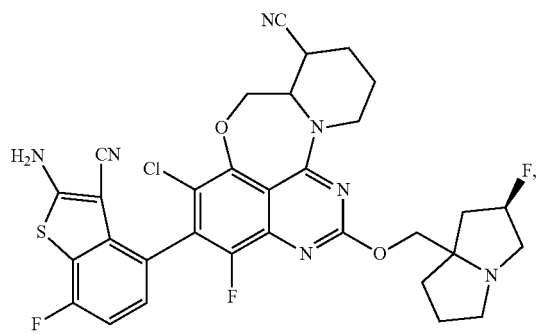

639
-continued
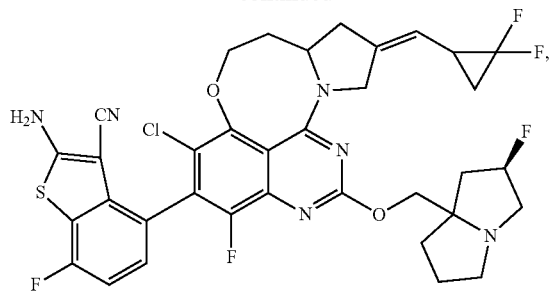
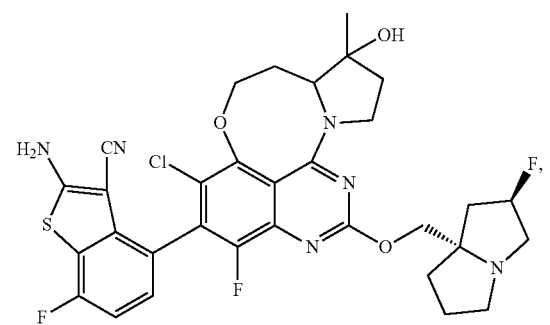
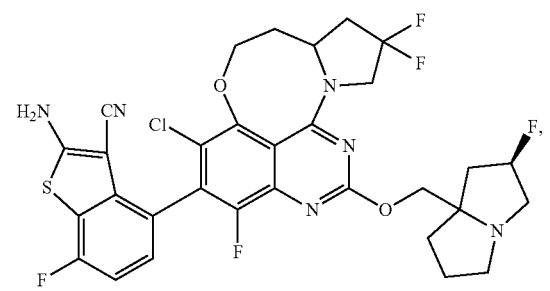
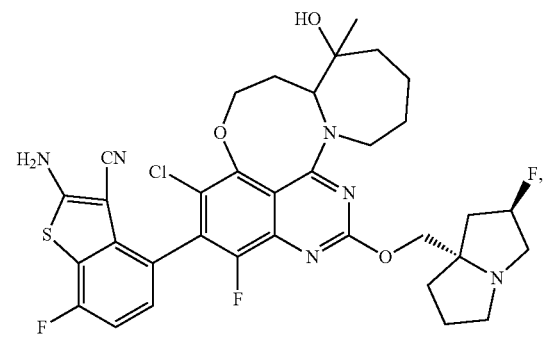
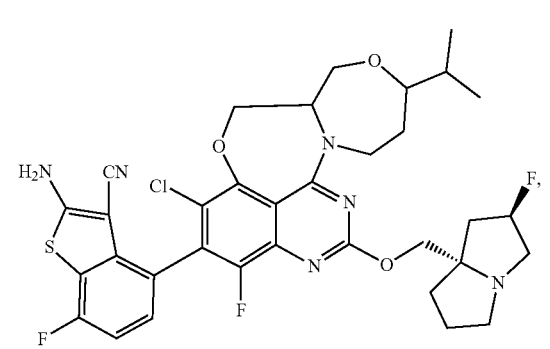
640
-continued
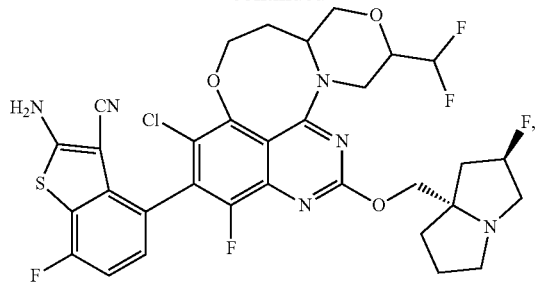
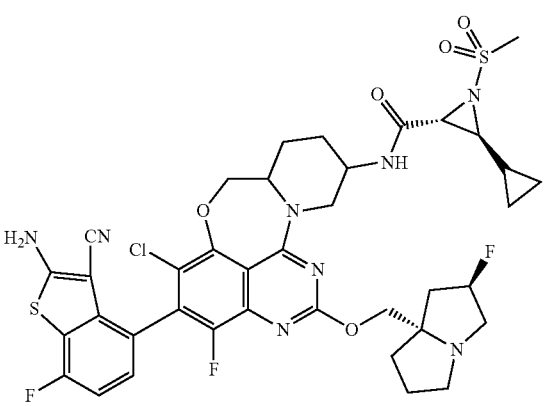
,
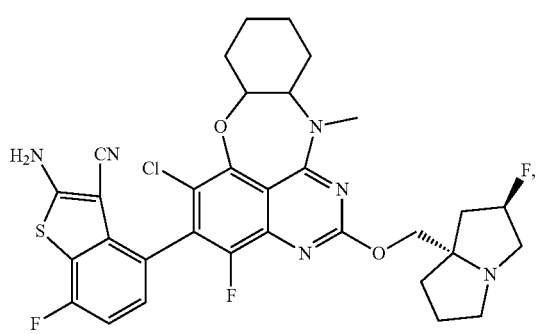
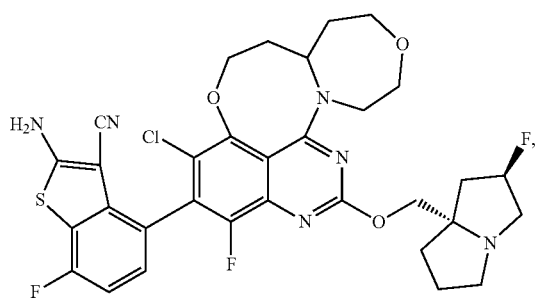
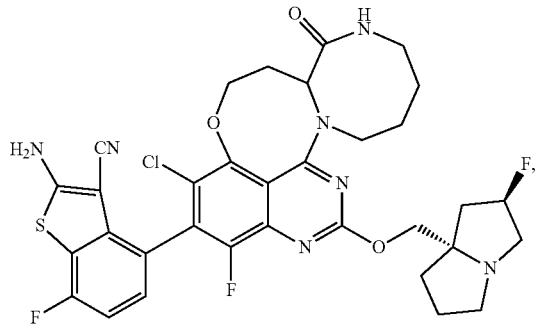

641
-continued
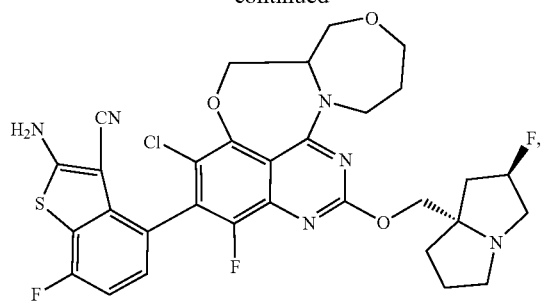
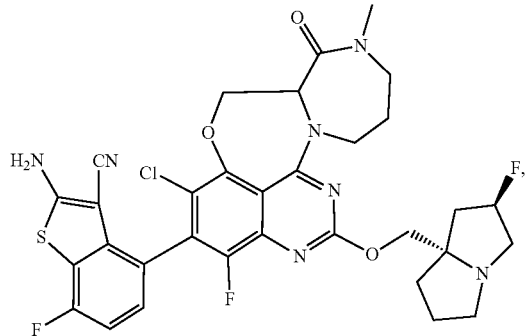
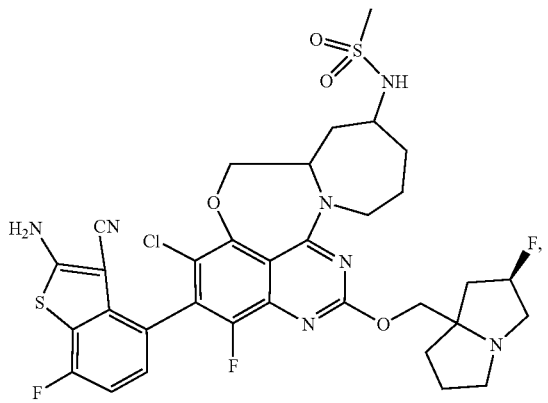
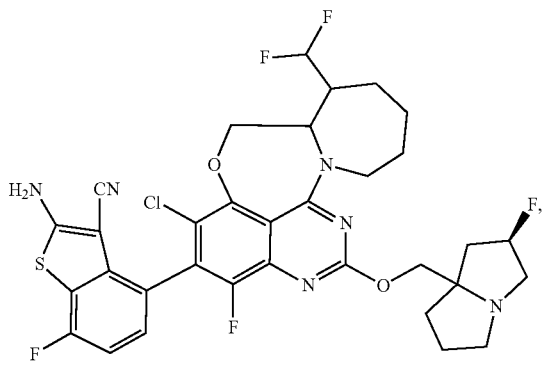
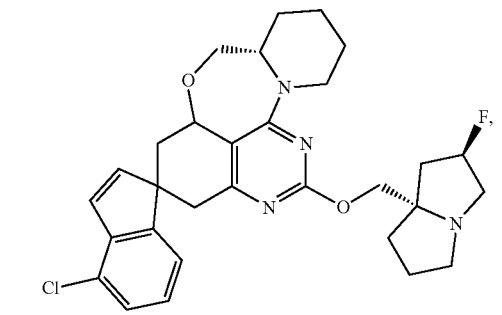
642
-continued
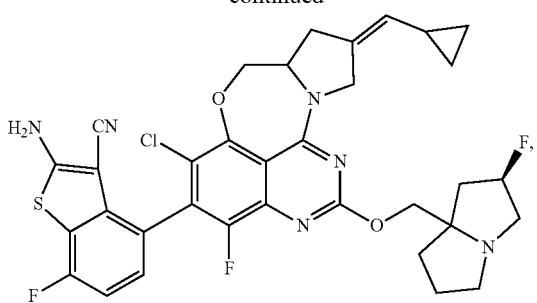
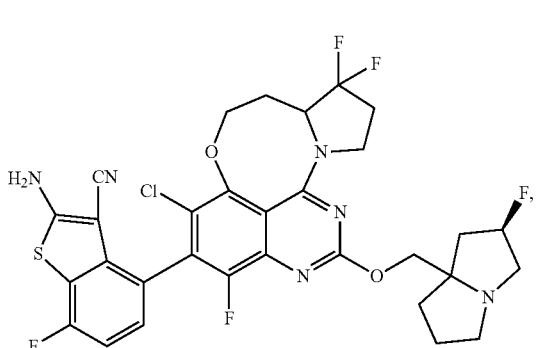
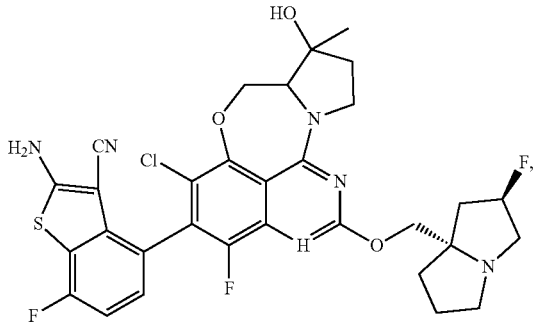
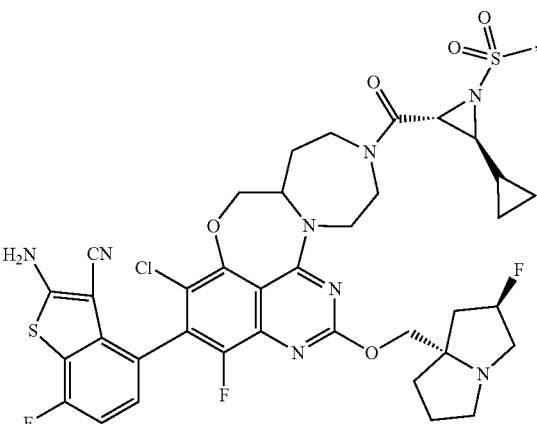
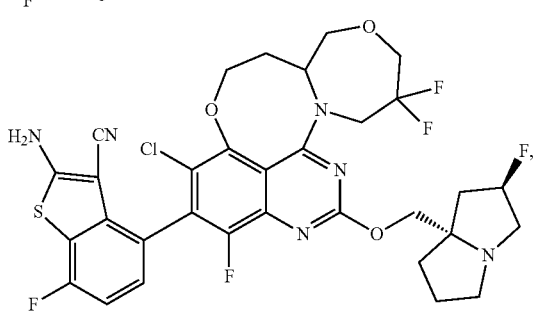

643
-continued
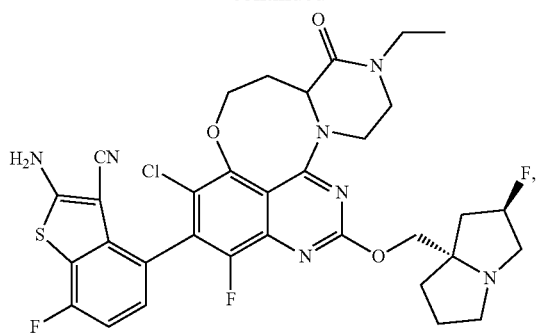
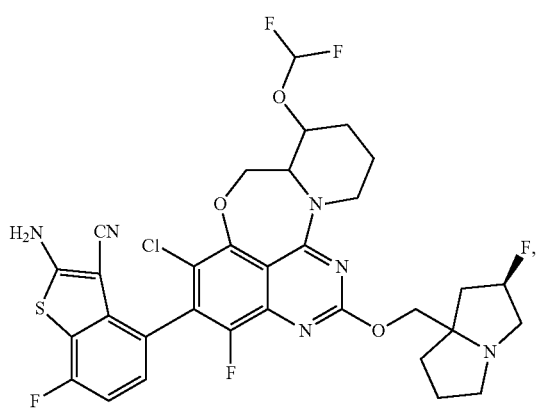
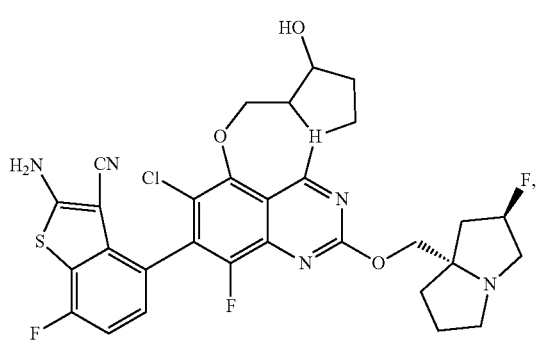
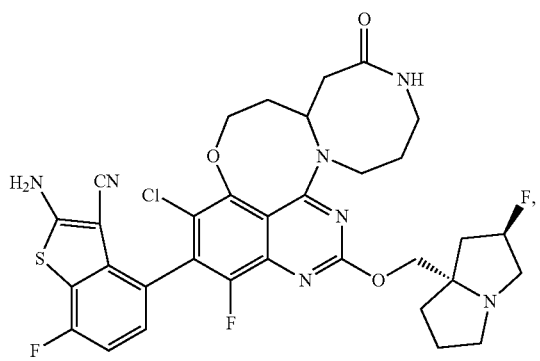
644
-continued
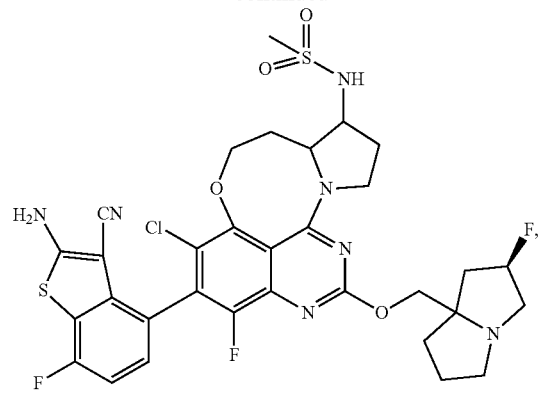
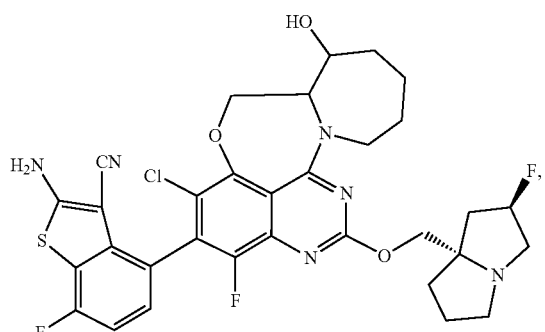
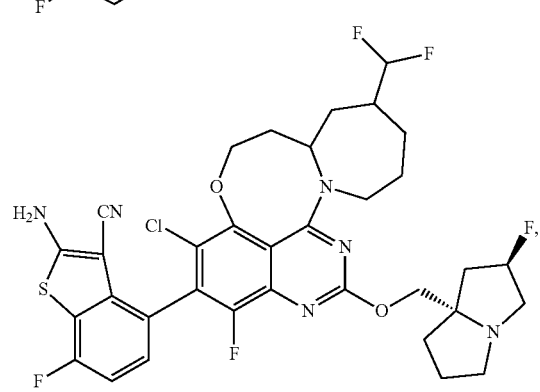
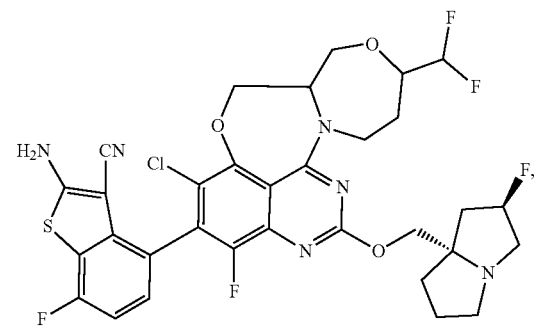
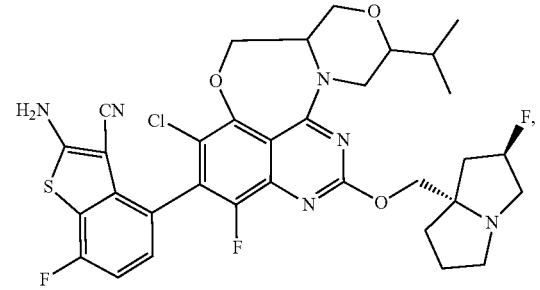

645
-continued
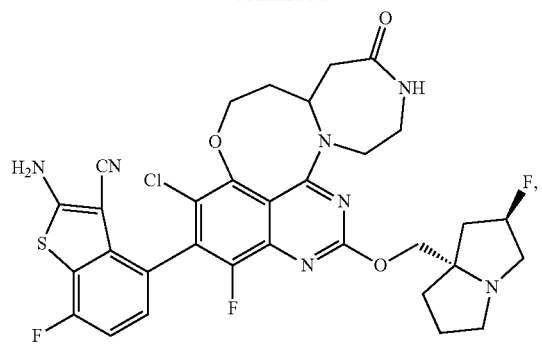
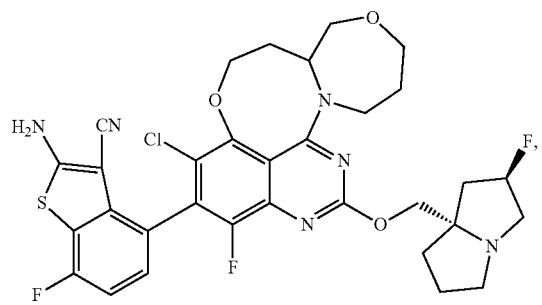
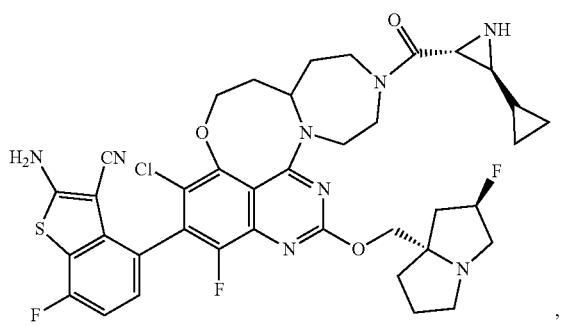
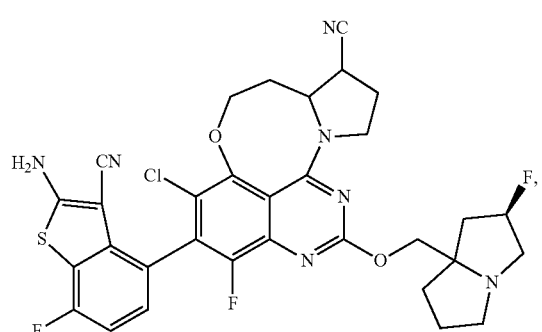
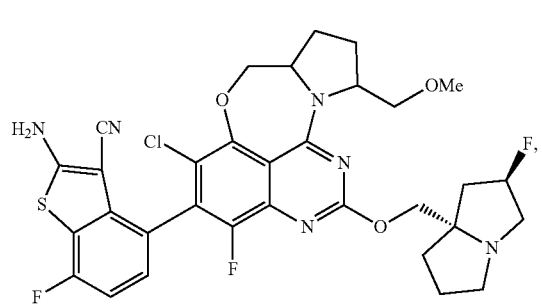
646
-continued
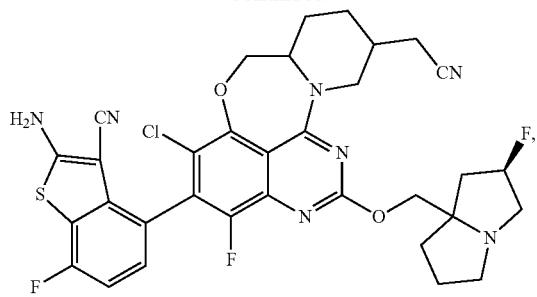
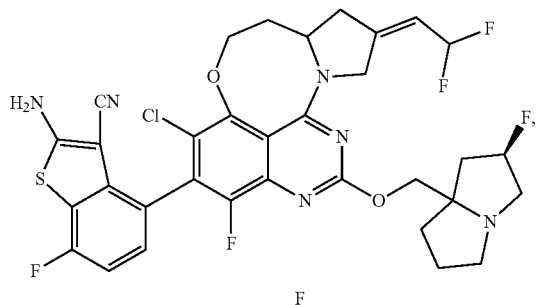
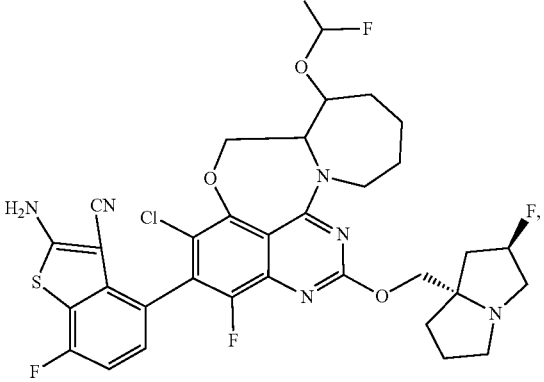
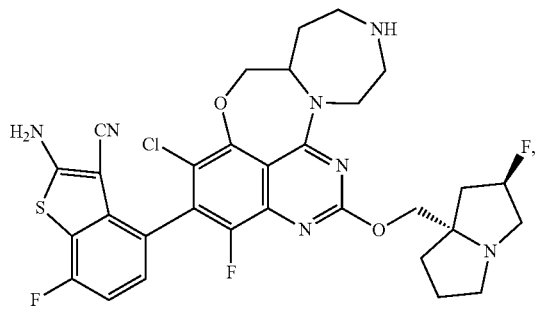
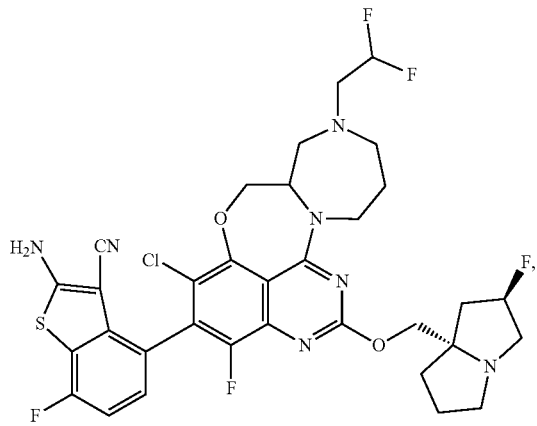

647
-continued
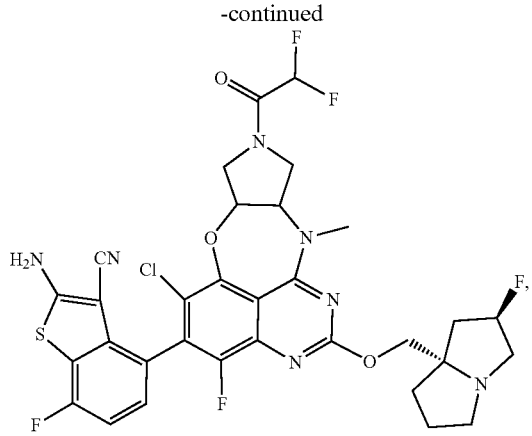
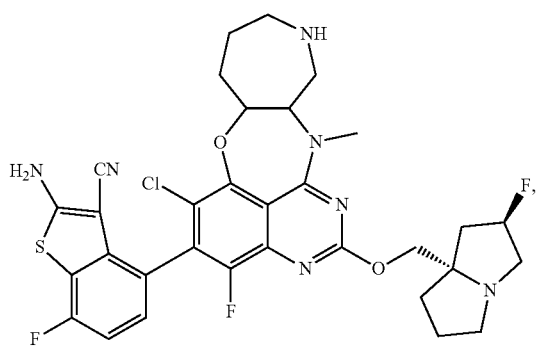
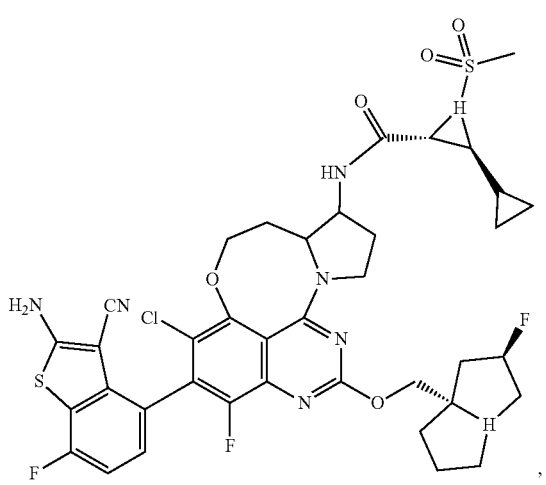
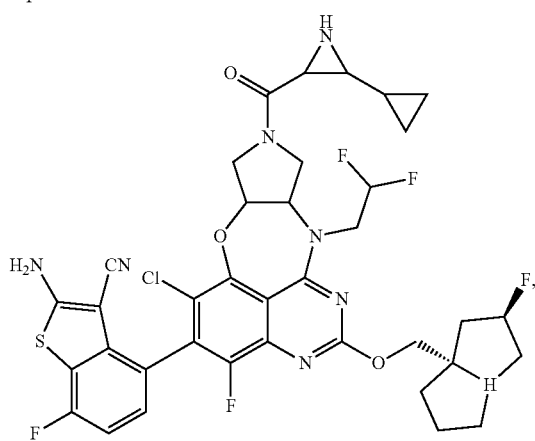
648
-continued
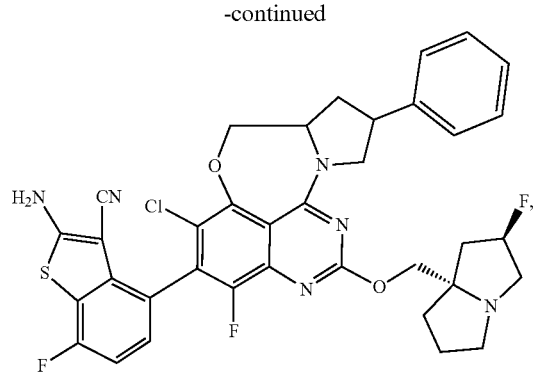
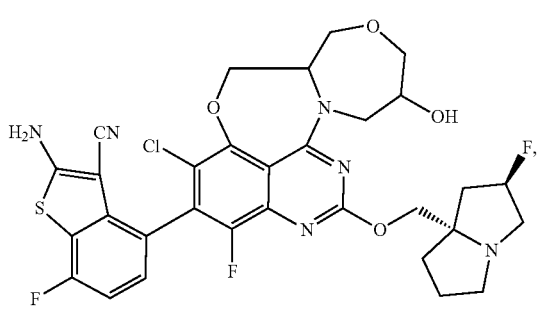
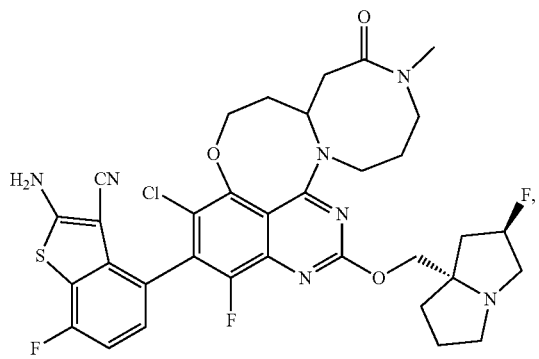
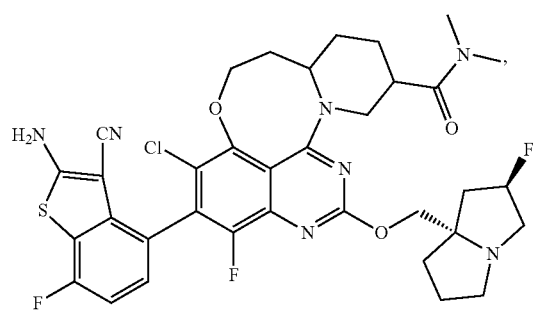

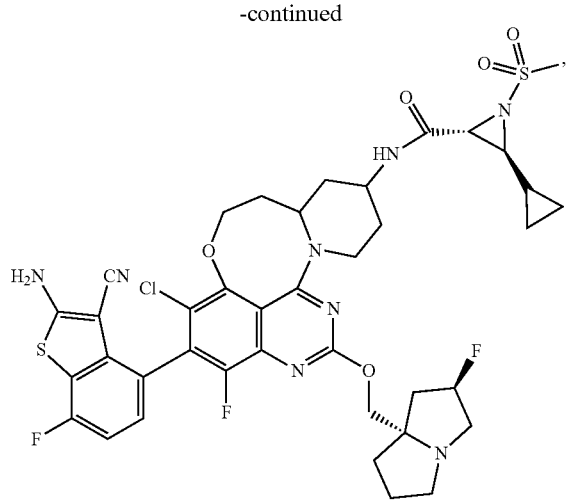
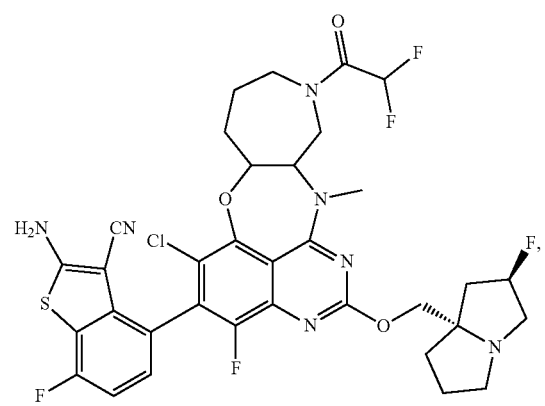
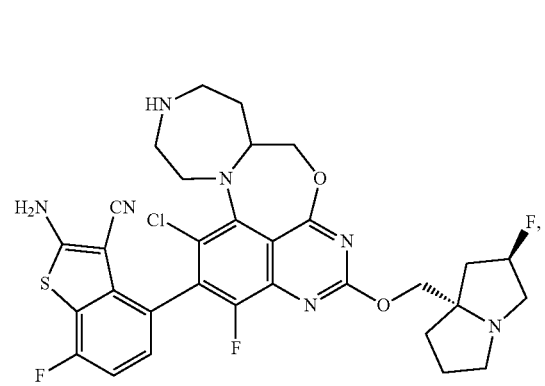
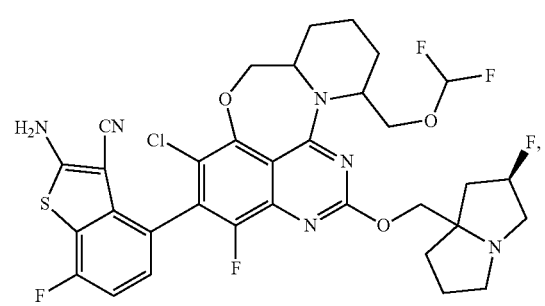
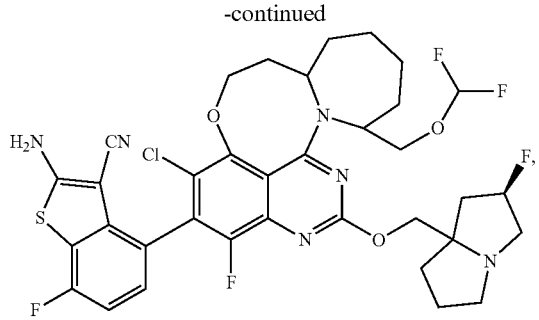
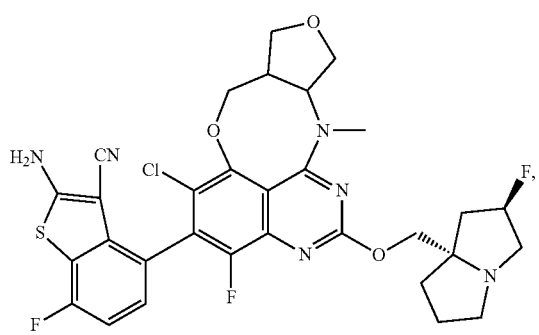
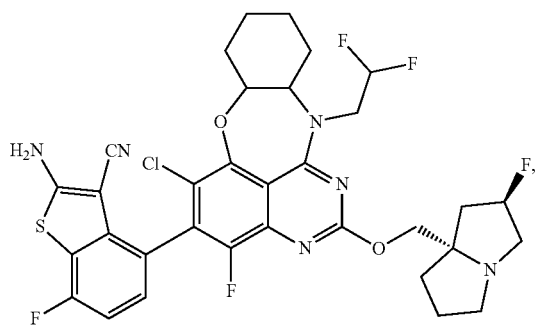
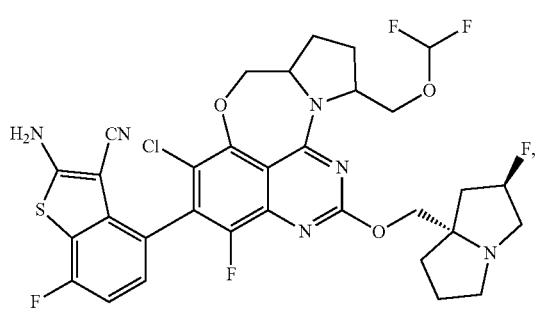
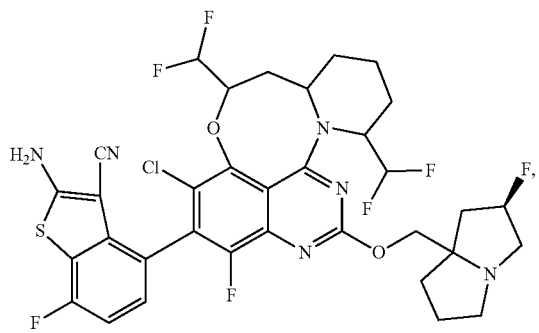

651
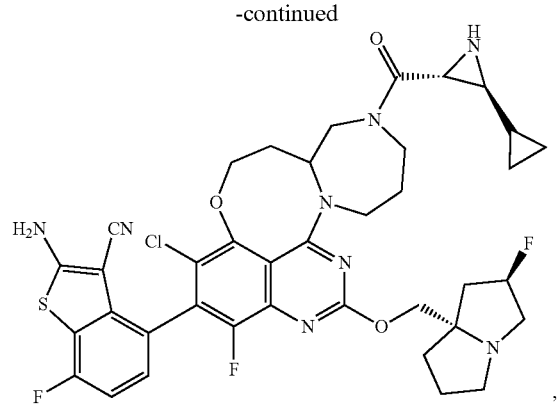
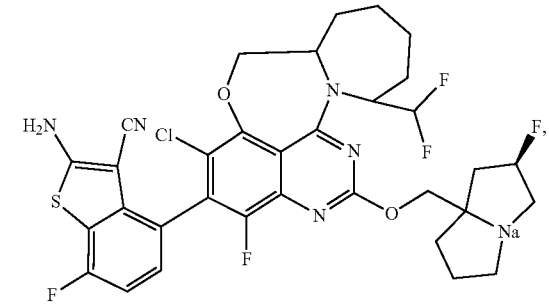
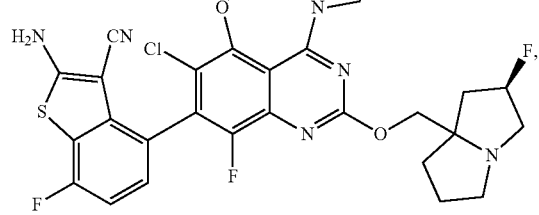
652
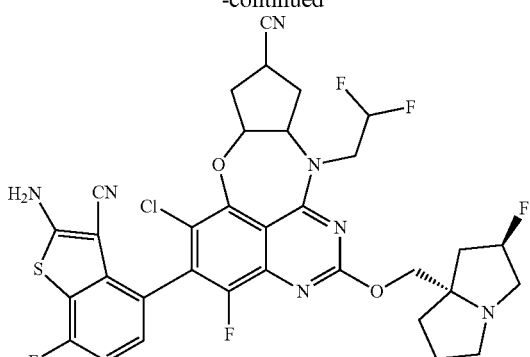
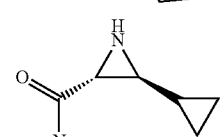
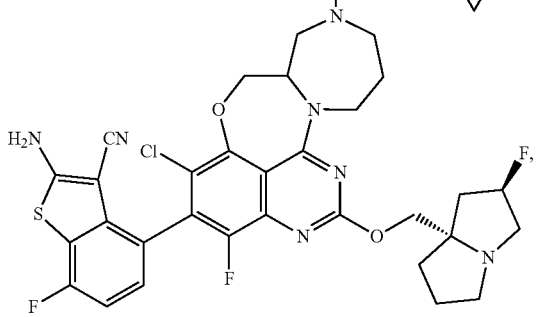
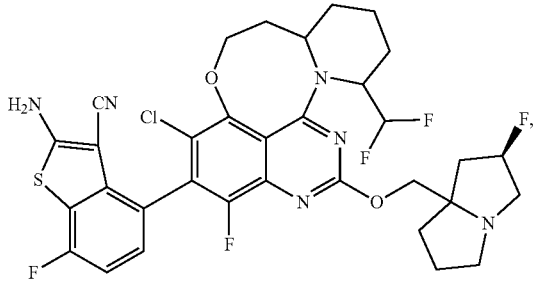
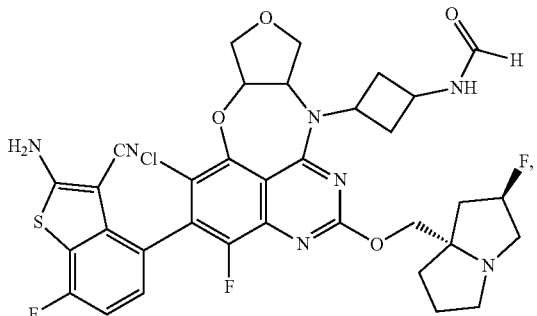
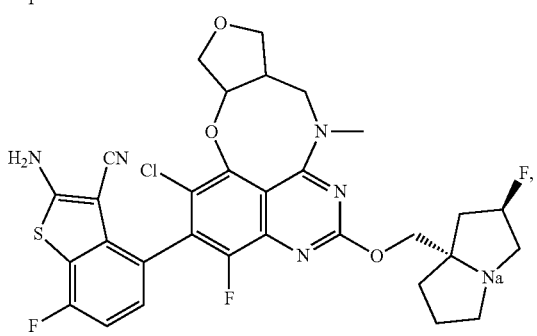

653
-continued
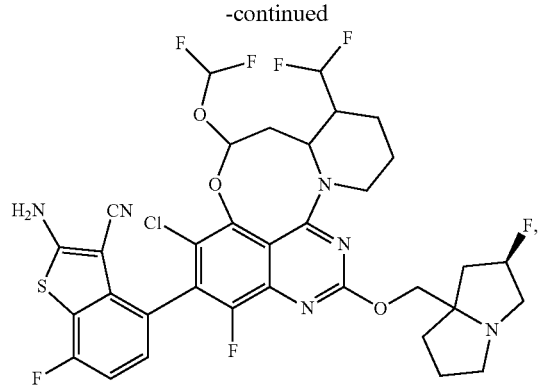
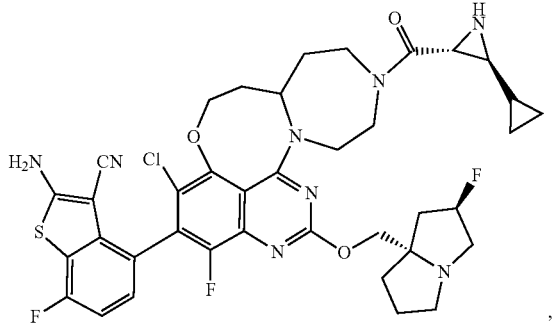
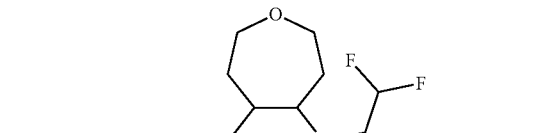
,
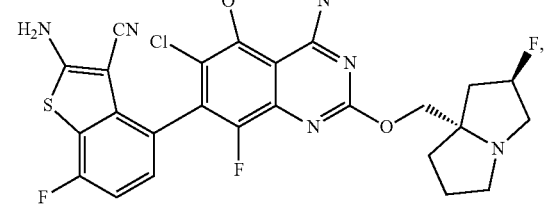
,
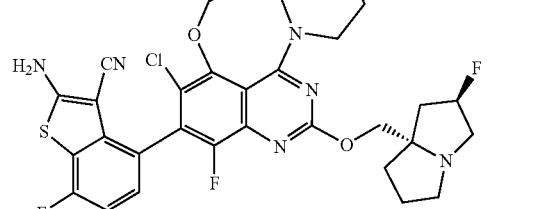
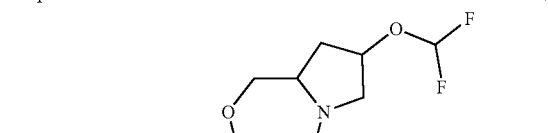
,
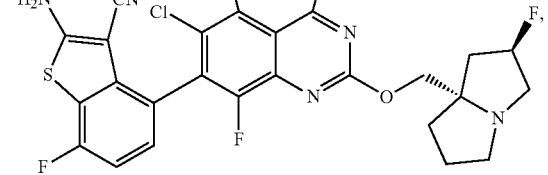
654
-continued
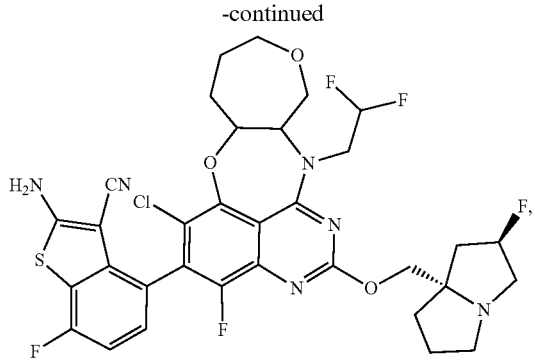
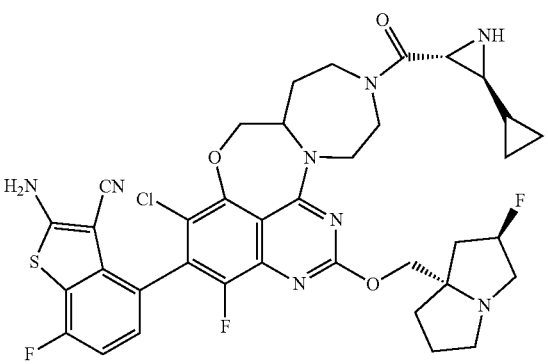
,
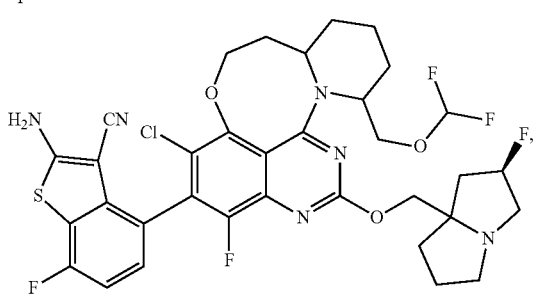
,
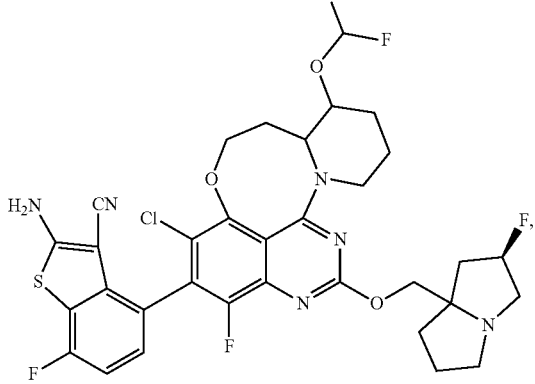
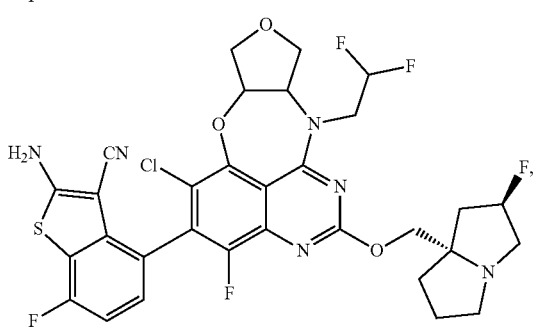

655
-continued
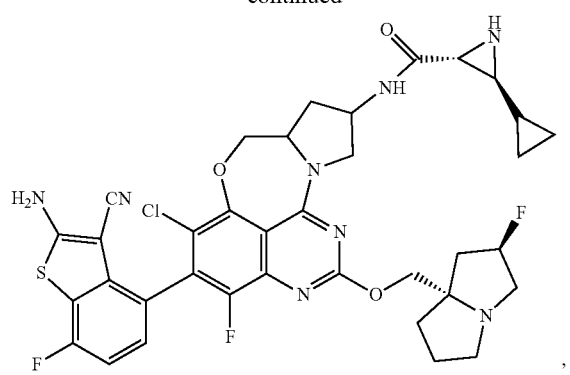
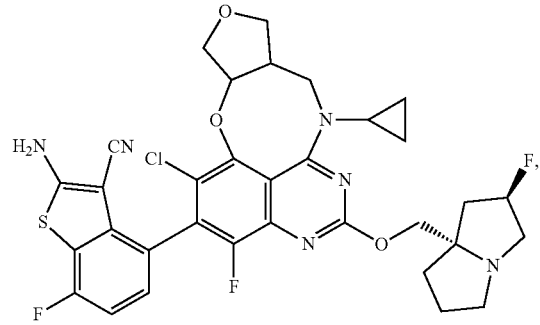
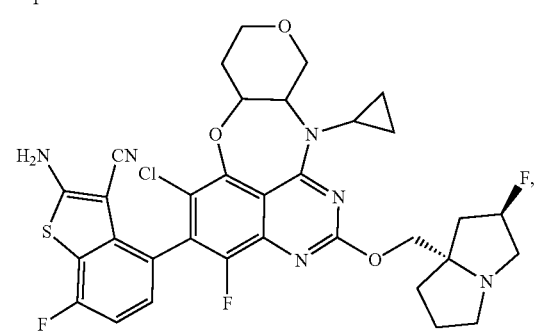
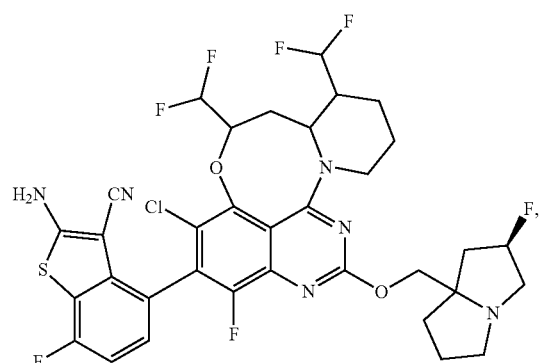
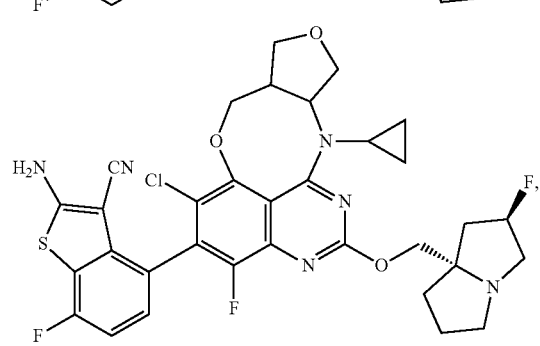
656
-continued
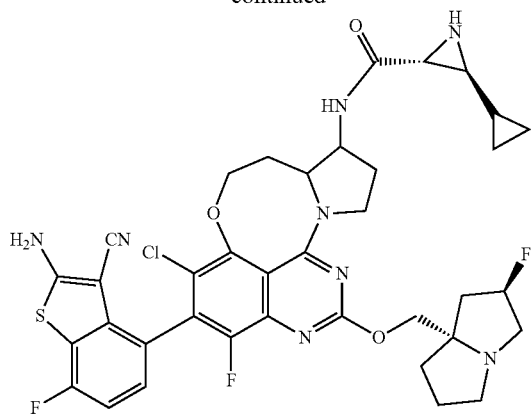
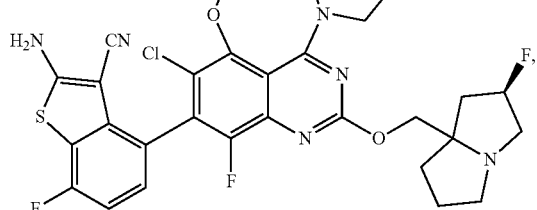
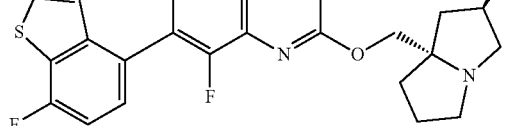
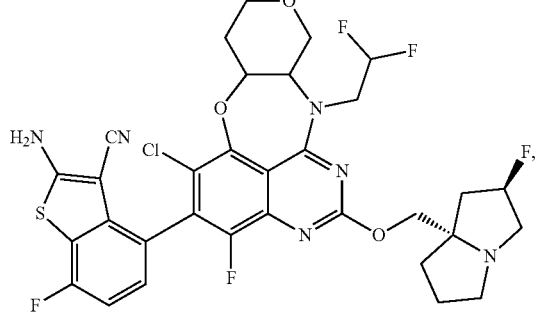

657
-continued
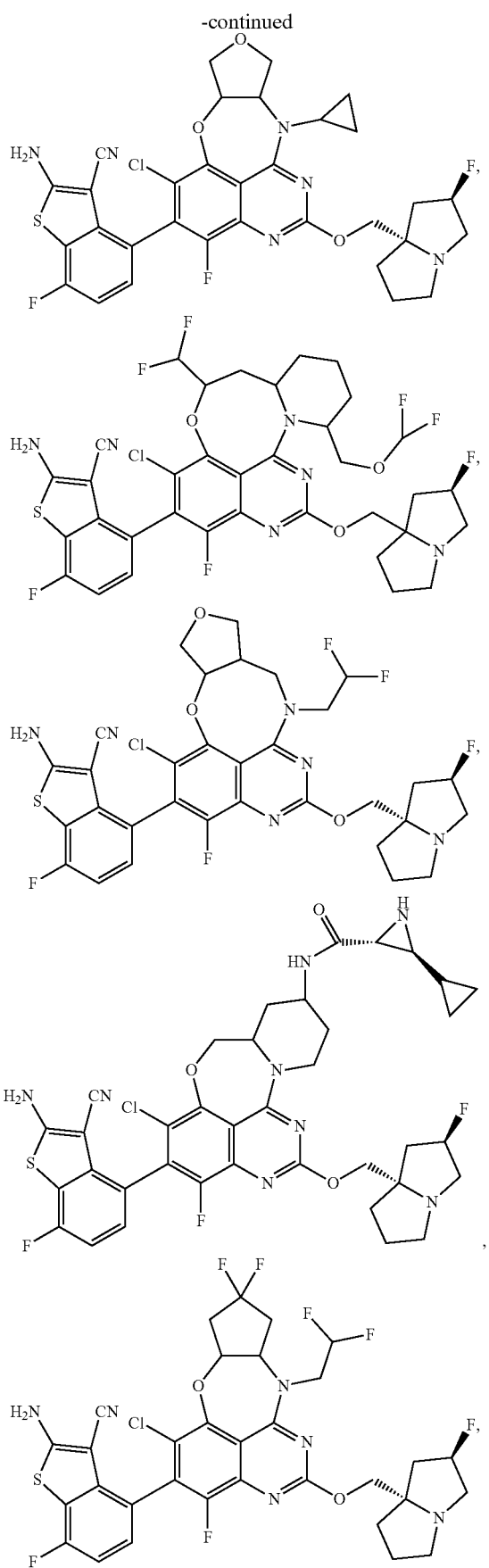
658
-continued
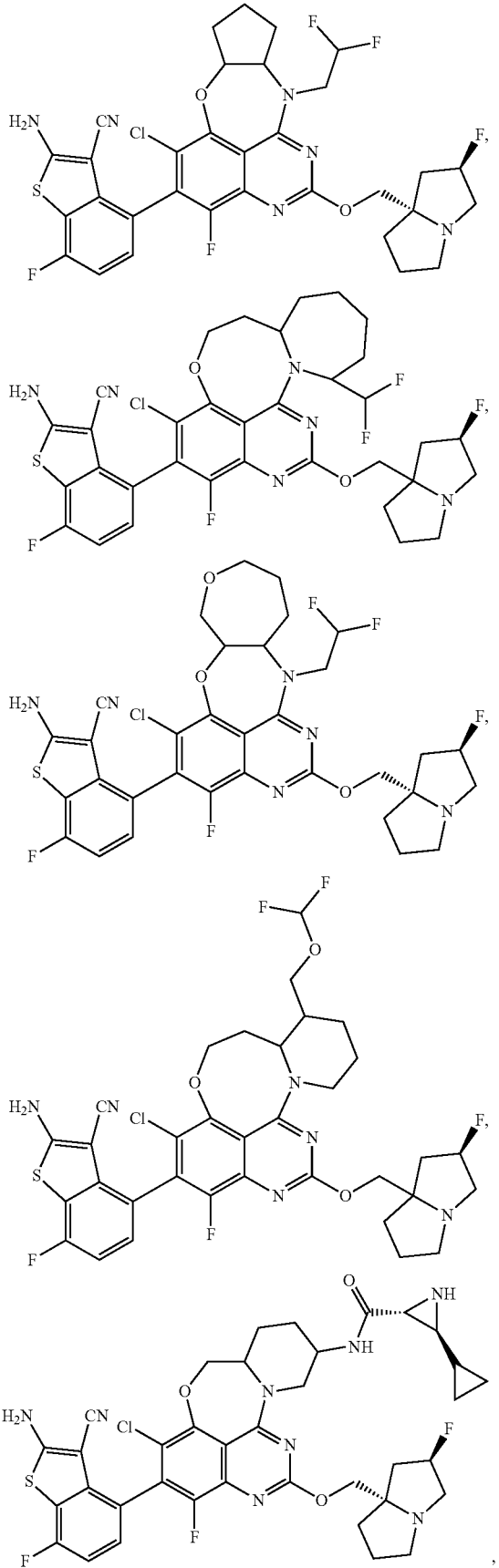

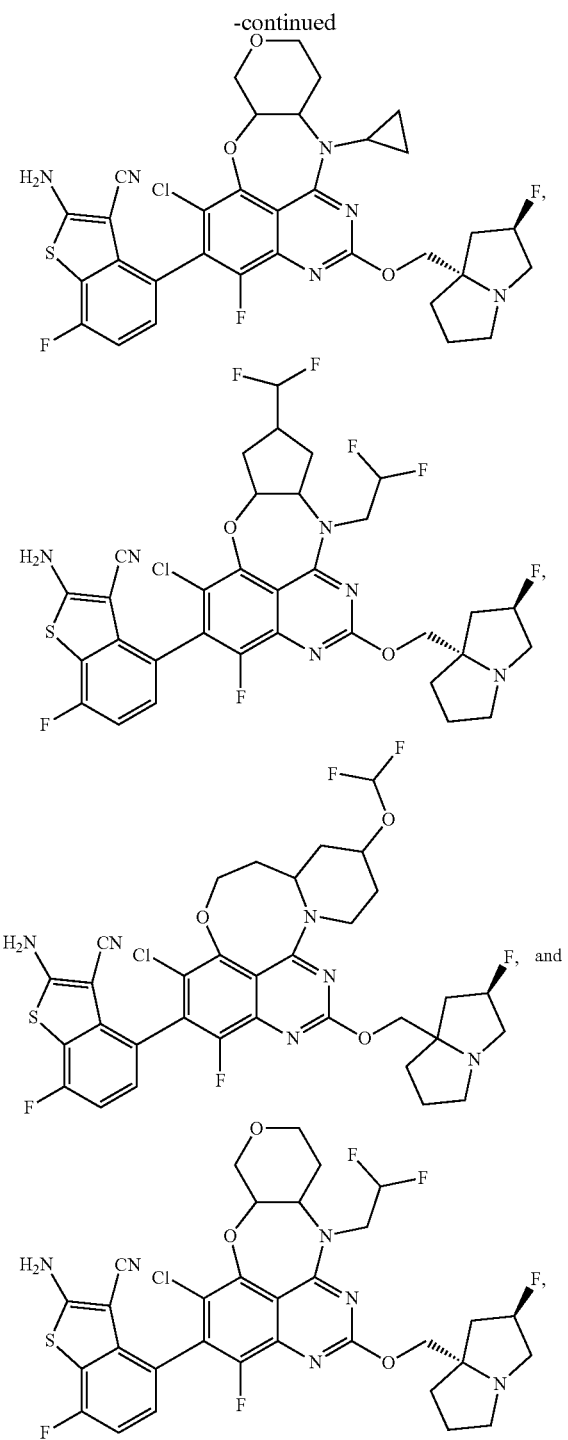

or a pharmaceutically acceptable salt or solvate thereof.

In an aspect is provided a compound having the formula A-L$^{AB}$-B wherein

A is a monovalent form of a compound described herein;
L$^{AB}$ is a covalent linker bonded to A and B; and
B is a monovalent form of a degradation enhancer.

In embodiments, the degradation enhancer is capable of binding a protein selected from E3A, mdm2, APC, EDD1, SOCS/BC-box/eloBC/CUL5/RING, LNXp80, CBX4, CBLL1, HACE1, HECTD1, HECTD2, HECTD3, HECTD4, HECW1, HECW2, HERC1, HERC2, HERC3, HERC4, HER5, HERC6, HUWE1, ITCH, NEDD4, NEDD4L, PPIL2, PRPF19, PIAS1, PIAS2, PIAS3, PIAS4, RANBP2, RNF4, RBX1, SMURF1, SMURF2, STUB1, TOPORS, TRIP12, UBE3A, UBE3B, UBE3C, UBE3D, UBE4A, UBE4B, UBOX5, UBR5, VHL (von-Hippel-Lindau ubiquitin ligase), WWP1, WWP2, Parkin, MKRN1, CMA (chaperon-mediated autophage), SCFb-TRCP (Skip-Cullin-F box (Beta-TRCP) ubiquitin complex), b-TRCP (b-transducing repeat-containing protein), cIAP1 (cellular inhibitor of apoptosis protein 1), APC/C (anaphase-promoting complex/cyclosome), CRBN (cereblon), CUL4-RBX1-DDB1-CRBN (CRL4$^{RBN}$) ubiquitin ligase, XIAP, IAP, KEAP1, DCAF15, RNF114, DCAF16, AhR, SOCS2, KLHL12, UBR2, SPOP, KLHL3, KLBL20, KLHDC2, SPSB1, SPSB2, SPSB4, SOCS6, FBXO4, FBXO31, BTRC, FBW7, CDC20, PML, TRIM21, TRIM24, TRIM33, GID4, avadomide, iberdomide, and CC-885. In embodiments, the degradation enhancer is capable of binding a protein selected from UBE2A, UBE2B, UBE2C, UBE2D1, UBE2D2, UBE2D3, UBE2DR, UBE2E1, UBE2E2, UBE2E3, UBE2F, UBE2G1, UBE2G2, UBE2H, UBE2I, UBE2J1, UBE2J2, UBE2K, UBE2L3, UBE2L6, UBE2L1, UBE2L2, UBE2L4, UBE2M, UBE2N, UBE2O, UBE2Q1, UBE2Q2, UBE2R1, UBE2R2, UBE2S, UBE2T, UBE2U, UBE2V1, UBE2V2, UBE2W, UBE2Z, ATG3, BIRC6, and UFC1. In embodiments, L$^{AB}$ is -L$^{AB1}$-L$^{AB2}$-L$^{AB3}$-L$^{AB4}$-L$^{AB5}$-;

L$^{AB1}$, L$^{AB2}$, L$^{AB3}$, L$^{AB4}$, and L$^{AB5}$ are independently a bond, —O—, —N(R$^{14}$)—, —C(O)—, —N(R$^{14}$)C(O)—, —C(O)N(R$^{14}$)—, —S—, —S(O)$_2$—, —S(O)—, —S(O)$_2$N(R$^{14}$)—, —S(O)N(R$^{14}$)—, —N(R$^{14}$)S(O)—, —N(R$^{14}$)S(O)$_2$—, C$_{1-6}$alkylene, (—O-C$_{1-6}$alkyl)$_z$, (-C$_{1-6}$alkyl-O)$_z$, C$_{2-6}$alkenylene, C$_{2-6}$alkynylene, C$_{1-6}$haloalkylene, C$_{3-12}$cycloalkylene, C$_{1-11}$heterocycloalkylene, C$_{6-12}$arylene, or C$_{1-11}$heteroarylene, wherein C$_{1-6}$alkylene, C$_{2-6}$alkenylene, C$_{2-6}$alkynylene, C$_{1-6}$haloalkylene, C$_{3-12}$cycloalkylene, C$_{1-11}$heterocycloalkylene, C$_{6-12}$arylene, or C$_{1-11}$heteroarylene, are optionally substituted with one, two, or three R$^{20n}$; wherein each C$_{1-6}$alkyl of (—O-C$_{1-6}$alkyl)$_z$- and (-C$_{1-6}$alkyl-O)$_z$- is optionally substituted with one, two, or three R$^{20n}$;

z is independently an integer from 0 to 10;

each R$^{12}$ is independently selected from hydrogen, C$_{1-6}$alkyl, C$_{2-6}$alkenyl, C$_{2-6}$alkynyl, C$_{3-10}$cycloalkyl, —CH$_2$-C$_{3-10}$cycloalkyl, C$_{2-9}$heterocycloalkyl, —CH$_2$-C$_{2-9}$heterocycloalkyl, C$_{6-10}$aryl, —CH$_2$-C$_{6-10}$aryl, —CH$_2$-C$_{1-9}$heteroaryl, and C$_{1-9}$heteroaryl, wherein C$_{1-6}$alkyl, C$_{2-6}$alkenyl, C$_{2-6}$alkynyl, C$_{3-10}$cycloalkyl, —CH$_2$-C$_{3-10}$cycloalkyl, C$_{2-9}$heterocycloalkyl, —CH$_2$-C$_{2-9}$heterocycloalkyl, C$_{6-10}$aryl, —CH$_2$-C$_{6-10}$aryl, —CH$_2$-C$_{1-9}$heteroaryl, and C$_{1-9}$heteroaryl are optionally substituted with one, two, or three R$^{20l}$;

each R$^{13}$ is independently selected from hydrogen, C$_{1-6}$alkyl, and C$_{1-6}$haloalkyl; or R$^{12}$ and R$^{13}$, together with the nitrogen to which they are attached, form a C$_{2-9}$heterocycloalkyl ring optionally substituted with one, two, or three R$^{20m}$;

each R$^{14}$ is independently selected from hydrogen, C$_{1-6}$alkyl, and C$_{1-6}$haloalkyl;

each R$^{15}$ is independently selected from C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl, wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl are optionally substituted with one, two, or three R$^{20o}$;

each $R^{20l}$, $R^{20m}$, $R^{20n}$, and $R^{20o}$ are each independently selected from halogen, —CN, $C_{1-6}$alkyl, $C_{2-6}$alkenyl, $C_{2-6}$alkynyl, $C_{3-10}$cycloalkyl, —$CH_2$-$C_{3-10}$cycloalkyl, $C_{2-9}$heterocycloalkyl, —$CH_2$-$C_{2-9}$heterocycloalkyl, $C_{6-10}$aryl, —$CH_2$-$C_{6-10}$aryl, —$CH_2$-$C_{1-9}$heteroaryl, $C_{1-9}$heteroaryl, —$OR^{21}$, —$SR^{21}$, —$N(R^{22})(R^{23})$, —$C(O)OR^{22}$, —$C(O)N(R^{22})(R^{23})$, —$C(O)C(O)N(R^{22})(R^{23})$, —$OC(O)N(R^{22})(R^{23})$, —$N(R^{24})C(O)N(R^{22})(R^{23})$, —$N(R^{24})C(O)OR^{25}$, —$N(R^{24})C(O)R^{25}$, —$N(R^{24})S(O)_2R^{25}$, —$C(O)R^{25}$, —$S(O)_2R^{25}$, —$S(O)_2N(R^{22})(R^{23})$, —$OCH_2C(O)OR^{22}$, and —$OC(O)R^{25}$, wherein $C_{1-6}$alkyl, $C_{2-6}$alkenyl, $C_{2-6}$alkynyl, $C_{3-10}$cycloalkyl, —$CH_2$-$C_{3-10}$cycloalkyl, $C_{2-9}$heterocycloalkyl, —$CH_2$-$C_{2-9}$heterocycloalkyl, $C_{6-10}$aryl, —$CH_2$-$C_{6-10}$aryl, —$CH_2$-$C_{1-9}$heteroaryl, and $C_{1-9}$heteroaryl are optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —$OR^{21}$, —$SR^{21}$, —$N(R^{22})(R^{23})$, —$C(O)OR^{22}$, —$C(O)N(R^{22})(R^{23})$, —$C(O)C(O)N(R^{22})(R^{23})$, —$OC(O)N(R^{22})(R^{23})$, —$N(R^{24})C(O)N(R^{22})(R^{23})$, —$N(R^{24})C(O)OR^{25}$, —$N(R^{24})C(O)R^{25}$, —$N(R^{24})S(O)_2R^{25}$, —$C(O)R^{25}$, —$S(O)_2R^{25}$, —$S(O)_2N(R^{22})(R^{23})$, and —$OC(O)R^{25}$;

each $R^{21}$ is independently selected from H, $C_{1-6}$alkyl, $C_{1-6}$haloalkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl;

each $R^{22}$ is independently selected from H, $C_{1-6}$alkyl, $C_{1-6}$haloalkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl;

each $R^{23}$ is independently selected from H and $C_{1-6}$alkyl;

each $R^{24}$ is independently selected from H and $C_{1-6}$alkyl; and each $R^{25}$ is independently selected from $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl.

In embodiments, $L^{AB}$ is —(O-$C_2$alkyl)$_z$— and z is an integer from 1 to 10. In embodiments, $L_{AB}$ is —($C_2$alkyl-O—)$_z$— and z is an integer from 1 to 10. In embodiments, $L_{AB}$ is —$(CH_2)_{zz1}L_{AB2}(CH_2O)_{zz2}$—, wherein $L^{AB2}$ is a bond, a 5 or 6 membered heterocycloalkylene or heteroarylene, phenylene, -($C_2$-$C_4$)alkynylene, —$SO_2$— or —NH—; and zz1 and zz2 are independently an integer from 0 to 10.

In embodiments, $L^{AB}$ is —$(CH_2)_{zz1}(CH_2O)_{zz2}$—, wherein zz1 and zz2 are each independently an integer from 0 to 10. In embodiments, $L^{AB}$ is a PEG linker. In embodiments, B is a monovalent form of a compound selected from

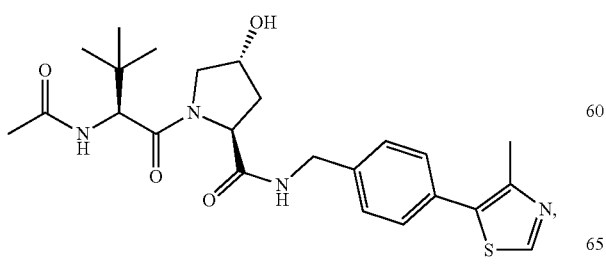

-continued

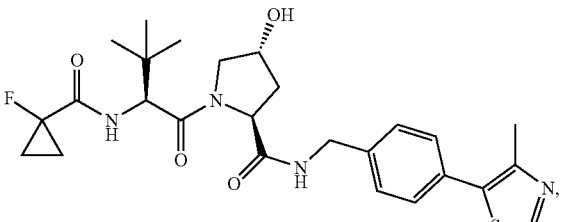

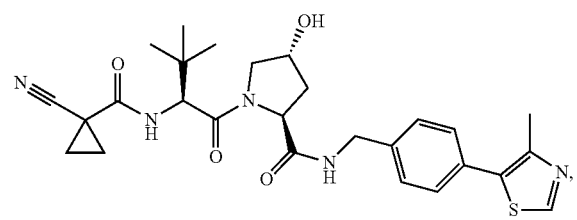

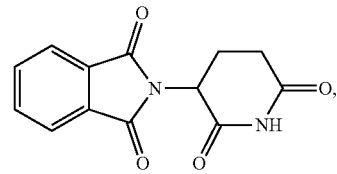

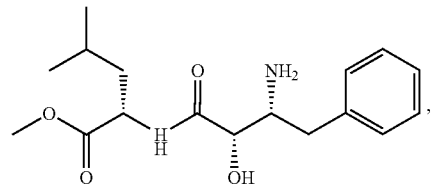

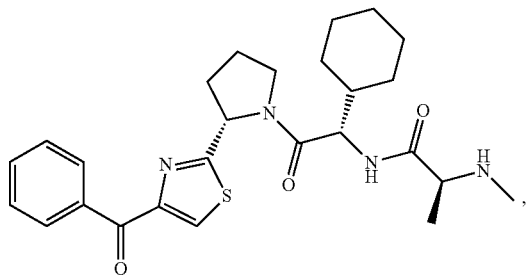

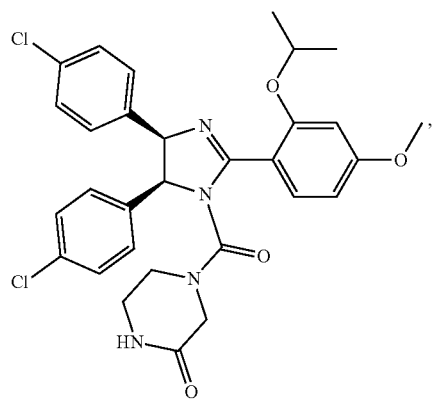

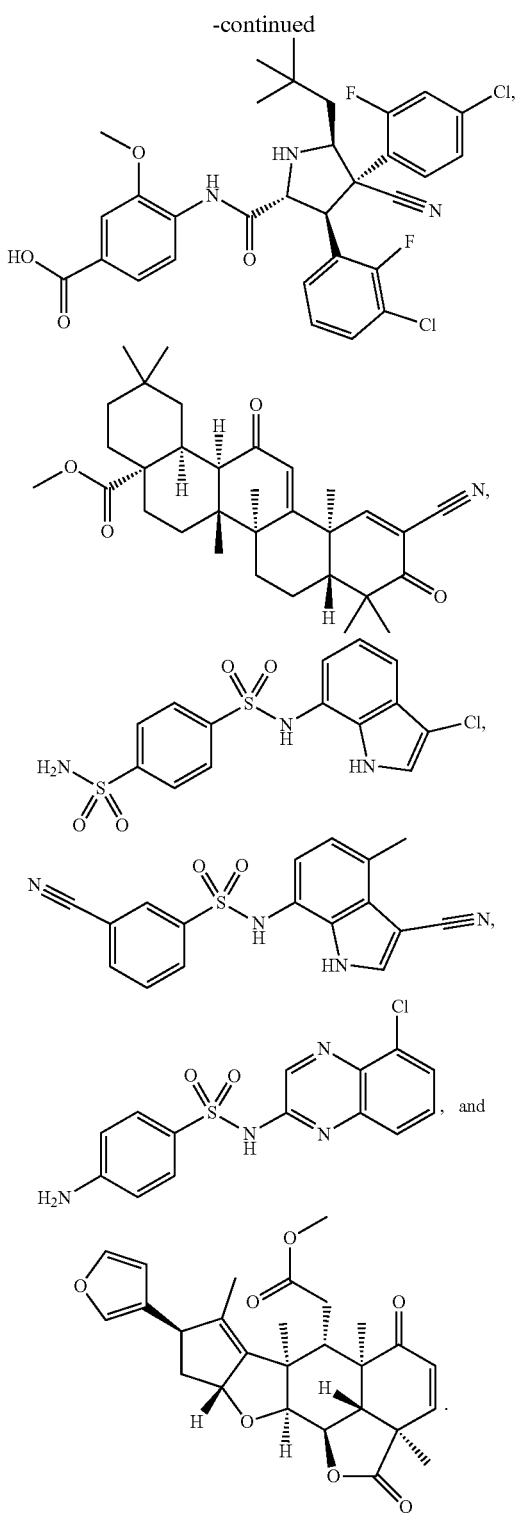

Further Forms of Compounds Disclosed Herein

Isomers

Furthermore, in some embodiments, the compounds described herein exist as geometric isomers. In some embodiments, the compounds described herein possess one or more double bonds. The compounds presented herein include all cis, trans, syn, anti, entgegen (E), and zusammen (Z) isomers as well as the corresponding mixtures thereof. In some situations, compounds exist as tautomers. The compounds described herein include all possible tautomers within the formulas described herein. In some situations, the compounds described herein possess one or more chiral centers and each center exists in the R configuration or S configuration. The compounds described herein include all diastereomeric, enantiomeric, and epimeric forms as well as the corresponding mixtures thereof. In additional embodiments of the compounds and methods provided herein, mixtures of enantiomers and/or diastereoisomers, resulting from a single preparative step, combination, or interconversion, are useful for the applications described herein. In some embodiments, the compounds described herein are prepared as optically pure enantiomers by chiral chromatographic resolution of the racemic mixture. In some embodiments, the compounds described herein are prepared as their individual stereoisomers by reacting a racemic mixture of the compound with an optically active resolving agent to form a pair of diastereoisomeric compounds, separating the diastereomers, and recovering the optically pure enantiomers. In some embodiments, dissociable complexes are preferred (e.g., crystalline diastereomeric salts). In some embodiments, the diastereomers have distinct physical properties (e.g., melting points, boiling points, solubilities, reactivity, etc.) and are separated by taking advantage of these dissimilarities. In some embodiments, the diastereomers are separated by chiral chromatography, or preferably, by separation/resolution techniques based upon differences in solubility. In some embodiments, the optically pure enantiomer is then recovered, along with the resolving agent, by any practical means that does not result in racemization.

Labeled Compounds

In some embodiments, the compounds described herein exist in their isotopically-labeled forms. In some embodiments, the methods disclosed herein include methods of treating diseases by administering such isotopically-labeled compounds. In some embodiments, the methods disclosed herein include methods of treating diseases by administering such isotopically-labeled compounds as pharmaceutical compositions. Thus, in some embodiments, the compounds disclosed herein include isotopically-labeled compounds, which are identical to those recited herein, but for the fact that one or more atoms are replaced by an atom having an atomic mass or mass number different from the atomic mass or mass number usually found in nature. Examples of isotopes that are incorporated into compounds described herein include isotopes of hydrogen, carbon, nitrogen, oxygen, phosphorous, sulfur, fluorine, and chloride, such as $^2H$, $^3H$, $^{13}C$, $^{14}C$, $^{35}N$, $^{17}O$, $^{18}O$, $^{31}P$, $^{32}P$, $^{35}S$, $^{18}F$, and $^{36}Cl$, respectively. Compounds described herein, and pharmaceutically acceptable salts, esters, solvate, hydrates, or derivatives thereof which contain the aforementioned isotopes and/or other isotopes of other atoms are within the scope of this invention. Certain isotopically-labeled compounds, for example those into which radioactive isotopes such as $^3H$ and $^{14}C$ are incorporated, are useful in drug and/or substrate tissue distribution assays. Tritiated, i. e., $^3H$ and carbon-14, i.e., $^{14}C$, isotopes are particularly preferred for their ease of preparation and detectability. Further, substitution with heavy isotopes such as deuterium, i.e., $^2H$, produces certain therapeutic advantages resulting from greater metabolic stability, for example increased in vivo half-life or reduced dosage requirements. In some embodiments, the isotopically labeled compounds, pharmaceutically acceptable salt, ester, solvate, hydrate, or derivative thereof is prepared by any suitable method.

In some embodiments, the compounds described herein are labeled by other means, including, but not limited to, the use of chromophores or fluorescent moieties, bioluminescent labels, or chemiluminescent labels.

Pharmaceutically Acceptable Salts

In some embodiments, the compounds described herein exist as their pharmaceutically acceptable salts. In some embodiments, the methods disclosed herein include methods of treating diseases by administering such pharmaceutically acceptable salts. In some embodiments, the methods disclosed herein include methods of treating diseases by administering such pharmaceutically acceptable salts as pharmaceutical compositions.

In some embodiments, the compounds described herein possess acidic or basic groups and therefore react with any of a number of inorganic or organic bases, and inorganic and organic acids, to form a pharmaceutically acceptable salt. In some embodiments, these salts are prepared in situ during the final isolation and purification of the compounds described herein, or by separately reacting a purified compound in its free form with a suitable acid or base, and isolating the salt thus formed.

Solvates

In some embodiments, the compounds described herein exist as solvates. In some embodiments are methods of treating diseases by administering such solvates. Further described herein are methods of treating diseases by administering such solvates as pharmaceutical compositions.

Solvates contain either stoichiometric or non-stoichiometric amounts of a solvent, and, in some embodiments, are formed during the process of crystallization with pharmaceutically acceptable solvents such as water, ethanol, and the like. Hydrates are formed when the solvent is water, or alcoholates are formed when the solvent is alcohol. Solvates of the compounds described herein are conveniently prepared or formed during the processes described herein. By way of example only, hydrates of the compounds described herein are conveniently prepared by recrystallization from an aqueous/organic solvent mixture, using organic solvents including, but not limited to, dioxane, tetrahydrofuran, or MeOH. In addition, the compounds provided herein exist in unsolvated as well as solvated forms. In general, the solvated forms are considered equivalent to the unsolvated forms for the purposes of the compounds and methods provided herein.

Synthesis of Compounds

In some embodiments, the synthesis of compounds described herein are accomplished using means described in the chemical literature, using the methods described herein, or by a combination thereof. In addition, solvents, temperatures and other reaction conditions presented herein may vary.

In other embodiments, the starting materials and reagents used for the synthesis of the compounds described herein are synthesized or are obtained from commercial sources, such as, but not limited to, Sigma-Aldrich, FischerScientific (Fischer Chemicals), and AcrosOrganics.

In further embodiments, the compounds described herein, and other related compounds having different substituents are synthesized using techniques and materials described herein as well as those that are recognized in the field, such as described, for example, in Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), Larock's Comprehensive Organic Transformations (VCH Publishers Inc., 1989), March, Advanced Organic Chemistry $4^{th}$ Ed., (Wiley 1992); Carey and Sundberg, Advanced Organic Chemistry $4^{th}$ Ed., Vols. A and B (Plenum 2000, 2001), and Green and Wuts, Protective Groups in Organic Synthesis $3^{rd}$ Ed., (Wiley 1999) (all of which are incorporated by reference for such disclosure). General methods for the preparation of compound as disclosed herein may be derived from reactions and the reactions may be modified by the use of appropriate reagents and conditions, for the introduction of the various moieties found in the formulae as provided herein. In some embodiments, the following synthetic method may be utilized.

In some embodiments, the compounds of the present invention exhibit one or more functional characteristics disclosed herein. For example, a subject compound binds to a Ras protein, Kras protein or a mutant form thereof. In some embodiments, a subject compound binds specifically and also inhibits a Ras protein, Kras protein or a mutant form thereof. In some embodiments, a subject compound selectively inhibits a Kras mutant relative to a wildtype Kras. In some embodiments, a subject compound selectively inhibits KrasG12D and/or KrasG12V relative to wildtype Kras. In some embodiments, the IC50 of a subject compound for a Kras mutant (e.g., including G12D) is less than about 5 µM, less than about 1 µM, less than about 50 n nM, less than about 10 nM, less than about 1 nM, less than about 0.5 nM, less than about 100 pM, or less than about 50 pM, as measured in an in vitro assay known in the art or exemplified herein. In some embodiments, a subject compound covalently binds to a Kras mutants (e.g., KrasG12D, KrasG12C, KrasG12S, and/or G13D).

In some embodiments, a subject compound of the present disclosure is capable of reducing Ras signaling output. Such reduction can be evidenced by one or more members of the following: (i) an increase in steady state level of GDP-bound Ras protein; (ii) a reduction of phosphorylated AKTs473, (iii) a reduction of phosphorylated ERKT202/y204, (iv) a reduction of phosphorylated S6S235/236, and (v) reduction (e.g., inhibition) of cell growth of Ras-driven tumor cells (e.g., those derived from a tumor cell line disclosed herein). In some cases, the reduction in Ras signaling output can be evidenced by two, three, four or all of (i)-(v) above.

It shall be understood that different aspects of the invention can be appreciated individually, collectively, or in combination with each other. Various aspects of the invention described herein may be applied to any of the particular applications disclosed herein. The compositions of matter including compounds of any formulae disclosed herein in the composition section of the present disclosure may be utilized in the method section including methods of use and production disclosed herein, or vice versa.

The chemical entities described herein can be synthesized according to one or more illustrative schemes herein and/or techniques known in the art. Materials used herein are either commercially available or prepared by synthetic methods generally known in the art. These schemes are not limited to the compounds listed in the examples or by any particular substituents, which are employed for illustrative purposes. Although various steps are described and depicted in Schemes 1-3 and Examples 1-6, the steps in some cases may be performed in a different order than the order shown in Schemes 1-3 and Examples 1-6. Various modifications to these synthetic reaction schemes may be made and will be suggested to one skilled in the art having referred to the present disclosure. Numberings or R groups in each scheme typically have the same meanings as those defined elsewhere herein unless otherwise indicated.

Unless specified to the contrary, the reactions described herein take place at atmospheric pressure, generally within a temperature range from −10° C. to 200° C. Further, except as otherwise specified, reaction times and conditions are intended to be approximate, e.g., taking place at about atmospheric pressure within a temperature range of about −10° C. to about 110° C. over a period of about 1 to about 24 hours; reactions left to run overnight average a period of about 16 hours. In general, compounds of the disclosure may be prepared by the following reaction schemes:

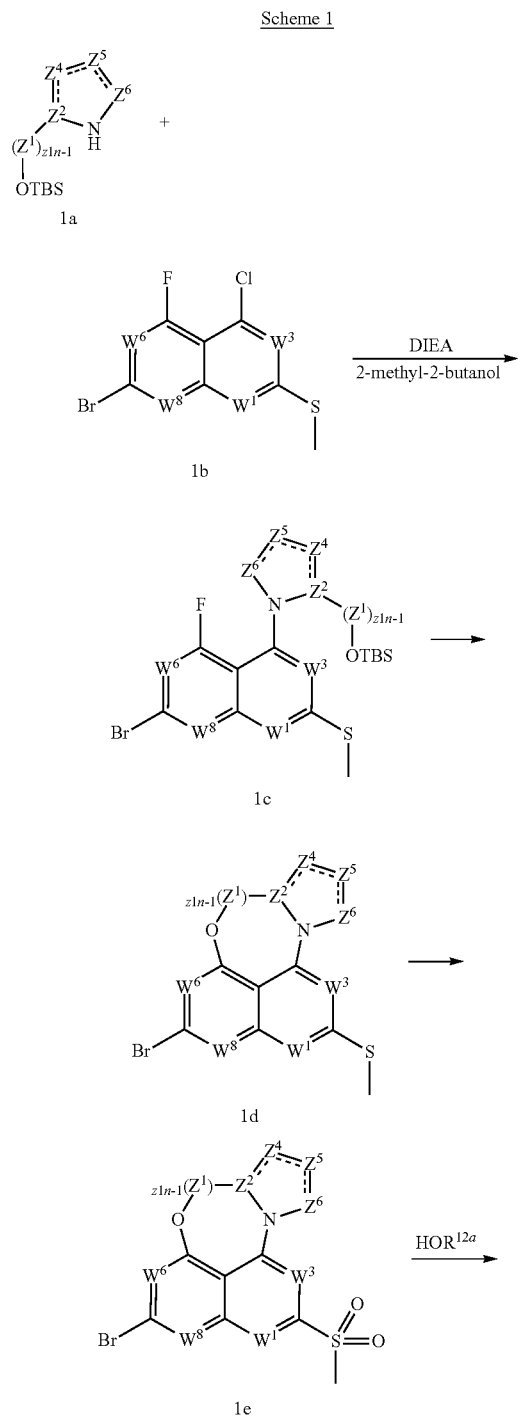

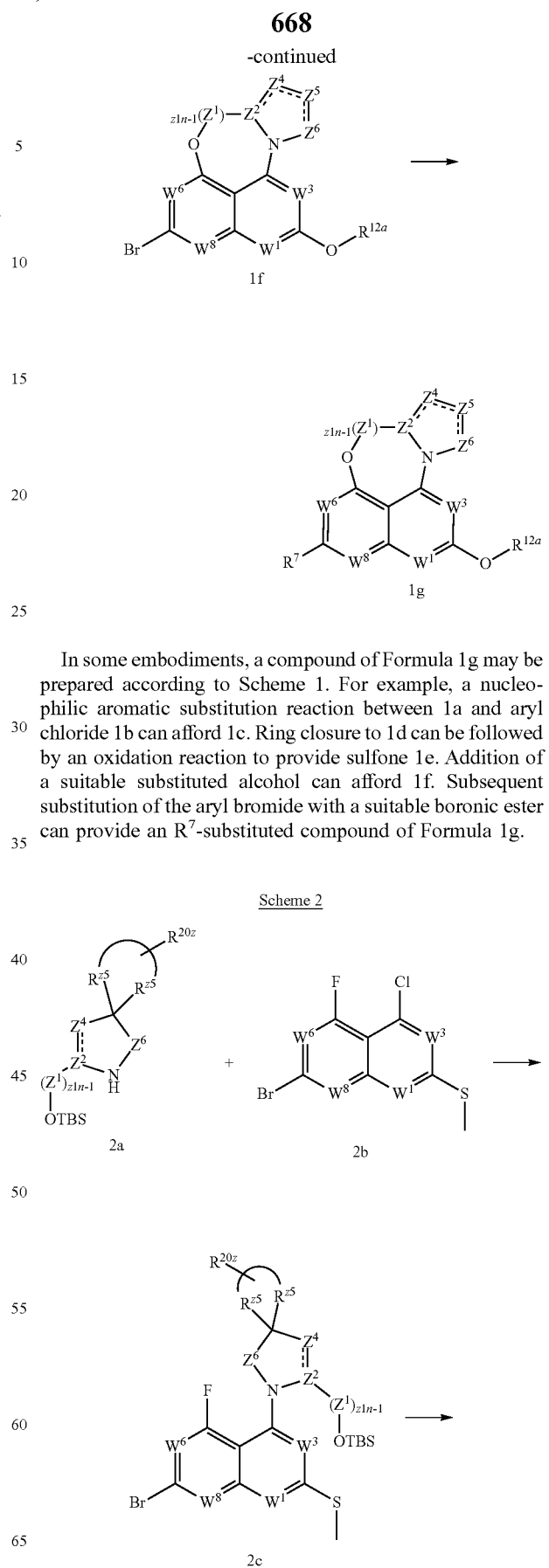

In some embodiments, a compound of Formula 1g may be prepared according to Scheme 1. For example, a nucleophilic aromatic substitution reaction between 1a and aryl chloride 1b can afford 1c. Ring closure to 1d can be followed by an oxidation reaction to provide sulfone 1e. Addition of a suitable substituted alcohol can afford 1f. Subsequent substitution of the aryl bromide with a suitable boronic ester can provide an $R^7$-substituted compound of Formula 1g.

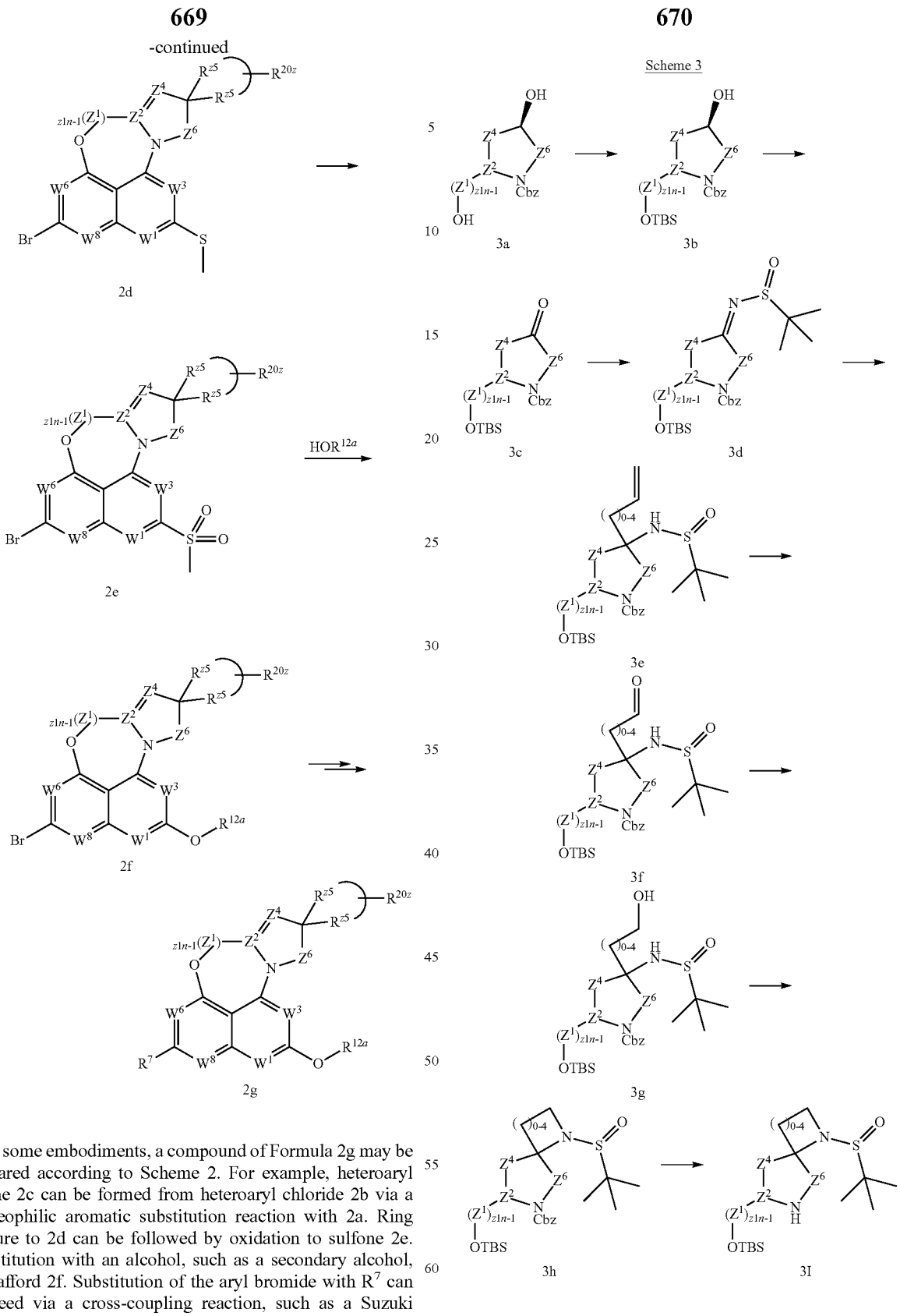

In some embodiments, a compound of Formula 2g may be prepared according to Scheme 2. For example, heteroaryl amine 2c can be formed from heteroaryl chloride 2b via a nucleophilic aromatic substitution reaction with 2a. Ring closure to 2d can be followed by oxidation to sulfone 2e. Substitution with an alcohol, such as a secondary alcohol, can afford 2f. Substitution of the aryl bromide with $R^7$ can proceed via a cross-coupling reaction, such as a Suzuki reaction with a suitable organoboron reagent, which can optionally be followed by one or more subsequent reactions—such as a deprotection and/or substitution reaction, for example, to modify $R^{20z}$—to provide a compound of Formula 2g.

In some embodiments, compound 2a is a compound of Formula 3i, which may be prepared according to Scheme 3. For example, protection of primary alcohol 3a, optionally utilizing a TBS protecting group, can afford silyl ester 3b. Oxidation, optionally using Dess-Martin periodinane, can give 3c, which can be reacted with 2-methylpropane-2-sulfinamide to provide imine 3d. The imine can undergo a Grignard reaction with a suitable reagent, such as allyl magnesium bromide, to give alkene 3e. Ozonolysis of the alkene can provide aldehyde 3f, which can be reduced (e.g., using NaBH$_4$) to primary alcohol 3g. Cyclization to spirocycle 3h can be followed by deprotection to reveal an amine of Formula 3i, which can readily be used in a nucleophilic aromatic substation reaction (e.g., as compound 2a of Scheme 2).

In some embodiments, a compound of the present disclosure is synthesized according to one of the general routes outlined in Schemes 1-3, Examples 1-6, or by methods generally known in the art. In some embodiments, exemplary compounds may include, but are not limited to, a compound selected from Table 1, or a salt or solvate thereof.

TABLE 1

| No. | Structure | Chemical Name | [M + H]$^+$ |
|---|---|---|---|
| 101 | 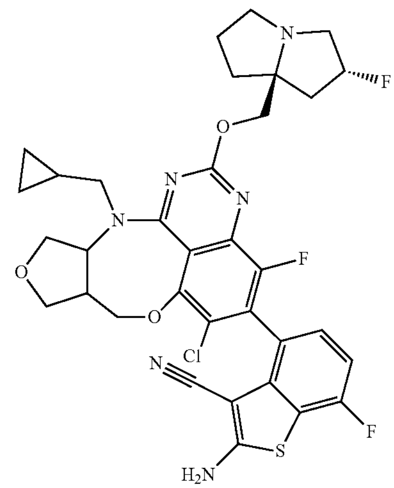 [SMILES: N#Cc1c(N)sc2c(F)ccc(-c3c(Cl)c4c5c(nc(OC[C@@]67CCCN6C[C@H](F)C7)nc5c3F)N(CC3CC3)C3COCC3CO4)c12] | 2-amino-4-(6-chloro-12-(cyclopropylmethyl)-4-fluoro-2-(((2R,7aS)-2-fluorotetrahydro-1H-pyrrolizin-7a(5H)-yl)methoxy)-8a,9,11a,12-tetrahydro-8H,11H-furo[3',4':6,7][1,5]oxazocino[4,3,2-de]quinazolin-5-yl)-7-fluorobenzo[b]thiophene-3-carbonitrile | 697.4 |
| 102 | 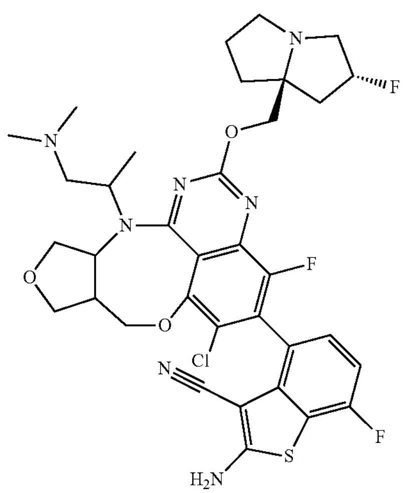 [SMILES: CC(CN(C)C)N1c2nc(OC[C@@]34CCCN3C[C@H](F)C4)nc3c(F)c(-c4ccc(F)c5sc(N)c(C#N)c45)c(Cl)c(c23)OCC2COCC21] | 2-amino-4-(6-chloro-12-(1-(dimethylamino)propan-2-yl)-4-fluoro-2-(((2R,7aS)-2-fluorotetrahydro-1H-pyrrolizin-7a(5H)-yl)methoxy)-8a,9,11a,12-tetrahydro-8H,11H-furo[3',4':6,7][1,5]oxazocino[4,3,2-de]quinazolin-5-yl)-7-fluorobenzo[b]thiophene-3-carbonitrile | 728.5 |
| 103 | 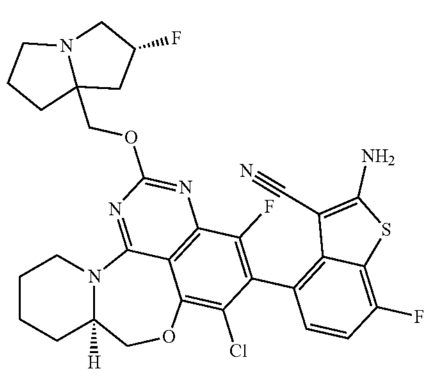 [SMILES: N#Cc1c(N)sc2c(F)ccc(-c3c(Cl)c4c5c(nc(OCC67CCCN6C[C@H](F)C7)nc5c3F)N3CCCC[C@@H]3CO4)c12] | 2-amino-4-((5aR)-3-chloro-1-fluoro-12-(((2R)-2-fluorotetrahydro-1H-pyrrolizin-7a(5H)-yl)methoxy)-5,5a,6,7,8,9-hexahydropyrido[2',1':3,4][1,4]oxazepino[5,6,7-de]quinazolin-2-yl)-7-fluorobenzo[b]thiophene-3-carbonitrile | 641.3 |

TABLE 1-continued

| No. | Structure | Chemical Name | [M + H]⁺ |
| --- | --- | --- | --- |
| 104 | 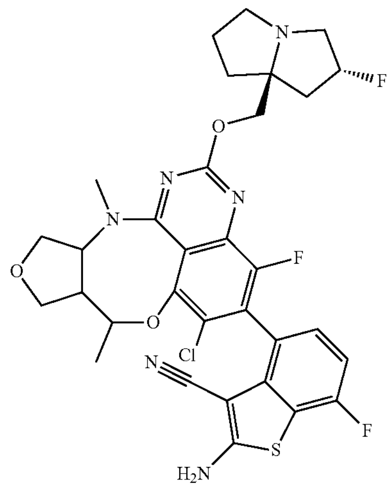 [SMILES: CC1Oc2c(Cl)c(-c3ccc(F)c4sc(N)c(C#N)c34)c(F)c3nc(OC[C@@]45CCCN4C[C@H](F)C5)nc(c23)N(C)C2COCC12] | 2-amino-4-(6-chloro-4-fluoro-2-(((2R,7aS)-2-fluorotetrahydro-1H-pyrrolizin-7a(5H)-yl)methoxy)-8,12-dimethyl-8a,9,11a,12-tetrahydro-8H,11H-furo[3',4':6,7][1,5]oxazocino[4,3,2-de]quinazolin-5-yl)-7-fluorobenzo[b]thiophene-3-carbonitrile | 671.3 |
| 105 [1] | 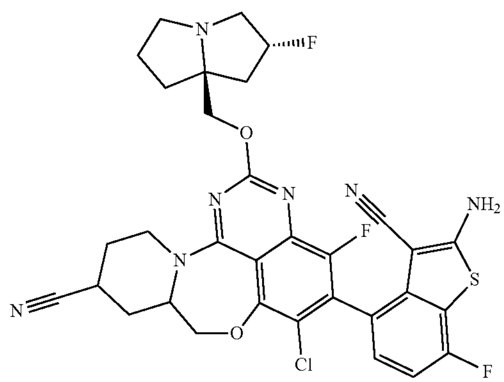 [SMILES: N#Cc1c(N)sc2c(F)ccc(-c3c(Cl)c4c5c(nc(OC[C@@]67CCCN6C[C@H](F)C7)nc5c3F)N3CCC(C#N)CC3CO4)c12] | 5-(2-amino-3-cyano-7-fluorobenzo[b]thiophen-4-yl)-6-chloro-4-fluoro-2-(((2R,7aS)-2-fluorotetrahydro-1H-pyrrolizin-7a(5H)-yl)methoxy)-8,8a,9,10,11,12-hexahydropyrido[2',1':3,4][1,4]oxazepino[5,6,7-de]quinazoline-10-carbonitrile | 666.25 |
| 106 | 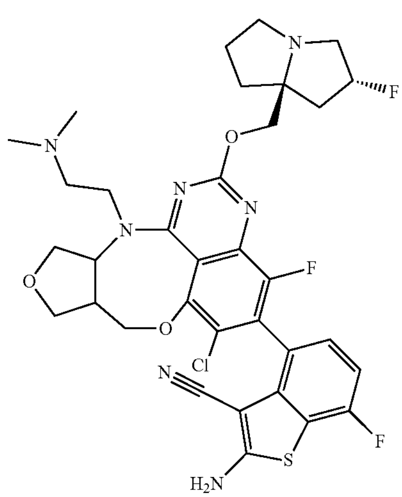 [SMILES: CN(C)CCN1c2nc(OC[C@@]34CCCN3C[C@H](F)C4)nc3c(F)c(-c4ccc(F)c5sc(N)c(C#N)c45)c(Cl)c(c23)OCC2COCC21] | 2-amino-4-(6-chloro-12-(2-(dimethylamino)ethyl)-4-fluoro-2-(((2R,7aS)-2-fluorotetrahydro-1H-pyrrolizin-7a(5H)-yl)methoxy)-8a,9,11a,12-tetrahydro-8H,11H-furo[3',4':6,7][1,5]oxazocino[4,3,2-de]quinazolin-5-yl)-7-fluorobenzo[b]thiophene-3-carbonitrile | 714.4 |

TABLE 1-continued

| No. | Structure | Chemical Name | [M + H]⁺ |
|---|---|---|---|
| 107 | 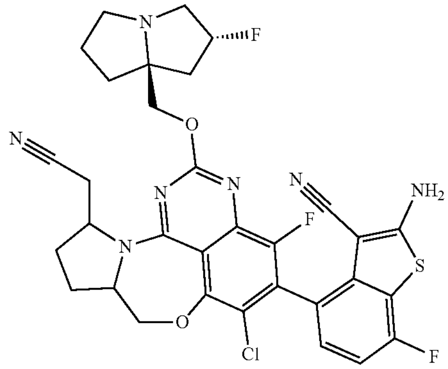 [SMILES: N#CCC1CCC2COc3c(Cl)c(-c4ccc(F)c5sc(N)c(C#N)c45)c(F)c4nc(OC[C@@]56CCCN5C[C@H](F)C6)nc(c34)N12] | 2-amino-4-(6-chloro-11-(cyanomethyl)-4-fluoro-2-(((2R,7aS)-2-fluorotetrahydro-1H-pyrrolizin-7a(5H)-yl)methoxy)-8a,9,10,11-tetrahydro-8H-pyrrolo[2',1':3,4][1,4]oxazepino[5,6,7-de]quinazolin-5-yl)-7-fluorobenzo[b]thiophene-3-carbonitrile | 666.7 |
| 108 | 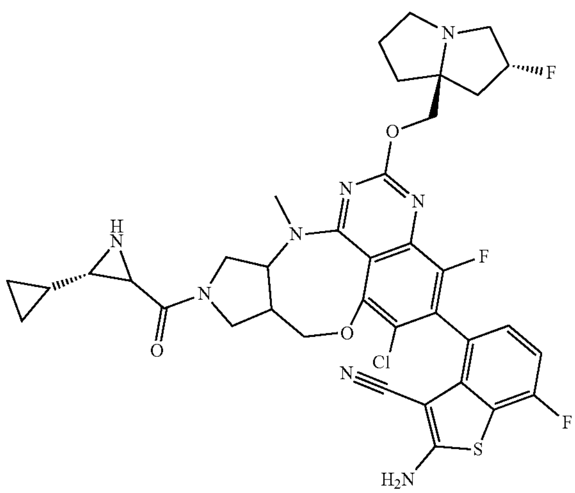 [SMILES: CN1c2nc(OC[C@@]34CCCN3C[C@H](F)C4)nc3c(F)c(-c4ccc(F)c5sc(N)c(C#N)c45)c(Cl)c(c23)OCC2CN(C(=O)C3N[C@H]3C3CC3)CC21] | 2-amino-4-(6-chloro-9-((3S)-3-cyclopropylaziridine-2-carbonyl)-4-fluoro-2-(((2R,7aS)-2-fluorotetrahydro-1H-pyrrolizin-7a(5H)-yl)methoxy)-11-methyl-7a,8,9,10,10a,11-hexahydropyrrolo[3',4':2,3][1,4]oxazepino[5,6,7-de]quinazolin-5-yl)-7-fluorobenzo[b]thiophene-3-carbonitrile | 751.3 |
| 109 | 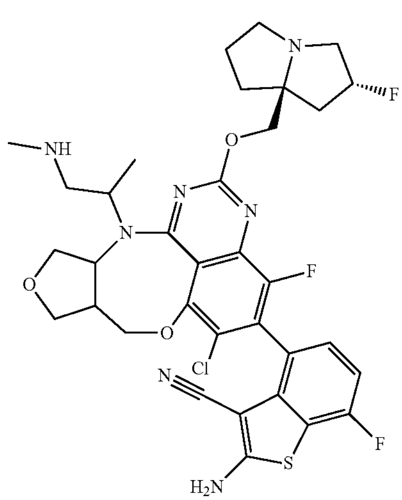 [SMILES: CNCC(C)N1c2nc(OC[C@@]34CCCN3C[C@H](F)C4)nc3c(F)c(-c4ccc(F)c5sc(N)c(C#N)c45)c(Cl)c(c23)OCC2COCC21] | 2-amino-4-(6-chloro-4-fluoro-2-(((2R,7aS)-2-fluorotetrahydro-1H-pyrrolizin-7a(5H)-yl)methoxy)-12-(1-(methylamino)propan-2-yl)-8a,9,11a,12-tetrahydro-8H,11H-furo[3',4':6,7][1,5]oxazocino[4,3,2-de]quinazolin-5-yl)-7-fluorobenzo[b]thiophene-3-carbonitrile | 714.4 |

TABLE 1-continued

| No. | Structure | Chemical Name | [M + H]+ |
|---|---|---|---|
| 110 [1] | 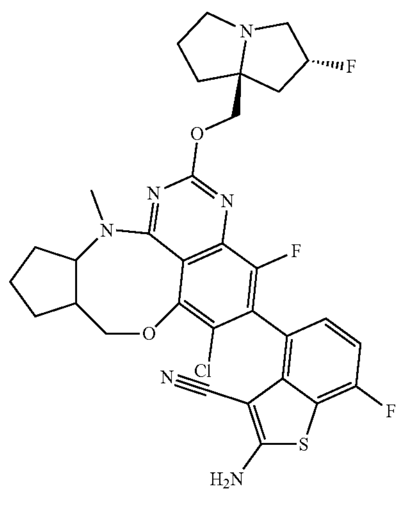 [SMILES: CN1c2nc(OC[C@@]34CCCN3C[C@H](F)C4)nc3c(F)c(-c4ccc(F)c5sc(N)c(C#N)c45)c(Cl)c(c23)OCC2CCCC21] | 2-amino-4-(6-chloro-4-fluoro-2-(((2R,7aS)-2-fluorotetrahydro-1H-pyrrolizin-7a(5H)-yl)methoxy)-12-methyl-8a,9,10,11,11a,12-hexahydro-8H-cyclopenta[6,7][1,5]oxazocino[4,3,2-de]quinazolin-5-yl)-7-fluorobenzo[b]thiophene-3-carbonitrile | 655.3 |
| 111 | 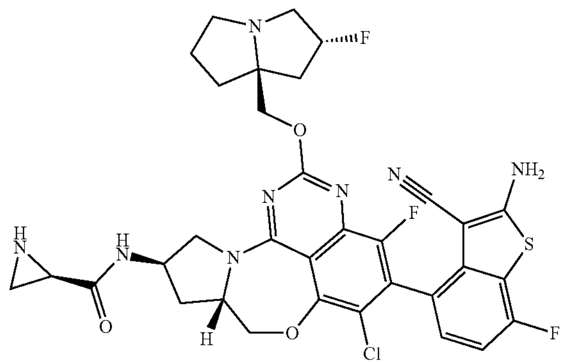 [SMILES: N#Cc1c(N)sc2c(F)ccc(-c3c(Cl)c4c5c(nc(OC[C@@]67CCCN6C[C@H](F)C7)nc5c3F)N3C[C@H](NC(=O)[C@H]5CN5)C[C@H]3CO4)c12] | (2R)-N-((8aS,10R)-5-(2-amino-3-cyano-7-fluorobenzo[b]thiophen-4-yl)-6-chloro-4-fluoro-2-(((2R,7aS)-2-fluorotetrahydro-1H-pyrrolizin-7a(5H)-yl)methoxy)-8a,9,10,11-tetrahydro-8H-pyrrolo[2',1':3,4][1,4]oxazepino[5,6,7-de]quinazolin-10-yl)aziridine-2-carboxamide | 711.3 |
| 112 | 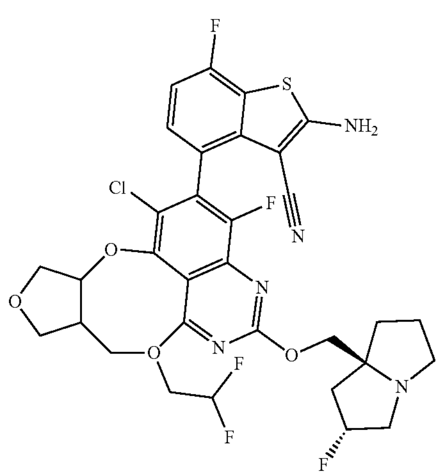 | 2-amino-4-(1-chloro-7-(2,2-difluoroethyl)-3-fluoro-5-(((2R,7aS)-2-fluorotetrahydro-1H-pyrrolizin-7a(5H)-yl)methoxy)-7,8,8a,9,11,11a-hexahydrofuro[3',4':7,8][1,5]oxazocino[4,3,2-de]quinazolin-2-yl)-7-fluorobenzo[b]thiophene-3-carbonitrile | 707.3 |

TABLE 1-continued

| No. | Structure | Chemical Name | [M + H]⁺ |
|---|---|---|---|
| 113 | 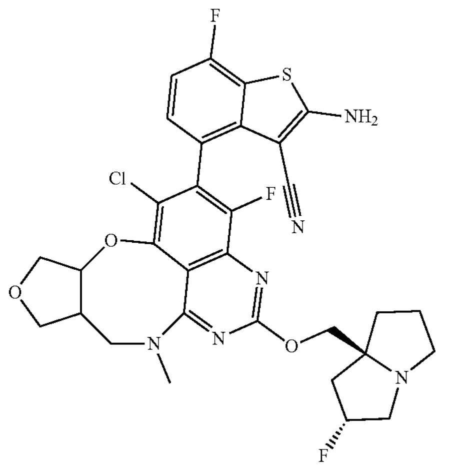 [SMILES: CN1CC2COCC2Oc2c(Cl)c(-c3ccc(F)c4sc(N)c(C#N)c34)c(F)c3nc(OC[C@@]45CCCN4C[C@H](F)C5)nc1c23] | 2-amino-4-(1-chloro-3-fluoro-5-(((2R,7aS)-2-fluorotetrahydro-1H-pyrrolizin-7a(5H)-yl)methoxy)-7-methyl-7,8,8a,9,11,11a-hexahydrofuro[3',4':7,8][1,5]oxazocino[4,3,2-de]quinazolin-2-yl)-7-fluorobenzo[b]thiophene-3-carbonitrile | 657.3 |
| 114 | 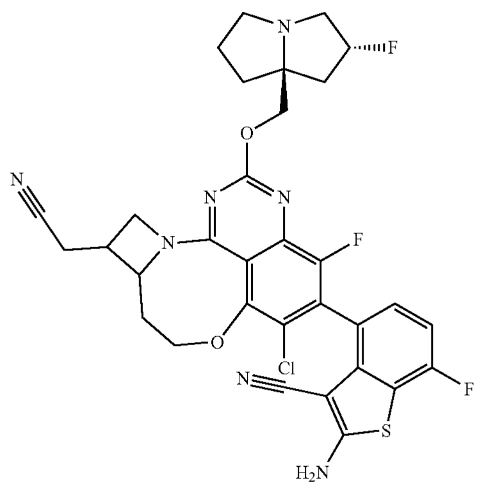 [SMILES: N#CCC1CN2c3nc(OC[C@@]45CCCN4C[C@H](F)C5)nc4c(F)c(-c5ccc(F)c6sc(N)c(C#N)c56)c(Cl)c(c34)OCCC12] | 2-amino-4-(9-chloro-1-(cyanomethyl)-7-fluoro-5-(((2R,7aS)-2-fluorotetrahydro-1H-pyrrolizin-7a(5H)-yl)methoxy)-1,11,12,12a-tetrahydro-2H-azeto[1',2':5,6][1,5]oxazocino[4,3,2-de]quinazolin-8-yl)-7-fluorobenzo[b]thiophene-3-carbonitrile | 666.35 |
| 115 | 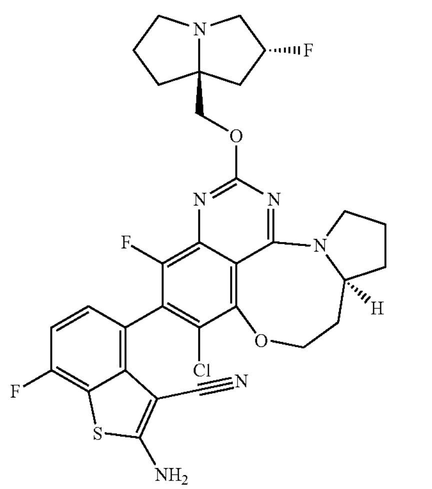 [SMILES: N#Cc1c(N)sc2c(F)ccc(-c3c(Cl)c4c5c(nc(OC[C@@]67CCCN6C[C@H](F)C7)nc5c3F)N3CCC[C@H]3CCO4)c12] | 2-amino-4-((13aS)-10-chloro-8-fluoro-6-(((2R,7aS)-2-fluorotetrahydro-1H-pyrrolizin-7a(5H)-yl)methoxy)-1,2,3,12,13,13a-hexahydropyrrolo[1',2':5,6][1,5]oxazocino[4,3,2-de]quinazolin-9-yl)-7-fluorobenzo[b]thiophene-3-carbonitrile | 641.4 |

TABLE 1-continued

| No. | Structure | Chemical Name | [M + H]⁺ |
|---|---|---|---|
| 116 | 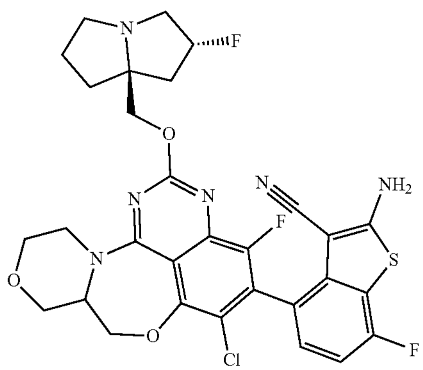 [SMILES: N#Cc1c(N)sc2c(F)ccc(-c3c(Cl)c4c5c(nc(OC[C@@]67CCCN6C[C@H](F)C7)nc5c3F)N3CCOCC3CO4)c12] | 2-amino-4-(6-chloro-4-fluoro-2-(((2R,7aS)-2-fluorotetrahydro-1H-pyrrolizin-7a(5H)-yl)methoxy)-8a,9,11,12-tetrahydro-8H-[1,4]oxazino[3',4':3,4][1,4]oxazepino[5,6,7-de]quinazolin-5-yl)-7-fluorobenzo[b]thiophene-3-carbonitrile | 643.2 |
| 117 [1] | 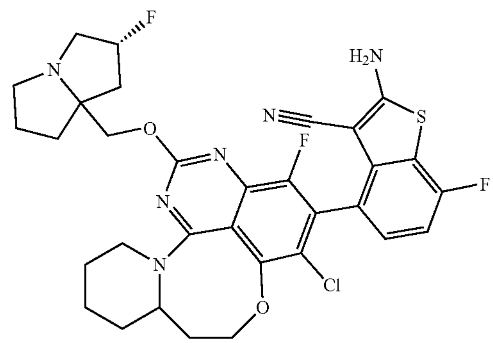 [SMILES: N#Cc1c(N)sc2c(F)ccc(-c3c(Cl)c4c5c(nc(OCC67CCCN6C[C@H](F)C7)nc5c3F)N3CCCCC3CCO4)c12] | 2-amino-4-(3-chloro-1-fluoro-13-(((2R)-2-fluorotetrahydro-1H-pyrrolizin-7a(5H)-yl)methoxy)-6,6a,7,8,9,10-hexahydro-5H-pyrido[1¹,2':5,6][1,5]oxazocino[4,3,2-de]quinazolin-2-yl)-7-fluorobenzo[b]thiophene-3-carbonitrile | 655.4 |
| 118 [1] | 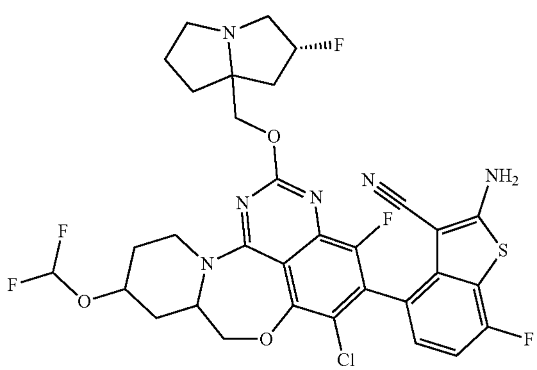 [SMILES: N#Cc1c(N)sc2c(F)ccc(-c3c(Cl)c4c5c(nc(OCC67CCCN6C[C@H](F)C7)nc5c3F)N3CCC(OC(F)F)CC3CO4)c12] | 2-amino-4-(6-chloro-10-(difluoromethoxy)-4-fluoro-2-(((2R)-2-fluorotetrahydro-1H-pyrrolizin-7a(5H)-yl)methoxy)-8,8a,9,10,11,12-hexahydropyrido[2',1':3,4][1,4]oxazepino[5,6,7-de]quinazolin-5-yl)-7-fluorobenzo[b]thiophene-3-carbonitrile | 707.3 |
| 119 | 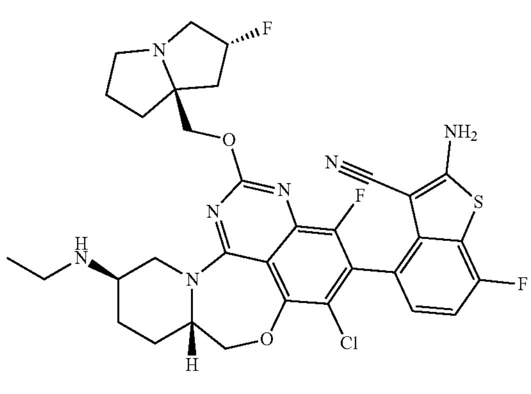 [SMILES: CCN[C@@H]1CC[C@H]2COc3c(Cl)c(-c4ccc(F)c5sc(N)c(C#N)c45)c(F)c4nc(OC[C@@]56CCCN5C[C@H](F)C6)nc(c34)N2C1] | 2-amino-4-((5aS,8R)-3-chloro-8-(ethylamino)-1-fluoro-12-(((2R,7aS)-2-fluorotetrahydro-1H-pyrrolizin-7a(5H)-yl)methoxy)-5,5a,6,7,8,9-hexahydropyrido[2',1':3,4][1,4]oxazepino[5,6,7-de]quinazolin-2-yl)-7-fluorobenzo[b]thiophene-3-carbonitrile | 684.3 |

TABLE 1-continued

| No. | Structure | Chemical Name | [M + H]+ |
|---|---|---|---|
| 120 | 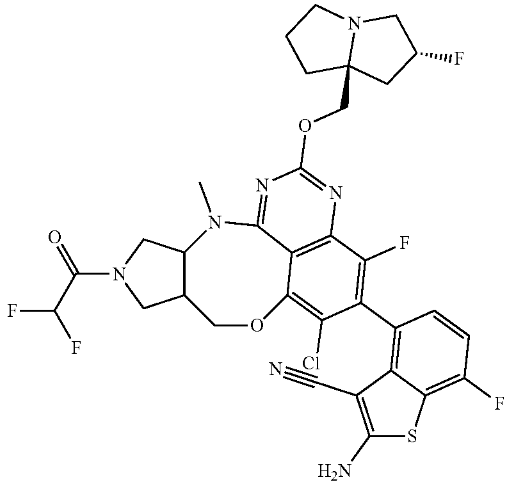 [SMILES: CN1c2nc(OC[C@@]34CCCN3C[C@H](F)C4)nc3c(F)c(-c4ccc(F)c5sc(N)c(C#N)c45)c(Cl)c(c23)OCC2CN(C(=O)C(F)F)CC21] | 2-amino-4-(6-chloro-10-(2,2-difluoroacetyl)-4-fluoro-2-(((2R,7aS)-2-fluorotetrahydro-1H-pyrrolizin-7a(5H)-yl)methoxy)-12-methyl-8a,9,10,11,11a,12-hexahydro-8H-pyrrolo[3',4':6,7][1,5]oxazocino[4,3,2-de]quinazolin-5-yl)-7-fluorobenzo[b]thiophene-3-carbonitrile | 734.3 |
| 121 | 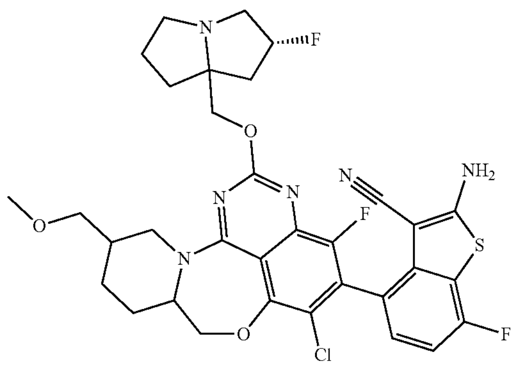 [SMILES: COCC1CCC2COc3c(Cl)c(-c4ccc(F)c5sc(N)c(C#N)c45)c(F)c4nc(OCC56CCCN5C[C@H](F)C6)nc(c34)N2C1] | 2-amino-4-(6-chloro-4-fluoro-2-(((2R)-2-fluorotetrahydro-1H-pyrrolizin-7a(5H)-yl)methoxy)-11-(methoxymethyl)-8,8a,9,10,11,12-hexahydropyrido[2',1':3,4][1,4]oxazepino[5,6,7-de]quinazolin-5-yl)-7-fluorobenzo[b]thiophene-3-carbonitrile | 685.3 |
| 122 [1] | 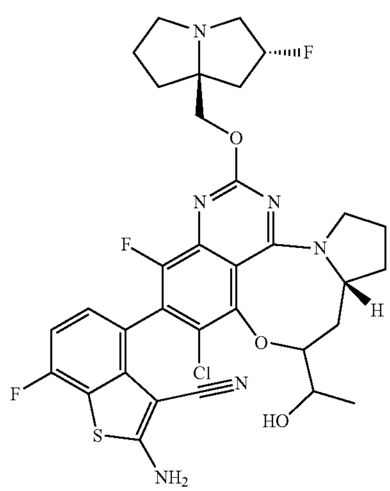 [SMILES: CC(O)C1C[C@H]2CCCN2c2nc(OC[C@@]34CCCN3C[C@H](F)C4)nc3c(F)c(-c4ccc(F)c5sc(N)c(C#N)c45)c(Cl)c(c23)O1] | 2-amino-4-((13aR)-10-chloro-8-fluoro-6-(((2R,7aS)-2-fluorotetrahydro-1H-pyrrolizin-7a(5H)-yl)methoxy)-12-(1-hydroxyethyl)-1,2,3,12,13,13a-hexahydropyrrolo[1',2':5,6][1,5]oxazocino[4,3,2-de]quinazolin-9-yl)-7-fluorobenzo[b]thiophene-3-carbonitrile | 685 |

TABLE 1-continued

| No. | Structure | Chemical Name | [M + H]⁺ |
|---|---|---|---|
| 123 [1] | 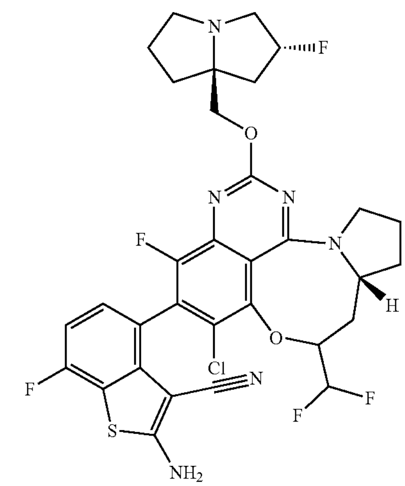 [SMILES: N#Cc1c(N)sc2c(F)ccc(-c3c(Cl)c4c5c(nc(OC[C@@]67CCCN6C[C@H](F)C7)nc5c3F)N3CCC[C@@H]3CC(C(F)F)O4)c12] | 2-amino-4-((13aR)-10-chloro-12-(difluoromethyl)-8-fluoro-6-(((2R,7aS)-2-fluorotetrahydro-1H-pyrrolizin-7a(5H)-yl)methoxy)-1,2,3,12,13,13a-hexahydropyrrolo[1',2':5,6][1,5]oxazocino[4,3,2-de]quinazolin-9-yl)-7-fluorobenzo[b]thiophene-3-carbonitrile | 690.95 |
| 124 | 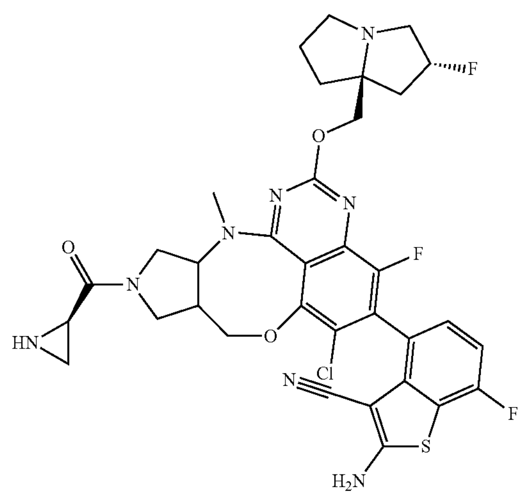 [SMILES: CN1c2nc(OC[C@@]34CCCN3C[C@H](F)C4)nc3c(F)c(-c4ccc(F)c5sc(N)c(C#N)c45)c(Cl)c(c23)OCC2CN(C(=O)[C@H]3CN3)CC21] | 2-amino-4-(10-((R)-aziridine-2-carbonyl)-6-chloro-4-fluoro-2-(((2R,7aS)-2-fluorotetrahydro-1H-pyrrolizin-7a(5H)-yl)methoxy)-12-methyl-8a,9,10,11,11a,12-hexahydro-8H-pyrrolo[3',4':6,7][1,5]oxazocino[4,3,2-de]quinazolin-5-yl)-7-fluorobenzo[b]thiophene-3-carbonitrile | 725.3 |
| 125 | 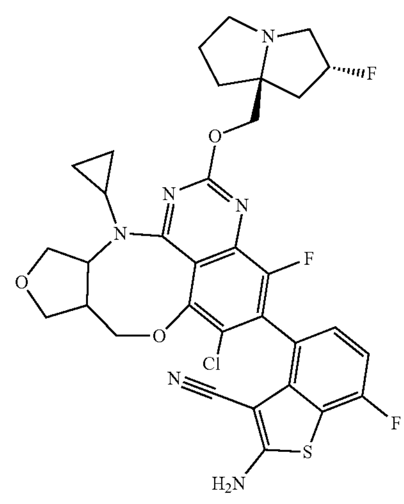 [SMILES: N#Cc1c(N)sc2c(F)ccc(-c3c(Cl)c4c5c(nc(OC[C@@]67CCCN6C[C@H](F)C7)nc5c3F)N(C3CC3)C3COCC3CO4)c12] | 2-amino-4-(6-chloro-12-cyclopropyl-4-fluoro-2-(((2R,7aS)-2-fluorotetrahydro-1H-pyrrolizin-7a(5H)-yl)methoxy)-8a,9,11a,12-tetrahydro-8H,11H-furo[3',4':6,7][1,5]oxazocino[4,3,2-de]quinazolin-5-yl)-7-fluorobenzo[b]thiophene-3-carbonitrile | 683.3 |

TABLE 1-continued

| No. | Structure | Chemical Name | [M + H]+ |
|---|---|---|---|
| 126 | 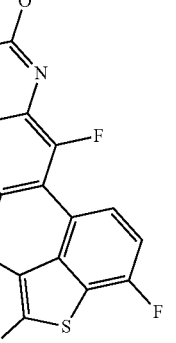 | 2-amino-4-(6-chloro-4-fluoro-2-(((2R,7aS)-2-fluorotetrahydro-1H-pyrrolizin-7a(5H)-yl)methoxy)-9-formyl-11-methyl-7a,8,9,10,10a,11-hexahydropyrrolo[3',4':2,3][1,4]oxazepino[5,6,7-de]quinazolin-5-yl)-7-fluorobenzo[b]thiophene-3-carbonitrile | 670.3 |
| 127 | 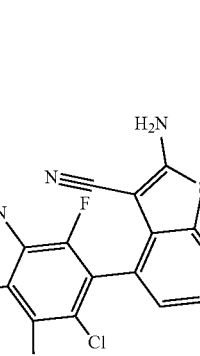 | 2-amino-4-(3-chloro-1'-(2,2-difluorocyclopropane-1-carbonyl)-1-fluoro-14-(((2R,7aS)-2-fluorotetrahydro-1H-pyrrolizin-7a(5H)-yl)methoxy)-5,6,6a,7,8,9-hexahydro-11H-spiro[azepino[1',2':5,6][1,5]oxazocino[4,3,2-de]quinazoline-10,3'-azetidin]-2-yl)-7-fluorobenzo[b]thiophene-3-carbonitrile | 814.2 |
| 128 [1] | 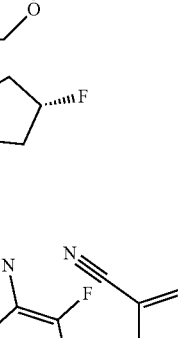 | 2-amino-4-(6-chloro-10-(difluoromethoxy)-4-fluoro-2-(((2R)-2-fluorotetrahydro-1H-pyrrolizin-7a(5H)-yl)methoxy)-8,8a,9,10,11,12-hexahydropyrido[2',1':3,4][1,4]oxazepino[5,6,7-de]quinazolin-5-yl)-7-fluorobenzo[b]thiophene-3-carbonitrile | 707.4 |
| 129 | 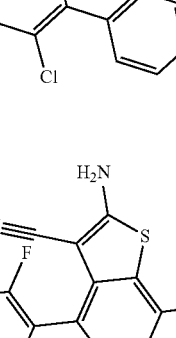 | 2-amino-4-(9-amino-3-chloro-1-fluoro-13-(((2R,7aS)-2-fluorotetrahydro-1H-pyrrolizin-7a(5H)-yl)methoxy)-6,6a,7,8,9,10-hexahydro-5H-pyrido[1',2':5,6][1,5]oxazocino[4,3,2-de]quinazolin-2-yl)-7-fluorobenzo[b]thiophene-3-carbonitrile | 670.2 |

TABLE 1-continued

| No. | Structure | Chemical Name | [M + H]⁺ |
|---|---|---|---|
| 130 (diastereomer 1) | 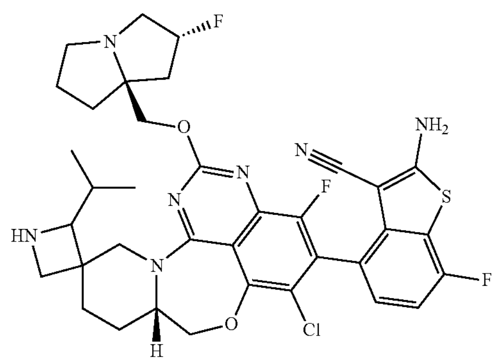 [SMILES: CC(C)C1NCC12CC[C@H]1COc3c(Cl)c(-c4ccc(F)c5sc(N)c(C#N)c45)c(F)c4nc(OC[C@@]56CCCN5C[C@H](F)C6)nc(c34)N1C2] | 2-amino-4-((5a'S)-3'-chloro-1'-fluoro-12'-(((2R,7aS)-2-fluorotetrahydro-1H-pyrrolizin-7a(5H)-yl)methoxy)-2-isopropyl-5',5a',6',7'-tetrahydro-9'H-spiro[azetidine-3,8'-pyrido[2',1':3,4][1,4]oxazepino[5,6,7-de]quinazolin]-2'-yl)-7-fluorobenzo[b]thiophene-3-carbonitrile | 724.5 |
| 131 | 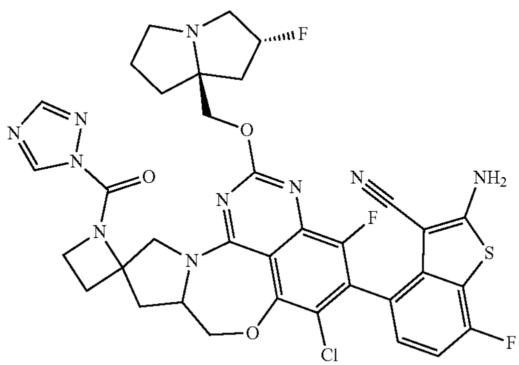 [SMILES: N#Cc1c(N)sc2c(F)ccc(-c3c(Cl)c4c5c(nc(OC[C@@]67CCCN6C[C@H](F)C7)nc5c3F)N3CC5(CCN5C(=O)n5cncn5)CC3CO4)c12] | 2-amino-4-(6'-chloro-4'-fluoro-2'-(((2R,7aS)-2-fluorotetrahydro-1H-pyrrolizin-7a(5H)-yl)methoxy)-1-(1H-1,2,4-triazole-1-carbonyl)-8a',9'-dihydro-8'H,11'H-spiro[azetidine-2,10'-pyrrolo[2',1':3,4][1,4]oxazepino[5,6,7-de]quinazolin]-5'-yl)-7-fluorobenzo[b]thiophene-3-carbonitrile | 763.4 |
| 132 | 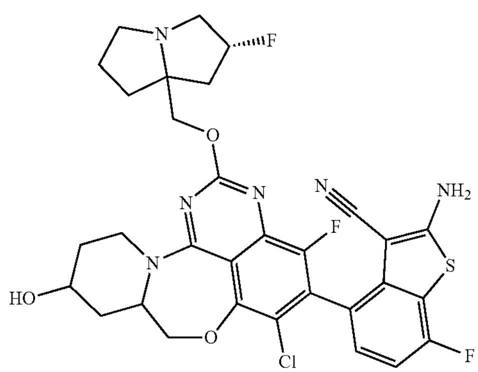 [SMILES: N#Cc1c(N)sc2c(F)ccc(-c3c(Cl)c4c5c(nc(OCC67CCCN6C[C@H](F)C7)nc5c3F)N3CCC(O)CC3CO4)c12] | 2-amino-4-(6-chloro-4-fluoro-2-(((2R)-2-fluorotetrahydro-1H-pyrrolizin-7a(5H)-yl)methoxy)-10-hydroxy-8,8a,9,10,11,12-hexahydropyrido[2',1':3,4][1,4]oxazepino[5,6,7-de]quinazolin-5-yl)-7-fluorobenzo[b]thiophene-3-carbonitrile | 657.3 |
| 133 | 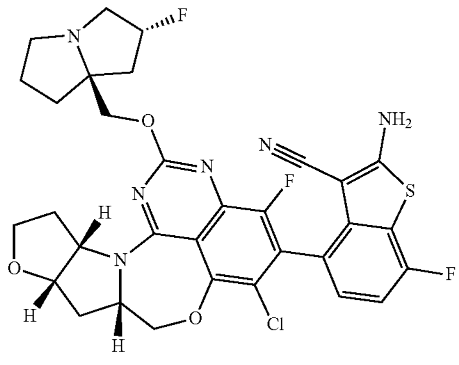 [SMILES: N#Cc1c(N)sc2c(F)ccc(-c3c(Cl)c4c5c(nc(OC[C@@]67CCCN6C[C@H](F)C7)nc5c3F)N3[C@H](CO4)C[C@@H]4OCC[C@@H]43)c12] | 2-amino-4-((8aS,9aS,12aS)-6-chloro-4-fluoro-2-(((2R,7aS)-2-fluorotetrahydro-1H-pyrrolizin-7a(5H)-yl)methoxy)-8a,9,9a,11,12,12a-hexahydro-8H-furo[2'',3'':4',5']pyrrolo[2',1':3,4][1,4]oxazepino[5,6,7-de]quinazolin-5-yl)-7-fluorobenzo[b]thiophene-3-carbonitrile | 669.2 |

TABLE 1-continued

| No. | Structure | Chemical Name | [M + H]+ |
|---|---|---|---|
| 134 | 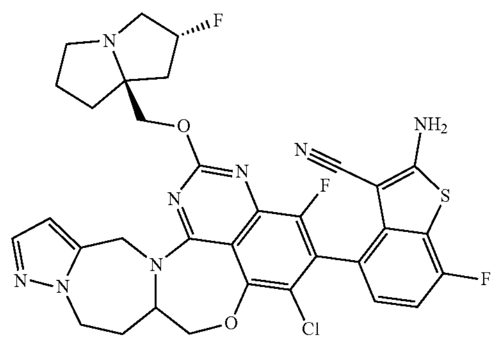 [SMILES: N#Cc1c(N)sc2c(F)ccc(-c3c(Cl)c4c5c(nc(OC[C@@]67CCCN6C[C@H](F)C7)nc5c3F)N3Cc5ccnn5CCC3CO4)c12] | 2-amino-4-(6-chloro-4-fluoro-2-(((2R,7aS)-2-fluorotetrahydro-1H-pyrrolizin-7a(5H)-yl)methoxy)-8,8a,9,10-tetrahydro-15H-pyrazolo[5'',1'':3',4'][1,4]diazepino[7,1':3,4][1,4]oxazepino[5,6,7-de]quinazolin-5-yl)-7-fluorobenzo[b]thiophene-3-carbonitrile | 693.6 |
| 135 [1] | 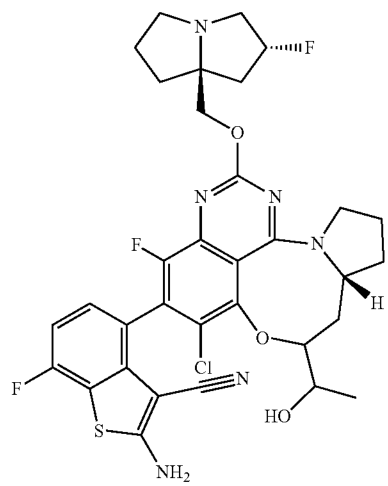 [SMILES: CC(O)C1C[C@H]2CCCN2c2nc(OC[C@@]34CCCN3C[C@H](F)C4)nc3c(F)c(-c4ccc(F)c5sc(N)c(C#N)c45)c(Cl)c(c23)O1] | 2-amino-4-((13aR)-10-chloro-8-fluoro-6-(((2R,7aS)-2-fluorotetrahydro-1H-pyrrolizin-7a(5H)-yl)methoxy)-12-(1-hydroxyethyl)-1,2,3,12,13,13a-hexahydropyrrolo[1',2':5,6][1,5]oxazocino[4,3,2-de]quinazolin-9-yl)-7-fluorobenzo[b]thiophene-3-carbonitrile | 685 |
| 136 | 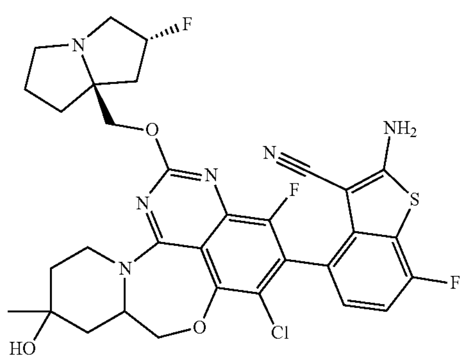 [SMILES: CC1(O)CCN2c3nc(OC[C@@]45CCCN4C[C@H](F)C5)nc4c(F)c(-c5ccc(F)c6sc(N)c(C#N)c56)c(Cl)c(c34)OCC2C1] | 2-amino-4-(3-chloro-1-fluoro-12-(((2R,7aS)-2-fluorotetrahydro-1H-pyrrolizin-7a(5H)-yl)methoxy)-7-hydroxy-7-methyl-5,5a,6,7,8,9-hexahydropyrido[2',1':3,4][1,4]oxazepino[5,6,7-de]quinazolin-2-yl)-7-fluorobenzo[b]thiophene-3-carbonitrile | 671.2 |
| 137 | 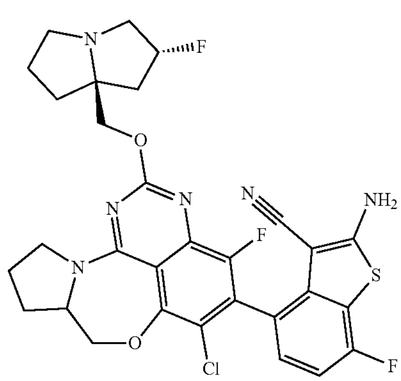 [SMILES: N#Cc1c(N)sc2c(F)ccc(-c3c(Cl)c4c5c(nc(OC[C@@]67CCCN6C[C@H](F)C7)nc5c3F)N3CCCC3CO4)c12] | 2-amino-4-(6-chloro-4-fluoro-2-(((2R,7aS)-2-fluorotetrahydro-1H-pyrrolizin-7a(5H)-yl)methoxy)-8a,9,10,11-tetrahydro-8H-pyrrolo[2',1':3,4][1,4]oxazepino[5,6,7-de]quinazolin-5-yl)-7-fluorobenzo[b]thiophene-3-carbonitrile | 628.3 |

TABLE 1-continued

| No. | Structure | Chemical Name | [M + H]+ |
|---|---|---|---|
| 138 | 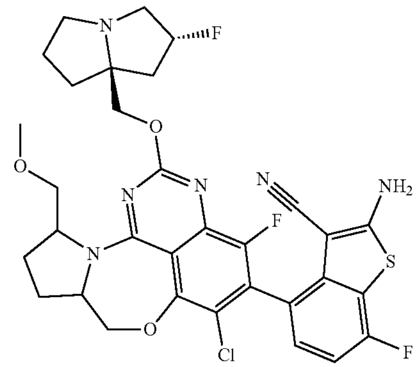 [SMILES: COCC1CCC2COc3c(Cl)c(-c4ccc(F)c5sc(N)c(C#N)c45)c(F)c4nc(OC[C@@]56CCCN5C[C@H](F)C6)nc(c34)N12] | 2-amino-4-(6-chloro-4-fluoro-2-(((2R,7aS)-2-fluorotetrahydro-1H-pyrrolizin-7a(5H)-yl)methoxy)-11-(methoxymethyl)-8a,9,10,11-tetrahydro-8H-pyrrolo[2',1':3,4][1,4]oxazepino[5,6,7-de]quinazolin-5-yl)-7-fluorobenzo[b]thiophene-3-carbonitrile | 671.3 |
| 139 | 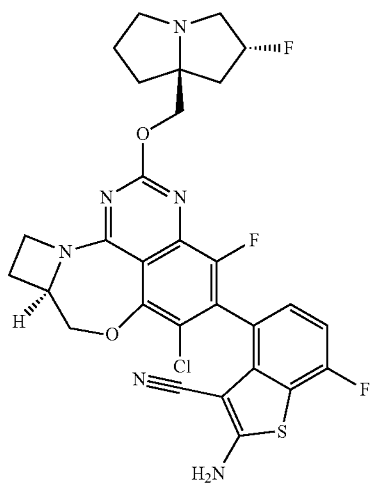 [SMILES: N#Cc1c(N)sc2c(F)ccc(-c3c(Cl)c4c5c(nc(OC[C@@]67CCCN6C[C@H](F)C7)nc5c3F)N3CC[C@@H]3CO4)c12] | 2-amino-4-((11aR)-9-chloro-7-fluoro-5-(((2R,7aS)-2-fluorotetrahydro-1H-pyrrolizin-7a(5H)-yl)methoxy)-1,2,11,11a-tetrahydroazeto[2',1':3,4][1,4]oxazepino[5,6,7-de]quinazolin-8-yl)-7-fluorobenzo[b]thiophene-3-carbonitrile | 613.3 |
| 140 | 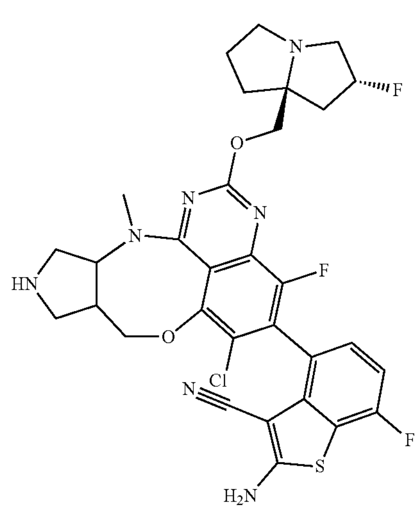 [SMILES: CN1c2nc(OC[C@@]34CCCN3C[C@H](F)C4)nc3c(F)c(-c4ccc(F)c5sc(N)c(C#N)c45)c(Cl)c(c23)OCC2CNCC21] | 2-amino-4-(6-chloro-4-fluoro-2-(((2R,7aS)-2-fluorotetrahydro-1H-pyrrolizin-7a(5H)-yl)methoxy)-12-methyl-8a,9,10,11,11a,12-hexahydro-8H-pyrrolo[3',4':6,7][1,5]oxazocino[4,3,2-de]quinazolin-5-yl)-7-fluorobenzo[b]thiophene-3-carbonitrile | 954.4 |

TABLE 1-continued

| No. | Structure | Chemical Name | [M + H]+ |
|---|---|---|---|
| 141 | 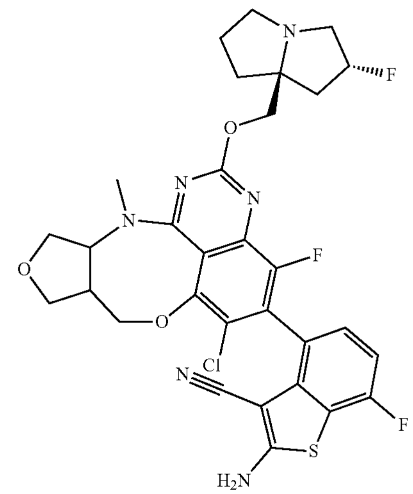 [SMILES: CN1c2nc(OC[C@@]34CCCN3C[C@H](F)C4)nc3c(F)c(-c4ccc(F)c5sc(N)c(C#N)c45)c(Cl)c(c23)OCC2COCC21] | 2-amino-4-(6-chloro-4-fluoro-2-(((2R,7aS)-2-fluorotetrahydro-1H-pyrrolizin-7a(5H)-yl)methoxy)-12-methyl-8a,9,11a,12-tetrahydro-8H,11H-furo[3',4':6,7][1,5]oxazocino[4,3,2-de]quinazolin-5-yl)-7-fluorobenzo[b]thiophene-3-carbonitrile | 657.4 |
| 142 | 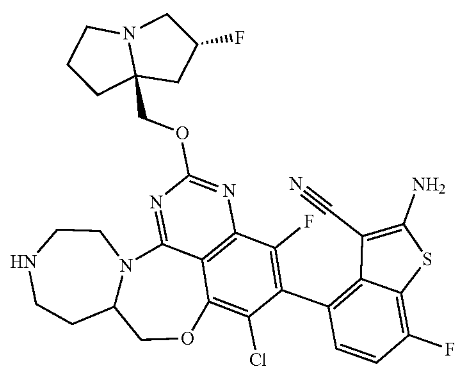 [SMILES: N#Cc1c(N)sc2c(F)ccc(-c3c(Cl)c4c5c(nc(OC[C@@]67CCCN6C[C@H](F)C7)nc5c3F)N3CCNCCC3CO4)c12] | 2-amino-4-(6-chloro-4-fluoro-2-(((2R,7aS)-2-fluorotetrahydro-1H-pyrrolizin-7a(5H)-yl)methoxy)-8a,9,10,11,12,13-hexahydro-8H-[1,4]diazepino[7',1':3,4][1,4]oxazepino[5,6,7-de]quinazolin-5-yl)-7-fluorobenzo[b]thiophene-3-carbonitrile | 656.4 |
| 143 [1] | 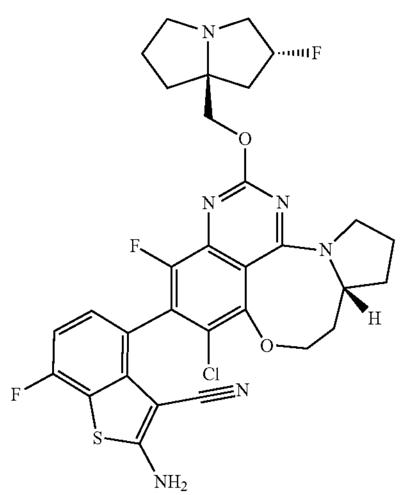 [SMILES: N#Cc1c(N)sc2c(F)ccc(-c3c(Cl)c4c5c(nc(OC[C@@]67CCCN6C[C@H](F)C7)nc5c3F)N3CCC[C@@H]3CCO4)c12] | 2-amino-4-((13aR)-10-chloro-8-fluoro-6-(((2R,7aS)-2-fluorotetrahydro-1H-pyrrolizin-7a(5H)-yl)methoxy)-1,2,3,12,13,13a-hexahydropyrrolo[1',2':5,6][1,5]oxazocino[4,3,2-de]quinazolin-9-yl)-7-fluorobenzo[b]thiophene-3-carbonitrile | 641.2 |

TABLE 1-continued

| No. | Structure | Chemical Name | [M + H]⁺ |
|---|---|---|---|
| 144 | 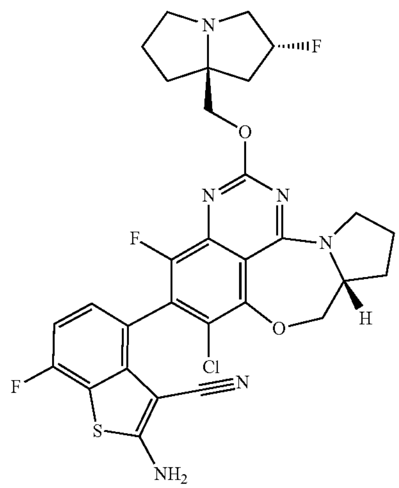 [SMILES: N#Cc1c(N)sc2c(F)ccc(-c3c(Cl)c4c5c(nc(OC[C@@]67CCCN6C[C@H](F)C7)nc5c3F)N3CCC[C@@H]3CO4)c12] | 2-amino-4-((12aR)-10-chloro-8-fluoro-6-(((2R,7aS)-2-fluorotetrahydro-1H-pyrrolizin-7a(5H)-yl)methoxy)-2,3,12,12a-tetrahydro-1H-pyrrolo[2',1':3,4][1,4]oxazepino[5,6,7-de]quinazolin-9-yl)-7-fluorobenzo[b]thiophene-3-carbonitrile | 627.4 |
| 145 [1] | 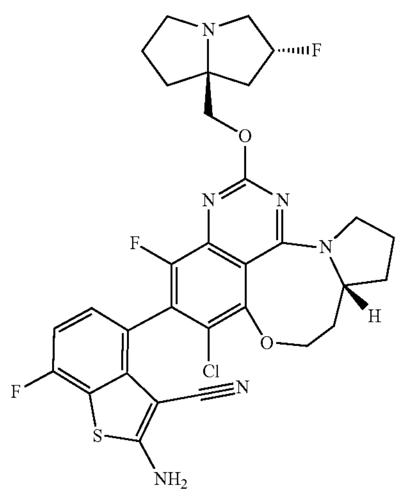 [SMILES: N#Cc1c(N)sc2c(F)ccc(-c3c(Cl)c4c5c(nc(OC[C@@]67CCCN6C[C@H](F)C7)nc5c3F)N3CCC[C@@H]3CCO4)c12] | 2-amino-4-((13aR)-10-chloro-8-fluoro-6-(((2R,7aS)-2-fluorotetrahydro-1H-pyrrolizin-7a(5H)-yl)methoxy)-1,2,3,12,13,13a-hexahydropyrrolo[1',2':5,6][1,5]oxazocino[4,3,2-de]quinazolin-9-yl)-7-fluorobenzo[b]thiophene-3-carbonitrile | 641.3 |
| 146 | 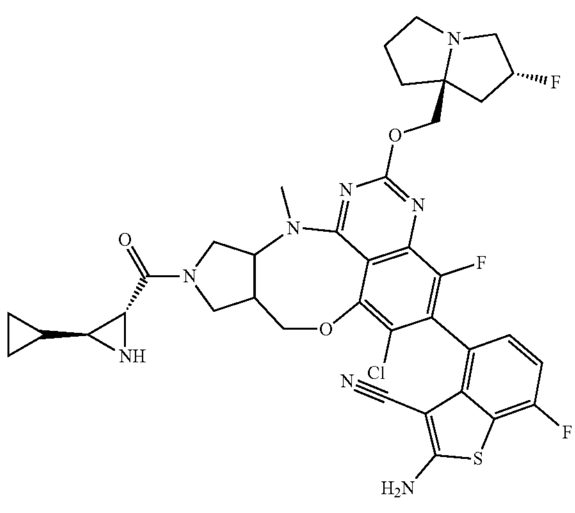 [SMILES: CN1c2nc(OC[C@@]34CCCN3C[C@H](F)C4)nc3c(F)c(-c4ccc(F)c5sc(N)c(C#N)c45)c(Cl)c(c23)OCC2CN(C(=O)[C@@H]3N[C@H]3C3CC3)CC21] | 2-amino-4-(6-chloro-10-((2R,3S)-3-cyclopropylaziridine-2-carbonyl)-4-fluoro-2-(((2R,7aS)-2-fluorotetrahydro-1H-pyrrolizin-7a(5H)-yl)methoxy)-12-methyl-8a,9,10,11,11a,12-hexahydro-8H-pyrrolo[3',4':6,7][1,5]oxazocino[4,3,2-de]quinazolin-5-yl)-7-fluorobenzo[b]thiophene-3-carbonitrile | 765.5 |

TABLE 1-continued

| No. | Structure | Chemical Name | [M + H]+ |
|---|---|---|---|
| 147 | 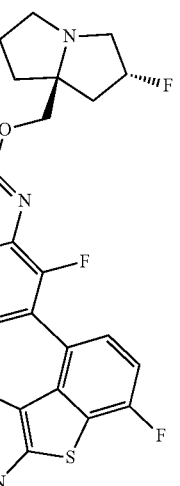 | 2-amino-4-(6-chloro-9-(2,2-difluoroacetyl)-4-fluoro-2-(((2R,7aS)-2-fluorotetrahydro-1H-pyrrolizin-7a(5H)-yl)methoxy)-11-methyl-7a,8,9,10,10a,11-hexahydropyrrolo[3',4':2,3][1,4]oxazepino[5,6,7-de]quinazolin-5-yl)-7-fluorobenzo[b]thiophene-3-carbonitrile | 720.3 |
| 148 [1] | 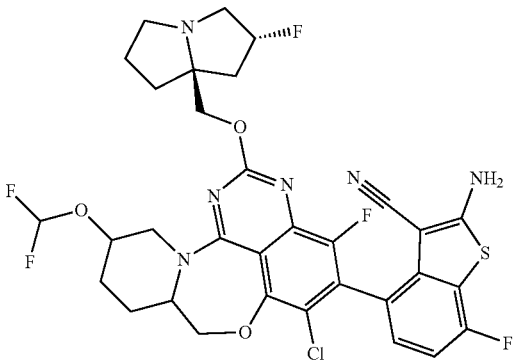 [SMILES: N#Cc1c(N)sc2c(F)ccc(-c3c(Cl)c4c5c(nc(OC[C@@]67CCCN6C[C@H](F)C7)nc5c3F)N3CC(OC(F)F)CCC3CO4)c12] | 2-amino-4-(6-chloro-11-(difluoromethoxy)-4-fluoro-2-(((2R,7aS)-2-fluorotetrahydro-1H-pyrrolizin-7a(5H)-yl)methoxy)-8,8a,9,10,11,12-hexahydropyrido[2',1':3,4][1,4]oxazepino[5,6,7-de]quinazolin-5-yl)-7-fluorobenzo[b]thiophene-3-carbonitrile | 707.2 |
| 149 | 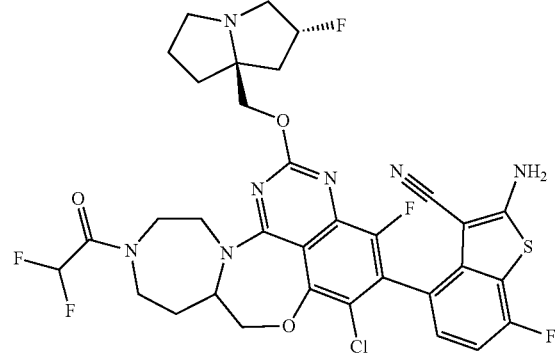 [SMILES: N#Cc1c(N)sc2c(F)ccc(-c3c(Cl)c4c5c(nc(OC[C@@]67CCCN6C[C@H](F)C7)nc5c3F)N3CCN(C(=O)C(F)F)CCC3CO4)c12] | 2-amino-4-(6-chloro-11-(2,2-difluoroacetyl)-4-fluoro-2-(((2R,7aS)-2-fluorotetrahydro-1H-pyrrolizin-7a(5H)-yl)methoxy)-8a,9,10,11,12,13-hexahydro-8H-[1,4]diazepino[7',1':3,4][1,4]oxazepino[5,6,7-de]quinazolin-5-yl)-7-fluorobenzo[b]thiophene-3-carbonitrile | 734.3 |
| 150 | 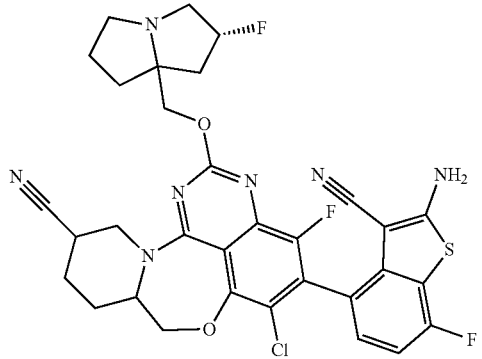 [SMILES: N#Cc1c(N)sc2c(F)ccc(-c3c(Cl)c4c5c(nc(OCC67CCCN6C[C@H](F)C7)nc5c3F)N3CC(C#N)CCC3CO4)c12] | 5-(2-amino-3-cyano-7-fluorobenzo[b]thiophen-4-yl)-6-chloro-4-fluoro-2-(((2R)-2-fluorotetrahydro-1H-pyrrolizin-7a(5H)-yl)methoxy)-8,8a,9,10,11,12-hexahydropyrido[2',1':3,4][1,4]oxazepino[5,6,7-de]quinazoline-11-carbonitrile | 666.35 |

TABLE 1-continued

| No. | Structure | Chemical Name | [M + H]+ |
|---|---|---|---|
| 151 | 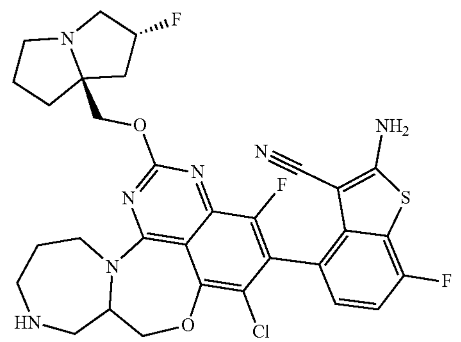 [SMILES: N#Cc1c(N)sc2c(F)ccc(-c3c(Cl)c4c5c(nc(OC[C@@]67CCCN6C[C@H](F)C7)nc5c3F)N3CCCNCC3CO4)c12] | 2-amino-4-(12-chloro-10-fluoro-8-(((2R,7aS)-2-fluorotetrahydro-1H-pyrrolizin-7a(5H)-yl)methoxy)-2,3,4,5,14,14a-hexahydro-1H-[1,4]diazepino[2',1':3,4][1,4]oxazepino[5,6,7-de]quinazolin-11-yl)-7-fluorobenzo[b]thiophene-3-carbonitrile | 656.3 |
| 152 | 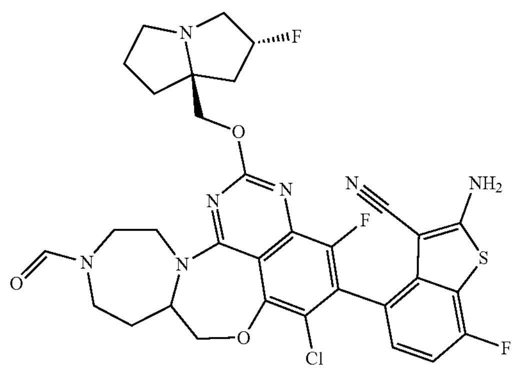 [SMILES: N#Cc1c(N)sc2c(F)ccc(-c3c(Cl)c4c5c(nc(OC[C@@]67CCCN6C[C@H](F)C7)nc5c3F)N3CCN(C=O)CCC3CO4)c12] | 2-amino-4-(6-chloro-4-fluoro-2-(((2R,7aS)-2-fluorotetrahydro-1H-pyrrolizin-7a(5H)-yl)methoxy)-11-formyl-8a,9,10,11,12,13-hexahydro-8H-[1,4]diazepino[7',1':3,4][1,4]oxazepino[5,6,7-de]quinazolin-5-yl)-7-fluorobenzo[b]thiophene-3-carbonitrile | 684.3 |
| 153 (diastereomer 1) | 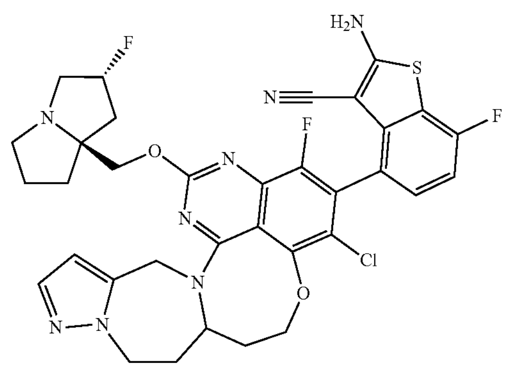 [SMILES: N#Cc1c(N)sc2c(F)ccc(-c3c(Cl)c4c5c(nc(OC[C@@]67CCCN6C[C@H](F)C7)nc5c3F)N3Cc5ccnn5CCC3CCO4)c12] | 2-amino-4-(3-chloro-1-fluoro-16-(((2R,7aS)-2-fluorotetrahydro-1H-pyrrolizin-7a(5H)-yl)methoxy)-6,6a,7,8-tetrahydro-5H,13H-pyrazolo[5'',1'':3',4'][1,4]diazepino[1',7':5,6][1,5]oxazocino[4,3,2-de]quinazolin-2-yl)-7-fluorobenzo[b]thiophene-3-carbonitrile | 707.2 |
| 154 | 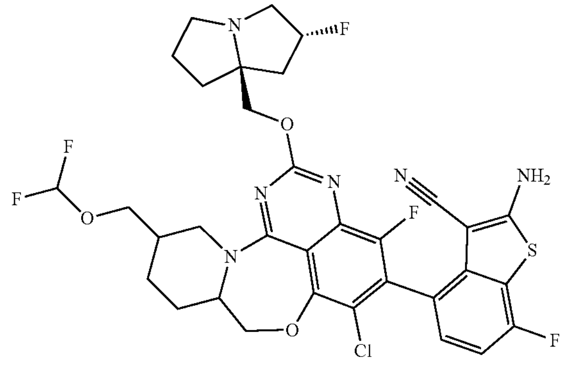 [SMILES: N#Cc1c(N)sc2c(F)ccc(-c3c(Cl)c4c5c(nc(OC[C@@]67CCCN6C[C@H](F)C7)nc5c3F)N3CC(COC(F)F)CCC3CO4)c12] | 2-amino-4-(6-chloro-11-((difluoromethoxy)methyl)-4-fluoro-2-(((2R,7aS)-2-fluorotetrahydro-1H-pyrrolizin-7a(5H)-yl)methoxy)-8,8a,9,10,11,12-hexahydropyrido[2',1':3,4][1,4]oxazepino[5,6,7-de]quinazolin-5-yl)-7-fluorobenzo[b]thiophene-3-carbonitrile | 721.2 |

TABLE 1-continued

| No. | Structure | Chemical Name | [M + H]+ |
|---|---|---|---|
| 155 | 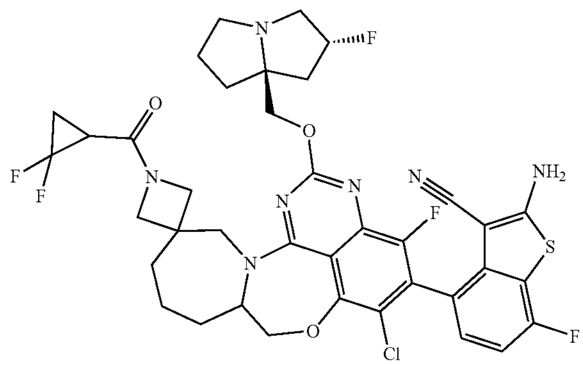 [SMILES: N#Cc1c(N)sc2c(F)ccc(-c3c(Cl)c4c5c(nc(OC[C@@]67CCCN6C[C@H](F)C7)nc5c3F)N3CC5(CCCC3CO4)CN(C(=O)C3CC3(F)F)C5)c12] | 2-amino-4-(6-chloro-1'-(2,2-difluorocyclopropane-1-carbonyl)-4-fluoro-2-(((2R,7aS)-2-fluorotetrahydro-1H-pyrrolizin-7a(5H)-yl)methoxy)-8a,9,10,11-tetrahydro-8H,13H-spiro[azepino[2',1':3,4][1,4]oxazepino[5,6,7-de]quinazoline-12,3'-azetidin]-5-yl)-7-fluorobenzo[b]thiophene-3-carbonitrile | 800.1 |
| 156 [1] | 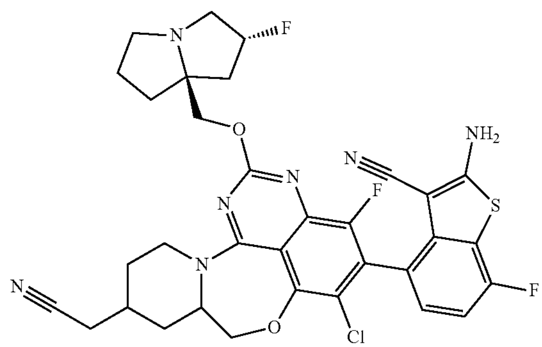 [SMILES: N#CCC1CCN2c3nc(OC[C@@]45CCCN4C[C@H](F)C5)nc4c(F)c(-c5ccc(F)c6sc(N)c(C#N)c56)c(Cl)c(c34)OCC2C1] | 2-amino-4-(3-chloro-7-(cyanomethyl)-1-fluoro-12-(((2R,7aS)-2-fluorotetrahydro-1H-pyrrolizin-7a(5H)-yl)methoxy)-5,5a,6,7,8,9-hexahydropyrido[2',1':3,4][1,4]oxazepino[5,6,7-de]quinazolin-2-yl)-7-fluorobenzo[b]thiophene-3-carbonitrile | 680.3 |
| 157 | 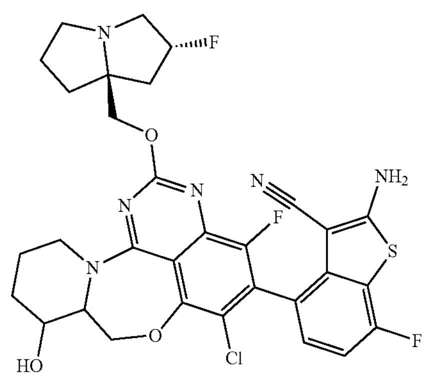 [SMILES: N#Cc1c(N)sc2c(F)ccc(-c3c(Cl)c4c5c(nc(OC[C@@]67CCCN6C[C@H](F)C7)nc5c3F)N3CCCC(O)C3CO4)c12] | 2-amino-4-(6-chloro-4-fluoro-2-(((2R,7aS)-2-fluorotetrahydro-1H-pyrrolizin-7a(5H)-yl)methoxy)-9-hydroxy-8,8a,9,10,11,12-hexahydropyrido[2',1':3,4][1,4]oxazepino[5,6,7-de]quinazolin-5-yl)-7-fluorobenzo[b]thiophene-3-carbonitrile | 657.2 |
| 158 | 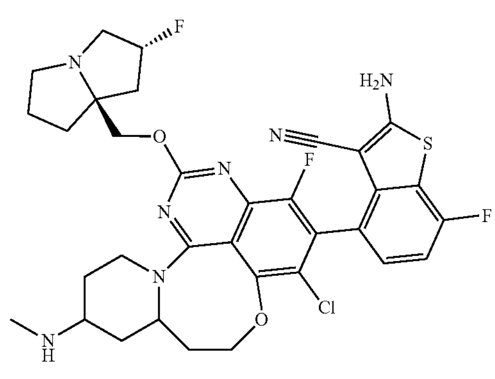 [SMILES: CNC1CCN2c3nc(OC[C@@]45CCCN4C[C@H](F)C5)nc4c(F)c(-c5ccc(F)c6sc(N)c(C#N)c56)c(Cl)c(c34)OCCC2C1] | 2-amino-4-(3-chloro-1-fluoro-13-(((2R,7aS)-2-fluorotetrahydro-1H-pyrrolizin-7a(5H)-yl)methoxy)-8-(methylamino)-6,6a,7,8,9,10-hexahydro-5H-pyrido[11,2':5,6][1,5]oxazocino[4,3,2-de]quinazolin-2-yl)-7-fluorobenzo[b]thiophene-3-carbonitrile | 684.2 |

TABLE 1-continued

| No. | Structure | Chemical Name | [M + H]+ |
|---|---|---|---|
| 159 | 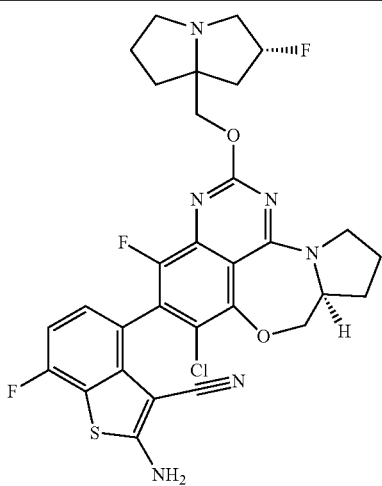 | 2-amino-4-((12aS)-10-chloro-8-fluoro-6-(((2R)-2-fluorotetrahydro-1H-pyrrolizin-7a(5H)-yl)methoxy)-2,3,12,12a-tetrahydro-1H-pyrrolo[2',1':3,4][1,4]oxazepino[5,6,7-de]quinazolin-9-yl)-7-fluorobenzo[b]thiophene-3-carbonitrile | 627.3 |
| 160 [1] | 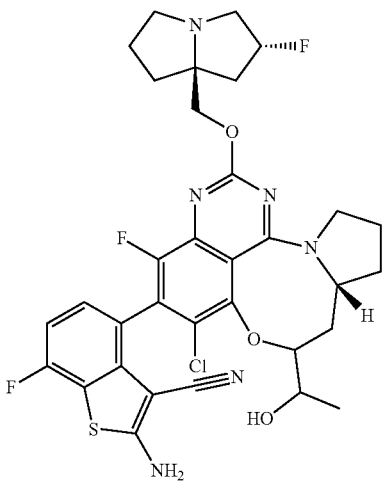 [SMILES: CC(O)C1C[C@H]2CCCN2c2nc(OC[C@@]34CCCN3C[C@H](F)C4)nc3c(F)c(-c4ccc(F)c5sc(N)c(C#N)c45)c(Cl)c(c23)O1] | 2-amino-4-((13aR)-10-chloro-8-fluoro-6-(((2R,7aS)-2-fluorotetrahydro-1H-pyrrolizin-7a(5H)-yl)methoxy)-12-(1-hydroxyethyl)-1,2,3,12,13,13a-hexahydropyrrolo[1',2':5,6][1,5]oxazocino[4,3,2-de]quinazolin-9-yl)-7-fluorobenzo[b]thiophene-3-carbonitrile | 685 |
| 161 | 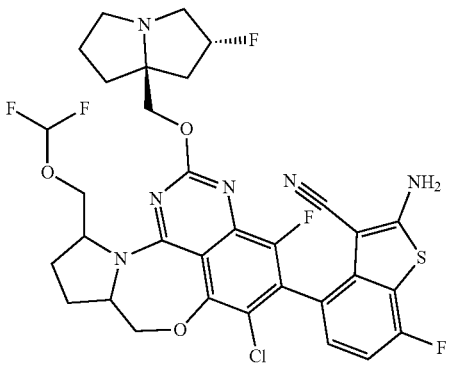 [SMILES: N#Cc1c(N)sc2c(F)ccc(-c3c(Cl)c4c5c(nc(OC[C@@]67CCCN6C[C@H](F)C7)nc5c3F)N3C(CCC3COC(F)F)CO4)c12] | 2-amino-4-(6-chloro-11-((difluoromethoxy)methyl)-4-fluoro-2-(((2R,7aS)-2-fluorotetrahydro-1H-pyrrolizin-7a(5H)-yl)methoxy)-8a,9,10,11-tetrahydro-8H-pyrrolo[2',1':3,4][1,4]oxazepino[5,6,7-de]quinazolin-5-yl)-7-fluorobenzo[b]thiophene-3-carbonitrile | 707.3 |

TABLE 1-continued

| No. | Structure | Chemical Name | [M + H]+ |
|---|---|---|---|
| 162 [1] | 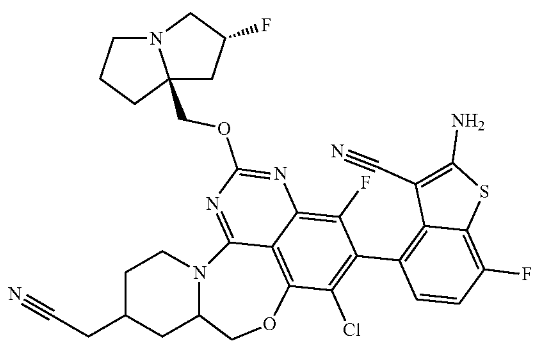 [SMILES: N#CCC1CCN2c3nc(OC[C@@]45CCCN4C[C@H](F)C5)nc4c(F)c(-c5ccc(F)c6sc(N)c(C#N)c56)c(Cl)c(c34)OCC2C1] | 2-amino-4-(3-chloro-7-(cyanomethyl)-1-fluoro-12-(((2R,7aS)-2-fluorotetrahydro-1H-pyrrolizin-7a(5H)-yl)methoxy)-5,5a,6,7,8,9-hexahydropyrido[2',1':3,4][1,4]oxazepino[5,6,7-de]quinazolin-2-yl)-7-fluorobenzo[b]thiophene-3-carbonitrile | 680.2 |
| 163 | 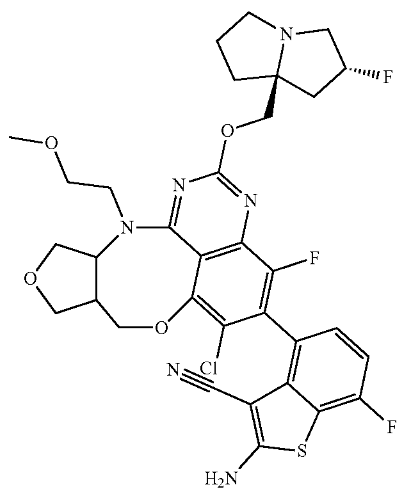 [SMILES: COCCN1c2nc(OC[C@@]34CCCN3C[C@H](F)C4)nc3c(F)c(-c4ccc(F)c5sc(N)c(C#N)c45)c(Cl)c(c23)OCC2COCC21] | 2-amino-4-(6-chloro-4-fluoro-2-(((2R,7aS)-2-fluorotetrahydro-1H-pyrrolizin-7a(5H)-yl)methoxy)-12-(2-methoxyethyl)-8a,9,11a,12-tetrahydro-8H,11H-furo[3',4':6,7][1,5]oxazocino[4,3,2-de]quinazolin-5-yl)-7-fluorobenzo[b]thiophene-3-carbonitrile | 701.3 |
| 164 | 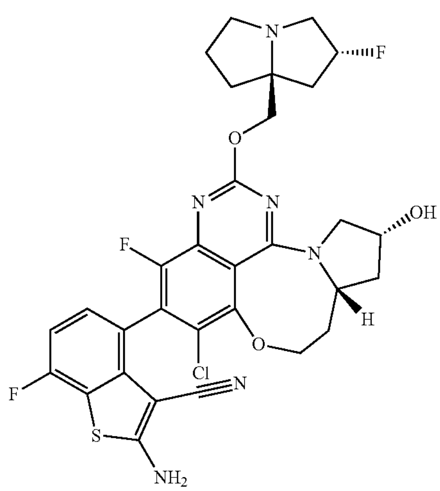 [SMILES: N#Cc1c(N)sc2c(F)ccc(-c3c(Cl)c4c5c(nc(OC[C@@]67CCCN6C[C@H](F)C7)nc5c3F)N3C[C@H](O)C[C@@H]3CCO4)c12] | 2-amino-4-((2R,13aS)-10-chloro-8-fluoro-6-(((2R,7aS)-2-fluorotetrahydro-1H-pyrrolizin-7a(5H)-yl)methoxy)-2-hydroxy-1,2,3,12,13,13a-hexahydropyrrolo[1',2':5,6][1,5]oxazocino[4,3,2-de]quinazolin-9-yl)-7-fluorobenzo[b]thiophene-3-carbonitrile | 657.4 |

TABLE 1-continued

| No. | Structure | Chemical Name | [M + H]⁺ |
|---|---|---|---|
| 165 | 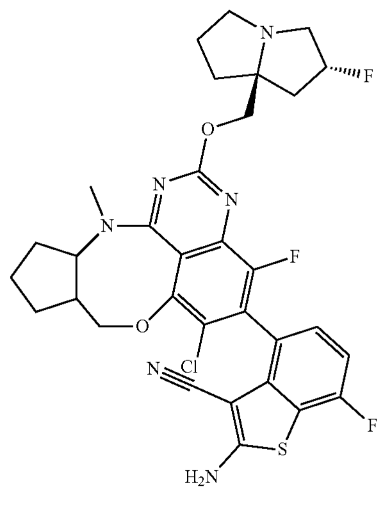 [SMILES: CN1c2nc(OC[C@@]34CCCN3C[C@H](F)C4)nc3c(F)c(-c4ccc(F)c5sc(N)c(C#N)c45)c(Cl)c(c23)OCC2CCCC21] | 2-amino-4-(6-chloro-4-fluoro-2-(((2R,7aS)-2-fluorotetrahydro-1H-pyrrolizin-7a(5H)-yl)methoxy)-12-methyl-8a,9,10,11,11a,12-hexahydro-8H-cyclopenta[6,7][1,5]oxazocino[4,3,2-de]quinazolin-5-yl)-7-fluorobenzo[b]thiophene-3-carbonitrile | 655.3 |
| 166 | 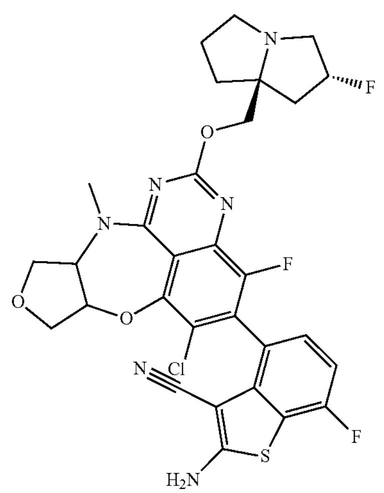 [SMILES: CN1c2nc(OC[C@@]34CCCN3C[C@H](F)C4)nc3c(F)c(-c4ccc(F)c5sc(N)c(C#N)c45)c(Cl)c(c23)OC2COCC21] | 2-amino-4-(6-chloro-4-fluoro-2-(((2R,7aS)-2-fluorotetrahydro-1H-pyrrolizin-7a(5H)-yl)methoxy)-11-methyl-7a,8,10a,11-tetrahydro-10H-furo[3',4':2,3][1,4]oxazepino[5,6,7-de]quinazolin-5-yl)-7-fluorobenzo[b]thiophene-3-carbonitrile | 643.2 |
| 167 | 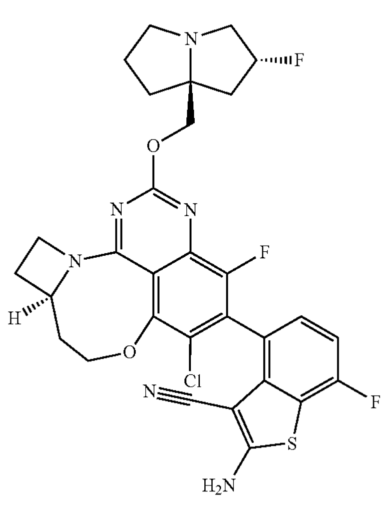 [SMILES: N#Cc1c(N)sc2c(F)ccc(-c3c(Cl)c4c5c(nc(OC[C@@]67CCCN6C[C@H](F)C7)nc5c3F)N3CC[C@@H]3CCO4)c12] | 2-amino-4-((12aR)-9-chloro-7-fluoro-5-(((2R,7aS)-2-fluorotetrahydro-1H-pyrrolizin-7a(5H)-yl)methoxy)-1,11,12,12a-tetrahydro-2H-azeto[1,2':5,6][1,5]oxazocino[4,3,2-de]quinazolin-8-yl)-7-fluorobenzo[b]thiophene-3-carbonitrile | 627.3 |

TABLE 1-continued

| No. | Structure | Chemical Name | [M + H]+ |
|---|---|---|---|
| 168 | 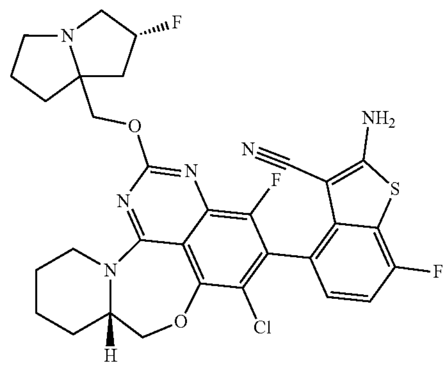 [SMILES: N#Cc1c(N)sc2c(F)ccc(-c3c(Cl)c4c5c(nc(OCC67CCCN6C[C@H](F)C7)nc5c3F)N3CCCC[C@H]3CO4)c12] | 2-amino-4-((5aS)-3-chloro-1-fluoro-12-(((2R)-2-fluorotetrahydro-1H-pyrrolizin-7a(5H)-yl)methoxy)-5,5a,6,7,8,9-hexahydropyrido[2',1':3,4][1,4]oxazepino[5,6,7-de]quinazolin-2-yl)-7-fluorobenzo[b]thiophene-3-carbonitrile | 641.4 |
| 169 [1] | 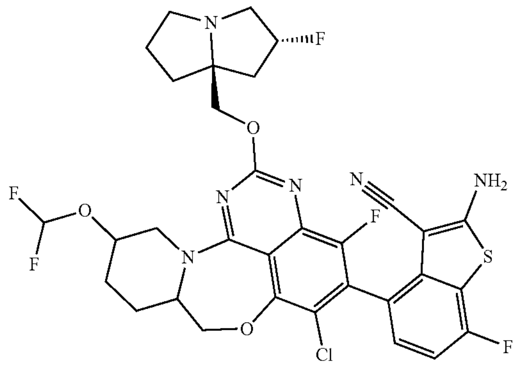 [SMILES: N#Cc1c(N)sc2c(F)ccc(-c3c(Cl)c4c5c(nc(OC[C@@]67CCCN6C[C@H](F)C7)nc5c3F)N3CC(OC(F)F)CCC3CO4)c12] | 2-amino-4-(6-chloro-11-(difluoromethoxy)-4-fluoro-2-(((2R,7aS)-2-fluorotetrahydro-1H-pyrrolizin-7a(5H)-yl)methoxy)-8,8a,9,10,11,12-hexahydropyrido[2',1':3,4][1,4]oxazepino[5,6,7-de]quinazolin-5-yl)-7-fluorobenzo[b]thiophene-3-carbonitrile | 707.3 |
| 170 | 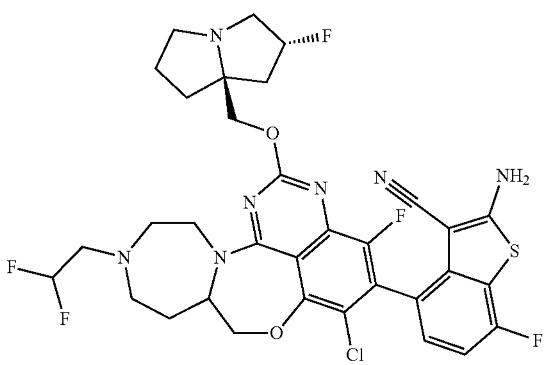 [SMILES: N#Cc1c(N)sc2c(F)ccc(-c3c(Cl)c4c5c(nc(OC[C@@]67CCCN6C[C@H](F)C7)nc5c3F)N3CCN(CC(F)F)CCC3CO4)c12] | 2-amino-4-(6-chloro-11-(2,2-difluoroethyl)-4-fluoro-2-(((2R,7aS)-2-fluorotetrahydro-1H-pyrrolizin-7a(5H)-yl)methoxy)-8a,9,10,11,12,13-hexahydro-8H-[1,4]diazepino[7',1':3,4][1,4]oxazepino[5,6,7-de]quinazolin-5-yl)-7-fluorobenzo[b]thiophene-3-carbonitrile | 720.3 |
| 171 | 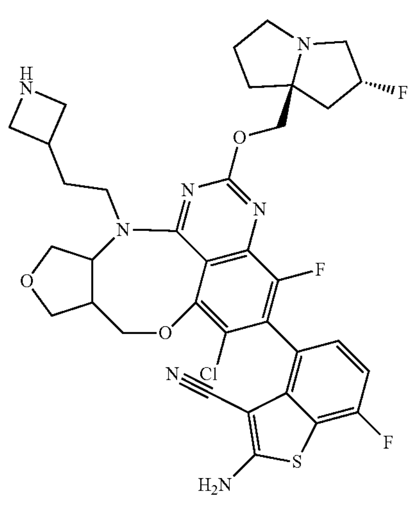 [SMILES: N#Cc1c(N)sc2c(F)ccc(-c3c(Cl)c4c5c(nc(OC[C@@]67CCCN6C[C@H](F)C7)nc5c3F)N(CCC3CNC3)C3COCC3CO4)c12] | 2-amino-4-(12-(2-(azetidin-3-yl)ethyl)-6-chloro-4-fluoro-2-(((2R,7aS)-2-fluorotetrahydro-1H-pyrrolizin-7a(5H)-yl)methoxy)-8a,9,11a,12-tetrahydro-8H,11H-furo[3',4':6,7][1,5]oxazocino[4,3,2-de]quinazolin-5-yl)-7-fluorobenzo[b]thiophene-3-carbonitrile | 726.3 |

TABLE 1-continued

| No. | Structure | Chemical Name | [M + H]+ |
|---|---|---|---|
| 172 | 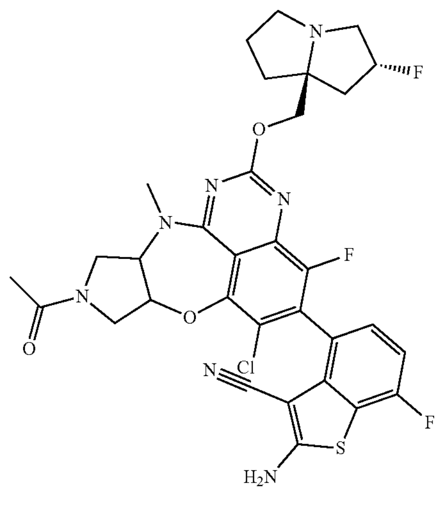 [SMILES: CC(=O)N1CC2Oc3c(Cl)c(-c4ccc(F)c5sc(N)c(C#N)c45)c(F)c4nc(OC[C@@]56CCCN5C[C@H](F)C6)nc(c34)N(C)C2C1] | 4-(9-acetyl-6-chloro-4-fluoro-2-(((2R,7aS)-2-fluorotetrahydro-1H-pyrrolizin-7a(5H)-yl)methoxy)-11-methyl-7a,8,9,10,10a,11-hexahydropyrrolo[3',4':2,3][1,4]oxazepino[5,6,7-de]quinazolin-5-yl)-2-amino-7-fluorobenzo[b]thiophene-3-carbonitrile | 684.2 |
| 173 (cis substitutions at azetidine) | 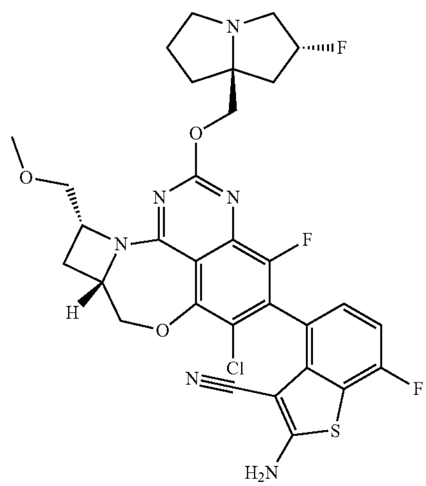 [SMILES: COC[C@H]1C[C@H]2COc3c(Cl)c(-c4ccc(F)c5sc(N)c(C#N)c45)c(F)c4nc(OC[C@@]56CCCN5C[C@H](F)C6)nc(c34)N21] | 2-amino-4-((8aS,10R)-6-chloro-4-fluoro-2-(((2R,7aS)-2-fluorotetrahydro-1H-pyrrolizin-7a(5H)-yl)methoxy)-10-(methoxymethyl)-8,8a,9,10-tetrahydroazeto[2',1':3,4][1,4]oxazepino[5,6,7-de]quinazolin-5-yl)-7-fluorobenzo[b]thiophene-3-carbonitrile | 657.3 |
| 175 | 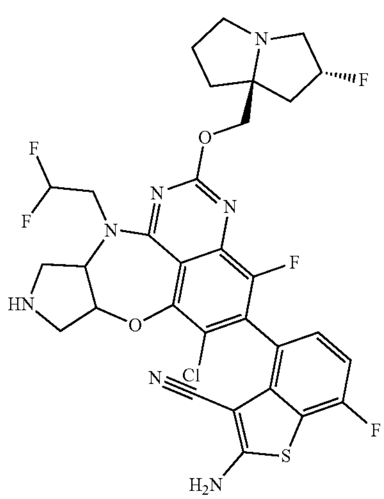 [SMILES: N#Cc1c(N)sc2c(F)ccc(-c3c(Cl)c4c5c(nc(OC[C@@]67CCCN6C[C@H](F)C7)nc5c3F)N(CC(F)F)C3CNCC3O4)c12] | 2-amino-4-(6-chloro-11-(2,2-difluoroethyl)-4-fluoro-2-(((2R,7aS)-2-fluorotetrahydro-1H-pyrrolizin-7a(5H)-yl)methoxy)-7a,8,9,10,10a,11-hexahydropyrrolo[3',4':2,3][1,4]oxazepino[5,6,7-de]quinazolin-5-yl)-7-fluorobenzo[b]thiophene-3-carbonitrile | 692.3 |

TABLE 1-continued

| No. | Structure | Chemical Name | [M + H]+ |
|---|---|---|---|
| 176 | 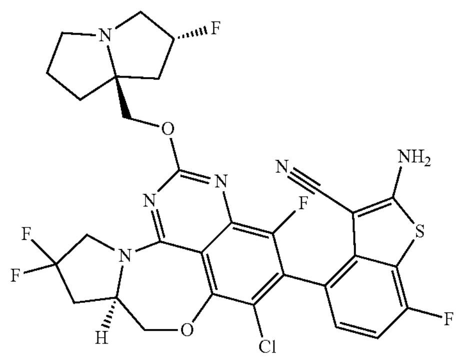 [SMILES: N#Cc1c(N)sc2c(F)ccc(-c3c(Cl)c4c5c(nc(OC[C@@]67CCCN6C[C@H](F)C7)nc5c3F)N3CC(F)(F)C[C@@H]3CO4)c12] | 2-amino-4-((8aR)-6-chloro-4,10,10-trifluoro-2-(((2R,7aS)-2-fluorotetrahydro-1H-pyrrolizin-7a(5H)-yl)methoxy)-8a,9,10,11-tetrahydro-8H-pyrrolo[2',1':3,4][1,4]oxazepino[5,6,7-de]quinazolin-5-yl)-7-fluorobenzo[b]thiophene-3-carbonitrile | 663.2 |
| 177 [1] | 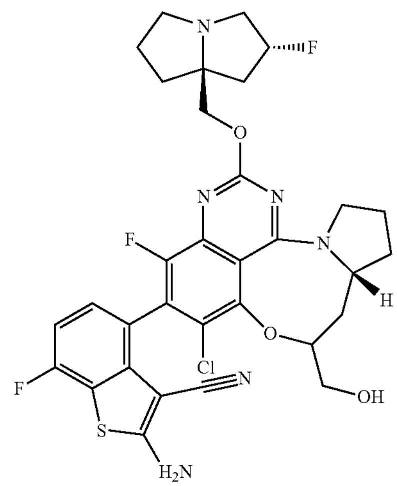 [SMILES: N#Cc1c(N)sc2c(F)ccc(-c3c(Cl)c4c5c(nc(OC[C@@]67CCCN6C[C@H](F)C7)nc5c3F)N3CCC[C@@H]3CC(CO)O4)c12] | 2-amino-4-((13aR)-10-chloro-8-fluoro-6-(((2R,7aS)-2-fluorotetrahydro-1H-pyrrolizin-7a(5H)-yl)methoxy)-12-(hydroxymethyl)-1,2,3,12,13,13a-hexahydropyrrolo[1',2':5,6][1,5]oxazocino[4,3,2-de]quinazolin-9-yl)-7-fluorobenzo[b]thiophene-3-carbonitrile | 671.1 |
| 178 | 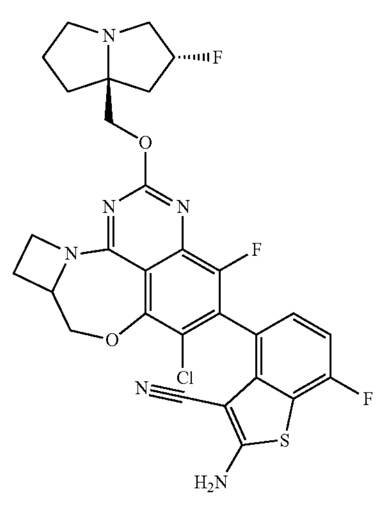 [SMILES: N#Cc1c(N)sc2c(F)ccc(-c3c(Cl)c4c5c(nc(OC[C@@]67CCCN6C[C@H](F)C7)nc5c3F)N3CCC3CO4)c12] | 2-amino-4-(6-chloro-4-fluoro-2-(((2R,7aS)-2-fluorotetrahydro-1H-pyrrolizin-7a(5H)-yl)methoxy)-8,8a,9,10-tetrahydroazeto[2',1':3,4][1,4]oxazepino[5,6,7-de]quinazolin-5-yl)-7-fluorobenzo[b]thiophene-3-carbonitrile | 613.3 |

TABLE 1-continued

| No. | Chemical Name | [M + H]+ |
|---|---|---|
| 179 (diastereomer 2) | 2-amino-4-((5a'S)-3'-chloro-1'-fluoro-12'-(((2R,7aS)-2-fluorotetrahydro-1H-pyrrolizin-7a(5H)-yl)methoxy)-2-isopropyl-5',5a',6',7'-tetrahydro-9'H-spiro[azetidine-3,8'-pyrido[2',1':3,4][1,4]oxazepino[5,6,7-de]quinazolin]-2'-yl)-7-fluorobenzo[b]thiophene-3-carbonitrile | 724.5 |
| 180 [1] | 2-amino-4-(((13aR)-10-chloro-8-fluoro-6-(((2R,7aS)-2-fluorotetrahydro-1H-pyrrolizin-7a(5H)-yl)methoxy)-12-(hydroxymethyl)-1,2,3,12,13,13a-hexahydropyrrolo[1',2':5,6][1,5]oxazocino[4,3,2-de]quinazolin-9-yl)-7-fluorobenzo[b]thiophene-3-carbonitrile | 671.1 |
| 181 | 2-amino-4-(((8aS)-6-chloro-4,10,10-trifluoro-2-(((2R,7aS)-2-fluorotetrahydro-1H-pyrrolizin-7a(5H)-yl)methoxy)-8a,9,10,11-tetrahydro-8H-pyrrolo[2',1':3,4][1,4]oxazepino[5,6,7-de]quinazolin-5-yl)-7-fluorobenzo[b]thiophene-3-carbonitrile | 663.2 |
| 182 | 2-amino-4-(6-chloro-4-fluoro-2-(((2R,7aS)-2-fluorotetrahydro-1H-pyrrolizin-7a(5H)-yl)methoxy)-11-methoxy-8,8a,9,10,11,12-hexahydropyrido[2',1':3,4][1,4]oxazepino[5,6,7-de]quinazolin-5-yl)-7-fluorobenzo[b]thiophene-3-carbonitrile | 671.2 |

TABLE 1-continued

| No. | Structure | Chemical Name | [M + H]+ |
|---|---|---|---|
| 183 | 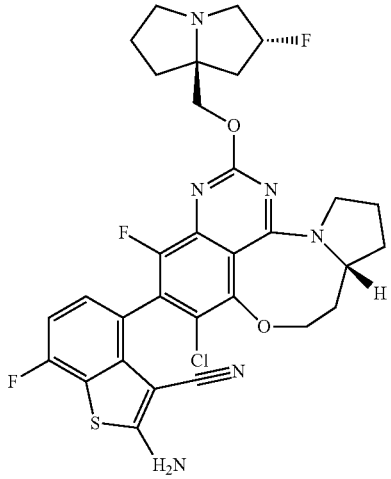 [SMILES: N#Cc1c(N)sc2c(F)ccc(-c3c(Cl)c4c5c(nc(OC[C@@]67CCCN6C[C@H](F)C7)nc5c3F)N3CCC[C@@H]3CCO4)c12] | 2-amino-4-((13aR)-10-chloro-8-fluoro-6-(((2R,7aS)-2-fluorotetrahydro-1H-pyrrolizin-7a(5H)-yl)methoxy)-1,2,3,12,13,13a-hexahydropyrrolo[1',2':5,6][1,5]oxazocino[4,3,2-de]quinazolin-9-yl)-7-fluorobenzo[b]thiophene-3-carbonitrile | 641.2 |
| 184 [1] | 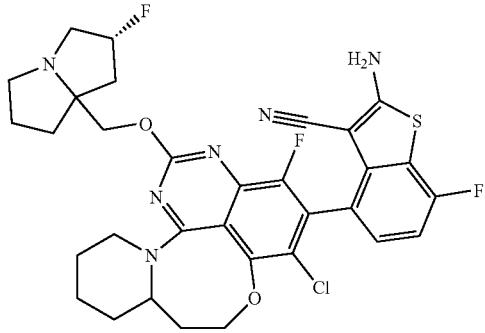 [SMILES: N#Cc1c(N)sc2c(F)ccc(-c3c(Cl)c4c5c(nc(OCC67CCCN6C[C@H](F)C7)nc5c3F)N3CCCCC3CCO4)c12] | 2-amino-4-(3-chloro-1-fluoro-13-(((2R)-2-fluorotetrahydro-1H-pyrrolizin-7a(5H)-yl)methoxy)-6,6a,7,8,9,10-hexahydro-5H-pyrido[11,2':5,6][1,5]oxazocino[4,3,2-de]quinazolin-2-yl)-7-fluorobenzo[b]thiophene-3-carbonitrile | 655.4 |
| 185 | 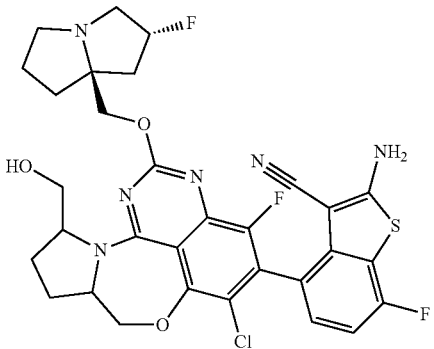 [SMILES: N#Cc1c(N)sc2c(F)ccc(-c3c(Cl)c4c5c(nc(OC[C@@]67CCCN6C[C@H](F)C7)nc5c3F)N3C(CO)CCC3CO4)c12] | 2-amino-4-(6-chloro-4-fluoro-2-(((2R,7aS)-2-fluorotetrahydro-1H-pyrrolizin-7a(5H)-yl)methoxy)-11-(hydroxymethyl)-8a,9,10,11-tetrahydro-8H-pyrrolo[2',1':3,4][1,4]oxazepino[5,6,7-de]quinazolin-5-yl)-7-fluorobenzo[b]thiophene-3-carbonitrile | 657.3 |

TABLE 1-continued

| No. | Structure | Chemical Name | [M + H]⁺ |
| --- | --- | --- | --- |
| 186 | 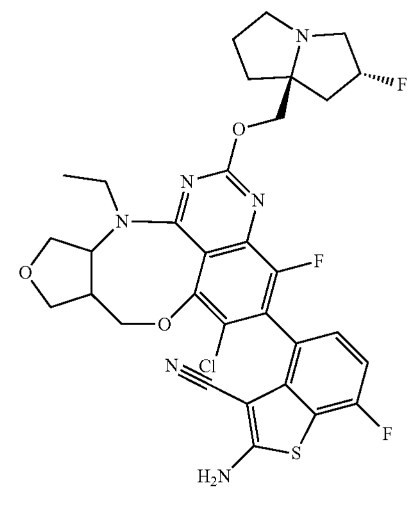 [SMILES: CCN1c2nc(OC[C@@]34CCCN3C[C@H](F)C4)nc3c(F)c(-c4ccc(F)c5sc(N)c(C#N)c45)c(Cl)c(c23)OCC2COCC21] | 2-amino-4-(6-chloro-12-ethyl-4-fluoro-2-(((2R,7aS)-2-fluorotetrahydro-1H-pyrrolizin-7a(5H)-yl)methoxy)-8a,9,11a,12-tetrahydro-8H,11H-furo[3',4':6,7][1,5]oxazocino[4,3,2-de]quinazolin-5-yl)-7-fluorobenzo[b]thiophene-3-carbonitrile | 671.4 |
| 187 | 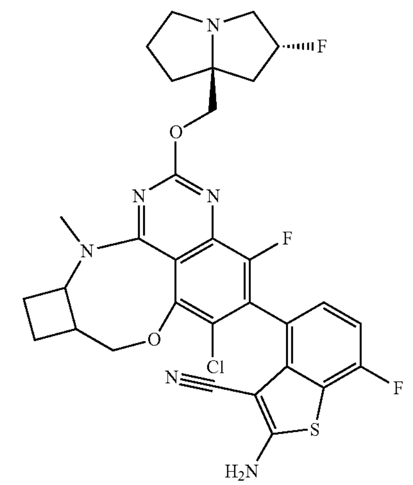 [SMILES: CN1c2nc(OC[C@@]34CCCN3C[C@H](F)C4)nc3c(F)c(-c4ccc(F)c5sc(N)c(C#N)c45)c(Cl)c(c23)OCC2CCC21] | 2-amino-4-(6-chloro-4-fluoro-2-(((2R,7aS)-2-fluorotetrahydro-1H-pyrrolizin-7a(5H)-yl)methoxy)-11-methyl-8,8a,9,10,10a,11-hexahydrocyclobuta[6,7][1,5]oxazocino[4,3,2-de]quinazolin-5-yl)-7-fluorobenzo[b]thiophene-3-carbonitrile | 641.3 |
| 188 | 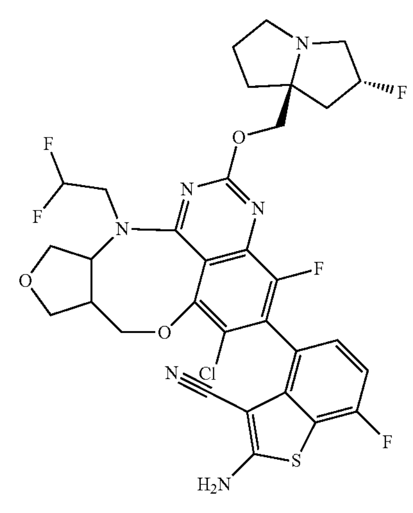 [SMILES: N#Cc1c(N)sc2c(F)ccc(-c3c(Cl)c4c5c(nc(OC[C@@]67CCCN6C[C@H](F)C7)nc5c3F)N(CC(F)F)C3COCC3CO4)c12] | 2-amino-4-(6-chloro-12-(2,2-difluoroethyl)-4-fluoro-2-(((2R,7aS)-2-fluorotetrahydro-1H-pyrrolizin-7a(5H)-yl)methoxy)-8a,9,11a,12-tetrahydro-8H,11H-furo[3',4':6,7][1,5]oxazocino[4,3,2-de]quinazolin-5-yl)-7-fluorobenzo[b]thiophene-3-carbonitrile\ | 707.2 |

TABLE 1-continued

| No. | Structure | Chemical Name | [M + H]+ |
|---|---|---|---|
| 189 | 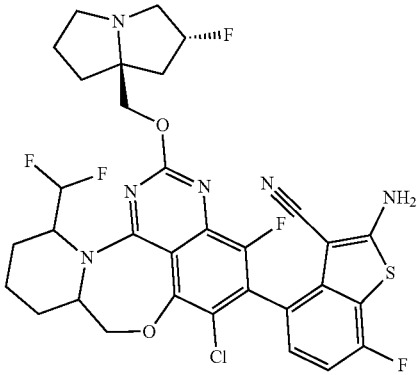 [SMILES: N#Cc1c(N)sc2c(F)ccc(-c3c(Cl)c4c5c(nc(OC[C@@]67CCCN6C[C@H](F)C7)nc5c3F)N3C(CCCC3C(F)F)CO4)c12] | 2-amino-4-(6-chloro-12-(difluoromethyl)-4-fluoro-2-(((2R,7aS)-2-fluorotetrahydro-1H-pyrrolizin-7a(5H)-yl)methoxy)-8,8a,9,10,11,12-hexahydropyrido[2',1':3,4][1,4]oxazepino[5,6,7-de]quinazolin-5-yl)-7-fluorobenzo[b]thiophene-3-carbonitrile | 691.2 |
| 190 [1] | 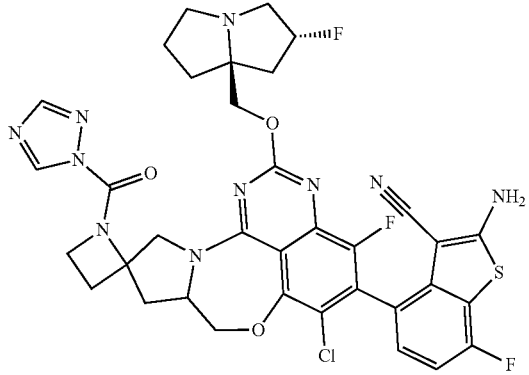 [SMILES: N#Cc1c(N)sc2c(F)ccc(-c3c(Cl)c4c5c(nc(OC[C@@]67CCCN6C[C@H](F)C7)nc5c3F)N3CC5(CCN5C(=O)n5cncn5)CC3CO4)c12] | 2-amino-4-(6'-chloro-4'-fluoro-2'-(((2R,7aS)-2-fluorotetrahydro-1H-pyrrolizin-7a(5H)-yl)methoxy)-1-(1H-1,2,4-triazole-1-carbonyl)-8a',9'-dihydro-8'H,11'H-spiro[azetidine-2,10'-pyrrolo[2',1':3,4][1,4]oxazepino[5,6,7-de]quinazolin]-5'-yl)-7-fluorobenzo[b]thiophene-3-carbonitrile | 763.3 |
| 191 | 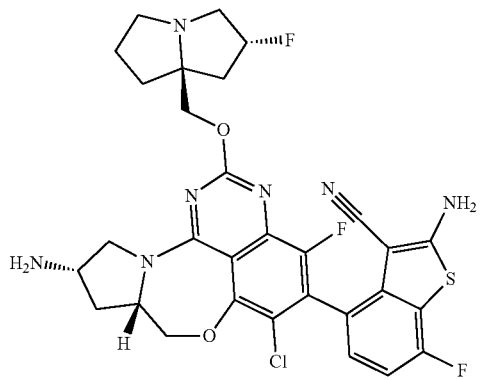 [SMILES: N#Cc1c(N)sc2c(F)ccc(-c3c(Cl)c4c5c(nc(OC[C@@]67CCCN6C[C@H](F)C7)nc5c3F)N3C[C@@H](N)C[C@H]3CO4)c12] | 2-amino-4-((8aS,10S)-10-amino-6-chloro-4-fluoro-2-(((2R,7aS)-2-fluorotetrahydro-1H-pyrrolizin-7a(5H)-yl)methoxy)-8a,9,10,11-tetrahydro-8H-pyrrolo[2',1':3,4][1,4]oxazepino[5,6,7-de]quinazolin-5-yl)-7-fluorobenzo[b]thiophene-3-carbonitrile | 642.3 |
| 192 | 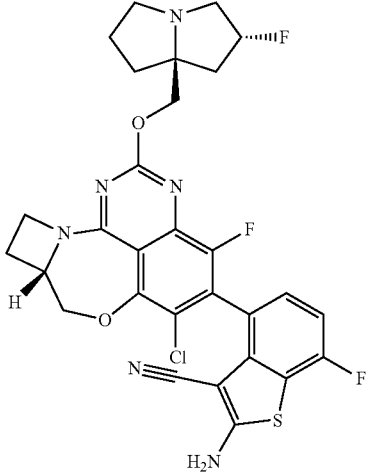 [SMILES: N#Cc1c(N)sc2c(F)ccc(-c3c(Cl)c4c5c(nc(OC[C@@]67CCCN6C[C@H](F)C7)nc5c3F)N3CC[C@H]3CO4)c12] | 2-amino-4-((11aS)-9-chloro-7-fluoro-5-(((2R,7aS)-2-fluorotetrahydro-1H-pyrrolizin-7a(5H)-yl)methoxy)-1,2,11,11a-tetrahydroazeto[2',1':3,4][1,4]oxazepino[5,6,7-de]quinazolin-8-yl)-7-fluorobenzo[b]thiophene-3-carbonitrile | 613.2 |

TABLE 1-continued

| No. | Structure | Chemical Name | [M + H]+ |
|---|---|---|---|
| 193 | 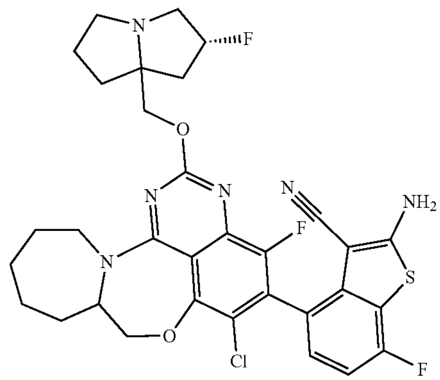 [SMILES: N#Cc1c(N)sc2c(F)ccc(-c3c(Cl)c4c5c(nc(OCC67CCCN6C[C@H](F)C7)nc5c3F)N3CCCCCC3CO4)c12] | 2-amino-4-(6-chloro-4-fluoro-2-(((2R)-2-fluorotetrahydro-1H-pyrrolizin-7a(5H)-yl)methoxy)-8a,9,10,11,12,13-hexahydro-8H-azepino[2',1':3,4][1,4]oxazepino[5,6,7-de]quinazolin-5-yl)-7-fluorobenzo[b]thiophene-3-carbonitrile | 655.3 |
| 194 | 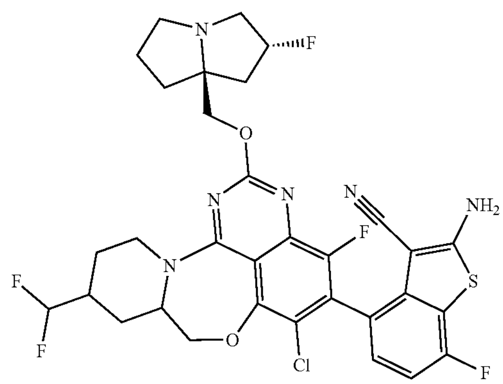 [SMILES: N#Cc1c(N)sc2c(F)ccc(-c3c(Cl)c4c5c(nc(OC[C@@]67CCCN6C[C@H](F)C7)nc5c3F)N3CCC(C(F)F)CC3CO4)c12] | 2-amino-4-(6-chloro-10-(difluoromethyl)-4-fluoro-2-(((2R,7aS)-2-fluorotetrahydro-1H-pyrrolizin-7a(5H)-yl)methoxy)-8,8a,9,10,11,12-hexahydropyrido[2',1':3,4][1,4]oxazepino[5,6,7-de]quinazolin-5-yl)-7-fluorobenzo[b]thiophene-3-carbonitrile | 691.2 |
| 195 | 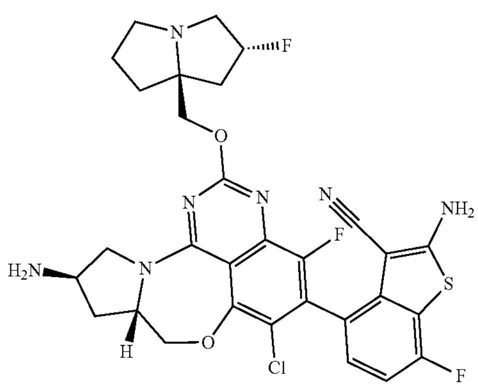 [SMILES: N#Cc1c(N)sc2c(F)ccc(-c3c(Cl)c4c5c(nc(OC[C@@]67CCCN6C[C@H](F)C7)nc5c3F)N3C[C@H](N)C[C@H]3CO4)c12] | 2-amino-4-((8aS,10R)-10-amino-6-chloro-4-fluoro-2-(((2R,7aS)-2-fluorotetrahydro-1H-pyrrolizin-7a(5H)-yl)methoxy)-8a,9,10,11-tetrahydro-8H-pyrrolo[2',1':3,4][1,4]oxazepino[5,6,7-de]quinazolin-5-yl)-7-fluorobenzo[b]thiophene-3-carbonitrile | 642.3 |
| 196 | 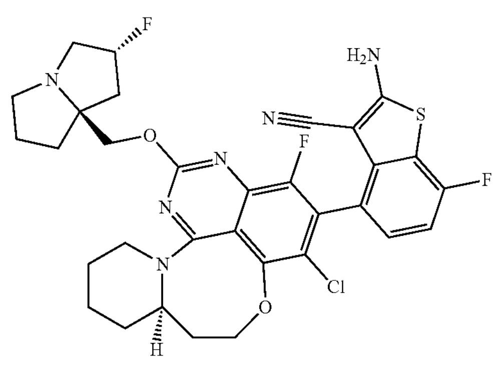 [SMILES: N#Cc1c(N)sc2c(F)ccc(-c3c(Cl)c4c5c(nc(OC[C@@]67CCCN6C[C@H](F)C7)nc5c3F)N3CCCC[C@@H]3CCO4)c12] | 2-amino-4-((6aR)-3-chloro-1-fluoro-13-(((2R,7aS)-2-fluorotetrahydro-1H-pyrrolizin-7a(5H)-yl)methoxy)-6,6a,7,8,9,10-hexahydro-5H-pyrido[11,2':5,6][1,5]oxazocino[4,3,2-de]quinazolin-2-yl)-7-fluorobenzo[b]thiophene-3-carbonitrile | 655.2 |

TABLE 1-continued

| No. | Structure | Chemical Name | [M + H]+ |
| --- | --- | --- | --- |
| 197 | 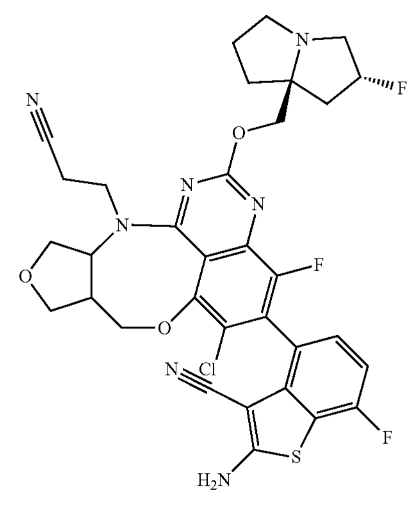 [SMILES: N#CCCN1c2nc(OC[C@@]34CCCN3C[C@H](F)C4)nc3c(F)c(-c4ccc(F)c5sc(N)c(C#N)c45)c(Cl)c(c23)OCC2COCC21] | 2-amino-4-(6-chloro-12-(2-cyanoethyl)-4-fluoro-2-(((2R,7aS)-2-fluorotetrahydro-1H-pyrrolizin-7a(5H)-yl)methoxy)-8a,9,11a,12-tetrahydro-8H,11H-furo[3',4':6,7][1,5]oxazocino[4,3,2-de]quinazolin-5-yl)-7-fluorobenzo[b]thiophene-3-carbonitrile | 696.4 |
| 198 | 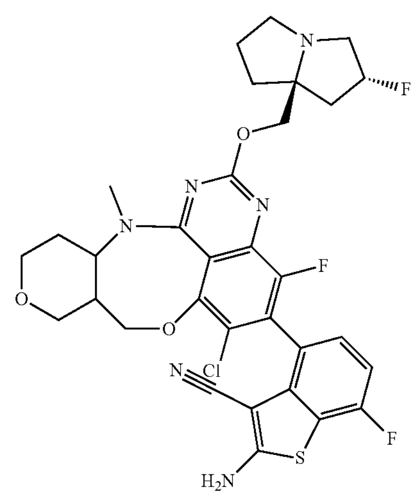 [SMILES: CN1c2nc(OC[C@@]34CCCN3C[C@H](F)C4)nc3c(F)c(-c4ccc(F)c5sc(N)c(C#N)c45)c(Cl)c(c23)OCC2COCCC21] | 2-amino-4-(6-chloro-4-fluoro-2-(((2R,7aS)-2-fluorotetrahydro-1H-pyrrolizin-7a(5H)-yl)methoxy)-13-methyl-8a,9,11,12,12a,13-hexahydro-8H-pyrano[4',3':6,7][1,5]oxazocino[4,3,2-de]quinazolin-5-yl)-7-fluorobenzo[b]thiophene-3-carbonitrile | 671.4 |
| 199 | 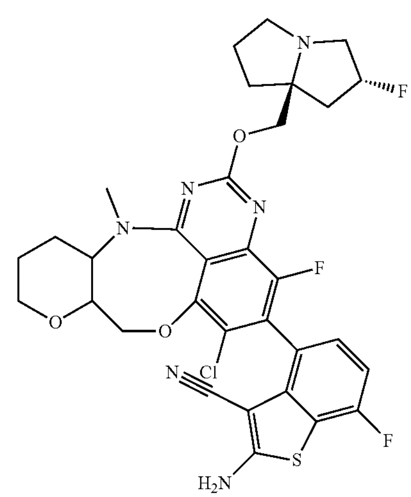 [SMILES: CN1c2nc(OC[C@@]34CCCN3C[C@H](F)C4)nc3c(F)c(-c4ccc(F)c5sc(N)c(C#N)c45)c(Cl)c(c23)OCC2OCCCC21] | 2-amino-4-(6-chloro-4-fluoro-2-(((2R,7aS)-2-fluorotetrahydro-1H-pyrrolizin-7a(5H)-yl)methoxy)-13-methyl-8,8a,11,12,12a,13-hexahydro-10H-pyrano[3',2':6,7][1,5]oxazocino[4,3,2-de]quinazolin-5-yl)-7-fluorobenzo[b]thiophene-3-carbonitrile | 671.3 |

TABLE 1-continued

| No. | Structure | Chemical Name | [M + H]⁺ |
|---|---|---|---|
| 200 | 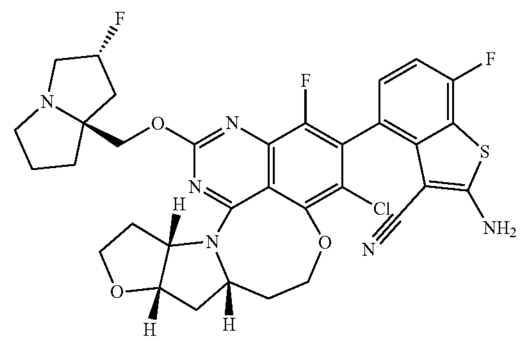 [SMILES: N#Cc1c(N)sc2c(F)ccc(-c3c(Cl)c4c5c(nc(OC[C@@]67CCCN6C[C@H](F)C7)nc5c3F)N3[C@H](CCO4)C[C@@H]4OCC[C@@H]43)c12] | 2-amino-4-((6aR,7aS,10aS)-3-chloro-1-fluoro-13-(((2R,7aS)-2-fluorotetrahydro-1H-pyrrolizin-7a(5H)-yl)methoxy)-5,6,6a,7,7a,9,10,10a-octahydrofuro[2'',3'':4',5']pyrrolo[1',2':5,6][1,5]oxazocino[4,3,2-de]quinazolin-2-yl)-7-fluorobenzo[b]thiophene-3-carbonitrile | 683.4 |
| 201 | 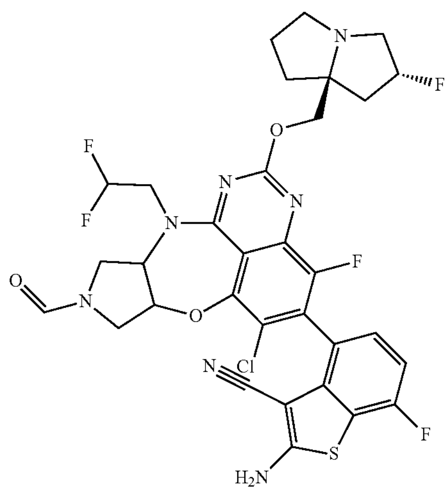 [SMILES: N#Cc1c(N)sc2c(F)ccc(-c3c(Cl)c4c5c(nc(OC[C@@]67CCCN6C[C@H](F)C7)nc5c3F)N(CC(F)F)C3CN(C=O)CC3O4)c12] | 2-amino-4-(6-chloro-11-(2,2-difluoroethyl)-4-fluoro-2-(((2R,7aS)-2-fluorotetrahydro-1H-pyrrolizin-7a(5H)-yl)methoxy)-9-formyl-7a,8,9,10,10a,11-hexahydropyrrolo[3',4':2,3][1,4]oxazepino[5,6,7-de]quinazolin-5-yl)-7-fluorobenzo[b]thiophene-3-carbonitrile | 720.4 |
| 202 [1] | 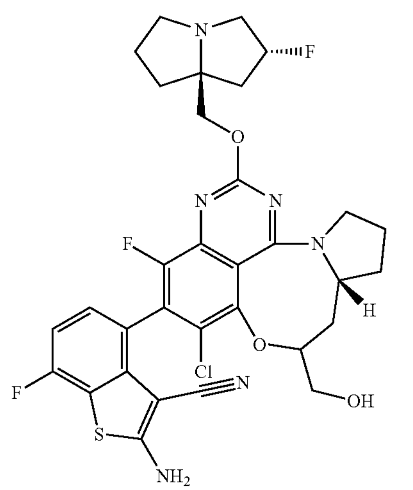 [SMILES: N#Cc1c(N)sc2c(F)ccc(-c3c(Cl)c4c5c(nc(OC[C@@]67CCCN6C[C@H](F)C7)nc5c3F)N3CCC[C@@H]3CC(CO)O4)c12] | 2-amino-4-((13aR)-10-chloro-8-fluoro-6-(((2R,7aS)-2-fluorotetrahydro-1H-pyrrolizin-7a(5H)-yl)methoxy)-12-(hydroxymethyl)-1,2,3,12,13,13a-hexahydropyrrolo[1',2':5,6][1,5]oxazocino[4,3,2-de]quinazolin-9-yl)-7-fluorobenzo[b]thiophene-3-carbonitrile | 671.1 |

TABLE 1-continued

| No. | Chemical Name | [M + H]+ |
|---|---|---|
| 203 | 2-amino-4-(6-chloro-4,10,10-trifluoro-2-(((2R,7aS)-2-fluorotetrahydro-1H-pyrrolizin-7a(5H)-yl)methoxy)-8,8a,9,10,11,12-hexahydropyrido[2',1':3,4][1,4]oxazepino[5,6,7-de]quinazolin-5-yl)-7-fluorobenzo[b]thiophene-3-carbonitrile | 677.5 |
| 204 | 2-amino-4-(6-chloro-11-(cyanomethyl)-4-fluoro-2-(((2R)-2-fluorotetrahydro-1H-pyrrolizin-7a(5H)-yl)methoxy)-8,8a,9,10,11,12-hexahydropyrido[2',1':3,4][1,4]oxazepino[5,6,7-de]quinazolin-5-yl)-7-fluorobenzo[b]thiophene-3-carbonitrile | 680.4 |
| 205 | 5-(2-amino-3-cyano-7-fluorobenzo[b]thiophen-4-yl)-6-chloro-4-fluoro-2-(((2R,7aS)-2-fluorotetrahydro-1H-pyrrolizin-7a(5H)-yl)methoxy)-8,8a,9,10,11,12-hexahydropyrido[2',1':3,4][1,4]oxazepino[5,6,7-de]quinazoline-10-carbonitrile | 666.3 |
| 206 (diastereomer 2) | 2-amino-4-(3-chloro-1-fluoro-16-(((2R,7aS)-2-fluorotetrahydro-1H-pyrrolizin-7a(5H)-yl)methoxy)-6,6a,7,8-tetrahydro-5H,13H-pyrazolo[5'',1'':3',4'][1,4]diazepino[1',7':5,6][1,5]oxazocino[4,3,2-de]quinazolin-2-yl)-7-fluorobenzo[b]thiophene-3-carbonitrile | 707.2 |

| No. | Structure | Chemical Name | [M + H]⁺ |
|---|---|---|---|
| 207 | 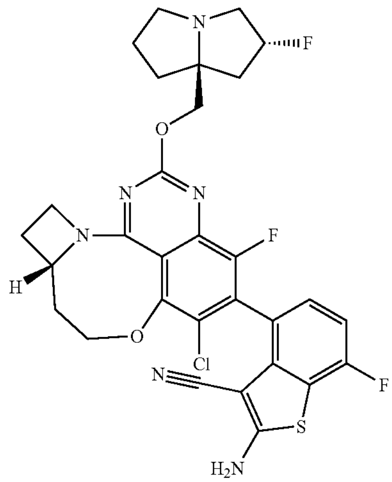 [SMILES: N#Cc1c(N)sc2c(F)ccc(-c3c(Cl)c4c5c(nc(OC[C@@]67CCCN6C[C@H](F)C7)nc5c3F)N3CC[C@H]3CCO4)c12] | 2-amino-4-((12aS)-9-chloro-7-fluoro-5-(((2R,7aS)-2-fluorotetrahydro-1H-pyrrolizin-7a(5H)-yl)methoxy)-1,11,12,12a-tetrahydro-2H-azeto[11,2':5,6][1,5]oxazocino[4,3,2-de]quinazolin-8-yl)-7-fluorobenzo[b]thiophene-3-carbonitrile | 627.3 |
| 208 | 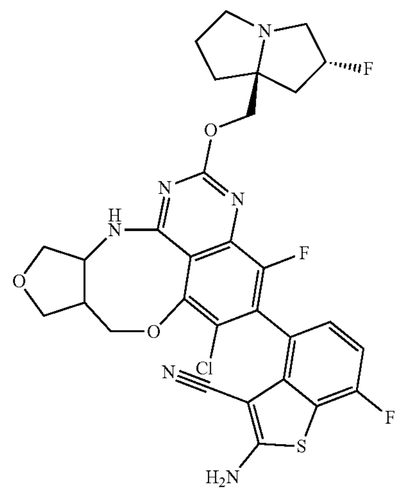 [SMILES: N#Cc1c(N)sc2c(F)ccc(-c3c(Cl)c4c5c(nc(OC[C@@]67CCCN6C[C@H](F)C7)nc5c3F)NC3COCC3CO4)c12] | 2-amino-4-(6-chloro-4-fluoro-2-(((2R,7aS)-2-fluorotetrahydro-1H-pyrrolizin-7a(5H)-yl)methoxy)-8a,9,11a,12-tetrahydro-8H,11H-furo[3',4':6,7][1,5]oxazocino[4,3,2-de]quinazolin-5-yl)-7-fluorobenzo[b]thiophene-3-carbonitrile | 643.3 |
| 209 | 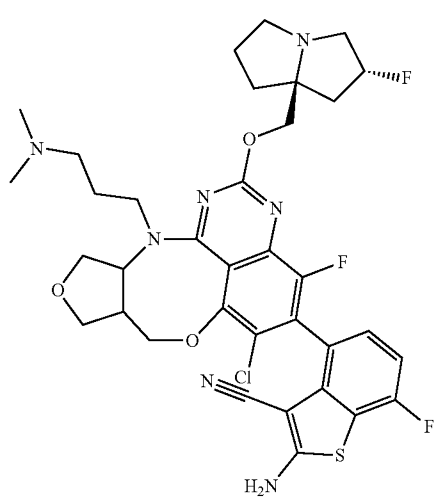 [SMILES: CN(C)CCCN1c2nc(OC[C@@]34CCCN3C[C@H](F)C4)nc3c(F)c(-c4ccc(F)c5sc(N)c(C#N)c45)c(Cl)c(c23)OCC2COCC21] | 2-amino-4-(6-chloro-12-(3-(dimethylamino)propyl)-4-fluoro-2-(((2R,7aS)-2-fluorotetrahydro-1H-pyrrolizin-7a(5H)-yl)methoxy)-8a,9,11a,12-tetrahydro-8H,11H-furo[3',4':6,7][1,5]oxazocino[4,3,2-de]quinazolin-5-yl)-7-fluorobenzo[b]thiophene-3-carbonitrile | 728.3 |

TABLE 1-continued

| No. | Structure | Chemical Name | [M + H]+ |
|---|---|---|---|
| 210 (cis substitutions at azetidine) | 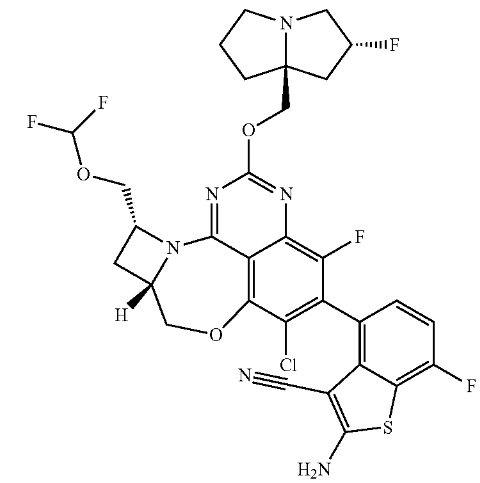 [SMILES: N#Cc1c(N)sc2c(F)ccc(-c3c(Cl)c4c5c(nc(OC[C@@]67CCCN6C[C@H](F)C7)nc5c3F)N3[C@H](CO4)C[C@@H]3COC(F)F)c12] | 2-amino-4-((8aS,10R)-6-chloro-10-((difluoromethoxy)methyl)-4-fluoro-2-(((2R,7aS)-2-fluorotetrahydro-1H-pyrrolizin-7a(5H)-yl)methoxy)-8,8a,9,10-tetrahydroazeto[2',1':3,4][1,4]oxazepino[5,6,7-de]quinazolin-5-yl)-7-fluorobenzo[b]thiophene-3-carbonitrile | 693.3 |
| 211 [1] | 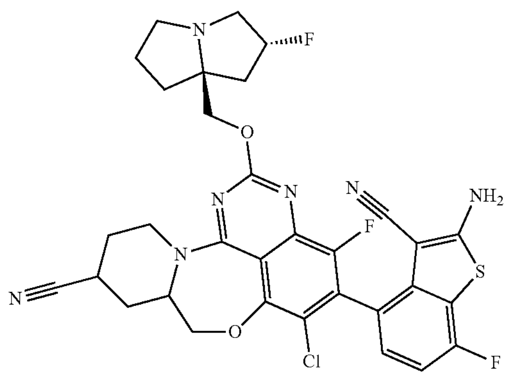 [SMILES: N#Cc1c(N)sc2c(F)ccc(-c3c(Cl)c4c5c(nc(OC[C@@]67CCCN6C[C@H](F)C7)nc5c3F)N3CCC(C#N)CC3CO4)c12] | 5-(2-amino-3-cyano-7-fluorobenzo[b]thiophen-4-yl)-6-chloro-4-fluoro-2-(((2R,7aS)-2-fluorotetrahydro-1H-pyrrolizin-7a(5H)-yl)methoxy)-8,8a,9,10,11,12-hexahydropyrido[2',1':3,4][1,4]oxazepino[5,6,7-de]quinazoline-10-carbonitrile | 666.2 |
| 212 [1] | 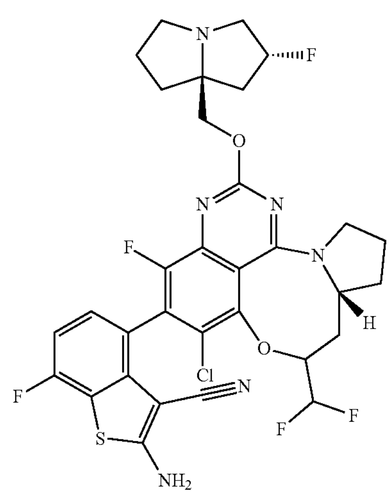 [SMILES: N#Cc1c(N)sc2c(F)ccc(-c3c(Cl)c4c5c(nc(OC[C@@]67CCCN6C[C@H](F)C7)nc5c3F)N3CCC[C@@H]3CC(C(F)F)O4)c12] | 2-amino-4-((13aR)-10-chloro-12-(difluoromethyl)-8-fluoro-6-(((2R,7aS)-2-fluorotetrahydro-1H-pyrrolizin-7a(5H)-yl)methoxy)-1,2,3,12,13,13a-hexahydropyrrolo[1',2':5,6][1,5]oxazocino[4,3,2-de]quinazolin-9-yl)-7-fluorobenzo[b]thiophene-3-carbonitrile | 691 |

TABLE 1-continued

| No. | Structure | Chemical Name | [M + H]+ |
|---|---|---|---|
| 213 [1] | 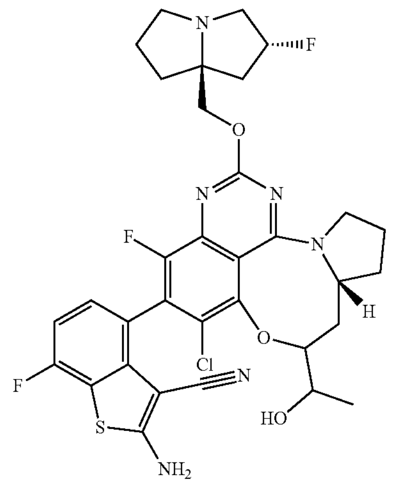 [SMILES: CC(O)C1C[C@H]2CCCN2c2nc(OC[C@@]34CCCN3C[C@H](F)C4)nc3c(F)c(-c4ccc(F)c5sc(N)c(C#N)c45)c(Cl)c(c23)O1] | 2-amino-4-((13aR)-10-chloro-8-fluoro-6-(((2R,7aS)-2-fluorotetrahydro-1H-pyrrolizin-7a(5H)-yl)methoxy)-12-(1-hydroxyethyl)-1,2,3,12,13,13a-hexahydropyrrolo[1',2':5,6][1,5]oxazocino[4,3,2-de]quinazolin-9-yl)-7-fluorobenzo[b]thiophene-3-carbonitrile | 685 |
| 214 | 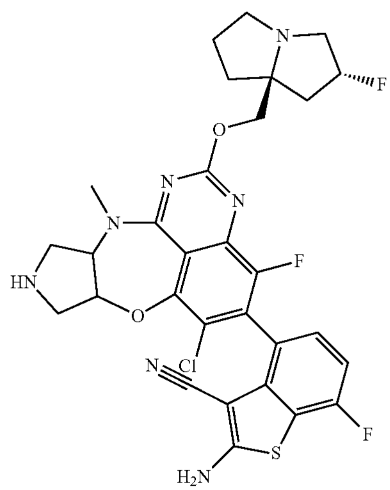 [SMILES: CN1c2nc(OC[C@@]34CCCN3C[C@H](F)C4)nc3c(F)c(-c4ccc(F)c5sc(N)c(C#N)c45)c(Cl)c(c23)OC2CNCC21] | 2-amino-4-(6-chloro-4-fluoro-2-(((2R,7aS)-2-fluorotetrahydro-1H-pyrrolizin-7a(5H)-yl)methoxy)-11-methyl-7a,8,9,10,10a,11-hexahydropyrrolo[3',4':2,3][1,4]oxazepino[5,6,7-de]quinazolin-5-yl)-7-fluorobenzo[b]thiophene-3-carbonitrile | 642.3 |
| 215 | 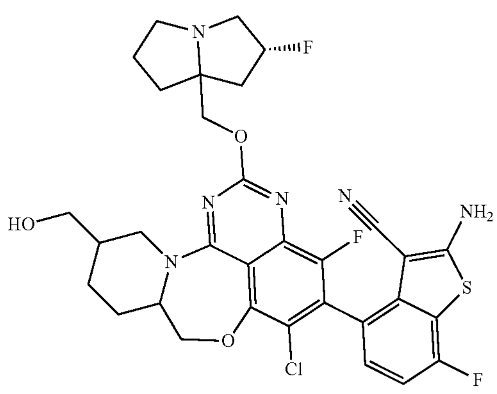 [SMILES: N#Cc1c(N)sc2c(F)ccc(-c3c(Cl)c4c5c(nc(OCC67CCCN6C[C@H](F)C7)nc5c3F)N3CC(CO)CCC3CO4)c12] | 2-amino-4-(6-chloro-4-fluoro-2-(((2R)-2-fluorotetrahydro-1H-pyrrolizin-7a(5H)-yl)methoxy)-11-(hydroxymethyl)-8,8a,9,10,11,12-hexahydropyrido[2',1':3,4][1,4]oxazepino[5,6,7-de]quinazolin-5-yl)-7-fluorobenzo[b]thiophene-3-carbonitrile | 671.3 |

[1] compound provided as partially purified isomer (e.g., HPLC purified as single peak, possible diastereomer/atropisomer purification without exact stereoisomer determination)
[2] compound provided as a single atropisomer (R)
[3] compound provided as a single atropisomer (S)
[4] Compound provided as a mixture of regioisomers (e.g., of optionally substituted imidazole, pyrazole, triazole, or tetrazole)
[5] Compound provided as a substantially pure single regioisomer (e.g., of optionally substituted imidazole, pyrazole, triazole, or tetrazole), though the structure provided has been tentatively assigned
[6] Compound provided as partially purified mixture of diastereomers and atropisomers
[7] Compound provided as tentatively assigned single diastereomer and single atropisomer It will be understood that when referring to one or more atropisomers of the compounds in the table above, the atropisomer is in reference to the orientation of the bonds attached to the atom of the substituent corresponding to the $R^7/R^{17}$ group of Formula (A) or B that is bonded to the $W^7$ atom of Formula (A) or B.

It will be understood that when two superscripted or parenthetical numbers above (e.g, 2 and 6) apply to a single compound and both numbers limit the same characteristic (e.g., atropisomer), the number with greater specificity will apply. For example, when a compound is classified as 2 and 6, the compound is a partially purified mixture of diastereomers and a single R atropisomer.

Unless indicated otherwise, when a compound of Table 1 may exist as atropisomers or diastereomers and a single isomer or limited mixture of isomers is not described in the chemical structure, name, or superscripted notes of Table 1, it will be understood that the compound may be provided as a mixture of two or more isomers. When two compounds are provided with identical chemical structures and/or names in Table 1 and the superscripted note or parenthetical note for each compound indicates a single atropisomer or partially purified mixture of isomers (e.g., diastereomers) without identifying the exact atropisomer or isomer (e.g., diastereomer), it will be understood that the two compounds are provided as different atropisomers, isomers (e.g., diastereomers), or partially purified mixtures of isomers.

In some instances, particularly for compounds denoted with a superscripted or parenthetical 4, two or more regioisomers may exist and the compound structures and corresponding chemical names provided have been tentatively assigned. In the preparation of certain compounds herein, such as compounds comprising a pyrazolyl, imidazolyl, triazolyl, or tetrazolyl, the starting material may exist in two or more tautomeric forms, thus the products may be isolated from the respective reaction mixtures as a single regioisomer or as a mixture of regioisomers that result from reaction with the two or more tautomeric forms of the starting material.

In some instances, particularly for compounds denoted with superscripted or parenthetical 5, one substantially pure regioisomer is provided and the compound structures and corresponding chemical names provided are tentatively assigned.

Unless indicated otherwise, where atropisomers of a compound are possible, the compound may be provided as a mixture of atropisomers. Unless indicated otherwise, where a compound includes a possible stereocenter (e.g., spirocyclic stereocenter) and no specific stereoisomer(s) is depicted, the compound may be provided as a mixture of stereoisomers.

Methods

The compounds described herein, or a pharmaceutically acceptable salt or solvate thereof, are Ras inhibitors capable of inhibiting a Ras protein. Ras proteins being inhibited can be Ras mutants (e.g., G12C, G12D, G12S, G1V, G13C, or G13D) from K-Ras, H-Ras or N-Ras. The compounds, a pharmaceutically acceptable salt or solvate thereof disclosed herein, have a wide range of applications in therapeutics, diagnostics, and other biomedical research.

In an aspect is provided a method of treating cancer in a subject in need thereof, comprising administering to the subject a therapeutically effective amount of a compound described herein, or a pharmaceutically acceptable salt or solvate thereof.

In an aspect is provided a method of treating cancer in a subject comprising a Ras mutant (e.g., G12C, G12D, G12S, G1V, G13C, or G13D) protein, comprising inhibiting the Ras mutant (e.g., G12C, G12D, G12S, G1V, G13C, or G13D) protein of said subject by administering to said subject a compound, wherein compound is characterized in that upon contacting the Ras mutant (e.g., G12C, G12D, G12S, G1V, G13C, or G13D) protein, said the Ras mutant (e.g., G12C, G12D, G12S, G1V, G13C, or G13D) protein activity or function is inhibited (e.g., partially inhibited or completely inhibited), such that said inhibited Ras mutant (e.g., G12C, G12D, G12S, G1V, G13C, or G13D) protein exhibits reduced Ras signaling output (e.g., compared to a corresponding Ras protein not contacted by the compound).

In an aspect is provided a method of modulating activity of a Ras protein (e.g., K-Ras, mutant K-Ras, G12C, G12D, G12S, G1V, G13C, or G13D), comprising contacting a Ras protein with an effective amount of a compound described herein, or a pharmaceutically acceptable salt or solvate thereof, thereby modulating the activity of the Ras protein.

In an aspect is provided a method of inhibiting cell growth, comprising administering an effective amount of a compound described herein, or a pharmaceutically acceptable salt or solvate thereof, to a cell expressing a Ras (e.g., K-Ras) protein, thereby inhibiting growth of said cells. In embodiments, the subject method comprises administering an additional agent to said cell.

In embodiments, the cancer is a solid tumor.

In embodiments, the cancer is a hematological cancer.

In practicing any of the methods disclosed herein, the Ras target to which a subject compound binds covalently can be a Ras mutant (e.g., G12C, G12D, G12S, G1V, G13C, or G13D), including a mutant of K-Ras, H-Ras, and N-Ras. In some embodiments, the methods of treating cancer can be applied to treat a solid tumor or a hematological cancer. In some embodiments, the cancer being treated can be, without limitation, prostate cancer, brain cancer, colon cancer, rectal cancer, renal-cell carcinoma, liver cancer, non-small cell carcinoma of the lung, cancer of the small intestine, cancer of the esophagus, melanoma, bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, Hodgkin's Disease, non-Hodgkin's lymphoma, cancer of the endocrine system, cancer of the thyroid gland, cancer of the parathyroid gland, cancer of the adrenal gland, sarcoma of soft tissue, cancer of the urethra, cancer of the penis, solid tumors of childhood, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers, combinations of said cancers, and metastatic lesions of said cancers. In some embodiments is a method of treating cancer in a subject in need thereof, comprising administering to the subject a therapeutically effective amount of a compound described herein, or a pharmaceutically acceptable salt or solvate thereof, wherein the cancer is a hematological cancer. In some embodiments is a method of treating cancer in a subject in need thereof, comprising administering to the subject a therapeutically effective amount of a compound described herein, or a pharmaceutically acceptable salt or solvate thereof, wherein the cancer is a hematological cancer selected from one or more of chronic lymphocytic leukemia (CLL), acute leukemias, acute lymphoid leukemia (ALL), B-cell acute lymphoid leukemia (B-ALL), T-cell acute lymphoid leukemia (T-ALL), chronic myelogenous leukemia (CML), B cell prolymphocytic leukemia, blastic plasmacytoid dendritic cell neoplasm, Burkitt's lymphoma, diffuse large B cell lymphoma, follicular lymphoma, hairy cell leukemia, small cell- or a large cell-follicular lymphoma, malignant lymphoproliferative conditions, MALT lymphoma, mantle cell lymphoma, marginal zone lymphoma, multiple myeloma, myelodysplasia and myelodysplastic syndrome, non-Hodgkin's lymphoma, Hodgkin's lymphoma, plasmablastic lymphoma, plasmacytoid dendritic cell neoplasm, Waldenstrom macroglobulinemia, and pre-leukemia. In some embodiments is a method of treating cancer in a subject in need thereof, comprising administering to the subject a therapeutically effective amount of a compound described herein, or a pharmaceutically acceptable salt or solvate thereof, wherein the cancer is one or more cancers selected from the group consisting of chronic lymphocytic leukemia (CLL), acute myeloid leukemia (AML), T-cell acute lymphoblastic leukemia (T-ALL), B cell acute lymphoblastic leukemia (B-ALL), and/or acute lymphoblastic leukemia (ALL).

Any of the treatment methods disclosed herein can be administered alone or in combination or in conjunction with another therapy or another agent. By "combination" it is meant to include (a) formulating a subject composition containing a subject compound together with another agent, and (b) using the subject composition separate from the another agent as an overall treatment regimen. By "conjunction" it is meant that the another therapy or agent is administered either simultaneously, concurrently or sequentially with a subject composition comprising a compound disclosed herein, with no specific time limits, wherein such conjunctive administration provides a therapeutic effect.

In some embodiment, a subject treatment method is combined with surgery, cellular therapy, chemotherapy, radiation, and/or immunosuppressive agents. Additionally, compositions of the present disclosure can be combined with other therapeutic agents, such as other anti-cancer agents, anti-allergic agents, anti-nausea agents (or anti-emetics), pain relievers, cytoprotective agents, immunostimulants, and combinations thereof.

In one embodiment, a subject treatment method is combined with a chemotherapeutic agent.

Exemplary chemotherapeutic agents include an anthracycline (e.g., doxorubicin (e.g., liposomal doxorubicin)), a vinca alkaloid (e.g., vinblastine, vincristine, vindesine, vinorelbine), an alkylating agent (e.g., cyclophosphamide, decarbazine, melphalan, ifosfamide, temozolomide), an immune cell antibody (e.g., alemtuzamab, gemtuzumab, rituximab, ofatumumab, tositumomab, brentuximab), an antimetabolite (including, e.g., folic acid antagonists, pyrimidine analogs, purine analogs and adenosine deaminase inhibitors (e.g., fludarabine)), a TNFR glucocorticoid induced TNFR related protein (GITR) agonist, a proteasome inhibitor (e.g., aclacinomycin A, gliotoxin or bortezomib), an immunomodulator such as thalidomide or a thalidomide derivative (e.g., lenalidomide). Additional chemotherapeutic agents contemplated for use in combination include busulfan (Myleran®), busulfan injection (Busulfex®), cladribine (Leustatin®), cyclophosphamide (Cytoxan® or Neosar®), cytarabine, cytosine arabinoside (Cytosar-U®), cytarabine liposome injection (DepoCyt®), daunorubicin hydrochloride (Cerubidine®), daunorubicin citrate liposome injection (DaunoXome®), dexamethasone, doxorubicin hydrochloride (Adriamycin®, Rubex®), etoposide (Vepeside), fludarabine phosphate (Fludara®), hydroxyurea (Hydrea®), Idarubicin (Idamycin®), mitoxantrone (Novantrone®), Gemtuzumab Ozogamicin (Mylotarg®), anastrozole (Arimidex®), bicalutamide (Casodex®), bleomycin sulfate (Blenoxane®), busulfan injection (Busulfex®), capecitabine (Xeloda®), N4-pentoxycarbonyl-5-deoxy-5-fluorocytidine, carboplatin (Paraplatin®), carmustine (BiCNU®), chlorambucil (Leukeran®), cisplatin (Platinol®), dacarbazine (DTIC-Dome®), dactinomycin (Actinomycin D, Cosmegan), dexamethasone, docetaxel (Taxotere®), 5-fluorouracil (Adrucil®, Efudex®), flutamide (Eulexin®), tezacitibine, Gemcitabine (difluorodeoxycitidine), ifosfamide (IFEX®), irinotecan (Camptosar®), L-asparaginase (ELSPAR®), leucovorin calcium, melphalan (Alkeran®), 6-mercaptopurine (Purinethol®), methotrexate (Folex®), mitoxantrone (Novantrone®), mylotarg, paclitaxel (Taxol®), phoenix (Yttrium90/MX-DTPA), pentostatin, polifeprosan 20 with carmustine implant (Gliadel®), tamoxifen citrate (Nolvadex®), teniposide (Vumon®), 6-thioguanine, thiotepa, tirapazamine (Tirazone®), topotecan hydrochloride for injection (Hycamptin®), vinblastine (Velban®), vincristine (Oncovin®), and vinorelbine (Navelbine®).

Anti-cancer agents of particular interest for combinations with a compound of the present invention include: anthracyclines; alkylating agents; antimetabolites; drugs that inhibit either the calcium dependent phosphatase calcineurin or the p70S6 kinase FK506) or inhibit the p70S6 kinase; mTOR inhibitors; immunomodulators; anthracyclines; vinca alkaloids; proteosome inhibitors; GITR agonists; protein tyrosine phosphatase inhibitors; a CDK4 kinase inhibitor; a BTK inhibitor; a MKN kinase inhibitor; a DGK kinase inhibitor; or an oncolytic virus.

Exemplary antimetabolites include, without limitation, pyrimidine analogs, purine analogs and adenosine deaminase inhibitors): methotrexate (Rheumatrex®, Trexall®), 5-fluorouracil (Adrucil®, Efudex®, Fluoroplex®), floxuridine (FUDF®), cytarabine (Cytosar-U®, Tarabine PFS), 6-mercaptopurine (Puri-Nethol®)), 6-thioguanine (Thioguanine Tabloid®), fludarabine phosphate (Fludara®), pentostatin (Nipent®), pemetrexed (Alimta®), raltitrexed (Tomudex®), cladribine (Leustatin®), clofarabine (Clofarex®, Clolar®), azacitidine (Vidaza®), decitabine and gemcitabine (Gemzar®). Preferred antimetabolites include, cytarabine, clofarabine and fludarabine.

Exemplary alkylating agents include, without limitation, nitrogen mustards, ethylenimine derivatives, alkyl sulfonates, nitrosoureas and triazenes): uracil mustard (Aminouracil Mustard®, Chlorethaminacil®, Demethyldopan®, Desmethyldopan®, Haemanthamine®, Nordopan®, Uracil nitrogen Mustard®, Uracillost®, Uracilmostaza®, Uramustin®, Uramustine®), chlormethine (Mustargen®), cyclophosphamide (Cytoxan®, Neosar®, Clafen®, Endoxan®, Procytox®, Revimmune™), ifosfamide (Mitoxana®), melphalan (Alkeran®), Chlorambucil (Leukeran®), pipobroman (Amedel®, Vercyte®), triethylenemelamine (Hemel®, Hexalen®, Hexastat®), triethylenethiophosphoramine, Temozolomide (Temodar®), thiotepa (Thioplex®), busulfan (Busilvex®, Myleran®), carmustine (BiCNU®), lomustine (CeeNU®), streptozocin (Zanosar®), and Dacarbazine (DTIC-Dome®). Additional exemplary alkylating agents include, without limitation, Oxaliplatin (Eloxatin®); Temozolomide (Temodar® and Temodal®); Dactinomycin (also known as actinomycin-D, Cosmegen®); Melphalan (also known as L-PAM, L-sarcolysin, and phenylalanine mustard, Alkeran®); Altretamine (also known as hexamethylmelamine (HMM), Hexalen®); Carmustine (BiCNU®); Bendamustine (Treanda®); Busulfan (Busulfex® and Myleran®); Carboplatin (Paraplatin®); Lomustine (also known as CCNU, CeeNU®); Cisplatin (also known as CDDP, Platinol® and Platinol®-AQ); Chlorambucil (Leukeran®); Cyclophosphamide (Cytoxan® and Neosar®); Dacarbazine (also known as DTIC, DIC and imidazole carboxamide, DTIC-Dome®); Altretamine (also known as hexamethylmelamine (HMM), Hexalen®); Ifosfamide (Ifex®); Prednumustine; Procarbazine (Matulane®); Mechlorethamine (also known as nitrogen mustard, mustine and mechloroethamine hydrochloride, Mustargen®); Streptozocin (Zanosar®); Thiotepa (also known as thiophosphoamide, TESPA and TSPA, Thioplex®); Cyclophosphamide (Endoxan®, Cytoxan®, Neosar®, Procytox®, Revimmune®); and Bendamustine HCl (Treanda®).

In an aspect, compositions provided herein can be administered in combination with radiotherapy such as radiation. Whole body radiation may be administered at 12 Gy. A radiation dose may comprise a cumulative dose of 12 Gy to the whole body, including healthy tissues. A radiation dose may comprise from 5 Gy to 20 Gy. A radiation dose may be 5 Gy, 6 Gy, 7 Gy, 8 Gy, 9 Gy, 10 Gy, 11 Gy, 12, Gy, 13 Gy, 14 Gy, 15 Gy, 16 Gy, 17 Gy, 18 Gy, 19 Gy, or up to 20 Gy. Radiation may be whole body radiation or partial body radiation. In the case that radiation is whole body radiation it may be uniform or not uniform. For example, when radiation may not be uniform, narrower regions of a body such as the neck may receive a higher dose than broader regions such as the hips.

Where desirable, an immunosuppressive agent can be used in conjunction with a subject treatment method. Exemplary immunosuppressive agents include but are not limited to cyclosporin, azathioprine, methotrexate, mycophenolate, and FK506, antibodies, or other immunoablative agents such as CAMPATH, anti-CD3 antibodies (e.g., muromonab, otelixizumab) or other antibody therapies, cytoxin, fludarabine, cyclosporin, FK506, rapamycin, mycophenolic acid, steroids, FR901228, cytokines, and irradiation, peptide vaccine, and any combination thereof. In accordance with the presently disclosed subject matter, the above-described various methods can comprise administering at least one immunomodulatory agent. In certain embodiments, the at least one immunomodulatory agent is selected from the group consisting of immunostimulatory agents, checkpoint immune blockade agents (e.g., blockade agents or inhibitors of immune checkpoint genes, such as, for example, PD-1, IDO, TIM3, LAG3, TIGIT, BTLA, VISTA, ICOS, KIRs and CD39), radiation therapy agents, chemotherapy agents, and combinations thereof. In some embodiments, the immunostimulatory agents are selected from the group consisting of IL-12, an agonist costimulatory monoclonal antibody, and combinations thereof. In one embodiment, the immunostimulatory agent is IL-12. In some embodiments, the agonist costimulatory monoclonal antibody is selected from the group consisting of an anti-4-1BB antibody (e.g., urelumab, PF-05082566), an anti-OX40 antibody (pogalizumab, tavolixizumab, PF-04518600), an anti-ICOS antibody (BMS986226, MEDI-570, GSK3359609, JTX-2011), and combinations thereof. In one embodiment, the agonist costimulatory monoclonal antibody is an anti-4-1 BB antibody. In some embodiments, the checkpoint immune blockade agents are selected from the group consisting of anti-PD-L1 antibodies (atezolizumab, avelumab, durvalumab, BMS-936559), anti-CTLA-4 antibodies (e.g., tremelimumab, ipilimumab), anti-PD-1 antibodies (e.g., pembrolizumab, nivolumab), anti-LAG3 antibodies (e.g., C9B7W, 410C9), anti-B7-H3 antibodies (e.g., DS-5573a), anti-TIM3 antibodies (e.g., F38-2E2), and combinations thereof. In one embodiment, the checkpoint immune blockade agent is an anti-PD-L1 antibody. In some cases, a compound of the present disclosure can be administered to a subject in conjunction with (e.g., before, simultaneously or following) bone marrow transplantation, T cell ablative therapy using either chemotherapy agents such as, fludarabine, external-beam radiation therapy (XRT), cyclophosphamide, or antibodies such as OKT3 or CAMPATH. In some cases, expanded cells can be administered before or following surgery. Alternatively, compositions comprising a compound described herein can be administered with immunostimulants Immunostimulants can be vaccines, colony stimulating agents, interferons, interleukins, viruses, antigens, co-stimulatory agents, immunogenicity agents, immunomodulators, or immunotherapeutic agents. An immunostimulant can be a cytokine such as an interleukin. One or more cytokines can be introduced with modified cells provided herein. Cytokines can be utilized to boost function of modified T lymphocytes (including adoptively transferred tumor-specific cytotoxic T lymphocytes) to expand within a tumor microenvironment. In some cases, IL-2 can be used to facilitate expansion of the modified cells described herein. Cytokines such as IL-15 can also be employed. Other relevant cytokines in the field of immunotherapy can also be utilized, such as IL-2, IL-7, IL-12, IL-15, IL-21, or any combination thereof. An interleukin can be IL-2, or aldesleukin. Aldesleukin can be administered in low dose or high dose. A high dose aldesleukin regimen can involve administering aldesleukin intravenously every 8 hours, as tolerated, for up to about 14 doses at about 0.037 mg/kg (600,000 IU/kg). An immunostimulant (e.g., aldesleukin) can be administered within 24 hours after a cellular administration. An immunostimulant (e.g., aldesleukin) can be administered in as an infusion over about 15 minutes about every 8 hours for up to about 4 days after a cellular infusion. An immunostimulant (e.g., aldesleukin) can be administered at a dose from about 100,000 IU/kg, 200,000 IU/kg, 300,000 IU/kg, 400,000 IU/kg, 500,000 IU/kg, 600,000 IU/kg, 700,000 IU/kg, 800,000 IU/kg, 900,000 IU/kg, or up to about 1,000,000 IU/kg. In some cases, aldesleukin can be administered at a dose from about 100,000 IU/kg to 300,000 IU/kg, from 300,000 IU/kg to 500,000 IU/kg, from 500,000 IU/kg to 700,000 IU/kg, from 700,000 IU/kg to about 1,000,000 IU/kg.

In some embodiments, any of the compounds herein that is capable of binding a Ras protein (e.g., KRAS) to modulate activity of such Ras protein may be administered in combination or in conjunction with one or more pharmacologically active agents comprising (1) an inhibitor of MEK (e.g., MEK1, MEK2) or of mutants thereof (e.g., trametinib, cobimetinib, binimetinib, selumetinib, refametinib); (2) an inhibitor of epidermal growth factor receptor (EGFR) and/or of mutants thereof (e.g., afatinib, erlotinib, gefitinib, lapatinib, cetuximab panitumumab, osimertinib, olmutinib, EGF-816); (3) an immunotherapeutic agent (e.g., checkpoint immune blockade agents, as disclosed herein); (4) a taxane (e.g., paclitaxel, docetaxel); (5) an anti-metabolite (e.g. antifolates such as methotrexate, raltitrexed, pyrimidine analogues such as 5-fluorouracil (5-FU), ribonucleoside and deoxyribonucleoside analogues, capecitabine and gemcitabine, purine and adenosine analogues such as mercaptopurine, thioguanine, cladribine and pentostatin, cytarabine (ara C), fludarabine); (6) an inhibitor of FGFR1 and/or FGFR2 and/or FGFR3 and/or of mutants thereof (e.g., nintedanib); (7) a mitotic kinase inhibitor (e.g., a CDK4/6 inhibitor, such as, for example, palbociclib, ribociclib, abemaciclib); (8) an anti-angiogenic drug (e.g., an anti-VEGF antibody, such as, for example, bevacizumab); (9) a topoisomerase inhibitor (e.g. epipodophyllotoxins such as for example etoposide and etopophos, teniposide, amsacrin, topotecan, irinotecan, mitoxantrone); (10) a platinum-containing compound (e.g. cisplatin, oxaliplatin, carboplatin); (11) an inhibitor of ALK and/or of mutants thereof (e.g. crizotinib, alectinib, entrectinib, brigatinib); (12) an inhibitor of c-MET and/or of mutants thereof (e.g., K252a, SU11274, PHA665752, PF2341066); (13) an inhibitor of BCR-ABL and/or of mutants thereof (e.g., imatinib, dasatinib, nilotinib); (14) an inhibitor of ErbB2 (Her2) and/or of mutants thereof (e.g., afatinib, lapatinib, trastuzumab, pertuzumab); (15) an inhibitor of AXL and/or of mutants thereof (e.g., R428, amuvatinib, XL-880); (16) an inhibitor of NTRK1 and/or of mutants thereof (e.g., Merestinib); (17) an inhibitor of RET and/or of mutants thereof (e.g., BLU-667, Lenvatinib); (18) an inhibitor of A-Raf and/or B-Raf and/or C-Raf and/or of mutants thereof (RAF-709, LY-3009120); (19) an inhibitor of ERK and/or of mutants thereof (e.g., ulixertinib); (20) an MDM2 inhibitor (e.g., HDM-201, NVP-CGM097, RG-71 12, MK-8242, RG-7388, SAR405838, AMG-232, DS-3032, RG-7775, APG-115); (21) an inhibitor of mTOR (e.g., rapamycin, temsirolimus, everolimus, ridaforolimus); (22) an inhibitor of BET (e.g., I-BET 151, I-BET 762, OTX-015, TEN-010, CPI-203, CPI-0610, olionon, RVX-208, ABBC-744, LY294002, AZD5153, MT-1, MS645); (23) an inhibitor of IGF1/2 and/or of IGF1-R (e.g., xentuzumab, MEDI-573); (24) an inhibitor of CDK9 (e.g., DRB, flavopiridol, CR8, AZD 5438, purvalanol B, AT7519, dinaciclib, SNS-032); (25) an inhibitor of farnesyl transferase (e.g., tipifarnib); (26) an inhibitor of SHIP pathway including SHIP2 inhibitor, as well as SHIP1 inhibitors; (27) an inhibitor of SRC (e.g., dasatinib); (28) an inhibitor of JAK (e.g. tofacitinib); (29) a PAR$^{12}$ inhibitor (e.g. Olaparib, Rucaparib, Niraparib, Talazoparib), (30) a BTK inhibitor (e.g. Ibrutinib, Acalabrutinib, Zanubrutinib), (31) a ROS1 inhibitor (e.g., entrectinib), (32) an inhibitor of SHP pathway including SHP2 inhibitor (e.g., 6-(4-amino-4-methylpiperidin-1-yl)-3-(2,3-dichlorophenyl)pyrazin-2-amine, as well as SHP1 inhibitors, or (33) an inhibitor of Src, FLT3, HDAC, VEGFR, PDGFR, LCK, Bcr-Abl or AKT or (34) an inhibitor of KrasG12C mutant (e.g., including but not limited to AMG510, MRTX849, and any covalent inhibitors binding to the cysteine residue 12 of Kras, the structures of these compounds are publically known) (e.g., an inhibitor of Ras G12C as described in US20180334454, US20190144444, US20150239900, US10246424, US20180086753, WO2018143315, WO2018206539, WO20191107519, WO2019141250, WO2019150305, U.S. Pat. No. 9,862,701, US20170197945, US20180086753, U.S. Pat. No. 10,144,724, US20190055211, US20190092767, US20180127396, US20180273523, U.S. Pat. No. 10,280,172, US20180319775, US20180273515, US20180282307, US20180282308, WO2019051291, WO2019213526, WO2019213516, WO2019217691, WO2019241157, WO2019217307, WO2020047192, WO2017087528, WO2018218070, WO2018218069, WO2018218071, WO2020027083, WO2020027084, WO2019215203, WO2019155399, WO2020035031, WO2014160200, WO2018195349, WO2018112240, WO2019204442, WO2019204449, WO2019104505, WO2016179558, WO2016176338, or related patents and applications, each of which is incorporated by reference in its entirety),), (35) a SHC inhibitor (e.g., PP2, AID371185), (36) a GAB inhibitor (e.g., GAB-0001), (37) a GRB inhibitor, (38) a PI-3 kinase inhibitor (e.g., Idelalisib, Copanlisib, Duvelisib, Alpelisib, Taselisib, Perifosine, Buparlisib, Umbralisib, NVP-BEZ235-AN), (39) a MARPK inhibitor, (40) CDK4/6 (e.g., palbociclib, ribociclib, abemaciclib), or (41) MAPK inhibitor (e.g., VX-745, VX-702, RO-4402257, SCIO-469, BIRB-796, SD-0006, PH-797804, AMG-548, LY2228820, SB-681323, GW-856553, RWJ67657, BCT-197), or (42) an inhibitor of SHP pathway including SHP2 inhibitor (e.g., 6-(4-amino-4-methylpiperidin-1-yl)-3-(2,3-dichlorophenyl) pyrazin-2-amine, RMC-4630, ERAS-601,

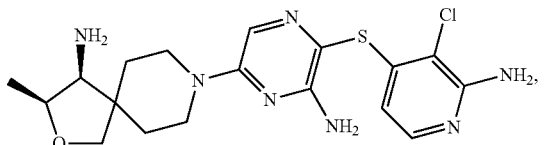

TNO155

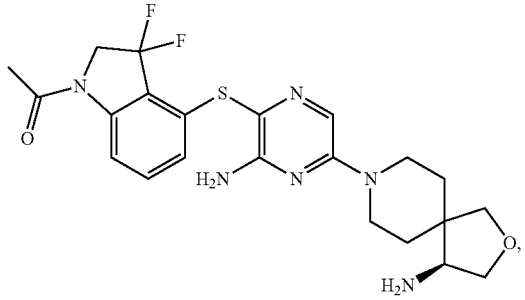

JAB-3068

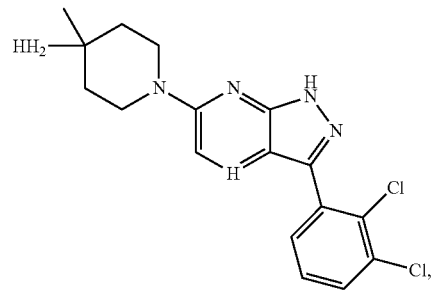

IACS-13909/BBP-398

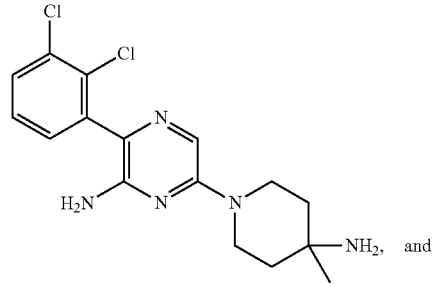

SHP099

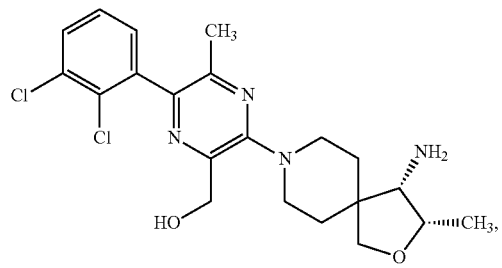

RMC-4550 as well as SHP1 inhibitors. In some embodiments, any of the compounds herein that is capable of binding a Ras protein (e.g., Kras) to modulate activity of such Ras protein may be administered in combination or in conjunction with one or more checkpoint immune blockade agents (e.g., anti-PD-1 and/or anti-PD-L1 antibody, anti-CLTA-4 antibody). In some embodiments, any of the compounds herein that is capable of binding a Ras protein (e.g., KRAS) to modulate activity of such Ras protein may be administered in combination or in conjunction with one or more pharmacologically active agents comprising an inhibitor against one or more targets selected from the group of: MEK, epidermal growth factor receptor (EGFR), FGFR1, FGFR2, FGFR3, mitotic kinase, topoisomerase, ALK, c-MET, ErbB2, AXL, NTRK1, RET, A-Raf, B-Raf, C-Raf, ERK, MDM2, mTOR, BET, IGF1/2, IGF1-R, CDK9, SHIP1, SHIP2, SHP2, SRC, JAK, PARP, BTK, FLT3, HDAC, VEGFR, PDGFR, LCK, Bcr-Abl, AKT, KrasG12C mutant, and ROS1. Where desired, the additional agent can be an inhibitor against one or more targets selected from the group of: MEK, epidermal growth factor receptor (EGFR), FGFR1, FGFR2, FGFR3, mitotic kinase, topoisomerase, ALK, c-MET, ErbB2, AXL, NTRK1, RET, A-Raf, B-Raf, C-Raf, ERK, MDM2, mTOR, BET, IGF1/2, IGF1-R, CDK9, SHP2, SRC, JAK, PARP, BTK, FLT3, HDAC, VEGFR, PDGFR, LCK, Bcr-Abl, AKT, KrasG12C mutant, and ROS1. In some embodiments, any of the compounds herein that is capable of binding a Ras protein (e.g., KRAS, mutant Ras protein) to modulate activity of such Ras mutant (e.g., G12C, G12D, G12S, G1V, G13C, or G13D) may be administered in combination or in conjunction with one or more additional pharmacologically active agents comprising an inhibitor of SOS (e.g., SOS1, SOS2) or of mutants thereof. In embodiments, the additional pharmacologically active agent administered in combination or in conjunction with a compound described herein (e.g., compound capable of binding a Ras protein) is an inhibitor of SOS (e.g., SOS1, SOS2). In embodiments, the additional pharmacologically active agent administered in combination or in conjunction with a compound (e.g., compound capable of binding a Ras protein) described herein is an inhibitor of SOS (e.g., SOS1, SOS2). In embodiments, the additional pharmacologically active agent administered in combination or in conjunction with a compound (e.g., compound capable of binding a Ras protein) described herein is an inhibitor of SOS (e.g., SOS1, SOS2) selected from RMC-5845, BI-1701963,

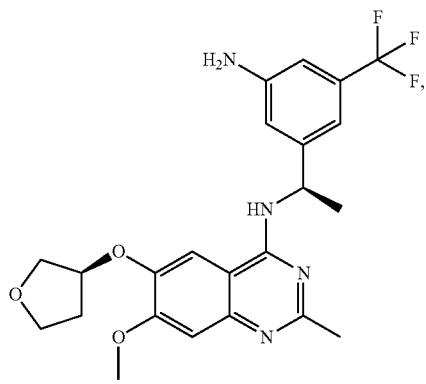

BI-3406

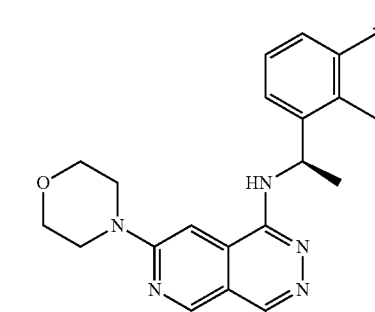

MRTX0902

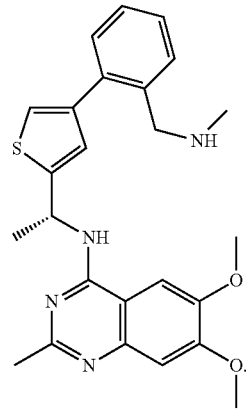

BAY 293

In embodiments, the additional pharmacologically active agent administered in combination or in conjunction with a compound described herein (e.g., compound capable of binding a Ras protein) is an inhibitor of SOS (e.g., SOS1, SOS2) described in WO2021092115, WO2018172250, WO2019201848, WO2019122129, WO2018115380, WO2021127429, WO2020180768, or WO2020180770, all of which are herein incorporated by reference in their entirety for all purposes.

In some embodiments, any of the compounds herein that is capable of binding a Ras protein (e.g., Kras) to modulate activity of such Ras protein may be administered in combination or in conjunction with one or more checkpoint immune blockade agents (e.g., anti-PD-1 and/or anti-PD-L1 antibody, anti-CLTA-4 antibody).

In some embodiments, any of the compounds described herein that is capable of binding a Ras protein (e.g., KRAS) may be administered in combination or in conjunction with one or more pharmacologically active agents comprising an inhibitor of: (1) SOS1 or a mutant thereof (e.g., RMC-5845, BI-3406, BAY-293, BI-1701963); (2) SHP2 or a mutant thereof (e.g., 6-(4-amino-4-methylpiperidin-1-yl)-3-(2,3-dichlorophenyl)pyrazin-2-amine, TN0155, RMC-4630, ERAS-601, JAB-3068, IACS-13909/BBP-398, SHP099, RMC-4550); (3) SHC or a mutant thereof (e.g., PP2, AID371185); (4) GAB or a mutant thereof (e.g., GAB-0001); (5) GRB or a mutant thereof; (6) JAK or a mutant thereof (e.g., tofacitinib); (7) A-RAF, B-RAF, C-RAF, or a mutant thereof (e.g., RAF-709, LY-3009120); (8) BRAF or a mutant thereof (e.g., sorafenib, vemurafenib, dabrafenib, encorafenib, regorafenib, GDC-879); (9) MEK or a mutant thereof (e.g., trametinib, cobimetinib, binimetinib, selumetinib, refametinib, AZD6244); (10) ERK or a mutant thereof (e.g., ulixertinib, MK-8353, LTT462, AZD0364, SCH772984, BIX02189, LY3214996, ravoxertinib); (11) PI3K or a mutant thereof (e.g., idelalisib, copanlisib, duvelisib, alpelisib, taselisib, perifosine, buparlisib, umbralisib, NVP-BEZ235-AN); (12) MAPK or a mutant thereof (e.g., VX-745, VX-702, RO-4402257, SCIO-469, BIRB-796, SD-0006, PH-797804, AMG-548, LY2228820, SB-681323, GW-856553, RWJ67657, BCT-197); (13) EGFR or a mutant thereof (e.g., afatinib, erlotinib, gefitinib, lapatinib, cetuximab panitumumab, osimertinib, olmutinib, EGF-816); (14) c-MET or a mutant thereof (e.g., K252a, SU11274, PHA665752, PF2341066); (15) ALK or a mutant thereof (e.g. crizotinib, alectinib, entrectinib, brigatinib); (16) FGFR1, FGFR-2, FGFR-3, FGFR-4 or a mutant thereof (e.g., nintedanib); (17) BCR-ABL or a mutant thereof (e.g., imatinib, dasatinib, nilotinib); (18) ErbB2 (Her2) or a mutant thereof (e.g., afatinib, lapatinib, trastuzumab, pertuzumab); (19) AXL or a mutant thereof (e.g., R428, amuvatinib, XL-880); (20) NTRK1 or a mutant thereof (e.g., merestinib); (21) ROS1 or a mutant thereof (e.g., entrectinib); (22) RET or a mutant thereof (e.g., BLU-667, Lenvatinib); (23) MDM2 or a mutant thereof (e.g., HDM-201, NVP-CGM097, RG-71 12, MK-8242, RG-7388, SAR405838, AMG-232, DS-3032, RG-7775, APG-115); (24) mTOR or a mutant thereof (e.g., rapamycin, temsirolimus, everolimus, ridaforolimus); (25) BET or a mutant thereof (e.g., I-BET 151, I-BET 762, OTX-015, TEN-010, CPI-203, CPI-0610, olionon, RVX-208, ABBC-744, LY294002, AZD5153, MT-1, MS645); (26) IGF1, IGF2, IGF1R, or a mutant thereof (e.g., xentuzumab, MEDI-573); (27) CDK9 or a mutant thereof (e.g., DRB, flavopiridol, CR8, AZD 5438, purvalanol B, AT7519, dinaciclib, SNS-032); or (28) CDK4/6 (e.g., palbociclib, ribociclib, abemaciclib).

In combination therapy, a compound provided herein and other anti-cancer agent(s) may be administered either simultaneously, concurrently or sequentially with no specific time limits, wherein such administration provides therapeutically effective levels of the two compounds in the body of the patient.

In some embodiments, the compound of the present disclosure and the other anti-cancer agent(s) are generally administered sequentially in any order by infusion or orally. The dosing regimen may vary depending upon the stage of the disease, physical fitness of the patient, safety profiles of the individual drugs, and tolerance of the individual drugs, as well as other criteria well-known to the attending physician and medical practitioner(s) administering the combination. The compound of the present invention and other anti-cancer agent(s) may be administered within minutes of each other, hours, days, or even weeks apart depending upon the particular cycle being used for treatment. In addition, the cycle could include administration of one drug more often than the other during the treatment cycle and at different doses per administration of the drug.

An antibiotic can be administered to a subject as part of a therapeutic regime. An antibiotic can be administered at a therapeutically effective dose. An antibiotic can kill or inhibit growth of bacteria. An antibiotic can be a broad spectrum antibiotic that can target a wide range of bacteria. Broad spectrum antibiotics, either a $3^{rd}$ or $4^{th}$ generation, can be cephalosporin or a quinolone. An antibiotic can also be a narrow spectrum antibiotic that can target specific types of bacteria. An antibiotic can target a bacterial cell wall such as penicillins and cephalosporins. An antibiotic can target a cellular membrane such as polymyxins. An antibiotic can interfere with essential bacterial enzymes such as antibiotics: rifamycins, lipiarmycins, quinolones, and sulfonamides.

An antibiotic can also be a protein synthesis inhibitor such as macrolides, lincosamides, and tetracyclines. An antibiotic can also be a cyclic lipopeptide such as daptomycin, glycylcyclines such as tigecycline, oxazolidiones such as linezolid, and lipiarmycins such as fidaxomicin. In some cases, an antibiotic can be $1^{st}$ generation, $2^{nd}$ generation, $3^{rd}$ generation, $4^{th}$ generation, or $5^{th}$ generation. A first-generation antibiotic can have a narrow spectrum. Examples of $1^{st}$ generation antibiotics can be penicillins (Penicillin G or Penicillin V), Cephalosporins (Cephazolin, Cephalothin, Cephapirin, Cephalethin, Cephradin, or Cephadroxin). In some cases, an antibiotic can be $2^{nd}$ generation. $2^{nd}$ generation antibiotics can be a penicillin (Amoxicillin or Ampicillin), Cephalosporin (Cefuroxime, Cephamandole, Cephoxitin, Cephaclor, Cephrozil, Loracarbef). In some cases, an antibiotic can be $3^{rd}$ generation. A $3^{rd}$ generation antibiotic can be penicillin (carbenicillin and ticarcillin) or cephalosporin (Cephixime, Cephtriaxone, Cephotaxime, Cephtizoxime, and Cephtazidime). An antibiotic can also be a $4^{th}$ generation antibiotic. A $4^{th}$ generation antibiotic can be Cephipime. An antibiotic can also be $5^{th}$ generation. $5^{th}$ generation antibiotics can be Cephtaroline or Cephtobiprole.

In some cases, an anti-viral agent may be administered as part of a treatment regime. In some cases, a herpes virus prophylaxis can be administered to a subject as part of a treatment regime. A herpes virus prophylaxis can be valacyclovir (Valtrex). Valtrex can be used orally to prevent the occurrence of herpes virus infections in subjects with positive HSV serology. It can be supplied in 500 mg tablets. Valacyclovir can be administered at a therapeutically effective amount.

In some cases, a treatment regime may be dosed according to a body weight of a subject. In subjects who are determined obese (BMI>35) a practical weight may need to be utilized. BMI is calculated by: BMI=weight (kg)/[height (m)]$^2$.

Body weight may be calculated for men as 50 kg+2.3* (number of inches over 60 inches) or for women 45.5 kg+2.3 (number of inches over 60 inches). An adjusted body weight may be calculated for subjects who are more than 20% of their ideal body weight. An adjusted body weight may be the sum of an ideal body weight+(0.4×(Actual body weight−ideal body weight)). In some cases, a body surface area may be utilized to calculate a dosage. A body surface area (BSA) may be calculated by: BSA (m2)=√Height (cm)*Weight (kg)/3600.

In an aspect is provided a method of modulating activity of a Ras (e.g., K-Ras) protein, comprising contacting a Ras protein with an effective amount of a compound described herein, or a pharmaceutically acceptable salt or solvate thereof, thereby modulating the activity of the Ras (e.g., K-Ras) protein.

In some embodiments, the subject method comprises administering an additional agent or therapy.

In some embodiments is a method of modulating activity of a Ras protein, comprising contacting a Ras protein with an effective amount of a compound described, or a pharmaceutically acceptable salt or solvate thereof, wherein said modulating comprises inhibiting the Ras (e.g., K-Ras) protein activity. In some embodiments is a method of modulating activity of a Ras protein including Ras mutant (e.g., G12C, G12D, G12S, G1V, G13C, or G13D) proteins such as K-Ras, H-Ras, and N-Ras, comprising contacting the Ras protein with an effective amount of a compound described herein, or a pharmaceutically acceptable salt or solvate thereof.

In some embodiments, provided is a method of reducing Ras signaling output in a cell by contacting the cell with a compound described herein. A reduction in Ras signaling can be evidenced by one or more members of the following: (i) an increase in steady state level of GDP-bound modified protein; (ii) a reduction of phosphorylated AKTs473, (iii) a reduction of phosphorylated ERKT202/y204, (iv) a reduction of phosphorylated S6S235/236, and (v) reduction of cell growth of a tumor cell expressing a Ras mutant (e.g., G12C, G12D, G12S, G1V, G13C, or G13D) protein, and (vi) reduction in Ras interaction with a Ras-pathway signaling protein. Non-limiting examples of Ras-pathway signaling protein include SOS (including SOS1 and SOS2), RAF, SHC, SHP (including SHP1 and SHP2), MEK, MAPK, ERK, GRB, RASA1, and GNAQ. In some cases, the reduction in Ras signaling output can be evidenced by two, three, four or all of (i)-(v) above. In some embodiments, the reduction any one or more of (i)-(v) can be 0.1-fold, 0.2-fold, 0.3-fold, 0.4-fold, 0.5-fold, 0.6-fold, 0.7-fold, 0.8-fold, 0.9-fold, 1-fold, 2-fold, 3-fold, 4-fold, 5-fold, 6-fold, 7-fold, 8-fold, 9-fold, 10-fold, 20-fold, 30-fold, 40-fold, 50-fold, 60-fold, 70-fold, 80-fold, 90-fold, 100-fold, 200-fold, 300-fold, 400-fold, 500-fold, 600-fold, 700-fold, 800-fold, 900-fold, 1000-fold, 2000-fold, 3000-fold, 4000-fold, 5000-fold, or more as compared to control untreated with a subject compound. A reduction in cell growth can be demonstrated with the use of tumor cells or cell lines. A tumor cell line can be derived from a tumor in one or more tissues, e.g., pancreas, lung, ovary, biliary tract, intestine (e.g., small intestine, large intestine (i.e. colon)), endometrium, stomach, hematopoietic tissue (e.g., lymphoid tissue), etc. Examples of the tumor cell line with a K-Ras mutation may include, but are not limited to, A549 (e.g., K-Ras G12S), AGS (e.g., K-Ras G12D), ASPC1 (e.g., K-Ras G12D), Calu-6 (e.g., K-Ras Q61K), CFPAC-1 (e.g., K-Ras G12V), CL40 (e.g., K-Ras G12D), COL0678 (e.g., K-Ras G12D), COR-L23 (e.g., K-Ras G12V), DAN-G (e.g., K-Ras G12V), GP2D (e.g., K-Ras G12D), GSU (e.g., K-Ras G12F), HCT116 (e.g., K-Ras G13D), HEC1A (e.g., K-Ras G12D), HEC1B (e.g., K-Ras G12F), HEC50B (e.g., K-Ras G12F), HEYA8 (e.g., K-Ras G12D or G13D), HPAC (e.g., K-Ras G12D), HPAFII (e.g., K-Ras G12D), HUCCT1 (e.g., K-Ras G12D), KARPAS620 (e.g., K-Ras G13D), KOPN8 (e.g., K-Ras G13D), KP-3 (e.g., K-Ras G12V), KP-4 (e.g., K-Ras G12D), L3.3 (e.g., K-Ras G12D), LoVo (e.g., K-Ras G13D), LS180 (e.g., K-Ras G12D), LS513 (e.g., K-Ras G12D), MCAS (e.g., K-Ras G12D), NB4 (e.g., K-Ras A18D), NCI-H1355 (e.g., K-Ras G13C), NCI-H1573 (e.g., K-Ras G12A), NCI-H1944 (e.g., K-Ras G13D), NCI-H2009 (e.g., K-Ras G12A), NCI-H441 (e.g., K-Ras G12V), NCI-H747 (e.g., K-Ras G13D), NOMO-1 (e.g., K-Ras G12D), OV7 (e.g., K-Ras G12D), PANCO203 (e.g., K-Ras G12D), PANC0403 (e.g., K-Ras G12D), PANC0504 (e.g., K-Ras G12D), PANC0813 (e.g., K-Ras G12D), PANC1 (e.g., K-Ras G12D), Panc-10.05 (e.g., K-Ras G12D), PaTu-8902 (e.g., K-Ras G12V), PK1 (e.g., K-Ras G12D), PK45H (e.g., K-Ras G12D), PK59 (e.g., K-Ras G12D), SK-CO-1 (e.g., K-Ras G12V), SKLU1 (e.g., K-Ras G12D), SKM-1 (e.g., K-Ras K117N), SNU1 (e.g., K-Ras G12D), SNU1033 (e.g., K-Ras G12D), SNU1197 (e.g., K-Ras G12D), SNU407 (e.g., K-Ras G12D), SNU410 (e.g., K-Ras G12D), SNU601 (e.g., K-Ras G12D), SNU61 (e.g., K-Ras G12D), SNU8 (e.g., K-Ras G12D), SNU869 (e.g., K-Ras G12D), SNU-C2A (e.g., K-Ras G12D), SU.86.86 (e.g., K-Ras G12D), SUIT2 (e.g., K-Ras G12D), SW1990 (e.g., K-Ras G12D), SW403 (e.g., K-Ras G12V), SW480 (e.g., K-Ras G12V), SW620 (e.g., K-Ras G12V), SW948 (e.g., K-Ras Q61L), T3M10 (e.g., K-Ras G12D), TCC-PAN2 (e.g., K-Ras G12R), TGBC11TKB (e.g., K-Ras G12D), and MIA Pa-Ca (e.g., MIA Pa-Ca 2 (e.g., K-Ras G12C)).

In an aspect is provided a modified Ras mutant protein comprising a compound described herein (or a remnant of a compound described herein wherein the remnant of said compound is modified from a stand alone compound described herein upon covalently bonding to the amino acid) covalently bonded to the amino acid corresponding to position 12 or 13 of SEQ ID No: 1. In some embodiments, such covalently bonded modified Ras mutant protein exhibits a reduced Ras signaling output (e.g., compared to a corresponding unmodified Ras mutant absent of the covalently bonded compound). In some embodiments, a modified Ras mutant protein is a K-Ras G12D mutant, an H-Ras G12D mutant, or a N-Ras G12D mutant. In some embodiments, a modified Ras mutant protein comprises an amino acid sequence selected from the group consisting of SEQ ID No. 2, SEQ ID No. 6, SEQ ID No. 8, and a respective fragment thereof comprising the aspartate residue corresponding to position 12 of SEQ ID No: 2. In embodiments, the modified Ras mutant protein comprises a compound described herein covalently bonded to the amino acid residue corresponding to position 12 or 13 of SEQ ID No: 1, wherein the Ras mutant protein is a human protein selected from KRas G12D, KRas G12C, KRas G12S, KRas G13D, KRas G13C, and KRas G13S. In embodiments, the modified Ras mutant protein comprises a compound described herein covalently bonded to the amino acid residue corresponding to position 12 or 13 of SEQ ID No: 1, wherein the Ras mutant protein is a—mammalian Ras protein (including human protein) selected from NRas G12D, NRas G12C, NRas G12S, NRas G13D, NRas G13C, and NRas G13S. In embodiments, the modified Ras mutant protein comprises a compound described herein covalently bonded to the amino acid residue corresponding to position 12 or 13 of SEQ ID No: 1, wherein the Ras mutant protein is a mammalian protein (including human protein) selected from HRas G12D, HRas G12C, HRas G12S, HRas G13D, HRas G13C, and HRas G13S. It will be understood that a compound described herein may be modified upon covalently binding an amino acid (e.g., mutant amino acid other than G) corresponding to position 12 or 13 of human KRas (e.g., SEQ ID. No: 1). A subject compound of the present disclosure encompasses a compound described herein immediately prior to covalently bonding the Ras mutant protein as well as the resulting compound covalently bonded to the modified Ras mutant protein. For example, a subject compound of the present disclosure can be covalently bonded to a mutant Ras protein to form a modified Ras mutant protein when a ring of the compound opened upon covalently bonding to the amino acid corresponding to position 12 or 13 of SEQ ID No: 1. The compound prior to and subsequent to such covalent binding are all considered a subject compound of the present invention.

In embodiments of a modified Ras mutant protein described herein, the reduced Ras signaling output is evidenced by one or more a reduced output selected from the group consisting of (i) an increase in steady state level of GDP-bound modified protein; (ii) a reduction of phosphorylated AKTs473, (iii) a reduction of phosphorylated ERK T202/Y204, (iv) a reduction of phosphorylated S6 S235/236, (v) reduction of cell growth of a tumor cell expressing a Ras mutant protein (e.g., G12D, G12C, G12S, G13D, G13C, or G13S), and (vi) reduction in Ras interaction with a Ras-pathway signaling protein In embodiments, the modified Ras mutant protein described herein is formed by contacting a compound described herein with the aspartate residue of an unmodified Ras G12D mutant protein, wherein the compound comprises a moiety susceptible to reacting with a nucleophilic aspartate residue corresponding to position 12 of SEQ ID No: 2. In some embodiments, the compound comprises a staying group and a leaving group, and wherein said contacting results in release of the leaving group and formation of said modified protein. In some embodiments, the compound selectively labels the aspartate residue corresponding to position 12 of SEQ ID No. 2 (a G12D mutant) relative to a valine (G12V) residue at the same position. In some embodiments, the compound selectively labels the aspartate residue as compared to (i) a serine residue of a K-Ras G12S mutant protein, said serine corresponding to residue 12 of SEQ ID NO: 4, and/or (ii) a valine residue of a K-Ras G12V mutant protein, said valine corresponding to residue 12 of SEQ ID NO: 3. In some embodiments, the compound selectively labels the aspartate residue as compared to (i) an serine residue of a K-Ras G12S mutant protein, said serine corresponding to residue 12 of SEQ ID NO: 4, and/or (ii) a valine residue of a K-Ras G12V mutant protein, said valine corresponding to residue 12 of SEQ ID NO: 3, by at least 1, 2, 3, 4, 5, 10 folds or more, when assayed under comparable conditions. In some embodiments, the compound selectively labels the aspartate residue corresponding to position 12 of SEQ ID No. 2 (a G12D KRas mutant) relative to a glycine residue at the same position in wildtype KRas.

In embodiments of the modified Ras mutant protein described herein, the compound interacts with the aspartate residue of an unmodified Ras G12D protein corresponding to position 12 of SEQ ID No: 2 in vitro.

In embodiments of the modified Ras mutant protein described herein, the compound contacts the aspartate residue of an unmodified K-Ras G12D protein corresponding to position 12 of SEQ ID No: 2 in vivo.

In an aspect is provided a method of treating cancer in a subject comprising a Ras mutant protein (e.g., KRas G12D, KRas G12C, KRas G12S, KRas G13D, KRas G13C, KRas G13S, NRas G12D, NRas G12C, NRas G12S, NRas G13D, NRas G13C, NRas G13S, HRas G12D, HRas G12C, HRas G12S, HRas G13D, HRas G13C, or HRas G13S), the method comprising modifying the Ras mutant protein of said subject by administering to said subject a compound described herein, wherein the compound is characterized in that upon contacting a Ras mutant protein, said Ras mutant protein is modified covalently at a residue corresponding to residue 12 or 13 of SEQ ID No: 1, such that said modified Ras mutant protein exhibits reduced Ras signaling output (e.g., compared to a control such as an unmodified Ras mutant protein not covalently bonded with any compound such as a compound disclosed herein).

In some aspects, a subject compound exhibits one or more of the following characteristics: it is capable of reacting with a mutant residue (e.g., KRas G12D, KRas G12C, KRas G12S, KRas G13D, KRas G13C, KRas G13S, NRas G12D, NRas G12C, NRas G12S, NRas G13D, NRas G13C, NRas G13S, HRas G12D, HRas G12C, HRas G12S, HRas G13D, HRas G13C, or HRas G13S) of a Ras mutant protein and covalently modify such Ras mutant and/or it comprises a moiety susceptible to reacting with a nucleophilic amino acid residue corresponding to position 12 or 13 of SEQ ID No: 1 (e.g., KRas G12D, KRas G12C, KRas G12S, KRas G13D, KRas G13C, KRas G13S, NRas G12D, NRas G12C, NRas G12S, NRas G13D, NRas G13C, NRas G13S, HRas G12D, HRas G12C, HRas G12S, HRas G13D, HRas G13C, or HRas G13S). In some embodiments, a subject compound when used to modify a Ras mutant protein, reduces the Ras protein's signaling output. In some embodiments, a subject compound exhibits an IC50 (against a mutant Ras (e.g., KRas G12D, KRas G12C, KRas G12S, KRas G13D, KRas G13C, KRas G13S, NRas G12D, NRas G12C, NRas G12S, NRas G13D, NRas G13C, NRas G13S, HRas G12D, HRas G12C, HRas G12S, HRas G13D, HRas G13C, or HRas G13S), as ascertained by reduction of Ras::SOS1 interaction) of less than 10 uM, 5 uM, 1 uM, 500 nM, less than 100 nM, less than 50 nM, 10 nM, 5 nM, 1nM, 500 pM, 50 pM, 10 pM or less.

In some embodiments, a modified Ras mutant protein disclosed herein exhibits a reduced Ras signaling output. A reduction of signaling output can be ascertained by a wide variety of methods known in the art. For example, phosphorylation of a substrate or a specific amino acid residue thereof can be detected and/or quantified one or more techniques, such as kinase activity assays, phospho-specific antibodies, Western blot, enzyme-linked immunosorbent assays (ELISA), cell-based ELISA, intracellular flow cytometry, mass spectrometry, and multi-analyte profiling. A host of readout can evidence a reduction of Ras signaling output including without limitation: (i) an increase in steady state level of GDP-bound modified protein; (ii) a reduction of phosphorylated AKTs473, (iii) a reduction of phosphorylated ERK T202/Y204, (iv) a reduction of phosphorylated S6 S235/236, and (v) reduction of cell growth of a tumor cell expressing a Ras mutant protein (e.g., KRas G12D, KRas G12C, KRas G12S, KRas G13D, KRas G13C, KRas G13S, NRas G12D, NRas G12C, NRas G12S, NRas G13D, NRas G13C, NRas G13S, HRas G12D, HRas G12C, HRas G12S, HRas G13D, HRas G13C, or HRas G13S), and (vi) reduction in Ras interaction with a Ras-pathway signaling protein. In some embodiments, a reduction is evidenced by 2, 3, 4 or more of items (i)-(vi). In some embodiments, the reduction in Ras signaling output can be evidenced by any one of (i)-(vi) as compared to control unmodified corresponding Ras proteins that is not covalently bonded to any compound disclosed herein. For example, a control Ras protein, as described herein, can be a Ras protein (e.g., wildtype or mutated) that is not complexed with any subject compound of the present disclosure. The increase in item (i) or reduction in items (ii) through (vi) can be at least about 0.1-fold, 0.2-fold, 0.3-fold, 0.4-fold, 0.5-fold, 0.6-fold, 0.7-fold, 0.8-fold, 0.9-fold, 1-fold, 2-fold, 3-fold, 4-fold, 5-fold, 6-fold, 7-fold, 8-fold, 9-fold, 10-fold, 20-fold, 30-fold, 40-fold, 50-fold, 60-fold, 70-fold, 80-fold, 90-fold, 100-fold, 200-fold, 300-fold, 400-fold, 500-fold, 600-fold, 700-fold, 800-fold, 900-fold, 1000-fold, 2000-fold, 3000-fold, 4000-fold, 5000-fold, or more as compared to the control Ras proteins. In some embodiments, a reduction in Ras interaction with a Ras-pathway signaling protein is established by a reduced interaction with SOS (including SOS1 and SOS2), RAF, SHC, SHP (including SHP1 and SHP2), MEK, MAPK, ERK, GRB, RASA1, or GNAQ.

In embodiments the modified Ras mutant protein described herein is formed by contacting a compound with the aspartate residue of an unmodified Ras G12D mutant protein, wherein the compound comprises a moiety susceptible to reacting with a nucleophilic aspartate residue corresponding to position 12 of SEQ ID No: 2. Non-limiting examples of a moiety susceptible to reaction with a nucleophilic serine residue of a K-Ras G12D protein comprise an optionally substituted aziridinyl.

Signaling output measured in terms of IC50 values can be obtained, a ratio of IC50 against one mutant relative to another mutant can be calculated. For instance, a selective reduction of K-Ras G12D signaling output can be evidenced by a ratio greater than one. In particular, a selective reduction of K-Ras G12D signaling relative to K-Ras G12S signaling is evidenced as the ratio of IC50 (against K-Ras G12S) to IC50 (against K-Ras G12D) is greater than 1.

It will be understood that when a compound described herein selectively labels the aspartate residue of a K-Ras G12D protein compared to another K-Ras protein(s) (e.g., WT, G12S, or G12V), the compound labels the K-Ras G12D protein with greater speed or to a greater degree or by any other quantifiable measurement compared to the other K-Ras protein (e.g., WT, G12S, G12V), under similar or identical reaction conditions for the proteins being compared. In some embodiments, the greater labeling of K-Ras G12D can be 0.1-fold, 0.2-fold, 0.3-fold, 0.4-fold, 0.5-fold, 0.6-fold, 0.7-fold, 0.8-fold, 0.9-fold, 1-fold, 2-fold, 3-fold, 4-fold, 5-fold, 6-fold, 7-fold, 8-fold, 9-fold, 10-fold, 20-fold, 30-fold, 40-fold, 50-fold, 60-fold, 70-fold, 80-fold, 90-fold, 100-fold, 200-fold, 300-fold, 400-fold, 500-fold, 600-fold, 700-fold, 800-fold, 900-fold, 1000-fold, 2000-fold, 3000-fold, 4000-fold, 5000-fold, or more as compared to another K-Ras protein (e.g., WT, G12S, or G12V).

In embodiments, the compounds described herein, or a pharmaceutically acceptable salt or solvate thereof, are Ras modulators (including Ras inhibitors) capable of covalently modifying a Ras protein. Ras proteins being modified can be Ras G12D mutants from K-Ras, H-Ras or N-Ras. The compounds, a pharmaceutically acceptable salt or solvate thereof disclosed herein, have a wide range of applications in therapeutics, diagnostics, and other biomedical research.

In an aspect is provided a method of treating cancer in a subject comprising a Ras G12D mutant protein, comprising modifying the Ras G12D mutant protein of said subject by administering to said subject a compound described herein, wherein said compound is characterized in that upon contacting the Ras G12D mutant protein, said the Ras G12D mutant protein is modified covalently at an aspartate residue corresponding to residue 12 of SEQ ID No: 2, such that said modified K-Ras G12D protein exhibits reduced Ras signaling output (e.g., compared to a corresponding unmodified Ras protein unbound to the covalent compound).

In an aspect is provided a method of modulating activity of a Ras protein (e.g., K-Ras, mutant K-Ras, K-Ras G12D), comprising contacting a Ras protein with an effective amount of a compound described herein, or a pharmaceutically acceptable salt or solvate thereof, thereby modulating the activity of the Ras protein.

In practicing any of the methods disclosed herein, the Ras target to which a subject compound binds covalently can be a Ras mutant (e.g., KRas G12D, KRas G12C, KRas G12S, KRas G13D, KRas G13C, KRas G13S, NRas G12D, NRas G12C, NRas G12S, NRas G13D, NRas G13C, NRas G13S, HRas G12D, HRas G12C, HRas G12S, HRas G13D, HRas G13C, or HRas G13S).

Pharmaceutical Compositions and Methods of Administration

In an aspect is provided a pharmaceutical composition comprising a compound described herein, or a pharmaceutically acceptable salt or solvate thereof, and a pharmaceutically acceptable excipient.

The compounds described herein, or a pharmaceutically acceptable salt or solvate thereof, are administered to subjects in a biologically compatible form suitable for administration to treat or prevent diseases, disorders or conditions. Administration of the compounds described herein can be in any pharmacological form including a therapeutically effective amount of a compound described herein, or a pharmaceutically acceptable salt or solvate thereof, alone or in combination with a pharmaceutically acceptable carrier.

In certain embodiments, the compounds described herein are administered as a pure chemical. In other embodiments, the compounds described herein are combined with a pharmaceutically suitable or acceptable carrier (also referred to herein as a pharmaceutically suitable (or acceptable) excipient, physiologically suitable (or acceptable) excipient, or physiologically suitable (or acceptable) carrier) selected on the basis of a chosen route of administration and standard pharmaceutical practice as described, for example, in Remington: The Science and Practice of Pharmacy (Gennaro, 21$^{st}$ Ed. Mack Pub. Co., Easton, PA (2005)).

Accordingly, provided herein is a pharmaceutical composition comprising at least one compound described herein, or a pharmaceutically acceptable salt, together with one or more pharmaceutically acceptable excipients. The excipient(s) (or carrier(s)) is acceptable or suitable if the excipient is compatible with the other ingredients of the composition and not deleterious to the recipient (i.e., the subject) of the composition.

In some embodiments of the methods described herein, the compounds described herein are administered either alone or in combination with pharmaceutically acceptable carriers, excipients or diluents, in a pharmaceutical composition. Administration of the compounds and compositions described herein can be affected by any method that enables delivery of the compounds to the site of action. These methods include, though are not limited to delivery via enteral routes (including oral, gastric or duodenal feeding tube, rectal suppository and rectal enema), parenteral routes (injection or infusion, including intraarterial, intracardiac, intradermal, intraduodenal, intramedullary, intramuscular, intraosseous, intraperitoneal, intrathecal, intravascular, intravenous, intravitreal, epidural and subcutaneous), inhalational, transdermal, transmucosal, sublingual, buccal and topical (including epicutaneous, dermal, enema, eye drops, ear drops, intranasal, vaginal) administration, although the most suitable route may depend upon for example the condition and disorder of the recipient. By way of example only, compounds described herein can be administered locally to the area in need of treatment, by for example, local infusion during surgery, topical application such as creams or ointments, injection, catheter, or implant. The administration can also be by direct injection at the site of a diseased tissue or organ.

In some embodiments of the methods described herein, pharmaceutical compositions suitable for oral administration are presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. In some embodiments, the active ingredient is presented as a bolus, electuary or paste.

Pharmaceutical compositions which can be used orally include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. In some embodiments, the tablets are coated or scored and are formulated so as to provide slow or controlled release of the active ingredient therein. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In some embodiments, stabilizers are added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or Dragee coatings for identification or to characterize different combinations of active compound doses.

In some embodiments of the methods described herein, pharmaceutical compositions are formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. The compositions may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described.

Pharmaceutical compositions for parenteral administration include aqueous and non-aqueous (oily) sterile injection solutions of the active compounds which may contain antioxidants, buffers, bacteriostats and solutes which render the formulation isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Pharmaceutical compositions may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example, as an emulsion in an acceptable oil) or ion exchange resins, or as sparingly soluble derivatives, for example, as a sparingly soluble salt Additional Embodiments (Embodiments 1-107)
1. A compound of Formula (A), or a pharmaceutically acceptable salt or solvate thereof:

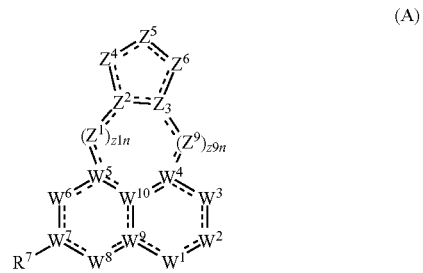

(A)

wherein:

$W^1$ is $N(R^1)$ or N;

$R^1$ is selected from hydrogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$C(O)OR^{12}$, —$OC(O)N(R^{12})(R^{13})$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20a}$;

$W^2$ is $C(R^2)$, $N(R^2)$, $C(R^2)_2$, $C(O)$, $S(O)$, $S(O)_2$, or N;

each $R^2$ is independently selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12a}$, —$SR^{12a}$, —$N(R^{12a}(R^{13})$, —$N=(R^{15})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$—, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20b}$;

$W^3$ is $C(R^3)$, $N(R^3)$, $C(R^3)_2$, $C(O)$, $S(O)$, $S(O)_2$, or N;

each $R^3$ is independently selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20c}$;

$W^4$ is $C(R^4)$, C, or N;

$R^4$ is selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —N($R^{14}$)C(O)$R^{15}$, —S(O)$_2$$R^{15}$, —S(O)$_2$N($R^{12}$)($R^{13}$), —S(=O)(=NH)N($R^{12}$)($R^{13}$), —CH$_2$C(O)N($R^{12}$)($R^{13}$), —CH$_2$N($R^{14}$)C(O)$R^{15}$, —CH$_2$S(O)$_2$$R^{15}$, and —CH$_2$S(O)$_2$N($R^{12}$)($R^{13}$), wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20d}$;

$W^5$ is C($R^5$), C, or N;

$R^5$ is selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —O$R^{12}$, —S$R^{12}$, —N($R^{12}$)($R^{13}$), —C(O)O$R^{12}$, —OC(O)N($R^{12}$)($R^{13}$), —N($R^{14}$)C(O)N($R^{12}$)($R^{13}$), —N($R^{14}$)C(O)O$R^{15}$, —N($R^{14}$)S(O)$_2$$R^{15}$, —C(O)$R^{15}$, —S(O)$R^{15}$, —OC(O)$R^{15}$, —C(O)N($R^{12}$)($R^{13}$), —C(O)C(O)N($R^{12}$)($R^{13}$), —N($R^{14}$)C(O)$R^{15}$, —S(O)$_2$$R^{15}$, —S(O)$_2$N($R^{12}$)($R^{13}$), —S(=O)(=NH)N($R^{12}$)($R^{13}$), —CH$_2$C(O)N($R^{12}$)($R^{13}$), —CH$_2$N($R^{14}$)C(O)$R^{15}$, —CH$_2$S(O)$_2$$R^{15}$, and —CH$_2$S(O)$_2$N($R^{12}$)($R^{13}$), wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20e}$;

$W^6$ is C($R^6$), N($R^6$), C($R^6$)$_2$, C(O), S(O), S(O)$_2$, or N;

each $R^6$ is independently selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —O$R^{12}$, —S$R^{12}$, —N($R^{12}$)($R^{13}$), —C(O)O$R^{12}$, —OC(O)N($R^{12}$)($R^{13}$), —N($R^{14}$)C(O)N($R^{12}$)($R^{13}$), —N($R^{14}$)C(O)O$R^{15}$, —N($R^{14}$)S(O)$_2$$R^{15}$, —C(O)$R^{15}$, —S(O)$R^{15}$, —OC(O)$R^{15}$, —C(O)N($R^{12}$)($R^{13}$), —C(O)C(O)N($R^{12}$)($R^{13}$), —N($R^{14}$)C(O)$R^{15}$, —S(O)$_2$$R^{15}$, —S(O)$_2$N($R^{12}$)($R^{13}$), —S(=O)(=NH)N($R^{12}$)($R^{13}$), —CH$_2$C(O)N($R^{12}$)($R^{13}$), —CH$_2$N($R^{14}$)C(O)$R^{15}$, —CH$_2$S(O)$_2$$R^{15}$, and —CH$_2$S(O)$_2$N($R^{12}$)($R^{13}$), wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20f}$;

$W^7$ is C($R^{7a}$), C, or N;

$R^{7a}$ is selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —O$R^{12}$, —S$R^{12}$, —N($R^{12}$)($R^{13}$), —C(O)O$R^{12}$, —OC(O)N($R^{12}$)($R^{13}$), —N($R^{14}$)C(O)N($R^{12}$)($R^{13}$), —N($R^{14}$)C(O)O$R^{15}$, —N($R^{14}$)S(O)$_2$$R^{15}$, —C(O)$R^{15}$, —S(O)$R^{15}$, —OC(O)$R^{15}$, —C(O)N($R^{12}$)($R^{13}$), —C(O)C(O)N($R^{12}$)($R^{13}$), —N($R^{14}$)C(O)$R^{15}$, —S(O)$_2$$R^{15}$, —S(O)$_2$N($R^{12}$)($R^{13}$), —S(=O)(=NH)N($R^{12}$)($R^{13}$), —CH$_2$C(O)N($R^{12}$)($R^{13}$), —CH$_2$N($R^{14}$)C(O)$R^{15}$, —CH$_2$S(O)$_2$$R^{15}$, and —CH$_2$S(O)$_2$N($R^{12}$)($R^{13}$), wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20g}$;

$R^7$ is -$L^7$—$R^{17}$;

$L^7$ is a bond, $C_1$-$C_4$alkyl, $C_2$-$C_4$alkenyl, $C_2$-$C_4$alkynyl, 2-4 membered heteroalkylene linker, —O—, —N($R^{7d}$)—, —C(O)—, —S—, —S(O)$_2$—, —S(O)—, —P(O)$R^{7d}$—, C$R^{7c}$$R^{7c}$, —OC$R^{7c}$$R^{7c}$—, —N($R^{7d}$)C$R^{7c}$$R^{7c}$—, —C(O)C$R^{7c}$$R^{7c}$—, —SC$R^{7c}$$R^{7c}$—, —S(O)$_2$C$R^{7c}$$R^{7c}$—, —S(O)C$R^{7c}$$R^{7c}$—, —P(O)$R^{7d}$C$R^{7c}$$R^{7c}$—, —C$R^{7c}$$R^{7c}$C$R^{7c}$$R^{7c}$—, —C$R^{7c}$$R^{7c}$O—, —C$R^{7c}$$R^{7c}$N($R^{7d}$)—, —C$R^{7c}$$R^{7c}$C(O)—, —C$R^{7c}$$R^{7c}$S—, —C$R^{7c}$$R^{7c}$S(O)$_2$—, —C$R^{7c}$$R^{7c}$S(O)—, —C$R^{7c}$$R^{7c}$P(O)$R^{7d}$—, —N($R^{7d}$)C(O)—, —N($R^{7d}$)S(O)$_2$—, —N($R^{7d}$)S(O)—, —N($R^{7d}$)P(O)$R^{7d}$—, —C(O)N($R^{7d}$)—, —S(O)$_2$N($R^{7d}$)—, —S(O)N($R^{7d}$)—, —P(O)$R^{7d}$N($R^{7d}$)—, —OC(O)—, —OS(O)$_2$—, —OS(O)—, —OP(O)$R^{7d}$—, —C(O)O—, —S(O)$_2$O—, —S(O)O—, or —P(O)$R^{7d}$O—; wherein the $C_1$-$C_4$alkyl, $C_2$-$C_4$alkenyl, $C_2$-$C_4$alkynyl, 2-4 membered heteroalkylene linker are optionally substituted with one, two, or three $R^{20g}$;

each $R^{7c}$ is independently selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —O$R^{12}$, —S$R^{12}$, —N($R^{12}$)($R^{13}$), —C(O)O$R^{12}$, —OC(O)N($R^{12}$)($R^{13}$), —N($R^{14}$)C(O)N($R^{12}$)($R^{13}$), —N($R^{14}$)C(O)O$R^{15}$, —N($R^{14}$)S(O)$_2$$R^{15}$, —C(O)$R^{15}$, —S(O)$R^{15}$, —OC(O)$R^{15}$, —C(O)N($R^{12}$)($R^{13}$), —C(O)C(O)N($R^{12}$)($R^{13}$), —N($R^{14}$)C(O)$R^{15}$, —S(O)$_2$$R^{15}$, —S(O)$_2$N($R^{12}$)($R^{13}$), S(=O)(=NH)N($R^{12}$)($R^{13}$), —CH$_2$C(O)N($R^{12}$)($R^{13}$), —CH$_2$N($R^{14}$)C(O)$R^{15}$, —CH$_2$S(O)$_2$$R^{15}$, and —CH$_2$S(O)$_2$N($R^{12}$)($R^{13}$), wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20g}$;

each $R^{7d}$ is independently selected from hydrogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —O$R^{12}$, —S$R^{12}$, —C(O)O$R^{12}$, —OC(O)N($R^{12}$)($R^{13}$), —C(O)$R^{15}$, —S(O)$R^{15}$, —OC(O)$R^{15}$, —C(O)N($R^{12}$)($R^{13}$), —C(O)C(O)N($R^{12}$)($R^{13}$), —S(O)$_2$$R^{15}$, —S(O)$_2$N($R^{12}$)($R^{13}$), —S(=O)(=NH)N($R^{12}$)($R^{13}$), —CH$_2$C(O)N($R^{12}$)($R^{13}$), —CH$_2$N($R^{14}$)C(O)$R^{15}$, —CH$_2$S(O)$_2$$R^{15}$, and —CH$_2$S(O)$_2$N($R^{12}$)($R^{13}$), wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20g}$;

$R^{17}$ is selected from $C_{3-10}$cycloalkyl, 3-10 membered heterocycloalkyl, $C_{6-10}$aryl, and 5-10 membered heteroaryl, wherein $C_{3-10}$cycloalkyl, 3-10 membered heterocycloalkyl, $C_{6-10}$aryl, and 5-10 membered heteroaryl are optionally substituted with one or more $R^{20q}$; or $L^7$ is a bond and $R^{7a}$ and $R^{17}$, together with the carbon to which they are attached, form $C_{3-10}$cycloalkyl or 3-10 membered heterocycloalkyl, wherein the $C_{3-10}$cycloalkyl and 3-10 membered heterocycloalkyl are optionally substituted with one or more $R^{20q}$;

$W^8$ is C($R^8$), N($R^8$), C($R^8$)$_2$, C(O), S(O), S(O)$_2$, or N;

each $R^8$ is independently selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —O$R^{12}$, —S$R^{12}$, —N($R^{12}$)($R^{13}$), —C(O)O$R^{12}$, —OC(O)N($R^{12}$)($R^{13}$), —N($R^{14}$)C(O)N($R^{12}$)($R^{13}$), —N($R^{14}$)C(O)O$R^{15}$, —N($R^{14}$)S(O)$_2$$R^{15}$, —C(O)$R^{15}$, —S(O)$R^{15}$, —OC(O)$R^{15}$, —C(O)N($R^{12}$)($R^{13}$), —C(O)C(O)N($R^{12}$)($R^{13}$), —N($R^{14}$)C(O)$R^{15}$, —S(O)$_2$$R^{15}$, —S(O)$_2$N($R^{12}$)($R^{13}$), —S(=O)(=NH)N($R^{12}$)($R^{13}$), —CH$_2$C(O)N($R^{12}$)($R^{13}$), —CH$_2$N($R^{14}$)C(O)$R^{15}$, —CH$_2$S(O)$_2$$R^{15}$, and —CH$_2$S(O)$_2$N($R^{12}$)($R^{13}$), wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20h}$;

$W^9$ is C($R^9$), C, or N;

$R^9$ is selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —O$R^{12}$, —S$R^{12}$, —N($R^{12}$)($R^{13}$), —C(O)O$R^{12}$, —OC(O)N($R^{12}$)($R^{13}$), —N($R^{14}$)C(O)N($R^{12}$)($R^{13}$), —N($R^{14}$)C(O)O$R^{15}$, —N($R^{14}$)S(O)$_2$$R^{15}$, —C(O)$R^{15}$, —S(O)$R^{15}$, —OC(O)$R^{15}$, —C(O)N($R^{12}$)($R^{13}$), —C(O)C(O)N($R^{12}$)($R^{13}$), —N($R^{14}$)C(O)$R^{15}$, —S(O)$_2$$R^{15}$, —S(O)$_2$N($R^{12}$)($R^{13}$), —S(=O)(=NH)N($R^{12}$)($R^{13}$), —$CH_2$C(O)N($R^{12}$)($R^{13}$), —$CH_2$N($R^{14}$)C(O)$R^{15}$, —$CH_2$S(O)$_2R^{15}$, and —$CH_2$S(O)$_2$N($R^{12}$)($R^{13}$), wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20i}$;

$W^{10}$ C($R^{10}$), C, or N;

$R^{10}$ is selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —N($R^{12}$)($R^{13}$), —C(O)$OR^{12}$, —OC(O)N($R^{12}$)($R^{13}$), —N($R^{14}$)C(O)N($R^{12}$)($R^{13}$), —N($R^{14}$)C(O)$OR^{15}$, —N($R^{14}$)S(O)$_2R^{15}$, —C(O)$R^{15}$, —S(O)$R^{15}$, —OC(O)$R^{15}$, —C(O)N($R^{12}$)($R^{13}$), —C(O)C(O)N($R^{12}$)($R^{13}$), —N($R^{14}$)C(O)$R^{15}$, —S(O)$_2R^{15}$, —S(O)$_2$N($R^{12}$)($R^{13}$), —S(=O)(=NH)N($R^{12}$)($R^{13}$), —$CH_2$C(O)N($R^{12}$)($R^{13}$), —$CH_2$N($R^{14}$)C(O)$R^{15}$, —$CH_2$S(O)$_2R^{15}$, and —$CH_2$S(O)$_2$N($R^{12}$)($R^{13}$), wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20j}$;

each $Z^1$ is independently C($R^{z1}$), N($R^{z1}$), C($R^{z1}$)$_2$, C(O), S(O), S(O)$_2$, O, S, or N;

z1n is 0, 1, 2, 3, or 4; wherein if z1n is 0 then $Z^2$ is directly bonded to $W^5$;

each $R^{z1}$ is independently selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —N($R^{12}$)($R^{13}$), —C(O)$OR^{12}$, —OC(O)N($R^{12}$)($R^{13}$), —N($R^{14}$)C(O)N($R^{12}$)($R^{13}$), —N($R^{14}$)C(O)$OR^{15}$, —N($R^{14}$)S(O)$_2R^{15}$, —C(O)$R^{15}$, —S(O)$R^{15}$, —OC(O)$R^{15}$, —C(O)N($R^{12}$)($R^{13}$), —C(O)C(O)N($R^{12}$)($R^{13}$), —N($R^{14}$)C(O)$R^{15}$, —S(O)$_2R^{15}$, —S(O)$_2$N($R^{12}$)($R^{13}$), —S(=O)(=NH)N($R^{12}$)($R^{13}$), —$CH_2$C(O)N($R^{12}$)($R^{13}$), —$CH_2$N($R^{14}$)C(O)$R^{15}$, —$CH_2$S(O)$_2R^{15}$, and —$CH_2$S(O)$_2$N($R^{12}$)($R^{13}$), wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20z1}$;

$Z^2$ is C($R^{z2}$), C, or N;

$R^{z2}$ is selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —N($R^{12}$)($R^{13}$), —C(O)$OR^{12}$, —OC(O)N($R^{12}$)($R^{13}$), —N($R^{14}$)C(O)N($R^{12}$)($R^{13}$), —N($R^{14}$)C(O)$OR^{15}$, —N($R^{14}$)S(O)$_2R^{15}$, —C(O)$R^{15}$, —S(O)$R^{15}$, —OC(O)$R^{15}$, —C(O)N($R^{12}$)($R^{13}$), —C(O)C(O)N($R^{12}$)($R^{13}$), —N($R^{14}$)C(O)$R^{15}$, —S(O)$_2R^{15}$, —S(O)$_2$N($R^{12}$)($R^{13}$), —S(=O)(=NH)N($R^{12}$)($R^{13}$), —$CH_2$C(O)N($R^{12}$)($R^{13}$), —$CH_2$N($R^{14}$)C(O)$R^{15}$, —$CH_2$S(O)$_2R^{15}$, and —$CH_2$S(O)$_2$N($R^{12}$)($R^{13}$), wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20z2}$;

$Z^3$ is C($R^{z3}$), C, or N;

$R^{z3}$ is selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —N($R^{12}$)($R^{13}$), —C(O)$OR^{12}$, —OC(O)N($R^{12}$)($R^{13}$), —N($R^{14}$)C(O)N($R^{12}$)($R^{13}$), —N($R^{14}$)C(O)$OR^{15}$, —N($R^{14}$)S(O)$_2R^{15}$, —C(O)$R^{15}$, —S(O)$R^{15}$, —OC(O)$R^{15}$, —C(O)N($R^{12}$)($R^{13}$), —C(O)C(O)N($R^{12}$)($R^{13}$), —N($R^{14}$)C(O)$R^{15}$, —S(O)$_2R^{15}$, —S(O)$_2$N($R^{12}$)($R^{13}$), —S(=O)(=NH)N($R^{12}$)($R^{13}$), —$CH_2$C(O)N($R^{12}$)($R^{13}$), —$CH_2$N($R^{14}$)C(O)$R^{15}$, —$CH_2$S(O)$_2R^{15}$, and —$CH_2$S(O)$_2$N($R^{12}$)($R^{13}$), wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20z3}$;

$Z^4$ is a bond, $Z^{4a}Z^{4b}$, $Z^{4a}Z^{4b}Z^{4c}$, $Z^{4a}Z^{4b}Z^{4c}Z^{4d}$, $Z^{4a}Z^{4b}Z^{4c}Z^{4d}4^{4e}$; wherein $Z^{4a}$ is directly bonded to $Z^2$; and wherein if $Z^4$ is a bond then $Z^2$ is directly bonded to $Z^5$;

$Z^{4a}$, $Z^{4b}$, $Z^{4c}$, $Z^{4d}$, and $Z^{4e}$ are independently C($R^{z4}$), N($R^{z4}$), C($R^{z4}$)$_2$, C(O), S(O), S(O)$_2$, S(O)(N$R^{z4}$), O, S, or N;

provided that if z9n is 0 and $Z^4$ is $Z^{4a}Z^{4b}$; then (1) $Z^{4b}$ is C($R^{z4}$), C($R^{z4}$)$_2$, C(O), S(O), S(O)$_2$, S(O)(N$R^{z4}$), O, S, or N, (2) $Z^{4b}$ is N($R^{z4}$) and $Z^{4a}$ is C(O), S(O), or S(O)$_2$; (3) $Z^{4b}$ is N($R^{z4}$) and $Z^5$ is C(O), S(O), or S(O)$_2$; or (4) $Z^{4b}$ is N($R^{z4}$) and $Z^3$ is C($R^{z3}$) or C;

each $R^{z4}$ is independently selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —N($R^{12}$)($R^{13}$), —C(O)$OR^{12}$, —OC(O)N($R^{12}$)($R^{13}$), —N($R^{14}$)C(O)N($R^{12}$)($R^{13}$), —N($R^{14}$)C(O)$OR^{15}$, —N($R^{14}$)S(O)$_2R^{15}$, —C(O)$OR^{12}$, —S(O)$R^{15}$, —OC(O)$R^{15}$, —C(O)N($R^{12}$)($R^{13}$), —C(O)C(O)N($R^{12}$)($R^{13}$), —N($R^{14}$)C(O)$R^{12}$, —S(O)$_2R^{15}$, —S(O)$_2$N($R^{12}$)($R^{13}$), —S(=O)(=NH)N($R^{12}$)($R^{13}$), —$CH_2$C(O)N($R^{12}$)($R^{13}$), —$CH_2$N($R^{14}$)C(O)$R^{15}$, —$CH_2$S(O)$_2R^{15}$, and —$CH_2$S(O)$_2$N($R^{12}$)($R^{13}$), wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20z4}$; or two $R^{z4}$ bonded to the same carbon are joined to form $C_{2-6}$alkenyl optionally substituted with one, two, or three $R^{20z4}$;

$Z^5$ is C($R^{z5}$), N($R^{z5}$), C($R^{z5}$)$_2$, C(O), S(O), S(O)$_2$, S(O)(N$R^{z5}$), O, S, or N;

each $R^{z5}$ is independently selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —N($R^{12}$)($R^{13}$), —C(O)$OR^{12}$, —OC(O)N($R^{12}$)($R^{13}$), —N($R^{14}$)C(O)N($R^{12}$)($R^{13}$), —N($R^{14}$)C(O)$OR^{15}$, —N($R^{14}$)S(O)$_2R^{15}$, —C(O)$OR^{12}$, —S(O)$R^{15}$, —OC(O)$R^{15}$, —C(O)N($R^{12}$)($R^{13}$), —C(O)C(O)N($R^{12}$)($R^{13}$), —N($R^{14}$)C(O)$R^{12}$, —S(O)$_2R^{15}$, —S(O)$_2$N($R^{12}$)($R^{13}$), —S(=O)(=NH)N($R^{12}$)($R^{13}$), —$CH_2$C(O)N($R^{12}$)($R^{13}$), —$CH_2$N($R^{14}$)C(O)$R^{15}$, —$CH_2$S(O)$_2R^{15}$, and —$CH_2$S(O)$_2$N($R^{12}$)($R^{13}$), wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20z5}$; or two $R^{z5}$ bonded to the same carbon are joined to form $C_{2-6}$alkenyl optionally substituted with one, two, or three $R^{20z5}$;

$Z^6$ is C($R^{z6}$), N($R^{z6}$), C($R^{z6}$)$_2$, C(O), S(O), S(O)$_2$, S(O)(N$R^{z6}$), O, S, or N;

each $R^{z6}$ is independently selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —N($R^{12}$)($R^{13}$), —C(O)$OR^{12}$, —OC(O)N($R^{12}$)($R^{13}$), —N($R^{14}$)C(O)N($R^{12}$)($R^{13}$), —N($R^{14}$)C(O)$OR^{15}$, —N($R^{14}$)S(O)$_2R^{15}$, —C(O)$OR^{12}$, —S(O)$R^{15}$, —OC(O)$R^{15}$, —C(O)N($R^{12}$)($R^{13}$), —C(O)C(O)N($R^{12}$)($R^{13}$), —N($R^{14}$)C(O)$R^{12}$, —S(O)$_2R^{15}$, —S(O)$_2$N($R^{12}$)($R^{13}$), —S(=O)(=NH)N($R^{12}$)($R^{13}$), —$CH_2$C(O)N($R^{12}$)($R^{13}$), —$CH_2$N($R^{14}$)C(O)$R^{15}$, —$CH_2$S(O)$_2R^{15}$, and —$CH_2$S(O)$_2$N($R^{12}$)($R^{13}$), wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20z6}$; or two $R^{z6}$ bonded to the same carbon are joined to form $C_{2-6}$alkenyl optionally substituted with one, two, or three $R^{20z6}$;

and further wherein the compound optionally comprises one of the following:

(1) two $R^{z4}$ bonded to the same carbon atom are joined to form monocyclic $C_{3-7}$cycloalkyl or monocyclic 3-7 membered heterocycloalkyl, wherein the monocyclic $C_{3-7}$cycloalkyl and monocyclic 3-7 membered heterocycloalkyl are optionally substituted with one, two, or three $R^{20z}$;

(2) two or more $R^{z4}$ bonded to adjacent atoms are joined to form monocyclic $C_{3-7}$cycloalkyl, monocyclic 3-7 membered heterocycloalkyl, phenyl, or monocyclic 5-6 membered heteroaryl, wherein the monocyclic $C_{3-7}$cycloalkyl, monocyclic 3-7 membered heterocycloalkyl, phenyl, and monocyclic 5-6 membered heteroaryl are optionally substituted with one, two, or three $R^{20z}$;

(3) two $R^{z5}$ bonded to the same carbon atom are joined to form monocyclic $C_{3-7}$cycloalkyl or monocyclic 3-7 membered heterocycloalkyl, wherein the monocyclic $C_{3-7}$cycloalkyl and monocyclic 3-7 membered heterocycloalkyl are optionally substituted with one, two, or three $R^{20z}$;

(4) one or two $R^{z4}$ bonded to one atom and one or two $R^{z5}$ bonded to an adjacent atom are joined to form monocyclic $C_{3-7}$cycloalkyl, monocyclic 3-7 membered heterocycloalkyl, phenyl, or monocyclic 5-6 membered heteroaryl, wherein the monocyclic $C_{3-7}$cycloalkyl, monocyclic 3-7 membered heterocycloalkyl, phenyl, and monocyclic 5-6 membered heteroaryl are optionally substituted with one, two, or three $R^{20z}$;

(5) one or two $R^{z4}$ bonded to one atom and one or two $R^{z5}$ bonded to a second atom are joined to form monocyclic $C_{3-7}$cycloalkyl or monocyclic 3-7 membered heterocycloalkyl, wherein the monocyclic $C_{3-7}$cycloalkyl and monocyclic 3-7 membered heterocycloalkyl are optionally substituted with one, two, or three $R^{20z}$;

(6) two $R^{z6}$ bonded to the same carbon atom are joined to form monocyclic $C_{3-7}$cycloalkyl or monocyclic 3-7 membered heterocycloalkyl, wherein the monocyclic $C_{3-7}$cycloalkyl and monocyclic 3-7 membered heterocycloalkyl are optionally substituted with one, two, or three $R^{20z}$;

(7) one or two $R^{z5}$ bonded to one atom and one or two $R^{z6}$ bonded to an adjacent atom are joined to form monocyclic $C_{3-7}$cycloalkyl, monocyclic 3-7 membered heterocycloalkyl, phenyl, or monocyclic 5-6 membered heteroaryl, wherein the monocyclic $C_{3-7}$cycloalkyl, monocyclic 3-7 membered heterocycloalkyl, phenyl, and monocyclic 5-6 membered heteroaryl are optionally substituted with one, two, or three $R^{20z}$; or (8) one or two $R^{z4}$ bonded to one atom and one or two $R^{z6}$ bonded to a second atom are joined to form monocyclic $C_{3-7}$cycloalkyl or monocyclic 3-7 membered heterocycloalkyl, wherein the monocyclic $C_{3-7}$cycloalkyl and monocyclic 3-7 membered heterocycloalkyl are optionally substituted with one, two, or three $R^{20z}$;

two $R^{20z}$ bonded to the same carbon atom are optionally joined to form monocyclic $C_{3-7}$cycloalkyl or monocyclic 3-7 membered heterocycloalkyl, wherein the monocyclic $C_{3-7}$cycloalkyl and monocyclic 3-7 membered heterocycloalkyl are optionally substituted with one, two, or three $R^{20zz}$; or two or more $R^{20z}$ bonded to two adjacent atoms are optionally joined to form monocyclic $C_{3-7}$cycloalkyl, monocyclic 3-7 membered heterocycloalkyl, phenyl, or monocyclic 5-6 membered heteroaryl, wherein the $C_{3-7}$cycloalkyl, monocyclic 3-7 membered heterocycloalkyl, phenyl, and monocyclic 5-6 membered heteroaryl are optionally substituted with one, two, or three $R^{20zz}$;

each $Z^9$ is independently $C(R^{z9})$, $N(R^{z9})$, $C(R^{z9})_2$, $C(O)$, $S(O)$, $S(O)_2$, $O$, $S$, or $N$;

z9n is 0, 1, 2, 3, or 4; wherein if z9n is 0 then $Z^3$ is directly bonded to $W^4$;

each $R^{z9}$ is independently selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20z9}$;

wherein the sum of z1n and z9n is 2, 3, or 4;

each $R^{12}$ is independently selected from hydrogen, $C_{1-6}$alkyl, $C_{2-6}$alkenyl, $C_{2-6}$alkynyl, $C_{3-10}$cycloalkyl, —$CH_2$-$C_{3-10}$cycloalkyl, $C_{2-9}$heterocycloalkyl, —$CH_2$-$C_{2-9}$heterocycloalkyl, $C_{6-10}$aryl, —$CH_2$-$C_{6-10}$aryl, —$CH_2$-$C_{1-9}$heteroaryl, and $C_{1-9}$heteroaryl, wherein $C_{1-6}$alkyl, $C_{2-6}$alkenyl, $C_{2-6}$alkynyl, $C_{3-10}$cycloalkyl, —$CH_2$-$C_{3-10}$cycloalkyl, $C_{2-9}$heterocycloalkyl, —$CH_2$-$C_{2-9}$heterocycloalkyl, $C_{6-10}$aryl, —$CH_2$-$C_{6-10}$aryl, —$CH_2$-$C_{1-9}$heteroaryl, and $C_{1-9}$heteroaryl are optionally substituted with one, two, or three $R^{20l}$;

each $R^{12a}$ is independently selected from hydrogen, $C_{1-6}$alkyl, $C_{2-6}$alkenyl, $C_{2-6}$alkynyl, $C_{3-10}$cycloalkyl, —$C(R^{12c})_2$-$C_{3-10}$cycloalkyl, $C_{2-9}$heterocycloalkyl, —$C(R^{12c})_2$-$C_{2-9}$heterocycloalkyl, $C_{6-10}$aryl, —$C(R^{12c})_2$-$C_{6-10}$aryl, —$C(R^{12c})_2$-$C_{1-9}$heteroaryl, and $C_{1-9}$heteroaryl, wherein $C_{1-6}$alkyl, $C_{2-6}$alkenyl, $C_{2-6}$alkynyl, $C_{3-10}$cycloalkyl, —$C(R^{12c})_2$-$C_{3-10}$cycloalkyl, $C_{2-9}$heterocycloalkyl, —$C(R^{12c})_2$-$C_{2-9}$heterocycloalkyl, $C_{6-10}$aryl, —$C(R^{12c})_2$-$C_{6-10}$aryl, —$C(R^{12c})_2$-$C_{1-9}$heteroaryl, and $C_{1-9}$heteroaryl are optionally substituted with one, two, or three $R^{20l}$;

each $R^{12c}$ is independently selected from hydrogen and $R^{20lc}$;

each $R^{13}$ is independently selected from hydrogen, $C_{1-6}$alkyl, and $C_{1-6}$haloalkyl; or $R^{12}$ and $R^{13}$, together with the nitrogen to which they are attached, form a $C_{1-9}$heterocycloalkyl ring optionally substituted with one, two, or three $R^{20m}$;

each $R^{14}$ is independently selected from hydrogen, $C_{1-6}$alkyl, and $C_{1-6}$haloalkyl;

each $R^{15}$ is independently selected from $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20o}$;

each $R^{20z1}$, $R^{20z2}$, $R^{20z3}$, $R^{20z4}$, $R^{20z5}$, $R^{20z6}$, and $R^{20z9}$ is independently selected from halogen, oxo, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{12}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{12}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20z}$;

each $R^{20z}$ is independently selected from halogen, oxo, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{12}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{12}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20zz}$;

each $R^{20a}$, $R^{20b}$, $R^{20c}$, $R^{20d}$, $R^{20e}$, $R^{20f}$, $R^{20g}$, $R^{20h}$, $R^{20i}$, $R^{20j}$, $R^{20l}$, $R^{20lc}$, $R^{20m}$, $R^{20o}$, $R^{20q}$, and $R^{20zz}$ is independently selected from halogen, oxo, —CN, $C_{1-6}$alkyl, $C_{2-6}$alkenyl, $C_{2-6}$alkynyl, $C_{3-10}$cycloalkyl, —$CH_2$-$C_{3-10}$cycloalkyl, $C_{2-9}$heterocycloalkyl, —$CH_2$-$C_{2-9}$heterocycloalkyl, $C_{6-10}$aryl, —$CH_2$-$C_{6-10}$aryl, —$CH_2$-$C_{1-9}$heteroaryl, $C_{1-9}$heteroaryl, —$OR^{21}$, —$SR^{21}$, —$N(R^{22})(R^{23})$, —$C(O)OR^{22}$, —$C(O)N(R^{22})(R^{23})$, —$C(O)C(O)N(R^{22})(R^{23})$, —$OC(O)N(R^{22})(R^{23})$, —$N(R^{24})C(O)N(R^{22})(R^{23})$, —$N(R^{24})C(O)OR^{25}$, —$N(R^{24})C(O)R^{21}$, —$N(R^{24})S(O)_2R^{25}$, —$C(O)R^{21}$, —$S(O)_2R^{25}$, —$S(O)_2N(R^{22})(R^{23})$, —$OCH_2C(O)OR^{22}$, =$NR^{21}$, and —$OC(O)R^{25}$; two $R^{20q}$ bonded to adjacent atoms are optionally joined to form a $C_{3-10}$cycloalkyl, $C_{2-9}$heterocycloalkyl, $C_{6-10}$aryl, or $C_{1-9}$heteroaryl; wherein $C_{1-6}$alkyl, $C_{2-6}$alkenyl, $C_{2-6}$alkynyl, $C_{3-10}$cycloalkyl, —$CH_2$-$C_{3-10}$cycloalkyl, $C_{2-9}$heterocycloalkyl, —$CH_2$-$C_{2-9}$heterocycloalkyl, $C_{6-10}$aryl, —$CH_2$-$C_{6-10}$aryl, —$CH_2$-$C_{1-9}$heteroaryl, and $C_{1-9}$heteroaryl are optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —$OR^{21}$, —$SR^{21}$, —$N(R^{22})(R^{23})$, —$C(O)OR^{22}$, —$C(O)N(R^{22})(R^{23})$, —$C(O)C(O)N(R^{22})(R^{23})$, —$OC(O)N(R^{22})(R^{23})$, —$N(R^{24})C(O)N(R^{22})(R^{23})$, —$N(R^{24})C(O)OR^{25}$, —$N(R^{24})C(O)R^{25}$, —$N(R^{24})S(O)_2R^{25}$, —$C(O)R^{25}$, —$S(O)_2R^{25}$, —$S(O)_2N(R^{22})(R^{23})$, and —$OC(O)R^{25}$;

each $R^{21}$ is independently selected from hydrogen, $C_{1-6}$alkyl, $C_{1-6}$haloalkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl;

each $R^{22}$ is independently selected from hydrogen, $C_{1-6}$alkyl, $C_{1-6}$haloalkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl;

each $R^{23}$ is independently selected from hydrogen and $C_{1-6}$alkyl;

each $R^{24}$ is independently selected from hydrogen and $C_{1-6}$alkyl;

each $R^{25}$ is independently selected from $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; and ----- indicates a single or double bond such that all valences are satisfied.

2. The compound of embodiment 1, or a pharmaceutically acceptable salt or solvate thereof, having the formula:

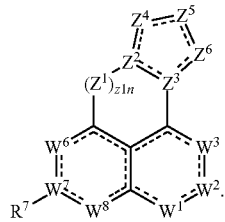

(A-1)

3. The compound of embodiment 1, or a pharmaceutically acceptable salt or solvate thereof, having the formula:

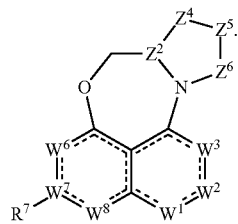

(A-2)

4. The compound of embodiment 1, or a pharmaceutically acceptable salt or solvate thereof, having the formula:

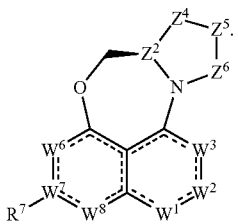

(A-2a)

5. The compound of embodiment 1, or a pharmaceutically acceptable salt or solvate thereof, having the formula:

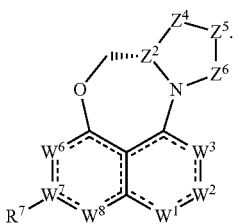

(A-2b)

6. The compound of embodiment 1, or a pharmaceutically acceptable salt or solvate thereof, having the formula:

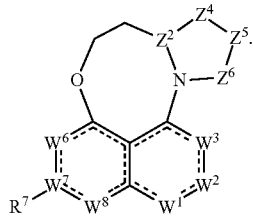

(A-3)

7. The compound of embodiment 1, or a pharmaceutically acceptable salt or solvate thereof, having the formula:

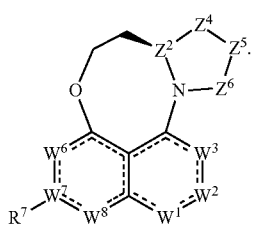

(A-3a)

8. The compound of embodiment 1, or a pharmaceutically acceptable salt or solvate thereof, having the formula:

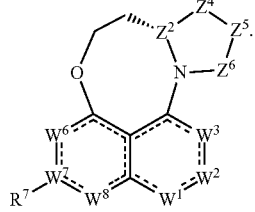

(A-3b)

9. The compound of embodiment 1, or a pharmaceutically acceptable salt or solvate thereof, having the formula:

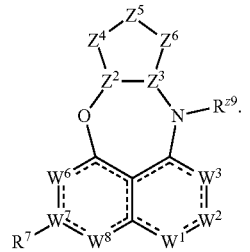

(A-6f)

10. The compound of any one of embodiments 3-8, or a pharmaceutically acceptable salt or solvate thereof, wherein

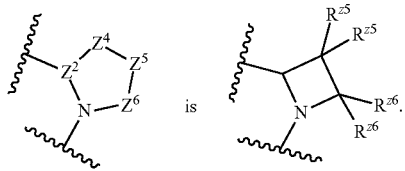 is 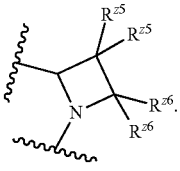

11. The compound of any one of embodiments 3-8, or a pharmaceutically acceptable salt or solvate thereof, wherein

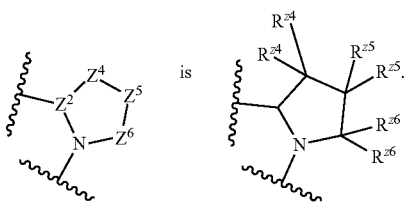 is 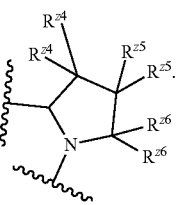

12. The compound of any one of embodiments 3-8, or a pharmaceutically acceptable salt or solvate thereof, wherein

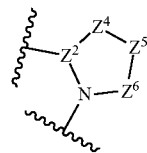

is selected from

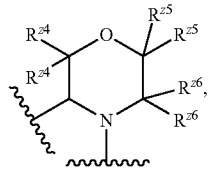 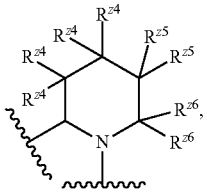

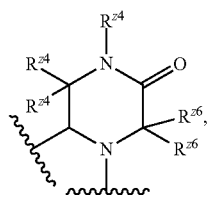 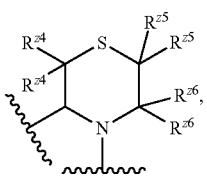

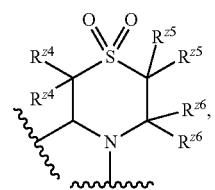 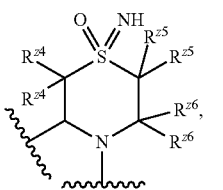 and

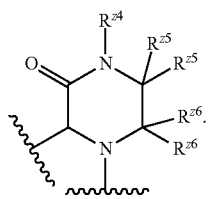
13. The compound of any one of embodiments 3-8, or a pharmaceutically acceptable salt or solvate thereof, wherein
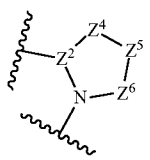
is selected from
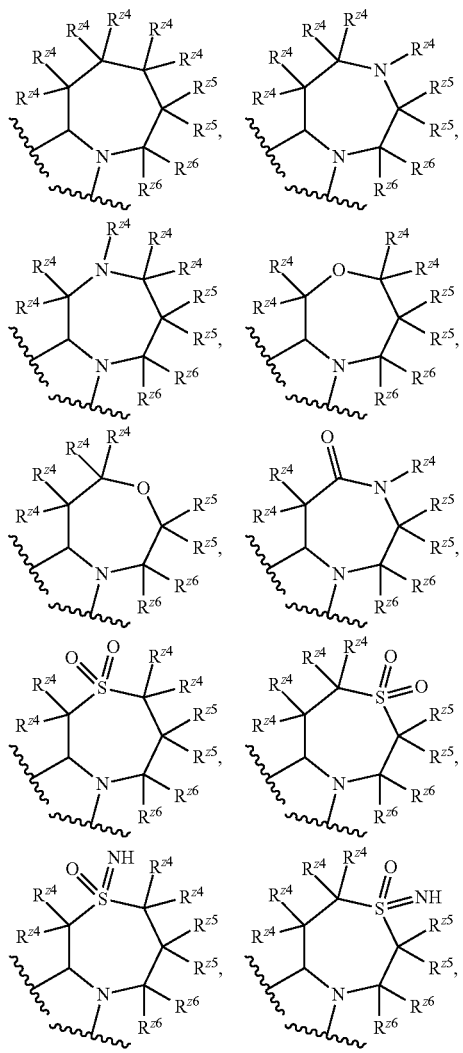
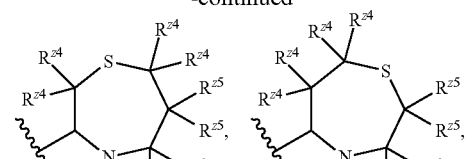
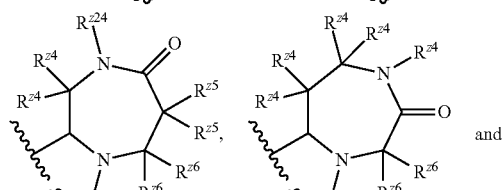
and
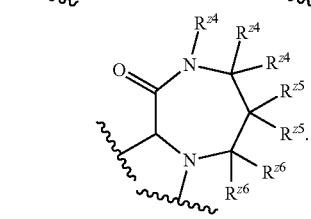
14. The compound of any one of embodiments 3-8, or a pharmaceutically acceptable salt or solvate thereof, wherein
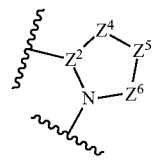
is selected from
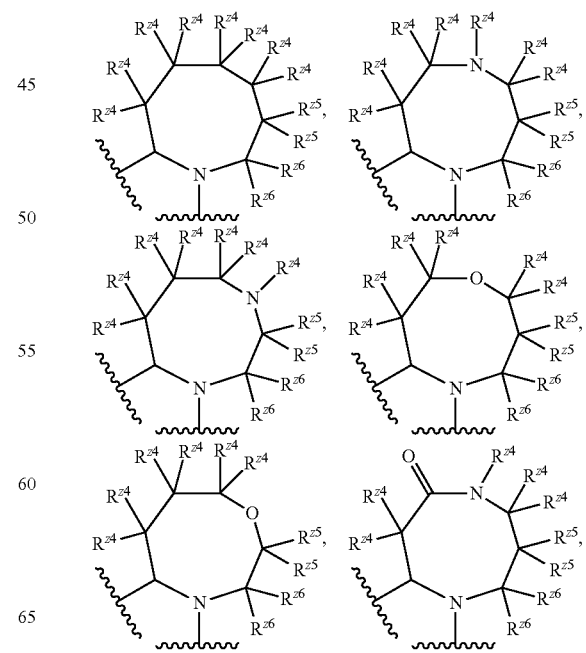

-continued

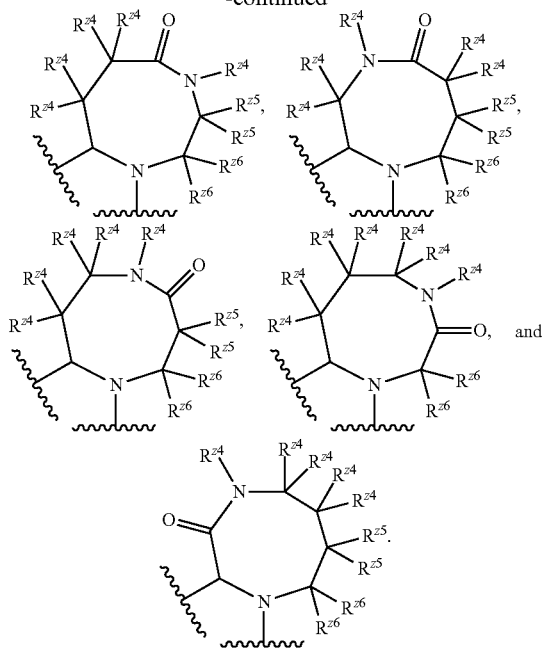

15. The compound of any one of embodiments 1-14, or a pharmaceutically acceptable salt or solvate thereof, wherein two $R^{z5}$ bonded to the same carbon atom are joined to form monocyclic $C_{3-7}$cycloalkyl or monocyclic 3-7 membered heterocycloalkyl, wherein the monocyclic $C_{3-7}$cycloalkyl and monocyclic 3-7 membered heterocycloalkyl are optionally substituted with one, two, or three $R^{20z}$.

16. The compound of any one of embodiments 1-14, or a pharmaceutically acceptable salt or solvate thereof, wherein two $R^{z5}$ bonded to the same carbon atom are joined to form monocyclic 4-membered heterocycloalkyl, wherein the 4 membered heterocycloalkyl is substituted with one, two, or three $R^{20z}$.

17. The compound of embodiment 16, or a pharmaceutically acceptable salt or solvate thereof, wherein

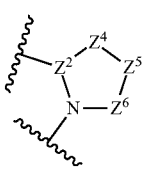

is selected from

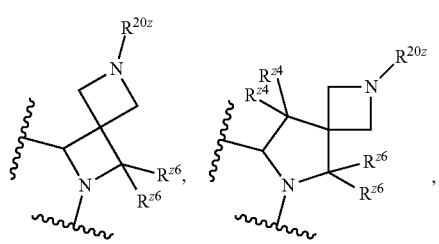

-continued

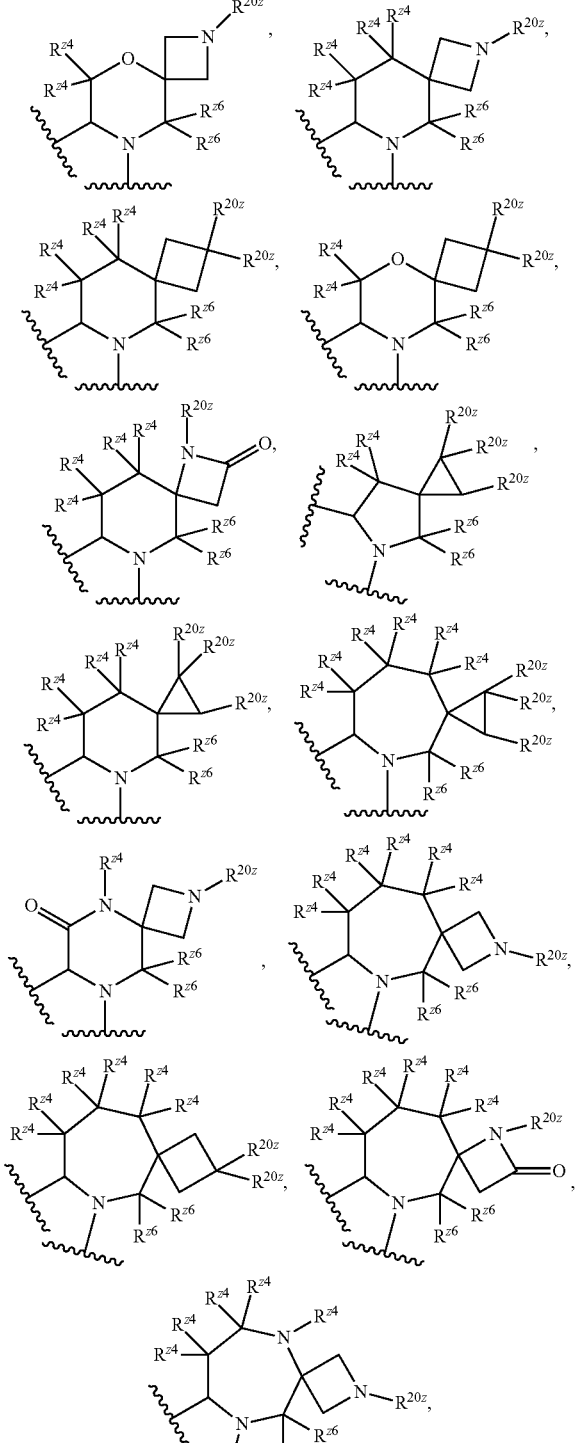

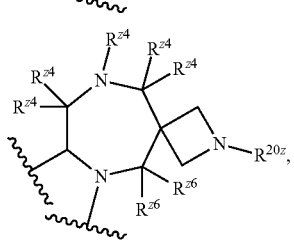

-continued
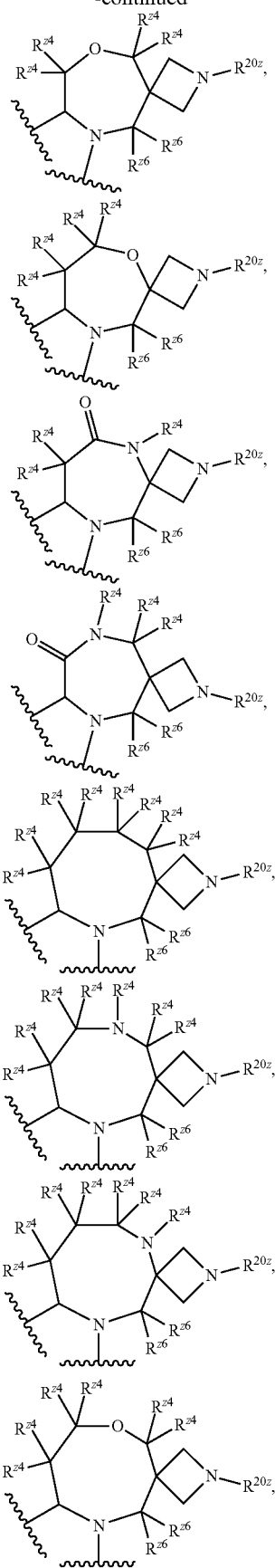
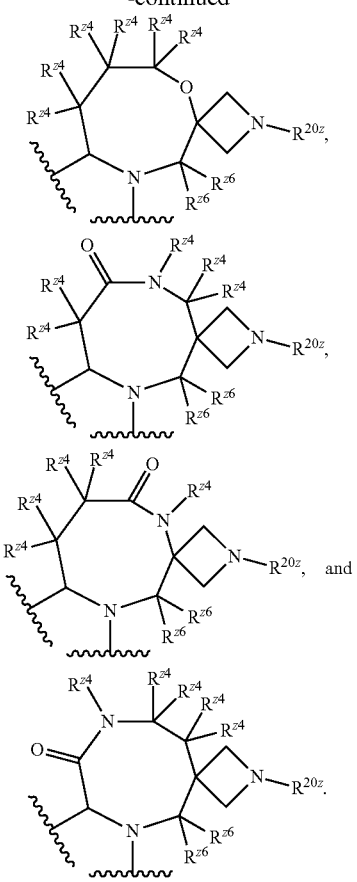
18. The compound of embodiment 16, or a pharmaceutically acceptable salt or solvate thereof, wherein
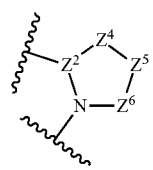
is selected from
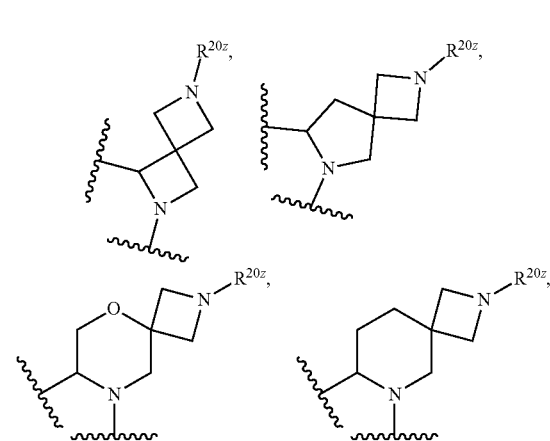

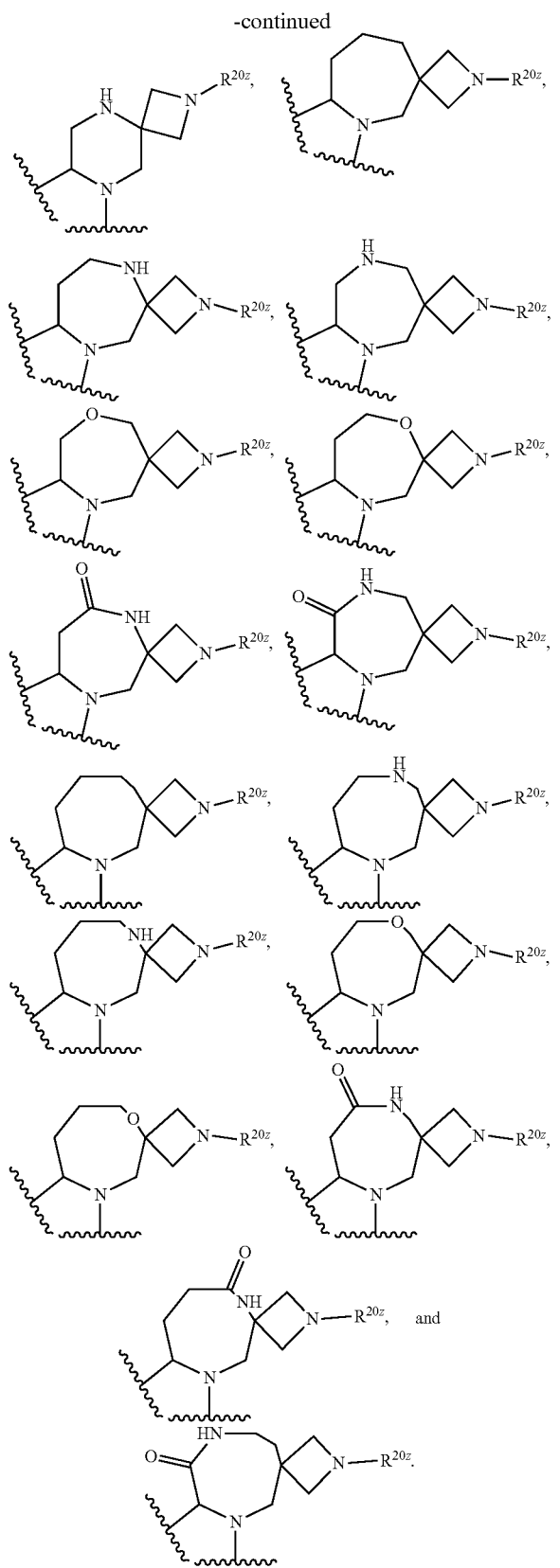

two $R^{z5}$ bonded to an adjacent atom are joined to form monocyclic $C_{3-7}$cycloalkyl, monocyclic 3-7 membered heterocycloalkyl, phenyl, or monocyclic 5-6 membered heteroaryl, wherein the monocyclic $C_{3-7}$cycloalkyl, monocyclic 3-7 membered heterocycloalkyl, phenyl, and monocyclic 5-6 membered heteroaryl are optionally substituted with one, two, or three $R^{20z}$.

20. The compound of any one of embodiments 1-14, or a pharmaceutically acceptable salt or solvate thereof, wherein one or two $R^{z4}$ bonded to one atom and one or two $R^{z5}$ bonded to an adjacent atom are joined to form monocyclic 5-6 membered heteroaryl, wherein the monocyclic 5-6 membered heteroaryl is optionally substituted with one, two, or three $R^{20z}$.

21. The compound of embodiment 20, or a pharmaceutically acceptable salt or solvate thereof, wherein the monocyclic 5-6 membered heteroaryl formed by the joining of one or two $R^{z4}$ bonded to one atom and one or two $R^{z5}$ bonded to an adjacent atom, is a triazolyl, pyrazolyl, imidazolyl, pyrrolyl, furanyl, thienyl, oxazolyl, isooxazolyl, pyridyl, pyridazinyl, pyrimidinyl, or pyrazinyl; each optionally substituted with one, two, or three $R^{20z}$.

22. The compound of embodiment 20, or a pharmaceutically acceptable salt or solvate thereof, wherein the monocyclic 5-6 membered heteroaryl formed by the joining of one or two $R^{z4}$ bonded to one atom and one or two $R^{z5}$ bonded to an adjacent atom, is a pyrazolyl optionally substituted with one, two, or three $R^{20z}$.

23. The compound of embodiment 22, or a pharmaceutically acceptable salt or solvate thereof, wherein

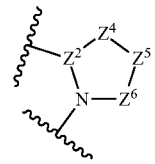

is selected from 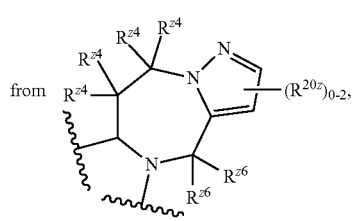

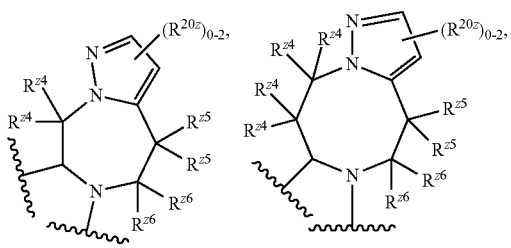

19. The compound of any one of embodiments 1-14, or a pharmaceutically acceptable salt or solvate thereof, wherein one or two $R^{z4}$ bonded to the atom and one or

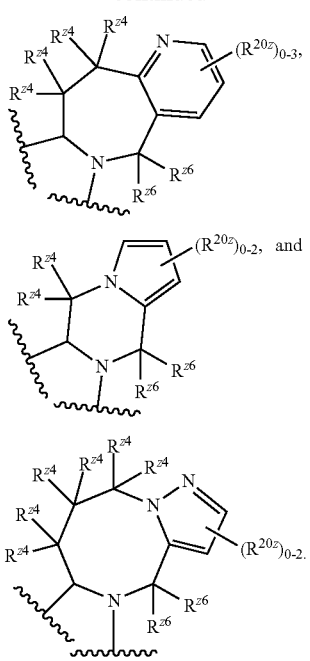

24. The compound of embodiment 22, or a pharmaceutically acceptable salt or solvate thereof, wherein is selected from

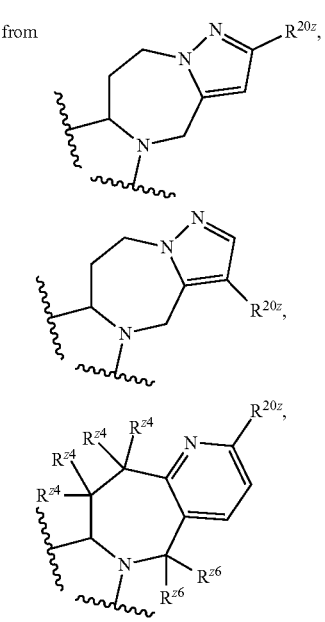

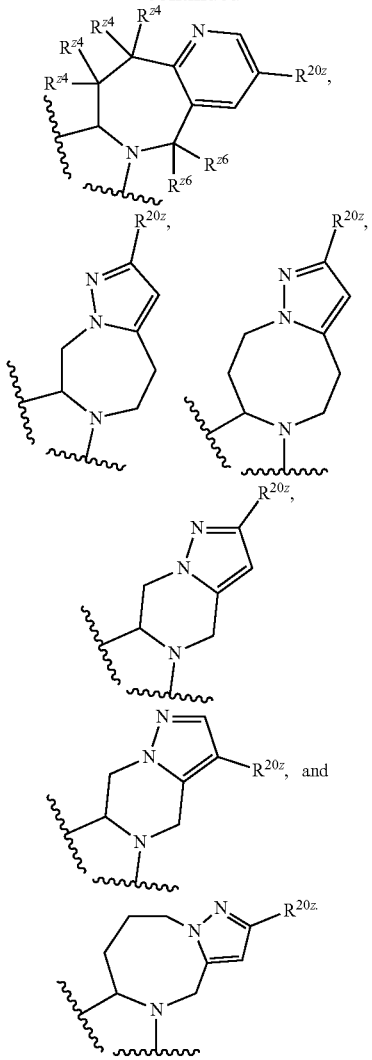

25. The compound of embodiment 1, or a pharmaceutically acceptable salt or solvate thereof, wherein z1n is 1, 2 or 3, and z9n is 1, 2, or 3.

26. The compound of embodiment 1, or a pharmaceutically acceptable salt or solvate thereof, wherein z1n is 0.

27. The compound of any one of embodiments 1-26, or a pharmaceutically acceptable salt or solvate thereof, wherein $W^1$ is N.

28. The compound of any one of embodiments 1-26, or a pharmaceutically acceptable salt or solvate thereof, wherein $W^1$ is $N(R^1)$.

29. The compound of any one of embodiments 1-28, or a pharmaceutically acceptable salt or solvate thereof, wherein $W^2$ is $C(R^2)$.

30. The compound of any one of embodiments 1-28, or a pharmaceutically acceptable salt or solvate thereof, wherein $W^2$ is $N(R^2)$.

31. The compound of any one of embodiments 1-28, or a pharmaceutically acceptable salt or solvate thereof, wherein $W^2$ is C(O).

32. The compound of any one of embodiments 1-31, or a pharmaceutically acceptable salt or solvate thereof, wherein $W^3$ is N.

33. The compound of any one of embodiments 1-31, or a pharmaceutically acceptable salt or solvate thereof, wherein $W^3$ is $C(R^3)$.
34. The compound of any one of embodiments 1-33, or a pharmaceutically acceptable salt or solvate thereof, wherein $W^4$ is C.
35. The compound of any one of embodiments 1-34, or a pharmaceutically acceptable salt or solvate thereof, wherein $W^5$ is C.
36. The compound of any one of embodiments 1-34, or a pharmaceutically acceptable salt or solvate thereof, wherein $W^5$ is $C(R^5)$.
37. The compound of any one of embodiments 1-36, or a pharmaceutically acceptable salt or solvate thereof, wherein $W^6$ is $C(R^6)$.
38. The compound of any one of embodiments 1-36, or a pharmaceutically acceptable salt or solvate thereof, wherein $W^6$ is $N(R^6)$.
39. The compound of any one of embodiments 1-38, or a pharmaceutically acceptable salt or solvate thereof, wherein $R^6$ is selected from hydrogen, halogen, —CN, $C_{1-6}$alkyl, $C_{3-6}$cycloalkyl, —$OR^{12}$, —$SR^{12}$, —$N(R^{12})(R^{13})$, 'C(O)$OR^{12}$, —C(O)$R^{15}$, —C(O)$N(R^{12})(R^{13})$, —S(O)$_2R^{15}$, and —S(O)$_2N(R^{12})(R^{13})$, wherein $C_{1-6}$alkyl and $C_{3-6}$cycloalkyl are optionally substituted with one, two, or three $R^{20f}$.
40. The compound of embodiment 39, or a pharmaceutically acceptable salt or solvate thereof, wherein $R^6$ is selected from hydrogen, halogen, —CN, $C_{1-6}$alkyl, and —$OR^{12}$, wherein $C_{1-6}$alkyl is optionally substituted with one, two, or three $R^{20f}$.
41. The compound of embodiment 39, or a pharmaceutically acceptable salt or solvate thereof, wherein $R^6$ is halogen.
42. The compound of any one of embodiments 1-36, or a pharmaceutically acceptable salt or solvate thereof, wherein $W^6$ is N.
43. The compound of any one of embodiments 1-42, or a pharmaceutically acceptable salt or solvate thereof, wherein $W^7$ is C.
44. The compound of any one of embodiments 1-42, or a pharmaceutically acceptable salt or solvate thereof, wherein $W^7$ is $C(R^{7a})$.
45. The compound of any one of embodiments 1-42, or a pharmaceutically acceptable salt or solvate thereof, wherein $W^7$ is N.
46. The compound of any one of embodiments 1-45, or a pharmaceutically acceptable salt or solvate thereof, wherein $W^8$ is $C(R^8)$.
47. The compound of any one of embodiments 1-46, or a pharmaceutically acceptable salt or solvate thereof, wherein $R^8$ is selected from hydrogen, halogen, —CN, $C_{1-6}$alkyl, —$OR^{12}$, —$SR^{12}$, —$N(R^{12})(R^{13})$, —C(O)$OR^{12}$, —C(O)$R^{15}$, —C(O)$N(R^{12})(R^{13})$, —S(O)$_2R^{15}$, and —S(O)$_2N(R^{12})(R^{13})$, wherein $C_{1-6}$alkyl is optionally substituted with one, two, or three $R^{20h}$.
48. The compound of embodiment 47, or a pharmaceutically acceptable salt or solvate thereof, wherein $R^8$ is selected from hydrogen, halogen, —CN, $C_{1-6}$alkyl, and —$OR^{12}$, wherein $C_{1-6}$alkyl is optionally substituted with one, two, or three $R^{20h}$.
49. The compound of embodiment 47, or a pharmaceutically acceptable salt or solvate thereof, wherein $R^8$ is halogen.
50. The compound of any one of embodiments 1-45, or a pharmaceutically acceptable salt or solvate thereof, wherein $W^8$ is N.
51. The compound of any one of embodiments 1-50, or a pharmaceutically acceptable salt or solvate thereof, wherein $W^9$ is C.
52. The compound of any one of embodiments 1-51, or a pharmaceutically acceptable salt or solvate thereof, wherein $W^{10}$ is C.
53. The compound of any one of embodiments 1-25, or a pharmaceutically acceptable salt or solvate thereof, wherein

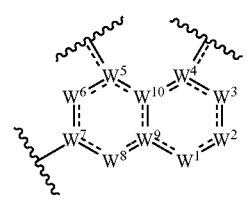

is selected from

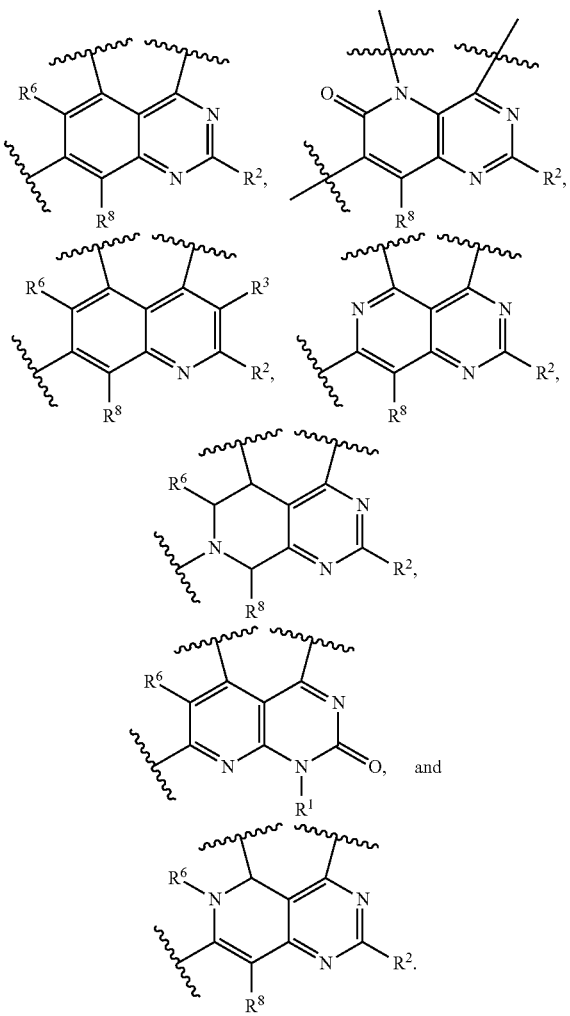

54. The compound of any one of embodiments 1-53, or a pharmaceutically acceptable salt or solvate thereof, wherein $L^7$ is a bond.
55. The compound of any one of embodiments 1-54, or a pharmaceutically acceptable salt or solvate thereof, wherein R[17] is selected from $C_{6-10}$aryl and 5-10 membered heteroaryl, each of which is optionally substituted with one, two, or three $R^{20q}$.

56. The compound of embodiment 55, or a pharmaceutically acceptable salt or solvate thereof, wherein R[17] is selected from $C_{10}$aryl and 9-membered heteroaryl, each of which is optionally substituted with one, two, or three $R^{20q}$.

57. The compound of embodiment 55, or a pharmaceutically acceptable salt or solvate thereof, wherein R[17] is selected from naphthalenyl and benzothiophenyl, each of which is optionally substituted with one, two, or three $R^{20q}$.

58. The compound of any one of embodiments 55 to 57, or a pharmaceutically acceptable salt or solvate thereof, wherein R[17] is substituted with one, two, or three substituents independently selected from halogen, —CN, $C_{1-3}$alkyl, $C_{2-3}$alkenyl, $C_{2-3}$alkynyl, —$OR^{21}$, and —$N(R^{22})(R^{23})$.

59. The compound of embodiment 58, or a pharmaceutically acceptable salt or solvate thereof, wherein R[17] is substituted with one, two, or three substituents independently selected from halogen, —CN, —$CH_3$, —C≡C, —OH, and —$NH_2$.

60. The compound of embodiment 58, or a pharmaceutically acceptable salt or solvate thereof, wherein R[17] is substituted with —F, —CN, and —$NH_2$.

61. The compound of any one of embodiments 1-54, or a pharmaceutically acceptable salt or solvate thereof, wherein R[17] is selected from

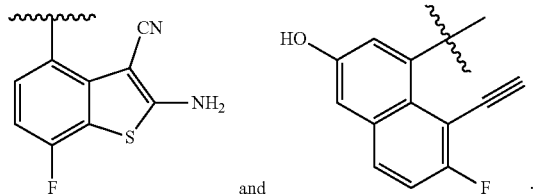 [SMILES: *c1ccc(F)c2sc(N)c(C#N)c12 ; "and" ; *c1cc(O)cc2ccc(F)c(C#C)c12]

and

62. The compound of any one of embodiments 1-54, or a pharmaceutically acceptable salt or solvate thereof, wherein R[17] is selected from

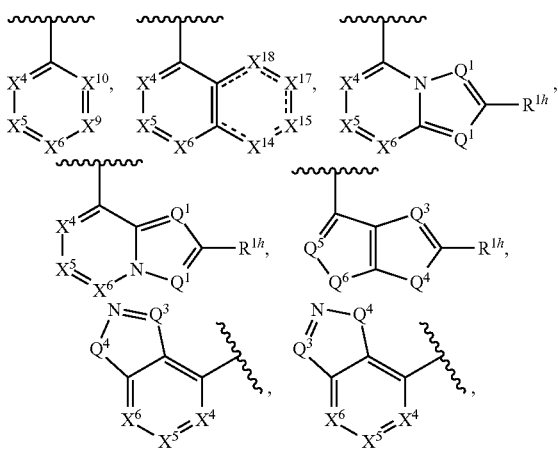

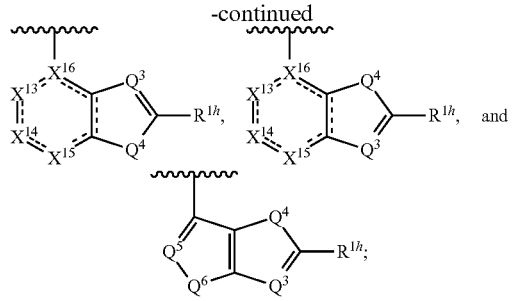

$Q^1$, $Q^3$, and $Q^5$ are independently selected from N and $C(R^{1d})$;

$Q^4$ and $Q^6$ are independently selected from O, S, $C(R^{1a})(R^{1b})$, and $N(R^{1c})$;

$X^4$, $X^5$, $X^6$, $X^9$, $X^{19}$ are independently selected from $C(R^{1a})$ and N;

$X^{13}$ is selected from a bond, $C(R^{1a})$, N, C(O), $C(R^{1a})(R^{1b})$, $C(O)C(R^{1a})(R^{1b})$, $C(R^{1a})(R^{1b})C(R^{1a})(R^{1b})$, $C(R^{1a})(R^{1b})N(R^{1c})$, and $N(R^{1c})$;

$X^{14}$, $X^{15}$, $X^{17}$, $X^{18}$ are independently selected from C(O), $C(R^{1a})$, N, $C(R^{1a})(R^{1b})$, and $N(R^{1c})$;

$X^{16}$ are independently selected from C, N, and $C(R^{1a})$;

each $R^{1a}$, $R^{1b}$, $R^{1d}$, and $R^{1h}$ is independently selected from hydrogen, halogen, —CN, $C_{1-6}$alkyl, $C_{1-6}$haloalkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{29q}$; or $R^{1a}$ and $R^{1b}$ bonded to the same carbon are joined to form a 3-10 membered heterocycloalkyl ring or a $C_{3-10}$cycloalkyl ring, wherein the 3-10 membered heterocycloalkyl ring or $C_{3-10}$cycloalkyl ring are optionally substituted with one, two, or three $R^{29q}$; or two $R^{1a}$ bonded to adjacent atoms are joined to form a 3-10 membered heterocycloalkyl ring, a $C_{6-10}$aryl ring, a 5-12 membered heteroaryl ring, or a $C_{3-10}$cycloalkyl ring, wherein the 3-10 membered heterocycloalkyl ring, $C_{6-10}$aryl ring, 5-12 membered heteroaryl ring, or $C_{3-10}$cycloalkyl ring are optionally substituted with one, two, or three $R^{29q}$; or $R^{1b}$ and one of $R^{1a}$, $R^{1b}$, $R^{1c}$, and $R^{1d}$ bonded to adjacent atoms are joined to form a 3-10 membered heterocycloalkyl ring, a $C_{6-10}$aryl ring, a 5-12 membered heteroaryl ring, or a $C_{3-10}$cycloalkyl ring, wherein the 3-10 membered heterocycloalkyl ring, a $C_{6-10}$aryl ring, a 5-12 membered heteroaryl ring, and $C_{6-10}$cycloalkyl ring are optionally substituted with one, two, or three $R^{29q}$; and each $R^{1c}$ is independently selected from hydrogen, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{29q}$.

63. The compound of any one of embodiments 1-54, or a pharmaceutically acceptable salt or solvate thereof, wherein $R^{17}$ is selected from:
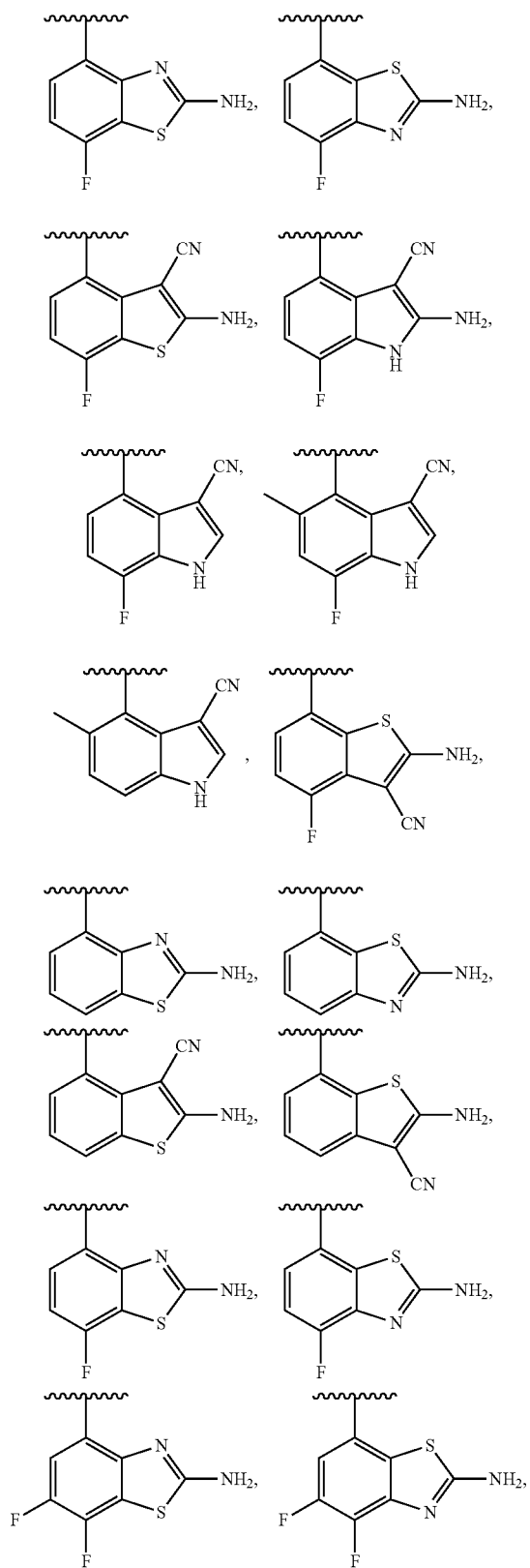
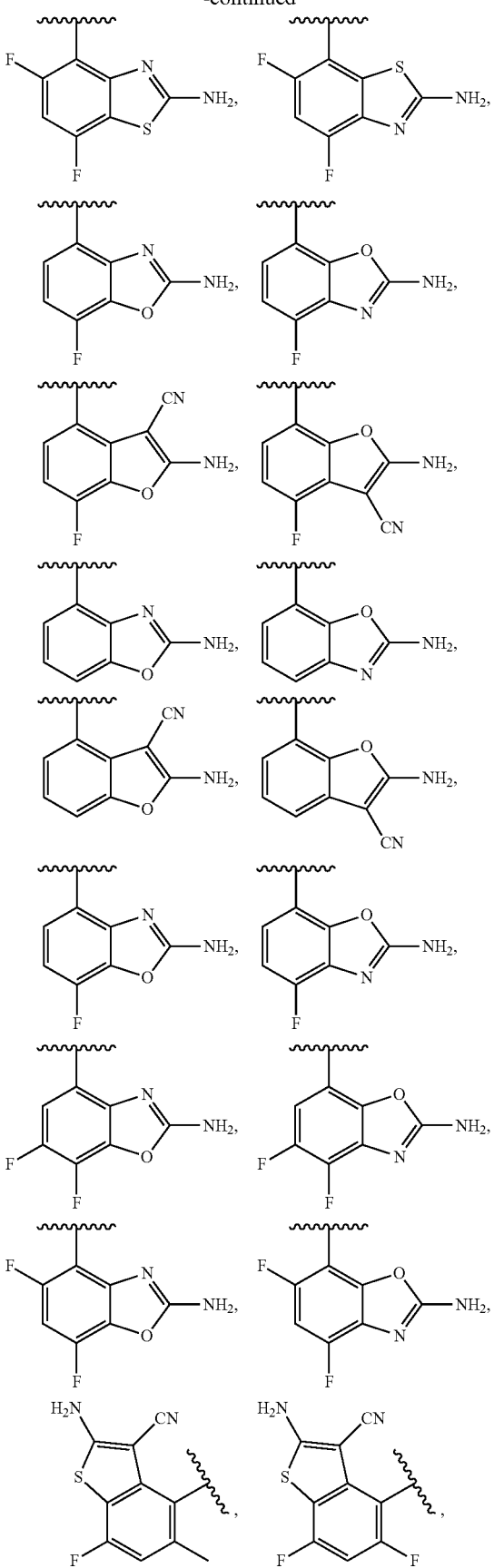

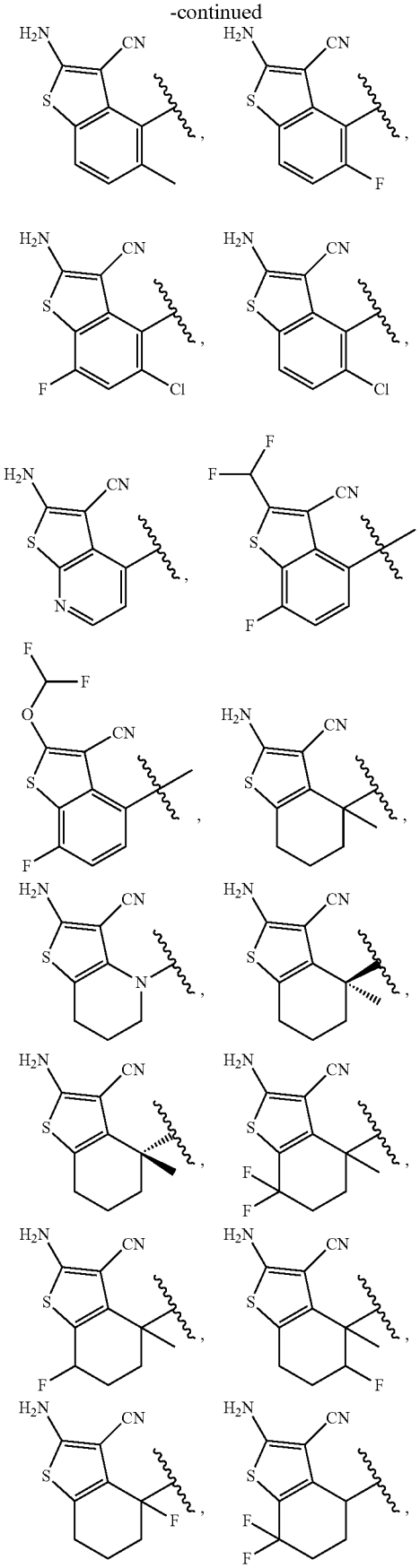
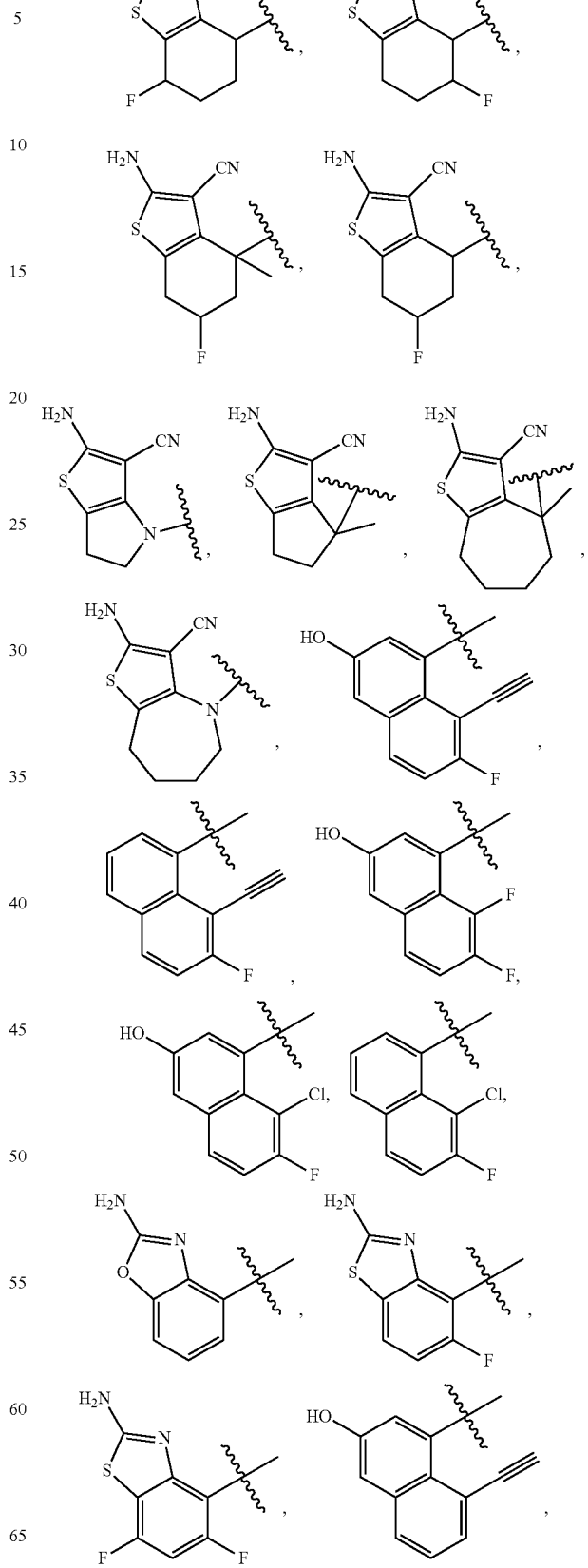

787
-continued
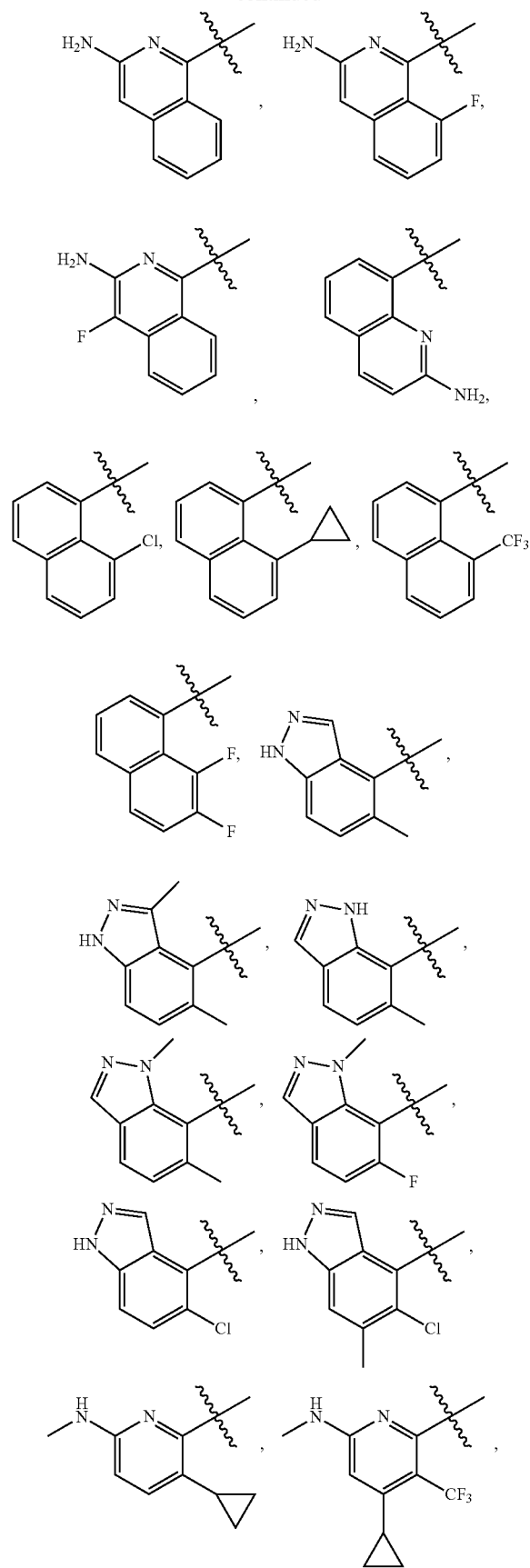
788
-continued
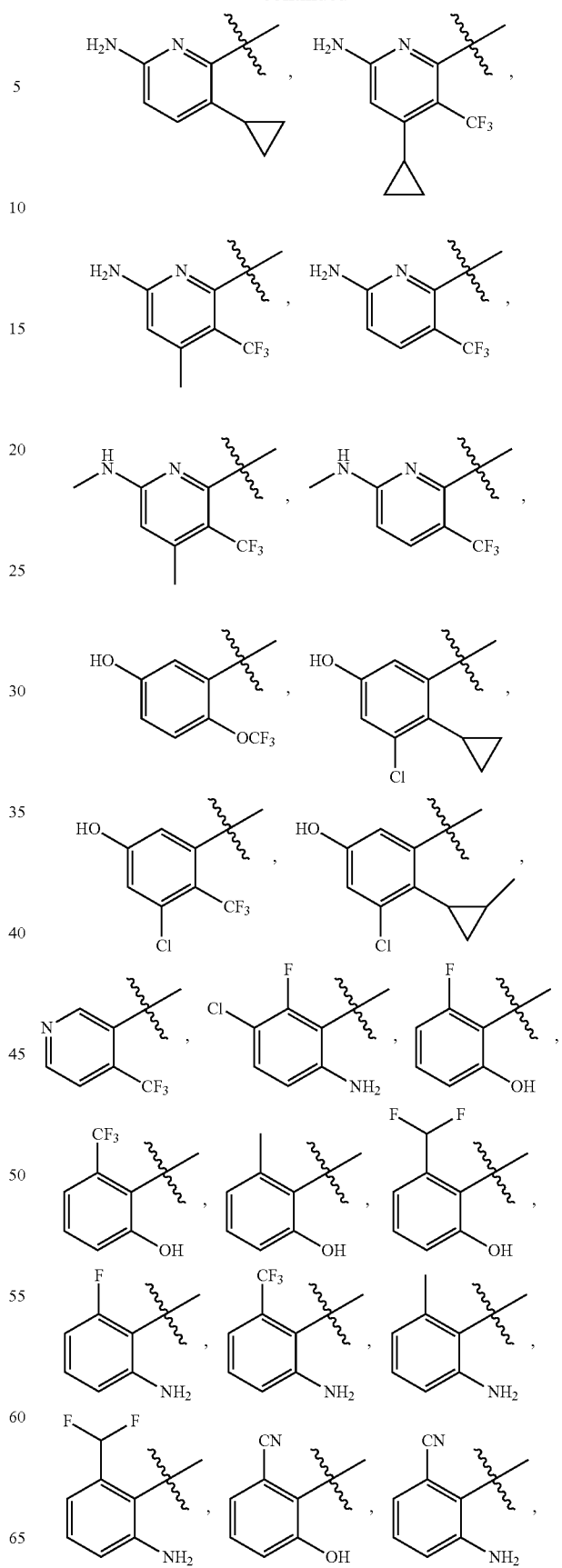

-continued
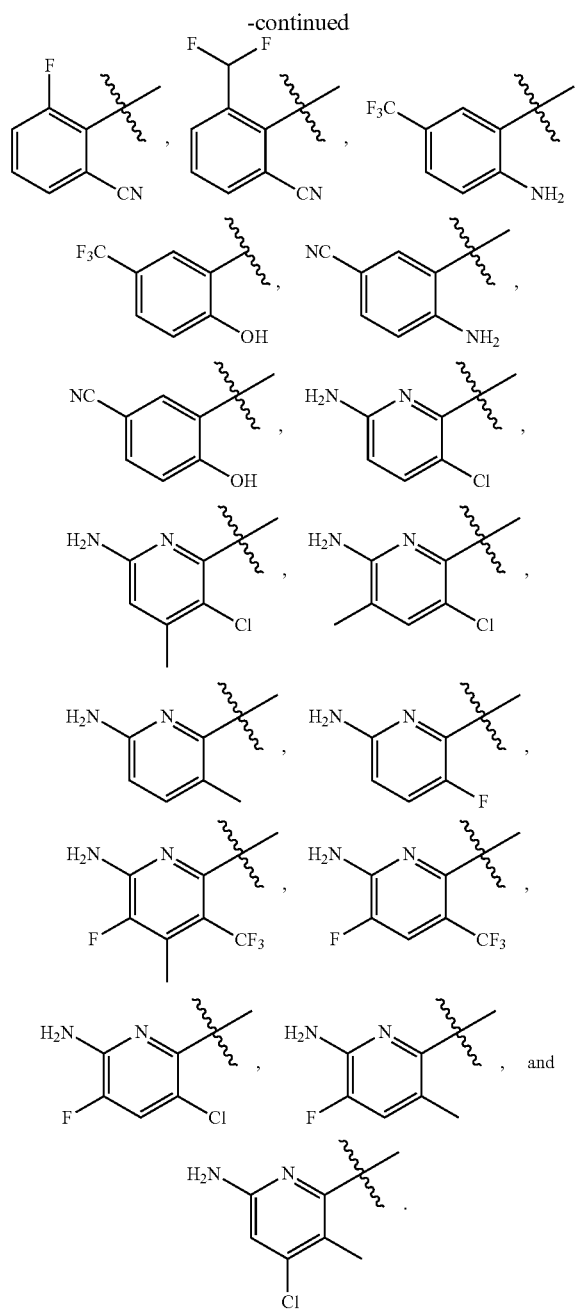
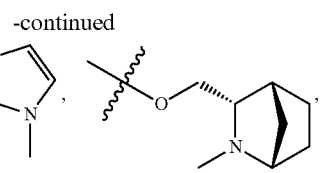
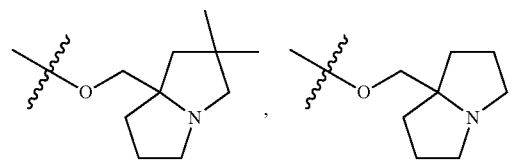
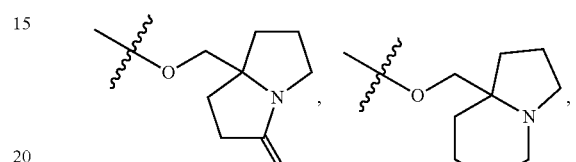
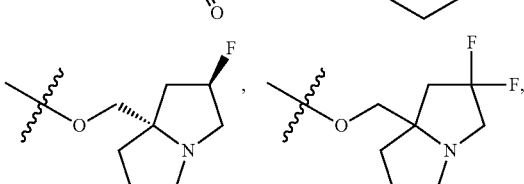
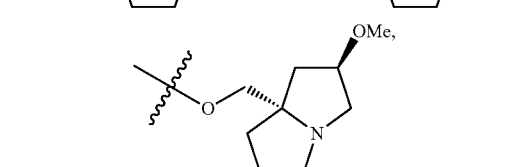
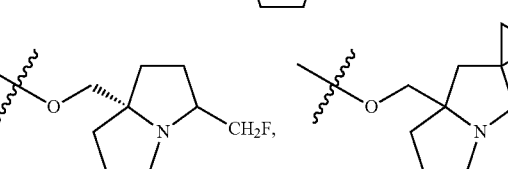
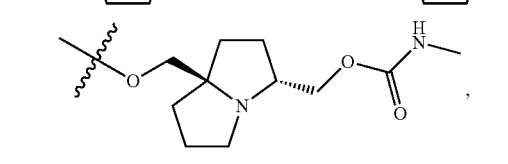
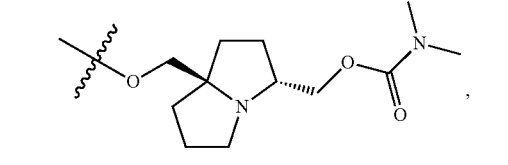
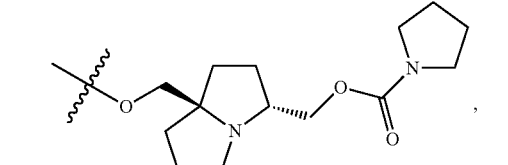
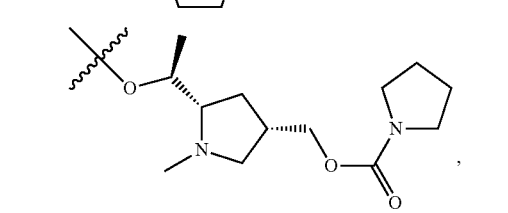
64. The compound of any one of embodiments 1-63, or a pharmaceutically acceptable salt or solvate thereof, wherein R² is independently —OR$^{12a}$.
65. The compound of any one of embodiments 1-63, or a pharmaceutically acceptable salt or solvate thereof, wherein R² is independently selected from
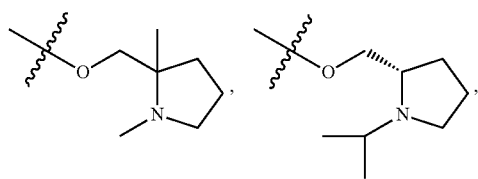

791
-continued
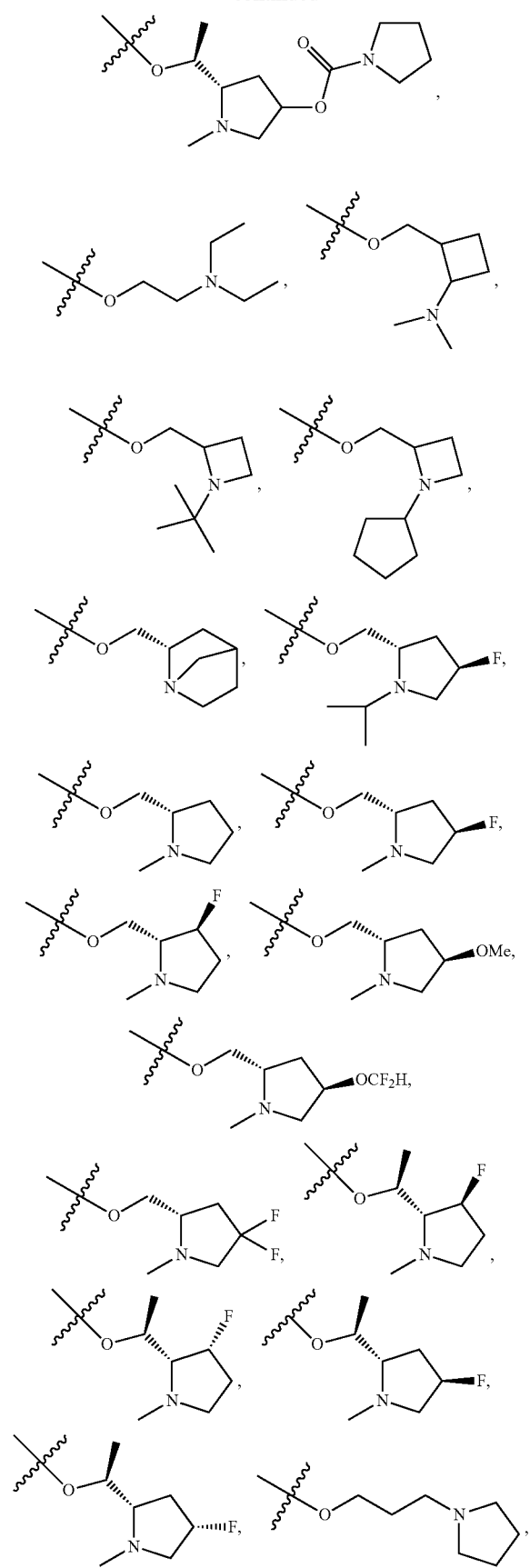
792
-continued
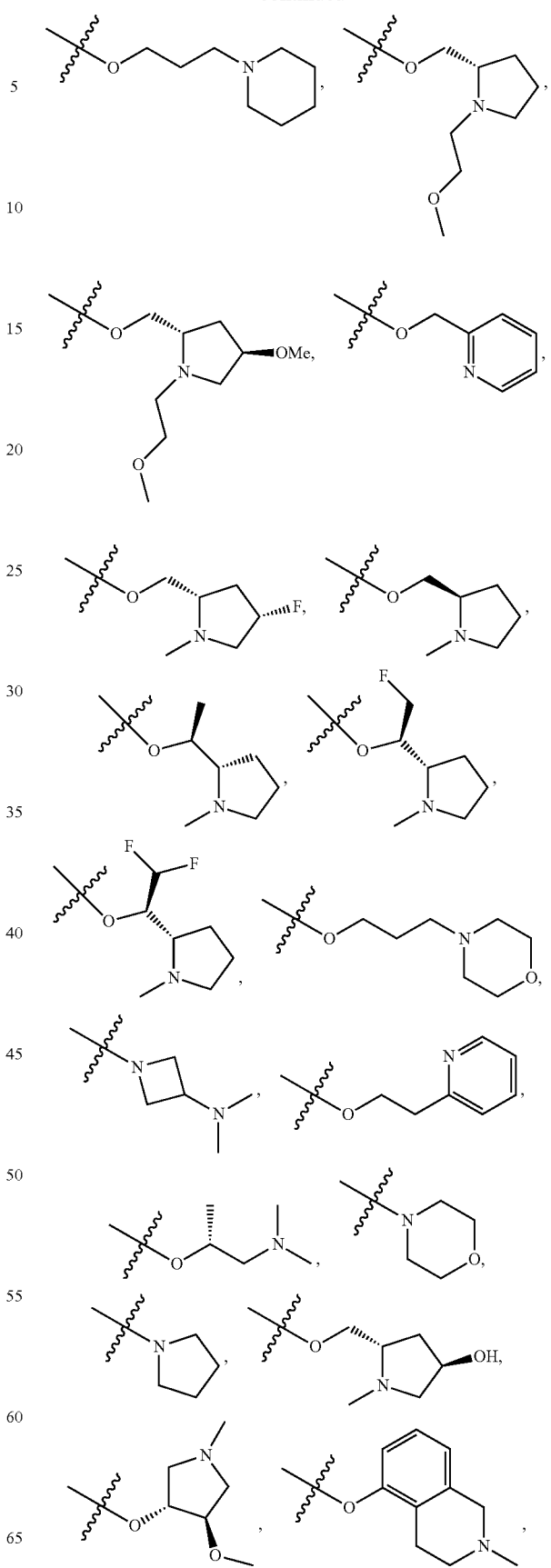

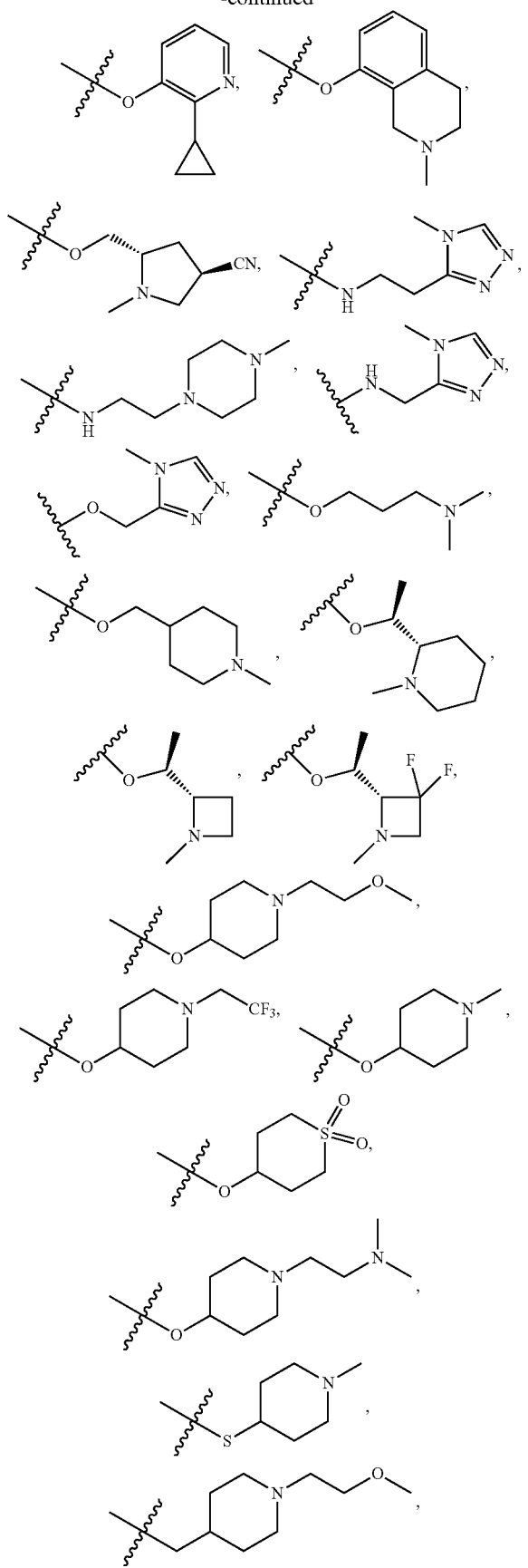
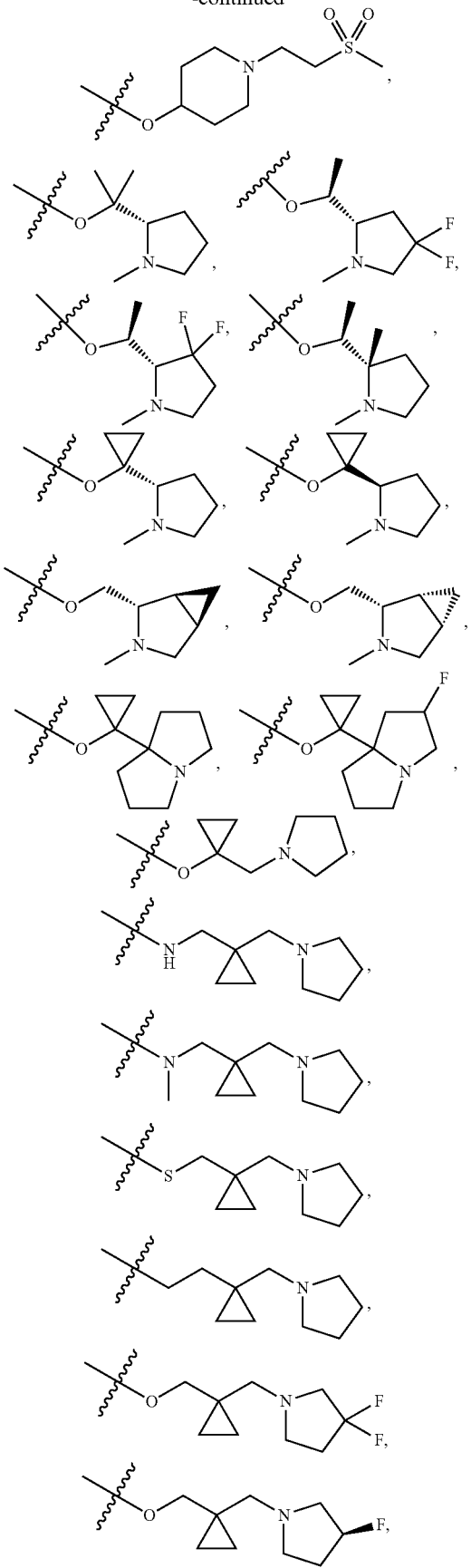

795
-continued
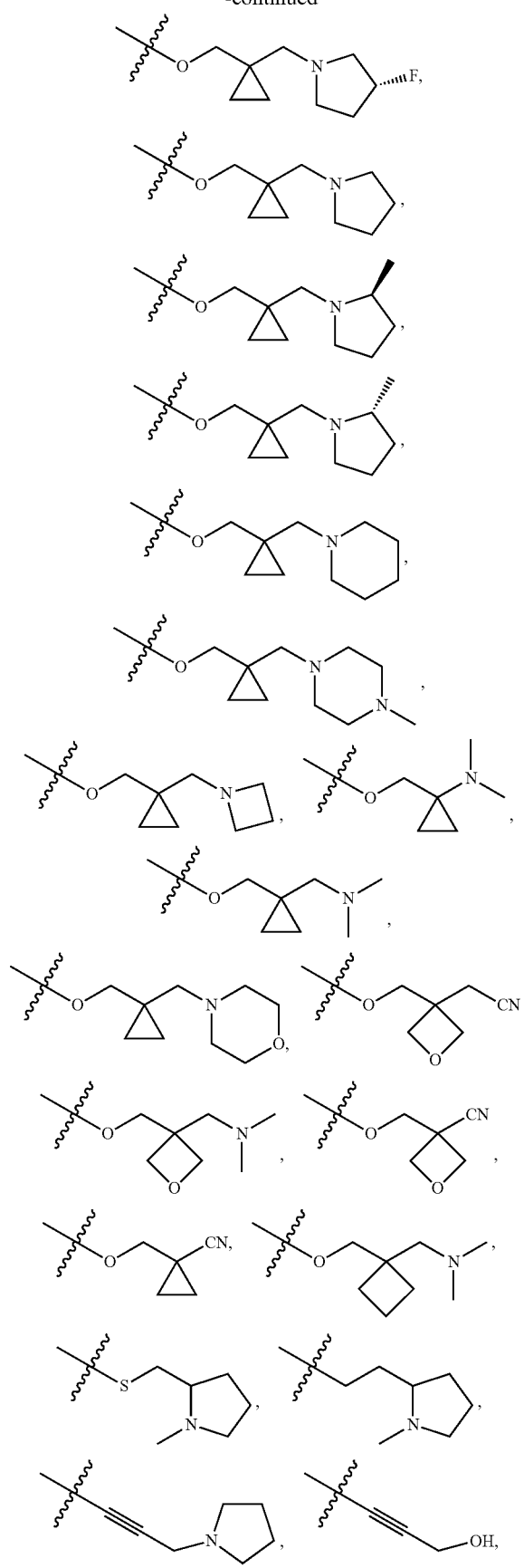
796
-continued
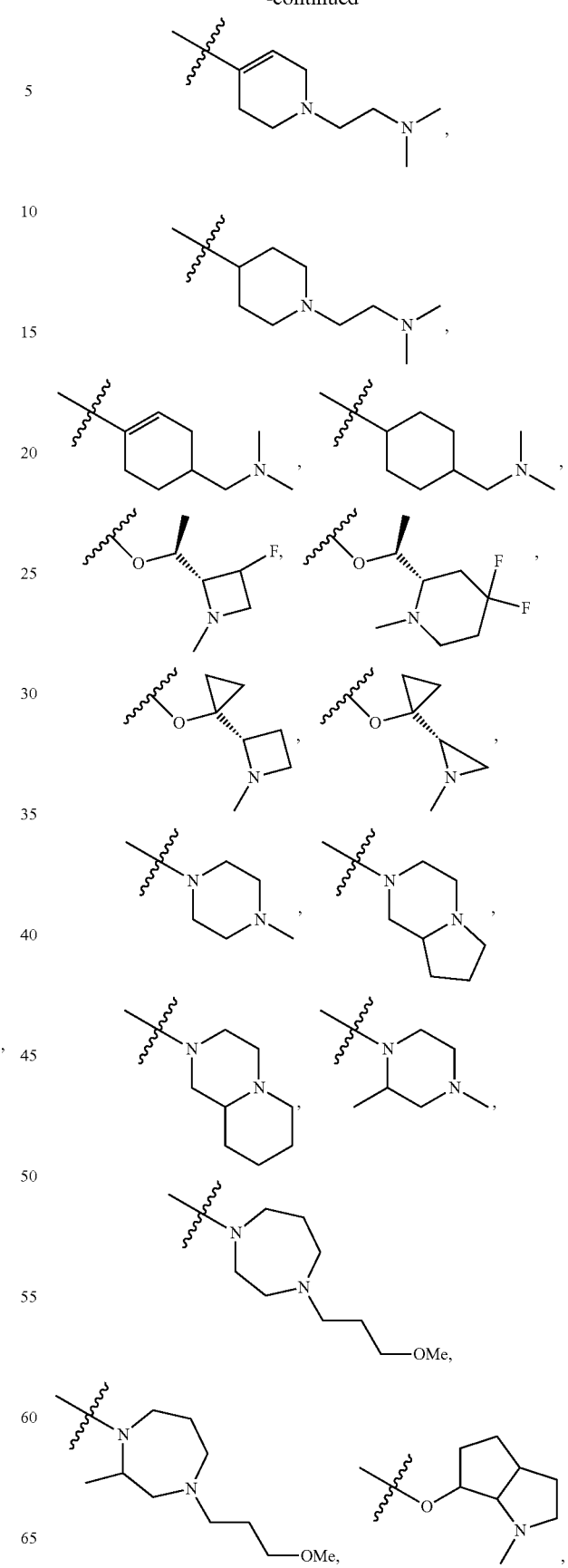

-continued

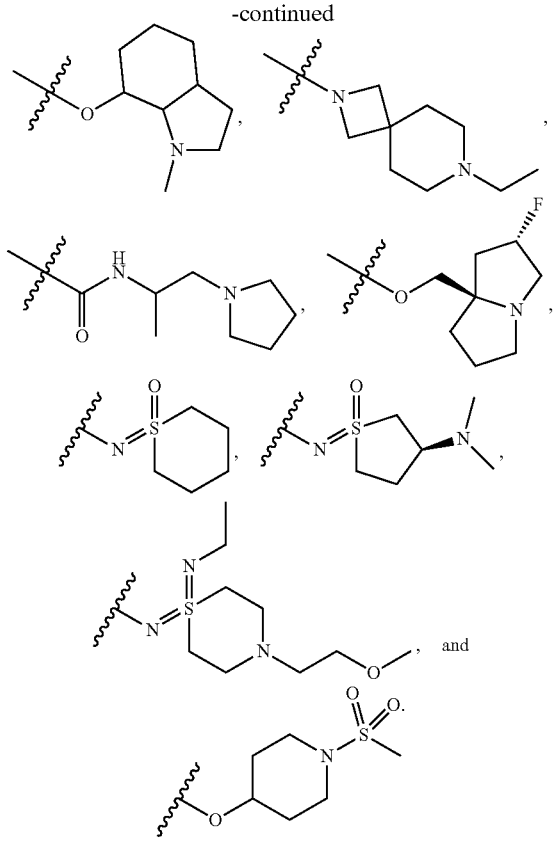

66. The compound of embodiment 65, or a pharmaceutically acceptable salt or solvate thereof, wherein $R^2$ is independently

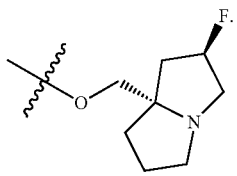

67. The compound of embodiment 1, or a pharmaceutically acceptable salt or solvate thereof, wherein $Z^4$ is a bond, $Z^{4a}$, $Z^{4a}Z^{4b}$, $Z^{4a}Z^{4b}Z^{4c}$, $Z^{4a}Z^{4b}Z^{4c}Z^{4d}$, or $Z^{4a}Z^{4b}Z^{4c}Z^{4d}Z^{4e}$;.
68. The compound of embodiment 1, or a pharmaceutically acceptable salt or solvate thereof, wherein $Z^4$ is $Z^{4a}$.
69. The compound of embodiment 1, or a pharmaceutically acceptable salt or solvate thereof, wherein $Z^4$ is $Z^{4a}Z^{4b}$.
70. The compound of embodiment 1, or a pharmaceutically acceptable salt or solvate thereof, wherein $Z^4$ is $Z^{4a}Z^{4b}Z^{4c}$.
71. The compound of embodiment 1, or a pharmaceutically acceptable salt or solvate thereof, wherein $Z^4$ is $Z^{4a}Z^{4b}Z^{4c}Z^{4d}$.
72. The compound of embodiment 1, or a pharmaceutically acceptable salt or solvate thereof, wherein $Z^4$ is $Z^{4a}Z^{4b}Z^{4c}Z^{4d}Z^{4e}$.
73. The compound of any one of embodiments 1-72, or a pharmaceutically acceptable salt or solvate thereof, wherein each $R^{z4}$ is independently selected from hydrogen, halogen, —CN, $C_{1-6}$alkyl, $C_{2-6}$alkenyl, $C_{3-10}$cycloalkyl, $C_{2-9}$heterocycloalkyl, $C_{1-9}$heteroaryl, —OR$^{12}$, —N(R$^{12}$)(R$^{13}$), —N(R$^{14}$)S(O)$_2$R$^{15}$, —C(O)R$^{12}$, —S(O)R$^{15}$, —OC(O)R$^{15}$, —C(O)N(R$^{12}$)(R$^{13}$), —N(R$^{14}$)C(O)R$^{12}$, —S(O)$_2$R$^{15}$, and —S(O)$_2$N(R$^{12}$)(R$^{13}$)—, wherein $C_{1-6}$alkyl, $C_{2-6}$alkenyl, $C_{3-10}$cycloalkyl, $C_{2-9}$heterocycloalkyl, and $C_{1-9}$heteroaryl are optionally substituted with one, two, or three $R^{20z4}$; or two $R^{z4}$ bonded to the same carbon are joined to form a $C_{2-6}$alkenyl that is optionally substituted with one, two, or three $R^{20z4}$.
74. The compound of any one of embodiments 1-72, or a pharmaceutically acceptable salt or solvate thereof, wherein each $R^{z4}$ is independently selected from hydrogen, halogen, —CN, $C_{3-10}$cycloalkyl, $C_{2-9}$heterocycloalkyl, $C_{1-9}$heteroaryl, —OR$^{12}$, —N(R$^{12}$)(R$^{13}$), —N(R$^{14}$)S(O)$_2$R$^{15}$, and —S(O)$_2$R$^{15}$, wherein $C_{1-6}$alkyl, $C_{3-10}$cycloalkyl, $C_{2-9}$heterocycloalkyl, and $C_{1-9}$heteroaryl are optionally substituted with one, two, or three $R^{20z4}$; or two $R^{z4}$ bonded to the same carbon are joined to form a $C_{2-6}$alkenyl that is optionally substituted with one, two, or three $R^{20z4}$.
75. The compound of any one of embodiments 1-74, or a pharmaceutically acceptable salt or solvate thereof, wherein each $R^{z5}$ is independently selected from hydrogen, halogen, —CN, $C_{2-6}$alkenyl, $C_{3-10}$cycloalkyl, $C_{2-9}$heterocycloalkyl, $C_{1-9}$heteroaryl, —OR$^{12}$, —N(R$^{12}$)(R$^{13}$), —N(R$^{14}$)S(O)$_2$R$^{15}$, —C(O)R$^{12}$, —S(O)R$^{15}$, —OC(O)R$^{15}$, —C(O)N(R$^{12}$)(R$^{13}$), —N(R$^{14}$)C(O)R$^{12}$, —S(O)$_2$R$^{15}$, and —S(O)$_2$N(R$^{12}$)(R$^{13}$)—, wherein $C_{1-6}$alkyl, $C_{2-6}$alkenyl, $C_{3-10}$cycloalkyl, $C_{2-9}$heterocycloalkyl, and $C_{1-9}$heteroaryl are optionally substituted with one, two, or three $R^{20z5}$; or two $R^{z5}$ bonded to the same carbon are joined to form a $C_{2-6}$alkenyl that is optionally substituted with one, two, or three $R^{20z5}$.
76. The compound of any one of embodiments 1-74, or a pharmaceutically acceptable salt or solvate thereof, wherein each $R^{z5}$ is independently selected from hydrogen, halogen, —CN, $C_{3-10}$cycloalkyl, $C_{2-9}$heterocycloalkyl, $C_{1-9}$heteroaryl, —OR$^{12}$, —N(R$^{12}$)(R$^{13}$), —N(R$^{14}$)S(O)$_2$R$^{15}$, and —S(O)$_2$R$^{15}$, wherein $C_{1-6}$alkyl, $C_{3-10}$cycloalkyl, $C_{2-9}$heterocycloalkyl, and $C_{1-9}$heteroaryl are optionally substituted with one, two, or three $R^{20z5}$; or two $R^{z5}$ bonded to the same carbon are joined to form a $C_{2-6}$alkenyl that is optionally substituted with one, two, or three $R^{20z5}$.
77. The compound of any one of embodiments 1-76, or a pharmaceutically acceptable salt or solvate thereof, wherein each $R^{z6}$ is independently selected from hydrogen, halogen, —CN, $C_{2-6}$alkenyl, $C_{3-10}$cycloalkyl, $C_{2-9}$heterocycloalkyl, $C_{1-9}$heteroaryl, —OR$^{12}$, —N(R$^{12}$)(R$^{13}$), —N(R$^{14}$)S(O)$_2$R$^{15}$, —C(O)R$^{12}$, —S(O)R$^{15}$, —OC(O)R$^{15}$, —C(O)N(R$^{12}$)(R$^{13}$), —N(R$^{14}$)C(O)R$^{12}$, —S(O)$_2$R$^{15}$, and —S(O)$_2$N(R$^{12}$)(R$^{13}$)—, wherein $C_{1-6}$alkyl, $C_{2-6}$alkenyl, $C_{3-10}$cycloalkyl, $C_{2-9}$heterocycloalkyl, and $C_{1-9}$heteroaryl are optionally substituted with one, two, or three $R^{20z6}$; or two $R^{z6}$ bonded to the same carbon are joined to form a $C_{2-6}$alkenyl that is optionally substituted with one, two, or three $R^{20z6}$.
78. The compound of any one of embodiments 1-76, or a pharmaceutically acceptable salt or solvate thereof, wherein each $R^{z6}$ is independently selected from hydrogen, halogen, —CN, $C_{3-10}$cycloalkyl, $C_{2-9}$heterocycloalkyl, $C_{1-9}$heteroaryl, —OR$^{12}$, —N(R$^{12}$)(R$^{13}$), —N($R^{14}$)S(O)$_2$$R^{15}$, and —S(O)$_2$$R^{15}$, wherein $C_{1-6}$alkyl, $C_{3-10}$cycloalkyl, $C_{2-9}$heterocycloalkyl, and $C_{1-9}$heteroaryl are optionally substituted with one, two, or three $R^{20z6}$; or two $R^{z6}$ bonded to the same carbon are joined to form a $C_{2-6}$alkenyl that is optionally substituted with one, two, or three $R^{20z6}$.

79. The compound of any one of embodiments 1-78, or a pharmaceutically acceptable salt or solvate thereof, wherein each $R^{20z}$ is independently selected from hydrogen, halogen, oxo, —CN, $C_{2-6}$alkenyl, $C_{3-10}$cycloalkyl, $C_{2-9}$heterocycloalkyl, $C_{1-9}$heteroaryl, —O$R^{12}$, —N($R^{12}$)($R^{13}$), —N($R^{14}$)S(O)$_2$$R^{15}$, —C(O)$R^{12}$, —S(O)$R^{15}$, —OC(O)$R^{15}$, —C(O)N($R^{12}$)($R^{13}$), —N($R^{14}$)C(O)$R^{12}$, —S(O)$_2$$R^{15}$, and —S(O)$_2$N($R^{12}$)($R^{13}$)—, wherein $C_{1-6}$alkyl, $C_{2-6}$alkenyl, $C_{3-10}$cycloalkyl, $C_{2-9}$heterocycloalkyl, and $C_{1-9}$heteroaryl are optionally substituted with one, two, or three $R^{20zz}$; or two $R^{20z}$ bonded to the same carbon are joined to form a $C_{2-6}$alkenyl that is optionally substituted with one, two, or three $R^{20zz}$.

80. The compound of any one of embodiments 1-78, or a pharmaceutically acceptable salt or solvate thereof, wherein each $R^{20z}$ is independently selected from hydrogen, halogen, oxo, —CN, $C_{3-10}$cycloalkyl, $C_{2-9}$heterocycloalkyl, $C_{1-9}$heteroaryl, —O$R^{12}$, —N($R^{12}$)($R^{13}$), —N($R^{14}$)S(O)$_2$$R^{15}$, and —S(O)$_2$$R^{15}$, wherein $C_{1-6}$alkyl, $C_{3-10}$cycloalkyl, $C_{2-9}$heterocycloalkyl, and $C_{1-9}$heteroaryl are optionally substituted with one, two, or three $R^{20zz}$; or two $R^{20z}$ bonded to the same carbon are joined to form a $C_{2-6}$alkenyl that is optionally substituted with one, two, or three $R^{20zz}$.

81. A compound having the formula A-$L^{AB}$-B wherein
A is a monovalent form of a compound of any one of embodiments 1-80;
$L^{AB}$ is a covalent linker bonded to A and B; and
B is a monovalent form of a degradation enhancer.

82. The compound of embodiment 81, wherein the degradation enhancer is capable of binding a protein selected from E3A, mdm2, APC, EDD1, SOCS/BC-box/eloBC/CUL5/RING, LNXp80, CBX4, CBLL1, HACE1, HECTD1, HECTD2, HECTD3, HECTD4, HECW1, HECW2, HERC1, HERC2, HERC3, HERC4, HER5, HERC6, HUWE1, ITCH, NEDD4, NEDD4L, PPIL2, PRPF19, PIAS1, PIAS2, PIAS3, PIAS4, RANBP2, RNF4, RBX1, SMURF1, SMURF2, STUB1, TOPORS, TRIP12, UBE3A, UBE3B, UBE3C, UBE3D, UBE4A, UBE4B, UBOX5, UBR5, VHL (von-Hippel-Lindau ubiquitin ligase), WWP1, WWP2, Parkin, MKRN1, CMA (chaperon-mediated autophage), SCFb-TRCP (Skip-Cullin-F box (Beta-TRCP) ubiquitin complex), b-TRCP (b-transducing repeat-containing protein), cIAP1 (cellular inhibitor of apoptosis protein 1), APC/C (anaphase-promoting complex/cyclosome), CRBN (cereblon), CUL4-RBX1-DDB1-CRBN (CRL4$^{CRBN}$) ubiquitin ligase, XIAP, IAP, KEAP1, DCAF15, RNF114, DCAF16, AhR, SOCS2, KLHL12, UBR2, SPOP, KLHL3, KLHL20, KLHDC2, SPSB1, SPSB2, SPSB4, SOCS6, FBXO4, FBXO31, BTRC, FBW7, CDC20, PML, TRIM21, TRIM24, TRIM33, GID4, avadomide, iberdomide, and CC-885.

83. The compound of embodiment 81, wherein the degradation enhancer is capable of binding a protein selected from UBE2A, UBE2B, UBE2C, UBE2D1, UBE2D2, UBE2D3, UBE2DR, UBE2E1, UBE2E2, UBE2E3, UBE2F, UBE2G1, UBE2G2, UBE2H, UBE2I, UBE2J1, UBE2J2, UBE2K, UBE2L3, UBE2L6, UBE2L1, UBE2L2, UBE2L4, UBE2M, UBE2N, UBE2O, UBE2Q1, UBE2Q2, UBE2R1, UBE2R2, UBE2S, UBE2T, UBE2U, UBE2V1, UBE2V2, UBE2W, UBE2Z, ATG3, BIRC6, and UFC1.

84. The compound of any one of embodiments 81-83, wherein $L^{AB}$ is -$L^{AB1}$-$L^{AB2}$-$L^{AB3}$-$L^{AB4}$-$L^{AB5}$;
$L^{AB1}$, $L^{AB2}$, $L^{AB3}$, $L^{AB4}$, and $L^{AB5}$ are independently a bond, —O—, —N($R^{14}$)—, —C(O)—, —N($R^{14}$)C(O)—, —C(O)N($R^{14}$)—, —S—, —S(O)$_2$—, —S(O)—, —S(O)$_2$N($R^{14}$)—, —S(O)N($R^{14}$)—, —N($R^{14}$)S(O)—, —N($R^{14}$)S(O)$_2$—, $C_{1-6}$alkylene, (—O-$C_{1-6}$alkyl)$_z$-, (-$C_{1-6}$alkyl-O)$_z$-, $C_{2-6}$alkenylene, $C_{2-6}$alkynylene, $C_{1-6}$haloalkylene, $C_{3-12}$cycloalkylene, $C_{1-11}$heterocycloalkylene, $C_{6-12}$arylene, or $C_{1-11}$heteroarylene, wherein $C_{1-6}$alkylene, $C_{2-6}$alkenylene, $C_{2-6}$alkynylene, $C_{1-6}$haloalkylene, $C_{3-12}$cycloalkylene, $C_{1-11}$heterocycloalkylene, $C_{6-12}$arylene, or $C_{1-11}$heteroarylene, are optionally substituted with one, two, or three $R^{20n}$; wherein each $C_{1-6}$alkyl of (—O-$C_{1-6}$alkyl)$_2$- and (-$C_{1-6}$alkyl-O)$_2$- is optionally substituted with one, two, or three $R^{20n}$.

z is independently an integer from 0 to 10;
each $R^{12}$ is independently selected from hydrogen, $C_{1-6}$alkyl, $C_{2-6}$alkenyl, $C_{2-6}$alkynyl, $C_{3-10}$cycloalkyl, —CH$_2$-$C_{3-10}$cycloalkyl, $C_{2-9}$heterocycloalkyl, —CH$_2$-$C_{2-9}$heterocycloalkyl, $C_{6-10}$aryl, —CH$_2$-$C_{6-10}$aryl, —CH$_2$-$C_{1-9}$heteroaryl, and $C_{1-9}$heteroaryl, wherein $C_{1-6}$alkyl, $C_{2-6}$alkenyl, $C_{2-6}$alkynyl, $C_{3-10}$cycloalkyl, —CH$_2$-$C_{3-10}$cycloalkyl, $C_{2-9}$heterocycloalkyl, —CH$_2$-$C_{2-9}$heterocycloalkyl, $C_{6-10}$aryl, —CH$_2$-$C_{6-10}$aryl, —CH$_2$-$C_{1-9}$heteroaryl, and $C_{1-9}$heteroaryl are optionally substituted with one, two, or three $R^{20l}$;
each $R^{13}$ is independently selected from hydrogen, $C_{1-6}$alkyl, and $C_{1-6}$haloalkyl; or $R^{12}$ and $R^{13}$, together with the nitrogen to which they are attached, form a $C_{2-9}$heterocycloalkyl ring optionally substituted with one, two, or three $R^{20m}$;
each $R^{14}$ is independently selected from hydrogen, $C_{1-6}$alkyl, and $C_{1-6}$haloalkyl;
each $R^{15}$ is independently selected from $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20o}$;
each $R^{20l}$, $R^{20m}$, $R^{20n}$, and $R^{20o}$ are each independently selected from halogen, —CN, $C_{1-6}$alkyl, $C_{2-6}$alkenyl, $C_{2-6}$alkynyl, $C_{3-10}$cycloalkyl, —CH$_2$-$C_{3-10}$cycloalkyl, $C_{2-9}$heterocycloalkyl, —CH$_2$-$C_{2-9}$heterocycloalkyl, $C_{6-10}$aryl, —CH$_2$-$C_{6-10}$aryl, —CH$_2$-$C_{1-9}$heteroaryl, $C_{1-9}$heteroaryl, —O$R^{21}$, —S$R^{21}$, —N($R^{22}$)($R^{23}$), —C(O)O$R^{22}$, —C(O)N($R^{22}$)($R^{23}$), —C(O)C(O)N($R^{22}$)($R^{23}$), —OC(O)N($R^{22}$)($R^{23}$), —N($R^{24}$)C(O)N($R^{22}$)($R^{23}$), —N($R^{24}$)C(O)O$R^{25}$, —N($R^{24}$)C(O)$R^{25}$, —N($R^{24}$)S(O)$_2$$R^{25}$, —C(O)$R^{25}$, —S(O)$_2$$R^{25}$, —S(O)$_2$N($R^{22}$)($R^{23}$), —OCH$_2$C(O)O$R^{22}$, and —OC(O)$R^{25}$, wherein $C_{1-6}$alkyl, $C_{2-6}$alkenyl, $C_{2-6}$alkynyl, $C_{3-10}$cycloalkyl, —CH$_2$-$C_{3-10}$cycloalkyl, $C_{2-9}$heterocycloalkyl, —CH$_2$-$C_{2-9}$heterocycloalkyl, $C_{6-10}$aryl, —CH$_2$-$C_{6-10}$aryl, —CH$_2$-$C_{1-9}$heteroaryl, and $C_{1-9}$heteroaryl are optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —O$R^{21}$, —S$R^{21}$, —N($R^{22}$)($R^{23}$), —C(O)

OR²², —C(O)N(R²²)(R²³), —C(O)C(O)N(R²²)(R²³), —OC(O)N(R²²)(R²³), —N(R²⁴)C(O)N(R²²)(R²³), —N(R²⁴)C(O)OR²⁵, —N(R²⁴)C(O)R²⁵, —N(R²⁴)S(O)₂R²⁵, —C(O)R²⁵, —S(O)₂R²⁵, —S(O)₂N(R²²)(R²³), and —OC(O)R²⁵;

each R²¹ is independently selected from H, $C_{1-6}$alkyl, $C_{1-6}$haloalkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl;

each R²² is independently selected from H, $C_{1-6}$alkyl, $C_{1-6}$haloalkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl;

each R²³ is independently selected from H and $C_{1-6}$alkyl;

each R²⁴ is independently selected from H and $C_{1-6}$alkyl; and each R²⁵ is independently selected from $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl.

85. The compound of any one of embodiments 81-83, wherein $L^{AB}$ is —(O-C₂alkyl)$_z$— and z is an integer from 1 to 10.

86. The compound of any one of embodiments 81-83, wherein $L^{AB}$ is -(C₂alkyl-O—)$_z$— and z is an integer from 1 to 10.

87. The compound of any one of embodiments 81-83, wherein $L^{AB}$ is —(CH₂)$_{zz1}$L$^{AB2}$(CH₂O)$_{zz2}$—, wherein $L^{AB2}$ is a bond, a 5 or 6 membered heterocycloalkylene or heteroarylene, phenylene, -(C₂-C₄)alkynylene, —SO₂— or —NH—; and zz1 and zz2 are independently an integer from 0 to 10.

88. The compound of any one of embodiments 81-83, wherein $L^{AB}$ is —(CH₂)$_{zz1}$(CH₂O)$_{zz2}$—, wherein zz1 and zz2 are each independently an integer from 0 to 10.

89. The compound of any one of embodiments 81-83, wherein $L^{AB}$ is a PEG linker.

90. The compound of any one of embodiments 81-89, wherein B is a monovalent form of a compound selected from

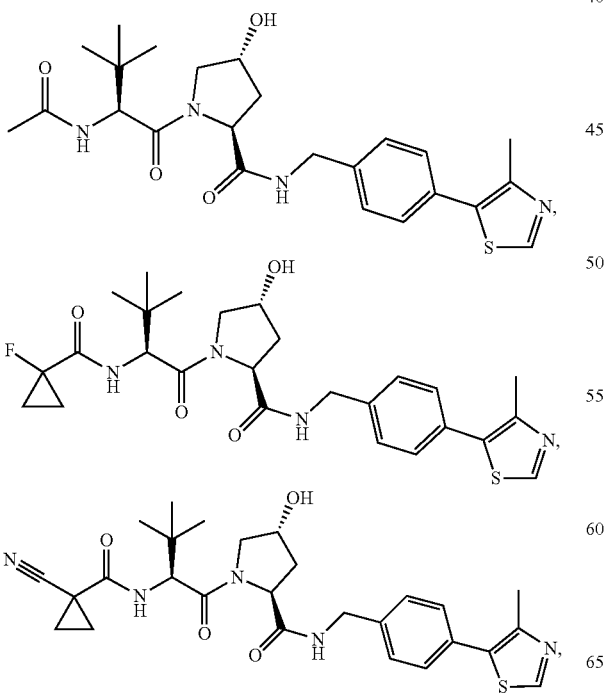

-continued

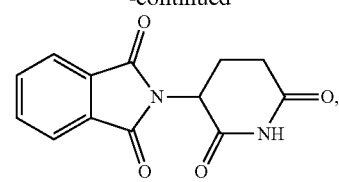

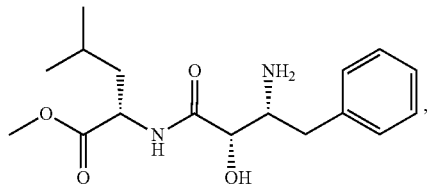

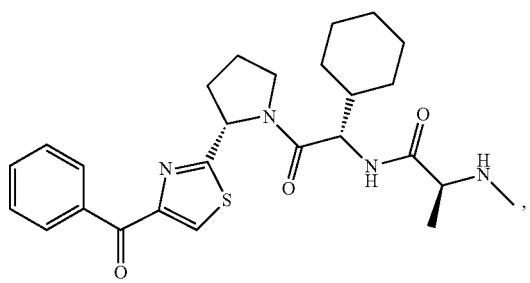

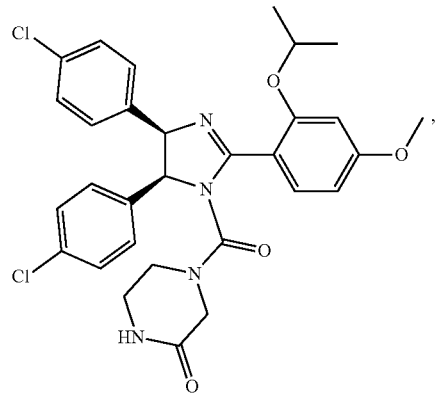

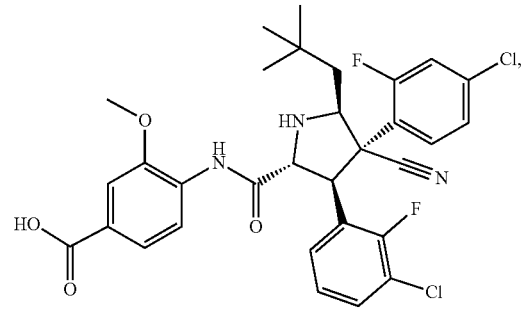

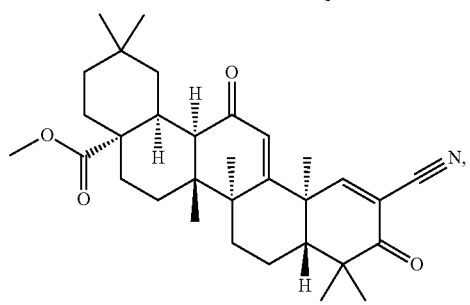

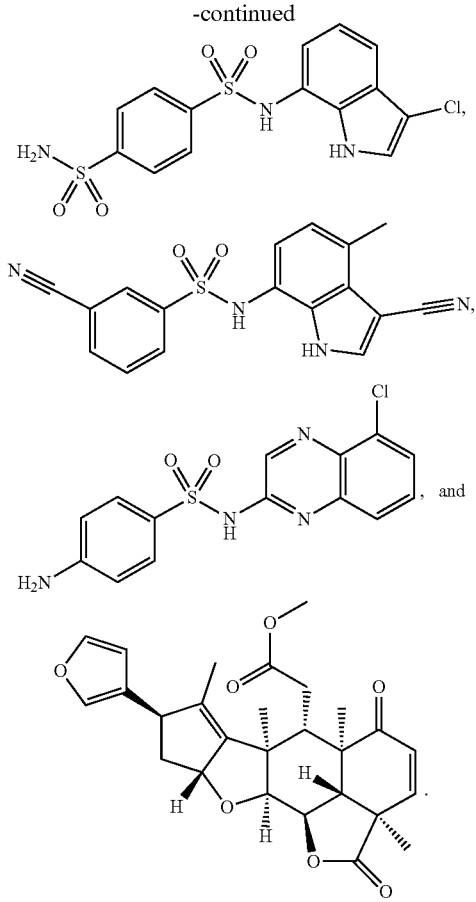

91. A pharmaceutical composition comprising a compound of any one of embodiments 1-90, or a pharmaceutically acceptable salt or solvate thereof, and a pharmaceutically acceptable excipient.
92. A method of treating cancer in a subject in need thereof, comprising administering to the subject a therapeutically effective amount of a compound of any one of embodiments 1-90, or a pharmaceutically acceptable salt or solvate thereof.
93. A method of treating cancer in a subject comprising a Ras mutant protein, the method comprising: modifying the Ras mutant protein of said subject by administering to said subject a compound, wherein the compound is characterized in that upon contacting the Ras mutant protein, said Ras mutant protein is modified covalently at a residue corresponding to residue 12 of SEQ ID No: 1, such that said modified Ras mutant protein exhibits reduced Ras signaling output.
94. The method of any one of embodiments 92 to 93, wherein the cancer is a solid tumor.
95. The method of any one of embodiments 92 to 93, wherein the cancer is a hematological cancer.
96. The method of any one of embodiments 92 to 93, wherein the compound is a compound of any one of embodiments 1-90.
97. A method of modulating signaling output of a Ras protein, comprising contacting a Ras protein with an effective amount of a compound of any one of embodiments 1-90, or a pharmaceutically acceptable salt or solvate thereof, thereby modulating the signaling output of the Ras protein.
98. A method of inhibiting cell growth, comprising administering an effective amount of a compound of any one of embodiments 1-90, or a pharmaceutically acceptable salt or solvate thereof, to a cell expressing a Ras protein, thereby inhibiting growth of said cells.
99. The method of embodiment any one of embodiments 92-98, comprising administering an additional agent.
100. The method of embodiment 99, wherein the additional agent comprises (1) an inhibitor of MEK; (2) an inhibitor of epidermal growth factor receptor (EGFR) and/or of mutants thereof; (3) an immunotherapeutic agent; (4) a taxane; (5) an anti-metabolite; (6) an inhibitor of FGFR1 and/or FGFR2 and/or FGFR3 and/or of mutants thereof; (7) a mitotic kinase inhibitor; (8) an anti-angiogenic drug; (9) a topoisomerase inhibitor; (10) a platinum-containing compound; (12) an inhibitor of c-MET and/or of mutants thereof; (13) an inhibitor of BCR-ABL and/or of mutants thereof; (14) an inhibitor of ErbB2 (Her2) and/or of mutants thereof; (15) an inhibitor of AXL and/or of mutants thereof; (16) an inhibitor of NTRK1 and/or of mutants thereof; (17) an inhibitor of RET and/or of mutants thereof; (18) an inhibitor of A-Raf and/or B-Raf and/or C-Raf and/or of mutants thereof; (19) an inhibitor of ERK and/or of mutants thereof; (20) an MDM2 inhibitor; (21) an inhibitor of mTOR; (23) an inhibitor of IGF1/2 and/or of IGF1-R; (24) an inhibitor of CDK9; (25) an inhibitor of farnesyl transferase; (26) an inhibitor of SHIP pathway; (27) an inhibitor of SRC; (28) an inhibitor of JAK; (29) a PAR$^{12}$ inhibitor, (31) a ROS1 inhibitor; (32) an inhibitor of SHP pathway, or (33) an inhibitor of Src, FLT3, HDAC, VEGFR, PDGFR, LCK, Bcr-Abl or AKT; (34) an inhibitor of KrasG12C mutant; (35) a SHC inhibitor (e.g., PP2, AID371185); (36) a GAB inhibitor; (38) a PI-3 kinase inhibitor; (39) a MARPK inhibitor; (40) CDK4/6 inhibitor; (41) MAPK inhibitor; (42) SHP2 inhibitor; (43) checkpoint immune blockade agents; (44) or SOS1 inhibitor; or (45) a SOS 2 inhibitor.
101. The method of embodiment 99, wherein the additional agent comprises an inhibitor of SHP2 selected from RMC-4630, ERAS-601,

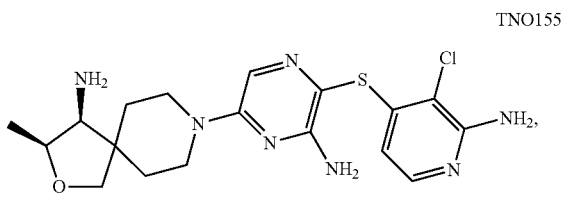

TNO155

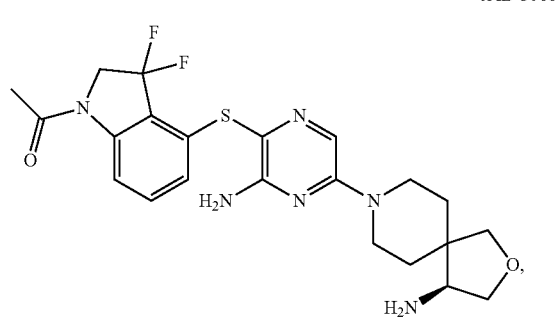

JAB-3068

-continued

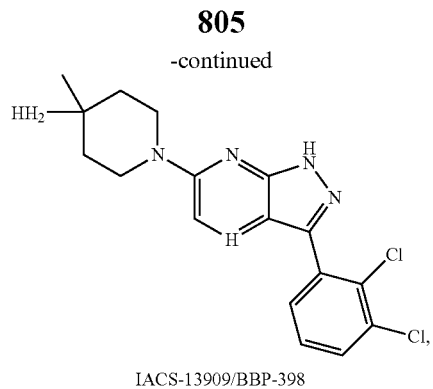

IACS-13909/BBP-398

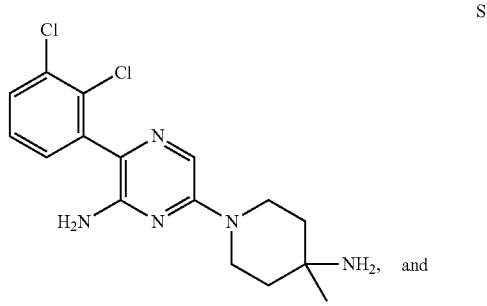

SHP099

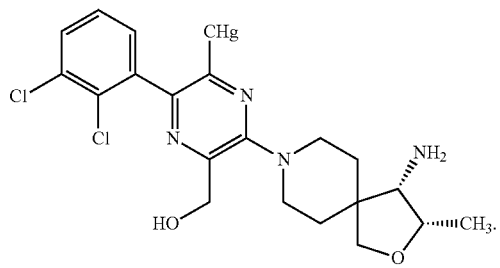

RMC-4550

102. The method of embodiment 99, wherein the additional agent comprises an inhibitor of SOS selected from RMC-5845, BI-1701963,

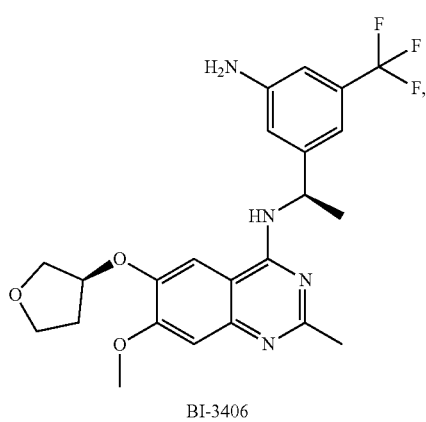

BI-3406

-continued

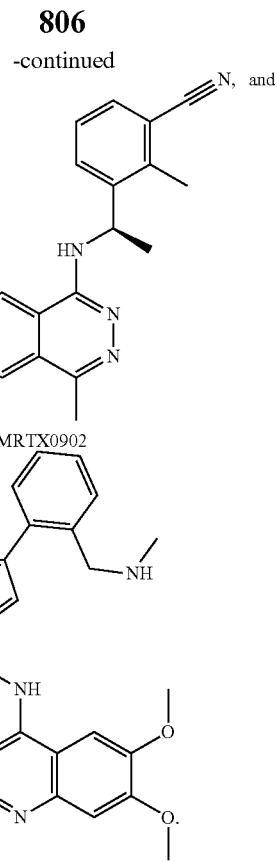

MRTX0902

BAY 293

103. The method of embodiment 99, wherein the additional agent comprises an inhibitor of EGFR selected from afatinib, erlotinib, gefitinib, lapatinib, cetuximab panitumumab, osimertinib, olmutinib, and EGF-816.

104. The method of embodiment 99, wherein the additional agent comprises an inhibitor of MEK selected from trametinib, cobimetinib, binimetinib, selumetinib, refametinib, and AZD6244.

105. The method of embodiment 99, wherein the additional agent comprises an inhibitor of ERK selected from ulixertinib, MK-8353, LTT462, AZD0364, SCH772984, BIX02189, LY3214996, and ravoxertinib.

106. The method of embodiment 99, wherein the additional agent comprises an inhibitor of CDK4/6 selected from palbociclib, ribociclib, and abemaciclib.

107. The method of embodiment 99, wherein the additional agent comprises an inhibitor of BRAF selected from sorafenib, vemurafenib, dabrafenib, encorafenib, regorafenib, and GDC-879.

EXAMPLES

The following examples are provided for illustrative purposes only and not to limit the scope of the claims provided herein. Unless noted otherwise, all materials, such as reagents, starting materials and solvents, were purchased from commercial suppliers, such as Sigma-Aldrich, VWR, and the like, and were used without further purification. Reactions were run under nitrogen atmosphere, unless noted otherwise. The progress of reactions was monitored by thin layer chromatography (TLC), analytical high performance liquid chromatography (anal. HPLC), and mass spectrometry, the details of which may be provided in specific examples.

Reactions were worked up as described specifically in each preparation; commonly, reaction mixtures were purified by extraction and other purification methods such as temperature- and solvent-dependent crystallization, and precipitation. In addition, reaction mixtures were routinely purified by preparative HPLC, for example, using Microsorb C18 or Microsorb BDS column packings and conventional eluents. Progress of reactions was typically monitored by liquid chromatography mass spectrometry (LCMS). Characterization of isomers was typically done by Nuclear Overhauser effect spectroscopy (NOE). Characterization of reaction products was routinely carried out by mass spectrometry and/or spectroscopy. For NMR measurement, samples were dissolved in deuterated solvent (CD$_3$OD, CDCl$_3$, or DMSO-d$_6$).

Example 1: Synthesis of 2-amino-4-(6-chloro-12-(cyclopropylmethyl)-4-fluoro-2-(((2R,7aS)-2-fluoro-tetrahydro-1H-pyrrolizin-7a(5H)-yl)methoxy)-8a,9,11a,12-tetrahydro-8H,11H-furo[3',4':6,7][1,5]oxazocino[4,3,2-de]quinazolin-5-yl)-7-fluorobenzo[b]thiophene-3-carbonitrile (101)

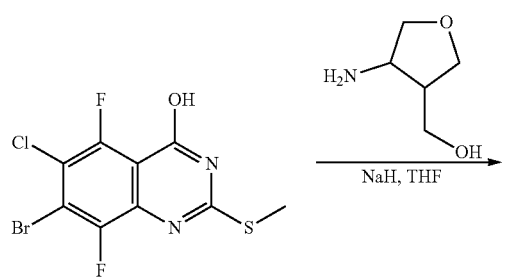

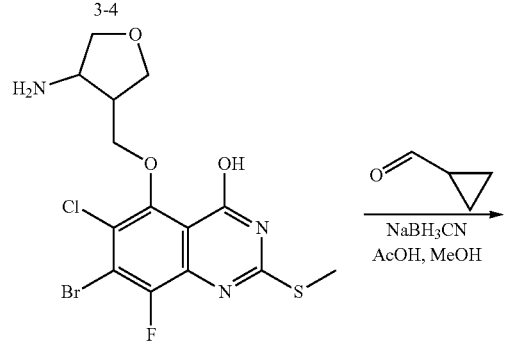

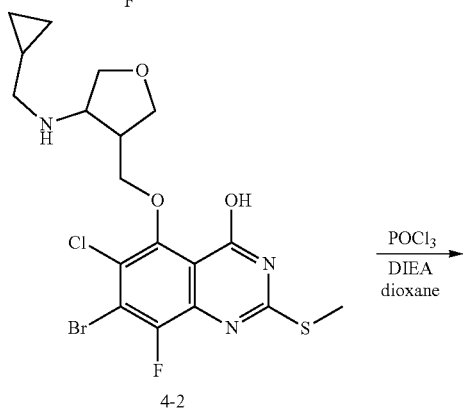

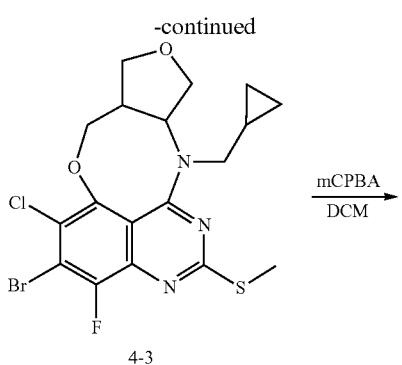

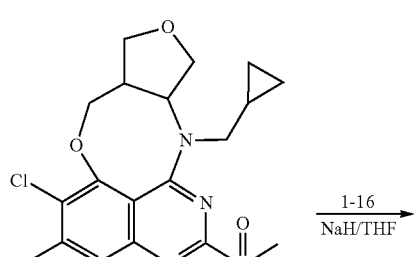

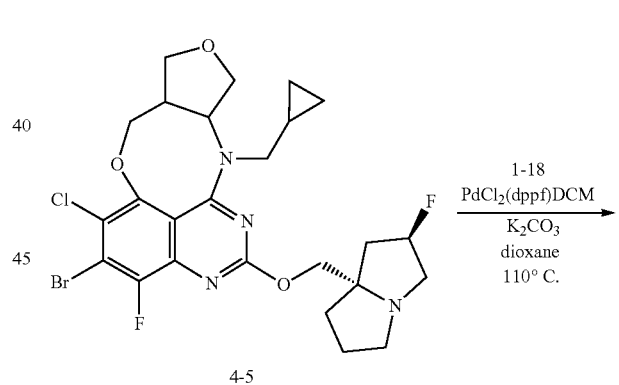

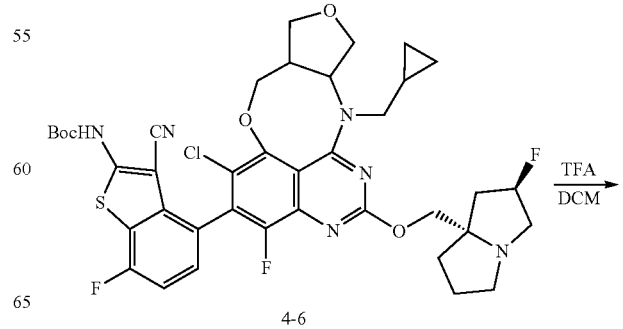

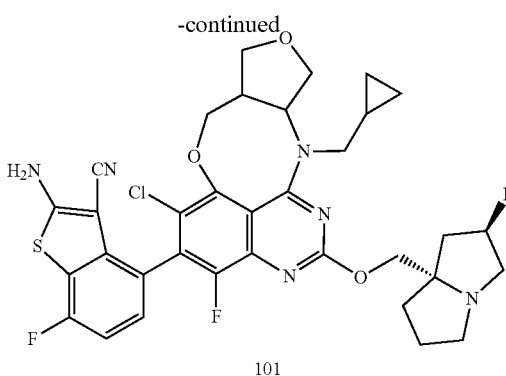

101

To a solution of (4-aminotetrahydrofuran-3-yl)methanol (136 mg, 1.17 mmol) in THF (20 mL) was added NaH (140 mg, 3.51 mmol). The resulting solution was stirred for 30 min at 0° C. Compound 3-4 (400 mg, 1.17 mmol) was added and the resulting mixture was stirred at RT for 2 h. The resulting solution was extracted with ethyl acetate and the organic layers were combined. The organic layer was washed with $H_2O$ and concentrated. The residue was purified on a silica gel column to afford compound 4-1 (115 mg). ESI-MS m/z: 436.9 [M+H]$^+$.

To a stirred solution of compound 4-1 (135 mg, 0.31 mmol) in MeOH (20 mL) was added $NaBH_3CN$ (24 mg, 0.39 mmol) and cyclopropanecarbaldehyde (18 mg, 0.26 mmol), and the resulting mixture was stirred at RT for 30 min. The mixture was partitioned between water and DCM. The organic layer was washed with brine, dried over $Na_2SO_4$, and concentrated in vacuo. The residue was purified by flash column chromatography on silica gel to afford compound 4-2 (58 mg). ESI-MS m/z: 491.0 [M+H]$^+$.

To a stirred solution of compound 4-2 (58 mg, 0.11 mmol) in dioxane (20 mL) was added $POCl_3$ (53 mg, 0.35 mmol) and DIEA (182 mg, 1.41 mmol), and the resulting mixture was stirred at RT overnight. The mixture was partitioned between water and EA. The organic layer was washed with brine, dried over $Na_2SO_4$, and concentrated in vacuo. The residue was purified by flash column chromatography on silica gel to afford compound 4-3 (32 mg). ESI-MS m/z: 473.0 [M+H]$^+$.

To a stirred solution of compound 4-3 (32 mg, 0.06 mmol) in DCM (20 mL), mCPBA (62 mg, 0.18 mmol) was added and the resulting mixture was stirred at 0° C. for 30 min. The mixture was partitioned between water and DCM. The organic layer was washed with brine, dried over $Na_2SO_4$, and concentrated in vacuo. The residue was purified by flash column chromatography on silica gel to afford compound 4-4 (33 mg). ESI-MS m/z: 504.9 [M+H]$^+$.

To a solution of compound 1-16 (62 mg, 0.39 mmol) in THF (20 mL) was added NaH (18 mg, 0.43 mmol) and the resulting solution was stirred for 30 min at 0° C. Compound 4-4 (33 mg, 0.06 mmol) was added and the resulting mixture was stirred at RT for 2 h. The mixture was extracted with ethyl acetate and the organic layers were combined. The organic layer was washed with $H_2O$ and concentrated. The residue was purified on a silica gel column eluting to afford compound 4-5 (33 mg). ESI-MS m/z: 584.1 [M+H]$^+$.

The mixture of compound 4-5 (33 mg, 0.05 mmol), compound 1-18 (46 mg, 0.11 mmol), $K_3CO_2$ (47 mg, 0.33 mmol), $PdCl_2$ (dtbpf) (9 mg, 0.011 mmol) in dioxane (6 mL) was stirred at 105° C. under argon overnight. The mixture was diluted with water (20 mL) and extracted with EtOAc (15 mL×2). The combined organic layer was washed with water and brine, dried over anhydrous $Na_2SO_4$, filtered, and concentrated in vacuo. The residue was purified by prep-TLC to afford compound 4-6 (8 mg) which was used in the next step directly. ESI-MS m/z: 796.24 [M+H]$^+$.

To a solution of compound 4-6 (8 mg, crude) in DCM (6 mL) at RT, TFA (2 mL) was added and the resulting mixture was stirred at RT for 30 min. The mixture was concentrated in vacuo to remove the solvent. The residue was purified by flash column chromatography on silica gel to afford compound 101 (1.5 mg). ESI-MS m/z: 696.19 [M+H]$^+$.

Example 2: Synthesis of 2-amino-4-(6-chloro-4-fluoro-2-((2R,7aS)-2-fluorotetrahydro-1H-pyrrolizin-7a(5H)-yl)methoxy)-8,12-dimethyl-8a,9,11a,12-tetrahydro-8H,11H-furo[3',4':6,7][1,5]oxazocino[4,3,2-de]quinazolin-5-yl)-7-fluorobenzo[b]thiophene-3-carbonitrile (104)

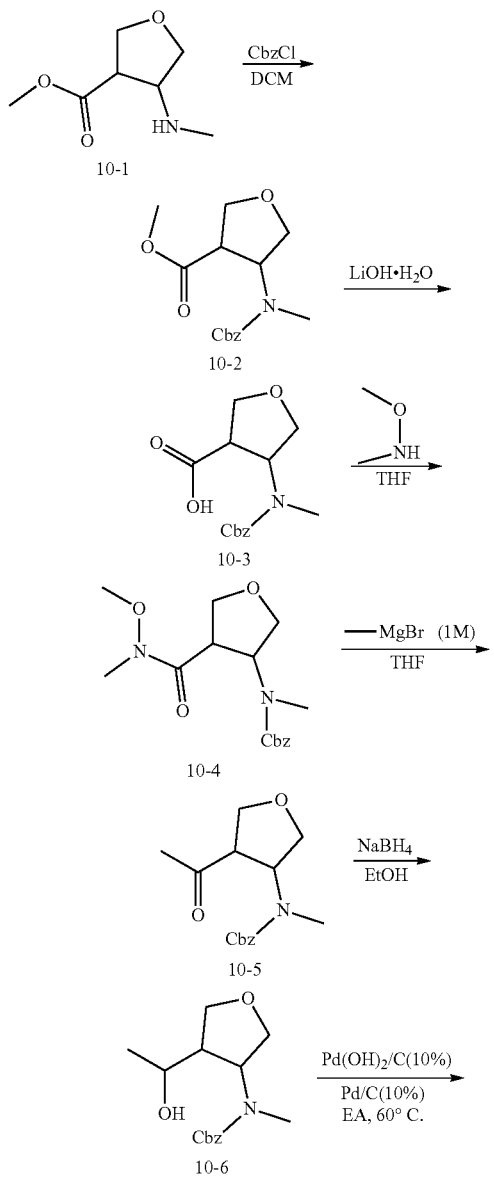

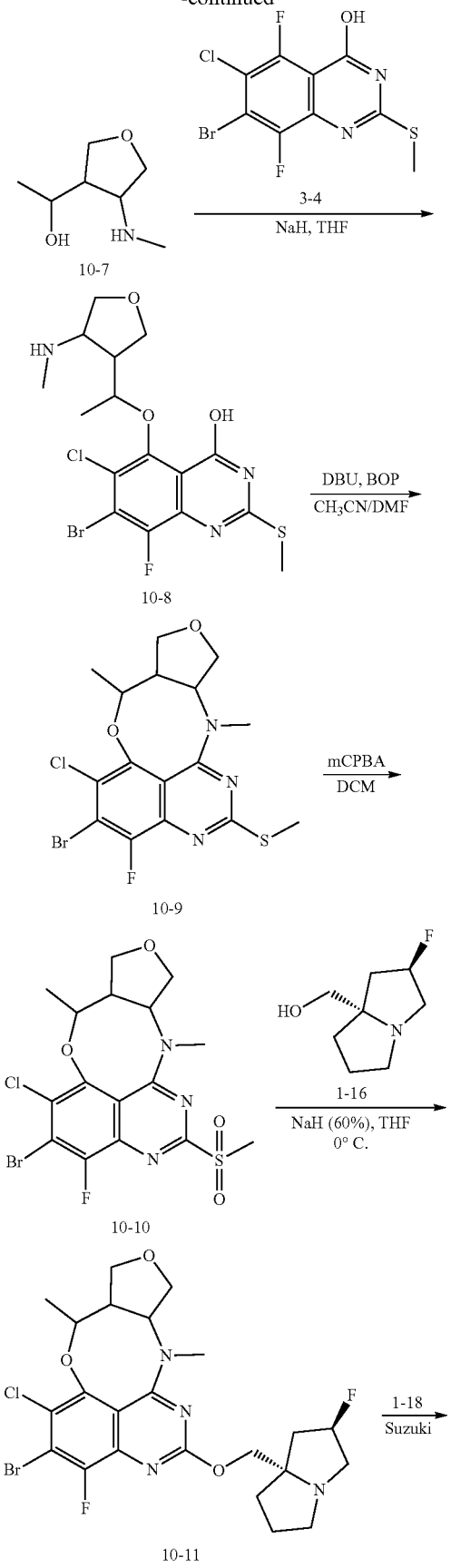

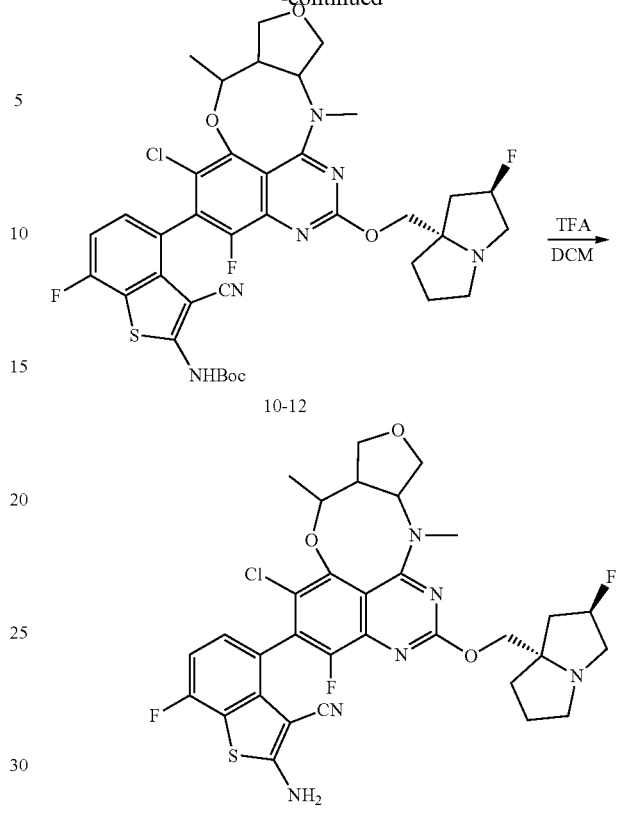

To a solution of methyl 4-(methylamino)tetrahydrofuran-3-carboxylate (10-1) (1.1 g, 6.9 mmol) in DCM (20 mL) was added TEA (2.09 g, 20.7 mmol) at 0° C., followed by CbzCl (1.77 g, 10.4 mmol) and the resulting mixture was stirred at RT overnight. The mixture was concentrated in vacuo and partitioned between DCM and water. The combined organic layer was concentrated in vacuo. The residue was purified on a silica gel column to afford compound 10-2 (0.7g). ESI-MS m/z: 293 [M+H]$^+$.

To a solution of compound 10-2 (0.8 g, 2.73 mmol) in THF/H$_2$O (8 mL/8 mL) was added LiOH·H$_2$O (172 mg, 4.1 mmol) and the resulting mixture was stirred at RT for 2 h. The mixture was concentrated in vacuo to afford compound 10-3 (0.8 g, crude) which was directly used in the next step. ESI-MS m/z: 279.1 [M+H]$^+$.

To a stirred solution of compound 10-3 (0.8 g, 2.86 mmol) in THF (30 mL) was added N,O-dimethylhydroxylamine (0.53 g, 5.73 mmol), DIEA (1.1 g, 8.58 mmol) and HATU (0.65 g, 5.01 mmol) and the resulting mixture was stirred at RT under Ar for 16 h. The mixture was partitioned between water and EA. The organic layer was washed with brine, dried over Na$_2$SO$_4$, filtered, and concentrated in vacuo. The residue was purified by flash column chromatography on silica gel to afford compound 10-4 (0.78 g). ESI-MS m/z: 322.2 [M+H]$^+$.

To a stirred solution of compound 10-4 (0.78 g, 2.42 mmol) in THF (10 mL) was added methylmagnesium bromide (1 M) (3.63 mL, 3.63 mmol) at 0° C. and the resulting mixture was stirred at RT under Ar for 1 h. The mixture was partitioned between water and EA. The organic layer was washed with brine, dried over Na$_2$SO$_4$, filtered, and concentrated in vacuo. The residue was purified by flash column chromatography on silica gel to afford product 10-5 (0.65 g). ESI-MS m/z: 277.0 [M+H]$^+$.

To a stirred solution of compound 10-5 (0.65 g, 2.36 mmol) in EtOH (10 mL) was added NaBH₄ (180 mg, 4.71 mmol) at 0° C. and the resulting mixture was stirred at RT under Ar for 1.5 h. The mixture was concentrated, and the residue was partitioned between water and EA. The organic layer was washed with brine, dried over Na₂SO₄, filtered, and concentrated in vacuo. The residue was purified by flash column chromatography on silica gel to afford product 10-6 (0.5 g). ESI-MS m/z: 279.2 [M+H]⁺.

To a stirred solution of compound 10-6 (0.5 g, 1.78 mmol) in EA (10 mL) was added Pd/C (10%) (50 mg) and Pd(OH)₂/C (20%) (50 mg) and the resulting mixture was stirred at 60° C. under H₂ for 18 h. The mixture was filtered and concentrated in vacuo to afford compound 10-7 (0.33 g). ESI-MS m/z: 145.1 [M+H]⁺.

To a stirred solution of 7-bromo-6-chloro-5,8-difluoro-2-(methylthio)quinazolin-4-ol (3-4) (400 mg, 1.11 mmol) in THF (10 mL) was added compound 10-7 (0.33 g) and NaH (60%) (222 mg, 5.55 mmol) and the resulting mixture was stirred at RT for 2 h. The mixture was partitioned between water and ethyl acetate. The organic layer was washed with brine, dried over Na₂SO₄, filtered, and concentrated in vacuo. The residue was purified by flash column chromatography on silica gel to afford compound 10-8 (367 mg). ESI-MS m/z: 467 [M+H]⁺.

To a stirred solution of compound 10-8 (0.37 g, 0.78 mmol) in MeCN/DMF (8 mL/8 mL) was added BOP (1.73 g, 3.92 mmol) and DBU (0.83 g, 5.49 mmol), and the resulting mixture was stirred at 60° C. under Ar for 13 h. The mixture was concentrated, and the residue was partitioned between water and EA. The organic layer was washed with brine, dried over Na₂SO₄, filtered, and concentrated in vacuo. The residue was purified by flash column chromatography on silica gel to afford compound 10-9 (0.19 g). ESI-MS m/z: 448.9 [M+H]⁺.

To a stirred solution of compound 10-9 (185 mg, 0.40 mmol) in DCM (15 mL), m-CPBA (209 mg, 1.21 mmol) was added, and the resulting mixture was stirred at RT for 1 h. The mixture was partitioned between water and dichloromethane. The organic layer was washed with brine, dried over Na₂SO₄, filtered, and concentrated in vacuo. The residue was purified by flash column chromatography on silica gel to afford compound 10-10 (185 mg). ES1-MS m/z: 480.9 [M+H]⁺.

To a stirred solution of compound 1-16 (379 mg, 2.4 mmol) in THF (15 mL) was added 60% NaH (96 mg, 2.4 mmol) at −20° C. and the mixture was stirred for 60 min under Ar. Compound 10-10 (185 mg, 0.40 mmol) was added and the resulting mixture was stirred at −20° C. for 1 h under Ar. The mixture was poured into ice water and partitioned between water and ethyl acetate. The organic layer was washed with brine, dried over Na₂SO₄, filtered, and concentrated in vacuo. The residue was purified by flash column chromatography on silica gel to afford compound 10-11 (140 mg). ESI-MS m/z: 561 [M+H]⁺.

To a stirred solution of compound 10-11 (140 mg, 0.25 mmol) in anhydrous toluene (15 mL) was added tert-butyl (3-cyano-4-(5,5-dimethyl-1,3,2-dioxaborinan-2-yl)-7-fluorobenzo[b]thiophen-2-yl)carbamate (1-18) (302 mg, 0.75 mmol), PdCl₂(dpephos) (35 mg, 0.05 mmol) and Cs₂CO₃ (244 mg, 0.75 mmol) and the resulting mixture was stirred at 105° C. under nitrogen for 28 h. The mixture was partitioned between water and ethyl acetate. The organic layer was washed with brine, dried over Na₂SO₄, filtered, and concentrated in vacuo. The residue was purified by flash column chromatography on silica gel to afford compound 10-12 (77 mg). ESI-MS m/z: 770 [M+H]⁺.

To a solution of compound 10-12 (70 mg) in DCM (6 mL) at RT, TFA (3 mL) was added and the resulting mixture was stirred at RT for 1.5 h. The mixture was concentrated in vacuo to remove the solvent. The residue was purified by flash column chromatography on silica gel to afford compound 104 (30 mg). ESI-MS m/z: 670 [M+H]⁺; ¹H NMR (400 MHz, CD₃OD): δ 7.22 (m, 1H), 7.06 (m, 1H), 5.44 (d, 1H), 4.55 (m, 2H), 4.39 (m, 2H), 4.16 (m, 1H), 3.54 (m, 4H), 3.35 (m, 3H), 2.45 (m, 2H), 2.22 (m, 3H), 2.03 (m, 2H), 1.59 (m, 3H), 1.30 (m, 3H).

Example 3: Synthesis of (2R)-N-((2R,12aS)-9-(2-amino-3-cyano-7-fluorobenzo[b]thiophen-4-yl)-10-chloro-8-fluoro-6-(((2R,7aS)-2-fluorotetrahydro-1H-pyrrolizin-7a(5H)-yl)methoxy)-2,3,12,12a-tetrahydro-1H-pyrrolo[2',1':,4][1,4]oxazepino[5,6,7-de]quinazolin-2-yl)aziridine-2-carboxamide (111)

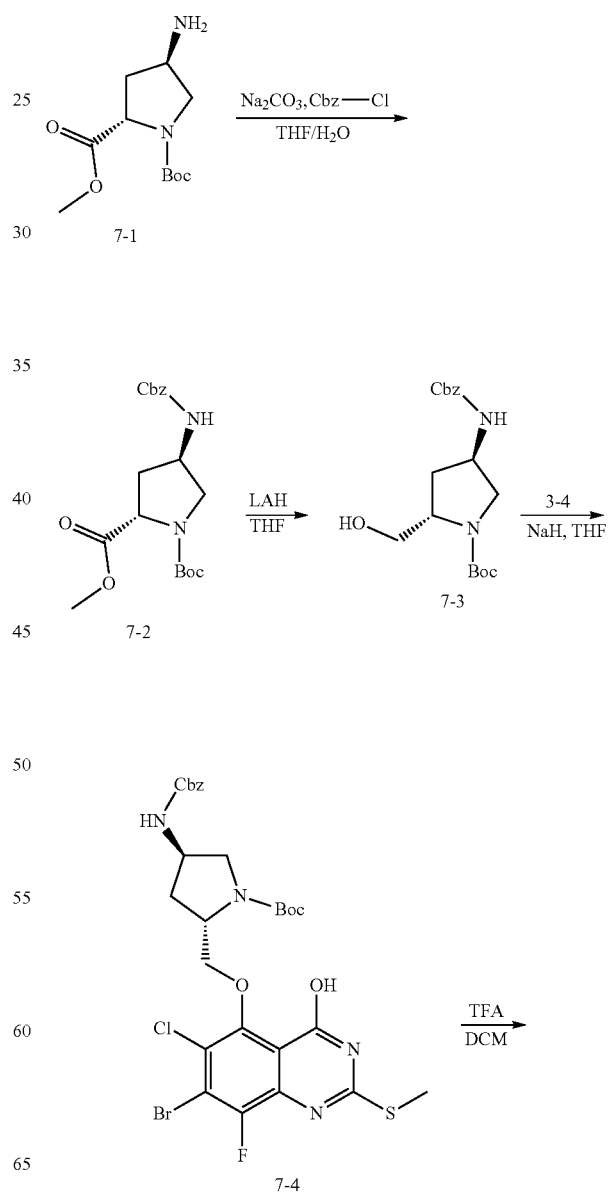

815
-continued

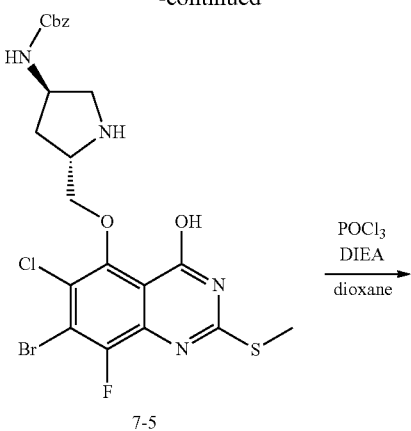
7-5

POCl₃
DIEA
dioxane
→

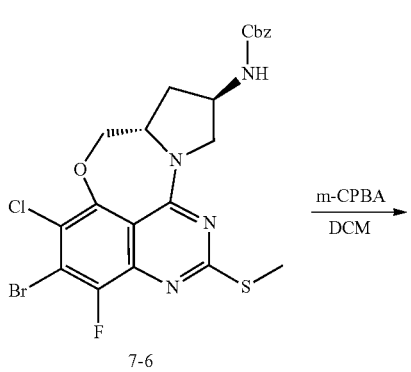
7-6 m-CPBA
DCM
→

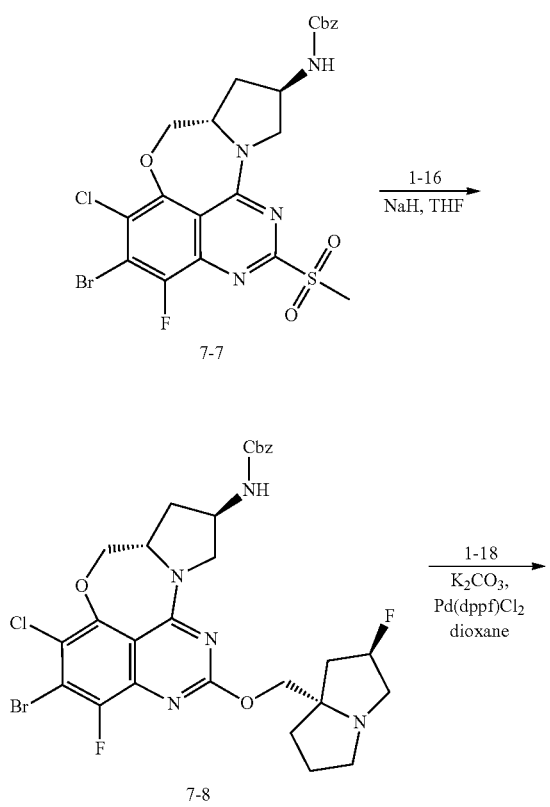
7-7

1-16
NaH, THF
→

7-8

1-18
K₂CO₃,
Pd(dppf)Cl₂
dioxane
→

816
-continued

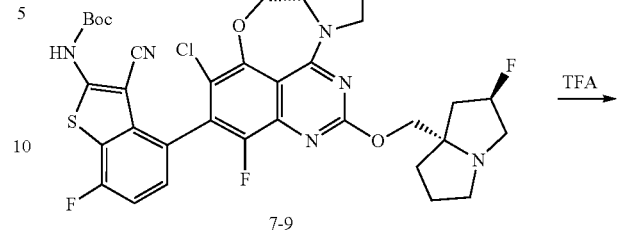
7-9

TFA
→

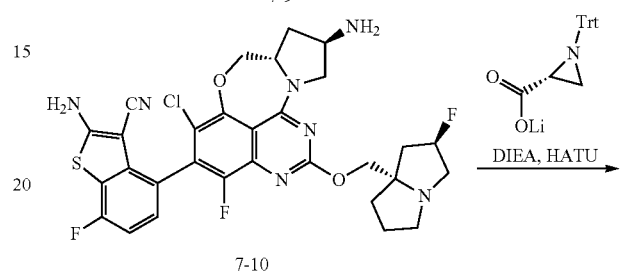
7-10

DIEA, HATU
→

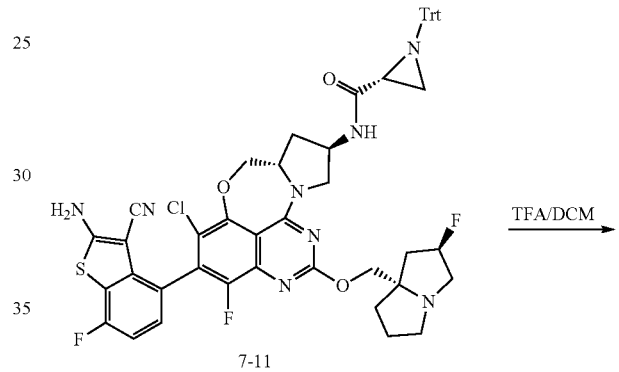
7-11

TFA/DCM
→

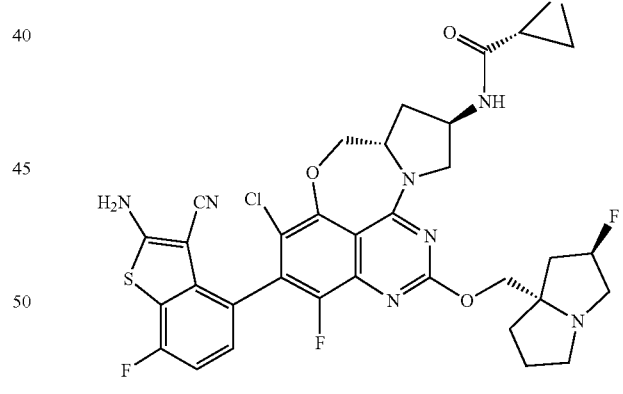
111

To a stirred solution of 1-(tert-butyl) 2-methyl (2S,4R)-4-aminopyrrolidine-1,2-dicarboxylate (7-1) (2 g, 8.18 mmol) in THF (10 mL) and H₂O (10 mL), was added Na₂CO₃ (2 g, 18.86 mmol) and Cbz-Cl (0.7 mL), and the resulting mixture was stirred at RT for 1 h. The mixture was diluted with water and extracted with ethyl acetate (50 mL×3). The combined organic layer was washed with water and brine, dried over anhydrous Na₂SO₄, and concentrated in vacuo. The residue was purified by silica gel column eluting with PE/EA (5:1) to afford compound 7-2 (3 g). ESI-MS m/z: 379.2 [M+H]⁺.

To a stirred solution of 7-2 (3 g, 7.91 mol) in THF (20 mL) was added LAH (110 mg, 2.09 mmol) at −20° C. and the resulting mixture was stirred at RT under argon for 1 h. The mixture was diluted with water (50 mL) and extracted with ethyl acetate (50 mL×3). The combined organic layer was washed with water and brine and concentrated in vacuo. The residue was purified by silica gel column eluting with DCM/MeOH (100:1 to 20:1) to afford compound 7-3 (1.9 g). ESI-MS m/z: 351.4 [M+H]$^+$.

A mixture of compound 7-3 (1.9 g, 5.42 mmol), compound 3-4 (1.8 g, 5.29 mmol), and NaH (1.14 g, 28.5 mmol) in THF (20 mL) was stirred at 0° C. under argon for 3 h. The mixture was diluted with water (20 mL) and extracted with ethyl acetate (20 mL×3). The combined organic layer was washed with water and brine, dried over anhydrous $Na_2SO_4$, and concentrated in vacuo. The residue was purified by silica gel column eluting with DCM/MeOH (100:1 to 10:1) to afford compound 7-4 (1.3 g). ESI-MS m/z: 652.1 [M+H]$^+$.

To a stirred solution of compound 7-4 (1.3 g, 1.99 mmol) in dichloromethane (12 mL) was added trifluoroacetic acid (4 mL) and the resulting mixture was stirred at RT for 1 h. The mixture was concentrated in vacuo to remove the solvent. The residue was dissolved in dichloromethane and treated with $NH_3$ in MeOH (7 N, 1 mL) and then concentrated in vacuo. The residue was purified by silica gel column eluting with DCM/MeOH (100:1 to 10:1) to afford compound 7-5 (490 mg). ESI-MS m/z: 552.0 [M+H]$^+$.

To a stirred solution of compound 7-5 (490 mg, 0.89 mmol) in dioxane (8 mL) was added DIPEA (2 mL) and $POCl_3$ (0.8 mL), and the resulting mixture was stirred at RT under argon for 2 h. The mixture was diluted with water (20 mL) and extracted with ethyl acetate (20 mL×2). The combined organic layer was washed with water and brine and concentrated in vacuo. The residue was purified by silica gel column eluting with DCM/MeOH (100:1 to 25:1) to afford compound 7-6 (390 mg). ESI-MS m/z: 553.0 [M+H]$^+$.

To a stirred solution of compound 7-6 (390 mg, 1.07 mmol) in DCM (5 mL), was added mCPBA (283 mg, 0.18 mmol) at 0° C. The resulting mixture was stirred at RT for 4 h. The mixture was diluted with water (20 mL) and extracted with ethyl acetate (15 mL×2). The combined organic layer was washed with water and brine and concentrated in vacuo. The residue was purified by silica gel column eluting with DCM/MeOH (100:1 to 20:1) to afford compound 7-7 (300 mg). ESI-MS m/z: 584.9 [M+H]$^+$.

To a stirred solution of 7-7 (300 mg, 0.51 mmol) in THF (5 mL) was added compound 1-16 (172 mg, 1.08 mmol) and NaH (43 mg, 1.07 mmol) at 0° C. The resulting mixture was stirred at RT for 16 h. The mixture was diluted with water (20 mL) and extracted with ethyl acetate (15 mL×2). The combined organic layer was washed with water and brine and concentrated in vacuo. The residue was purified by silica gel column eluting with DCM/MeOH (100:1 to 10:1) to afford compound 7-8 (98 mg). ESI-MS m/z: 664.1 [M+H]$^+$.

To a stirred solution of compound 7-8 (98 mg, 0.14 mmol) in dioxane (4 mL) were added compound 1-18 (118 mg, 0.29 mmol), $K_2CO_3$ (101 mg, 0.73 mmol) and Pd(dppf)$Cl_2$ (60 mg, 0.07 mmol), and the resulting mixture was stirred at 105° C. under Ar for 4 h. The mixture was diluted with water (20 mL) and extracted with ethyl acetate (20 mL×2). The combined organic layer was washed with water and brine and concentrated in vacuo. The residue was purified by prep-TLC to afford compound 7-9 (70 mg). ESI-MS m/z: 876.3 [M+H]$^+$.

The mixture of 7-9 (70 mg, 0.084 mmol) in TFA (4 mL) was stirred at 50° C. for 16 h. The mixture was concentrated in vacuo to remove the solvent. The residue was dissolved in dichloromethane and treated with $NH_3$ in MeOH (7 N, 1 mL) and then concentrated in vacuo. The residue was purified by prep-TLC to afford compound 7-10 (45 mg). ESI-MS m/z: 642.2 [M+H]$^+$.

To a stirred solution of compound 7-10 (45 mg, 0.07 mmol) in DMF (4 mL) was added DIPEA (0.02 mL), lithium (R)-1-tritylaziridine-2-carboxylate (16 mg, 0.05 mmol) and HATU (16 mg, 0.04 mmol), and the resulting mixture was stirred at RT for 16 h. The mixture was diluted with water (10 mL) and extracted with ethyl acetate (10 mL×2). The combined organic layer was washed with water and brine and concentrated in vacuo. The residue was purified by prep-TLC to afford compound 7-11 (4 mg). ESI-MS m/z: 953.3 [M+H]$^+$.

To a stirred solution of compound 7-11 (4 mg, 0.01 mmol) in dichloromethane (3 mL) was added trifluoroacetic acid (1 mL) and the resulting mixture was stirred at RT for 1 h. The mixture was concentrated in vacuo to remove the solvent. The residue was dissolved in dichloromethane and treated with $NH_3$ in MeOH (7 N, 1 mL) and then concentrated in vacuo. The residue was purified by prep-HPLC to afford compound 111 (1 mg). ESI-MS m/z: 711.18 [M+H]$^+$.

Example 4: Synthesis of 2-amino-4-(1-chloro-3-fluoro-5-(((2R,7aS)-2-fluorotetrahydro-1H-pyrrolizin-7a(5H)-yl)methoxy)-7-methyl-7,8,8a,9,11,11a-hexahydrofuro[3',4':7,8][1,5]oxazocino[4,3,2-de]quinazolin-2-yl)-7-fluorobenzo[b]thiophene-3-carbonitrile (113)

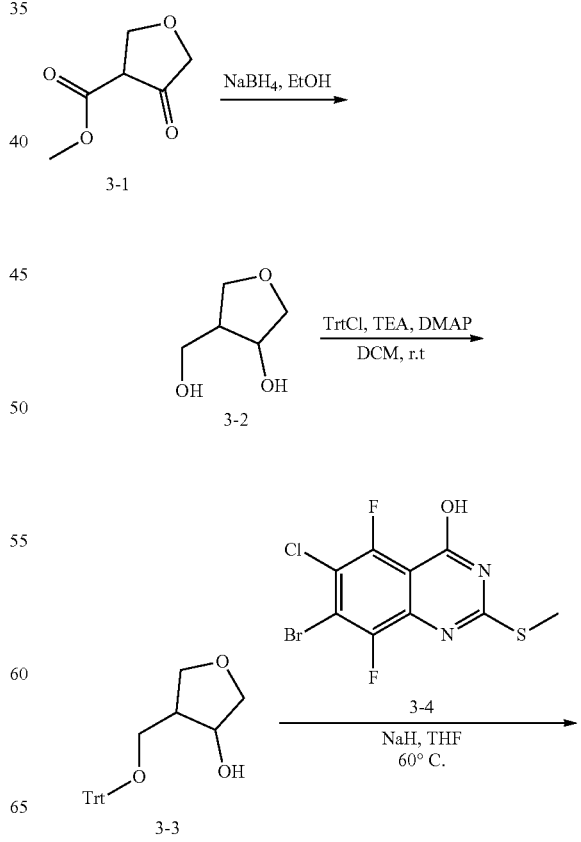

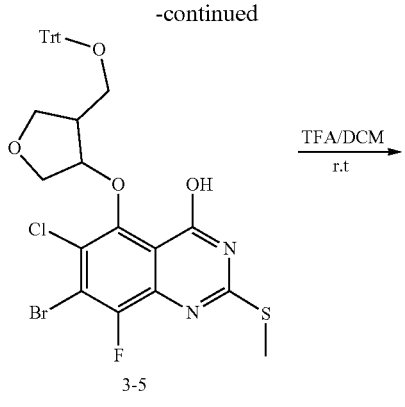
3-5
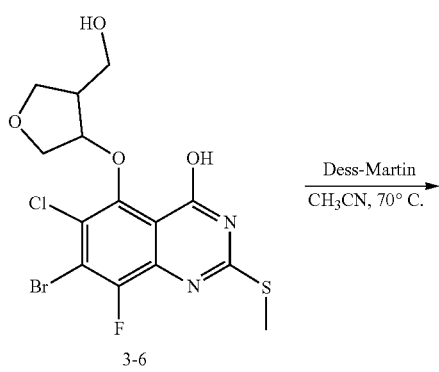
3-6
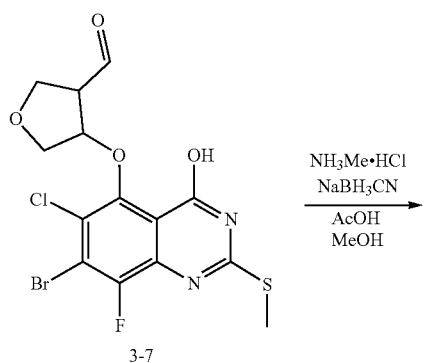
3-7
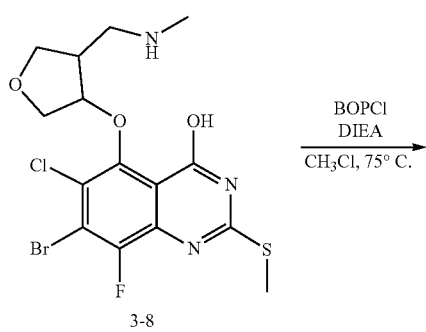
3-8
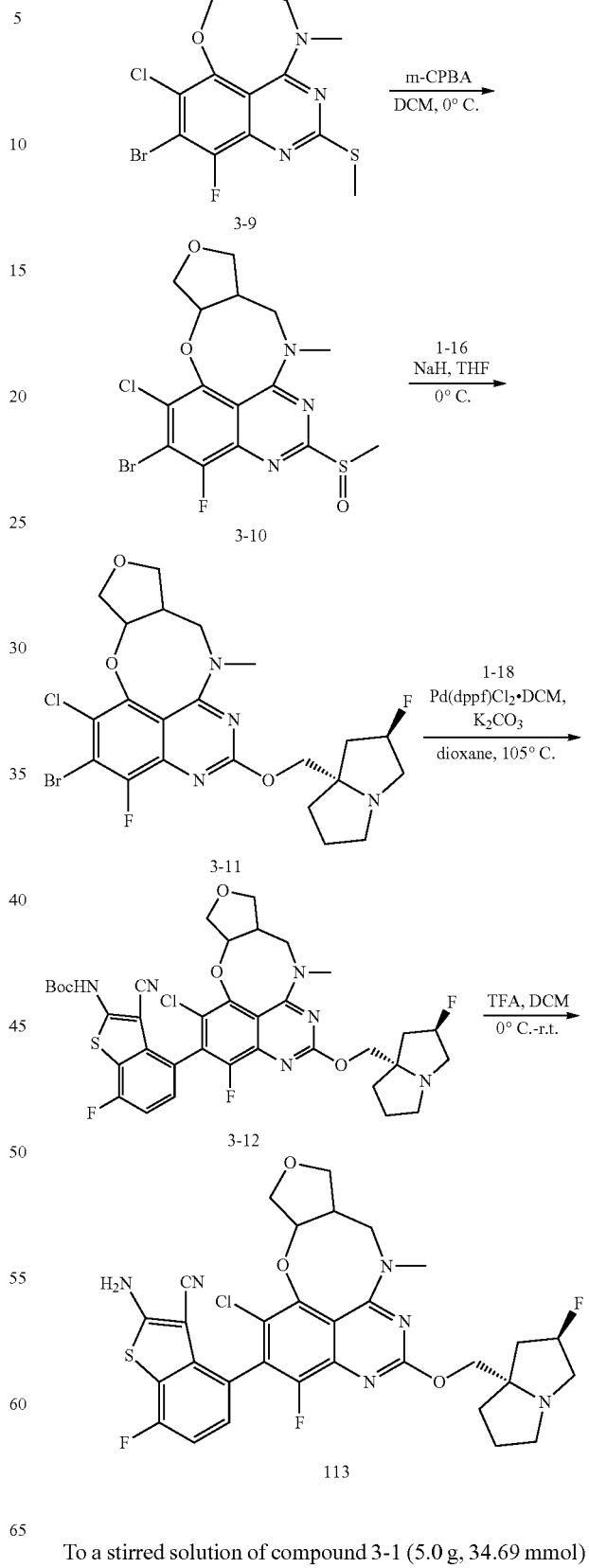
To a stirred solution of compound 3-1 (5.0 g, 34.69 mmol) in EtOH (100 mL) at −30° C. NaBH₄ (6.6 g, 173.45 mmol)

was added in portions and the mixture was stirred at RT overnight. The mixture was diluted with 1N HCl (6.6 mL) and then concentrated in vacuo. The residue was diluted with (DCM/MeOH=4/1 200 mL). The mixture was filtered and concentrated in vacuo. The residue was purified by silica gel column eluting with DCM/MeOH (10:1) to afford compound 3-2 (2.0 g). ESI-MS m/z: 119.0 [M+H]$^+$.

To a stirred solution of compound 3-2 (820 mg, 6.94 mmol), TEA (1.4 g, 13.88 mmol) and DMAP (30 mg) in DCM (15 mL) was added TrtCl (1.94 g, 6.94 mmol). The mixture was stirred at RT overnight, diluted with water, and extracted with DCM. The combined organic layer was washed with water and brine, dried over anhydrous $Na_2SO_4$, and concentrated in vacuo. The residue was purified by silica gel column eluting with DCM/MeOH (50:1) to afford compound 3-3 (800 mg). ESI-MS m/z: 361 [M+H]$^+$.

To a solution of compound 3-4 (360 mg, 1.0 mmol) and compound 3-3 (300 mg, 0.88 mmol) in anhydrous THF (15 mL) was added NaH (176 mg, 4.4 mmol) in portions. The mixture was stirred at RT overnight, diluted with $NH_4Cl$ (aq), extracted with ethyl acetate (15 mL×2). The combined organic layer was washed with water and brine, dried over anhydrous $Na_2SO_4$, and concentrated in vacuo. The residue was purified by silica gel column eluting with DCM/MeOH (50:1) to afford compound 3-5 (450 mg). ESI-MS m/z: 681 [M+H]$^+$.

To a solution of 3-5 (290 mg, 0.42 mmol) in 10 mL of DCM at 0° C. was added TFA (3 mL) and the resulting mixture was stirred at RT for 2 h. The mixture was diluted with $NaHCO_3$ (aq) and extracted with DCM (15 mL×2). The combined organic layer was washed with water and brine, dried over anhydrous $Na_2SO_4$, and concentrated in vacuo. The residue was purified by silica gel column eluting with DCM/MeOH (30:1) to afford compound 3-6 (100 mg). ESI-MS m/z: 439 [M+H]$^+$.

The mixture of 3-6 (80 mg, 0.18 mmol) and Dess-Martin reagent (308 mg, 0.73 mmol) in 10 mL of $CH_3CN$ was stirred at 71° C. for 2 h under argon. The mixture was cooled to RT, poured into ice-water, and extracted with EA/MeOH=10/1 (11 mL×2). The combined organic layer was washed with water and brine, dried over anhydrous $Na_2SO_4$, and concentrated in vacuo to afford compound 3-7 (70 mg) without further purification. ESI-MS m/z: 437 [M+H]$^+$.

A solution of 3-7 (70 mg, 0.16 mmol), methylamine hydrochloride (54 mg, 0.8 mmol) and AcOH (2 mg, 0.032 mmol) in 7 mL of MeOH was stirred at RT for 20 min. $NaBH_3CN$ (52 mg, 0.8 mmol) was added and stirred at RT for 2 h. The mixture was concentrated in vacuo and the residue was purified by silica gel column eluting with DCM/MeOH (30:1) to afford compound 3-8 (50 mg). ESI-MS m/z: 452 [M+H]$^+$.

The mixture of compound 3-8 (45 mg, 0.1 mmol), BOPCl (76 mg, 0.3 mmol) and DIPEA (77 mg, 0.6 mmol) in 8 mL of $CH_3Cl$ was stirred at 75° C. overnight under argon. The mixture was allowed to cool to RT, diluted with $H_2O$ (10 mL), and extracted with DCM (10 mL×2). The combined organic layer was washed with water and brine, dried over anhydrous $Na_2SO_4$, and concentrated in vacuo. The residue was purified by silica gel column eluting with PE/EA (1:1) to afford compound 3-9 (25 mg). ESI-MS m/z: 434 [M+H]$^+$.

To a solution of compound 3-9 (25 mg, 0.057 mmol) in 5 mL of DCM at 0° C., m-CPBA (25 mg, 0.14 mmol) was added. The mixture was stirred at 0° C. for 1 h, diluted with $NaHCO_3$ (aq), and extracted with DCM (10 mL×2). The combined organic layer was washed with water and brine, dried over anhydrous $Na_2SO_4$, and concentrated in vacuo.

The residue was purified by silica gel column eluting with DCM/MeOH (30:1) to afford compound 3-10 (20 mg). ESI-MS m/z: 450 [M+H]$^+$.

To a solution of compound 3-10 (20 mg, 0.044 mmol) and compound 1-16 (55 mg, 0.34 mmol) in 5 mL of anhydrous THF at 0° C. was added NaH (13 mg, 0.34 mmol). The mixture was stirred at 0° C. for 2 h, diluted with $NH_4Cl$ (aq), and extracted with EtOAc (10 mL×2). The combined organic layer was washed with water and brine, dried over anhydrous $Na_2SO_4$, and concentrated in vacuo. The residue was purified by prep-TLC plate to afford the compound 3-11 (17 mg). ESI-MS m/z: 545 [M+H]$^+$.

The mixture of compound 3-11 (17 mg, 0.031 mmol), compound 1-18 (31 mg, 0.078 mmol), Pd(dppf)Cl$_2$ (3.8 mg, 0.0047 mmol) and $K_2CO_3$ (13 mg, 0.0933 mmol) in 8 mL of dioxane was stirred at 105° C. for 4 h. The mixture was diluted with water, extracted with EtOAc (10 mL×2). The combined organic layer was washed with water and brine, dried over anhydrous $Na_2SO_4$, and concentrated in vacuo. The residue was purified by prep-TLC plate to afford the compound 3-12 (10 mg). ESI-MS m/z: 757.2 [M+H]$^+$.

To a stirred solution of compound 3-12 (10 mg, 0.012 mmol) in dichloromethane (4 mL) was added trifluoroacetic acid (1 mL) and the resulting mixture was stirred at RT for 1 h. The mixture was concentrated in vacuo to remove the solvent. The residue was dissolved in dichloromethane and treated with $NH_3$ in MeOH (7 N, 1 mL) and then concentrated in vacuo. The residue was purified by prep-HPLC to afford compound 113 (2.2 mg). ESI-MS m/z: 656.2 [M+H]$^+$.

Example 5: Synthesis of 2-amino-4-(10-((R)-aziridine-2-carbonyl)-6-chloro-4-fluoro-2-(((2R,7aS)-2-fluorotetrahydro-1H-pyrrolizin-7a(5H)-yl)methoxy)-12-methyl-8a,9,10,11,11a,12-hexahydro-8H-pyrrolo[3',4':6,7][1,5]oxazocino[4,3,2-de]quinazolin-5-yl)-7-fluorobenzo[b]thiophene-3-carbonitrile (124)

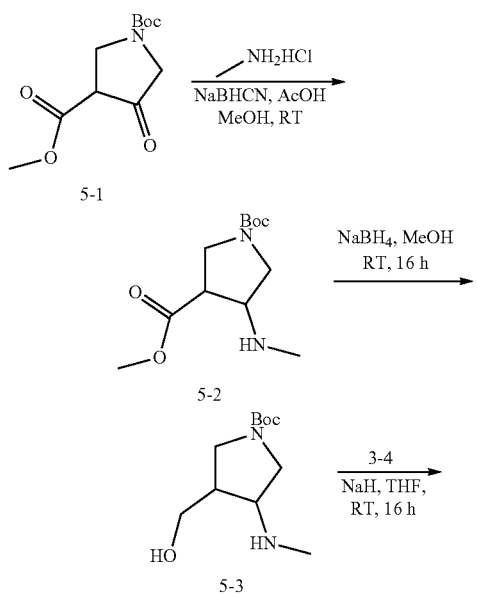

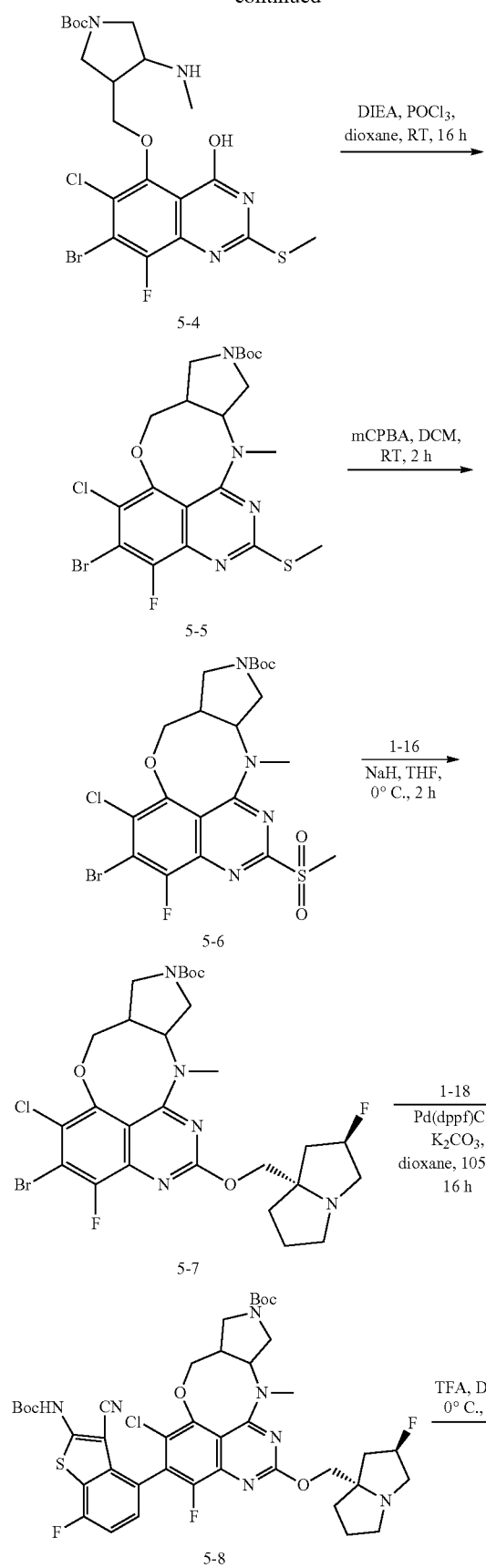

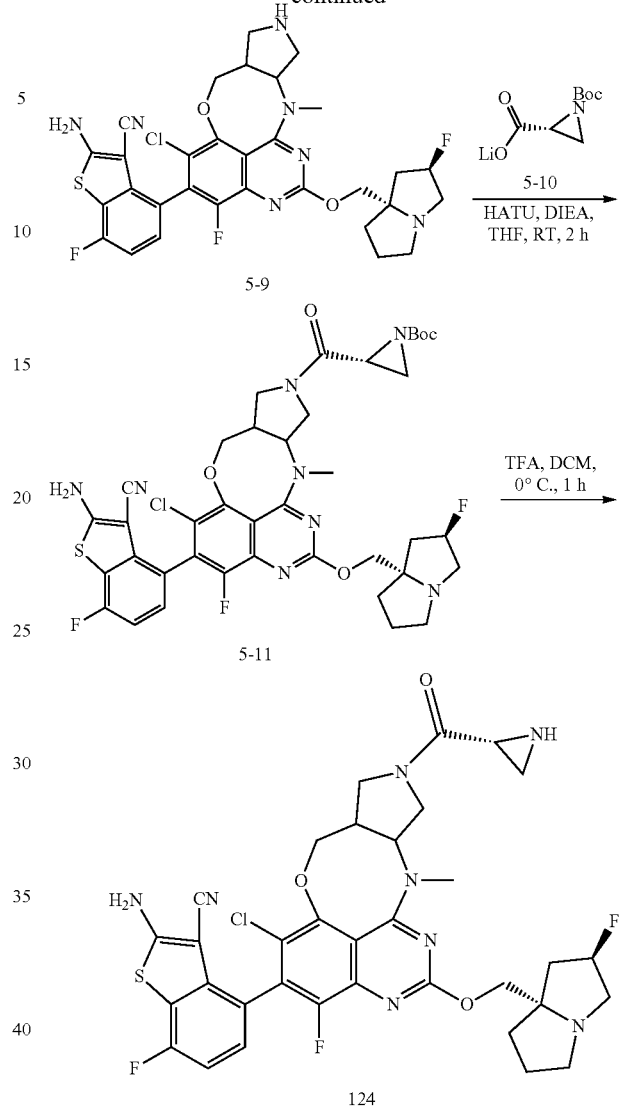

To a stirred solution of compound 5-1 (500 mg, 2.06 mmol) and methanamine hydrochloride (833 mg, 12.34 mmol) in MeOH (10 mL) was added AcOH (1 mL) at 0° C., and the resulting mixture was stirred at RT for 16 h. The mixture was diluted with water (50 mL) and extracted with ethyl acetate (50 mL×2). The combined organic layer was washed with water and brine, dried over anhydrous $Na_2SO_4$, and concentrated in vacuo. The residue was purified by silica gel column eluting with DCM/MeOH (100:1 to 50:1) to afford compound 5-2 (500 mg). ESI-MS m/z: 259 [M+H]⁺.

To a stirred solution of compound 5-2 (500 mg, 1.94 mmol) in MeOH (10 mL) was added $NaBH_4$ (366 mg, 9.69 mmol) at 0° C., and the resulting mixture was stirred at RT for 16 h. The mixture was diluted with water (50 mL) and extracted with ethyl acetate (50 mL×2). The combined organic layer was washed with water and brine and concentrated in vacuo. The residue was purified by silica gel column eluting with DCM/MeOH (100:1 to 50:1) to afford compound 5-3 (200 mg). ESI-MS m/z: 231 [M+H]⁺.

To a stirred solution of compound 5-3 (200 mg, 0.86 mmol) and compound 3-4 (295 mg, 0.86 mmol) in THF (5 mL) was added NaH (346 mg, 8.65 mmol) at 0° C., and the resulting mixture was stirred at RT for 16 h. The mixture was diluted with water (25 mL) and extracted with ethyl acetate (25 mL×2). The combined organic layer was washed with water and brine and concentrated in vacuo. The residue was purified by silica gel column eluting with DCM/MeOH (100:1 to 50:1) to afford compound 5-4 (100 mg). ESI-MS m/z: 552 [M+H]+.

To a stirred solution of compound 5-4 (100 mg, 0.18 mmol) in dioxane (5 mL), DIEA (187 mg, 1.45 mmol) was added, followed by POCl₃ (111 mg, 0.73 mmol) at 0° C., and the resulting mixture was stirred at RT for 16 h. The mixture was diluted with water (25 mL) and extracted with ethyl acetate (25 mL×2). The combined organic layer was washed with water and brine and concentrated in vacuo. The residue was purified by silica gel column eluting with PE/EA (10:1 to 4:1) to afford compound 5-5 (90 mg). ESI-MS m/z: 533 [M+H]+.

To a stirred solution of compound 5-5 (90 mg, 0.17 mmol) in DCM (5 mL) was added mCPBA (87 mg, 0.51 mmol) at 0° C., and the resulting mixture was stirred at RT for 2 h. The mixture was diluted with water (25 mL) and extracted with ethyl acetate (25 mL×2). The combined organic layer was washed with water and brine and concentrated in vacuo. The residue was purified by silica gel column eluting with PE/EA (10:1 to 4:1) to afford compound 5-6 (90 mg). ESI-MS m/z: 566 [M+H]+.

To a stirred solution of compound 5-6 (90 mg, 0.16 mmol) and compound 1-16 (76 mg, 0.48 mmol) in THF (5 mL) was added NaH (22 mg, 0.56 mmol) at 0° C., and the resulting mixture was stirred at RT for 2 h. The mixture was diluted with water (25 mL) and extracted with ethyl acetate (25 mL×2). The combined organic layer was washed with water and brine and concentrated in vacuo. The residue was purified by silica gel column eluting with DCM/MeOH (100:1 to 50:1) to afford compound 5-7 (100 mg). ESI-MS m/z: 646 [M+H]+.

A mixture of compound 5-7 (100 mg, 0.155 mmol), compound 1-18 (125 mg, 0.310 mmol), K₂CO₃ (64 mg, 0.465 mmol), Pd(dppf)Cl₂ (25 mg, 0.031 mmol) in dioxane (10 mL) was stirred at 105° C. under argon for 16 h. The mixture was diluted with water (20 mL) and extracted with ethyl acetate (15 mL×2). The combined organic layer was washed with water and brine, dried over anhydrous Na₂SO₄ and concentrated in vacuo. The residue was purified by prep-TLC plate to afford the compound 5-8 (80 mg). ESI-MS m/z: 856 [M+H]+.

To a stirred solution of compound 5-8 (80 mg, 0.094 mmol) in dichloromethane (6 mL) was added trifluoroacetic acid (2 mL) and the resulting mixture was stirred at RT for 1 h. The mixture was concentrated in vacuo to remove the solvent. The residue was dissolved in dichloromethane and treated with NH₃ in MeOH (7 N, 1 mL) and then concentrated in vacuo. The residue was purified by prep-HPLC to afford compound 5-9 (60 mg). ESI-MS m/z: 657 [M+H]+.

To a stirred solution of compound 5-10 (18 mg, 0.092 mmol) and DIEA (35 mg, 0.275 mmol) in THF (3 mL), HATU (52 mg, 0.137 mmol) was added, followed by compound 5-9 (60 mg, 0.092 mmol) in THF (2 mL) at 0° C. The resulting mixture was stirred at RT for 2 h. The mixture was diluted with water (15 mL) and extracted with ethyl acetate (15 mL×2). The combined organic layer was washed with water and brine and concentrated in vacuo. The residue was purified by prep-HPLC to afford compound 5-11 (10 mg). ESI-MS m/z: 825 [M+H]+.

To a stirred solution of compound 5-11 (10 mg, 0.012 mmol) in dichloromethane (3 mL) was added trifluoroacetic acid (1 mL) and the resulting mixture was stirred at RT for 1 h. The mixture was concentrated in vacuo to remove the solvent. The residue was dissolved in dichloromethane and treated with NH₃ in MeOH (7 N, 1 mL) and then concentrated in vacuo. The residue was purified by prep-HPLC to afford compound 124 (2 mg). ESI-MS m/z: 725 [M+H]+.

Example 6: Synthesis of 2-amino-4-(6-chloro-4-fluoro-2-(((2R,7aS)-2-fluorotetrahydro-1H-pyrrolizin-7a(5H)-yl)methoxy)-9-formyl-11-methyl-7a,8,9,10,10a,11-hexahydropyrrolo[3',4':2,3][1,4]oxazepino[5,6,7-de]quinazolin-5-yl)-7-fluorobenzo[b]thiophene-3-carbonitrile (126)

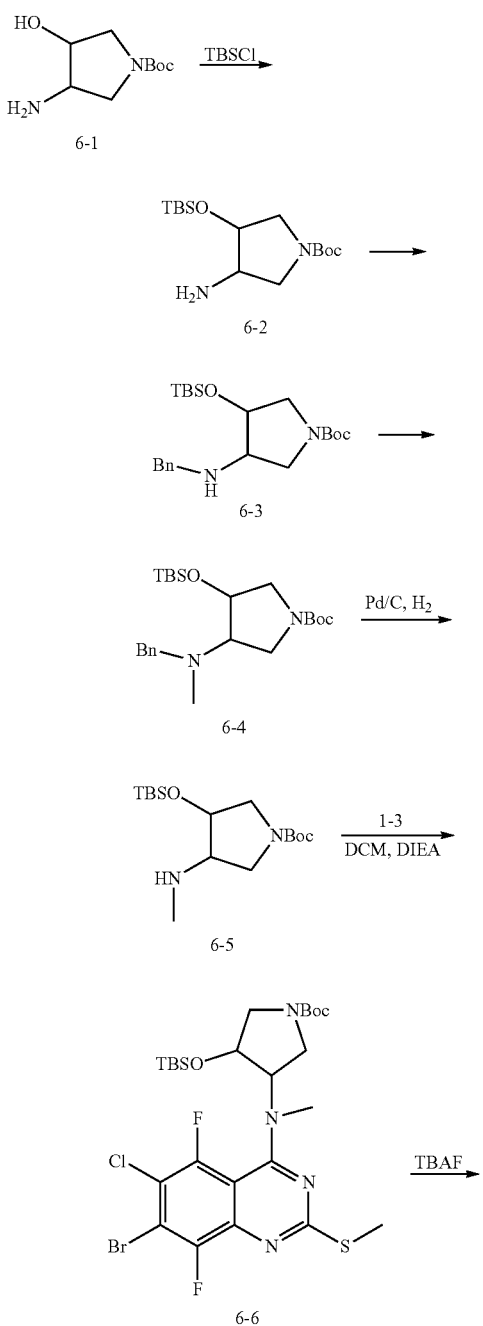

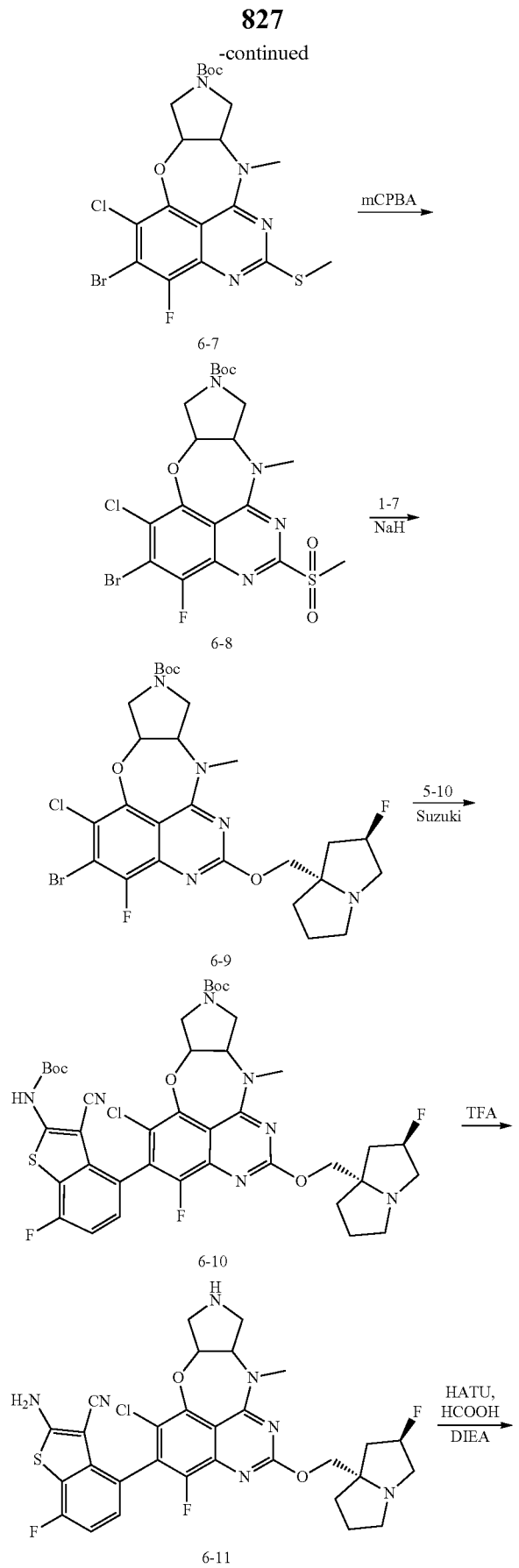

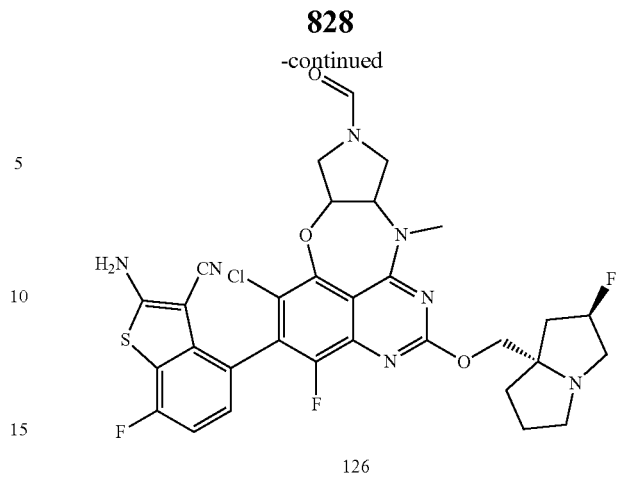

126

Step A: Preparation of tert-butyl 3-amino-4-((tert-butyldimethylsilyl)oxy)pyrrolidine-1-carboxylate (6-2). To a solution of (S)-tert-butyl 3-amino-4-hydroxyl)yrrolidine-1-carboxylate (6-1) (250 mg, 2.17 mmol) in DCM (30 mL) at 0° C., imidazole (162 mg, 2.38 mmol) and TBSCl (627 mg, 4.16 mmol) were added and the resulting mixture was stirred at room temperature overnight. The reaction mixture was extracted with DCM, washed with NaHCO$_3$ (aq) and brine, dried over Na$_2$SO$_4$, concentrated and the residue was purified by flash chromatography on silica gel (2% MeOH/DCM) to afford compound 6-2 (490 mg).

Step B: Preparation of tert-butyl 3-(benzylamino)-4-((tert-butyldimethylsilyl)oxy)pyrrolidine-1-carboxylate (6-3). To a solution of compound 6-2 (490 mg, 2.12 mmol) and benzaldehyde (197 mg, 2.54 mmol) in MeOH (20 mL) at 0° C., 3 drops of AcOH and NaBH$_3$CN (146 mg, 3.18 mmol) were added and the resulting mixture was stirred at room temperature for 3 h. The reaction mixture was extracted with DCM, washed with water and brine, dried over Na$_2$SO$_4$, concentrated and the residue was purified by flash chromatography on silica gel (25% EA/PE) to afford compound 6-3 (490 mg).

Step C: Preparation of tert-butyl 3-(benzyl(methyl)amino)-4-((tert-butyldimethylsilyl)oxy)pyrrolidine-1-carboxylate (6-4). To a solution of to compound 6-3 (490 mg, 1.20 mmol) in MeOH (10 mL), HCHO (43.34 mg, 1.44 mmol), NaBH$_3$CN (114 mg, 1.80 mmol) and 3 drops of AcOH were added and the resulting mixture was stirred under Ar at room temperature for 3 h. The reaction mixture was extracted with ethyl acetate, washed with water and brine, dried over Na$_2$SO$_4$, concentrated and the residue was purified by flash chromatography on silica gel (10% EA/PE) to afford compound 6-4 (306 mg). ESI-MS m/z: 421 [M+H]$^+$.

Step D: Preparation of tert-butyl 3-((tert-butyldimethylsilyl)oxy)-4-(methylamino)pyrrolidine-1-carboxylate (6-5). To a solution of compound 6-4 (306 mg, 0.73 mmol) in MeOH (20 mL), Pd/C (60 mg) was added, and the resulting mixture was stirred under H$_2$ overnight. The reaction mixture was filtered and concentrated in vacuo to afford compound 6-5 (230 mg). ESI-MS m/z: 331 [M+H]$^+$.

Step E: Preparation of tert-butyl 3-((7-bromo-6-chloro-5,8-difluoro-2-(methylthio)quinazolin-4-yl)(methyl)amino)-4-((tert-butyldimethylsilyl)oxy)pyrrolidine-1-carboxylate (6-6). To a solution of compound 6-5 (230 mg, 0.7 mmol) in DCM (20 mL), 1-3 (250 mg, 0.7 mmol) and DIEA (269 mmol, 2.1 mmol) were added and the resulting mixture was stirred under argon at room temperature for 3 h. The reaction mixture was quenched with water, extracted with ethyl acetate, washed with brine, dried over Na$_2$SO$_4$, concentrated and the residue was purified by flash chromatography on silica gel (17% PE/EA) to afford compound 6-6 (180 mg). ESI-MS m/z: 655 [M+H]$^+$.

Step F: Preparation of tert-butyl 5-bromo-6-chloro-4-fluoro-11-methyl-2-(methylthio)-7a,8,10a,11-tetrahydropyrrolo[3',4':2,3][1,4]oxazepino[5,6,7-de]quinazoline-9(10H)-carboxylate (6-7). To a solution of compound 6-6 (180 mg, 0.27 mmol) in THF (1 mL), TBAF (5 mL, 1 M in THF) was added and the resulting mixture was stirred under argon at room temperature for 16 h. The reaction mixture was extracted with ethyl acetate, washed with water and brine, dried over Na$_2$SO$_4$, concentrated and the residue was purified by flash chromatography on silica gel (25% EA/PE) to afford compound 6-7 (130 mg). ESI-MS m/z: 519 [M+H]$^+$.

Step G: Preparation of tert-butyl 5-bromo-6-chloro-4-fluoro-11-methyl-2-(methylsulfonyl)-7a,8,10a,11-tetrahydropyrrolo[3',4':2,3][1,4]oxazepino[5,6,7-de]quinazoline-9(10H)-carboxylate (6-8). To a solution of compound 6-7 (130 mg, 0.25 mmol) in DCM (20 mL) at 0° C., mCPBA (129 mg, 0.75 mmol) was added and the resulting mixture was stirred at room temperature for 1 h. The reaction mixture was quenched with Na$_2$SO$_3$ (aq), extracted with DCM, washed with water and brine, dried over Na$_2$SO$_4$, concentrated and the residue was purified by flash chromatography on silica gel (50% EA/PE) to afford compound 6-8 (71 mg). ESI-MS m/z: 551 [M+H]$^+$.

Step H: Preparation of tert-butyl 5-bromo-6-chloro-4-fluoro-2-((2R,7aS)-2-fluorotetrahydro-1H-pyrrolizin-7a(5H)-yl)methoxy)-11-methyl-7a,8,10a,11-tetrahydropyrrolo[3',4':2,3][1,4]oxazepino[5,6,7-de]quinazoline-9(10H)-carboxylate (6-9). To a mixture of NaH (52 mg, 1.3 mmol) in THF (10 mL) at 0° C. under argon, 1-7 (204 mg, 1.28 mmol) was added and the resulting mixture was stirred at room temperature for 30 min. To this mixture, compound 6-8 (71 mg, 0.13 mmol) was added and the resulting mixture was stirred at room temperature for 1 h. The reaction mixture was quenched with water, extracted with ethyl acetate, washed with brine, dried over Na$_2$SO$_4$, concentrated and the residue was purified by flash chromatography on silica gel (5% MeOH/DCM) to afford compound 6-9 (56 mg). ESI-MS m/z: 631 [M+H]$^+$.

Step I: Preparation of tert-butyl 5-(2-((tert-butoxycarbonyl)amino)-3-cyano-7-fluorobenzo[b]thiophen-4-yl)-6-chloro-4-fluoro-2-((2R,7aS)-2-fluorotetrahydro-1H-pyrrolizin-7a(5H)-yl)methoxy)-11-methyl-7a,8,10a,11-tetrahydropyrrolo[3',4':2,3][1,4]oxazepino[5,6,7-de]quinazoline-9(10H)-carboxylate (6-10). To a solution of compound 6-9 (56 mg, 0.089 mmol) and 5-10 (72 mg, 0.17 mmol) in toluene (10 mL), Cs$_2$CO$_3$ (87 mg, 0.27 mmol), DPEphosPdCl$_2$ (13 mg, 0.018 mmol) were added, and the mixture was purged with argon. The resulting mixture was stirred at 105° C. for 16 h. The reaction mixture was concentrated, diluted with ethyl acetate, washed with water and brine, dried over Na$_2$SO$_4$, concentrated and the residue was purified by flash chromatography on silica gel (5% MeOH/DCM) to afford compound 6-10 (37 mg). ESI-MS m/z: 841 [M+H]$^+$.

Step J: Preparation of 2-amino-4-(6-chloro-4-fluoro-2-((2R,7aS)-2-fluorotetrahydro-1H-pyrrolizin-7a(5H)-yl)methoxy)-11-methyl-7a,8,9,10,10a,11-hexahydropyrrolo[3',4':2,3][1,4]oxazepino[5,6,7-de]quinazolin-5-yl)-7-fluorobenzo[b]thiophene-3-carbonitrile (6-11). To a solution of compound 6-10 (37 mg, 0.044 mmol) in DCM (3 mL) at 0° C., TFA (1 mL) was added, and the resulting mixture was stirred at room temperature for 1 h. The reaction mixture was concentrated to remove TFA, diluted with DCM and basified with NaHCO$_3$ (aq). The mixture was extracted with DCM, washed with brine, dried over Na$_2$SO$_4$, concentrated and the residue was purified by flash chromatography on silica gel (10% MeOH/DCM) to afford compound 6-11 (20 mg). ESI-MS m/z: 641 [M+H]$^+$.

Step K: Preparation of 2-amino-4-(6-chloro-4-fluoro-2-((2R,7aS)-2-fluorotetrahydro-1H-pyrrolizin-7a(5H)-yl)methoxy)-9-formyl-11-methyl-7a,8,9,10,10a,11-hexahydropyrrolo[3',4':2,3][1,4]oxazepino[5,6,7-de]quinazolin-5-yl)-7-fluorobenzo[b]thiophene-3-carbonitrile (126). To a solution of compound 6-11 (20 mg, 0.031 mmol) in DCM (10 mL) at 0° C., HATU (18 mg, 0.046 mmol) and DIEA (12 mg, 0.09 mmol) were added followed by HCOOH (2 mg, 0.06 mmol). The resulting mixture was stirred at 0° C., under argon. The reaction mixture was diluted with DCM, washed with water and brine, dried over Na$_2$SO$_4$, concentrated and the residue was purified by flash chromatography on silica gel (5% MeOH/DCM) to afford the title compound (4.2 mg). ESI-MS m/z: 671 [M+H]$^+$; $^1$HNMR (400 MHz, CD$_3$OD) δ: 8.24 (s, 1H), 7.26 (m, 1H), 7.06 (m, 1H), 5.46 (m, 1H), 5.12 (m, 1H), 4.64 (m, 4H), 4.40 (m, 1H), 3.94 (m, 5H), 3.42 (s, 3H), 2.59 (m, 1H), 2.3-2.20 (m, 4H), 1.6 (m, 2H).

Example 7: Synthesis of 2-Amino-4-(10'-chloro-8'-fluoro-6'-(((2R,7aS)-2-fluorotetrahydro-1H-pyrrolizin-7a(5H)-yl)methoxy)-1-(1H-1,2,4-triazole-1-carbonyl)-12',12a'-dihydro-1'H,3'H-spiro[azetidine-2,2'-pyrrolo[2',1':3,4][1,4]oxazepino[5,6,7-de]quinazolin]-9'-yl)-7-fluorobenzo[b]thiophene-3-carbonitrile (131)

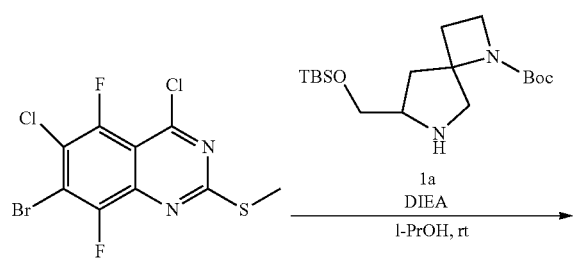

-continued
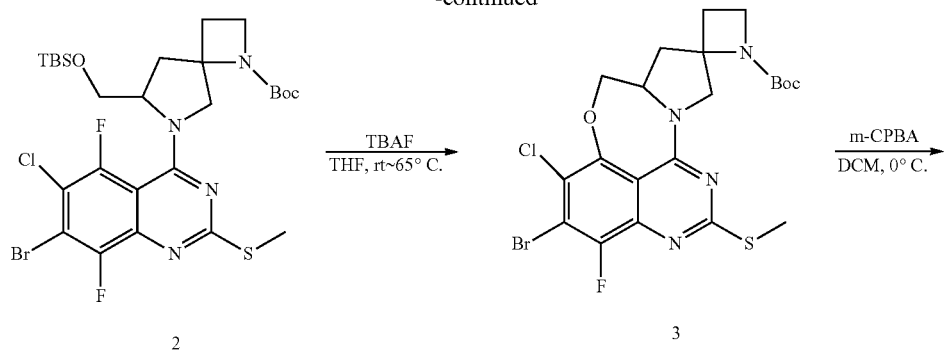
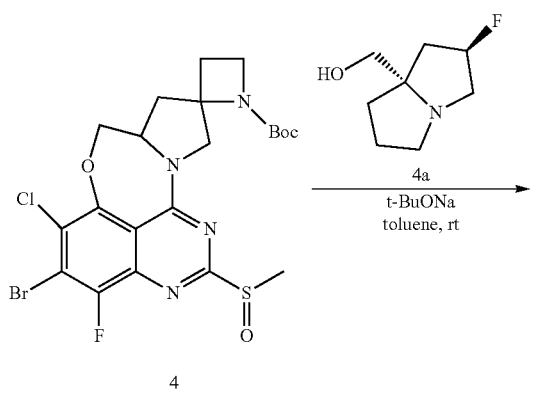
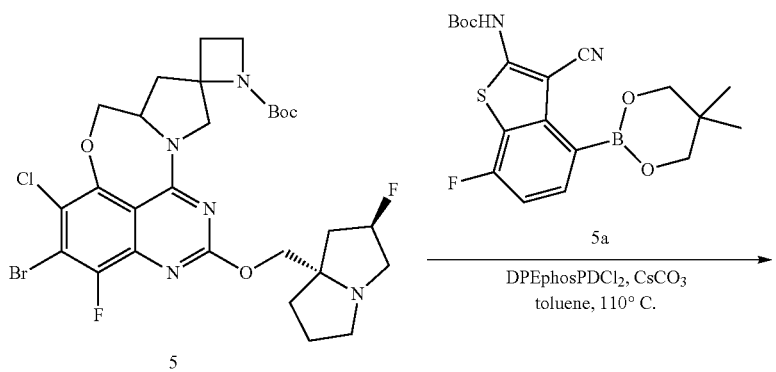
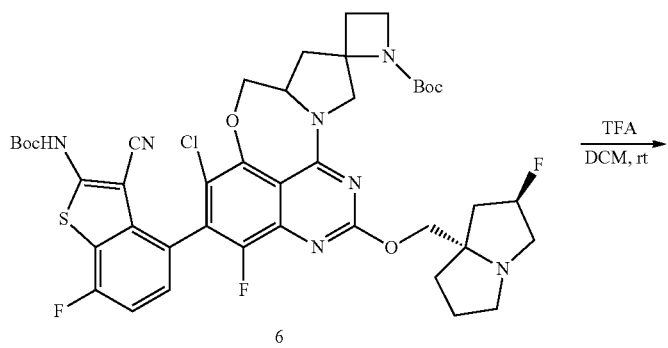

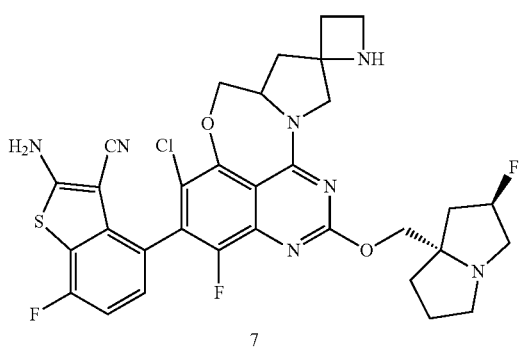

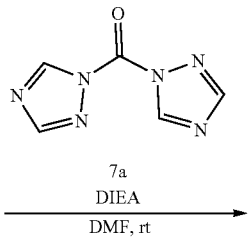

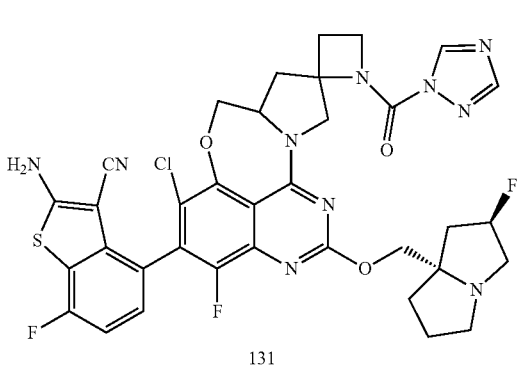

The mixture of compound 1 (600 mg, 1.68 mmol), compound 1a (599 mg, 1.68 mmol) and DIEA (651 mg, 5.04 mmol) in 9 mL of i-PrOH was stirred at 25° C. for 1 h. The mixture was poured into water (70 mL), and the solution was extracted with ethyl acetate (100 mL×3). The organic layer was washed with brine (100 mL), dried over anhydrous sodium sulfate, filtered and the filtrate was concentrated to dryness under reduced pressure. The crude was purified by Prep-TLC (PE/EA=10/1) to give compound 2-P1 (460 mg) and compound 2-P2 (360 mg). MS m/z (ESI): 679.2 [M+H]$^+$.

To a solution of compound 2 (450 mg, 0.66 mmol) in 9 mL of THF was added 1 M TBAF (0.79 mL), and the reaction mixture was stirred at 25° C. for 1 h under $N_2$ atmosphere then warmed up to 65° C. for 1 h. The mixture was poured into water (70 mL), and the solution was extracted with ethyl acetate (50 mL×3). The organic layer was washed with water (50 mL×3), dried over anhydrous sodium sulfate, filtered and the filtrate was concentrated to dryness under reduced pressure resulting in the crude product, compound 3 (380 mg, crude). MS m/z (ESI): 545.3 [M+H]$^+$.

To a solution of compound 3 (380 mg, 0.70 mmol) in 5 mL of DCM was added 80% m-CPBA (151 mg, 0.70 mmol). The reaction mixture was stirred at 0° C. for 30 min. The reaction solution was quenched with $Na_2S_2O_3$ at 0° C. The mixture was poured into water (10 mL), and the solution was extracted with ethyl acetate (30 mL×3). The organic layer was washed with water (30 mL), dried over anhydrous sodium sulfate, filtered and the filtrate was concentrated to dryness under reduced pressure, resulting in the crude product, compound 4 (260 mg, crude). MS m/z (ESI): 561.3 [M+H]$^+$.

To a solution of compound 4a (95 mg, 0.60 mmol) in 4 mL of toluene was added t-BuONa (58 mg, 0.60 mmol) at room temperature under $N_2$ atmosphere. After stirring at room temperature for 10 min, a solution of compound 4 (110 mg, 0.20 mmol) in anhydrous toluene (1 mL) was added via syringe. The reaction mixture was stirred at RT for 2 h. The mixture was poured into water (10 mL), and the solution was extracted with ethyl acetate (20 mL×3). The organic layer was washed with water (20 mL), dried over anhydrous sodium sulfate, filtered and the filtrate was concentrated to dryness under reduced pressure. The residue was purified by HPLC (20~60% ACN/water with 0.03% formic acid) to provide desired compound 5 (70 mg). MS m/z (ESI): 656.3 [M+H]$^+$.

To a solution of compound 5 (75 mg, 0.11 mmol), compound 5a (69 mg, 0.17 mmol), and $Cs_2CO_3$ (111 mg, 0.34 mmol) in toluene (5 mL) was added DPEPhosPDCl$_2$ (16 mg, 0.023 mmol). The mixture was stirred at 110° C. under nitrogen for 2 h. The mixture was poured into water (20 mL), and the solution was extracted with ethyl acetate (20 mL×3). The organic layer was washed with brine (20 mL), dried over anhydrous sodium sulfate, filtered and the filtrate was concentrated to dryness under reduced pressure. The residue was purified by silica gel column (PE/EA=1/1) to give compound 6 (50 mg). MS m/z (ESI): 868.2 [M+H]$^+$.

To a solution of compound 6 (50 mg, 0.058 mmol) in DCM (1 mL) was added TFA (1 mL). The reaction mixture was stirred at 25° C. for 30 min. The solvent was removed under reduced pressure. The reaction mixture was diluted with aq. NaHCO$_3$ (10 mL) and DCM/MeOH=10/1 (10 mL×3). The organic layer was washed with brine, dried over sodium sulfate, filtered, and concentrated to afford compound 7 (40 mg, crude). MS m/z (ESI): 668.1 [M+H]$^+$.

To a solution of compound 7 (40 mg, 0.06 mmol) and DIEA (23 mg, 0.18 mmol) in 1 mL of DMF, was added compound 7a (30 mg, 0.18 mmol). The reaction mixture was then stirred at RT for 1 h. The crude was purified by prep-HPLC (FA) to give compound 131 (9.9 mg). MS m/z (ESI): 763.3 [M+H]⁺; ¹H NMR (400 MHz, DMSO-d₆) δ 9.11 (d, J=19.8 Hz, 1H), 8.34 (s, 1H), 8.25 (d, J=1.2 Hz, 1H), 8.18-8.02 (m, 2H), 7.30-7.09 (m, 2H), 5.27 (d, J=54.4 Hz, 1H), 4.80-3.94 (m, 10H), 3.12-2.88 (m, 5H), 2.32-1.73 (m, 8H).
Example 8: Synthesis of 2-amino-4-(3-chloro-1-fluoro-12-((2R,7aS)-2-fluorotetrahydro-1H-pyrrolizin-7a(5H)-yl)methoxy)-7-hydroxy-5,5a,6,7,8,9-hexahydropyrido[2',1':3,4][1,4]oxazepino[5,6,7-de]quinazolin-2-yl)-7-fluorobenzo[b]thiophene-3-carbonitrile (132)
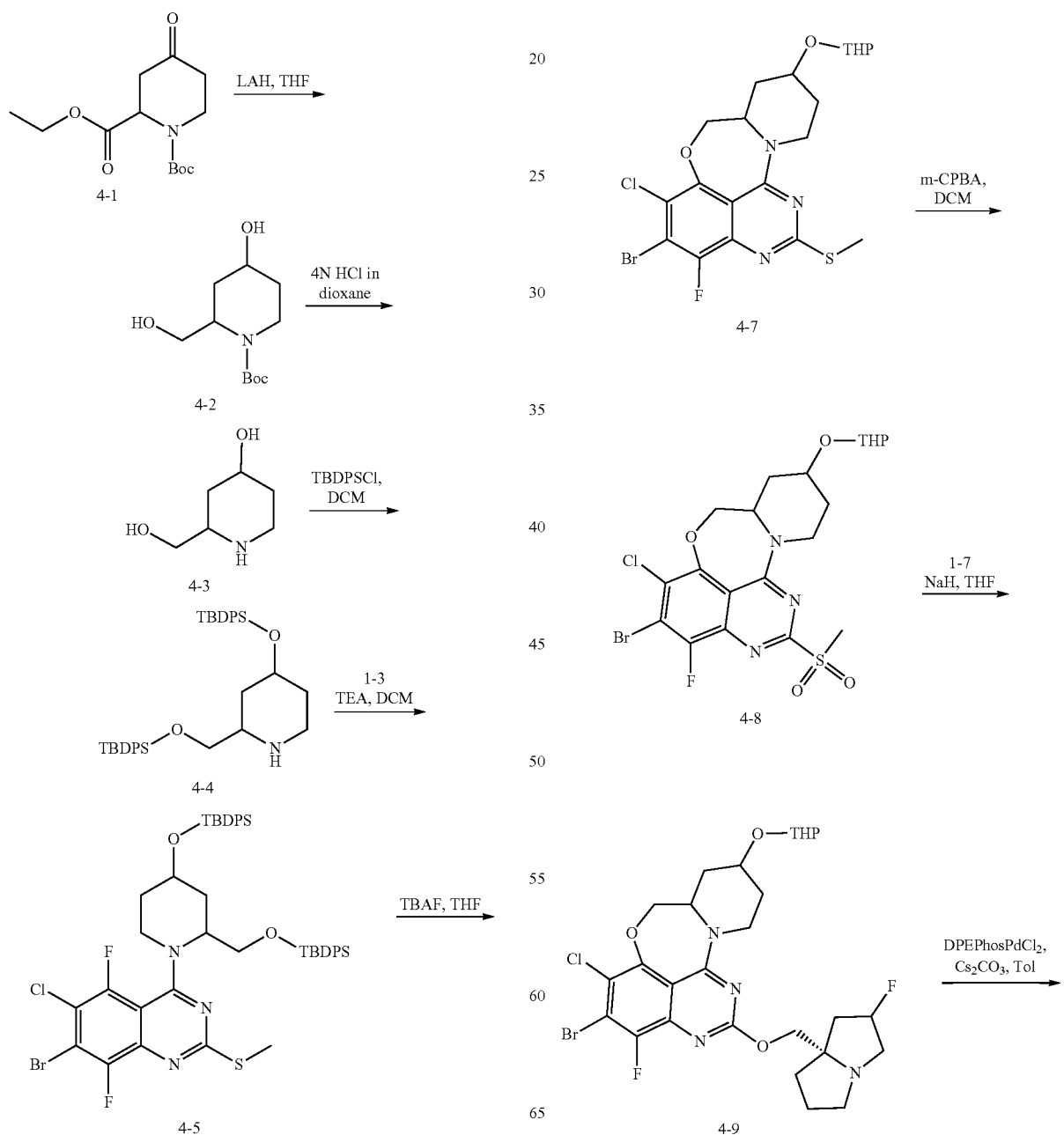

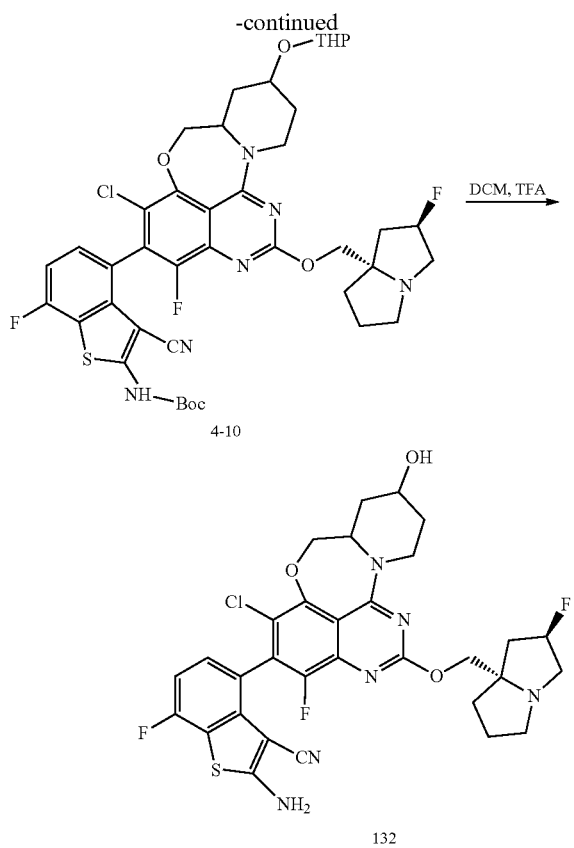

Step A: Preparation of tert-butyl 4-hydroxy-2-(hydroxymethyl)piperidine-1-carboxylate (4-2). To a solution of 1-(tert-butyl) 2-ethyl 4-oxopiperidine-1,2-dicarboxylate (4-1) (500 mg, 1.84 mmol) in THF (10 mL) was added LiAlH₄ (210 mg, 5.5 mmol) at −78° C. The resulting mixture was stirred for 5 hours at room temperature when LCMS showed the reaction was completed. The reaction mixture was quenched with 10% sodium hydroxide solution (0.2 mL) and water (0.5 mL). It was filtered through celite and the celite pad was washed with ethyl acetate. The organics were combined, washed with brine and dried over Na₂SO₄, then filtered and solvent removed under reduced pressure to give a crude residue. The crude product was used in the next step without further purification. ESI-MS m/z: 232[M+H]⁺.

Step B: Preparation of 2-(hydroxymethyl)piperidin-4-ol (4-3). An HCl solution (4M in dioxane, 10 mL) was added to 4-2 (450 mg, 1.95 mmol) at room temperature and the resultant mixture was stirred for 1 hour. Solvent was removed in vacuo to give the desired product which was used in the next step without purification. ESI-MS m/z: 132[M+H]⁺.

Step C: Preparation of 4-((tert-butyldiphenylsilyl)oxy)-2-(((tert-butyldiphenylsilyl)oxy)methyl)piperidine (4-4). To a solution of 4-3 (240 mg, 1.83 mmol) and imidazole (311 mg, 4.5 mmol) in dry DMF (10 mL) was added TBDPSCl (1.1 g, 4.0 mmol) at 0° C. The resulting mixture was stirred for 3 hours at room temperature. The reaction mixture was extracted with ethyl acetate (15 mL×2), washed with NH₄Cl (aq) and brine, and dried over Na₂SO₄, then filtered and solvent removed under reduced pressure to give a crude residue. The crude residue was purified by flash chromatography on silica gel (dichloromethane:methyl alcohol=95:5) to give the desired product as an oil. ESI-MS m/z: 608[M+H]⁺.

Step D: Preparation of 7-bromo-4-(4-((tert-butyldiphenylsilyl)oxy)-2-(((tert-butyldiphenylsilyl)oxy)methyl)piperidin-1-yl)-6-chloro-5,8-difluoro-2-(methylthio)quinazoline (4-5). To solution of 1-3 (300 mg, 0.83 mmol) and Et₃N (252 mg, 2.5 mmol) in dry DCM (20 mL) was added 4-4 (556 mg, 0.91 mmol) at 0° C. The resulting mixture was stirred for 16 hours at room temperature. The reaction mixture was extracted with DCM (20 mL×2), washed with NH₄Cl (aq) and brine, and dried over Na₂SO₄, then filtered and solvent removed under reduced pressure to give a crude. The crude was purified by flash chromatography on silica gel (petroleum ether:ethyl acetate=5:1) to give the desired product as a solid.

Step E: Preparation of 2-bromo-3-chloro-1-fluoro-12-(methylthio)-5,5a,6,7,8,9-hexahydropyrido[2',1':3,4][1,4]oxazepino[5,6,7-de]quinazolin-7-ol (4-6). To a solution of 4-5 (600 mg, 0.64 mmol) in dry THF (2 mL) was added TBAF (1.0 M, 6.0 mL). The resulting mixture was stirred for 16 hours at room temperature under argon. The reaction mixture was extracted with ethyl acetate (20 mL×2), washed with NH₄Cl (aq) and brine, and dried over Na₂SO₄, then filtered and solvent removed under reduced pressure to give a crude residue. The crude residue was purified by flash chromatography on silica gel (petroleum ether:ethyl acetate=3:1) to give the desired product as a solid. ESI-MS m/z: 435[M+H]⁺.

Step F: Preparation of 2-bromo-3-chloro-1-fluoro-12-(methylthio)-7-((tetrahydro-2H-pyran-2-yl)oxy)-5,5a,6,7,8,9-hexahydropyrido[2',1':3,4][1,4]oxazepino[5,6,7-de]quinazoline (4-7). To a solution of 4-6 (250 mg, 0.57 mmol) in DCM (10 mL) was added 3,4-dihydro-2H-pyran (97 mg, 1.2 mmol) and ppTs (20 mg, 0.12 mmol). The resulting mixture was stirred for 16 hours at room temperature and was extracted with ethyl acetate. The combined organics were washed with water and brine and dried over Na₂SO₄, then filtered and solvent removed under reduced pressure to give a crude residue. The crude residue was purified by flash chromatography on silica gel (petroleum ether:ethyl acetate=4:1) to give the desired product as a solid. ESI-MS m/z: 519 [M+H]⁺.

Step G: Preparation of 2-bromo-3-chloro-1-fluoro-12-(methylsulfonyl)-7-((tetrahydro-2H-pyran-2-yl)oxy)-5,5a,6,7,8,9-hexahydropyrido[2',1'3,4][1,4]oxazepino[5,6,7-de]quinazoline (4-8). To a solution of 4-7 (130 mg, 0.25 mmol) in dry DCM (15 mL) was added m-CPBA (128 mg, 0.75 mmol) at 0° C. The resulting mixture was stirred for 1.5 hours at room temperature. The reaction mixture was quenched with Na₂SO₃ (aq) and extracted with DCM (15 mL×2). The organics were combined, washed with water and brine, and dried over Na₂SO₄, then filtered and solvent removed under reduced pressure to give a crude residue. The crude residue was purified by flash chromatography on silica gel (DCM:MeOH=30:1) to give the desired product as a solid. ESI-MS m/z: 551[M+H]⁺.

Step H: Preparation of 2-bromo-3-chloro-1-fluoro-12-(((2R,7aS)-2-fluorotetrahydro-1H-pyrrolizin-7a(5H)-yl)methoxy)-7-((tetrahydro-2H-pyran-2-yl)oxy)-5,5a,6,7,8,9-hexahydropyrido[2',1':3,4][1,4]oxazepino[5,6,7-de]quinazoline (4-9). To a solution of 1-7 (186 mg, 1.18 mmol) in THF (20 mL) at 0° C. was added NaH (60%, 48 mg, 1.18 mmol) and the resulting mixture was stirred for 30 min at 0° C. under argon. Then, 4-8 (100 mg, 0.24 mmol) was added slowly at 0° C. and the resulting mixture was stirred for 1 hour at room temperature. The reaction mixture was filtered and solvent was removed under reduced pressure to give a crude residue. The crude residue was purified by flash chromatography on silica gel (DCM:MeOH=20:1) to give the desired product as a solid. ESI-MS m/z: 630 [M+H]⁺.

Step I: Preparation of tert-butyl (4-(3-chloro-1-fluoro-12-(((2R,7aS)-2-fluorotetrahydro-1H-pyrrolizin-7a(5H)-yl)methoxy)-7-((tetrahydro-2H-pyran-2-yl)oxy)-5,5a,6,7,8,9-hexahydropyrido[2',1':3,4][1,4]oxazepino[5,6,7-de]quinazolin-2-yl)-3-cyano-7-fluorobenzo[b]thiophen-2-yl)carbamate (4-10). To a solution of 4-9 (87 mg, 0.14 mmol) in toluene (15 mL) was added tert-butyl (3-cyano-4-(5,5-dimethyl-1,3,2-dioxaborinan-2-yl)-7-fluorobenzo[b]thiophen-2-yl)carbamate (112 mg, 0.28 mmol), Cs$_2$CO$_3$ (135 mg, 0.41 mmol) and DPEPhosPdCl$_2$ (20 mg, 0.03 mmol). The resulting mixture was heated at 95° C. under argon and stirred for 16 hours. It was cooled down to room temperature and ethyl acetate (15 mL) was added. The organics were washed with brine and dried over Na$_2$SO$_4$, then filtered and solvent removed under reduced pressure to give a crude residue. The crude residue was purified by flash chromatography on silica gel (dichloromethane:methyl alcohol=20:1) to afford the desired product as a solid. ESI-MS m/z: 842 [M+H]⁺.

Step J: Preparation of 2-amino-4-(3-chloro-1-fluoro-12-(((2R,7aS)-2-fluorotetrahydro-1H-pyrrolizin-7a(5H)-yl)methoxy)-7-hydroxy-5,5a,6,7,8,9-hexahydropyrido[2',1':3,4][1,4]oxazepino[5,6,7-de]quinazolin-2-yl)-7-fluorobenzo[b]thiophene-3-carbonitrile (132). To a solution of 4-10 (40 mg, 0.05 mmol) in DCM (6 mL) was added TFA (3 mL) slowly at 0° C. The resulting mixture was stirred for 1 hour at room temperature. The reaction mixture was concentrated to remove TFA. The resultant residue was partitioned between saturated NaHCO$_3$ (5 mL) and dichloromethane (5 mL). The aqueous layer was extracted with dichloromethane (10 mL×2). The organics were combined, washed with brine, and dried over Na$_2$SO$_4$, then filtered and solvent removed under reduced pressure to give a crude residue. The crude residue was purified by TLC (DCM:MeOH=15:1) to afford the title compound as a solid. ESI-MS m/z: 658 [M+H]⁺. ¹HNMR (MeOD, 400 MHz): 7.12-7.07 (m, 1 H), 6.95-6.90 (m, 1 H), 5.48-5.35 (m, 1 H), 5.03-4.99 (m, 1 H), 4.42-4.62 (m, 3 H), 4.22-4.38 (m, 2 H), 4.18-2.02 (1 H, brs), 3.93-3.64 (m, 3 H), 3.35-3.42 (m, 1 H), 3.24-3.28 (m, 1 H), 2.41-2.62 (m, 2 H), 2.22-2.32 (m, 1 H), 2.18-2.22 (m, 2H), 1.82-2.03 (m, 2 H), 1.66-1.83 (m, 3 H).

Example 9: Synthesis of 2-amino-4-((5aS,6aS,9aS)-3-chloro-1-fluoro-12-(((2R,7aS)-2-fluorotetrahydro-1H-pyrrolizin-7a(5H)-yl)methoxy)-5a,6,6a,8,9,9a-hexahydro-5H-furo[2",3":4',5']pyrrolo[2',1':3,4][1,4]oxazepino[5,6,7-de]quinazolin-2-yl)-7-fluorobenzo[b]thiophene-3-carbonitrile (133)

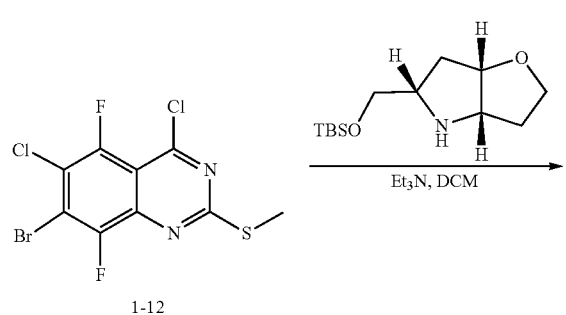
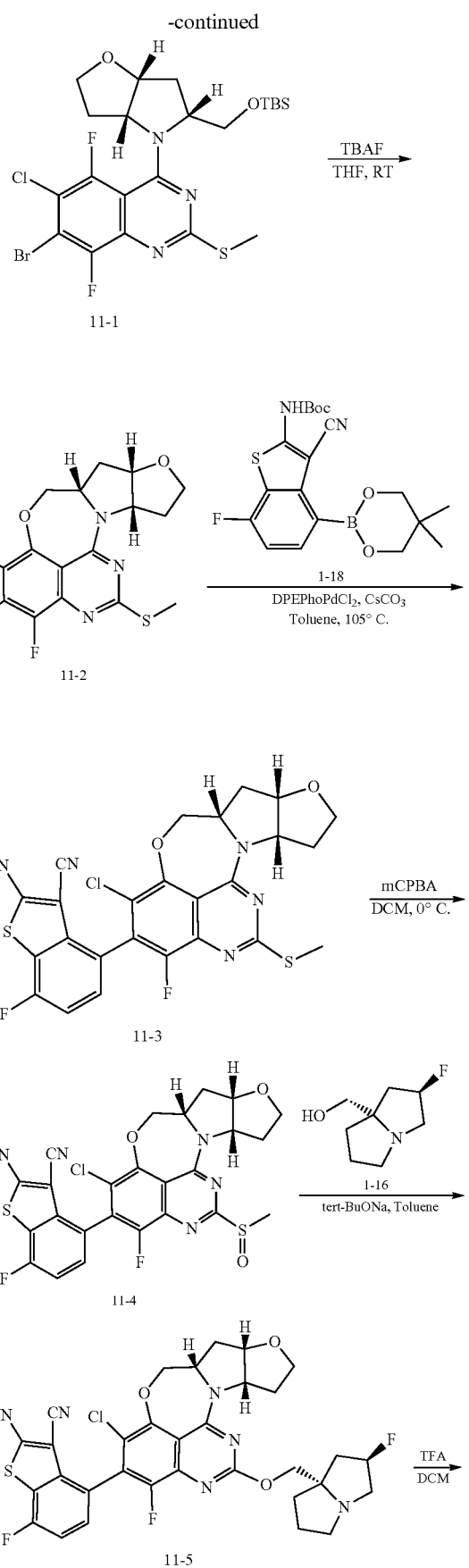

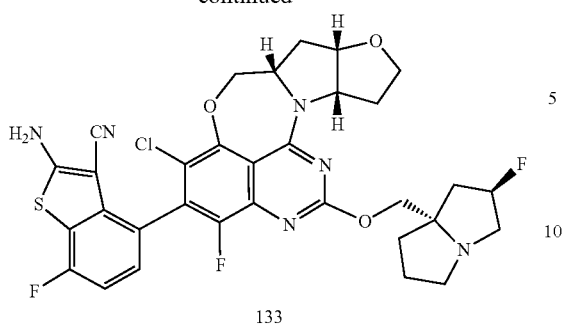

133

To a stirred solution of compound 1-12 (210 mg, 0.58 mmol) in DCM (10 mL) was added Et₃N (88 mg, 0.88 mmol) and (3aS,5S,6aS)-5-(((tert-butyldimethylsilyl)oxy)methyl)hexahydro-2H-furo[3,2-b]pyrrole (149 mg, 0.58 mmol), and the resulting mixture was stirred at RT overnight. The mixture was diluted with water and extracted with ethyl acetate (25 mL×2). The combined organic layer was concentrated in vacuo. The residue was purified by silica gel column eluting with Hex/EA to afford compound 11-1 (285 mg). ESI-MS m/z: 580.0 [M+H]⁺.

To a stirred solution of 11-1 (285 mg, 0.49 mmol) in THF (12 mL), TBAF in THF solution (1 M, 1.5 mL, 1.5 mmol) was added, and the resulting mixture was stirred at RT overnight. The mixture was diluted with water and extracted with ethyl acetate (25 mL×2). The combined organic layer was concentrated in vacuo. The residue was purified by silica gel column eluting with Hex/EA to afford compound 11-2 (18.0 mg). ESI-MS m/z: 446.0 [M+H]⁺.

A mixture of compound 11-2 (18.0 mg, 0.04 mmol), compound 1-18 (22.8 mg, 0.056 mmol), Cs₂CO₃ (22 mg, 0.06 mmol), DPEPhosPdCl₂ (10 mg, 0.014 mmol) in Toluene (5 mL) was stirred at 105° C. under argon for 3 h. The mixture was diluted with water (3 mL) and extracted with ethyl acetate (15 mL×2). The combined organic layer was concentrated in vacuo. The residue was purified by silica gel column eluting with Hex/EA to afford compound 11-3 (16.3 mg). ESI-MS m/z: 658.1 [M+H]⁺.

To a stirred solution of compound 11-3 (16.3 mg, 0.024 mmol) in DCM (5 mL) at 0° C., was added mCPBA (8.5 mg, 0.048 mmol). The resulting mixture was stirred at 0° C. for 15 min. The mixture was concentrated, and the residue was purified by silica gel column eluting with Hex/EA to afford compound 11-4 (12.3 mg). ESI-MS m/z: 674.1 [M+H]⁺.

To a stirred solution of compound 11-4 (12.3 mg, 0.018 mmol) in toluene (3 mL) was added ((2R,7aS)-2-fluorotetrahydro-1H-pyrrolizin-7a(5H)-yl)methanol (1-16) (8.6 mg, 0.054 mmol), cooled in ice/water bath for 15 min with argon protection, and tert-BuONa (5.2 mg, 0.054 mmol) was added. The resulting mixture was stirred in the ice/water bath under argon for 10 min. The mixture was purified with reverse phase column eluting with H₂O/ACN to afford compound 11-5 (5.2 mg). ESI-MS m/z: 769.2 [M+H]⁺.

To a stirred solution of compound 11-5 (5.2 mg, 0.0067 mmol) in DCM (2 mL) was added TFA (0.5 mL) and the mixture was stirred at RT for 1 h. The mixture was concentrated in vacuo to remove the solvent. The residue was purified by prep-HPLC to afford compound 133 (2.7 mg). ESI-MS m/z: 669.2 [M+H]⁺.

Example 10: Synthesis of 2-amino-4-(3-chloro-1-fluoro-15-(((2R,7aS)-2-fluorotetrahydro-1H-pyrrolizin-7a(5H)-yl)methoxy)-5,5a,6,7-tetrahydro-12H-pyrazolo[5'',1'':3',4'][1,4]diazepino[7',1':3,4][1,4]oxazepino[5,6,7-de]quinazolin-2-yl)-7-fluorobenzo[b]thiophene-3-carbonitrile (134)

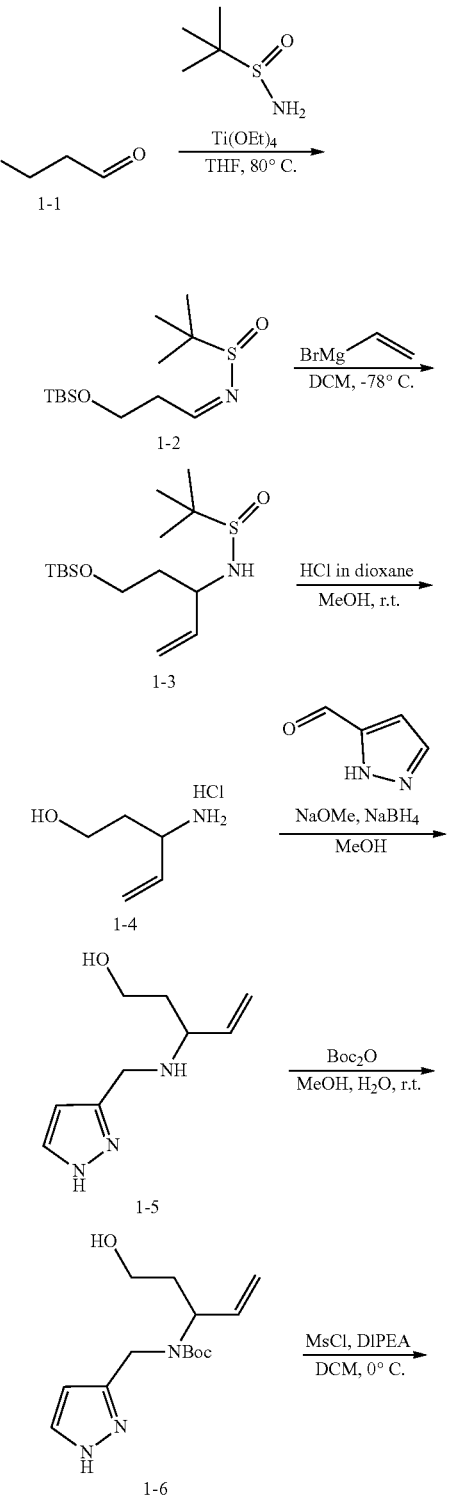

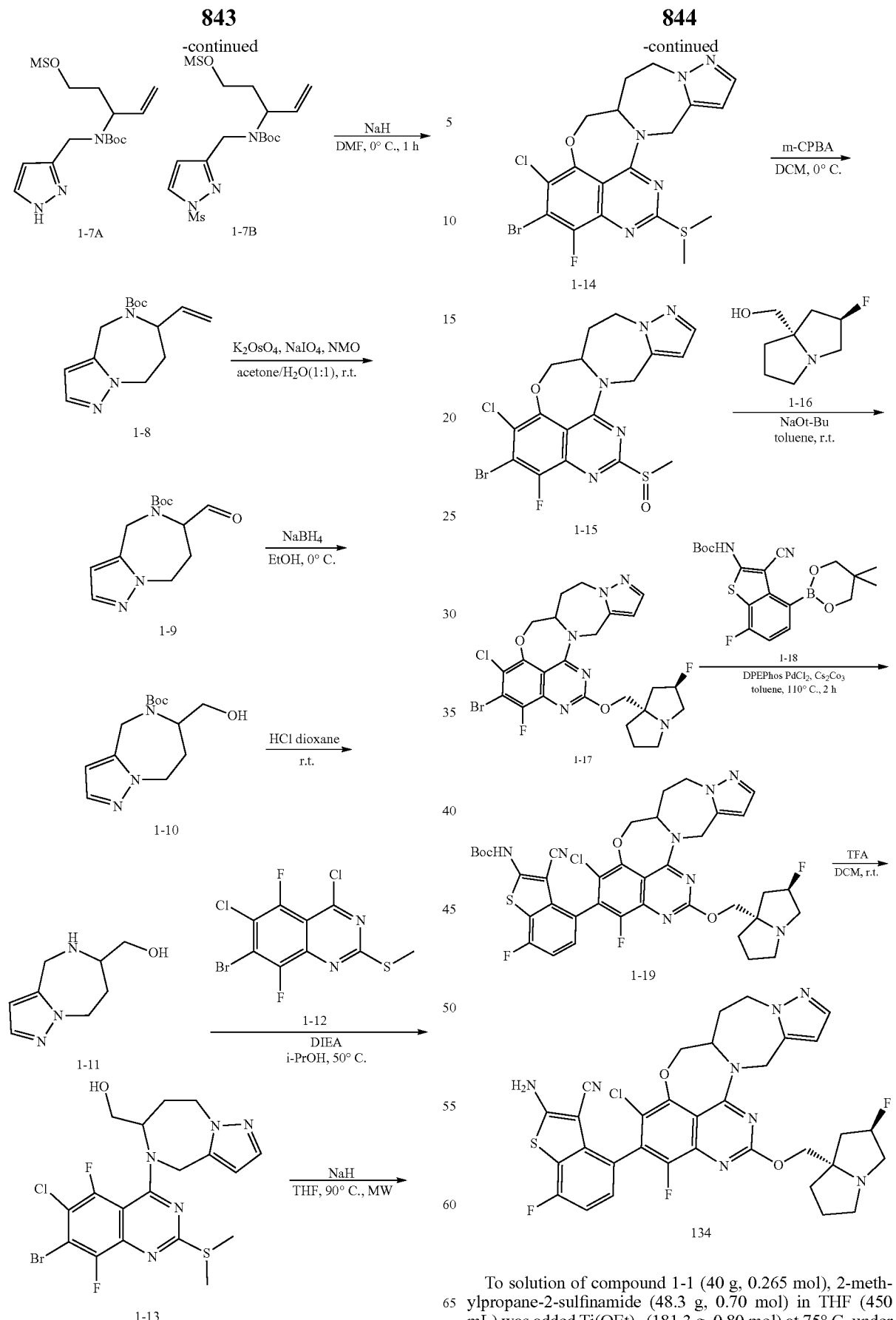
To solution of compound 1-1 (40 g, 0.265 mol), 2-methylpropane-2-sulfinamide (48.3 g, 0.70 mol) in THF (450 mL) was added Ti(OEt)$_4$ (181.3 g, 0.80 mol) at 75° C. under argon and stirred for 1 h. The mixture was cooled to room temperature and poured into an ice bath (1 L), filtered, and the solid was washed with ethyl acetate (500 mL×3). The combined organic layer was dried over anhydrous sodium sulfate, filtered, and concentrated in vacuo. The residue was purified by silica gel column (PE:EA=6:1) to give compound 1-2 (56.6 g).

To a stirred solution of compound 1-2 (54.5 g, 0.19 mol) in dichloromethane (1.0 L) was added vinylmagnesium bromide (560 mL, 0.56 mol) at −78° C. and stirred for 1 h. The reaction was quenched with saturated $NH_4Cl$ (600 mL) and extracted with DCM (500 mL×3). The combined organic layer was dried over anhydrous sodium sulfate, filtered, and concentrated in vacuo. The residue was purified by silica gel column (PE:EA=4:1) to give compound 1-3 (56.6 g).

To a solution of compound 1-3 (17.2 g, 54.1 mmol) in MeOH (80 mL) was added HCl in dioxane (80 mL) at room temperature under argon. The mixture was stirred at room temperature for 2 h. After completed, the mixture was concentrated to give crude compound 1-4 which was directly used in the next step.

A mixture of compound 1-4 (crude, 54.1 mmol) and NaOMe (2.92 g, 54.1 mmol) in MeOH (250 mL) was stirred at room temperature under argon for 1 h. Then 1H-pyrazole-5-carbaldehyde (4.33 g, 45.1 mmol) was added and the resulting mixture was stirred at room temperature for another 1 h. The mixture was cooled to 0° C. and $NaBH_4$ (2.05 g, 54.1 mmol) was added and stirred at 0° C. for 1 h. The mixture was quenched with water and $Boc_2O$ (11.81 g, 54.1 mmol) was added and stirred at room temperature for 48 h. The mixture was quenched with $NH_4Cl$ aqueous solution and extracted with DCM (400 mL×3). The organic layer was dried with anhydrous $NaSO_4$ and concentrated under vacuum. The residue was purified by silica gel column (DCM:MeOH=20:1) to give compound 1-6 (8.05 g). ESI-MS m/z: 282.2 $[M+H]^+$.

To a solution of compound 1-6 (8.05 g, 28.6 mmol) in DCM (100 mL) was added DIPEA (11.1 g, 85.8 mmol) and MsCl (4.9 g, 42.9 mmol) under argon at 0° C. The mixture was stirred at 0° C. for 1 h. The mixture was diluted with DCM (300 mL) and washed with aqueous $NaHCO_3$ (100 mL). The organic layer was dried with anhydrous $NaSO_4$ and concentrated under vacuum to give compound 1-7 (mixture of 1-7A and 1-7B). The crude product was directly used in the next step. ESI-MS m/z: 460.0 $[M+H]^+$.

To a solution of compound 1-7 (crude, 28.6 mmol) in DMF (80 mL) was added NaH (60%) (1.72 g, 42.9 mmol) under argon at 0° C. The mixture was stirred at 0° C. for 1 h, diluted with EA (300 mL) and washed with brine (150 mL×3). The organic layer was dried with anhydrous $Na_2SO_4$ and concentrated under vacuum. The residue was purified by silica gel column (PE:EA=2:1) to give compound 1-8 (4.7 g). ESI-MS m/z: 264.1 $[M+H]^+$.

To a solution of compound 1-8 (2.63 g, 10.0 mmol) in acetone/$H_2O$ (50 mL/50 mL) was added $K2OsO4·2H_2O$ (190 mg, 0.5 mmol), NMO (2.34 g, 20.0 mmol) and $NaIO_4$ (4.30 g, 20.0 mmol) under argon at room temperature. The mixture was stirred at room temperature for 24 h, diluted with EA (200 mL) and washed with water (60 mL×3). The organic layer was dried with anhydrous $Na_2SO_4$ and concentrated under vacuum. The residue was purified by silica gel column (DCM:MeOH=20:1) to give compound 1-9 (1.4 g). ESI-MS m/z: 284.2 $[M+H]^+$.

To a solution of compound 1-9 (1.4 g, 5.28 mmol) in EtOH (30 mL) was added $NaBH_4$ (400 mg, 10.57 mmol) under argon at 0° C. The mixture was stirred at 0° C. for 1 h, quenched with saturated $NH_4Cl$ aqueous solution, and extracted with EA (80 mL×3). The organic layer was dried with anhydrous $Na_2SO_4$ and concentrated under vacuum. The residue was purified by silica gel column (DCM:MeOH=10:1) to give compound 1-10 (520 mg).

To a solution of compound 1-10 (500 mg, 1.87 mmol) in MeOH (8 mL) was added HCl in dioxane (8 mL) at room temperature. The mixture was stirred for 1 h and concentrated to give compound 1-11 which was directly used in the next step. ESI-MS m/z: 168.3 $[M+H]^+$.

To a solution of compound 1-11 (crude, 1.87 mmol) and DIPEA (967 mg, 7.48 mmol) in i-PrOH (15 mL) was added compound 1-12 (673 mg, 1.87 mmol) at room temperature. The mixture was stirred at 50° C. for 4 h. The mixture was filtered and the solid was washed with PE to give compound 1-13 (360 mg). ESI-MS m/z: 49.1.9 $[M+H]^+$.

To a solution of compound 1-13 (90 mg, 0.18 mmol) in THF (10 mL) was added NaH (60%) (60 mg, 1.47 mmol) at room temperature. The mixture was stirred at 90° C. for 3 h under microwave. After completed, the four batches were combined, the mixture was quenched with ice water and extracted with DCM (50 mL×3). The organic layer was dried with anhydrous $Na_2SO_4$ and concentrated. The residue was purified by silica gel column (DCM:MeOH=20:1) to give compound 1-14 (178 mg). ESI-MS m/z: 471.9 $[M+H]^+$.

To a solution of compound 1-14 (178 mg, 0.38 mmol) in DCM (50 mL) was added m-CPBA (72 mg, 0.38 mmol) at 0° C. under argon. The mixture was stirred at 0° C. for 1 h. After completed, the mixture was quenched with saturated $Na_2S_2O_4$ aqueous solution and extracted with EA (80 mL×2). The organic layer was dried with anhydrous $Na_2SO_4$ and concentrated under vacuum to give compound 1-15 (205 mg) which was directly used in the next step. ESI-MS m/z: 487.9 $[M+H]^+$.

To a solution of compound 1-16 (302 mg, 1.9 mmol) in toluene (15 mL) was added NaOt-Bu (183 mg, 1.9 mmol) at room temperature under argon. The mixture was stirred for 20 min, then compound 1-15 (205 mg crude, 0.3 mmol) was added, and the mixture was stirred at room temperature for 2 h. After completion, the mixture was diluted with water and extracted with EA (50 mL×2). The organic layer was dried with anhydrous $Na_2SO_4$ and concentrated under vacuum. The crude was purified by Prep-TLC (DCM:MeOH=10:1) to give compound 1-17 (62 mg). ESI-MS m/z: 582.8 $[M+H]^+$.

To a solution of compound 1-17 (62 mg, 0.11 mmol), compound 1-18 (65 mg, 0.16 mmol) and $Cs_2CO_3$ (107 mg, 0.66 mmol) in toluene (10 mL) was added $DPEphosPdCl_2$ (32 mg, 0.044 mmol) at room temperature under argon. The mixture was stirred at 110° C. for 40 min, then the mixture was cooled and diluted with EA (50 mL). The mixture was washed with water (20 mL×3). The organic layer was dried with anhydrous $Na_2SO_4$ and concentrated under vacuum. The crude was purified by Prep-TLC (DCM:MeOH=10:1) to give compound 1-19 (50 mg). ESI-MS m/z: 793.7 $[M+H]^+$.

To a solution of compound 1-19 (50 mg, 0.063 mmol) in DCM (2 mL) was added TFA (1 mL) at room temperature under argon. The mixture was stirred at room temperature for 1 h, then the mixture was concentrated. The crude residue was purified by Prep-TLC (DCM:$NH_3$ in MeOH (7N)=10:1) to give compound 134 (12.1 mg). ESI-MS m/z: 693.6 $[M+H]^+$; $^1$H NMR (400 MHz, $d_6$-DMSO): δ 8.07 (d, J=10.6 Hz, 2H), 7.22 (ddd, J=16.7, 8.0, 2.7 Hz, 2H), 7.11 (dd, J=8.4, 6.6 Hz, 1H), 6.22 (s, 1H), 6.02 (t, J=13.6 Hz, 1H), 5.30 (d, J=55.3 Hz, 1H), 4.79 (dd, J=12.8, 4.5 Hz, 1H), 4.58-4.28 (m, 5H), 4.19-3.84 (m, 2H), 3.13 (s, 2H), 3.05 (s, 1H), 2.86 (s, 1H), 2.34-2.14 (m, 2H), 2.06 (s, 2H), 1.90-1.73 (m, 4H).

Example 11: Synthesis of 2-amino-4-(6-chloro-10-((2R,3S)-3-cyclopropylaziridine-2-carbonyl)-4-fluoro-2-(((2R,7aS)-2-fluorotetrahydro-1H-pyrrolizin-7a(5H)-yl)methoxy)-12-methyl-8a,9,10,11,11a,12-hexahydro-8H-pyrrolo[3',4':6,7][1,5]oxazocino[4,3,2-de]quinazolin-5-yl)-7-fluorobenzo[b]thiophene-3-carbonitrile (146)

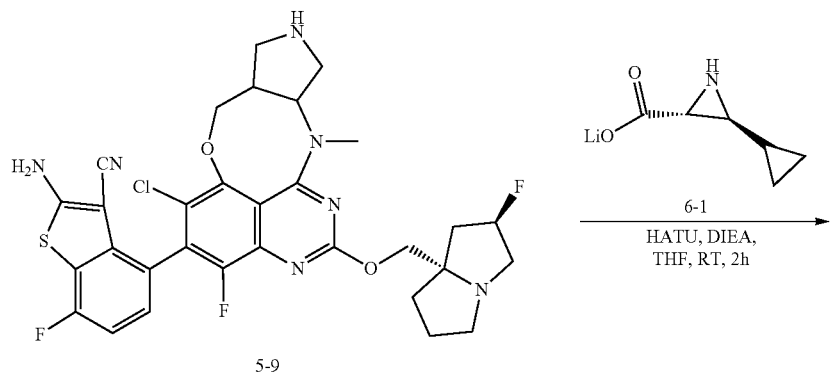

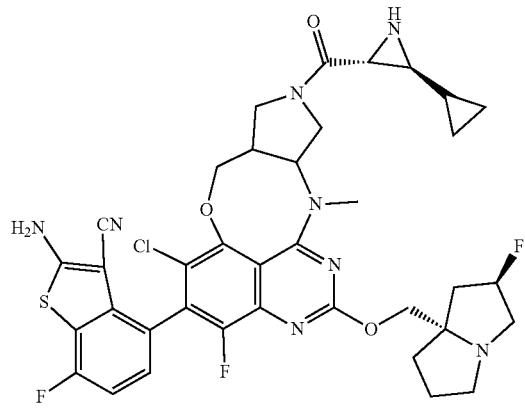

146

To a stirred solution of lithium (2R,3S)-3-cyclopropylaziridine-2-carboxylate (6-1) (10 mg, 0.076 mmol) and DIEA (29 mg, 0.23 mmol) in THF (3 mL), HATU (44 mg, 0.11 mmol) was added, and then compound 5-9 (50 mg, 0.076 mmol) in THF (2 mL) was added at 0° C. The resulting mixture was stirred at RT for 2 h. The mixture was diluted with water (15 mL) and extracted with ethyl acetate (15 mL×2). The combined organic layer was washed with water and brine and concentrated in vacuo. The residue was purified by prep-HPLC to afford compound 146 (8 mg). ESI-MS m/z: 765 [M+H]$^+$.

Example 12: Synthesis of 2-amino-4-(12-chloro-10-fluoro-8-(((2R,7aS)-2-fluorotetrahydro-1H-pyrrolizin-7a(5H)-yl)methoxy)-3-formyl-2,3,4,5,14,14a-hexahydro-1H-[1,4]diazepino[7',1':3,4][1,4]oxazepino[5,6,7-de]quinazolin-11-yl)-7-fluorobenzo[b]thiophene-3-carbonitrile (152)

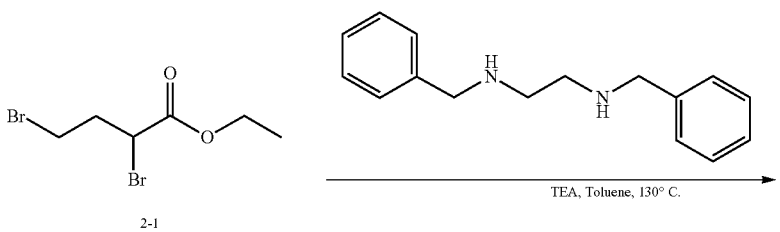

-continued
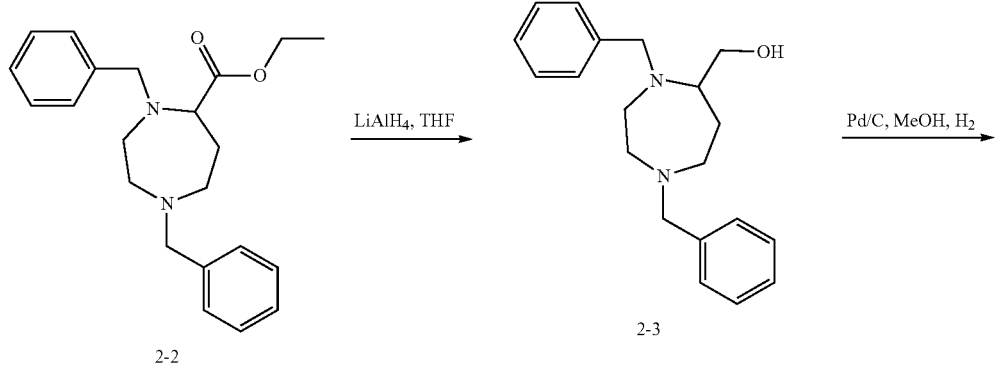
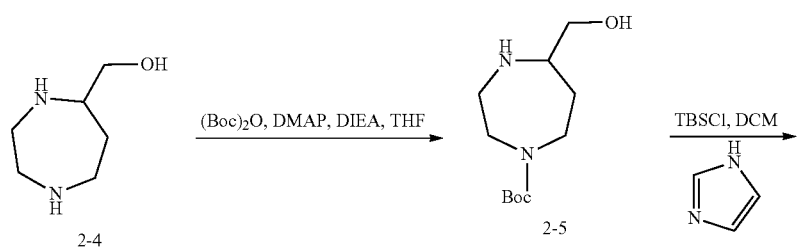
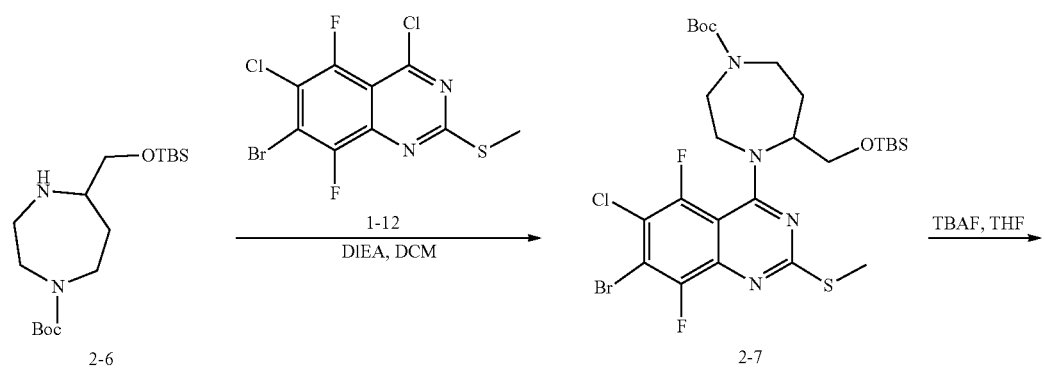
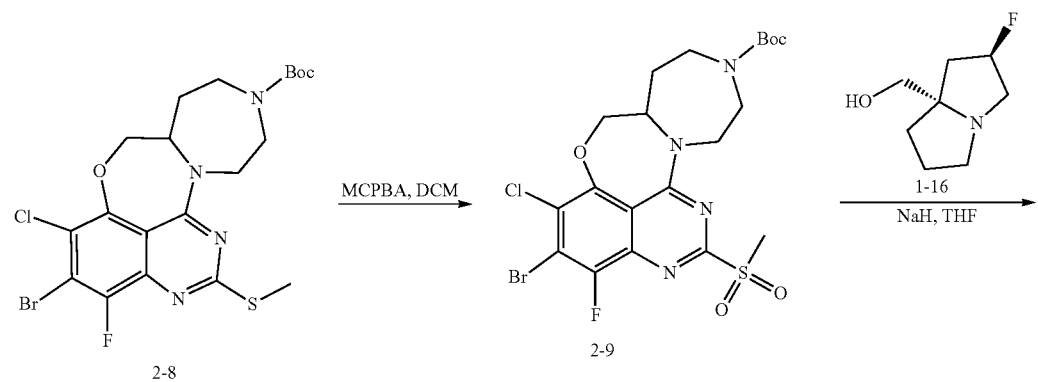 [SMILES: CSc1nc2c3c(c(Cl)c(Br)c(F)c3n1)OCC1CCN(C(=O)OC(C)(C)C)CCN21 ; CC(C)(C)OC(=O)N1CCC2COc3c(Cl)c(Br)c(F)c4nc(S(C)(=O)=O)nc(c34)N2CC1 ; OC[C@@]12CCCN1C[C@H](F)C2]

-continued
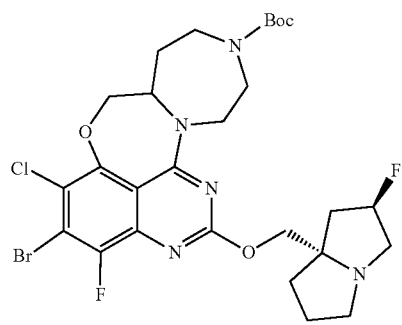
2-10
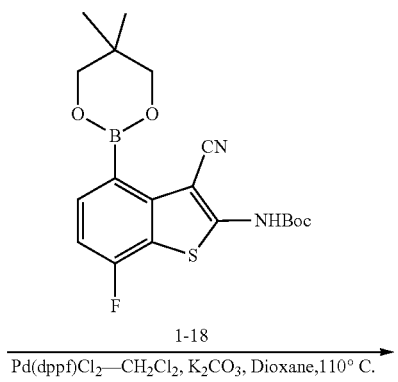
1-18
Pd(dppf)Cl₂—CH₂Cl₂, K₂CO₃, Dioxane, 110° C.
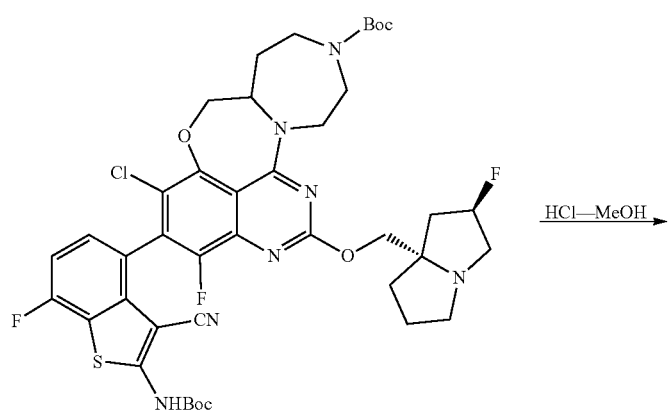
2-11
HCl—MeOH
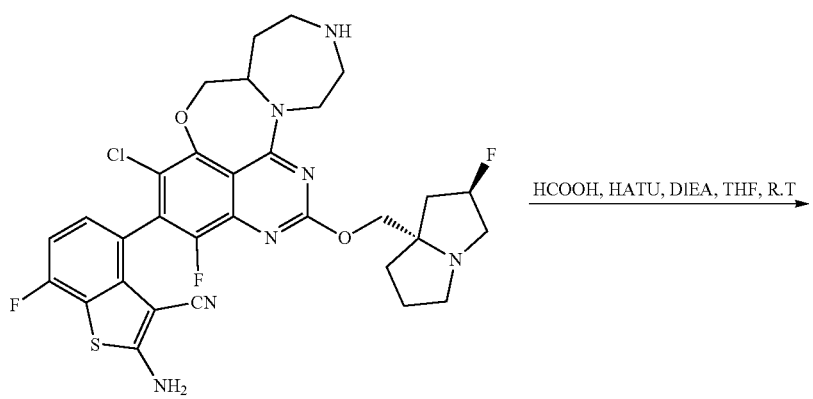
2-12
HCOOH, HATU, DIEA, THF, R.T

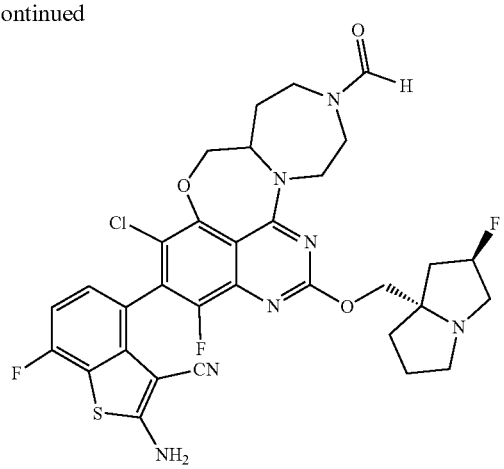

152

To a stirred solution of compound 2-1 (6 g, 21.9 mmol) in Toluene (20 mL) was added TEA (6.6 g, 65.7 mmol) and $N_1$, $N_2$-dibenzylethane-1,2-diamine (6.3 g, 26.2 mmol), and the resulting mixture was stirred at 130° C. for 16 h. The mixture was diluted with water and extracted with ethyl acetate (100 mL×2). The combined organic layer was washed with water and brine, dried over anhydrous $Na_2SO_4$, and concentrated in vacuo. The residue was purified by silica gel column eluting with PE/EA (5:1) to afford compound 2-2 (7.1 g). ESI-MS m/z: 353.1 [M+H]$^+$.

To a stirred solution of compound 2-2 (7.1 g, 20 mmol) in THF (100 mL) was added LiAlH$_4$ (2.3 g, 60.5 mmol), and the resulting mixture was stirred at RT for 1 h. The reaction mixture was quenched with water. The mixture was diluted with water (100 mL) and extracted with ethyl acetate (100 mL×2). The combined organic layer was washed with water, brine and concentrated in vacuo. The residue was purified by silica gel column eluting with DCM/MeOH (100:1 to 50:1) to afford compound 2-3 (5.4 g). ESI-MS m/z: 311.0 [M+H]$^+$.

To a stirred solution of compound 2-3 (2 g, 6.4 mmol) in MeOH (30 mL) was added Pd/C (300 mg), and the resulting mixture was stirred at 60° C. for 16 h under $H_2$. The mixture was filtered, and the filtrate was concentrated to afford compound 2-4 (1.1 g). ESI-MS m/z: 131.3 [M+H]$^+$.

To a stirred solution of compound 2-4 (1.1 g, 8.46 mmol) in THF (20 mL) was added DIEA (3.2 g, 25.4 mmol), (Boc)$_2$O (2.2 g, 10.1 mmol) and DMAP (206 mg, 1.69 mmol), and the resulting mixture was stirred at 60° C. for 16 h. The mixture was diluted with water and extracted with ethyl acetate (50 mL×2). The combined organic layer was washed with water and brine, dried over anhydrous $Na_2SO_4$, and concentrated in vacuo. The residue was purified by silica gel column eluting with DCM/MeOH (10:1) to afford compound 2-5 (1.5 g). ESI-MS m/z: 231.0 [M+H]$^+$.

To a stirred solution of compound 2-5 (1.5 g, 6.5 mmol) in DCM (20 mL) was added 1H-imidazole (1.3 g, 19.5 mmol) and TBSCl (1.4 g, 9.78 mmol), and the resulting mixture was stirred at R.T for 16 h. The mixture was diluted with water and extracted with DCM (50 mL×2). The combined organic layer was washed with water and brine, dried over anhydrous $Na_2SO_4$, and concentrated in vacuo. The residue was purified by silica gel column eluting with DCM/MeOH (50:1) to afford compound 2-6 (850 mg). ESI-MS m/z: 345.0 [M+H]$^+$.

To a stirred solution of compound 2-6 (390 mg, 1.13 mmol) in DCM (20 mL) was added DIEA (438 mg, 3.4 mmol) and compound 1-12 (404 mg, 1.13 mmol), and the resulting mixture was stirred at R.T for 16 h. The mixture was diluted with water and extracted with DCM (50 mL×2). The combined organic layer was washed with water and brine, dried over anhydrous $Na_2SO_4$, and concentrated in vacuo. The residue was purified by silica gel column eluting with PE/EA (7:1) to afford compound 2-7 (620 mg). ESI-MS m/z: 667.0 [M+H]$^+$.

To a stirred solution of 2-7 (620 mg, 0.93 mmol) in THF (10 mL) was added TBAF (5 mL), and the resulting mixture was stirred at 80° C. for 2 h. The mixture was diluted with water and extracted with ethyl acetate (50 mL×2). The combined organic layer was washed with water and brine, dried over anhydrous $Na_2SO_4$, and concentrated in vacuo. The residue was purified by silica gel column eluting with PE/EA (4:1) to afford compound 2-8 (320 mg). ESI-MS m/z: 533.0 [M+H]$^+$.

To a stirred solution of compound 2-8 (320 mg, 0.6 mmol) in DCM (10 mL) was added MCPBA (310 mg,1.8 mmol), and the resulting mixture was stirred at R.T for 2 h. The mixture was diluted with water and extracted with DCM (50 mL×2). The combined organic layer was washed with water and brine, dried over anhydrous $Na_2SO_4$, and concentrated in vacuo. The residue was purified by silica gel column eluting with DCM/MeOH (100:1) to afford compound 2-9 (340 mg). ESI-MS m/z: 565.0 [M+H]$^+$.

To a stirred solution of compound 1-16 (573 mg, 3.6 mmol) in THF (10 mL), NaH (144 mg, 3.6 mmol) was added, and the resulting mixture was stirred at 0° C. for 0.5 h. Compound 2-9 (340 mg, 0.6 mmol) was added at 0° C. and then stirred for 0.5 h. The reaction mixture was quenched with water. The mixture was diluted with water and extracted with ethyl acetate (50 mL×2). The combined organic layer was washed with water and brine, dried over anhydrous $Na_2SO_4$, and concentrated in vacuo. The residue was purified by silica gel column eluting with DCM/MeOH (50:1) to afford compound 2-10 (410 mg). ESI-MS m/z: 644.0 [M+H]$^+$.

To a stirred solution of 2-10 (410 mg, 0.63 mmol) in dioxane (20 mL), was added compound 1-18 (513 mg, 1.27 mmol), Pd(dppf)Cl$_2$—CH$_2$Cl$_2$ (102 mg, 0.127 mmol), and K$_2$CO$_3$, and the resulting mixture was stirred at 110° C. for 16 h. The mixture was diluted with water and extracted with ethyl acetate (50 mL×2). The combined organic layer was washed with water and brine, dried over anhydrous Na$_2$SO$_4$, and concentrated in vacuo. The residue was purified by silica gel column eluting with DCM/MeOH (50:1) to afford compound 2-11 (260 mg). ESI-MS m/z: 856.0 [M+H]$^+$.

The mixture of compound 2-11 (260 mg, 0.3 mmol) in HCl-MeOH (10 mL) was stirred at R.T for 2 h. The mixture was concentrated in vacuo to afford compound 2-12 (210 mg) which was directly used in the next step. ESI-MS m/z: 656.0 [M+H]$^+$.

To a stirred solution of 2-12 (20 mg, 0.03 mmol) in THF (20 mL) was added HCOOH (2.8 mg, 0.06 mmol), HATU (23 mg, 0.06 mmol), DIEA (11.8 mg, 0.09 mmol), and the resulting mixture was stirred at R.T for 16 h. The mixture was diluted with water and extracted with ethyl acetate (50 mL×2). The combined organic layer was washed with water and brine, dried over anhydrous Na$_2$SO$_4$, and concentrated in vacuo. The residue was purified by prep-HPLC to afford compound 152 (1.9 mg). ESI-MS m/z: 684.3 [M+H]$^+$; $^1$H NMR (400 MHz, CD$_3$OD): δ 7.12-7.06 (m, 1H), 6.94-6.91 (m, 1H), 5.37-5.23 (m, 1H), 5.12-5.06 (m, 1H), 4.63-4.58 (m, 1H), 4.40-4.23 (m, 3H), 4.09-4.02 (m, 1H), 3.61-3.30 (m, 6H), 3.13-3.03 (m, 2H), 2.28-1.83 (m, 9H).

Example 13: Synthesis of 2-amino-4-(3-chloro-1'-(2,2-difluorocyclopropane-1-carbonyl)-1-fluoro-13-(((2R,7aS)-2-fluorotetrahydro-1H-pyrrolizin-7a(5H)-yl)methoxy)-5a,6,7,8-tetrahydro-5H,10H-spiro[azepino[2',1':3,4][1,4]oxazepino[5,6,7-de]quinazoline-9,3'-azetidin]-2-yl)-7-fluorobenzo[b]thiophene-3-carbonitrile (155)

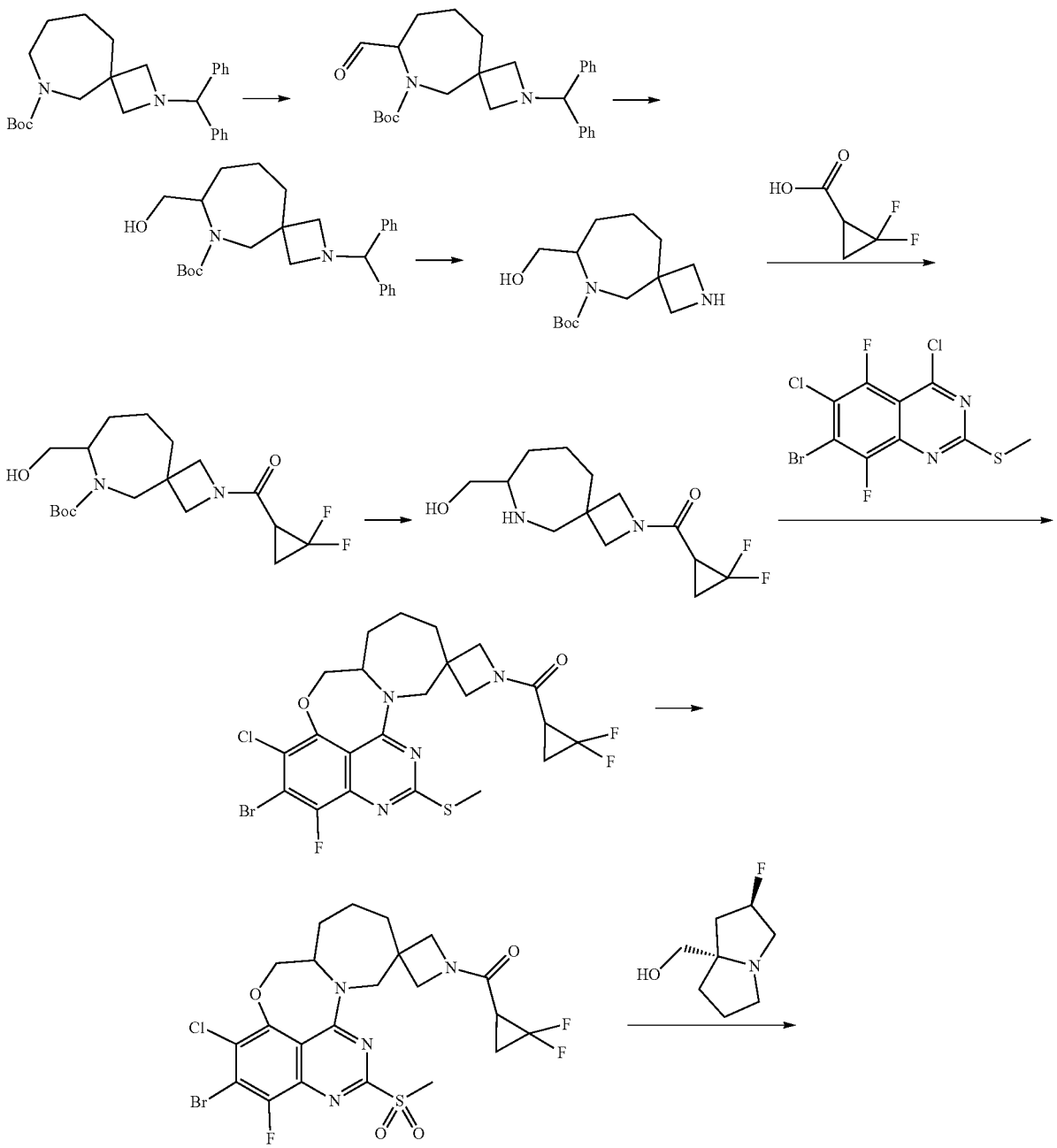

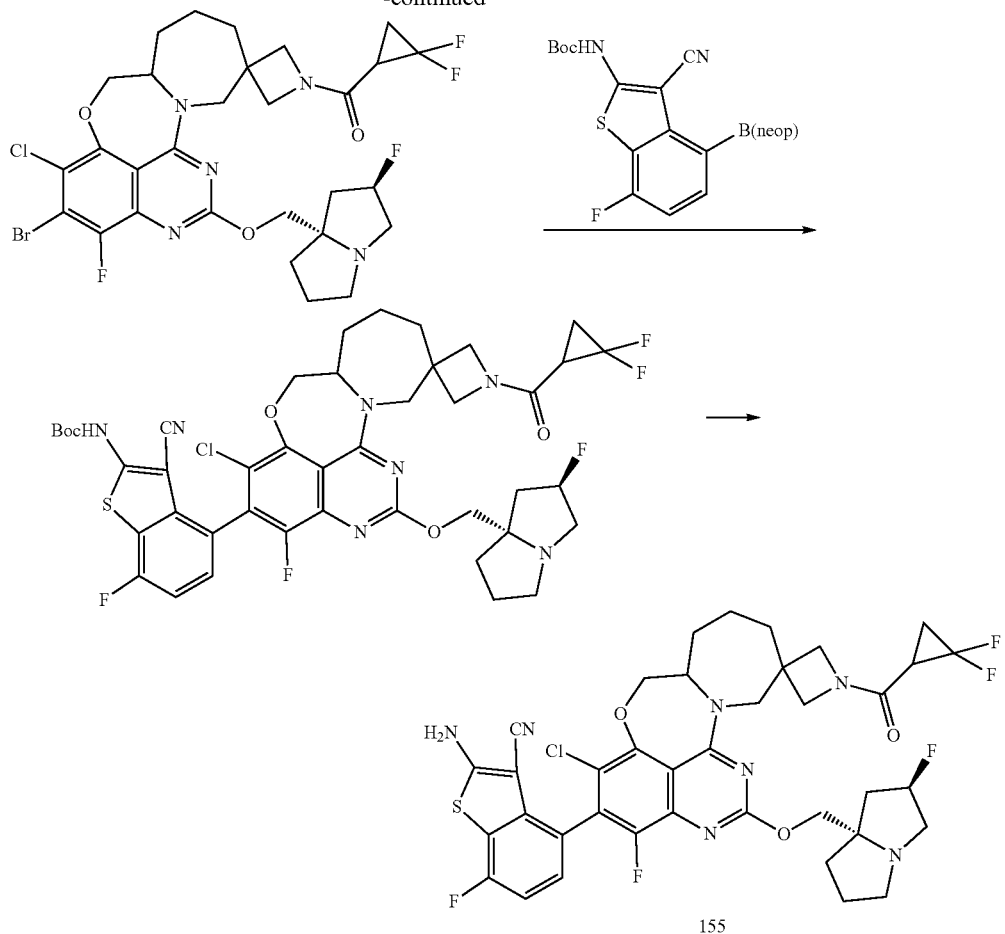

155

Step 1: tert-butyl 2-benzhydryl-7-formyl-2,6-diazaspiro[3.6]decane-6-carboxylate A reaction flask charged with magnetic stir bar under argon, tert-butyl 2-benzhydryl-2,6-diazaspiro[3.6]decane-6-carboxylate (810 mg, 2.0 mmol, 1.0 eq), and TMEDA (0.75 mL, 5.0 mmol, 2.5 eq) was subjected to anhydrous diethyl ether (20 ml). s-BuLi (2.85 mL, 4 mmol, 1.4 M in hexenes) was added dropwise to the reaction mixture at −78° C. over 30 minutes. Upon finishing addition, the reaction was allowed to warm up from −20° C. to −15° C. and stirred for 4 hours. Then anhydrous DMF (4 mL) was added slowly to the reaction mixture at −78° C. The mixture was allowed to warm to room temperature and stirred overnight. Water (20 mL) and ethyl acetate (10 mL) were added to the reaction mixture at 0° C. The layers were separated, the aqueous was extracted with ethyl acetate (2×10 mL). The organics were combined and dried over $Na_2SO_4$. The resulting product was filtered and solvent was removed under reduced pressure to give a crude. The crude was used for the next step without purification. LCMS calc. for $C_{27}H_{35}N_2O_3$ [M+H]$^+$: m/z=435.3; Found: 435.3.

Step 2: tert-butyl 2-benzhydryl-7-(hydroxymethyl)-2,6-diazaspiro[3.6]decane-6-carboxylate The crude from the last step was dissolved with 15 ml MeOH (15 mL) in a round bottom flask charged with a stir bar. $NaBH_4$ (151 mg, 4.0 mmol, 2.0 eq) was added to the reaction mixture in portions at 0° C. and the resulting mixture was stirring at room temperature for 1 hour. Then saturated $NH_4Cl$ solution was added slowly to the reaction mixture at 0° C., followed by ethyl acetate (20 mL). The organic layers were separated and dried over $Na_2SO_4$. The resulting product was filtered and solvent was removed under reduced pressure to give a crude. The crude was purified by silica gel chromatography eluting with 0 to 40% ethyl acetate/hexane. The desired product was obtained as clear oil. LCMS calc. for $C_{27}H_{37}N_2O_3$ [M+H]$^+$: m/z=437.3.3; Found: 437.4.

Step 3: tert-butyl 7-(hydroxymethyl)-2,6-diazaspiro[3.6]decane-6-carboxylate Tert-butyl 2-benzhydryl-7-(hydroxymethyl)-2,6-diazaspiro[3.6]decane-6-carboxylate (400 mg, 0.92 mmol, 1.0 eq), Pd(OH)$_2$ (13 mg, 0.09 mmol, 10 mmol %) and ammonium formate (113 mg, 1.8 mmol, 2.0 eq) were added to MeOH (10 mL). The mixture was allowed to stir at 60° C. for 4 hours and then cooled down to room temperature. Solvent was removed and the residue obtained was purified by silica gel chromatography eluting with 0 to 30% MeOH/ dichloromethane. The desired product was obtained as oil. LCMS calc. for $C_{14}H_{27}N_2O_3$ [M+H]$^+$: m/z=271.2; Found: 271.2.

Step 4: tert-butyl 2-(2,2-difluorocyclopropane-1-carbonyl)-7-(hydroxymethyl)-2,6-diazaspiro[3.6]decane-6-carboxylate Tert-butyl 2-benzhydryl-7-(hydroxymethyl)-2,6-diazaspiro[3.6]decane-6-carboxylate (100 mg, 0.37 mmol, 1.0 eq), 2,2-difluorocyclopropane-1-carboxylic acid (54 mg, 0.44 mmol, 1.2 eq), 1 [bis(dimethylamino)methylene]-1H-1,2,3-triazolo[4,5-b]pyridinium 3-oxide hexafluorophosphate (54 mg, 0.74 mmol, 2.0 eq) and N-methyl morpholine (81 µL, 0.74 mmol, 2.0 eq) were added to anhydrous dichloromethane (6 mL) in a round bottom flask. The mixture was stirred for 2 hours at room temperature and the solvent was removed under reduced pressure to give a crude. The crude was purified by silica gel chromatography eluting with 0 to 40% ethyl acetate/hexane. The desired product was obtained as white solid. LCMS calc. for $C_{18}H_{29}F_2N_2O_4$ [M+H]$^+$: m/z=375.2; Found: 375.3.

Step 5: (2,2-difluorocyclopropyl)(7-(hydroxymethyl)-2,6-diazaspiro[3.6]decan-2-yl)methanone Tert-butyl 2-(2,2-difluorocyclopropane-1-carbonyl)-7-(hydroxymethyl)-2,6-diazaspiro[3.6]-decane-6-carboxylate (70 mg, 0.19 mmol) was dissolved in dichloromethane (6 mL). Then TFA (0.6 mL) was added dropwise at 0° C. and the reaction mixture was allowed to stir at room temperature for 1 hour. Solvent was removed to give a crude which is used directly in the next step without further purification. LCMS calc. for $C_{13}H_{21}F_2N_2O_2$ [M+H]$^+$: m/z=275.2; Found: 275.1.

Step 6: (6-(7-bromo-6-chloro-5,8-difluoro-2-(methylthio)quinazolin-4-yl)-7-(hydroxymethyl)-2,6-diazaspiro[3.6]decan-2-yl)(2,2-difluorocyclopropyl)methanone The crude from the previous step was added to 7-bromo-4,6-dichloro-5,8-difluoro-2-(methylthio)quinazoline (68 mg, 0.19 mmol, 1.0 eq), N,N-Diisopropylethylamine (165 µL, 0.95 mmol, 5.0 eq) in dichloromethane (5 mL). The reaction mixture was stirred at room temperature for 3 hours. Solvent was removed under reduced pressure to give a crude which was purified by silica gel chromatography, eluting with 0 to 80% ethyl acetate/hexane. The desired compound was obtained as a white solid. LCMS calc. for $C_{22}H_{23}BrClF_4N_4O_2S$ [M+H]$^+$: m/z=597.0; Found: 597.2.

Step 7: (2-bromo-3-chloro-1-fluoro-13-(methylthio)-5a,6,7,8-tetrahydro-5H,10H-spiro[azepino[2',1':3,4][1,4]oxazepino[5,6,7-de]quinazoline-9,3'-azetidin]-1'-yl)(2,2-difluorocyclopropyl)methanone 6-(7-bromo-6-chloro-5,8-difluoro-2-(methylthio)quinazolin-4-yl)-7-(hydroxymethyl)-2,6-diazaspiro[3.6]decan-2-yl)(2,2-difluorocyclopropyl)methanone (83 mg, 0.14 mmol, 1.0 eq) was dissolved with THF (5 mL) in a round bottom flask charged with a magnetic bar. Then tetrabutylammonium fluoride (0.42 mL, 0.42 mmol, 3.0 eq, 1 M in hexenes) was added slowly and the resulting mixture was allowed to stir at room temperature for 1 hour. Water (10 mL) was added, followed by ethyl acetate (6 mL). The organic layers were separated, and aqueous was extracted with ethyl acetate (2×6 mL). The organics were combined, washed with brine, and dried over sodium sulfate. The resulting product was filtered and solvent was removed under reduced pressure to give a crude. The crude was purified by silica gel chromatography eluting with 0 to 60% ethyl acetate/hexane to afford the desired product as a white solid. LCMS calc. for $C_{22}H_{22}BrClF_3N_4O_2S$ [M+H]$^+$: m/z=577.0; Found: 577.3.

Step 8: (2-bromo-3-chloro-1-fluoro-13-(methylsulfonyl)-5a,6,7,8-tetrahydro-5H,10H-spiro[azepino[2',1':3,4][1,4]oxazepino[5,6,7-de]quinazoline-9,3'-azetidin]-1'-yl)(2,2-difluorocyclopropyl)methanone (2-bromo-3-chloro-1-fluoro-13-(methylthio)-5a,6,7,8-tetrahydro-5H,10H-spiro[azepino-[2',1':3,4][1,4]oxazepino[5,6,7-de]quinazoline-9,3'-azetidin]-1'-yl)(2,2-difluorocyclopropyl)-methanone (16 mg, 0.028 mmol, 1.0 eq) was dissolved in dichloromethane (4 mL). m-chloroperoxybenzoic acid (16 mg, 0.062 mmol, 2.2 eq) was added slowly at ° C. and the reaction mixture was allowed to stir at room temperature for 30 minutes and quenched with $Na_2S_2O_3$ (5 mL 10% aq.). The organic layers were separated, combined, and dried over $Na_2SO_4$. The resulting product was filtered and solvent was removed to give a crude. The crude was purified by silica gel chromatography p eluting with 0 to 10% MeOH/DCM to afford the desired product as a white solid. LCMS calc. for $C_{22}H_{22}BrClF_3N_4O_4S$ [M+H]$^+$: m/z=609.1; Found: 609.5.

Step 9: (2-bromo-3-chloro-1-fluoro-13-(((2R,7aS)-2-fluorotetrahydro-1H-pyrrolizin-7a(5H)-yl)methoxy)-5a,6,7,8-tetrahydro-5H,10H-spiro[azepino[2',1':3,4][1,4]oxazepino-[5,6,7-de]quinazoline-9,3'-azetidin]-1'-yl)(2,2-difluorocyclopropyl)methanone (2-bromo-3-chloro-1-fluoro-13-(methylsulfonyl)-5a,6,7,8-tetrahydro-5H,10H-spiro[azepino-[2',1':3,4][1,4]oxazepino[5,6,7-de]quinazoline-9,3'-azetidin]-1'-yl)(2,2-difluorocyclopropyl)-methanone (13 mg, 0.02 mmol, 1.0 eq), ((2R,7aS)-2-fluorotetrahydro-1H-pyrrolizin-7a(5H)-yl)methanol (7.8 mg, 0.06 mmol, 3.0 eq), and 4 Å MS (15 mg) were added to a reaction vial in toluene (2 mL). The mixture was allowed to stir at room temperature for 10 min under nitrogen before NaOtBu (6.0 mg, 0.06 mmol, 3.0 eq) was added. It was stirred for 1 hour at room temperature and solvent was removed under reduced pressure to give a crude. The crude was purified by silica gel chromatography eluting with 0 to 20% MeOH/DCM to afford the desired product as a white solid. LCMS calc. for $C_{29}H_{32}BrClF_4N_5O_3$ [M+H]$^+$: m/z=688.1; Found: 688.5.

Step 10: tert-butyl (4-(3-chloro-1'-(2,2-difluorocyclopropane-1-carbonyl)-1-fluoro-13-((2R,7aS)-2-fluorotetrahydro-1H-pyrrolizin-7a(5H)-yl)methoxy)-5a,6,7,8-tetrahydro-5H,10H-spiro[azepino[2',1':3,4][1,4]oxazepino[5,6,7-de]quinazoline-9,3'-azetidin]-2-yl)-3-cyano-7-fluorobenzo[b]thiophen-2-yl)carbamate (2-bromo-3-chloro-1-fluoro-13-((2R,7aS)-2-fluorotetrahydro-1H-pyrrolizin-7a(5H)-yl)methoxy)-5a,6,7,8-tetrahydro-5H,10H-spiro[azepino[2',1':3,4][1,4]oxazepino[5,6,7-de]quinazoline-9,3'-azetidin]-1'-yl)(2,2-difluorocyclopropyl)methanone (10 mg, 0.014 mmol, 1.0 eq), tert-butyl (3-cyano-4-(5,5-dimethyl-1,3,2-dioxaborinan-2-yl)-7-fluorobenzo[b]thiophen-2-yl)carbamate (10.0 mg, 0.026 mmol, 1.8 eq), dichlorobis(diphenylphosphinophenyl)ether palladium (II) (1.56 mg, 0.002 mmol, 15 mol %), and cesium carbonate (9 mg, 0.029 mmol, 2.0 eq) were added to a round bottom flask. The reaction system was vacuumed and refilled with nitrogen three times. Then anhydrous toluene (2 mL) was added via syringe. The mixture was vacuumed and refilled with nitrogen three times before stirring at 100° C. for 2 hours. Then the reaction mixture was allowed to cool down to room temperature and solvent was removed to give a crude. The crude was purified via silica gel chromatography eluting with 0-20% MeOH/DCM to afford the desired product as a beige solid. LCMS calc. for $C_{43}H_{44}ClF_5N_7O_5S$ $[M+H]^+$: m/z=900.3; Found: 900.3.

Step 11: 2-amino-4-(3-chloro-1'-(2,2-difluorocyclopropane-1-carbonyl)-1-fluoro-13-((2R,7aS)-2-fluorotetrahydro-1H-pyrrolizin-7a(5H)-yl)methoxy)-5a,6,7,8-tetrahydro-5H,10H-spiro[azepino[2',1':3,4][1,4]oxazepino[5,6,7-de]quinazoline-9,3'-azetidin]-2-yl)-7-fluorobenzo[b]thiophene-3-carbonitrile Tert-butyl (4-(3-chloro-1'-(2,2-difluorocyclopropane-1-carbonyl)-1-fluoro-13-((2R,7aS)-2-fluorotetrahydro-1H-pyrrolizin-7a(5H)-yl)methoxy)-5a,6,7,8-tetrahydro-5H,10H-spiro[azepino-[2',1':3,4][1,4]oxazepino[5,6,7-de]quinazoline-9,3'-azetidin]-2-yl)-3-cyano-7-fluorobenzo[b]-thiophen-2-yl)carbamate (4.5 mg, 0.005 mmol) was dissolved with dichloromethane (2 mL) in a scintillation vial charged with stir bar. Then TFA (0.2 mL) was added dropwise at 0° C. After stirring for 30 minutes, solvent was removed under reduced pressure to give a crude. The crude was purified by reverse phase chromatography eluting with 0-60% ACN/H₂O (0.1% formic acid) to afford the desired product as white solid. LCMS calc. for $C_{38}H_{36}ClF_5N_7O_3S$ $[M+H]^+$: m/z=800.2; Found: 800.1.

Example 14: Synthesis of 2-amino-4-(6-chloro-4-fluoro-2-((2R,7aS)-2-fluorotetrahydro-1H-pyrrolizin-7a(5H)-yl)methoxy)-11-methyl-7a,8,10a,11-tetrahydro-10H-furo[3',4':2,3][1,4]oxazepino[5,6,7-de]quinazolin-5-yl)-7-fluorobenzo[b]thiophene-3-carbonitrile (166)

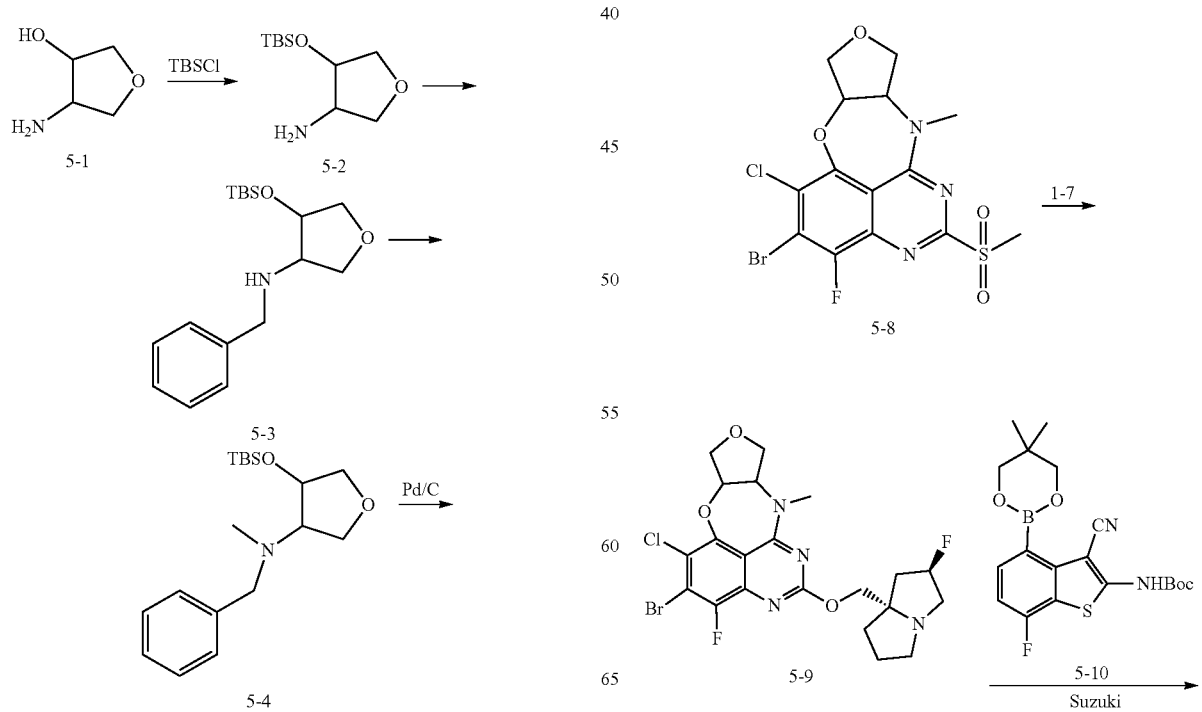

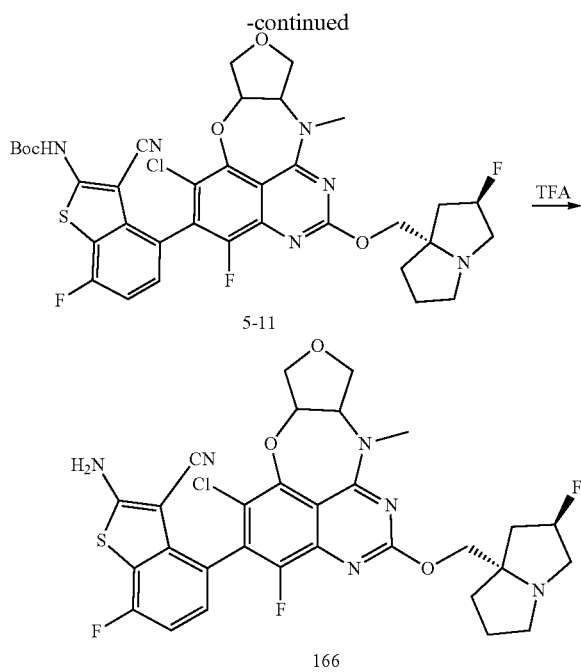

5-11

166

Step A: Preparation of 4-((tert-butyldimethylsilyl)oxy)tetrahydrofuran-3-amine (5-2). To a solution of 4-aminotetrahydrofuran-3-ol (5-1) (2 g, 19.39 mmol) and 1H-imidazole (1.3 g, 58.18 mmol) in DMF (10 mL) at 0° C., TBSCl (3.5 g, 23.27 mmol) was slowly added, and the resulting mixture was stirred at room temperature for 4 h. The reaction mixture was extracted with ethyl acetate, washed with $H_2O$ and brine, dried over $Na_2SO_4$, concentrated in vacuo and the residue was purified by flash chromatography on silica gel (2% MeOH/DCM) to afford compound 5-2 (2 g). ESI-MS m/z: 218 [M+H]$^+$.

Step B: Preparation of N-benzyl-4-((tert-butyldimethylsilyl)oxy)tetrahydrofuran-3-amine (5-3). To a solution of compound 5-2 (500 mg, 2.30 mmol) and benzaldehyde (244.0 mg, 2.30 mmol) in MeOH (10 mL) at 0° C., NaBH$_3$CN (213.9 mg, 3.45 mmol) was slowly added followed by 2 drops of AcOH. The resulting mixture was stirred at room temperature for 16 h. The reaction mixture was extracted with ethyl acetate, washed with $H_2O$, dried over $Na_2SO_4$, concentrated in vacuo and the residue was purified by flash chromatography on silica gel (15% EA/PE) to afford compound 5-3 (240 mg). ESI-MS m/z: 308 [M+H]$^+$.

Step C: Preparation of N-benzyl-4-((tert-butyldimethylsilyl)oxy)-N-methyltetrahydrofuran-3-amine (5-4). To a solution of compound 5-3 (700 mg, 2.28 mmol) and acetaldehyde (68.4 mg, 2.28 mmol) in MeOH (10 mL) at 0° C., NaBH$_3$CN (212.0 mg, 3.42 mmol) was slowly added followed by 2 drops of AcOH. The resulting mixture was stirred at room temperature for 16 h. The reaction mixture was extracted with ethyl acetate, washed with $H_2O$, dried over $Na_2SO_4$, concentrated in vacuo and the residue was purified by flash chromatography on silica gel (25% EA/PE) to afford compound 5-4 (500 mg). ESI-MS m/z: 322 [M+H]$^+$.

Step D: Preparation of 4-((tert-butyldimethylsilyl)oxy)-N-methyltetrahydrofuran-3-amine (5-5). A mixture of compound 5-4 (500 mg, 1.56 mmol) and Pd/C (500 mg) in MeOH (10 mL) was stirred under $H_2$ at room temperature for 16 h. The reaction mixture was filtered, and the filtrate was concentrated in vacuo to afford compound 5-5 (350 mg). ESI-MS m/z: 232 [M+H]$^+$.

Step E: Preparation of 7-bromo-N-(4-((tert-butyldimethylsilyl)oxy)tetrahydrofuran-3-yl)-6-chloro-5,8-difluoro-N-methyl-2-(methylthio)quinazolin-4-amine (5-6). To a solution of 1-3 (500 mg, 1.39 mmol) and DMA (537.5 mg, 2.08 mmol) in THF (10 mL) at 0° C., compound 5-5 (320 mg, 1.39 mmol) was added and the resulting mixture was stirred at room temperature for 2 h. The reaction mixture was extracted with ethyl acetate, washed with $H_2O$, dried over $Na_2SO_4$, concentrated in vacuo and the residue was purified by flash chromatography on silica gel (5% EA/PE) to afford compound 5-6 (300 mg). ESI-MS m/z: 556 [M+H]$^+$.

Step F: Preparation of 5-bromo-6-chloro-4-fluoro-11-methyl-2-(methylthio)-7a,8,10a,11-tetrahydro-10H-furo[3',4':2,3][1,4]oxazepino[5,6,7-de]quinazoline (5-7). To a solution of compound 5-6 (170 mg, 0.306 mmol) in THF (5 mL) at 0° C., TBAF (0.92 mL, 1M in THF, 0.92 mmol) was slowly added and the resulting mixture was stirred at room temperature for 2 h. The reaction mixture was extracted with ethyl acetate, washed with $H_2O$, dried over $Na_2SO_4$, concentrated in vacuo and the residue was purified by flash chromatography on silica gel (10% EA/PE) to afford compound 5-7 (120 mg). ESI-MS m/z: 422 [M+H]$^+$.

Step G: Preparation of 5-bromo-6-chloro-4-fluoro-11-methyl-2-(methylsulfonyl)-7a,8,10a,11-tetrahydro-10H-furo[3',4':2,3][1,4]oxazepino[5,6,7-de]quinazoline (5-8). To a solution of compound 5-7 (120 mg, 0.29 mmol) in DCM (10 mL) at 0° C., mCPBA (147.1 mg, 0.86 mmol) was added slowly and the resulting mixture was stirred at room temperature for 2 h. The reaction mixture was extracted with ethyl acetate, washed with $H_2O$, dried over $Na_2SO_4$, concentrated in vacuo and the residue was purified by flash chromatography on silica gel (2% MeOH/DCM) to afford compound 5-8 (40 mg). ESI-MS m/z: 454 [M+H]$^+$.

Step H: Preparation of 5-bromo-6-chloro-4-fluoro-2-(((2R,7aS)-2-fluorotetrahydro-1H-pyrrolizin-7a(5H)-yl)methoxy)-11-methyl-7a,8,10a,11-tetrahydro-10H-furo[3',4':2,3][1,4]oxazepino[5,6,7-de]quinazoline (5-9). To a solution of 1-7 (28.13 mg, 0.177 mmol) in THF (5 mL) at 0° C., NaH (7.77 mg, 0.194 mmol) was added and the resulting mixture was stirred for 20 min. Compound 5-8 (40 mg, 0.088 mmol) was added to this mixture. The resulting mixture was stirred at room temperature for 2 h. The reaction mixture was extracted with ethyl acetate, washed with $H_2O$, dried over $Na_2SO_4$, concentrated in vacuo and the residue was purified by flash chromatography on silica gel (2% MeOH/DCM) to afford compound 5-9 (35 mg). ESI-MS m/z: 533 [M+H]$^+$.

Step I: Preparation of tert-butyl (4-(6-chloro-4-fluoro-2-(((2R,7aS)-2-fluorotetrahydro-1H-pyrrolizin-7a(5H)-yl)methoxy)-11-methyl-7a,8,10a,11-tetrahydro-10H-furo[3',4':2,3][1,4]oxazepino[5,6,7-de]quinazolin-5-yl)-3-cyano-7-fluorobenzo[b]thiophen-2-yl)carbamate (5-11). To a solution of compound 5-9 (35 mg, 0.066 mmol) and tert-butyl (3-cyano-4-(5,5-dimethyl-1,3,2-dioxaborinan-2-yl)-7-fluorobenzo[b]thiophen-2-yl)carbamate (5-10) (53.06 mg, 0.13 mmol) in toluene (10 mL), Cs$_2$CO$_3$ (64 mg, 0.19 mmol) and DPEphosPdCl$_2$ (23.5 mg, 0.033 mmol) were added and the mixture was purged with argon. The resulting mixture was stirred at 105° C. for 16 h. The reaction mixture was concentrated and extracted with ethyl acetate. The organic layer was washed with water and brine, dried over $Na_2SO_4$, concentrated in vacuo and the residue was purified by flash chromatography on silica gel (5% MeOH/DCM) to afford compound 5-11 (20 mg). ESI-MS m/z: 743 [M+H]$^+$.

Step J: Preparation of 2-amino-4-(6-chloro-4-fluoro-2-(((2R,7aS)-2-fluorotetrahydro-1H-pyrrolizin-7a(5H)-yl)

methoxy)-11-methyl-7a,8,10a,11-tetrahydro-10H-furo[3',4':
2,3][1,4]oxazepino[5,6,7-de]quinazolin-5-yl)-7-fluorobenzo[b]thiophene-3-carbonitrile (166). To a solution of compound 5-11 (20 mg, 0.027 mmol) in DCM (2 mL) at 0° C., TFA (1 mL) was added slowly, and the resulting mixture was stirred at room temperature for 1 h. The reaction mixture was basified with NaHCO$_3$ aqueous solution, extracted with DCM, washed with brine, dried over Na$_2$SO$_4$, concentrated in vacuo and the residue was purified by flash chromatography on silica gel (10% MeOH/DCM) to afford the title compound (2 mg). ESI-MS m/z: 643 [M+H]$^+$.

Example 15: Synthesis of 2-amino-4-((5aS)-3-chloro-1-fluoro-12-(((2R,7aS)-2-fluorohexahydro-1H-pyrrolizin-7a-yl)methoxy)-5,5a,6,7,8,9-hexahydropyrido[2',1':3,4][1,4]oxazepino[5,6,7-de]quinazolin-2-yl)-7-fluorobenzo[b]thiophene-3-carbonitrile (168)

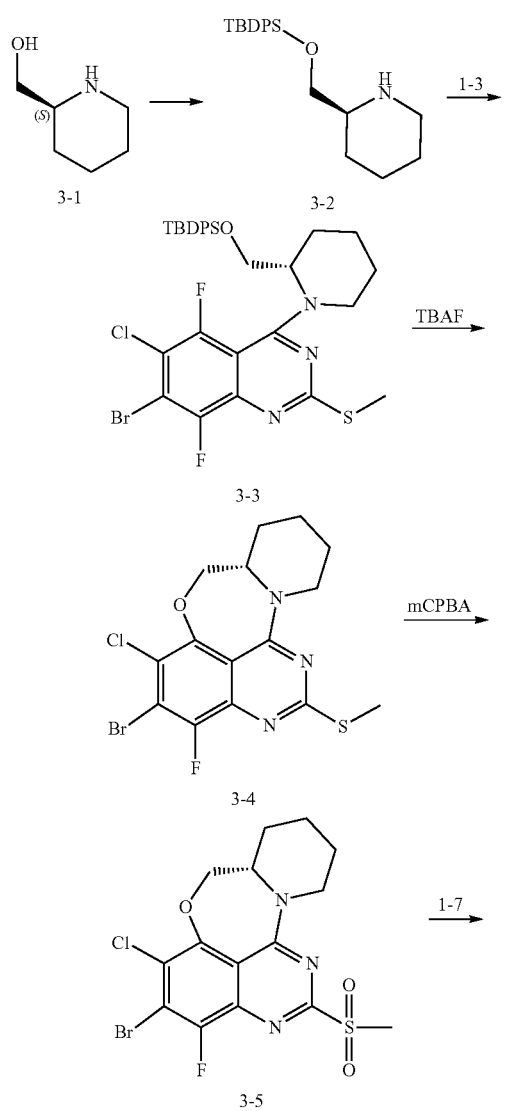

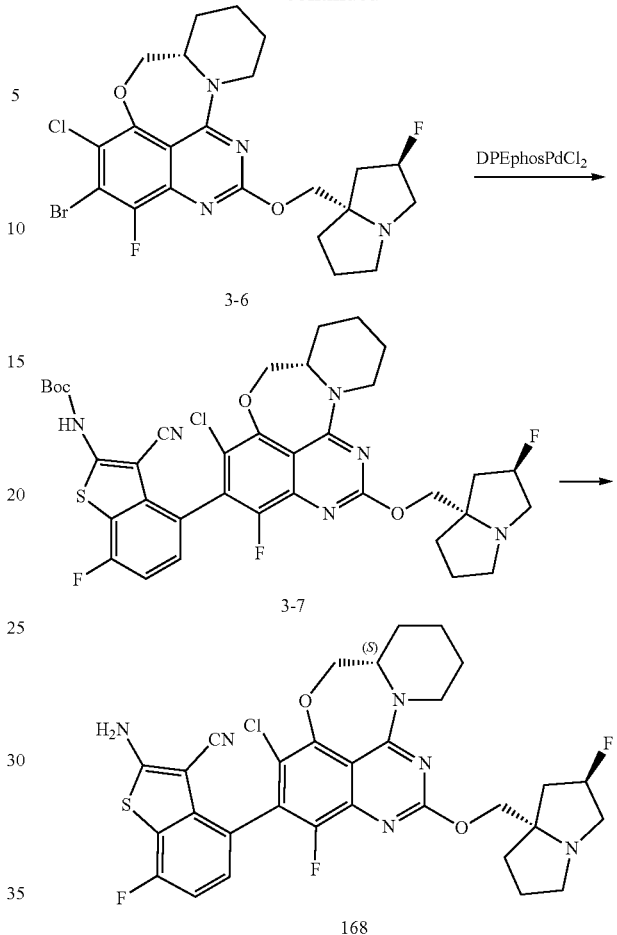

Step A: Preparation of (S)-2-(((tert-butyldiphenylsilyl)oxy)methyl)piperidine (3-2). To a solution of (S)-piperidin-2-ylmethanol (3-1) (250 mg, 2.17 mmol) in DCM (30 mL) was added imidazole (162 mg, 2.38 mmol) and DMAP (20 mg) slowly at 0° C., followed by the addition of TBDPSCl at the same temperature. The resulting mixture was stirred for 3 hours at room temperature. The reaction mixture was extracted with DCM, washed with NaHCO$_3$ (aq) and brine, and dried over Na$_2$SO$_4$, then filtered and solvent removed under reduced pressure to give a crude residue. The crude residue was purified by flash chromatography on silica gel (2% MeOH/DCM) to afford the desired product (3-2).

Step B: Preparation of (S)-7-bromo-4-(2-(((tert-butyldiphenylsilyl)oxy)methyl)piperidin-1-yl)-6-chloro-5,8-difluoro-2-(methylthio)quinazoline (3-3). To a solution of 1-3 (200 mg, 0.55 mmol) and 3-2 (232 mg, 0.66 mmol) in DCM (30 mL) was added DIPEA (212 mg, 1.65 mmol) at 0° C. The resulting mixture was stirred for 1 hour at room temperature. The reaction mixture was extracted with DCM, washed with water and brine, and dried over Na$_2$SO$_4$, then filtered and solvent removed under reduced pressure to give a crude residue. The crude residue was purified by flash chromatography on silica gel (10% ethyl acetate/ petroleum) to afford the desired product Step C: Preparation of (S)-2-bromo-3-chloro-1-fluoro-12-(methylthio)-5,5a,6,7,8,9-hexahydropyrido[2',1':3,4][1,4]oxazepino[5,6,7-de]quinazoline (3-4). To a solution of 3-3 (341 mg, 0.50 mmol) in THF (1 mL) was added TBAF (5 mL, 1M in THF). The resulting mixture was stirred for 16 hours under Ar at room temperature. The reaction mixture was extracted with ethyl acetate, washed with water and brine, and dried over $Na_2SO_4$, then filtered and solvent removed under reduced pressure to give a crude residue. The crude residue was purified by flash chromatography on silica gel (10% ethyl acetate/petroleum) to afford the desired product. ESI-MS m/z: 419 [M+H]$^+$.

Step D: Preparation of (S)-2-bromo-3-chloro-1-fluoro-12-(methylsulfonyl)-5,5a,6,7,8,9-hexahydropyrido[2',1':3,4][1,4]oxazepino[5,6,7-de]quinazoline (3-5). To a solution of 3-4 (120 mg, 0.28 mmol) in DCM (20 mL) was added m-CPBA (144 mg, 0.84 mmol) slowly at 0° C. The resulting mixture was stirred for 1 hour at room temperature. The reaction mixture was quenched with $Na_2SO_3$ (aq), extracted with DCM, washed with water and brine, and dried over $Na_2SO_4$, then filtered and solvent removed under reduced pressure to give a crude residue. The crude residue was purified by flash chromatography on silica gel (50% ethyl acetate/petroleum) to afford the desired product. ESI-MS m/z: 451 [M+H]$^+$.

Step E: Preparation of (S)-2-bromo-3-chloro-1-fluoro-12-(((2R,7aS)-2-fluorohexahydro-1H-pyrrolizin-7a-yl)methoxy)-5,5a,6,7,8,9-hexahydropyrido[2',1':3,4][1,4]oxazepino[5,6,7-de]quinazoline (3-6). To a solution of NaH (92 mg, 2.3 mmol) in THF (20 mL) in a three mouth flask was added 1-7 (182 mg, 1.15 mmol) at 0° C. under Ar. The mixture was stirred for 30 min at room temperature. 3-5 (106 mg, 0.23 mmol) was added slowly at 0° C. and the resulting mixture was stirred for an additional 1 hour at room temperature. The reaction mixture was quenched with water, extracted with ethyl acetate, washed with brine, and dried over $Na_2SO_4$, then filtered and solvent removed under reduced pressure to give a crude residue. The crude residue was purified by flash chromatography on silica gel (5% MeOH/DCM) to afford the desired product. ESI-MS m/z: 531 [M+H]$^+$.

Step F: Preparation of tert-butyl (4-((5aS)-3-chloro-1-fluoro-12-(((2R,7aS)-2-fluorohexahydro-1H-pyrrolizin-7a-yl)methoxy)-5,5a,6,7,8,9-hexahydropyrido[2',1':3,4][1,4]oxazepino[5,6,7-de]quinazolin-2-yl)-3-cyano-7-fluorobenzo[b]thiophen-2-yl)carbamate (3-7). To a solution of 3-6 (40 mg, 0.075 mmol) and tert-butyl (3-cyano-4-(5,5-dimethyl-1,3,2-dioxaborinan-2-yl)-7-fluorobenzo[b]thiophen-2-yl)carbamate (60 mg, 0.15 mmol) in toluene (10 mL) were added $Cs_2CO_3$ (73 mg, 0.225 mmol) and DPEphos-PdCl$_2$ (10 mg, 0.015 mmol), then the mixture was degassed and back filled with Ar three times. The resulting mixture was heated to 100° C. for 16 hours with stirring. The reaction mixture was cooled to room temperature and concentrated to remove most of the toluene. It was then extracted with ethyl acetate, washed with water and brine, and dried over $Na_2SO_4$, then filtered and solvent removed under reduced pressure to give a crude residue. The crude residue was purified by flash chromatography on silica gel (5% MeOH/DCM) to afford the desired product. ESI-MS m/z: 741 [M+H]$^+$.

Step G: Preparation of 2-amino-4-((5aS)-3-chloro-1-fluoro-12-(((2R,7aS)-2-fluorohexahydro-1H-pyrrolizin-7a-yl)methoxy)-5,5a,6,7,8,9-hexahydropyrido[2',1':3,4][1,4]oxazepino[5,6,7-de]quinazolin-2-yl)-7-fluorobenzo[b]thiophene-3-carbonitrile (168). To a solution of 3-7 (35 mg, 0.047 mmol) in DCM (3 mL) was added TFA (1 mL) slowly at 0° C. The resulting mixture was stirred for 1 hour at room temperature. The reaction mixture was concentrated to remove TFA and diluted with DCM. It was treated with NaHCO$_3$ (aq), extracted with DCM, washed with brine, and dried over $Na_2SO_4$, then filtered and solvent removed under reduced pressure to give a crude residue. The crude residue was purified by flash chromatography on silica gel (10% MeOH/DCM) to afford the title compound. ESI-MS m/z: 641 [M+H]$^+$. $^1$H NMR (400 MHz, DMSO-d$_6$) δ: 8.11 (s, 2 H), 7.25-7.21 (m, 1 H), 7.17-7.13 (m, 1 H), 5.53-5.40 (m, 1 H), 5.08-5.04 (m, 1 H), 4.56-4.33 (m, 3 H), 4.01-3.95 (m, 1 H), 3.58-3.49 (m, 1 H), 3.17-3.11 (m, 1 H), 3.08-3.01 (m, 1 H), 2.41-2.31 (m, 2 H), 2.22-2.17 (m, 1 H), 2.08-1.78 (m, 9 H), 1.70-1.46 (m, 3 H).

Example 16: Synthesis of 2-amino-4-(9-chloro-7-fluoro-5-(((2R,7aS)-2-fluorotetrahydro-1H-pyrrolizin-7a(5H)-yl)methoxy)-2-(methoxymethyl)-1,2,11,11a-tetrahydroazeto[2',1':3,4][1,4]-oxazepino[5,6,7-de]quinazolin-8-yl)-7-fluorobenzo[b]thiophene-3-carbonitrile (173)

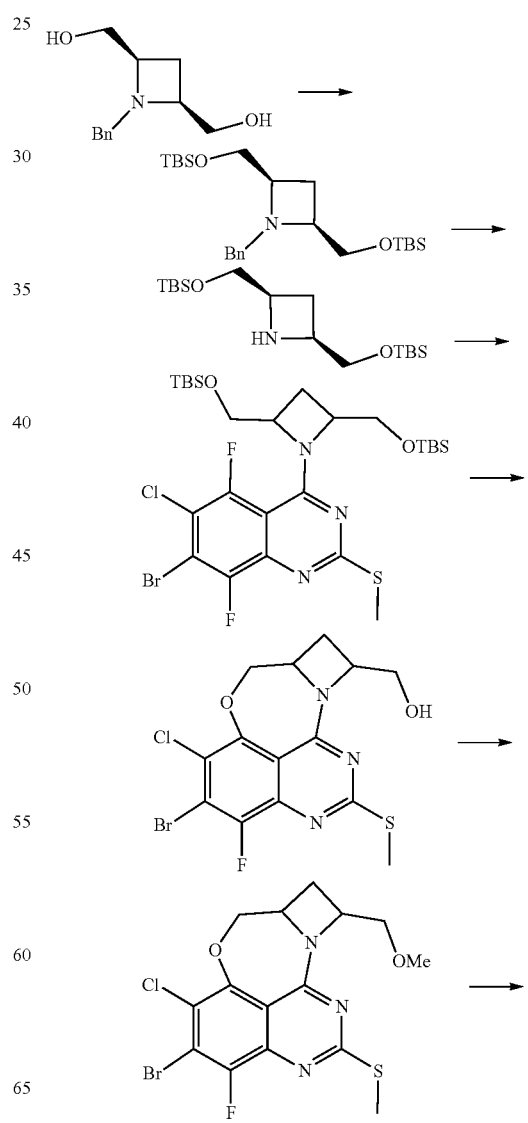

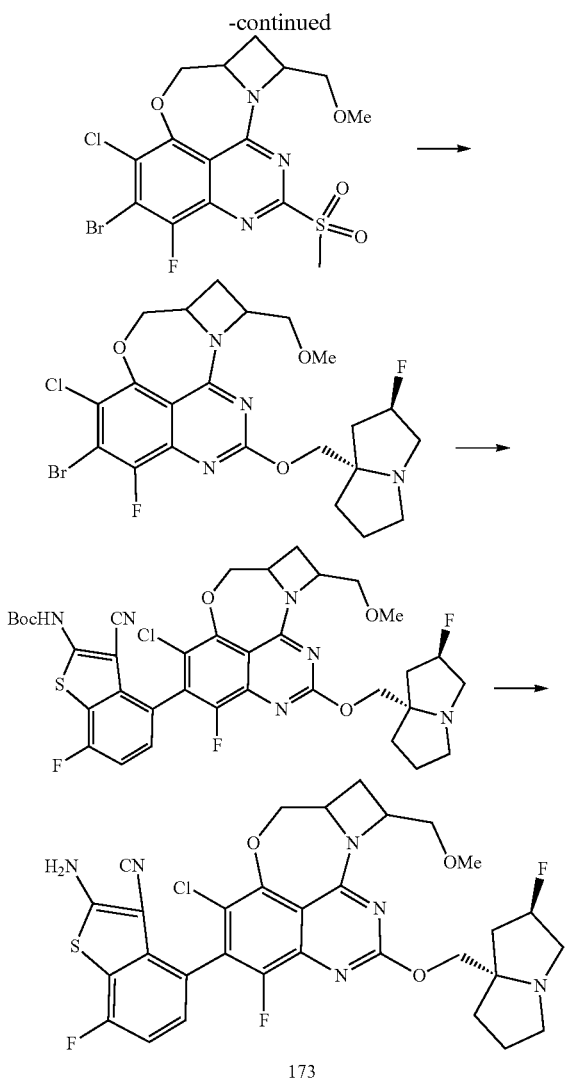

Step 1: (2R,4S)-1-benzyl-2,4-bis(((tert-butyldimethylsilyl)oxy)methyl)azetidine

To a solution of ((2R,4S)-1-benzylazetidine-2,4-diyl)dimethanol (500 mg, 2.42 mmol) and imidazole (411 mg, 6.04 mmol) in dry dichloromethane (25 mL) was added TBSCl (912 mg, 6.04 mmol) at 0° C. The resulting mixture was stirred for 3 hours at room temperature. The reaction mixture was then extracted with dichloromethane (15 mL×2), washed with NH$_4$Cl (aq) and brine, dried over Na$_2$SO$_4$. The resulting product was filtered and solvent was removed under reduced pressure to give a crude. The crude was purified by flash chromatography on silica gel (petroleum ether:ethyl acetate=10:1) to give the desired product as an oil. ESI-MS m/z: 436 [M+H]$^+$.

Step 2: (2R,4S)-2,4-bis(((tert-butyldimethylsilyl)oxy)methyl)azetidine

A solution of (2R,4S)-1-benzyl-2,4-bis(((tert-butyldimethylsilyl)oxy)methyl)azetidine (650 mg, 1.49 mmol), Pd/C (130 mg, 0.2 eq) and Pd(OH)$_2$ (130 mg, 0.2 eq) in dry MeOH (25 mL) was stirred for 16 hours at room temperature under hydrogen atmosphere. The resulting product was diluted with dichloromethane (15 mL), filtered and solvent was removed under reduced pressure to give the desired product as an oil which was used directly in the next step without further purification. ESI-MS m/z: 346 [M+H]$^+$.

Step 3: 4-(2,4-bis(((tert-butyldimethylsilyl)oxy)methyl)azetidin-1-yl)-7-bromo-6-chloro-5,8-difluoro-2-(methylthio)quinazoline To a solution of 7-bromo-4,6-dichloro-5,8-difluoro-2-(methylthio)quinazoline (283 mg, 0.79 mmol) and Et$_3$N (471 mg, 4.65 mmol) in dry dichloromethane (25 mL) was added (2R,4S)-2,4-bis(((tert-butyldimethylsilyl)oxy)methyl)azetidine (320 mg, 0.93 mmol) at 0° C. The resulting mixture was stirred for 5 hours at RT. The reaction mixture was extracted with dichloromethane (20 mL×2), washed with NH$_4$Cl (aq) and brine, dried over Na$_2$SO$_4$. The resulting product was filtered and solvent was removed under reduced pressure to give a crude. The crude was purified by flash chromatography on silica gel (petroleum ether:ethyl acetate=5:1) to give the desired product as a solid. ESI-MS m/z: 668 [M+H]$^+$.

Step 4: (8-bromo-9-chloro-7-fluoro-5-(methylthio)-1,2,11,11a-tetrahydroazeto[2',1':3,4]-[1,4]oxazepino[5,6,7-de]quinazolin-2-yl)methanol To a solution of 4-(2,4-bis(((tert-butyldimethylsilyl)oxy)methyl)azetidin-1-yl)-7-bromo-6-chloro-5,8-difluoro-2-(methylthio)quinazoline (383 mg, 0.57 mmol) in dry THF (3 mL) was added TBAF (1.0 M, 6.0 mL). The resulting mixture was stirred for 16 hours at room temperature under argon and extracted with ethyl acetate (20 mL×2). The extracts were combined, washed with NH$_4$Cl (aq) and brine, dried over Na$_2$SO$_4$. The resulting product was filtered and solvent was removed under reduced pressure to give a crude. The crude was purified by flash chromatography on silica gel (petroleum ether:ethyl acetate=3:1) to give the desired product as a solid. ESI-MS m/z: 420 [M+H]$^+$;

Step 5: 8-bromo-9-chloro-7-fluoro-2-(methoxymethyl)-5-(methylthio)-1,2,11,11a-tetrahydroazeto[2',1':3,4][1,4]oxazepino[5,6,7-de]quinazoline To a solution of (8-bromo-9-chloro-7-fluoro-5-(methylthio)-1,2,11,11a-tetrahydroazeto[2',1':3,4]-[1,4]oxazepino[5,6,7-de]quinazolin-2-yl)methanol (180 mg, 0.43 mmol) in dry THF (15 mL), was added NaH (60%, 35 mg, 0.86 mmol) at 0° C. The resulting mixture was stirred for 0.5 hours at room temperature and iodomethane (92 mg, 0.65 mmol) was added. The resulting mixture was stirred for 1.5 hours at room temperature. The reaction mixture was quenched with NH$_4$Cl (aq) and extracted with ethyl acetate (15 mL×2). The extracts were combined, washed with water and brine, dried over Na$_2$SO$_4$. The resulting product was filtered and solvent was removed under reduced pressure to give a crude. The crude was purified by flash chromatography on silica gel (petroleum ether:ethyl acetate=3:1) to give the desired product as a solid. ESI-MS m/z: 433 [M+H]$^+$;

Step 6: 8-bromo-9-chloro-7-fluoro-2-(methoxymethyl)-5-(methylsulfonyl)-1,2,11,11a-tetrahydroazeto[2',1':3,4][1,4]oxazepino[5,6,7-de]quinazoline To a solution of 8-bromo-9-chloro-7-fluoro-2-(methoxymethyl)-5-(methylthio)-1,2,11,11a-tetrahydroazeto[2',1':3,4][1,4]oxazepino[5,6,7-de]quinazo (90 mg, 0.21 mmol) in dry DCM (15 mL) was added m-CPBA (90 mg, 0.52 mmol) at 0° C. The resulting mixture was stirred for 1.5 hours at room temperature. The reaction mixture was quenched with Na₂SO₃ (aq) and extracted with dichloromethane (15 mL×2). The extracts were combined, washed with water and brine, dried over Na₂SO₄. The resulting product was filtered and solvent was removed under reduced pressure to give a crude. The crude was purified by flash chromatography on silica gel (DCM:MeOH=30:1) to give the desired product as a solid. ESI-MS m/z: 466 [M+H]⁺;

Step 7: 8-bromo-9-chloro-7-fluoro-5-(((2R,7aS)-2-fluorotetrahydro-1H-pyrrolizin-7a(5H)-yl)methoxy)-2-(methoxymethyl)-1,2,11,11a-tetrahydroazeto[2',1':3,4][1,4]oxazepino[5,6,7-de]quinazoline To a solution of ((2R,7aS)-2-fluorohexahydro-1H-pyrrolizin-7a-yl)methanol (77 mg, 1.11 mmol) in THF (20 mL) was added NaH (60%, 20 mg, 0.48 mmol) at 0° C. and the resulting mixture was stirred for 30 minutes at 0° C. under argon. 8-bromo-9-chloro-7-fluoro-2-(methoxymethyl)-5-(methylsulfonyl)-1,2,11,11a-tetrahydroazeto[2',1':3,4][1,4]oxazepino[5,6,7-de]quinazoline (45 mg, 0.10 mmol) was added slowly at 0° C. and the resulting mixture was stirred for 1 hour at room temperature. The resulting product was filtered and solvent was removed under reduced pressure to give a crude. The crude was purified by flash chromatography on silica gel (DCM:MeOH=20:1) to give the desired product as a solid. ESI-MS m/z: 545 [M+H]⁺;

Step 8: tert-butyl (4-(9-chloro-7-fluoro-5-(((2R,7aS)-2-fluorotetrahydro-1H-pyrrolizin-7a(5H)-yl)methoxy)-2-(methoxymethyl)-1,2,11,11a-tetrahydroazeto[2',1':3,4][1,4]-oxazepino[5,6,7-de]quinazolin-8-yl)-3-cyano-7-fluorobenzo[b]thiophen-2-yl)carbamate To a mixture of 8-bromo-9-chloro-7-fluoro-5-(((2R,7aS)-2-fluorotetrahydro-1H-pyrrolizin-7a(5H)-yl)methoxy)-2-(methoxymethyl)-1,2,11,11a-tetrahydroazeto[2',1':3,4][1,4]oxazepino-[5,6,7-de]quinazoline (30 mg, 0.055 mmol) in dioxane (15 mL) was added tert-butyl (3-cyano-4-(5,5-dimethyl-1,3,2-dioxaborinan-2-yl)-7-fluorobenzo[b]thiophen-2-yl)carbamate (67 mg, 0.17 mmol), K₂CO₃ (46 mg, 0.33 mmol) and Pd(dppf)Cl₂ (dichloromethane) (9 mg 0.01 mmol). The resulting mixture was heated at 110° C. under argon and stirred for 16 hours. The resulting product was cooled to room temperature and ethyl acetate (15 mL) was added. The organics were washed with brine, dried over Na₂SO₄. The resulting product was filtered and solvent was removed under reduced pressure to give a crude. The crude was purified by flash chromatography on silica gel (dichloromethane:methyl alcohol=20:1) to afford the desired product as a solid. ESI-MS m/z: 757 [M+H]⁺;

Step 9: 2-amino-4-(9-chloro-7-fluoro-5-(((2R,7aS)-2-fluorotetrahydro-1H-pyrrolizin-7a(5H)-yl)methoxy)-2-(methoxymethyl)-1,2,11,11a-tetrahydroazeto[2',1':3,4][1,4]oxazepino[5,6,7-de]quinazolin-8-yl)-7-fluorobenzo[b]thiophene-3-carbonitrile To a solution of tert-butyl (4-(9-chloro-7-fluoro-5-(((2R,7aS)-2-fluorotetrahydro-1H-pyrrolizin-7a(5H)-yl)methoxy)-2-(methoxymethyl)-1,2,11,11a-tetrahydroazeto[2',1':3,4][1,4]-oxazepino-[5,6,7-de]quinazolin-8-yl)-3-cyano-7-fluorobenzo[b]thiophen-2-yl)carbamate (20 mg, 0.03 mmol) in dichloromethane (3 mL) was added TFA (1.5 mL) slowly at 0° C. The resulting mixture was stirred for 1 hour at room temperature. The reaction mixture was concentrated to remove TFA and the residue was partitioned between saturated NaHCO₃ (5 mL) and dichloromethane (5 mL). The aqueous layer was extracted with dichloromethane (10 mL×2). The organics were combined, washed with brine, and dried over Na₂SO₄. The resulting product was filtered and solvent was removed under reduced pressure to give a crude. The crude was purified by TLC (DCM: MeOH=15:1) to afford the desired product as a solid. ESI-MS m/z: 657 [M+H]⁺; ¹HNMR (400 MHz, MeOD) : 7.19 (m, 1H), 7.05 (m, 1H), 5.45 (m, 1H), 4.61 (m, 6H), 3.79 (m, 2H), 2.29 (m, 6H), 1.60 (m, 4H), 0.97 (m, 4H).

Example 17: Synthesis of 2-amino-((12aS)-10-chloro-2,2,8-trifluoro-6-(((2R,7aS)-2-fluorotetrahydro-1H-pyrrolizin-7a(5H)-yl)methoxy)-2,3,12,12a-tetrahydro-1H-pyrrolo[2',1':3,4][1,4]oxazepino[5,6,7-de]quinazolin-9-yl)-7-fluorobenzo[b]thiophene-3-carbonitrile (181)

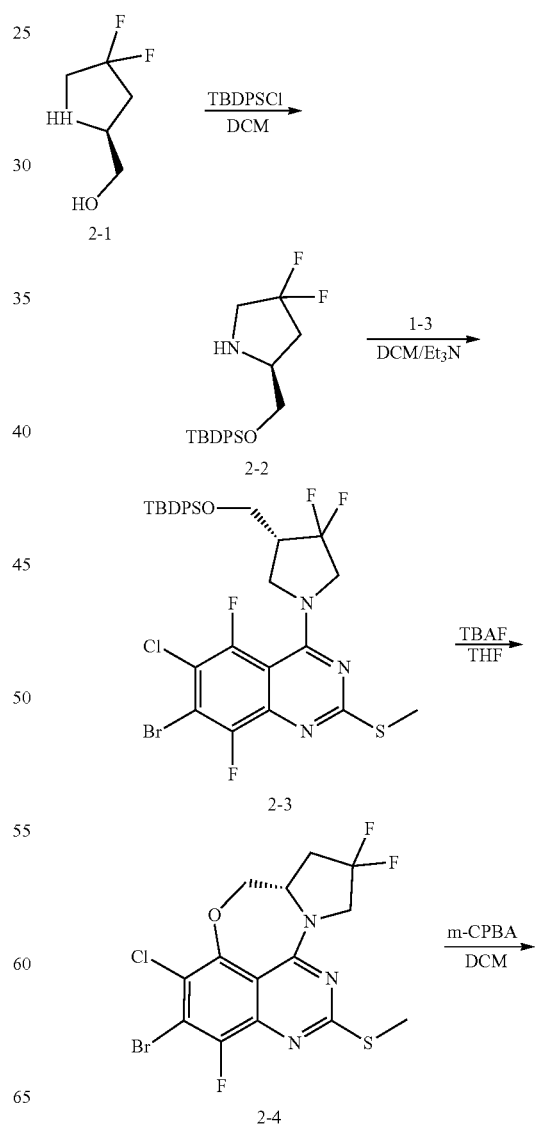

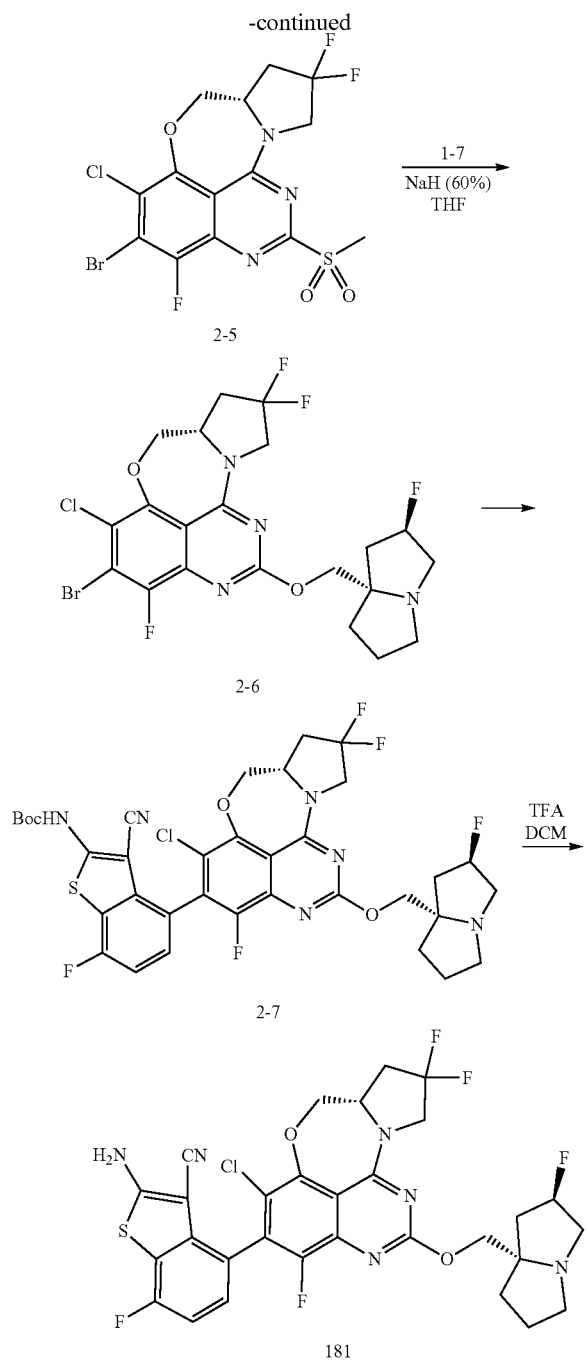

Step A: Preparation of (S)-2-(((tert-butyldimethylsilyl)oxy)methyl)-4,4-difluoropyrrolidine (2-2). To a solution of (S)-(4,4-difluoropyrrolidin-2-yl)methanol (150 mg, 1.10 mmol) and imidazole (149 mg, 2.19 mmol) in dry DCM (15 mL) was added TBSCl (197 mg, 1.32 mmol) at 0° C. The resulting mixture was stirred for 3 hours at room temperature. The reaction mixture was extracted with DCM (15 mL×2). The organics were combined, washed with NH₄Cl (aq) and brine, and dried over Na₂SO₄, then filtered and solvent removed under reduced pressure to give a crude residue. The crude residue was purified by flash chromatography on silica gel (dichloromethane:methyl alcohol=95:5) to give the desired product as an oil. ESI-MS m/z: 252[M+H]⁺.

Step B: Preparation of (S)-7-bromo-4-(2-(((tert-butyldimethylsilyl)oxy)methyl)-3,3-difluoropyrrolidin-1-yl)-6-chloro-5,8-difluoro-2-(methylthio)quinazoline (2-3). To a solution of 1-3 (208 mg, 0.58 mmol) and Et₃N (586 mg, 5.80 mmol) in dry DCM (20 mL) was added (S)-2-(((tert-butyldiphenylsilyl)oxy)methyl)-4,4-difluoropyrrolidine (240 mg, 0.64 mmol) at 0° C. The resulting mixture was stirred for 16 hours at room temperature. The reaction mixture was extracted with DCM (20 mL×2). The organics were combined, washed with NH₄Cl (aq) and brine, and dried over Na₂SO₄, then filtered and solvent removed under reduced pressure to give a crude residue. The crude residue was purified by flash chromatography on silica gel (petroleum ether:ethyl acetate=5:1) to give 2-3 as a solid.

Step C: Preparation of (S)-9-bromo-10-chloro-2,2,8-trifluoro-6-(methylthio)-2,3,12,12a-tetrahydro-1H-pyrrolo[2',1':3,4][1,4]oxazepino[5,6,7-de]quinazoline (2-4). To a solution of 2-3 (216 mg, 0.38 mmol) in dry THF (2 mL) was added TBAF (1 M, 6.0 mL). The resulting mixture was stirred for 16 hours at room temperature under argon. The reaction mixture was extracted with ethyl acetate (20 mL×2), washed with NH₄Cl (aq) and brine, and dried over Na₂SO₄, then filtered and solvent removed under reduced pressure to give a crude. The crude was purified by flash chromatography on silica gel (petroleum ether:ethyl acetate=3:1) to give the desired product as a solid. ESI-MS m/z: 440 [M+H]⁺.

Step D: Preparation of (S)-9-bromo-10-chloro-2,2,8-trifluoro-6-(methylsulfonyl)-2,3,12,12a-tetrahydro-1H-pyrrolo[2',1':3,4][1,4]oxazepino[5,6,7-de]quinazoline (2-5). To a solution of 2-4 (160 mg, 0.37 mmol) in dry DCM (15 mL) was added m-CPBA (157 mg, 0.91 mmol) at 0° C. The resulting mixture was stirred for 1.5 hours at room temperature. The reaction mixture was quenched with Na₂SO₃ (aq) and extracted with DCM (15 mL×2). The organics were combined, washed with water and brine, and dried over Na₂SO₄, then filtered and solvent removed under reduced pressure to give a crude residue. The crude residue was purified by flash chromatography on silica gel (DCM:MeOH=30:1) to give the desired product as a solid. ESI-MS m/z: 472 [M+H]⁺.

Step E: Preparation of (S)-9-bromo-10-chloro-2,2,8-trifluoro-6-((2R,7aS)-2-fluorotetrahydro-1H-pyrrolizin-7a(5H)-yl)methoxy)-2,3,12,12a-tetrahydro-1H-pyrrolo[2',1':3,4][1,4]oxazepino[5,6,7-de]quinazoline (2-6). To a solution of 1-7 (253 mg, 1.59 mmol) in THF (20 ml) was added NaH (60%, 64 mg, 1.59 mmol) at 0° C. and the resulting mixture was stirred for 30 min at 0° C. under argon. Then, 2-5 (150 mg, 0.32 mmol) was added slowly at 0° C. and the resulting mixture was stirred for an additional 1 hour at room temperature. The product was extracted with ethyl acetate. The organics were combined, washed with brine, and dried over Na₂SO₄, then filtered and solvent removed under reduced pressure to give a crude residue. The crude residue was purified by flash chromatography on silica gel (DCM:MeOH=20:1) to give the desired product as a solid. ESI-MS m/z: 551 [M+H]⁺.

Step F: Preparation of tert-butyl (4-((12aS)-10-chloro-2,2,8-trifluoro-6-((2R,7aS)-2-fluorotetrahydro-1H-pyrrolizin-7a(5H)-yl)methoxy)-2,3,12,12a-tetrahydro-1H-pyrrolo[2',1':3,4][1,4]oxazepino[5,6,7-de]quinazolin-9-yl)-3-cyano-7-fluorobenzo[b]thiophen-2-yl)carbamate (2-7). To a solution of 2-6 (120 mg, 0.22 mmol) in dioxane (20 mL) was added tert-butyl (3-cyano-4-(5,5-dimethyl-1,3,2-dioxaborinan-2-yl)-7-fluorobenzo[b]thiophen-2-yl)carbamate (177 mg, 0.44 mmol), K₂CO₃ (152 mg, 1.10 mmol) and Pd(dppf)Cl₂·DCM (28 mg, 0.04 mmol). The resulting mixture was heated at 110° C. under argon and stirred for 16 hours, then cooled to room temperature and ethyl acetate (15 mL) added. The organics were washed with brine and dried over Na₂SO₄, then filtered and solvent removed under reduced pressure to give a crude residue. The crude residue was purified by flash chromatography on silica gel (dichloromethane:methyl alcohol=20:1) to afford the desired product as a solid. ESI-MS m/z: 763 [M+H]⁺.

Step G: Preparation of 2-amino-4-((12a5)-10-chloro-2,2,8-trifluoro-6-((2R,7aS)-2-fluorotetrahydro-1H-pyrrolizin-7a(5H)-yl)methoxy)-2,3,12,12a-tetrahydro-1H-pyrrolo[2',1':3,4][1,4]oxazepino[5,6,7-de]quinazolin-9-yl)-7-fluorobenzo[b]thiophene-3-carbonitrile (181). To a solution of 2-7 (100 mg, 0.14 mmol) in DCM (10 mL) was added TFA (4 ml) slowly at 0° C. The resulting mixture was stirred for 1 hour at room temperature. The reaction mixture was concentrated to remove TFA, then the resultant residue was partitioned between saturated NaHCO₃ (5 mL) and dichloromethane (5 mL). The aqueous layer was extracted with dichloromethane (15 mL×2). The organics were washed with brine and dried over Na₂SO₄, then filtered and solvent removed under reduced pressure to give a crude residue. The crude residue was purified by prep-TLC (DCM:MeOH=15:1) to afford the desired product as a solid. ESI-MS m/z: 663 [M+H]⁺. ¹HNMR (400 MHz, MeOD): 7.19 (m, 1 H), 7.04 (m, 1 H), 5.72-5.49 (m, 1 H), 4.569-4.63 (m, 4 H), 3.92 (m, 4 H), 2.54 (m, 1 H), 2.23-2.32 (2 H, m), 2.02-2.16 (m, 2 H), 1.30 (m, 6 H).

Example 18: Synthesis of 2-amino-4-(6-chloro-12-(2,2-difluoroethyl)-4-fluoro-2-(((2R,7aS)-2-fluorotetrahydro-1H-pyrrolizin-7a(5H)-yl)methoxy)-8a,9,11a,12-tetrahydro-8H,11H-furo[3',4':6,7][1,5]oxazocino[4,3,2-de]quinazolin-5-yl)-7-fluorobenzo[b]thiophene-3-carbonitrile (188)

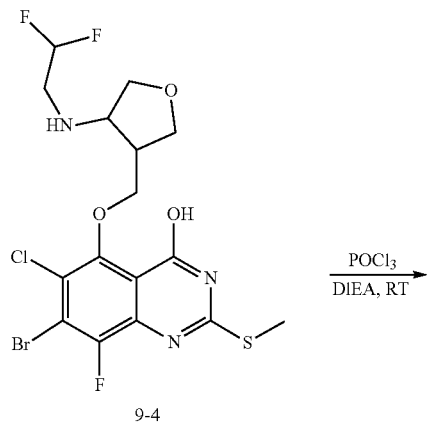
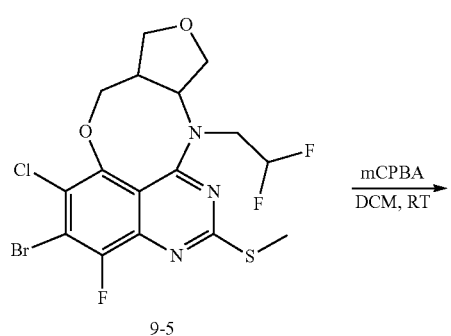
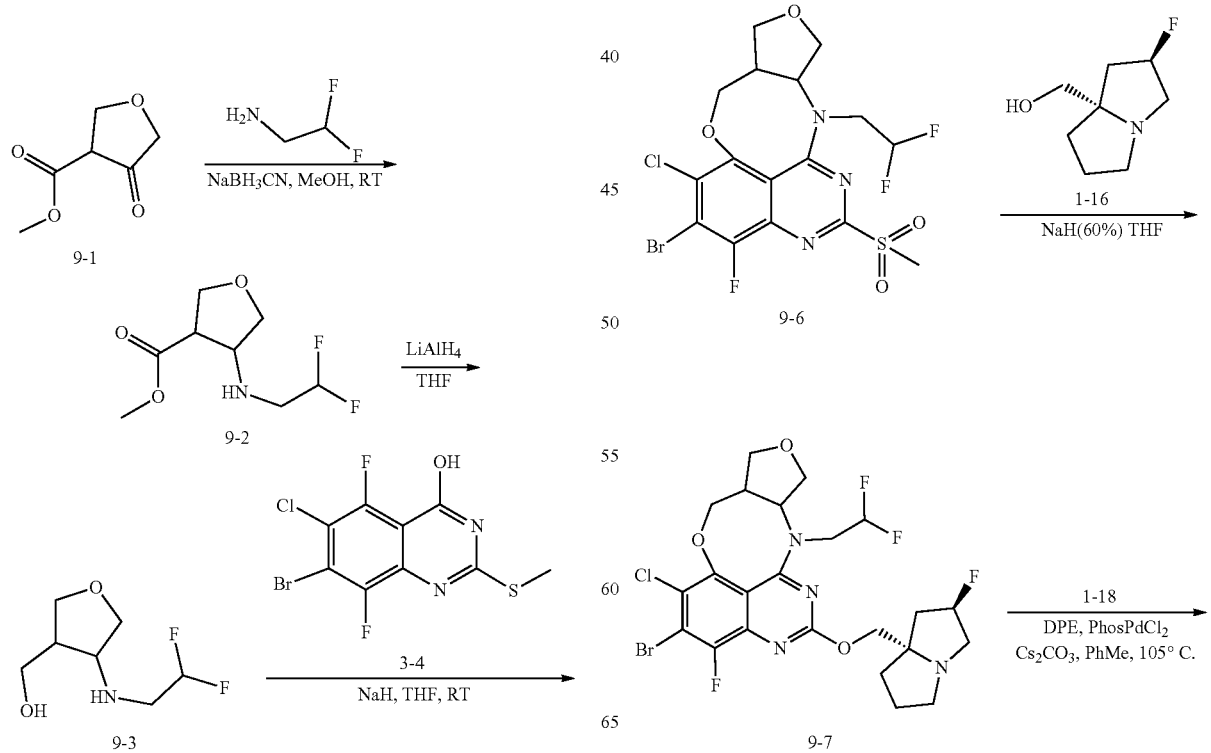

-continued

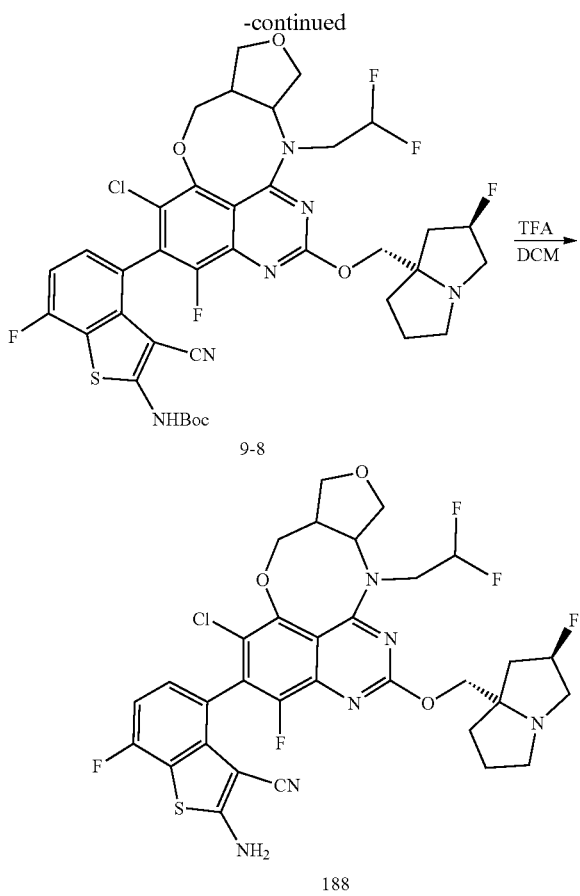

To a solution of methyl 4-oxotetrahydrofuran-3-carboxylate (9-1) (0.5 g, 3.47 mmol) in MeOH (20 mL), 2,2-difluoroethan-1-amine (0.42 g, 5.22 mmol) was added AcOH (0.1 mL) and NaBH$_3$CN (374 mg, 5.22 mmol) and the resulting mixture was stirred at RT overnight. The mixture was concentrated in vacuo. then partitioned between DCM and water. The combined organic layer was concentrated in vacuo. The residue was purified on a silica gel column to afford compound 9-2 (0.6 g). ESI-MS m/z: 209.9 [M+H]$^+$.

To a stirred solution of compound 9-2 (0.6 g, 3.1 mmol) in THF (20 mL) was added LHA (0.3 g, 0.69 mmol) at −30° C. and the resulting mixture was stirred at RT under Ar for 1.5 h. The mixture was partitioned between water and EA. The organic layer was washed with brine, dried over Na$_2$SO$_4$, filtered, and concentrated in vacuo. The residue was purified by flash column chromatography on silica gel to afford product compound 9-3 (0.23 g). ESI-MS m/z: 181.1 [M+H]$^+$.

To a stirred solution of 7-bromo-6-chloro-5,8-difluoro-2-(methylthio)quinazolin-4-ol (3-4) (230 mg, 0.61 mmol) in THF (10 mL) was added compound 9-3 and NaH (60%, 70 mg, 0.29 mmol) and the resulting mixture was stirred at RT for 2 h. The mixture was partitioned between water and ethyl acetate. The organic layer was washed with brine, dried over Na$_2$SO$_4$, filtered, and concentrated in vacuo. The residue was purified by flash column chromatography on silica gel to afford compound 9-4 (125 mg). ESI-MS m/z: 502 [M+H]$^+$.

To a stirred solution of compound 9-4 (125 mg, 0.25 mmol) in dioxane (4 mL), POCl$_3$ (114.3 mg, 0.73 mmol) was added, followed by DMA (253 mg, 2.7 mmol) dropwise. The resulting mixture was stirred at RT for 1 h. The mixture was partitioned between water and dichloromethane. The organic layer was washed with brine, dried over Na$_2$SO$_4$, filtered, and concentrated in vacuo. The residue was purified by flash column chromatography on silica gel to afford 9-5 (100 mg). ESI-MS m/z: 484.0 [M+H]$^+$.

To a stirred solution of compound 9-5 (100 mg, 0.25 mmol) in DCM (15 mL), m-CPBA (103 mg, 0.54 mmol) was added, and the resulting mixture was stirred at RT for 1 h. The mixture was partitioned between water and dichloromethane. The organic layer was washed with brine, dried over Na$_2$SO$_4$, filtered, and concentrated in vacuo. The residue was purified by flash column chromatography on silica gel to afford compound 9-6 (140 mg).

To a stirred solution of ((2R,7aS)-2-fluorohexahydro-1H-pyrrolizin-7a-yl)methanol (1-16) (288 mg, 1.78 mmol) in THF (10 mL), 60% NaH (58 mg, 1.78 mmol) was added at −20° C. and stirred for 60 min under Ar. Compound 9-6 (140 mg) was added and the resulting mixture was stirred at RT for 1 h under Ar. The mixture was poured into ice water and partitioned between water and ethyl acetate. The organic layer was washed with brine, dried over Na$_2$SO$_4$, filtered, and concentrated in vacuo. The residue was purified by flash column chromatography on silica gel to afford compound 9-7 (60 mg). ESI-MS m/z: 594.1 [M+H]$^+$.

To a stirred solution of compound 9-7 (60 mg, 0.10 mmol) in anhydrous toluene (5 mL) was added compound 1-18 (122 mg, 0.31 mmol), PdCl$_2$ (dpephos) (15 mg, 0.02 mmol) and Cs$_2$CO$_3$ (98 mg, 0.31 mmol) and the resulting mixture was stirred at 105° C. under nitrogen for 18 h. The mixture was partitioned between water and ethyl acetate. The organic layer was washed with brine, dried over Na$_2$SO$_4$, filtered, and concentrated in vacuo. The residue was purified by flash column chromatography on silica gel to afford compound 9-8 (60 mg). ESI-MS m/z: 806.2 [M+H]$^+$.

To a solution of compound 9-8 (60 mg) in DCM (6 mL) at RT, TFA (2 mL) was added and the resulting mixture was stirred at RT for 1.5 h. The mixture was concentrated in vacuo to remove the solvent. The residue was purified by flash column chromatography on silica gel to afford compound 188 (20 mg). ESI-MS m/z: 706.2 [M+H]$^+$; $^1$HNMR (400 MHz, CD$_3$OD): δ 7.18 (m, 1H), 7.11 (m, 1H), 6.94 (m, 2H), 6.41 (t, 1H), 5.36 (d, 1H), 4.43 (m, 3H), 4.20 (m, 1H), 4.05 (m, 2H), 3.88 (m, 1H), 3.57 (m, 4H), 2.89 (m,1H), 2.42 (m, 3H), 2.11 (m, 5H), 1.96 (m, 2H).

Example 19: Synthesis of 2-amino-4-(3-chloro-1-fluoro-13-(((2R,7aS)-2-fluorotetrahydro-1H-pyrrolizin-7a(5H)-yl)methoxy)-5a,6,7,8,9,10-hexahydro-5H-azepino[2',1':3,4][1,4]oxazepino[5,6,7-de]quinazolin-2-yl)-7-fluorobenzo[b]thiophene-3-carbonitrile (193)

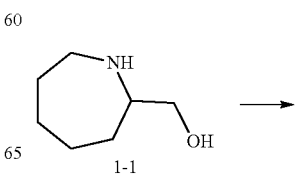

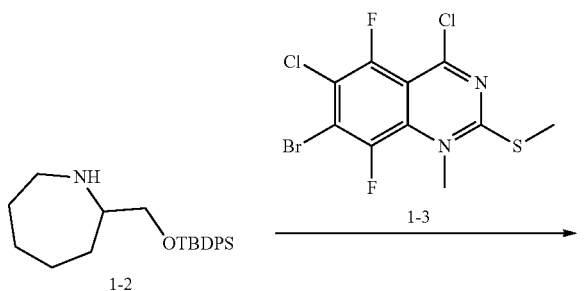

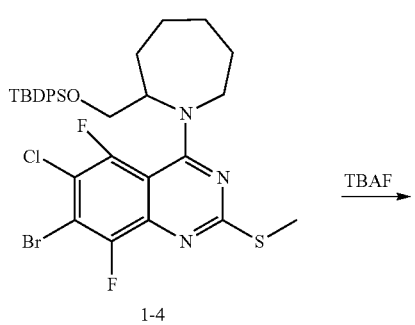

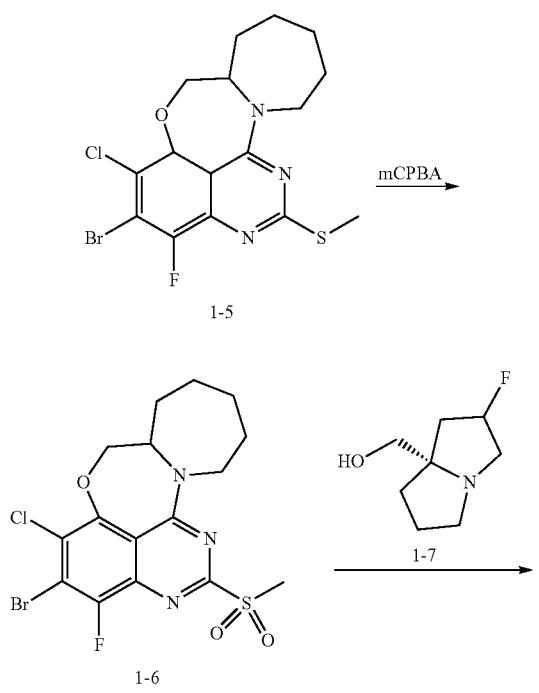

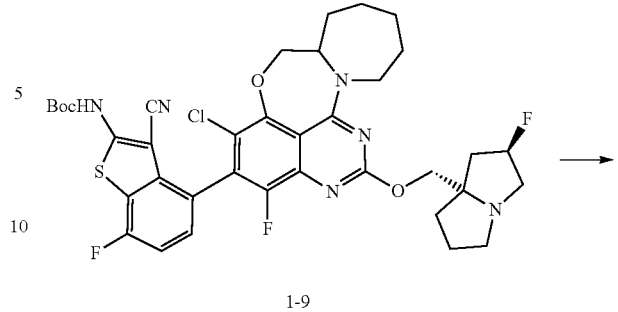

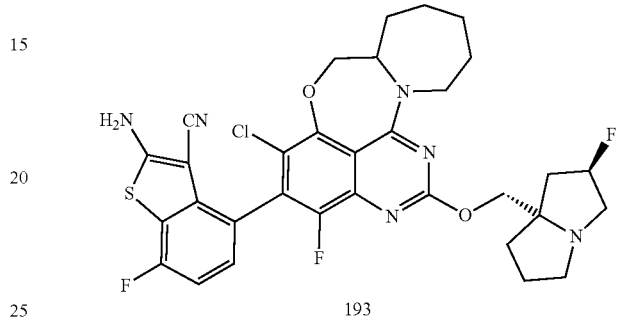

Step A: Preparation of 2-(((tert-butyldiphenylsilyl)oxy)methyl)azepane (1-2). To a solution of azepan-2-ylmethanol (400 mg, 3.10 mmol) in DCM (30 mL) was added imidazole (231 mg, 3.25 mmol) and DMAP (30 mg) slowly at 0° C., followed by addition of TBDPSCl at the same temperature. The resulting mixture was stirred for 3 hours at room temperature. The reaction mixture was extracted with DCM. The combined organics were washed with NaHCO$_3$ (aq) and brine, then dried over Na$_2$SO$_4$, filtered and concentrated to give a crude residue. The residue was purified by flash chromatography on silica gel (2% MeOH/DCM) to afford the desired product.

Step B: Preparation of 7-bromo-4-(2-(((tert-butyldiphenylsilyl)oxy)methyl)azepan-1-yl)-6-chloro-5,8-difluoro-2-(methylthio)quinazoline (1-4). To a solution of 7-bromo-4,6-dichloro-5,8-difluoro-2-(methylthio)quinazoline (1-3) (210 mg, 0.58 mmol) and 1-2 (270 mg, 0.73 mmol) in DCM (30 mL) was added Et$_3$N (300 mg, 2.97 mmol) at 0° C. The resulting mixture was gradually warmed to room temperature and stirred for 1 hour. The reaction mixture was extracted with DCM, washed with water and brine, and dried over Na$_2$SO$_4$, then filtered and concentrated to give a crude residue. The crude residue was purified by flash chromatography on silica gel (10% ethyl acetate/petroleum) to afford the desired product.

Step C: Preparation of 2-bromo-3-chloro-1-fluoro-13-(methylthio)-5a,6,7,8,9,10-hexahydro-5H-azepino[2',1'3,4][1,4]oxazepino[5,6,7-de]quinazoline (1-5). To a solution of 1-4 (380 mg, 0.55 mmol) in THF (1 mL) was added TBAF (5 mL, 1M in THF). The resulting mixture was stirred under Ar at room temperature for 16 hours. The reaction mixture was extracted with ethyl acetate, washed with water and brine, and dried over Na$_2$SO$_4$, then filtered and concentrated to give a crude residue. The crude residue was purified by flash chromatography on silica gel (10% ethyl acetate/petroleum) to afford the 1-5. ESI-MS m/z: 433 [M+H]$^+$.

Step D: Preparation of 2-bromo-3-chloro-1-fluoro-13-(methylsulfinyl)-5a,6,7,8,9,10-hexahydro-5H-azepino[2',1':3,4][1,4]oxazepino[5,6,7-de]quinazoline (1-6). To a solution of 1-5 (230 mg, 0.53 mmol) in DCM (20 mL) was added m-CPBA (107 mg, 0.62 mmol) slowly at 0° C. The resulting mixture was stirred for 1 hour at room temperature. The reaction mixture was quenched with Na$_2$SO$_3$ (aq) and extracted with DCM. The organics were combined, washed with brine, and dried over Na$_2$SO$_4$, then filtered and solvent removed under reduced pressure to give a crude residue. The crude residue was purified by flash chromatography on silica gel (5% MeOH/DCM) to afford the 1-6. ESI-MS m/z: 465[M+H]$^+$.

Step E: Preparation of 2-bromo-3-chloro-1-fluoro-13-((2R,7aS)-2-fluorotetrahydro-1H-pyrrolizin-7a(5H)-yl)methoxy)-5a,6,7,8,9,10-hexahydro-5H-azepino[2',1':3,4][1,4]oxazepino[5,6,7-de]quinazoline (1-8). To a suspension of NaH (67 mg, 1.67 mmol) in THF (20 mL) was added ((2R,7aS)-2-fluorohexahydro-1H-pyrrolizin-7a-yl)methanol (1-7) (400 mg, 2.51 mmol) at 0° C. under Ar. The mixture was stirred for 30 min at room temperature, then 1-6 (180 mg, 0.27 mmol) was added slowly at 0° C. After completion of the addition, the resulting mixture was stirred for 1 hour at room temperature. The reaction mixture was quenched with water and extracted with ethyl acetate, washed with brine, and dried over Na$_2$SO$_4$, then filtered and solvent removed under reduced pressure to give a crude residue. The crude residue was purified by flash chromatography on silica gel (5% MeOH/DCM) to afford 1-8. ESI-MS m/z: 545 [M+H]$^+$.

Step F: Preparation of tert-butyl (4-(3-chloro-1-fluoro-13-(((2R,7aS)-2-fluorotetrahydro-1H-pyrrolizin-7a(5H)-yl)methoxy)-5a,6,7,8,9,10-hexahydro-5H-azepino[2',1':3,4][1,4]oxazepino[5,6,7-de]quinazolin-2-yl)-3-cyano-7-fluorobenzo[b]thiophen-2-yl)carbamate (1-9). To a solution of 1-8 (140 mg, 0.257 mmol) and tert-butyl (3-cyano-4-(5,5-dimethyl-1,3,2-dioxaborinan-2-yl)-7-fluorobenzo[b]thiophen-2-yl)carbamate (260 mg, 0.65 mmol) in toluene (10 mL) were added Cs$_2$CO$_3$ (338 mg, 1.09 mmol), DPEphos-PdCl$_2$ (60 mg, 0.09 mmol), then the resulting mixture was degassed with Ar for three times. The reaction mixture was heated to 100° C. for 16 hours, then cooled to room temperature and most of the solvent removed under reduced pressure. The product was extracted in ethyl acetate. The combined organics were washed with brine and dried over Na$_2$SO$_4$, then filtered and solvent removed under reduced pressure to give a crude residue. The crude residue was purified by flash chromatography on silica gel (5% MeOH/DCM) to afford 1-9. ESI-MS m/z: 755[M+H]$^+$.

Step G: Preparation of 2-amino-4-(3-chloro-1-fluoro-13-(((2R,7aS)-2-fluorotetrahydro-1H-pyrrolizin-7a(5H)-yl)methoxy)-5a,6,7,8,9,10-hexahydro-5H-azepino[2',1':3,4][1,4]oxazepino[5,6,7-de]quinazolin-2-yl)-7-fluorobenzo[b]thiophene-3-carbonitrile (193). To a solution of 1-9 (35 mg, 0.051 mmol) in DCM (3 mL) was added TFA (1 mL) slowly at 0° C. The resulting mixture was stirred for 1 hour at room temperature. The reaction mixture was concentrated to remove TFA, then taken up in DCM, treated with NaHCO$_3$ (aq), and extracted with DCM. The organics were combined, washed with brine, and dried over Na$_2$SO$_4$, then filtered and solvent removed under reduced pressure to give a crude residue. The crude residue was purified by flash chromatography on silica gel (10% MeOH/DCM) to afford the title compound. ESI-MS m/z: 655 [M+H]$^+$. HNMR (400 MHz, DMSO-d$_6$): 8.13-8.10 (m, 2 H), 7.28-7.25 (m, 1 H), 7.18-7.13 (m, 1 H), 5.59-5.46 (m, 1 H), 4.84-4.67 (m, 2 H), 4.50-4.31 (m, 3 H), 4.12-4.07 (m, 1 H), 3.72-3.68 (m, 3 H), 3.24 (brs, 1 H), 2.48-2.42 (m, 2 H), 2.28-2.26 (m, 1 H), 2.13-1.89 (m, 5 H), 1.70-1.48 (m, 6 H), 1.41 (s, 1 H).

Example 20: Synthesis of 2-amino-4-((6aR,7aS,10aS)-3-chloro-1-fluoro-13-(((2R,7aS)-2-fluorotetrahydro-1H-pyrrolizin-7a(5H)-yl)methoxy)-5,6,6a,7,7a,9,10,10a-octahydrofuro[2'',3'':4',5']pyrrolo[1',2':5,6][1,5]oxazocino[4,3,2-de]quinazolin-2-yl)-7-fluorobenzo[b]thiophene-3-carbonitrile (200)

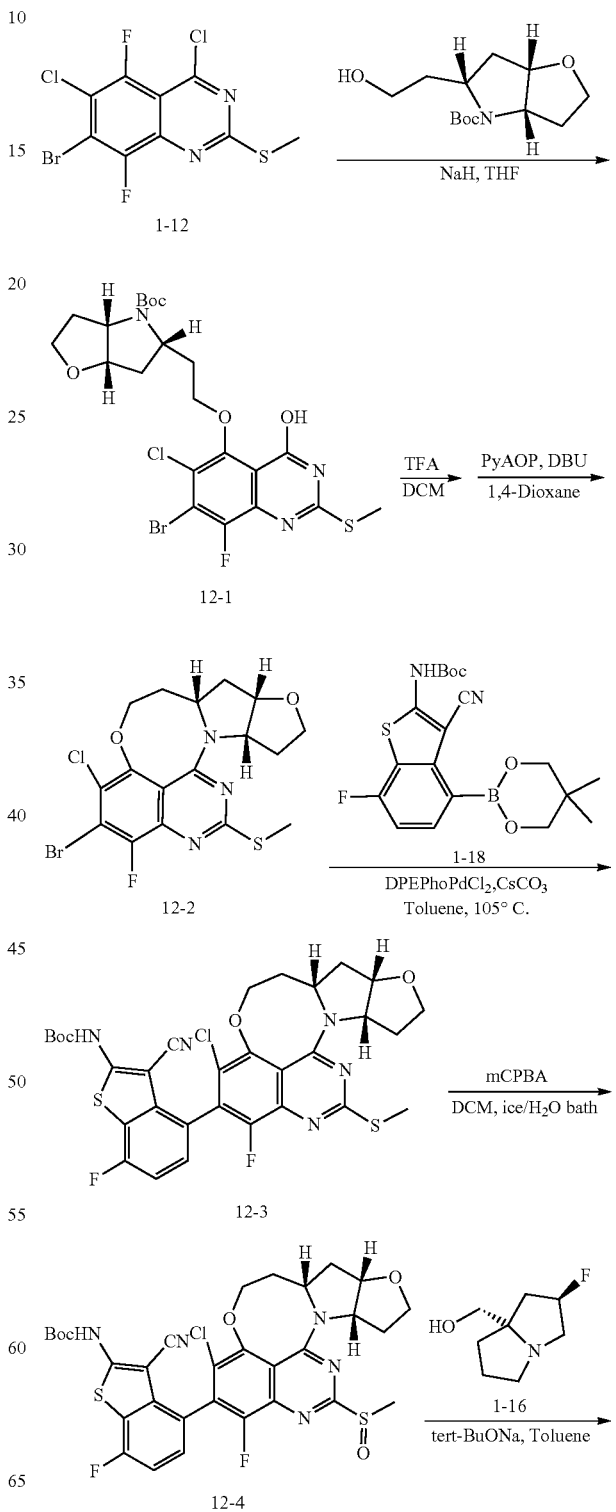

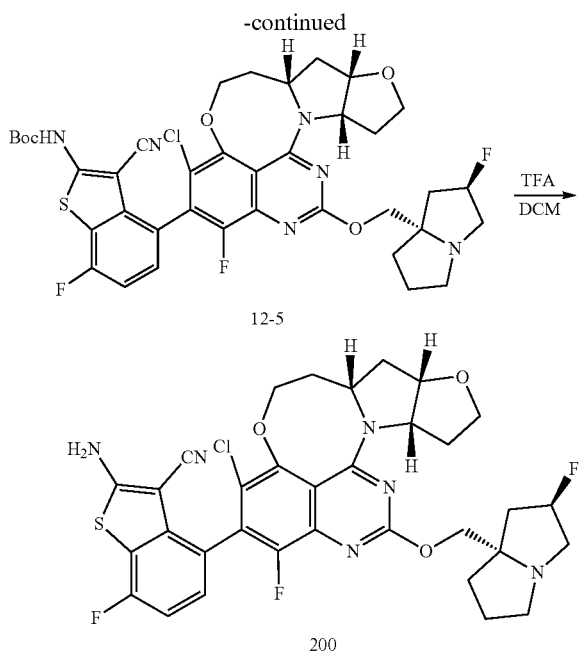

To a stirred solution of compound 1-12 (210 mg, 0.58 mmol) in THF (10 mL), tert-butyl (3aS,5R,6aS)-5-(2-hydroxyethyl)hexahydro-4H-furo[3,2-b]pyrrole-4-carboxylate (106 mg, 0.41 mmol) was added. The mixture was cooled in the ice/water bath, NaH (60%) (82 mg, 2.0 mmol) was added and the resulting mixture was stirred at RT for 2 h. The mixture was diluted with water and extracted with ethyl acetate (25 mL×2). The combined organic layer was concentrated in vacuo. The residue was purified by silica gel column eluting with Hex/EA to afford compound 12-1 (172.4 mg). ESI-MS m/z: 577.1 [M+H]$^+$.

To a stirred solution of 12-1 (172.0 mg, 0.30 mmol) in DCM (10 mL), TFA (2.0 mL) was added, and the resulting mixture was stirred at RT for 2 h. The mixture was concentrated in vacuo. The residue was dissolved in 1,4-Dioxane (12 mL), then DBU (182 mg, 1.2 mmol) and PyAOP (172 mg, 0.33 mmol) were added, and the resulting mixture was stirred at RT overnight. The mixture was diluted with water and extracted with ethyl acetate (25 mL×2). The combined organic layer was concentrated in vacuo. The residue was purified by silica gel column eluting with Hex/EA to afford compound 12-2 (79 mg). ESI-MS m/z: 459.2 [M+H]$^+$.

A mixture of compound 12-2 (79.0 mg, 0.17 mmol), compound 1-18 (97.0 mg, 0.24 mmol), Cs$_2$CO$_3$ (92 mg, 0.26 mmol), DPEPhosPdCl$_2$ (20 mg, 0.028 mmol) in Toluene (7 mL) was stirred at 105° C. under argon for 3 h. The mixture was diluted with water (3 mL) and extracted with ethyl acetate (15 mL×2). The combined organic layer was concentrated in vacuo. The residue was purified by silica gel column eluting with Hex/EA to afford compound 12-3 (60.2 mg). ESI-MS m/z: 671.0 [M+H]$^+$.

To a stirred solution of compound 12-3 (60.2 mg, 0.090 mmol) in DCM (5 mL) at 0° C., mCPBA (30.9 mg, 0.18 mmol) was added. The resulting mixture was stirred at 0° C. for 15 min. The mixture was concentrated, and the residue was purified by silica gel column eluting with Hex/EA to afford compound 12-4 (39.2 mg). ESI-MS m/z: 688.2 [M+H]$^+$.

To a stirred solution of 12-4 (39.2 mg, 0.057 mmol) in toluene (3 mL), ((2R,7aS)-2-fluorotetrahydro-1H-pyrrolizin-7a(5H)-yl)methanol (1-16) (13.6 mg, 0.086 mmol) was added, cooled in ice/water bath for 15 min with argon protection, then tert-BuONa (16.4 mg, 0.17 mmol) was added. The resulting mixture was stirred in the ice/water bath under argon for 10 min. The mixture was concentrated in vacuo and the residue was purified with reverse phase column eluting with H$_2$O/ACN to afford compound 12-5 (23 mg). ESI-MS m/z: 783.2 [M+H]$^+$.

To a stirred solution of compound 12-5 (5.2 mg, 0.0067 mmol) in DCM (2 mL) was added TFA (0.5 mL) and the mixture was stirred at RT for 1 h. The mixture was concentrated in vacuo to remove the solvent. The residue was purified by prep-HPLC to afford compound 200 (13.9 mg). ESI-MS m/z: 683.4 [M+H]$^+$.

Example 21: Ras Sequences

```
Human K-Ras Wildtype sequence
                                                      (SEQ ID NO. 1)
  1 MTEYKLVVVG AGGVGKSALT IQLIQNHFVD EYDPTIEDSY RKQVVIDGET
 51 CLLDILDTAG QEEYSAMRDQ YMRTGEGFLC VFAINNTKSF EDIHHYREQI
101 KRVKDSEDVP MVLVGNKCDL PSRTVDTKQA QDLARSYGIP FIETSAKTRQ
151 GVDDAFYTLV REIRKHKEKM SKDGKKKKKK SKTKCVIM Human K-Ras G12D
                                                      (SEQ ID NO. 2)
  1 MTEYKLVVVG ADGVGKSALT IQLIQNHFVD EYDPTIEDSY RKQVVIDGET
 51 CLLDILDTAG QEEYSAMRDQ YMRTGEGFLC VFAINNTKSF EDIHHYREQI
101 KRVKDSEDVP MVLVGNKCDL PSRTVDTKQA QDLARSYGIP FIETSAKTRQ
151 GVDDAFYTLV REIRKHKEKM SKDGKKKKKK SKTKCVIM Human K-Ras G12V
                                                      (SEQ ID NO. 3)
  1 MTEYKLVVVG AVGVGKSALT IQLIQNHFVD EYDPTIEDSY RKQVVIDGET
 51 CLLDILDTAG QEEYSAMRDQ YMRTGEGFLC VFAINNTKSF EDIHHYREQI
101 KRVKDSEDVP MVLVGNKCDL PSRTVDTKQA QDLARSYGIP FIETSAKTRQ
151 GVDDAFYTLV REIRKHKEKM SKDGKKKKKK SKTKCVIM Human K-Ras G12S (SEQ ID NO. 4):
  1 MTEYKLVVVG ASGVGKSALT IQLIQNHFVD EYDPTIEDSY RKQVVIDGET
 51 CLLDILDTAG QEEYSAMRDQ YMRTGEGFLC VFAINNTKSF EDIHHYREQI
101 KRVKDSEDVP MVLVGNKCDL PSRTVDTKQA QDLARSYGIP FIETSAKTRQ
151 GVDDAFYTLV REIRKHKEKM SKDGKKKKKK SKTKCVIM
```

```
Human N-Ras wildtype
                                                        (SEQ ID NO. 5)
  1 MTEYKLVVVG AGGVGKSALT IQLIQNHFVD EYDPTIEDSY RKQVVIDGET
 51 CLLDILDTAG QEEYSAMRDQ YMRTGEGFLC VFAINNSKSF ADINLYREQI
101 KRVKDSDDVP MVLVGNKCDL PTRTVDTKQA HELAKSYGIP FIETSAKTRQ
151 GVEDAFYTLV REIRQYRMKK LNSSDDGTQG CMGLPCVVM H-Ras G12D
                                                        (SEQ ID NO. 6)
  1 MTEYKLVVVG ADGVGKSALT IQLIQNHFVD EYDPTIEDSY RKQVVIDGET
 51 CLLDILDTAG QEEYSAMRDQ YMRTGEGFLC VFAINNTKSF EDIHQYREQI
101 KRVKDSDDVP MVLVGNKCDL AARTVESRQA QDLARSYGIP YIETSAKTRQ
151 GVEDAFYTLV REIRQHKLRK LNPPDESGPG CMSCKCVLS H-Ras wildtype
                                                        (SEQ ID NO. 7)
  1 MTEYKLVVVG AGGVGKSALT IQLIQNHFVD EYDPTIEDSY RKQVVIDGET
 51 CLLDILDTAG QEEYSAMRDQ YMRTGEGFLC VFAINNTKSF EDIHQYREQI
101 KRVKDSDDVP MVLVGNKCDL AARTVESRQA QDLARSYGIP YIETSAKTRQ
151 GVEDAFYTLV REIRQHKLRK LNPPDESGPG CMSCKCVLS Human N-Ras G12D
                                                        (SEQ ID NO. 8)
  1 MTEYKLVVVG ADGVGKSALT IQLIQNHFVD EYDPTIEDSY RKQVVIDGET
 51 CLLDILDTAG QEEYSAMRDQ YMRTGEGFLC VFAINNSKSF ADINLYREQI
101 KRVKDSDDVP MVLVGNKCDL PTRTVDTKQA HELAKSYGIP FIETSAKTRQ
151 GVEDAFYTLV REIRQYRMKK LNSSDDGTQG CMGLPCVVM
```

Example 22: Protein Expression

DNA expression constructs encoding one or more protein sequences of interest (e.g., Kras fragments thereof, mutant variants thereof, etc.) and its corresponding DNA sequences are optimized for expression in *E. coli* and synthesized by, for example, the GeneArt Technology at Life Technologies. In some cases, the protein sequences of interest are fused with a tag (e.g., glutathione S-transferase (GST), histidine (His), or any other affinity tags) to facilitate recombinant expression and purification of the protein of interest. Such tag can be cleaved subsequent to purification. Alternatively, such tag may remain intact to the protein of interest and may not interfere with activities (e.g., target binding and/or phosphorylation) of the protein of interest A resulting expression construct is additionally encoded with (i) att-site sequences at the 5' and 3' ends for subcloning into various destination vectors using, for example, the Gateway Technology, as well as (ii) a Tobacco Etch Virus (TEV) protease site for proteolytic cleavage of one or more tag sequences. The applied destination vectors can be a pET vector series from Novagen (e.g., with ampicillin resistance gene), which provides an N-terminal fusion of a GST-tag to the integrated gene of interest and/or a pET vector series (e.g., with ampicillin resistance gene), which provides an N-terminal fusion of a HIS-tag to the integrated gene. To generate the final expression vectors, the expression construct of the protein of interest is cloned into any of the applied destination vectors. The expression vectors are transformed into an *E. coli* strain, e.g., BL21 (DE3). Cultivation of the transformed strains for expression is performed in a 10 L or 1 L fermenter. The cultures are grown, for example, in Terrific Broth media (MP Biomedicals, Kat. #1 13045032) with 200 μg/mL ampicillin at a temperature of 37° C. to a density of 0.6 (OD600), shifted to a temperature of ~27° C. (for K-Ras expression vectors) induced for expression with 100 mM IPTG, and further cultivated for 24 hours. After cultivation, the transformed *E. coli* cells are harvested by centrifugation and the resulting pellet is suspended in a lysis buffer, as provided below, and lysed by passing three-times through a high pressure device. The lysate is centrifuged (49000 g, 45 min, 4° C.) and the supernatant is used for further purification.

Example 23: Ras Protein Purification

A Ras (e.g., K-Ras wildtype or a mutant such as K-Ras G12S, K-Ras G12D, K-Ras G12V or K-Ras G12C) construct or a variant thereof is tagged with GST. *E. coli* culture from a 10 L fermenter is lysed in lysis buffer (50 mM Tris HCl 7.5, 500 mM NaCl, 1 mM DTT, 0.5% CHAPS, Complete Protease Inhibitor Cocktail—(Roche)). As a first chromatography step, the centrifuged lysate is incubated with 50 mL Glutathione Agarose 4B (Macherey-Nagel; 745500.100) in a spinner flask (16 h, 10° C.). The Glutathione Agarose 4B loaded with protein is transferred to a chromatography column connected to a chromatography system, e.g., an Akta chromatography system. The column is washed with wash buffer (50 mM Tris HCl 7.5, 500 mM NaCl, 1 mM DTT) and the bound protein is eluted with elution buffer (50 mM Tris HCl 7.5, 500 mM NaCl, 1 mM DTT, 15 mM Glutathione). The main fractions of the elution peak (monitored by OD280) are pooled. For further purification by size-exclusion chromatography, the above eluate volume is applied to a column Superdex 200 HR prep grade (GE Healthcare) and the resulting peak fractions of the eluted fusion protein is collected. Native mass spectrometry analyses of the final purified protein construct can be performed to assess its homogeneous load with GDP.

Example 24: HTRF (Homogenous Time-Resolved Fluorescence) Resonance Energy Transfer Assay The ability of a compound of the present disclosure to reduce a Ras signaling output can be demonstrated by an HTRF assay. This assay can be also used to assess a selective inhibition or reduction of signaling output of a mutant Ras protein relative to a wildtype, or relative to a different mutant Ras protein. For example, the equilibrium interaction of wildtype Kras or K-Ras mutant (e.g., wildtype or a mutant thereof) with SOS1 (e.g., hSOS1) can be assessed as a proxy or an indication for a subject compound's ability to bind and inhibit Ras protein. HTRF assay detects from (i) a fluorescence resonance energy transfer (FRET) donor (e.g., anti-GST-Europium) that is bound to GST-tagged K-Ras mutant to (ii) a FRET acceptor (e.g., anti-6His-XL665) bound to a His-tagged hSOS1.

The assay buffer can contain ~5 mM HEPES pH 7.4, ~150 mM NaCl, ~1 mM DTT, 0.05% BSA and 0.0025% (v/v) Igepal. A Ras working solution is prepared in an assay buffer containing typically a suitable amount of the protein construct (e.g., GST-tagged K-Ras mutant) and the FRET donor (e.g., antiGST-Eu(K) from Cisbio, France). A SOS1 working solution is prepared in an assay buffer containing suitable amount of the protein construct (e.g., His-hSOS1) and the FRET acceptor (e.g., anti-6His-XL665 from Cisbio, France). A suitable amount of the protein construct will depend on the range of activity or range of IC50 values being detected or under investigation. For detecting IC50 within a range of 500 nM, the protein constructs of the same range of molarity can be utilized. An inhibitor control solution is prepared in an assay buffer containing comparable amount of the FRET acceptor without the SOS1 protein.

A fixed volume of DMSO with or without test compound is transferred into a 384-well plate. Ras working solution is added to all wells of the test plate. SOS1 working solution is added to all wells except for those that are subsequently filled the inhibitor control solution. Upon incubation for about 10 minutes or longer, the fluorescence is measured with a M1000Pro plate reader (Tecan) using HTRF detection (excitation 337 nm, emission 1: 620 nm, emission 2: 665 nm). Compounds are tested in duplicate at different concentrations (for example, 10 µM, 2.5 µM, 0.63 µM, 0.16 µM, 0.04 µM, 0.01 µM test compound). The ratiometric data (i.e., emission 2 divided by emission 1) is used to calculate IC50 values against Ras using GraphPad Prism (GraphPad software). Following this general procedure, samples are tested with or without a subject compound disclosed herein including compounds exemplified in Table 1 to assess their abilities to inhibit a mutant K-Ras relative to another K-Ras (e.g., different mutant or wildtype). Signaling output measured in terms of IC50 values can be obtained, a ratio of IC50 against one mutant relative to another mutant can be calculated. For instance, a selective reduction of K-Ras G12D signaling output can be evidenced by a ratio greater than one. In particular, a selective reduction of K-Ras G12D signaling relative to K-Ras WT signaling is evidenced if the ratio of IC50 (against K-Ras WT) to IC50 (against K-Ras G12D) is greater than 1. In some embodiments, one or more subject compounds disclosed herein are expected to exhibit selective inhibition of a Ras mutant (e.g., G12C, G12D, G12S, G12V, G13C, or G13D) over WT by at least 1-fold, and in some instances greater than 2-, 3-, 4- or 5-fold. In some embodiments, one or more subject compounds exhibited potent inhibition across wildtype and mutant K-Ras proteins including K-Ras G12D, K-Ras G12S, and K-Ras G12V.

Table 2 shows the resulting IC50 values of selected compounds against K-Ras G12D, K-Ras G12S, K-Ras G12V, and wildtype K-Ras using the HTRF assay described herein. Compound numbers correspond to the numbers and structures provided in Table 1 and Examples 1-20.

TABLE 2

| | <5 µM (+++) | ≥5 µM (++) |
|---|---|---|
| PPI-HTRF-5 nM (K-Ras G12D IC$_{50}$) | 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 211, 212, 213, 214, 215 | 210 |
| PPI-HTRF-5 nM (K-Ras G12S IC$_{50}$) | 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 175, 176, 177, 178, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 211, 212, 213, 214, 215 | 179, 210 |
| PPI-HTRF-5 nM (K-Ras G12V IC$_{50}$) | 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 211, 212, 213, 214, 215 | 210 |
| PPI-HTRF-5 nM (K-Ras wt IC$_{50}$) | 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 211, 212, 213, 214, 215 | 210 |

Example 25: GTPase Activity Assay

The ability of a compound of the present disclosure to inhibit Ras protein signaling can be demonstrated by a reduced GTPase activity. This assay can also be used to assess selective inhibition of a mutant Ras protein relative to a wildtype, or relative to a different mutant Ras protein. For instance, the assay can be used to establish a subject compound's ability to selectively inhibit Kras G12D relative to wildtype, Kras G12S relative to wildtype, Kras G12V relative to wildtype, Kras G12S relative Kras G12V, Kras G12S relative Kras G12D, Kras G12D relative Kras G12S, or Kras G12D relative Kras G12V. In particular, intrinsic and GTPase-activating protein (GAP)-stimulated GTPase activity for a K-Ras construct or a mutant thereof can be measured using EnzCheck phosphate assay system (Life Technologies). For example, K-Ras WT, K-Ras D154Q mutant, K-Ras G12D mutant, K-Ras G12S mutant, and K-Ras G12D/D154Q mutant proteins (2.5 mg/mL) in buffer (20 mmol/L Tris, pH 8.0, 50 mM NaCl) is loaded with GTP at room temperature for 2 hours by exposing to exchange buffer containing EDTA. Proteins are buffer exchanged to assay buffer (30 mM Tris, pH 7.5, 1 mM DTT) and the concentration is adjusted to 2 mg/mL. GTP loading is verified by back extraction of nucleotide using 6M urea and evaluation of nucleotide peaks by HPLC using an ion-exchange column. The assay is performed in a clear 384-well plate (Costar) by combining GTP-loaded K-Ras proteins (50 mM final) with 2-amino-6-mercapto-7-methylpurine ribonucleoside (MESG) (200 mM final), and purine nucleotide phosphorylase (5 U/mL final). GTP hydrolysis is initiated by the addition of $MgCl_2$ at a working concentration of 40 mM. For GAP stimulation, Ras p21 protein activator 1 (P120GAP) can be included at 50 mM. Absorbance at 360 nm can be measured every 8 to 15 s for 1,000 s at 20° C. Samples are tested with or without a subject compound disclosed herein to assess each compound's ability to inhibit signaling of a given Ras protein (e.g., a given mutant Kras) of interest.

Example 26: Nucleotide Exchange Assay

The ability of a compound of the present disclosure to inhibit Ras protein signaling can be demonstrated by reduced nucleotide exchange activity. This assay can be also used to assess selective inhibition of a mutant Ras protein relative to a wildtype, or relative to a different mutant Ras protein. For example, 250 nM or 500 nM GDP-loaded K-Ras protein (e.g., wildtype or a mutant thereof including those mentioned in Example 25) is incubated with different concentrations of compounds (for example ~60 µM, ~20 µM, ~6.7 µM, ~2.2 µM, ~0.7 µM, or ~0.2 µM subject compound). A control reaction without subject compound is also included. SOS1 (catalytic domain) protein is added to the K-Ras protein solution. The nucleotide exchange reaction is initiated by adding fluorescent labelled GDP (Guanosine 5'-Diphosphate, BODIPY™ FL 2'-(or-3')-O-(N-(2-Aminoethyl) Urethane) to a final concentration of 0.36 µM. Fluorescence is measured every 30 s for 70 minutes at 490 nm/515 nm (excitation/emission) in a M1000Pro plate reader (Tecan). Data is exported and analyzed to calculate an IC50 using GraphPad Prism (GraphPad Software). Sample(s) can be tested with or without a subject compound disclosed herein to assess the compound's ability to inhibit K-Ras signaling or its IC50 against a given Ras protein (e.g., a given mutant K-Ras) of interest.

Example 27: Testing for Modification of Ras Protein

Test compounds are prepared as 10 mM stock solutions in DMSO (Fisher cat #BP231-100). KRAS protein (e.g., His-tagged GDP-loaded wildtype 1-169, His-tagged GDP-loaded G12C 1-169, His-tagged GDP-loaded G12D 1-169, or His-tagged GDP-loaded G12S 1-169) is diluted to ~2 µM in appropriate buffer (e.g., a Hepes buffer at physiological conditions). For testing KRAS modification, compounds are diluted to 50× final test concentration in DMSO in 96-well storage plates. 1 µL of the diluted 50× compounds are added to appropriate wells in the PCR plate (Fisher cat #AB-0800). ~49 µL of the stock protein solution is added to each well of the 96-well PCR plate. Reactions are mixed carefully. The plate is sealed well with aluminum plate seal and stored in a drawer at room temperature for 24 hrs. 5 µL of 2% formic acid (Fisher cat #A117-50) in MilliQ $H_2O$ is then added to each well followed by mixing with a pipette. The plate is then resealed with aluminum seal and stored until mass spectrometry analysis. The extent of covalent modification of KRAS proteins can be determined by liquid chromatography electrospray mass spectrometry analysis of the intact proteins on a Thermo Q-Exactive Plus mass spectrometer. 20 µL of sample is injected onto a bioZen 3.6 µm Intact C4 column (Phenomenex cat #00B-4767-AN) placed in a column oven set to 40° C. and separated using a suitable LC gradient from ~20% to ~60% solvent B. Solvent A is 0.1% formic acid and solvent B is 0.1% formic acid in acetonitrile. HESI source settings are set to 40, 5 and 1 for the sheath, auxiliary and sweep gas flow, respectively. The spray voltage is 4 kV, and the capillary temperature is 320° C. S-lens RF level is 50 and auxiliary gas heater temperature is set to 200° C. The mass spectrometry is acquired using a scan range from 650 to 1750 m/z using positive polarity at a mass resolution of 70,000, AGC target of 1e6 ions and maximum injection time of 250 ms. The recorded protein mass spectrum is deconvoluted from the raw data file using Protein Deconvolution v4.0 (Thermo). The protein mass and adduct masses are exported with their peak intensities. The peak intensities for the unmodified and modified protein are used to calculate the percent covalent modification of the KRAS protein based on the following equation:

% KRAS protein modification=((KRAS-compound)/ (KRAS)+(KRAS-Compound))*100.

Example 28: Ras Cellular Assay

The ability of a compound of the present disclosure to inhibit Ras protein signaling can be demonstrated by inhibiting growth of a given Kras mutant cell line. For example, this assay can be also used to assess selective growth inhibition of a mutant Ras protein relative to a wildtype, or relative to a different mutant Ras protein.

a. Growth of Cells with K-Ras G12C Mutation

MIA PaCa-2 (ATCC CRL-1420) and NCI-H1792 (ATCC CRL-5895) cell lines comprise a G12C mutation and can be used to assess Ras cellular signaling in vitro, e.g., in response to an inhibitor compound of the present disclosure. This cellular assay can also be used to discern selective inhibition of a subject compound against certain types of Kras mutants, e.g., more potent inhibition against Kras G12D relative to Kras G12C mutant, by comparing inhibition of MIA PaCa-2 (G12C driven tumor cell line) to inhibition of GP2d (G12D driven tumor cell line). MIA PaCa-2 culture medium is prepared with DMEM/Ham's F12 (e.g., with stable Glutamine), 10% FCS, and 2.5% Horse Serum. NCI-H1792 culture medium is prepared with RPMI 1640 (e.g., with stable Glutamine) and 10% FCS.

On a first day (e.g., Day 1), Softagar (Select Agar, Invitrogen, 3% in $ddH_2O$ autoclaved) is boiled and tempered at 48° C. Appropriate culture medium (i.e., medium) is tempered to 37° C. Agar (3%) is diluted 1:5 in medium (=0.6%) and plated into 96 well plates (Corning, #3904), then incubated at room temperature for agar solidification. A 3% agar is diluted to 0.25% in medium (1:12 dilution) and tempered at 42° C. Cells are trypsinized, counted, and tempered at 37° C. The cells (e.g., MIA PaCa-2 at about 125-150 cells, NCI-H1792 at about 1000 cells) are resuspended in 100 mL 0.25% Agar and plated, followed by incubation at room temperature for agar solidification. The wells are overlaid with 50 mL of the medium. Sister wells in a separate plate are plated for time zero determination. All plates are incubated overnight at 37° C. and 5% $CO_2$.

On a second day (e.g., Day 2), time zero values are measured. A 40 mL volume of Cell Titer 96 Aqueous Solution (Promega) is added to each well and incubated in the dark at 37° C. and 5% $CO_2$. Absorption can be measured at 490 nm and reference wavelength 660 nm. DMSO-prediluted test compounds are added to wells of interest, e.g., with HP Dispenser, to one or more desired concentrations (e.g., a final DMSO concentration of 0.3%).

On a tenth day (e.g., Day 10), absorption by wells treated with the test compounds and control wells are measured with, for example, Cell Titer 96 AQueous and analyzed in comparison to the time zero measurements. The IC50 values are determined using the four parameter fit. The resulting IC50 value is a measurement of the ability of the test compound to reduce cell growth of Ras-driven cells (e.g., tumor cell lines) in vitro and/or in vivo. One or more compounds disclosed herein is expected to exhibit an IC50 value less than 5 μM, 1 μM, 100 nM, or even less, against one or more KRas G12C cell line (including MIA PaCa-2 and NCI-H1792).

b. Growth of Cells with K-Ras G12D Mutation

ASPC-1 (ATCC CRL-1682), Panc-10.05 (ATCC CRL-2547), A427, GP2d cell lines or any other cell lines comprising a G12D mutation can be used to assess Ras cellular signaling in vitro, e.g., in response to a compound described herein. For example, ASPC-1 culture medium is prepared with RPMI-1640 and 10% heat-inactivated FBS. Panc-10.05 culture medium is prepared with RPMI-1640, 10 Units/mL human recombinant insulin, and 10% FBS. A427 cell culture is prepared with RPMI-1640 and 10% heat-inactivated FBS. A CellTiter-Glo (CTG) luminescent based assay (Promega) is used to assess growth of the cells, as a measurement of the ability of the compounds herein to inhibit Ras signaling in the cells. The cells (e.g., 800 per well) are seeded in their respective culture medium in standard tissue culture-treated 384-well format plates (Falcon #08-772-116) or ultra-low attachment surface 384-well format plates (S-Bio #MS-9384UZ). The day after plating, cells are treated with a dilution series (e.g., a 9 point 3-fold dilution series) of the compounds herein (e.g., approximately 40 μL final volume per well). Cell viability can be monitored (e.g., approximately 5 days later) according to the manufacturer's recommended instructions, where the CellTiter-Glo reagent is added (e.g., approximately 10 μL), vigorously mixed, covered, and placed on a plate shaker (e.g., approximately for 20 min) to ensure sufficient cell lysis prior to assessment of luminescent signal. The IC50 values are determined using the four parameter fit. The resulting IC50 value is a measurement of the ability of the test compound to reduce cell growth of Ras-driven cells (e.g., tumor cell lines) in vitro and/or in vivo. One or more compounds disclosed herein is expected to exhibit an IC50 value less than 5 μM, 1 μM, 100 nM, or even less, against one or more KRas G12D cell line (including GP2D, HPAC, AsPC-1, Panc04.03).

c. Growth of Cells with K-Ras G12S Mutation

A549 (ATCC CRL-185) and LS123 (ATCC CRL-255) cell lines comprise a G12S mutation and can be used to assess Ras cellular signaling in vitro, e.g., in response to treatment with a compound described herein. A549 culture medium is prepared with RPMI-1640 and 10% heat-inactivated FBS. LS123 culture medium is prepared with RPMI-1640 and 10% heat-inactivated FBS. A CellTiter-Glo (CTG) luminescent based assay (Promega) is used to assess growth of the cells, as a measurement of the ability of the compounds herein to inhibit Ras signaling in the cells. The cells (e.g., 800 per well) are seeded in their respective culture medium in standard tissue culture-treated 384-well format plates (Falcon #08-772-116) or ultra-low attachment surface 384-well format plates (S-Bio #MS-9384WZ). The day after plating, cells are treated with a dilution series (e.g., a 10 point, 3-fold dilution series) of the compounds herein (e.g., approximately 40 μL final volume per well). Cell viability can be monitored (e.g., approximately 6 days later) according to the manufacturer's recommended instructions, where CellTiter-Glo reagent is added (e.g., approximately 10 μL), vigorously mixed, covered, and placed on a plate shaker (e.g., approximately for 20 min) to ensure sufficient cell lysis prior to assessment of luminescent signal. The IC50 values are determined using the four parameter fit. The resulting IC50 value is a measurement of the ability of the test compound to reduce cell growth of Ras-driven cells (e.g., tumor cell lines) in vitro and/or in vivo. One or more compounds disclosed herein possess the ability to inhibit growth of KRAS G12S cell line (e.g., A549 or LS123) and/or KRAS G12C cell lines (e.g., MIA PaCa-2).

In some embodiments, one or more subject compounds exhibited potent cell growth inhibition of GP2D, A549, and/or SW620 cells. Table 3 shows the resulting IC50 values of selected compounds against KRas mutant cells using the cellular assay described herein. Compound numbers correspond to the numbers and structures provided in Table 1 and Examples 1-20.

TABLE 3

|  | <5 μM (+++) | ≥5 μM (++) |
|---|---|---|
| Cell Proliferation (GP2D IC$_{50}$) | 101, 102, 103, 104, 105, 106, 107, 108, 113, 114, 115, 116, 117, 120, 121, 124, 125, 126, 127, 129, 131, 132, 133, 134, 135, 136, 137, 138, 139, 140, 141, 142, 143, 144, 146, 148, 149, 150, 151, 152, 153, 154, 155, 157, 159, 161, 162, 164, 167, 168, 170, 171, 173, 175, 176, 177, 178, 180, 181, 182, 183, 184, 185, 186, 187, 188, 189, 190, 192, 193, 196, 197, 200, 204, 205, 207, 208, 209, 211, 212, 215 | 109, 110, 111, 112, 156, 158, 172, 214 |
| Cell Proliferation (A549 IC$_{50}$) | 101, 103, 105, 107, 114, 115, 116, 117, 121, 125, 126, 131, 132, 133, 134, 136, 137, 138, 140, 141, 142, 143, 144, 149, 150, 151, 152, 153, 154, 155, 156, 157, 159, 161, 162, 167, 168, 170, 173, 175, 176, 178, 181, 182, 183, 184, 185, 186, 188, 189, 190, 192, 193, 196, 200, 204, 205, 207, 211, 215 | 108, 110, 120, 124, 127, 139, 146, 148, 171, 172, 214 |
| Cell Proliferation (SW620 IC$_{50}$) | 101, 103, 104, 105, 106, 107, 110, 112, 113, 114, 115, 116, 117, 120, 121, 124, 125, 126, 127, 131, 132, 133, 134, 136, 137, 138, 139, 140, 141, 142, 143, 144, 146, 148, 149, 150, 151, 152, 153, 154, 155, 156, 157, 158, 159, 161, 162, 164, 167, 168, 170, 173, 175, 176, 177, 178, | 102, 108, 109, 111, 129, 135, 171, 172, 214 |

TABLE 3-continued

| <5 µM (+++) | ≥5 µM (++) |
|---|---|
| 180, 181, 182, 183, 184, 185, 186, 187, 188, 189, 190, 192, 193, 196, 197, 200, 204, 205, 207, 208, 209, 211, 212, 215, | |

All compounds in Table 1 that are not listed in Table 3 have not been measured in the assays used for Table 3.

Example 29: In Vivo Ras Inhibition

The in vivo reduction in Ras signaling output by a compound of the present disclosure is determined in a mouse tumor xenograft model, such as a K-Ras G12D model utilizing cells including a KRas G12D mutant or a K-Ras G12C model utilizing cells including a KRas G12C mutant. Xenograft with K-Ras G12D, G12C, or G12S Mutation Tumor xenografts are established by administration of tumor cells with a K-Ras G12D mutation (e.g., ASPC-1 cells) a K-Ras G12C mutation (e.g., MIA PaCa-2 cells), or a K-Ras G12S mutation (e.g., A549 or LS123 cells) into mice. Female 6- to 8-week-old athymic BALB/c nude (NCr) nu/nu mice are used for xenografts. The tumor cells (e.g., approximately 5×10$^6$) are harvested on the day of use and injected in growth-factor-reduced Matrigel/PBS (e.g., 50% final concentration in 100 µL). One flank is inoculated subcutaneously per mouse. Mice are monitored daily, weighed twice weekly, and caliper measurements begin when tumors become visible. For efficacy studies, animals are randomly assigned to treatment groups by an algorithm that assigns animals to groups to achieve best case distributions of mean tumor size with lowest possible standard deviation. Tumor volume can be calculated by measuring two perpendicular diameters using the following formula: (L×w$^2$)/2, in which L and w refer to the length and width of the tumor, respectively. Percent tumor volume change can be calculated using the following formula: $(V_{final} - V_{initial})/V_{initial} \times 100$. Percent of tumor growth inhibition (% TGI) can be calculated using the following formula: % TGI=100×(1−(average $V_{final} - V_{initial}$ of treatment group)/(average $V_{final} - V_{initial}$ of control group). When tumors reach a threshold average size (e.g., approximately 200-400 mm$^3$), mice are randomized into 3-10 mice per group and are treated with vehicle (e.g., 100% Labrasol®) or a compound disclosed herein, using, for example, a daily schedule by oral gavage. Results can be expressed as mean and standard deviation of the mean.

Example 30: Metabolic (Microsomal) Stability Assay

The metabolic stability of a test compound is assayed at 37° C. using pooled liver microsomes (mouse or human liver microsomes). An aliquot of 10 µL of 50 µM test compound is mixed with 490 µL of 0.611 mg/mL liver microsomes, then 50 µL of the mixtures are dispensed to the 96 well tubes and warmed at 37° C. for 10 minutes. The reactions are initiated by adding 50 µL of the pre-warmed NADPH regeneration system solution (add 1.2 µL solution, 240 µL solution B, mix with 10.56 mL KPBS) and then incubated at 37° C. The final incubation solution contains 100 mM potassium phosphate (pH 7.4), 1.3 mM NADP$^+$, 3.3 mM glucose 6-phosphate, 0.4 unit/mL of glucose 6-phosphate dehydrogenase, 3.3 mM magnesium chloride, 0.3 mg/mL liver microsomes and 0.5 µM test article. After 0, 15, 30 and 60 minutes in a shaking incubator, the reactions are terminated by adding 100 µL of acetonitrile containing 200 nM buspirone as an internal standard. All incubations are conducted in duplicate. Plates are vortexed vigorously by using Fisher Scientific microplate vortex mixer (Henry Troemner, US). Samples are then centrifuged at 3500 rpm for 10 minutes (4° C.) using Sorvall Legend XRT Centrifuge (Thermo Scientific, GE). Supernatants (40 µL) are transferred into clean 96-deep well plates. To each well is added with 160 µL of ultrapure water (Milli-Q, Millipore Corporation) with 0.1% (v/v) formic acid (Fisher Chemical) and the resulting solutions mixed thoroughly and subjected to LC/MS/MS analysis in MRM positive ionization mode.

All samples are measured using a mass spectrometer (QTrap 5500 quadrupole/ion trap) coupled with a Shimadzu HPLC system. The HPLC system consists of a Shimadzu series degasser, binary quaternary gradient pumps, column heater coupled to an autosampler, and a Phenomenex Gemini-NX, C18, 3.0 µm or Phenomenex Lunar, C8, 5.0 µM HPLC column (Phenomenex, Torrance, CA), eluting with a mobile phase gradient consisting of Solution A (0.1% formic acid water) and Solution B (0.1% formic acid acetonitrile). The column temperature is maintained at 40° C. All the analytes are detected with positive-mode electrospray ionization (ES+).

The half-life for the metabolic degradation of the test compound is calculated by plotting the time-course disappearance of the test compound during the incubation with liver microsomes. Each plot is fitted to a first-order equation for the elimination of the test compound (% remaining compound) versus time using non-linear regression (Equation 1).

$$\frac{C_t}{C_0} = e^{-kt} \quad \text{Equation 1}$$

where $C_t$ is the mean relative substrate concentration at time t and $C_0$ is the initial concentration (0.5 µM) at time 0. Note that the area ratio of the substrate peak to an internal standard peak is proportional to the analyte concentration and is used for regression analysis to derive a value of k.

The half-life $t_{1/2}$ for metabolic (microsome) stability is derived from the test compound elimination constant k using Equation 2 below.

$$t_{1/2} = \frac{0.693}{k} \quad \text{Equation 2}$$

Example 31: CYP2C19 Inhibition Assay

Some xenobiotics can inhibit cytochrome P450 (CYP) enzyme function, which alters their ability to metabolize drugs. Administration of a CYP inhibitor with a drug whose clearance is dependent on CYP metabolism can result in increased plasma concentrations of this concomitant drug, leading to potential toxicity. The inhibition of CYP2C19 by a test compound is assayed in human liver microsomes using S-mephenytoin as a CYP2C19 substrate. The stock solution of the test compound or known CYP2C19 inhibitor as a positive control (10 mM) is diluted with KPBS to 40 µM. In a similar way, the stock solutions of the human liver microsomes and S-mephenytoin are diluted with KPBS buffer. The pre-incubations are started by incubating a plate containing 25 µL human liver microsomes (final concentration of 0.2 mg/mL), 25 µL NADPH-generating system, and a 25 µL test compound (final concentration 10 µM) or the positive control for 30 min at 37±1° C. After the pre-incubation, 25 µL S-mephenytoin (final concentration 200 µM) is added and incubated another 12 minutes at 37±1° C. for substrate metabolism. The reactions are terminated by addition of 100 µL of ice-cold acetonitrile containing an internal standard (buspirone). Precipitated proteins are removed by centrifugation at 3500 rpm for 10 minutes at 4° C. (Allegra 25R, Beckman Co. Fullerton, CA), then an aliquot of the supernatant is transferred to an assay plate.

All the samples are assessed using a mass spectrometer (QTrap 5500 quadrupole/ion trap) coupled with a Shimadzu HPLC system following the manufacturer's instructions. The metabolism of S-mephenytoin in human liver microsomes is monitored by LC/MS/MS as representative of CYP2C19 inhibitory activity. The amount of metabolite formed is assessed by the peak area ratio (metabolite/IS) and % inhibition at 10 µM is expressed as a percentage of the metabolite signal reduced compared to the control (i.e. an incubation that contained no inhibitor and represented 100% enzyme activity): % inhibition=(1−A/B)×100%, where A is the metabolite peak area ratio formed in the presence of test compound or inhibitor at 10 µM and B is the metabolite peak area ratio formed without test compound or inhibitor in the incubation.

Example 32: Mouse and Human Protein Binding Assay to Assess Free Drug Concentration This assay can be used to determine the plasma protein binding of the test compound in the plasma of human and animal species using a Rapid Equilibrium Dialysis (RED) device for equilibrium dialysis and LC-MS/MS for sample analysis. Test compound is spiked in. The stock solution of the test compound is prepared at 5 mM concentration. One µL of 5 mM working solution is added into 1000 µL plasma to achieve a final concentration of 5 µM. The spiked plasma is placed on a rocker and gently agitated for approximately 20 minutes. A volume of 300 µL of the plasma sample containing 5 µM test compound from each species is added to designated RED device donor chambers followed by addition of 500 µL of potassium phosphate buffer to the corresponding receiver chambers in duplicate. The RED device is then sealed with sealing tape and shaken at 150 RPM for 4 hours at 37° C. Post-dialysis donor and receiver compartment samples are prepared for LC-MS/MS analysis, including spiking samples with an internal standard for the bioanalytical analysis. Warfarin and propranolol are purchased from Sigma-Aldrich (St. Louis, MO), and used as positive controls for low and high plasma protein binding, respectively.

All the samples are analyzed using an Agilent Technologies 6430 Triple Quad LC/MS system. The HPLC system consists of an Agilent 1290 Infinity Liquid Chromatograph coupled to an autosampler (Agilent 1290 Infinity LC Injector HTC), and a Phenomenex Gemini-NX, C18, 3.0 µm or Phenomenex Lunar, C8, 5.0 µM HPLC column (Phenomenex, Torrance, CA), eluting with a mobile phase gradient consisting of Solution A (0.1% formic acid water) and Solution B (0.1% formic acid acetonitrile). The column temperature is maintained at 40° C. All the analytes are detected with positive-mode electrospray ionization (ES+). The percentage of the test compound bound to plasma is calculated following Equations 3 and 4.

Equation 3

$$\% \text{ Free test compound} = \frac{\text{Peak ratio}\left(\frac{\text{test compound}}{\text{Internal standard}}\right), \text{receiver compartment}}{\text{Peak ratio}\left(\frac{\text{test compound}}{\text{Internal standard}}\right), \text{donor compartment}} * 100$$

Equation 4

$$\% \text{ Plasma protein bound test compound} = 100 - \% \text{ Free test compound}$$

Example 33: hERG (Automated Patch-Clamp) Assay

The human ether-a-go-go related gene (hERG) encodes the voltage gated potassium channel in the heart (IKr) which is involved in cardiac repolarization. Inhibition of the hERG causes QT interval prolongation and can lead to potential fatal events in humans. It is thus important to assess hERG inhibition early in drug discovery. A hERG automated patch-clamp assay is done using a hERG CHO-K1 cell line using an incubation time of 5 min. The degree of hERG inhibition (%) is obtained by measuring the tail current amplitude, which is induced by a one second test pulse to −40 mV after a two second pulse to +20 mV, before and after drug incubation (the current difference is normalized to control and multiplied by 100 to obtain the percent of inhibition). The percent hERG inhibition is measured in the presence of 10 µM test compound.

Example 34: Rat Oral Exposure (% F)

A pharmacokinetic profile for a test compound is measured by single dosing in jugular vein cannulated male Sprague-Dawley rats. Animal weights are typically over 200 grams, and animals are allowed to acclimate to their new environment for at least 3 days prior to the initiation of any studies. One set of animals is dosed intravenously (IV) with test compound (2 mg/kg in 20% HP-beta-CD or 20% Captisol, pH adjusted to ~4 by citric acid). The IV dosing solution concentration is 0.4 mg/mL test compound. Blood is sampled at 5 minutes, 15 minutes, 30 minutes, 90 minutes, 360 minutes, and 24 hours following IV dosing. Another set of animals is dosed oral (po) with test compound (10 mg/kg in 20% HP-beta-CD or 20% Captisol, pH adjusted to ~4 by citric acid). The oral dosing solution concentration is 1 mg/mL test compound. Blood is sampled at 15 minutes, 30 minutes, 90 minutes, 180 minutes, 360 minutes and 24 hours following oral (po) dosing. Blood samples (~0.2 mL/sample) is collected via the jugular vein, placed in tubes containing EDTA-K2 and stored on ice until centrifuged. The blood samples are centrifuged at approximately 6800 g for 6 minutes at 2-8° C. and the resulting plasma is separated and stored frozen at approximately −80° C.

The plasma samples are analyzed using an Agilent Technologies 6430 Triple Quad LC/MS system, following the manufacturer's instructions. The analytes are detected with positive-mode electrospray ionization (ES+). A standard curve for each test compound is generated and used to measure test compound concentrations in the rat plasma samples. Based on the time course sampling, an area under the curve is calculated for the oral dose group and the intravenous dose group. Percentage rat bioavailability is calculated based on equation 5.

$$\% \ F(\text{rat}) = \frac{AUC_{po} * Dose_{IV}}{AUC_{V} * Dose_{po}}, \quad \text{Equation 5}$$

where F is bioavailability, $AUC_{po}$ is area under curve of oral drug, $AUC_{IV}$ is area under curve of intravenous drug, $Dose_{IV}$ is the intravenous dose and $Dose_{po}$ is the oral dose.

The invention claimed is:

1. A compound of the formula:

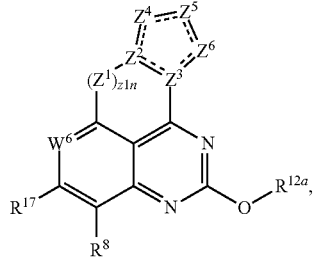

or a pharmaceutically acceptable salt or solvate thereof, wherein:

$W^6$ is $C(R^6)$ or N;

$R^6$ is selected from hydrogen, halogen, and methyl, wherein methyl is optionally substituted with one, two, or three halogen;

$R^8$ is selected from hydrogen and halogen;

$R^{17}$ is selected from $C_{6-10}$aryl and 5-10 membered heteroaryl, each of which is optionally substituted with one, two, three, or four $R^{20q}$;

each $Z^1$ is independently $C(R^{z1})_2$ or O;

z1n is 2 or 3;

each $R^{z1}$ is independently selected from hydrogen, halogen, —CN, $C_{1-6}$alkyl, $C_{2-6}$alkenyl, and $C_{2-6}$alkynyl, wherein $C_{1-6}$alkyl, $C_{2-6}$alkenyl, and $C_{2-6}$alkynyl are optionally substituted with one, two, or three $R^{20z1}$;

each $R^{20z1}$ is independently selected from halogen, oxo, —CN, —$OR^{12}$, and —$N(R^{12})(R^{13})$;

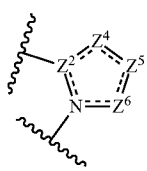

is selected from

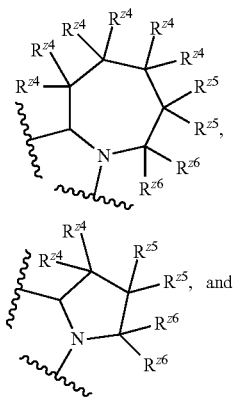

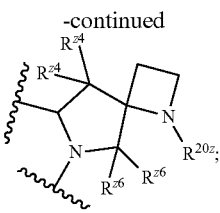

one $R^{z5}$, $R^{20z}$, or $R^{20zz}$ is E, wherein E is a moiety capable of covalently binding to a Ras mutant protein at an amino acid corresponding to G12D or G12S of human K-Ras mutant G12D or G12S protein, respectively;

each $R^{z4}$ is hydrogen; each $R^{z5}$ is independently selected from E, hydrogen, —$C(O)R^{12}$, and —$N(R^{14})C(O)R^{12}$; and one $R^{z4}$ and one $R^{z5}$ may be joined to form a monocyclic 3-7 membered heterocycloalkyl, wherein the monocyclic 3-7 membered heterocycloalkyl is optionally substituted with one, two, or three $R^{20z}$;

each $R^{z6}$ is hydrogen;

each $R^{12}$ is independently selected from hydrogen, $C_{1-6}$alkyl, $C_{2-6}$alkenyl, $C_{2-6}$alkynyl, $C_{3-10}$cycloalkyl, —$CH_2$-$C_{3-10}$cycloalkyl, $C_{2-9}$heterocycloalkyl, —$CH_2$-$C_{2-9}$heterocycloalkyl, $C_{3-10}$aryl, —$CH_2$-$C_{6-10}$aryl, —$CH_2$-$C_{1-9}$heteroaryl, and $C_{1-9}$heteroaryl, wherein $C_{1-6}$alkyl, $C_{2-6}$alkenyl, $C_{2-6}$alkynyl, $C_{3-10}$cycloalkyl, —$CH_2$-$C_{3-10}$cycloalkyl, $C_{2-9}$heterocycloalkyl, —$CH_2$-$C_{2-9}$heterocycloalkyl, $C_{6-10}$aryl, —$CH_2$-$C_{6-10}$aryl, —$CH_2$-$C_{1-9}$heteroaryl, and $C_{1-9}$heteroaryl are optionally substituted with one, two, or three $R^{20l}$;

each $R^{12a}$ is —$C(R^{12c})_2$-$C_{2-9}$heterocycloalkyl, wherein —$C(R^{12c})_2$-$C_{2-9}$heterocycloalkyl is optionally substituted with one, two, or three $R^{20l}$;

each $R^{12c}$ is independently selected from hydrogen and $R^{20lc}$;

each $R^{13}$ is independently selected from hydrogen, $C_{1-6}$alkyl, and $C_{1-6}$haloalkyl; or $R^{12}$ and $R^{13}$, together with the nitrogen to which they are attached, form a $C_{2-9}$heterocycloalkyl ring optionally substituted with one, two, or three $R^{20m}$;

each $R^{14}$ is independently selected from hydrogen, $C_{1-6}$alkyl, and $C_{1-6}$haloalkyl;

each $R^{15}$ is independently selected from $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20o}$;

each $R^{20z}$ is independently selected from E, halogen, oxo, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{12}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{12}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20zz}$;

each $R^{20lc}$, $R^{20l}$, $R^{20m}$, $R^{20o}$, and $R^{20q}$ is independently selected from halogen, oxo, —CN, $C_{1-6}$alkyl, $C_{2-6}$alkenyl, $C_{2-6}$alkynyl, $C_{3-10}$cycloalkyl, —$CH_2$-$C_{3-10}$cycloalkyl, $C_{2-9}$heterocycloalkyl, —$CH_2$-$C_{2-9}$heterocycloalkyl, $C_{6-10}$aryl, —$CH_2$-$C_{6-10}$aryl, —$CH_2$-$C_{1-9}$heteroaryl, $C_{1-9}$heteroaryl, —$N(R^{22})(R^{23})$, —$C(O)OR^{22}$, —$C(O)N(R^{22})(R^{23})$, —$C(O)C(O)N(R^{22})(R^{23})$, —$OC(O)N(R^{22})(R^{23})$, —$N(R^{24})C(O)N(R^{22})(R^{23})$, —$N(R^{24})C(O)OR^{25}$, —$N(R^{24})C(O)R^{21}$, —$N(R^{24})S(O)_2R^{25}$, —$C(O)R^{21}$, —$S(O)_2R^{25}$, —$S(O)_2N(R^{22})(R^{23})$, —$OCH_2C(O)OR^{22}$, =$NR^{21}$, and —$OC(O)R^{25}$; two $R^{20q}$ bonded to adjacent atoms are optionally joined to form a $C_{3-10}$cycloalkyl, $C_{2-9}$heterocycloalkyl, $C_{6-10}$aryl, or $C_{1-9}$heteroaryl; wherein $C_{1-6}$alkyl, $C_{2-6}$alkenyl, $C_{2-6}$alkynyl, $C_{3-10}$cycloalkyl, —$CH_2$-$C_{3-10}$cycloalkyl, $C_{2-9}$heterocycloalkyl, —$CH_2$-$C_{2-9}$heterocycloalkyl, $C_{6-10}$aryl, —$CH_2$-$C_{6-10}$aryl, —$CH_2$-$C_{1-9}$heteroaryl, and $C_{1-9}$heteroaryl are optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —$OR^{21}$, —$SR^{21}$, —$N(R^{22})(R^{23})$, —$C(O)OR^{22}$, —$C(O)N(R^{22})(R^{23})$, —$C(O)C(O)N(R^{22})(R^{23})$, —$OC(O)N(R^{22})(R^{23})$, —$N(R^{24})C(O)N(R^{22})(R^{23})$, —$N(R^{24})C(O)OR^{25}$, —$N(R^{24})C(O)R^{25}$, —$N(R^{24})S(O)_2R^{25}$, —$C(O)R^{25}$, —$S(O)_2R^{25}$, —$S(O)_2N(R^{22})(R^{23})$, and —$OC(O)R^{25}$;

each $R^{20zz}$ is independently selected from E, halogen, oxo, —CN, $C_{1-6}$alkyl, $C_{2-6}$alkenyl, $C_{2-6}$alkynyl, $C_{3-10}$cycloalkyl, —$CH_2$-$C_{3-10}$cycloalkyl, $C_{2-9}$heterocycloalkyl, —$CH_2$-$C_{2-9}$heterocycloalkyl, $C_{3-10}$aryl, —$CH_2$-$C_{6-10}$aryl, —$CH_2$-$C_{1-9}$heteroaryl, $C_{1-9}$heteroaryl, —$OR^{21}$, —$SR^{21}$, —$N(R^{22})(R^{23})$, —$C(O)OR^{22}$, —$C(O)N(R^{22})(R^{23})$, —$C(O)C(O)N(R^{22})(R^{23})$, —$OC(O)N(R^{22})(R^{23})$, —$N(R^{24})C(O)N(R^{22})(R^{23})$, —$N(R^{24})C(O)OR^{25}$, —$N(R^{24})C(O)R^{21}$, —$N(R^{24})S(O)_2R^{25}$, —$C(O)R^{21}$, —$S(O)_2R^{25}$, —$S(O)_2N(R^{22})(R^{23})$, —$OCH_2C(O)OR^{22}$, =$NR^{21}$, and —$OC(O)R^{25}$; wherein $C_{1-6}$alkyl, $C_{2-6}$alkenyl, $C_{2-6}$alkynyl, $C_{3-10}$cycloalkyl, —$CH_2$-$C_{3-10}$cycloalkyl, $C_{2-9}$heterocycloalkyl, —$CH_2$-$C_{2-9}$heterocycloalkyl, $C_{3-10}$aryl, —$CH_2$-$C_{6-10}$aryl, —$CH_2$-$C_{1-9}$heteroaryl, and $C_{1-9}$heteroaryl are optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —$OR^{21}$, —$SR^{21}$, —$N(R^{22})(R^{23})$, —$C(O)OR^{22}$, —$C(O)N(R^{22})(R^{23})$, —$C(O)C(O)N(R^{22})(R^{23})$, —$OC(O)N(R^{22})(R^{23})$, —$N(R^{24})C(O)N(R^{22})(R^{23})$, —$N(R^{24})C(O)OR^{25}$, —$N(R^{24})C(O)R^{25}$, —$N(R^{24})S(O)_2R^{25}$, —$C(O)R^{25}$, —$S(O)_2R^{25}$, —$S(O)_2N(R^{22})(R^{23})$, and —$OC(O)R^{25}$;

each $R^{21}$ is independently selected from hydrogen, $C_{1-6}$alkyl, $C_{1-6}$haloalkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl;

each $R^{22}$ is independently selected from hydrogen, $C_{1-6}$alkyl, $C_{1-6}$haloalkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl;

each $R^{23}$ is independently selected from hydrogen and $C_{1-6}$alkyl;

each $R^{24}$ is independently selected from hydrogen and $C_{1-6}$alkyl;

each $R^{25}$ is independently selected from $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; and ----- indicates a single or double bond such that all valences are satisfied.

2. The compound of claim 1, or a pharmaceutically acceptable salt or solvate thereof, wherein $W^6$ is N.

3. The compound of claim 1, or a pharmaceutically acceptable salt or solvate thereof, wherein $W^6$ is $C(R^6)$; and $R^6$ is selected from halogen and methyl, wherein the methyl is optionally substituted with one, two, or three halogen.

4. The compound of claim 1, or a pharmaceutically acceptable salt or solvate thereof, wherein one $R^{z5}$ is —$C(O)R^{12}$ or —$N(H)C(O)R^{12}$; and the $R^{12}$ is a 3-membered heterocycloalkyl which comprises one or more nitrogen ring atoms and is optionally substituted with one, two, or three $R^{20l}$.

5. The compound of claim 1, or a pharmaceutically acceptable salt or solvate thereof, wherein one $R^{20z}$ is —$C(O)R^{12}$ or —$N(H)C(O)R^{12}$; and the $R^{12}$ is a 5-membered heteroaryl which comprises two, three, or four ring nitrogen atoms and is optionally substituted with one, two, or three $R^{20l}$.

6. The compound of claim 1, or a pharmaceutically acceptable salt or solvate thereof, wherein $R^8$ is halogen.

7. The compound of claim 1, or a pharmaceutically acceptable salt or solvate thereof, wherein $R^{17}$ is phenyl optionally substituted with one, two, three, or four $R^{20q}$.

8. The compound of claim 1, or a pharmaceutically acceptable salt or solvate thereof, wherein $R^{17}$ is selected from naphthyl and benzothiophenyl, each of which is optionally substituted with one, two, or three substituents independently selected from halogen, —CN, $C_{1-3}$alkyl, $C_{2-3}$alkenyl, $C_{2-3}$alkynyl, —$OR^{21}$, and —$N(R^{22})(R^{23})$.

9. The compound of claim 1, or a pharmaceutically acceptable salt or solvate thereof, wherein $R^{17}$ is selected from:

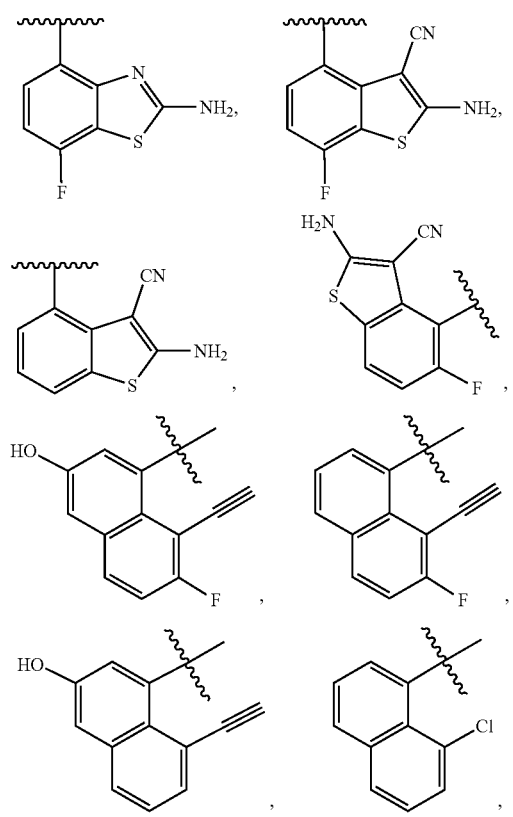

-continued

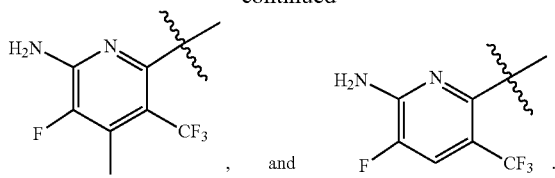
, and

10. The compound of claim 1, or a pharmaceutically acceptable salt or solvate thereof, wherein —OR$^{12a}$ is selected from

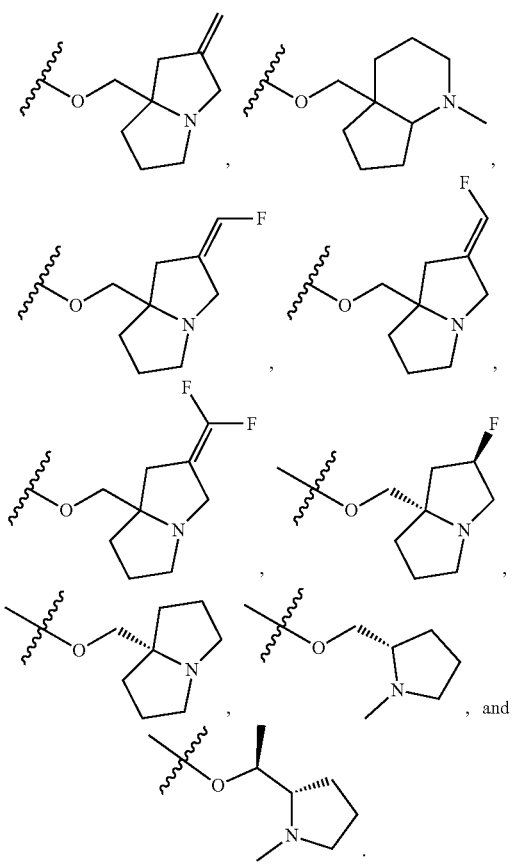

11. The compound of claim 1, or a pharmaceutically acceptable salt or solvate thereof, wherein —OR$^{12a}$ is

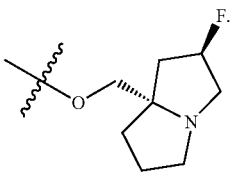 [SMILES: *OC[C@@]12CCCN1C[C@H](F)C2]

12. The compound of claim 1, or a pharmaceutically acceptable salt or solvate thereof, wherein the compound covalently binds to a KRas G12D mutant.

13. The compound of claim 1, or a pharmaceutically acceptable salt or solvate thereof, wherein the compound covalently binds to a KRas G12S mutant.

14. A pharmaceutical composition comprising a compound of claim 1, or a pharmaceutically acceptable salt or solvate thereof, and a pharmaceutically acceptable excipient.

15. A method of treating cancer in a subject comprising a Ras mutant protein, the method comprising: modifying the Ras mutant protein of said subject by administering to said subject a compound of claim 1, wherein the compound is characterized in that upon contacting the Ras mutant protein, said Ras mutant protein is modified covalently at a residue corresponding to residue 12 of SEQ ID No: 1, such that said modified Ras mutant protein exhibits reduced Ras signaling output.

16. The method of claim 15, wherein the Ras mutant protein is a KRas G12D or G12S mutant protein.

17. The method of claim 15, wherein the cancer is a solid tumor or a hematological cancer.

18. The method of claim 15, comprising administering an additional agent.

19. A method of modulating signaling output of a Ras protein, comprising contacting a Ras protein with an effective amount of a compound of claim 1, or a pharmaceutically acceptable salt or solvate thereof, thereby modulating the signaling output of the Ras protein.

20. The method of claim 19, wherein the Ras protein is a KRas G12D or G12S mutant protein.

* * * * *

UNITED STATES PATENT AND TRADEMARK OFFICE
CERTIFICATE OF CORRECTION

PATENT NO. : 12,059,425 B2  
APPLICATION NO. : 18/439666  
DATED : August 13, 2024  
INVENTOR(S) : Wu et al.

Page 1 of 1

It is certified that error appears in the above-identified patent and that said Letters Patent is hereby corrected as shown below:

In the Claims

Claim 1, Column 902, Line 25, delete "$C_{3-10}$aryl," and insert -- $C_{6-10}$aryl, --.

Claim 1, Column 903, Line 3, delete "$C_{1-9}$heteroaryl," and insert -- $C_{1-9}$heteroaryl, -$OR^{21}$, -$SR^{21}$, --.

Claim 1, Column 903, Line 28, delete "$C_{3-10}$aryl," and insert -- $C_{6-10}$aryl, --.

Claim 1, Column 903, Line 38, delete "$C_{3-10}$aryl," and insert -- $C_{6-10}$aryl, --.

Signed and Sealed this  
Seventeenth Day of June, 2025

Coke Morgan Stewart  
*Acting Director of the United States Patent and Trademark Office*

```
                              SEQUENCE LISTING

Sequence total quantity: 13
SEQ ID NO: 1            moltype = AA  length = 188
FEATURE                 Location/Qualifiers
source                  1..188
                        mol_type = protein
                        organism = Homo sapiens
SEQUENCE: 1
MTEYKLVVVG AGGVGKSALT IQLIQNHFVD EYDPTIEDSY RKQVVIDGET CLLDILDTAG   60
QEEYSAMRDQ YMRTGEGFLC VFAINNTKSF EDIHHYREQI KRVKDSEDVP MVLVGNKCDL  120
PSRTVDTKQA QDLARSYGIP FIETSAKTRQ GVDDAFYTLV REIRKHKEKM SKDGKKKKKK  180
SKTKCVIM                                                          188

SEQ ID NO: 2            moltype = AA  length = 188
FEATURE                 Location/Qualifiers
source                  1..188
                        mol_type = protein
                        organism = Homo sapiens
SEQUENCE: 2
MTEYKLVVVG ADGVGKSALT IQLIQNHFVD EYDPTIEDSY RKQVVIDGET CLLDILDTAG   60
QEEYSAMRDQ YMRTGEGFLC VFAINNTKSF EDIHHYREQI KRVKDSEDVP MVLVGNKCDL  120
PSRTVDTKQA QDLARSYGIP FIETSAKTRQ GVDDAFYTLV REIRKHKEKM SKDGKKKKKK  180
SKTKCVIM                                                          188

SEQ ID NO: 3            moltype = AA  length = 188
FEATURE                 Location/Qualifiers
source                  1..188
                        mol_type = protein
                        organism = Homo sapiens
SEQUENCE: 3
MTEYKLVVVG AVGVGKSALT IQLIQNHFVD EYDPTIEDSY RKQVVIDGET CLLDILDTAG   60
QEEYSAMRDQ YMRTGEGFLC VFAINNTKSF EDIHHYREQI KRVKDSEDVP MVLVGNKCDL  120
PSRTVDTKQA QDLARSYGIP FIETSAKTRQ GVDDAFYTLV REIRKHKEKM SKDGKKKKKK  180
SKTKCVIM                                                          188

SEQ ID NO: 4            moltype = AA  length = 188
FEATURE                 Location/Qualifiers
source                  1..188
                        mol_type = protein
                        organism = Homo sapiens
SEQUENCE: 4
MTEYKLVVVG ASGVGKSALT IQLIQNHFVD EYDPTIEDSY RKQVVIDGET CLLDILDTAG   60
QEEYSAMRDQ YMRTGEGFLC VFAINNTKSF EDIHHYREQI KRVKDSEDVP MVLVGNKCDL  120
PSRTVDTKQA QDLARSYGIP FIETSAKTRQ GVDDAFYTLV REIRKHKEKM SKDGKKKKKK  180
SKTKCVIM                                                          188

SEQ ID NO: 5            moltype = AA  length = 189
FEATURE                 Location/Qualifiers
source                  1..189
                        mol_type = protein
                        organism = Homo sapiens
SEQUENCE: 5
MTEYKLVVVG AGGVGKSALT IQLIQNHFVD EYDPTIEDSY RKQVVIDGET CLLDILDTAG   60
QEEYSAMRDQ YMRTGEGFLC VFAINNSKSF ADINLYREQI KRVKDSDDVP MVLVGNKCDL  120
PTRTVDTKQA HELAKSYGIP FIETSAKTRQ GVEDAFYTLV REIRQYRMKK LNSSDDGTQG  180
CMGLPCVVM                                                         189

SEQ ID NO: 6            moltype = AA  length = 189
FEATURE                 Location/Qualifiers
source                  1..189
                        mol_type = protein
                        organism = Homo sapiens
SEQUENCE: 6
MTEYKLVVVG ADGVGKSALT IQLIQNHFVD EYDPTIEDSY RKQVVIDGET CLLDILDTAG   60
QEEYSAMRDQ YMRTGEGFLC VFAINNTKSF EDIHQYREQI KRVKDSDDVP MVLVGNKCDL  120
```

```
AARTVESRQA QDLARSYGIP YIETSAKTRQ GVEDAFYTLV REIRQHKLRK LNPPDESGPG    180
CMSCKCVLS                                                           189

SEQ ID NO: 7            moltype = AA  length = 189
FEATURE                 Location/Qualifiers
source                  1..189
                        mol_type = protein
                        organism = Homo sapiens
SEQUENCE: 7
MTEYKLVVVG AGGVGKSALT IQLIQNHFVD EYDPTIEDSY RKQVVIDGET CLLDILDTAG    60
QEEYSAMRDQ YMRTGEGFLC VFAINNTKSF EDIHQYREQI KRVKDSDDVP MVLVGNKCDL    120
AARTVESRQA QDLARSYGIP YIETSAKTRQ GVEDAFYTLV REIRQHKLRK LNPPDESGPG    180
CMSCKCVLS                                                           189

SEQ ID NO: 8            moltype = AA  length = 189
FEATURE                 Location/Qualifiers
source                  1..189
                        mol_type = protein
                        organism = Homo sapiens
SEQUENCE: 8
MTEYKLVVVG ADGVGKSALT IQLIQNHFVD EYDPTIEDSY RKQVVIDGET CLLDILDTAG    60
QEEYSAMRDQ YMRTGEGFLC VFAINNSKSF ADINLYREQI KRVKDSDDVP MVLVGNKCDL    120
PTRTVDTKQA HELAKSYGIP FIETSAKTRQ GVEDAFYTLV REIRQYRMKK LNSSDDGTQG    180
CMGLPCVVM                                                           189

SEQ ID NO: 9            moltype = AA  length = 108
FEATURE                 Location/Qualifiers
source                  1..108
                        mol_type = protein
                        organism = Homo sapiens
SEQUENCE: 9
MTEYKLVVVG AGGVGKSALT IQLIQNHFVD EYDPTIEDSY RKQVVIDGET CLLDILDTAG    60
QEEYSAMRDQ YMRTGEGFLC VFAINNTKSF EDIHHYREQI KRVKDSED                108

SEQ ID NO: 10           moltype = AA  length = 108
FEATURE                 Location/Qualifiers
source                  1..108
                        mol_type = protein
                        organism = Homo sapiens
SEQUENCE: 10
MTEYKLVVVG AGGVGKSALT IQLIQNHFVD EYDPTIEDSY RKQVVIDGET CLLDILDTAG    60
QEEYSAMRDQ YMRTGEGFLC VFAINNTKSF EDIHQYREQI KRVKDSDD                108

SEQ ID NO: 11           moltype = AA  length = 108
FEATURE                 Location/Qualifiers
source                  1..108
                        mol_type = protein
                        organism = Homo sapiens
SEQUENCE: 11
MTEYKLVVVG AGGVGKSALT IQLIQNHFVD EYDPTIEDSY RKQVVIDGET CLLDILDTAG    60
QEEYSAMRDQ YMRTGEGFLC VFAINNSKSF ADINLYREQI KRVKDSDD                108

SEQ ID NO: 12           moltype = AA  length = 119
FEATURE                 Location/Qualifiers
source                  1..119
                        mol_type = protein
                        organism = Homo sapiens
SEQUENCE: 12
MAANKPKGQN SLALHKVIMV GSGGVGKSAL TLQFMYDEFV EDYEPTKADS YRKKVVLDGE    60
EVQIDILDTA GQEDYAAIRD NYFRSGEGFL CVFSITEMES FAATADFREQ ILRVKEDEN    119

SEQ ID NO: 13           moltype = AA  length = 120
FEATURE                 Location/Qualifiers
source                  1..120
                        mol_type = protein
                        organism = Homo sapiens
SEQUENCE: 13
MAANKSKGQS SLALHKVIMV GSGGVGKSAL TLQFMYDEFV EDYEPTKADS YRKKVVLDGE    60
EVQIDILDTA GQEDYAAIRD NYFRSGEGFL LVFSITEHES FTATAEFREQ ILRVKAEEDK    120
```